US012503436B2

(12) United States Patent
Venkatraman et al.

(10) Patent No.: US 12,503,436 B2
(45) Date of Patent: Dec. 23, 2025

(54) COMPOUNDS AND COMPOSITIONS FOR TREATING CONDITIONS ASSOCIATED WITH STING ACTIVITY

(71) Applicant: NOVARTIS PHARMA AG, Basel (CH)

(72) Inventors: Shankar Venkatraman, Lansdale, PA (US); Jason Katz, Newton, MA (US); William R. Roush, Boston, MA (US); Hans Martin Seidel, Concord, MA (US)

(73) Assignee: NOVARTIS PHARMA AG, Basel (CH)

( * ) Notice: Subject to any disclaimer, the term of this patent is extended or adjusted under 35 U.S.C. 154(b) by 0 days.

(21) Appl. No.: 17/884,933

(22) Filed: Aug. 10, 2022

(65) Prior Publication Data

US 2023/0167057 A1 Jun. 1, 2023

Related U.S. Application Data

(60) Provisional application No. 63/369,343, filed on Jul. 25, 2022, provisional application No. 63/298,889, filed on Jan. 12, 2022, provisional application No. 63/231,672, filed on Aug. 10, 2021.

(51) Int. Cl.

| | |
|---|---|
| ***C07D 209/40*** | (2006.01) |
| ***A61K 31/4439*** | (2006.01) |
| ***A61K 31/454*** | (2006.01) |
| ***A61K 45/06*** | (2006.01) |
| ***A61P 35/00*** | (2006.01) |
| ***C07D 401/06*** | (2006.01) |
| ***C07D 401/12*** | (2006.01) |
| ***C07D 401/14*** | (2006.01) |
| ***C07D 403/06*** | (2006.01) |
| ***C07D 403/12*** | (2006.01) |
| ***C07D 405/12*** | (2006.01) |
| ***C07D 405/14*** | (2006.01) |
| ***C07D 407/12*** | (2006.01) |
| ***C07D 417/12*** | (2006.01) |
| ***C07D 451/02*** | (2006.01) |
| ***C07D 471/04*** | (2006.01) |
| ***C07D 487/08*** | (2006.01) |

(52) U.S. Cl.

CPC ........ *C07D 209/40* (2013.01); *A61K 31/4439* (2013.01); *A61K 31/454* (2013.01); *A61K 45/06* (2013.01); *A61P 35/00* (2018.01); *C07D 401/06* (2013.01); *C07D 401/12* (2013.01); *C07D 401/14* (2013.01); *C07D 403/06* (2013.01); *C07D 403/12* (2013.01); *C07D 405/12* (2013.01); *C07D 405/14* (2013.01); *C07D 407/12* (2013.01); *C07D 417/12* (2013.01); *C07D 451/02* (2013.01); *C07D 471/04* (2013.01); *C07D 487/08* (2013.01); *C07B 2200/05* (2013.01)

(58) Field of Classification Search

CPC .. C07D 209/40; C07D 401/12; C07D 401/14; C07D 403/06; C07D 403/12; C07D 405/12; C07D 405/14; C07D 417/12; C07D 471/04; C07D 487/08; A61K 45/06; C07B 2200/05

See application file for complete search history.

(56) References Cited

U.S. PATENT DOCUMENTS

| | | | | |
|---|---|---|---|---|
| 5,189,054 | A | 2/1993 | Salituro et al. | |
| 6,043,248 | A | 3/2000 | Nugent et al. | |
| 6,124,306 | A | 9/2000 | Morris et al. | |
| 7,511,136 | B2 | 3/2009 | Amici et al. | |
| 7,927,613 | B2 | 4/2011 | Almarsson et al. | |
| 8,981,085 | B2 | 3/2015 | Le Huerou et al. | |
| 10,000,481 | B2 | 6/2018 | Stokes et al. | |
| 2004/0106667 | A1 | 6/2004 | Damour et al. | |
| 2004/0254177 | A1* | 12/2004 | Amici ..................... | A61P 13/08 514/254.06 |

(Continued)

FOREIGN PATENT DOCUMENTS

| | | |
|---|---|---|
| CN | 106146493 | 11/2016 |
| CN | 110105356 | 8/2019 |

(Continued)

OTHER PUBLICATIONS

By S. Rivara, et al. (Synthesis of (E)-8-(3-Chlorostyryl)caffeine Analogues Leading to 9-Deazaxanthine Derivatives as Dual A2A Antagonists/MAO-B Inhibitors, J. Med. Chem. 2013, VL-56, IS-3, p. 1247-1261, doi: 10.1021/jm301686s. (Year: 2013).*

M. Sklepari, et al. (Synthesis, Docking Study and Kinase Inhibitory Activity of a No. of New Substituted Pyrazolo[3,4-c]pyridines , Chemical and Pharmaceutical Bulletin, 2017, vol. 65, Issue 1, pp. 66-81, https://doi.org/10.1248/cpb.c16-00704. (Year: 2017).*

Double patenting over copending U.S. Appl. No. 18/095,717 (US20230250060A1). (Year: 2023).*

J. Martin et al. J. (Org. Chem. Aug. 5, 2021, 86, 17, 11333-11340. (Year: 2021).*

J. Martin et al. J. Org. Chem. Aug. 5, 2021, 86, 17, 11333-11340. doi/10.1021/acs.joc. 1c00652. (Year: 2021).*

(Continued)

*Primary Examiner* — James H Strum-Acevedo
*Assistant Examiner* — Manahil Mirghani Ali Abdalhameed
(74) *Attorney, Agent, or Firm* — Adil R. Zhugralin

(57) ABSTRACT

This disclosure features chemical entities (e.g., a compound or a pharmaceutically acceptable salt, and/or hydrate, and/or cocrystal, and/or drug combination of the compound) that inhibit (e.g., antagonize) Stimulator of Interferon Genes (STING). Said chemical entities are useful, e.g., for treating a condition, disease or disorder in which increased (e.g., excessive) STING activation (e.g., STING signaling) contributes to the pathology and/or symptoms and/or progression of the condition, disease or disorder (e.g., cancer) in a subject (e.g., a human). This disclosure also features compositions containing the same as well as methods of using and making the same.

86 Claims, No Drawings

(56) References Cited

U.S. PATENT DOCUMENTS

2008/0312301 A1 12/2008 Merla et al.
2010/0234324 A1 9/2010 Eggenweiler et al.
2012/0202848 A1 8/2012 Greene et al.
2013/0178460 A1 7/2013 Chen et al.
2015/0056224 A1 2/2015 Dubensky et al.
2016/0289196 A1 10/2016 Choi et al.
2017/0283397 A1 10/2017 Vankayalapati et al.
2020/0172534 A1 6/2020 Roush et al.
2021/0236466 A1 8/2021 Roush et al.
2022/0024906 A1 1/2022 Venkatraman et al.
2022/0024919 A1 1/2022 Venkatraman et al.
2022/0227760 A1 7/2022 Venkatraman et al.
2022/0242852 A1 8/2022 Venkatraman et al.
2022/0388957 A1 12/2022 Seidel et al.
2023/0002320 A1 1/2023 Seidel et al.
2023/0002373 A1 1/2023 Seidel et al.
2023/0021448 A1 1/2023 Seidal et al.
2023/0047905 A1 2/2023 Venkatraman et al.
2023/0092163 A1 3/2023 Katz et al.
2023/0106899 A1 4/2023 Glick et al.
2023/0115274 A1 4/2023 Roush et al.
2023/0127839 A1 4/2023 Seidel et al.
2023/0250060 A1* 8/2023 Venkatraman ....... C07D 403/12 514/415
2023/0250088 A1 8/2023 Venkatraman et al.
2023/0250106 A1 8/2023 Venkatraman et al.
2023/0271941 A1 8/2023 Venkatraman et al.
2023/0365553 A1 11/2023 Venkatraman et al.
2024/0041843 A1 2/2024 Glick et al.
2024/0051970 A1 2/2024 Venkatraman et al.
2024/0060982 A1 2/2024 Glick et al.
2024/0076285 A1 3/2024 Venkatraman
2024/0083879 A1 3/2024 Venkatraman et al.
2024/0083895 A1 3/2024 Roush et al.
2024/0100017 A1 3/2024 Glick et al.
2024/0101556 A1 3/2024 Venkatraman et al.

FOREIGN PATENT DOCUMENTS

EP 0029546 6/1981
EP 0606489 7/1994
EP 1710233 10/2006
EP 2243772 10/2010
EP 3056210 8/2016
EP 3184521 6/2017
EP 3556362 10/2019
JP 2004-530655 A 10/2004
KR 2014019055 A * 2/2014
WO WO 2002/050073 6/2002
WO WO 2002/067865 A2 9/2002
WO WO 2003/028720 4/2003
WO WO 2003/028724 4/2003
WO WO-03068773 A1 * 8/2003 ........... C07D 471/04
WO WO 2005/005415 1/2005
WO WO 2005/123674 12/2005
WO WO 2006/094235 9/2006
WO WO 2007/076423 7/2007
WO WO 2007/090493 8/2007
WO WO 2007/139856 12/2007
WO WO 2008/061109 5/2008
WO WO 2008/090048 7/2008
WO WO 2008/154241 12/2008
WO WO 2009/010824 1/2009
WO WO 2009/013126 1/2009
WO WO 2009/089352 7/2009
WO WO 2009/140320 11/2009
WO WO 2010/069966 6/2010
WO WO 2010/118390 10/2010
WO WO 2011/050316 4/2011
WO WO 2011/133888 10/2011
WO WO 2012/077932 6/2012
WO WO 2012/110190 8/2012
WO WO 2012/129338 9/2012
WO WO 2012/163456 12/2012
WO WO 2012/178123 12/2012
WO WO 2013/114113 8/2013
WO WO 2015/061294 4/2015
WO WO 2015/112854 7/2015
WO WO 2015/127125 8/2015
WO WO 2016/055028 4/2016
WO WO 2017/153952 9/2017
WO WO 2017/165495 9/2017
WO WO 2017/175156 10/2017
WO WO 2018/083105 5/2018
WO WO 2018/098206 A1 5/2018
WO WO 2018/122232 7/2018
WO WO 2018/138684 8/2018
WO WO 2019/069275 4/2019
WO WO 2019/104067 5/2019
WO WO 2019/122202 6/2019
WO WO 2019/185525 10/2019
WO WO 2019/201939 10/2019
WO WO-2019201939 A1 * 10/2019 ........... A61K 31/404
WO WO 2020/010092 1/2020
WO WO 2020/010155 1/2020
WO WO 2020/106736 5/2020
WO WO 2020/106741 5/2020
WO WO 2020/150417 7/2020
WO WO 2020/150439 7/2020
WO WO 2020/236586 11/2020
WO WO 2020/243519 12/2020
WO WO 2020/252240 12/2020
WO WO 2020/257621 12/2020
WO WO 2021/067791 4/2021
WO WO 2021/067801 4/2021
WO WO 2021/067805 4/2021
WO WO 2021/138419 7/2021
WO WO 2021/138434 7/2021
WO WO 2021/236405 11/2021
WO WO 2022/015938 1/2022
WO WO 2022/015957 1/2022
WO WO 2022/015975 1/2022
WO WO 2022/015977 1/2022
WO WO 2022/015979 1/2022
WO WO 2022/133046 6/2022
WO WO 2022/133098 6/2022
WO WO 2022/140387 6/2022
WO WO 2022/140397 6/2022
WO WO 2022/140403 6/2022
WO WO 2022/140410 6/2022
WO WO 2022/150543 7/2022
WO WO 2022/150549 7/2022
WO WO 2022/150560 7/2022
WO WO 2022/150585 7/2022
WO 2023016434 A1 2/2023
WO 2023018236 A1 2/2023
WO WO 2023/018781 2/2023
WO WO 2023/137034 7/2023
WO WO 2023/137041 7/2023
WO WO 2024/064358 A1 3/2024
WO WO 2024/151919 A1 7/2024

OTHER PUBLICATIONS

F. Li et al. (Aging Dis. Oct. 1, 2021;12(7):1658-1674. doi: 10.14336/AD.2021.0304. (Year: 2021).*

N. Reich (Semin Immunol. 2019; 43: 101282. doi:10.1016/j.smim.2019.101282. (Year: 2019).*

Caballero et al., "Binding Studies and Quantitative Structure-Activity Relationship of 3-Amino-1H-Indazoles as Inhibitors of GSK3β," Chemical Biological & Drug Design, Oct. 2011, 78(4):631-641.

CAS No. 1090528-21-4, "Benzamide, N-1H-indazol-3-yl-4-(1-piperidinylmethyl)-," Dec. 28, 2008, retrieved on Oct. 13, 2021, XP55850936, 1 page.

CAS No. 1455710-19-6, "Benzamide, N-1H-indazol-3-yl-4-(1-methylethyl)," Oct. 6, 2013, retrieved on Oct. 13, 2021, XP55851222, 1 page.

CAS No. 1840149-63-4, "1H-Pyrrolo[2,3-b)pyridine-3-sulfonamide, 4-chloro-N-(3-methyl-4-piperidinyl)," dated Jan. 3, 2016, 1 page.

(56) References Cited

OTHER PUBLICATIONS

CAS No. 2305399-80-6, "Acetic acid, 2-[4-[(1H-indazol-3-ylamino)carbonyl]-2,6-dimethylphenoxy]-," Apr. 24, 2019, retrieved on Oct. 13, 2021, XP55851086, 1 page.
CAS No. 63607-40-9, "N-indol-3-yl-toluene-4-sulfonamide," retrieved on Aug. 23, 2023, retrieved from URL <https://www.molbase.com/moldata/26700121.html#>, 2 pages.
CAS No. RN 220265-46-3, "Benzenepropanamide, N-(2-benzoyl-6-chloro-1H-indol-3-yl)-," Mar. 9, 1999, retrieved on Feb. 25, 2023, 15 pages.
CAS Nos. 1457319-48-0, 1457185-97-5, "CN-Benzamide, 4-ethoxy-N-1H-indazol-3-yl-," Oct. 13, 2013, retrieved on Oct. 13, 2021, XP55850930, 1 page.
CAS Nos. 1458486-88-8, 1458303-04-02, "Benzamide, N-1H-indazol-3-yl-4-[(methylthio)methyl]-," Oct. 15, 2013, retrieved on Oct. 13, 2021, XP55851079, 1 page.
Cui et al., "Optimization of 1H-indazol-3-amine derivatives as potent fibroblast growth factor receptor inhibitors," Bioorganic & Medicinal Chemistry Letters, Aug. 15, 2017, 27(16):3782-3786.
Feneyrolles et al., "Discovering novel 7-azaindole-based series as potent AXL kinase inhibitors," Bioorganic & Medicinal Chemistry Letters, Feb. 15, 2017, 27(4):862-866.
Filipski et al., "Intestinal Targeting of Drugs: Rational Design Approaches and Challenges," Current Topics in Medicinal Chemistry, 2013, 13:776-802.
Gao et al., "Discovery of dual death-associated protein related apoptosis inducing protein kinase 1 and 2 inhibitors by a scaffold hopping approach," Journal of Medicinal Chemistry, Sep. 2, 2014, 57(18):7624-7643.
Haag et al., "Targeting STING with covalent small-molecule inhibitors," Nature, Jul. 2018, 559(7713):269-273.
Harmon et al., "The reaction of arylsulfonyl azides with N-methylindole," J. of Organic Chemistry, Jan. 1973, 38:1:11-16.
Huang et al., "Identification of pyrazolopyridine derivatives as novel spleen tyrosine kinase inhibitors," Archiv Der Pharmazie, Aug. 2018, 351(8):1800083.
International Preliminary Report on Patentability in International Appln. No. PCT/US2020/013786, mailed on Jul. 29, 2021, 28 pages.
International Preliminary Report on Patentability in International Appln. No. PCT/US2020/013824, mailed on Jun. 16, 2021, 12 pages.
International Preliminary Report on Patentability in International Appln. No. PCT/US2021/041792, mailed on Jan. 26, 2023, 8 pages.
International Preliminary Report on Patentability in International Appln. No. PCT/US2021/041817, mailed on Jan. 26, 2023, 9 pages.
International Preliminary Report on Patentability in International Appln. No. PCT/US2021/041820, mailed on Jan. 26, 2023, 11 pages.
International Preliminary Report on Patentability in International Appln. No. PCT/US2021/041823, mailed on Jan. 26, 2023, 9 pages.
International Preliminary Report on Patentablity in International Appln. No. PCT/US2021/041758, mailed on Jan. 26, 2023, 10 pages.
International Search Report and Written Opinion in International Appl. No. PCT/US2020/013824, mailed on May 11, 2020, 14 pages.
International Search Report and Written Opinion in International Appln. No. PCT/US2020/013786, mailed on Jul. 16, 2020, 45 pages.
International Search Report and Written Opinion in International Appln. No. PCT/US2021/041758, mailed on Oct. 15, 2021, 13 pages.
International Search Report and Written Opinion in International Appln. No. PCT/US2021/041792, mailed on Oct. 14, 2021, 9 pages.
International Search Report and Written Opinion in International Appln. No. PCT/US2021/041817, mailed on Oct. 20, 2021, 12 pages.
International Search Report and Written Opinion in International Appln. No. PCT/US2021/041820, mailed on Oct. 22, 2021, 15 pages.
International Search Report and Written Opinion in International Appln. No. PCT/US2021/041823, mailed on Oct. 27, 2021, 15 pages.
International Search Report and Written Opinion in International Appln. No. PCT/US2022/039931, mailed on Nov. 25, 2022, 10 pages.
International Search Report and Written Opinion in International Appln. No. PCT/US2023/010550, mailed on Mar. 15, 2023, 16 pages.
International Search Report and Written Opinion in International Appln. No. PCT/US2023/010561, mailed on Mar. 16, 2023, 15 pages.
Invitation to Pay Additional Fees in International Appln. No. PCT/US2020/013786, mailed Apr. 20, 2020, 32 pages.
Kumaran et al., "Synthesis, Spectral Characterization and Anti microbial Studies of New 3- and 4-substituted in 7-Aza Indole Derivatives," International Journal of Pharma Tech Research, Jan.-Mar. 2012, 4(1):169-175.
Lammers et al., "Effect of Intratumoral Injection on the Biodistribution and the Therapeutic Potential of HPMACopolymer-Based Drug Delivery Systems," Neoplasia, 2006, 10:788-795.
Lesuisse et al., "Rational design of potent GSK3β inhibitors with selectivity for Cdk1 and Cdk2," Bioorganic & Medicinal Chemistry Letters, Mar. 15, 2010, 20(6):1985-1989.
Liu et al., "Design, synthesis and biological evaluation of novel FGFR inhibitors bearing an indazole scaffold," Organic & Biomolecular Chemistry, Jul. 28, 2015, 13(28):7643-7654.
Magedov et al., "Antiproliferative activity of 2,3-disubstituted indoles toward apoptosis-resistant cancers cells," Bioorganic & Medicinal Chemistry Letters, Jun. 1, 2013, 23(11):3277-3282.
Morphy, "Selectively Nonselective Kinase Inhibition: Striking the Right Balance," Journal of Medicinal Chemistry, Feb. 25, 2010, 53(4):1413-1437.
Postow et al., "Immune Checkpoint Blockade in Cancer Therapy," J. Clin. Oncol., 2015, 33:17:1974-82.
Przheval'skii et al., "Fischer Synthesis of 3-(N-Acylamino)-2-phenylindoles," Chemistry of Heterocyclic Compounds, 2002, 38(9):1055-1061.
Reekie et al., "Rapid access to N-(indol-2-y1)amides and N-(indol-3-yl)amides as unexplored pharmacophores," Organic & Biomolecular Chemistry, 2017, 15:576-580.
Stec et al., "Synthesis, biological evaluation, and structure-activity relationships of N-benzoyl-2-hydroxybenzamides as agents active against *P. falciparum* (K1 strain), trypanosomes, and leishmania," Journal of Medicinal Chemistry, Apr. 12, 2012, 55(7), 13 pages.
Suresh et al., "Synthesis and Antitumor Activity Evaluation of 2-Aminothiazoles Appended 5-methylisoxazoline and Pyridine-piperazine Hybrid Molecules," Letters in Organic Chemistry, 2018, 15(12):1070-1077.
Verdonck et al., "Synthesis and Structure-Activity Relationships of 3, 5-Disubstituted-pyrrolo [2,3-b] pyridines as Inhibitors of Adaptor-Associated Kinase 1 with Antiviral Activity," Journal of Medicinal Chemistry, Jun. 27, 2019, 62(12):5810-5831.
Wang et al., "Discovery of novel pyrazolo[1,5-a]pyrimidines as potent pan-Pim inhibitors by structure- and property-based drug design," Bioorganic & Medicinal Chemistry Letters, Apr. 17, 2013, 23(11):3149-3153.
Warren et al., "A Critical Assessment of Docking Programs and Scoring Functions," Journal of Medicinal Chemistry, Oct. 1, 2006, 49(20):5912-5931.
Zhao et al., "Discovery of Substituted 1H-Pyrazolo[3,4-b]pyridine Derivatives as Potent and Selective FGFR Kinase Inhibitors," ACS Medicinal Chemistry Letters, Apr. 20, 2016, 7(6):629-634.
CAS No. RN 1069766-41-1, "1H-Tetrazole-1-acetamide, N-1H-indol-3-yl-," dated Nov. 2, 2008, 3 pages.
CAS No. RN 2389944-78-7, "3-Piperidineacetamide, N-(5-bromo-1H-indol-3-yl)-, (3R)-," dated Dec. 12, 2019, 3 pages.
International Preliminary Report on Patentability in International Appln. No. PCT/US2022/039931, mailed on Feb. 22, 2024, 8 pages.
CAS No. 1214421-60-9 "Benzenepropanamide, N-1H-indol-3-yl-4- [(methylamino)sulfonyl], "retrieved on Jun. 26, 2024, 3 pages.

(56) References Cited

OTHER PUBLICATIONS

CAS No. 1196510-99-2 “Benzeneacetamide, N-(5-bromo-4-fluoro-1H- pyrrolo[2,3-b]pyridin-3-yl)-,” retrieved on Jun. 26, 2024, 9 pages.
International Preliminary Report on Patentability in International Appln. No. PCT/US2023/010550, mailed on Jul. 25, 2024, 8 pages.
International Preliminary Report on Patentability in International Appln. No. PCT/US2023/010561, mailed on Jul. 25, 2024, 7 pages.

* cited by examiner

COMPOUNDS AND COMPOSITIONS FOR TREATING CONDITIONS ASSOCIATED WITH STING ACTIVITY

CROSS REFERENCE TO RELATED APPLICATIONS

This application claims the benefit of U.S. Provisional Application No. 63/231,672, filed on Aug. 10, 2021, U.S. Provisional Application No. 63/298,889, filed on Jan. 12, 2022, and U.S. Provisional Application No. 63/369,343, filed on Jul. 25, 2022, each of these prior applications is incorporated by reference in its entirety.

TECHNICAL FIELD

This disclosure features chemical entities (e.g., a compound or a pharmaceutically acceptable salt, and/or hydrate, and/or cocrystal, and/or drug combination of the compound) that inhibit (e.g., antagonize) Stimulator of Interferon Genes (STING). Said chemical entities are useful, e.g., for treating a condition, disease or disorder in which increased (e.g., excessive) STING activation (e.g., STING signaling) contributes to the pathology and/or symptoms and/or progression of the condition, disease or disorder (e.g., cancer) in a subject (e.g., a human). This disclosure also features compositions containing the same as well as methods of using and making the same.

BACKGROUND

STING, also known as transmembrane protein 173 (TMEM173) and MPYS/MITA/ERIS, is a protein that in humans is encoded by the TMEM173 gene. STING has been shown to play a role in innate immunity. STING induces type I interferon production when cells are infected with intracellular pathogens, such as viruses, mycobacteria and intracellular parasites. Type I interferon, mediated by STING, protects infected cells and nearby cells from local infection in an autocrine and paracrine manner.

The STING pathway is pivotal in mediating the recognition of cytosolic DNA. In this context, STING, a transmembrane protein localized to the endoplasmic reticulum (ER), acts as a second messenger receptor for 2', 3' cyclic GMP-AMP (hereafter cGAMP), which is produced by cGAS after dsDNA binding. In addition, STING can also function as a primary pattern recognition receptor for bacterial cyclic dinucleotides (CDNs) and small molecule agonists. The recognition of endogenous or prokaryotic CDNs proceeds through the carboxy-terminal domain of STING, which faces into the cytosol and creates a V-shaped binding pocket formed by a STING homodimer. Ligand-induced activation of STING triggers its re-localization to the Golgi, a process essential to promote the interaction of STING with TBK1. This protein complex, in turn, signals through the transcription factors IRF-3 to induce type I interferons (IFNs) and other co-regulated antiviral factors. In addition, STING was shown to trigger NF-κB and MAP kinase activation. Following the initiation of signal transduction, STING is rapidly degraded, a step considered important in terminating the inflammatory response.

Excessive activation of STING is associated with a subset of monogenic autoinflammatory conditions, the so-called type I interferonopathies. Examples of these diseases include a clinical syndrome referred to as STING-associated vasculopathy with onset in infancy (SAVI), which is caused by gain-of-function mutations in TMEM173 (the gene name of STING). Moreover, STING is implicated in the pathogenesis of Aicardi-Goutières Syndrome (AGS) and genetic forms of lupus. As opposed to SAVI, it is the dysregulation of nucleic acid metabolism that underlies continuous innate immune activation in AGS. Apart from these genetic disorders, emerging evidence points to a more general pathogenic role for STING in a range of inflammation-associated disorders such as systemic lupus erythematosus, rheumatoid arthritis and cancer. Thus, small molecule-based pharmacological interventions into the STING signaling pathway hold significant potential for the treatment of a wide spectrum of diseases

SUMMARY

This disclosure features chemical entities (e.g., a compound or a pharmaceutically acceptable salt, and/or hydrate, and/or cocrystal, and/or drug combination of the compound) that inhibit (e.g., antagonize) Stimulator of Interferon Genes (STING). Said chemical entities are useful, e.g., for treating a condition, disease or disorder in which increased (e.g., excessive) STING activation (e.g., STING signaling) contributes to the pathology and/or symptoms and/or progression of the condition, disease or disorder (e.g., cancer) in a subject (e.g., a human). This disclosure also features compositions containing the same as well as methods of using and making the same.

An "antagonist" of STING includes compounds that, at the protein level, directly bind or modify STING such that an activity of STING is decreased, e.g., by inhibition, blocking or dampening agonist-mediated responses, altered distribution, or otherwise. STING antagonists include chemical entities, which interfere or inhibit STING signaling.

In one aspect, compounds of Formula (I), or a pharmaceutically acceptable salt thereof, are featured:

(I)

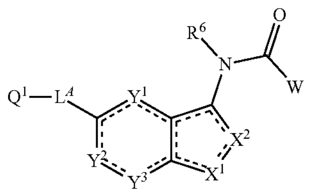

in which $Q^1$, $L^A$, $Y^1$, $Y^2$, $Y^3$, $X^1$, $X^2$, $R^6$, and W can be as defined anywhere herein.

In one aspect, pharmaceutical compositions are featured that include a chemical entity described herein (e.g., a compound described generically or specifically herein or a pharmaceutically acceptable salt thereof or compositions containing the same) and one or more pharmaceutically acceptable excipients.

In one aspect, methods for inhibiting (e.g., antagonizing) STING activity are featured that include contacting STING with a chemical entity described herein (e.g., a compound described generically or specifically herein or a pharmaceutically acceptable salt thereof or compositions containing the same). Methods include in vitro methods, e.g., contacting a sample that includes one or more cells comprising STING (e.g., innate immune cells, e.g., mast cells, macrophages, dendritic cells (DCs), and natural killer cells) with the chemical entity. Methods can also include in vivo methods; e.g., administering the chemical entity to a subject (e.g., a human) having a disease in which increased (e.g., excessive) STING signaling contributes to the pathology and/or symptoms and/or progression of the disease.

In one aspect, methods of treating a condition, disease or disorder ameliorated by antagonizing STING are featured, e.g., treating a condition, disease or disorder in which increased (e.g., excessive) STING activation (e.g., STING signaling) contributes to the pathology and/or symptoms and/or progression of the condition, disease or disorder (e.g., cancer) in a subject (e.g., a human). The methods include administering to a subject in need of such treatment an effective amount of a chemical entity described herein (e.g., a compound described generically or specifically herein or a pharmaceutically acceptable salt thereof or compositions containing the same).

In another aspect, methods of treating cancer are featured that include administering to a subject in need of such treatment an effective amount of a chemical entity described herein (e.g., a compound described generically or specifically herein or a pharmaceutically acceptable salt thereof or compositions containing the same).

In a further aspect, methods of treating other STING-associated conditions are featured, e.g., type I interferonopathies (e.g., STING-associated vasculopathy with onset in infancy (SAVI)), Aicardi-Goutières Syndrome (AGS), genetic forms of lupus, and inflammation-associated disorders such as systemic lupus erythematosus, and rheumatoid arthritis. The methods include administering to a subject in need of such treatment an effective amount of a chemical entity described herein (e.g., a compound described generically or specifically herein or a pharmaceutically acceptable salt thereof or compositions containing the same).

In another aspect, methods of suppressing STING-dependent type I interferon production in a subject in need thereof are featured that include administering to the subject an effective amount of a chemical entity described herein (e.g., a compound described generically or specifically herein or a pharmaceutically acceptable salt thereof or compositions containing the same).

In a further aspect, methods of treating a disease in which increased (e.g., excessive) STING activation (e.g., STING signaling) contributes to the pathology and/or symptoms and/or progression of the disease are featured. The methods include administering to a subject in need of such treatment an effective amount of a chemical entity described herein (e.g., a compound described generically or specifically herein or a pharmaceutically acceptable salt thereof or compositions containing the same).

In another aspect, methods of treatment are featured that include administering an effective amount of a chemical entity described herein (e.g., a compound described generically or specifically herein or a pharmaceutically acceptable salt thereof or compositions containing the same) to a subject; wherein the subject has (or is predisposed to have) a disease in which increased (e.g., excessive) STING activation (e.g., STING signaling) contributes to the pathology and/or symptoms and/or progression of the disease.

In a further aspect, methods of treatment that include administering to a subject a chemical entity described herein (e.g., a compound described generically or specifically herein or a pharmaceutically acceptable salt thereof or compositions containing the same), wherein the chemical entity is administered in an amount effective to treat a disease in which increased (e.g., excessive) STING activation (e.g., STING signaling) contributes to the pathology and/or symptoms and/or progression of the disease, thereby treating the disease.

In another aspect, there is provided is a compound, or a pharmaceutically acceptable salt or tautomer thereof, as described herein, for use in the treatment of a disease, condition or disorder modulated by STING inhibition.

In another aspect, there is provided a compound, or a pharmaceutically acceptable salt or tautomer thereof, as described herein for use in the treatment of a condition, disease or disorder associated with increased (e.g., excessive) STING activation.

In another aspect, there is provided a compound, or a pharmaceutically acceptable salt or tautomer thereof, described herein for use in the treatment of cancer.

In another aspect, there is provided a compound, or a pharmaceutically acceptable salt or tautomer thereof, as described herein for use in the treatment of cancer selected from the group consisting of melanoma, cervical cancer, breast cancer, ovarian cancer, prostate cancer, testicular cancer, urothelial carcinoma, bladder cancer, non-small cell lung cancer, small cell lung cancer, sarcoma, colorectal adenocarcinoma, gastrointestinal stromal tumors, gastroesophageal carcinoma, colorectal cancer, pancreatic cancer, kidney cancer, hepatocellular cancer, malignant mesothelioma, leukemia, lymphoma, myelodysplasia syndrome, multiple myeloma, transitional cell carcinoma, neuroblastoma, plasma cell neoplasms, Wilm's tumor, or hepatocellular carcinoma.

In another aspect, there is provided a compound, or a pharmaceutically acceptable salt or tautomer thereof, as described herein for use in the treatment of type I interferonopathies.

In another aspect, there is provided a compound, or a pharmaceutically acceptable salt or tautomer thereof, as described herein for use in the treatment of type I interferonopathies selected from STING-associated vasculopathy with onset in infancy (SAVI)), Aicardi-Goutières Syndrome (AGS), genetic forms of lupus, and inflammation-associated disorders such as systemic lupus erythematosus, and rheumatoid arthritis.

In another aspect, there is provided the use of a compound, or a pharmaceutically acceptable salt or tautomer thereof, as described herein in the manufacture of a medicament for the treatment of a condition, disease or disorder associated with increased (e.g., excessive) STING activation.

In another aspect, there is provided the use of a compound, or a pharmaceutically acceptable salt or tautomer thereof, as described herein in the manufacture of a medicament for the treatment of cancer.

In another aspect, there is provided the use of a compound, or a pharmaceutically acceptable salt or tautomer thereof, as described herein in the manufacture of a medicament for the treatment of cancer selected from the group consisting of melanoma, cervical cancer, breast cancer, ovarian cancer, prostate cancer, testicular cancer, urothelial carcinoma, bladder cancer, non-small cell lung cancer, small cell lung cancer, sarcoma, colorectal adenocarcinoma, gastrointestinal stromal tumors, gastroesophageal carcinoma, colorectal cancer, pancreatic cancer, kidney cancer, hepatocellular cancer, malignant mesothelioma, leukemia, lymphoma, myelodysplasia syndrome, multiple myeloma, transitional cell carcinoma, neuroblastoma, plasma cell neoplasms, Wilm's tumor, or hepatocellular carcinoma.

In another aspect, there is provided the use of a compound, or a pharmaceutically acceptable salt or tautomer thereof, as described herein in the manufacture of a medicament for the treatment of type I interferonopathies.

In another aspect, there is provided the use of a compound, or a pharmaceutically acceptable salt or tautomer thereof, as described herein for use in the manufacture of a medicament for the treatment of type I interferonopathies selected from STING-associated vasculopathy with onset in infancy (SAVI)), Aicardi-Goutières Syndrome (AGS), genetic forms of lupus, and inflammation-associated disorders such as systemic lupus erythematosus, and rheumatoid arthritis.

In another aspect, there is provided the use of a compound, or a pharmaceutically acceptable salt or tautomer thereof, as described herein, for the treatment of a disease, condition or disorder modulated by STING inhibition.

In another aspect, there is provided the use of a compound, or a pharmaceutically acceptable salt or tautomer thereof, as described herein for the treatment of a condition, disease or disorder associated with increased (e.g., excessive) STING activation.

In another aspect, there is provided the use of a compound, or a pharmaceutically acceptable salt or tautomer thereof, as described herein for the treatment of cancer.

In another aspect, there is provided the use of a compound, or a pharmaceutically acceptable salt or tautomer thereof, as described herein for the treatment of cancer selected from the group consisting of melanoma, cervical cancer, breast cancer, ovarian cancer, prostate cancer, testicular cancer, urothelial carcinoma, bladder cancer, non-small cell lung cancer, small cell lung cancer, sarcoma, colorectal adenocarcinoma, gastrointestinal stromal tumors, gastroesophageal carcinoma, colorectal cancer, pancreatic cancer, kidney cancer, hepatocellular cancer, malignant mesothelioma, leukemia, lymphoma, myelodysplasia syndrome, multiple myeloma, transitional cell carcinoma, neuroblastoma, plasma cell neoplasms, Wilm's tumor, or hepatocellular carcinoma.

In another aspect, there is provided the use of a compound, or a pharmaceutically acceptable salt or tautomer thereof, as described herein for the treatment of type I interferonopathies.

In another aspect, there is provided the use of a compound, or a pharmaceutically acceptable salt or tautomer thereof, as described herein for the treatment of type I interferonopathies selected from STING-associated vasculopathy with onset in infancy (SAVI)), Aicardi-Goutières Syndrome (AGS), genetic forms of lupus, and inflammation-associated disorders such as systemic lupus erythematosus, and rheumatoid arthritis.

Embodiments can include one or more of the following features.

The chemical entity can be administered in combination with one or more additional therapeutic agents and/or regimens. For examples, methods can further include administering one or more (e.g., two, three, four, five, six, or more) additional agents.

The chemical entity can be administered in combination with one or more additional therapeutic agents and/or regimens that are useful for treating other STING-associated conditions, e.g., type I interferonopathies (e.g., STING-associated vasculopathy with onset in infancy (SAVI)), Aicardi-Goutières Syndrome (AGS), genetic forms of lupus, and inflammation-associated disorders such as systemic lupus erythematosus, and rheumatoid arthritis.

The chemical entity can be administered in combination with one or more additional cancer therapies (e.g., surgery, radiotherapy, chemotherapy, toxin therapy, immunotherapy, cryotherapy or gene therapy, or a combination thereof, e.g., chemotherapy that includes administering one or more (e.g., two, three, four, five, six, or more) additional chemotherapeutic agents. Non-limiting examples of additional chemotherapeutic agents is selected from an alkylating agent (e.g., cisplatin, carboplatin, mechlorethamine, cyclophosphamide, chlorambucil, ifosfamide and/or oxaliplatin); an anti-metabolite (e.g., azathioprine and/or mercaptopurine); a terpenoid (e.g., a *vinca* alkaloid and/or a taxane; e.g., Vincristine, Vinblastine, Vinorelbine and/or Vindesine Taxol, Pacllitaxel and/or Docetaxel); a topoisomerase (e.g., a type I topoisomerase and/or a type 2 topoisomerase; e.g., camptothecins, such as irinotecan and/or topotecan; amsacrine, etoposide, etoposide phosphate and/or teniposide); a cytotoxic antibiotic (e.g., actinomycin, anthracyclines, doxorubicin, daunorubicin, valrubicin, idarubicin, epirubicin, bleomycin, plicamycin and/or mitomycin); a hormone (e.g., a lutenizing hormone releasing hormone agonist; e.g., leuprolidine, goserelin, triptorelin, histrelin, bicalutamide, flutamide and/or nilutamide); an antibody (e.g., Abciximab, Adalimumab, Alemtuzumab, Atlizumab, Basiliximab, Belimumab, Bevacizumab, Bretuximab vedotin, Canakinumab, Cetuximab, Ceertolizumab pegol, Daclizumab, Denosumab, Eculizumab, Efalizumab, Gemtuzumab, Golimumab, Golimumab, Ibritumomab tiuxetan, Infliximab, Ipilimumab, Muromonab-CD3, Natalizumab, Ofatumumab, Omalizumab, Palivizumab, Panitumuab, Ranibizumab, Rituximab, Tocilizumab, Tositumomab and/or Trastuzumab); an anti-angiogenic agent; a cytokine; a thrombotic agent; a growth inhibitory agent; an anti-helminthic agent; and an immune checkpoint inhibitor that targets an immune checkpoint receptor selected from the group consisting of CTLA-4, PD-1, PD-L1, PD-1-PD-L1, PD-1-PD-L2, interleukin-2 (IL-2), indoleamine 2,3-dioxygenase (IDO), IL-10, transforming growth factor-β (TGFβ), T cell immunoglobulin and mucin 3 (TIM3 or HAVCR2), Galectin 9-TIM3, Phosphatidylserine-TIM3, lymphocyte activation gene 3 protein (LAG3), MHC class II-LAG3, 4-1BB-4-1BB ligand, OX40-OX40 ligand, GITR, GITR ligand-GITR, CD27, CD70-CD27, TNFRSF25, TNFRSF25-TL1A, CD40L, CD40-CD40 ligand, HVEM-LIGHT-LTA, HVEM, HVEM-BTLA, HVEM-CD160, HVEM-LIGHT, HVEM-BTLA-CD160, CD80, CD80-PDL-1, PDL2-CD80, CD244, CD48-CD244, CD244, ICOS, ICOS—ICOS ligand, B7-H3, B7-H4, VISTA, TMIGD2, HHLA2-TMIGD2, Butyrophilins, including BTNL2, Siglec family, TIGIT and PVR family members, KIRs, ILTs and LIRs, NKG2D and NKG2A, MICA and MICB, CD244, CD28, CD86-CD28, CD86-CTLA, CD80-CD28, CD39, CD73 Adenosine-CD39-CD73, CXCR4-CXCL12, Phosphatidylserine, TIM3, Phosphatidylserine-TIM3, SIRPA-CD47, VEGF, Neuropilin, CD160, CD30, and CD155 (e.g., CTLA-4 or PD1 or PD-L1).

The subject can have cancer; e.g., the subject has undergone and/or is undergoing and/or will undergo one or more cancer therapies.

Non-limiting examples of cancer include melanoma, cervical cancer, breast cancer, ovarian cancer, prostate cancer, testicular cancer, urothelial carcinoma, bladder cancer, non-small cell lung cancer, small cell lung cancer, sarcoma, colorectal adenocarcinoma, gastrointestinal stromal tumors, gastroesophageal carcinoma, colorectal cancer, pancreatic cancer, kidney cancer, hepatocellular cancer, malignant mesothelioma, leukemia, lymphoma, myelodysplasia syndrome, multiple myeloma, transitional cell carcinoma, neuroblastoma, plasma cell neoplasms, Wilm's tumor, or hepatocellular carcinoma. In certain embodiments, the cancer can be a refractory cancer.

The chemical entity can be administered intratumorally.

The methods can further include identifying the subject.

Other embodiments include those described in the Detailed Description and/or in the claims.

Additional Definitions

To facilitate understanding of the disclosure set forth herein, a number of additional terms are defined below. Generally, the nomenclature used herein and the laboratory procedures in organic chemistry, medicinal chemistry, and pharmacology described herein are those well-known and commonly employed in the art. Unless defined otherwise, all technical and scientific terms used herein generally have the same meaning as commonly understood by one of ordinary skill in the art to which this disclosure belongs. Each of the patents, applications, published applications, and other publications that are mentioned throughout the specification and the attached appendices are incorporated herein by reference in their entireties.

As used herein, the term "STING" is meant to include, without limitation, nucleic acids, polynucleotides, oligonucleotides, sense and antisense polynucleotide strands, complementary sequences, peptides, polypeptides, proteins, homologous and/or orthologous STING molecules, isoforms, precursors, mutants, variants, derivatives, splice variants, alleles, different species, and active fragments thereof.

The term "acceptable" with respect to a formulation, composition or ingredient, as used herein, means having no persistent detrimental effect on the general health of the subject being treated.

"API" refers to an active pharmaceutical ingredient.

The terms "effective amount" or "therapeutically effective amount," as used herein, refer to a sufficient amount of a chemical entity being administered which will relieve to some extent one or more of the symptoms of the disease or condition being treated. The result includes reduction and/or alleviation of the signs, symptoms, or causes of a disease, or any other desired alteration of a biological system. For example, an "effective amount" for therapeutic uses is the amount of the composition comprising a compound as disclosed herein required to provide a clinically significant decrease in disease symptoms. An appropriate "effective" amount in any individual case is determined using any suitable technique, such as a dose escalation study.

The term "excipient" or "pharmaceutically acceptable excipient" means a pharmaceutically-acceptable material, composition, or vehicle, such as a liquid or solid filler, diluent, carrier, solvent, or encapsulating material. In one embodiment, each component is "pharmaceutically acceptable" in the sense of being compatible with the other ingredients of a pharmaceutical formulation, and suitable for use in contact with the tissue or organ of humans and animals without excessive toxicity, irritation, allergic response, immunogenicity, or other problems or complications, commensurate with a reasonable benefit/risk ratio. See, e.g., *Remington: The Science and Practice of Pharmacy,* 21st ed.; Lippincott Williams & Wilkins: Philadelphia, PA, 2005*; Handbook of Pharmaceutical Excipients, 6th* ed.; Rowe et al., Eds.; The Pharmaceutical Press and the American Pharmaceutical Association: 2009*; Handbook of Pharmaceutical Additives, 3rd ed.*; Ash and Ash Eds.; Gower Publishing Company: 2007*; Pharmaceutical Preformulation and Formulation, 2nd ed.*; Gibson Ed.; CRC Press LLC: Boca Raton, FL, 2009.

The term "pharmaceutically acceptable salt" refers to a formulation of a compound that does not cause significant irritation to an organism to which it is administered and does not abrogate the biological activity and properties of the compound. In certain instances, pharmaceutically acceptable salts are obtained by reacting a compound described herein, with acids such as hydrochloric acid, hydrobromic acid, sulfuric acid, nitric acid, phosphoric acid, methanesulfonic acid, ethanesulfonic acid, p-toluenesulfonic acid, salicylic acid and the like. In some instances, pharmaceutically acceptable salts are obtained by reacting a compound having acidic group described herein with a base to form a salt such as an ammonium salt, an alkali metal salt, such as a sodium or a potassium salt, an alkaline earth metal salt, such as a calcium or a magnesium salt, a salt of organic bases such as dicyclohexylamine, N-methyl-D-glucamine, tris(hydroxymethyl)methylamine, and salts with amino acids such as arginine, lysine, and the like, or by other methods previously determined. The pharmacologically acceptable salt s not specifically limited as far as it can be used in medicaments. Examples of a salt that the compounds described herein from with a base include the following: salts thereof with inorganic bases such as sodium, potassium, magnesium, calcium, and aluminum; salts thereof with organic bases such as methylamine, ethylamine and ethanolamine; salts thereof with basic amino acids such as lysine and ornithine; and ammonium salt. The salts may be acid addition salts, which are specifically exemplified by acid addition salts with the following: mineral acids such as hydrochloric acid, hydrobromic acid, hydroiodic acid, sulfuric acid, nitric acid, and phosphoric acid:organic acids such as formic acid, acetic acid, propionic acid, oxalic acid, malonic acid, succinic acid, fumaric acid, maleic acid, lactic acid, malic acid, tartaric acid, citric acid, methanesulfonic acid, and ethanesulfonic acid; acidic amino acids such as aspartic acid and glutamic acid.

The term "pharmaceutical composition" refers to a mixture of a compound described herein with other chemical components (referred to collectively herein as "excipients"), such as carriers, stabilizers, diluents, dispersing agents, suspending agents, and/or thickening agents. The pharmaceutical composition facilitates administration of the compound to an organism. Multiple techniques of administering a compound exist in the art including, but not limited to: rectal, oral, intravenous, aerosol, parenteral, ophthalmic, pulmonary, and topical administration.

The term "subject" refers to an animal, including, but not limited to, a primate (e.g., human), monkey, cow, pig, sheep, goat, horse, dog, cat, rabbit, rat, or mouse. The terms "subject" and "patient" are used interchangeably herein in reference, for example, to a mammalian subject, such as a human.

The terms "treat," "treating," and "treatment," in the context of treating a disease or disorder, are meant to include alleviating or abrogating a disorder, disease, or condition, or one or more of the symptoms associated with the disorder, disease, or condition; or to slowing the progression, spread or worsening of a disease, disorder or condition or of one or more symptoms thereof. The "treatment of cancer", refers to one or more of the following effects: (1) inhibition, to some extent, of tumor growth, including, (i) slowing down and (ii) complete growth arrest; (2) reduction in the number of tumor cells; (3) maintaining tumor size; (4) reduction in tumor size; (5) inhibition, including (i) reduction, (ii) slowing down or (iii) complete prevention, of tumor cell infiltration into peripheral organs; (6) inhibition, including (i) reduction, (ii) slowing down or (iii) complete prevention, of metastasis; (7) enhancement of anti-tumor immune response, which may result in (i) maintaining tumor size, (ii) reducing tumor size, (iii) slowing the growth of a tumor, (iv) reducing, slowing or preventing invasion and/or (8) relief, to some extent, of the severity or number of one or more symptoms associated with the disorder.

The term "halo" refers to fluoro (F), chloro (Cl), bromo (Br), or iodo (I).

The term "alkyl" refers to a saturated acyclic hydrocarbon radical that may be a straight chain or branched chain, containing the indicated number of carbon atoms. For example, $C_{1-10}$ indicates that the group may have from 1 to 10 (inclusive) carbon atoms in it. Alkyl groups can either be unsubstituted or substituted with one or more substituents. Non-limiting examples include methyl, ethyl, iso-propyl, tert-butyl, n-hexyl. The term "saturated" as used in this context means only single bonds present between constituent carbon atoms and other available valences occupied by hydrogen and/or other substituents as defined herein.

The term "haloalkyl" refers to an alkyl, in which one or more hydrogen atoms is/are replaced with an independently selected halo.

The term "alkoxy" refers to an —O-alkyl radical (e.g., $—OCH_3$).

The term "alkylene" refers to a divalent alkyl (e.g., $—CH_2—$).

The term "alkenyl" refers to an acyclic hydrocarbon chain that may be a straight chain or branched chain having one or more carbon-carbon double bonds. The alkenyl moiety contains the indicated number of carbon atoms. For example, $C_{2-6}$ indicates that the group may have from 2 to 6 (inclusive) carbon atoms in it. Alkenyl groups can either be unsubstituted or substituted with one or more substituents.

The term "alkynyl" refers to an acyclic hydrocarbon chain that may be a straight chain or branched chain having one or more carbon-carbon triple bonds. The alkynyl moiety contains the indicated number of carbon atoms. For example, $C_{2-6}$ indicates that the group may have from 2 to 6 (inclusive) carbon atoms in it. Alkynyl groups can either be unsubstituted or substituted with one or more substituents.

The term "aryl" refers to a 6-20 carbon mono-, bi-, tri- or polycyclic group wherein at least one ring in the system is aromatic (e.g., 6-carbon monocyclic, 10-carbon bicyclic, or 14-carbon tricyclic aromatic ring system); and wherein 0, 1, 2, 3, or 4 atoms of each ring may be substituted by a substituent. Examples of aryl groups include phenyl, naphthyl, tetrahydronaphthyl, dihydro-1H-indenyl and the like.

The term "cycloalkyl" as used herein refers to cyclic saturated hydrocarbon groups having, e.g., 3 to 20 ring carbons, preferably 3 to 16 ring carbons, and more preferably 3 to 12 ring carbons or 3-10 ring carbons or 3-6 ring carbons, wherein the cycloalkyl group may be optionally substituted. Examples of cycloalkyl groups include, without limitation, cyclopropyl, cyclobutyl, cyclopentyl, cyclohexyl, cycloheptyl, and cyclooctyl. Cycloalkyl may include multiple fused and/or bridged rings. Non-limiting examples of fused/bridged cycloalkyl includes: bicyclo[1.1.0]butanyl, bicyclo[2.1.0]pentanyl, bicyclo[1.1.1]pentanyl, bicyclo[3.1.0]hexanyl, bicyclo[2.1.1]hexanyl, bicyclo[3.2.0]heptanyl, bicyclo[4.1.0]heptanyl, bicyclo[2.2.1]heptanyl, bicyclo[3.1.1]heptanyl, bicyclo[4.2.0]octanyl, bicyclo[3.2.1]octanyl, bicyclo[2.2.2]octanyl, and the like. Cycloalkyl also includes spirocyclic rings (e.g., spirocyclic bicycle wherein two rings are connected through just one atom). Non-limiting examples of spirocyclic cycloalkyls include spiro[2.2]pentanyl, spiro[2.5]octanyl, spiro[3.5]nonanyl, spiro[3.5]nonanyl, spiro[3.5]nonanyl, spiro[4.4]nonanyl, spiro[2.6]nonanyl, spiro[4.5]decanyl, spiro[3.6]decanyl, spiro[5.5]undecanyl, and the like. The term "saturated" as used in this context means only single bonds present between constituent carbon atoms.

The term "cycloalkenyl" as used herein means partially unsaturated cyclic hydrocarbon groups having 3 to 20 ring carbons, preferably 3 to 16 ring carbons, and more preferably 3 to 12 ring carbons or 3-10 ring carbons or 3-6 ring carbons, wherein the cycloalkenyl group may be optionally substituted. Examples of cycloalkenyl groups include, without limitation, cyclopentenyl, cyclohexenyl, cycloheptenyl, and cyclooctenyl. As partially unsaturated cyclic hydrocarbon groups, cycloalkenyl groups may have any degree of unsaturation provided that one or more double bonds is present in the ring, none of the rings in the ring system are aromatic, and the cycloalkenyl group is not fully saturated overall. Cycloalkenyl may include multiple fused and/or bridged and/or spirocyclic rings.

The term "heteroaryl", as used herein, means a mono-, bi-, tri- or polycyclic group having 5 to 20 ring atoms, alternatively 5, 6, 9, 10, or 14 ring atoms; and having 6, 10, or 14 pi electrons shared in a cyclic array; wherein at least one ring in the system is aromatic, and at least one ring in the system contains one or more heteroatoms independently selected from the group consisting of N, O, and S (but does not have to be a ring which contains a heteroatom, e.g. tetrahydroisoquinolinyl, e.g., tetrahydroquinolinyl). Heteroaryl groups can either be unsubstituted or substituted with one or more substituents. Examples of heteroaryl include thienyl, pyridinyl, furyl, oxazolyl, oxadiazolyl, pyrrolyl, imidazolyl, triazolyl, thiodiazolyl, pyrazolyl, isoxazolyl, thiadiazolyl, pyranyl, pyrazinyl, pyrimidinyl, pyridazinyl, triazinyl, thiazolyl benzothienyl, benzoxadiazolyl, benzofuranyl, benzimidazolyl, benzotriazolyl, cinnolinyl, indazolyl, indolyl, isoquinolinyl, isothiazolyl, naphthyridinyl, purinyl, thienopyridinyl, pyrido[2,3-d]pyrimidinyl, pyrrolo[2,3-b]pyridinyl, quinazolinyl, quinolinyl, thieno[2,3-c]pyridinyl, pyrazolo[3,4-b]pyridinyl, pyrazolo[3,4-c]pyridinyl, pyrazolo[4,3-c]pyridinyl, pyrazolo[4,3-b]pyridinyl, tetrazolyl, chromanyl, 2,3-dihydrobenzo[b][1,4]dioxinyl, benzo[d][1,3]dioxolyl, 2,3-dihydrobenzofuranyl, tetrahydroquinolinyl, 2,3-dihydrobenzo[b][1,4]oxathiinyl, isoindolinyl, and others. In some embodiments, the heteroaryl is selected from thienyl, pyridinyl, furyl, pyrazolyl, imidazolyl, isoindolinyl, pyranyl, pyrazinyl, and pyrimidinyl.

The term "heterocyclyl" refers to a mon-, bi-, tri-, or polycyclic saturated ring system with 3-16 ring atoms (e.g., 5-8 membered monocyclic, 8-12 membered bicyclic, or 11-14 membered tricyclic ring system) having 1-3 heteroatoms if monocyclic, 1-6 heteroatoms if bicyclic, or 1-9 heteroatoms if tricyclic or polycyclic, said heteroatoms selected from O, N, or S (e.g., carbon atoms and 1-3, 1-6, or 1-9 heteroatoms of N, O, or S if monocyclic, bicyclic, or tricyclic, respectively), wherein 0, 1, 2 or 3 atoms of each ring may be substituted by a substituent. Examples of heterocyclyl groups include piperazinyl, pyrrolidinyl, dioxanyl, morpholinyl, tetrahydrofuranyl, and the like. Heterocyclyl may include multiple fused and bridged rings. Non-limiting examples of fused/bridged heterocyclyl includes: 2-azabicyclo[1.1.0]butanyl, 2-azabicyclo[2.1.0]pentanyl, 2-azabicyclo[1.1.1]pentanyl, 3-azabicyclo[3.1.0]hexanyl, 5-azabicyclo[2.1.1]hexanyl, 3-azabicyclo[3.2.0]heptanyl, octahydrocyclopenta[c]pyrrolyl, 3-azabicyclo[4.1.0]heptanyl, 7-azabicyclo[2.2.1]heptanyl, 6-azabicyclo[3.1.1]heptanyl, 7-azabicyclo[4.2.0]octanyl, 2-azabicyclo[2.2.2]octanyl, 3-azabicyclo[3.2.1]octanyl, 2-oxabicyclo[1.1.0]butanyl, 2-oxabicyclo[2.1.0]pentanyl, 2-oxabicyclo[1.1.1]pentanyl, 3-oxabicyclo[3.1.0]hexanyl, 5-oxabicyclo[2.1.1]hexanyl, 3-oxabicyclo[3.2.0]heptanyl, 3-oxabicyclo[4.1.0]heptanyl, 7-oxabicyclo[2.2.1]heptanyl, 6-oxabicyclo[3.1.1]heptanyl, 7-oxabicyclo[4.2.0]octanyl, 2-oxabicyclo[2.2.2]octanyl, 3-oxabicyclo[3.2.1]octanyl, and the like. Heterocyclyl also includes spirocyclic rings (e.g., spirocyclic bicycle wherein two rings are connected through just one atom). Non-limiting examples of spirocyclic heterocyclyls include 2-azaspiro[2.2]pentanyl, 4-azaspiro[2.5]octanyl, 1-azaspiro[3.5]nonanyl, 2-azaspiro[3.5]nonanyl, 7-azaspiro[3.5]nonanyl, 2-azaspiro[4.4]nonanyl, 6-azaspiro[2.6]nonanyl, 1,7-diazaspiro[4.5]decanyl, 7-azaspiro[4.5]decanyl 2,5-diazaspiro[3.6]decanyl, 3-azaspiro[5.5]undecanyl, 2-oxaspiro[2.2]pentanyl, 4-oxaspiro[2.5]octanyl, 1-oxaspiro[3.5]nonanyl, 2-oxaspiro[3.5]nonanyl, 7-oxaspiro[3.5]nonanyl, 2-oxaspiro[4.4]nonanyl, 6-oxaspiro[2.6]nonane, 1,7-dioxaspiro[4.5]decanyl, 2,5-dioxaspiro[3.6]decanyl, 1-oxaspiro[5.5]undecanyl, 3-oxaspiro[5.5]undecanyl, 3-oxa-9-azaspiro[5.5]undecanyl and the like. The term "saturated" as used in this context means only single bonds present between constituent ring atoms and other available valences occupied by hydrogen and/or other substituents as defined herein.

The term "heterocycloalkenyl" as used herein means partially unsaturated cyclic ring system with 3-16 ring atoms (e.g., 5-8 membered monocyclic, 8-12 membered bicyclic, or 11-14 membered tricyclic ring system) having 1-3 heteroatoms if monocyclic, 1-6 heteroatoms if bicyclic, or 1-9 heteroatoms if tricyclic or polycyclic, said heteroatoms selected from O, N, or S (e.g., carbon atoms and 1-3, 1-6, or 1-9 heteroatoms of N, O, or S if monocyclic, bicyclic, or tricyclic, respectively), wherein 0, 1, 2 or 3 atoms of each ring may be substituted by a substituent. Examples of heterocycloalkenyl groups include, without limitation, tetrahydropyridyl, dihydropyrazinyl, dihydropyridyl, dihydropyrrolyl, dihydrofuranyl, dihydrothiophenyl. As partially unsaturated cyclic groups, heterocycloalkenyl groups may have any degree of unsaturation provided that one or more double bonds is present in the ring, none of the rings in the ring system are aromatic, and the heterocycloalkenyl group is not fully saturated overall. Heterocycloalkenyl may include multiple fused and/or bridged and/or spirocyclic rings.

As used herein, when a ring is described as being "aromatic", it means said ring has a continuous, delocalized π-electron system. Typically, the number of out of plane π-electrons corresponds to the Hückel rule (4n+2). Examples of such rings include: benzene, pyridine, pyrimidine, pyrazine, pyridazine, pyridone, pyrrole, pyrazole, oxazole, thioazole, isoxazole, isothiazole, and the like.

As used herein, when a ring is described as being "partially unsaturated", it means said ring has one or more additional degrees of unsaturation (in addition to the degree of unsaturation attributed to the ring itself, e.g., one or more double or tirple bonds between constituent ring atoms), provided that the ring is not aromatic. Examples of such rings include: cyclopentene, cyclohexene, cycloheptene, dihydropyridine, tetrahydropyridine, dihydropyrrole, dihydrofuran, dihydrothiophene, and the like.

For the avoidance of doubt, and unless otherwise specified, for rings and cyclic groups (e.g., aryl, heteroaryl, heterocyclyl, heterocycloalkenyl, cycloalkenyl, cycloalkyl, and the like described herein) containing a sufficient number of ring atoms to form bicyclic or higher order ring systems (e.g., tricyclic, polycyclic ring systems), it is understood that such rings and cyclic groups encompass those having fused rings, including those in which the points of fusion are located (i) on adjacent ring atoms (e.g., [x.x.0] ring systems, in which 0 represents a zero atom bridge (e.g., 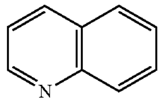 ));

(ii) a single ring atom (spiro-fused ring systems)

(e.g., 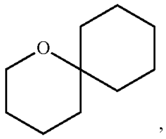 , 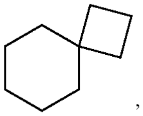 , or

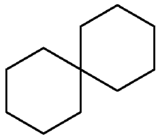 ), or (iii) a contiguous array of ring atoms (bridged ring systems having all bridge lengths>0)

(e.g.,  , 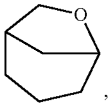 , or 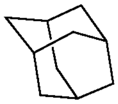 ).

In addition, atoms making up the compounds of the present embodiments are intended to include all isotopic forms of such atoms. Isotopes, as used herein, include those atoms having the same atomic number but different mass numbers. By way of general example and without limitation, isotopes of hydrogen include tritium and deuterium, and isotopes of carbon include $^{13}C$ and $^{14}C$.

In addition, the compounds generically or specifically disclosed herein are intended to include all tautomeric forms. Thus, by way of example, a compound containing the moiety:

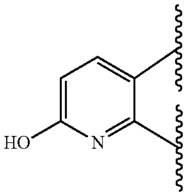 [SMILES: *c1ccc(O)nc1*]

encompasses the tautomeric form containing the moiety:

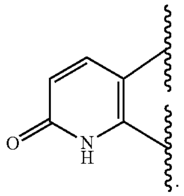 [SMILES: *c1ccc(=O)[nH]c1*].

Similarly, a pyridinyl or pyrimidinyl moiety that is described to be optionally substituted with hydroxyl encompasses pyridone or pyrimidone tautomeric forms.

As used herein, the phrase "optionally substituted" when used in conjunction with a structural moiety (e.g., alkyl) is intended to encompass both the unsubstituted structural moiety (i.e., none of the substitutable hydrogen atoms are replaced with one or more non-hydrogen substituents) and substituted structural moieties substituted with the indicated range of non-hydrogen substituents. For example, "$C_1$-$C_4$ alkyl optionally substituted with 1-4 $R^a$" is intended to encompass both unsubstituted $C_1$-$C_4$ alkyl and $C_1$-$C_4$ alkyl substituted with 1-4 $R^a$.

The details of one or more embodiments of the invention are set forth in the accompanying drawings and the description below. Other features and advantages of the invention will be apparent from the description and drawings, and from the claims.

DETAILED DESCRIPTION

This disclosure features chemical entities (e.g., a compound or a pharmaceutically acceptable salt, and/or hydrate, and/or cocrystal, and/or drug combination of the compound) that inhibit (e.g., antagonize) Stimulator of Interferon Genes (STING). Said chemical entities are useful, e.g., for treating a condition, disease or disorder in which increased (e.g., excessive) STING activation (e.g., STING signaling) contributes to the pathology and/or symptoms and/or progression of the condition, disease or disorder (e.g., cancer) in a subject (e.g., a human). This disclosure also features compositions containing the same as well as methods of using and making the same.

Formula I Compounds

In one aspect, the disclosure features a compound of Formula (I):

Formula I

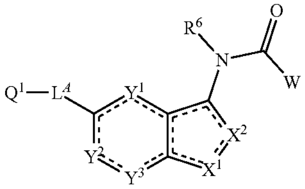

or a pharmaceutically acceptable salt thereof or a tautomer thereof, wherein:

$L^A$ is $-(L^1)_{a1}-(L^2)_{a2}-(L^3)_{a3}-(L^4)_{a4}-(L^5)_{a5}-*$, wherein * represents the point of attachment to $Q^1$;

a1, a2, a3, a4, and a5 are each independently 0 or 1, provided that a1+a2+a3+a4+a5≥1, and each of $L^1$, $L^3$, and $L^5$ is independently selected from the group consisting of: —O—, —N(H)—, —N($R^d$)—, $S(O)_{0-2}$, and —C(═O)—;

provided that when one or both of a2 and a4 is 0, then the combinations of $L^1$, $L^3$, and $L^5$ cannot form O—O, N—O, N—N, O—S, S—S, or N—$S(O)_0$ bonds, and each of $L^2$ and $L^4$ is independently selected from the group consisting of:

straight-chain $C_{1-6}$ alkylene, straight-chain $C_{2-6}$ alkenylene, or straight-chain $C_{2-6}$ alkynylene, each of which is optionally substituted with 1-6 $R^b$;

$C_{3-10}$ cycloalkylene or $C_{3-10}$ cycloalkenylene, each of which is optionally substituted with 1-3 $R^c$, provided the $C_{3-10}$ cycloalkylene or $C_{3-10}$ cycloalkenylene is not directly connected to the 6-membered ring containing $Y^1$, $Y^2$, and $Y^3$; and heterocyclylene or heterocycloalkenylene, each having 4-10 ring atoms wherein 1-3 ring atoms are ring heteroatoms each independently selected from the group consisting of: N, N(H), N($R^d$), O, and $S(O)_{0-2}$, wherein the heterocyclylene or heterocycloalkenylene is optionally substituted with 1-3 $R^c$, provided the heterocyclylene or heterocycloalkenylene is not directly connected to the 6-membered ring containing $Y^1$, $Y^2$, and $Y^3$;

$Q^1$ is —$R^g$;

$Y^1$, $Y^2$, and $Y^3$ are each independently selected from the group consisting of $CR^1$, C(═O), N, and $NR^2$;

$X^1$ is selected from the group consisting of O, S, N, $NR^2$, and $CR^1$;

$X^2$ is selected from the group consisting of O, S, N, $NR^4$, and $CR^5$;

each ═══ is independently a single bond or a double bond, provided that the five-membered ring comprising $X^1$ and $X^2$ is heteroaryl, and that the six-membered ring comprising $Y^1$, $Y^2$, and $Y^3$ is aryl or heteroaryl;

each occurrence of $R^1$ and $R^5$ is independently selected from the group consisting of: H; $R^c$; $R^g$; and $-(L^g)_{bg}-R^g$;

each occurrence of $R^2$ and $R^4$ is independently selected from the group consisting of: H; $R^d$; $R^g$; and $-(L^g)_{bg}-R^g$;

$R^6$ is selected from the group consisting of: H; $R^d$; and $R^g$;

W is selected from the group consisting of:

H;

$C_{1-10}$ alkyl, $C_{2-10}$ alkenyl, or $C_{2-10}$ alkynyl, each of which is optionally substituted with 1-6 $R^{a2}$;

monocyclic $C_{3-8}$ cycloalkyl or $C_{3-8}$ cycloalkenyl, each of which is optionally substituted with 1-4 substituents independently selected from the group consisting of oxo and $R^c$; and monocyclic heterocyclyl or heterocycloalkenyl of 3-8 ring atoms, wherein 1-3 ring atoms are heteroatoms, each independently selected from the group consisting of N, N(H), N($R^d$), O, and $S(O)_{0-2}$, and wherein the heterocyclyl or heterocycloalkenyl is optionally substituted with 1-4 substituents independently selected from the group consisting of oxo and $R^c$, provided that when W is heterocyclyl or heterocycloalkenyl, it is attached to the C(═O)$NR^6$ group via a ring carbon atom;

each occurrence of $R^a$ and $R^{a2}$ is independently selected from the group consisting of: —OH; -halo; —$NR^eR^f$; $C_{1-4}$ alkoxy; $C_{1-4}$ haloalkoxy; —C(═O)O($C_{1-4}$ alkyl); —C(═O)($C_{1-4}$ alkyl); —C(═O)OH; —CONR'R"; —$S(O)_{1-2}$NR'R"; —$S(O)_{1-2}$($C_{1-4}$ alkyl); and cyano;

each occurrence of $R^b$ and $R^c$ is independently selected from the group consisting of: halo; cyano; $C_{1-10}$ alkyl which is optionally substituted with 1-6 independently selected $R^a$; $C_{2-6}$ alkenyl; $C_{2-6}$ alkynyl; $C_{1-4}$ alkoxy; $C_{1-4}$ haloalkoxy; —$S(O)_{1-2}$($C_{1-4}$ alkyl); —S(O)(═NH)($C_{1-4}$ alkyl); —$NR^eR^f$; —OH; —$S(O)_{1-2}$NR'R"; —$C_{1-4}$ thioalkoxy; —$NO_2$; —C(═O)($C_{1-10}$ alkyl); —C(═O)O($C_{1-4}$ alkyl); —C(═O)OH; —C(═O)NR'R"; and —$SF_5$;

each occurrence of $R^d$ is independently selected from the group consisting of: $C_{1-6}$ alkyl optionally substituted with 1-3 independently selected $R^a$; —C(O)($C_{1-4}$ alkyl); —C(O)O($C_{1-4}$ alkyl); —CONR'R"; —$S(O)_{1-2}$NR'R"; —$S(O)_{1-2}$($C_{1-4}$ alkyl); —OH; and $C_{1-4}$ alkoxy;

each occurrence of $R^e$ and $R^f$ is independently selected from the group consisting of: H; $C_{1-6}$ alkyl optionally substituted with 1-3 substituents each independently selected from the group consisting of NR'R", —OH, halo, $C_{1-4}$ alkoxy, and $C_{1-4}$ haloalkoxy; —C(O)($C_{1-4}$ alkyl); —C(O)O($C_{1-4}$ alkyl); —CONR'R"; —$S(O)_{1-2}$NR'R"; —$S(O)_{1-2}$($C_{1-4}$ alkyl); —OH; and $C_{1-4}$ alkoxy;

each occurrence of $R^g$ is independently selected from the group consisting of:

$C_{3-12}$ cycloalkyl or $C_{3-12}$ cycloalkenyl, each of which is optionally substituted with 1-4 substituents independently selected from the group consisting of oxo and $R^c$;

heterocyclyl or heterocycloalkenyl of 3-12 ring atoms, wherein 1-3 ring atoms are heteroatoms, each independently selected from the group consisting of N, N(H), N($R^d$), O, and $S(O)_{0-2}$, and wherein the heterocyclyl or heterocycloalkenyl is optionally substituted with 1-4 substituents independently selected from the group consisting of oxo and $R^c$;

heteroaryl of 5-12 ring atoms, wherein 1-4 ring atoms are heteroatoms, each independently selected from the group consisting of N, N(H), N($R^d$), O, and $S(O)_{0-2}$, and wherein the heteroaryl is optionally substituted with 1-4 $R^c$; and $C_{6-10}$ aryl optionally substituted with 1-4 $R^c$, each occurrence of $L^g$ is independently selected from the group consisting of: —O—, —NH—, —$NR^d$, —$S(O)_{0-2}$, C(O), and $C_{1-3}$ alkylene optionally substituted with 1-3 $R^a$;

each occurrence of bg is independently 1, 2, or 3; and each occurrence of R' and R" is independently selected from the group consisting of: H; —OH; and $C_{1-4}$ alkyl.

In another aspect, this disclosure features a compound of Formula (I):

Formula I

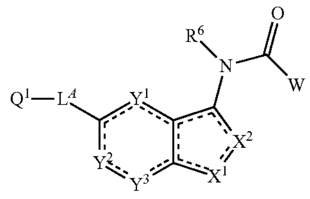

or a pharmaceutically acceptable salt thereof or a tautomer thereof, wherein:

$L^A$ is $-(L^1)_{a1}-(L^2)_{a2}-(L^3)_{a3}-(L^4)_{a4}-(L^5)_{a5}-*$, wherein * represents the point of attachment to $Q^1$;

a1, a2, a3, a4, and a5 are each independently 0 or 1, provided that a1+a2+a3+a4+a5≥1, and each of $L^1$, $L^3$, and $L^5$ is independently selected from the group consisting of: —O—, —N(H)—, —N($R^d$)—, $S(O)_{0-2}$, and —C(=O)—;

provided that when one or both of a2 and a4 is 0, then the combinations of $L^1$, $L^3$, and $L^5$ cannot form O—O, N—O, N—N, O—S, S—S, or N—$S(O)_0$ bonds, and each of $L^2$ and $L^4$ is independently selected from the group consisting of:

straight-chain $C_{1-6}$ alkylene, straight-chain $C_{2-6}$ alkenylene, or straight-chain $C_{2-6}$ alkynylene, each of which is optionally substituted with 1-6 $R^b$;

$C_{3-10}$ cycloalkylene or $C_{3-10}$ cycloalkenylene, each of which is optionally substituted with 1-3 $R^e$ provided the $C_{3-10}$ cycloalkylene or $C_{3-10}$ cycloalkenylene is not directly connected to the 6-membered ring containing $Y^1$, $Y^2$, and $Y^3$; and heterocyclylene or heterocycloalkenylene, each having 4-10 ring atoms wherein 1-3 ring atoms are ring heteroatoms each independently selected from the group consisting of: N, N(H), N($R^d$), O, and $S(O)_{0-2}$, wherein the heterocyclylene or heterocycloalkenylene is optionally substituted with 1-3 $R^c$, provided the heterocyclylene or heterocycloalkenylene is not directly connected to the 6-membered ring containing $Y^1$, $Y^2$, and $Y^3$;

$Q^1$ is —$R^g$;

$Y^1$, $Y^2$, and $Y^3$ are each independently selected from the group consisting of $CR^1$, C(=O), N, and $NR^2$;

$X^1$ is selected from the group consisting of O, S, N, $NR^2$, and $CR^1$;

$X^2$ is selected from the group consisting of O, S, N, $NR^4$, and $CR^5$;

each ⎓ is independently a single bond or a double bond, provided that the five-membered ring comprising $X^1$ and $X^2$ is heteroaryl, and that the six-membered ring comprising $Y^1$, $Y^2$, and $Y^3$ is aryl or heteroaryl;

further provided that $L^A$ cannot include a cyclic group directly attached to the 6-membered ring containing $Y^1$, $Y^2$, and $Y^3$;

each occurrence of $R^1$ and $R^5$ is independently selected from the group consisting of: H; $R^c$; $R^g$; and $-(L^g)_{bg}-R^g$;

each occurrence of $R^2$ and $R^4$ is independently selected from the group consisting of: H; $R^d$; $R^g$; and $-(L^g)_{bg}-R^g$;

$R^6$ is selected from the group consisting of: H; $R^d$; and $R^g$;

W is selected from the group consisting of:

H;

$C_{1-10}$ alkyl, $C_{2-10}$ alkenyl, or $C_{2-10}$ alkynyl, each of which is optionally substituted with 1-6 $R^{a2}$, wherein one or more of the internal optionally substituted methylene group can be replaced by one or more heteroatom selected from O or S, wherein when W is alkenyl or alkynyl, the heteroatom is not directed connected to the $sp^2$ or sp carbon;

monocyclic $C_{3-8}$ cycloalkyl or $C_{3-8}$ cycloalkenyl, each of which is optionally substituted with 1-4 substituents independently selected from the group consisting of oxo and $R^c$; and monocyclic heterocyclyl or heterocycloalkenyl of 3-8 ring atoms, wherein 1-3 ring atoms are heteroatoms, each independently selected from the group consisting of N, N(H), N($R^d$), O, and $S(O)_{0-2}$, and wherein the heterocyclyl or heterocycloalkenyl is optionally substituted with 1-4 substituents independently selected from the group consisting of oxo and $R^c$, provided that when W is heterocyclyl or heterocycloalkenyl, it is attached to the C(=O)$NR^6$ group via a ring carbon atom;

each occurrence of $R^a$ and $R^{a2}$ is independently selected from the group consisting of: —OH; -halo; —$NR^eR^f$; $C_{1-4}$ alkoxy; $C_{1-4}$ haloalkoxy; —C(=O)O($C_{1-4}$ alkyl); —C(=O)($C_{1-4}$ alkyl); —C(=O)OH; —CONR'R"; —$S(O)_{1-2}$NR'R"; —$S(O)_{1-2}$($C_{1-4}$ alkyl); and cyano;

each occurrence of $R^b$ and $R^c$ is independently selected from the group consisting of: halo; cyano; $C_{1-10}$ alkyl which is optionally substituted with 1-6 independently selected $R^a$; $C_{2-6}$ alkenyl; $C_{2-6}$ alkynyl; $C_{1-4}$ alkoxy; $C_{1-4}$ haloalkoxy; —$S(O)_{1-2}$($C_{1-4}$ alkyl); —S(O)(=NH)($C_{1-4}$ alkyl); —$NR^eR^f$; —OH; —$S(O)_{1-2}$NR'R"; —$C_{1-4}$ thioalkoxy; —$NO_2$; —C(═O)($C_{1-10}$ alkyl); —C(═O)O($C_{1-4}$ alkyl); —C(═O)OH; —C(═O)NR'R"; and —$SF_5$;

each occurrence of $R^d$ is independently selected from the group consisting of: $C_{1-6}$ alkyl optionally substituted with 1-3 independently selected $R^a$; —C(O)($C_{1-4}$ alkyl); —C(O)O($C_{1-4}$ alkyl); —CONR'R"; —$S(O)_{1-2}$NR'R"; —$S(O)_{1-2}$($C_{1-4}$ alkyl); —OH; and $C_{1-4}$ alkoxy;

each occurrence of $R^e$ and $R^f$ is independently selected from the group consisting of: H; $C_{1-6}$ alkyl optionally substituted with 1-3 substituents each independently selected from the group consisting of NR'R", —OH, halo, $C_{1-4}$ alkoxy, and $C_{1-4}$ haloalkoxy; —C(O)($C_{1-4}$ alkyl); —C(O)O($C_{1-4}$ alkyl); —CONR'R"; —$S(O)_{1-2}$NR'R"; —$S(O)_{1-2}$($C_{1-4}$ alkyl); —OH; and $C_{1-4}$ alkoxy;

each occurrence of $R^g$ is independently selected from the group consisting of:

$C_{3-12}$ cycloalkyl or $C_{3-12}$ cycloalkenyl, each of which is optionally substituted with 1-4 substituents independently selected from the group consisting of oxo and $R^c$;

heterocyclyl or heterocycloalkenyl of 3-12 ring atoms, wherein 1-3 ring atoms are heteroatoms, each independently selected from the group consisting of N, N(H), N($R^d$), O, and $S(O)_{0-2}$, and wherein the heterocyclyl or heterocycloalkenyl is optionally substituted with 1-4 substituents independently selected from the group consisting of oxo and $R^c$;

heteroaryl of 5-12 ring atoms, wherein 1-4 ring atoms are heteroatoms, each independently selected from the group consisting of N, N(H), N($R^d$), O, and $S(O)_{0-2}$, and wherein the heteroaryl is optionally substituted with 1-4 $R^c$; and $C_{6-10}$ aryl optionally substituted with 1-4 $R^c$;

each occurrence of $L^g$ is independently selected from the group consisting of: —O—, —NH—, —$NR^d$, —$S(O)_{0-2}$, C(O), and $C_{1-3}$ alkylene optionally substituted with 1-3 $R^a$;

each occurrence of bg is independently 1, 2, or 3; and each occurrence of R' and R" is independently selected from the group consisting of: H; —OH; and $C_{1-4}$ alkyl.

In another aspect, this disclosure features a compound of Formula (I):

Formula I

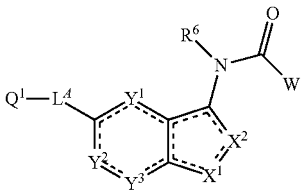

or a pharmaceutically acceptable salt thereof or a tautomer thereof, wherein:

$L^A$ is $-(L^1)_{a1}-(L^2)_{a2}-(L^3)_{a3}-(L^4)_{a4}-(L^5)_{a5}-*$, wherein * represents the point of attachment to $Q^1$;

a1, a2, a3, a4, and a5 are each independently 0 or 1, provided that a1+a2+a3+a4+a5≥1, and each of $L^1$, $L^3$, and $L^5$ is independently selected from the group consisting of: —O—, —N(H)—, —N($R^d$)—, $S(O)_{0-2}$, and —C(═O)—;

provided that when one or both of a2 and a4 is 0, then the combinations of $L^1$, $L^3$, and $L^5$ cannot form O—O, N—O, N—N, O—S, S—S, or N—$S(O)_0$ bonds, and each of $L^2$ and $L^4$ is independently selected from the group consisting of:

straight-chain $C_{1-6}$ alkylene, straight-chain $C_{2-6}$ alkenylene, or straight-chain $C_{2-6}$ alkynylene, each of which is optionally substituted with 1-6 $R^b$;

$C_{3-10}$ cycloalkylene or $C_{3-10}$ cycloalkenylene, each of which is optionally substituted with 1-3 $R^c$ provided the $C_{3-10}$ cycloalkylene or $C_{3-10}$ cycloalkenylene is not directly connected to the 6-membered ring containing $Y^1$, $Y^2$, and $Y^3$; and heterocyclylene or heterocycloalkenylene, each having 4-10 ring atoms wherein 1-3 ring atoms are ring heteroatoms each independently selected from the group consisting of: N, N(H), N($R^d$), O, and $S(O)_{0-2}$, wherein the heterocyclylene or heterocycloalkenylene is optionally substituted with 1-3 $R^c$, provided the heterocyclylene or heterocycloalkenylene is not directly connected to the 6-membered ring containing $Y^1$, $Y^2$, and $Y^3$;

$Q^1$ is —$R^g$;

$Y^1$, $Y^2$, and $Y^3$ are each independently selected from the group consisting of $CR^1$, C(═O), N, and $NR^2$;

$X^1$ is selected from the group consisting of O, S, N, $NR^2$, and $CR^1$;

$X^2$ is selected from the group consisting of O, S, N, $NR^4$, and $CR^5$;

each ⎓ is independently a single bond or a double bond, provided that the five-membered ring comprising $X^1$ and $X^2$ is heteroaryl, and that the six-membered ring comprising $Y^1$, $Y^2$, and $Y^3$ is aryl or heteroaryl;

further provided that $L^A$ cannot include a cyclic group directly attached to the 6 membered ring containing $Y^1$, $Y^2$, and $Y^3$;

each occurrence of $R^1$ and $R^5$ is independently selected from the group consisting of: H; $R^c$; $R^g$; and $-(L^g)_{bg}-R^g$;

each occurrence of $R^2$ and $R^4$ is independently selected from the group consisting of: H; $R^d$; $R^g$; and $-(L^g)_{bg}-R^g$;

$R^6$ is selected from the group consisting of: H; $R^d$; and $R^g$;

W is selected from the group consisting of:

H;

$C_{1-10}$ alkyl, $C_{2-10}$ alkenyl, or $C_{2-10}$ alkynyl, each of which is optionally substituted with 1-6 $R^{a2}$, wherein one or more of the internal optionally substituted methylene group can be replaced by one or more heteroatom selected from O or S, wherein when W is alkenyl or alkynyl, the heteroatom is not directed connected to the $sp^2$ or sp carbon;

monocyclic $C_{3-8}$ cycloalkyl or $C_{3-8}$ cycloalkenyl, each of which is optionally substituted with 1-4 substituents independently selected from the group consisting of oxo and $R^c$; and monocyclic heterocyclyl or heterocycloalkenyl of 3-8 ring atoms, wherein 1-3 ring atoms are heteroatoms, each independently selected from the group consisting of N, N(H), N($R^d$), O, and $S(O)_{0-2}$, and wherein the heterocyclyl or heterocycloalkenyl is optionally substituted with 1-4 substituents independently selected from the group consisting of oxo and $R^c$, provided that when W is heterocyclyl or heterocycloalkenyl, it is attached to the C(═O)$NR^6$ group via a ring carbon atom;

each occurrence of $R^a$ and $R^{a2}$ is independently selected from the group consisting of: —OH; -halo; —$NR^eR^f$;

$C_{1-4}$ alkoxy; $C_{1-4}$ haloalkoxy; —C(=O)O($C_{1-4}$ alkyl); —C(=O)($C_{1-4}$ alkyl); —C(=O)OH; —CONR'R"; —$S(O)_{1-2}$NR'R"; —$S(O)_{1-2}$($C_{1-4}$ alkyl); and cyano;

each occurrence of $R^b$ and $R^c$ is independently selected from the group consisting of: halo; cyano; $C_{1-10}$ alkyl which is optionally substituted with 1-6 independently selected $R^a$; $C_{2-6}$ alkenyl; $C_{2-6}$ alkynyl; $C_{1-4}$ alkoxy; $C_{1-4}$ haloalkoxy; —$S(O)_{1-2}$($C_{1-4}$ alkyl); —S(O)(=NH)($C_{1-4}$ alkyl); —$NR^eR^f$; —OH; —$S(O)_{1-2}$NR'R"; —$C_{1-4}$ thioalkoxy; —$NO_2$; —C(=O)($C_{1-10}$ alkyl); —C(=O)O($C_{1-4}$ alkyl); —C(=O)OH; —C(=O)NR'R"; and —$SF_5$;

each occurrence of $R^d$ is independently selected from the group consisting of: $C_{1-6}$ alkyl optionally substituted with 1-3 independently selected $R^a$; —C(O)($C_{1-4}$ alkyl); —C(O)O($C_{1-4}$ alkyl); —CONR'R"; —$S(O)_{1-2}$NR'R"; —$S(O)_{1-2}$($C_{1-4}$ alkyl); —OH; and $C_{1-4}$ alkoxy;

each occurrence of $R^e$ and $R^f$ is independently selected from the group consisting of: H; $C_{1-6}$ alkyl optionally substituted with 1-3 substituents each independently selected from the group consisting of NR'R", —OH, halo, $C_{1-4}$ alkoxy, and $C_{1-4}$ haloalkoxy; —C(O)($C_{1-4}$ alkyl); —C(O)O($C_{1-4}$ alkyl); —CONR'R"; —$S(O)_{1-2}$NR'R"; —$S(O)_{1-2}$($C_{1-4}$ alkyl); —OH; and $C_{1-4}$ alkoxy;

each occurrence of $R^g$ is independently selected from the group consisting of:

$C_{3-12}$ cycloalkyl or $C_{3-12}$ cycloalkenyl, each of which is optionally substituted with 1-4 substituents independently selected from the group consisting of oxo, $R^c$, and $R^h$;

heterocyclyl or heterocycloalkenyl of 3-12 ring atoms, wherein 1-3 ring atoms are heteroatoms, each independently selected from the group consisting of N, N(H), N($R^d$), O, and $S(O)_{0-2}$, and wherein the heterocyclyl or heterocycloalkenyl is optionally substituted with 1-4 substituents independently selected from the group consisting of oxo, $R^c$, and $R^h$;

heteroaryl of 5-12 ring atoms, wherein 1-4 ring atoms are heteroatoms, each independently selected from the group consisting of N, N(H), N($R^d$), O, and $S(O)_{0-2}$, and wherein the heteroaryl is optionally substituted with 1-4 substituents independently selected from the group consisting of oxo, $R^c$, and $R^h$; and $C_{6-10}$ aryl optionally substituted with 1-4 substituents independently selected from the group consisting of oxo, $R^c$, and $R^h$;

each occurrence of $R^h$ is independently selected from the group consisting of:

$C_{3-12}$ cycloalkyl or $C_{3-12}$ cycloalkenyl, each of which is optionally substituted with 1-4 $R^i$;

heterocyclyl or heterocycloalkenyl of 3-12 ring atoms, wherein 1-3 ring atoms are heteroatoms, each independently selected from the group consisting of N, N(H), N($R^d$), O, and $S(O)_{0-2}$, and wherein the heterocyclyl or heterocycloalkenyl is optionally substituted with 1-4 $R^i$;

heteroaryl of 5-12 ring atoms, wherein 1-3 ring atoms are heteroatoms, each independently selected from the group consisting of N, N(H), N($R^d$), O, and $S(O)_{0-2}$, and wherein the heteroaryl is optionally substituted with 1-4 $R^i$; and $C_{6-10}$ aryl optionally substituted with 1-4 $R^i$;

each occurrence of $R^1$ is independently selected from the group consisting of: $C_{1-6}$ alkyl; $C_{1-4}$ haloalkyl; $C_{1-4}$ alkoxy; $C_{1-4}$ haloalkoxy; and halo;

each occurrence of $L^g$ is independently selected from the group consisting of: —O—, —NH—, —$NR^d$, —$S(O)_{0-2}$, C(O), and $C_{1-3}$ alkylene optionally substituted with 1-3 $R^a$;

each occurrence of bg is independently 1, 2, or 3; and each occurrence of R' and R" is independently selected from the group consisting of: H; —OH; and $C_{1-4}$ alkyl.

In still another aspect, this disclosure features A compound of Formula (I):

Formula I

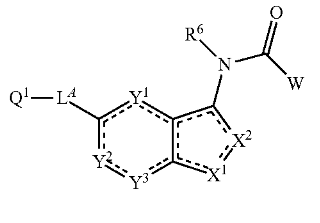

or a pharmaceutically acceptable salt thereof or a tautomer thereof, wherein:

$L^A$ is -$(L^1)_{a1}$-$(L^2)_{a2}$-$(L^3)_{a3}$-$(L^4)_{a4}$-$(L^5)_{a5}$-*, wherein * represents the point of attachment to $Q^1$;

a1, a2, a3, a4, and a5 are each independently 0 or 1, provided that a1+a2+a3+a4+a5≥1, and each of $L^1$, $L^3$, and $L^5$ is independently selected from the group consisting of: —O—, —N(H)—, —N($R^d$)—, $S(O)_{0-2}$, and —C(=O)—;

provided that when one or both of a2 and a4 is 0, then the combinations of $L^1$, $L^3$, and $L^5$ cannot form O—O, N—O, N—N, O—S, S—S, or N—$S(O)_0$ bonds, and each of $L^2$ and $L^4$ is independently selected from the group consisting of:

straight-chain $C_{1-6}$ alkylene, straight-chain $C_{2-6}$ alkenylene, or straight-chain $C_{2-6}$ alkynylene, each of which is optionally substituted with 1-6 $R^b$;

$C_{3-10}$ cycloalkylene or $C_{3-10}$ cycloalkenylene, each of which is optionally substituted with 1-3 $R^c$ provided the $C_{3-10}$ cycloalkylene or $C_{3-10}$ cycloalkenylene is not directly connected to the 6-membered ring containing $Y^1$, $Y^2$, and $Y^3$; and heterocyclylene or heterocycloalkenylene, each having 4-10 ring atoms wherein 1-3 ring atoms are ring heteroatoms each independently selected from the group consisting of: N, N(H), N($R^d$), O, and $S(O)_{0-2}$, wherein the heterocyclylene or heterocycloalkenylene is optionally substituted with 1-3 $R^c$, provided the heterocyclylene or heterocycloalkenylene is not directly connected to the 6-membered ring containing $Y^1$, $Y^2$, and $Y^3$;

$Q^1$ is —$R^g$;

$Y^1$, $Y^2$, and $Y^3$ are each independently selected from the group consisting of $CR^1$, C(=O), N, and $NR^2$;

$X^1$ is selected from the group consisting of O, S, N, $NR^2$, and $CR^1$;

$X^2$ is selected from the group consisting of O, S, N, $NR^4$, and $CR^5$;

each ⎓ is independently a single bond or a double bond, provided that the five-membered ring comprising $X^1$ and $X^2$ is heteroaryl, and that the six-membered ring comprising $Y^1$, $Y^2$, and $Y^3$ is aryl or heteroaryl;

further provided that $L^A$ cannot include a cyclic group directly attached to the 6 membered ring containing $Y^1$, $Y^2$, and $Y^3$;

each occurrence of $R^1$ and $R^5$ is independently selected from the group consisting of: H; $R^c$; $R^g$; and $-(L^g)_{bg}-R^g$;

each occurrence of $R^2$ and $R^4$ is independently selected from the group consisting of: H; $R^d$; $R^g$; and $-(L^g)_{bg}-R^g$;

$R^6$ is selected from the group consisting of: H; $R^d$; and $R^g$;

W is selected from the group consisting of:

H;

$C_{1-10}$ alkyl, $C_{2-10}$ alkenyl, or $C_{2-10}$ alkynyl, each of which is optionally substituted with 1-6 $R^{a2}$, wherein one or more of the internal optionally substituted methylene group can be replaced by one or more heteroatom selected from O or S, wherein when W is alkenyl or alkynyl, the heteroatom is not directed connected to the $sp^2$ or sp carbon;

monocyclic $C_{3-8}$ cycloalkyl or $C_{3-8}$ cycloalkenyl, each of which is optionally substituted with 1-4 substituents independently selected from the group consisting of oxo and $R^c$; and monocyclic heterocyclyl or heterocycloalkenyl of 3-8 ring atoms, wherein 1-3 ring atoms are heteroatoms, each independently selected from the group consisting of N, N(H), N($R^d$), O, and $S(O)_{0-2}$, and wherein the heterocyclyl or heterocycloalkenyl is optionally substituted with 1-4 substituents independently selected from the group consisting of oxo and $R^c$, provided that when W is heterocyclyl or heterocycloalkenyl, it is attached to the C(═O)$NR^6$ group via a ring carbon atom;

each occurrence of $R^a$ and $R^{a2}$ is independently selected from the group consisting of: —OH; -halo; —$NR^eR^f$; $C_{1-4}$ alkoxy; $C_{1-4}$ haloalkoxy; —C(═O)O($C_{1-4}$ alkyl); —C(═O)($C_{1-4}$ alkyl); —C(═O)OH; —CONR'R"; —$S(O)_{1-2}$NR'R"; —$S(O)_{1-2}$($C_{1-4}$ alkyl); and cyano;

each occurrence of $R^b$ and $R^c$ is independently selected from the group consisting of: halo; cyano; $C_{1-10}$ alkyl which is optionally substituted with 1-6 independently selected $R^a$; $C_{2-6}$ alkenyl; $C_{2-6}$ alkynyl; $C_{1-4}$ alkoxy; $C_{1-4}$ haloalkoxy; —$S(O)_{1-2}$($C_{1-4}$ alkyl); —S(O)(═NH)($C_{1-4}$ alkyl); —$NR^eR^f$; —OH; —$S(O)_{1-2}$NR'R"; —$C_{1-4}$ thioalkoxy; —$NO_2$; —C(═O)($C_{1-10}$ alkyl); —C(═O)O($C_{1-4}$ alkyl); —C(═O)OH; —C(═O)NR'R"; —NR'C(═O)($C_{1-4}$ alkyl) and —$SF_5$;

each occurrence of $R^d$ is independently selected from the group consisting of: $C_{1-6}$ alkyl optionally substituted with 1-3 independently selected $R^a$; —C(O)($C_{1-4}$ alkyl); —C(O)O($C_{1-4}$ alkyl); —CONR'R"; —$S(O)_{1-2}$NR'R"; —$S(O)_{1-2}$($C_{1-4}$ alkyl); —OH; and $C_{1-4}$ alkoxy;

each occurrence of $R^e$ and $R^f$ is independently selected from the group consisting of: H; $C_{1-6}$ alkyl optionally substituted with 1-3 substituents each independently selected from the group consisting of NR'R", —OH, halo, $C_{1-4}$ alkoxy, and $C_{1-4}$ haloalkoxy; —C(O)($C_{1-4}$ alkyl); —C(O)O($C_{1-4}$ alkyl); —CONR'R"; —$S(O)_{1-2}$NR'R"; —$S(O)_{1-2}$($C_{1-4}$ alkyl); —OH; and $C_{1-4}$ alkoxy;

each occurrence of $R^g$ is independently selected from the group consisting of:

$C_{3-12}$ cycloalkyl or $C_{3-12}$ cycloalkenyl, each of which is optionally substituted with 1-4 substituents independently selected from the group consisting of oxo, $R^c$, and $R^h$;

heterocyclyl or heterocycloalkenyl of 3-12 ring atoms, wherein 1-3 ring atoms are heteroatoms, each independently selected from the group consisting of N, N(H), N($R^d$), O, and $S(O)_{0-2}$, and wherein the heterocyclyl or heterocycloalkenyl is optionally substituted with 1-4 substituents independently selected from the group consisting of oxo, $R^c$, and $R^h$;

heteroaryl of 5-12 ring atoms, wherein 1-4 ring atoms are heteroatoms, each independently selected from the group consisting of N, N(H), N($R^d$), O, and $S(O)_{0-2}$, and wherein the heteroaryl is optionally substituted with 1-4 substituents independently selected from the group consisting of oxo, $R^c$, and $R^h$; and $C_{6-10}$ aryl optionally substituted with 1-4 substituents independently selected from the group consisting of oxo, $R^c$, and $R^h$;

each occurrence of $R^h$ is independently selected from the group consisting of:

$C_{3-12}$ cycloalkyl or $C_{3-12}$ cycloalkenyl, each of which is optionally substituted with 1-4 $R^i$;

heterocyclyl or heterocycloalkenyl of 3-12 ring atoms, wherein 1-3 ring atoms are heteroatoms, each independently selected from the group consisting of N, N(H), N($R^d$), O, and $S(O)_{0-2}$, and wherein the heterocyclyl or heterocycloalkenyl is optionally substituted with 1-4 $R^i$;

heteroaryl of 5-12 ring atoms, wherein 1-3 ring atoms are heteroatoms, each independently selected from the group consisting of N, N(H), N($R^d$), O, and $S(O)_{0-2}$, and wherein the heteroaryl is optionally substituted with 1-4 $R^i$; and $C_{6-10}$ aryl optionally substituted with 1-4 $R^i$ each occurrence of $R^i$ is independently selected from the group consisting of: $C_{1-6}$ alkyl; $C_{1-4}$ haloalkyl; $C_{1-4}$ alkoxy; $C_{1-4}$ haloalkoxy; and halo;

each occurrence of $L^g$ is independently selected from the group consisting of: —O—, —NH—, —$NR^d$, —$S(O)_{0-2}$, C(O), and $C_{1-3}$ alkylene optionally substituted with 1-3 $R^a$;

each occurrence of bg is independently 1, 2, or 3; and each occurrence of R' and R" is independently selected from the group consisting of: H; —OH; and $C_{1-4}$ alkyl.

Variable $L^A$ ($-(L)_{a1}-(L^2)_{a2}-(L^3)_{a3}-(L^4)_{a4}-(L^5)_{a5}-*$, Wherein * Represents the Point of Attachment to $Q^1$)

In some embodiments, $L^A$ is a divalent moiety having a 1-6 (e.g., 2-6 (e.g., 2, 3, or 4)) linear array of substituted or unsubstituted carbon and/or heteroatoms. In some embodiments, $L^A$ is a divalent moiety having a combination of a cyclic moiety and a 1-6 (e.g., 2-6 (e.g., 2, 3, or 4)) linear array of substituted or unsubstituted carbon and/or heteroatoms. For example, one cyclic moiety (e.g., C3-6, e.g., C4 cycloalkylene), and an acyclic moiety (e.g., O).

In some embodiments, provided that when a3 is 0; and a4 is 1, then $L^4$ is other than straight-chain $C_{1-6}$ alkylene, straight-chain $C_{2-6}$ alkenylene, or straight-chain $C_{2-6}$ alkynylene, each of which is optionally substituted with 1-6 $R^b$.

In some embodiments, a2 is 1. In some embodiments, a2 is 0.

In certain embodiments (when a2 is 1), $L^2$ is straight-chain $C_{1-6}$ alkylene, straight-chain $C_{2-6}$ alkenylene, or straight-chain $C_{2-6}$ alkynylene, each of which is optionally substituted with 1-6 $R^b$.

In certain of the foregoing embodiments, $L^2$ is straight-chain $C_{1-6}$ alkylene, which is optionally substituted with 1-6 $R^b$.

In certain of the foregoing embodiments, $L^2$ is straight-chain $C_{1-3}$ alkylene, which is optionally substituted with 1-3 $R^b$.

In certain embodiments, $L^2$ is selected from the group consisting of: $—CH_2—$, $—CHR^b—$ and $—C(R^b)_2—$. For example, $L^2$ can be $—CH_2—$.

In certain embodiments (when $L^2$ is straight-chain $C_{1-6}$ alkylene, which is optionally substituted with 1-6 $R^b$), $L^2$ is straight-chain $C_{2-3}$ alkylene which is optionally substituted with 1-3 $R^b$.

In certain of these embodiments, $L^2$ is straight-chain $C_2$ alkylene which is optionally substituted with 1-3 $R^b$. In certain of the foregoing embodiments, $L^2$ is selected from the group consisting of: $—CH_2CH_2—$, $—CH_2CH(R^b)—*$, and $—CH_2C(R^b)_2—*$, wherein the asterisk represents point of attachment to $-(L^3)_{a3}-$. For example, $L^2$ can be $—CH_2CH_2—$.

In certain embodiments, $L^2$ is straight-chain $C_3$ alkylene which is optionally substituted with 1-3 $R^b$. For example, $L^2$ can be selected from the group consisting of:

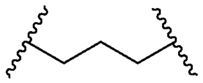,
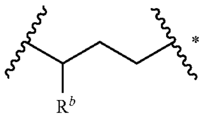,
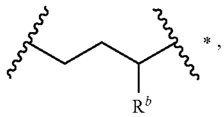, and
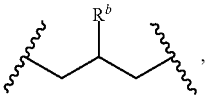, wherein the asterisk represents point of attachment to $-(L^3)_{a3}-$.

In certain embodiments (when a2 is 1), $L^2$ is straight-chain $C_{2-6}$ alkenylene, which is optionally substituted with 1-6 $R^b$. In certain of these embodiments, $L^2$ is straight-chain $C_{2-4}$ alkenylene, which is optionally substituted with 1-3 $R^b$. For example, $L^2$ can be selected from the group consisting of:

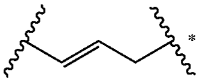 and
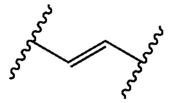, wherein the asterisk represents the point of attachment to $-(L^3)_{a3}-$.

In certain embodiments (when a2 is 1), $L^2$ is selected from the group consisting of:

- $C_{3-10}$ cycloalkylene or $C_{3-10}$ cycloalkenylene, each of which is optionally substituted with 1-3 $R^c$; and
- heterocyclylene or heterocycloalkenylene, each having 4-10 ring atoms wherein 1-3 ring atoms are ring heteroatoms each independently selected from the group consisting of: N, N(H), $N(R^d)$, O, and $S(O)_{0-2}$, wherein the heterocyclylene or heterocycloalkenylene is optionally substituted with 1-3 $R^c$.

In certain of these embodiments, $L^2$ is selected from the group consisting of:

- $C_{3-8}$ cycloalkylene, which is optionally substituted with 1-3 $R^c$; and
- heterocyclylene having 4-8 ring atoms wherein 1-3 ring atoms are ring heteroatoms each independently selected from the group consisting of: N, N(H), $N(R^d)$, O, and $S(O)_{0-2}$, wherein the heterocyclylene is optionally substituted with 1-3 $R^c$.

In certain of the foregoing embodiments, $L^2$ is:

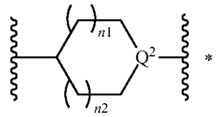

which is optionally substituted with 1-2 $R^c$, wherein n1 and n2 are independently 0, 1, or 2; $Q^2$ is CH, $CR^c$, or N; and the asterisk represents the point of attachment to $-(L^3)_{a3}-$.

In certain of these embodiments, $Q^2$ is CH.

In certain embodiments (when $L^2$ is:

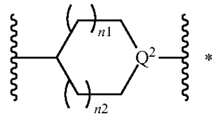

as defined supra), n1 and n2 are each 0.

As a non-limiting example (when $L^2$ is:

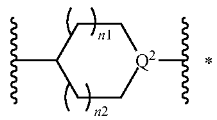

as defined supra), $L^2$ can be

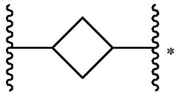, wherein the asterisk represents the point of attachment to $-(L^3)_{a3}-$ or $-(L^1)_{a1}$, e.g., $-(L^1)_{a1}$, in which at is 1. For example, $L^2$ can be

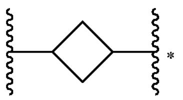, wherein the asterisk represents the point of attachment to $-(L^1)_{a1}$. In certain of these embodiments, $-(L^1)_{a1}$ is O. In certain of the foregoing embodiments, each of a3, a4, and a5 is 0.

In some embodiments, at is 1. In some embodiments, a1 is 0.

In certain embodiments (when at is 1), $L^1$ is selected from the group consisting of: —O—, —N(H)—, $—N(R^d)—$, and —S—. In certain of these embodiments, $L^1$ is —O—.

In some embodiments, a3 is 1. In some embodiments, a3 is 0.

In certain embodiments (when a3 is 1), $L^3$ is selected from the group consisting of —O—, —N(H)—, $—N(R^d)—$, and —S—. In certain of these embodiments, $L^3$ is —O—. In certain other embodiments, $L^3$ is —N(H)— or $—N(R^d)—$ (e.g., —N(H)—).

In some embodiments, a4 is 1. In some embodiments, a4 is 0.

In certain embodiments (when a4 is 1), $L^4$ is straight-chain $C_{1-3}$ alkylene, which is optionally substituted with 1-3 $R^b$. In certain of these embodiments, $L^4$ is —$CH_2$—.

In certain embodiments (when a4 is 1), $L^4$ is selected from the group consisting of:

$C_{3-8}$ cycloalkylene, which is optionally substituted with 1-3 $R^c$; and heterocyclylene having 4-8 ring atoms wherein 1-3 ring atoms are ring heteroatoms each independently selected from the group consisting of N, N(H), N($R^d$), O, and $S(O)_{0-2}$, wherein the heterocyclylene is optionally substituted with 1-3 $R^c$.

In certain of these embodiments, $L^4$ is:

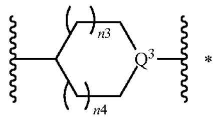

which is optionally substituted with 1-2 $R^c$, wherein n3 and n4 are independently 0, 1, or 2; $Q^3$ is CH, $CR^c$, or N; and the asterisk represents the point of attachment to -$(L^5)_{a5}$-.

In certain embodiments (when $L^4$ is:

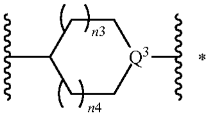

), n3 and n4 are each 1. In certain embodiments (when $L^4$ is:

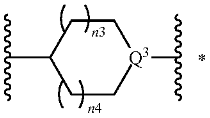

), $Q^3$ is N.

As a non-limiting example of the foregoing embodiments, $L^4$ can be

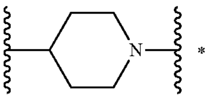

, wherein the asterisk represents the point of attachment to -$(L^5)_{a5}$-.

In some embodiments, a5 is 0.

Non-Limiting Combinations of -$(L^1)_{a1}$-$(L^2)_{a2}$-$(L^3)_{a3}$-$(L^4)_{a4}$-$(L^5)_{a5}$-*

In some embodiments, -$(L^1)_{a1}$$(L^2)_{a2}$-$(L^3)_{a3}$-$(L^4)_{a4}$-$(L)_{a5}$-* has a length of from 1 atom to 8 atoms (as used here and for counting purposes only, moieties such as $CH_2$, C(O), $CF_2$ and the like, whether present in acyclic or cyclic moieties, count as 1 atom); e.g., from 1 atom to 6 atoms, or from 1 atom to 5 atoms, or from 1 atom to 4 atoms; or from 1 atom to 3 atoms; or from 2 atoms to 6 atoms; or from 2 atoms to 4 atoms.

In certain embodiments, one of at, a3, and a5 is 1, and the other two of at, a3, and a5 are 0. In certain embodiments, at is 1, e.g., when $L^2$ is a cyclic group (e.g., cycloalkylene).

In certain embodiments, one of a2 and a4 is 1, and the other of a2 and a4 is 0 or 1.

In certain of the foregoing embodiments, one of at, a3, and a5 is 1, and the other two of at, a3, and a5 are 0; and one of a2 and a4 is 1, and the other of a2 and a4 is 0 or 1.

In certain embodiments, 1≤a1+a2+a3+a4+a5≤4. In certain of these embodiments, 1≤a1+a2+a3+a4+a5≤3.

In certain embodiments, at and a2 are each 1.

[AA1] In certain embodiments, at and a2 are each 1;

L is —O—, —N(H)—, or —N($R^d$)—;

$L^2$ is selected from the group consisting of:

straight-chain $C_{1-3}$ alkylene, which is optionally substituted with 1-3 $R^b$;

$C_{3-8}$ cycloalkylene, which is optionally substituted with 1-3 $R^c$; and heterocyclylene having 4-8 ring atoms wherein 1-3 ring atoms are ring heteroatoms each independently selected from the group consisting of: N, N(H), N($R^d$), O, and $S(O)_{0-2}$, wherein the heterocyclylene is optionally substituted with 1-3 $R^c$.

[AA2] In certain embodiments, a1 and a2 are each 1;

$L^1$ is —O—; and $L^2$ is straight-chain $C_{1-3}$ alkylene, which is optionally substituted with 1-3 $R^b$.

[AA3] In certain embodiments, a1 and a2 are each 1;

$L^1$ is —O—; and $L^2$ is selected from the group consisting of: —$CH_2$—, —$CHR^b$—, and —$C(R^b)_2$—.

[AA4] In certain embodiments, a1 and a2 are each 1;

$L^1$ is —O—; and $L^2$ is straight-chain $C_{2-3}$ alkylene which is optionally substituted with 1-3 $R^b$.

In certain embodiments of [AA4], $L^2$ is straight-chain $C_2$ alkylene which is optionally substituted with 1-3 $R^b$. As non-limiting examples of the foregoing embodiments, $L^2$ can be selected from the group consisting of: —$CH_2CH_2$—, —$CH_2CH(R^b)$—*, and —$CH_2C(R^b)_2$—*, wherein the asterisk represents point of attachment to -$(L^3)_{a3}$-. For example, $L^2$ can be —$CH_2CH_2$—.

[AA5] In certain embodiments, a1 and a2 are each 1;

$L^1$ is —O—;

$L^2$ is selected from the group consisting of:

$C_{3-8}$ cycloalkylene, which is optionally substituted with 1-3 $R^c$; and heterocyclylene having 4-8 ring atoms wherein 1-3 ring atoms are ring heteroatoms each independently selected from the group consisting of: N, N(H), N($R^d$), O, and $S(O)_{0-2}$, wherein the heterocyclylene is optionally substituted with 1-3 $R^c$.

In certain embodiments of [AA5], $L^2$ is:

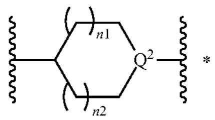

which is optionally substituted with 1-2 $R^c$, wherein n1 and n2 are independently 0, 1, or 2; $Q^2$ is CH, $CR^C$, or N; and the asterisk represents the point of attachment to $-(L^3)_{a3}-$.

In certain of these embodiments, n1 and n2 are independently 0 or 1, optionally 0; and $Q^2$ is CH. For example, n1 and n2 can both be 0; and $Q^2$ can be CH, e.g., $L^2$ can be optionally substituted cyclobutane-diyl, e.g, optionally substituted cyclobutane-1,3-diyl.

In certain embodiments when at and a2 are each 1, a3, a4, and a5 are each 0.

In certain embodiments of [AA1], a3, a4, and a5 are each 0. In certain embodiments of [AA2], a3, a4, and a5 are each 0. In certain embodiments of [AA3], a3, a4, and a5 are each 0. In certain embodiments of [AA4], a3, a4, and a5 are each 0. In certain embodiments of [AA5], a3, a4, and a5 are each 0.

In certain embodiments when at and a2 are each 1, a3 and a5 are 0; and a4 is 1.

In certain embodiments of [AA1], a3 and a5 are 0; and a4 is 1. In certain embodiments of [AA2], a3 and a5 are 0; and a4 is 1. In certain embodiments of [AA3], a3 and a5 are 0; and a4 is 1. In certain embodiments of [AA4], a3 and a5 are 0; and a4 is 1. In certain embodiments of [AA5], a3 and a5 are 0; and a4 is 1.

In certain embodiments (when at and a2 are each 1, a3 and a5 are 0; and a4 is 1), $L^4$ is selected from the group consisting of:

$C_{3-8}$ cycloalkylene, which is optionally substituted with 1-3 $R^c$; and heterocyclylene having 4-8 ring atoms wherein 1-3 ring atoms are ring heteroatoms each independently selected from the group consisting of: N, N(H), $N(R^d)$, O, and $S(O)_{0-2}$, wherein the heterocyclylene is optionally substituted with 1-3 $R^c$.

In certain of these embodiments, $L^4$ is:

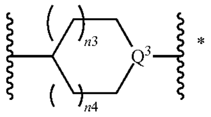

which is optionally substituted with 1-2 $R^c$, wherein n3 and n4 are independently 0, 1, or 2; $Q^3$ is CH, $CR^c$, or N; and the asterisk represents the point of attachment to $-(L^5)_{a5}-$. In certain of the foregoing embodiments, n3 and n4 are independently 0 or 1; and $Q^3$ is N.

In certain embodiments, at is 0; and a2 is 1.

[BB1] In certain embodiments, at is 0; a2 is 1; and $L^2$ is straight-chain $C_{1-6}$ alkylene, which is optionally substituted with 1-6 $R^b$.

In certain embodiments of [BB1], $L^2$ is straight-chain $C_{1-3}$ alkylene, which is optionally substituted with 1-3 $R^b$. In certain of the foregoing embodiments, $L^2$ is selected from the group consisting of: $—CH_2—$, $—CHR^b—$, and $—C(R^b)_2—$. For example, $L^2$ can be $—CH_2—$.

In certain embodiments of [BB1], $L^2$ is straight-chain $C_{2-3}$ alkylene which is optionally substituted with 1-3 $R^b$. In certain of the foregoing embodiments, $L^2$ is straight-chain $C_2$ alkylene, which is optionally substituted with 1-3 $R^b$. As non-limiting examples, $L^2$ can be selected from the group consisting of: $—CH_2CH_2—$, $—CH_2CH(R^b)—*$, and $—CH_2C(R^b)_2—*$, wherein the asterisk represents point of attachment to $-(L^3)_{a3}-$. For example, $L^2$ can be $—CH_2CH_2—$.

In certain embodiments of [BB1], $L^2$ is straight-chain $C_3$ alkylene, which is optionally substituted with 1-3 $R^b$. In certain of these embodiments, $L^2$ is selected from the group consisting of:

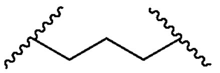
,
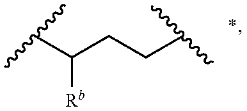
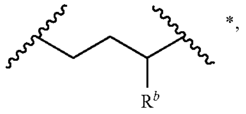
and
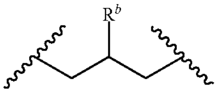
, wherein the asterisk represents point of attachment to $-(L^3)_{a3}-$.

In certain embodiments (when a1 is 0; and a2 is 1), a3 is 0; and a4 is 0.

In certain embodiments of [BB1], a3 is 0; and a4 is 0.

In certain embodiments (when at is 0; and a2 is 1), a3 is 1. In certain embodiments of [BB1], a3 is 1.

In certain embodiments (when a1 is 0; and a2 is 1) or in certain embodiments of [BB1], a3 is 1; and $L^3$ is selected from the group consisting of: is —O—, —N(H)—, and $—N(R^d)—$. In certain of these embodiments, a3 is 1; and $L^3$ is —O—. In certain other embodiments, a3 is 1; and $L^3$ is —N(H)— or $—N(R^d)—$, optionally —N(H)—.

In certain embodiments (when a1 is 0; and a2 is 1) or in certain embodiments of [BB1], a4 is 1; and $L^4$ is straight-chain $C_{1-3}$ alkylene, which is optionally substituted with 1-3 $R^b$. In certain of these embodiments, a4 is 1; and $L^4$ is $—CH_2—$.

In certain embodiments (when a1 is 0; and a2 is 1) or in certain embodiments of [BB1], a4 is 0.

[CC1] In certain embodiments, a1 is 0; a2 is 1; $L^2$ is straight-chain $C_{2-4}$ alkenylene, which is optionally substituted with 1-3 $R^b$.

In certain embodiments of [CC1], $L^2$ is selected from the group consisting of:

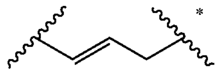
and
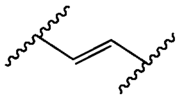
, wherein the asterisk represents the point of attachment to $-(L^3)_{a3}-$.

In certain embodiments of [CC1], a3 is 0; and a4 is 0.

For the avoidance of doubt when any one or more of a1, a2, a3, a4, and a5 are 0, this means that the corresponding variable ($L^1$-$L^5$) is absent from $L^A$. For example, when each of a3, a4, and a5 are 0, this means that $L^A$ has the formula $-L^1-L^2-$.

In certain embodiments, $L^A$ is $-L^1-L^2-$.

In certain embodiments, $L^A$ is $-L^2-L^3-$.

In certain embodiments, $L^A$ is $-L^2-L^3-L^4-$.

In certain embodiments, $L^A$ can be $—CH_2CH_2—O—*$, wherein * represents the point of attachment to $Q^1$.

In certain embodiments, $L^A$ can be $—O—CH_2CH_2—*$, wherein * represents the point of attachment to $Q^1$.

In certain embodiments, $L^A$ can be $—CH_2—O—CH_2—$.

In certain embodiments, $L^A$ can be

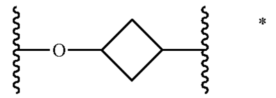 [SMILES: *OC1CC(*)C1]

(such as

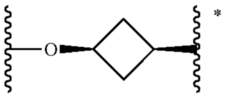

or

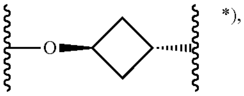

), wherein * represents the point of attachment to $Q^1$.

Variable $Q^1$

In some embodiments, $Q^1$ is selected from the group consisting of:

- heteroaryl of 5-12 ring atoms, wherein 1-4 ring atoms are heteroatoms, each independently selected from the group consisting of N, N(H), $N(R^d)$, O, and $S(O)_{0-2}$, and wherein the heteroaryl is optionally substituted with 1-4 $R^e$; and
- $C_{6-10}$ aryl optionally substituted with 1-4 $R^c$.

In certain of these embodiments, $Q^1$ is selected from the group consisting of:

- heteroaryl of 5-6 ring atoms, wherein 1-4 ring atoms are heteroatoms, each independently selected from the group consisting of N, N(H), $N(R^d)$, O, and $S(O)_{0-2}$, and wherein the heteroaryl is optionally substituted with 1-3 $R^c$; and
- phenyl optionally substituted with 1-3 $R^c$.

In certain of the foregoing embodiments, $Q^1$ is selected from the group consisting of:

- heteroaryl of 6 ring atoms, wherein 1-2 ring atoms are ring nitrogen atoms, and wherein the heteroaryl is optionally substituted with 1-3 $R^c$; and
- phenyl optionally substituted with 1-3 $R^c$.

In certain embodiments, $Q^1$ is phenyl optionally substituted with 1-3 $R^c$. In certain of these embodiments, $Q^1$ is selected from the group consisting of:

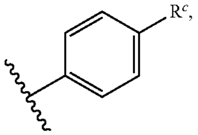

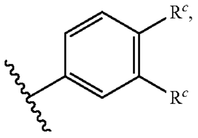

-continued and

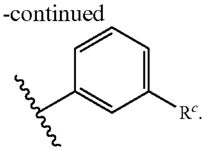

In certain embodiments, $Q^1$ is heteroaryl of 6 ring atoms, wherein 1-2 ring atoms are ring nitrogen atoms, and wherein the heteroaryl is optionally substituted with 1-3 $R^c$In certain of these embodiments, $Q^1$ is pyridyl, which is optionally substituted with 1-3 $R^c$In certain of the foregoing embodiments $Q^1$ is selected from the group consisting of.

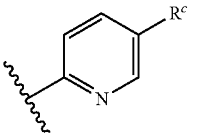

and

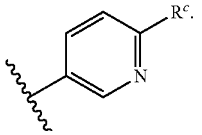

In certain embodiments, $Q^1$ is heterocyclyl or heterocycloalkenyl of 3-12 ring atoms, wherein 1-3 ring atoms are heteroatoms, each independently selected from the group consisting of N, N(H), $N(R^d)$, O, and $S(O)_{0-2}$, and wherein the heterocyclyl or heterocycloalkenyl is optionally substituted with 1-4 substituents independently selected from the group consisting of oxo and $R^c$.

In certain of these embodiments, $Q^1$ is heterocyclyl of 4-10 ring atoms, wherein 1-3 ring atoms are heteroatoms, each independently selected from the group consisting of N, N(H), $N(R^d)$, O, and $S(O)_{0-2}$, and wherein the heterocyclyl is optionally substituted with 1-4 substituents independently selected from the group consisting of oxo and $R^c$.

In certain of the foregoing embodiments, $Q^1$ is heterocyclyl of 4-8 ring atoms, wherein 1-2 ring atoms are heteroatoms, each independently selected from the group consisting of N, N(H), $N(R^d)$, O, and $S(O)_{0-2}$, provided that one ring atom is $N(R^d)$, and wherein the heterocyclyl is optionally substituted with 1-4 substituents independently selected from the group consisting of oxo and $R^c$.

As non-limiting examples of the foregoing embodiments, $Q^1$ can be

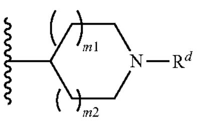

or

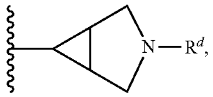

wherein m1 and m2 are each independently 0, 1, or 2; and wherein $Q^1$ is optionally substituted with 1-2 $R^c$. For example, $Q^1$ can be

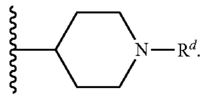

As another non-limiting example, $Q^1$ can be

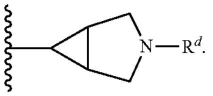

In certain embodiments, each $R^d$ present in $Q^1$ is independently selected from the group consisting of: —C(O)O($C_{1-4}$ alkyl); and $C_{1-6}$ alkyl optionally substituted with 1-3 independently selected $R^a$.

In certain of the foregoing embodiments, each $R^d$ present in $Q^1$ is $C_{1-6}$ alkyl optionally substituted with 1-3 independently selected halo.

In certain of the foregoing embodiments, each $R^d$ present in $Q^1$ is $C_{1-4}$ alkyl substituted with 1-3 —F. In certain embodiments, each $R^d$ present in $Q^1$ is $C_{2-3}$ alkyl substituted with 1-3 —F. For example, each $R^d$ present in $Q^1$ can be —$CH_2CF_3$.

In certain embodiments, each $R^c$ present in $Q^1$ is independently selected from the group consisting of: halo; cyano; $C_{1-4}$ alkoxy; $C_{1-4}$ haloalkoxy; and $C_{1-10}$ alkyl which is optionally substituted with 1-6 independently selected $R^a$.

In certain embodiments, each $R^c$ present in $Q^1$ is independently selected from the group consisting of: halo; cyano; $C_{1-4}$ alkoxy; $C_{1-4}$ haloalkoxy; and $C_{1-6}$ alkyl which is optionally substituted with 1-6 independently selected halo.

In certain of the foregoing embodiments, each $R^c$ present in $Q^1$ is independently selected from the group consisting of: halo and $C_{1-3}$ alkyl which is optionally substituted with 1-6 independently selected halo.

In certain embodiments, each $R^c$ present in $Q^1$ is $C_{1-3}$ alkyl which is optionally substituted with 1-6 —F. For example, each $R^c$ present in $Q^1$ can be $CF_3$.

In certain embodiments, each $R^c$ present in $Q^1$ is an independently selected halo (e.g., —F or —Cl).

Variables $Y^1$, $Y^2$, $Y^3$, $X^1$, and $X^2$

In some embodiments, $Y^1$ is $CR^1$.

In some embodiments, $Y^2$ is $CR^1$.

In some embodiments, $Y^3$ is $CR^1$.

In certain embodiments, each occurrence of $R^1$ is independently H or $R^e$. In certain of these embodiments, each occurrence of $R^1$ is H.

In certain other embodiments, 1-2 occurrence of $R^1$ is $R^c$; and each remaining occurrence of $R^1$ is H. For example, one occurrence of $R^1$ can be halo (e.g., —F or —Cl); and each remaining occurrence of $R^1$ can be H.

In certain embodiments, $Y^1$, $Y^2$, and $Y^3$ are each independently selected $CR^1$.

In certain embodiments, $Y^1$, $Y^2$, and $Y^3$ are each CH.

In certain embodiments, one of $Y^1$, $Y^2$, and $Y^3$ is $CR^C$, optionally C-halo; and each of the remaining two $Y^1$, $Y^2$, and $Y^3$ is CH.

In some embodiments, $X^1$ is $NR^2$. In certain of these embodiments, $X^1$ is NH.

In some embodiments, $X^2$ is $CR^5$. In certain of these embodiments, $X^2$ is CH.

In certain embodiments, $X^1$ is $NR^2$; and $X^2$ is $CR^5$. In certain of the foregoing embodiments, $X^1$ is NH; and $X^2$ is CH.

In certain embodiments, $Y^1$, $Y^2$, and $Y^3$ are each an independently selected $CR^1$; $X^1$ is $NR^2$; and $X^2$ is $CR^5$. In certain of the foregoing embodiments, $Y^1$, $Y^2$, and $Y^3$ are each CH; $X^1$ is NH; and $X^2$ is CH.

Variables $R^6$ and W

In some embodiments, $R^6$ is H.

In some embodiments, W is $C_{1-10}$ alkyl, $C_{2-10}$ alkenyl, or $C_{2-10}$ alkenyl, each of which is optionally substituted with 1-6 $R^{a2}$.

In certain of these embodiments, W is $C_{1-10}$ alkyl, which is optionally substituted with 1-6 $R^{a2}$. In certain of the foregoing embodiments, W is $C_{1-6}$ alkyl, which is optionally substituted with 1-6 $R^{a2}$.

In certain embodiments, W is $C_{1-4}$ alkyl, which is optionally substituted with 1-6 $R^{a2}$.

In certain of the foregoing embodiments, W is unsubstituted $C_{1-4}$ alkyl. As non-limiting examples of the foregoing embodiments, W can be selected from the group consisting of: methyl, ethyl, n-propyl, isopropyl, and isobutyl. For example, W can be methyl or ethyl.

In some embodiments, W is $C_{1-10}$ alkyl, $C_{2-10}$ alkenyl, or $C_{2-10}$ alkenyl, each of which is optionally substituted with 1-6 $R^{a2}$, wherein one or more of the internal optionally substituted methylene group is replaced by one or more heteroatom selected from O or S, wherein when W is alkenyl or alkynyl, the heteroatom is not directed connected to the $sp^2$ or sp carbon;

In certain embodiments, W is $C_{1-4}$ alkyl, which is optionally substituted with 1-6 $R^{a2}$, wherein one or more of the internal optionally substituted methylene group is replaced by one or more heteroatom selected from O or S, wherein when W is alkenyl or alkynyl, the heteroatom is not directed connected to the $sp^2$ or sp carbon;

In certain embodiments, W is $C_{1-4}$ alkyl, which is optionally substituted with one $R^{a2}$, wherein one or more of the internal methylene group is replaced by O.

In certain embodiments, W is —$CH_2$—O—$(CH_2)_2$—$OCH_3$.

In certain embodiments, W is $C_{1-4}$ alkyl, which is substituted with 1-6 $R^{a2}$.

In certain of these embodiments, each $R^{a2}$ is independently selected from the group consisting of: —OH; -halo; —$NR^eR^f$; $C_{1-4}$ alkoxy; $C_{1-4}$ haloalkoxy; —C(=O)O($C_{1-4}$ alkyl); —C(=O)($C_{1-4}$ alkyl); and cyano. For example, each $R^{a2}$ can be independently selected from the group consisting of halo; —OH; $C_{1-4}$ alkoxy; and $C_{1-4}$ haloalkoxy.

In certain embodiments, W is $C_{1-4}$ alkyl which is substituted with 1-3 substituents each independently selected from the group consisting of: halo; —OH; $C_{1-4}$ alkoxy; and $C_{1-4}$ haloalkoxy. As non-limiting examples, W can be

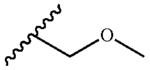,

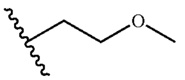,

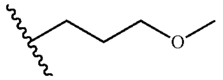, and

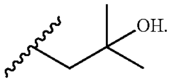

As another non-limiting example of the foregoing embodiments, W can be

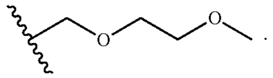 [SMILES: *COCCOC]

In some embodiments, W is selected from the group consisting of:

- monocyclic $C_{3-8}$ cycloalkyl or $C_{3-8}$ cycloalkenyl, each of which is optionally substituted with 1-4 substituents independently selected from the group consisting of oxo and $R^c$; and
- monocyclic heterocyclyl or heterocycloalkenyl of from 3-8 ring atoms, wherein 1-3 ring atoms are heteroatoms, each independently selected from the group consisting of N, N(H), N($R^d$), O, and $S(O)_{0-2}$, and wherein the heterocyclyl or heterocycloalkenyl is optionally substituted with 1-4 substituents independently selected from the group consisting of oxo and $R^c$.

In certain of the foregoing embodiments, W is monocyclic $C_{3-8}$ cycloalkyl or $C_{3-8}$ cycloalkenyl, each of which is optionally substituted with 1-4 substituents independently selected from the group consisting of oxo and $R^c$.

In certain of these embodiments, W is monocyclic $C_{3-8}$ cycloalkyl, which is optionally substituted with 1-4 substituents independently selected from the group consisting of oxo and $R^c$.

In certain embodiments, W is unsubstituted $C_{3-8}$ cycloalkyl. As non-limiting examples of the foregoing embodiments, W can be cyclopropyl, cyclobutyl, cyclopentyl, or cyclohexyl. For example, W can be cyclobutyl.

In some embodiments, W is H.

Non-Limiting Combinations

In certain embodiments, the compound is a compound of Formula (I-a):

Formula (I-a)

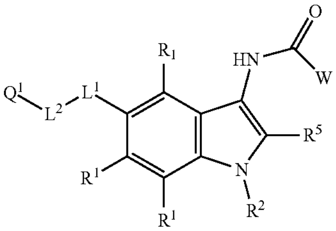

or a pharmaceutically acceptable salt thereof, wherein:

- $L^1$ is selected from the group consisting of: —O—, —N(H)—, and —N($R^d$)—;
- $L^2$ is selected from the group consisting of:
  - straight-chain $C_{1-3}$ alkylene, which is optionally substituted with 1-3 $R^b$;
  - $C_{3-8}$ cycloalkylene, which is optionally substituted with 1-3 $R^c$; and
  - heterocyclylene having 4-8 ring atoms wherein 1-3 ring atoms are ring heteroatoms each independently selected from the group consisting of: N, N(H), N($R^d$), O, and $S(O)_{0-2}$, wherein the heterocyclylene is optionally substituted with 1-3 $R^c$.

In certain embodiments of Formula (I-a), $L^1$ is —O—.

In certain embodiments of Formula (I-a), $L^2$ is straight-chain $C_{1-3}$ alkylene, which is optionally substituted with 1-3 $R^b$.

In certain embodiments of Formula (I-a), $L^2$ is selected from the group consisting of: —$CH_2$—, —$CHR^b$—, and —$C(R^b)_2$—, optionally wherein $L^2$ is —$CH_2$—.

In certain embodiments of Formula (I-a), $L^2$ is straight-chain $C_2$ alkylene which is optionally substituted with 1-3 $R^b$. In certain of these embodiments, $L^2$ is selected from the group consisting of: —$CH_2CH_2$—, —$CH_2CH(R^b)$—*, and —$CH_2C(R^b)_2$—*, wherein the asterisk represents point of attachment to -$Q^1$. For example, $L^2$ can be —$CH_2CH_2$—.

In certain embodiments of Formula (I-a), $L^2$ is straight-chain $C_3$ alkylene which is optionally substituted with 1-3 $R^b$.

In certain embodiments of Formula (I-a), $L^2$ is:

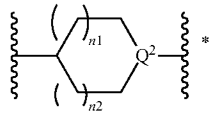

which is optionally substituted with 1-2 $R^c$, wherein n1 and n2 are independently 0, 1, or 2; $Q^2$ is CH, $CR^C$, or N; and the asterisk represents the point of attachment to $Q^1$.

In certain of these embodiments, n1 and n2 are independently 0 or 1, optionally 0; and $Q^2$ is CH. For example, n1 and n2 can both be 0; and $Q^2$ can be CH, e.g., $L^2$ can be optionally substituted optionally substituted cyclobutane-diyl, e.g, optionally substituted cyclobutane-1,3-diyl.

In certain embodiments of Formula (I-a), $L^1$ is —O—; and $L^2$ is:

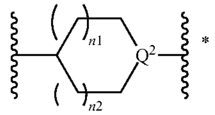

which is optionally substituted with 1-2 $R^c$, wherein n1 and n2 are independently 0 or 1, optionally 0; and $Q^2$ is CH. For example, n1 and n2 can both be 0; and $Q^2$ can be CH, e.g., $L^2$ can be optionally substituted cyclobutane-diyl, e.g, optionally substituted 1,3-cyclobutane-1,3-diyl, e.g., unsubstituted cyclobutane-diyl, e.g, unsubstituted cyclobutane-1, 3-diy.

In certain embodiments of Formula (I-a), $L^1$ is —O—; and $L^2$ is straight-chain $C_{2-3}$ alkylene which is optionally substituted with 1-3 $R^b$.

In certain of the foregoing embodiments of Formula (I-a), $L^2$ is straight-chain $C_2$ alkylene which is optionally substituted with 1-3 $R^b$.

In certain of the foregoing embodiments, $L^2$ is selected from the group consisting of: —$CH_2CH_2$—, —$CH_2CH(R^b)$—*, and —$CH_2C(R^b)_2$—*, wherein the asterisk represents point of attachment to -$Q^1$. For example, $L^2$ can be —$CH_2CH_2$—.

In certain embodiments of Formula (I-a), $L^1$ is —O—; and $L^2$ is selected from the group consisting of: —$CH_2$—, —$CHR^b$—, and —$C(R^b)_2$. For example, $L^2$ can be —$CH_2$—.

In certain embodiments, the compound is a compound of Formula (I-b):

Formula (I-b)

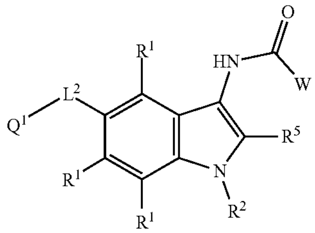

or a pharmaceutically acceptable salt thereof, wherein:

$L^2$ is straight-chain $C_{1-6}$ alkylene or straight-chain $C_{2-6}$ alkenylene, each of which is optionally substituted with 1-6 $R^b$.

In certain embodiments of Formula (I-b), $L^2$ is straight-chain $C_{2-3}$ alkylene which is optionally substituted with 1-3 $R^b$.

In certain embodiments of Formula (I-b), $L^2$ is straight-chain $C_2$ alkylene which is optionally substituted with 1-3 $R^b$. In certain of these embodiments, $L^2$ is selected from the group consisting of: $—CH_2CH_2—$, $—CH_2CH(R^b)—*$, and $—CH_2C(R^b)_2—*$, wherein the asterisk represents point of attachment to $-Q^1$. For example, $L^2$ can be $—CH_2CH_2—$.

In certain embodiments of Formula (I-b), $L^2$ is straight-chain $C_3$ alkylene which is optionally substituted with 1-3 $R^b$. In certain of these embodiments, $L^2$ is selected from the group consisting of:

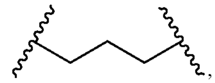,
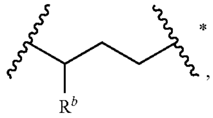,
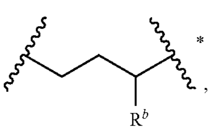, and
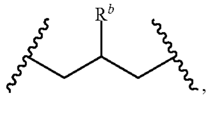, wherein the asterisk represents point of attachment to $-Q^1$. For example, $L^2$ can be

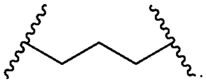 [SMILES: *CCC*].

In certain embodiments of Formula (I-b), $L^2$ is straight-chain $C_{2-4}$ alkenylene, which is optionally substituted with 1-3 $R^b$.

In certain of these embodiments, $L^2$ is selected from the group consisting of:

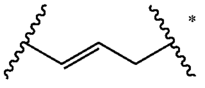 and 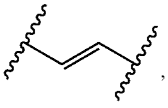, wherein the asterisk represents the point of attachment to $-Q^1$.

In certain embodiments, the compound is a compound of Formula (I-c):

Formula (I-c)

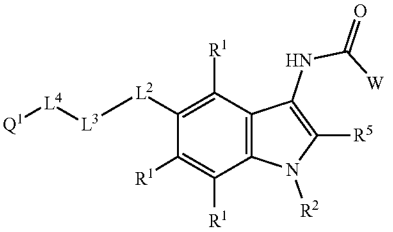

or a pharmaceutically acceptable salt thereof, wherein:

$L^2$ and $L^4$ are independently selected straight-chain $C_{1-3}$ alkylene which is optionally substituted with 1-6 $R^b$; and $L^3$ is selected from the group consisting of: —O—, —N(H)—, and $—N(R^d)—$.

In certain embodiments of Formula (I-c), $L^2$ and $L^4$ are independently selected from the group consisting of: $—CH_2—$, $—CHR^b—$, and $—C(R^b)_2$. In certain of these embodiments, $L^2$ and $L^4$ are each $—CH_2—$.

In certain embodiments of Formula (I-c), $L^3$ is —O—.

In certain embodiments of Formula (I-c), $L^3$ is —N(H)— or $—N(R^d)—$. For example, $L^3$ can be —N(H)—.

In certain embodiments, the compound is a compound of Formula (I-d):

Formula (I-d)

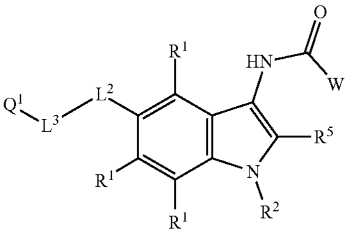

or a pharmaceutically acceptable salt thereof, wherein:

$L^2$ is straight-chain $C_{1-3}$ alkylene which is optionally substituted with 1-6 $R^b$; and $L^3$ is selected from the group consisting of: —O—, —N(H)—, and $—N(R^d)—$.

In certain embodiments of Formula (I-d), $L^2$ is selected from the group consisting of: $—CH_2—$, $—CHR^b—$, and $—C(R^b)_2$.

In certain embodiments of Formula (I-d), $L^2$ is straight-chain $C_2$ alkylene which is optionally substituted with 1-3 $R^b$. In certain of these embodiments, $L^2$ is selected from the group consisting of: $—CH_2CH_2—$, $—CH_2CH(R^b)—*$, and $—CH_2C(R^b)_2—*$, wherein the asterisk represents point of attachment to $-L^3$. For example, $L^2$ can be $—CH_2CH_2—$.

In certain embodiments of Formula (I-d), $L^3$ is —O—.

In certain embodiments of Formula (I-d), $L^3$ is —N(H)— or $—N(R^d)—$. For example, $L^3$ can be —N(H)—.

In certain embodiments of Formula (I-a), (I-b), (I-c) or (I-d), $Q^1$ is selected from the group consisting of:

- heteroaryl of 5-6 ring atoms, wherein 1-4 ring atoms are heteroatoms, each independently selected from the group consisting of N, N(H), $N(R^d)$, O, and $S(O)_{0-2}$, and wherein the heteroaryl is optionally substituted with 1-3 $R^c$; and
- phenyl optionally substituted with 1-3 $R^c$.

In certain embodiments of Formula (I-a), (I-b), (I-c) or (I-d), $Q^1$ is selected from the group consisting of:

heteroaryl of 6 ring atoms, wherein 1-2 ring atoms are ring nitrogen atoms, and wherein the heteroaryl is optionally substituted with 1-3 $R^c$; and phenyl optionally substituted with 1-3 $R^c$.

In certain embodiments of Formula (I-a), (I-b), (I-c) or (I-d), $Q^1$ is phenyl or pyridyl, each optionally substituted with 1-3 $R^c$.

In certain embodiments of Formula (I-a), (I-b), (I-c) or (I-d), $Q^1$ is

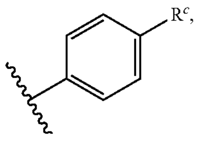
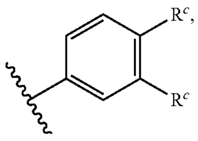
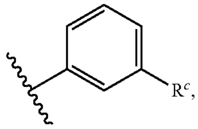
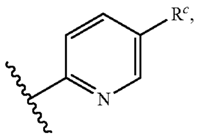
or
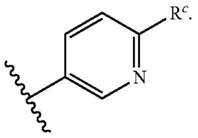

In certain embodiments of Formula (I-a), (I-b), (I-c) or (I-d), $Q^1$ is phenyl or pyridyl, each optionally substituted with 1-3 $R^c$, wherein each $R^c$ present in $Q^1$ is independently selected from the group consisting of: halo and $C_{1-3}$ alkyl which is optionally substituted with 1-6 independently selected halo.

In certain embodiments of Formula (I-a), (I-b), (I-c) or (I-d), $Q^1$ is

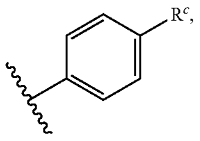
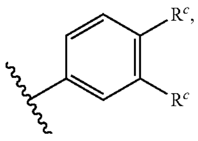
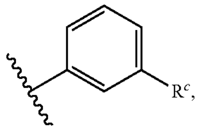
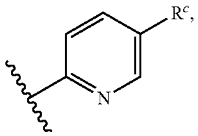
or
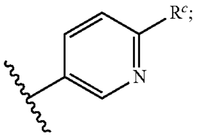

and each $R^c$ present in $Q^1$ is independently selected from the group consisting of: —F, —Cl, and —$CF_3$.

In certain embodiments of Formula (I-a), (I-b), (I-c) or (I-d), $Q^1$ is heterocyclyl of 4-10 ring atoms, wherein 1-3 ring atoms are heteroatoms, each independently selected from the group consisting of N, N(H), N($R^d$), O, and $S(O)_{0-2}$, and wherein the heterocyclyl is optionally substituted with 1-4 substituents independently selected from the group consisting of oxo and $R^c$.

In certain embodiments of Formula (I-a), (I-b), (I-c) or (I-d), $Q^1$ is:

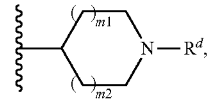

wherein m1 and m2 are each independently 0, 1, or 2.

In certain embodiments of Formula (I-a), (I-b), (I-c) or (I-d), $Q^1$ is

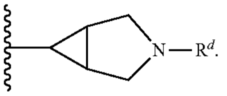

In certain embodiments of Formula (I-a), (I-b), (I-c) or (I-d), $Q^1$ is:

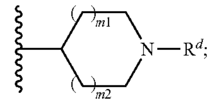

and the $R^d$ present in $Q^1$ is selected from the group consisting of: —C(O)O($C_{1-4}$ alkyl); and $C_{1-6}$ alkyl optionally substituted with 1-3 independently selected $R^a$; or wherein the $R^d$ present in $Q^1$ is $C_{2-3}$ alkyl substituted with 1-3 —F.

In certain embodiments of Formula (I-a), (I-b), (I-c) or (I-d), $Q^1$ is:

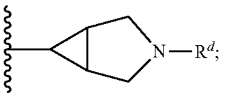

and the $R^d$ present in $Q^1$ is selected from the group consisting of: —C(O)O($C_{1-4}$ alkyl); and $C_{1-6}$ alkyl optionally substituted with 1-3 independently selected $R^a$; or wherein the $R^d$ present in $Q^1$ is $C_{2-3}$ alkyl substituted with 1-3 —F.

In certain embodiments of Formula (I-a), (I-b), (I-c) or (I-d), each $R^1$ is H.

In certain embodiments of Formula (I-a), (I-b), (I-c) or (I-d), one occurrence of $R^1$ is $R^c$; and each remaining $R^1$ is H.

In certain embodiments of Formula (I-a), (I-b), (I-c) or (I-d), $R^2$ is H; and $R^5$ is H.

In certain embodiments of Formula (I-a), (I-b), (I-c) or (I-d), W is $C_{1-6}$ alkyl, which is optionally substituted with 1-6 $R^{a2}$.

In certain embodiments of Formula (I-a), (I-b), (I-c) or (I-d), W is $C_{1-6}$ alkyl, which is optionally substituted with 1-6 $R^{a2}$, wherein one or more of the internal optionally substituted methylene group is replaced by one or more heteroatom selected from O or S, wherein when W is alkenyl or alkynyl, the heteroatom is not directed connected to the $sp^2$ or sp carbon;

In certain embodiments of Formula (I-a), (I-b), (I-c) or (I-d), W is unsubstituted $C_{1-4}$ alkyl. For example, W can be methyl or ethyl.

In certain embodiments of Formula (I-a), (I-b), (I-c) or (I-d), W is $C_{1-4}$ alkyl, which is substituted with 1-6 $R^{a2}$.

In certain of these embodiments, W is: $C_{1-4}$ alkyl which is substituted with 1-3 substituents each independently selected from the group consisting of: halo; —OH; $C_{1-4}$ alkoxy; and $C_{1-4}$ haloalkoxy.

As non-limiting examples of the foregoing embodiments, W can be

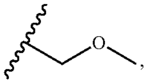,
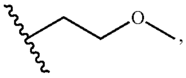,
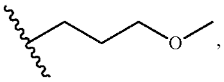, or
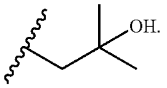

As another non-limiting example of the foregoing embodiments, W can be

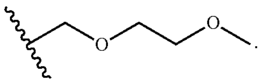 [SMILES: *COCCOC]

In certain embodiments of Formula (I-a), (I-b), (I-c) or (I-d), W is selected from the group consisting of:

monocyclic $C_{3-8}$ cycloalkyl or $C_{3-8}$ cycloalkenyl, each of which is optionally substituted with 1-4 substituents independently selected from the group consisting of oxo and $R^c$; and monocyclic heterocyclyl or heterocycloalkenyl of from 3-8 ring atoms, wherein 1-3 ring atoms are heteroatoms, each independently selected from the group consisting of N, N(H), N($R^d$), O, and $S(O)_{0-2}$, and wherein the heterocyclyl or heterocycloalkenyl is optionally substituted with 1-4 substituents independently selected from the group consisting of oxo and $R^c$.

In certain embodiments of Formula (I-a), (I-b), (I-c) or (I-d), W is monocyclic $C_{3-8}$ cycloalkyl, which is optionally substituted with 1-4 substituents independently selected from the group consisting of oxo and $R^c$. In certain of these embodiments, W is unsubstituted $C_{3-8}$ cycloalkyl. For example, W can be cyclobutyl.

Non-Limiting Exemplary Compounds

In some embodiments, the compound is selected from the group consisting of the compounds delineated in Table C1 or a pharmaceutically acceptable salt thereof.

TABLE C1

| Compound No. | Structure | LC-MS |
|---|---|---|
| 101 | 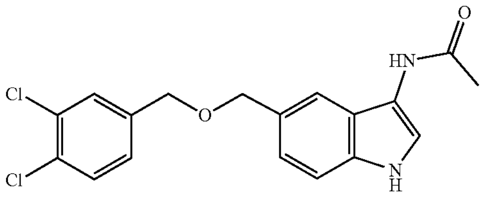 [SMILES: CC(=O)Nc1c[nH]c2ccc(COCc3ccc(Cl)c(Cl)c3)cc12] N-(5-(((3,4-dichlorobenzyl)oxy)methyl)-1H-indol-3-yl)acetamide | 361.0 |
| 102 | 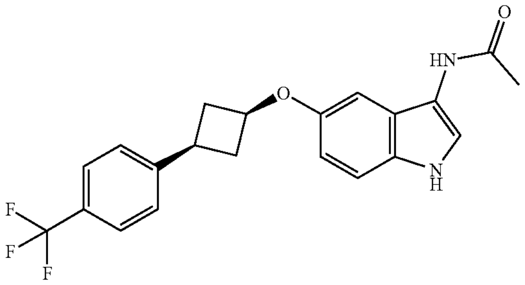 [SMILES: CC(=O)Nc1c[nH]c2ccc(O[C@H]3C[C@@H](c4ccc(C(F)(F)F)cc4)C3)cc12] N-(5-(cis-3-(4-(trifluoromethyl)phenyl)cyclobutoxy)-1H-indol-3-yl)acetamide | 387.2 |

TABLE C1-continued

| Compound No. | Structure | LC-MS |
|---|---|---|
| 103 | 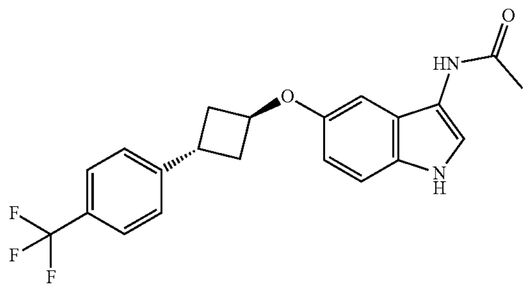 [SMILES: CC(=O)Nc1c[nH]c2ccc(O[C@H]3C[C@H](c4ccc(C(F)(F)F)cc4)C3)cc12]<br>N-(5-(trans-3-(4-(trifluoromethyl)phenyl)cyclobutoxy)-1H-indol-3-yl)acetamide | 389.3 |
| 104 | 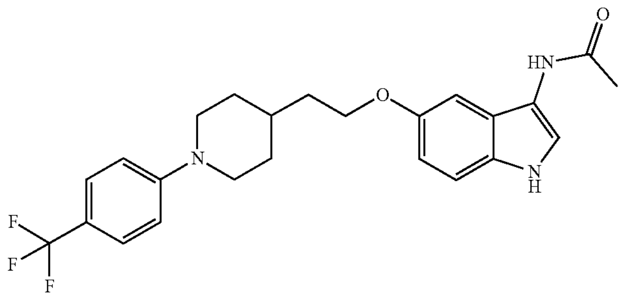 [SMILES: CC(=O)Nc1c[nH]c2ccc(OCCC3CCN(c4ccc(C(F)(F)F)cc4)CC3)cc12]<br>N-(5-(2-(1-(4-(trifluoromethyl)phenyl)piperidin-4-yl)ethoxy)-1H-indol-3-yl)acetamide | 446.2 |
| 105 | 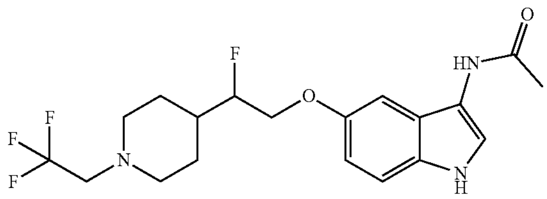 [SMILES: CC(=O)Nc1c[nH]c2ccc(OCC(F)C3CCN(CC(F)(F)F)CC3)cc12]<br>N-(5-(2-fluoro-2-(1-(2,2,2-trifluoroethyl)piperidin-4-yl)ethoxy)-1H-indol-3-yl)acetamide | 402.2 |
| 106 | 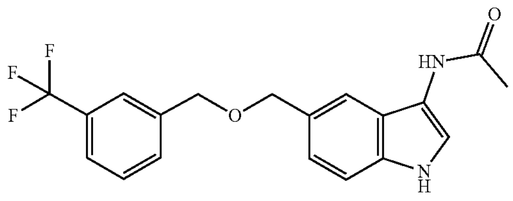 [SMILES: CC(=O)Nc1c[nH]c2ccc(COCc3cccc(C(F)(F)F)c3)cc12]<br>N-(5-(((3-(trifluoromethyl)benzyl)oxy)methyl)-1H-indol-3-yl)acetamide | 361.2 |
| 107 | 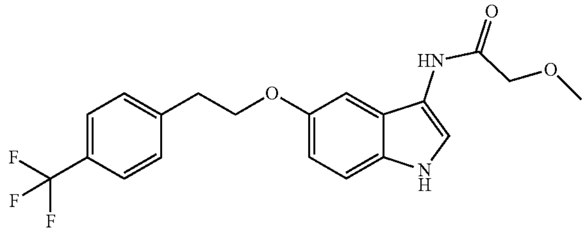 [SMILES: COCC(=O)Nc1c[nH]c2ccc(OCCc3ccc(C(F)(F)F)cc3)cc12]<br>2-methoxy-N-(5-(4-(trifluoromethyl)phenethoxy)-1H-indol-3-yl)acetamide | 393.3 |

TABLE C1-continued

| Compound No. | Structure | LC-MS |
|---|---|---|
| 108 | 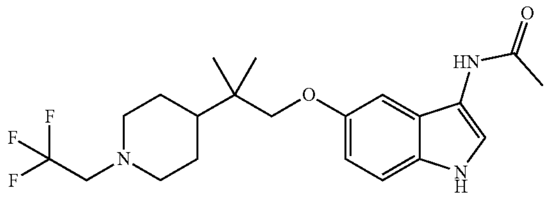 [SMILES: CC(=O)Nc1c[nH]c2ccc(OCC(C)(C)C3CCN(CC(F)(F)F)CC3)cc12] N-(5-(2-methyl-2-(1-(2,2,2-trifluoroethyl)piperidin-4-yl)propoxy)-1H-indol-3-yl)acetamide | 412.4 |
| 109 | 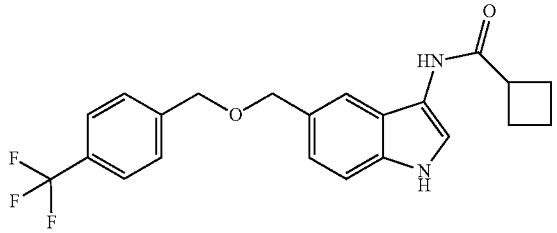 [SMILES: O=C(Nc1c[nH]c2ccc(COCc3ccc(C(F)(F)F)cc3)cc12)C1CCC1] N-(5-(((4-(trifluoromethyl)benzyl)oxy)methyl)-1H-indol-3-yl)cyclobutanecarboxamide | 401.2 |
| 110 | 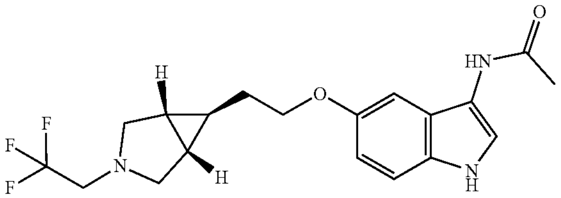 [SMILES: CC(=O)Nc1c[nH]c2ccc(OCC[C@@H]3[C@H]4CN(CC(F)(F)F)C[C@@H]34)cc12] N-(5-(2-((1R,5S,6s)-3-(2,2,2-trifluoroethyl)-3-azabicyclo[3.1.0]hexan-6-yl)ethoxy)-1H-indol-3-yl)acetamide | 382.2 |
| 111 | 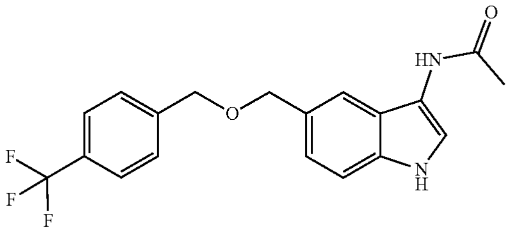 [SMILES: CC(=O)Nc1c[nH]c2ccc(COCc3ccc(C(F)(F)F)cc3)cc12] N-(5-(((4-(trifluoromethyl)benzyl)oxy)methyl)-1H-indol-3-yl)acetamide | 363.1 |
| 112 | 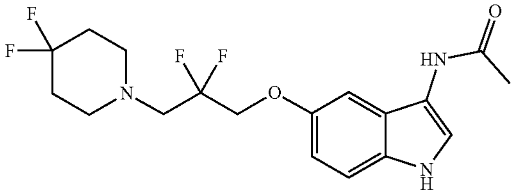 [SMILES: CC(=O)Nc1c[nH]c2ccc(OCC(F)(F)CN3CCC(F)(F)CC3)cc12] N-(5-(3-(4,4-difluoropiperidin-1-yl)-2,2-difluoropropoxy)-1H-indol-3-yl)acetamide | 388.3 |

TABLE C1-continued
| Compound No. | Structure | LC-MS |
|---|---|---|
| 113 | 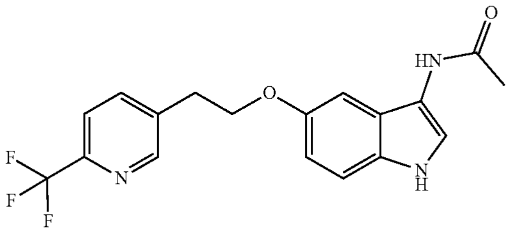 [SMILES: CC(=O)Nc1c[nH]c2ccc(OCCc3ccc(C(F)(F)F)nc3)cc12] N-(5-(2-(6-(trifluoromethyl)pyridin-3-yl)ethoxy)-1H-indol-3-yl)acetamide | 364.1 |
| 114 | 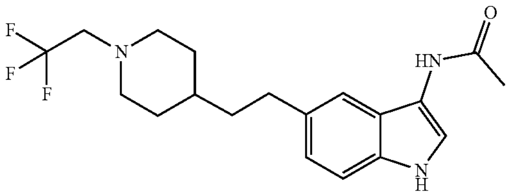 [SMILES: CC(=O)Nc1c[nH]c2ccc(CCC3CCN(CC(F)(F)F)CC3)cc12] N-(5-(2-(1-(2,2,2-trifluoroethyl)piperidin-4-yl)ethyl)-1H-indol-3-yl)acetamide | 368.1 |
| 115 | 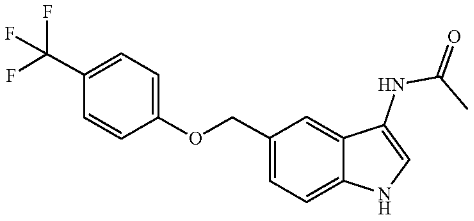 [SMILES: CC(=O)Nc1c[nH]c2ccc(COc3ccc(C(F)(F)F)cc3)cc12] N-(5-((4-(trifluoromethyl)phenoxy)methyl)-1H-indol-3-yl)acetamide | 347.15 |
| 116 | 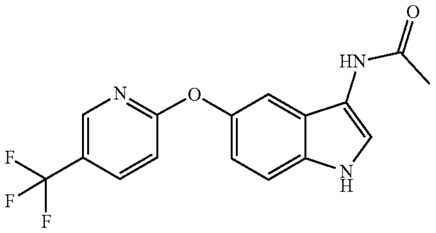 [SMILES: CC(=O)Nc1c[nH]c2ccc(Oc3ccc(C(F)(F)F)cn3)cc12] N-(5-((5-(trifluoromethyl)pyridin-2-yl)oxy)-1H-indol-3-yl)acetamide | 336.05 |
| 117 | 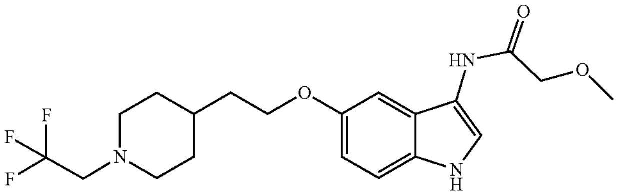 [SMILES: COCC(=O)Nc1c[nH]c2ccc(OCCC3CCN(CC(F)(F)F)CC3)cc12] 2-methoxy-N-(5-(2-(1-(2,2,2-trifluoroethyl)piperidin-4-yl)ethoxy)-1H-indol-3-yl)acetamide | 414.1 |

TABLE C1-continued

| Compound No. | Structure | LC-MS |
|---|---|---|
| 118 | 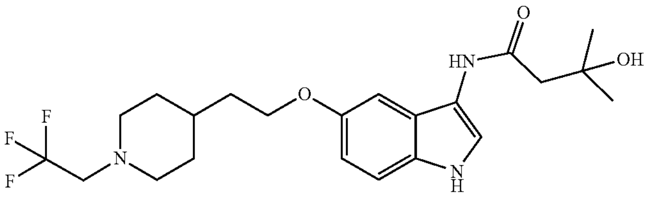 [SMILES: CC(C)(O)CC(=O)Nc1c[nH]c2ccc(OCCC3CCN(CC(F)(F)F)CC3)cc12] 3-hydroxy-3-methyl-N-(5-(2-(1-(2,2,2-trifluoroethyl)piperidin-4-yl)ethoxy)-1H-indol-3-yl)butanamide | 442.3 |
| 119 | 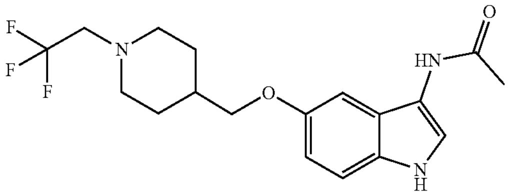 [SMILES: CC(=O)Nc1c[nH]c2ccc(OCC3CCN(CC(F)(F)F)CC3)cc12] N-(5-((1-(2,2,2-trifluoroethyl)piperidin-4-yl)methoxy)-1H-indol-3-yl)acetamide | 370.3 |
| 120 | 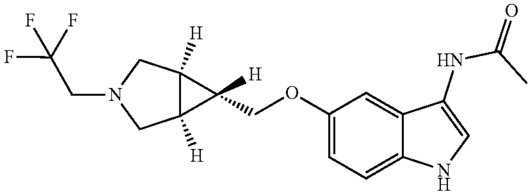 [SMILES: CC(=O)Nc1c[nH]c2ccc(OC[C@@H]3[C@H]4CN(CC(F)(F)F)C[C@@H]34)cc12] N-(5-(((1R,5S,6r)-3-(2,2,2-trifluoroethyl)-3-azabicyclo[3.1.0]hexan-6-yl)methoxy)-1H-indol-3-yl)acetamide | 368.3 |
| 121 | 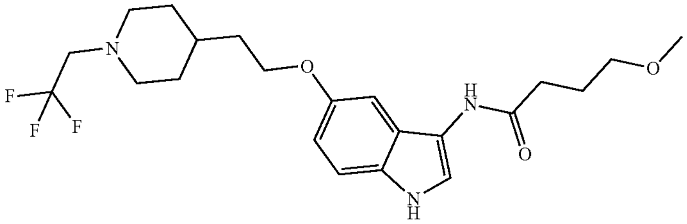 [SMILES: COCCCC(=O)Nc1c[nH]c2ccc(OCCC3CCN(CC(F)(F)F)CC3)cc12] 4-methoxy-N-(5-(2-(1-(2,2,2-trifluoroethyl)piperidin-4-yl)ethoxy)-1H-indol-3-yl)butanamide | 442.2 |
| 122 | 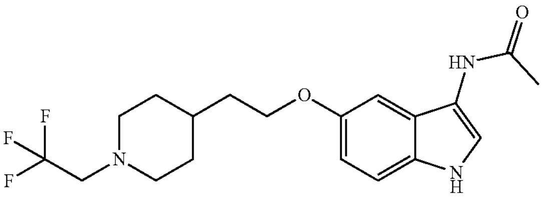 [SMILES: CC(=O)Nc1c[nH]c2ccc(OCCC3CCN(CC(F)(F)F)CC3)cc12] N-(5-(2-(1-(2,2,2-trifluoroethyl)piperidin-4-yl)ethoxy)-1H-indol-3-yl)acetamide | 384.1 |

TABLE C1-continued
| Compound No. | Structure | LC-MS |
|---|---|---|
| 123 | 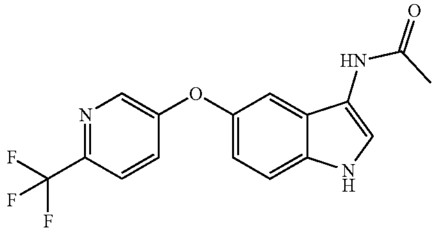 [SMILES: CC(=O)Nc1c[nH]c2ccc(Oc3ccc(C(F)(F)F)nc3)cc12] N-(5-((6-(trifluoromethyl)pyridin-3-yl)oxy)-1H-indol-3-yl)acetamide | 336.0 |
| 124 | 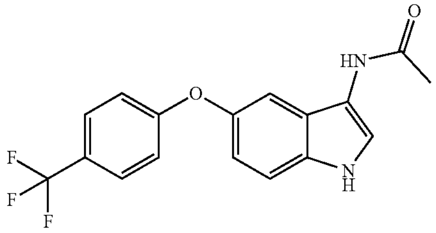 [SMILES: CC(=O)Nc1c[nH]c2ccc(Oc3ccc(C(F)(F)F)cc3)cc12] N-(5-(4-(trifluoromethyl)phenoxy)-1H-indol-3-yl)acetamide | 335.2 |
| 125 | 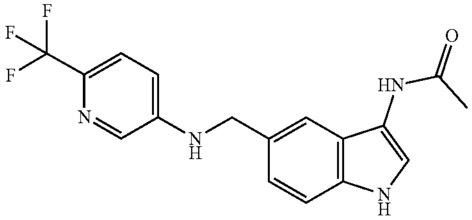 [SMILES: CC(=O)Nc1c[nH]c2ccc(CNc3ccc(C(F)(F)F)nc3)cc12] N-(5-(((6-(trifluoromethyl)pyridin-3-yl)amino)methyl)-1H-indol-3-yl)acetamide | 349.0 |
| 126 | 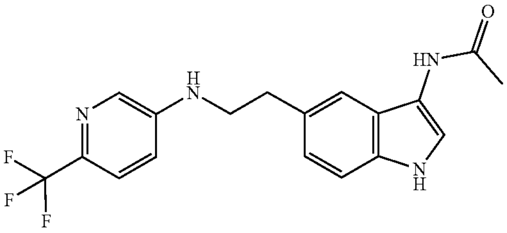 [SMILES: CC(=O)Nc1c[nH]c2ccc(CCNc3ccc(C(F)(F)F)nc3)cc12] N-(5-(2-((6-(trifluoromethyl)pyridin-3-yl)amino)ethyl)-1H-indol-3-yl)acetamide | 363.1 |
| 127 | 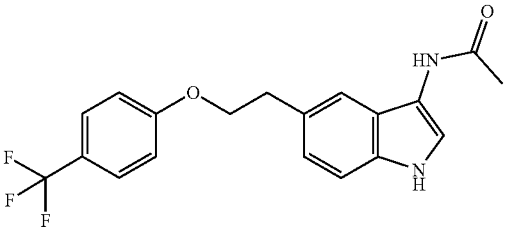 [SMILES: CC(=O)Nc1c[nH]c2ccc(CCOc3ccc(C(F)(F)F)cc3)cc12] N-(5-(2-(4-(trifluoromethyl)phenoxy)ethyl)-1H-indol-3-yl)acetamide | 363.1 |

TABLE C1-continued
| Compound No. | Structure | LC-MS |
|---|---|---|
| 128 | 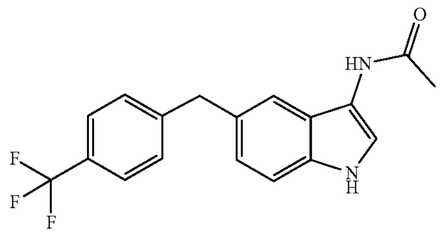 [SMILES: CC(=O)Nc1c[nH]c2ccc(Cc3ccc(C(F)(F)F)cc3)cc12] N-(5-(4-(trifluoromethyl)benzyl)-1H-indol-3-yl)acetamide | 333.1 |
| 129 | 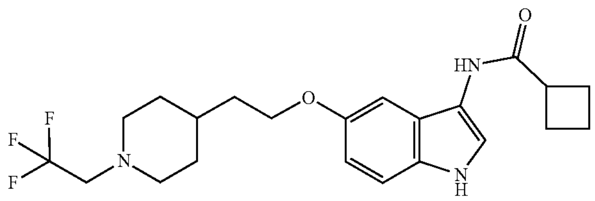 [SMILES: O=C(Nc1c[nH]c2ccc(OCCC3CCN(CC(F)(F)F)CC3)cc12)C1CCC1] N-(5-(2-(1-(2,2,2-trifluoroethyl)piperidin-4-yl)ethoxy)-1H-indol-3-yl)cyclobutanecarboxamide | 424.1 |
| 130 | 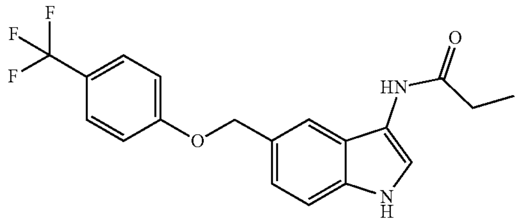 [SMILES: CCC(=O)Nc1c[nH]c2ccc(COc3ccc(C(F)(F)F)cc3)cc12] N-(5-((4-(trifluoromethyl)phenoxy)methyl)-1H-indol-3-yl)propionamide | 361.1 |
| 131 | 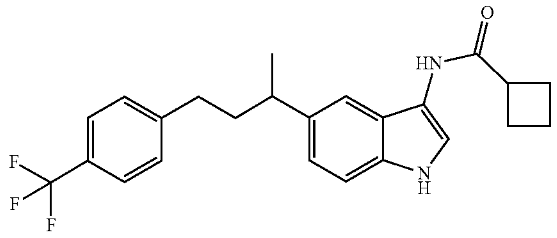 [SMILES: CC(CCc1ccc(C(F)(F)F)cc1)c1ccc2[nH]cc(NC(=O)C3CCC3)c2c1] N-(5-(4-(4-(trifluoromethyl)phenyl)butan-2-yl)-1H-indol-3-yl)cyclobutanecarboxamide | 415.2 |
| 132 | 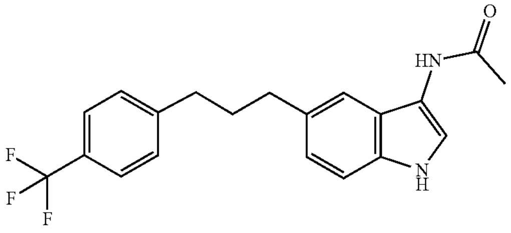 [SMILES: CC(=O)Nc1c[nH]c2ccc(CCCc3ccc(C(F)(F)F)cc3)cc12] N-(5-(3-(4-(trifluoromethyl)phenyl)propyl)-1H-indol-3-yl)acetamide | 359.1 |

TABLE C1-continued
| Compound No. | Structure | LC-MS |
|---|---|---|
| 133 | 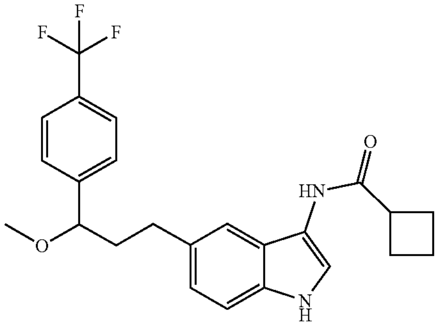 [SMILES: COC(CCc1ccc2[nH]cc(NC(=O)C3CCC3)c2c1)c1ccc(C(F)(F)F)cc1] N-(5-(3-methoxy-3-(4-(trifluoromethyl)phenyl)propyl)-1H-indol-3-yl)cyclobutanecarboxamide | 431.2 |
| 134 | 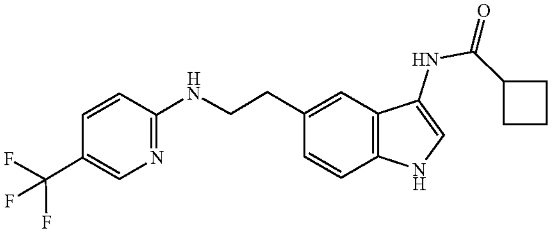 [SMILES: O=C(Nc1c[nH]c2ccc(CCNc3ccc(C(F)(F)F)cn3)cc12)C1CCC1] N-(5-(2-((5-(trifluoromethyl)pyridin-2-yl)amino)ethyl)-1H-indol-3-yl)cyclobutanecarboxamide | 403.2 |
| 135 | 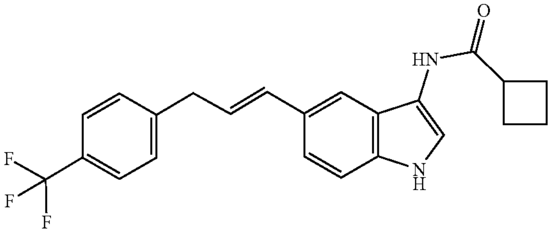 [SMILES: O=C(Nc1c[nH]c2ccc(/C=C/Cc3ccc(C(F)(F)F)cc3)cc12)C1CCC1] (E)-N-(5-(3-(4-(trifluoromethyl)phenyl)prop-1-en-1-yl)-1H-indol-3-yl)cyclobutanecarboxamide | 399.2 |
| 136 | 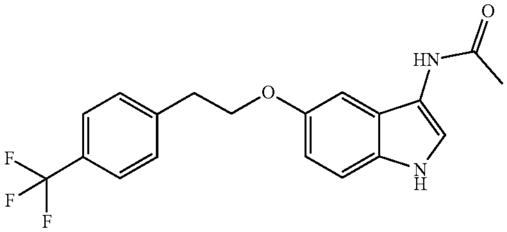 [SMILES: CC(=O)Nc1c[nH]c2ccc(OCCc3ccc(C(F)(F)F)cc3)cc12] N-(5-(4-(trifluoromethyl)phenethoxy)-1H-indol-3-yl)acetamide | 363.1 |
| 137 | 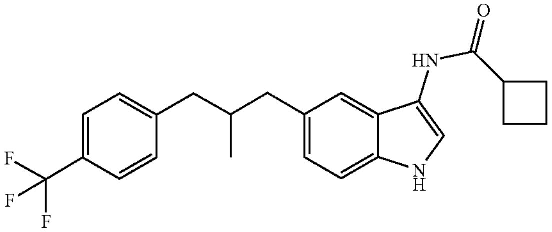 [SMILES: CC(Cc1ccc(C(F)(F)F)cc1)Cc1ccc2[nH]cc(NC(=O)C3CCC3)c2c1] | 415.1 |

TABLE C1-continued

| Compound No. | Structure | LC-MS |
|---|---|---|
| | N-(5-(2-methyl-3-(4-(trifluoromethyl)phenyl)propyl)-1H-indol-3-yl)cyclobutanecarboxamide | |
| 138 | 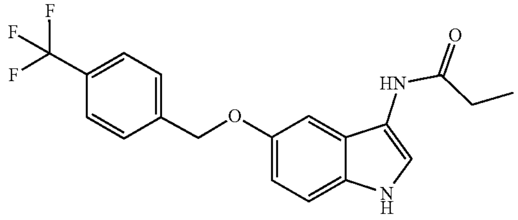 N-(5-((4-(trifluoromethyl)benzyl)oxy)-1H-indol-3-yl)propionamide | 363.1 |
| 139 | 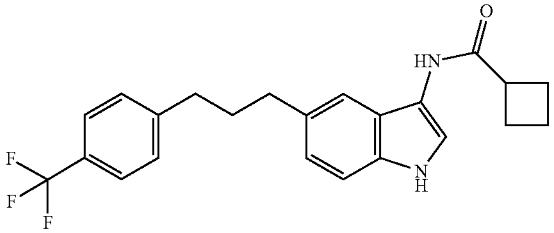 [SMILES: O=C(Nc1c[nH]c2ccc(CCCc3ccc(C(F)(F)F)cc3)cc12)C1CCC1] N-(5-(3-(4-(trifluoromethyl)phenyl)propyl)-1H-indol-3-yl)cyclobutanecarboxamide | 401.2 |
| 140 | 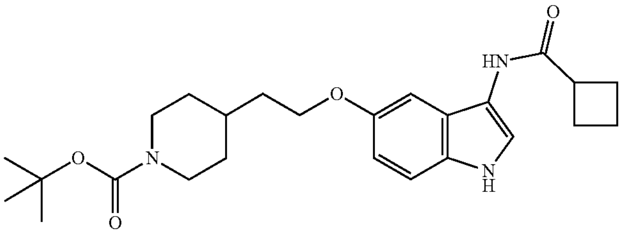 [SMILES: CC(C)(C)OC(=O)N1CCC(CCOc2ccc3[nH]cc(NC(=O)C4CCC4)c3c2)CC1] tert-butyl 4-(2-((3-(cyclobutanecarboxamido)-1H-indol-5-yl)oxy)ethyl)piperidine-1-carboxylate | 440.2 |
| 141 | 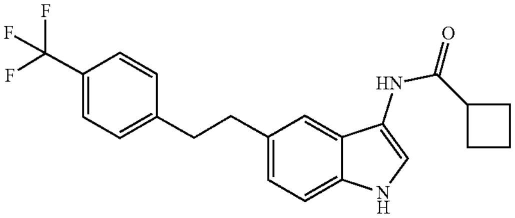 [SMILES: O=C(Nc1c[nH]c2ccc(CCc3ccc(C(F)(F)F)cc3)cc12)C1CCC1] N-(5-(4-(trifluoromethyl)phenethyl)-1H-indol-3-yl)cyclobutanecarboxamide | 385.2 |
| 142 | 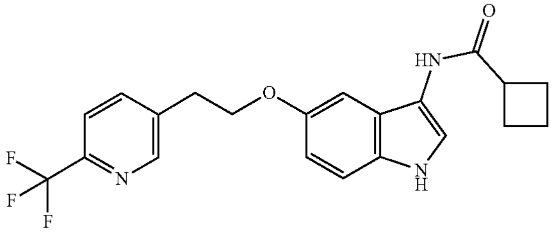 [SMILES: O=C(Nc1c[nH]c2ccc(OCCc3ccc(C(F)(F)F)nc3)cc12)C1CCC1] N-(5-(2-(6-(trifluoromethyl)pyridin-3-yl)ethoxy)-1H-indol-3-yl)cyclobutanecarboxamide | 404.1 |

TABLE C1-continued

| Compound No. | Structure | LC-MS |
|---|---|---|
| 143 | 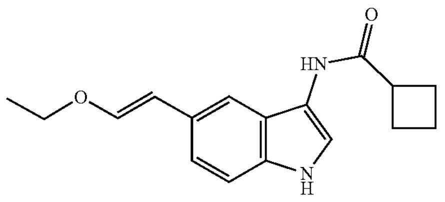 [SMILES: CCO/C=C/c1ccc2[nH]cc(NC(=O)C3CCC3)c2c1] (E)-N-(5-(2-ethoxyvinyl)-1H-indol-3-yl)cyclobutanecarboxamide | 285.2 |
| 144 | 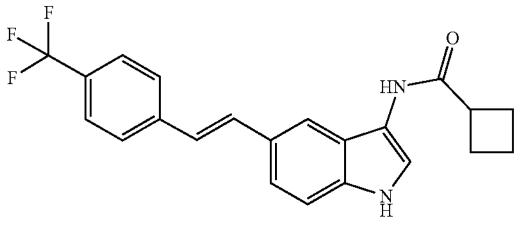 [SMILES: O=C(Nc1c[nH]c2ccc(/C=C/c3ccc(C(F)(F)F)cc3)cc12)C1CCC1] (E)-N-(5-(4-(trifluoromethyl)styryl)-1H-indol-3-yl)cyclobutanecarboxamide | 385.2 |
| 145 | 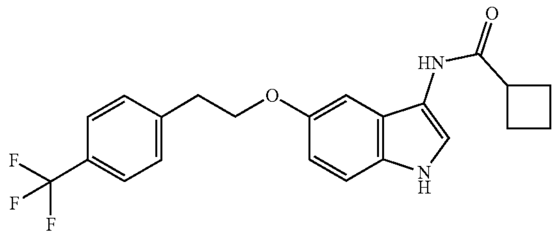 [SMILES: O=C(Nc1c[nH]c2ccc(OCCc3ccc(C(F)(F)F)cc3)cc12)C1CCC1] N-(5-(2-(4-(trifluoromethyl)phenoxy)ethyl)-1H-indol-3-yl)cyclobutanecarboxamide | 403.1 |
| 146 | 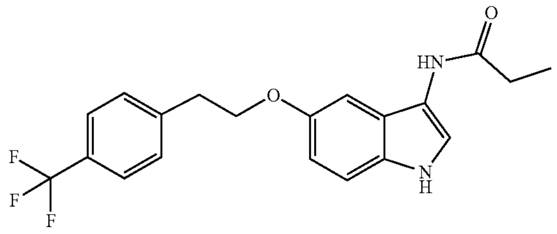 [SMILES: CCC(=O)Nc1c[nH]c2ccc(OCCc3ccc(C(F)(F)F)cc3)cc12] N-(5-(4-(trifluoromethyl)phenethoxy)-1H-indol-3-yl)propionamide | 377.1 |
| 147 | 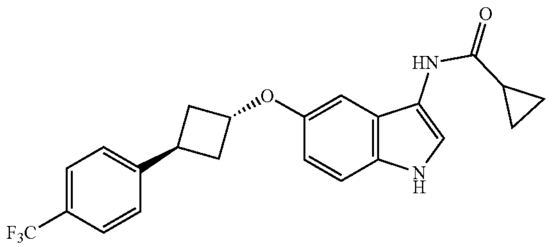 [SMILES: O=C(Nc1c[nH]c2ccc(O[C@H]3C[C@H](c4ccc(C(F)(F)F)cc4)C3)cc12)C1CC1] trans-N-(5-(-3-(4-(trifluoromethyl)phenyl)cyclobutoxy)-1H-indol-3-yl)cyclopropanecarboxamide | 415.1 |

TABLE C1-continued

| Compound No. | Structure | LC-MS |
|---|---|---|
| 148 | 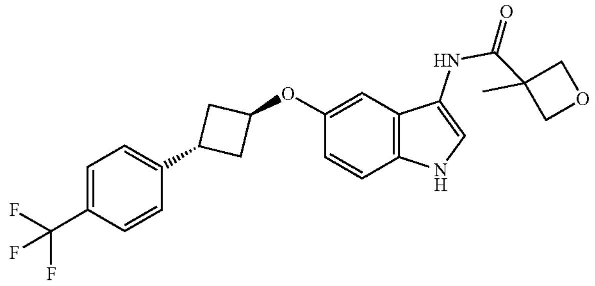 [SMILES: CC1(C(=O)Nc2c[nH]c3ccc(O[C@H]4C[C@H](c5ccc(C(F)(F)F)cc5)C4)cc23)COC1] 3-methyl-N-(5-(trans-3-(4-(trifluoromethyl)phenyl)cyclobutoxy)-1H-indol-3-yl)oxetane-3-carboxamide | 445.3 |
| 149 | 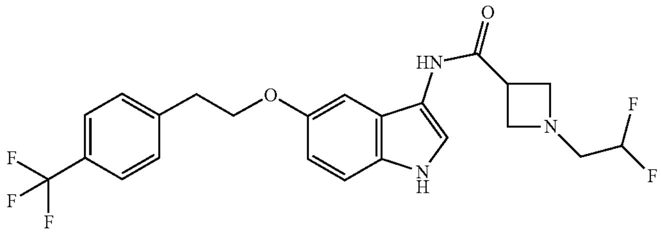 [SMILES: O=C(Nc1c[nH]c2ccc(OCCc3ccc(C(F)(F)F)cc3)cc12)C1CN(CC(F)F)C1] 1-(2,2-difluoroethyl)-N-(5-(4-(trifluoromethyl)phenethoxy)-1H-indol-3-yl)azetidine-3-carboxamide | 466.1 |
| 150 | 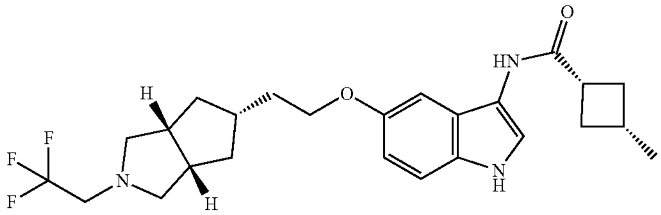 [SMILES: C[C@H]1C[C@@H](C(=O)Nc2c[nH]c3ccc(OCC[C@@H]4C[C@@H]5CN(CC(F)(F)F)C[C@@H]5C4)cc23)C1] (1s,3S)-3-methyl-N-(5-(2-((3aR,5r,6aS)-2-(2,2,2-trifluoroethyl)octahydrocyclopenta[c]pyrrol-5-yl)ethoxy)-1H-indol-3-yl)cyclobutane-1-carboxamide | 464.4 |
| 151 | 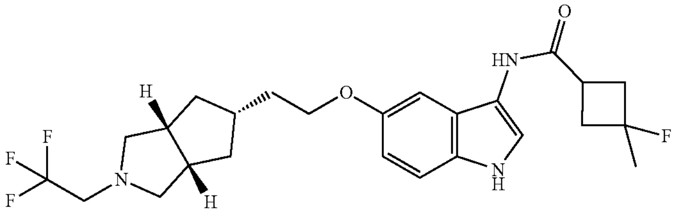 [SMILES: CC1(F)CC(C(=O)Nc2c[nH]c3ccc(OCC[C@@H]4C[C@@H]5CN(CC(F)(F)F)C[C@@H]5C4)cc23)C1] 3-fluoro-3-methyl-N-(5-(2-((3aR,5r,6aS)-2-(2,2,2-trifluoroethyl)octahydrocyclopenta[c]pyrrol-5-yl)ethoxy)-1H-indol-3-yl)cyclobutane-1-carboxamide | 482.1 |
| 152 | 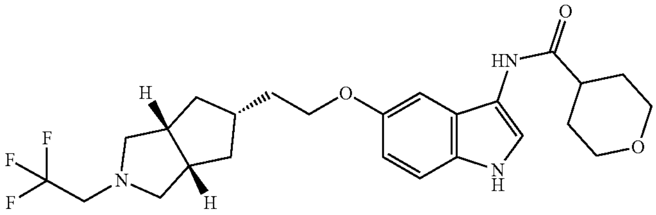 [SMILES: O=C(Nc1c[nH]c2ccc(OCC[C@@H]3C[C@@H]4CN(CC(F)(F)F)C[C@@H]4C3)cc12)C1CCOCC1] | 480.1 |

TABLE C1-continued

| Compound No. | Structure | LC-MS |
|---|---|---|
| | N-(5-(2-((3aR,5r,6aS)-2-(2,2,2-trifluoroethyl)octahydrocyclopenta[c]pyrrol-5-yl)ethoxy)-1H-indol-3-yl)tetrahydro-2H-pyran-4-carboxamide | |
| 153 | 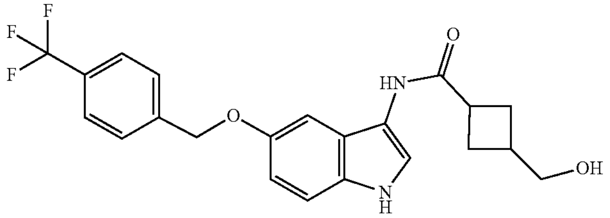 [SMILES: O=C(Nc1c[nH]c2ccc(OCc3ccc(C(F)(F)F)cc3)cc12)C1CC(CO)C1] 3-(hydroxymethyl)-N-(5-((4-(trifluoromethyl)benzyl)oxy)-1H-indol-3-yl)cyclobutane-1-carboxamide | 419.3 |
| 154 | 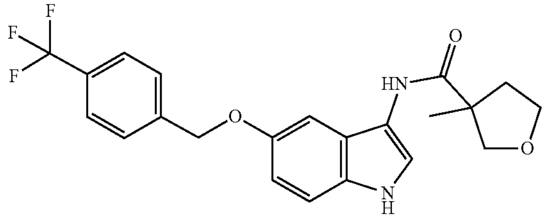 [SMILES: CC1(C(=O)Nc2c[nH]c3ccc(OCc4ccc(C(F)(F)F)cc4)cc23)CCOC1] 3-methyl-N-(5-((4-(trifluoromethyl)benzyl)oxy)-1H-indol-3-yl)tetrahydrofuran-3-carboxamide | 419.3 |
| 155 | 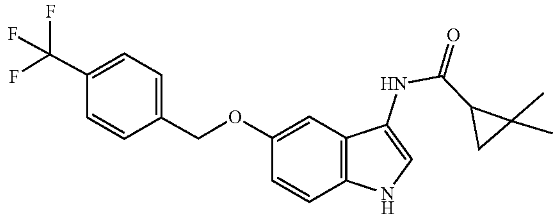 [SMILES: CC1(C)CC1C(=O)Nc1c[nH]c2ccc(OCc3ccc(C(F)(F)F)cc3)cc12] 2,2-dimethyl-N-(5-((4-(trifluoromethyl)benzyl)oxy)-1H-indol-3-yl)cyclopropane-1-carboxamide | 403.3 |
| 156 | 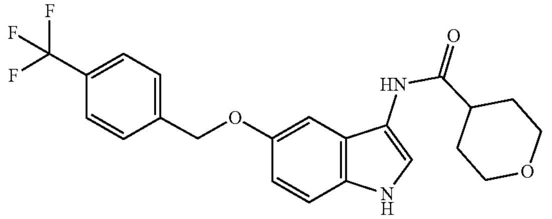 [SMILES: O=C(Nc1c[nH]c2ccc(OCc3ccc(C(F)(F)F)cc3)cc12)C1CCOCC1] N-(5-((4-(trifluoromethyl)benzyl)oxy)-1H-indol-3-yl)tetrahydro-2H-pyran-4-carboxamide | 419.3 |
| 157 | 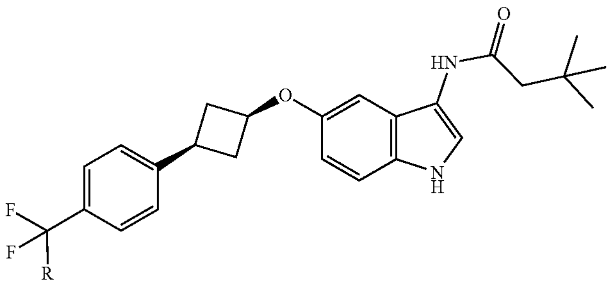 | 445.4 |

TABLE C1-continued

| Compound No. | Structure | LC-MS |
|---|---|---|
| | 3,3-dimethyl-N-(5-(cis-3-(4-(trifluoromethyl)phenyl)cyclobutoxy)-1H-indol-3-yl)butanamide | |
| 158 | 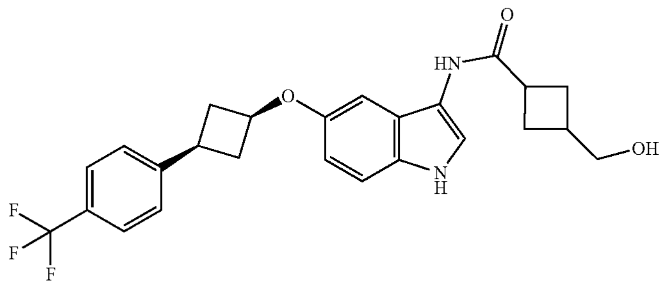 [SMILES: O=C(Nc1c[nH]c2ccc(O[C@H]3C[C@@H](c4ccc(C(F)(F)F)cc4)C3)cc12)C1CC(CO)C1] 3-(hydroxymethyl)-N-(5-(cis-3-(4-(trifluoromethyl)phenyl)cyclobutoxy)-1H-indol-3-yl)cyclobutane-1-carboxamide | 459.3 |
| 159 | 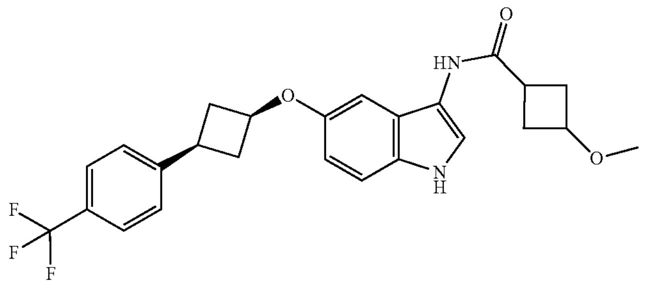 [SMILES: COC1CC(C(=O)Nc2c[nH]c3ccc(O[C@H]4C[C@@H](c5ccc(C(F)(F)F)cc5)C4)cc23)C1] 3-methoxy-N-(5-(cis-3-(4-(trifluoromethyl)phenyl)cyclobutoxy)-1H-indol-3-yl)cyclobutane-1-carboxamide | 459.3 |
| 160 | 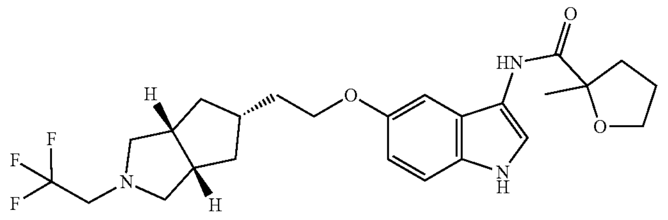 [SMILES: CC1(C(=O)Nc2c[nH]c3ccc(OCC[C@@H]4C[C@@H]5CN(CC(F)(F)F)C[C@@H]5C4)cc23)CCCO1] 2-methyl-N-(5-(2-((3aR,5r,6aS)-2-(2,2,2-trifluoroethyl)octahydrocyclopenta[c]pyrrol-5-yl)ethoxy)-1H-indol-3-yl)tetrahydrofuran-2-carboxamide | 480.3 |
| 161 | 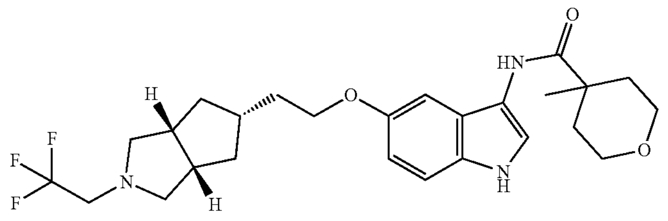 [SMILES: CC1(C(=O)Nc2c[nH]c3ccc(OCC[C@@H]4C[C@@H]5CN(CC(F)(F)F)C[C@@H]5C4)cc23)CCOCC1] 4-methyl-N-(5-(2-((3aR,5r,6aS)-2-(2,2,2-trifluoroethyl)octahydrocyclopenta[c]pyrrol-5-yl)ethoxy)-1H-indol-3-yl)tetrahydro-2H-pyran-4-carboxamide | 494.4 |

TABLE C1-continued

| Compound No. | Structure | LC-MS |
|---|---|---|
| 162 | 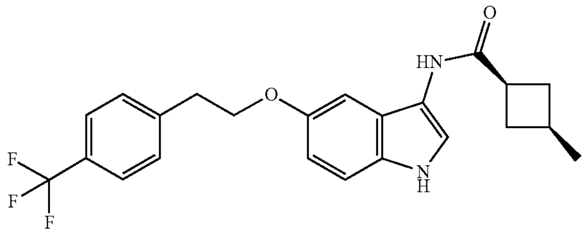 [SMILES: C[C@H]1C[C@@H](C(=O)Nc2c[nH]c3ccc(OCCc4ccc(C(F)(F)F)cc4)cc23)C1]<br>cis-3-methyl-N-(5-(4-(trifluoromethyl)phenethoxy)-1H-indol-3-yl)cyclobutane-1-carboxamide | 417.3 |
| 163 | 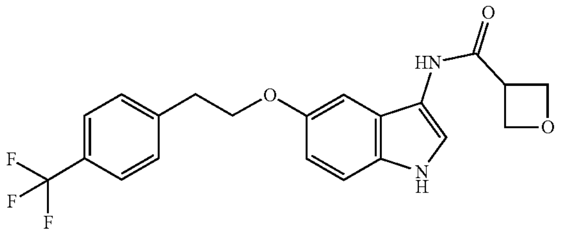 [SMILES: O=C(Nc1c[nH]c2ccc(OCCc3ccc(C(F)(F)F)cc3)cc12)C1COC1]<br>N-(5-(4-(trifluoromethyl)phenethoxy)-1H-indol-3-yl)oxetane-3-carboxamide | 405.2 |
| 164 | 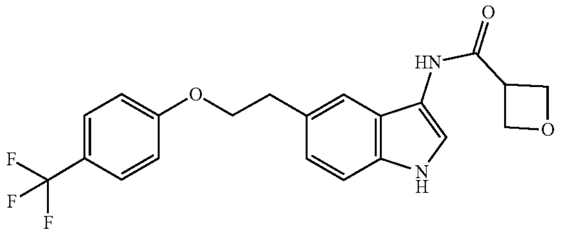 [SMILES: O=C(Nc1c[nH]c2ccc(CCOc3ccc(C(F)(F)F)cc3)cc12)C1COC1]<br>N-(5-(2-(4-(trifluoromethyl)phenoxy)ethyl)-1H-indol-3-yl)oxetane-3-carboxamide | 403.05 |
| 165 | 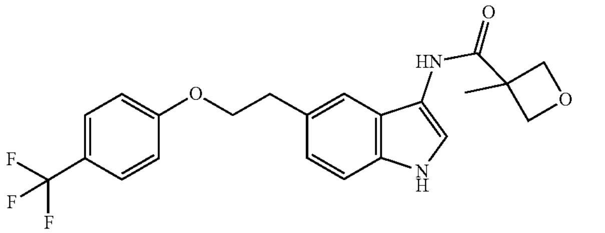 [SMILES: CC1(C(=O)Nc2c[nH]c3ccc(CCOc4ccc(C(F)(F)F)cc4)cc23)COC1]<br>3-methyl-N-(5-(2-(4-(trifluoromethyl)phenoxy)ethyl)-1H-indol-3-yl)oxetane-3-carboxamide | 417.1 |
| 166 | 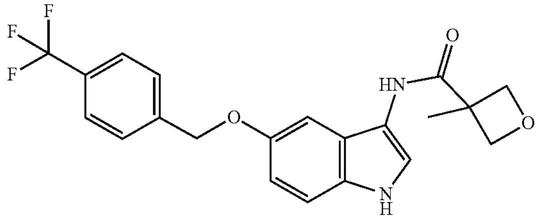 [SMILES: CC1(C(=O)Nc2c[nH]c3ccc(OCc4ccc(C(F)(F)F)cc4)cc23)COC1]<br>3-methyl-N-(5-((4-(trifluoromethyl)benzyl)oxy)-1H-indol-3-yl)oxetane-3-carboxamide | 405.1 |

TABLE C1-continued
| Compound No. | Structure | LC-MS |
| --- | --- | --- |
| 167 | 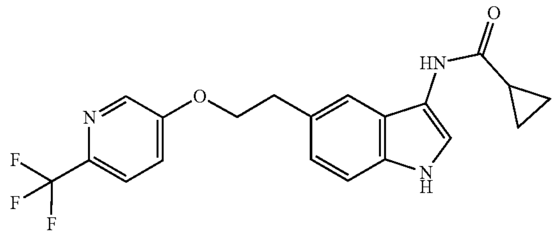 [SMILES: O=C(Nc1c[nH]c2ccc(CCOc3ccc(C(F)(F)F)nc3)cc12)C1CC1] N-(5-(2-((6-(trifluoromethyl)pyridin-3-yl)oxy)ethyl)-1H-indol-3-yl)cyclopropanecarboxamide | 390.1 |
| 168 | 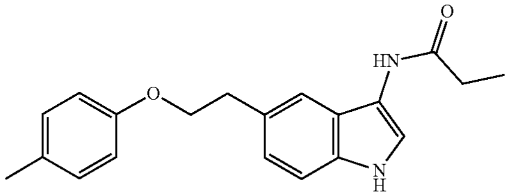 [SMILES: CCC(=O)Nc1c[nH]c2ccc(CCOc3ccc(C)cc3)cc12] N-(5-(2-(p-tolyloxy)ethyl)-1H-indol-3-yl)propionamide | 323.15 |
| 169 | 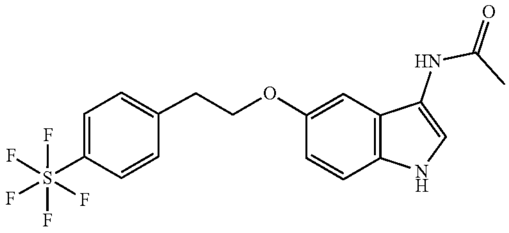 [SMILES: CC(=O)Nc1c[nH]c2ccc(OCCc3ccc(S(F)(F)(F)(F)F)cc3)cc12] N-(5-(4-(pentafluoro-16-sulfaneyl)phenethoxy)-1H-indol-3-yl)acetamide | 419.05 |
| 170 | 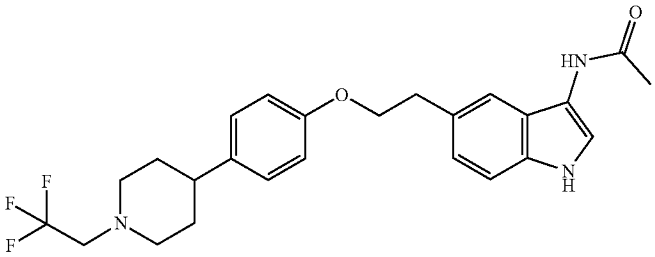 [SMILES: CC(=O)Nc1c[nH]c2ccc(CCOc3ccc(C4CCN(CC(F)(F)F)CC4)cc3)cc12] N-(5-(2-(4-(1-(2,2,2-trifluoroethyl)piperidin-4-yl)phenoxy)ethyl)-1H-indol-3-yl)acetamide | 460.25 |
| 171 | 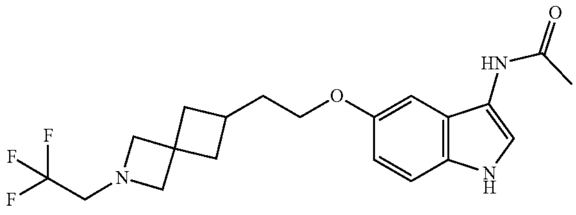 [SMILES: CC(=O)Nc1c[nH]c2ccc(OCCC3CC4(C3)CN(CC(F)(F)F)C4)cc12] N-(5-(2-(2-(2,2,2-trifluoroethyl)-2-azaspiro[3.3]heptan-6-yl)ethoxy)-1H-indol-3-yl)acetamide | 396.3 |

TABLE C1-continued

| Compound No. | Structure | LC-MS |
|---|---|---|
| 172 | 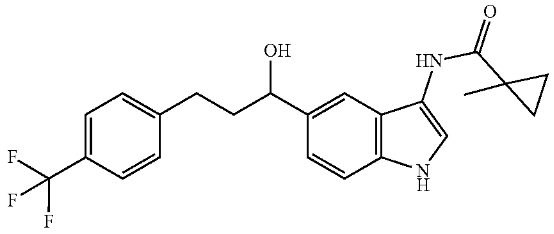 [SMILES: CC1(C(=O)Nc2c[nH]c3ccc(C(O)CCc4ccc(C(F)(F)F)cc4)cc23)CC1]<br>N-(5-(1-hydroxy-3-(4-(trifluoromethyl)phenyl)propyl)-1H-indol-3-yl)-1-methylcyclopropane-1-carboxamide | 417.1 |
| 173 | 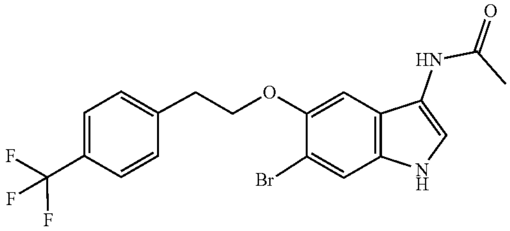 [SMILES: CC(=O)Nc1c[nH]c2cc(Br)c(OCCc3ccc(C(F)(F)F)cc3)cc12]<br>N-(6-bromo-5-(4-(trifluoromethyl)phenethoxy)-1H-indol-3-yl)acetamide | 440.95 |
| 174 | 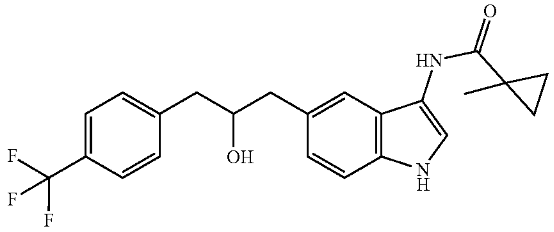 [SMILES: CC1(C(=O)Nc2c[nH]c3ccc(CC(O)Cc4ccc(C(F)(F)F)cc4)cc23)CC1]<br>N-(5-(2-hydroxy-3-(4-(trifluoromethyl)phenyl)propyl)-1H-indol-3-yl)-1-methylcyclopropane-1-carboxamide | 417.05 |
| 175 | 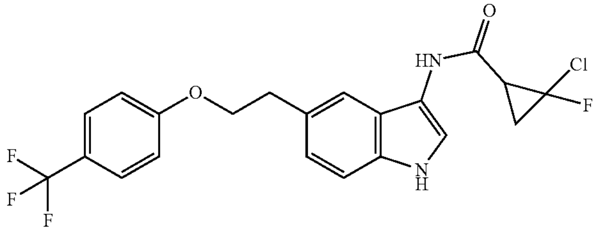 [SMILES: O=C(Nc1c[nH]c2ccc(CCOc3ccc(C(F)(F)F)cc3)cc12)C1CC1(F)Cl]<br>2-chloro-2-fluoro-N-(5-(2-(4-(trifluoromethyl)phenoxy)ethyl)-1H-indol-3-yl)cyclopropane-1-carboxamide | 441.1 |
| 176 | 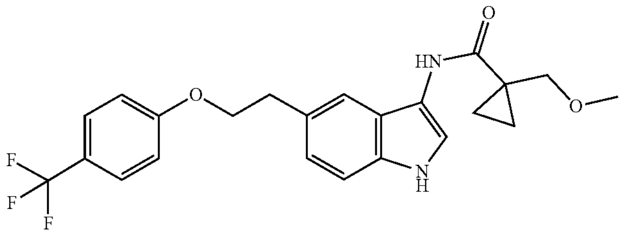 [SMILES: COCC1(C(=O)Nc2c[nH]c3ccc(CCOc4ccc(C(F)(F)F)cc4)cc23)CC1]<br>1-(methoxymethyl)-N-(5-(2-(4-(trifluoromethyl)phenoxy)ethyl)-1H-indol-3-yl)cyclopropane-1-carboxamide | 433.2 |

TABLE C1-continued

| Compound No. | Structure | LC-MS |
|---|---|---|
| 177 | 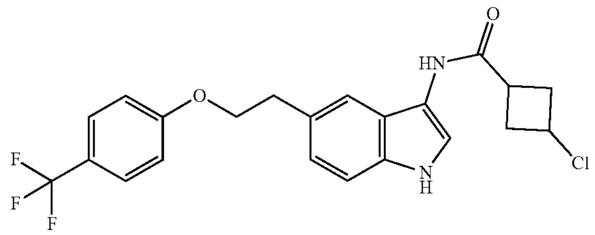 [SMILES: O=C(Nc1c[nH]c2ccc(CCOc3ccc(C(F)(F)F)cc3)cc12)C1CC(Cl)C1] 3-chloro-N-(5-(2-(4-(trifluoromethyl)phenoxy)ethyl)-1H-indol-3-yl)cyclobutane-1-carboxamide | 437.2 |
| 178 | 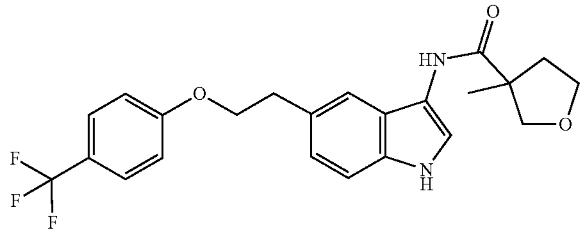 [SMILES: CC1(C(=O)Nc2c[nH]c3ccc(CCOc4ccc(C(F)(F)F)cc4)cc23)CCOC1] 3-methyl-N-(5-(2-(4-(trifluoromethyl)phenoxy)ethyl)-1H-indol-3-yl)tetrahydrofuran-3-carboxamide | 433.3 |
| 179 | 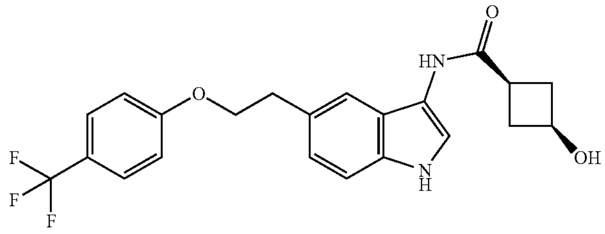 [SMILES: O=C(Nc1c[nH]c2ccc(CCOc3ccc(C(F)(F)F)cc3)cc12)[C@H]1C[C@@H](O)C1] cis-3-hydroxy-N-(5-(2-(4-(trifluoromethyl)phenoxy)ethyl)-1H-indol-3-yl)cyclobutane-1-carboxamide | 419.2 |
| 180 | 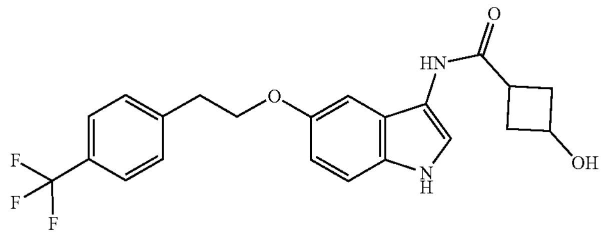 [SMILES: O=C(Nc1c[nH]c2ccc(OCCc3ccc(C(F)(F)F)cc3)cc12)C1CC(O)C1] 3-hydroxy-N-(5-(4-(trifluoromethyl)phenethoxy)-1H-indol-3-yl)cyclobutane-1-carboxamide | 419.2 |
| 181 | 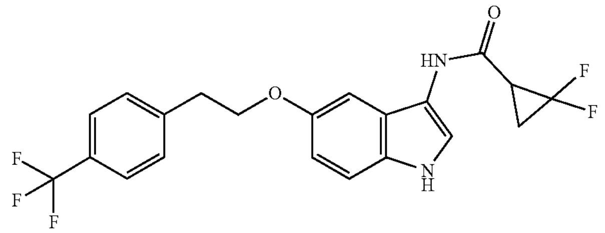 [SMILES: O=C(Nc1c[nH]c2ccc(OCCc3ccc(C(F)(F)F)cc3)cc12)C1CC1(F)F] | 425.2 |

TABLE C1-continued

| Compound No. | Structure | LC-MS |
|---|---|---|
| | 2,2-difluoro-N-(5-(4-(trifluoromethyl)phenethoxy)-1H-indol-3-yl)cyclopropane-1-carboxamide | |
| 182 | 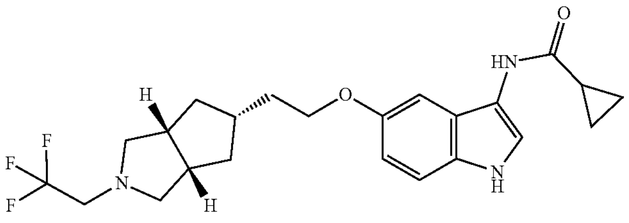 [SMILES: O=C(Nc1c[nH]c2ccc(OCC[C@@H]3C[C@@H]4CN(CC(F)(F)F)C[C@@H]4C3)cc12)C1CC1] N-(5-(2-((3aR,5r,6aS)-2-(2,2,2-trifluoroethyl)octahydrocyclopenta[c]pyrrol-5-yl)ethoxy)-1H-indol-3-yl)cyclopropanecarboxamide | 436.15 |
| 183 | 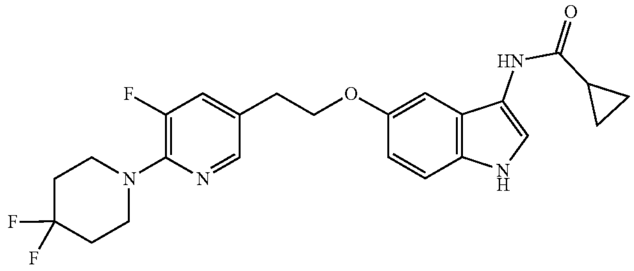 [SMILES: O=C(Nc1c[nH]c2ccc(OCCc3cnc(N4CCC(F)(F)CC4)c(F)c3)cc12)C1CC1] N-(5-(2-(6-(4,4-difluoropiperidin-1-yl)-5-fluoropyridin-3-yl)ethoxy)-1H-indol-3-yl)cyclopropanecarboxamide | 459.2 |
| 184 | 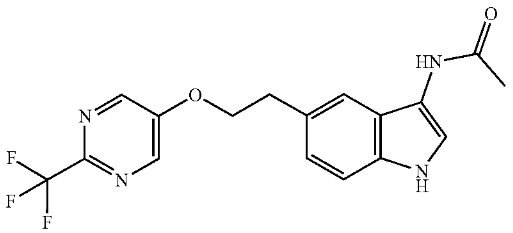 [SMILES: CC(=O)Nc1c[nH]c2ccc(CCOc3cnc(C(F)(F)F)nc3)cc12] N-(5-(2-((2-(trifluoromethyl)pyrimidin-5-yl)oxy)ethyl)-1H-indol-3-yl)acetamide | 364.32 |
| 185 | 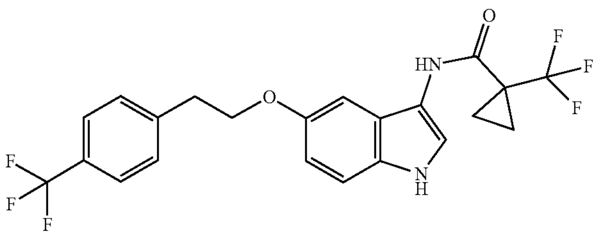 [SMILES: O=C(Nc1c[nH]c2ccc(OCCc3ccc(C(F)(F)F)cc3)cc12)C1(C(F)(F)F)CC1] 1-(trifluoromethyl)-N-(5-(4-(trifluoromethyl)phenethoxy)-1H-indol-3-yl)cyclopropane-1-carboxamide | 457.1 |

TABLE C1-continued

| Compound No. | Structure | LC-MS |
|---|---|---|
| 186 | 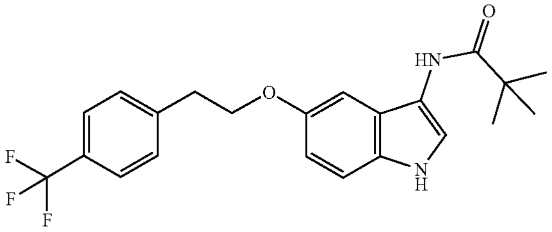 [SMILES: CC(C)(C)C(=O)Nc1c[nH]c2ccc(OCCc3ccc(C(F)(F)F)cc3)cc12] N-(5-(4-(trifluoromethyl)phenethoxy)-1H-indol-3-yl)pivalamide | 405.1 |
| 187 | 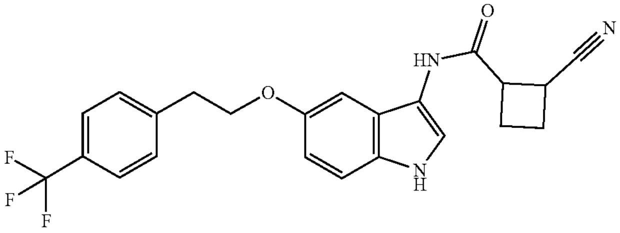 [SMILES: N#CC1CCC1C(=O)Nc1c[nH]c2ccc(OCCc3ccc(C(F)(F)F)cc3)cc12] 2-cyano-N-(5-(4-(trifluoromethyl)phenethoxy)-1H-indol-3-yl)cyclobutane-1-carboxamide | 428.1 |
| 188 | 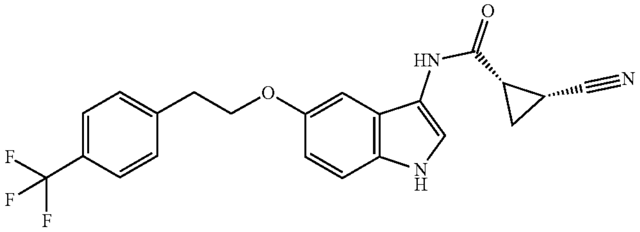 [SMILES: N#C[C@@H]1C[C@@H]1C(=O)Nc1c[nH]c2ccc(OCCc3ccc(C(F)(F)F)cc3)cc12] (1S,2R)-2-cyano-N-(5-(4-(trifluoromethyl)phenethoxy)-1H-indol-3-yl)cyclopropane-1-carboxamide | 414.2 |
| 189 | 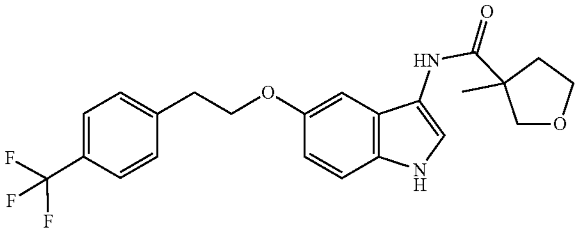 [SMILES: CC1(C(=O)Nc2c[nH]c3ccc(OCCc4ccc(C(F)(F)F)cc4)cc23)CCOC1] 3-methyl-N-(5-(4-(trifluoromethyl)phenethoxy)-1H-indol-3-yl)tetrahydrofuran-3-carboxamide | 433.2 |
| 190 | 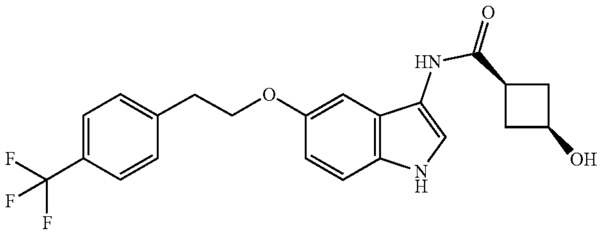 cis-3-hydroxy-N-(5-(4-(trifluoromethyl)phenethoxy)-1H-indol-3-yl)cyclobutane-1-carboxamide | 419.1 |

TABLE C1-continued

| Compound No. | Structure | LC-MS |
|---|---|---|
| 191 | 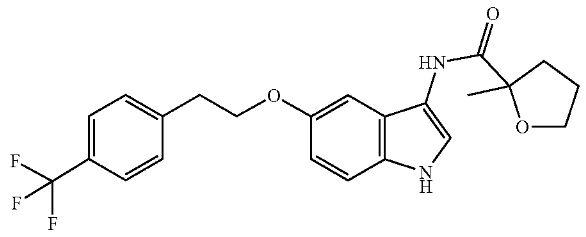 [SMILES: CC1(C(=O)Nc2c[nH]c3ccc(OCCc4ccc(C(F)(F)F)cc4)cc23)CCCO1] 2-methyl-N-(5-(4-(trifluoromethyl)phenethoxy)-1H-indol-3-yl)tetrahydrofuran-2-carboxamide | 433.2 |
| 192 | 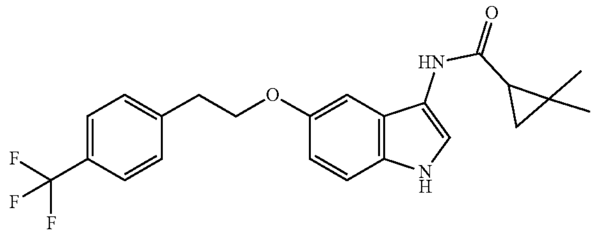 [SMILES: CC1(C)CC1C(=O)Nc1c[nH]c2ccc(OCCc3ccc(C(F)(F)F)cc3)cc12] 2,2-dimethyl-N-(5-(4-(trifluoromethyl)phenethoxy)-1H-indol-3-yl)cyclopropane-1-carboxamide | 417.1 |
| 193 | 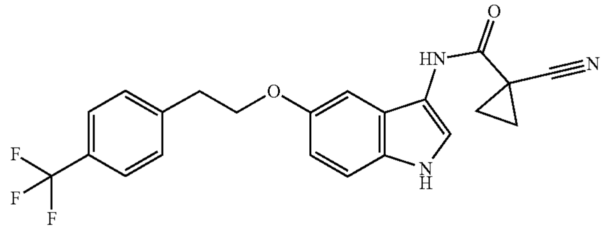 [SMILES: N#CC1(C(=O)Nc2c[nH]c3ccc(OCCc4ccc(C(F)(F)F)cc4)cc23)CC1] 1-cyano-N-(5-(4-(trifluoromethyl)phenethoxy)-1H-indol-3-yl)cyclopropane-1-carboxamide | 414.2 |
| 194 | 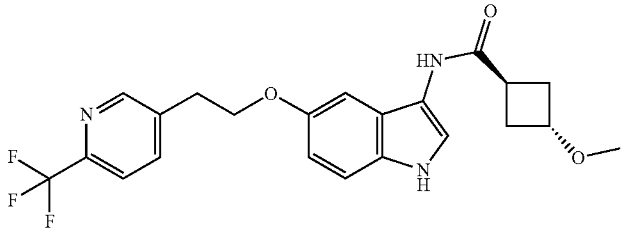 [SMILES: CO[C@H]1C[C@H](C(=O)Nc2c[nH]c3ccc(OCCc4ccc(C(F)(F)F)nc4)cc23)C1] trans-3-methoxy-N-(5-(2-(6-(trifluoromethyl)pyridin-3-yl)ethoxy)-1H-indol-3-yl)cyclobutane-1-carboxamide | 434.0 |
| 195 | 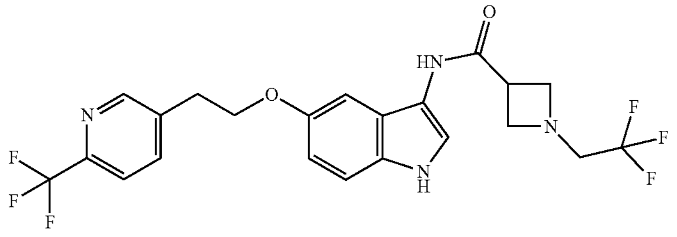 [SMILES: O=C(Nc1c[nH]c2ccc(OCCc3ccc(C(F)(F)F)nc3)cc12)C1CN(CC(F)(F)F)C1] 1-(2,2,2-trifluoroethyl)-N-(5-(2-(6-(trifluoromethyl)pyridin-3-yl)ethoxy)-1H-indol-3-yl)azetidine-3-carboxamide | 487.15 |

TABLE C1-continued

| Compound No. | Structure | LC-MS |
|---|---|---|
| 196 | 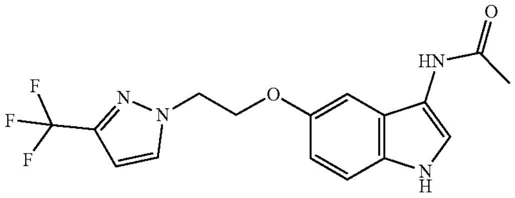 [SMILES: CC(=O)Nc1c[nH]c2ccc(OCCn3ccc(C(F)(F)F)n3)cc12] N-(5-(2-(3-(trifluoromethyl)-1H-pyrazol-1-yl)ethoxy)-1H-indol-3-yl)acetamide | 351.1 |
| 197 | 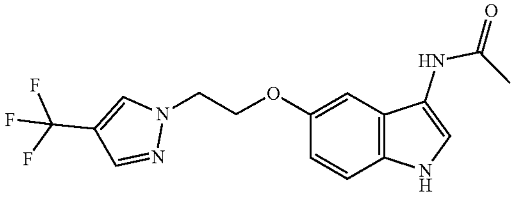 [SMILES: CC(=O)Nc1c[nH]c2ccc(OCCn3cc(C(F)(F)F)cn3)cc12] N-(5-(2-(4-(trifluoromethyl)-1H-pyrazol-1-yl)ethoxy)-1H-indol-3-yl)acetamide | 353.05 |
| 198 | 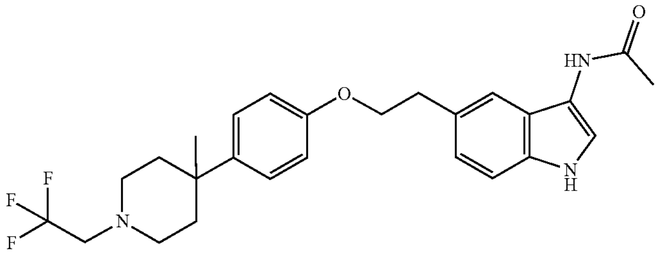 [SMILES: CC(=O)Nc1c[nH]c2ccc(CCOc3ccc(C4(C)CCN(CC(F)(F)F)CC4)cc3)cc12] N-(5-(2-(4-(4-methyl-1-(2,2,2-trifluoroethyl)piperidin-4-yl)phenoxy)ethyl)-1H-indol-3-yl)acetamide | 474.2 |
| 199 | 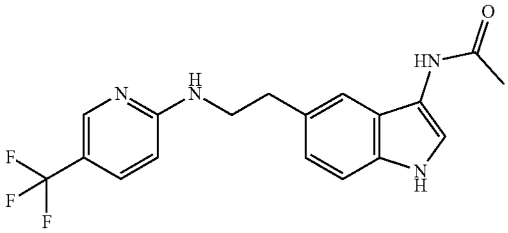 [SMILES: CC(=O)Nc1c[nH]c2ccc(CCNc3ccc(C(F)(F)F)cn3)cc12] N-(5-(2-((5-(trifluoromethyl)pyridin-2-yl)amino)ethyl)-1H-indol-3-yl)acetamide | 363.05 |
| 200 | 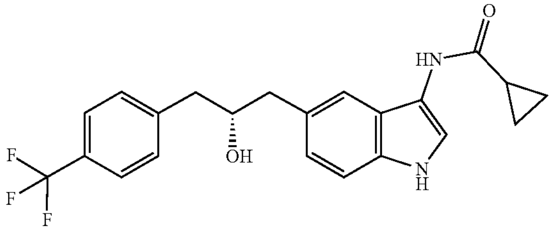 [SMILES: O=C(Nc1c[nH]c2ccc(C[C@H](O)Cc3ccc(C(F)(F)F)cc3)cc12)C1CC1] (R)-N-(5-(2-hydroxy-3-(4-(trifluoromethyl)phenyl)propyl)-1H-indol-3-yl)cyclopropanecarboxamide | 401.1 |

TABLE C1-continued
| Compound No. | Structure | LC-MS |
|---|---|---|
| 201 | 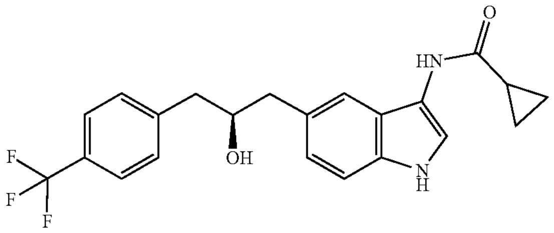 [SMILES: O=C(Nc1c[nH]c2ccc(C[C@@H](O)Cc3ccc(C(F)(F)F)cc3)cc12)C1CC1] (S)-N-(5-(2-hydroxy-3-(4-(trifluoromethyl)phenyl)propyl)-1H-indol-3-yl)cyclopropanecarboxamide | 401.15 |
| 202 | 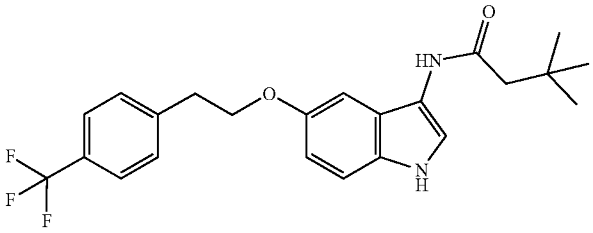 [SMILES: CC(C)(C)CC(=O)Nc1c[nH]c2ccc(OCCc3ccc(C(F)(F)F)cc3)cc12] 3,3-dimethyl-N-(5-(4-(trifluoromethyl)phenethoxy)-1H-indol-3-yl)butanamide | 419.2 |
| 203 | 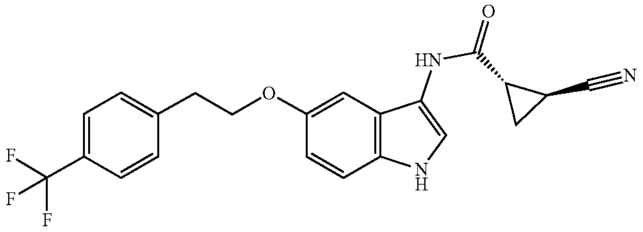 [SMILES: N#C[C@H]1C[C@@H]1C(=O)Nc1c[nH]c2ccc(OCCc3ccc(C(F)(F)F)cc3)cc12] (1S,2S)-2-cyano-N-(5-(4-(trifluoromethyl)phenethoxy)-1H-indol-3-yl)cyclopropane-1-carboxamide | 414.2 |
| 204 | 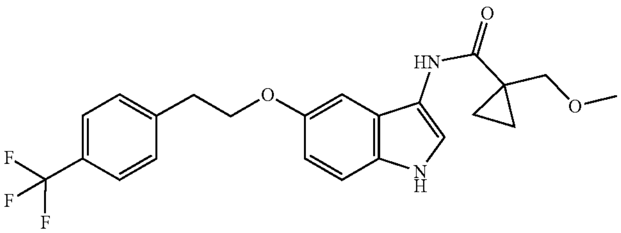 [SMILES: COCC1(C(=O)Nc2c[nH]c3ccc(OCCc4ccc(C(F)(F)F)cc4)cc23)CC1] 1-(methoxymethyl)-N-(5-(4-(trifluoromethyl)phenethoxy)-1H-indol-3-yl)cyclopropane-1-carboxamide | 433.2 |
| 205 | 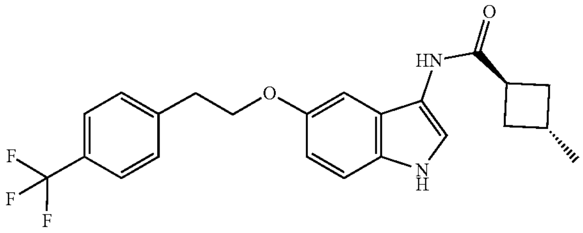 [SMILES: C[C@H]1C[C@H](C(=O)Nc2c[nH]c3ccc(OCCc4ccc(C(F)(F)F)cc4)cc23)C1] | 417.3 |

TABLE C1-continued

| Compound No. | Structure | LC-MS |
|---|---|---|
| | trans-3-methyl-N-(5-(4-(trifluoromethyl)phenethoxy)-1H-indol-3-yl)cyclobutane-1-carboxamide | |
| 206 | 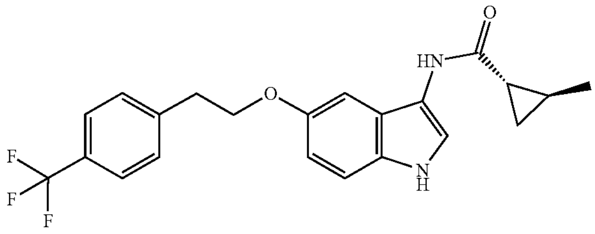 [SMILES: C[C@H]1C[C@@H]1C(=O)Nc1c[nH]c2ccc(OCCc3ccc(C(F)(F)F)cc3)cc12] | 403.2 |
| | (1S,2S)-2-methyl-N-(5-(4-(trifluoromethyl)phenethoxy)-1H-indol-3-yl)cyclopropane-1-carboxamide | |
| 207 | 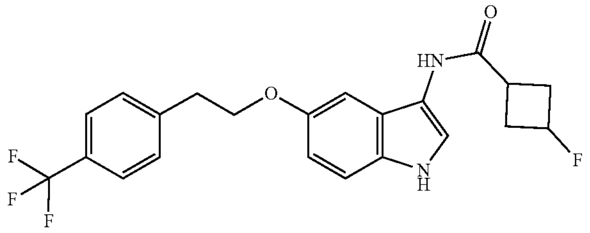 [SMILES: O=C(Nc1c[nH]c2ccc(OCCc3ccc(C(F)(F)F)cc3)cc12)C1CC(F)C1] | 421.2 |
| | 3-fluoro-N-(5-(4-(trifluoromethyl)phenethoxy)-1H-indol-3-yl)cyclobutane-1-carboxamide | |
| 208 | 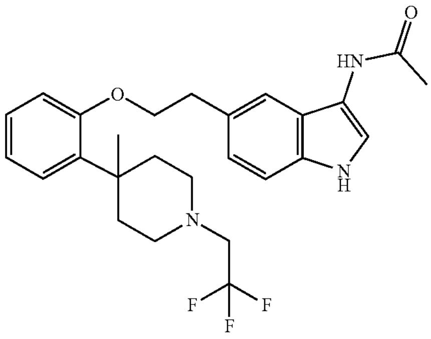 [SMILES: CC(=O)Nc1c[nH]c2ccc(CCOc3ccccc3C3(C)CCN(CC(F)(F)F)CC3)cc12] | 474.25 |
| | N-(5-(2-(2-(4-methyl-1-(2,2,2-trifluoroethyl)piperidin-4-yl)phenoxy)ethyl)-1H-indol-3-yl)acetamide | |
| 209 | 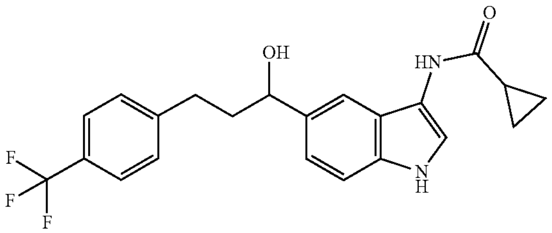 [SMILES: O=C(Nc1c[nH]c2ccc(C(O)CCc3ccc(C(F)(F)F)cc3)cc12)C1CC1] | 401.1 |
| | N-(5-(1-hydroxy-3-(4-(trifluoromethyl)phenyl)propyl)-1H-indol-3-yl)cyclopropanecarboxamide | |

TABLE C1-continued

| Compound No. | Structure | LC-MS |
|---|---|---|
| 210 | 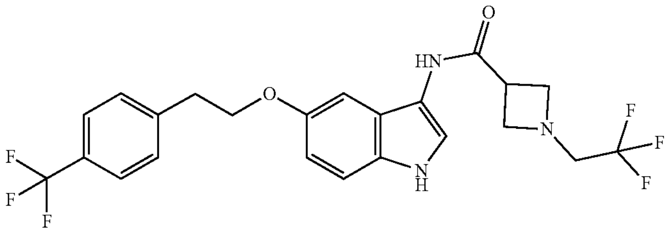 [SMILES: O=C(Nc1c[nH]c2ccc(OCCc3ccc(C(F)(F)F)cc3)cc12)C1CN(CC(F)(F)F)C1]<br>1-(2,2,2-trifluoroethyl)-N-(5-(4-(trifluoromethyl)phenethoxy)-1H-indol-3-yl)azetidine-3-carboxamide | 484.0 |
| 211 | 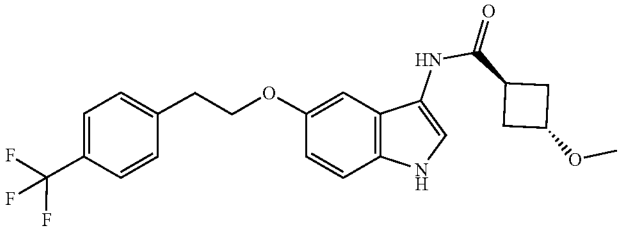 [SMILES: CO[C@H]1C[C@H](C(=O)Nc2c[nH]c3ccc(OCCc4ccc(C(F)(F)F)cc4)cc23)C1]<br>trans-3-methoxy-N-(5-(4-(trifluoromethyl)phenethoxy)-1H-indol-3-yl)cyclobutane-1-carboxamide | 431.1 |
| 212 | 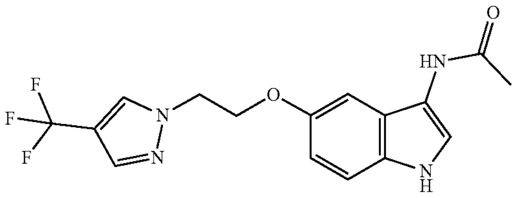 [SMILES: CC(=O)Nc1c[nH]c2ccc(OCCn3cc(C(F)(F)F)cn3)cc12]<br>N-(5-(3-(4-(trifluoromethyl)-1H-pyrazol-1-yl)propyl)-1H-indol-3-yl)acetamide | 350.95 |
| 213 | 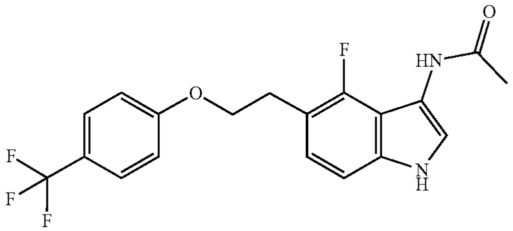 [SMILES: CC(=O)Nc1c[nH]c2ccc(CCOc3ccc(C(F)(F)F)cc3)c(F)c12]<br>N-(4-fluoro-5-(2-(4-(trifluoromethyl)phenoxy)ethyl)-1H-indol-3-yl)acetamide | 379.0 |
| 214 | 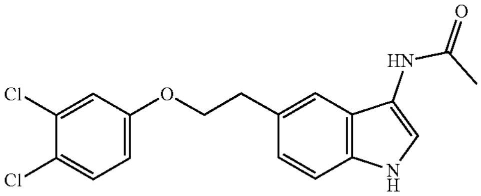 [SMILES: CC(=O)Nc1c[nH]c2ccc(CCOc3ccc(Cl)c(Cl)c3)cc12]<br>N-(5-(2-(3,4-dichlorophenoxy)ethyl)-1H-indol-3-yl)acetamide | 363.05 |

TABLE C1-continued

| Compound No. | Structure | LC-MS |
|---|---|---|
| 215 | 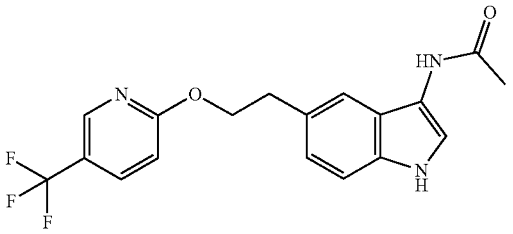 [SMILES: CC(=O)Nc1c[nH]c2ccc(CCOc3ccc(C(F)(F)F)cn3)cc12]<br>N-(5-(2-((5-(trifluoromethyl)pyridin-2-yl)oxy)ethyl)-1H-indol-3-yl)acetamide | 364.1 |
| 216 | 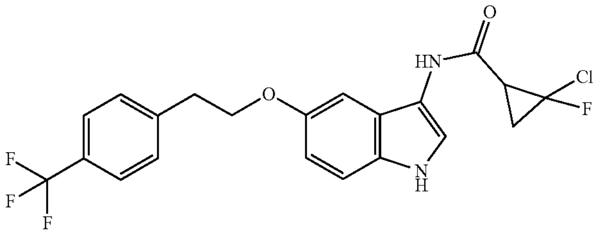 [SMILES: O=C(Nc1c[nH]c2ccc(OCCc3ccc(C(F)(F)F)cc3)cc12)C1CC1(F)Cl]<br>2-chloro-2-fluoro-N-(5-(4-(trifluoromethyl)phenethoxy)-1H-indol-3-yl)cyclopropane-1-carboxamide | 441.1 |
| 217 | 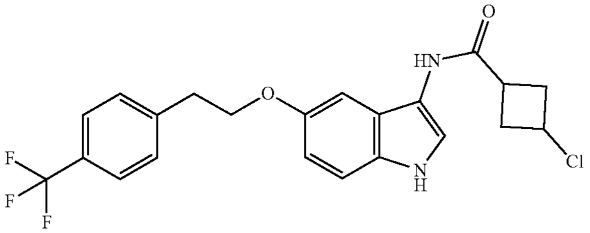 [SMILES: O=C(Nc1c[nH]c2ccc(OCCc3ccc(C(F)(F)F)cc3)cc12)C1CC(Cl)C1]<br>3-chloro-N-(5-(4-(trifluoromethyl)phenethoxy)-1H-indol-3-yl)cyclobutane-1-carboxamide | 437.1 |
| 218 | 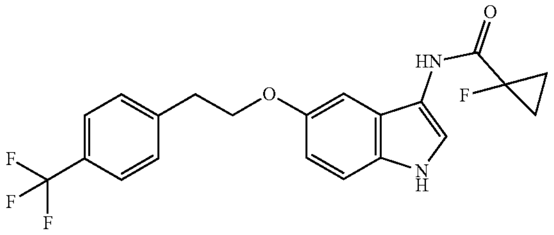 [SMILES: O=C(Nc1c[nH]c2ccc(OCCc3ccc(C(F)(F)F)cc3)cc12)C1(F)CC1]<br>1-fluoro-N-(5-(4-(trifluoromethyl)phenethoxy)-1H-indol-3-yl)cyclopropane-1-carboxamide | 407.2 |
| 219 | 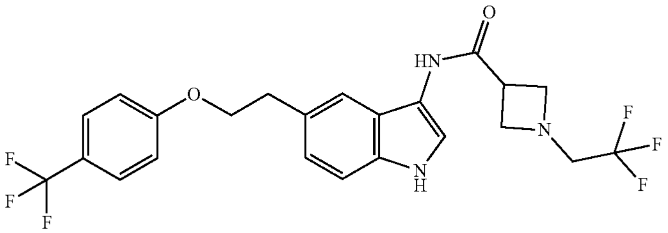 [SMILES: O=C(Nc1c[nH]c2ccc(CCOc3ccc(C(F)(F)F)cc3)cc12)C1CN(CC(F)(F)F)C1]<br>1-(2,2,2-trifluoroethyl)-N-(5-(2-(4-(trifluoromethyl)phenoxy)ethyl)-1H-indol-3-yl)azetidine-3-carboxamide | 486.1 |

TABLE C1-continued

| Compound No. | Structure | LC-MS |
|---|---|---|
| 220 | 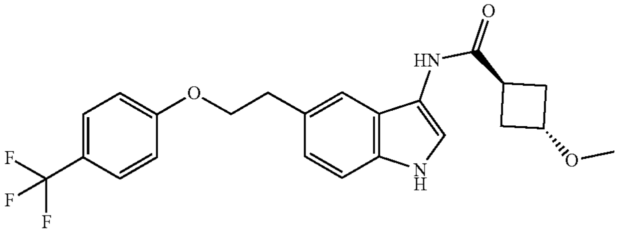 [SMILES: CO[C@H]1C[C@H](C(=O)Nc2c[nH]c3ccc(CCOc4ccc(C(F)(F)F)cc4)cc23)C1]<br>trans-3-methoxy-N-(5-(2-(4-(trifluoromethyl)phenoxy)ethyl)-1H-indol-3-yl)cyclobutane-1-carboxamide | 431.1 |
| 221 | 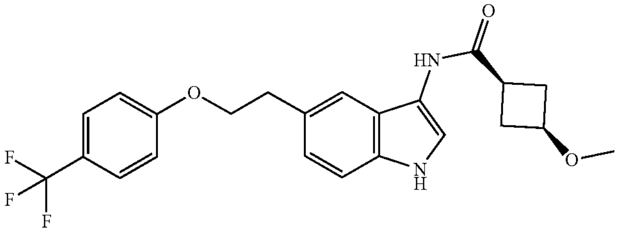 [SMILES: CO[C@H]1C[C@@H](C(=O)Nc2c[nH]c3ccc(CCOc4ccc(C(F)(F)F)cc4)cc23)C1]<br>cis-3-methoxy-N-(5-(2-(4-(trifluoromethyl)phenoxy)ethyl)-1H-indol-3-yl)cyclobutane-1-carboxamide | 431.15 |
| 222 | 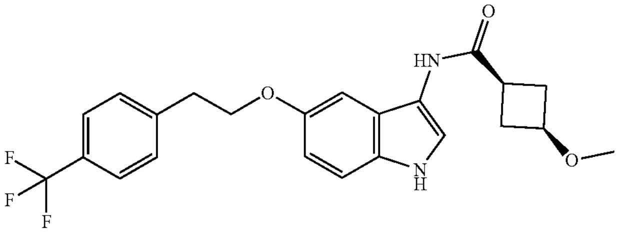 [SMILES: CO[C@H]1C[C@@H](C(=O)Nc2c[nH]c3ccc(OCCc4ccc(C(F)(F)F)cc4)cc23)C1]<br>cis-3-methoxy-N-(5-(4-(trifluoromethyl)phenethoxy)-1H-indol-3-yl)cyclobutane-1-carboxamide | 431.1 |
| 223 | 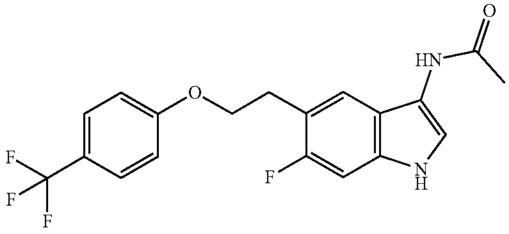 [SMILES: CC(=O)Nc1c[nH]c2cc(F)c(CCOc3ccc(C(F)(F)F)cc3)cc12]<br>N-(6-fluoro-5-(2-(4-(trifluoromethyl)phenoxy)ethyl)-1H-indol-3-yl)acetamide | 379.1 |
| 224 | 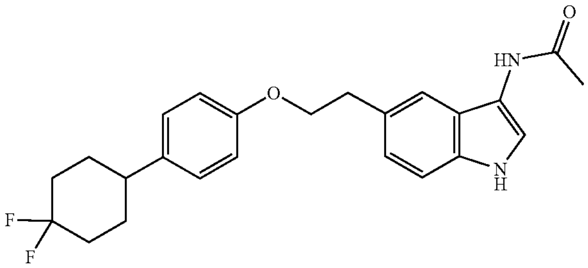 [SMILES: CC(=O)Nc1c[nH]c2ccc(CCOc3ccc(C4CCC(F)(F)CC4)cc3)cc12] | 411.15 |

TABLE C1-continued

| Compound No. | Structure | LC-MS |
|---|---|---|
| | N-(5-(2-(4-(4,4-difluorocyclohexyl)phenoxy)ethyl)-1H-indol-3-yl)acetamide | |
| 225 | 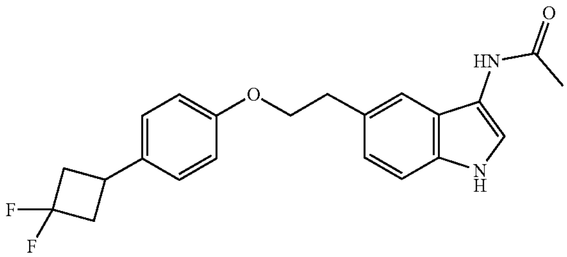 [SMILES: CC(=O)Nc1c[nH]c2ccc(CCOc3ccc(C4CC(F)(F)C4)cc3)cc12]<br>N-(5-(2-(4-(3,3-difluorocyclobutyl)phenoxy)ethyl)-1H-indol-3-yl)acetamide | |
| 226 | 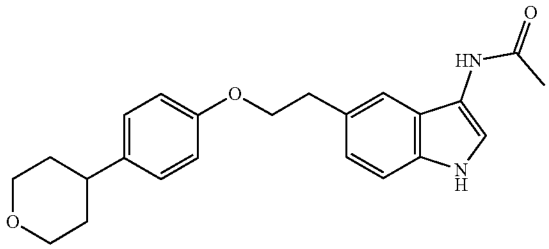 [SMILES: CC(=O)Nc1c[nH]c2ccc(CCOc3ccc(C4CCOCC4)cc3)cc12]<br>N-(5-(2-(4-(tetrahydro-2H-pyran-4-yl)phenoxy)ethyl)-1H-indol-3-yl)acetamide | 377.0 |
| 227 | 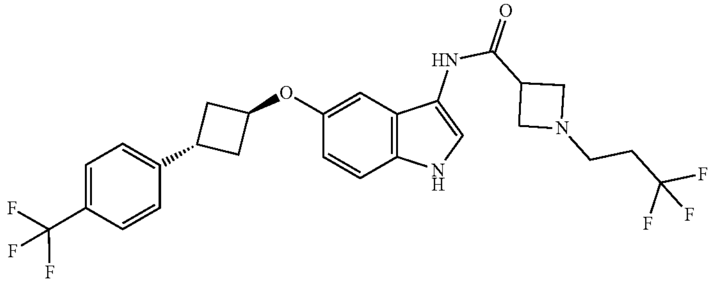 [SMILES: O=C(Nc1c[nH]c2ccc(O[C@H]3C[C@H](c4ccc(C(F)(F)F)cc4)C3)cc12)C1CN(CCC(F)(F)F)C1]<br>N-(5-(trans-3-(4-(trifluoromethyl)phenyl)cyclobutoxy)-1H-indol-3-yl)-1-(3,3,3-trifluoropropyl)azetidine-3-carboxamide | 524.15 |
| 228 | 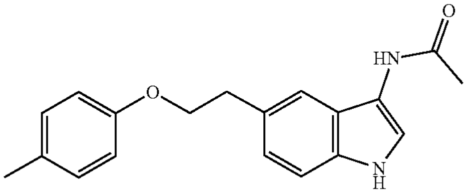 [SMILES: CC(=O)Nc1c[nH]c2ccc(CCOc3ccc(C)cc3)cc12]<br>N-(5-(2-(p-tolyloxy)ethyl)-1H-indol-3-yl)acetamide | 307.1 |

TABLE C1-continued
| Compound No. | Structure | LC-MS |
|---|---|---|
| 229 | 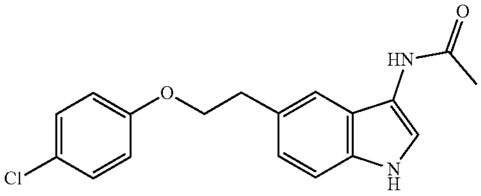 [SMILES: CC(=O)Nc1c[nH]c2ccc(CCOc3ccc(Cl)cc3)cc12] N-(5-(2-(4-chlorophenoxy)ethyl)-1H-indol-3-yl)acetamide | 327.05 |
| 230 | 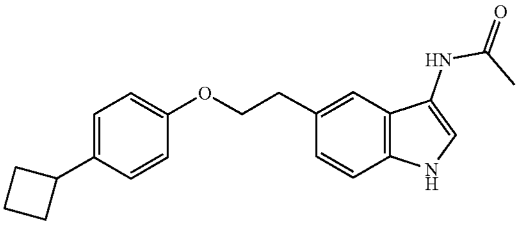 [SMILES: CC(=O)Nc1c[nH]c2ccc(CCOc3ccc(C4CCC4)cc3)cc12] N-(5-(2-(4-cyclobutylphenoxy)ethyl)-1H-indol-3-yl)acetamide | 347.15 |
| 231 | 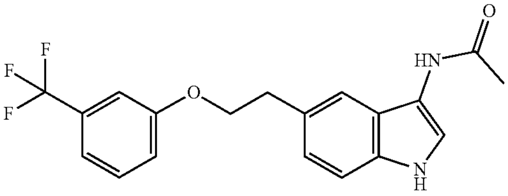 [SMILES: CC(=O)Nc1c[nH]c2ccc(CCOc3cccc(C(F)(F)F)c3)cc12] N-(5-(2-(3-(trifluoromethyl)phenoxy)ethyl)-1H-indol-3-yl)acetamide | 361.1 |
| 232 | 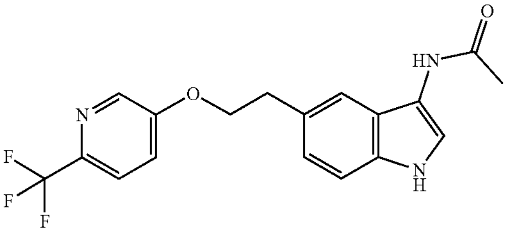 [SMILES: CC(=O)Nc1c[nH]c2ccc(CCOc3ccc(C(F)(F)F)nc3)cc12] N-(5-(2-((6-(trifluoromethyl)pyridin-3-yl)oxy)ethyl)-1H-indol-3-yl)acetamide | 364.1 |
| 233 | 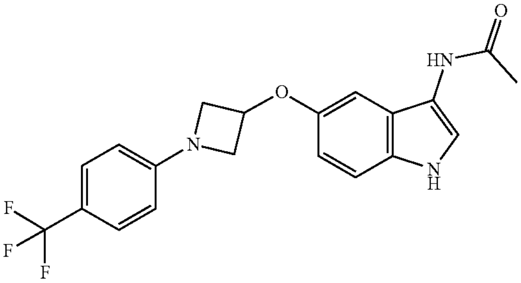 [SMILES: CC(=O)Nc1c[nH]c2ccc(OC3CN(c4ccc(C(F)(F)F)cc4)C3)cc12] N-(5-((1-(4-(trifluoromethyl)phenyl)azetidin-3-yl)oxy)-1H-indol-3-yl)acetamide | 390.1 |

TABLE C1-continued

| Compound No. | Structure | LC-MS |
|---|---|---|
| 234 | 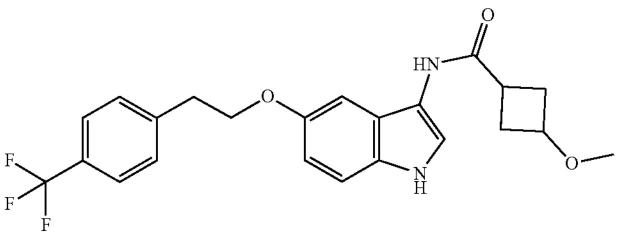 [SMILES: COC1CC(C(=O)Nc2c[nH]c3ccc(OCCc4ccc(C(F)(F)F)cc4)cc23)C1]<br>3-methoxy-N-(5-(4-(trifluoromethyl)phenethoxy)-1H-indol-3-yl)cyclobutane-1-carboxamide | 433.2 |
| 235 | 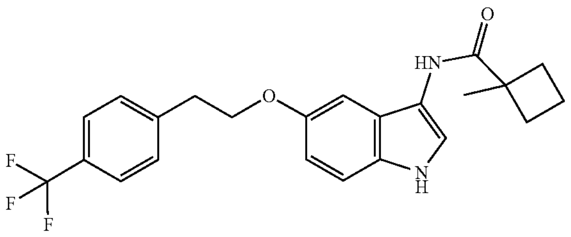 [SMILES: CC1(C(=O)Nc2c[nH]c3ccc(OCCc4ccc(C(F)(F)F)cc4)cc23)CCC1]<br>1-methyl-N-(5-(4-(trifluoromethyl)phenethoxy)-1H-indol-3 -yl)cyclobutane-1-carboxamide | 417.2 |
| 236 | 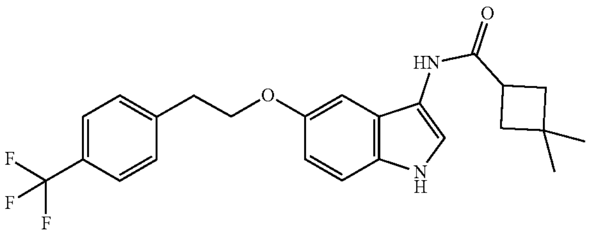 [SMILES: CC1(C)CC(C(=O)Nc2c[nH]c3ccc(OCCc4ccc(C(F)(F)F)cc4)cc23)C1]<br>3,3-dimethyl-N-(5-(4-(trifluoromethyl)phenethoxy)-1H-indol-3-yl)cyclobutane-1-carboxamide | 431.2 |
| 237 | 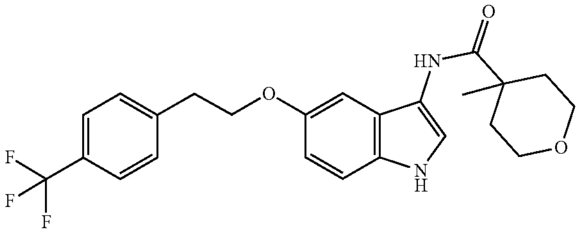 [SMILES: CC1(C(=O)Nc2c[nH]c3ccc(OCCc4ccc(C(F)(F)F)cc4)cc23)CCOCC1]<br>4-methyl-N-(5-(4-(trifluoromethyl)phenethoxy)-1H-indol-3-yl)tetrahydro-2H-pyran-4-carboxamide | 447.2 |
| 238 | 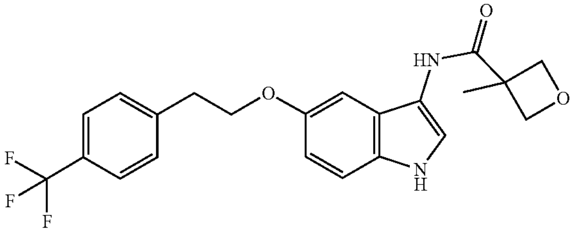<br>3-methyl-N-(5-(4-(trifluoromethyl)phenethoxy)-1H-indol-3-yl)oxetane-3-carboxamide | 419.2 |

TABLE C1-continued

| Compound No. | Structure | LC-MS |
|---|---|---|
| 239 | 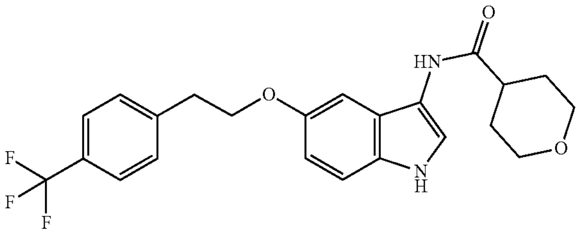 [SMILES: O=C(Nc1c[nH]c2ccc(OCCc3ccc(C(F)(F)F)cc3)cc12)C1CCOCC1] N-(5-(4-(trifluoromethyl)phenethoxy)-1H-indol-3-yl)tetrahydro-2H-pyran-4-carboxamide | 433.2 |
| 240 | 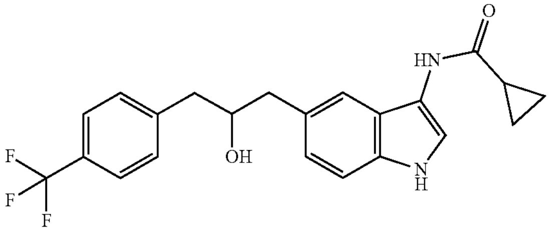 [SMILES: O=C(Nc1c[nH]c2ccc(CC(O)Cc3ccc(C(F)(F)F)cc3)cc12)C1CC1] N-(5-(2-hydroxy-3-(4-(trifluoromethyl)phenyl)propyl)-1H-indol-3-yl)cyclopropanecarboxamide | 401.1 |
| 241 | 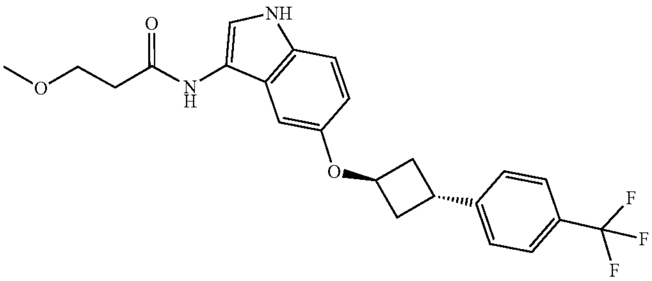 [SMILES: COCCC(=O)Nc1c[nH]c2ccc(O[C@H]3C[C@H](c4ccc(C(F)(F)F)cc4)C3)cc12] 3-methoxy-N-(5-((1r,3r)-3-(4-(trifluoromethyl)phenyl)cyclobutoxy)-1H-indol-3-yl)propanamide | 433.05 |
| 242 | 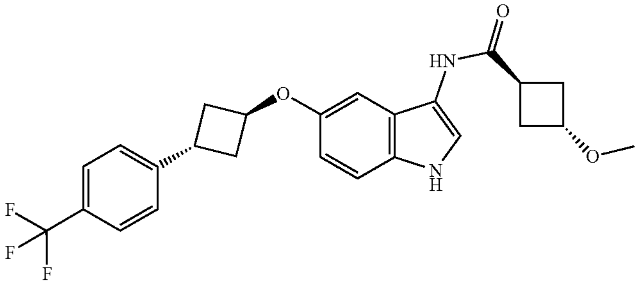 [SMILES: CO[C@H]1C[C@H](C(=O)Nc2c[nH]c3ccc(O[C@H]4C[C@H](c5ccc(C(F)(F)F)cc5)C4)cc23)C1] trans-3-methoxy-N-(5-(trans-3-(4-(trifluoromethyl)phenyl)cyclobutoxy)-1H-indol-3-yl)cyclobutane-1-carboxamide | 459.3 |

TABLE C1-continued

| Compound No. | Structure | LC-MS |
|---|---|---|
| 243 | 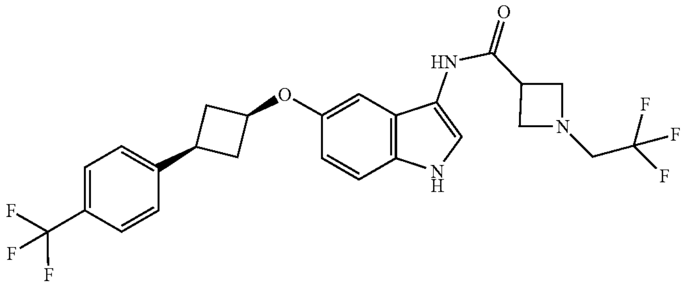 [SMILES: O=C(Nc1c[nH]c2ccc(O[C@H]3C[C@@H](c4ccc(C(F)(F)F)cc4)C3)cc12)C1CN(CC(F)(F)F)C1]<br>1-(2,2,2-trifluoroethyl)-N-(5-(cis-3-(4-(trifluoromethyl)phenyl)cyclobutoxy)-1H-indol-3-yl)azetidine-3-carboxamide | 510.15 |
| 244 | 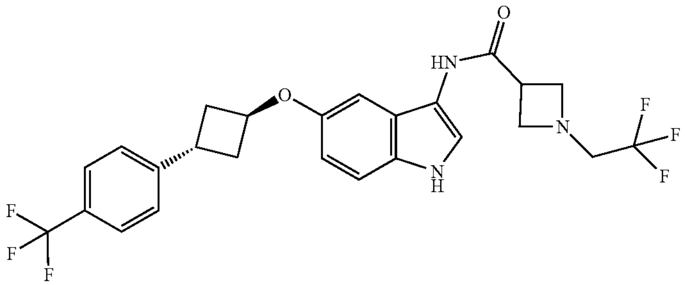 [SMILES: O=C(Nc1c[nH]c2ccc(O[C@H]3C[C@H](c4ccc(C(F)(F)F)cc4)C3)cc12)C1CN(CC(F)(F)F)C1]<br>1-(2,2,2-trifluoroethyl)-N-(5-(trans-3-(4-(trifluoromethyl)phenyl)cyclobutoxy)-1H-indol-3-yl)azetidine-3-carboxamide | 510.15 |
| 245 | 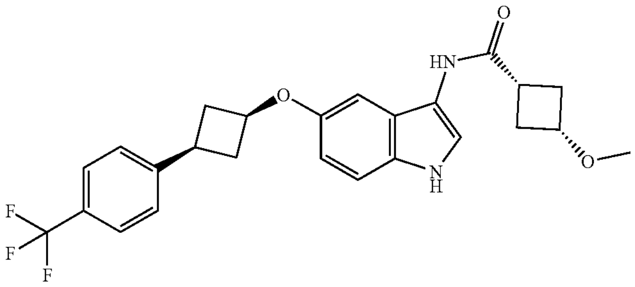 [SMILES: CO[C@H]1C[C@@H](C(=O)Nc2c[nH]c3ccc(O[C@H]4C[C@@H](c5ccc(C(F)(F)F)cc5)C4)cc23)C1]<br>cis-3-methoxy-N-(5-(cis-3-(4-(trifluoromethyl)phenyl)cyclobutoxy)-1H-indol-3-yl)cyclobutane-1-carboxamide | 459.2 |
| 246 | 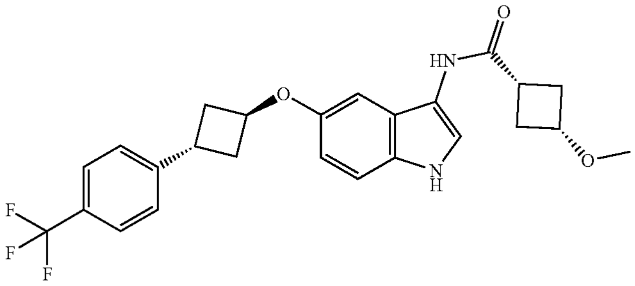<br>cis-3-methoxy-N-(5-(trans-3-(4-(trifluoromethyl)phenyl)cyclobutoxy)-1H-indol-3-yl)cyclobutane-1-carboxamide | 459.2 |

TABLE C1-continued

| Compound No. | Structure | LC-MS |
|---|---|---|
| 247 | 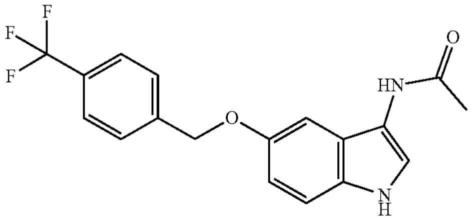 [SMILES: CC(=O)Nc1c[nH]c2ccc(OCc3ccc(C(F)(F)F)cc3)cc12] N-(5-((4-(trifluoromethyl)benzyl)oxy)-1H-indol-3-yl)acetamide | 349.0 |
| 248 | 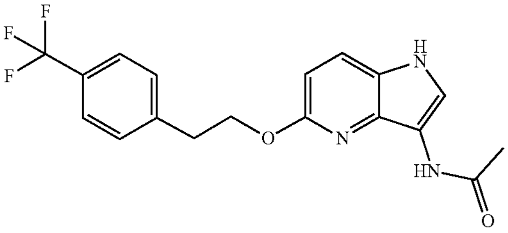 [SMILES: CC(=O)Nc1c[nH]c2ccc(OCCc3ccc(C(F)(F)F)cc3)nc12] N-(5-(4-(trifluoromethyl)phenethoxy)-1H-pyrrolo[3,2-b]pyridin-3-yl)acetamide | 364.05 |
| 249 | 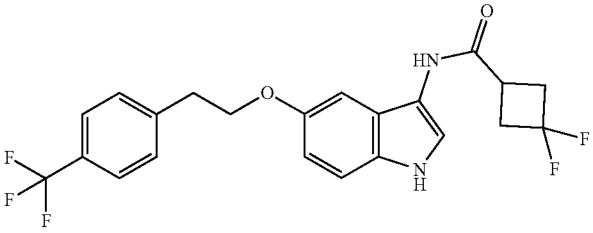 [SMILES: O=C(Nc1c[nH]c2ccc(OCCc3ccc(C(F)(F)F)cc3)cc12)C1CC(F)(F)C1] 3,3-difluoro-N-(5-(4-(trifluoromethyl)phenethoxy)-1H-indol-3-yl)cyclobutane-1-carboxamide | 437.15 |
| 250 | 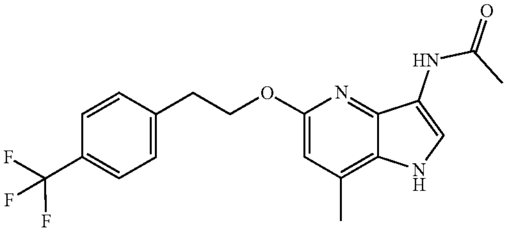 [SMILES: CC(=O)Nc1c[nH]c2c(C)cc(OCCc3ccc(C(F)(F)F)cc3)nc12] N-(7-methyl-5-(4-(trifluoromethyl)phenethoxy)-1H-pyrrolo[3,2-b]pyridin-3-yl)acetamide | 376.1 |
| 251 | 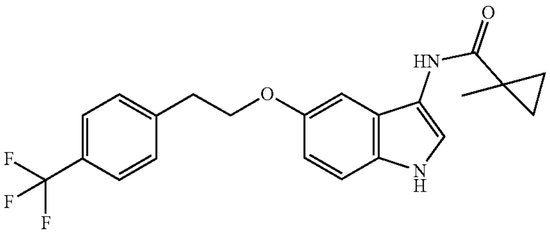 [SMILES: CC1(C(=O)Nc2c[nH]c3ccc(OCCc4ccc(C(F)(F)F)cc4)cc23)CC1] 1-methyl-N-(5-(4-(trifluoromethyl)phenethoxy)-1H-indol-3-yl)cyclopropane-1-carboxamide | 403.3 |

TABLE C1-continued
| Compound No. | Structure | LC-MS |
|---|---|---|
| 252 | 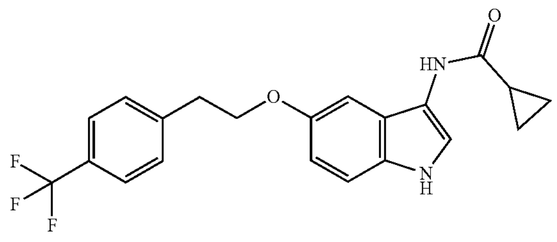 [SMILES: O=C(Nc1c[nH]c2ccc(OCCc3ccc(C(F)(F)F)cc3)cc12)C1CC1] N-(5-(4-(trifluoromethyl)phenethoxy)-1H-indol-3-yl)cyclopropanecarboxamide | 387.1 |
| 253 | 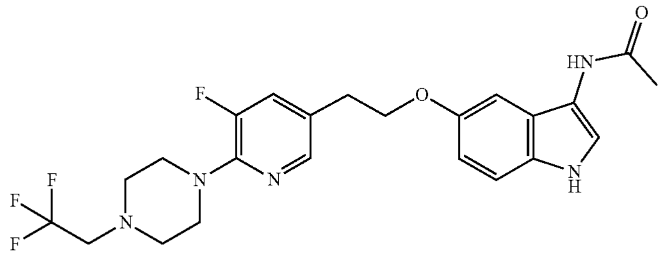 [SMILES: CC(=O)Nc1c[nH]c2ccc(OCCc3cnc(N4CCN(CC(F)(F)F)CC4)c(F)c3)cc12] N-(5-(2-(5-fluoro-6-(4-(2,2,2-trifluoroethyl)piperazin-1-yl)pyridin-3-yl)ethoxy)-1H-indol-3-yl)acetamide | 480.3 |
| 254 | 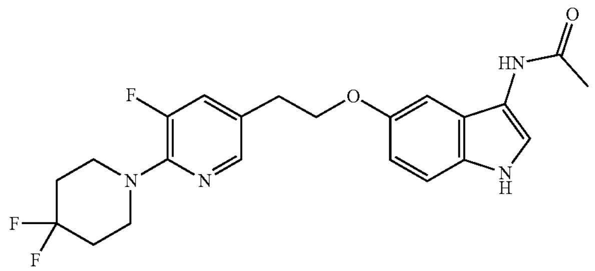 [SMILES: CC(=O)Nc1c[nH]c2ccc(OCCc3cnc(N4CCC(F)(F)CC4)c(F)c3)cc12] N-(5-(2-(6-(4,4-difluoropiperidin-1-yl)-5-fluoropyridin-3-yl)ethoxy)-1H-indol-3-yl)acetamide | 433.2 |
| 255 | 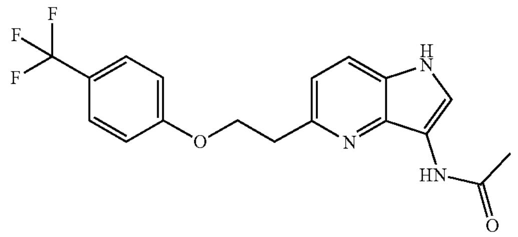 [SMILES: CC(=O)Nc1c[nH]c2ccc(CCOc3ccc(C(F)(F)F)cc3)nc12] N-(5-(2-(4-(trifluoromethyl)phenoxy)ethyl)-1H-pyrrolo[3,2-b]pyridin-3-yl)acetamide | 364.2 |
| 256 | 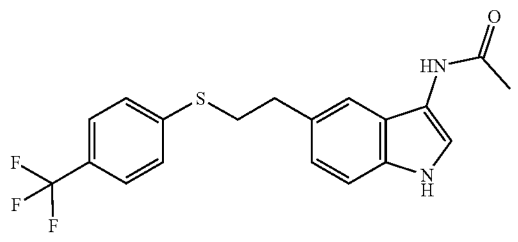 | 377.1 |

TABLE C1-continued

| Compound No. | Structure | LC-MS |
|---|---|---|
| | N-(5-(2-((4-(trifluoromethyl)phenyl)thio)ethyl)-1H-indol-3-yl)acetamide | |
| 257 | 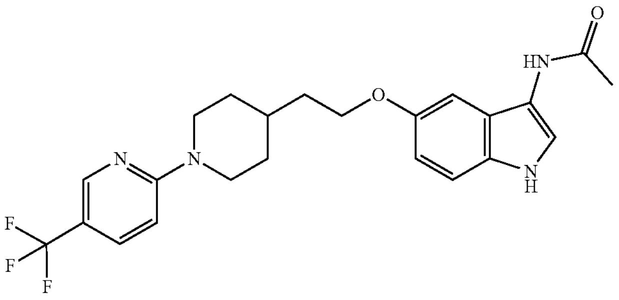 [SMILES: CC(=O)Nc1c[nH]c2ccc(OCCC3CCN(c4ccc(C(F)(F)F)cn4)CC3)cc12] N-(5-(2-(1-(5-(trifluoromethyl)pyridin-2-yl)piperidin-4-yl)ethoxy)-1H-indol-3-yl)acetamide | 447.4 |
| 258 | 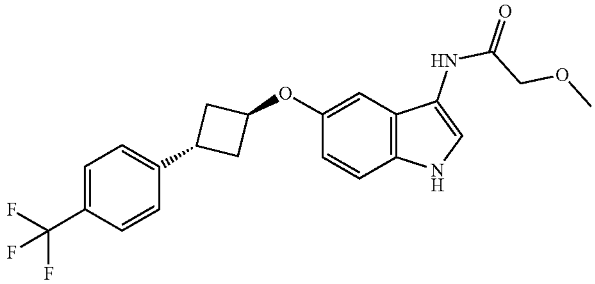 [SMILES: COCC(=O)Nc1c[nH]c2ccc(O[C@H]3C[C@H](c4ccc(C(F)(F)F)cc4)C3)cc12] 2-methoxy-N-(5-(trans-3-(4-(trifluoromethyl)phenyl)cyclobutoxy)-1H-indol-3-yl)acetamide | 419.1 |
| 259 | 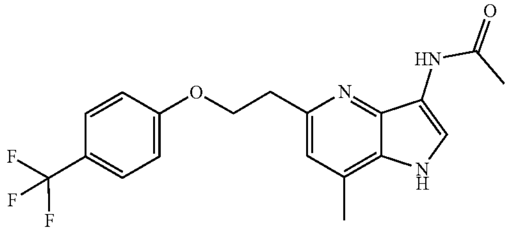 [SMILES: CC(=O)Nc1c[nH]c2c(C)cc(CCOc3ccc(C(F)(F)F)cc3)nc12] N-(7-methyl-5-(2-(4-(trifluoromethyl)phenoxy)ethyl)-1H-pyrrolo[3,2-b]pyridin-3-yl)acetamide | 378.3 |
| 260 | 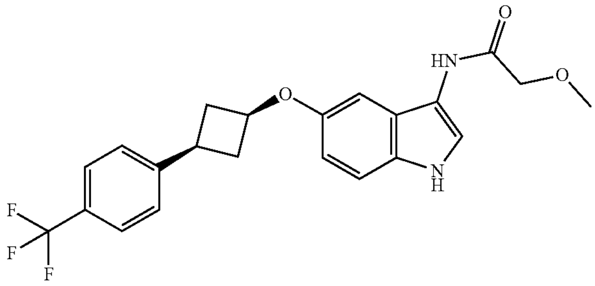 [SMILES: COCC(=O)Nc1c[nH]c2ccc(O[C@H]3C[C@@H](c4ccc(C(F)(F)F)cc4)C3)cc12] 2-methoxy-N-(5-(cis-3-(4-(trifluoromethyl)phenyl)cyclobutoxy)-1H-indol-3-yl)acetamide | 419.2 |

TABLE C1-continued
| Compound No. | Structure | LC-MS |
|---|---|---|
| 261 | 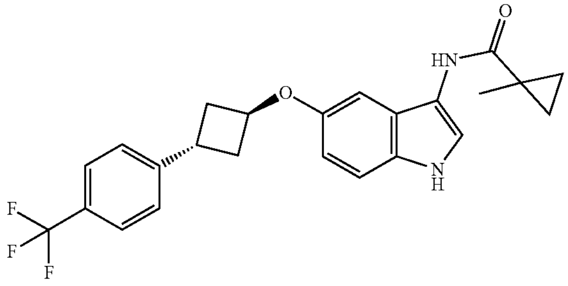 [SMILES: CC1(C(=O)Nc2c[nH]c3ccc(O[C@H]4C[C@H](c5ccc(C(F)(F)F)cc5)C4)cc23)CC1]<br>1-methyl-N-(5-(trans-3-(4-(trifluoromethyl)phenyl)cyclobutoxy)-1H-indol-3-yl)cyclopropane-1-carboxamide | 429.0 |
| 262 | 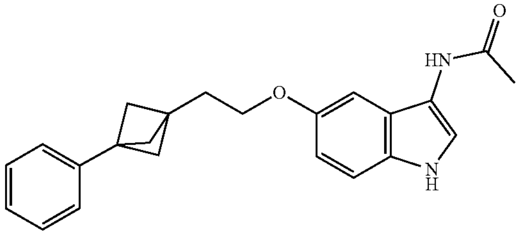 [SMILES: CC(=O)Nc1c[nH]c2ccc(OCCC34CC(c5ccccc5)(C3)C4)cc12]<br>N-(5-(2-(3-phenylbicyclo[1.1.1]pentan-1-yl)ethoxy)-1H-indol-3-yl)acetamide | 359.2 |
| 263 | 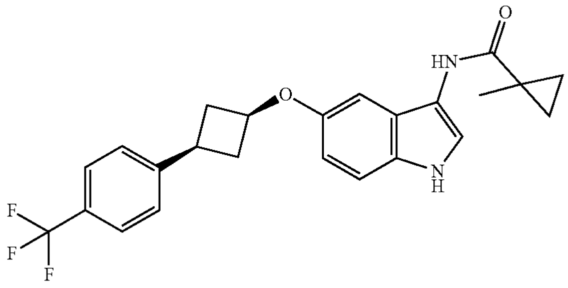 [SMILES: CC1(C(=O)Nc2c[nH]c3ccc(O[C@H]4C[C@@H](c5ccc(C(F)(F)F)cc5)C4)cc23)CC1]<br>1-methyl-N-(5-(cis-3-(4-(trifluoromethyl)phenyl)cyclobutoxy)-1H-indol-3-yl)cyclopropane-1-carboxamide | 429.15 |
| 264 | 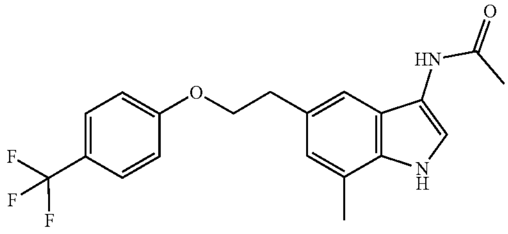 [SMILES: CC(=O)Nc1c[nH]c2c(C)cc(CCOc3ccc(C(F)(F)F)cc3)cc12]<br>N-(7-methyl-5-(2-(4-(trifluoromethyl)phenoxy)ethyl)-1H-indol-3-yl)acetamide | 375.15 |

TABLE C1-continued

| Compound No. | Structure | LC-MS |
|---|---|---|
| 265 | 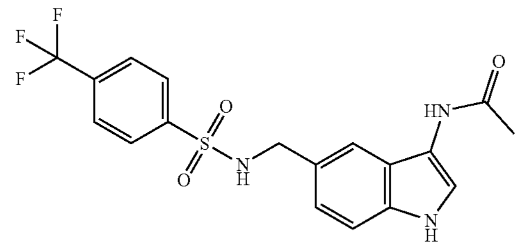 [SMILES: CC(=O)Nc1c[nH]c2ccc(CNS(=O)(=O)c3ccc(C(F)(F)F)cc3)cc12] N-(5-(((4-(trifluoromethyl)phenyl)sulfonamido)methyl)-1H-indol-3-yl)acetamide | 412.1 |
| 266 | 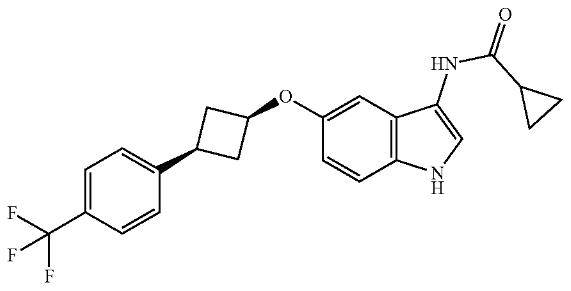 [SMILES: O=C(Nc1c[nH]c2ccc(O[C@H]3C[C@@H](c4ccc(C(F)(F)F)cc4)C3)cc12)C1CC1] N-(5-(cis-3-(4-(trifluoromethyl)phenyl)cyclobutoxy)-1H-indol-3-yl)cyclopropanecarboxamide | 415.1 |
| 267 | 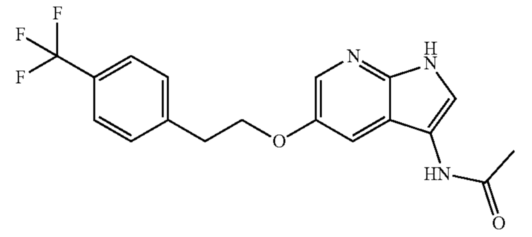 [SMILES: CC(=O)Nc1c[nH]c2ncc(OCCc3ccc(C(F)(F)F)cc3)cc12] N-(5-(4-(trifluoromethyl)phenethoxy)-1H-pyrrolo[2,3-b]pyridin-3-yl)acetamide | 364.1 |
| 268 | 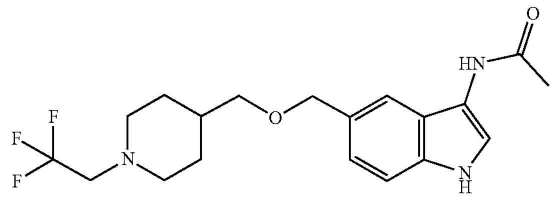 [SMILES: CC(=O)Nc1c[nH]c2ccc(COCC3CCN(CC(F)(F)F)CC3)cc12] N-(5-(((1-(2,2,2-trifluoroethyl)piperidin-4-yl)methoxy)methyl)-1H-indol-3-yl)acetamide | 382.2 |
| 270 | 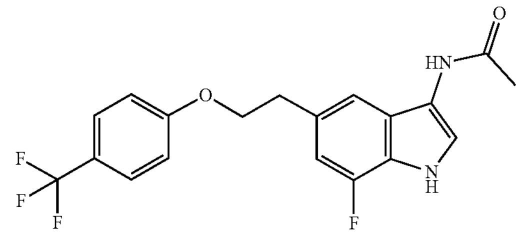 [SMILES: CC(=O)Nc1c[nH]c2c(F)cc(CCOc3ccc(C(F)(F)F)cc3)cc12] N-(7-fluoro-5-(2-(4-(trifluoromethyl)phenoxy)ethyl)-1H-indol-3-yl)acetamide | 379.1 |

TABLE C1-continued

| Compound No. | Structure | LC-MS |
|---|---|---|
| 271 | 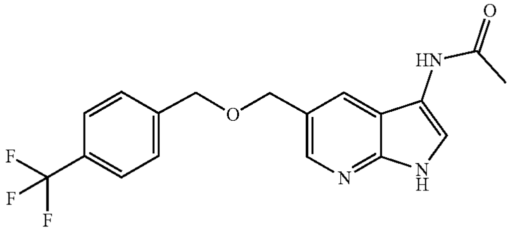 [SMILES: CC(=O)Nc1c[nH]c2ncc(COCc3ccc(C(F)(F)F)cc3)cc12] N-(5-(((4-(trifluoromethyl)benzyl)oxy)methyl)-1H-pyrrolo[2,3-b]pyridin-3-yl)acetamide | 364.05 |
| 272 | 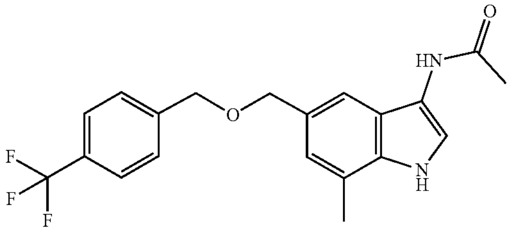 [SMILES: CC(=O)Nc1c[nH]c2c(C)cc(COCc3ccc(C(F)(F)F)cc3)cc12] N-(7-methyl-5-(((4-(trifluoromethyl)benzyl)oxy)methyl)-1H-indol-3-yl)acetamide | 375.15 |
| 273 | 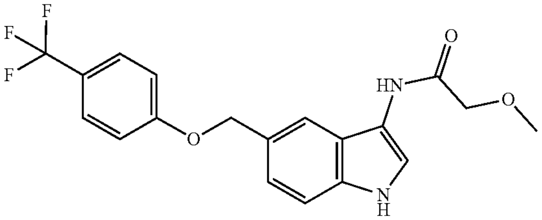 [SMILES: COCC(=O)Nc1c[nH]c2ccc(COc3ccc(C(F)(F)F)cc3)cc12] 2-methoxy-N-(5-((4-(trifluoromethyl)phenoxy)methyl)-1H-indol-3-yl)acetamide | 378.15 |
| 274 | 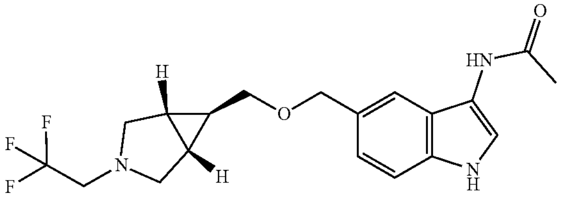 [SMILES: CC(=O)Nc1c[nH]c2ccc(COC[C@@H]3[C@H]4CN(CC(F)(F)F)C[C@@H]34)cc12] N-(5-((((1R,5S,6r)-3-(2,2,2-trifluoroethyl)-3-azabicyclo[3.1.0]hexan-6-yl)methoxy)methyl)-1H-indol-3-yl)acetamide | 381.05 |
| 275 | 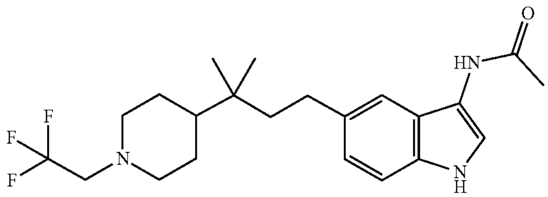 [SMILES: CC(=O)Nc1c[nH]c2ccc(CCC(C)(C)C3CCN(CC(F)(F)F)CC3)cc12] N-(5-(3-methyl-3-(1-(2,2,2-trifluoroethyl)piperidin-4-yl)butyl)-1H-indol-3-yl)acetamide | 410.4 |

TABLE C1-continued
| Compound No. | Structure | LC-MS |
|---|---|---|
| 276 | 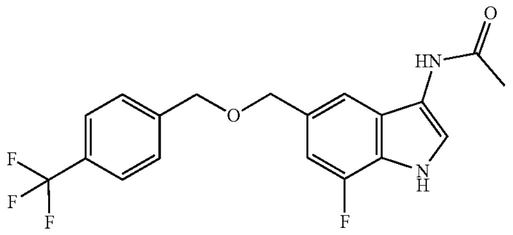 [SMILES: CC(=O)Nc1c[nH]c2c(F)cc(COCc3ccc(C(F)(F)F)cc3)cc12] N-(7-fluoro-5-(((4-(trifluoromethyl)benzyl)oxy)methyl)-1H-indol-3-yl)acetamide | 379.15 |
| 277 | 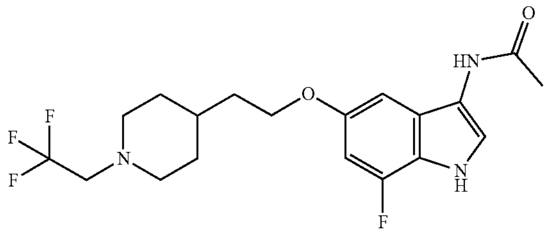 [SMILES: CC(=O)Nc1c[nH]c2c(F)cc(OCCC3CCN(CC(F)(F)F)CC3)cc12] N-(7-fluoro-5-(2-(1-(2,2,2-trifluoroethyl)piperidin-4-yl)ethoxy)-1H-indol-3-yl)acetamide | 402.3 |
| 278 | 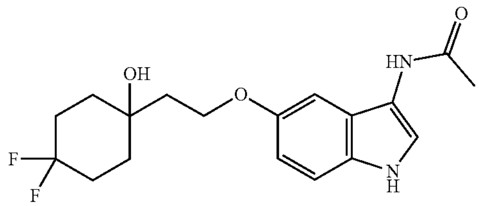 [SMILES: CC(=O)Nc1c[nH]c2ccc(OCCC3(O)CCC(F)(F)CC3)cc12] N-(5-(2-(4,4-difluoro-1-hydroxycyclohexyl)ethoxy)-1H-indol-3-yl)acetamide | 353.15 |
| 279 | 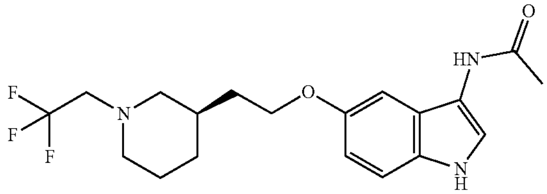 [SMILES: CC(=O)Nc1c[nH]c2ccc(OCC[C@H]3CCCN(CC(F)(F)F)C3)cc12] (R)-N-(5-(2-(1-(2,2,2-trifluoroethyl)piperidin-3-yl)ethoxy)-1H-indol-3-yl)acetamide | 384.25 |
| 280 | 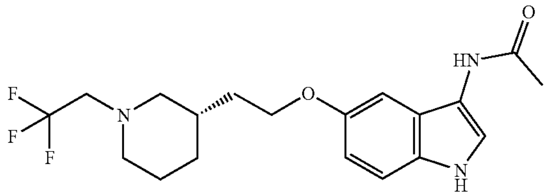 [SMILES: CC(=O)Nc1c[nH]c2ccc(OCC[C@@H]3CCCN(CC(F)(F)F)C3)cc12] (S)-N-(5-(2-(1-(2,2,2-trifluoroethyl)piperidin-3-yl)ethoxy)-1H-indol-3-yl)acetamide | 384.2 |

TABLE C1-continued

| Compound No. | Structure | LC-MS |
|---|---|---|
| 281 | 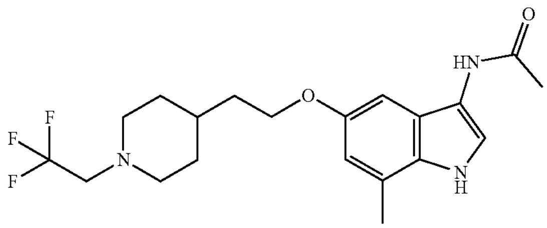 [SMILES: CC(=O)Nc1c[nH]c2c(C)cc(OCCC3CCN(CC(F)(F)F)CC3)cc12]<br>N-(7-methyl-5-(2-(1-(2,2,2-trifluoroethyl)piperidin-4-yl)ethoxy)-1H-indol-3-yl)acetamide | 398.3 |
| 282 | 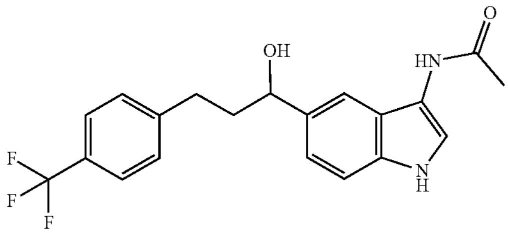 [SMILES: CC(=O)Nc1c[nH]c2ccc(C(O)CCc3ccc(C(F)(F)F)cc3)cc12]<br>N-(5-(1-hydroxy-3-(4-(trifluoromethyl)phenyl)propyl)-1H-indol-3-yl)acetamide | 375.1 |
| 283 | 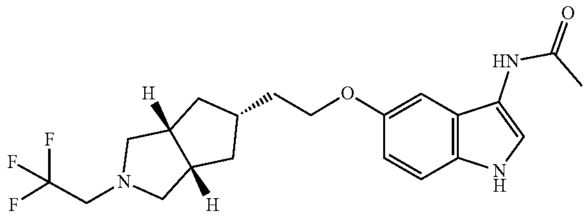 [SMILES: CC(=O)Nc1c[nH]c2ccc(OCC[C@@H]3C[C@@H]4CN(CC(F)(F)F)C[C@@H]4C3)cc12]<br>N-(5-(2-((3aR,5r,6aS)-2-(2,2,2-trifluoroethyl)octahydrocyclopenta[c]pyrrol-5-yl)ethoxy)-1H-indol-3-yl)acetamide | 410.2 |
| 284 | 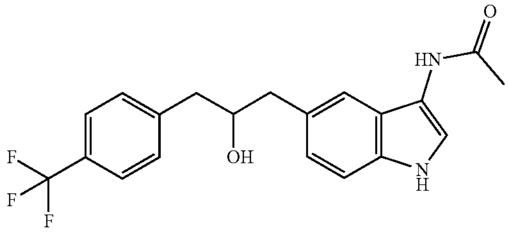 [SMILES: CC(=O)Nc1c[nH]c2ccc(CC(O)Cc3ccc(C(F)(F)F)cc3)cc12]<br>N-(5-(2-hydroxy-3-(4-(trifluoromethyl)phenyl)propyl)-1H-indol-3-yl)acetamide | 375.1 |
| 285 | 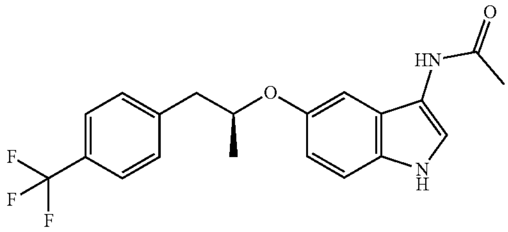 [SMILES: CC(=O)Nc1c[nH]c2ccc(O[C@@H](C)Cc3ccc(C(F)(F)F)cc3)cc12]<br>(S)-N-(5-((1-(4-(trifluoromethyl)phenyl)propan-2-yl)oxy)-1H-indol-3-yl)acetamide | 377.15 |

TABLE C1-continued
| Compound No. | Structure | LC-MS |
|---|---|---|
| 286 | 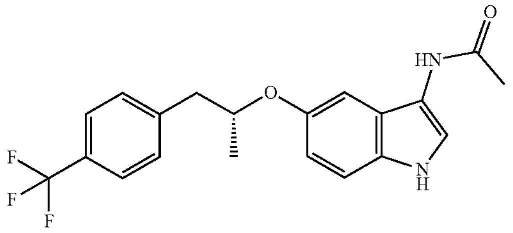 [SMILES: CC(=O)Nc1c[nH]c2ccc(O[C@H](C)Cc3ccc(C(F)(F)F)cc3)cc12] (R)-N-(5-((1-(4-(trifluoromethyl)phenyl)propan-2-yl)oxy)-1H-indol-3-yl)acetamide | 377.15 |
| 287 | 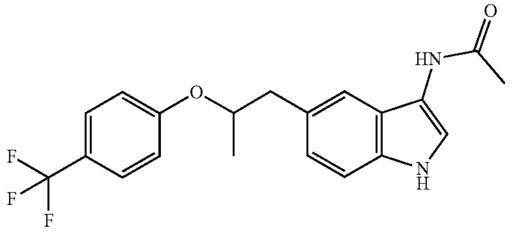 [SMILES: CC(=O)Nc1c[nH]c2ccc(CC(C)Oc3ccc(C(F)(F)F)cc3)cc12] N-(5-(2-(4-(trifluoromethyl)phenoxy)propyl)-1H-indol-3-yl)acetamide | 375.0 |
| 288 | 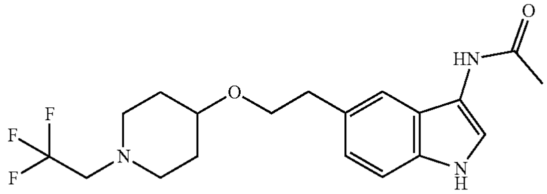 [SMILES: CC(=O)Nc1c[nH]c2ccc(CCOC3CCN(CC(F)(F)F)CC3)cc12] N-(5-(2-((1-(2,2,2-trifluoroethyl)piperidin-4-yl)oxy)ethyl)-1H-indol-3-yl)acetamide | 384.35 |
| 289 | 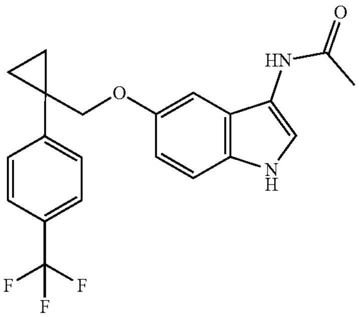 [SMILES: CC(=O)Nc1c[nH]c2ccc(OCC3(c4ccc(C(F)(F)F)cc4)CC3)cc12] N-(5-((1-(4-(trifluoromethyl)phenyl)cyclopropyl)methoxy)-1H-indol-3-yl)acetamide | 389.15 |
| 290 | 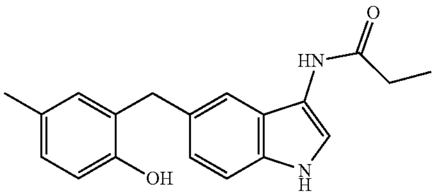 [SMILES: CCC(=O)Nc1c[nH]c2ccc(Cc3cc(C)ccc3O)cc12] N-(5-(2-hydroxy-5-methylbenzyl)-1H-indol-3-yl)propionamide | 308.0 |

TABLE C1-continued

| Compound No. | Structure | LC-MS |
|---|---|---|
| 291 | 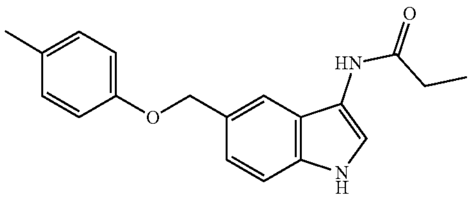 [SMILES: CCC(=O)Nc1c[nH]c2ccc(COc3ccc(C)cc3)cc12] N-(5-((p-tolyloxy)methyl)-1H-indol-3-yl)propionamide | 308.0 |
| 292 | 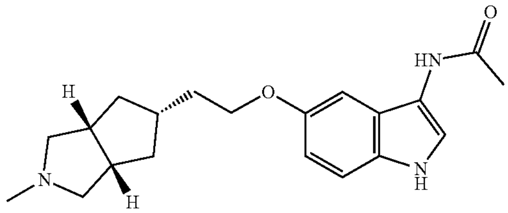 [SMILES: CC(=O)Nc1c[nH]c2ccc(OCC[C@@H]3C[C@@H]4CN(C)C[C@@H]4C3)cc12] N-(5-(2-((3aR,5r,6aS)-2-methyloctahydrocyclopenta[c]pyrrol-5-yl)ethoxy)-1H-indol-3-yl)acetamide | 342.15 |
| 293 | 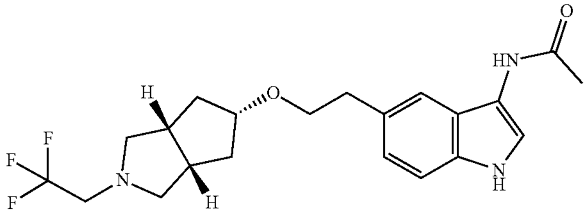 [SMILES: CC(=O)Nc1c[nH]c2ccc(CCO[C@@H]3C[C@@H]4CN(CC(F)(F)F)C[C@@H]4C3)cc12] N-(5-(2-((3aR,5r,6aS)-2-(2,2,2-trifluoroethyl)octahydrocyclopenta[c]pyrrol-5-yl)oxy)ethyl)-1H-indol-3-yl)acetamide | 410.2 |
| 294 | 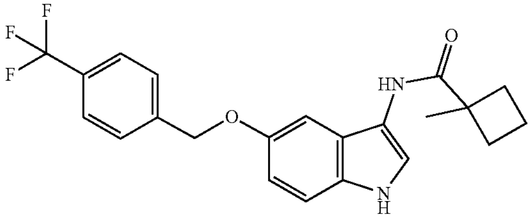 [SMILES: CC1(C(=O)Nc2c[nH]c3ccc(OCc4ccc(C(F)(F)F)cc4)cc23)CCC1] 1-methyl-N-(5-((4-(trifluoromethyl)benzyl)oxy)-1H-indol-3-yl)cyclobutane-1-carboxamide | 403.3 |
| 295 | 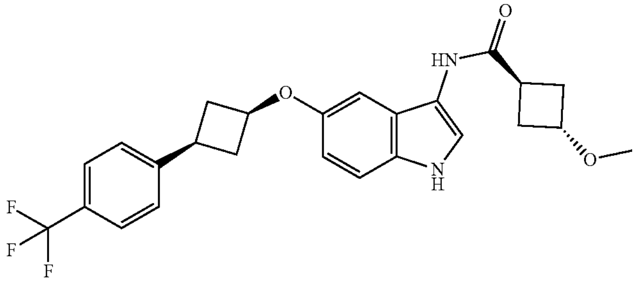 [SMILES: CO[C@H]1C[C@H](C(=O)Nc2c[nH]c3ccc(O[C@H]4C[C@@H](c5ccc(C(F)(F)F)cc5)C4)cc23)C1] trans-3-methoxy-N-(5-(cis-3-(4-(trifluoromethyl)phenyl)cyclobutoxy)-1H-indol-3-yl)cyclobutane-1-carboxamide | 459.4 |

TABLE C1-continued

| Compound No. | Structure | LC-MS |
|---|---|---|
| 296 | 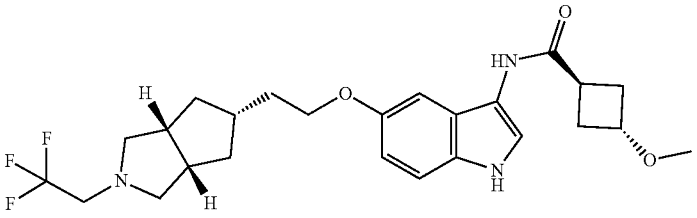 [SMILES: CO[C@H]1C[C@H](C(=O)Nc2c[nH]c3ccc(OCC[C@@H]4C[C@@H]5CN(CC(F)(F)F)C[C@@H]5C4)cc23)C1] trans-3-methoxy-N-(5-(2-((3aR,5r,6aS)-2-(2,2,2-trifluoroethyl)octahydrocyclopenta[c]pyrrol-5-yl)ethoxy)-1H-indol-3-yl)cyclobutane-1-carboxamide | 480.4 |
| 297 | 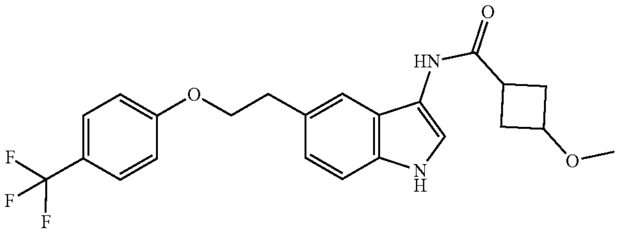 [SMILES: COC1CC(C(=O)Nc2c[nH]c3ccc(CCOc4ccc(C(F)(F)F)cc4)cc23)C1] 3-methoxy-N-(5-(2-(4-(trifluoromethyl)phenoxy)ethyl)-1H-indol-3-yl)cyclobutane-1-carboxamide | 433.2 |
| 298 | 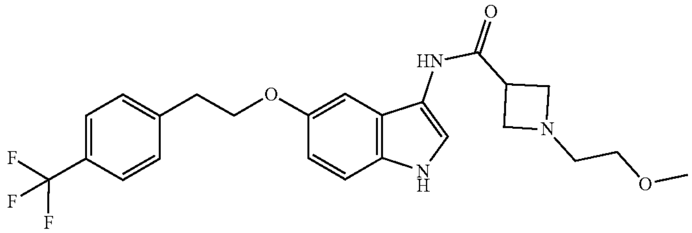 [SMILES: COCCN1CC(C(=O)Nc2c[nH]c3ccc(OCCc4ccc(C(F)(F)F)cc4)cc23)C1] 1-(2-methoxyethyl)-N-(5-(4-(trifluoromethyl)phenethoxy)-1H-indol-3-yl)azetidine-3-carboxamide | 462.3 |
| 299 | 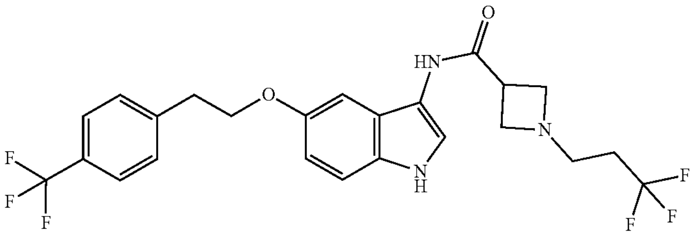 [SMILES: O=C(Nc1c[nH]c2ccc(OCCc3ccc(C(F)(F)F)cc3)cc12)C1CN(CCC(F)(F)F)C1] N-(5-(4-(trifluoromethyl)phenethoxy)-1H-indol-3-yl)-1-(3,3,3-trifluoropropyl)azetidine-3-carboxamide | 500.1 |
| 300 | 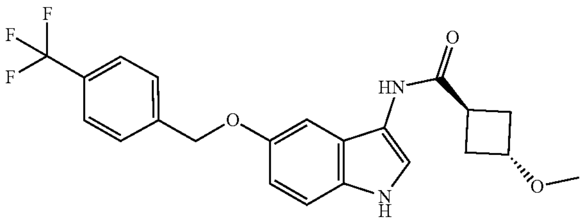 [SMILES: CO[C@H]1C[C@H](C(=O)Nc2c[nH]c3ccc(OCc4ccc(C(F)(F)F)cc4)cc23)C1] | 419.3 |

TABLE C1-continued

| Compound No. | Structure | LC-MS |
|---|---|---|
| | trans-3-methoxy-N-(5-((4-(trifluoromethyl)benzyl)oxy)-1H-indol-3-yl)cyclobutane-1-carboxamide | |
| 301 | 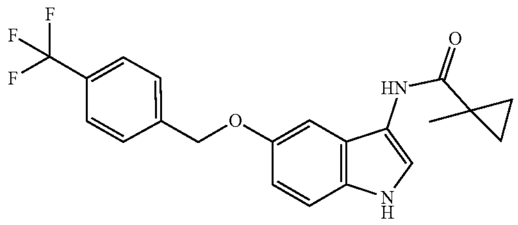 1-methyl-N-(5-((4-(trifluoromethyl)benzyl)oxy)-1H-indol-3-yl)cyclopropane-1-carboxamide | 389.3 |
| 302 | 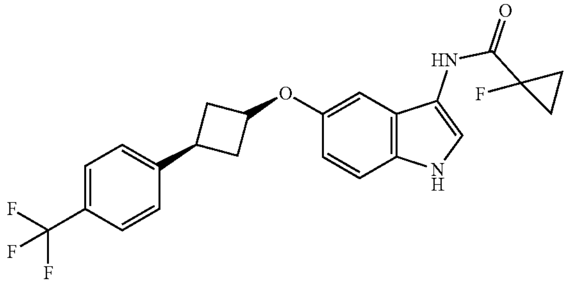 1-fluoro-N-(5-(cis-3-(4-(trifluoromethyl)phenyl)cyclobutoxy)-1H-indol-3-yl)cyclopropane-1-carboxamide | 433.3 |
| 303 | 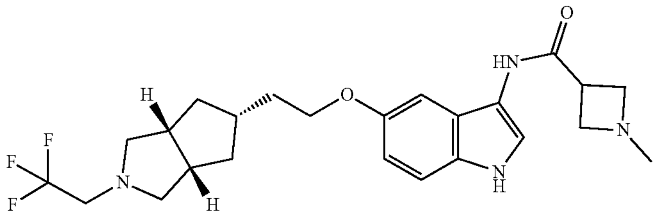 [SMILES: CN1CC(C(=O)Nc2c[nH]c3ccc(OCC[C@@H]4C[C@@H]5CN(CC(F)(F)F)C[C@@H]5C4)cc23)C1] 1-methyl-N-(5-(2-((3aR,5r,6aS)-2-(2,2,2-trifluoroethyl)octahydrocyclopenta[c]pyrrol-5-yl)ethoxy)-1H-indol-3-yl)azetidine-3-carboxamide | 465.4 |
| 304 | 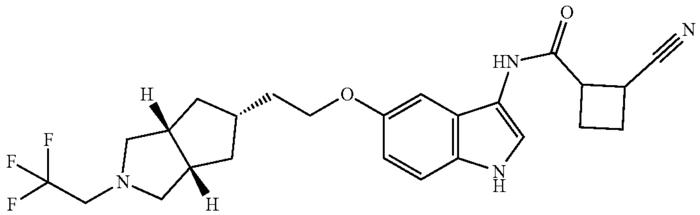 [SMILES: N#CC1CCC1C(=O)Nc1c[nH]c2ccc(OCC[C@@H]3C[C@@H]4CN(CC(F)(F)F)C[C@@H]4C3)cc12] 2-cyano-N-(5-(2-((3aR,5r,6aS)-2-(2,2,2-trifluoroethyl)octahydrocyclopenta[c]pyrrol-5-yl)ethoxy)-1H-indol-3-yl)cyclobutane-1-carboxamide | 475.4 |
| 305 | 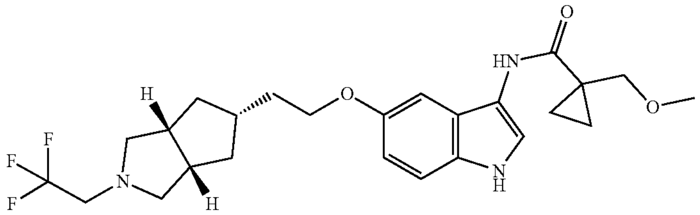 [SMILES: COCC1(C(=O)Nc2c[nH]c3ccc(OCC[C@@H]4C[C@@H]5CN(CC(F)(F)F)C[C@@H]5C4)cc23)CC1] | 480.4 |

TABLE C1-continued

| Compound No. | Structure | LC-MS |
|---|---|---|
| | 1-(methoxymethyl)-N-(5-(2-((3aR,5r,6aS)-2-(2,2,2-trifluoroethyl)octahydrocyclopenta[c]pyrrol-5-yl)ethoxy)-1H-indol-3-yl)cyclopropane-1-carboxamide | |
| 306 | 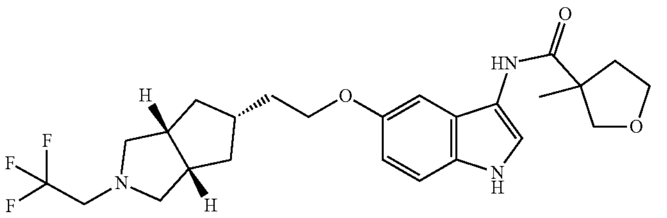 [SMILES: CC1(C(=O)Nc2c[nH]c3ccc(OCC[C@@H]4C[C@@H]5CN(CC(F)(F)F)C[C@@H]5C4)cc23)CCOC1]<br>3-methyl-N-(5-(2-((3aR,5r,6aS)-2-(2,2,2-trifluoroethyl)octahydrocyclopenta[c]pyrrol-5-yl)ethoxy)-1H-indol-3-yl)tetrahydrofuran-3-carboxamide | 480.4 |
| 307 | 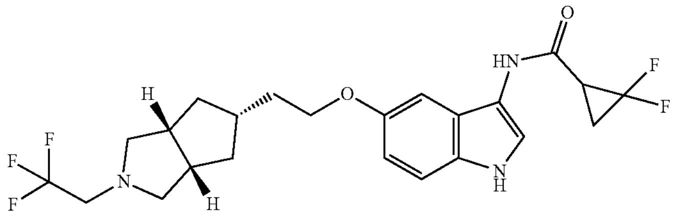 [SMILES: O=C(Nc1c[nH]c2ccc(OCC[C@@H]3C[C@@H]4CN(CC(F)(F)F)C[C@@H]4C3)cc12)C1CC1(F)F]<br>2,2-difluoro-N-(5-(2-((3aR,5r,6aS)-2-(2,2,2-trifluoroethyl)octahydrocyclopenta[c]pyrrol-5-yl)ethoxy)-1H-indol-3-yl)cyclopropane-1-carboxamide | 472.3 |
| 308 | 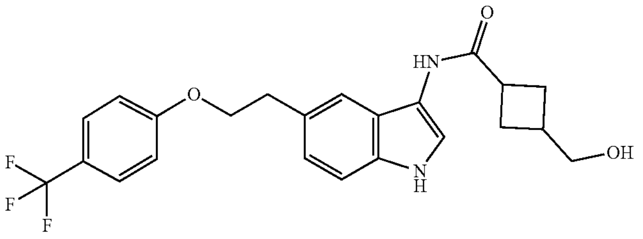 [SMILES: O=C(Nc1c[nH]c2ccc(CCOc3ccc(C(F)(F)F)cc3)cc12)C1CC(CO)C1]<br>3-(hydroxymethyl)-N-(5-(2-(4-(trifluoromethyl)phenoxy)ethyl)-1H-indol-3-yl)cyclobutane-1-carboxamide | 433.3 |
| 309 | 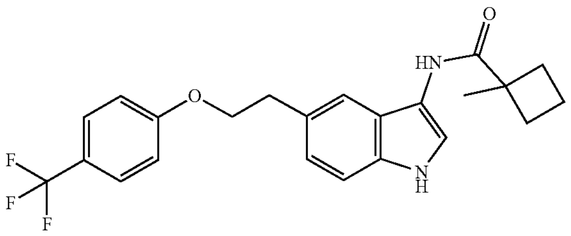 [SMILES: CC1(C(=O)Nc2c[nH]c3ccc(CCOc4ccc(C(F)(F)F)cc4)cc23)CCC1]<br>1-methyl-N-(5-(2-(4-(trifluoromethyl)phenoxy)ethyl)-1H-indol-3-yl)cyclobutane-1-carboxamide | 417.3 |

TABLE C1-continued

| Compound No. | Structure | LC-MS |
|---|---|---|
| 310 | 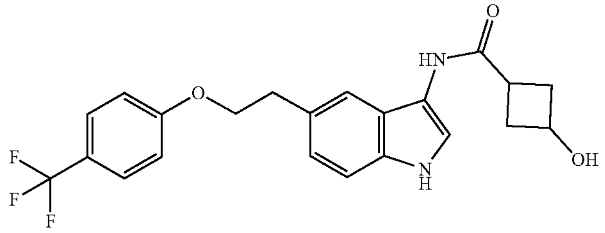 [SMILES: O=C(Nc1c[nH]c2ccc(CCOc3ccc(C(F)(F)F)cc3)cc12)C1CC(O)C1]<br>3-hydroxy-N-(5-(2-(4-(trifluoromethyl)phenoxy)ethyl)-1H-indol-3-yl)cyclobutane-1-carboxamide | 419.0 |
| 311 | 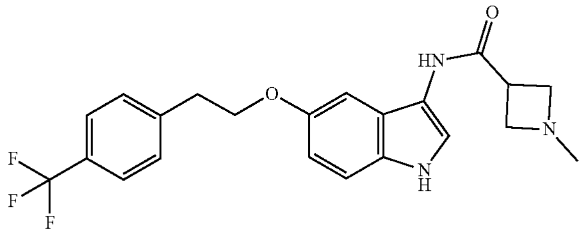 [SMILES: CN1CC(C(=O)Nc2c[nH]c3ccc(OCCc4ccc(C(F)(F)F)cc4)cc23)C1]<br>1-methyl-N-(5-(4-(trifluoromethyl)phenethoxy)-1H-indol-3-yl)azetidine-3-carboxamide | 418.0 |
| 312 | 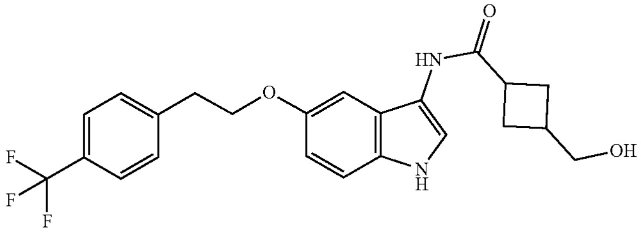 [SMILES: O=C(Nc1c[nH]c2ccc(OCCc3ccc(C(F)(F)F)cc3)cc12)C1CC(CO)C1]<br>3-(hydroxymethyl)-N-(5-(4-(trifluoromethyl)phenethoxy)-1H-indol-3-yl)cyclobutane-1-carboxamide | 433.3 |
| 313 | 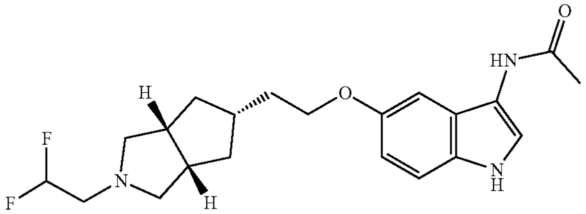 [SMILES: CC(=O)Nc1c[nH]c2ccc(OCC[C@@H]3C[C@@H]4CN(CC(F)F)C[C@@H]4C3)cc12]<br>N-(5-(2-((3aR,5r,6aS)-2-(2,2-difluoroethyl)octahydrocyclopenta[c]pyrrol-5-yl)ethoxy)-1H-indol-3-yl)acetamide | 392.25 |
| 314 | 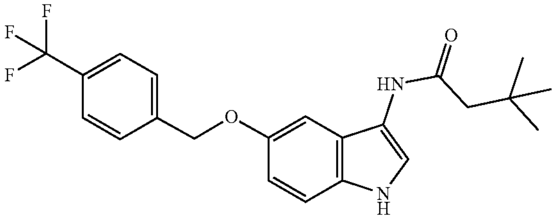 [SMILES: CC(C)(C)CC(=O)Nc1c[nH]c2ccc(OCc3ccc(C(F)(F)F)cc3)cc12]<br>3,3-dimethyl-N-(5-((4-(trifluoromethyl)benzyl)oxy)-1H-indol-3-yl)butanamide | 300.15 |

TABLE C1-continued

| Compound No. | Structure | LC-MS |
|---|---|---|
| 315 | 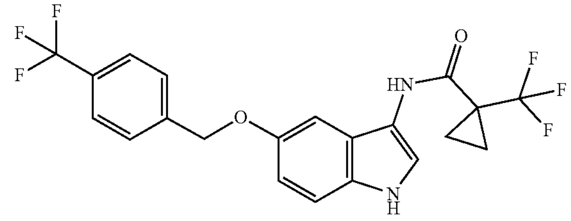 [SMILES: O=C(Nc1c[nH]c2ccc(OCc3ccc(C(F)(F)F)cc3)cc12)C1(C(F)(F)F)CC1]<br>1-(trifluoromethyl)-N-(5-((4-(trifluoromethyl)benzyl)oxy)-1H-indol-3-yl)cyclopropane-1-carboxamide | 423.3 |
| 316 | 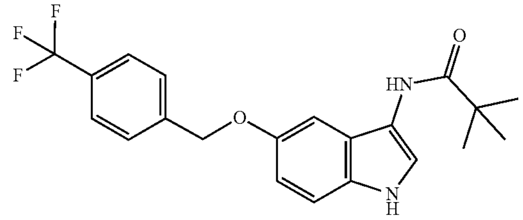 [SMILES: CC(C)(C)C(=O)Nc1c[nH]c2ccc(OCc3ccc(C(F)(F)F)cc3)cc12]<br>N-(5-((4-(trifluoromethyl)benzyl)oxy)-1H-indol-3-yl)pivalamide | 405.0 |
| 317 | 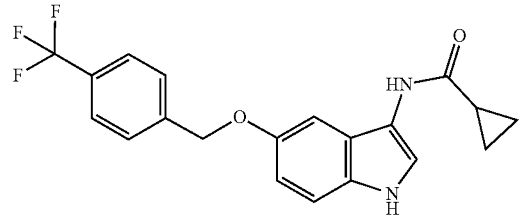 [SMILES: O=C(Nc1c[nH]c2ccc(OCc3ccc(C(F)(F)F)cc3)cc12)C1CC1]<br>N-(5-((4-(trifluoromethyl)benzyl)oxy)-1H-indol-3-yl)cyclopropanecarboxamide | 443.0 |
| 318 | 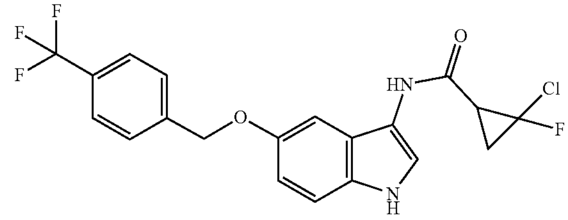 [SMILES: O=C(Nc1c[nH]c2ccc(OCc3ccc(C(F)(F)F)cc3)cc12)C1CC1(F)Cl]<br>2-chloro-2-fluoro-N-(5-((4-(trifluoromethyl)benzyl)oxy)-1H-indol-3-yl)cyclopropane-1-carboxamide | 391.0 |
| 319 | 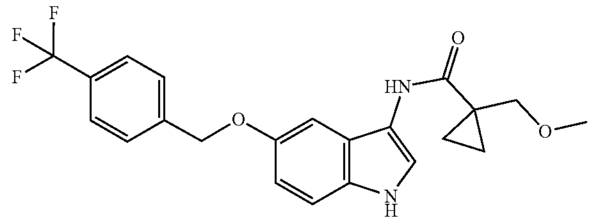 [SMILES: COCC1(C(=O)Nc2c[nH]c3ccc(OCc4ccc(C(F)(F)F)cc4)cc23)CC1]<br>1-(methoxymethyl)-N-(5-((4-(trifluoromethyl)benzyl)oxy)-1H-indol-3-yl)cyclopropane-1-carboxamide | 375.0 |

TABLE C1-continued

| Compound No. | Structure | LC-MS |
|---|---|---|
| 320 | 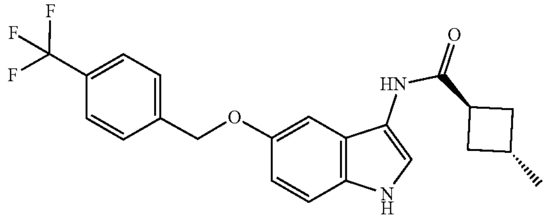 [SMILES: C[C@H]1C[C@H](C(=O)Nc2c[nH]c3ccc(OCc4ccc(C(F)(F)F)cc4)cc23)C1] trans-3-methyl-N-(5-((4-(trifluoromethyl)benzyl)oxy)-1H-indol-3-yl)cyclobutane-1-carboxamide | 427.2 |
| 321 | 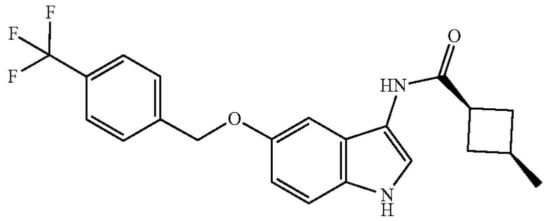 [SMILES: C[C@H]1C[C@@H](C(=O)Nc2c[nH]c3ccc(OCc4ccc(C(F)(F)F)cc4)cc23)C1] cis-3-methyl-N-(5-((4-(trifluoromethyl)benzyl)oxy)-1H-indol-3-yl)cyclobutane-1-carboxamide | 419.0 |
| 322 | 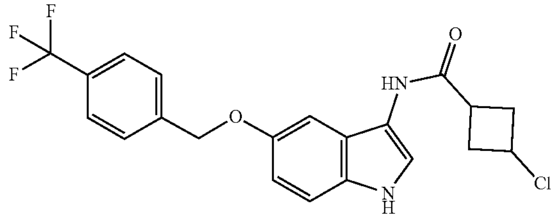 [SMILES: O=C(Nc1c[nH]c2ccc(OCc3ccc(C(F)(F)F)cc3)cc12)C1CC(Cl)C1] 3-chloro-N-(5-((4-(trifluoromethyl)benzyl)oxy)-1H-indol-3-yl)cyclobutane-1-carboxamide | 403.3 |
| 323 | 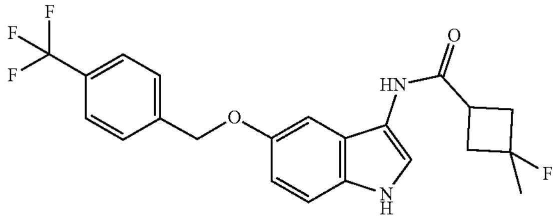 [SMILES: CC1(F)CC(C(=O)Nc2c[nH]c3ccc(OCc4ccc(C(F)(F)F)cc4)cc23)C1] 3-fluoro-3-methyl-N-(5-((4-(trifluoromethyl)benzyl)oxy)-1H-indol-3-yl)cyclobutane-1-carboxamide | 403.3 |
| 324 | 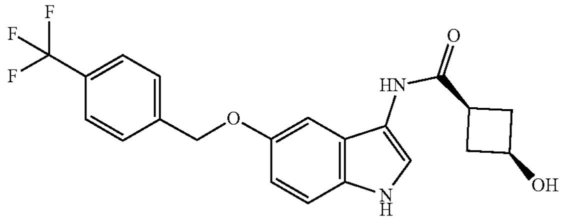 [SMILES: O=C(Nc1c[nH]c2ccc(OCc3ccc(C(F)(F)F)cc3)cc12)[C@H]1C[C@@H](O)C1] cis-3-hydroxy-N-(5-((4-(trifluoromethyl)benzyl)oxy)-1H-indol-3-yl)cyclobutane-1-carboxamide | 423.2 |

TABLE C1-continued

| Compound No. | Structure | LC-MS |
|---|---|---|
| 325 | 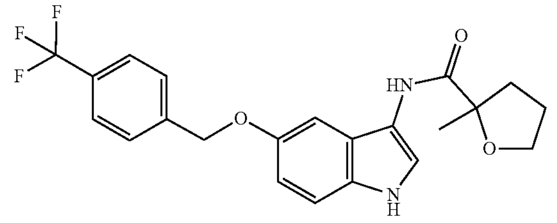 [SMILES: CC1(C(=O)Nc2c[nH]c3ccc(OCc4ccc(C(F)(F)F)cc4)cc23)CCCO1]<br>2-methyl-N-(5-((4-(trifluoromethyl)benzyl)oxy)-1H-indol-3-yl)tetrahydrofuran-2-carboxamide | 421.3 |
| 326 | 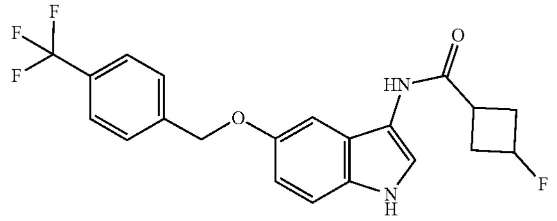 [SMILES: O=C(Nc1c[nH]c2ccc(OCc3ccc(C(F)(F)F)cc3)cc12)C1CC(F)C1]<br>3-fluoro-N-(5-((4-(trifluoromethyl)benzyl)oxy)-1H-indol-3-yl)cyclobutane-1-carboxamide | 405.3 |
| 327 | 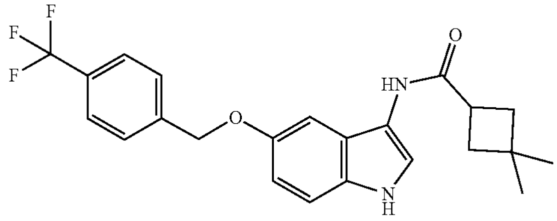 [SMILES: CC1(C)CC(C(=O)Nc2c[nH]c3ccc(OCc4ccc(C(F)(F)F)cc4)cc23)C1]<br>3,3-dimethyl-N-(5-((4-(trifluoromethyl)benzyl)oxy)-1H-indol-3-yl)cyclobutane-1-carboxamide | 419.0 |
| 328 | 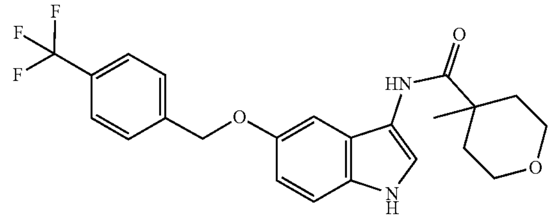 [SMILES: CC1(C(=O)Nc2c[nH]c3ccc(OCc4ccc(C(F)(F)F)cc4)cc23)CCOCC1]<br>4-methyl-N-(5-((4-(trifluoromethyl)benzyl)oxy)-1H-indol-3-yl)tetrahydro-2H-pyran-4-carboxamide | 407.0 |
| 329 | 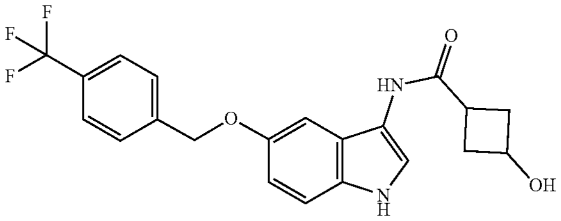 [SMILES: O=C(Nc1c[nH]c2ccc(OCc3ccc(C(F)(F)F)cc3)cc12)C1CC(O)C1]<br>3-hydroxy-N-(5-((4-(trifluoromethyl)benzyl)oxy)-1H-indol-3-yl)cyclobutane-1-carboxamide | 417.3 |

TABLE C1-continued

| Compound No. | Structure | LC-MS |
|---|---|---|
| 330 | 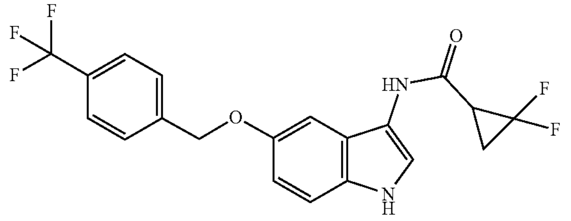 [SMILES: O=C(Nc1c[nH]c2ccc(OCc3ccc(C(F)(F)F)cc3)cc12)C1CC1(F)F] 2,2-difluoro-N-(5-((4-(trifluoromethyl)benzyl)oxy)-1H-indol-3-yl)cyclopropane-1-carboxamide | 433.0 |
| 331 | 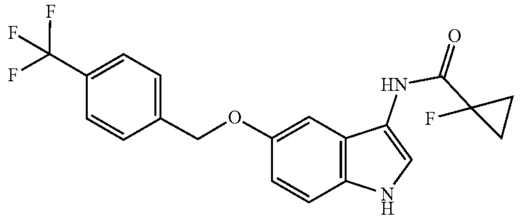 [SMILES: O=C(Nc1c[nH]c2ccc(OCc3ccc(C(F)(F)F)cc3)cc12)C1(F)CC1] 1-fluoro-N-(5-((4-(trifluoromethyl)benzyl)oxy)-1H-indol-3-yl)cyclopropane-1-carboxamide | 405.3 |
| 332 | 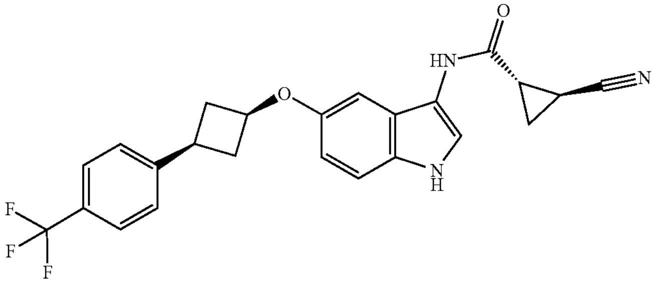 [SMILES: N#C[C@H]1C[C@@H]1C(=O)Nc1c[nH]c2ccc(O[C@H]3C[C@@H](c4ccc(C(F)(F)F)cc4)C3)cc12] cis-2-cyano-N-(5-(cis-3-(4-(trifluoromethyl)phenyl)cyclobutoxy)-1H-indol-3-yl)cyclopropane-1-carboxamide | 411.2 |
| 333 | 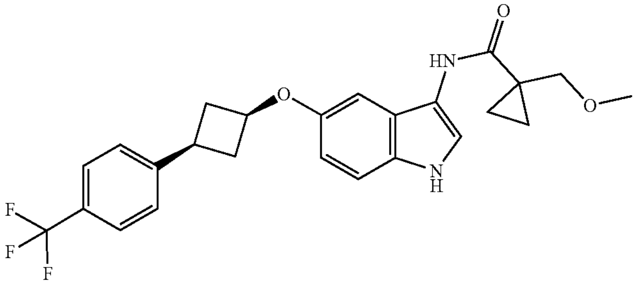 [SMILES: COCC1(C(=O)Nc2c[nH]c3ccc(O[C@H]4C[C@@H](c5ccc(C(F)(F)F)cc5)C4)cc23)CC1] 1-(methoxymethyl)-N-(5-(cis-3-(4-(trifluoromethyl)phenyl)cyclobutoxy)-1H-indol-3-yl)cyclopropane-1-carboxamide | 393.0 |

TABLE C1-continued

| Compound No. | Structure | LC-MS |
|---|---|---|
| 334 | 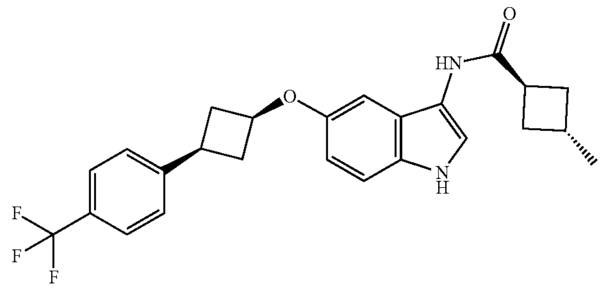 [SMILES: C[C@H]1C[C@H](C(=O)Nc2c[nH]c3ccc(O[C@H]4C[C@@H](c5ccc(C(F)(F)F)cc5)C4)cc23)C1] trans-3-methyl-N-(5-(cis-3-(4-(trifluoromethyl)phenyl)cyclobutoxy)-1H-indol-3-yl)cyclobutane-1-carboxamide | 440.3 |
| 335 | 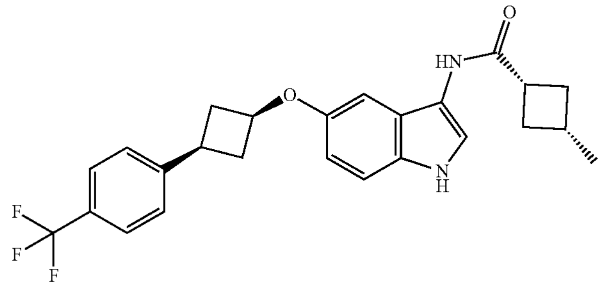 cis-3-methyl-N-(5-(cis-3-(4-(trifluoromethyl)phenyl)cyclobutoxy)-1H-indol-3-yl)cyclobutane-1-carboxamide | 459.1 |
| 336 | 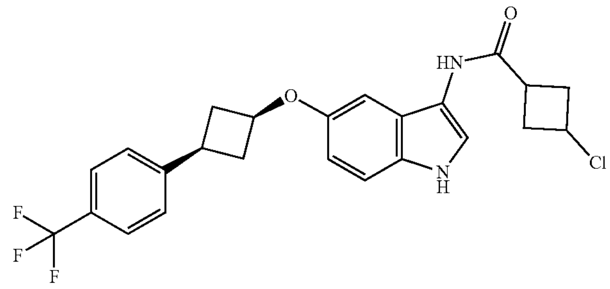 [SMILES: O=C(Nc1c[nH]c2ccc(O[C@H]3C[C@@H](c4ccc(C(F)(F)F)cc4)C3)cc12)C1CC(Cl)C1] 3-chloro-N-(5-(cis-3-(4-(trifluoromethyl)phenyl)cyclobutoxy)-1H-indol-3-yl)cyclobutane-1-carboxamide | 443.3 |
| 337 | 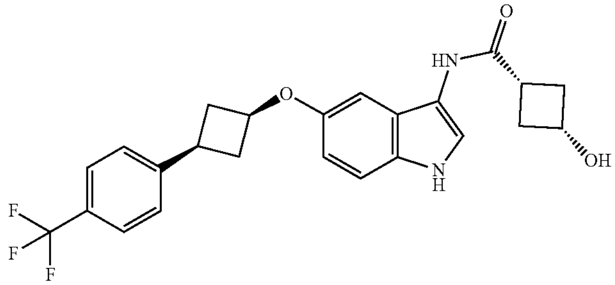 cis-3-hydroxy-N-(5-(cis-3-(4-(trifluoromethyl)phenyl)cyclobutoxy)-1H-indol-3-yl)cyclobutane-1-carboxamide | 443.3 |

TABLE C1-continued

| Compound No. | Structure | LC-MS |
|---|---|---|
| 338 | 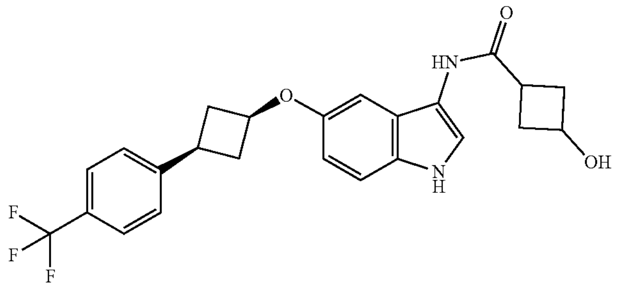 3-hydroxy-N-(5-(cis-3-(4-(trifluoromethyl)phenyl)cyclobutoxy)-1H-indol-3-yl)cyclobutane-1-carboxamide | 463.1 |
| 339 | 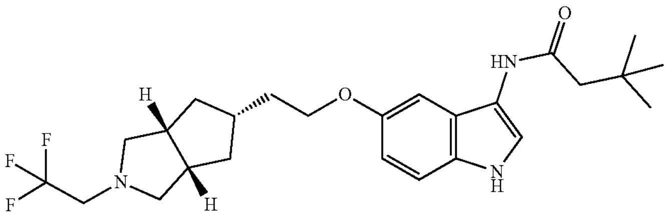 [SMILES: CC(C)(C)CC(=O)Nc1c[nH]c2ccc(OCC[C@@H]3C[C@@H]4CN(CC(F)(F)F)C[C@@H]4C3)cc12] 3,3-dimethyl-N-(5-(2-((3aR,5r,6aS)-2-(2,2,2-trifluoroethyl)octahydrocyclopenta[c]pyrrol-5-yl)ethoxy)-1H-indol-3-yl)butanamide | 445.3 |
| 340 | 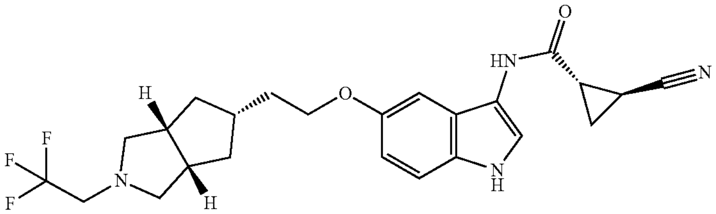 (1S,2S)-2-cyano-N-(5-(2-((3aR,5r,6aS)-2-(2,2,2-trifluoroethyl)octahydrocyclopenta[c]pyrrol-5-yl)ethoxy)-1H-indol-3-yl)cyclopropane-1-carboxamide | 445.2 |
| 341 | 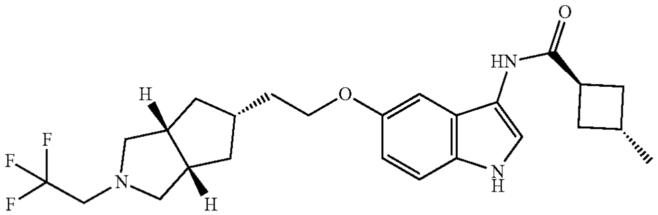 [SMILES: C[C@H]1C[C@H](C(=O)Nc2c[nH]c3ccc(OCC[C@@H]4C[C@@H]5CN(CC(F)(F)F)C[C@@H]5C4)cc23)C1] (1r,3R)-3-methyl-N-(5-(2-((3aR,5r,6aS)-2-(2,2,2-trifluoroethyl)octahydrocyclopenta[c]pyrrol-5-yl)ethoxy)-1H-indol-3-yl)cyclobutane-1-carboxamide | 466.4 |
| 342 | 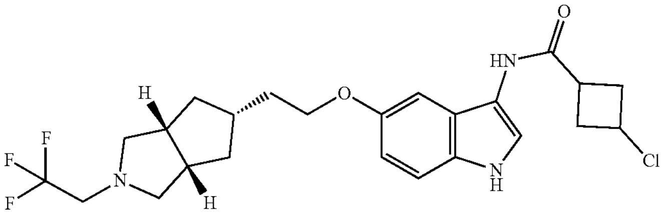 [SMILES: O=C(Nc1c[nH]c2ccc(OCC[C@@H]3C[C@@H]4CN(CC(F)(F)F)C[C@@H]4C3)cc12)C1CC(Cl)C1] | 461.4 |

TABLE C1-continued

| Compound No. | Structure | LC-MS |
| --- | --- | --- |
| | 3-chloro-N-(5-(2-((3aR,5r,6aS)-2-(2,2,2-trifluoroethyl)octahydrocyclopenta[c]pyrrol-5-yl)ethoxy)-1H-indol-3-yl)cyclobutane-1-carboxamide | |
| 343 | 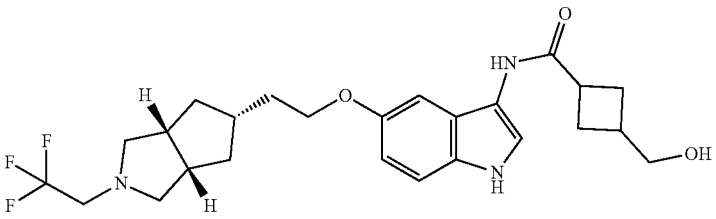 [SMILES: O=C(Nc1c[nH]c2ccc(OCC[C@@H]3C[C@@H]4CN(CC(F)(F)F)C[C@@H]4C3)cc12)C1CC(CO)C1]<br>3-(hydroxymethyl)-N-(5-(2-((3aR,5r,6aS)-2-(2,2,2-trifluoroethyl)octahydrocyclopenta[c]pyrrol-5-yl)ethoxy)-1H-indol-3-yl)cyclobutane-1-carboxamide | 464.4 |
| 344 | 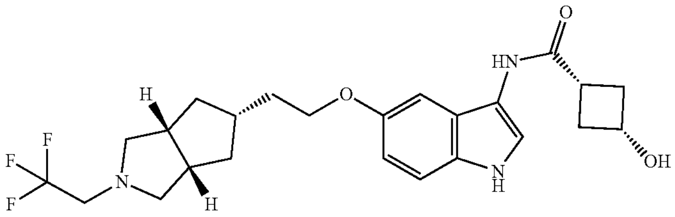 [SMILES: O=C(Nc1c[nH]c2ccc(OCC[C@@H]3C[C@@H]4CN(CC(F)(F)F)C[C@@H]4C3)cc12)[C@H]1C[C@@H](O)C1]<br>cis-3-hydroxy-N-(5-(2-((3aR,5r,6aS)-2-(2,2,2-trifluoroethyl)octahydrocyclopenta[c]pyrrol-5-yl)ethoxy)-1H-indol-3-yl)cyclobutane-1-carboxamide | 484.0 |
| 345 | 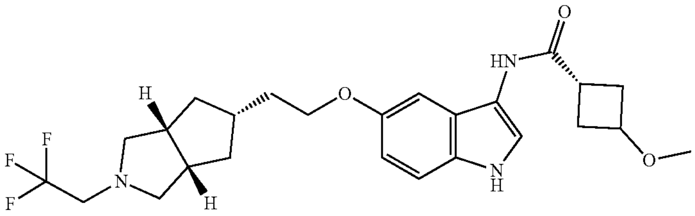<br>3-methoxy-N-(5-(2-((3aR,5r,6aS)-2-(2,2,2-trifluoroethyl)octahydrocyclopenta[c]pyrrol-5-yl)ethoxy)-1H-indol-3-yl)cyclobutane-1-carboxamide | 480.3 |
| 346 | 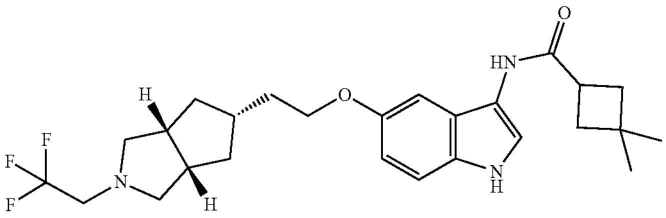 [SMILES: CC1(C)CC(C(=O)Nc2c[nH]c3ccc(OCC[C@@H]4C[C@@H]5CN(CC(F)(F)F)C[C@@H]5C4)cc23)C1]<br>3,3-dimethyl-N-(5-(2-((3aR,5r,6aS)-2-(2,2,2-trifluoroethyl)octahydrocyclopenta[c]pyrrol-5-yl)ethoxy)-1H-indol-3-yl)cyclobutane-1-carboxamide | 466.4 |

TABLE C1-continued

| Compound No. | Structure | LC-MS |
|---|---|---|
| 347 | 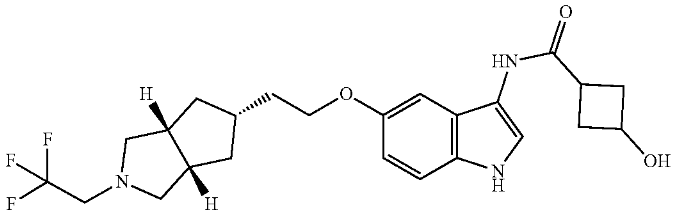 [SMILES: O=C(Nc1c[nH]c2ccc(OCC[C@@H]3C[C@@H]4CN(CC(F)(F)F)C[C@@H]4C3)cc12)C1CC(O)C1]<br>3-hydroxy-N-(5-(2-((3aR,5r,6aS)-2-(2,2,2-trifluoroethyl)octahydrocyclopenta[c]pyrrol-5-yl)ethoxy)-1H-indol-3-yl)cyclobutane-1-carboxamide | 480.1 |
| 348 | 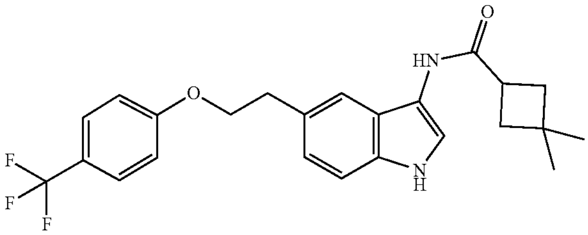 [SMILES: CC1(C)CC(C(=O)Nc2c[nH]c3ccc(CCOc4ccc(C(F)(F)F)cc4)cc23)C1]<br>3,3-dimethyl-N-(5-(2-(4-(trifluoromethyl)phenoxy)ethyl)-1H-indol-3-yl)cyclobutane-1-carboxamide | 478.1 |
| 349 | 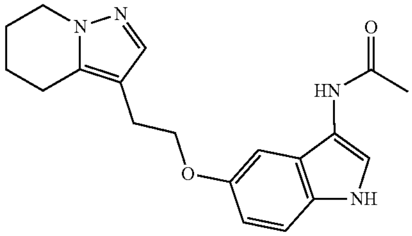 [SMILES: CC(=O)Nc1c[nH]c2ccc(OCCc3cnn4c3CCCC4)cc12]<br>N-(5-(2-(4,5,6,7-tetrahydropyrazolo[1,5-a]pyridin-3-yl)ethoxy)-1H-indol-3-yl)acetamide | 466.1 |
| 350 | 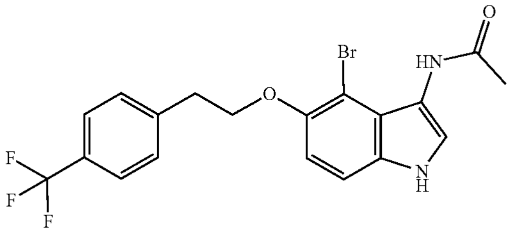 [SMILES: CC(=O)Nc1c[nH]c2ccc(OCCc3ccc(C(F)(F)F)cc3)c(Br)c12]<br>N-(4-bromo-5-(4-(trifluoromethyl)phenethoxy)-1H-indol-3-yl)acetamide | 431.3 |
| 351 | 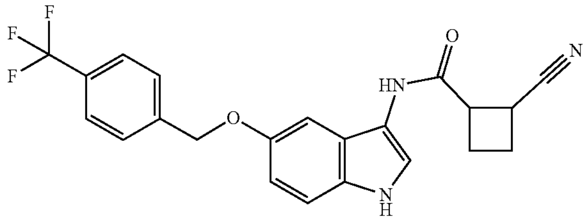 [SMILES: N#CC1CCC1C(=O)Nc1c[nH]c2ccc(OCc3ccc(C(F)(F)F)cc3)cc12]<br>2-cyano-N-(5-((4-(trifluoromethyl)benzyl)oxy)-1H-indol-3-yl)cyclobutane-1-carboxamide | 339.1 |

TABLE C1-continued

| Compound No. | Structure | LC-MS |
| --- | --- | --- |
| 352 | 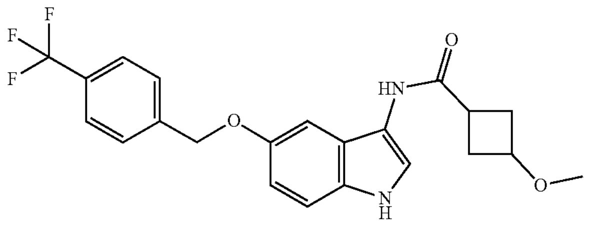 [SMILES: COC1CC(C(=O)Nc2c[nH]c3ccc(OCc4ccc(C(F)(F)F)cc4)cc23)C1]<br>3-methoxy-N-(5-((4-(trifluoromethyl)benzyl)oxy)-1H-indol-3-yl)cyclobutane-1-carboxamide | 441.0 |
| 353 | 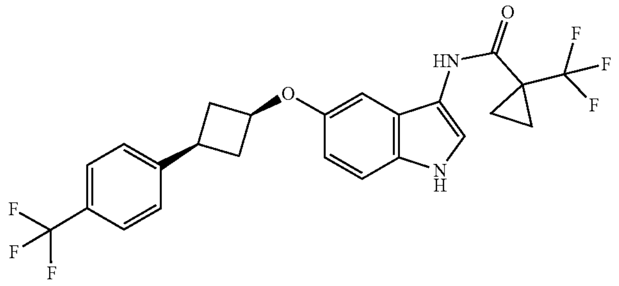 [SMILES: O=C(Nc1c[nH]c2ccc(O[C@H]3C[C@@H](c4ccc(C(F)(F)F)cc4)C3)cc12)C1(C(F)(F)F)CC1]<br>1-(trifluoromethyl)-N-(5-(cis-3-(4-(trifluoromethyl)phenyl)cyclobutoxy)-1H-indol-3-yl)cyclopropane-1-carboxamide | 414.3 |
| 354 | 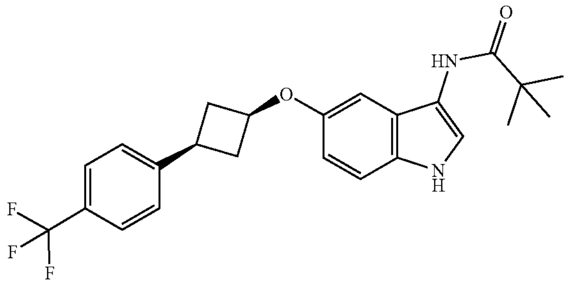 [SMILES: CC(C)(C)C(=O)Nc1c[nH]c2ccc(O[C@H]3C[C@@H](c4ccc(C(F)(F)F)cc4)C3)cc12]<br>N-(5-(cis-3-(4-(trifluoromethyl)phenyl)cyclobutoxy)-1H-indol-3-yl)pivalamide | 419.3 |
| 355 | 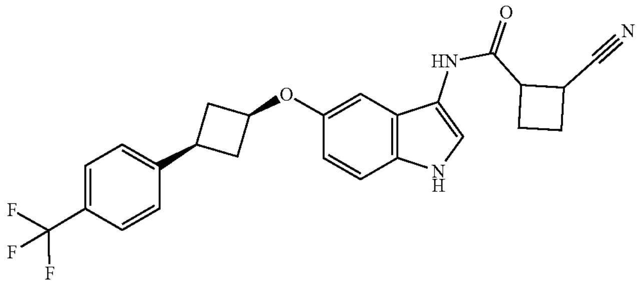 [SMILES: N#CC1CCC1C(=O)Nc1c[nH]c2ccc(O[C@H]3C[C@@H](c4ccc(C(F)(F)F)cc4)C3)cc12]<br>2-cyano-N-(5-(cis-3-(4-(trifluoromethyl)phenyl)cyclobutoxy)-1H-indol-3-yl)cyclobutane-1-carboxamide | 483.3 |

TABLE C1-continued

| Compound No. | Structure | LC-MS |
|---|---|---|
| 356 | 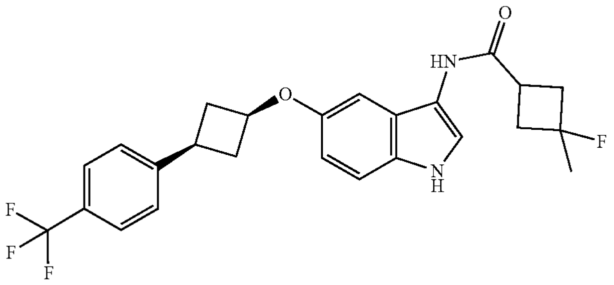 [SMILES: CC1(F)CC(C(=O)Nc2c[nH]c3ccc(O[C@H]4C[C@@H](c5ccc(C(F)(F)F)cc5)C4)cc23)C1]<br>3-fluoro-3-methyl-N-(5-(cis-3-(4-(trifluoromethyl)phenyl)cyclobutoxy)-1H-indol-3-yl)cyclobutane-1-carboxamide | 431.4 |
| 357 | 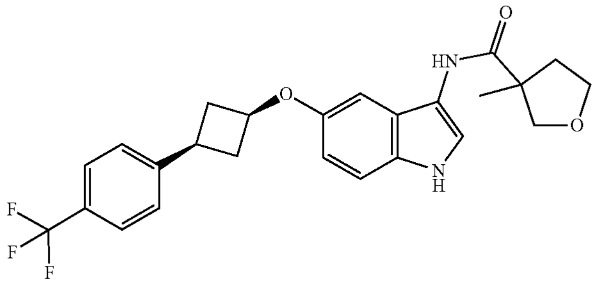 [SMILES: CC1(C(=O)Nc2c[nH]c3ccc(O[C@H]4C[C@@H](c5ccc(C(F)(F)F)cc5)C4)cc23)CCOC1]<br>3-methyl-N-(5-(cis-3-(4-(trifluoromethyl)phenyl)cyclobutoxy)-1H-indol-3-yl)tetrahydrofuran-3-carboxamide | 454.3 |
| 358 | 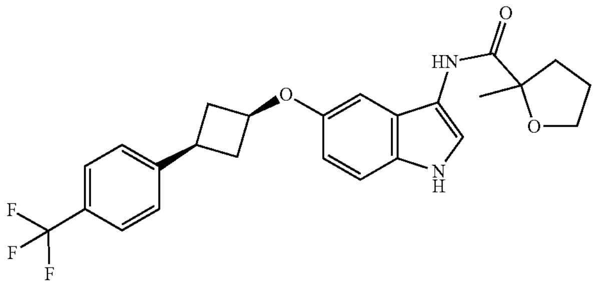 [SMILES: CC1(C(=O)Nc2c[nH]c3ccc(O[C@H]4C[C@@H](c5ccc(C(F)(F)F)cc5)C4)cc23)CCCO1]<br>2-methyl-N-(5-(cis-3-(4-(trifluoromethyl)phenyl)cyclobutoxy)-1H-indol-3-yl)tetrahydrofuran-2-carboxamide | 461.3 |
| 359 | 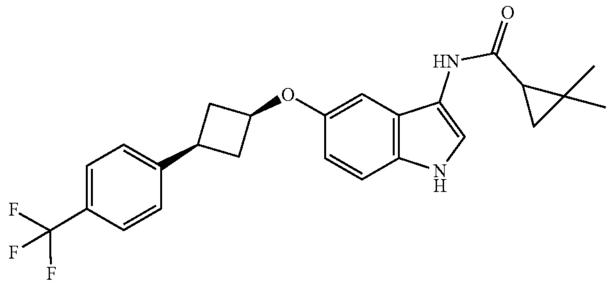 [SMILES: CC1(C)CC1C(=O)Nc1c[nH]c2ccc(O[C@H]3C[C@@H](c4ccc(C(F)(F)F)cc4)C3)cc12]<br>2,2-dimethyl-N-(5-(cis-3-(4-(trifluoromethyl)phenyl)cyclobutoxy)-1H-indol-3-yl)cyclopropane-1-carboxamide | 459.3 |

TABLE C1-continued

| Compound No. | Structure | LC-MS |
|---|---|---|
| 360 | 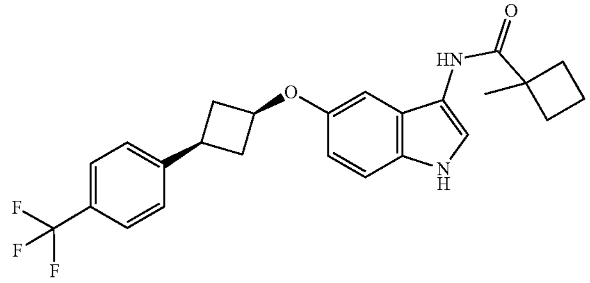 [SMILES: CC1(C(=O)Nc2c[nH]c3ccc(O[C@H]4C[C@@H](c5ccc(C(F)(F)F)cc5)C4)cc23)CCC1] 1-methyl-N-(5-(cis-3-(4-(trifluoromethyl)phenyl)cyclobutoxy)-1H-indol-3-yl)cyclobutane-1-carboxamide | 459.3 |
| 361 | 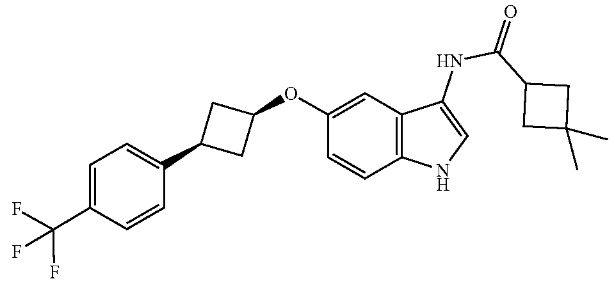 [SMILES: CC1(C)CC(C(=O)Nc2c[nH]c3ccc(O[C@H]4C[C@@H](c5ccc(C(F)(F)F)cc5)C4)cc23)C1] 3,3-dimethyl-N-(5-(cis-3-(4-(trifluoromethyl)phenyl)cyclobutoxy)-1H-indol-3-yl)cyclobutane-1-carboxamide | 443.4 |
| 362 | 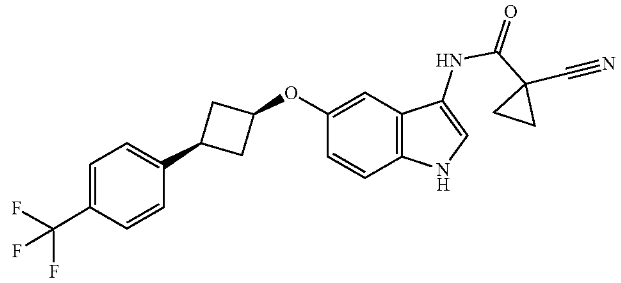 [SMILES: N#CC1(C(=O)Nc2c[nH]c3ccc(O[C@H]4C[C@@H](c5ccc(C(F)(F)F)cc5)C4)cc23)CC1] 1-cyano-N-(5-(cis-3-(4-(trifluoromethyl)phenyl)cyclobutoxy)-1H-indol-3-yl)cyclopropane-1-carboxamide | 443.3 |
| 363 | 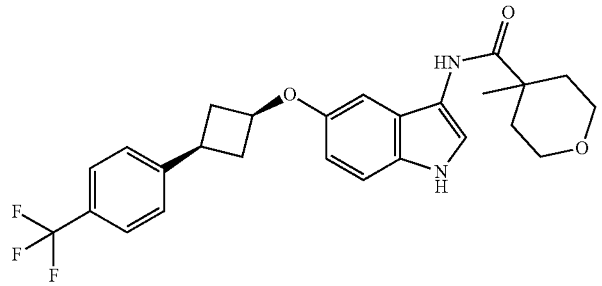 [SMILES: CC1(C(=O)Nc2c[nH]c3ccc(O[C@H]4C[C@@H](c5ccc(C(F)(F)F)cc5)C4)cc23)CCOCC1] 4-methyl-N-(5-(cis-3-(4-(trifluoromethyl)phenyl)cyclobutoxy)-1H-indol-3-yl)tetrahydro-2H-pyran-4-carboxamide | 457.3 |

TABLE C1-continued

| Compound No. | Structure | LC-MS |
|---|---|---|
| 364 | 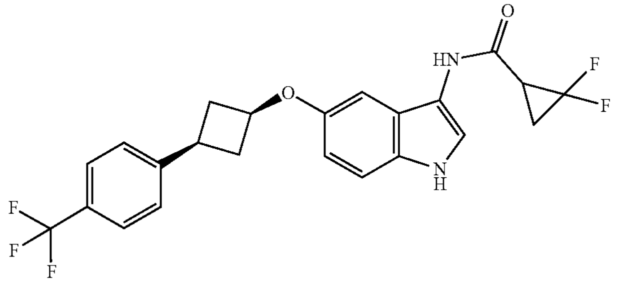 [SMILES: O=C(Nc1c[nH]c2ccc(O[C@H]3C[C@@H](c4ccc(C(F)(F)F)cc4)C3)cc12)C1CC1(F)F] 2,2-difluoro-N-(5-(cis-3-(4-(trifluoromethyl)phenyl)cyclobutoxy)-1H-indol-3-yl)cyclopropane-1-carboxamide | 440.3 |
| 365 | 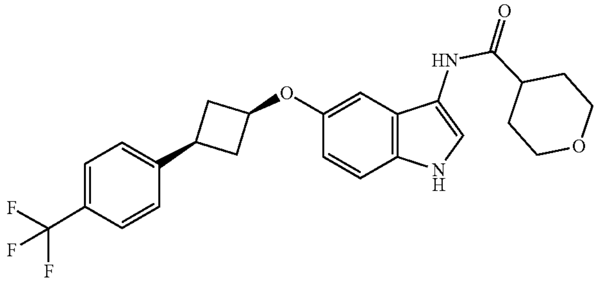 [SMILES: O=C(Nc1c[nH]c2ccc(O[C@H]3C[C@@H](c4ccc(C(F)(F)F)cc4)C3)cc12)C1CCOCC1] N-(5-(cis-3-(4-(trifluoromethyl)phenyl)cyclobutoxy)-1H-indol-3-yl)tetrahydro-2H-pyran-4-carboxamide | 473.3 |
| 366 | 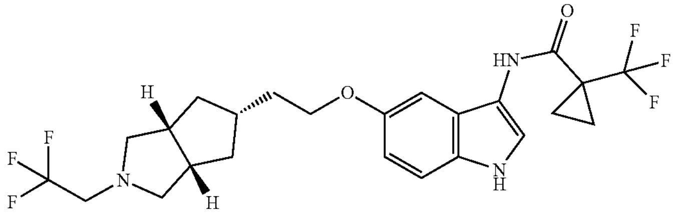 [SMILES: O=C(Nc1c[nH]c2ccc(OCC[C@@H]3C[C@@H]4CN(CC(F)(F)F)C[C@@H]4C3)cc12)C1(C(F)(F)F)CC1] N-(5-(2-((3aR,5r,6aS)-2-(2,2,2-trifluoroethyl)octahydrocyclopenta[c]pyrrol-5-yl)ethoxy)-1H-indol-3-yl)-1-(trifluoromethyl)cyclopropane-1-carboxamide | 451.3 |
| 367 | 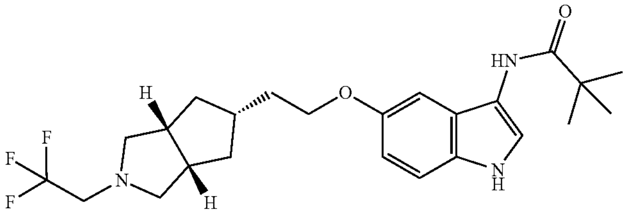 [SMILES: CC(C)(C)C(=O)Nc1c[nH]c2ccc(OCC[C@@H]3C[C@@H]4CN(CC(F)(F)F)C[C@@H]4C3)cc12] N-(5-(2-((3aR,5r,6aS)-2-(2,2,2-trifluoroethyl)octahydrocyclopenta[c]pyrrol-5-yl)ethoxy)-1H-indol-3-yl)pivalamide | 459.3 |
| 368 | 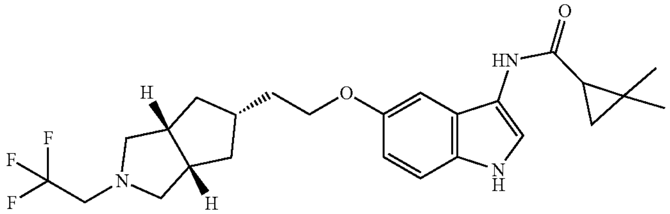 [SMILES: CC1(C)CC1C(=O)Nc1c[nH]c2ccc(OCC[C@@H]3C[C@@H]4CN(CC(F)(F)F)C[C@@H]4C3)cc12] | 484.4 |

TABLE C1-continued

| Compound No. | Structure | LC-MS |
|---|---|---|
| | 2,2-dimethyl-N-(5-(2-((3aR,5r,6aS)-2-(2,2,2-trifluoroethyl)octahydrocyclopenta[c]pyrrol-5-yl)ethoxy)-1H-indol-3-yl)cyclopropane-1-carboxamide | |
| 369 | 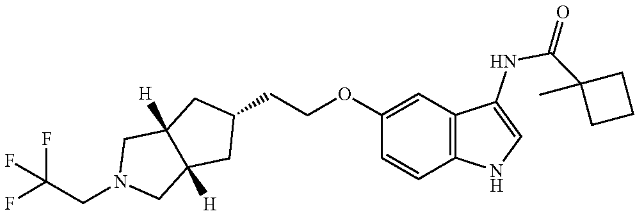 [SMILES: CC1(C(=O)Nc2c[nH]c3ccc(OCC[C@@H]4C[C@@H]5CN(CC(F)(F)F)C[C@@H]5C4)cc23)CCC1] 1-methyl-N-(5-(2-((3aR,5r,6aS)-2-(2,2,2-trifluoroethyl)octahydrocyclopenta[c]pyrrol-5-yl)ethoxy)-1H-indol-3-yl)cyclobutane-1-carboxamide | 504.4 |
| 370 | 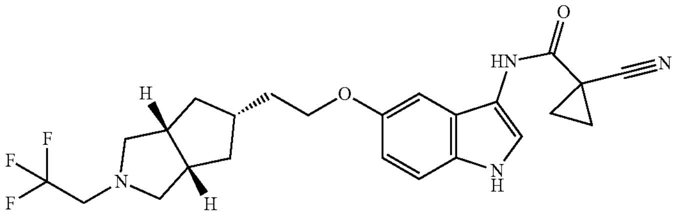 [SMILES: N#CC1(C(=O)Nc2c[nH]c3ccc(OCC[C@@H]4C[C@@H]5CN(CC(F)(F)F)C[C@@H]5C4)cc23)CC1] 1-cyano-N-(5-(2-((3aR,5r,6aS)-2-(2,2,2-trifluoroethyl)octahydrocyclopenta[c]pyrrol-5-yl)ethoxy)-1H-indol-3-yl)cyclopropane-1-carboxamide | 452.4 |
| 371 | 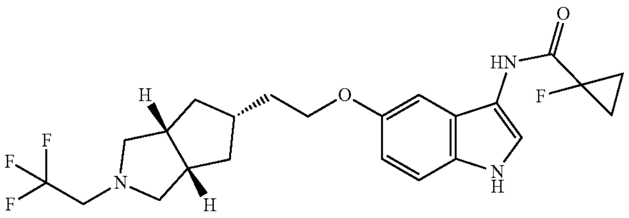 [SMILES: O=C(Nc1c[nH]c2ccc(OCC[C@@H]3C[C@@H]4CN(CC(F)(F)F)C[C@@H]4C3)cc12)C1(F)CC1] 1-fluoro-N-(5-(2-((3aR,5r,6aS)-2-(2,2,2-trifluoroethyl)octahydrocyclopenta[c]pyrrol-5-yl)ethoxy)-1H-indol-3-yl)cyclopropane-1-carboxamide | 464.4 |
| 372 | 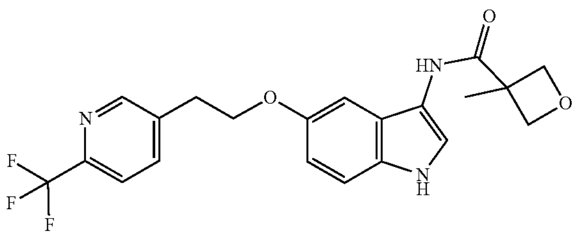 [SMILES: CC1(C(=O)Nc2c[nH]c3ccc(OCCc4ccc(C(F)(F)F)nc4)cc23)COC1] 3-methyl-N-(5-(2-(6-(trifluoromethyl)pyridin-3-yl)ethoxy)-1H-indol-3-yl)oxetane-3-carboxamide | 464.4 |

TABLE C1-continued

| Compound No. | Structure | LC-MS |
|---|---|---|
| 373 | 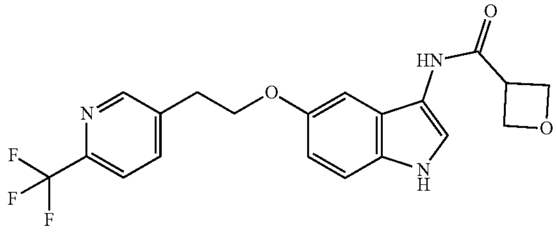 [SMILES: O=C(Nc1c[nH]c2ccc(OCCc3ccc(C(F)(F)F)nc3)cc12)C1COC1] N-(5-(2-(6-(trifluoromethyl)pyridin-3-yl)ethoxy)-1H-indol-3-yl)oxetane-3-carboxamide | 461.4 |
| 374 | 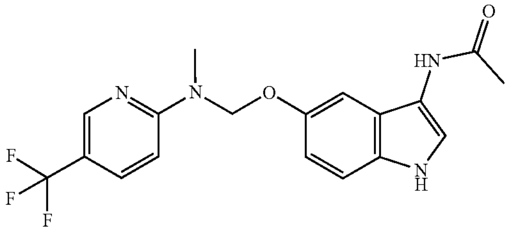 [SMILES: CC(=O)Nc1c[nH]c2ccc(OCN(C)c3ccc(C(F)(F)F)cn3)cc12] N-(5-(2-(methyl(5-(trifluoromethyl)pyridin-2-yl)amino)ethyl)-1H-indol-3-yl)acetamide | 454.4 |
| 375 | 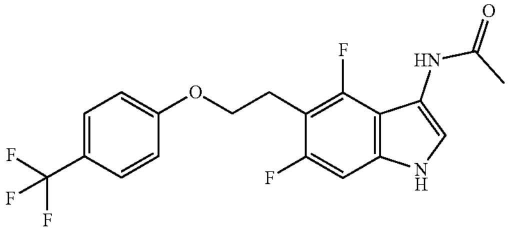 [SMILES: CC(=O)Nc1c[nH]c2cc(F)c(CCOc3ccc(C(F)(F)F)cc3)c(F)c12] N-(4,6-difluoro-5-(2-(4-(trifluoromethyl)phenoxy)ethyl)-1H-indol-3-yl)acetamide | 420.05 |
| 376 | 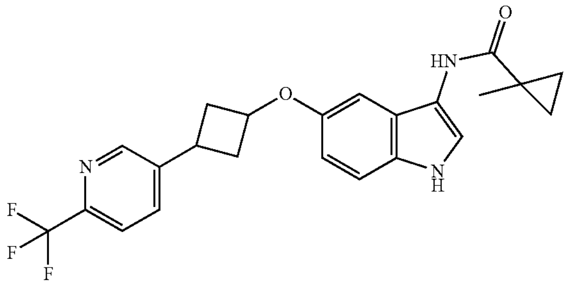 [SMILES: CC1(C(=O)Nc2c[nH]c3ccc(OC4CC(c5ccc(C(F)(F)F)nc5)C4)cc23)CC1] 1-methyl-N-(5-(3-(6-(trifluoromethyl)pyridin-3-yl)cyclobutoxy)-1H-indol-3-yl)cyclopropane-1-carboxamide | 406.15 |
| 377 | 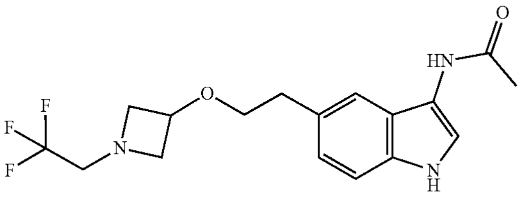 [SMILES: CC(=O)Nc1c[nH]c2ccc(CCOC3CN(CC(F)(F)F)C3)cc12] N-(5-(2-((1-(2,2,2-trifluoroethyl)azetidin-3-yl)oxy)ethyl)-1H-indol-3-yl)acetamide | 377.15 |

TABLE C1-continued

| Compound No. | Structure | LC-MS |
|---|---|---|
| 378 | 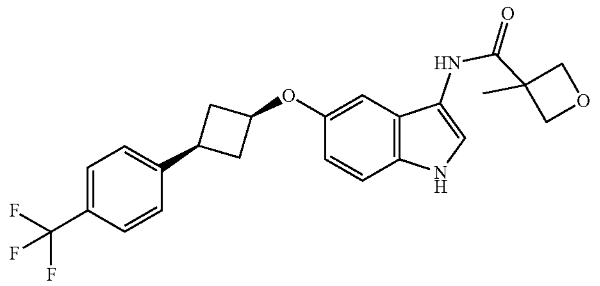 [SMILES: CC1(C(=O)Nc2c[nH]c3ccc(O[C@H]4C[C@@H](c5ccc(C(F)(F)F)cc5)C4)cc23)COC1] 3-methyl-N-(5-(cis-3-(4-(trifluoromethyl)phenyl)cyclobutoxy)-1H-indol-3-yl)oxetane-3-carboxamide | 396.9 |
| 379 | 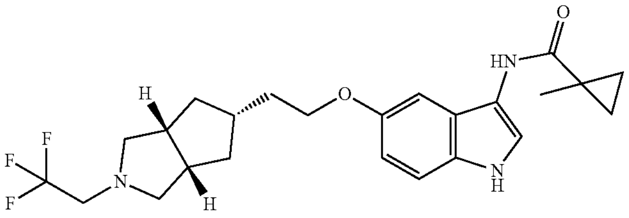 [SMILES: CC1(C(=O)Nc2c[nH]c3ccc(OCC[C@@H]4C[C@@H]5CN(CC(F)(F)F)C[C@@H]5C4)cc23)CC1] 1-methyl-N-(5-(2-((3aR,5r,6aS)-2-(2,2,2-trifluoroethyl)octahydrocyclopenta[c]pyrrol-5-yl)ethoxy)-1H-indol-3-yl)cyclopropane-1-carboxamide | 430.05 |
| 380 | 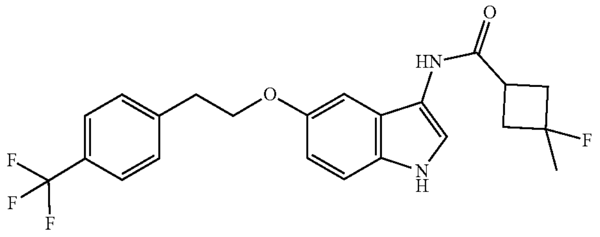 [SMILES: CC1(F)CC(C(=O)Nc2c[nH]c3ccc(OCCc4ccc(C(F)(F)F)cc4)cc23)C1] 3-fluoro-3-methyl-N-(5-(4-(trifluoromethyl)phenethoxy)-1H-indol-3-yl)cyclobutane-1-carboxamide | 356.05 |
| 381 | 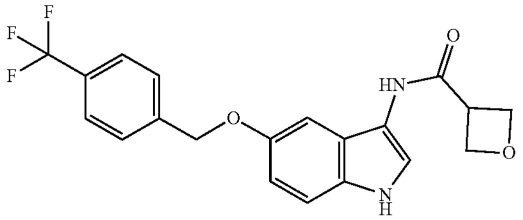 [SMILES: O=C(Nc1c[nH]c2ccc(OCc3ccc(C(F)(F)F)cc3)cc12)C1COC1] N-(5-((4-(trifluoromethyl)benzyl)oxy)-1H-indol-3-yl)oxetane-3-carboxamide | 463.3 |
| 382 | 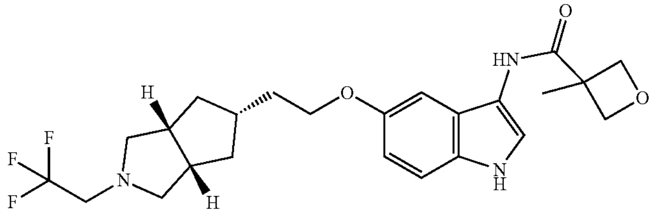 [SMILES: CC1(C(=O)Nc2c[nH]c3ccc(OCC[C@@H]4C[C@@H]5CN(CC(F)(F)F)C[C@@H]5C4)cc23)COC1] | 445.2 |

TABLE C1-continued

| Compound No. | Structure | LC-MS |
|---|---|---|
| | 3-methyl-N-(5-(2-((3aR,5r,6aS)-2-(2,2,2-trifluoroethyl)octahydrocyclopenta[c]pyrrol-5-yl)ethoxy)-1H-indol-3-yl)oxetane-3-carboxamide | |
| 383 | 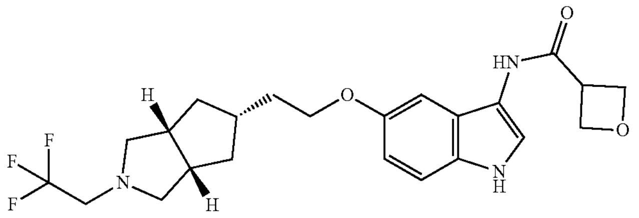 [SMILES: O=C(Nc1c[nH]c2ccc(OCC[C@@H]3C[C@@H]4CN(CC(F)(F)F)C[C@@H]4C3)cc12)C1COC1] N-(5-(2-((3aR,5r,6aS)-2-(2,2,2-trifluoroethyl)octahydrocyclopenta[c]pyrrol-5-yl)ethoxy)-1H-indol-3-yl)oxetane-3-carboxamide | 450.4 |
| 384 | 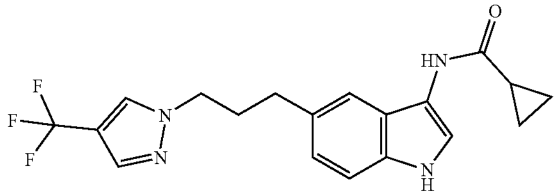 [SMILES: O=C(Nc1c[nH]c2ccc(CCCn3cc(C(F)(F)F)cn3)cc12)C1CC1] N-(5-(3-(4-(trifluoromethyl)-1H-pyrazol-1-yl)propyl)-1H-indol-3-yl)cyclopropanecarboxamide | 435.2 |
| 385 | 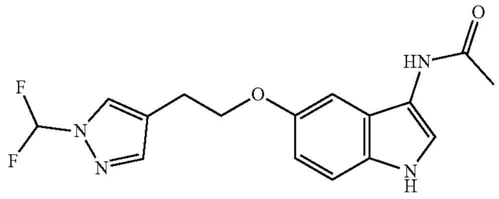 [SMILES: CC(=O)Nc1c[nH]c2ccc(OCCc3cnn(C(F)F)c3)cc12] N-(5-(2-(1-(difluoromethyl)-1H-pyrazol-4-yl)ethoxy)-1H-indol-3-yl)acetamide | 391.05 |
| 386 | 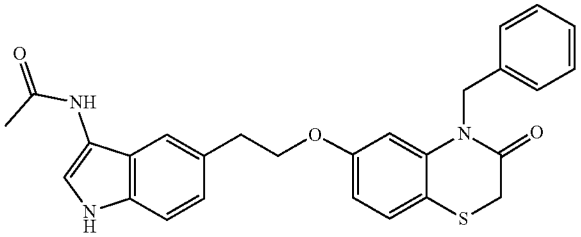 [SMILES: CC(=O)Nc1c[nH]c2ccc(CCOc3ccc4c(c3)N(Cc3ccccc3)C(=O)CS4)cc12] N-(5-(2-((4-benzyl-3-oxo-3,4-dihydro-2H-benzo[b][1,4]thiazin-6-yl)oxy)ethyl)-1H-indol-3-yl)acetamide | 466.2 |
| 387 | 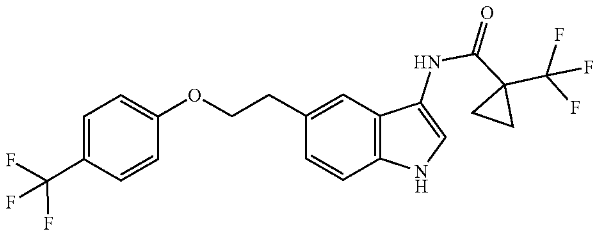 [SMILES: O=C(Nc1c[nH]c2ccc(CCOc3ccc(C(F)(F)F)cc3)cc12)C1(C(F)(F)F)CC1] 1-(trifluoromethyl)-N-(5-(2-(4-(trifluoromethyl)phenoxy)ethyl)-1H-indol-3-yl)cyclopropane-1-carboxamide | 452.15 |

TABLE C1-continued
| Compound No. | Structure | LC-MS |
|---|---|---|
| 388 | 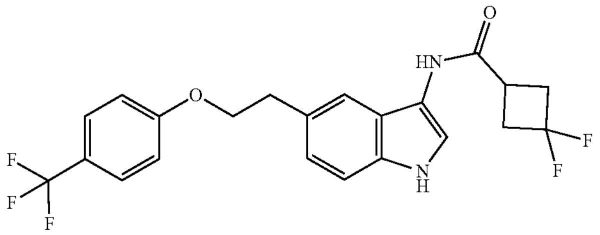 [SMILES: O=C(Nc1c[nH]c2ccc(CCOc3ccc(C(F)(F)F)cc3)cc12)C1CC(F)(F)C1] 3,3-difluoro-N-(5-(2-(4-(trifluoromethyl)phenoxy)ethyl)-1H-indol-3-yl)cyclobutane-1-carboxamide | 377.15 |
| 389 | 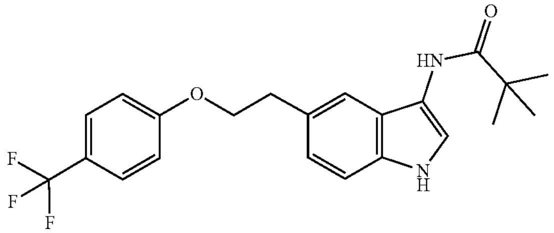 [SMILES: CC(C)(C)C(=O)Nc1c[nH]c2ccc(CCOc3ccc(C(F)(F)F)cc3)cc12] N-(5-(2-(4-(trifluoromethyl)phenoxy)ethyl)-1H-indol-3-yl)pivalamide | 333.05 |
| 390 | 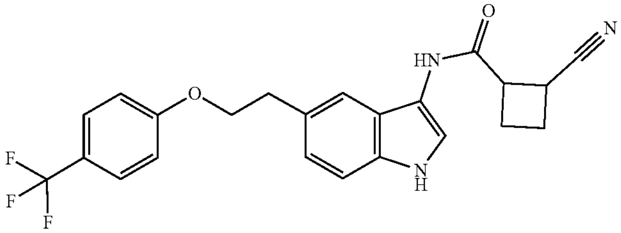 [SMILES: N#CC1CCC1C(=O)Nc1c[nH]c2ccc(CCOc3ccc(C(F)(F)F)cc3)cc12] 2-cyano-N-(5-(2-(4-(trifluoromethyl)phenoxy)ethyl)-1H-indol-3-yl)cyclobutane-1-carboxamide | 470.1 |
| 391 | 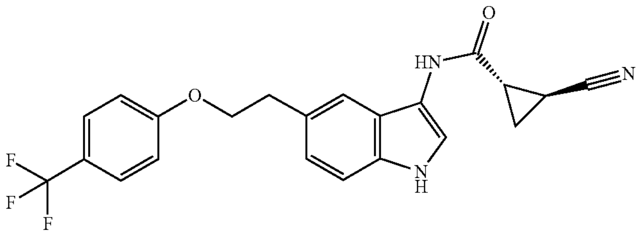 [SMILES: N#C[C@H]1C[C@@H]1C(=O)Nc1c[nH]c2ccc(CCOc3ccc(C(F)(F)F)cc3)cc12] (1S,2S)-2-cyano-N-(5-(2-(4-(trifluoromethyl)phenoxy)ethyl)-1H-indol-3-yl)cyclopropane-1-carboxamide | 437.3 |
| 392 | 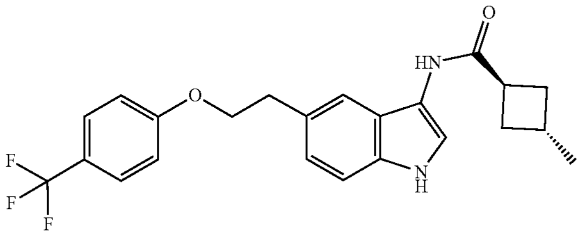 [SMILES: C[C@H]1C[C@H](C(=O)Nc2c[nH]c3ccc(CCOc4ccc(C(F)(F)F)cc4)cc23)C1] | 457.2 |

TABLE C1-continued

| Compound No. | Structure | LC-MS |
|---|---|---|
| | trans-3-methyl-N-(5-(2-(4-(trifluoromethyl)phenoxy)ethyl)-1H-indol-3-yl)cyclobutane-1-carboxamide | |
| 393 | 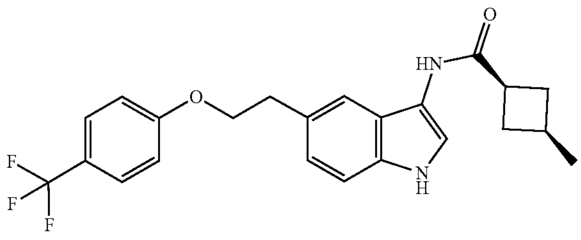 [SMILES: C[C@H]1C[C@@H](C(=O)Nc2c[nH]c3ccc(CCOc4ccc(C(F)(F)F)cc4)cc23)C1] cis-3-methyl-N-(5-(2-(4-(trifluoromethyl)phenoxy)ethyl)-1H-indol-3-yl)cyclobutane-1-carboxamide | 439.2 |
| 394 | 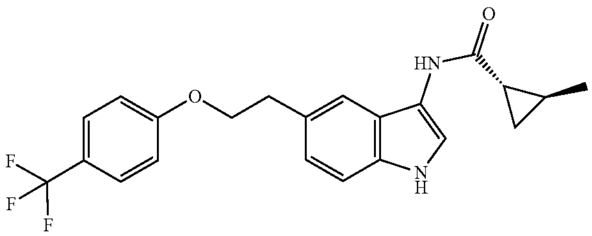 [SMILES: C[C@H]1C[C@@H]1C(=O)Nc1c[nH]c2ccc(CCOc3ccc(C(F)(F)F)cc3)cc12] (1S,2S)-2-methyl-N-(5-(2-(4-(trifluoromethyl)phenoxy)ethyl)-1H-indol-3-yl)cyclopropane-1-carboxamide | 405.3 |
| 395 | 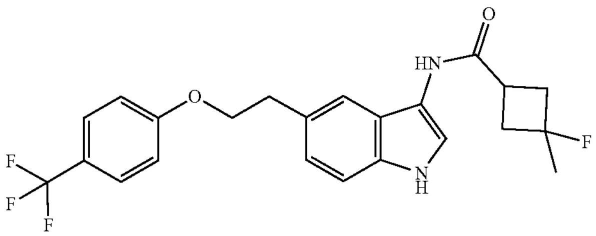 [SMILES: CC1(F)CC(C(=O)Nc2c[nH]c3ccc(CCOc4ccc(C(F)(F)F)cc4)cc23)C1] 3-fluoro-3-methyl-N-(5-(2-(4-(trifluoromethyl)phenoxy)ethyl)-1H-indol-3-yl)cyclobutane-1-carboxamide | 428.2 |
| 396 | 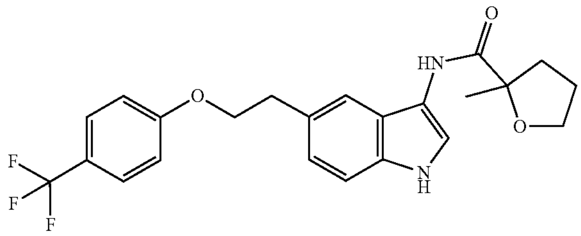 [SMILES: CC1(C(=O)Nc2c[nH]c3ccc(CCOc4ccc(C(F)(F)F)cc4)cc23)CCCO1] 2-methyl-N-(5-(2-(4-(trifluoromethyl)phenoxy)ethyl)-1H-indol-3-yl)tetrahydrofuran-2-carboxamide | 414.2 |

TABLE C1-continued

| Compound No. | Structure | LC-MS |
| --- | --- | --- |
| 397 | 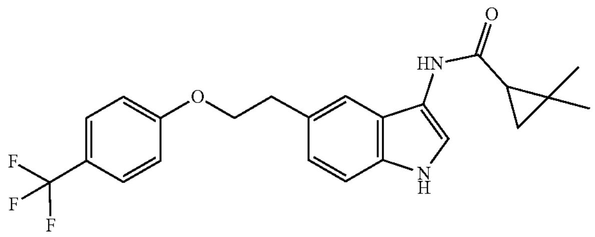 [SMILES: CC1(C)CC1C(=O)Nc1c[nH]c2ccc(CCOc3ccc(C(F)(F)F)cc3)cc12]<br>2,2-dimethyl-N-(5-(2-(4-(trifluoromethyl)phenoxy)ethyl)-1H-indol-3-yl)cyclopropane-1-carboxamide | 417.2 |
| 398 | 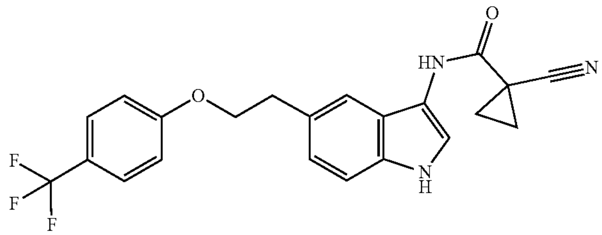 [SMILES: N#CC1(C(=O)Nc2c[nH]c3ccc(CCOc4ccc(C(F)(F)F)cc4)cc23)CC1]<br>1-cyano-N-(5-(2-(4-(trifluoromethyl)phenoxy)ethyl)-1H-indol-3-yl)cyclopropane-1-carboxamide | 417.3 |
| 399 | 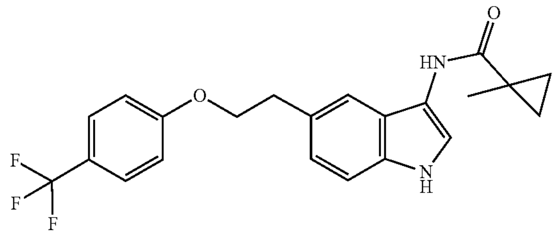 [SMILES: CC1(C(=O)Nc2c[nH]c3ccc(CCOc4ccc(C(F)(F)F)cc4)cc23)CC1]<br>1-methyl-N-(5-(2-(4-(trifluoromethyl)phenoxy)ethyl)-1H-indol-3-yl)cyclopropane-1-carboxamide | 403.2 |
| 400 | 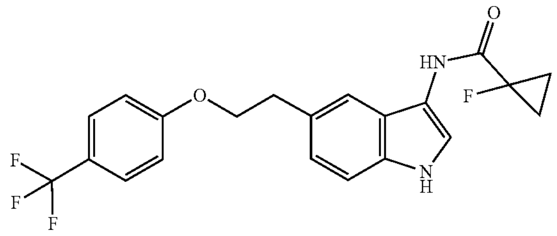 [SMILES: O=C(Nc1c[nH]c2ccc(CCOc3ccc(C(F)(F)F)cc3)cc12)C1(F)CC1]<br>1-fluoro-N-(5-(2-(4-(trifluoromethyl)phenoxy)ethyl)-1H-indol-3-yl)cyclopropane-1-carboxamide | 435.3 |
| 401 | 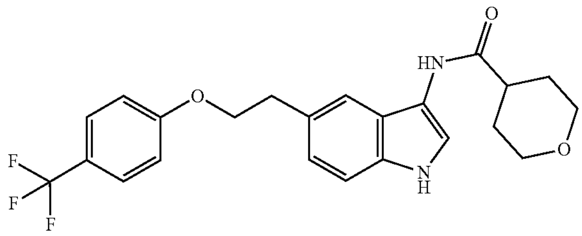 [SMILES: O=C(Nc1c[nH]c2ccc(CCOc3ccc(C(F)(F)F)cc3)cc12)C1CCOCC1]<br>N-(5-(2-(4-(trifluoromethyl)phenoxy)ethyl)-1H-indol-3-yl)tetrahydro-2H-pyran-4-carboxamide | 431.2 |

TABLE C1-continued
| Compound No. | Structure | LC-MS |
|---|---|---|
| 402 | 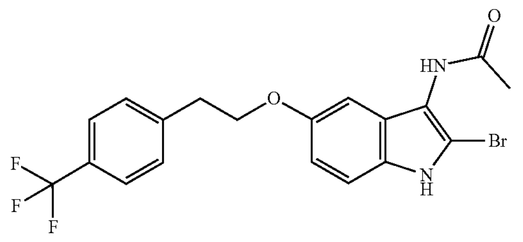 [SMILES: CC(=O)Nc1c(Br)[nH]c2ccc(OCCc3ccc(C(F)(F)F)cc3)cc12] N-(2-bromo-5-(4-(trifluoromethyl)phenethoxy)-1H-indol-3-yl)acetamide | 417.3 |
| 404 | 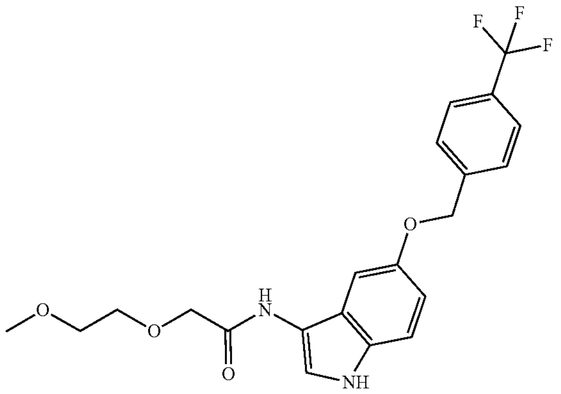 [SMILES: COCCOCC(=O)Nc1c[nH]c2ccc(OCc3ccc(C(F)(F)F)cc3)cc12] 2-(2-methoxyethoxy)-N-(5-((4-(trifluoromethyl)benzyl)oxy)-1H-indol-3-yl)acetamide | 403.2 |
| 405 | 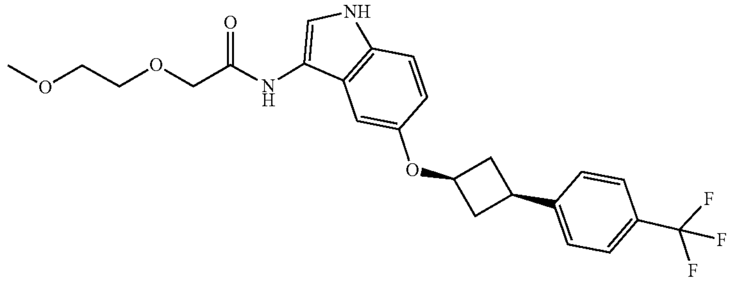 [SMILES: COCCOCC(=O)Nc1c[nH]c2ccc(O[C@H]3C[C@@H](c4ccc(C(F)(F)F)cc4)C3)cc12] 2-(2-methoxyethoxy)-N-(5-(cis-3-(4-(trifluoromethyl)phenyl)cyclobutoxy)-1H-indol-3-yl)acetamide | 407.2 |
| 406 | 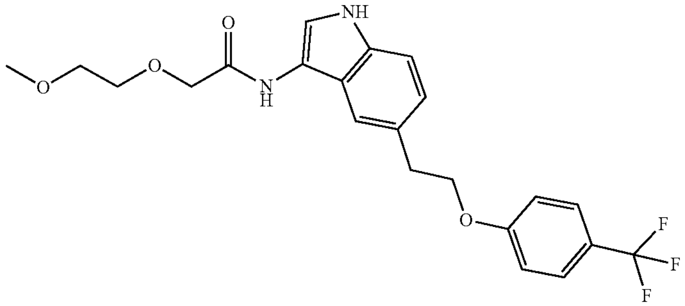 [SMILES: COCCOCC(=O)Nc1c[nH]c2ccc(CCOc3ccc(C(F)(F)F)cc3)cc12] 2-(2-methoxyethoxy)-N-(5-(2-(4-(trifluoromethyl)phenoxy)ethyl)-1H-indol-3-yl)acetamide | 433.3 |

TABLE C1-continued

| Compound No. | Structure | LC-MS |
| --- | --- | --- |
| 407 | 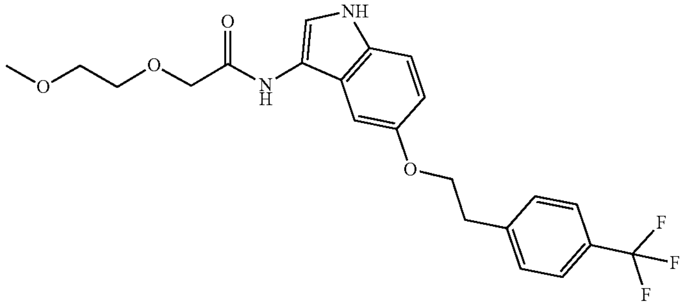 [SMILES: COCCOCC(=O)Nc1c[nH]c2ccc(OCCc3ccc(C(F)(F)F)cc3)cc12]<br>2-(2-methoxyethoxy)-N-(5-(4-(trifluoromethyl)phenethoxy)-1H-indol-3-yl)acetamide | |
| 408 | 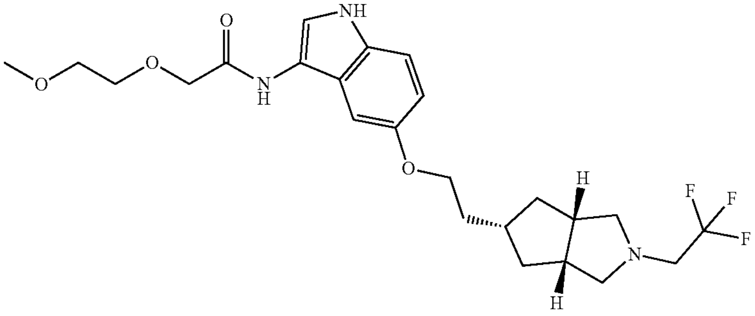 [SMILES: COCCOCC(=O)Nc1c[nH]c2ccc(OCC[C@@H]3C[C@@H]4CN(CC(F)(F)F)C[C@@H]4C3)cc12]<br>2-(2-methoxyethoxy)-N-(5-(2-((3aR,5r,6aS)-2-(2,2,2-trifluoroethyl)octahydrocyclopenta[c]pyrrol-5-yl)ethoxy)-1H-indol-3-yl)acetamide | 440.8 |
| 409 | 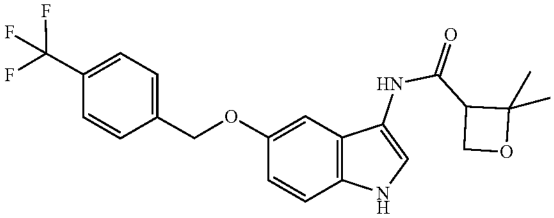 [SMILES: CC1(C)OCC1C(=O)Nc1c[nH]c2ccc(OCc3ccc(C(F)(F)F)cc3)cc12]<br>2,2-dimethyl-N-(5-((4-(trifluoromethyl)benzyl)oxy)-1H-indol-3-yl)oxetane-3-carboxamide | 419.15 |
| 410 | 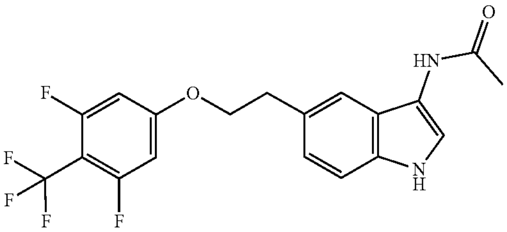 [SMILES: CC(=O)Nc1c[nH]c2ccc(CCOc3cc(F)c(C(F)(F)F)c(F)c3)cc12]<br>N-(5-(2-(3,5-difluoro-4-(trifluoromethyl)phenoxy)ethyl)-1H-indol-3-yl)acetamide | 399.2 |

TABLE C1-continued

| Compound No. | Structure | LC-MS |
|---|---|---|
| 411 | 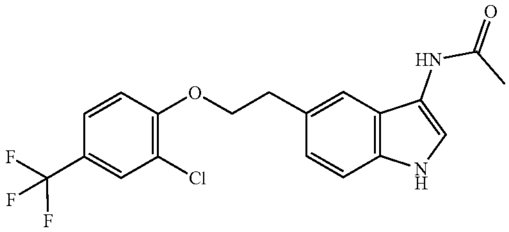 [SMILES: CC(=O)Nc1c[nH]c2ccc(CCOc3ccc(C(F)(F)F)cc3Cl)cc12]<br>N-(5-(2-(2-chloro-4-(trifluoromethyl)phenoxy)ethyl)-1H-indol-3-yl)acetamide | 397.1 |
| 412 | 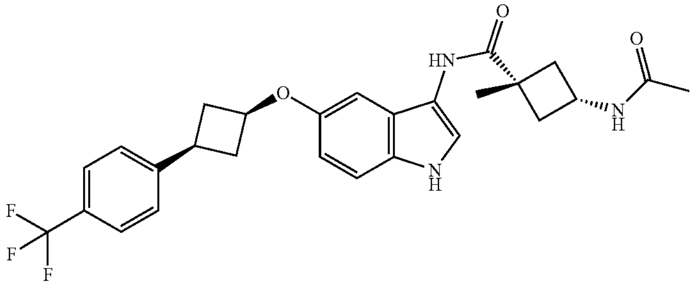 [SMILES: CC(=O)N[C@H]1C[C@@](C)(C(=O)Nc2c[nH]c3ccc(O[C@H]4C[C@@H](c5ccc(C(F)(F)F)cc5)C4)cc23)C1]<br>cis-3-acetamido-1-methyl-N-(5-(cis-3-(4-(trifluoromethyl)phenyl)cyclobutoxy)-1H-indol-3-yl)cyclobutane-1-carboxamide | 500.2 |
| 413 | 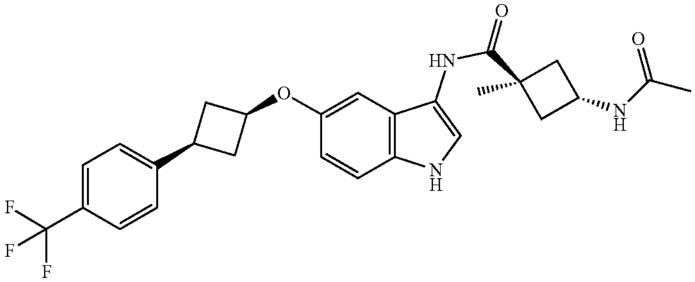 [SMILES: CC(=O)N[C@H]1C[C@](C)(C(=O)Nc2c[nH]c3ccc(O[C@H]4C[C@@H](c5ccc(C(F)(F)F)cc5)C4)cc23)C1]<br>trans-3-acetamido-1-methyl-N-(5-(cis-3-(4-(trifluoromethyl)phenyl)cyclobutoxy)-1H-indol-3-yl)cyclobutane-1-carboxamide | 500.2 |
| 414 | 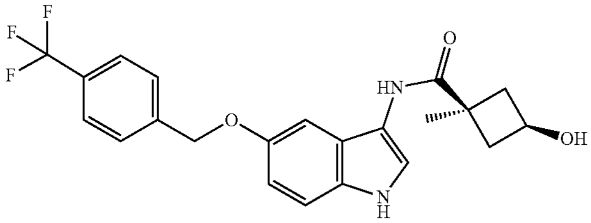 [SMILES: C[C@]1(C(=O)Nc2c[nH]c3ccc(OCc4ccc(C(F)(F)F)cc4)cc23)C[C@@H](O)C1]<br>cis-3-hydroxy-1-methyl-N-(5-((4-(trifluoromethyl)benzyl)oxy)-1H-indol-3-yl)cyclobutane-1-carboxamide | 419.15 |
| 415 | 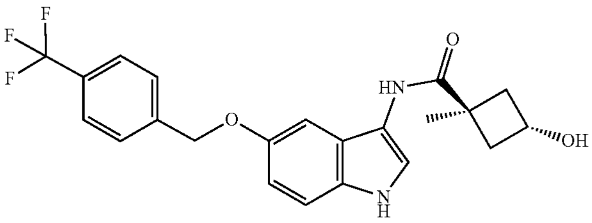 [SMILES: C[C@]1(C(=O)Nc2c[nH]c3ccc(OCc4ccc(C(F)(F)F)cc4)cc23)C[C@H](O)C1] | 419.15 |

TABLE C1-continued

| Compound No. | Structure | LC-MS |
|---|---|---|
| | trans-3-hydroxy-1-methyl-N-(5-((4-(trifluoromethyl)benzyl)oxy)-1H-indol-3-yl)cyclobutane-1-carboxamide | |
| 416 | 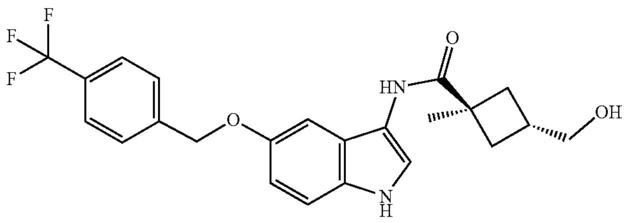 [SMILES: C[C@]1(C(=O)Nc2c[nH]c3ccc(OCc4ccc(C(F)(F)F)cc4)cc23)C[C@H](CO)C1] trans-3-(hydroxymethyl)-1-methyl-N-(5-((4-(trifluoromethyl)benzyl)oxy)-1H-indol-3-yl)cyclobutane-1-carboxamide | 433.15 |
| 417 | 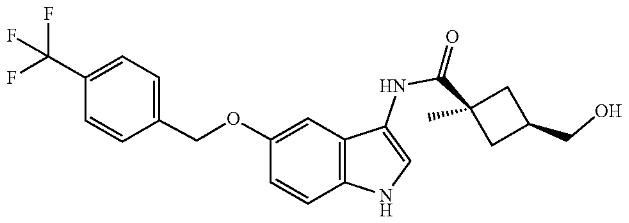 [SMILES: C[C@]1(C(=O)Nc2c[nH]c3ccc(OCc4ccc(C(F)(F)F)cc4)cc23)C[C@@H](CO)C1] cis-3-(hydroxymethyl)-1-methyl-N-(5-((4-(trifluoromethyl)benzyl)oxy)-1H-indol-3-yl)cyclobutane-1-carboxamide | 433.25 |
| 418 | 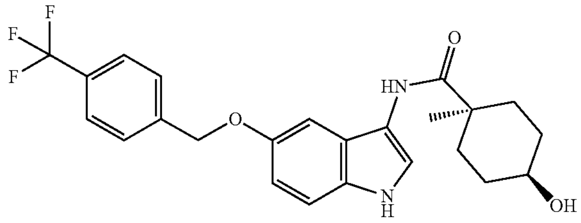 [SMILES: C[C@]1(C(=O)Nc2c[nH]c3ccc(OCc4ccc(C(F)(F)F)cc4)cc23)CC[C@@H](O)CC1] trans-4-hydroxy-1-methyl-N-(5-((4-(trifluoromethyl)benzyl)oxy)-1H-indol-3-yl)cyclohexane-1-carboxamide | 447.2 |
| 419 | 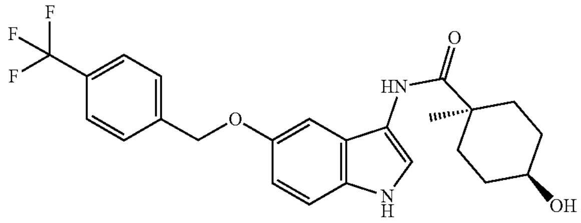 [SMILES: C[C@]1(C(=O)Nc2c[nH]c3ccc(OCc4ccc(C(F)(F)F)cc4)cc23)CC[C@@H](O)CC1] trans-4-hydroxy-1-methyl-N-(5-((4-(trifluoromethyl)benzyl)oxy)-1H-indol-3-yl)cyclohexane-1-carboxamide | 447.25 |

TABLE C1-continued

| Compound No. | Structure | LC-MS |
|---|---|---|
| 420 | 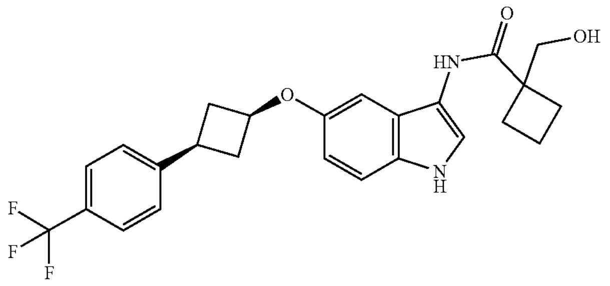 [SMILES: O=C(Nc1c[nH]c2ccc(O[C@H]3C[C@@H](c4ccc(C(F)(F)F)cc4)C3)cc12)C1(CO)CCC1] 1-(hydroxymethyl)-N-(5-(cis-3-(4-(trifluoromethyl)phenyl)cyclobutoxy)-1H-indol-3-yl)cyclobutane-1-carboxamide | 459.15 |
| 421 | 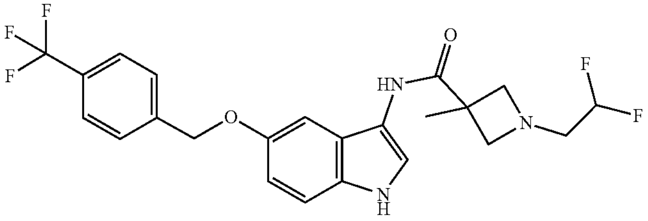 [SMILES: CC1(C(=O)Nc2c[nH]c3ccc(OCc4ccc(C(F)(F)F)cc4)cc23)CN(CC(F)F)C1] 1-(2,2-difluoroethyl)-3-methyl-N-(5-((4-(trifluoromethyl)benzyl)oxy)-1H-indol-3-yl)azetidine-3-carboxamide | 468.1 |
| 422 | 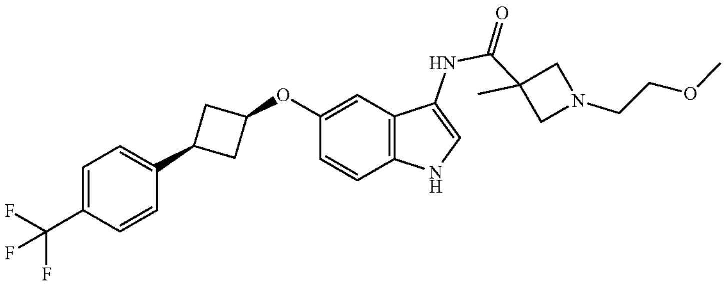 [SMILES: COCCN1CC(C)(C(=O)Nc2c[nH]c3ccc(O[C@H]4C[C@@H](c5ccc(C(F)(F)F)cc5)C4)cc23)C1] 1-(2-methoxyethyl)-3-methyl-N-(5-(cis-3-(4-(trifluoromethyl)phenyl)cyclobutoxy)-1H-indol-3-yl)azetidine-3-carboxamide | 502.2 |
| 423 | 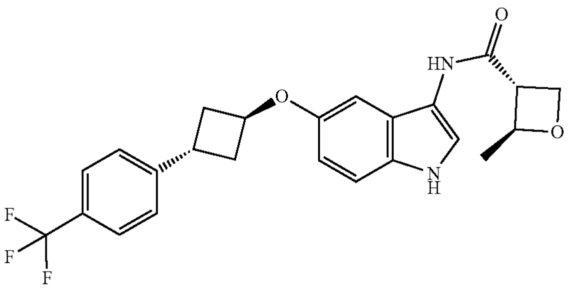 [SMILES: C[C@@H]1OC[C@H]1C(=O)Nc1c[nH]c2ccc(O[C@H]3C[C@H](c4ccc(C(F)(F)F)cc4)C3)cc12] (2S,3R)-2-methyl-N-(5-(trans-3-(4-(trifluoromethyl)phenyl)cyclobutoxy)-1H-indol-3-yl)oxetane-3-carboxamide | 445.1 |

TABLE C1-continued

| Compound No. | Structure | LC-MS |
|---|---|---|
| 424 | 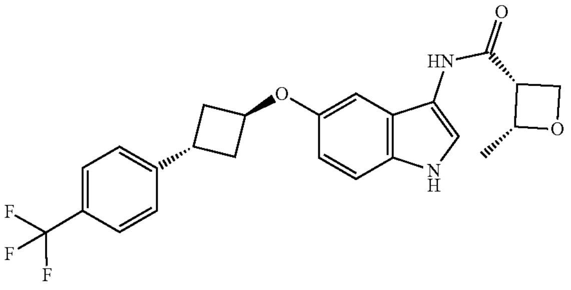 [SMILES: C[C@H]1OC[C@H]1C(=O)Nc1c[nH]c2ccc(O[C@H]3C[C@H](c4ccc(C(F)(F)F)cc4)C3)cc12]<br>(2R,3R)-2-methyl-N-(5-(trans-3-(4-(trifluoromethyl)phenyl)cyclobutoxy)-1H-indol-3-yl)oxetane-3-carboxamide | 445.25 |
| 425 | 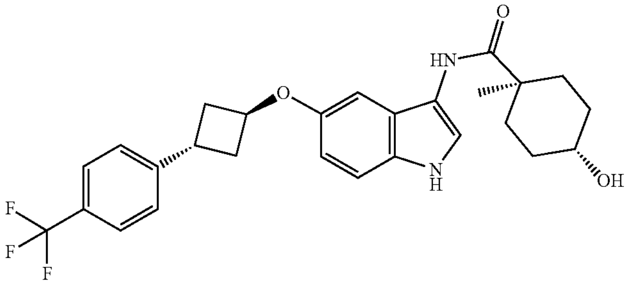 [SMILES: C[C@]1(C(=O)Nc2c[nH]c3ccc(O[C@H]4C[C@H](c5ccc(C(F)(F)F)cc5)C4)cc23)CC[C@H](O)CC1]<br>4-hydroxy-1-methyl-N-(5-(trans-3-(4-(trifluoromethyl)phenyl)cyclobutoxy)-1H-indol-3-yl)cyclohexane-1-carboxamide | 487.2 |
| 426 | 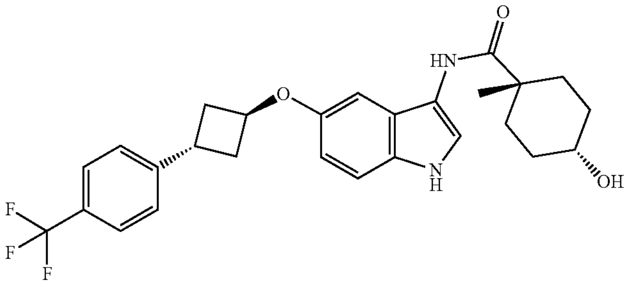 [SMILES: C[C@]1(C(=O)Nc2c[nH]c3ccc(O[C@H]4C[C@H](c5ccc(C(F)(F)F)cc5)C4)cc23)CC[C@@H](O)CC1]<br>cis-4-hydroxy-1-methyl-N-(5-(trans-3-(4-(trifluoromethyl)phenyl)cyclobutoxy)-1H-indol-3-yl)cyclohexane-1-carboxamide | 487.3 |
| 427 | 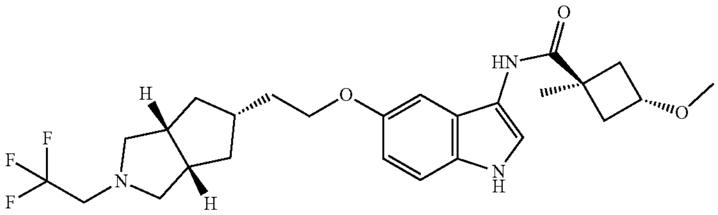 [SMILES: CO[C@H]1C[C@](C)(C(=O)Nc2c[nH]c3ccc(OCC[C@@H]4C[C@@H]5CN(CC(F)(F)F)C[C@@H]5C4)cc23)C1]<br>(1r,3R)-3-methoxy-1-methyl-N-(5-(2-((3aR,5r,6aS)-2-(2,2,2-trifluoroethyl)octahydrocyclopenta[c]pyrrol-5-yl)ethoxy)-1H-indol-3-yl)cyclobutane-1-carboxamide | 494.2 |

TABLE C1-continued
| Compound No. | Structure | LC-MS |
|---|---|---|
| 428 | 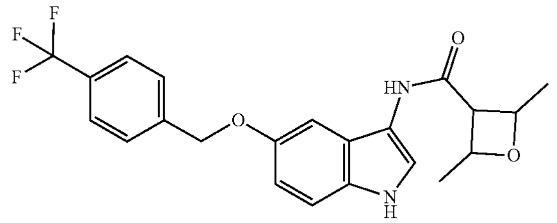 [SMILES: CC1OC(C)C1C(=O)Nc1c[nH]c2ccc(OCc3ccc(C(F)(F)F)cc3)cc12]<br>2,4-dimethyl-N-(5-((4-(trifluoromethyl)benzyl)oxy)-1H-indol-3-yl)oxetane-3-carboxamide | 419.15 |
| 429 | 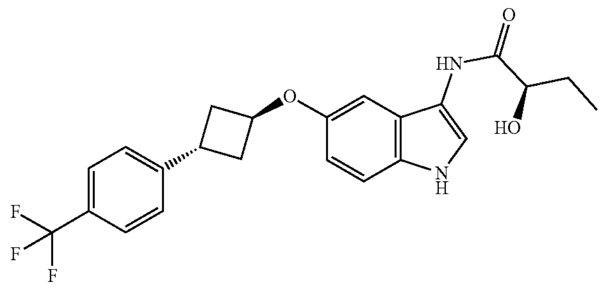 [SMILES: CC[C@@H](O)C(=O)Nc1c[nH]c2ccc(O[C@H]3C[C@H](c4ccc(C(F)(F)F)cc4)C3)cc12]<br>(R)-2-hydroxy-N-(5-(trans-3-(4-(trifluoromethyl)phenyl)cyclobutoxy)-1H-indol-3-yl)butanamide | 433.25 |
| 430 | 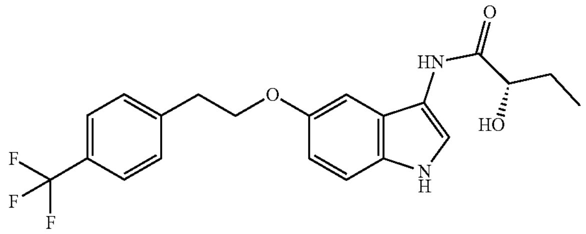 [SMILES: CC[C@H](O)C(=O)Nc1c[nH]c2ccc(OCCc3ccc(C(F)(F)F)cc3)cc12]<br>(S)-2-hydroxy-N-(5-(4-(trifluoromethyl)phenethoxy)-1H-indol-3-yl)butanamide | 407.15 |
| 431 | 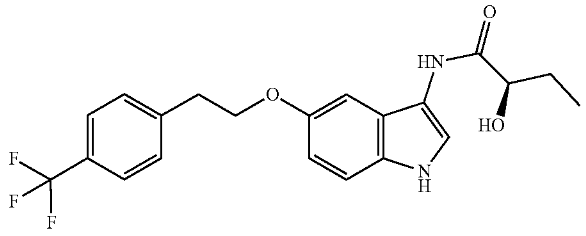 [SMILES: CC[C@@H](O)C(=O)Nc1c[nH]c2ccc(OCCc3ccc(C(F)(F)F)cc3)cc12]<br>(R)-2-hydroxy-N-(5-(4-(trifluoromethyl)phenethoxy)-1H-indol-3-yl)butanamide | 407.2 |

TABLE C1-continued

| Compound No. | Structure | LC-MS |
|---|---|---|
| 432 | 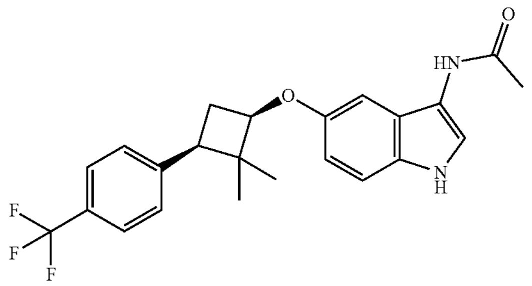 [SMILES: CC(=O)Nc1c[nH]c2ccc(O[C@@H]3C[C@H](c4ccc(C(F)(F)F)cc4)C3(C)C)cc12] N-(5-((1R,3R)-2,2-dimethyl-3-(4-(trifluoromethyl)phenyl)cyclobutoxy)-1H-indol-3-yl)acetamide | 417.2 |
| 433 | 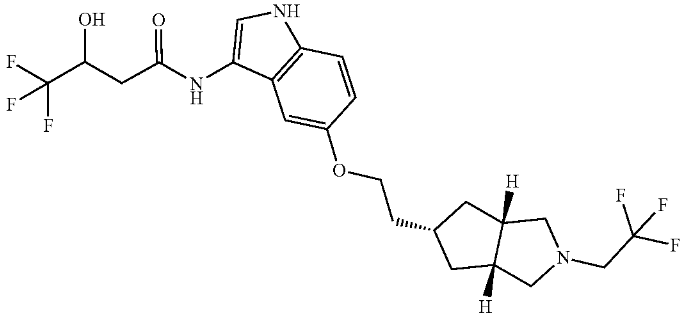 [SMILES: O=C(CC(O)C(F)(F)F)Nc1c[nH]c2ccc(OCC[C@@H]3C[C@@H]4CN(CC(F)(F)F)C[C@@H]4C3)cc12] 4,4,4-trifluoro-3-hydroxy-N-(5-(2-((3aR,5r,6aS)-2-(2,2,2-trifluoroethyl)octahydrocyclopenta[c]pyrrol-5-yl)ethoxy)-1H-indol-3-yl)butanamide | 508.2 |
| 434 | 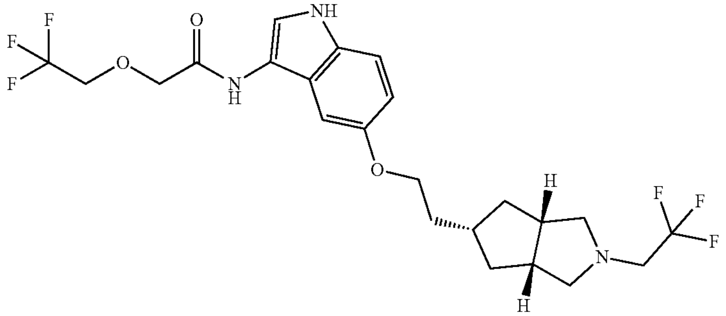 [SMILES: O=C(COCC(F)(F)F)Nc1c[nH]c2ccc(OCC[C@@H]3C[C@@H]4CN(CC(F)(F)F)C[C@@H]4C3)cc12] 2-(2,2,2-trifluoroethoxy)-N-(5-(2-((3aR,5r,6aS)-2-(2,2,2-trifluoroethyl)octahydrocyclopenta[c]pyrrol-5-yl)ethoxy)-1H-indol-3-yl)acetamide | 508.2 |
| 435 | 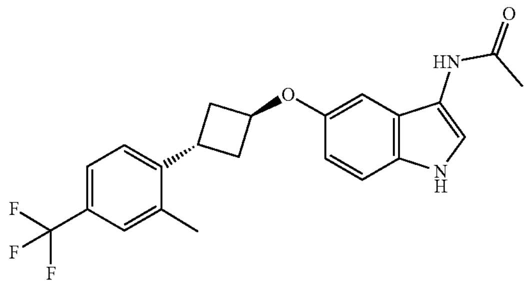 [SMILES: CC(=O)Nc1c[nH]c2ccc(O[C@H]3C[C@H](c4ccc(C(F)(F)F)cc4C)C3)cc12] N-(5-(trans-3-(2-methyl-4-(trifluoromethyl)phenyl)cyclobutoxy)-1H-indol-3-yl)acetamide | 403.15 |

TABLE C1-continued

| Compound No. | Structure | LC-MS |
|---|---|---|
| 436 | 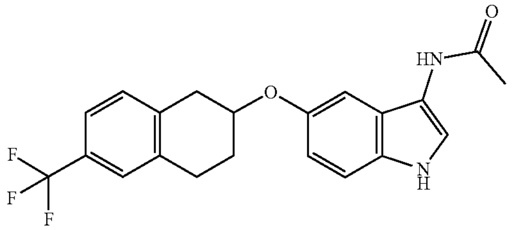 [SMILES: CC(=O)Nc1c[nH]c2ccc(OC3CCc4cc(C(F)(F)F)ccc4C3)cc12] N-(5-((6-(trifluoromethyl)-1,2,3,4-tetrahydronaphthalen-2-yl)oxy)-1H-indol-3-yl)acetamide | 389.05 |
| 437 | 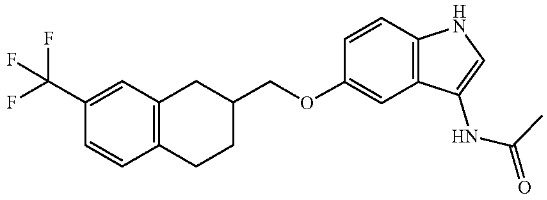 [SMILES: CC(=O)Nc1c[nH]c2ccc(OCC3CCc4ccc(C(F)(F)F)cc4C3)cc12] N-(5-((7-(trifluoromethyl)-1,2,3,4-tetrahydronaphthalen-2-yl)methoxy)-1H-indol-3-yl)acetamide | 401.1 |
| 438 | 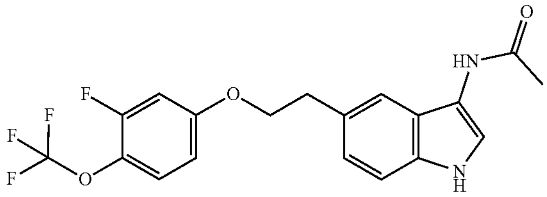 [SMILES: CC(=O)Nc1c[nH]c2ccc(CCOc3ccc(OC(F)(F)F)c(F)c3)cc12] N-(5-(2-(3-fluoro-4-(trifluoromethoxy)phenoxy)ethyl)-1H-indol-3-yl)acetamide | 397.3 |
| 439 | 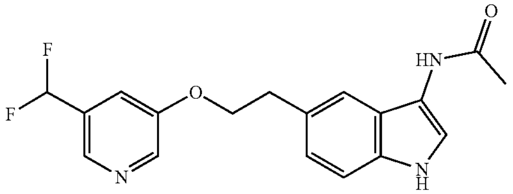 [SMILES: CC(=O)Nc1c[nH]c2ccc(CCOc3cncc(C(F)F)c3)cc12] N-(5-(2-((5-(difluoromethyl)pyridin-3-yl)oxy)ethyl)-1H-indol-3-yl)acetamide | 346.2 |
| 440 | 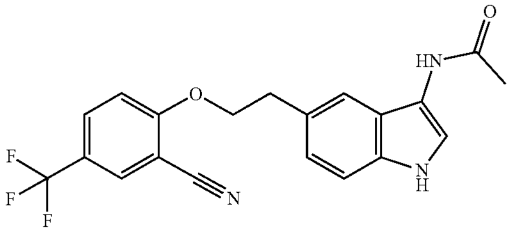 [SMILES: CC(=O)Nc1c[nH]c2ccc(CCOc3ccc(C(F)(F)F)cc3C#N)cc12] N-(5-(2-(2-cyano-4-(trifluoromethyl)phenoxy)ethyl)-1H-indol-3-yl)acetamide | 388.2 |

TABLE C1-continued

| Compound No. | Structure | LC-MS |
|---|---|---|
| 441 | 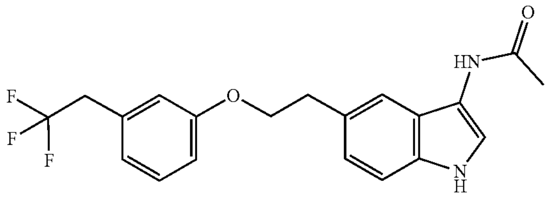 [SMILES: CC(=O)Nc1c[nH]c2ccc(CCOc3cccc(CC(F)(F)F)c3)cc12] N-(5-(2-(3-(2,2,2-trifluoroethyl)phenoxy)ethyl)-1H-indol-3-yl)acetamide | 421.2 |
| 442 | 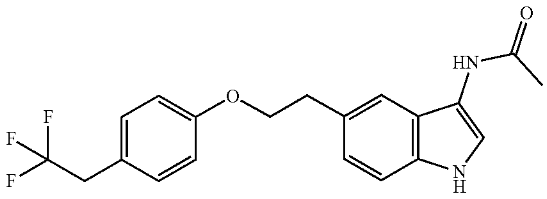 [SMILES: CC(=O)Nc1c[nH]c2ccc(CCOc3ccc(CC(F)(F)F)cc3)cc12] N-(5-(2-(4-(2,2,2-trifluoroethyl)phenoxy)ethyl)-1H-indol-3-yl)acetamide | 421.1 |
| 443 | 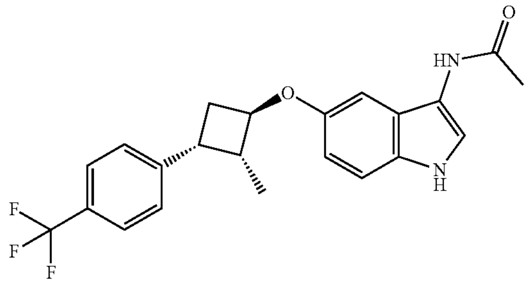 [SMILES: CC(=O)Nc1c[nH]c2ccc(O[C@@H]3C[C@@H](c4ccc(C(F)(F)F)cc4)[C@H]3C)cc12] N-(5-((1R,2R,3R)-2-methyl-3-(4-(trifluoromethyl)phenyl)cyclobutoxy)-1H-indol-3-yl)acetamide | 401.1 |
| 444 | 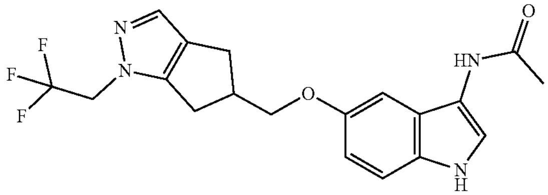 [SMILES: CC(=O)Nc1c[nH]c2ccc(OCC3Cc4cnn(CC(F)(F)F)c4C3)cc12] N-(5-((1-(2,2,2-trifluoroethyl)-1,4,5,6-tetrahydrocyclopenta[c]pyrazol-5-yl)methoxy)-1H-indol-3-yl)acetamide | 393.35 |
| 445 | 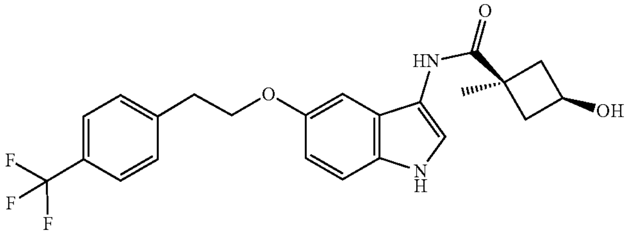 [SMILES: C[C@]1(C(=O)Nc2c[nH]c3ccc(OCCc4ccc(C(F)(F)F)cc4)cc23)C[C@@H](O)C1] (cis)-3-hydroxy-1-methyl-N-(5-(4-(trifluoromethyl)phenethoxy)-1H-indol-3-yl)cyclobutane-1-carboxamide | 433.15 |

TABLE C1-continued

| Compound No. | Structure | LC-MS |
|---|---|---|
| 446 | 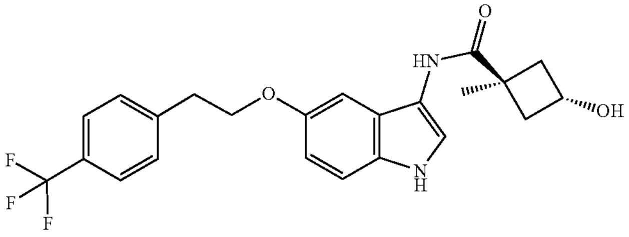 [SMILES: C[C@]1(C(=O)Nc2c[nH]c3ccc(OCCc4ccc(C(F)(F)F)cc4)cc23)C[C@H](O)C1] trans-3-hydroxy-1-methyl-N-(5-(4-(trifluoromethyl)phenethoxy)-1H-indol-3-yl)cyclobutane-1-carboxamide | 433.1 |
| 447 | 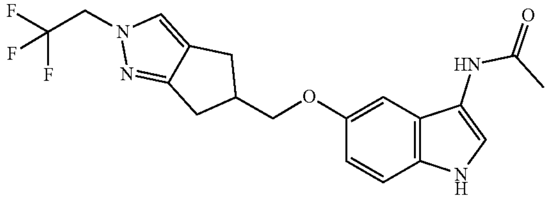 [SMILES: CC(=O)Nc1c[nH]c2ccc(OCC3Cc4cn(CC(F)(F)F)nc4C3)cc12] N-(5-((2-(2,2,2-trifluoroethyl)-2,4,5,6-tetrahydrocyclopenta[c]pyrazol-5-yl)methoxy)-1H-indol-3-yl)acetamide | 393.1 |
| 448 | 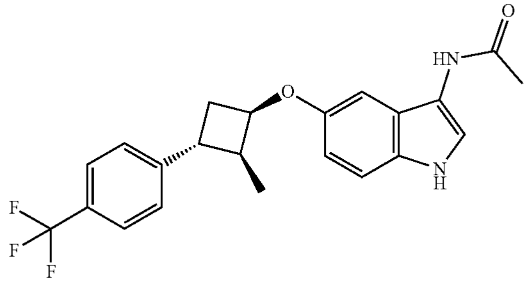 [SMILES: CC(=O)Nc1c[nH]c2ccc(O[C@@H]3C[C@@H](c4ccc(C(F)(F)F)cc4)[C@@H]3C)cc12] N-(5-((1R,2S,3R)-2-methyl-3-(4-(trifluoromethyl)phenyl)cyclobutoxy)-1H-indol-3-yl)acetamide | 401.1 |
| 449 | 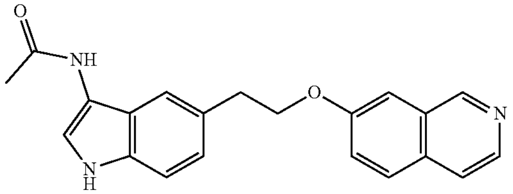 [SMILES: CC(=O)Nc1c[nH]c2ccc(CCOc3ccc4ccncc4c3)cc12] N-(5-(2-(isoquinolin-7-yloxy)ethyl)-1H-indol-3-yl)acetamide | 346.2 |
| 450 | 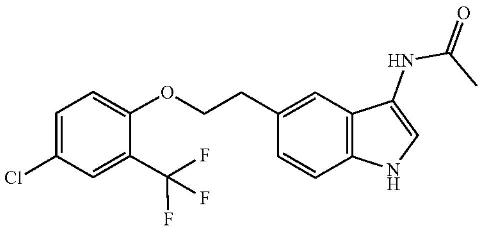 [SMILES: CC(=O)Nc1c[nH]c2ccc(CCOc3ccc(Cl)cc3C(F)(F)F)cc12] N-(5-(2-(4-chloro-2-(trifluoromethyl)phenoxy)ethyl)-1H-indol-3-yl)acetamide | 397.2 |

TABLE C1-continued
| Compound No. | Structure | LC-MS |
|---|---|---|
| 451 | 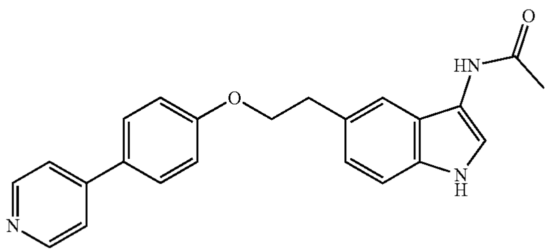 [SMILES: CC(=O)Nc1c[nH]c2ccc(CCOc3ccc(-c4ccncc4)cc3)cc12] N-(5-(2-(4-(pyridin-4-yl)phenoxy)ethyl)-1H-indol-3-yl)acetamide | 372.2 |
| 452 | 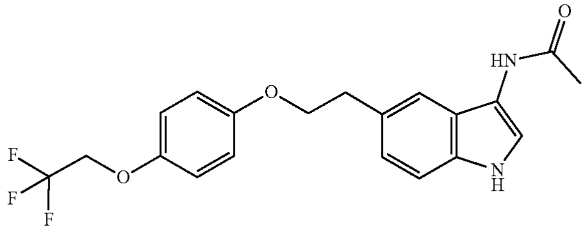 [SMILES: CC(=O)Nc1c[nH]c2ccc(CCOc3ccc(OCC(F)(F)F)cc3)cc12] N-(5-(2-(4-(2,2,2-trifluoroethoxy)phenoxy)ethyl)-1H-indol-3-yl)acetamide | 393.2 |
| 453 | 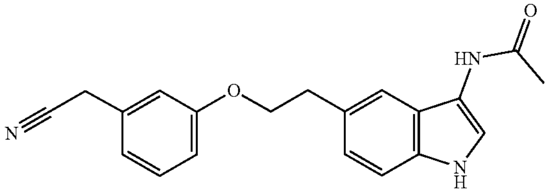 [SMILES: CC(=O)Nc1c[nH]c2ccc(CCOc3cccc(CC#N)c3)cc12] N-(5-(2-(3-(cyanomethyl)phenoxy)ethyl)-1H-indol-3-yl)acetamide | 334.3 |
| 454 | 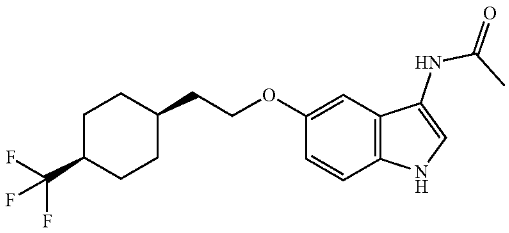 [SMILES: CC(=O)Nc1c[nH]c2ccc(OCC[C@H]3CC[C@@H](C(F)(F)F)CC3)cc12] N-(5-(2-(cis-4-(trifluoromethyl)cyclohexyl)ethoxy)-1H-indol-3-yl)acetamide | 369.35 |
| 455 | 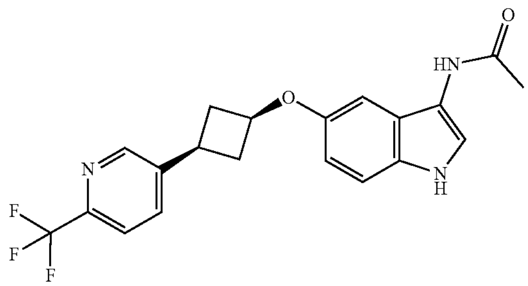 [SMILES: CC(=O)Nc1c[nH]c2ccc(O[C@H]3C[C@@H](c4ccc(C(F)(F)F)nc4)C3)cc12] N-(5-(cis-3-(6-(trifluoromethyl)pyridin-3-yl)cyclobutoxy)-1H-indol-3-yl)acetamide | 390.1 |

TABLE C1-continued
| Compound No. | Structure | LC-MS |
|---|---|---|
| 456 | 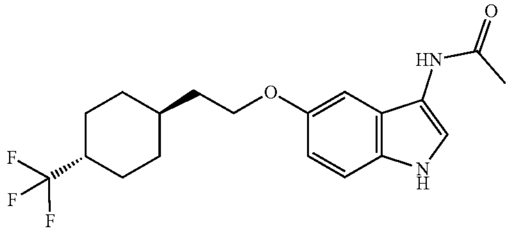 [SMILES: CC(=O)Nc1c[nH]c2ccc(OCC[C@H]3CC[C@H](C(F)(F)F)CC3)cc12] N-(5-(2-(trans-4-(trifluoromethyl)cyclohexyl)ethoxy)-1H-indol-3-yl)acetamide | 369.35 |
| 457 | 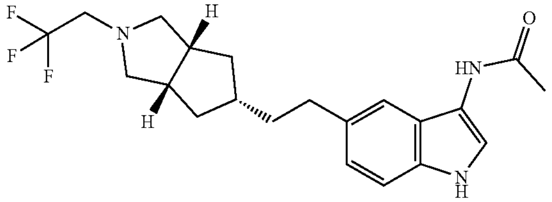 [SMILES: CC(=O)Nc1c[nH]c2ccc(CC[C@@H]3C[C@@H]4CN(CC(F)(F)F)C[C@@H]4C3)cc12] N-(5-(2-((3aR,5r,6aS)-2-(2,2,2-trifluoroethyl)octahydrocyclopenta[c]pyrrol-5-yl)ethyl)-1H-indol-3-yl)acetamide | 394.15 |
| 458 | 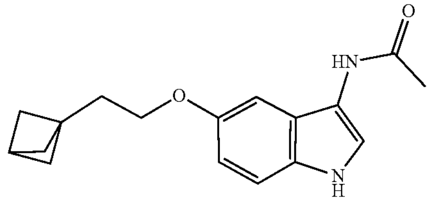 [SMILES: CC(=O)Nc1c[nH]c2ccc(OCCC34CC(C3)C4)cc12] N-(5-(2-(bicyclo[1.1.1]pentan-1-yl)ethoxy)-1H-indol-3-yl)acetamide | 285.15 |
| 459 | 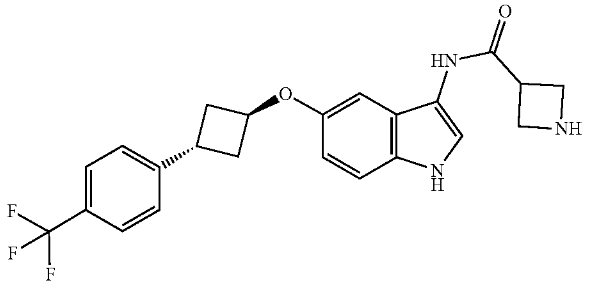 [SMILES: O=C(Nc1c[nH]c2ccc(O[C@H]3C[C@H](c4ccc(C(F)(F)F)cc4)C3)cc12)C1CNC1] N-(5-(trans-3-(4-(trifluoromethyl)phenyl)cyclobutoxy)-1H-indol-3-yl)azetidine-3-carboxamide | 430.3 |
| 460 | 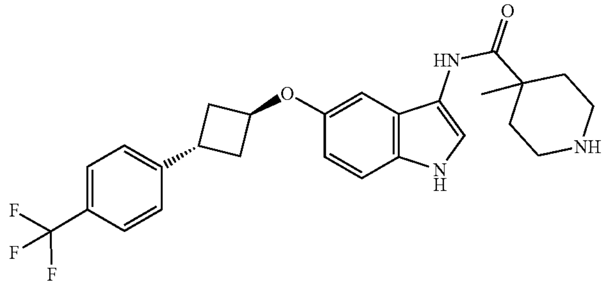 [SMILES: CC1(C(=O)Nc2c[nH]c3ccc(O[C@H]4C[C@H](c5ccc(C(F)(F)F)cc5)C4)cc23)CCNCC1] | 472.3 |

TABLE C1-continued

| Compound No. | Structure | LC-MS |
|---|---|---|
| | 4-methyl-N-(5-(trans-3-(4-(trifluoromethyl)phenyl)cyclobutoxy)-1H-indol-3-yl)piperidine-4-carboxamide | |
| 461 | 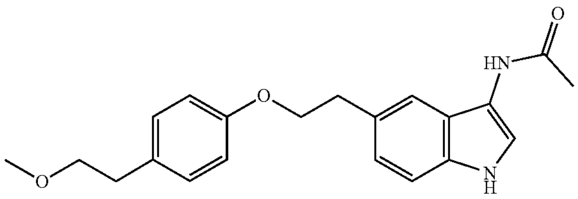 [SMILES: COCCc1ccc(OCCc2ccc3[nH]cc(NC(C)=O)c3c2)cc1] N-(5-(2-(4-(2-methoxyethyl)phenoxy)ethyl)-1H-indol-3-yl)acetamide | 353.3 |
| 462 | 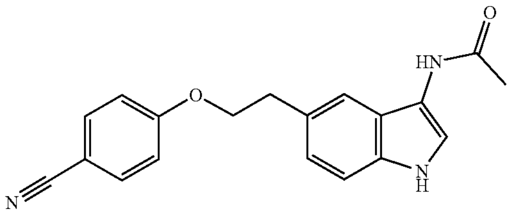 [SMILES: CC(=O)Nc1c[nH]c2ccc(CCOc3ccc(C#N)cc3)cc12] N-(5-(2-(4-cyanophenoxy)ethyl)-1H-indol-3-yl)acetamide | 320.2 |
| 463 | 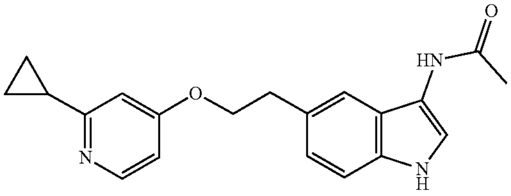 [SMILES: CC(=O)Nc1c[nH]c2ccc(CCOc3ccnc(C4CC4)c3)cc12] N-(5-(2-((2-cyclopropylpyridin-4-yl)oxy)ethyl)-1H-indol-3-yl)acetamide | 336.3 |
| 464 | 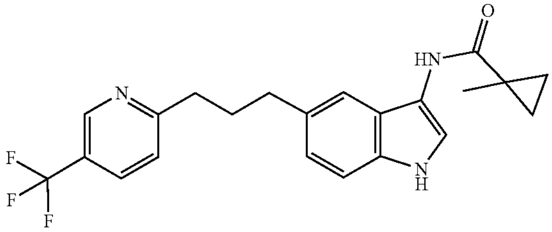 [SMILES: CC1(C(=O)Nc2c[nH]c3ccc(CCCc4ccc(C(F)(F)F)cn4)cc23)CC1] 1-methyl-N-(5-(3-(5-(trifluoromethyl)pyridin-2-yl)propyl)-1H-indol-3-yl)cyclopropane-1-carboxamide | 402.1 |
| 465 | 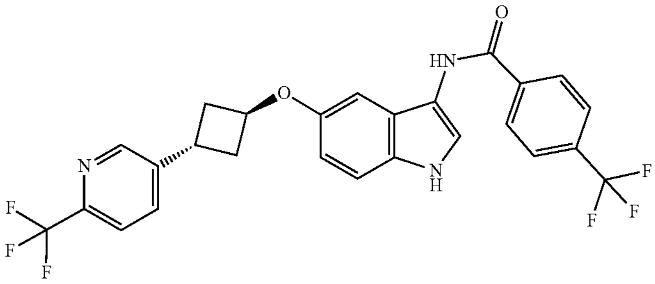 [SMILES: O=C(Nc1c[nH]c2ccc(O[C@H]3C[C@H](c4ccc(C(F)(F)F)nc4)C3)cc12)c1ccc(C(F)(F)F)cc1] 4-(trifluoromethyl)-N-(5-(trans-3-(6-(trifluoromethyl)pyridin-3-yl)cyclobutoxy)-1H-indol-3-yl)benzamide | 518.1 |

TABLE C1-continued

| Compound No. | Structure | LC-MS |
|---|---|---|
| 466 | 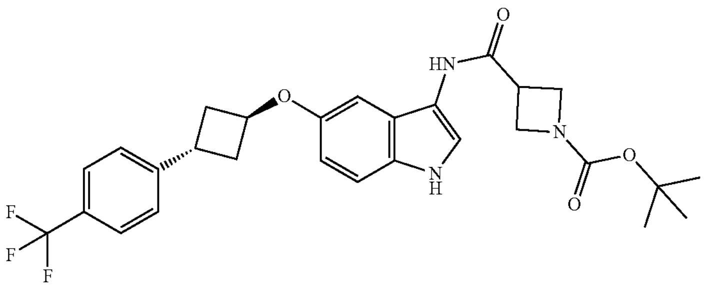 [SMILES: CC(C)(C)OC(=O)N1CC(C(=O)Nc2c[nH]c3ccc(O[C@H]4C[C@H](c5ccc(C(F)(F)F)cc5)C4)cc23)C1] tert-butyl 3-((5-(trans-3-(4-(trifluoromethyl)phenyl)cyclobutoxy)-1H-indol-3-yl)carbamoyl)azetidine-1-carboxylate | 529.3 |
| 467 | 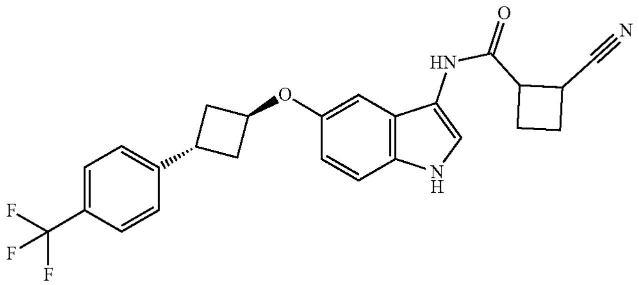 [SMILES: N#CC1CCC1C(=O)Nc1c[nH]c2ccc(O[C@H]3C[C@H](c4ccc(C(F)(F)F)cc4)C3)cc12] 2-cyano-N-(5-(trans-3-(4-(trifluoromethyl)phenyl)cyclobutoxy)-1H-indol-3-yl)cyclobutane-1-carboxamide | 454.3 |
| 468 | 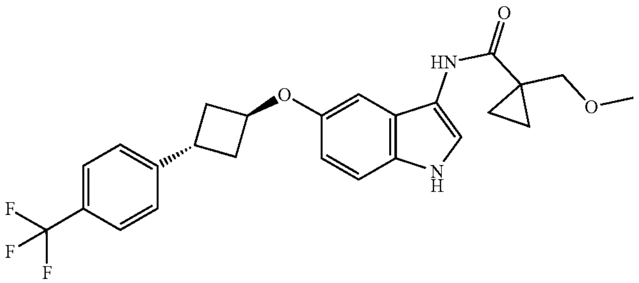 [SMILES: COCC1(C(=O)Nc2c[nH]c3ccc(O[C@H]4C[C@H](c5ccc(C(F)(F)F)cc5)C4)cc23)CC1] 1-(methoxymethyl)-N-(5-(trans-3-(4-(trifluoromethyl)phenyl)cyclobutoxy)-1H-indol-3-yl)cyclopropane-1-carboxamide | 459.3 |
| 469 | 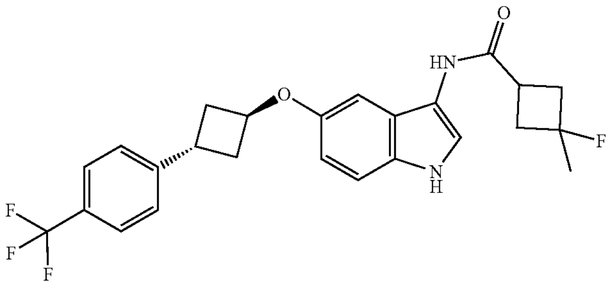 [SMILES: CC1(F)CC(C(=O)Nc2c[nH]c3ccc(O[C@H]4C[C@H](c5ccc(C(F)(F)F)cc5)C4)cc23)C1] 3-fluoro-3-methyl-N-(5-(trans-3-(4-(trifluoromethyl)phenyl)cyclobutoxy)-1H-indol-3-yl)cyclobutane-1-carboxamide | 461.3 |

TABLE C1-continued
| Compound No. | Structure | LC-MS |
|---|---|---|
| 470 | 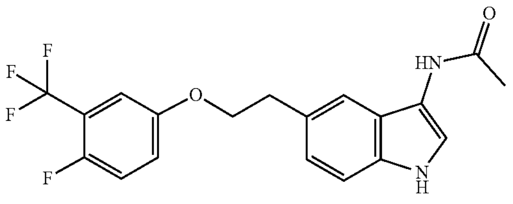 [SMILES: CC(=O)Nc1c[nH]c2ccc(CCOc3ccc(F)c(C(F)(F)F)c3)cc12] N-(5-(2-(4-fluoro-3-(trifluoromethyl)phenoxy)ethyl)-1H-indol-3-yl)acetamide | 381.2 |
| 471 | 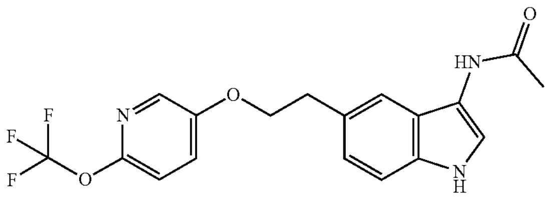 [SMILES: CC(=O)Nc1c[nH]c2ccc(CCOc3ccc(OC(F)(F)F)nc3)cc12] N-(5-(2-((6-(trifluoromethoxy)pyridin-3-yl)oxy)ethyl)-1H-indol-3-yl)acetamide | 380.2 |
| 472 | 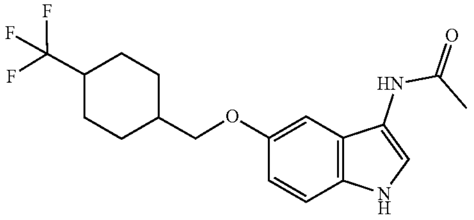 [SMILES: CC(=O)Nc1c[nH]c2ccc(OCC3CCC(C(F)(F)F)CC3)cc12] N-(5-((4-(trifluoromethyl)cyclohexyl)methoxy)-1H-indol-3-yl)acetamide | 355.25 |
| 473 | 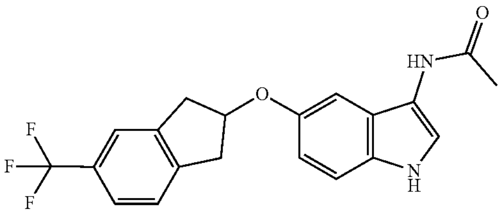 [SMILES: CC(=O)Nc1c[nH]c2ccc(OC3Cc4ccc(C(F)(F)F)cc4C3)cc12] N-(5-((5-(trifluoromethyl)-2,3-dihydro-1H-inden-2-yl)oxy)-1H-indol-3-yl)acetamide | 375.25 |
| 474 | 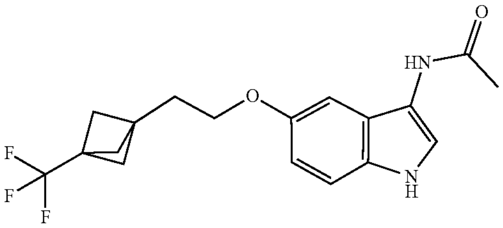 [SMILES: CC(=O)Nc1c[nH]c2ccc(OCCC34CC(C(F)(F)F)(C3)C4)cc12] N-(5-(2-(3-(trifluoromethyl)bicyclo[1.1.1]pentan-1-yl)ethoxy)-1H-indol-3-yl)acetamide | 353.15 |

TABLE C1-continued

| Compound No. | Structure | LC-MS |
|---|---|---|
| 475 | 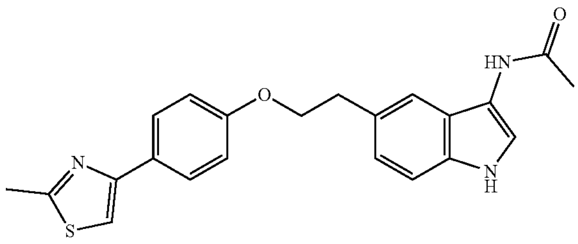 [SMILES: CC(=O)Nc1c[nH]c2ccc(CCOc3ccc(-c4csc(C)n4)cc3)cc12] N-(5-(2-(4-(2-methylthiazol-4-yl)phenoxy)ethyl)-1H-indol-3-yl)acetamide | 392.2 |
| 476 | 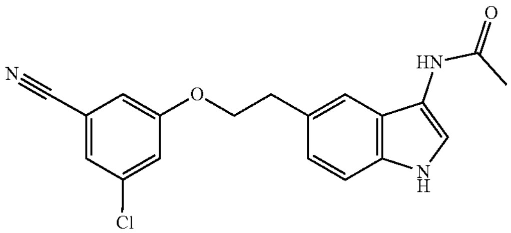 [SMILES: CC(=O)Nc1c[nH]c2ccc(CCOc3cc(Cl)cc(C#N)c3)cc12] N-(5-(2-(3-chloro-5-cyanophenoxy)ethyl)-1H-indol-3-yl)acetamide | 354.2 |
| 477 | 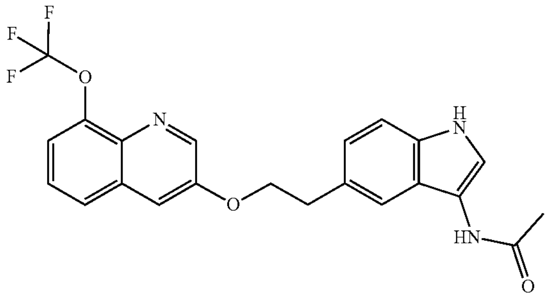 [SMILES: CC(=O)Nc1c[nH]c2ccc(CCOc3cnc4c(OC(F)(F)F)cccc4c3)cc12] N-(5-(2-((8-(trifluoromethoxy)quinolin-3-yl)oxy)ethyl)-1H-indol-3-yl)acetamide | 430.3 |
| 478 | 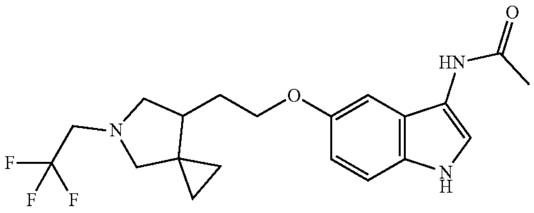 [SMILES: CC(=O)Nc1c[nH]c2ccc(OCCC3CN(CC(F)(F)F)CC34CC4)cc12] N-(5-(2-(5-(2,2,2-trifluoroethyl)-5-azaspiro[2.4]heptan-7-yl)ethoxy)-1H-indol-3-yl)acetamide | 396.1 |
| 479 | 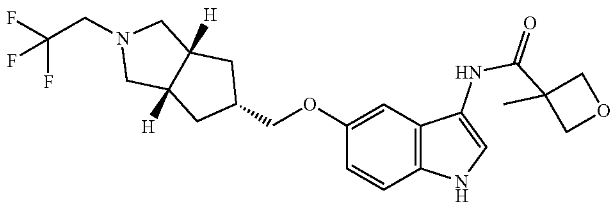 [SMILES: CC1(C(=O)Nc2c[nH]c3ccc(OC[C@@H]4C[C@@H]5CN(CC(F)(F)F)C[C@@H]5C4)cc23)COC1] 3-methyl-N-(5-(((3aR,5r,6aS)-2-(2,2,2-trifluoroethyl)octahydrocyclopenta[c]pyrrol-5-yl)methoxy)-1H-indol-3-yl)oxetane-3-carboxamide | 452.15 |

TABLE C1-continued

| Compound No. | Structure | LC-MS |
|---|---|---|
| 480 | 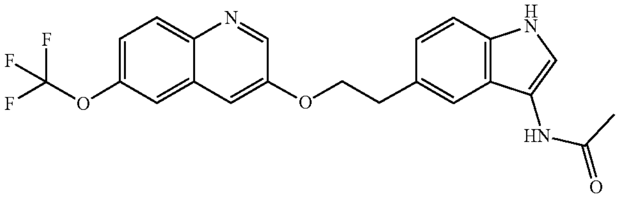 [SMILES: CC(=O)Nc1c[nH]c2ccc(CCOc3cnc4ccc(OC(F)(F)F)cc4c3)cc12] N-(5-(2-((6-(trifluoromethoxy)quinolin-3-yl)oxy)ethyl)-1H-indol-3-yl)acetamide | 430.3 |
| 481 | 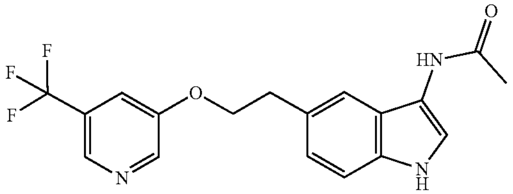 [SMILES: CC(=O)Nc1c[nH]c2ccc(CCOc3cncc(C(F)(F)F)c3)cc12] N-(5-(2-((5-(trifluoromethyl)pyridin-3-yl)oxy)ethyl)-1H-indol-3-yl)acetamide | 364.2 |
| 482 | 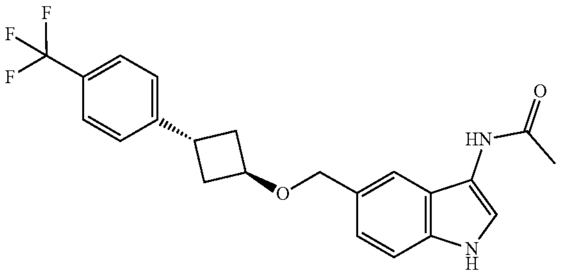 [SMILES: CC(=O)Nc1c[nH]c2ccc(CO[C@H]3C[C@H](c4ccc(C(F)(F)F)cc4)C3)cc12] N-(5-((trans-3-(4-(trifluoromethyl)phenyl)cyclobutoxy)methyl)-1H-indol-3-yl)acetamide | 401.1 |
| 483 | 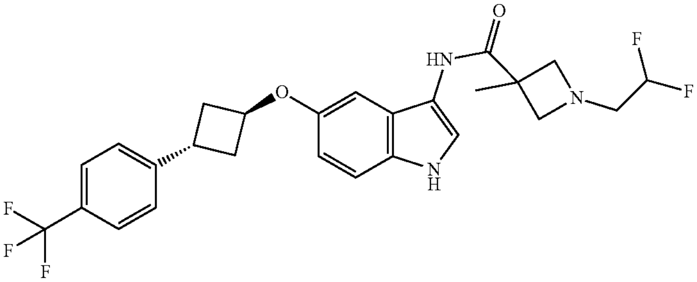 [SMILES: CC1(C(=O)Nc2c[nH]c3ccc(O[C@H]4C[C@H](c5ccc(C(F)(F)F)cc5)C4)cc23)CN(CC(F)F)C1] 1-(2,2-difluoroethyl)-3-methyl-N-(5-(trans-3-(4-(trifluoromethyl)phenyl)cyclobutoxy)-1H-indol-3-yl)azetidine-3-carboxamide | 508.2 |
| 484 | 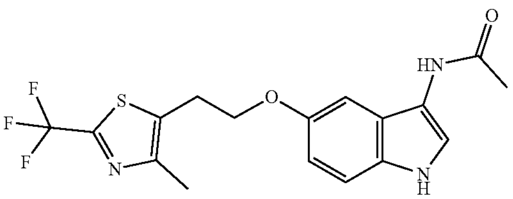 [SMILES: CC(=O)Nc1c[nH]c2ccc(OCCc3sc(C(F)(F)F)nc3C)cc12] N-(5-(2-(4-methyl-2-(trifluoromethyl)thiazol-5-yl)ethoxy)-1H-indol-3-yl)acetamide | 382.05 |

TABLE C1-continued

| Compound No. | Structure | LC-MS |
|---|---|---|
| 485 | 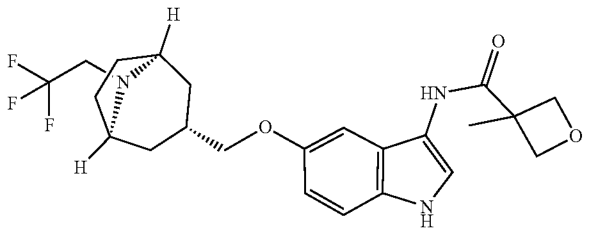 [SMILES: CC1(C(=O)Nc2c[nH]c3ccc(OC[C@@H]4C[C@H]5CC[C@@H](C4)N5CC(F)(F)F)cc23)COC1]<br>3-methyl-N-(5-(((1R,3s,5S)-8-(2,2,2-trifluoroethyl)-8-azabicyclo[3.2.1]octan-3-yl)methoxy)-1H-indol-3-yl)oxetane-3-carboxamide | 452.1 |
| 486 | 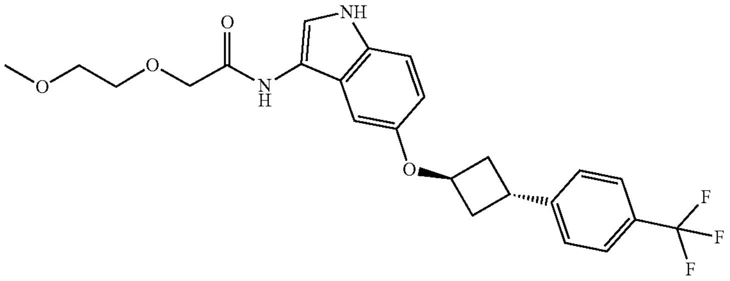 [SMILES: COCCOCC(=O)Nc1c[nH]c2ccc(O[C@H]3C[C@H](c4ccc(C(F)(F)F)cc4)C3)cc12]<br>2-(2-methoxyethoxy)-N-(5-((trans)-3-(4-(trifluoromethyl)phenyl)cyclobutoxy)-1H-indol-3-yl)acetamide | 463.3 |
| 487 | 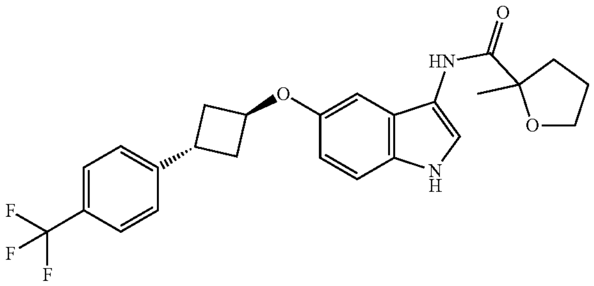 [SMILES: CC1(C(=O)Nc2c[nH]c3ccc(O[C@H]4C[C@H](c5ccc(C(F)(F)F)cc5)C4)cc23)CCCO1]<br>2-methyl-N-(5-(trans-3-(4-(trifluoromethyl)phenyl)cyclobutoxy)-1H-indol-3-yl)tetrahydrofuran-2-carboxamide | 459.3 |
| 488 | 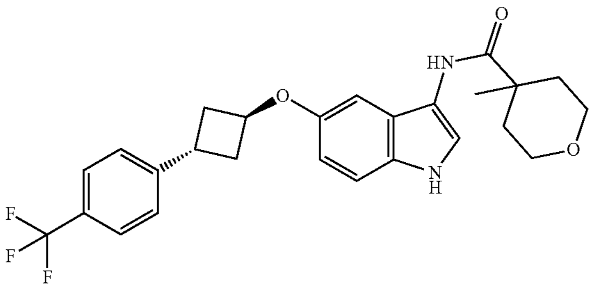<br>4-methyl-N-(5-(trans-3-(4-(trifluoromethyl)phenyl)cyclobutoxy)-1H-indol-3-yl)tetrahydro-2H-pyran-4-carboxamide | 473.4 |

TABLE C1-continued
| Compound No. | Structure | LC-MS |
|---|---|---|
| 489 | 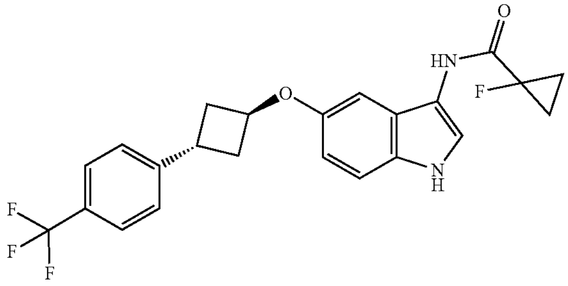 [SMILES: O=C(Nc1c[nH]c2ccc(O[C@H]3C[C@H](c4ccc(C(F)(F)F)cc4)C3)cc12)C1(F)CC1] 1-fluoro-N-(5-(trans-3-(4-(trifluoromethyl)phenyl)cyclobutoxy)-1H-indol-3-yl)cyclopropane-1-carboxamide | 433.2 |
| 490 | 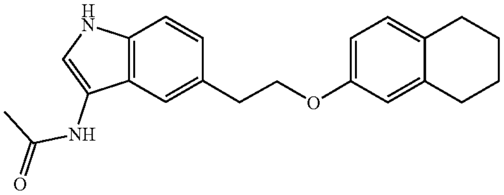 [SMILES: CC(=O)Nc1c[nH]c2ccc(CCOc3ccc4c(c3)CCCC4)cc12] N-(5-(2-((5,6,7,8-tetrahydronaphthalen-2-yl)oxy)ethyl)-1H-indol-3-yl)acetamide | 349.3 |
| 491 | 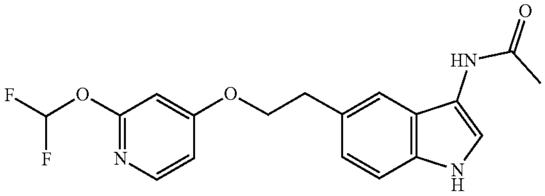 [SMILES: CC(=O)Nc1c[nH]c2ccc(CCOc3ccnc(OC(F)F)c3)cc12] N-(5-(2-((2-(difluoromethoxy)pyridin-4-yl)oxy)ethyl)-1H-indol-3-yl)acetamide | 362.2 |
| 492 | 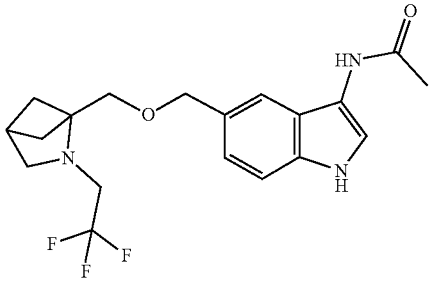 [SMILES: CC(=O)Nc1c[nH]c2ccc(COCC34CC(CN3CC(F)(F)F)C4)cc12] N-(5-(((2-(2,2,2-trifluoroethyl)-2-azabicyclo[2.1.1]hexan-1-yl)methoxy)methyl)-1H-indol-3-yl)acetamide | 382.05 |
| 493 | 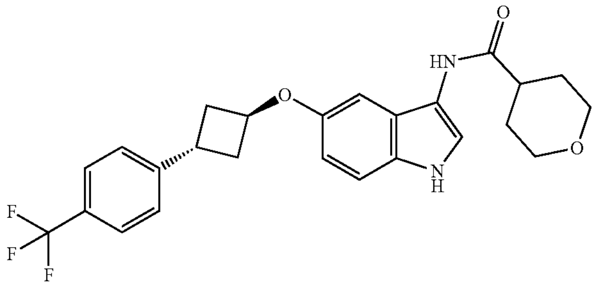 [SMILES: O=C(Nc1c[nH]c2ccc(O[C@H]3C[C@H](c4ccc(C(F)(F)F)cc4)C3)cc12)C1CCOCC1] | 459.3 |

TABLE C1-continued

| Compound No. | Structure | LC-MS |
|---|---|---|
| | N-(5-(trans-3-(4-(trifluoromethyl)phenyl)cyclobutoxy)-1H-indol-3-yl)tetrahydro-2H-pyran-4-carboxamide | |
| 494 | 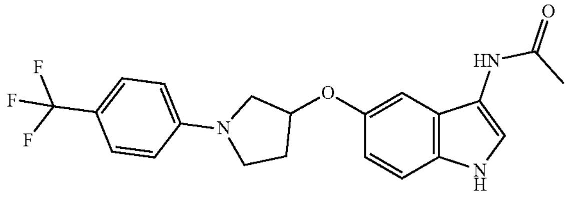 [SMILES: CC(=O)Nc1c[nH]c2ccc(OC3CCN(c4ccc(C(F)(F)F)cc4)C3)cc12] N-(5-((1-(4-(trifluoromethyl)phenyl)pyrrolidin-3-yl)oxy)-1H-indol-3-yl)acetamide | 404.05 |
| 495 | 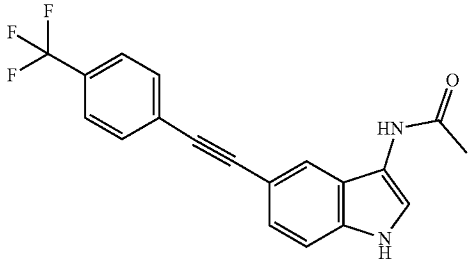 [SMILES: CC(=O)Nc1c[nH]c2ccc(C#Cc3ccc(C(F)(F)F)cc3)cc12] N-(5-((4-(trifluoromethyl)phenyl)ethynyl)-1H-indol-3-yl)acetamide | 341.05 |
| 496 | 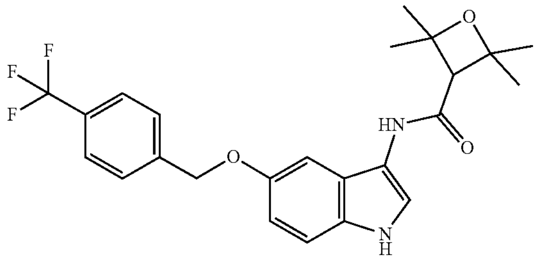 [SMILES: CC1(C)OC(C)(C)C1C(=O)Nc1c[nH]c2ccc(OCc3ccc(C(F)(F)F)cc3)cc12] 2,2,4,4-tetramethyl-N-(5-((4-(trifluoromethyl)benzyl)oxy)-1H-indol-3-yl)oxetane-3-carboxamide | 445.1 |
| 497 | 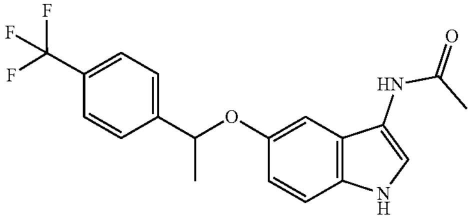 [SMILES: CC(=O)Nc1c[nH]c2ccc(OC(C)c3ccc(C(F)(F)F)cc3)cc12] N-(5-(1-(4-(trifluoromethyl)phenyl)ethoxy)-1H-indol-3-yl)acetamide | 361.05 |
| 498 | 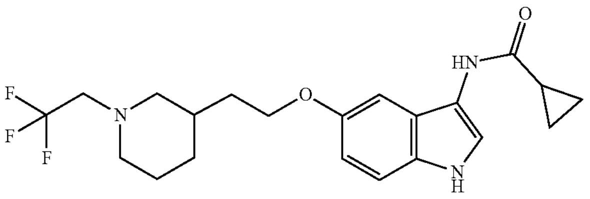 [SMILES: O=C(Nc1c[nH]c2ccc(OCCC3CCCN(CC(F)(F)F)C3)cc12)C1CC1] | 410.15 |

TABLE C1-continued

| Compound No. | Structure | LC-MS |
|---|---|---|
| | N-(5-(2-(1-(2,2,2-trifluoroethyl)piperidin-3-yl)ethoxy)-1H-indol-3-yl)cyclopropanecarboxamide | |
| 499 | 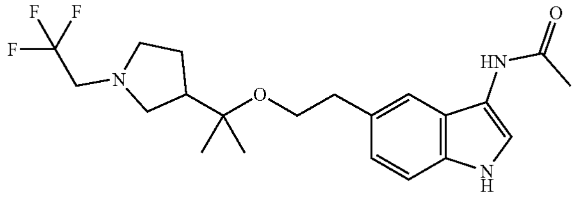 [SMILES: CC(=O)Nc1c[nH]c2ccc(CCOC(C)(C)C3CCN(CC(F)(F)F)C3)cc12] N-(5-(2-((2-(1-(2,2,2-trifluoroethyl)pyrrolidin-3-yl)propan-2-yl)oxy)ethyl)-1H-indol-3-yl)acetamide | 412.2 |
| 500 | 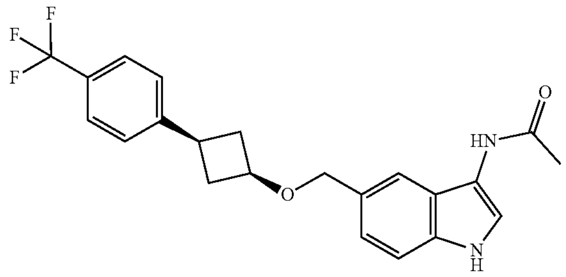 [SMILES: CC(=O)Nc1c[nH]c2ccc(CO[C@H]3C[C@@H](c4ccc(C(F)(F)F)cc4)C3)cc12] N-(5-((cis-3-(4-(trifluoromethyl)phenyl)cyclobutoxy)methyl)-1H-indol-3-yl)acetamide | 401.1 |
| 501 | 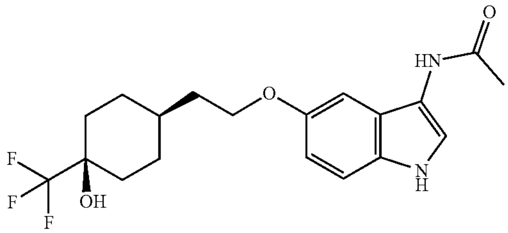 [SMILES: CC(=O)Nc1c[nH]c2ccc(OCC[C@H]3CC[C@](O)(C(F)(F)F)CC3)cc12] N-(5-(2-(trans-4-hydroxy-4-(trifluoromethyl)cyclohexyl)ethoxy)-1H-indol-3-yl)acetamide | 385.05 |
| 504 | 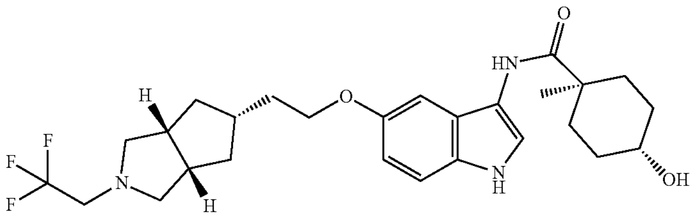 [SMILES: C[C@]1(C(=O)Nc2c[nH]c3ccc(OCC[C@@H]4C[C@@H]5CN(CC(F)(F)F)C[C@@H]5C4)cc23)CC[C@H](O)CC1] (1r,4R)-4-hydroxy-1-methyl-N-(5-(2-((3aR,5r,6aS)-2-(2,2,2-trifluoroethyl)octahydrocyclopenta[c]pyrrol-5-yl)ethoxy)-1H-indol-3-yl)cyclohexane-1-carboxamide | 508.2 |

TABLE C1-continued

| Compound No. | Structure | LC-MS |
|---|---|---|
| 505 | 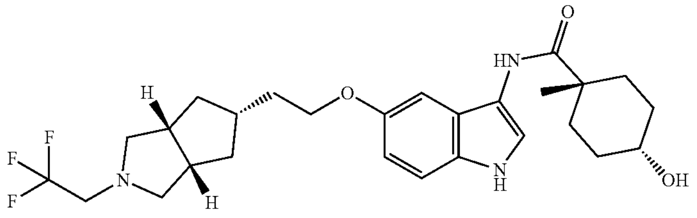 [SMILES: C[C@]1(C(=O)Nc2c[nH]c3ccc(OCC[C@@H]4C[C@@H]5CN(CC(F)(F)F)C[C@@H]5C4)cc23)CC[C@@H](O)CC1] (1s,4S)-4-hydroxy-1-methyl-N-(5-(2-((3aR,5r,6aS)-2-(2,2,2-trifluoroethyl)octahydrocyclopenta[c]pyrrol-5-yl)ethoxy)-1H-indol-3-yl)cyclohexane-1-carboxamide | 508.2 |
| 506 | 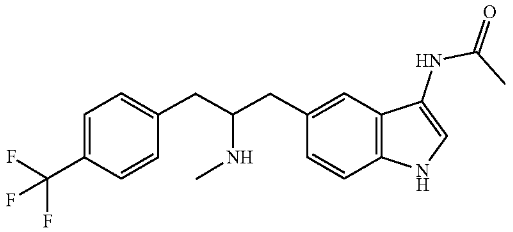 [SMILES: CNC(Cc1ccc(C(F)(F)F)cc1)Cc1ccc2[nH]cc(NC(C)=O)c2c1] N-(5-(2-(methylamino)-3-(4-(trifluoromethyl)phenyl)propyl)-1H-indol-3-yl)acetamide | 390.15 |
| 507 | 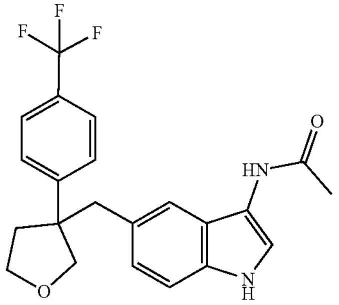 [SMILES: CC(=O)Nc1c[nH]c2ccc(CC3(c4ccc(C(F)(F)F)cc4)CCOC3)cc12] N-(5-((3-(4-(trifluoromethyl)phenyl)tetrahydrofuran-3-yl)methyl)-1H-indol-3-yl)acetamide | 403.05 |
| 508 | 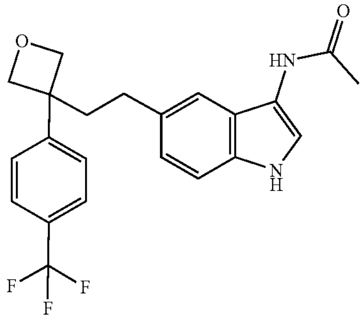 [SMILES: CC(=O)Nc1c[nH]c2ccc(CCC3(c4ccc(C(F)(F)F)cc4)COC3)cc12] N-(5-(2-(3-(4-(trifluoromethyl)phenyl)oxetan-3-yl)ethyl)-1H-indol-3-yl)acetamide | 403.05 |

TABLE C1-continued

| Compound No. | Structure | LC-MS |
|---|---|---|
| 509 | 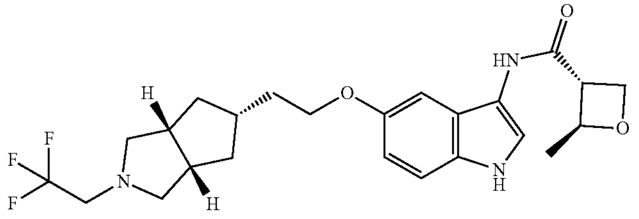 [SMILES: C[C@@H]1OC[C@H]1C(=O)Nc1c[nH]c2ccc(OCC[C@@H]3C[C@@H]4CN(CC(F)(F)F)C[C@@H]4C3)cc12] (2S,3R)-2-methyl-N-(5-(2-((3aR,5r,6aS)-2-(2,2,2-trifluoroethyl)octahydrocyclopenta[c]pyrrol-5-yl)ethoxy)-1H-indol-3-yl)oxetane-3-carboxamide | 466.2 |
| 510 | 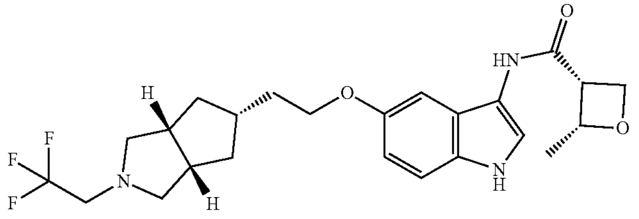 [SMILES: C[C@H]1OC[C@H]1C(=O)Nc1c[nH]c2ccc(OCC[C@@H]3C[C@@H]4CN(CC(F)(F)F)C[C@@H]4C3)cc12] (2R,3R)-2-methyl-N-(5-(2-((3aR,5r,6aS)-2-(2,2,2-trifluoroethyl)octahydrocyclopenta[c]pyrrol-5-yl)ethoxy)-1H-indol-3-yl)oxetane-3-carboxamide | 466.2 |
| 511 | 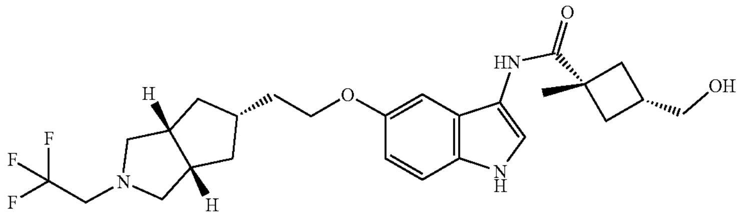 [SMILES: C[C@]1(C(=O)Nc2c[nH]c3ccc(OCC[C@@H]4C[C@@H]5CN(CC(F)(F)F)C[C@@H]5C4)cc23)C[C@@H](CO)C1] (1s,3S)-3-(hydroxymethyl)-1-methyl-N-(5-(2-((3aR,5r,6aS)-2-(2,2,2-trifluoroethyl)octahydrocyclopenta[c]pyrrol-5-yl)ethoxy)-1H-indol-3-yl)cyclobutane-1-carboxamide | 494.2 |
| 512 | 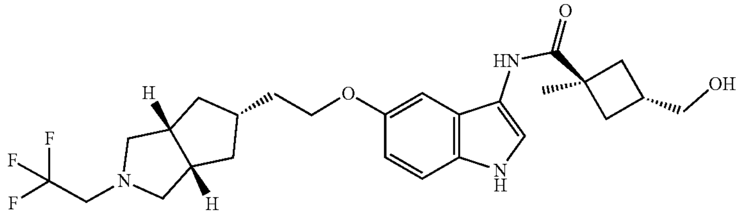 [SMILES: C[C@]1(C(=O)Nc2c[nH]c3ccc(OCC[C@@H]4C[C@@H]5CN(CC(F)(F)F)C[C@@H]5C4)cc23)C[C@H](CO)C1] (1r,3R)-3-(hydroxymethyl)-1-methyl-N-(5-(2-((3aR,5r,6aS)-2-(2,2,2-trifluoroethyl)octahydrocyclopenta[c]pyrrol-5-yl)ethoxy)-1H-indol-3-yl)cyclobutane-1-carboxamide | 494.2 |
| 513 | 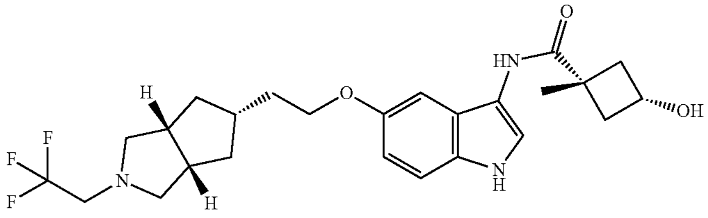 [SMILES: C[C@]1(C(=O)Nc2c[nH]c3ccc(OCC[C@@H]4C[C@@H]5CN(CC(F)(F)F)C[C@@H]5C4)cc23)C[C@@H](O)C1] (1s,3S)-3-hydroxy-1-methyl-N-(5-(2-((3aR,5r,6aS)-2-(2,2,2- | 480.2 |

TABLE C1-continued

| Compound No. | Structure | LC-MS |
|---|---|---|
| | trifluoroethyl)octahydrocyclopenta[c]pyrrol-5-yl)ethoxy)-1H-indol-3-yl)cyclobutane-1-carboxamide | |
| 514 | 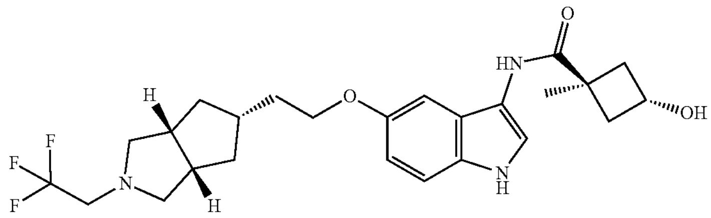 [SMILES: C[C@]1(C(=O)Nc2c[nH]c3ccc(OCC[C@@H]4C[C@@H]5CN(CC(F)(F)F)C[C@@H]5C4)cc23)C[C@H](O)C1] (1r,3R)-3-hydroxy-1-methyl-N-(5-(2-((3aR,5r,6aS)-2-(2,2,2-trifluoroethyl)octahydrocyclopenta[c]pyrrol-5-yl)ethoxy)-1H-indol-3-yl)cyclobutane-l-carboxamide | 480.2 |
| 515 | 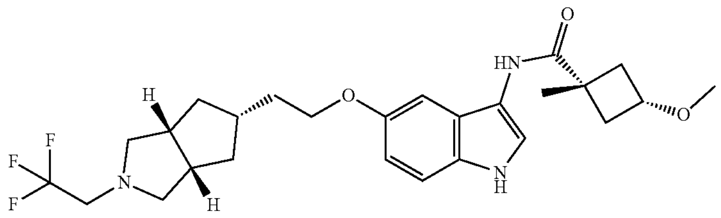 [SMILES: CO[C@H]1C[C@@](C)(C(=O)Nc2c[nH]c3ccc(OCC[C@@H]4C[C@@H]5CN(CC(F)(F)F)C[C@@H]5C4)cc23)C1] (1s,3S)-3-methoxy-1-methyl-N-(5-(2-((3aR,5r,6aS)-2-(2,2,2-trifluoroethyl)octahydrocyclopenta[c]pyrrol-5-yl)ethoxy)-1H-indol-3-yl)cyclobutane-1-carboxamide | 494.2 |
| 516 | 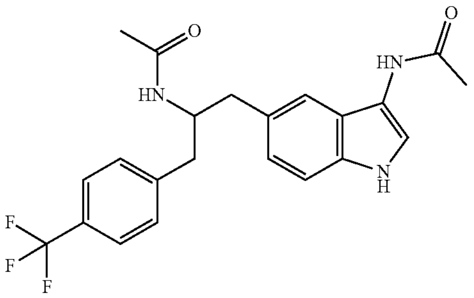 [SMILES: CC(=O)Nc1c[nH]c2ccc(CC(Cc3ccc(C(F)(F)F)cc3)NC(C)=O)cc12] N-(1-(3-acetamido-1H-indol-5-yl)-3-(4-(trifluoromethyl)phenyl)propan-2-yl)acetamide | 418.15 |
| 517 | 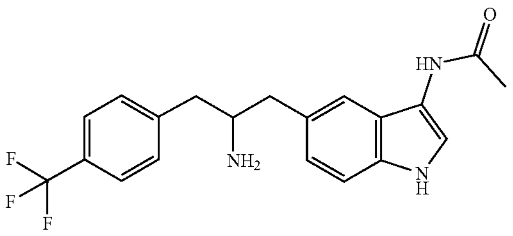 [SMILES: CC(=O)Nc1c[nH]c2ccc(CC(N)Cc3ccc(C(F)(F)F)cc3)cc12] N-(5-(2-amino-3-(4-(trifluoromethyl)phenyl)propyl)-1H-indol-3-yl)acetamide | 376.1 |

TABLE C1-continued

| Compound No. | Structure | LC-MS |
|---|---|---|
| 518 | 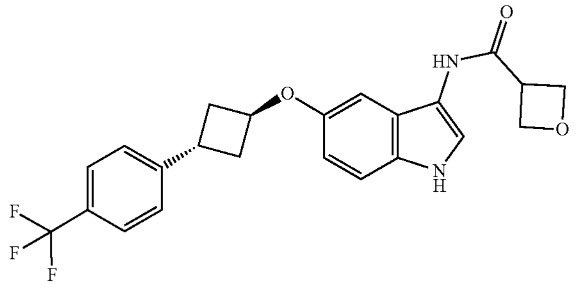 [SMILES: O=C(Nc1c[nH]c2ccc(O[C@H]3C[C@H](c4ccc(C(F)(F)F)cc4)C3)cc12)C1COC1] N-(5-(trans-3-(4-(trifluoromethyl)phenyl)cyclobutoxy)-1H-indol-3-yl)oxetane-3-carboxamide | 431.1 |
| 519 | 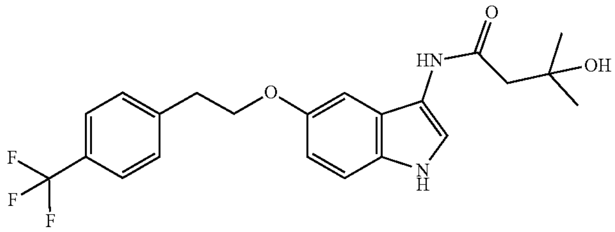 [SMILES: CC(C)(O)CC(=O)Nc1c[nH]c2ccc(OCCc3ccc(C(F)(F)F)cc3)cc12] 3-hydroxy-3-methyl-N-(5-(4-(trifluoromethyl)phenethoxy)-1H-indol-3-yl)butanamide | 421.15 |
| 520 | 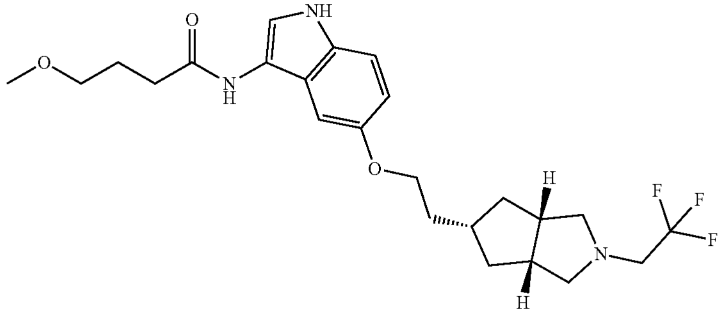 [SMILES: COCCCC(=O)Nc1c[nH]c2ccc(OCC[C@@H]3C[C@@H]4CN(CC(F)(F)F)C[C@@H]4C3)cc12] 4-methoxy-N-(5-(2-((3aR,5r,6aS)-2-(2,2,2-trifluoroethyl)octahydrocyclopenta[c]pyrrol-5-yl)ethoxy)-1H-indol-3-yl)butanamide | 468.25 |
| 521 | 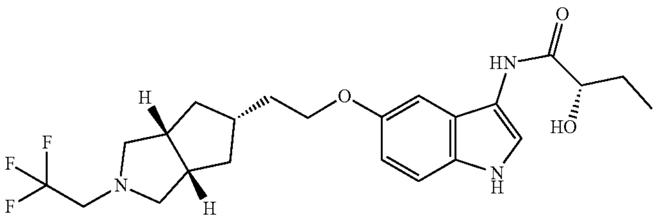 [SMILES: CC[C@H](O)C(=O)Nc1c[nH]c2ccc(OCC[C@@H]3C[C@@H]4CN(CC(F)(F)F)C[C@@H]4C3)cc12] (S)-2-hydroxy-N-(5-(2-((3aR,5r,6aS)-2-(2,2,2-trifluoroethyl)octahydrocyclopenta[c]pyrrol-5-yl)ethoxy)-1H-indol-3-yl)butanamide | 454.2 |

TABLE C1-continued

| Compound No. | Structure | LC-MS |
| --- | --- | --- |
| 522 | 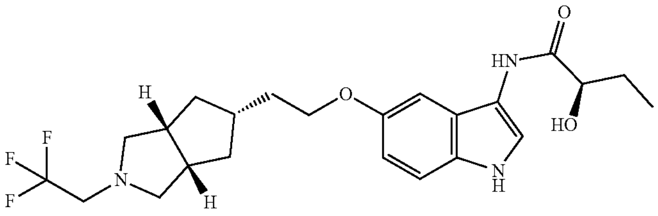 [SMILES: CC[C@@H](O)C(=O)Nc1c[nH]c2ccc(OCC[C@@H]3C[C@@H]4CN(CC(F)(F)F)C[C@@H]4C3)cc12]<br>(R)-2-hydroxy-N-(5-(2-((3aR,5r,6aS)-2-(2,2,2-trifluoroethyl)octahydrocyclopenta[c]pyrrol-5-yl)ethoxy)-1H-indol-3-yl)butanamide | 454.2 |
| 523 | 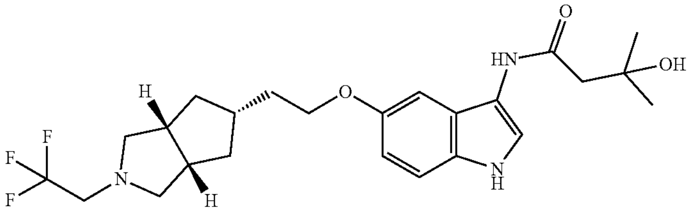 [SMILES: CC(C)(O)CC(=O)Nc1c[nH]c2ccc(OCC[C@@H]3C[C@@H]4CN(CC(F)(F)F)C[C@@H]4C3)cc12]<br>3-hydroxy-3-methyl-N-(5-(2-((3aR,5r,6aS)-2-(2,2,2-trifluoroethyl)octahydrocyclopenta[c]pyrrol-5-yl)ethoxy)-1H-indol-3-yl)butanamide | 468.15 |
| 525 | 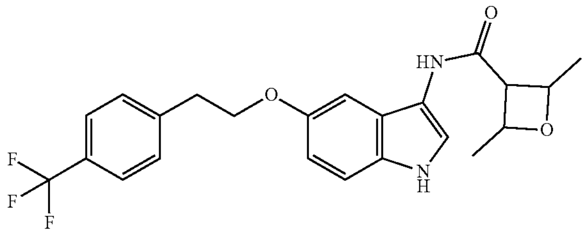 [SMILES: CC1OC(C)C1C(=O)Nc1c[nH]c2ccc(OCCc3ccc(C(F)(F)F)cc3)cc12]<br>2,4-dimethyl-N-(5-(4-(trifluoromethyl)phenethoxy)-1H-indol-3-yl)oxetane-3-carboxamide | 433.1 |
| 526 | 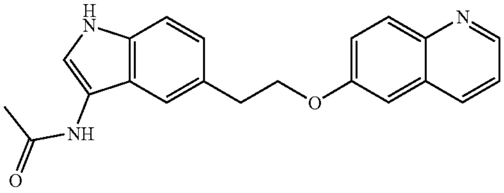 [SMILES: CC(=O)Nc1c[nH]c2ccc(CCOc3ccc4ncccc4c3)cc12]<br>N-(5-(2-(quinolin-6-yloxy)ethyl)-1H-indol-3-yl)acetamide | 346.2 |
| 527 | 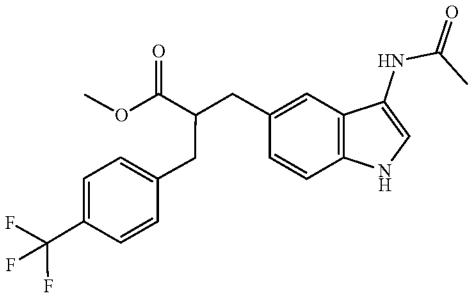 [SMILES: COC(=O)C(Cc1ccc(C(F)(F)F)cc1)Cc1ccc2[nH]cc(NC(C)=O)c2c1]<br>methyl 3-(3-acetamido-1H-indol-5-yl)-2-(4-(trifluoromethyl)benzyl)propanoate | 419.3 |

TABLE C1-continued

| Compound No. | Structure | LC-MS |
|---|---|---|
| 528 | 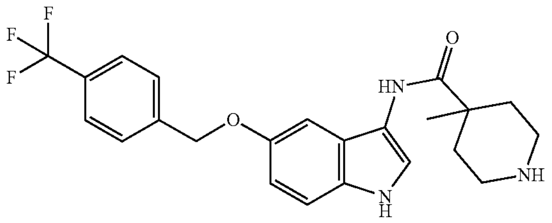 [SMILES: CC1(C(=O)Nc2c[nH]c3ccc(OCc4ccc(C(F)(F)F)cc4)cc23)CCNCC1]<br>4-methyl-N-(5-((4-(trifluoromethyl)benzyl)oxy)-1H-indol-3-yl)piperidine-4-carboxamide | 432.4 |
| 529 | 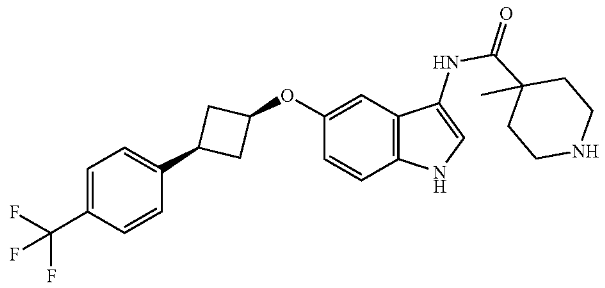 [SMILES: CC1(C(=O)Nc2c[nH]c3ccc(O[C@H]4C[C@@H](c5ccc(C(F)(F)F)cc5)C4)cc23)CCNCC1]<br>4-methyl-N-(5-(cis-3-(4-(trifluoromethyl)phenyl)cyclobutoxy)-1H-indol-3-yl)piperidine-4-carboxamide | 472.3 |
| 530 | 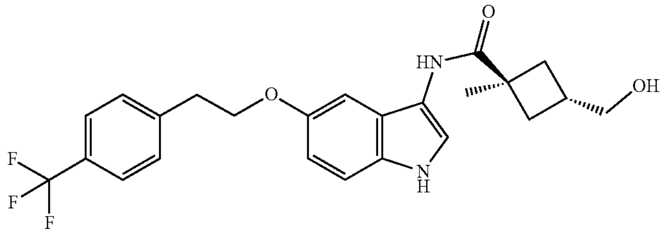 [SMILES: C[C@]1(C(=O)Nc2c[nH]c3ccc(OCCc4ccc(C(F)(F)F)cc4)cc23)C[C@H](CO)C1]<br>trans-3-(hydroxymethyl)-1-methyl-N-(5-(4-(trifluoromethyl)phenethoxy)-1H-indol-3-yl)cyclobutane-1-carboxamide | 447.2 |
| 531 | 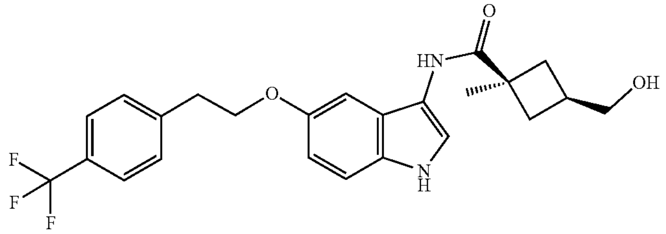 [SMILES: C[C@]1(C(=O)Nc2c[nH]c3ccc(OCCc4ccc(C(F)(F)F)cc4)cc23)C[C@@H](CO)C1]<br>cis-3-(hydroxymethyl)-1-methyl-N-(5-(4-(trifluoromethyl)phenethoxy)-1H-indol-3-yl)cyclobutane-1-carboxamide | 447.15 |

TABLE C1-continued
| Compound No. | Structure | LC-MS |
|---|---|---|
| 532 | 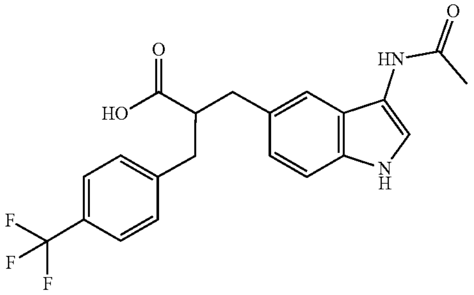 [SMILES: CC(=O)Nc1c[nH]c2ccc(CC(Cc3ccc(C(F)(F)F)cc3)C(=O)O)cc12]<br>3-(3-acetamido-1H-indol-5-yl)-2-(4-(trifluoromethyl)benzyl)propanoic acid | 403.0 |
| 533 | 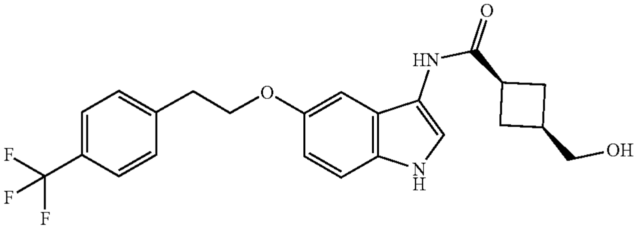 [SMILES: O=C(Nc1c[nH]c2ccc(OCCc3ccc(C(F)(F)F)cc3)cc12)[C@H]1C[C@@H](CO)C1]<br>cis-3-(hydroxymethyl)-N-(5-(4-(trifluoromethyl)phenethoxy)-1H-indol-3-yl)cyclobutane-1-carboxamide | 433.1 |
| 534 | 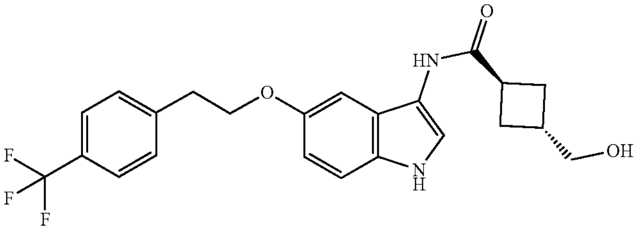 [SMILES: O=C(Nc1c[nH]c2ccc(OCCc3ccc(C(F)(F)F)cc3)cc12)[C@H]1C[C@H](CO)C1]<br>trans-3-(hydroxymethyl)-N-(5-(4-(trifluoromethyl)phenethoxy)-1H-indol-3-yl)cyclobutane-1-carboxamide | 433.15 |
| 536 | 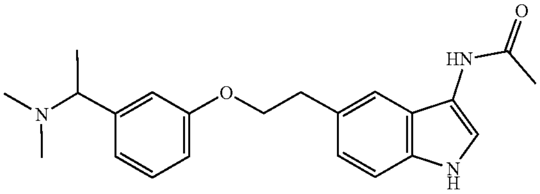 [SMILES: CC(=O)Nc1c[nH]c2ccc(CCOc3cccc(C(C)N(C)C)c3)cc12]<br>N-(5-(2-(3-(1-(dimethylamino)ethyl)phenoxy)ethyl)-1H-indol-3-yl)acetamide | 366.3 |
| 537 | 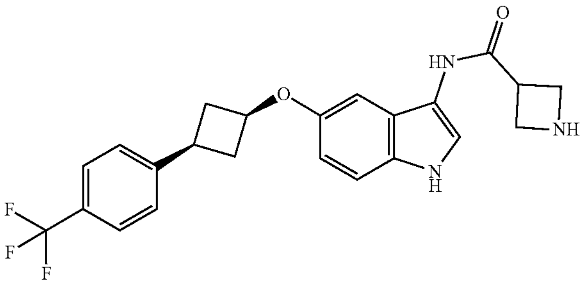 [SMILES: O=C(Nc1c[nH]c2ccc(O[C@H]3C[C@@H](c4ccc(C(F)(F)F)cc4)C3)cc12)C1CNC1] | 430.3 |

TABLE C1-continued

| Compound No. | Structure | LC-MS |
| --- | --- | --- |
| | N-(5-(cis-3-(4-(trifluoromethyl)phenyl)cyclobutoxy)-1H-indol-3-yl)azetidine-3-carboxamide | |
| 538 | 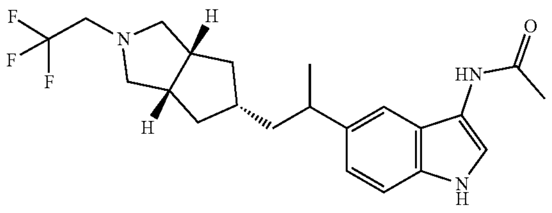 [SMILES: CC(=O)Nc1c[nH]c2ccc(C(C)C[C@@H]3C[C@@H]4CN(CC(F)(F)F)C[C@@H]4C3)cc12] | 408.2 |
| | N-(5-(1-((3aR,5r,6aS)-2-(2,2,2-trifluoroethyl)octahydrocyclopenta[c]pyrrol-5-yl)propan-2-yl)-1H-indol-3-yl)acetamide | |
| 539 | 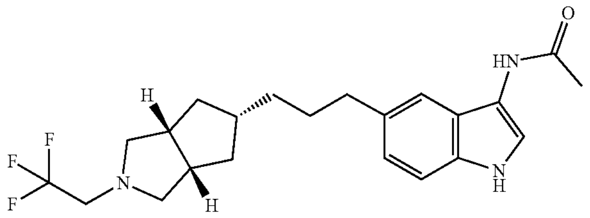 [SMILES: CC(=O)Nc1c[nH]c2ccc(CCC[C@@H]3C[C@@H]4CN(CC(F)(F)F)C[C@@H]4C3)cc12] | 408.2 |
| | N-(5-(3-((3aR,5r,6aS)-2-(2,2,2-trifluoroethyl)octahydrocyclopenta[c]pyrrol-5-yl)propyl)-1H-indol-3-yl)acetamide | |
| 540 | 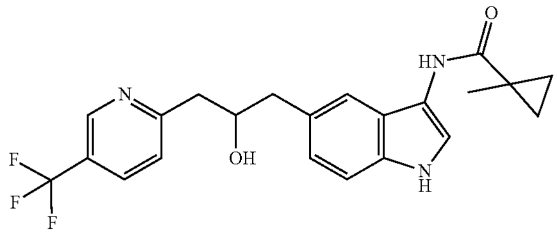 [SMILES: CC1(C(=O)Nc2c[nH]c3ccc(CC(O)Cc4ccc(C(F)(F)F)cn4)cc23)CC1] | 418.2 |
| | N-(5-(2-hydroxy-3-(5-(trifluoromethyl)pyridin-2-yl)propyl)-1H-indol-3-yl)-1-methylcyclopropane-1-carboxamide | |
| 541 | 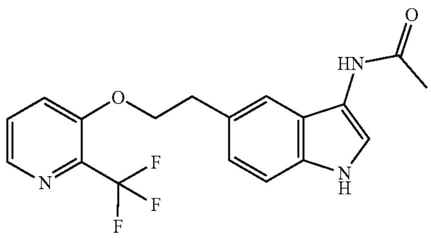 [SMILES: CC(=O)Nc1c[nH]c2ccc(CCOc3cccnc3C(F)(F)F)cc12] | 364.3 |
| | N-(5-(2-((2-(trifluoromethyl)pyridin-3-yl)oxy)ethyl)-1H-indol-3-yl)acetamide | |
| 542 | 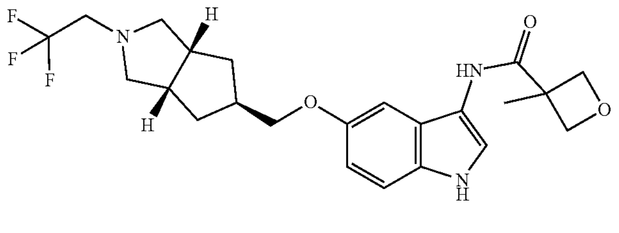 [SMILES: CC1(C(=O)Nc2c[nH]c3ccc(OC[C@H]4C[C@@H]5CN(CC(F)(F)F)C[C@@H]5C4)cc23)COC1] | 452.15 |

TABLE C1-continued

| Compound No. | Structure | LC-MS |
|---|---|---|
| | 3-methyl-N-(5-(((3aR,5s,6aS)-2-(2,2,2-trifluoroethyl)octahydrocyclopenta[c]pyrrol-5-yl)methoxy)-1H-indol-3-yl)oxetane-3-carboxamide | |
| 543 | 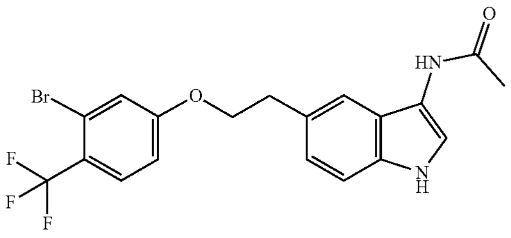 [SMILES: CC(=O)Nc1c[nH]c2ccc(CCOc3ccc(C(F)(F)F)c(Br)c3)cc12] N-(5-(2-(3-bromo-4-(trifluoromethyl)phenoxy)ethyl)-1H-indol-3-yl)acetamide | 439.0 |
| 544 | 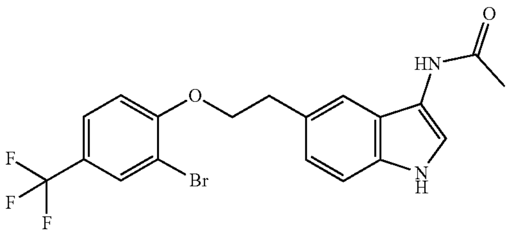 [SMILES: CC(=O)Nc1c[nH]c2ccc(CCOc3ccc(C(F)(F)F)cc3Br)cc12] N-(5-(2-(2-bromo-4-(trifluoromethyl)phenoxy)ethyl)-1H-indol-3-yl)acetamide | 438.95 |
| 545 | 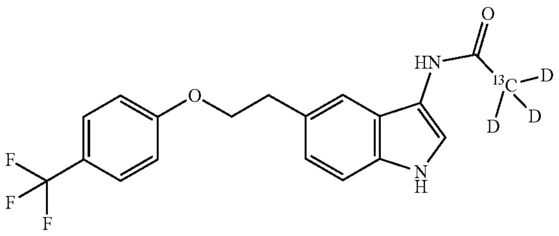 [SMILES: [2H][13C]([2H])([2H])C(=O)Nc1c[nH]c2ccc(CCOc3ccc(C(F)(F)F)cc3)cc12] N-(5-(2-(4-(trifluoromethyl)phenoxy)ethyl)-1H-indol-3-yl)acetamide-2-13C-2,2,2-d3 | 365.0 |
| 546 | 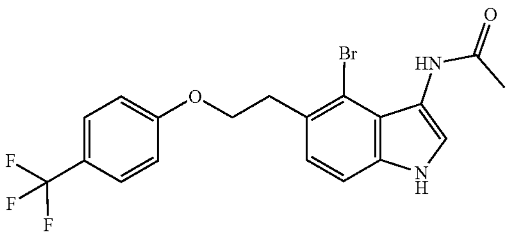 [SMILES: CC(=O)Nc1c[nH]c2ccc(CCOc3ccc(C(F)(F)F)cc3)c(Br)c12] N-(4-bromo-5-(2-(4-(trifluoromethyl)phenoxy)ethyl)-1H-indol-3-yl)acetamide | 441.05 |

TABLE C1-continued
| Compound No. | Structure | LC-MS |
|---|---|---|
| 547 | 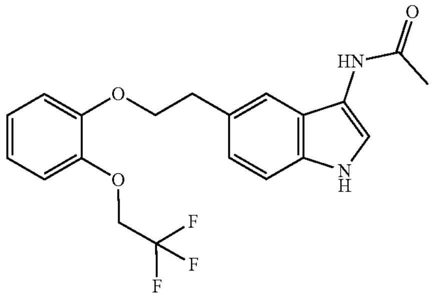 [SMILES: CC(=O)Nc1c[nH]c2ccc(CCOc3ccccc3OCC(F)(F)F)cc12] N-(5-(2-(2-(2,2,2-trifluoroethoxy)phenoxy)ethyl)-1H-indol-3-yl)acetamide | 393.3 |
| 548 | 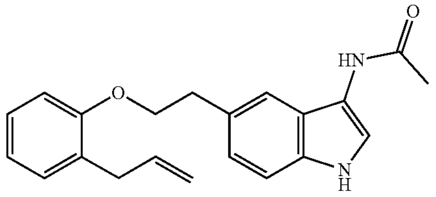 [SMILES: C=CCc1ccccc1OCCc1ccc2[nH]cc(NC(C)=O)c2c1] N-(5-(2-(2-allylphenoxy)ethyl)-1H-indol-3-yl)acetamide | 335.3 |
| 549 | 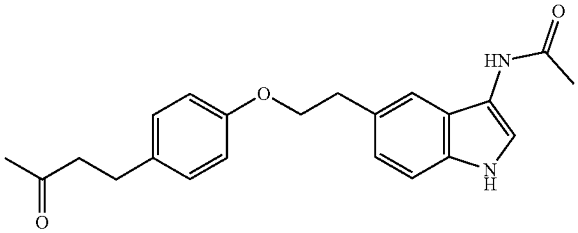 [SMILES: CC(=O)CCc1ccc(OCCc2ccc3[nH]cc(NC(C)=O)c3c2)cc1] N-(5-(2-(4-(3-oxobutyl)phenoxy)ethyl)-1H-indol-3-yl)acetamide | 365.3 |
| 550 | 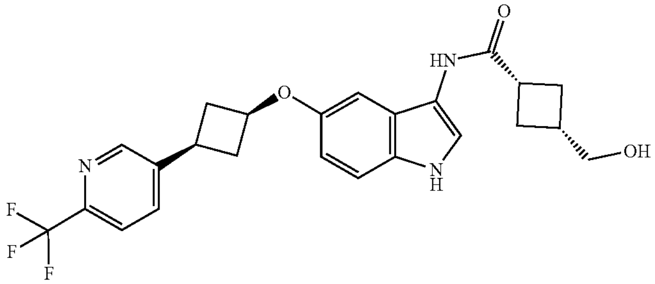 [SMILES: O=C(Nc1c[nH]c2ccc(O[C@H]3C[C@@H](c4ccc(C(F)(F)F)nc4)C3)cc12)[C@H]1C[C@@H](CO)C1] cis-3-(hydroxymethyl)-N-(5-(cis-3-(6-(trifluoromethyl)pyridin-3-yl)cyclobutoxy)-1H-indol-3-yl)cyclobutane-1-carboxamide | 460.1 |

TABLE C1-continued

| Compound No. | Structure | LC-MS |
|---|---|---|
| 551 | 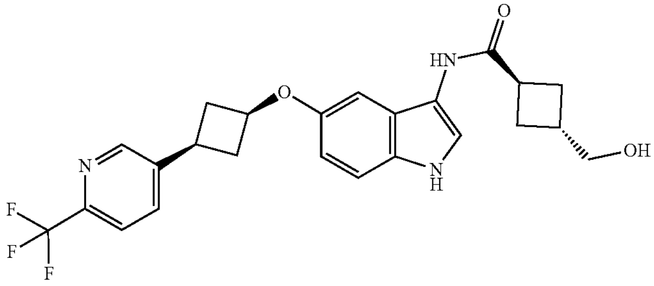 [SMILES: O=C(Nc1c[nH]c2ccc(O[C@H]3C[C@@H](c4ccc(C(F)(F)F)nc4)C3)cc12)[C@H]1C[C@H](CO)C1] trans-3-(hydroxymethyl)-N-(5-(cis-3-(6-(trifluoromethyl)pyridin-3-yl)cyclobutoxy)-1H-indol-3-yl)cyclobutane-1-carboxamide | 460.1 |
| 552 | 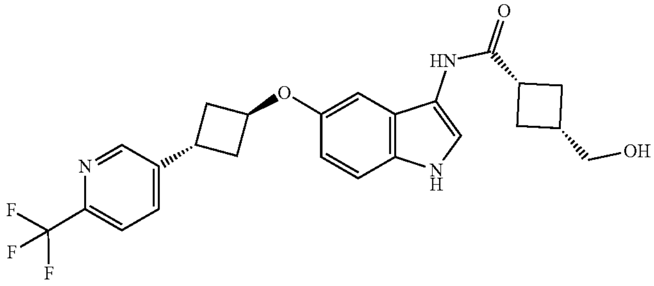 [SMILES: O=C(Nc1c[nH]c2ccc(O[C@H]3C[C@H](c4ccc(C(F)(F)F)nc4)C3)cc12)[C@H]1C[C@@H](CO)C1] cis-3-(hydroxymethyl)-N-(5-(trans-3-(6-(trifluoromethyl)pyridin-3-yl)cyclobutoxy)-1H-indol-3-yl)cyclobutane-1-carboxamide | 458.1 |
| 553 | 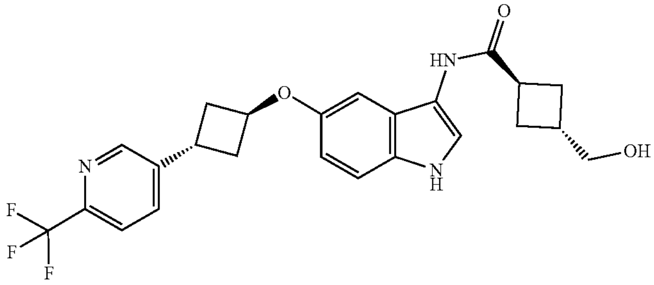 [SMILES: O=C(Nc1c[nH]c2ccc(O[C@H]3C[C@H](c4ccc(C(F)(F)F)nc4)C3)cc12)[C@H]1C[C@H](CO)C1] trans-3-(hydroxymethyl)-N-(5-(trans-3-(6-(trifluoromethyl)pyridin-3-yl)cyclobutoxy)-1H-indol-3-yl)cyclobutane-1-carboxamide | 458.1 |
| 554 | 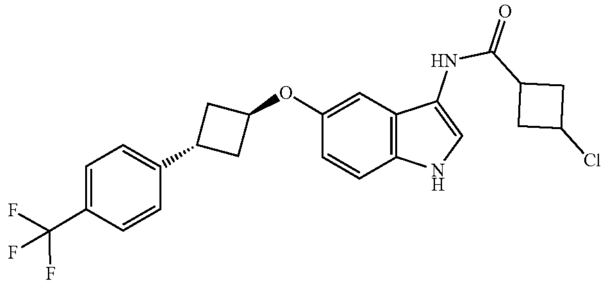 [SMILES: O=C(Nc1c[nH]c2ccc(O[C@H]3C[C@H](c4ccc(C(F)(F)F)cc4)C3)cc12)C1CC(Cl)C1] 3-chloro-N-(5-(trans-3-(4-(trifluoromethyl)phenyl)cyclobutoxy)-1H-indol-3-yl)cyclobutane-1-carboxamide | 463.2 |

TABLE C1-continued
| Compound No. | Structure | LC-MS |
|---|---|---|
| 555 | 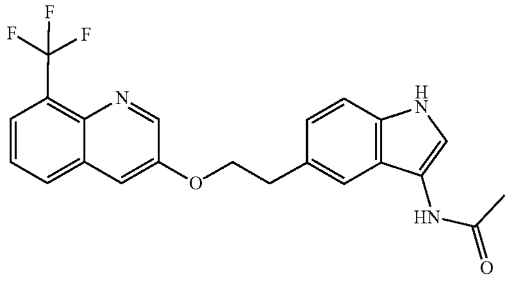 [SMILES: CC(=O)Nc1c[nH]c2ccc(CCOc3cnc4c(C(F)(F)F)cccc4c3)cc12]<br>N-(5-(2-((8-(trifluoromethyl)quinolin-3-yl)oxy)ethyl)-1H-indol-3-yl)acetamide | 414.3 |
| 556 | 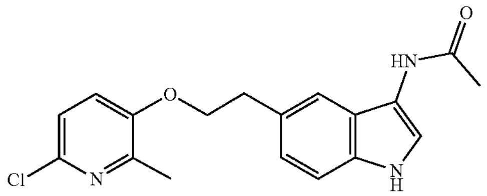 [SMILES: CC(=O)Nc1c[nH]c2ccc(CCOc3ccc(Cl)nc3C)cc12]<br>N-(5-(2-((6-chloro-2-methylpyridin-3-yl)oxy)ethyl)-1H-indol-3-yl)acetamide | 344.2 |
| 557 | 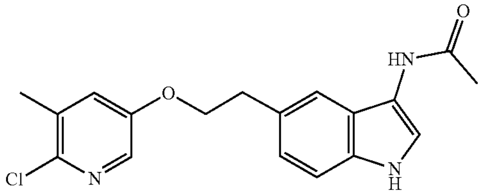 [SMILES: CC(=O)Nc1c[nH]c2ccc(CCOc3cnc(Cl)c(C)c3)cc12]<br>N-(5-(2-((6-chloro-5-methylpyridin-3-yl)oxy)ethyl)-1H-indol-3-yl)acetamide | 344.2 |
| 558 | 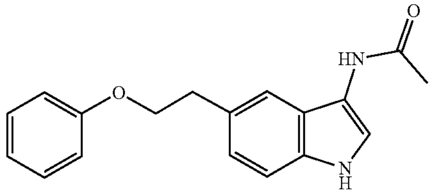 [SMILES: CC(=O)Nc1c[nH]c2ccc(CCOc3ccccc3)cc12]<br>N-(5-(2-phenoxyethyl)-1H-indol-3-yl)acetamide | 295.2 |
| 559 | 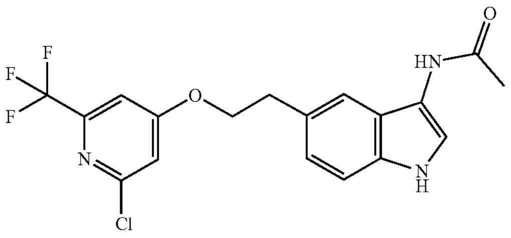 [SMILES: CC(=O)Nc1c[nH]c2ccc(CCOc3cc(Cl)nc(C(F)(F)F)c3)cc12]<br>N-(5-(2-((2-chloro-6-(trifluoromethyl)pyridin-4-yl)oxy)ethyl)-1H-indol-3-yl)acetamide | 398.2 |

TABLE C1-continued

| Compound No. | Structure | LC-MS |
|---|---|---|
| 560 | 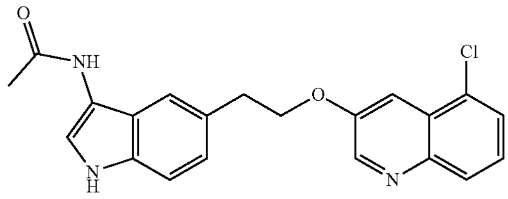 [SMILES: CC(=O)Nc1c[nH]c2ccc(CCOc3cnc4cccc(Cl)c4c3)cc12]<br>N-(5-(2-((5-chloroquinolin-3-yl)oxy)ethyl)-1H-indol-3-yl)acetamide | 380.2 |
| 561 | 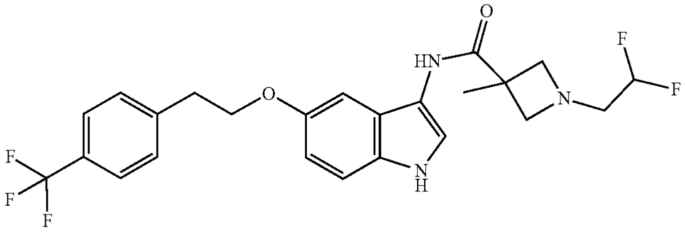 [SMILES: CC1(C(=O)Nc2c[nH]c3ccc(OCCc4ccc(C(F)(F)F)cc4)cc23)CN(CC(F)F)C1]<br>1-(2,2-difluoroethyl)-3-methyl-N-(5-(4-(trifluoromethyl)phenethoxy)-1H-indol-3-yl)azetidine-3-carboxamide | 480.15 |
| 562 | 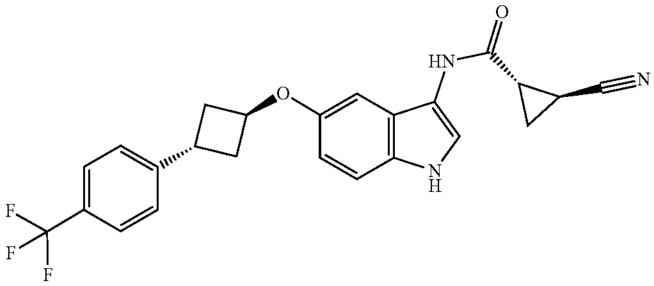 [SMILES: N#C[C@H]1C[C@@H]1C(=O)Nc1c[nH]c2ccc(O[C@H]3C[C@H](c4ccc(C(F)(F)F)cc4)C3)cc12]<br>(1s,2s)-2-cyano-N-(5-((trans)-3-(4-(trifluoromethyl)phenyl)cyclobutoxy)-1H-indol-3-yl)cyclopropane-1-carboxamide | 440.2 |
| 563 | 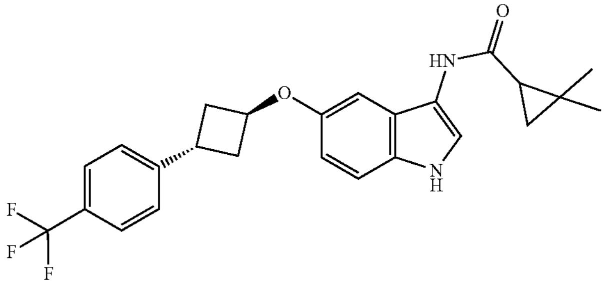 [SMILES: CC1(C)CC1C(=O)Nc1c[nH]c2ccc(O[C@H]3C[C@H](c4ccc(C(F)(F)F)cc4)C3)cc12]<br>2,2-dimethyl-N-(5-(trans-3-(4-(trifluoromethyl)phenyl)cyclobutoxy)-1H-indol-3-yl)cyclopropane-1-carboxamide | 443.3 |

TABLE C1-continued

| Compound No. | Structure | LC-MS |
|---|---|---|
| 564 | 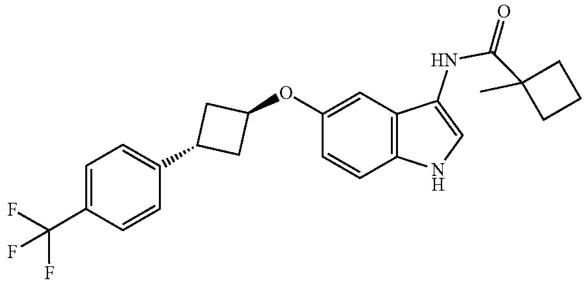 [SMILES: CC1(C(=O)Nc2c[nH]c3ccc(O[C@H]4C[C@H](c5ccc(C(F)(F)F)cc5)C4)cc23)CCC1] 1-methyl-N-(5-(trans-3-(4-(trifluoromethyl)phenyl)cyclobutoxy)-1H-indol-3-yl)cyclobutane-1-carboxamide | 443.3 |
| 565 | 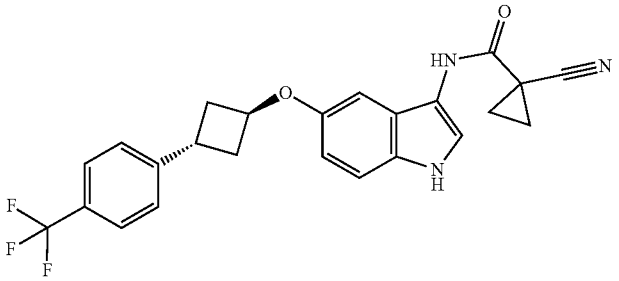 [SMILES: N#CC1(C(=O)Nc2c[nH]c3ccc(O[C@H]4C[C@H](c5ccc(C(F)(F)F)cc5)C4)cc23)CC1] 1-cyano-N-(5-(trans-3-(4-(trifluoromethyl)phenyl)cyclobutoxy)-1H-indol-3-yl)cyclopropane-1-carboxamide | 440.3 |
| 567 | 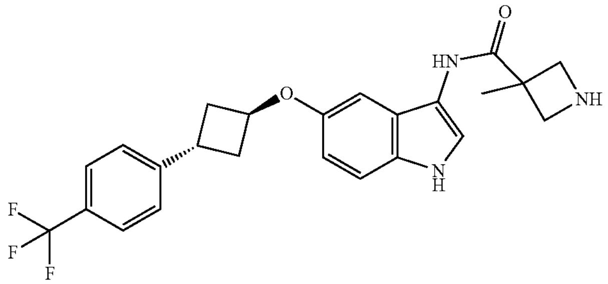 [SMILES: CC1(C(=O)Nc2c[nH]c3ccc(O[C@H]4C[C@H](c5ccc(C(F)(F)F)cc5)C4)cc23)CNC1] 3-methyl-N-(5-(trans-3-(4-(trifluoromethyl)phenyl)cyclobutoxy)-1H-indol-3-yl)azetidine-3-carboxamide | 444.25 |
| 568 | 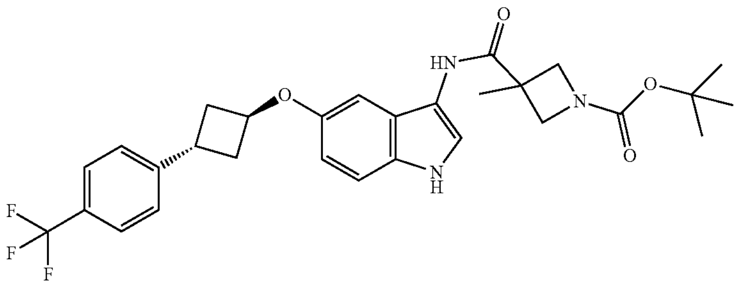 [SMILES: CC(C)(C)OC(=O)N1CC(C)(C(=O)Nc2c[nH]c3ccc(O[C@H]4C[C@H](c5ccc(C(F)(F)F)cc5)C4)cc23)C1] tert-butyl 3-methyl-3-((5-(trans-3-(4-(trifluoromethyl)phenyl)cyclobutoxy)-1H-indol-3-yl)carbamoyl)azetidine-1-carboxylate | 542.15 |

TABLE C1-continued

| Compound No. | Structure | LC-MS |
| --- | --- | --- |
| 569 | 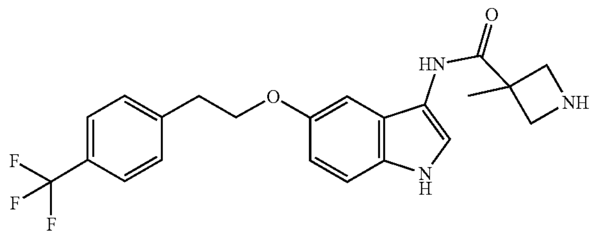 [SMILES: CC1(C(=O)Nc2c[nH]c3ccc(OCCc4ccc(C(F)(F)F)cc4)cc23)CNC1] 3-methyl-N-(5-(4-(trifluoromethyl)phenethoxy)-1H-indol-3-yl)azetidine-3-carboxamide | 418.15 |
| 570 | 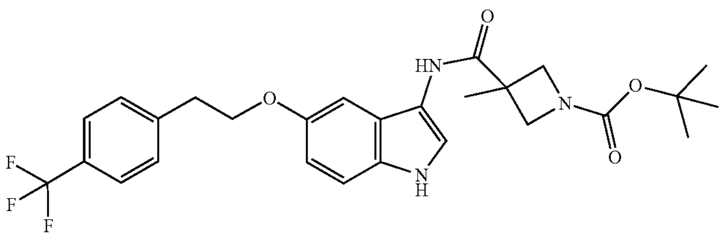 [SMILES: CC(C)(C)OC(=O)N1CC(C)(C(=O)Nc2c[nH]c3ccc(OCCc4ccc(C(F)(F)F)cc4)cc23)C1] tert-butyl 3-methyl-3-((5-(4-(trifluoromethyl)phenethoxy)-1H-indol-3-yl)carbamoyl)azetidine-1-carboxylate | 516.15 |
| 571 | 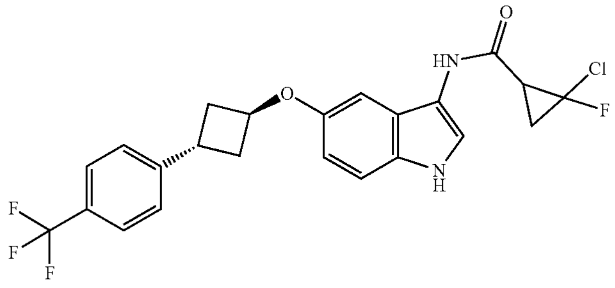 [SMILES: O=C(Nc1c[nH]c2ccc(O[C@H]3C[C@H](c4ccc(C(F)(F)F)cc4)C3)cc12)C1CC1(F)Cl] 2-chloro-2-fluoro-N-(5-(trans-3-(4-(trifluoromethyl)phenyl)cyclobutoxy)-1H-indol-3-yl)cyclopropane-1-carboxamide | 467.2 |
| 572 | 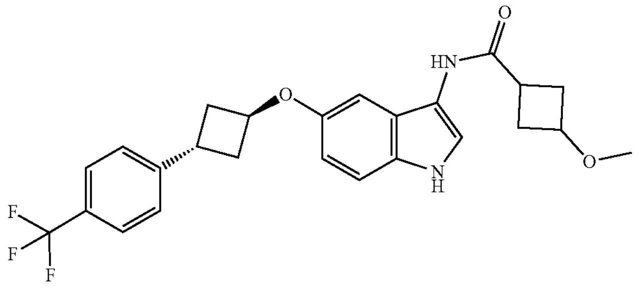 [SMILES: COC1CC(C(=O)Nc2c[nH]c3ccc(O[C@H]4C[C@H](c5ccc(C(F)(F)F)cc5)C4)cc23)C1] 3-methoxy-N-(5-(trans-3-(4-(trifluoromethyl)phenyl)cyclobutoxy)-1H-indol-3-yl)cyclobutane-1-carboxamide | 459.2 |

TABLE C1-continued

| Compound No. | Structure | LC-MS |
|---|---|---|
| 573 | 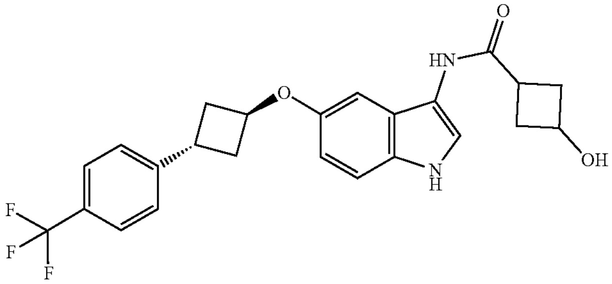 [SMILES: O=C(Nc1c[nH]c2ccc(O[C@H]3C[C@H](c4ccc(C(F)(F)F)cc4)C3)cc12)C1CC(O)C1] 3-hydroxy-N-(5-(trans-3-(4-(trifluoromethyl)phenyl)cyclobutoxy)-1H-indol-3-yl)cyclobutane-1-carboxamide | 445.2 |
| 574 | 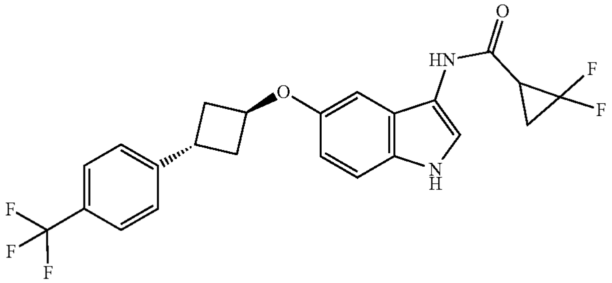 [SMILES: O=C(Nc1c[nH]c2ccc(O[C@H]3C[C@H](c4ccc(C(F)(F)F)cc4)C3)cc12)C1CC1(F)F] 2,2-difluoro-N-(5-(trans-3-(4-(trifluoromethyl)phenyl)cyclobutoxy)-1H-indol-3-yl)cyclopropane-1-carboxamide | 451.2 |
| 575 | 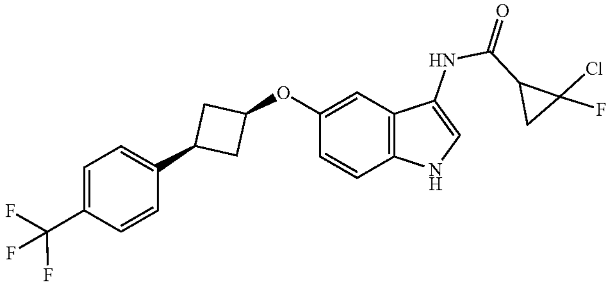 [SMILES: O=C(Nc1c[nH]c2ccc(O[C@H]3C[C@@H](c4ccc(C(F)(F)F)cc4)C3)cc12)C1CC1(F)Cl] 2-chloro-2-fluoro-N-(5-(cis-3-(4-(trifluoromethyl)phenyl)cyclobutoxy)-1H-indol-3-yl)cyclopropane-1-carboxamide | 467.3 |
| 576 | 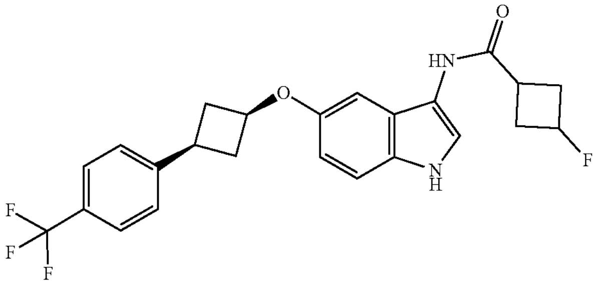 [SMILES: O=C(Nc1c[nH]c2ccc(O[C@H]3C[C@@H](c4ccc(C(F)(F)F)cc4)C3)cc12)C1CC(F)C1] 3-fluoro-N-(5-(cis-3-(4-(trifluoromethyl)phenyl)cyclobutoxy)-1H-indol-3-yl)cyclobutane-1-carboxamide | 447.2 |

TABLE C1-continued

| Compound No. | Structure | LC-MS |
| --- | --- | --- |
| 577 | 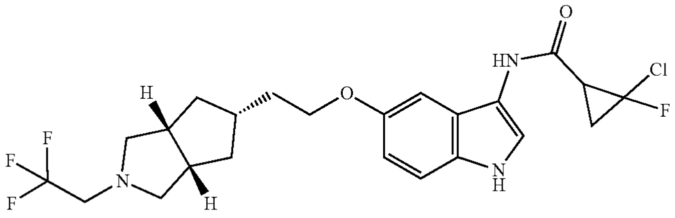 [SMILES: O=C(Nc1c[nH]c2ccc(OCC[C@@H]3C[C@@H]4CN(CC(F)(F)F)C[C@@H]4C3)cc12)C1CC1(F)Cl]<br>2-chloro-2-fluoro-N-(5-(2-((3aR,5r,6aS)-2-(2,2,2-trifluoroethyl)octahydrocyclopenta[c]pyrrol-5-yl)ethoxy)-1H-indol-3-yl)cyclopropane-1-carboxamide | 488.3 |
| 578 | 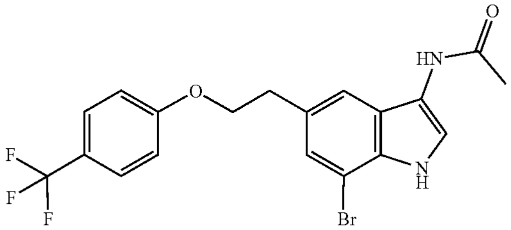 [SMILES: CC(=O)Nc1c[nH]c2c(Br)cc(CCOc3ccc(C(F)(F)F)cc3)cc12]<br>N-(7-bromo-5-(2-(4-(trifluoromethyl)phenoxy)ethyl)-1H-indol-3-yl)acetamide | 440.8 |
| 579 | 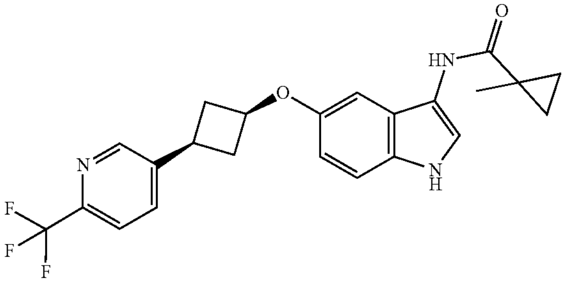 [SMILES: CC1(C(=O)Nc2c[nH]c3ccc(O[C@H]4C[C@@H](c5ccc(C(F)(F)F)nc5)C4)cc23)CC1]<br>1-methyl-N-(5-(cis-3-(6-(trifluoromethyl)pyridin-3-yl)cyclobutoxy)-1H-indol-3-yl)cyclopropane-1-carboxamide | 430.15 |
| 580 | 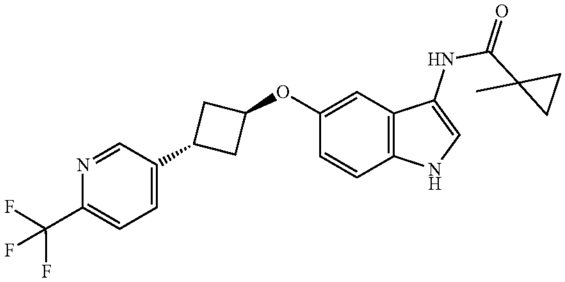 [SMILES: CC1(C(=O)Nc2c[nH]c3ccc(O[C@H]4C[C@H](c5ccc(C(F)(F)F)nc5)C4)cc23)CC1]<br>1-methyl-N-(5-(cis-3-(6-(trifluoromethyl)pyridin-3-yl)cyclobutoxy)-1H-indol-3-yl)cyclopropane-1-carboxamide | 430.15 |
| 581 | 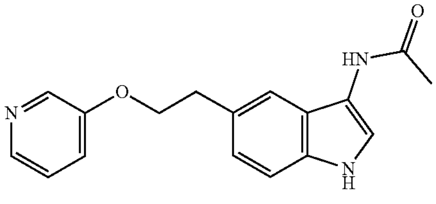 [SMILES: CC(=O)Nc1c[nH]c2ccc(CCOc3cccnc3)cc12] | 296.2 |

TABLE C1-continued

| Compound No. | Structure | LC-MS |
|---|---|---|
| | N-(5-(2-(pyridin-3-yloxy)ethyl)-1H-indol-3-yl)acetamide | |
| 582 | 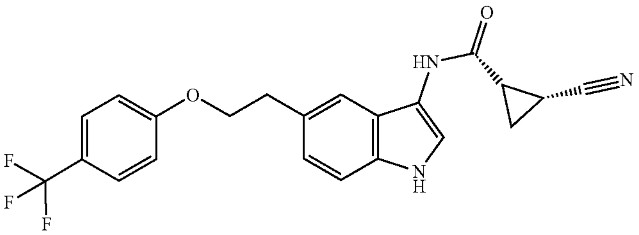 (1S,2R)-2-cyano-N-(5-(2-(4-(trifluoromethyl)phenoxy)ethyl)-1H-indol-3-yl)cyclopropane-1-carboxamide | 412.1 |
| 584 | 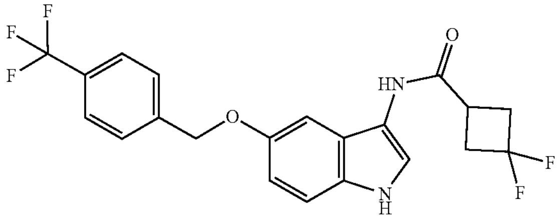 [SMILES: O=C(Nc1c[nH]c2ccc(OCc3ccc(C(F)(F)F)cc3)cc12)C1CC(F)(F)C1] 3,3-difluoro-N-(5-((4-(trifluoromethyl)benzyl)oxy)-1H-indol-3-yl)cyclobutane-1-carboxamide | 425.3 |
| 585 | 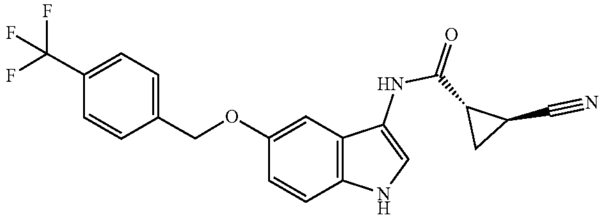 [SMILES: N#C[C@H]1C[C@@H]1C(=O)Nc1c[nH]c2ccc(OCc3ccc(C(F)(F)F)cc3)cc12] (1S,2S)-2-cyano-N-(5-((4-(trifluoromethyl)benzyl)oxy)-1H-indol-3-yl)cyclopropane-1-carboxamide | 400.3 |
| 586 | 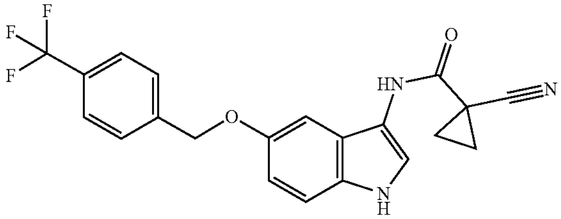 [SMILES: N#CC1(C(=O)Nc2c[nH]c3ccc(OCc4ccc(C(F)(F)F)cc4)cc23)CC1] 1-cyano-N-(5-((4-(trifluoromethyl)benzyl)oxy)-1H-indol-3-yl)cyclopropane-1-carboxamide | 400.3 |
| 587 | 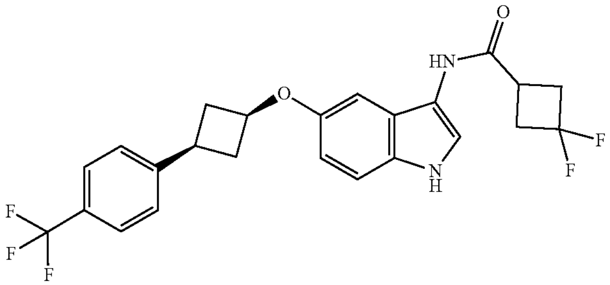 [SMILES: O=C(Nc1c[nH]c2ccc(O[C@H]3C[C@@H](c4ccc(C(F)(F)F)cc4)C3)cc12)C1CC(F)(F)C1] | 465.3 |

TABLE C1-continued

| Compound No. | Structure | LC-MS |
|---|---|---|
| | 3,3-difluoro-N-(5-(cis-3-(4-(trifluoromethyl)phenyl)cyclobutoxy)-1H-indol-3-yl)cyclobutane-1-carboxamide | |
| 588 | 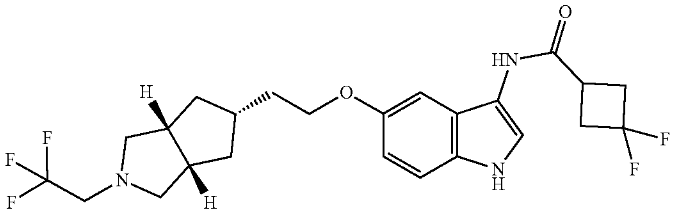 [SMILES: O=C(Nc1c[nH]c2ccc(OCC[C@@H]3C[C@@H]4CN(CC(F)(F)F)C[C@@H]4C3)cc12)C1CC(F)(F)C1] 3,3-difluoro-N-(5-(2-((3aR,5r,6aS)-2-(2,2,2-trifluoroethyl)octahydrocyclopenta[c]pyrrol-5-yl)ethoxy)-1H-indol-3-yl)cyclobutane-1-carboxamide | 486.4 |
| 589 | 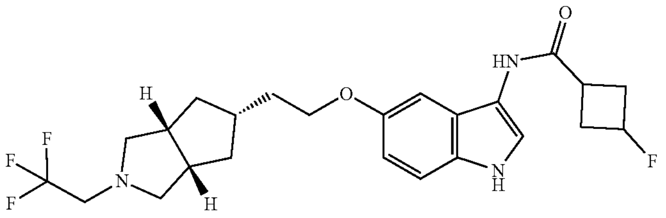 [SMILES: O=C(Nc1c[nH]c2ccc(OCC[C@@H]3C[C@@H]4CN(CC(F)(F)F)C[C@@H]4C3)cc12)C1CC(F)C1] 3-fluoro-N-(5-(2-((3aR,5r,6aS)-2-(2,2,2-trifluoroethyl)octahydrocyclopenta[c]pyrrol-5-yl)ethoxy)-1H-indol-3-yl)cyclobutane-1-carboxamide | 468.3 |
| 590 | 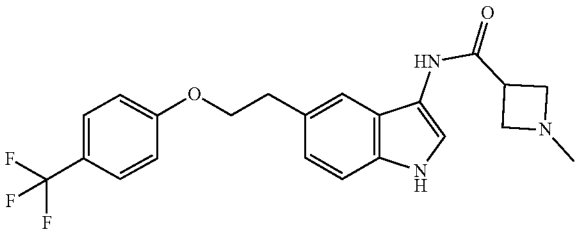 [SMILES: CN1CC(C(=O)Nc2c[nH]c3ccc(CCOc4ccc(C(F)(F)F)cc4)cc23)C1] 1-methyl-N-(5-(2-(4-(trifluoromethyl)phenoxy)ethyl)-1H-indol-3-yl)azetidine-3-carboxamide | 418.3 |
| 591 | 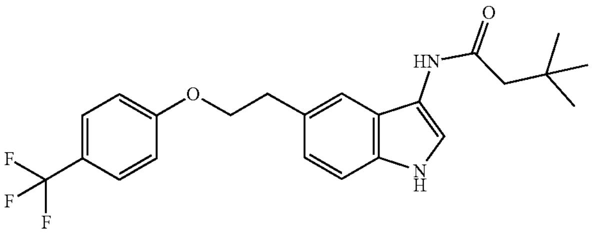 [SMILES: CC(C)(C)CC(=O)Nc1c[nH]c2ccc(CCOc3ccc(C(F)(F)F)cc3)cc12] 3,3-dimethyl-N-(5-(2-(4-(trifluoromethyl)phenoxy)ethyl)-1H-indol-3-yl)butanamide | 419.3 |

TABLE C1-continued

| Compound No. | Structure | LC-MS |
|---|---|---|
| 592 | 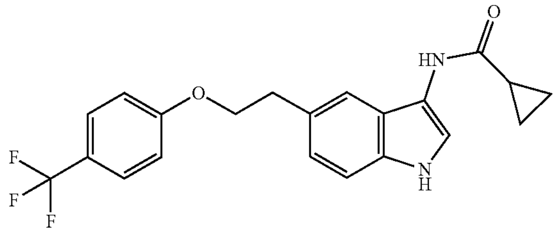 [SMILES: O=C(Nc1c[nH]c2ccc(CCOc3ccc(C(F)(F)F)cc3)cc12)C1CC1]<br>N-(5-(2-(4-(trifluoromethyl)phenoxy)ethyl)-1H-indol-3-yl)cyclopropanecarboxamide | 389.2 |
| 593 | 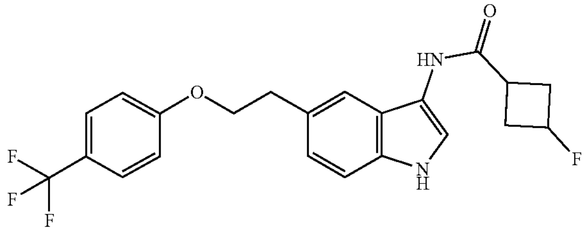 [SMILES: O=C(Nc1c[nH]c2ccc(CCOc3ccc(C(F)(F)F)cc3)cc12)C1CC(F)C1]<br>3-fluoro-N-(5-(2-(4-(trifluoromethyl)phenoxy)ethyl)-1H-indol-3-yl)cyclobutane-1-carboxamide | 421.2 |
| 594 | 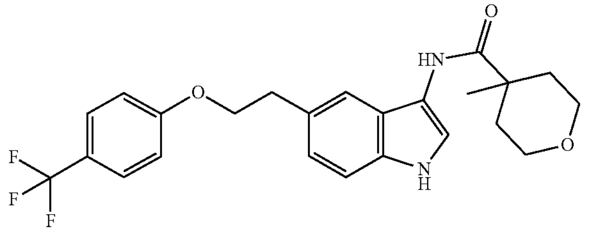 [SMILES: CC1(C(=O)Nc2c[nH]c3ccc(CCOc4ccc(C(F)(F)F)cc4)cc23)CCOCC1]<br>4-methyl-N-(5-(2-(4-(trifluoromethyl)phenoxy)ethyl)-1H-indol-3-yl)tetrahydro-2H-pyran-4-carboxamide | 447.3 |
| 595 | 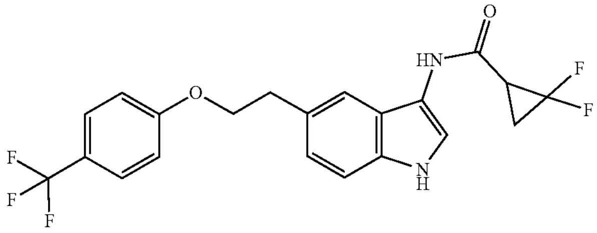 [SMILES: O=C(Nc1c[nH]c2ccc(CCOc3ccc(C(F)(F)F)cc3)cc12)C1CC1(F)F]<br>2,2-difluoro-N-(5-(2-(4-(trifluoromethyl)phenoxy)ethyl)-1H-indol-3-yl)cyclopropane-1-carboxamide | 425.2 |
| 596 | 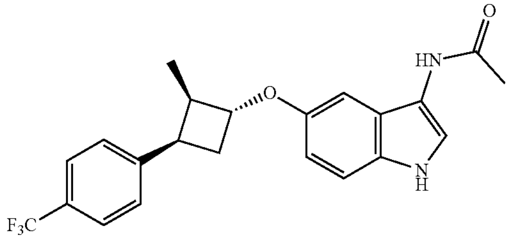 [SMILES: CC(=O)Nc1c[nH]c2ccc(O[C@@H]3C[C@@H](c4ccc(C(F)(F)F)cc4)[C@H]3C)cc12] | 401.1 |

Pharmaceutical Compositions and Administration

General

In some embodiments, a chemical entity (e.g., a compound that inhibits (e.g., antagonizes) STING, or a pharmaceutically acceptable salt, and/or hydrate, and/or cocrystal, and/or drug combination thereof) is administered as a pharmaceutical composition that includes the chemical entity and one or more pharmaceutically acceptable excipients, and optionally one or more additional therapeutic agents as described herein.

In some embodiments, the chemical entities can be administered in combination with one or more conventional pharmaceutical excipients. Pharmaceutically acceptable excipients include, but are not limited to, ion exchangers, alumina, aluminum stearate, lecithin, self-emulsifying drug delivery systems (SEDDS) such as d-α-tocopherol polyethylene glycol 1000 succinate, surfactants used in pharmaceutical dosage forms such as Tweens, poloxamers or other similar polymeric delivery matrices, serum proteins, such as human serum albumin, buffer substances such as phosphates, tris, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium-chloride, zinc salts, colloidal silica, magnesium trisilicate, polyvinyl pyrrolidone, cellulose-based substances, polyethylene glycol, sodium carboxymethyl cellulose, polyacrylates, waxes, polyethylene-polyoxypropylene-block polymers, and wool fat. Cyclodextrins such as α-, β, and γ-cyclodextrin, or chemically modified derivatives such as hydroxyalkylcyclodextrins, including 2- and 3-hydroxypropyl-β-cyclodextrins, or other solubilized derivatives can also be used to enhance delivery of compounds described herein. Dosage forms or compositions containing a chemical entity as described herein in the range of 0.005% to 100% with the balance made up from non-toxic excipient may be prepared. The contemplated compositions may contain 0.001%-100% of a chemical entity provided herein, in one embodiment 0.1-95%, in another embodiment 75-85%, in a further embodiment 20-80%. Actual methods of preparing such dosage forms are known, or will be apparent, to those skilled in this art; for example, see *Remington: The Science and Practice of Pharmacy,* $22^{nd}$ Edition (Pharmaceutical Press, London, U K. 2012).

Routes of Administration and Composition Components

In some embodiments, the chemical entities described herein or a pharmaceutical composition thereof can be administered to subject in need thereof by any accepted route of administration. Acceptable routes of administration include, but are not limited to, buccal, cutaneous, endocervical, endosinusial, endotracheal, enteral, epidural, interstitial, intra-abdominal, intra-arterial, intrabronchial, intrabursal, intracerebral, intracisternal, intracoronary, intradermal, intraductal, intraduodenal, intradural, intraepidermal, intraesophageal, intragastric, intragingival, intraileal, intralymphatic, intramedullary, intrameningeal, intramuscular, intraovarian, intraperitoneal, intraprostatic, intrapulmonary, intrasinal, intraspinal, intrasynovial, intratesticular, intrathecal, intratubular, intratumoral, intrauterine, intravascular, intravenous, nasal, nasogastric, oral, parenteral, percutaneous, peridural, rectal, respiratory (inhalation), subcutaneous, sublingual, submucosal, topical, transdermal, transmucosal, transtracheal, ureteral, urethral and vaginal. In certain embodiments, a preferred route of administration is parenteral (e.g., intratumoral).

Compositions can be formulated for parenteral administration, e.g., formulated for injection via the intravenous, intramuscular, sub-cutaneous, or even intraperitoneal routes. Typically, such compositions can be prepared as injectables, either as liquid solutions or suspensions; solid forms suitable for use to prepare solutions or suspensions upon the addition of a liquid prior to injection can also be prepared; and the preparations can also be emulsified. The preparation of such formulations will be known to those of skill in the art in light of the present disclosure.

The pharmaceutical forms suitable for injectable use include sterile aqueous solutions or dispersions; formulations including sesame oil, peanut oil, or aqueous propylene glycol; and sterile powders for the extemporaneous preparation of sterile injectable solutions or dispersions. In all cases the form must be sterile and must be fluid to the extent that it may be easily injected. It also should be stable under the conditions of manufacture and storage and must be preserved against the contaminating action of microorganisms, such as bacteria and fungi.

The carrier also can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion, and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques, which yield a powder of the active ingredient, plus any additional desired ingredient from a previously sterile-filtered solution thereof.

Intratumoral injections are discussed, e.g., in Lammers, et al., "*Effect of Intratumoral Injection on the Biodistribution and the Therapeutic Potential of HPMA Copolymer-Based Drug Delivery Systems*" *Neoplasia.* 2006, 10, 788-795.

Pharmacologically acceptable excipients usable in the rectal composition as a gel, cream, enema, or rectal suppository, include, without limitation, any one or more of cocoa butter glycerides, synthetic polymers such as polyvinylpyrrolidone, PEG (like PEG ointments), glycerine, glycerinated gelatin, hydrogenated vegetable oils, poloxamers, mixtures of polyethylene glycols of various molecular weights and fatty acid esters of polyethylene glycol Vaseline, anhydrous lanolin, shark liver oil, sodium saccharinate, menthol, sweet almond oil, sorbitol, sodium benzoate, anoxid SBN, vanilla essential oil, aerosol, parabens in phenoxyethanol, sodium methyl p-oxybenzoate, sodium propyl p-oxybenzoate, diethylamine, carbomers, carbopol, methyloxybenzoate, macrogol cetostearyl ether, cocoyl caprylocaprate, isopropyl alcohol, propylene glycol, liquid paraffin, xanthan gum, carboxy-metabisulfite, sodium edetate, sodium benzoate, potassium metabisulfite, grapefruit seed extract, methyl sulfonyl methane (MSM), lactic acid, glycine, vitamins, such as vitamin A and E and potassium acetate.

In certain embodiments, suppositories can be prepared by mixing the chemical entities described herein with suitable non-irritating excipients or carriers such as cocoa butter, polyethylene glycol or a suppository wax which are solid at ambient temperature but liquid at body temperature and therefore melt in the rectum and release the active compound. In other embodiments, compositions for rectal administration are in the form of an enema.

In other embodiments, the compounds described herein or a pharmaceutical composition thereof are suitable for local delivery to the digestive or GI tract by way of oral administration (e.g., solid or liquid dosage forms.).

Solid dosage forms for oral administration include capsules, tablets, pills, powders, and granules. In such solid dosage forms, the chemical entity is mixed with one or more pharmaceutically acceptable excipients, such as sodium citrate or dicalcium phosphate and/or: a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents. Solid compositions of a similar type may also be employed as fillers in soft and hard-filled gelatin capsules using such excipients as lactose or milk sugar as well as high molecular weight polyethylene glycols and the like.

In one embodiment, the compositions will take the form of a unit dosage form such as a pill or tablet and thus the composition may contain, along with a chemical entity provided herein, a diluent such as lactose, sucrose, dicalcium phosphate, or the like; a lubricant such as magnesium stearate or the like; and a binder such as starch, gum acacia, polyvinylpyrrolidine, gelatin, cellulose, cellulose derivatives or the like. In another solid dosage form, a powder, marume, solution or suspension (e.g., in propylene carbonate, vegetable oils, PEG's, poloxamer 124 or triglycerides) is encapsulated in a capsule (gelatin or cellulose base capsule). Unit dosage forms in which one or more chemical entities provided herein or additional active agents are physically separated are also contemplated; e.g., capsules with granules (or tablets in a capsule) of each drug; two-layer tablets; two-compartment gel caps, etc. Enteric coated or delayed release oral dosage forms are also contemplated.

Other physiologically acceptable compounds include wetting agents, emulsifying agents, dispersing agents or preservatives that are particularly useful for preventing the growth or action of microorganisms. Various preservatives are well known and include, for example, phenol and ascorbic acid.

In certain embodiments the excipients are sterile and generally free of undesirable matter. These compositions can be sterilized by conventional, well-known sterilization techniques. For various oral dosage form excipients such as tablets and capsules sterility is not required. The USP/NF standard is usually sufficient.

In certain embodiments, solid oral dosage forms can further include one or more components that chemically and/or structurally predispose the composition for delivery of the chemical entity to the stomach or the lower GI; e.g., the ascending colon and/or transverse colon and/or distal colon and/or small bowel. Exemplary formulation techniques are described in, e.g., Filipski, K. J., et al., *Current Topics in Medicinal Chemistry,* 2013, 13, 776-802, which is incorporated herein by reference in its entirety.

Examples include upper-GI targeting techniques, e.g., Accordion Pill (Intec Pharma), floating capsules, and materials capable of adhering to mucosal walls.

Other examples include lower-GI targeting techniques. For targeting various regions in the intestinal tract, several enteric/pH-responsive coatings and excipients are available. These materials are typically polymers that are designed to dissolve or erode at specific pH ranges, selected based upon the GI region of desired drug release. These materials also function to protect acid labile drugs from gastric fluid or limit exposure in cases where the active ingredient may be irritating to the upper GI (e.g., hydroxypropyl methylcellulose phthalate series, Coateric (polyvinyl acetate phthalate), cellulose acetate phthalate, hydroxypropyl methylcellulose acetate succinate, Eudragit series (methacrylic acid-methyl methacrylate copolymers), and Marcoat). Other techniques include dosage forms that respond to local flora in the GI tract, Pressure-controlled colon delivery capsule, and Pulsincap.

Ocular compositions can include, without limitation, one or more of any of the following: viscogens (e.g., Carboxymethylcellulose, Glycerin, Polyvinylpyrrolidone, Polyethylene glycol); Stabilizers (e.g., Pluronic (triblock copolymers), Cyclodextrins); Preservatives (e.g., Benzalkonium chloride, ETDA, SofZia (boric acid, propylene glycol, sorbitol, and zinc chloride; Alcon Laboratories, Inc.), Purite (stabilized oxychloro complex; Allergan, Inc.)).

Topical compositions can include ointments and creams. Ointments are semisolid preparations that are typically based on petrolatum or other petroleum derivatives. Creams containing the selected active agent are typically viscous liquid or semisolid emulsions, often either oil-in-water or water-in-oil. Cream bases are typically water-washable, and contain an oil phase, an emulsifier and an aqueous phase. The oil phase, also sometimes called the "internal" phase, is generally comprised of petrolatum and a fatty alcohol such as cetyl or stearyl alcohol; the aqueous phase usually, although not necessarily, exceeds the oil phase in volume, and generally contains a humectant. The emulsifier in a cream formulation is generally a nonionic, anionic, cationic or amphoteric surfactant. As with other carriers or vehicles, an ointment base should be inert, stable, nonirritating and non-sensitizing.

In any of the foregoing embodiments, pharmaceutical compositions described herein can include one or more one or more of the following: lipids, interbilayer crosslinked multilamellar vesicles, biodegradeable poly(D,L-lactic-co-glycolic acid) [PLGA]-based or poly anhydride-based nanoparticles or microparticles, and nanoporous particle-supported lipid bilayers.

Dosages

The dosages may be varied depending on the requirement of the patient, the severity of the condition being treating and the particular compound being employed. Determination of the proper dosage for a particular situation can be determined by one skilled in the medical arts. The total daily dosage may be divided and administered in portions throughout the day or by means providing continuous delivery.

In some embodiments, the compounds described herein are administered at a dosage of from about 0.001 mg/Kg to about 500 mg/Kg (e.g., from about 0.01 mg/Kg to about 100 mg/Kg; from about 0.01 mg/Kg to about 10 mg/Kg; from about 0.01 mg/Kg to about 1 mg/Kg; from about 0.01 mg/Kg to about 0.1 mg/Kg; from about 0.1 mg/Kg to about 100 mg/Kg; from about 0.1 mg/Kg to about 10 mg/Kg).

Regimens

The foregoing dosages can be administered on a daily basis (e.g., as a single dose or as two or more divided doses) or non-daily basis (e.g., every other day, every two days, every three days, once weekly, twice weeks, once every two weeks, once a month).

In some embodiments, the period of administration of a compound described herein is for 1 day, 2 days, 3 days, 4 days, 5 days, 6 days, 7 days, 8 days, 9 days, 10 days, 11 days, 12 days, 13 days, 14 days, 3 weeks, 4 weeks, 5 weeks, 6 weeks, 7 weeks, 8 weeks, 9 weeks, 10 weeks, 11 weeks, 12 weeks, 4 months, 5 months, 6 months, 7 months, 8 months, 9 months, 10 months, 11 months, 12 months, or more. In a further embodiment, a period of during which administration is stopped is for 1 day, 2 days, 3 days, 4 days, 5 days, 6 days, 7 days, 8 days, 9 days, 10 days, 11 days, 12 days, 13 days, 14 days, 3 weeks, 4 weeks, 5 weeks, 6 weeks, 7 weeks, 8 weeks, 9 weeks, 10 weeks, 11 weeks, 12 weeks, 4 months, 5 months, 6 months, 7 months, 8 months, 9 months, 10 months, 11 months, 12 months, or more. In an embodiment, a therapeutic compound is administered to an individual for a period of time followed by a separate period of time. In another embodiment, a therapeutic compound is administered for a first period and a second period following the first period, with administration stopped during the second period, followed by a third period where administration of the therapeutic compound is started and then a fourth period following the third period where administration is stopped. In an aspect of this embodiment, the period of administration of a therapeutic compound followed by a period where administration is stopped is repeated for a determined or undetermined period of time. In a further embodiment, a period of administration is for 1 day, 2 days, 3 days, 4 days, 5 days, 6 days, 7 days, 8 days, 9 days, 10 days, 11 days, 12 days, 13 days, 14 days, 3 weeks, 4 weeks, 5 weeks, 6 weeks, 7 weeks, 8 weeks, 9 weeks, 10 weeks, 11 weeks, 12 weeks, 4 months, 5 months, 6 months, 7 months, 8 months, 9 months, 10 months, 11 months, 12 months, or more. In a further embodiment, a period of during which administration is stopped is for 1 day, 2 days, 3 days, 4 days, 5 days, 6 days, 7 days, 8 days, 9 days, 10 days, 11 days, 12 days, 13 days, 14 days, 3 weeks, 4 weeks, 5 weeks, 6 weeks, 7 weeks, 8 weeks, 9 weeks, 10 weeks, 11 weeks, 12 weeks, 4 months, 5 months, 6 months, 7 months, 8 months, 9 months, 10 months, 11 months, 12 months, or more.

Methods of Treatment

In some embodiments, methods for treating a subject having condition, disease or disorder in which increased (e.g., excessive)STING activity (e.g., e.g., STING signaling) contributes to the pathology and/or symptoms and/or progression of the condition, disease or disorder (e.g., immune disorders, cancer) are provided.

Indications

In some embodiments, the condition, disease or disorder is cancer. Non-limiting examples of cancer include melanoma, carcinoma, lymphoma, blastoma, sarcoma, and leukemia or lymphoid malignancies. More particular examples of such cancers include breast cancer, colon cancer, rectal cancer, colorectal cancer, kidney or renal cancer, clear cell cancer lung cancer including small-cell lung cancer, non-small cell lung cancer, adenocarcinoma of the lung and squamous carcinoma of the lung, squamous cell cancer (e.g. epithelial squamous cell cancer), cervical cancer, ovarian cancer, prostate cancer, prostatic neoplasms, liver cancer, bladder cancer, cancer of the peritoneum, hepatocellular cancer, gastric or stomach cancer including gastrointestinal cancer, gastrointestinal stromal tumor, pancreatic cancer, head and neck cancer, glioblastoma, retinoblastoma, astrocytoma, thecomas, arrhenoblastomas, hepatoma, hematologic malignancies including non-Hodgkins lymphoma (NHL), multiple myeloma, myelodysplasia disorders, myeloproliferative disorders, chronic myelogenous leukemia, and acute hematologic malignancies, endometrial or uterine carcinoma, endometriosis, endometrial stromal sarcoma, fibrosarcomas, choriocarcinoma, salivary gland carcinoma, vulval cancer, thyroid cancer, esophageal carcinomas, hepatic carcinoma, anal carcinoma, penile carcinoma, nasopharyngeal carcinoma, laryngeal carcinomas, Kaposi's sarcoma, mast cell sarcoma, ovarian sarcoma, uterine sarcoma, melanoma, malignant mesothelioma, skin carcinomas, Schwannoma, oligodendroglioma, neuroblastomas, neuroectodermal tumor, rhabdomyosarcoma, osteogenic sarcoma, leiomyosarcomas, Ewing Sarcoma, peripheral primitive neuroectodermal tumor, urinary tract carcinomas, thyroid carcinomas, Wilm's tumor, as well as abnormal vascular proliferation associated with phakomatoses, edema (such as that associated with brain tumors), and Meigs' syndrome. In some cases, the cancer is melanoma.

In some embodiments, the condition, disease or disorder is a neurological disorder, which includes disorders that involve the central nervous system (brain, brainstem and cerebellum), the peripheral nervous system (including cranial nerves), and the autonomic nervous system (parts of which are located in both central and peripheral nervous system). Non-limiting examples of neurological disorders include acquired epileptiform aphasia; acute disseminated encephalomyelitis; adrenoleukodystrophy; age-related macular degeneration; agenesis of the corpus callosum; agnosia; Aicardi syndrome; Alexander disease; Alpers' disease; alternating hemiplegia; Alzheimer's disease; Vascular dementia; amyotrophic lateral sclerosis; anencephaly; Angelman syndrome; angiomatosis; anoxia; aphasia; apraxia; arachnoid cysts; arachnoiditis; Anronl-Chiari malformation; arteriovenous malformation; Asperger syndrome; ataxia telegiectasia; attention deficit hyperactivity disorder; autism; autonomic dysfunction; back pain; Batten disease; Behcet's disease; Bell's palsy; benign essential blepharospasm; benign focal; amyotrophy; benign intracranial hypertension; Binswanger's disease; blepharospasm; Bloch Sulzberger syndrome; brachial plexus injury; brain abscess; brain injury; brain tumors (including glioblastoma multiforme); spinal tumor; Brown-Sequard syndrome; Canavan disease; carpal tunnel syndrome; causalgia; central pain syndrome; central pontine myelinolysis; cephalic disorder; cerebral aneurysm; cerebral arteriosclerosis; cerebral atrophy; cerebral gigantism; cerebral palsy; Charcot-Marie-Tooth disease; chemotherapy-induced neuropathy and neuropathic pain; Chiari malformation; chorea; chronic inflammatory demyelinating polyneuropathy; chronic pain; chronic regional pain syndrome; Coffin Lowry syndrome; coma, including persistent vegetative state; congenital facial diplegia; corticobasal degeneration; cranial arteritis; craniosynostosis; Creutzfeldt-Jakob disease; cumulative trauma disorders; Cushing's syndrome; cytomegalic inclusion body disease; cytomegalovirus infection; dancing eyes-dancing feet syndrome; Dandy-Walker syndrome; Dawson disease; De Morsier's syndrome; Dejerine-Klumke palsy; dementia; dermatomyositis; diabetic neuropathy; diffuse sclerosis; dysautonomia; dysgraphia; dyslexia; dystonias; early infantile epileptic encephalopathy; empty sella syndrome; encephalitis; encephaloceles; encephalotrigeminal angiomatosis; epilepsy; Erb's palsy; essential tremor; Fabry's disease; Fahr's syndrome; fainting; familial spastic paralysis; febrile seizures; Fisher syndrome; Friedreich's ataxia; fronto-temporal dementia and other "tauopathies"; Gaucher's disease; Gerstmann's syndrome; giant cell arteritis; giant cell inclusion disease; globoid cell leukodystrophy; Guillain-Barre syndrome; HTLV-1-associated myelopathy; Hallervorden-Spatz disease; head injury; headache; hemifacial spasm; hereditary spastic paraplegia; heredopathia atactica polyneuritiformis; herpes zoster oticus; herpes zoster; Hirayama syndrome; HIV-associated dementia and neuropathy (also neurological manifestations of AIDS); holoprosencephaly; Huntington's disease and other polyglutamine repeat diseases; hydranencephaly; hydrocephalus; hypercortisolism; hypoxia; immune-mediated encephalomyelitis; inclusion body myositis; incontinentia pigmenti; infantile phytanic acid storage disease; infantile refsum disease; infantile spasms; inflammatory myopathy; intracranial cyst; intracranial hypertension; Joubert syndrome; Kearns-Sayre syndrome; Kennedy disease Kinsbourne syndrome; Klippel Feil syndrome; Krabbe disease; Kugelberg-Welander disease; kuru; Lafora disease; Lambert-Eaton myasthenic syndrome; Landau-Kleffner syndrome; lateral medullary (Wallenberg) syndrome; learning disabilities; Leigh's disease; Lennox-Gustaut syndrome; Lesch-Nyhan syndrome; leukodystrophy; Lewy body dementia; Lissencephaly; locked-in syndrome; Lou Gehrig's disease (i.e., motor neuron disease or amyotrophic lateral sclerosis); lumbar disc disease; Lyme disease-neurological sequelae; Machado-Joseph disease; macrencephaly; megalencephaly; Melkersson-Rosenthal syndrome; Menieres disease; meningitis; Menkes disease; metachromatic leukodystrophy; microcephaly; migraine; Miller Fisher syndrome; mini-strokes; mitochondrial myopathies; Mobius syndrome; monomelic amyotrophy; motor neuron disease; Moyamoya disease; mucopolysaccharidoses; milti-infarct dementia; multifocal motor neuropathy; multiple sclerosis and other demyelinating disorders; multiple system atrophy with postural hypotension; p muscular dystrophy; myasthenia gravis; myelinoclastic diffuse sclerosis; myoclonic encephalopathy of infants; myoclonus; myopathy; myotonia congenital; narcolepsy; neurofibromatosis; neuroleptic malignant syndrome; neurological manifestations of AIDS; neurological sequelae of lupus; neuromyotonia; neuronal ceroid lipofuscinosis; neuronal migration disorders; Niemann-Pick disease; O'Sullivan-McLeod syndrome; occipital neuralgia; occult spinal dysraphism sequence; Ohtahara syndrome; olivopontocerebellar atrophy; opsoclonus myoclonus; optic neuritis; orthostatic hypotension; overuse syndrome; paresthesia; Parkinson's disease; paramyotonia congenital; paraneoplastic diseases; paroxysmal attacks; Parry Romberg syndrome; Pelizaeus-Merzbacher disease; periodic paralyses; peripheral neuropathy; painful neuropathy and neuropathic pain; persistent vegetative state; pervasive developmental disorders; photic sneeze reflex; phytanic acid storage disease; Pick's disease; pinched nerve; pituitary tumors; polymyositis; porencephaly; post-polio syndrome; postherpetic neuralgia; postinfectious encephalomyelitis; postural hypotension; Prader-Willi syndrome; primary lateral sclerosis; prion diseases; progressive hemifacial atrophy; progressive multifocal leukoencephalopathy; progressive sclerosing poliodystrophy; progressive supranuclear palsy; pseudotumor cerebri; Ramsay-Hunt syndrome (types I and II); Rasmussen's encephalitis; reflex sympathetic dystrophy syndrome; Refsum disease; repetitive motion disorders; repetitive stress injuries; restless legs syndrome; retrovirus-associated myelopathy; Rett syndrome; Reye's syndrome; Saint Vitus dance; Sandhoff disease; Schilder's disease; schizencephaly; septo-optic dysplasia; shaken baby syndrome; shingles; Shy-Drager syndrome; Sjögren's syndrome; sleep apnea; Soto's syndrome; spasticity; spina bifida; spinal cord injury; spinal cord tumors; spinal muscular atrophy; Stiff-Person syndrome; stroke; Sturge-Weber syndrome; subacute sclerosing panencephalitis; subcortical arteriosclerotic encephalopathy; Sydenham chorea; syncope; syringomyelia; tardive dyskinesia; Tay-Sachs disease; temporal arteritis; tethered spinal cord syndrome; Thomsen disease; thoracic outlet syndrome; Tic Douloureux; Todd's paralysis; Tourette syndrome; transient ischemic attack; transmissible spongiform encephalopathies; transverse myelitis; traumatic brain injury; tremor; trigeminal neuralgia; tropical spastic paraparesis; tuberous sclerosis; vascular dementia (multi-infarct dementia); vasculitis including temporal arteritis; Von Hippel-Lindau disease; Wallenberg's syndrome; Werdnig-Hoffman disease; West syndrome; whiplash; Williams syndrome; Wildon's disease; amyotrophe lateral sclerosis and Zellweger syndrome.

In some embodiments, the condition, disease or disorder is STING-associated conditions, e.g., type I interferonopathies (e.g., STING-associated vasculopathy with onset in infancy (SAVI)), Aicardi-Goutieres Syndrome (AGS), genetic forms of lupus, and inflammation-associated disorders such as systemic lupus erythematosus, and rheumatoid arthritis. In certain embodiments, the condition, disease or disorder is an autoimmune disease (e.g., a cytosolic DNA-triggered autoinflammatory disease). Non-limiting examples include rheumatoid arthritis, systemic lupus erythematosus, multiple sclerosis, inflammatory bowel diseases (IBDs) comprising Crohn disease (CD) and ulcerative colitis (UC), which are chronic inflammatory conditions with polygenic susceptibility. In certain embodiments, the condition is an inflammatory bowel disease. In certain embodiments, the condition is Crohn's disease, autoimmune colitis, iatrogenic autoimmune colitis, ulcerative colitis, colitis induced by one or more chemotherapeutic agents, colitis induced by treatment with adoptive cell therapy, colitis associated by one or more alloimmune diseases (such as graft-vs-host disease, e.g., acute graft vs. host disease and chronic graft vs. host disease), radiation enteritis, collagenous colitis, lymphocytic colitis, microscopic colitis, and radiation enteritis. In certain of these embodiments, the condition is alloimmune disease (such as graft-vs-host disease, e.g., acute graft vs. host disease and chronic graft vs. host disease), celiac disease, irritable bowel syndrome, rheumatoid arthritis, lupus, scleroderma, psoriasis, cutaneous T-cell lymphoma, uveitis, and mucositis (e.g., oral mucositis, esophageal mucositis or intestinal mucositis).

In some embodiments, modulation of the immune system by STING provides for the treatment of diseases, including diseases caused by foreign agents. Exemplary infections by foreign agents which may be treated and/or prevented by the method of the present invention include an infection by a bacterium (e.g., a Gram-positive or Gram-negative bacterium), an infection by a fungus, an infection by a parasite, and an infection by a virus. In one embodiment of the present invention, the infection is a bacterial infection (e.g., infection by *E. coli, Klebsiella pneumoniae, Pseudomonas aeruginosa, Salmonella* spp., *Staphylococcus aureus, Streptococcus* spp., or vancomycin-resistant *enterococcus*), or sepsis. In another embodiment, the infection is a fungal infection (e.g. infection by a mould, a yeast, or a higher fungus). In still another embodiment, the infection is a parasitic infection (e.g., infection by a single-celled or multicellular parasite, including *Giardia duodenalis, Cryptosporidium parvum, Cyclospora cayetanensis*, and *Toxoplasma gondiz*). In yet another embodiment, the infection is a viral infection (e.g., infection by a virus associated with AIDS, avian flu, chickenpox, cold sores, common cold, gastroenteritis, glandular fever, influenza, measles, mumps, pharyngitis, pneumonia, rubella, SARS, lower or upper respiratory tract infection (e.g., respiratory syncytial virus), Ebola, Zika, and SARS-CoV-2 (COVID19)).

In some embodiments, the condition, disease or disorder is hepatits B (see, e.g., WO 2015/061294).

In some embodiments, the condition, disease or disorder is selected from cardiovascular diseases (including e.g., myocardial infarction).

In some embodiments, the condition, disease or disorder is age-related macular degeneration.

In some embodiments, the condition, disease or disorder is mucositis, also known as stomatitits, which can occur as a result of chemotherapy or radiation therapy, either alone or in combination as well as damage caused by exposure to radiation outside of the context of radiation therapy.

In some embodiments, the condition, disease or disorder is uveitis, which is inflammation of the uvea (e.g., anterior uveitis, e.g., iridocyclitis or iritis; intermediate uveitis (also known as pars planitis); posterior uveitis; or chorioretinitis, e.g., pan-uveitis).

In some embodiments, the condition, disease or disorder is selected from the group consisting of a cancer, a neurological disorder, an autoimmune disease, hepatitis B, uveitis, a cardiovascular disease, age-related macular degeneration, and mucositis.

In some embodiments, the condition, disease or disorder is selected from the group consisting of Familial Chilblain Lupus, RVCL (autosomal dominant retinal vasculopathy with cerebral leukodystrophy), lupus nephritis (LN), Sjogren's Syndrome (SS), lung inflammation, acute lung inflammation, idiopathic pulmonary fibrosis, liver and renal fibrosis, nonalcoholic steatohepatitis (NASH), cirrhosis, endomyocardial fibrosis, acute and chronic kidney injury, APOL1-associated podocytopathy, acute pancreatitis, chronic obstructive pulmonary disease (COPD), senescence, and aging.

Still other examples can include those indications discussed herein and below in contemplated combination therapy regimens.

Combination Therapy

This disclosure contemplates both monotherapy regimens as well as combination therapy regimens.

In some embodiments, the methods described herein can further include administering one or more additional therapies (e.g., one or more additional therapeutic agents and/or one or more therapeutic regimens) in combination with administration of the compounds described herein.

In certain embodiments, the methods described herein can further include administering one or more additional cancer therapies.

The one or more additional cancer therapies can include, without limitation, surgery, radiotherapy, chemotherapy, toxin therapy, immunotherapy, cryotherapy, cancer vaccines (e.g., HPV vaccine, hepatitis B vaccine, Oncophage, Provenge) and gene therapy, as well as combinations thereof. Immunotherapy, including, without limitation, adoptive cell therapy, the derivation of stem cells and/or dendritic cells, blood transfusions, lavages, and/or other treatments, including, without limitation, freezing a tumor.

In some embodiments, the one or more additional cancer therapies is chemotherapy, which can include administering one or more additional chemotherapeutic agents.

In certain embodiments, the additional chemotherapeutic agent is an immunomodulatory moiety, e.g., an immune checkpoint inhibitor. In certain of these embodiments, the immune checkpoint inhibitor targets an immune checkpoint receptor selected from the group consisting of CTLA-4, PD-1, PD-L1, PD-1-PD-L1, PD-1-PD-L2, interleukin-2 (IL-2), indoleamine 2,3-dioxygenase (IDO), IL-10, transforming growth factor-β (TGFβ), T cell immunoglobulin and mucin 3 (TIM3 or HAVCR2), Galectin 9-TIM3, Phosphatidylserine-TIM3, lymphocyte activation gene 3 protein (LAG3), MHC class II-LAG3, 4-1BB-4-1BB ligand, OX40-OX40 ligand, GITR, GITR ligand-GITR, CD27, CD70-CD27, TNFRSF25, TNFRSF25-TL1A, CD40L, CD40-CD40 ligand, HVEM-LIGHT-LTA, HVEM, HVEM-BTLA, HVEM-CD160, HVEM-LIGHT, HVEM-BTLA-CD160, CD80, CD80-PDL-1, PDL2-CD80, CD244, CD48-CD244, CD244, ICOS, ICOS—ICOS ligand, B7-H3, B7-H4, VISTA, TMIGD2, HHLA2-TMIGD2, Butyrophilins, including BTNL2, Siglec family, TIGIT and PVR family members, KIRs, ILTs and LIRs, NKG2D and NKG2A, MICA and MICB, CD244, CD28, CD86-CD28, CD86-CTLA, CD80-CD28, CD39, CD73 Adenosine-CD39-CD73, CXCR4-CXCL12, Phosphatidylserine, TIM3, Phosphatidylserine-TIM3, SIRPA-CD47, VEGF, Neuropilin, CD160, CD30, and CD155; e.g., CTLA-4 or PD1 or PD-L1). See, e.g., Postow, M. *J. Clin. Oncol.* 2015, 33, 1.

In certain of these embodiments, the immune checkpoint inhibitor is selected from the group consisting of: Urelumab, PF-05082566, MEDI6469, TRX518, Varlilumab, CP-870893, Pembrolizumab (PD1), Nivolumab (PD1), Atezolizumab (formerly MPDL3280A) (PDL1), MEDI4736 (PD-L1), Avelumab (PD-L1), PDR001 (PD1), BMS-986016, MGA271, Lirilumab, IPH2201, Emactuzumab, INCB024360, Galunisertib, Ulocuplumab, BKT140, Bavituximab, CC-90002, Bevacizumab, and MNRP1685A, and MGA271.

In certain embodiments, the additional chemotherapeutic agent is an alkylating agent. Alkylating agents are so named because of their ability to alkylate many nucleophilic functional groups under conditions present in cells, including, but not limited to cancer cells. In a further embodiment, an alkylating agent includes, but is not limited to, Cisplatin, carboplatin, mechlorethamine, cyclophosphamide, chlorambucil, ifosfamide and/or oxaliplatin. In an embodiment, alkylating agents can function by impairing cell function by forming covalent bonds with the amino, carboxyl, sulfhydryl, and phosphate groups in biologically important molecules or they can work by modifying a cell's DNA. In a further embodiment an alkylating agent is a synthetic, semisynthetic or derivative.

In certain embodiments, the additional chemotherapeutic agent is an anti-metabolite. Anti-metabolites masquerade as purines or pyrimidines, the building-blocks of DNA and in general, prevent these substances from becoming incorporated in to DNA during the "S" phase (of the cell cycle), stopping normal development and division. Anti-metabolites can also affect RNA synthesis. In an embodiment, an antimetabolite includes, but is not limited to azathioprine and/or mercaptopurine. In a further embodiment an anti-metabolite is a synthetic, semisynthetic or derivative.

In certain embodiments, the additional chemotherapeutic agent is a plant alkaloid and/or terpenoid. These alkaloids are derived from plants and block cell division by, in general, preventing microtubule function. In an embodiment, a plant alkaloid and/or terpenoid is a *vinca* alkaloid, a podophyllotoxin and/or a taxane. *Vinca* alkaloids, in general, bind to specific sites on tubulin, inhibiting the assembly of tubulin into microtubules, generally during the M phase of the cell cycle. In an embodiment, a *vinca* alkaloid is derived, without limitation, from the Madagascar periwinkle, Catharanthus *roseus* (formerly known as *Vinca rosea*). In an embodiment, a *vinca* alkaloid includes, without limitation, Vincristine, Vinblastine, Vinorelbine and/or Vindesine. In an embodiment, a taxane includes, but is not limited, to Taxol, Paclitaxel and/or Docetaxel. In a further embodiment a plant alkaloid or terpernoid is a synthetic, semisynthetic or derivative. In a further embodiment, a podophyllotoxin is, without limitation, an etoposide and/or teniposide. In an embodiment, a taxane is, without limitation, docetaxel and/or ortataxel. [021] In an embodiment, a cancer therapeutic is a topoisomerase. Topoisomerases are essential enzymes that maintain the topology of DNA. Inhibition of type I or type II topoisomerases interferes with both transcription and replication of DNA by upsetting proper DNA supercoiling. In a further embodiment, a topoisomerase is, without limitation, a type I topoisomerase inhibitor or a type II topoisomerase inhibitor. In an embodiment a type I topoisomerase inhibitor is, without limitation, a camptothecin. In another embodiment, a camptothecin is, without limitation, exatecan, irinotecan, lurtotecan, topotecan, BNP 1350, CKD 602, DB 67 (AR67) and/or ST 1481. In an embodiment, a type II topoisomerase inhibitor is, without limitation, epipodophyllotoxin. In a further embodiment an epipodophyllotoxin is, without limitation, an amsacrine, etoposid, etoposide phosphate and/or teniposide. In a further embodiment a topoisomerase is a synthetic, semisynthetic or derivative, including those found in nature such as, without limitation, epipodophyllotoxins, substances naturally occurring in the root of American Mayapple (*Podophyllum peltatum*).

In certain embodiments, the additional chemotherapeutic agent is a stilbenoid. In a further embodiment, a stilbenoid includes, but is not limited to, Resveratrol, Piceatannol, Pinosylvin, Pterostilbene, Alpha-Viniferin, Ampelopsin A, Ampelopsin E, Diptoindonesin C, Diptoindonesin F, Epsilon-Vinferin, Flexuosol A, Gnetin H, Hemsleyanol D, Hopeaphenol, Trans-Diptoindonesin B, Astringin, Piceid and Diptoindonesin A. In a further embodiment a stilbenoid is a synthetic, semisynthetic or derivative.

In certain embodiments, the additional chemotherapeutic agent is a cytotoxic antibiotic. In an embodiment, a cytotoxic antibiotic is, without limitation, an actinomycin, an anthracenedione, an anthracycline, thalidomide, dichloroacetic acid, nicotinic acid, 2-deoxyglucose and/or chlofazimine. In an embodiment, an actinomycin is, without limitation, actinomycin D, bacitracin, colistin (polymyxin E) and/or polymyxin B. In another embodiment, an antracenedione is, without limitation, mitoxantrone and/or pixantrone. In a further embodiment, an anthracycline is, without limitation, bleomycin, doxorubicin (Adriamycin), daunorubicin (daunomycin), epirubicin, idarubicin, mitomycin, plicamycin and/or valrubicin. In a further embodiment a cytotoxic antibiotic is a synthetic, semisynthetic or derivative.

In certain embodiments, the additional chemotherapeutic agent is selected from endostatin, angiogenin, angiostatin, chemokines, angioarrestin, angiostatin (plasminogen fragment), basement-membrane collagen-derived anti-angiogenic factors (tumstatin, canstatin, or arrestin), anti-angiogenic antithrombin III, signal transduction inhibitors, cartilage-derived inhibitor (CDI), CD59 complement fragment, fibronectin fragment, gro-beta, heparinases, heparin hexasaccharide fragment, human chorionic gonadotropin (hCG), interferon alpha/beta/gamma, interferon inducible protein (IP-10), interleukin-12, kringle 5 (plasminogen fragment), metalloproteinase inhibitors (TIMPs), 2-methoxyestradiol, placental ribonuclease inhibitor, plasminogen activator inhibitor, platelet factor-4 (PF4), prolactin 16 kD fragment, proliferin-related protein (PRP), various retinoids, tetrahydrocortisol-S, thrombospondin-1 (TSP-1), transforming growth factor-beta (TGF-β), vasculostatin, vasostatin (calreticulin fragment) and the like.

In certain embodiments, the additional chemotherapeutic agent is selected from abiraterone acetate, altretamine, anhydrovinblastine, auristatin, bexarotene, bicalutamide, BMS 184476, 2,3,4,5,6-pentafluoro-N-(3-fluoro-4-methoxyphenyl)benzene sulfonamide, bleomycin, N,N-dimethyl-L-valyl-L-valyl-N-methyl-L-valyl-L-proly-1-Lproline-t-butylamide, cachectin, cemadotin, chlorambucil, cyclophosphamide, 3',4'-didehydro-4'-deoxy-8'-norvincaleukoblastine, docetaxol, doxetaxel, cyclophosphamide, carboplatin, carmustine, cisplatin, cryptophycin, cyclophosphamide, cytarabine, dacarbazine (DTIC), dactinomycin, daunorubicin, decitabine dolastatin, doxorubicin (adriamycin), etoposide, 5-fluorouracil, finasteride, flutamide, hydroxyurea and hydroxyureataxanes, ifosfamide, liarozole, lonidamine, lomustine (CCNU), MDV3100, mechlorethamine (nitrogen mustard), melphalan, mivobulin isethionate, rhizoxin, sertenef, streptozocin, mitomycin, methotrexate, taxanes, nilutamide, onapristone, paclitaxel, prednimustine, procarbazine, RPR109881, stramustine phosphate, tamoxifen, tasonermin, taxol, tretinoin, vinblastine, vincristine, vindesine sulfate, and vinflunine.

In certain embodiments, the additional chemotherapeutic agent is platinum, cisplatin, carboplatin, oxaliplatin, mechlorethamine, cyclophosphamide, chlorambucil, azathioprine, mercaptopurine, vincristine, vinblastine, vinorelbine, vindesine, etoposide and teniposide, paclitaxel, docetaxel, irinotecan, topotecan, amsacrine, etoposide, etoposide phosphate, teniposide, 5-fluorouracil, leucovorin, methotrexate, gemcitabine, taxane, leucovorin, mitomycin C, tegafur-uracil, idarubicin, fludarabine, mitoxantrone, ifosfamide and doxorubicin. Additional agents include inhibitors of mTOR (mammalian target of rapamycin), including but not limited to rapamycin, everolimus, temsirolimus and deforolimus.

In still other embodiments, the additional chemotherapeutic agent can be selected from those delineated in U.S. Pat. No. 7,927,613, which is incorporated herein by reference in its entirety.

In some embodiments, the additional therapeutic agent and/or regimen are those that can be used for treating other STING-associated conditions, e.g., type I interferonopathies (e.g., STING-associated vasculopathy with onset in infancy (SAVI)), Aicardi-Goutieres Syndrome (AGS), genetic forms of lupus, and inflammation-associated disorders such as systemic lupus erythematosus, and rheumatoid arthritis and the like.

Non-limiting examples of additional therapeutic agents and/or regimens for treating rheumatoid arthritis include non-steroidal anti-inflammatory drugs (NSAIDs; e.g., ibuprofen and naproxen), corticosteroids (e.g, prednisone), disease-modifying antirheumatic drugs (DMARDs; e.g., methotrexate (Trexall®, Otrexup®, Rasuvo®, Rheumatrex®), leflunomide (Arava®), hydroxychloroquine (Plaquenil), PF-06650833, iguratimod, tofacitinib (Xeljanz®), ABBV-599, evobrutinib, and sulfasalazine (Azulfidine®)), and biologics (e.g., abatacept (Orencia®), adalimumab (Humira®), anakinra (Kineret®), certolizumab (Cimzia®), etanercept (Enbrel®), golimumab (Simponi®), infliximab (Remicade®), rituximab (Rituxan®), tocilizumab (Actemra®), vobarilizumab, sarilumab (Kevzara®), secukinumab, ABP 501, CHS-0214, ABC-3373, and tocilizumab (ACTEMRA®)).

Non-limiting examples of additional therapeutic agents and/or regimens for treating lupus include steroids, topical immunomodulators (e.g., tacrolimus ointment (Protopic®) and pimecrolimus cream (Elidel®)), thalidomide (Thalomid®), non-steroidal anti-inflammatory drugs (NSAIDs; e.g., ibuprofen and naproxen), antimalarial drugs (e.g., Hydroxychloroquine (Plaquenil)), corticosteroids (e.g, prednisone) and immunomodulators (e.g., evobrutinib, iberdomide, voclosporin, cenerimod, azathioprine (Imuran®), cyclophosphamide (Cytoxan®, Neosar®, Endoxan®), and cyclosporine (Neoral, Sandimmune®, Gengraf®), and mycophenolate mofetil) baricitinb, iguratimod, filogotinib, GS-9876, rapamycin, and PF-06650833), and biologics (e.g., belimumab (Benlysta®), anifrolumab, prezalumab, MEDI0700, obinutuzumab, vobarilizumab, lulizumab, atacicept, PF-06823859, and lupizor, rituximab, BT063, BI655064, BIIB059, aldesleukin (Proleukin®), dapirolizumab, edratide, IFN-α-kinoid, OMS721, RC18, RSLV-132, theralizumab, XmAb5871, and ustekinumab (Stelara®)). For example, non-limiting treatments for systemic lupus erythematosus include non-steroidal anti-inflammatory drugs (NSAIDs; e.g., ibuprofen and naproxen), antimalarial drugs (e.g., Hydroxychloroquine (Plaquenil)), corticosteroids (e.g, prednisone) and immunomodulators (e.g., iberdomide, voclosporin, azathioprine (Imuran®), cyclophosphamide (Cytoxan®, Neosar®, Endoxan®), and cyclosporine (Neoral, Sandimmune®, Gengraf®), and mycophenolate mofetil, baricitinb, filogotinib, and PF-06650833), and biologics (e.g., belimumab (Benlysta®), anifrolumab, prezalumab, MEDIO700, vobarilizumab, lulizumab, atacicept, PF-06823859, lupizor, rituximab, BT063, BI655064, BIIB059, aldesleukin (Proleukin®), dapirolizumab, edratide, IFN-α-kinoid, RC18, RSLV-132, theralizumab, XmAb5871, and ustekinumab (Stelara®)). As another example, non-limiting examples of treatments for cutaneous lupus include steroids, immunomodulators (e.g., tacrolimus ointment (Protopic®) and pimecrolimus cream (Elidel®)), GS-9876, filogotinib, and thalidomide (Thalomid®). Agents and regimens for treating drug-induced and/or neonatal lupus can also be administered.

Non-limiting examples of additional therapeutic agents and/or regimens for treating STING-associated vasculopathy with onset in infancy (SAVI) include JAK inhibitors (e.g., tofacitinib, ruxolitinib, filgotinib, and baricitinib).

Non-limiting examples of additional therapeutic agents and/or regimens for treating Aicardi-Goutières Syndrome (AGS) include physiotherapy, treatment for respiratory complications, anticonvulsant therapies for seizures, tube-feeding, nucleoside reverse transcriptase inhibitors (e.g., emtricitabine (e.g., Emtriva®), tenofovir (e.g., Viread®), emtricitabine/tenofovir (e.g., Truvada®), zidovudine, lamivudine, and abacavir), and JAK inhibitors (e.g., tofacitinib, ruxolitinib, filgotinib, and baricitinib).

Non-limiting examples of additional therapeutic agents and/or regimens for treating IBDs include 6-mercaptopurine, AbGn-168H, ABX464, ABT-494, adalimumab, AJM300, alicaforsen, AMG139, anrukinzumab, apremilast, ATR-107 (PF0530900), autologous CD34-selected peripheral blood stem cells transplant, azathioprine, bertilimumab, BI 655066, BMS-936557, certolizumab pegol (Cimzia®), cobitolimod, corticosteroids (e.g., prednisone, Methylprednisolone, prednisone), CP-690,550, CT-P13, cyclosporine, DIMS0150, E6007, E6011, etrasimod, etrolizumab, fecal microbial transplantation, figlotinib, fingolimod, firategrast (SB-683699) (formerly T-0047), GED0301, GLPG0634, GLPG0974, guselkumab, golimumab, GSK1399686, HMPL-004 (Andrographis *paniculata* extract), IMU-838, infliximab, Interleukin 2 (IL-2), Janus kinase (JAK) inhibitors, laquinimod, masitinib (AB1010), matrix metalloproteinase 9 (MMP 9) inhibitors (e.g., GS-5745), MEDI2070, mesalamine, methotrexate, mirikizumab (LY3074828), natalizumab, NNC 0142-0000-0002, NNC0114-0006, ozanimod, peficitinib (JNJ-54781532), PF-00547659, PF-04236921, PF-06687234, QAX576, RHB-104, rifaximin, risankizumab, RPC1063, SB012, SHP647, sulfasalazine, TD-1473, thalidomide, tildrakizumab (MK 3222), TJ301, TNF-Kinoid®, tofacitinib, tralokinumab, TRK-170, upadacitinib, ustekinumab, UTTR1147A, V565, vatelizumab, VB-201, vedolizumab, and vidofludimus.

Non-limiting examples of additional therapeutic agents and/or regimens for treating irritable bowel syndrome include alosetron, bile acid sequesterants (e.g., cholestyramine, colestipol, colesevelam), chloride channel activators (e.g., lubiprostone), coated peppermint oil capsules, desipramine, dicyclomine, ebastine, eluxadoline, farnesoid X receptor agonist (e.g., obeticholic acid), fecal microbiota transplantation, fluoxetine, gabapentin, guanylate cyclase-C agonists (e.g., linaclotide, plecanatide), ibodutant, imipramine, JCM-16021, loperamide, lubiprostone, nortriptyline, ondansetron, opioids, paroxetine, pinaverium, polyethylene glycol, pregabalin, probiotics, ramosetron, rifaximin, and tanpanor.

Non-limiting examples of additional therapeutic agents and/or regimens for treating scleroderma include non-steroidal anti-inflammatory drugs (NSAIDs; e.g., ibuprofen and naproxen), corticosteroids (e.g, prednisone), immunomodulators (e.g., azathioprine, methotrexate (Trexall®, Otrexup®, Rasuvo®, Rheumatrex®), cyclophosphamide (Cytoxan®, Neosar®, Endoxan®), and cyclosporine (Neoral®, Sandimmune®, Gengraf®), antithymocyte globulin, mycophenolate mofetil, intravenous immunoglobulin, rituximab, sirolimus, and alefacept), calcium channel blockers (e.g., nifedipine), alpha blockers, serotonin receptor antagonists, angiotensin II receptor inhibitors, statins, local nitrates, iloprost, phosphodiesterase 5 inhibitors (e.g., sildenafil), bosentan, tetracycline antibiotics, endothelin receptor antagonists, prostanoids, and tyrosine kinase inhibitors (e.g., imatinib, nilotinib and dasatinib).

Non-limiting examples of additional therapeutic agents and/or regimens for treating Crohn's Disease (CD) include adalimumab, autologous CD34-selected peripheral blood stem cells transplant, 6-mercaptopurine, azathioprine, certolizumab pegol (Cimzia®), corticosteroids (e.g., prednisone), etrolizumab, E6011, fecal microbial transplantation, figlotinib, guselkumab, infliximab, IL-2, JAK inhibitors, matrix metalloproteinase 9 (MMP 9) inhibitors (e.g., GS-5745), MEDI2070, mesalamine, methotrexate, natalizumab, ozanimod, RHB-104, rifaximin, risankizumab, SHP647, sulfasalazine, thalidomide, upadacitinib, V565, and vedolizumab.

Non-limiting examples of additional therapeutic agents and/or regimens for treating UC include AbGn-168H, ABT-494, ABX464, apremilast, PF-00547659, PF-06687234, 6-mercaptopurine, adalimumab, azathioprine, bertilimumab, brazikumab (MEDI2070), cobitolimod, certolizumab pegol (Cimzia®), CP-690,550, corticosteroids (e.g., multimax budesonide, Methylprednisolone), cyclosporine, E6007, etrasimod, etrolizumab, fecal microbial transplantation, figlotinib, guselkumab, golimumab, IL-2, IMU-838, infliximab, matrix metalloproteinase 9 (MMP9) inhibitors (e.g., GS-5745), mesalamine, mesalamine, mirikizumab (LY3074828), RPC1063, risankizumab (BI 6555066), SH1P647, sulfasalazine, TD-1473, TJ301, tildrakizumab (MK 3222), tofacitinib, tofacitinib, ustekinumab, UTTR1147A, and vedolizumab.

Non-limiting examples of additional therapeutic agents and/or regimens for treating autoimmune colitis include corticosteroids (e.g., budesonide, prednisone, prednisolone, Beclometasone dipropionate), diphenoxylate/atropine, infliximab, loperamide, mesalamine, TIP60 inhibitors (see, e.g., U.S. Patent Application Publication No. 2012/0202848), and vedolizumab.

Non-limiting examples of additional therapeutic agents and/or regimens for treating iatrogenic autoimmune colitis include corticosteroids (e.g., budesonide, prednisone, prednisolone, Beclometasone dipropionate), diphenoxylate/atropine, infliximab, loperamide, TIP60 inhibitors (see, e.g., U.S. Patent Application Publication No. 2012/0202848), and vedolizumab.

Non-limiting examples of additional therapeutic agents and/or regimens for treating colitis induced by one or more chemotherapeutics agents include corticosteroids (e.g., budesonide, prednisone, prednisolone, beclometasone dipropionate), diphenoxylate/atropine, infliximab, loperamide, mesalamine, TIP60 inhibitors (see, e.g., U.S. Patent Application Publication No. 2012/0202848), and vedolizumab.

Non-limiting examples of additional therapeutic agents and/or regimens for treating colitis induced by treatment with adoptive cell therapy include corticosteroids (e.g., budesonide, prednisone, prednisolone, beclometasone dipropionate), diphenoxylate/atropine, infliximab, loperamide, TIP60 inhibitors (see, e.g., U.S. Patent Application Publication No. 2012/0202848), and vedolizumab.

Non-limiting examples of additional therapeutic agents and/or regimens for treating colitis associated with one or more alloimmune diseases include corticosteroids (e.g., budesonide, prednisone, prednisolone, beclometasone dipropionate), sulfasalazine, and eicopentaenoic acid.

Non-limiting examples of additional therapeutic agents and/or regimens for treating radaiation enteritis include teduglutide, amifostine, angiotensin-converting enzyme (ACE) inhibitors (e.g., benazepril, captopril, enalapril, fosinopril, lisinopril, moexipril, perindopril, quinapril, ramipril, and trandolapril), probiotics, selenium supplementation, statins (e.g., atorvastatin, fluvastatin, lovastatin, pravastatin, rosuvastatin, simvastatin, and pitavastatin), sucralfate, and vitamin E.

Non-limiting examples of additional therapeutic agents and/or regimens for treating collagenous colitis include 6-mercaptopurine, azathaioprine, bismuth subsalicate, *Boswellia serrata* extract, cholestyramine, colestipol, corticosteroids (e.g., budesonide, prednisone, prednisolone, beclometasone dipropionate), loperamide, mesalamine, methotrexate, probiotics, and sulfasalazine.

Non-limiting examples of additional therapeutic agents and/or regimens for treating lyphocytic colitis include 6-mercaptopurine, azathioprine, bismuth subsalicylate, cholestyramine, colestipol, corticosteroids (e.g., budesonide, prednisone, prednisolone, beclometasone dipropionate), loperamide, mesalamine, methotrexate, and sulfasalazine.

Non-limiting examples of additional therapeutic agents and/or regimens for treating microscopic colitis include 6-mercaptopurine, azathioprine, bismuth subsalicylate, *Boswellia serrata* extract, cholestyramine, colestipol, corticosteroids (e.g., budesonide, prednisone, prednisolone, beclometasone dipropionate), fecal microbial transplantation, loperamide, mesalamine, methotrexate, probiotics, and sulfasalazine.

Non-limiting examples of additional therapeutic agents and/or regimens for treating alloimmune disease include intrauterine platelet transfusions, intravenous immunoglobin, maternal steroids, abatacept, alemtuzumab, alphal-antitrypsin, AMG592, antithymocyte globulin, barcitinib, basiliximab, bortezomib, brentuximab, cannabidiol, corticosteroids (e.g., methylprednisone, prednisone), cyclosporine, dacilzumab, defribrotide, denileukin diftitox, glasdegib, ibrutinib, IL-2, infliximab, itacitinib, LBH589, maraviroc, mycophenolate mofetil, natalizumab, neihulizumab, pentostatin, pevonedistat, photobiomodulation, photopheresis, ruxolitinib, sirolimus, sonidegib, tacrolimus, tocilizumab, and vismodegib.

Non-limiting examples of additional therapeutic agents and/or regimens for treating multiple sclerosis (MS) include alemtuzumab (Lemtrada®), ALKS 8700, amiloride, ATX-MS-1467, azathioprine, baclofen (Lioresal®), beta interferons (e.g., IFN-β-1a, IFN-β-1b), cladribine, corticosteroids (e.g., methylprednisolone), daclizumab, dimethyl fumarate (Tecfidera®), fingolimod (Gilenya®), fluoxetine, glatiramer acetate (Copaxone®), hydroxychloroquine, ibudilast, idebenone, laquinimod, lipoic acid, losartan, masitinib, MD1003 (biotin), mitoxantrone, montelukast, natalizumab (Tysabri®), NeuroVax™, ocrelizumab, ofatumumab, pioglitazone, and RPC1063.

Non-limiting examples of additional therapeutic agents and/or regimens for treating graft-vs-host disease include abatacept, alemtuzumab, alphal-antitrypsin, AMG592, antithymocyte globulin, barcitinib, basiliximab, bortezomib, brentuximab, cannabidiol, corticosteroids (e.g., methylprednisone, prednisone), cyclosporine, dacilzumab, defribrotide, denileukin diftitox, glasdegib, ibrutinib, IL-2, imatinib, infliximab, itacitinib, LBH589, maraviroc, mycophenolate mofetil, natalizumab, neihulizumab, pentostatin, pevonedistat, photobiomodulation, photopheresis, ruxolitinib, sirolimus, sonidegib, tacrolimus, tocilizumab, and vismodegib.

Non-limiting examples of additional therapeutic agents and/or regimens for treating acute graft-vs-host disease include alemtuzumab, alpha-1 antitrypsin, antithymocyte globulin, basiliximab, brentuximab, corticosteroids (e.g., methylprednisone, prednisone), cyclosporine, dacilzumab, defribrotide, denileukin diftitox, ibrutinib, infliximab, itacitinib, LBH589, mycophenolate mofetil, natalizumab, neihulizumab, pentostatin, photopheresis, ruxolitinib, sirolimus, tacrolimus, and tocilizumab.

Non-limiting examples of additional therapeutic agents and/or regimens for treating chronic graft vs. host disease include abatacept, alemtuzumab, AMG592, antithymocyte globulin, basiliximab, bortezomib, corticosteroids (e.g., methylprednisone, prednisone), cyclosporine, dacilzumab, denileukin diftitox, glasdegib, ibrutinib, IL-2, imatinib, infliximab, mycophenolate mofetil, pentostatin, photobiomodulation, photopheresis, ruxolitinib, sirolimus, sonidegib, tacrolimus, tocilizumab, and vismodegib.

Non-limiting examples of additional therapeutic agents and/or regimens for treating celiac disease include AMG 714, AMY01, *Aspergillus niger* prolyl endoprotease, BL-7010, CALY-002, GBR 830, Hu-Mik-Beta-1, IMGX003, KumaMax, Larazotide Acetate, Nexvan2®, pancrelipase, TIMP-GLIA, vedolizumab, and ZED1227.

Non-limiting examples of additional therapeutic agents and/or regimens for treating psoriasis include topical corticosteroids, topical crisaborole/AN2728, topical SNA-120, topical SAN021, topical tapinarof, topical tocafinib, topical IDP-118, topical M518101, topical calcipotriene and betamethasone dipropionate (e.g., MC2-01 cream and Taclonex®), topical P-3073, topical LEO 90100 (Enstilar®), topical betamethasone dipropriate (Sernivo®), halobetasol propionate (Ultravate®), vitamin D analogues (e.g., calcipotriene (Dovonex®) and calcitriol (Vectical®)), anthralin (e.g., Dritho-scalp® and Dritho-creme®), topical retinoids (e.g., tazarotene (e.g., Tazorac® and Avage®)), calcineurin inhibitors (e.g., tacrolimus (Prograf®) and pimecrolimus (Elidel®)), salicylic acid, coal tar, moisturizers, phototherapy (e.g., exposure to sunlight, UVB phototherapy, narrow band UVB phototherapy, Goeckerman therapy, psoralen plus ultraviolet A (PUVA) therapy, and excimer laser), retinoids (e.g., acitretin (Soriatane®)), methotrexate (Trexall®, Otrexup®, Rasuvo®, Rheumatrex®), Apo805K1, baricitinib, FP187, KD025, prurisol, VTP-43742, XP23829, ZPL-389, CF101 (piclidenoson), LAS41008, VPD-737 (serlopitant), upadacitinib (ABT-494), aprmilast, tofacitibin, cyclosporine (Neoral®, Sandimmune®, Gengraf®), biologics (e.g., etanercept (Enbrel®), entanercept-szzs (Elrezi®), infliximab (Remicade®), adalimumab (Humira®), adalimumab-adbm (Cyltezo®), ustekinumab (Stelara®), golimumab (Simponi®), apremilast (Otezla®), secukinumab (Cosentyx®), certolixumab pegol, secukinumab, tildrakizumab-asmn, infliximab-dyyb, abatacept, ixekizumab (Taltz®), ABP 710, BCD-057, BI695501, bimekizumab (UCB4940), CHS-1420, GP2017, guselkumab (CNTO 1959), HD203, M923, MSB11022, Mirikizumab (LY3074828), PF-06410293, PF-06438179, risankizumab (BI655066), SB2, SB4, SB5, siliq (brodalumab), namilumab (MT203, tildrakizumab (MK-3222), and ixekizumab (Taltz®)), thioguanine, and hydroxyurea (e.g., Droxia® and Hydrea®).

Non-limiting examples of additional therapeutic agents and/or regimens for treating cutaneous T-cell lymphoma include phototherapy (e.g., exposure to sunlight, UVB phototherapy, narrow band UVB phototherapy, Goeckerman therapy, psoralen plus ultraviolet A (PUVA) therapy, and excimer laser), extracorporeal photopheresis, radiation therapy (e.g., spot radiation and total skin body electron beam therapy), stem cell transplant, corticosteroids, imiquimod, bexarotene gel, topical bis-chloroethyl-nitrourea, mechlorethamine gel, vorinostat (Zolinza®), romidepsin (Istodax®), pralatrexate (Folotyn®) biologics (e.g., alemtuzumab (Campath®), brentuximab vedotin (SGN-35), mogamulizumab, and IPH4102).

Non-limiting examples of additional therapeutic agents and/or regimens for treating uveitis include corticosteroids (e.g., intravitreal triamcinolone acetonide injectable suspensions), antibiotics, antivirals (e.g., acyclovir), dexamethasone, immunomodulators (e.g., tacrolimus, leflunomide, cyclophosphamide (Cytoxan®, Neosar®, Endoxan®), and cyclosporine (Neoral®, Sandimmune®, Gengraf®), chlorambucil, azathioprine, methotrexate, and mycophenolate mofetil), biologics (e.g., infliximab (Remicade®), adalimumab (Humira®), etanercept (Enbrel@), golimumab (Simponi®), certolizumab (Cimzia®), rituximab (Rituxan®), abatacept (Orencia®), basiliximab (Simulect®), anakinra (Kineret®), canakinumab (Ilaris®), gevokixumab (XOMA052), tocilizumab (Actemra®), alemtuzumab (Campath®), efalizumab (Raptiva®), LFG316, sirolimus (Santen®), abatacept, sarilumab (Kevzara®), and daclizumab (Zenapax®)), cytotoxic drugs, surgical implant (e.g., fluocinolone insert), and vitrectomy.

on-limiting examples of additional therapeutic agents and/or regimens for treating mucositis include AG013, SGX942 (dusquetide), amifostine (Ethyol®), cryotherapy, cepacol lonzenges, capsaicin lozenges, mucoadhesives (e.g., MuGard®) oral diphenhydramine (e.g., Benadry® elixir), oral bioadherents (e.g., polyvinylpyrrolidone-sodium hyaluronate gel (Gelclair®)), oral lubricants (e.g., Oral Balance®), caphosol, *chamomilla recutita* mouthwash, edible grape plant exosome, antiseptic mouthwash (e.g., chlorhexidine gluconate (e.g., Peridex® or Periogard®), topical pain relievers (e.g., lidocaine, benzocaine, dyclonine hydrochloride, xylocaine (e.g., viscous xylocaine 2%), and Ulcerease® (0.6% phenol)), corticosteroids (e.g., prednisone), pain killers (e.g., ibuprofen, naproxen, acetaminophen, and opioids), GC4419, palifermin (keratinocyte growth factor; Kepivance®), ATL-104, clonidine lauriad, IZN-6N4, SGX942, rebamipide, nepidermin, soluble β-1,3/1,6 glucan, P276, LP-0004-09, CR-3294, ALD-518, IZN-6N4, quercetin, granules comprising *vaccinium myrtillus* extract, macleaya *cordata* alkaloids and *echinacea angustifolia* extract (e.g., SAMITAL®), and gastrointestinal cocktail (an acid reducer such aluminum hydroxide and magnesium hydroxide (e.g., Maalox), an antifungal (e.g., nystatin), and an analgesic (e.g., hurricane liquid)). For example, non-limiting examples of treatments for oral mucositis include AG013, amifostine (Ethyol®), cryotherapy, cepacol lonzenges, mucoadhesives (e.g., MuGard®) oral diphenhydramine (e.g., Benadry® elixir), oral bioadherents (e.g., polyvinylpyrrolidone-sodium hyaluronate gel (Gelclair®)), oral lubricants (e.g., Oral Balance®), caphosol, *chamomilla recutita* mouthwash, edible grape plant exosome, antiseptic mouthwash (e.g., chlorhexidine gluconate (e.g., Peridex® or Periogard®), topical pain relievers (e.g., lidocaine, benzocaine, dyclonine hydrochloride, xylocaine (e.g., viscous xylocaine 2%), and Ulcerease® (0.6% phenol)), corticosteroids (e.g., prednisone), pain killers (e.g., ibuprofen, naproxen, acetaminophen, and opioids), GC4419, palifermin (keratinocyte growth factor; Kepivance®), ATL-104, clonidine lauriad, IZN-6N4, SGX942, rebamipide, nepidermin, soluble β-1,3/1,6 glucan, P276, LP-0004-09, CR-3294, ALD-518, IZN-6N4, quercetin, and gastrointestinal cocktail (an acid reducer such aluminum hydroxide and magnesium hydroxide (e.g., Maalox), an antifungal (e.g., nystatin), and an analgesic (e.g., hurricane liquid)). As another example, non-limiting examples of treatments for esophageal mucositis include xylocaine (e.g., gel viscous Xylocaine 2%). As another example, treatments for intestinal mucositis, treatments to modify intestinal mucositis, and treatments for intestinal mucositis signs and symptoms include gastrointestinal cocktail (an acid reducer such aluminum hydroxide and magnesium hydroxide (e.g., Maalox), an antifungal (e.g., nystatin), and an analgesic (e.g., hurricane liquid)).

In certain embodiments, the second therapeutic agent or regimen is administered to the subject prior to contacting with or administering the chemical entity (e.g., about one hour prior, or about 6 hours prior, or about 12 hours prior, or about 24 hours prior, or about 48 hours prior, or about 1 week prior, or about 1 month prior).

In other embodiments, the second therapeutic agent or regimen is administered to the subject at about the same time as contacting with or administering the chemical entity. By way of example, the second therapeutic agent or regimen and the chemical entity are provided to the subject simultaneously in the same dosage form. As another example, the second therapeutic agent or regimen and the chemical entity are provided to the subject concurrently in separate dosage forms.

In still other embodiments, the second therapeutic agent or regimen is administered to the subject after contacting with or administering the chemical entity (e.g., about one hour after, or about 6 hours after, or about 12 hours after, or about 24 hours after, or about 48 hours after, or about 1 week after, or about 1 month after).

Patient Selection

In some embodiments, the methods described herein further include the step of identifying a subject (e.g., a patient) in need of such treatment (e.g., by way of biopsy, endoscopy, or other conventional method known in the art). In certain embodiments, the STING protein can serve as a biomarker for certain types of cancer, e.g., colon cancer and prostate cancer. In other embodiments, identifying a subject can include assaying the patient's tumor microenvironment for the absence of T-cells and/or presence of exhausted T-cells, e.g., patients having one or more cold tumors. Such patients can include those that are resistant to treatment with checkpoint inhibitors. In certain embodiments, such patients can be treated with a chemical entity herein, e.g., to recruit T-cells into the tumor, and in some cases, further treated with one or more checkpoint inhibitors, e.g., once the T-cells become exhausted.

In some embodiments, the chemical entities, methods, and compositions described herein can be administered to certain treatment-resistant patient populations (e.g., patients resistant to checkpoint inhibitors; e.g., patients having one or more cold tumors, e.g., tumors lacking T-cells or exhausted T-cells).

Compound Preparation

As can be appreciated by the skilled artisan, methods of synthesizing the compounds of the formulae herein will be evident to those of ordinary skill in the art. Synthetic chemistry transformations and protecting group methodologies (protection and deprotection) useful in synthesizing the compounds described herein are known in the art and include, for example, those such as described in R. Larock, Comprehensive Organic Transformations, VCH Publishers (1989); T. W. Greene and RGM. Wuts, Protective Groups in Organic Synthesis, 2d. Ed., John Wiley and Sons (1991); L. Fieser and M. Fieser, Fieser and Fieser's Reagents for Organic Synthesis, John Wiley and Sons (1994); and L. Paquette, ed., Encyclopedia of Reagents for Organic Synthesis, John Wiley and Sons (1995), and subsequent editions thereof. The starting materials used in preparing the compounds of the invention are known, made by known methods, or are commercially available. The skilled artisan will also recognize that conditions and reagents described herein that can be interchanged with alternative art-recognized equivalents. For example, in many reactions, triethylamine can be interchanged with other bases, such as non-nucleophilic bases (e.g. diisopropylamine, 1,8-diazabicycloundec-7-ene, 2,6-di-tert-butylpyridine, or tetrabutylphosphazene).

The skilled artisan will recognize a variety of analytical methods that can be used to characterize the compounds described herein, including, for example, $^1H$ NMR, heteronuclear NMR, mass spectrometry, liquid chromatography, and infrared spectroscopy. The foregoing list is a subset of characterization methods available to a skilled artisan and is not intended to be limiting.

To further illustrate the foregoing, the following non-limiting, exemplary synthetic schemes are included. Variations of these examples within the scope of the claims are within the purview of one skilled in the art and are considered to fall within the scope of the invention as described, and claimed herein. The reader will recognize that the skilled artisan, provided with the present disclosure, and skill in the art is able to prepare and use the invention without exhaustive examples.

EXAMPLES

Abbreviation of Chemical Terms

Ac=acetyl
ADDP=1,1'-(azodicarbonyl)-dipiperidine
ACN=acetonitrile
$Boc_2O$=di-tert-butyl pyrocarbornate
Bu=butyl
BOP=Benzotriazol-1-yloxytris(dimethylamino)-phosphonium hexafluoro-phosphate
Bn=benzyl
Bz=benzoyl
CataCxium A=Bis(adamant-1-yl)(butyl)phosphine
CMPB=(Cyanomethylene)tri-n-butylphosphorane
DAST=Diethylaminosulphur trifluoride
DBAD=di-tert-butyl azodiformate
DCE=dichloroethane
DCM=dichloromethane
DEAD=diethyl azodiformate
DIBAL-H=Diisobutylaluminum hydride
DIAD=diisopropyl azodicarboxylate
DIEA=N,N-diisopropylethylamine
DMA=Dimethylacetamide
DMAP=4-dimethylaminopyridine
DMF=N,N-dimethylformamide
DMF-DMA=N,N-dimethylformamide dimethyl acetal
DMSO=dimethyl sulfoxide
DPPA=diphenyl azidophosphate
Dppf=bis(diphenylphosphino)ferrocene
DtBPF=1,1'-Bis[bis(1,1-dimethylethyl)phosphino]ferrocene
Grubbs $1^{st}$=Grubbs Catalyst 1st Generation
FA=Formic acid
HATU=2-(7-Azabenzotriazol-1-yl)-N,N,N',N'-tetramethyluronium hexafluorophosphateHMDS=1,1,1,3,3,3-Hexamethyldisilazane
$H_2O$=Water
HPLC=high performance liquid chromatography
IBX=2-iodoxybenzoic acid
LAH=Lithium aluminum hydride
LC-MS=liquid chromatography-mass spectrometry
Me=methyl
NMI=1-methylimidazole
NMR=nuclear magnetic resonance
POT=tris(2-methylphenyl)phosphine
Pr=propyl
Py=pyridine
RT=retention time
TBDPS=t-butyl-diphenylsilyl
TBS=tert-Butyldimethylsilyl
TBUP=Tri-n-butylphosphine
TCFH=N,N,N',N'-tetramethylchloroformamidinium-hexafluorophosphate
TEA=trimethylamine
Tf=trifluoromethanesulfonyl
TFA=trifluoroacetic acid
$Tf_2O$=trifluoromethanesulfonic anhydride
THE=tetrahydrofuran TMS=Trimethylsilyl Tol=methylbenzene $T_3P$=2,4,6-tripropyl-2,4,6-trioxo-1,3,5,2,4,6-trioxatriphosphorinane Ts=Tosyl t-AmOH=2-methylbutan-2-ol XPhos=(2-(2,4,6-triisopropylphenethyl)phenyl)dicyclohexylphosphine $Na_2SO_4$=Sodium sulfate Speedvac=Savant SC250EXP SpeedVac Concentrator DMSO=Dimethyl Sulfoxide Cs2CO3=Cesium carbonate TCFH=N-(chloro(dimethylamino)methylene)-N-methylmethanaminium hexafluorophosphateN—

HPLC-1=high-performance liquid chromatography

Materials and Methods

For schemes 1-51 and examples 1-195 and, the LC-MS methods and prep-HPLC methods are one of the following methods.

LCMS Method A: Kinetex EVO C18 100A, 30*3 mm, 0.5 μL injection, 1.2 mL/min flowrate, 90-900 amu scan range, 254 nm UV detection. Mobile Phase A (MPA): Water/5 mM $NH_4HCO_3$ and Mobile Phase B (MPB): Acetonitrile. Elution 10% MPB to 95% in 2.00 min, hold at 95% MPB for 0.30 min, 95% MPB to 10% in 0.10 min.

LCMS Method B: Xselect CSH C18, 50*3 mm, 1.0 μL injection, 1.2 mL/min flowrate, 90-900 amu scan range, 254 nm UV detection. Mobile Phase A (MPA): Water/0.1% FA and Mobile Phase B (MPB): Acetonitrile/0.1% FA. Elution 5% MPB to 100% in 2.00 min, hold at 100% MPB for 0.70 min, 100% MPB to 5% in 0.05 min, then equilibration to 5% MPB for 0.15 min.

LCMS Method C: XBridge Shield RP18, 50*4.6 mm, 0.5 μL injection, 1.2 mL/min flowrate, 90-900 amu scan range, 254 nm UV detection. Mobile Phase A (MPA): Water/0.04% $NH_3.H_2O$ and Mobile Phase B (MPB): Acetonitrile. Elution 10% MPB to 95% in 2.00 min, hold at 95% MPB for 0.79 min, 95% MPB to 10% in 0.06 min, then equilibration to 10% MPB for 0.15 min.

LCMS Method D: kinetex 2.6 μm EVO, 50*3 mm, 0.5 μL injection, 1.2 mL/min flowrate, 30-2000 amu scan range, 254 nm UV detection. Mobile Phase A (MPA): Water/5 mM $NH_4HCO_3$ and Mobile Phase B (MPB): Acetonitrile. Elution 10% MPB to 95% in 2.00 min, hold at 95% MPB for 0.70 min, 95% MPB to 10% in 0.05 min, then equilibration to 10% MPB for 0.25 min.

LCMS Method E: HALOC18, 30*3 mm, 0.5 μL injection, 1.5 mL/min flowrate, 30-2000 amu scan range, 254 nm UV detection. Mobile Phase A (MPA): Water/0.05% TFA and Mobile Phase B (MPB): Acetonitrile/0.05% TFA. Elution 5% MPB to 100% in 1.20 min, hold at 100% MPB for 0.60 min, 100% MPB to 5% in 0.02 min, then equilibration to 5% MPB for 0.18 min.

LCMS Method F: Shim-pack Scepter C18-120, 33*3 mm, 0.5 μL injection, 1.5 mL/min flowrate, 30-2000 amu scan range, 254 nm UV detection. Mobile Phase A (MPA): Water/5 mM $NH_4HCO_3$ and Mobile Phase B (MPB): Acetonitrile. Elution 50% MPB to 95% in 2.00 min, hold at 95% MPB for 0.60 min, 95% MPB to 10% in 0.05 min, then equilibration to 10% MPB for 0.25 min.

LCMS Method G: Poroshell HPH C18, 50*3 mm, 0.5 μL injection, 1.2 mL/min flowrate, 30-2000 amu scan range, 254 nm UV detection. Mobile Phase A (MPA): Water/5 mM $NH_4HCO_3$+5 mM $NH_4OH$ and Mobile Phase B (MPB): Acetonitrile. Elution 10% MPB to 95% in 2.00 min, hold at 95% MPB for 0.70 min, 95% MPB to 5% in 0.05 min, then equilibration to 5% MPB for 0.25 min.

Method A

Instrument: Agilent LCMS system equipped with DAD and ELSD detector

Ion mode: Positive

Column: Waters X-Bridge C18, 50*2.1 mm*5 m or equivalent

Mobile Phase: A: $H_2O$ (0.04% TFA); B: $CH_3CN$ (0.02% TFA)

Gradient: 4.5 min gradient method, actual method would depend on clogP of compound.

Flow Rate: 0.6 mL/min or 0.8 mL/min

Column Temp: 40° C. or 50° C.

UV: 220 nm

Method B

Instrument: Agilent LCMS system equipped with DAD and ELSD detector

Ion mode: Positive

Column: Waters X-Bridge ShieldRP18, 50*2.1 mm*5 m or equivalent

Mobile Phase:A: $H_2O$ (0.05% $NH_3.H_2O$) or 10 mM ammonia bicarbonate; B: $CH_3CN$ Gradient: 4.5 min gradient method; actual method would depend on the clogP of the compound.

Flow Rate: 0.6 mL/min or 0.8 mL/min

Column Temp: 40° C.

UV: 220 nm

Prep. HPLC Condition

Instrument:

1. GILSON 281 and Shimadzu LCMS 2010A
2. GILSON 215 and Shimadzu LC-20AP
3. GILSON 215

Mobile Phase:

A: $NH_4OH/H_2O$=0.05% v/v; B: ACN

A: $FA/H_2O$=0.225% v/v; B: ACN

Column

Xtimate C18 150*25 mm*5 μm

Flow rate: 25 mL/min or 30 mL/min

Monitor wavelength: 220&254 nm

Gradient: actual method would depend on clog P of compound

Detector: MS Trigger or UV

NMR was recorded on BRUKER NMR 300.03 Mz, DUL-C—H, ULTRASHIELD™ 300, AVANCE II 300 B-ACS™ 120 or BRUKER NMR 400.13 Mz, BBFO, ULTRASHIELD™ 400, AVANCE III 400, B-ACS™ 120.

For scheme 52-75 and examples 196-289, the LC-MS, NMR, Prep-HPLC are conducted using one of the following methods.

LCMS Method A: Kinetex EVO C18 100A, 30*3 mm, 0.5 μL injection, 1.2 mL/min flowrate, 90-900 amu scan range, 254 nm UV detection. Mobile Phase A (MPA): Water/5 mM $NH_4HCO_3$ and Mobile Phase B (MPB): Acetonitrile. Elution 10% MPB to 95% in 2.00 min, hold at 95% MPB for 0.30 min, 95% MPB to 10% in 0.10 min.

LCMS Method B: Xselect CSH C18, 50*3 mm, 1.0 μL injection, 1.2 mL/min flowrate, 90-900 amu scan range, 254 nm UV detection. Mobile Phase A (MPA): Water/0.1% FA and Mobile Phase B (MPB): Acetonitrile/0.1% FA. Elution 5% MPB to 100% in 2.00 min, hold at 100% MPB for 0.70 min, 100% MPB to 5% in 0.05 min, then equilibration to 5% MPB for 0.15 min.

LCMS Method C: XBridge Shield RP18, 50*4.6 mm, 0.5 μL injection, 1.2 mL/min flowrate, 90-900 amu scan range, 254 nm UV detection. Mobile Phase A (MPA): Water/0.04% $NH_3 \cdot H_2O$ and Mobile Phase B (MPB): Acetonitrile. Elution 10% MPB to 95% in 2.00 min, hold at 95% MPB for 0.79 min, 95% MPB to 10% in 0.06 min, then equilibration to 10% MPB for 0.15 min.

LCMS Method D: kinetex 2.6 μm EVO, 50*3 mm, 0.5 μL injection, 1.2 mL/min flowrate, 30-2000 amu scan range, 254 nm UV detection. Mobile Phase A (MPA): Water/5 mM $NH_4HCO_3$ and Mobile Phase B (MPB): Acetonitrile. Elution 10% MPB to 95% in 2.00 min, hold at 95% MPB for 0.70 min, 95% MPB to 10% in 0.05 min, then equilibration to 10% MPB for 0.25 min.

LCMS Method E: HALOC18, 30*3 mm, 0.5 μL injection, 1.5 mL/min flowrate, 30-2000 amu scan range, 254 nm UV detection. Mobile Phase A (MPA): Water/0.05% TFA and Mobile Phase B (MPB): Acetonitrile/0.05% TFA. Elution 5% MPB to 100% in 1.20 min, hold at 100% MPB for 0.60 min, 100% MPB to 5% in 0.02 min, then equilibration to 5% MPB for 0.18 min.

LCMS Method F: Shin-pack Scepter C18-120, 33*3 mm, 0.5 μL injection, 1.5 mL/min flowrate, 30-2000 amu scan range, 254 nm UV detection. Mobile Phase A (MPA): Water/5 mM $NH_4HCO_3$ and Mobile Phase B (MPB): Acetonitrile. Elution 50% MPB to 95% in 2.00 min, hold at 95% MPB for 0.60 min, 95% MPB to 10% in 0.05 min, then equilibration to 10% MPB for 0.25 min.

Method A

- Instrument: Agilent LCMS system equipped with DAD and ELSD detector
- Ion mode: Positive
- Column: Waters X-Bridge C18, 50*2.1 mm*5 m or equivalent
- Mobile Phase: A: $H_2O$ (0.04% TFA); B: $CH_3CN$ (0.02% TFA)
- Gradient: 4.5 min gradient method, actual method would depend on clogP of compound.
- Flow Rate: 0.6 mL/min or 0.8 mL/min
- Column Temp: 40° C. or 50° C.
- UV: 220 nm Method B

- Instrument: Agilent LCMS system equipped with DAD and ELSD detector
- Ion mode: Positive
- Column: Waters X-Bridge ShieldRP18, 50*2.1 mm*5 m or equivalent
- Mobile Phase:A: $H_2O$ (0.05% $NH_3.H_2O$) or 10 mM ammonia bicarbonate; B: $CH_3CN$
- Gradient: 4.5 min gradient method; actual method would depend on the clogP of the compound.
- Flow Rate: 0.6 mL/min or 0.8 mL/min
- Column Temp: 40° C.
- UV: 220 nm Prep. HPLC-1 Condition-1

Instrument:

1. GILSON 281 and Shimadzu LCMS 2010A
2. GILSON 215 and Shimadzu LC-20AP
3. GILSON 215

Mobile Phase:

- A: $NH_4OH/H_2O$=0.05% v/v; B: ACN
- A: $FA/H_2O$=0.225% v/v; B: ACN

Column

- Xtimate C18 150*25 mm*5 μm
- Flow rate: 25 mL/min or 30 mL/min
- Monitor wavelength: 220&254 nm
- Gradient: actual method would depend on clog P of compound
- Detector: MS Trigger or UV NMR was recorded on BRUKER NMR 300.03 Mz, DUL-C—H, ULTRASHIELD™ 300, AVANCE II 300 B-ACS™ 120 or BRUKER NMR 400.13 Mz, BBFO, ULTRASHIELD™ 400, AVANCE III 400, B-ACS™ 120.

Preparative Examples

Scheme for the preparation of Key Intermediates: Schemes below illustrate the preparation of key intermediates.

Scheme 1: Synthesis of intermediate 1 and intermediate 2 (N-(5-bromo-1H-indol-3-yl)acetamide and tert-butyl 3-acetamido-5-bromo-1H-indole-1-carboxylate)

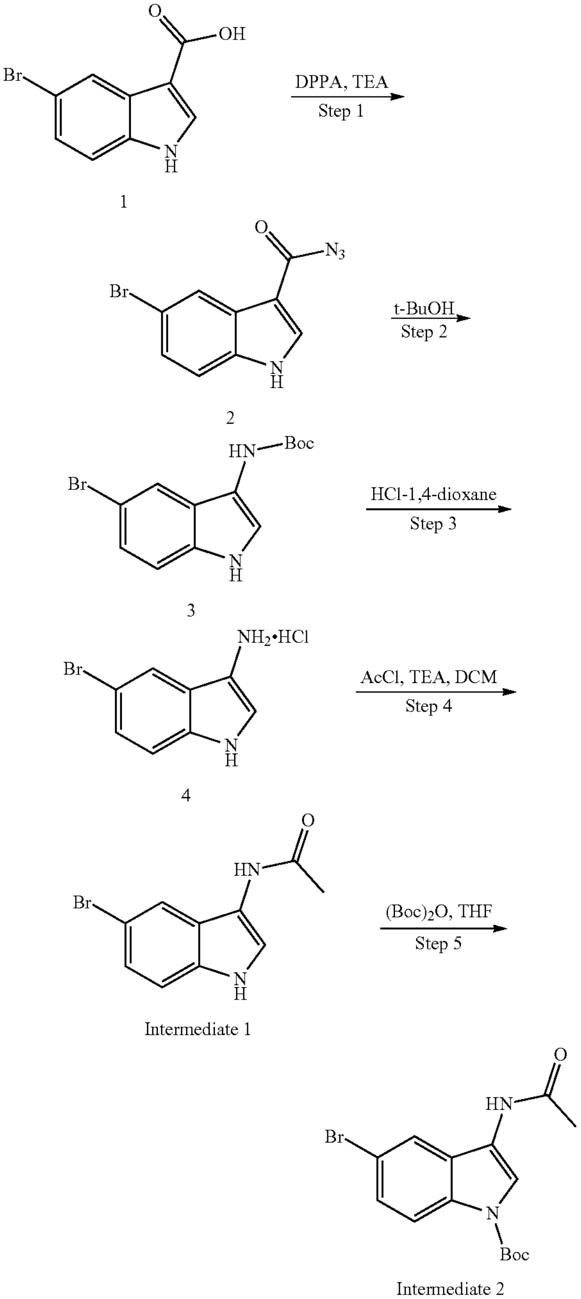

1

2

3

4

Intermediate 1

Intermediate 2

Step 1: 5-bromo-1H-indole-3-carbonyl azide

5-Bromo-1H-indole-3-carboxylic acid (30.0 g, 124.9 mmol, 1.0 equiv.) was dissolved in THE (150 mL), then TEA (26.1 mL, 187.4 mmol, 1.5 equiv.) and DPPA (37.8 g, 137.4 mmol, 1.1 equiv.) were added. The reaction mixture was stirred for 12 hours at ambient temperature, then quenched by the addition of water and stirred for an additional 10 min. The precipitated solid was collected by filtration and dried to give 5-bromo-1H-indole-3-carbonyl azide (33.6 g) as an off-white solid. LCMS Method B: $[M-H]^-=263$.

Step 2: tert-butyl (5-bromo-1H-indol-3-yl)carbamate

5-Bromo-1H-indole-3-carbonyl azide (33.6 g, 126.7 mmol, 1.0 equiv.) was dissolved in t-BuOH (300 mL). The reaction mixture was heated to 80° C. for 12 hours, then cooled to ambient temperature and concentrated under vacuum. The residue was purified by flash column chromatography on silica gel, eluting with ethyl acetate/petroleum ether (1:10) to give tert-butyl (5-bromo-1H-indol-3-yl)carbamate (22.1 g) as a pale white solid. LCMS Method A: $[M+H]^+=311$.

Step 3: 5-bromo-1H-indol-3-amine hydrochloride tert-Butyl (5-bromo-1H-indol-3-yl)carbamate (20.0 g, 64.2 mmol, 1.0 equiv.) was dissolved in HCl/1,4-dioxane (4 M, 150 mL). The reaction mixture was stirred for 2 hours at ambient temperature and then concentrated under vacuum to give 5-bromo-1H-indol-3-amine hydrochloride (18.7 g) as a brown solid. LCMS Method A: $[M+H]^+=211$.

Step 4: N-(5-bromo-1H-indol-3-yl)acetamide

5-Bromo-1H-indol-3-amine (18.7 g, 88.6 mmol, 1.0 equiv.) and TEA (37.1 mL, 265.8 mmol, 3.0 equiv.) were dissolved in DCM (200 mL) and the solution was cooled to 0° C. Then AcCl (6.9 mL, 97.4 mmol, 1.1 equiv.) was added dropwise, maintaining the solution at 0° C. The reaction mixture was stirred for 3 hours at ambient temperature, then quenched by the addition of water. The resulting solution was extracted with DCM, washed with brine, dried over anhydrous $Na_2SO_4$ and concentrated under vacuum. The residue was purified by flash column chromatography on silica gel, eluting with ethyl acetate/petroleum ether (1:3) to give N-(5-bromo-1H-indol-3-yl)acetamide (15.0 g) as a brown solid. LCMS Method A: $[M+H]^+=253$.

Step 5: tert-butyl 5-bromo-3-acetamidoindole-1-carboxylate

N-(5-bromo-1H-indol-3-yl)acetamide (1.0 g, 4.0 mmol, 1.0 equiv.) was dissolved in THF (30 mL), then TEA (1.1 mL, 7.9 mmol, 2 equiv.), $Boc_2O$ (862.3 mg, 4.0 mmol, 1.0 equiv.) and DMAP (48.3 mg, 0.4 mmol, 0.1 equiv.) were added. The reaction mixture was stirred for 50 min at ambient temperature, then quenched by the addition of water. The resulting solution was extracted with ethyl acetate, washed with brine, dried over anhydrous $Na_2SO_4$ and concentrated under vacuum. The residue was purified by flash column chromatography on silica gel, eluting with ethyl acetate/petroleum ether (1:5) to give tert-butyl 5-bromo-3-acetamidoindole-1-carboxylate (800.0 mg) as a pale yellow solid. LCMS Method C: $[M+H]^+=3M53$.

The intermediates in the following table were prepared using the same method described for Intermediates 1 and 2.

| Intermediate | Structure | LCMS data |
|---|---|---|
| Intermediate 3 | 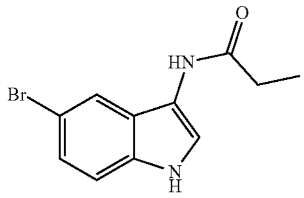 | Method A: MS-ESI: 267 $[M + H]^+$ |
| Intermediate 4 | 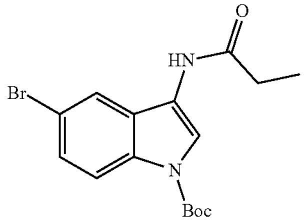 [SMILES: CCC(=O)Nc1cn(C(=O)OC(C)(C)C)c2ccc(Br)cc12] | Method A: MS-ESI: 367 $[M + H]^+$ |
| Intermediate 5 | 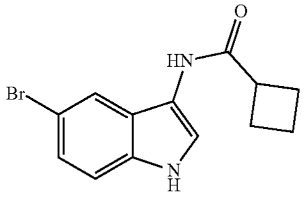 [SMILES: O=C(Nc1c[nH]c2ccc(Br)cc12)C1CCC1] | Method A: MS-ESI: 293 $[M + H]^+$ |
| Intermediate 6 | 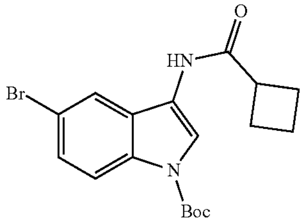 [SMILES: CC(C)(C)OC(=O)n1cc(NC(=O)C2CCC2)c2cc(Br)ccc21] | Method A: MS-ESI: 393 $[M + H]^+$ |

Scheme 2: Synthesis of intermediate 7 (N-(5-hydroxy-1H-indol-3-yl)acetamide

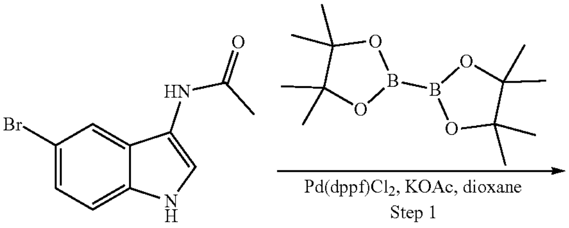

Intermediate 1

-continued

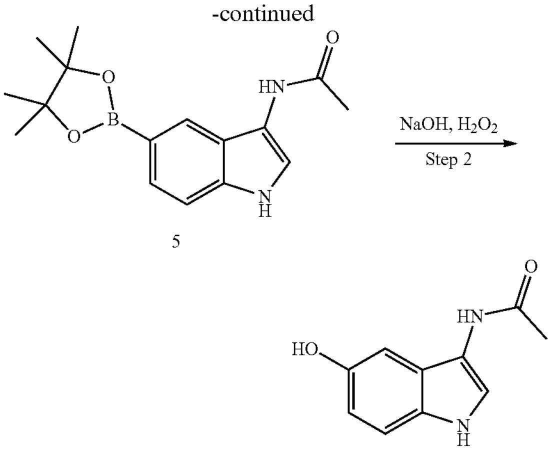

5

Intermediate 7

Step 1: N-(5-(4,4,5,5-tetramethyl-1,3,2-dioxaborolan-2-yl)-1H-indol-3-yl)acetamide N-(5-bromo-1H-indol-3-yl)acetamide (10.0 g, 39.5 mmol, 1.0 equiv.) was dissolved in 1,4-dioxane (100 mL), then 4,4,4',4',5,5,5',5'-octamethyl-2,2'-bi(1,3,2-dioxaborolane) (20.1 g, 79.0 mmol, 2.0 equiv.), KOAc (7.7 g, 79.0 mmol, 2.0 equiv.) and Pd(dppf)$Cl_2$·$CH_2Cl_2$ (2.8 g, 3.9 mmol, 0.1 equiv.) were added under an atmosphere of nitrogen. The reaction mixture was heated to 100° C. for 6 hours, then cooled to ambient temperature and quenched by the addition of water. The resulting solution was extracted with ethyl acetate, washed with brine, dried over anhydrous $Na_2SO_4$ and concentrated under vacuum. The residue was purified by flash column chromatography on silica gel, eluting with dichloromethane/methanol (20:1) to give N-(5-(4,4,5,5-tetramethyl-1,3,2-dioxaborolan-2-yl)-1H-indol-3-yl)acetamide (9.1 g) as a brown solid. LCMS Method A: $[M+H]^+$ =301.

Step 2: N-(5-hydroxy-1H-indol-3-yl)acetamide

N-(5-(4,4,5,5-tetramethyl-1,3,2-dioxaborolan-2-yl)-1H-indol-3-yl)acetamide (6.5 g, 21.6 mmol, 1.0 equiv.) was dissolved in THE (50 mL) and water (50 mL), then NaOH (1.7 g, 42.5 mmol, 2.0 equiv.) was added. This was followed by the addition of $H_2O_2$ (30% wt. in water, 28.0 mL, 420.0 mmol, 20.0 equiv.) dropwise at 0° C. The reaction mixture was stirred for 2 hours at ambient temperature, then quenched by the addition of saturated aqueous $NH_4Cl$. The resulting solution was extracted with ethyl acetate, washed with brine and concentrated under vacuum. The residue was purified by flash column chromatography on silica gel, eluting with dichloromethane/methanol (10:1) to give N-(5-hydroxy-1H-indol-3-yl)acetamide (2.5 g) as a grey solid. LCMS Method A: $[M+H]^+$=191.

The intermediates in the following table were prepared using the same method described for Intermediate 7.

| Intermediate | Starting material | Structure | LCMS data |
|---|---|---|---|
| Intermediate 8 | 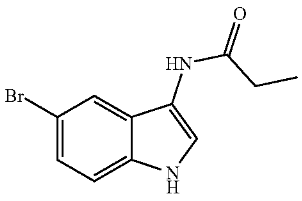 Intermediate 3 | 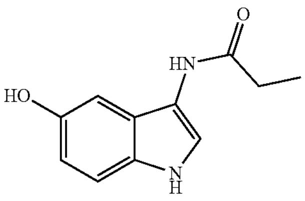 | Method A: MS-ESI: 205 $[M + H]^+$ |
| Intermediate 9 | 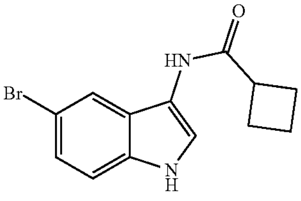 Intermediate 5 | 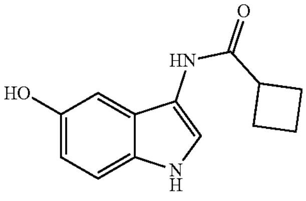 [SMILES: O=C(Nc1c[nH]c2ccc(O)cc12)C1CCC1] | Method A: MS-ESI: 231 $[M + H]^+$ |

Scheme 3: Synthesis of intermediate 10 (tert-butyl 3-acetamido-5-hydroxy-1H-indole-1-carboxylate)

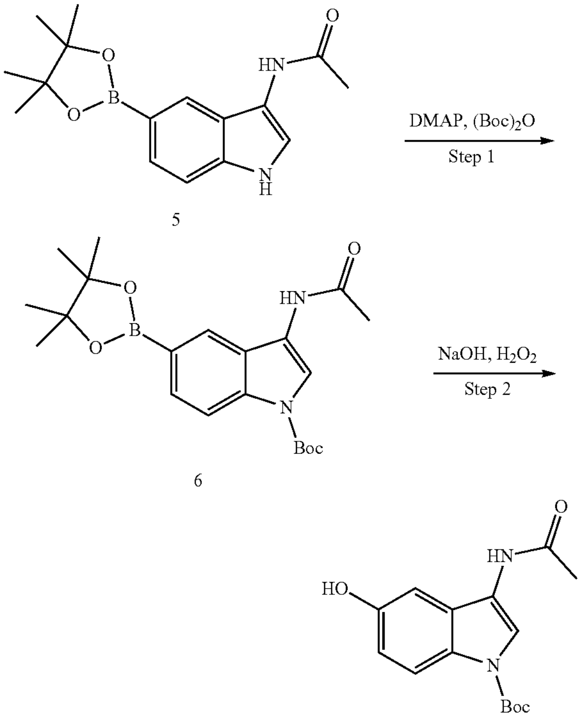

5

6

Intermediate 10

Step 1: tert-butyl 3-acetamido-5-(4,4,5,5-tetramethyl-1,3,2-dioxaborolan-2-yl)indole-1-carboxylate N-[5-(4,4,5,5-tetramethyl-1,3,2-dioxaborolan-2-yl)-1H-indol-3-yl]acetamide (1.0 g, 3.3 mmol, 1.0 equiv.) and $Boc_2O$ (872.5 mg, 4.0 mmol, 1.2 equiv.) were dissolved in THF, then TEA (0.9 mL, 6.7 mmol, 2.0 equiv.) and DMAP (40.7 mg, 0.3 mmol, 0.1 equiv.) were added. The reaction mixture was stirred overnight at ambient temperature, then quenched by the addition of water. The resulting solution was extracted with ethyl acetate, washed with brine, dried over anhydrous $Na_2SO_4$ and concentrated under vacuum. The residue was purified by flash column chromatography on silica gel, eluting with ethyl acetate/petroleum ether (1:7) to give tert-butyl 3-acetamido-5-(4,4,5,5-tetramethyl-1,3,2-dioxaborolan-2-yl)indole-1-carboxylate (907.5 mg) as a yellow solid. LCMS Method B: $[M+H]^+$=401.

Step 2: tert-butyl 3-acetamido-5-hydroxyindole-1-carboxylate tert-Butyl 3-acetamido-5-(4,4,5,5-tetramethyl-1,3,2-dioxaborolan-2-yl)indole-1-carboxylate (1.0 g, 2.5 mmol, 1.0 equiv.) was dissolved in THE (10 mL), then aqueous NaOH (2% wt., 10 mL, 5.0 mmol, 2.0 equiv.) and $H_2O_2$ (30% wt., 2.6 mL, 25.0 mmol, 10.0 equiv.) were added. The reaction mixture was stirred for 2 hours at ambient temperature and then quenched by the addition of water. The resulting solution was adjusted to pH 6 with saturated aqueous $NH_4HCO_3$, then extracted with ethyl acetate and the combined organic layers were concentrated under vacuum. The residue was purified by flash column chromatography on silica gel, eluting with dichloromethane/methanol (20:1) to give tert-butyl 3-acetamido-5-hydroxyindole-1-carboxylate (690.0 mg) as a grey solid. LCMS Method B: $[M+H]^+$=291.

Scheme 4: Synthesis of intermediate 11 (tert-butyl 3-acetamdio-5-(2-hydroxyethyl)-1H-indole-1-carboxylate)

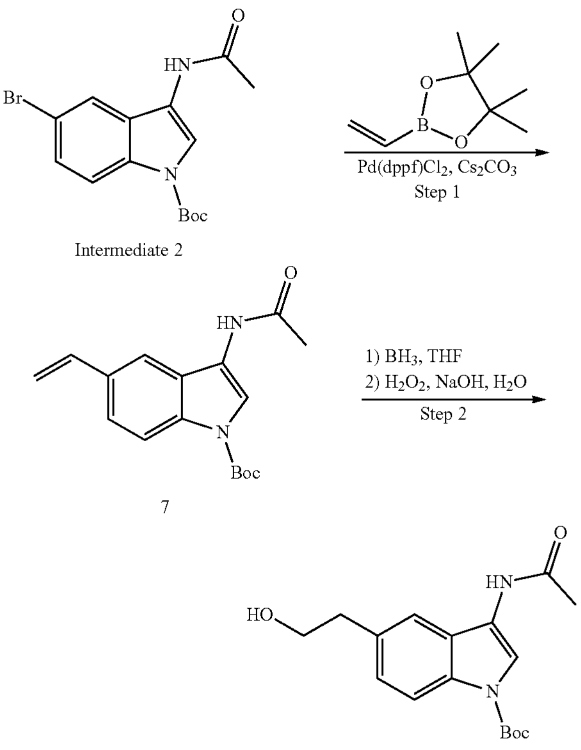

Intermediate 2

7

Intermediate 11

Step 1: tert-butyl 3-acetamido-5-ethenylindole-1-carboxylate tert-Butyl 5-bromo-3-acetamidoindole-1-carboxylate (660.0 mg, 1.9 mmol, 1.0 equiv.) was dissolved in 1,4-dioxane (4 mL) and water (1 mL), then 2-ethenyl-4,4,5,5-tetramethyl-1,3,2-dioxaborolane (575.6 mg, 3.7 mmol, 2.0 equiv.), $Cs_2CO_3$ (1.2 g, 3.7 mmol, 2.0 equiv.) and Pd(dppf)$Cl_2$ (273.4 mg, 0.4 mmol, 0.2 equiv.) were added under an atmosphere of nitrogen. The reaction mixture was heated to 85° C. for 4 hours, then cooled to ambient temperature and concentrated under vacuum. The residue was purified by flash column chromatography on silica gel, eluting with ethyl acetate/petroleum ether (1:4) to give tert-butyl 3-acetamido-5-ethenylindole-1-carboxylate (400.0 mg %) as a pale yellow solid. LCMS Method C: $[M+H]^+$=301.

Step 2: tert-butyl 3-acetamido-5-(2-hydroxyethyl)-1H-indole-1-carboxylate tert-Butyl 3-acetamido-5-ethenylindole-1-carboxylate (500.0 mg, 1.7 mmol, 1.0 equiv.) was dissolved in THE (20 mL), then $BH_3$-THF (1 M, 2.5 mL, 2.5 mmol, 1.5 equiv.) was added dropwise. The reaction mixture was stirred for 40 min at ambient temperature. Then a solution of aqueous NaOH (1 M, 3.3 mL, 3.3 mmol, 2.0 equiv.) was added and the reaction mixture was cooled to 0° C. This was followed by the dropwise addition of $H_2O_2$ (30% wt. in water, 1.3 mL, 3.3 mmol, 2.0 equiv.), maintaining the reaction mixture at 0° C. The reaction mixture was stirred for additional 30 min at 0° C., then quenched by the addition of saturated aqueous $NH_4Cl$. The resulting solution was extracted with ethyl acetate, washed with brine, dried over anhydrous $Na_2SO_4$ and concentrated under vacuum. The residue was purified by flash column chromatography on silica gel, eluting with dichloromethane/methanol (12:1) to give tert-butyl 3-acetamido-5-(2-hydroxyethyl) indole-1-carboxylate (300.0 mg) as a pale yellow solid. LCMS Method A: $[M+H]^+$=319.

The intermediate in the following table was prepared using the same method described for Intermediate 11.

| Intermediate | Starting material | Structure | LCMS data |
|---|---|---|---|
| Intermediate 12 | 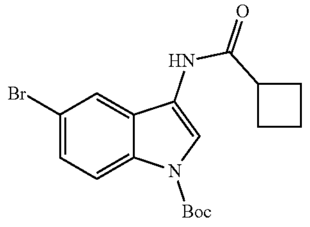 Intermediate 6 | 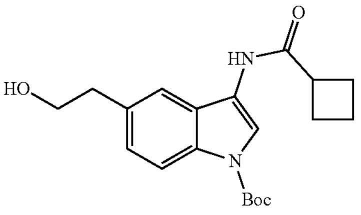 [SMILES: CC(C)(C)OC(=O)n1cc(NC(=O)C2CCC2)c2cc(CCO)ccc21] | Method A: MS-ESI: 359 $[M + H]^+$ |

Scheme 5: Synthesis of intermediate 13 (tert-butyl 3-acetamido-5-(hydroxymethyl)-1H-indole-1-carboxylate)

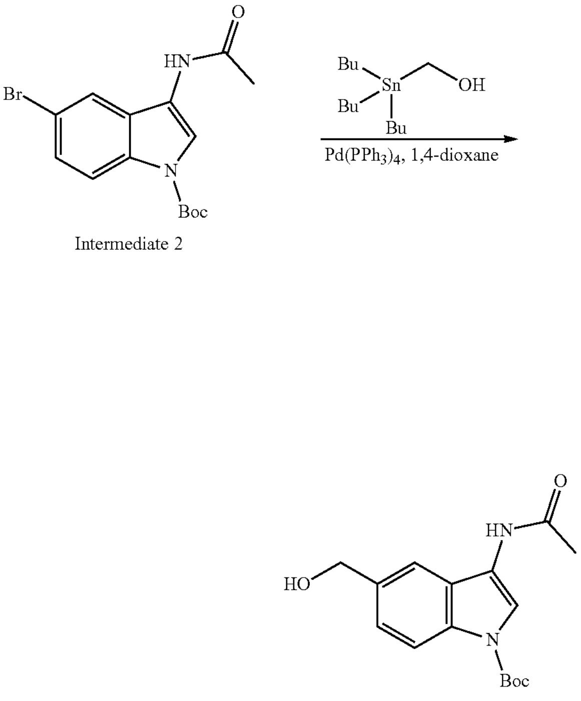

Intermediate 2

Intermediate 13 tert-Butyl 5-bromo-3-acetamidoindole-1-carboxylate (500.0 mg, 1.4 mmol, 1.0 equiv.) was dissolved in 1,4-dioxane (5 mL), then (tributylstannyl)methanol (909.1 mg, 2.8 mmol, 2.0 equiv.) and $Pd(PPh_3)_4$ (327.2 mg, 0.3 mmol, 0.2 equiv.) were added under an atmosphere of nitrogen. The reaction mixture was heated to 85° C. for 4 hours, then cooled to ambient temperature and concentrated under vacuum. The residue was purified by flash column chromatography on silica gel, eluting with ethyl acetate/petroleum ether (1:5) to give tert-butyl 3-acetamido-5-(hydroxymethyl)indole-1-carboxylate (262.5 mg) as a pale yellow solid. LCMS Method C: $[M+H]^+$=305.

The intermediate in the following table was prepared using the same method described for Intermediate 13.

| Intermediate | Starting material | Structure | LCMS data |
|---|---|---|---|
| Intermediate 14 | 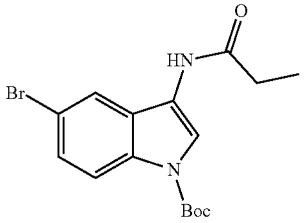 Intermediate 4 | 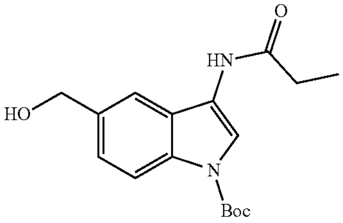 [SMILES: CCC(=O)Nc1cn(C(=O)OC(C)(C)C)c2ccc(CO)cc12] | Method C: MS-ESI: 319 [M + H]$^+$ |

Scheme 6: Synthesis of intermediate 15 (tert-butyl 3-acetamido-5-(2-oxoethyl)-1H-indole-1-carboxylate)

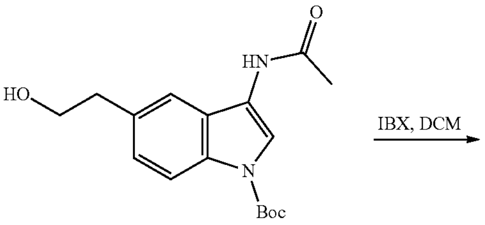

Intermediate 11

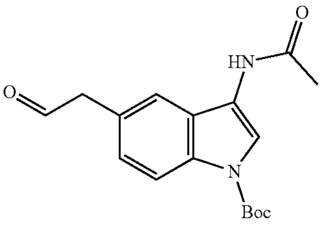

Intermediate 15

Scheme 7: Synthesis of intermediate 17 (tert-butyl 3-acetamido-5-formyl-1H-indole-1-carboxylate)

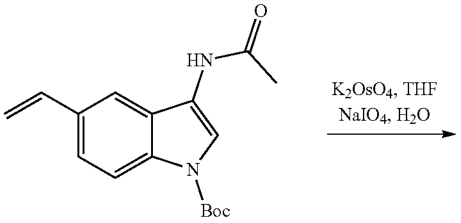

7

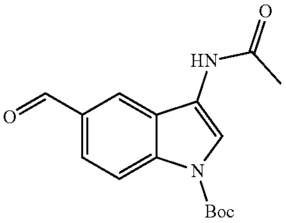

Intermediate 17 tert-Butyl 3-acetamido-5-(2-hydroxyethyl)indole-1-carboxylate (320.0 mg, 1.0 mmol, 1.0 equiv.) was dissolved in DCM (25 mL), then IBX (562.9 mg, 2.0 mmol, 2.0 equiv.) was added. The reaction mixture was heated to 50° C. for 3 hours, the cooled to ambient temperature and the solids were removed by filtration. The filtrate was concentrated under vacuum to give tert-butyl 3-acetamido-5-(2-oxoethyl)indole-1-carboxylate (311.2 mg) as a pale yellow solid. LCMS Method A: $[M+H]^+=317$.

The intermediate in the following table was prepared using the same method described for Intermediate 15.

tert-Butyl 3-acetamido-5-ethenylindole-1-carboxylate (400.0 mg, 1.3 mmol, 1.0 equiv.) was dissolved in THE (15 mL) and water (15 mL), then $K_2O_sO_4.2H_2O$ (98.1 mg, 0.3 mmol, 0.2 equiv.) and $NaIO_4$ (1.1 g, 5.3 mmol, 4.0 equiv.) were added. The reaction mixture was stirred for 2 hours at ambient temperature and then diluted with water. The resulting solution was extracted with ethyl acetate, washed with brine, dried over anhydrous $Na_2SO_4$ and concentrated under vacuum to give tert-butyl 3-acetamido-5-formylindole-1-carboxylate (350.0 mg) as a dark yellow solid. LCMS Method B: $[M+H]^+=303$.

| Intermediate | Starting material | Structure | LCMS data |
|---|---|---|---|
| Intermediate 16 | 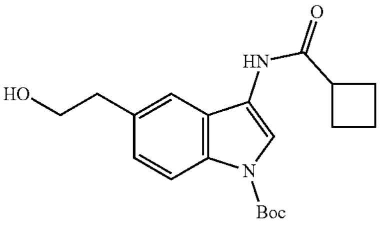 Intermediate 12 | 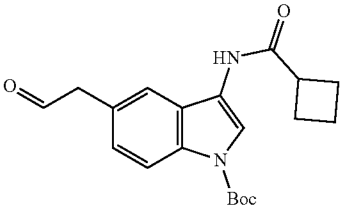 [SMILES: CC(C)(C)OC(=O)n1cc(NC(=O)C2CCC2)c2cc(CC=O)ccc21] | Method A: MS-ESI: 357 [M + H]$^+$ |

Scheme 8: Synthesis of intermediate 18 (2-fluoro-2-(1-(2,2,2-trifluoroethyl)piperidin-4-yl)ethan-1-ol)

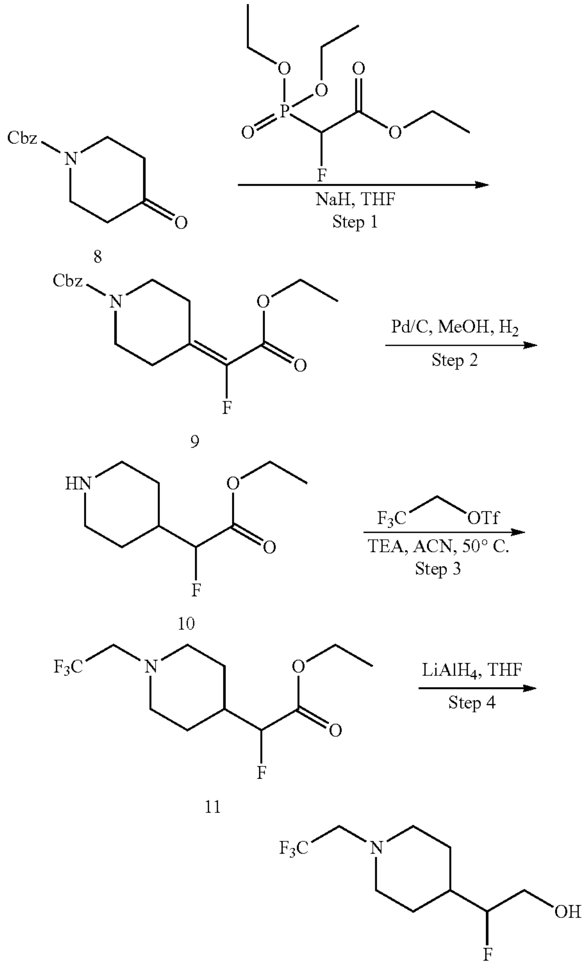

8

9

10

11

Intermediate 18

Step 1: benzyl 4-(2-ethoxy-1-fluoro-2-oxoethylidene)piperidine-1-carboxylate

Ethyl 2-(diethoxyphosphoryl)-2-fluoroacetate (1.6 g, 6.4 mmol, 1.5 equiv.) was dissolved in THE (20 mL) and cooled to 0° C., then NaH (60% wt., 342.9 mg, 8.6 mmol, 2.0 equiv.) was added, maintaining the reaction mixture at 0° C. The reaction mixture was stirred for 30 min at ambient temperature. This was followed by the dropwise addition of benzyl 4-oxopiperidine-1-carboxylate (1.0 g, 4.3 mmol, 1.0 equiv.) at 0° C. The resulting mixture was stirred for an additional 2 hours at ambient temperature, then quenched by the addition of water. The resulting solution was extracted with ethyl acetate, washed with brine, dried over anhydrous $Na_2SO_4$ and concentrated under vacuum. The residue was purified by flash column chromatography on silica gel, eluting with ethyl acetate/petroleum ether (1:1) to give benzyl 4-(2-ethoxy-1-fluoro-2-oxoethylidene)piperidine-1-carboxylate (1.2 g) as a colorless oil. LCMS Method A: $[M+H]^+$=322.

Step 2: ethyl 2-fluoro-2-(piperidin-4-yl)acetate

Benzyl 4-(2-ethoxy-1-fluoro-2-oxoethylidene)piperidine-1-carboxylate (1.2 g, 3.7 mmol, 1.0 equiv.) was dissolved in MeOH (20 mL), then Pd/C (120.0 mg, 10% wt.) was added under an atmosphere of nitrogen. The mixture was sparged with nitrogen, placed under an atmosphere of hydrogen gas (balloon), then stirred for 2 hours at ambient temperature. The solids were removed by filtration and the filtrate was concentrated under vacuum. The residue was purified by flash column chromatography on silica gel, eluting with ethyl acetate/petroleum ether (1:1) to give ethyl 2-fluoro-2-(piperidin-4-yl)acetate (650.0 mg) as a colorless oil. LCMS Method A: $[M+H]^+$=190.

Step 3: ethyl 2-fluoro-2-(1-(2,2,2-trifluoroethyl)piperidin-4-yl)acetate

Ethyl 2-fluoro-2-(piperidin-4-yl)acetate (1.0 g, 5.3 mmol, 1.0 equiv.) and TEA (1.5 mL, 10.6 mmol, 2.0 equiv.) were dissolved in ACN (20 mL), then 2,2,2-trifluoroethyl trifluoromethanesulfonate (1.8 g, 7.9 mmol, 1.5 equiv.) was added. The reaction mixture was stirred for 4 hours at ambient temperature and then concentrated under vacuum. The residue was purified by flash column chromatography on silica gel, eluting with ethyl acetate/petroleum ether (1:1) to give ethyl 2-fluoro-2-(1-(2,2,2-trifluoroethyl)piperidin-4-yl)acetate (820.0 mg) as a colorless oil. LCMS Method A: $[M+H]^+$=272.

Step 4: 2-fluoro-2-(1-(2,2,2-trifluoroethyl)piperidin-4-yl)ethan-1-ol

Ethyl 2-fluoro-2-(1-(2,2,2-trifluoroethyl)piperidin-4-yl) acetate (400.0 mg, 1.5 mmol, 1.0 equiv.) was dissolved in THE (15 mL) and cooled to 0° C., then $LiAlH_4$ (111.9 mg, 2.9 mmol, 2.0 equiv.) was added, maintaining the solution at 0° C. The reaction mixture was stirred for 2 hours at ambient temperature and then quenched by the addition of $Na_2SO_4.10H_2O$. The solid was removed by filtration, then the filtrate was concentrated under vacuum. The residue was purified by flash column chromatography on silica gel, eluting with ethyl acetate/petroleum ether (1:2) to give 2-fluoro-2-(1-(2,2,2-trifluoroethyl)piperidin-4-yl)ethan-1-ol (310.0 mg) as a colorless oil. LCMS Method A: $[M+H]^+$=230.

Scheme 9: Synthesis of intermediate 19 (2-(1-(4-(trifluoromethyl)phenyl)piperidin-4-yl)ethan-1-ol)

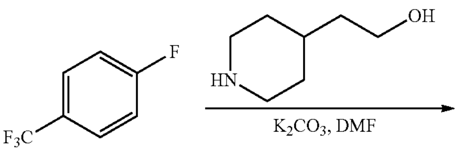

12

-continued

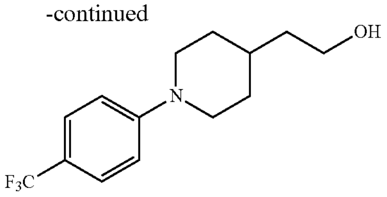

Intermediate 19

1-Fluoro-4-(trifluoromethyl)benzene (500.0 mg, 3.0 mmol, 1.0 equiv.) was dissolved in DMF (10 mL), then $K_2CO_3$ (842.1 mg, 6.0 mmol, 2.0 equiv.) and 4-piperidineethanol (393.6 mg, 3.0 mmol, 1.0 equiv.) were added. The reaction mixture was heated to 120° C. overnight, then cooled to ambient temperature and quenched by the addition of aqueous HCl (2N). The resulting solution was extracted with ethyl acetate, washed with brine, dried over anhydrous $Na_2SO_4$ and concentrated under vacuum. The residue was purified by flash column chromatography on silica gel, eluting with ethyl acetate/petroleum ether (1:1) to give 2-[1-[4-(trifluoromethyl)phenyl]piperidin-4-yl]ethanol (280.0 mg) as a pale yellow solid. LCMS Method A: $[M+H]^+$=274.

The intermediates in the following table were prepared using the same method described for Intermediate 19.

Scheme 10: Synthesis of intermediate 23 (2-methyl-2-(1-(2,2,2-trifluoroethyl)piperidin-4-yl)propan-1-ol)

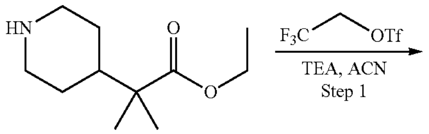

13

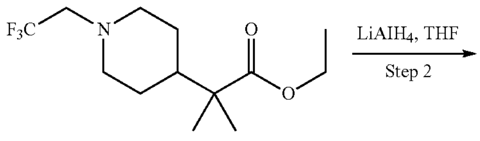

14

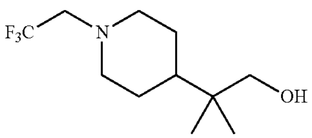

Intermediate 23

| Intermediate | Starting material A | Starting material B | Structure | LCMS data |
|---|---|---|---|---|
| Intermediate 20 | 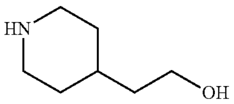 | 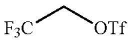 | 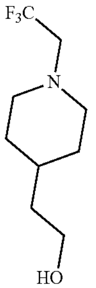 [SMILES: OCCC1CCN(CC(F)(F)F)CC1] | Method A: MS-ESI: 212 $[M + H]^+$ |
| Intermediate 21 | 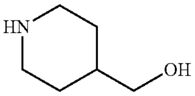 | 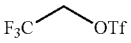 | 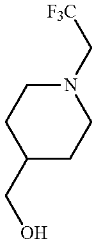 [SMILES: OCC1CCN(CC(F)(F)F)CC1] | Method A: MS-ESI: 198 $[M + H]^+$ |
| Intermediate 22 | 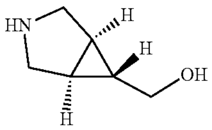 | 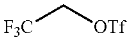 | 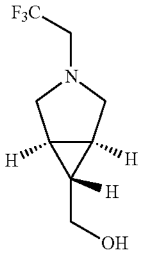 [SMILES: OC[C@@H]1[C@H]2CN(CC(F)(F)F)C[C@@H]12] | Method A: MS-ESI: 196 $[M + H]^+$ |

Step 1: ethyl 2-methyl-2-[1-(2,2,2-trifluoroethyl)piperidin-4-yl]propanoate

Ethyl 2-methyl-2-(piperidin-4-yl)propanoate (500.0 mg, 2.5 mmol, 1.0 equiv.) and TEA (0.5 mL, 3.8 mmol, 1.5 equiv.) were dissolved in ACN (25 mL), then 2,2,2-trifluoroethyl trifluoromethanesulfonate (873.5 mg, 3.8 mmol, 1.5 equiv.) was added. The reaction mixture was heated to 65° C. for 6 hours, then cooled to ambient temperature and concentrated under vacuum. The residue was purified by flash column chromatography on silica gel, eluting with ethyl acetate/petroleum ether (1:5) to give ethyl 2-methyl-2-[1-(2,2,2-trifluoroethyl)piperidin-4-yl]propanoate (205.5 mg) as a yellow oil. LCMS Method C: $[M+H]^+$=282.

Step 2: 2-methyl-2-[1-(2,2,2-trifluoroethyl)piperidin-4-yl]propan-1-ol

Ethyl 2-methyl-2-[1-(2,2,2-trifluoroethyl)piperidin-4-yl]propanoate (200.0 mg, 0.7 mmol, 1.0 equiv.) was dissolved in THF (100 mL) and cooled to 0° C. Then $LiAlH_4$ (40.5 mg, 1.1 mmol, 1.5 equiv.) was added. The reaction mixture was stirred for 2 hours at ambient temperature and then quenched by the addition of water. The solid was removed by filtration and the filtrate was concentrated under vacuum. The residue was purified by flash column chromatography on silica gel, eluting with ethyl acetate/petroleum ether (1:5) to give 2-methyl-2-[1-(2,2,2-trifluoroethyl)piperidin-4-yl]propan-1-ol (21.3 mg) as a yellow oil. LCMS Method C: $[M+H]^+$=240.

Scheme 11: Synthesis of intermediate 24 (2-((1R,5S,6s)-3-(2,2,2-trifluoroethyl)-3-azabicyclo[3.1.0]hexan-6-yl)ethan-1-ol)

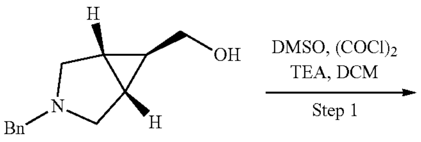

15

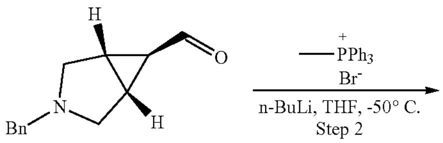

16

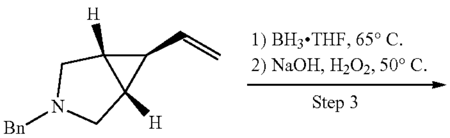

17

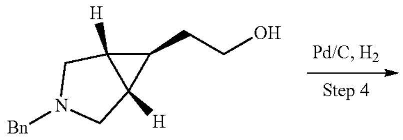

18

-continued

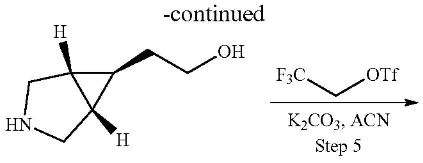

19

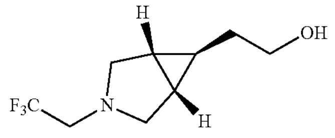

Intermediate 24

Step 1: (1R,5S,6S)-3-benzyl-3-azabicyclo[3.1.0]hexane-6-carbaldehyde

Oxalyl chloride (1.0 mL, 12.3 mmol, 2.5 equiv.) was dissolved in DCM (30 mL) and cooled to −78° C., then DMSO (1.7 mL, 24.6 mmol, 5.0 equiv.) was added dropwise. The reaction mixture was stirred for 1 hour at −78° C. under an atmosphere of nitrogen. This was followed by the dropwise addition of a solution of [(1R,5S,6S)-3-benzyl-3-azabicyclo[3.1.0]hexan-6-yl]methanol (1.0 g, 4.9 mmol, 1.0 equiv.) in DCM (20 mL), maintaining the solution at −78° C. The reaction mixture was stirred for an additional 2 hours at −78° C., then TEA (6.9 mL, 49.2 mmol, 10.0 equiv.) was added dropwise and the resulting solution was stirred for another 4 hours at ambient temperature. The reaction was quenched by the addition of water, extracted with ethyl acetate, washed with brine, dried over anhydrous $Na_2SO_4$ and concentrated under vacuum to give (1R,5S,6S)-3-benzyl-3-azabicyclo[3.1.0]hexane-6-carbaldehyde (980.0 mg) as a pale yellow liquid. LCMS Method A: $[M+H]^+$=202.

Step 2: (1R,5S,6S)-3-benzyl-6-ethenyl-3-azabicyclo[3.1.0]hexane

Methyltriphenylphosphonium bromide (2.0 g, 5.7 mmol, 1.5 equiv.) was dissolved in THF (20 mL) and cooled to −50° C., then n-BuLi (3M in THF, 1.9 mL, 5.7 mmol, 1.5 equiv.) was added dropwise under an atmosphere of nitrogen, maintaining the solution at −50° C. After 30 min at −50° C., a solution of (1R,5S,6S)-3-benzyl-3-azabicyclo[3.1.0]hexane-6-carbaldehyde (760.0 mg, 3.8 mmol, 1.0 equiv.) in THE (5 mL) was added dropwise. The resulting mixture was stirred for additional 4 hours at ambient temperature and then quenched by the addition of saturated aqueous $NH_4Cl$. The resulting solution was extracted with ethyl acetate, washed with brine, dried over anhydrous $Na_2SO_4$ and concentrated under vacuum. The residue was purified by flash column chromatography on silica gel, eluting with ethyl acetate/petroleum ether (1:5) to give (1R,5S,6S)-3-benzyl-6-ethenyl-3-azabicyclo[3.1.0]hexane (480.0 mg) as a pale yellow oil. LCMS Method A: $[M+H]^+$=200.

Step 3: 2-[(1R,5S,6S)-3-benzyl-3-azabicyclo[3.1.0]hexan-6-yl]ethanol (1R,5S,6S)-3-benzyl-6-ethenyl-3-azabicyclo[3.1.0]hexane (480.0 mg, 2.4 mmol, 1.0 equiv.) was dissolved in THE (20 mL), then $BH_3$—$SMe_2$ (0.80 mL, 2.4 mmol, 1.0 equiv.) was added dropwise. The reaction mixture was stirred for 1 hour at 65° C., then cooled down to 0° C. Then a solution of NaOH (578.0 mg, 14.4 mmol, 6.0 equiv.) in $H_2O$ (2 mL) was added, followed by the dropwise addition of $H_2O_2$ (30% aqueous, 1.5 mL, 14.4 mmol, 6.0 equiv.). The resulting mixture was heated to 50° C. overnight, then cooled to ambient temperature and quenched by the addition of saturated aqueous $NH_4Cl$. The resulting solution was extracted with ethyl acetate, washed with brine, dried over anhydrous $Na_2SO_4$ and concentrated under vacuum. The residue was purified by flash column chromatography on silica gel, eluting with ethyl acetate/petroleum ether (1:1) to give 2-[(1R,5S,6S)-3-benzyl-3-azabicyclo[3.1.0]hexan-6-yl]ethanol (510.0 mg) as a pale yellow oil. LCMS Method A: $[M+H]^+$=218.

Step 4: 2-[(1R,5S,6S)-3-azabicyclo[3.1.0]hexan-6-yl]ethanol

2-[(1R,5S,6S)-3-benzyl-3-azabicyclo[3.1.0]hexan-6-yl]ethanol (450.0 mg, 2.1 mmol, 1.0 equiv.) was dissolved in MeOH (20 mL), then Pd/C (10% wt., 44.1 mg) was added. The mixture was sparged with nitrogen, placed under an atmosphere of hydrogen gas (balloon), then stirred for 6 hours at 45° C. The solids were removed by filtration and the filtrate was concentrated under vacuum to give 2-[(1R,5S,6S)-3-azabicyclo[3.1.0]hexan-6-yl]ethanol (250.0 mg) as a pale yellow oil. LCMS Method A: $[M+H]^+$=128.

Step 5: 2-[(1R,5S,6S)-3-(2,2,2-trifluoroethyl)-3-azabicyclo[3.1.0]hexan-6-yl]ethanol 2-[(1R,5S,6S)-3-azabicyclo[3.1.0]hexan-6-yl]ethanol (250.0 mg, 2.0 mmol, 1.0 equiv.) was dissolved in ACN (5 mL) and cooled to 0° C., then $K_2CO_3$ (543.3 mg, 3.9 mmol, 2.0 equiv.) and 2,2,2-trifluoroethyl trifluoromethanesulfonate (684.3 mg, 2.9 mmol, 1.5 equiv.) were added. The reaction mixture was heated to 80° C. for 50 min, the cooled to ambient temperature and quenched by the addition of water. The resulting solution was extracted with ethyl acetate, washed with brine, dried over anhydrous $Na_2SO_4$ and concentrated under vacuum. The residue was purified by flash column chromatography on silica gel, eluting with ethyl acetate/petroleum ether (1:1) to give 2-[(1R,5S,6S)-3-(2,2,2-trifluoroethyl)-3-azabicyclo[3.1.0]hexan-6-yl]ethanol (260.0 mg) as a pale yellow oil. LCMS Method A: $[M+H]^+$=210.

Scheme 12: Synthesis of intermediates 25/26 (cis-3-(4-(trifluoromethyl)phenyl)cyclobutan-1-ol and trans-3-(4-(trifluoromethyl)phenyl)cyclobutan-1-ol)

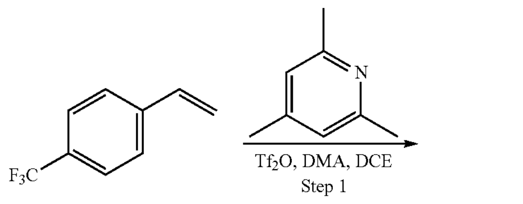

21

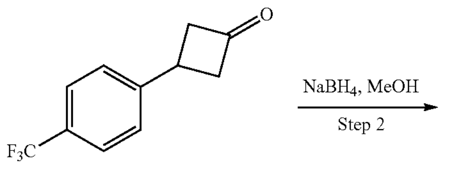

22

-continued

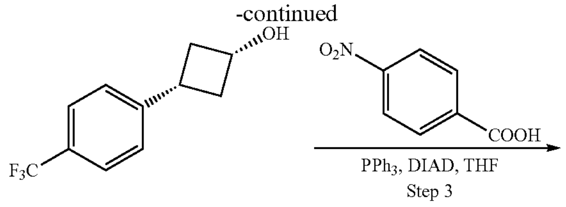

Intermediate 25

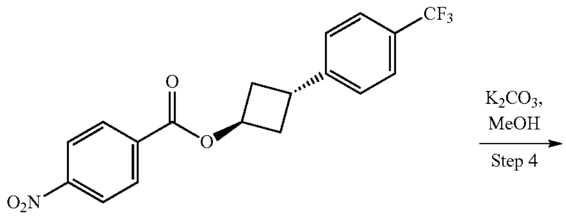

23

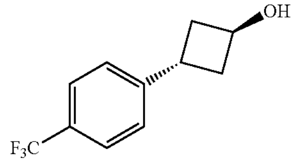

Intermediate 26

Step 1: 3-[4-(trifluoromethyl)phenyl]cyclobutan-1-one

DMA (1.3 mL, 13.9 mmol, 1.2 equiv.) was dissolved in DCE (30 mL) and cooled to 5° C., then $Tf_2O$ (2.7 mL, 16.3 mmol, 1.4 equiv.) was added dropwise, maintaining the solution at 5° C. The reaction mixture was stirred for 30 min at 5° C. This was followed by the addition of a solution of 1-ethenyl-4-(trifluoromethyl) benzene (840.0 mg, 4.9 mmol, 1.0 equiv.) and 2,4,6-collidine (2.0 g, 16.3 mmol, 1.4 equiv.) in DCE (10 mL) dropwise at 5° C. The resulting mixture was heated to 80° C. overnight, then cooled to ambient temperature and concentrated under vacuum. The residue was diluted with water, extracted with ethyl acetate, washed with brine, dried over anhydrous $Na_2SO_4$ and concentrated under vacuum. The residue was purified by flash column chromatography on silica gel, eluting with ethyl acetate/petroleum ether (1:7) to give 3-[4-(trifluoromethyl)phenyl]cyclobutan-1-one (450.0 mg) as a pale yellow oil. $^1H$ NMR (400 MHz, Chloroform-d) δ 7.64 (d, J=8.0 Hz, 2H), 7.45 (d, J=8.0 Hz, 2H), 3.79-3.75 (m, 1H), 3.63-3.50 (m, 2H), 3.34-3.23 (m, 2H).

Step 2: cis-3-[4-(trifluoromethyl)phenyl]cyclobutan-1-ol

3-[4-(Trifluoromethyl)phenyl]cyclobutan-1-one (300.0 mg, 1.4 mmol, 1.0 equiv.) was dissolved in MeOH (15 mL) and cooled to −10° C., then $NaBH_4$ (106.0 mg, 2.8 mmol, 2.0 equiv.) was added, maintaining the solution at −10° C. The reaction mixture was stirred for 50 min at −10° C. under an atmosphere of nitrogen and then quenched by the addition of ice-water. The resulting solution was extracted with ethyl acetate, washed with brine, dried over anhydrous $Na_2SO_4$ and concentrated under vacuum to give cis-3-[4-(trifluoromethyl)phenyl]cyclobutan-1-ol (260.0 mg) as a pale yellow oil. LCMS Method A: $[M+H]^+$=217.

Step 3: trans-3-[4-(trifluoromethyl)phenyl]cyclobutyl 4-nitrobenzoate

Cis-3-[4-(trifluoromethyl)phenyl]cyclobutan-1-ol (130.0 mg, 0.6 mmol, 1.0 equiv.) was dissolved in THE (2 mL), then p-nitrobenzoic acid (100.5 mg, 0.6 mmol, 1.0 equiv.), $PPh_3$ (315.4 mg, 1.2 mmol, 2.0 equiv.) and DIAD (243.2 mg, 1.2 mmol, 2.0 equiv.) were added. The reaction mixture was stirred for 4 hours at ambient temperature, then concentrated under vacuum. The residue was purified by flash column chromatography on silica gel, eluting with ethyl acetate/petroleum ether (1:6) to give trans-3-[4-(trifluoromethyl)phenyl]cyclobutyl 4-nitrobenzoate (160.0 mg) as a pale yellow solid. LCMS Method A: $[M+H]^+$=366.

Step 4: trans-3-[4-(trifluoromethyl)phenyl]cyclobutan-1-ol

Trans-3-[4-(trifluoromethyl)phenyl]cyclobutyl 4-nitrobenzoate (300.0 mg, 0.8 mmol, 1.0 equiv.) was dissolved in MeOH (4 mL) and water (1 mL), then $K_2CO_3$ (227.0 mg, 1.6 mmol, 2.0 equiv.) was added. The reaction mixture was heated to 65° C. for 2 hours, then cooled to ambient temperature and quenched by the addition of water. The resulting solution was extracted with ethyl acetate, washed with brine, dried over anhydrous $Na_2SO_4$ and concentrated under vacuum to give trans-3-[4-(trifluoromethyl)phenyl]cyclobutan-1-ol (155.2 mg) as a pale yellow oil. LCMS Method A: $[M+H]^+$=217.

Scheme 12A: Synthesis of intermediate 25 (cis-3-(4-(trifluoromethyl)phenyl)cyclobutan-1-ol)

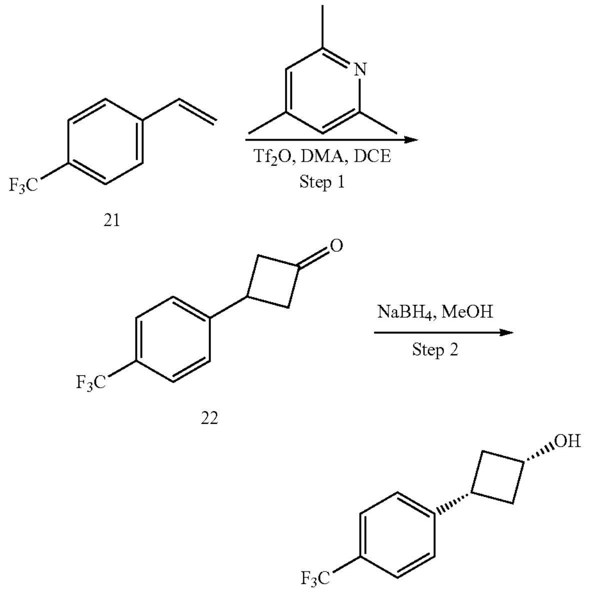

21

22 intermediate 25

Step 1: 3-[4-(trifluoromethyl)phenyl]cyclobutan-1-one

DMA (12.1 g, 138.9 mmol, 1.2 equiv.) was dissolved in DCE (400 mL) and cooled to 0° C., then $Tf_2O$ (46.0 g, 163.0 mmol, 1.4 equiv.) was added dropwise at 0-5° C., over the course of 30 min. The resulting mixture was stirred for 1 hour at 5° C., then 2,4,6-collidine (19.7 g, 162.5 mmol, 1.4 equiv.) and 1-ethenyl-4-(trifluoromethyl)benzene (20.0 g, 116.2 mmol, 1.0 equiv.) were added at 5° C. The resulting solution heated to 80° C. for 48 hours, then cooled to ambient temperature and concentrated under vacuum. The residue was diluted with 300 mL of water, extracted with ethyl acetate and concentrated under vacuum. The residue was purified by flash column chromatography on silica gel, eluting with ethyl acetate/petroleum ether (3:7) to give 3-(4-(trifluoromethyl)phenyl)cyclobutan-1-one (8.0 g) as a yellow oil. $^1H$ NMR (400 MHz, Chloroform-d) δ 7.64 (d, J=8.0 Hz, 2H), 7.45 (d, J=8.0 Hz, 2H), 3.79-3.75 (m, 1H), 3.63-3.50 (m, 2H), 3.34-3.23 (m, 2H).

Step 2: cis-3-[4-(trifluoromethyl)phenyl]cyclobutan-1-ol 3-(4-(trifluoromethyl)phenyl)cyclobutan-1-one (7.9 g, 36.9 mmol, 1.0 equiv.) was dissolved in MeOH (50 mL) and cooled to 0° C., then $NaBH_4$ (2.1 g, 55.3 mmol, 1.5 equiv.) was added in portions, while maintaining the reaction mixture at 0° C. The resulting mixture was stirred for 1 hour at 0° C., then quenched by the addition of ice-water. The resulting solution was extracted with ethyl acetate, dried over anhydrous $Na_2SO_4$ and concentrated under vacuum. The residue was purified by flash column chromatography on silica gel, eluting with DCM/MeOH (99:1) to afford cis-3-(4-(trifluoromethyl)phenyl)cyclobutan-1-ol (60.5 g) as a yellow oil. $^1H$ NMR (400 MHz, DMSO-$d_6$) δ 7.65 (d, J=8.4 Hz, 2H), 7.45 (d, J=8.0 Hz, 2H), 5.14 (d, J=7.2 Hz, 1H), 4.11-4.01 (m, 1H), 3.02-2.93 (m, 1H), 2.66-2.60 (m, 2H), 1.95-1.86 (m, 2H).

Scheme 13: Synthesis of intermediates 27 (2-(6-trifluoromethyl)pyridin-3-yl)ethyl 4-methylbenzenesulfonate)

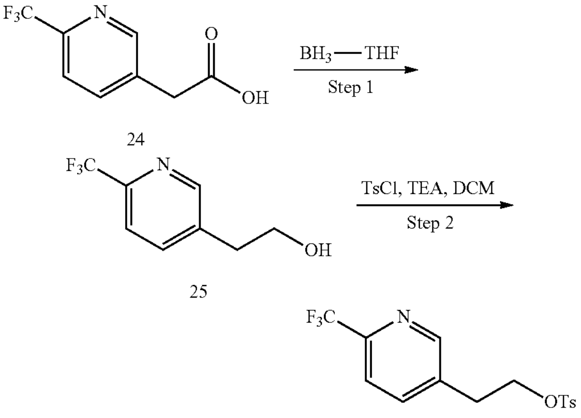

24

25

Intermediate 27

Step 1: 2-[6-(trifluoromethyl)pyridin-3-yl]ethanol

[6-(Trifluoromethyl)pyridin-3-yl]acetic acid (500.0 mg, 2.4 mmol, 1.0 equiv.) was dissolved in THF (30 mL) and cooled to 0° C. Then $BH_3$·THF (1 M, 4.9 mL, 4.9 mmol, 1.5 equiv.) was added, maintaining the solution at 0° C. The reaction mixture was stirred overnight at ambient temperature and the quenched by the addition of water. The resulting solution was extracted with ethyl acetate, washed with brine, dried over anhydrous $Na_2SO_4$ and concentrated under vacuum to give 2-[6-(trifluoromethyl)pyridin-3-yl]ethanol (330.0 mg) as a yellow oil. LCMS Method A: $[M+H]^+=192$.

Step 2: 2-[6-(trifluoromethyl)pyridin-3-yl]ethyl 4-methylbenzenesulfonate

2-[6-(Trifluoromethyl)pyridin-3-yl]ethanol (300.0 mg, 1.6 mmol, 1.0 equiv.) and TEA (1.1 mL, 7.8 mmol, 5.0 equiv.) were dissolved in DCM (3 mL), then TsCl (897.6 mg, 4.7 mmol, 3.0 equiv.) was added. The reaction mixture was stirred for 16 hours at ambient temperature and then quenched by the addition of water. The resulting solution was extracted with DCM, dried over anhydrous $Na_2SO_4$ and concentrated under vacuum. The residue was purified by flash column chromatography on silica gel, eluting with ethyl acetate/petroleum ether (1:1) to give 2-[6-(trifluoromethyl)pyridin-3-yl]ethyl 4-methylbenzenesulfonate (500.0 mg) as a yellow solid. LCMS Method A: $[M+H]^+=346$.

Scheme 14: Synthesis of intermediate 28 (3-(4,4-difluoropiperidin-1-yl)-2,2-difluoropropyl 4-methylbenzenesulfonate)

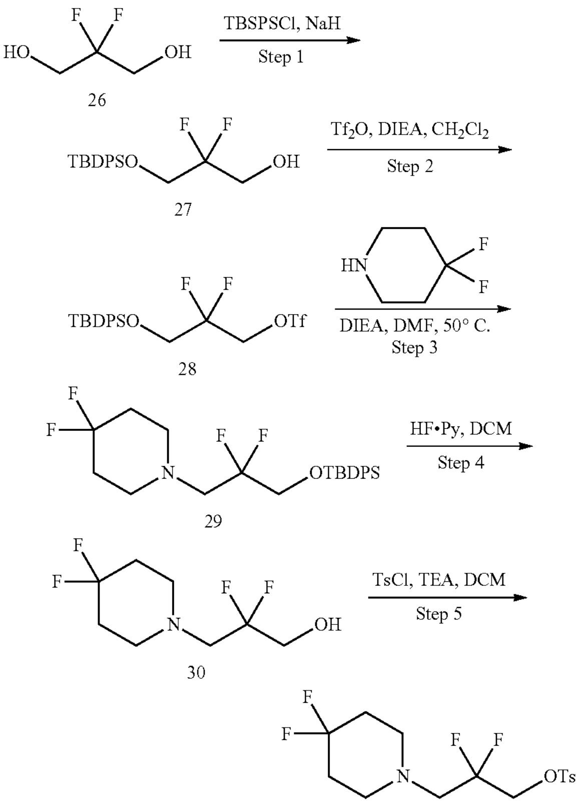

26

27

28

29

30

Intermediate 28

Step 1: 3-[(tert-butyldiphenylsilyl)oxy]-2,2-difluoro-propan-1-ol 2,2-Difluoropropane-1,3-diol (2.0 g, 17.8 mmol, 1.0 equiv.) was dissolved in THE (20.0 mL) and cooled to 0° C., then NaH (60% wt., 1.0 g, 26.7 mmol, 1.5 equiv.) was added, maintaining the solution at 0° C. After 2 hours at 0° C., TBDPSCl (9.8 g, 35.6 mmol, 2.0 equiv.) was added. The resulting mixture was stirred for an additional 2 hours at ambient temperature and then quenched by the addition of water. The resulting solution was extracted with ethyl acetate, washed with brine, dried over anhydrous $Na_2SO_4$ and concentrated under vacuum. The resulting mixture was concentrated under vacuum. The residue was purified by flash column chromatography on silica gel, eluting with ethyl acetate/petroleum ether (1:1) to give 3-[(tert-butyldiphenylsilyl)oxy]-2,2-difluoropropan-1-ol (5.1 g) as a yellow oil. LCMS Method C: $[M+H]^+=351$.

Step 2: 3-[(tert-butyldiphenylsilyl)oxy]-2,2-difluoro-propyl trifluoromethanesulfonate 3-[(tert-Butyldiphenylsilyl)oxy]-2,2-difluoropropan-1-ol (4.9 g, 14.0 mmol, 1.0 equiv.) was dissolved in DCE (20 mL) and cooled to −70° C., then DIEA (9.7 mL, 55.9 mmol, 4.0 equiv.) and trifluoromethanesulfonic anhydride (4.7 mL, 27.9 mmol, 2.0 equiv.) were added dropwise at −70° C. under an atmosphere of nitrogen. The reaction mixture was stirred for 2 hours at −20° C. and then concentrated under vacuum. The residue was purified by flash column chromatography on silica gel, eluting with ethyl acetate/petroleum ether (1:2) to give 3-[(tert-butyldiphenylsilyl)oxy]-2,2-difluoropropyl trifluoromethanesulfonate (5.2 g) as a yellow oil. LCMS Method A: $[M+H]^+=483$.

Step 3: 1-[3-[(tert-butyldiphenylsilyl)oxy]-2,2-difluoropropyl]-4,4-difluoropiperidine 3-[(tert-Butyldiphenylsilyl)oxy]-2,2-difluoropropyl trifluoromethanesulfonate (5.0 g, 10.3 mmol, 1.0 equiv.) was dissolved in DMF (20 mL), then 4,4-difluoropiperidine (1.5 g, 12.4 mmol, 1.2 equiv.) and DIEA (3.5 mL, 20.7 mmol, 2.0 equiv.) were added. The reaction mixture was heated to 50° C., then cooled to ambient temperature and quenched by the addition of water. The resulting solution was extracted with ethyl acetate, washed with brine, dried over anhydrous $Na_2SO_4$ and concentrated under vacuum. The residue was purified by flash column chromatography on silica gel, eluting with ethyl acetate/petroleum ether (1:1) to give 1-[3-[(tert-butyldiphenylsilyl)oxy]-2,2-difluoropropyl]-4,4-difluoropiperidine (3.8 g) as a yellow oil. LCMS Method A: $[M+H]^+=454$.

Step 4: 3-(4,4-difluoropiperidin-1-yl)-2,2-difluoro-propan-1-ol

1-[3-[(tert-Butyldiphenylsilyl)oxy]-2,2-difluoropropyl]-4,4-difluoropiperidine (3.6 g, 7.9 mmol, 1.0 equiv.) was dissolved in DCM (10 mL), then HF·Py (70% wt., 1.1 mL, 31.7 mmol, 4.0 equiv.) was added. The reaction mixture was stirred for 12 hours at ambient temperature and concentrated under vacuum. The residue was purified by flash column chromatography on silica gel, eluting with ethyl acetate/petroleum ether (1:4) to give 3-(4,4-difluoropiperidin-1-yl)-2,2-difluoropropan-1-ol (1.0 g) as a yellow oil. LCMS Method A: $[M+H]^+=216$.

Step 5: 3-(4,4-difluoropiperidin-1-yl)-2,2-difluoropropyl 4-methylbenzenesulfonate 3-(4,4-Difluoropiperidin-1-yl)-2,2-difluoropropan-1-ol (220.0 mg, 1.0 mmol, 1.0 equiv.) and TEA (0.3 mL, 2.0 mmol, 2.0 equiv.) were dissolved in DCM (10 mL), then TsCl (389.8 mg, 2.0 mmol, 2.0 equiv.) was added. The reaction mixture was stirred for 12 hours at ambient temperature and then concentrated under vacuum. The residue was purified by flash column chromatography on silica gel, eluting with ethyl acetate/petroleum ether (1:1) to give 3-(4,4-difluoropiperidin-1-yl)-2,2-difluoropropyl 4-methylbenzenesulfonate (320.0 mg) as a white solid. LCMS Method A: $[M+H]^+=370$.

Scheme 15: Synthesis of intermediate 29 (5-(4-(trifluoromethyl)phenoxy)-1H-indol-3-amine hydrochloride)

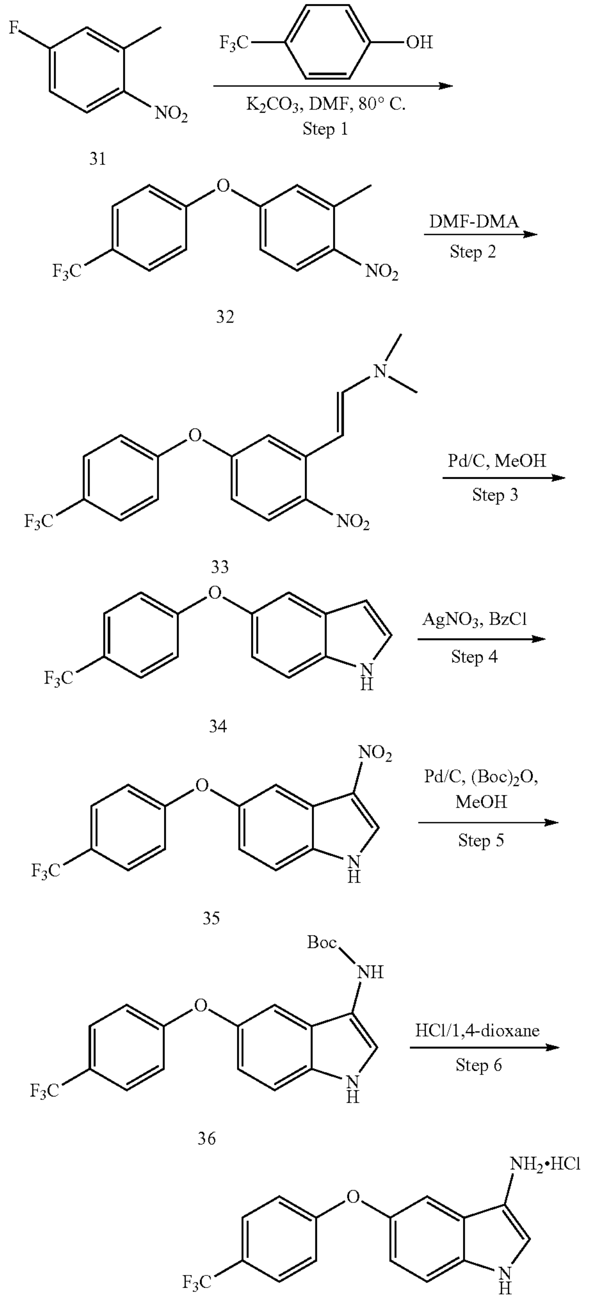

31

32

33

34

35

36

Intermediate 29

Step 1: 2-methyl-1-nitro-4-(4-(trifluoromethyl)phenoxy)benzene

4-Fluoro-2-methyl-1-nitrobenzene (19.0 g, 122.5 mmol, 1.0 equiv.) was dissolved in DMF (100 mL), then $K_2CO_3$ (50.8 g, 367.4 mmol, 3.0 equiv.) and 4-(trifluoromethyl) phenol (23.8 g, 146.9 mmol, 1.2 equiv.) were added. The reaction mixture was heated to 80° C. for 2 hours, then cooled to ambient temperature and quenched by the addition of water. The resulting solution was extracted with ethyl acetate, dried over anhydrous $Na_2SO_4$ and concentrated under vacuum. The residue was purified by flash column chromatography on silica gel, eluting with ethyl acetate/petroleum ether (1:9) to give 2-methyl-1-nitro-4-(4-(trifluoromethyl)phenoxy)benzene (30.0 g) as a yellow solid.

Step 2: (E)-N,N-dimethyl-2-(2-nitro-5-(4-(trifluoromethyl)phenoxy)phenyl)ethen-1-amine 2-Methyl-1-nitro-4-(4-(trifluoromethyl)phenoxy)benzene (20.0 g, 67.3, 1.0 equiv.) was dissolved in DMF (100 mL), then DMF-DMA (10.7 mL, 80.7 mmol, 1.2 equiv.) was added. The reaction mixture was heated to 140° C. for 2 hours, then cooled to ambient temperature and quenched by the addition of water. The resulting solution was extracted with ethyl acetate, washed with brine, dried over anhydrous $Na_2SO_4$ and concentrated under vacuum to give (E)-N,N-dimethyl-2-(2-nitro-5-(4-(trifluoromethyl)phenoxy)phenyl) ethen-1-amine (24.0 g) as a red solid. LCMS Method A: $[M+H]^+=353$.

Step 3: 5-(4-(trifluoromethyl)phenoxy)-1H-indole (E)-N,N-dimethyl-2-(2-nitro-5-(4-(trifluoromethyl)phenoxy)phenyl)ethen-1-amine (24.0 g, 68.1 mmol, 1.0 equiv.) was dissolved in ethyl acetate (250 mL), then Pd/C (10% wt., 2.5 g) was added. The mixture was sparged with nitrogen, placed under an atmosphere of hydrogen gas (balloon), then stirred for 36 hours at ambient temperature. The solids were removed by filtration and the filtrate was concentrated under vacuum. The residue was purified by flash column chromatography on silica gel, eluting with ethyl acetate/petroleum ether (1:6) to give 5-(4-(trifluoromethyl)phenoxy)-1H-indole (11.5 g) as a green solid. LCMS Method A: $[M+H]^+=278$.

Step 4: 3-nitro-5-(4-(trifluoromethyl)phenoxy)-1H-indole

A mixture of $AgNO_3$ (3.6 g, 21.6 mmol, 1.2 equiv.) and ACN (50 mL) was cooled to 0° C., then benzoyl chloride (2.5 mL, 21.6 mmol, 1.2 equiv.) was added dropwise, maintaining the solution at 0° C. The reaction mixture was stirred for 10 min at 0° C., then a solution of 5-(4-(trifluoromethyl)phenoxy)-1H-indole (5.0 g, 18.0 mmol, 1.0 equiv.) in ACN (5 mL) was added dropwise. The resulting solution was stirred for 1 hour at ambient temperature and then quenched by the addition of water. The resulting solution was extracted with ethyl acetate, washed with brine, dried over anhydrous $Na_2SO_4$ and concentrated under vacuum. The residue was purified by flash column chromatography on silica gel, eluting with ethyl acetate/petroleum ether (1:5) to give 3-nitro-5-(4-(trifluoromethyl)phenoxy)-1H-indole (3.1 g) as a black solid. LCMS Method B: $[M-H]^-=321$.

Step 5: tert-butyl (5-(4-(trifluoromethyl)phenoxy)-1H-indol-3-yl)carbamate

3-Nitro-5-(4-(trifluoromethyl)phenoxy)-1H-indole (3.1 g, 9.7 mmol, 1.0 equiv.) was dissolved in MeOH (50 mL), then $(Boc)_2O$ (4.2 g, 19.4 mmol, 2.0 equiv.) and Pd/C (10% wt., 0.4 g) were added. The mixture was sparged with nitrogen, placed under an atmosphere of hydrogen gas (balloon), then stirred for 10 hours at ambient temperature. The solids were removed by filtration and the filtrate was concentrated under vacuum. The residue was purified by flash column chromatography on silica gel, eluting with ethyl acetate/petroleum ether (1:4) to give tert-butyl (5-(4-(trifluoromethyl)phenoxy)-1H-indol-3-yl)carbamate (1.3 g) as a brown solid. LCMS Method A: $[M+H]^+$=393.

Step 6: 5-(4-(trifluoromethyl)phenoxy)-1H-indol-3-amine hydrochloride tert-Butyl (5-(4-(trifluoromethyl)phenoxy)-1H-indol-3-yl)carbamate (1.3 g, 3.3 mmol, 1.0 equiv.) was dissolved in HCl/1,4-dioxane (4N, 15 mL). The reaction mixture was stirred for 2 hours at ambient temperature and then concentrated under vacuum to give 5-(4-(trifluoromethyl)phenoxy)-1H-indol-3-amine hydrochloride (910.0 mg) as a green solid. LCMS Method A: $[M+H]^+$=293.

The intermediates in the following table were prepared using the same method described for Intermediate 29.

-continued

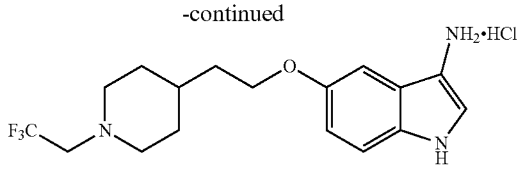

Intermediate 32

Step 1: tert-butyl N-(5-[2-[1-(2,2,2-trifluoroethyl)piperidin-4-yl]ethoxy]-1H-indol-3-yl)carbamate tert-Butyl N-(5-hydroxy-1H-indol-3-yl)carbamate (300.0 mg, 1.2 mmol, 1.0 equiv.) was dissolved in DCM (20 mL) and cooled to 0° C., then 2-[1-(2,2,2-trifluoroethyl)piperidin-4-yl]ethanol (306.3 mg, 1.5 mmol, 1.2 equiv.) and $P(n\text{-}Bu)_3$ (733.4 mg, 3.6 mmol, 3.0 equiv.) were added under an atmosphere of nitrogen. This was followed by the dropwise addition of a solution of ADDP (609.8 mg, 2.4 mmol, 2.0 equiv.) in DCM (5 mL), maintaining the solution at 0° C. The reaction mixture was stirred for 4 hours at ambient temperature and then concentrated under vacuum. The residue was purified by flash column chromatography on silica gel, eluting with ethyl acetate/petroleum ether (1:5) to give tert-butyl N-(5-[2-[1-(2,2,2-trifluoroethyl)piperidin-4-yl]ethoxy]-1H-indol-3-yl)carbamate (285.0 mg) as a pale yellow solid. LCMS Method C: $[M+H]^+$=442.

| Intermediate | Starting material A | Starting material B | Structure | LCMS data |
| --- | --- | --- | --- | --- |
| Intermediate 30 | 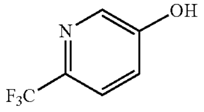 | 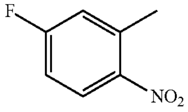 | 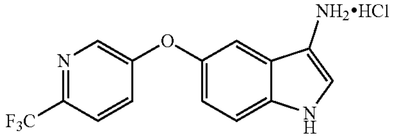 | Method A: MS-ESI: 294 $[M + H]^+$ |
| Intermediate 31 | 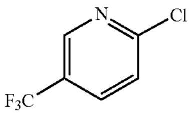 | 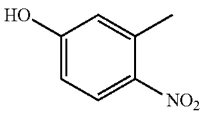 | 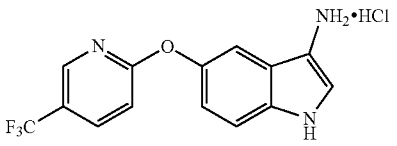 | Method A: MS-ESI: 294 $[M + H]^+$ |

Scheme 16: Synthesis of intermediate 32 (5-(2-(1-(2,2,2-trifluoroethyl)piperidin-4-yl)ethoxy)-1H-indol-3-anine hydrochloride)

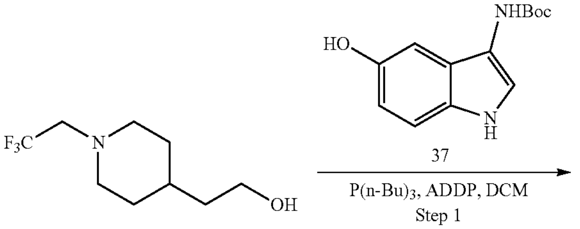

Intermediate 20

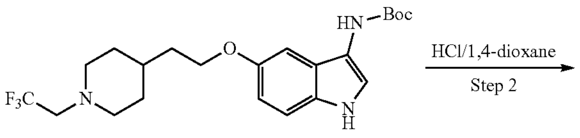

38

Step 2: 5-(2-(1-(2,2,2-trifluoroethyl)piperidin-4-yl)ethoxy)-1H-indol-3-amine hydrochloride tert-Butyl N-(5-[2-[1-(2,2,2-trifluoroethyl)piperidin-4-yl]ethoxy]-1H-indol-3-yl)carbamate (1.0 g, 2.3 mmol, 1.0 equiv.) was dissolved in HCl/1,4-dioxane (4N, 10 mL). The reaction mixture was stirred for 40 min at ambient temperature and then concentrated under vacuum to give 5-(2-(1-(2,2,2-trifluoroethyl)piperidin-4-yl)ethoxy)-1H-indol-3-amine hydrochloride (910.0 mg) as a yellow solid. LCMS Method A: $[M+H]^+$=342.

The intermediate in the following table was prepared using the same method described for Intermediate 32.

| Intermediate | Starting material | Structure | LCMS data |
|---|---|---|---|
| Intermediate 33 | 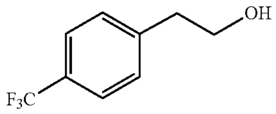 | 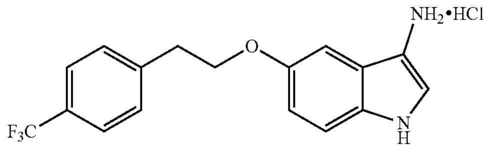 | Method C: MS-ESI: 321 [M-H]$^-$ |

Scheme 17: Synthesis of intermediate 34 ((E)-4,4,5,5-tetramethyl-2-(3-(4-(trifluoromethyl)phenyl)prop-1-en-1-yl)-1,3,2-dioxaborolane)

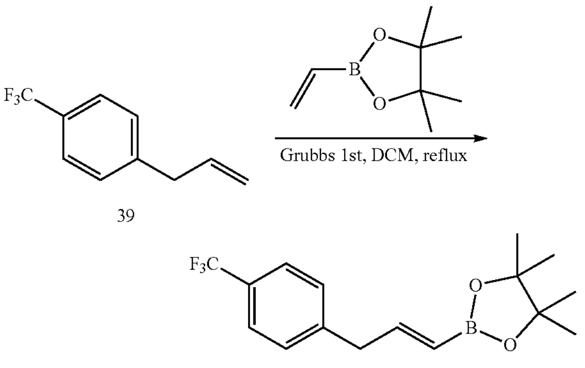

39

Intermediate 34

1-Allyl-4-(trifluoromethyl)benzene (1.0 g, 5.4 mmol, 1.0 equiv.) was dissolved in DCM (10 mL), then 4,4,5,5-tetramethyl-2-vinyl-1,3,2-dioxaborolane (1.7 g, 10.7 mmol, 2.0 equiv.) and Grubbs 1st (224.8 mg, 0.3 mmol, 0.05 equiv.) were added under an atmosphere of nitrogen. The reaction mixture was heated to 50° C. for 16 hours, then cooled to ambient temperature and quenched by the addition of water. The resulting solution was extracted with ethyl acetate, washed with brine, dried over anhydrous $Na_2SO_4$ and concentrated under vacuum. The residue was purified by flash column chromatography on silica gel, eluting with ethyl acetate/petroleum ether (1:4) to give (E)-4,4,5,5-tetramethyl-2-(3-(4-(trifluoromethyl)phenyl)prop-1-en-1-yl)-1,3,2-dioxaborolane (640 mg) as a brown liquid. LCMS Method A: $[M+H]^+$=313.

Scheme 18: Synthesis of intermediate 35 (1-(2-methylallyl)-4-(trifluoromethyl)benzene)

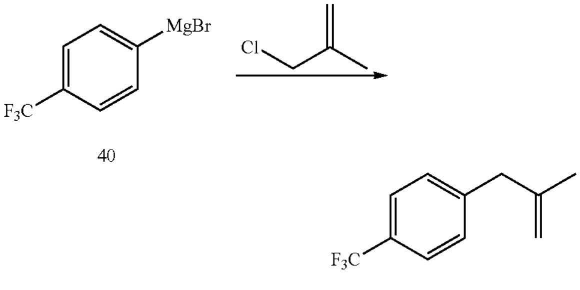

40

Intermediate 35

Bromo[4-(trifluoromethyl)phenyl]magnesium (8 mL, 0.5 mol/L, 4.0 mmol, 1.0 equiv.) was dissolved in THE (30 mL) and cooled to 0° C. Then 3-chloro-2-methylpropene (0.4 g, 4.0 mmol, 1.0 equiv.) was added, maintaining the solution at 0° C. The reaction mixture was stirred for 4 hours at 0° C. and then quenched by the addition of ice-water. The resulting solution was extracted with ethyl acetate, washed with brine, dried over anhydrous $Na_2SO_4$ and concentrated under vacuum. The residue was purified by flash column chromatography on silica gel, eluting with petroleum ether (100%) to give 1-(2-methylprop-2-en-1-yl)-4-(trifluoromethyl)benzene (410.0 mg) as a light yellow solid. $^1$H NMR (400 MHz, Chloroform-d) δ 7.57 (d, J=7.6 Hz, 2H), 7.33 (d, J=8.0 Hz, 2H), 4.89-4.87 (m, 1H), 4.77-4.75 (m, 1H), 3.39 (s, 2H), 1.70 (s, 3H).

Scheme 19: Synthesis of intermediate 36 (1-(2-methylallyl)-4-(trifluoromethyl)benzene)

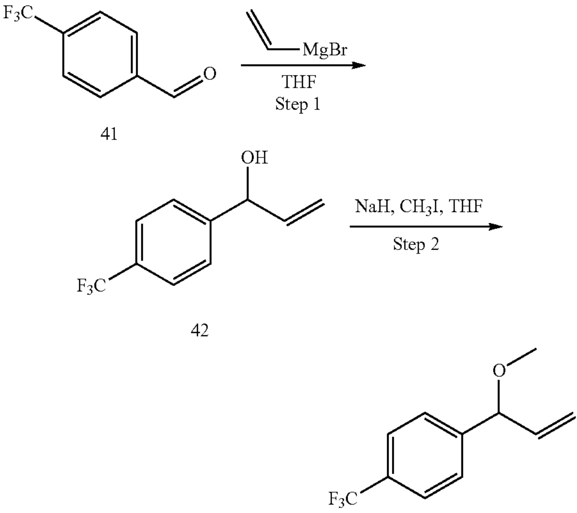

41

42

Intermediate 36

Step 1: 1-[4-(trifluoromethyl)phenyl]prop-2-en-1-ol 4-(Trifluoromethyl)benzaldehyde (2.0 g, 11.5 mmol, 1.0 equiv.) was dissolved in THF (30 mL) and cooled to 0° C., then bromo(ethenyl)magnesium (1M in THF, 13.8 mL, 13.8 mmol, 1.2 equiv.) was added dropwise under an atmosphere of nitrogen, maintaining the solution at 0° C. The reaction mixture was stirred for 2 hours at ambient temperature, then quenched by the addition of ice-water. The resulting solution was extracted with ethyl acetate, washed with brine, dried over anhydrous $Na_2SO_4$ and concentrated under vacuum. The residue was purified by flash column chromatography on silica gel, eluting with ethyl acetate/petroleum ether (1:2) to give 1-[4-(trifluoromethyl)phenyl]prop-2-en-1-ol (1.0 g) as a pale yellow solid. LCMS Method A: $[M+H]^+$=203.

Step 2: 1-(1-methoxyprop-2-en-1-yl)-4-(trifluoromethyl)benzene

1-[4-(Trifluoromethyl)phenyl]prop-2-en-1-ol (1.0 g, 4.9 mmol, 1.0 equiv.) was dissolved in THE (30 mL) and cooled to 0° C., then NaH (60% wt., 0.4 g, 9.9 mmol, 2.0 equiv.) was added. This was followed by the dropwise addition of $CH_3I$ (0.6 mL, 9.9 mmol, 2.0 equiv.) while maintaining the internal reaction temperature at 0° C. The reaction mixture was allowed to warm to ambient temperature and for 2 hours, then quenched by the addition of ice water. The resulting solution was extracted with ethyl acetate, washed with brine, dried over anhydrous $Na_2SO_4$ and concentrated under vacuum to give 1-(1-methoxyprop-2-en-1-yl)-4-(trifluoromethyl)benzene (0.9 g) as a pale yellow solid. $^1H$ NMR (400 MHz, Chloroform-d) δ 7.63 (d, J=8.0 Hz, 2H), 7.48 (d, J=8.0 Hz, 2H), 5.97-5.82 (m, 1H), 5.37-5.23 (m, 2H), 4.70 (d, J=6.8 Hz, 1H), 3.38 (s, 3H). LCMS Method A: $[M+H]^+$=217.

Scheme 20: Synthesis of intermediate 37 (N-(5-bromo-1H-indol-3-yl)cyclopropanecarboxamide)

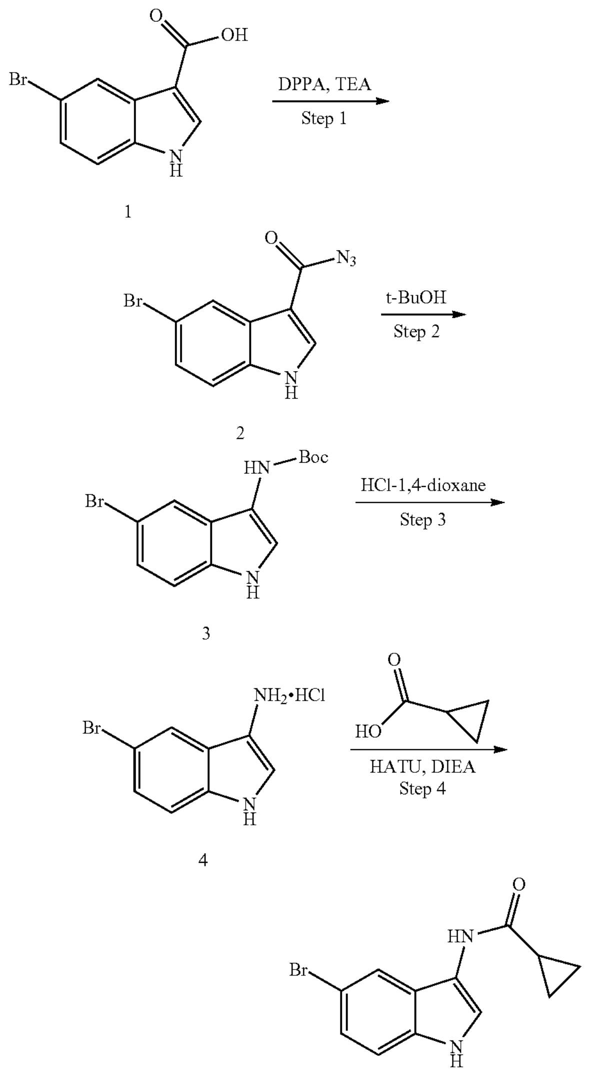

1

2

3

4

Intermediate 37

Step 1: 5-bromo-1H-indole-3-carbonyl azide

5-Bromo-1H-indole-3-carboxylic acid (30.0 g, 124.9 mmol, 1.0 equiv.) was dissolved in THE (150 mL), then TEA (26.1 mL, 187.4 mmol, 1.5 equiv.) and DPPA (37.8 g, 137.4 mmol, 1.1 equiv.) were added. The reaction mixture was stirred for 12 hours at ambient temperature, then quenched by the addition of water and stirred for an additional 10 min. The precipitated solid was collected by filtration and dried to give 5-bromo-1H-indole-3-carbonyl azide (33.6 g) as an off-white solid. LCMS Method B: $[M-H]^-$=263.

Step 2: tert-butyl (5-bromo-1H-indol-3-yl)carbamate

5-Bromo-1H-indole-3-carbonyl azide (33.6 g, 126.7 mmol, 1.0 equiv.) was dissolved in t-BuOH (300 mL). The reaction mixture was heated to 80° C. for 12 hours, then cooled to ambient temperature and concentrated under vacuum. The residue was purified by flash column chromatography on silica gel, eluting with ethyl acetate/petroleum ether (1:10) to give tert-butyl (5-bromo-1H-indol-3-yl)carbamate (22.1 g) as a pale white solid. LCMS Method A: $[M+H]^+$=311.

Step 3: 5-bromo-1H-indol-3-amine hydrochloride tert-Butyl (5-bromo-1H-indol-3-yl)carbamate (20.0 g, 64.2 mmol, 1.0 equiv.) was dissolved in HCl/1,4-dioxane (4 M, 150 mL). The reaction mixture was stirred for 2 hours at ambient temperature and then concentrated under vacuum to give 5-bromo-1H-indol-3-amine hydrochloride (18.7 g) as a brown solid. LCMS Method A: $[M+H]^+$=211.

Step 4: N-(5-bromo-1H-indol-3-yl)cyclopropanecarboxamide

Cyclopropanecarboxylic acid (172.0 mg, 2.0 mmol, 1.0 equiv.) was dissolved in DCM (20 mL), then DIEA (1.0 mL, 6.0 mmol, 3.0 equiv.), HATU (1.1 g, 3.0 mmol, 1.5 equiv.) and 5-bromo-1H-indol-3-amine hydrogen chloride (500.0 mg, 2.0 mmol, 1.0 equiv.) were added. The reaction mixture was stirred for 2 hours at ambient temperature and then quenched by the addition of water. The resulting solution was extracted with ethyl acetate, washed with brine, dried over anhydrous $Na_2SO_4$ and concentrated under vacuum. The residue was purified by flash column chromatography on silica gel, eluting with ethyl acetate/petroleum ether (1:1) to give N-(5-bromo-1H-indol-3-yl)cyclopropanecarboxamide (510.0 mg) as a white solid. LCMS Method A: $[M+H]^+$=279.

The intermediates in the following Table were prepared using the same method described for Intermediate 37.

| Intermediate | Structure | LCMS data |
| --- | --- | --- |
| Intermediate 38 | 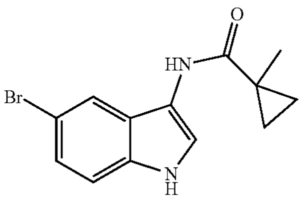 [SMILES: CC1(C(=O)Nc2c[nH]c3ccc(Br)cc23)CC1] | Method A: MS-ESI: 293 $[M + H]^+$ |

-continued

| Intermediate | Structure | LCMS data |
|---|---|---|
| Intermediate 39 | 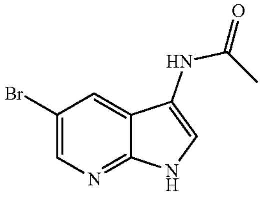 | Method A: MS-ESI: 254 [M + H]+ |
| Intermediate 40 | 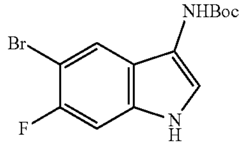 [SMILES: CC(C)(C)OC(=O)Nc1c[nH]c2cc(F)c(Br)cc12] | Method A: MS-ESI: 329 [M + H]+ |

Scheme 21: Synthesis of intermediate 41 (N-(5-bromo-7-fluoro-1H-indol-3-yl)acetamide)

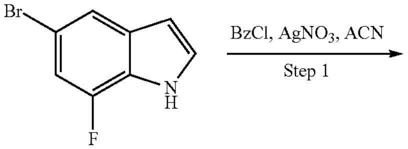

5

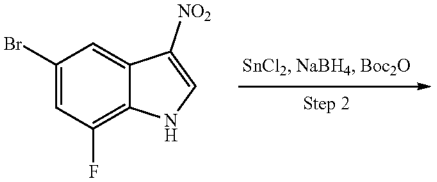

6

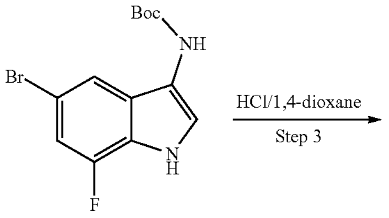

7

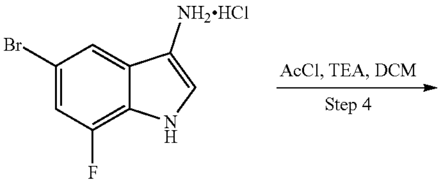

8

-continued

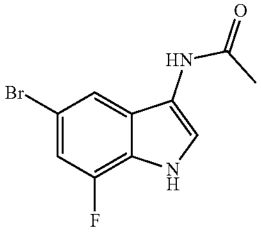

Intermediate 41

Step 1: 5-bromo-7-fluoro-3-nitro-1H-indole

5-Bromo-7-fluoro-1H-indole (8.5 g, 39.7 mmol, 1.0 equiv.) was dissolved in in ACN (150 mL) and cooled to 0° C., then $AgNO_3$ (10.1 g, 59.6 mmol, 1.5 equiv.) was added. The resulting mixture was stirred for 15 min, then benzoyl chloride (8.4 g, 59.6 mmol, 1.5 equiv.) was added batchwise, maintaining the reaction mixture at 0° C. The reaction mixture was stirred for 3 hours at 0° C., then quenched by the addition of ice-water. The resulting solution was extracted with ethyl acetate, washed with brine, dried over anhydrous $Na_2SO_4$ and concentrated under vacuum. The residue was purified by flash column chromatography on silica gel, eluting with ethyl acetate/petroleum ether (1:1) to give 5-bromo-7-fluoro-3-nitro-1H-indole (7.4 g) as a black solid. LCMS Method A: $[M+H]^+$=259.

Step 2: tert-butyl (5-bromo-7-fluoro-1H-indol-3-yl)carbamate

5-Bromo-7-fluoro-3-nitro-1H-indole (3.0 g, 11.6 mmol, 1.0 equiv.) was dissolved in MeOH (50 mL) then $(Boc)_2O$ (3.0 g, 13.8 mmol, 1.2 equiv.) was added. This was followed by the portionwise addition of $SnCl_2$ (6.6 g, 34.7 mmol, 3.0 equiv.) and $NaBH_4$ (1.3 g, 34.7 mmol, 3.0 equiv.), while maintain the reaction mixture at 0° C. The reaction mixture was stirred for 4 hours at 0° C., then quenched by the addition of ice-water. The resulting solution was extracted with ethyl acetate, washed with brine, dried over anhydrous $Na_2SO_4$ and concentrated under vacuum. The residue was purified by flash column chromatography on silica gel, eluting with ethyl acetate/petroleum ether (1:9) to give tert-butyl (5-bromo-7-fluoro-1H-indol-3-yl)carbamate (1.3 g) as a yellow solid. LCMS Method A: $[M+H]^+$=329.

Step 3: 5-bromo-7-fluoro-1H-indol-3-amine hydrochloride tert-Butyl (5-bromo-7-fluoro-1H-indol-3-yl)carbamate (1.3 g, 3.9 mmol, 1.0 equiv.) was dissolved in HCl/1,4-dioxane (4N, 15 mL). The reaction mixture was stirred for 2 hours at ambient temperature then concentrated under vacuum to give 5-bromo-7-fluoro-1H-indol-3-amine hydrochloride (980.0 mg) as a grey solid. LCMS Method A: $[M+H]^+$=229.

Step 4: N-(5-bromo-7-fluoro-1H-indol-3-yl)acetamide

5-Bromo-7-fluoro-1H-indol-3-amine (980.0 mg, 4.3 mmol, 1.0 equiv.) and TEA (2.3 mL, 17.1 mmol, 4.0 equiv.) were dissolved in DCM (10 mL), then acetyl chloride (0.4 mL, 5.1 mmol, 1.2 equiv.) was added. The reaction mixture was stirred for 2 hours at ambient temperature, then quenched by the addition of water. The resulting solution was extracted with dichloromethane, washed with brine, dried over anhydrous $Na_2SO_4$ and concentrated under vacuum. The residue was purified by flash column chromatography on silica gel, eluting with dichloromethane/methanol (20:1) to give N-(5-bromo-7-fluoro-1H-indol-3-yl)acetamide (800.0 mg) as a brown solid. LCMS Method A: $[M+H]^+$=271.

The intermediates in the following table were prepared using the same method described for Intermediate 41.

| Intermediate | Structure | LCMS data |
| --- | --- | --- |
| Intermediate 42 | 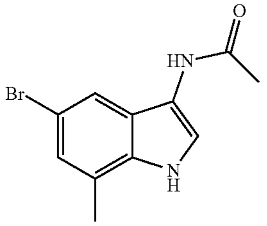 | Method A: MS-ESI: 267 $[M + H]^+$ |
| Intermediate 43 | 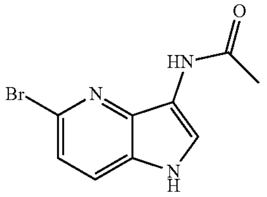 | Method A: MS-ESI: 254 [M + H]+ |
| Intermediate 44 | 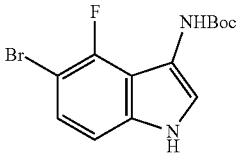 [SMILES: CC(C)(C)OC(=O)Nc1c[nH]c2ccc(Br)c(F)c12] | Method A: MS-ESI: 329 [M + H]+ |

Scheme 22: Synthesis of intermediate 45 (N-(7-fluoro-5-hydroxy-1H-indol-3-yl)acetamide)

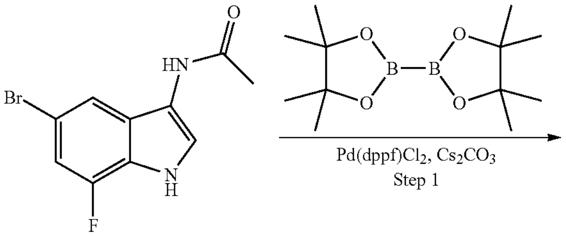

Intermediate 41

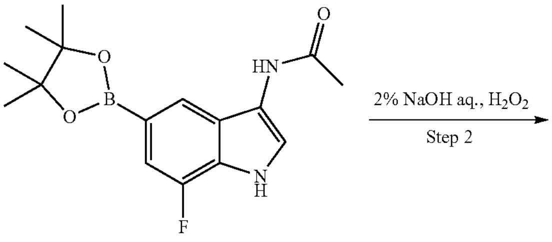

9

-continued

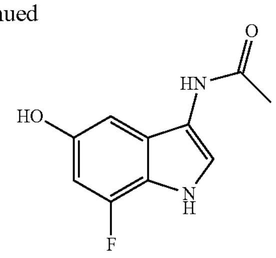

Intermediate 45

Step 1: N-(7-fluoro-5-(4,4,5,5-tetramethyl-1,3,2-dioxaborolan-2-yl)-1H-indol-3-yl)acetamide N-(5-Bromo-7-fluoro-1H-indol-3-yl)acetamide (1.0 g, 3.8 mmol, 1.0 equiv.) was dissolved in 1,4-dioxane (100 mL), then 4,4,4',4',5,5,5',5'-octamethyl-2,2'-bi(1,3,2-dioxaborolane) (1.5 g, 5.8 mmol, 1.5 equiv.), $Cs_2CO_3$ (2.5 g, 7.7 mmol, 2.0 equiv.) and Pd(dppf)$Cl_2$·$CH_2Cl_2$ (0.3 g, 0.4 mmol, 0.1 equiv.) were added under an atmosphere of nitrogen. The reaction mixture was heated to 100° C. for 2 hours, then cooled to ambient temperature and quenched by the addition of water. The resulting solution was extracted with ethyl acetate, washed with brine, dried over anhydrous $Na_2SO_4$ and concentrated under vacuum. The residue was purified by flash column chromatography on silica gel, eluting with ethyl acetate/petroleum ether (1:2) to give N-(7-fluoro-5-(4,4,5,5-tetramethyl-1,3,2-dioxaborolan-2-yl)-1H-indol-3-yl)acetamide (880 mg) as a brown solid. LCMS Method A: $[M+H]^+$=319.

Step 2: N-(7-fluoro-5-hydroxy-1H-indol-3-yl)acetamide

N-(7-fluoro-5-(4,4,5,5-tetramethyl-1,3,2-dioxaborolan-2-yl)-1H-indol-3-yl)acetamide (830.0 mg, 2.6 mmol, 1.0 equiv.) was dissolved in THE (10 mL) and cooled to 0° C., then a solution of NaOH in water (2% wt./wt., 11 mL, 5.5 mmol, 2.0 equiv.) was added. This was followed by the addition of $H_2O_2$ (30% wt./wt. in water, 2 mL, 19.2 mmol, 7.5 equiv.) dropwise at 0° C. The reaction mixture was stirred for 2 hours at ambient temperature, then quenched by the addition of saturated aqueous $NH_4Cl$. The resulting solution was extracted with ethyl acetate, washed with brine and concentrated under vacuum. The residue was purified by flash column chromatography on silica gel, eluting with dichloromethane/methanol (10:1) to give N-(7-fluoro-5-hydroxy-1H-indol-3-yl)acetamide (174.0 mg) as a black solid. LCMS Method A: $[M+H]^+$=209.

Scheme 23: Synthesis of intermediate 46 (N-(5-hydroxy-7-methyl-1H-indol-3-yl)acetamide)

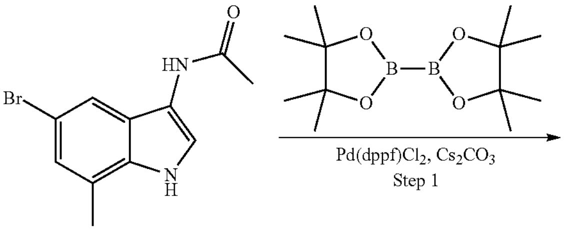

Intermediate 42

-continued

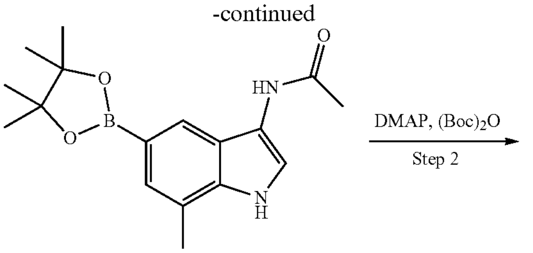

10

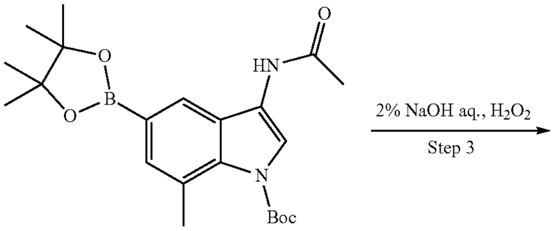

11

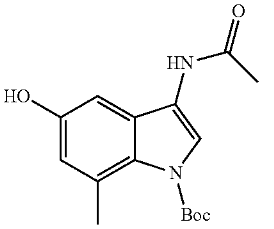

Intermediate 46

Step 1: N-[7-methyl-5-(4,4,5,5-tetramethyl-1,3,2-dioxaborolan-2-yl)-1H-indol-3-yl]acetamide N-(5-Bromo-7-methyl-1H-indol-3-yl)acetamide (150.0 mg, 0.6 mmol, 1.0 equiv.) was dissolved in 1,4-dioxane (100 mL), then 4,4,4',4',5,5,5',5'-octamethyl-2,2'-bi(1,3,2-dioxaborolane) (213.9 mg, 0.8 mmol, 1.5 equiv.), KOAc (110.2 mg, 1.1 mmol, 2.0 equiv.) and $Pd(dppf)Cl_2 \cdot CH_2Cl_2$ (41.1 mg, 0.06 mmol, 0.1 equiv.) were added under an atmosphere of nitrogen. The reaction mixture was heated to 85° C. for 6 hours, then cooled to ambient temperature and quenched by the addition of water. The resulting solution was extracted with ethyl acetate, washed with brine, dried over anhydrous $Na_2SO_4$ and concentrated under vacuum. The residue was purified by flash column chromatography on silica gel, eluting with ethyl acetate/petroleum ether (1:5) to give N-[7-methyl-5-(4,4,5,5-tetramethyl-1,3,2-dioxaborolan-2-yl)-1H-indol-3-yl]acetamide (100.0 mg) as a pale yellow solid. LCMS Method B: $[M+H]^+$=315.

Step 2: tert-butyl 3-acetamido-7-methyl-5-(4,4,5,5-tetramethyl-1,3,2-dioxaborolan-2-yl)indole-1-carboxylate N-[7-Methyl-5-(4,4,5,5-tetramethyl-1,3,2-dioxaborolan-2-yl)-1H-indol-3-yl]acetamide (50.0 mg, 0.2 mmol, 1.0 equiv.) and $Boc_2O$ (41.7 mg, 0.2 mmol, 1.2 equiv.) were dissolved in THE (5 mL), then TEA (0.1 mL, 0.3 mmol, 2.0 equiv.) and DMAP (4.0 mg, 0.03 mmol, 0.2 equiv.) were added. The reaction mixture was stirred overnight at ambient temperature, then quenched by the addition of water. The resulting solution was extracted with ethyl acetate, washed with brine, dried over anhydrous $Na_2SO_4$ and concentrated under vacuum. The residue was purified by flash column chromatography on silica gel, eluting with ethyl acetate/petroleum ether (1:7) to give tert-butyl 3-acetamido-7-methyl-5-(4,4,5,5-tetramethyl-1,3,2-dioxaborolan-2-yl)indole-1-carboxylate (45.8 mg) as a pale yellow solid. LCMS Method B: $[M+H]^+$=415.

Step 3: tert-butyl 3-acetamido-5-hydroxy-7-methylindole-1-carboxylate tert-Butyl 3-acetamido-7-methyl-5-(4,4,5,5-tetramethyl-1,3,2-dioxaborolan-2-yl)indole-1-carboxylate (200.0 mg, 0.5 mmol, 1.0 equiv.) was dissolved in THE (10 mL) and cooled to 0° C., then aqueous NaOH (2% wt./wt., 2 mL, 1.0 mmol, 1.0 equiv.) was added. This was followed by the addition of $H_2O_2$ (30% wt./wt. in water, 0.5 mL, 5.0 mmol, 10.0 equiv.) dropwise at 0° C. The reaction mixture was stirred for 2 hours at ambient temperature, then quenched by the addition of saturated aqueous $NH_4Cl$. The resulting solution was extracted with ethyl acetate and concentrated under vacuum. The residue was purified by flash column chromatography on silica gel, eluting with dichloromethane/methanol (20:1) to give tert-butyl 3-acetamido-5-hydroxy-7-methylindole-1-carboxylate (60.0 mg) as a light yellow solid. LCMS Method B: $[M+H]^+$=305.

The intermediates in the following table were prepared using the same method described for Intermediate 46.

| Intermediate | Starting material | Structure | LCMS data |
| --- | --- | --- | --- |
| Intermediate 47 | 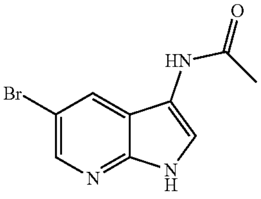 Intermediate 39 | 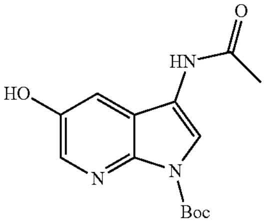 [SMILES: CC(=O)Nc1cn(C(=O)OC(C)(C)C)c2ncc(O)cc12] | Method A: MS-ESI: 292 $[M + H]^+$ |

Scheme 24: Synthesis of intermediate 48 (N-(5-(2-hydroxyethyl)-1H-indol-3-yl)acetamide)

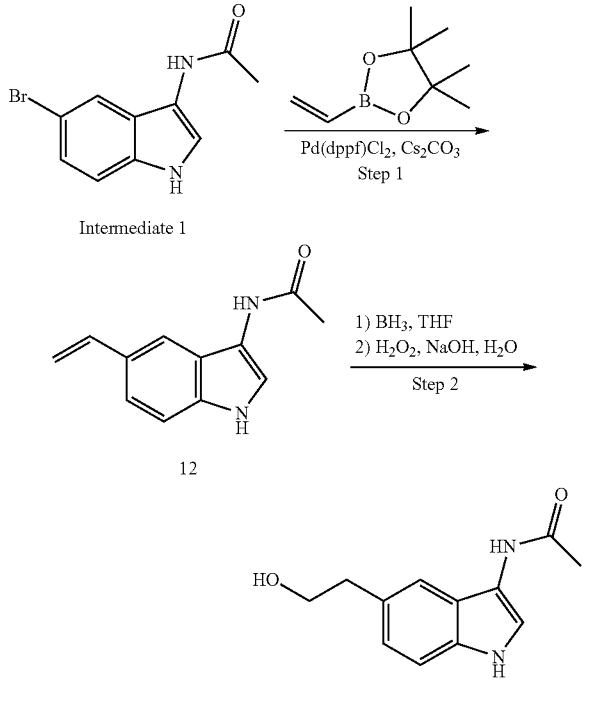

Step 1: N-(5-vinyl-1H-indol-3-yl)acetamide

N-(5-bromo-1H-indol-3-yl)acetamide (3.0 g, 11.9 mmol, 1.0 equiv.) was dissolved in 1,4-dioxane (30 mL) and water (3 mL), then $Pd(dppf)Cl_2 \cdot CH_2Cl_2$ (1.9 g, 2.3 mmol, 0.2 equiv.), $Cs_2CO_3$ (7.7 g, 23.7 mmol, 2.0 equiv.) and 4,4,5,5-tetramethyl-2-vinyl-1,3,2-dioxaborolane (2.2 g, 14.2 mmol, 1.2 equiv.) were added under atmosphere of nitrogen. The reaction mixture was heated to 100° C. for 16 hours, then cooled to ambient temperature and concentrated under vacuum. The residue was purified by flash column chromatography on silica gel, eluting with ethyl acetate/petroleum ether (1:1) to give N-(5-vinyl-1H-indol-3-yl)acetamide (1.5 g) as a brown solid. LCMS Method C: $[M+H]^+$=201.

Step 2: N-(5-(2-hydroxyethyl)-1H-indol-3-yl)acetamide

N-(5-vinyl-1H-indol-3-yl)acetamide (1.0 g, 5.0 mmol, 1.0 equiv.) was dissolved in THF (30 mL) and cooled to 0° C., then $BH_3$-THF (1 M, 20 mL, 20.0 mmol, 4.0 equiv.) was added dropwise. After 2 hours at ambient temperature, a solution of aqueous NaOH (1 M, 10 mL, 10.0 mmol, 2.0 equiv.) was added. This was followed by the addition of $H_2O_2$ (30% wt./wt. in water, 1.3 mL, 38.2 mmol, 7.6 equiv.), maintaining the reaction mixture at 0° C. The reaction mixture was stirred for an additional 30 min at 0° C., then quenched by the addition of saturated aqueous $NH_4Cl$. The resulting solution was adjusted to pH 6-7 with aqueousHCl (6M), extracted with ethyl acetate, washed with brine, dried over anhydrous $Na_2SO_4$ and concentrated under vacuum. The residue was purified by flash column chromatography on silica gel, eluting with ethyl acetate/petroleum ether (3:2) to give N-(5-(2-hydroxyethyl)-1H-indol-3-yl)acetamide (294.0 mg) as a pale brown solid. LCMS Method A: $[M+H]^+$=219.

The intermediates in the following table were prepared using the same method described for Intermediate 48.

| Intermediate | Starting material | Structure | LCMS data |
|---|---|---|---|
| Intermediate 49 | 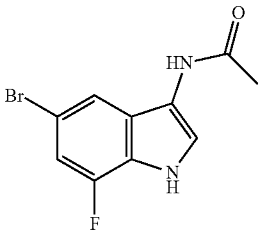 Intermediate 41 | 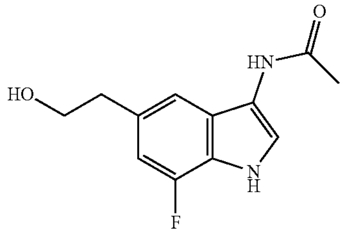 [SMILES: CC(=O)Nc1c[nH]c2c(F)cc(CCO)cc12] | Method A: MS-ESI: 237 $[M + H]^+$ |
| Intermediate 50 | 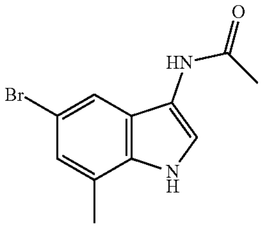 Intermediate 42 | 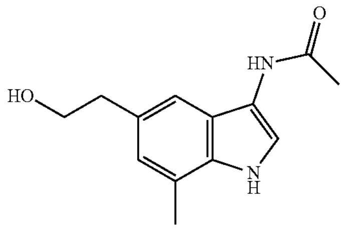 [SMILES: CC(=O)Nc1c[nH]c2c(C)cc(CCO)cc12] | Method A: MS-ESI: 233 $[M + H]^+$ |

-continued

| Intermediate | Starting material | Structure | LCMS data |
|---|---|---|---|
| Intermediate 51 | 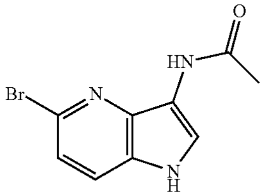 Intermediate 43 | 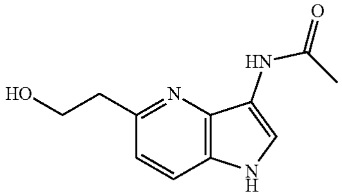 [SMILES: CC(=O)Nc1c[nH]c2ccc(CCO)nc12] | Method A: MS-ESI: 220 [M + H]+ |
| Intermediate 52 | 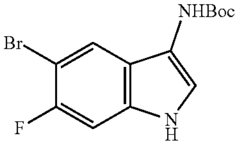 Intermediate 40 | 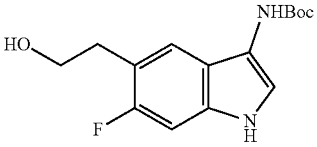 [SMILES: CC(C)(C)OC(=O)Nc1c[nH]c2cc(F)c(CCO)cc12] | Method A: MS-ESI: 295 [M + H]+ |
| Intermediate 53 | 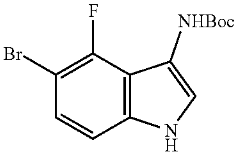 Intermediate 44 | 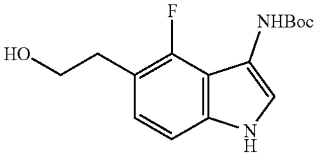 [SMILES: CC(C)(C)OC(=O)Nc1c[nH]c2ccc(CCO)c(F)c12] | Method A: MS-ESI: 295 [M + H]+ |
| Intermediate 54 | 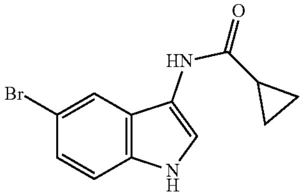 Intermediate 37 | 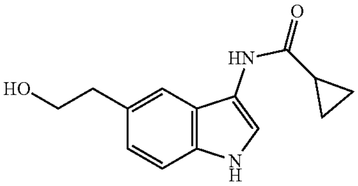 [SMILES: O=C(Nc1c[nH]c2ccc(CCO)cc12)C1CC1] | Method A: MS-ESI: 245 [M + H]+ |
| Intermediate 55 | 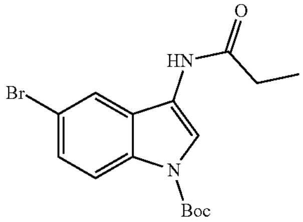 Intermediate 4 | 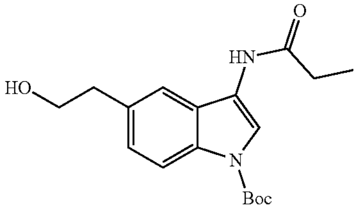 [SMILES: CCC(=O)Nc1cn(C(=O)OC(C)(C)C)c2ccc(CCO)cc12] | Method A: MS-ESI: 333 [M + H]+ |

Scheme 25: Synthesis of intermediate 56 (tert-butyl 5-(hydroxymethyl)-3-(2-(methylamino)-2-oxoacetamido)-1H-indole-1-carboxylate)

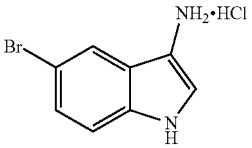

4

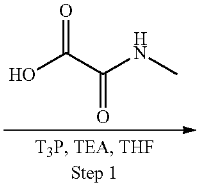

-continued

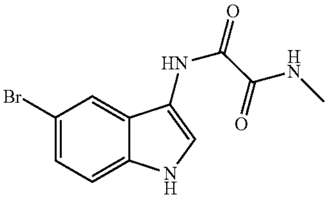

13

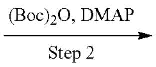

-continued

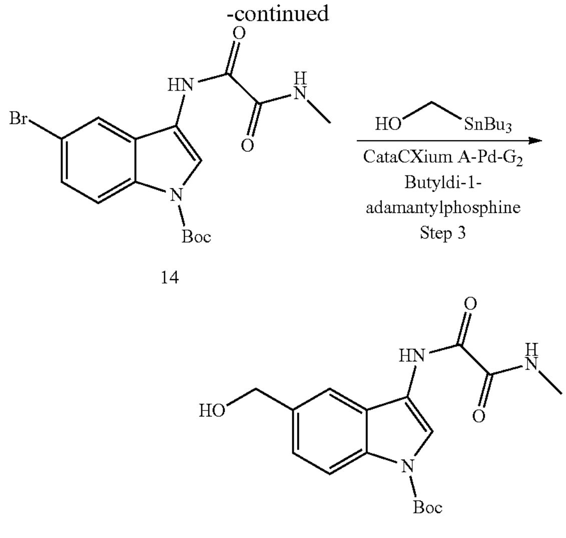

14

Intermediate 56

Step 1: N1-(5-bromo-1H-indol-3-yl)-N2-methyloxalamide

5-Bromo-1H-indol-3-amine (1.7 g, 8.0 mmol, 1.0 equiv.) was dissolved in THE (20 mL), then TEA (3.3 mL, 24.1 mmol, 3.0 equiv.), 2-(methylamino)-2-oxoacetic acid (830.2 mg, 8.0 mmol, 1.0 equiv.) and $T_3P$ (50% wt., 3.84 g, 12.0 mmol, 1.5 equiv.) were added. The reaction mixture was stirred for 30 min at ambient temperature, then quenched by the addition of water. The resulting solution was extracted with ethyl acetate, washed with brine, dried over anhydrous sodium sulfate and concentrated under vacuum. The residue was purified by flash column chromatography on silica gel, eluting with ethyl acetate/petroleum ether (1:1) to give N1-(5-bromo-1H-indol-3-yl)-N2-methyloxalamide (1.2 g) as a brown solid. LCMS Method A: $[M+H]^+$=296.

Step 2: tert-butyl 5-bromo-3-(2-(methylamino)-2-oxoacetamido)-1H-indole-1-carboxylate N1-(5-Bromo-1H-indol-3-yl)-N2-methyloxalamide (1.2 g, 4.0 mmol, 1.0 equiv.) was dissolved in DCM (12 mL), then DMAP (50.0 mg, 0.4 mmol, 0.1 equiv.) and $(Boc)_2O$ (1.0 g, 4.8 mmol, 1.2 equiv.) were added. The reaction mixture was stirred for 1 hour at ambient temperature, then quenched by the addition of water. The resulting solution was extracted with ethyl acetate, washed with brine, dried over anhydrous sodium sulfate and concentrated under vacuum. The residue was purified by flash column chromatography on silica gel, eluting with ethyl acetate/petroleum ether (1:2) to give tert-butyl 5-bromo-3-(2-(methylamino)-2-oxoacetamido)-1H-indole-1-carboxylate (950.0 mg) as a white solid. LCMS Method A: $[M+H]^+$=396

Step 3: tert-butyl 5-(hydroxymethyl)-3-(2-(methylamino)-2-oxoacetamido)-1H-indole-1-carboxylate tert-Butyl 5-bromo-3-(2-(methylamino)-2-oxoacetamido)-1H-indole-1-carboxylate (900.0 mg, 2.2 mmol, 1.0 equiv.) was dissolved in 1,4-dioxane (10 mL), then (tributylstannyl)methanol (1823.2 mg, 5.6 mmol, 2.5 equiv.), butyl di-1-adamanthylphosphine (162.8 mg, 0.4 mmol, 0.20 equiv.) and CataCXium A-Pd-G2 (151.8 mg, 0.2 mmol, 0.1 equiv.) were added under an atmosphere of nitrogen. The reaction mixture was heated to 100° C. for 6 hours, then cooled to ambient temperature and quenched by the addition of water. The resulting solution was extracted with ethyl acetate, washed with brine, dried over anhydrous sodium sulfate and concentrated under vacuum. The residue was purified by flash column chromatography on silica gel, eluting with ethyl acetate/petroleum ether (2:1) to give tert-butyl 5-(hydroxymethyl)-3-(2-(methylamino)-2-oxoacetamido)-1H-indole-1-carboxylate (750.0 mg) as an off-white solid. LCMS Method C: $[M+H]^+$=348.

The intermediates in the following table were prepared using the same method described for Intermediate 56.

| Intermediate | Starting material | Structure | LCMS data |
| --- | --- | --- | --- |
| Intermediate 57 | 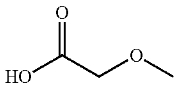 | 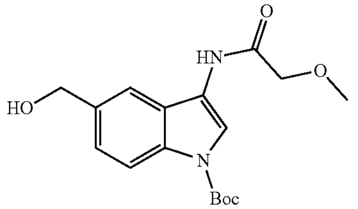 [SMILES: COCC(=O)Nc1cn(C(=O)OC(C)(C)C)c2ccc(CO)cc12] | Method C: MS-ESI: 335 $[M + H]^+$ |

Scheme 26: Synthesis of intermediate 58 (N-(5-(2-hydroxyethyl)-7-methyl-1H-pyrrolo[3,2-b]pyridin-3-yl)acetamide)

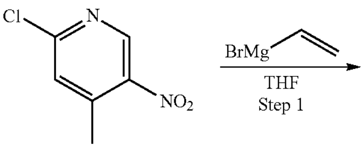

15

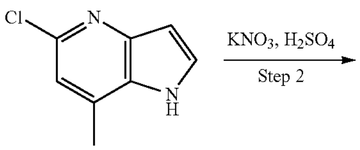

16

-continued

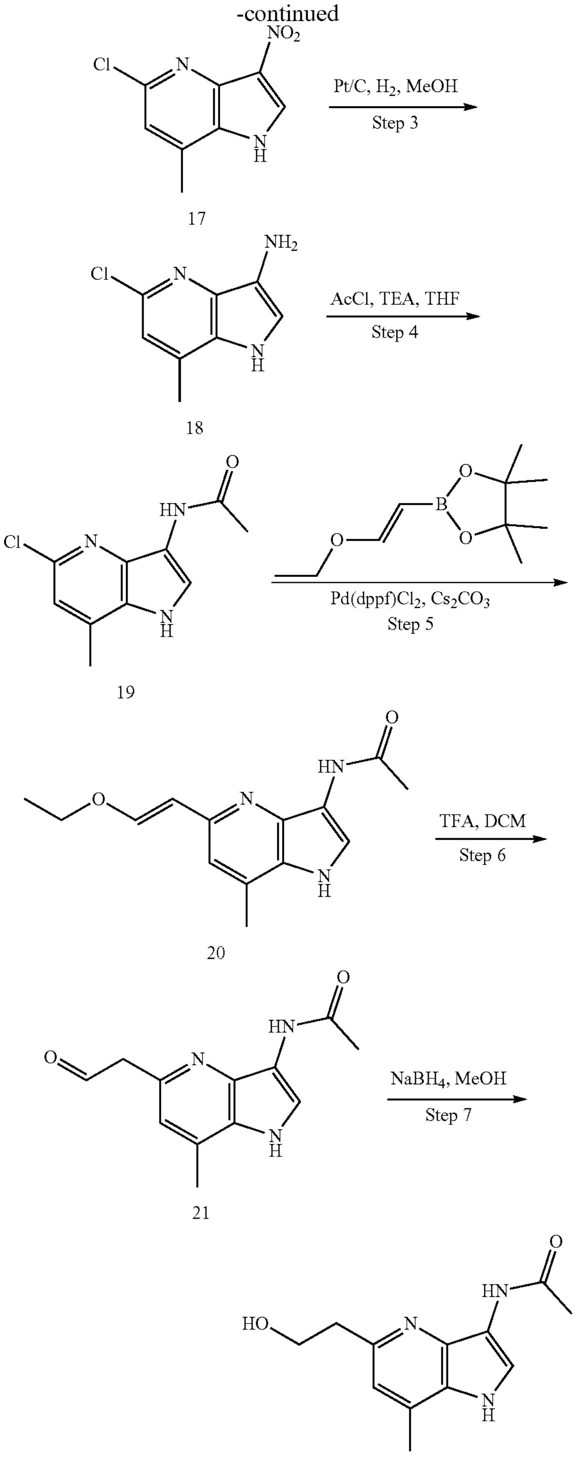

17

18

19

20

21

Intermediate 58

Step 1: 5-chloro-7-methyl-1H-pyrrolo[3,2-b]pyridine

2-Chloro-4-methyl-5-nitropyridine (10 g, 57.9 mmol, 1.0 equiv.) was dissolved in THF (50 mL) and cooled to −60° C., then bromo(ethenyl)magnesium (1M in THF, 173.8 mL, 173.8 mmol, 3.0 equiv.) was added dropwise under an atmosphere of nitrogen, maintaining the solution at −60° C. The reaction mixture was stirred overnight at ambient temperature, then quenched by the addition of saturated $NH_4Cl$ aqueous at 0° C. The reaction mixture was extracted with ethyl acetate, washed with brine, dried over anhydrous $Na_2SO_4$ and concentrated under vacuum. The residue was purified by flash column chromatography on silica gel, eluting with ethyl acetate/petroleum ether (1:5) to give 5-chloro-7-methyl-1H-pyrrolo[3,2-b]pyridine (1.6 g) as a light yellow solid. LCMS Method A: $[M+H]^+$=167.

Step 2: 5-chloro-7-methyl-3-nitro-1H-pyrrolo[3,2-b]pyridine

5-Chloro-7-methyl-1H-pyrrolo[3,2-b]pyridine (1.0 g, 6.0 mmol, 1.0 equiv.) was dissolved in $H_2SO_4$ (15 mL) and cooled to 0° C., then $KNO_3$ (900.0 mg, 9.0 mmol, 1.5 equiv.) was added in portions, maintaining the solution at 0° C. The reaction mixture was stirred for 40 min at ambient temperature, then cooled to 0° C. and quenched by the addition of ice-water. The precipitated solids were collected by filtration, washed with ethyl acetate and dried under vacuum to give 5-chloro-7-methyl-3-nitro-1H-pyrrolo[3,2-b]pyridine (890.0 mg) as a pale yellow solid. LCMS Method A: $[M+H]^+$=212.

Step 3: 5-chloro-7-methyl-1H-pyrrolo[3,2-b]pyridin-3-amine

5-Chloro-7-methyl-3-nitro-1H-pyrrolo[3,2-b]pyridine (800.0 mg, 3.8 mmol, 1.0 equiv.) was dissolved in MeOH (20 mL), then Pt/C (147.5 mg, 0.8 mmol, 0.2 equiv.) was added. The mixture was sparged with nitrogen, placed under an atmosphere of hydrogen gas (balloon), then stirred overnight at ambient temperature. The solids were removed by filtration and the filtrate was concentrated under vacuum. This gave 5-chloro-7-methyl-1H-pyrrolo[3,2-b] pyridin-3-amine (550.0 mg) as a yellow solid. LCMS Method A: $[M+H]^+$=182.

Step 4: N-{5-chloro-7-methyl-1H-pyrrolo[3,2-b]pyridin-3-yl}acetamide

5-Chloro-7-methyl-1H-pyrrolo[3,2-b]pyridin-3-amine (550.0 mg, 3.0 mmol, 1.0 equiv.) and TEA (0.8 mL, 6.1 mmol, 2.0 equiv.) were dissolved in THE (20 mL) and cooled to 0° C., then acetyl chloride (0.3 mL, 3.6 mmol, 1.2 equiv.) was added, maintaining the solution at 0° C. The reaction mixture was stirred for 4 hours at ambient temperature, then quenched by the addition of MeOH. The resulting solution was concentrated under vacuum and the residue was purified by flash column chromatography on silica gel, eluting with ethyl acetate/petroleum ether (1:1) to give N-{5-chloro-7-methyl-1H-pyrrolo[3,2-b]pyridin-3-yl}acetamide (600.0 mg) as a yellow solid. LCMS Method A: $[M+H]^+$=224.

Step 5: N-{5-[(E)-2-ethoxyethenyl]-7-methyl-1H-pyrrolo[3,2-b]pyridin-3-yl}acetamide N-{5-Chloro-7-methyl-1H-pyrrolo[3,2-b]pyridin-3-yl}acetamide (300.0 mg, 1.3 mmol, 1.0 equiv.) was dissolved in 1.4-dioxane (3 mL) and water (0.5 mL), then 2-[(E)-2-ethoxyethenyl]-4,4,5,5-tetramethyl-1,3,2-dioxaborolane (398.5 mg, 2.0 mmol, 1.5 equiv.), $Cs_2CO_3$ (874.1 mg, 2.7 mmol, 2.0 equiv.), and Pd(dppf)$Cl_2$ (196.3 mg, 0.3 mmol, 0.2 equiv.) were added under an atmosphere of nitrogen. The reaction mixture was heated to 90° C. overnight, then cooled to ambient temperature and concentrated under vacuum. The residue was purified by flash column chromatography on silica gel, eluting with ethyl acetate/petroleum ether (1:2) to give N-{5-[(E)-2-ethoxyethenyl]-7-methyl-1H-pyrrolo[3,2-b]pyridin-3-yl}acetamide (200.0 mg) as a yellow solid. LCMS Method A: $[M+H]^+$=260.

Step 6: N-[7-methyl-5-(2-oxoethyl)-1H-pyrrolo[3,2-b]pyridin-3-yl]acetamide

N-{5-[(E)-2-ethoxyethenyl]-7-methyl-1H-pyrrolo[3,2-b]pyridin-3-yl}acetamide (200.0 mg, 0.8 mmol, 1.0 equiv.) was dissolved in DCM (10 mL) and TFA (1 mL). The reaction mixture was stirred for 2 hours at 60° C., then cooled to ambient temperature and concentrated under vacuum to give N-[7-methyl-5-(2-oxoethyl)-1H-pyrrolo[3,2-b]pyridin-3-yl]acetamide (175.0 mg) as a brown solid, which was used in next step directly without further purification. LCMS Method A: $[M+H]^+$=232.

Step 7: N-[5-(2-hydroxyethyl)-7-methyl-1H-pyrrolo[3,2-b]pyridin-3-yl]acetamide

N-[7-methyl-5-(2-oxoethyl)-1H-pyrrolo[3,2-b]pyridin-3-yl]acetamide (175.0 mg, 0.8 mmol, 1.0 equiv.) was dissolved in MeOH (10 mL) and cooled to 0° C., then $NaBH_4$ (114.5 mg, 3.0 mmol, 3.8 equiv.) was added. The reaction mixture was stirred for 1 hour at ambient temperature, then concentrated under vacuum. The residue was purified by reverse flash chromatography using the following conditions: column, C18 silica gel; mobile phase, MeCN in water, 5% to 100% gradient in 10 min; detector, UV 254 nm. This gave in N-[5-(2-hydroxyethyl)-7-methyl-1H-pyrrolo[3,2-b]pyridin-3-yl]acetamide (85.0 mg) as a pale yellow solid. LCMS Method A: $[M+H]^+$=234.

Scheme 27: Synthesis of intermediate 59 (tert-butyl (5-(2-hydroxypropyl)-1H-indol-3-yl)carbamate)

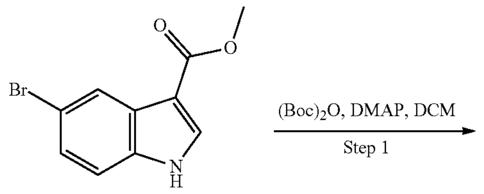

22

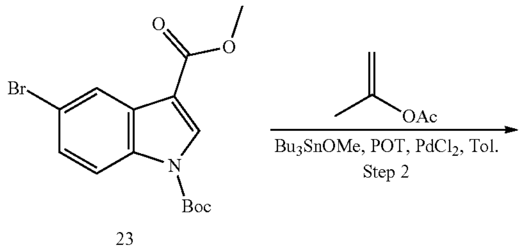

23

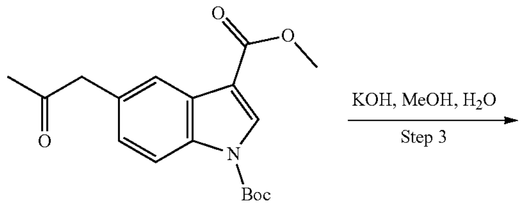

24

-continued

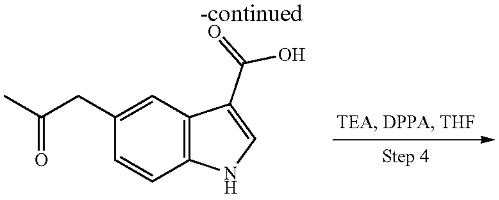

25

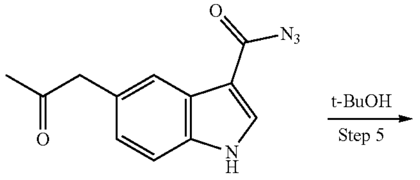

26

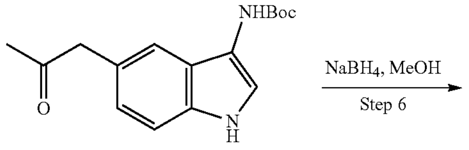

27

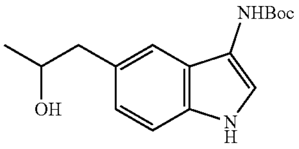

Intermediate 59

Step 1: 1-tert-butyl 3-methyl 5-bromoindole-1,3-dicarboxylate

Methyl 5-bromo-1H-indole-3-carboxylate (5.0 g, 19.6 mmol, 1.0 equiv.) was dissolved in DCM (100 mL), then $Boc_2O$ (8.6 g, 39.3 mmol, 2.0 equiv.) and DMAP (480.8 mg, 3.9 mmol, 0.2 equiv.) were added. The reaction mixture was stirred for 3 hours at ambient temperature, then quenched by the addition of water. The resulting solution was extracted with DCM, washed with brine, dried over anhydrous $Na_2SO_4$ and concentrated under vacuum. The residue was purified by flash column chromatography on silica gel, eluting with ethyl acetate/petroleum ether (1:5) to give 1-tert-butyl 3-methyl 5-bromoindole-1,3-dicarboxylate (6.5 g) as a white solid. LCMS Method A: $[M+H]^+$=354.

Step 2: 1-tert-butyl 3-methyl 5-(2-oxopropyl)indole-1,3-dicarboxylate 1-tert-Butyl 3-methyl 5-bromoindole-1,3-dicarboxylate (3.0 g, 8.4 mmol, 1.0 equiv.) and 1-propen-2-ol acetate (1.7 g, 16.9 mmol, 2.0 equiv.) were dissolved in toluene (60 mL), then $Bu_3SnOMe$ (3.2 g, 10.1 mmol, 1.2 equiv.), $PdCl_2$ (0.3 g, 1.6 mmol, 0.2 equiv) and POT (0.6 g, 2.1 mmol, 0.2 equiv.) were added under an atmosphere of nitrogen. The reaction mixture was heated to 100° C. for 3 hours, then cooled to ambient temperature and concentrated under vacuum. The residue was diluted with water, extracted with ethyl acetate, washed with brine, dried over anhydrous $Na_2SO_4$ and concentrated under vacuum. The residue was purified by flash column chromatography on silica gel, eluting with ethyl acetate/petroleum ether (1:5) to give 1-tert-butyl 3-methyl 5-(2-oxopropyl)indole-1,3-dicarboxylate (2.5 g) as a white solid. LCMS Method A: $[M+H]^+$=332.

Step 3: 5-(2-oxopropyl)-1H-indole-3-carboxylic acid 1-tert-Butyl 3-methyl 5-(2-oxopropyl)indole-1,3-dicarboxylate (2.5 g, 7.5 mmol, 1.0 equiv.) was dissolved in MeOH (20 mL) and water (4 mL), then KOH (0.8 g, 15.0 mmol, 2.0 equiv.) was added. The reaction mixture was heated to 80° C. overnight, then cooled to ambient temperature and concentrated under vacuum. The residue was diluted with water and adjusted to pH 2 with aqueous HCl (2 N). The resulting solution was extracted with ethyl acetate, washed with brine, dried over anhydrous $Na_2SO_4$ and concentrated under vacuum to give 5-(2-oxopropyl)-1H-indole-3-carboxylic acid (1.5 g) as a white solid. LCMS Method B: $[M-H]^-$=216.

Step 4: 5-(2-oxopropyl)-1H-indole-3-carbonyl azide 5-(2-Oxopropyl)-1H-indole-3-carboxylic acid (1.5 g, 6.9 mmol, 1.0 equiv.) was dissolved in THF (20 mL), then TEA (2.9 mL, 20.7 mmol, 3.0 equiv.) and DPPA (2.8 g, 10.3 mmol, 1.5 equiv.) were added. The reaction mixture was stirred overnight at ambient temperature, then concentrated under vacuum to give 5-(2-oxopropyl)-1H-indole-3-carbonyl azide (1.1 g) as a white solid, which was used in the next step directly without further purification. LCMS Method A: $[M+H]^+$=243.

Step 5: tert-butyl N-[5-(2-oxopropyl)-1H-indol-3-yl]carbamate 5-(2-Oxopropyl)-1H-indole-3-carbonyl azide (1.0 g, 4.1 mmol, 1.0 equiv.) was dissolved in 2-methyl-2-propanol (30 mL). The reaction mixture was heated to 90° C. overnight, then cooled to ambient temperature and concentrated under vacuum. The residue was purified by reverse flash chromatography with the following conditions: column, C18; mobile phase, ACN in water (0.5% $NH_4HCO_3$), 0% ACN to 100% gradient in 15 min; detector, UV 254 nm. This gave tert-butyl N-[5-(2-oxopropyl)-1H-indol-3-yl]carbamate (600.0 mg) as a white solid. LCMS Method A: $[M+H]^+$=289.

Step 6: tert-butyl N-[5-(2-hydroxypropyl)-1H-indol-3-yl]carbamate tert-Butyl N-[5-(2-oxopropyl)-1H-indol-3-yl]carbamate (550.0 mg, 1.9 mmol, 1.0 equiv.) was dissolved in MeOH (15 mL), then $NaBH_4$ (144.3 mg, 3.8 mmol, 2.0 equiv.) was added. The reaction mixture was stirred for 4 hours at ambient temperature, then concentrated under vacuum. The residue was diluted with water, extracted with ethyl acetate, washed with brine, dried over anhydrous $Na_2SO_4$ and concentrated under vacuum to give tert-butyl N-[5-(2-hydroxypropyl)-1H-indol-3-yl]carbamate (550.0 mg) as a white solid. LCMS Method A: $[M+H]^+$=291.

Scheme 28: Synthesis of intermediate 60 (1-[4-(trifluoromethyl)phenyl]azetidin-3-ol)

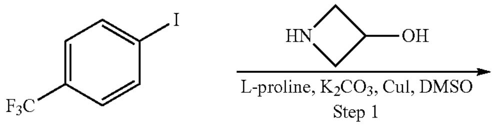

28

-continued

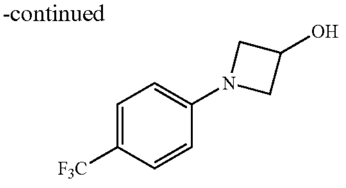

Intermediate 60

1-Iodo-4-(trifluoromethyl)benzene (1.0 g, 3.7 mmol, 1.0 equiv.) and azetidin-3-ol (0.5 g, 7.4 mmol, 2.0 equiv.) were dissolved in DMSO (5 mL), then L-proline (0.4 g, 3.7 mmol, 1.0 equiv.), $K_2CO_3$ (1.0 g, 7.4 mmol, 2.0 equiv.) and CuI (0.4 g, 1.8 mmol, 0.5 equiv.) were added under an atmosphere of nitrogen. The reaction mixture was stirred overnight at 90° C., then cooled to ambient temperature and quenched by the addition of water. The resulting solution was extracted with ethyl acetate, washed with brine, dried over anhydrous $Na_2SO_4$ and concentrated under vacuum. The residue was purified by flash column chromatography on silica gel, eluting with ethyl acetate/petroleum ether (1:1) to give 1-[4-(trifluoromethyl)phenyl]azetidin-3-ol (600.0 mg) as an off-white solid. LCMS Method B: $[M+H]^+$=218.

Scheme 29: Synthesis of intermediate 61 (2-(6-(trifluoromethyl)pyridin-3-yl)ethan-1-ol)

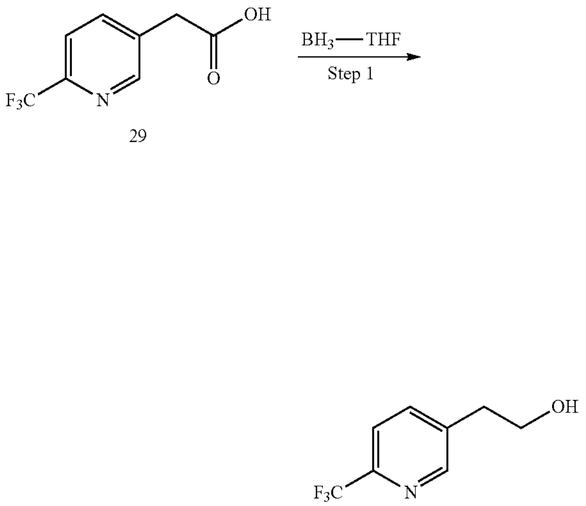

29

Intermediate 61

[6-(Trifluoromethyl)pyridin-3-yl]acetic acid (4.8 g, 23.2 mmol, 1.0 equiv.) was dissolved in THF (100 mL) and cooled to 0° C., then $BH_3$-THF (1M, 69.5 mL, 69.5 mmol, 3.0 equiv.) was added dropwise, maintaining the solution at 0° C. The reaction mixture was stirred for 1 hour at ambient temperature, then quenched by the addition of ice-water. The resulting solution was extracted with ethyl acetate, washed with brine, dried over anhydrous $Na_2SO_4$ and concentrated under vacuum. The residue was purified by flash column chromatography on silica gel, eluting with dichloromethane/methanol (95:5) to give 2-[6-(trifluoromethyl)pyridin-3-yl]ethanol (4.3 g) as a yellow oil. LCMS Method A: $[M+H]^+$=192.

The intermediates in the following table were prepared using the same method described for Intermediate 61.

| Intermediate | Starting material | Structure | LCMS data |
|---|---|---|---|
| Intermediate 62 | 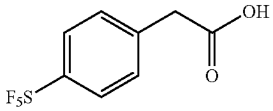 | 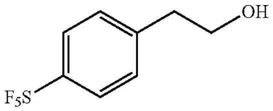 | Method C: MS-ESI: 249 $[M + H]^+$ |

Scheme 30: Synthesis of intermediate 63 (2-(2-(2,2,2-trifluoroethyl)-2-azaspiro[3.3]heptan-6-yl)ethan-1-ol)

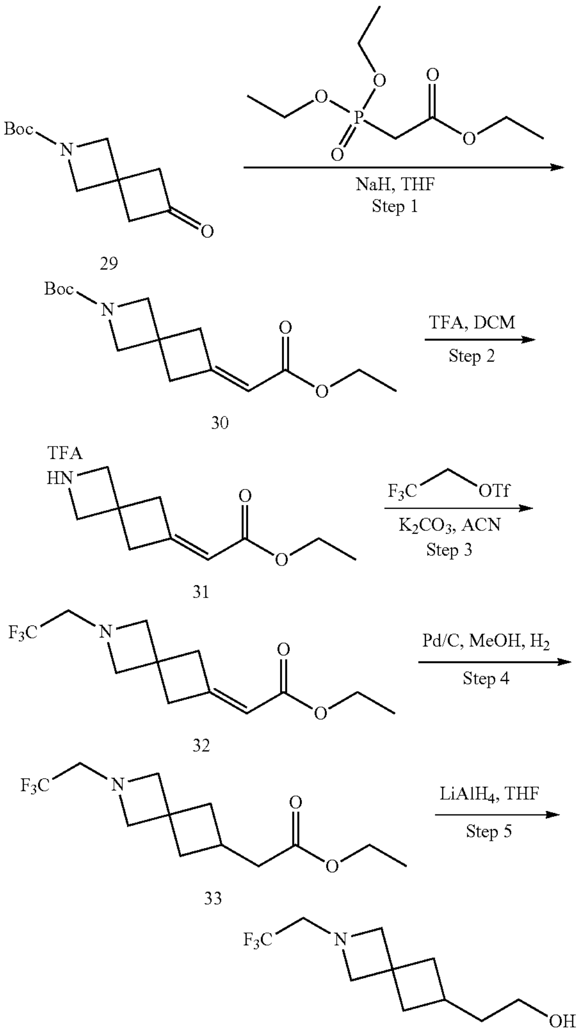

29

30

31

32

33

Intermediate 63

Step 1: tert-butyl 6-(2-ethoxy-2-oxoethylidene)-2-azaspiro[3.3]heptane-2-carboxylate Triethyl phosphonoacetate (1.3 g, 5.7 mmol, 1.2 equiv.) was dissolved in THF (50 mL) and cooled to 0° C., then NaH (60% wt. in mineral oil, 0.3 g, 7.1 mmol, 1.5 equiv.). After 30 min at 0° C., tert-butyl 6-oxo-2-azaspiro[3.3]heptane-2-carboxylate (1.0 g, 4.7 mmol, 1.0 equiv.) was added. The reaction mixture was stirred for an additional 2 hours at ambient temperature, then quenched by the addition of ice-water. The resulting solution was extracted with ethyl acetate, washed with brine, dried over anhydrous $Na_2SO_4$ and concentrated under vacuum to give tert-butyl 6-(2-ethoxy-2-oxoethylidene)-2-azaspiro[3.3]heptane-2-carboxylate (1.3 g) as a yellow oil. LCMS Method A: $[M+H]^+$=282.

Step 2: ethyl 2-{2-azaspiro[3.3]heptan-6-ylidene}acetate TFA salt tert-Butyl 6-(2-ethoxy-2-oxoethylidene)-2-azaspiro[3.3]heptane-2-carboxylate (1.3 g, 4.6 mmol, 1.0 equiv.) was dissolved in DCM (40 mL) and TFA (2 mL). The reaction mixture was stirred for 40 min at ambient temperature, then concentrated under vacuum to give in ethyl 2-{2-azaspiro[3.3]heptan-6-ylidene}acetate TFA salt (1.0 g) as a yellow oil. LCMS Method A: $[M+H]^+$=182.

Step 3: ethyl 2-[2-(2,2,2-trifluoroethyl)-2-azaspiro[3.3]heptan-6-ylidene]acetate Ethyl 2-{2-azaspiro[3.3]heptan-6-ylidene}acetate TFA salt (1.0 g, 5.5 mmol, 1.0 equiv.) was dissolved in ACN (40 mL), then $K_2CO_3$ (1.5 g, 11.0 mmol, 2.0 equiv.) and 2,2,2-trifluoroethyl trifluoromethanesulfonate (1.4 g, 6.1 mmol, 1.1 equiv.) were added. The reaction mixture was heated to 80° C. for 2 hours, then cooled to ambient temperature and quenched by the addition of water. The resulting solution was extracted with ethyl acetate, washed with brine, dried over anhydrous $Na_2SO_4$ and concentrated under vacuum to give ethyl 2-[2-(2,2,2-trifluoroethyl)-2-azaspiro[3.3]heptan-6-ylidene]acetate (1.4 g) as a light yellow oil. LCMS Method A: $[M+H]^+$=264.

Step 4: ethyl 2-[2-(2,2,2-trifluoroethyl)-2-azaspiro[3.3]heptan-6-yl]acetate

Ethyl 2-[2-(2,2,2-trifluoroethyl)-2-azaspiro[3.3]heptan-6-ylidene]acetate (1.2 g, 4.6 mmol, 1.0 equiv.) was dissolved in MeOH (40 mL), then Pd/C (120.0 mg, 10% wt.) was added under an atmosphere of nitrogen. The reaction mixture was sparged with nitrogen, placed under an atmosphere of hydrogen gas (balloon), then stirred for 2 hours at ambient temperature. The solids were removed by filtration and the filtrate was concentrated under vacuum. The residue was purified by flash column chromatography on silica gel, eluting with ethyl acetate/petroleum ether (1:3) to give ethyl 2-[2-(2,2,2-trifluoroethyl)-2-azaspiro[3.3]heptan-6-yl]acetate (260.0 mg) as a light yellow oil. LCMS Method A: $[M+H]^+$=266.

Step 5: 2-[2-(2,2,2-trifluoroethyl)-2-azaspiro[3.3]heptan-6-yl]ethanol

Ethyl 2-[2-(2,2,2-trifluoroethyl)-2-azaspiro[3.3]heptan-6-yl]acetate (260.0 mg, 1.0 mmol, 1.0 equiv.) was dissolved in THF (15 mL) and cooled to 0° C., then $LiAlH_4$ (74.4 mg, 2.0 mmol, 2.0 equiv.) was added. The reaction mixture was stirred for 60 min at ambient temperature, then cooled to 0° C. and quenched by the addition of ice-water. The resulting solution was extracted with ethyl acetate, washed with brine, dried over anhydrous $Na_2SO_4$ and concentrated under vacuum to give 2-[2-(2,2,2-trifluoroethyl)-2-azaspiro[3.3]heptan-6-yl]ethanol (210.0 mg) as a light yellow oil. LCMS Method A: $[M+H]^+=224$.

The intermediates in the following table were prepared using the same method described for Intermediate 63.

| Intermediate | Starting material | Structure | LCMS data |
|---|---|---|---|
| Intermediate 64 | 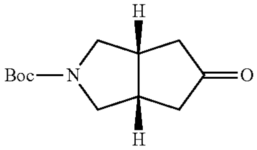 [SMILES: CC(C)(C)OC(=O)N1C[C@H]2CC(=O)C[C@H]2C1] | 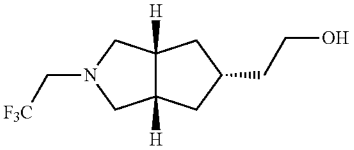 [SMILES: OCC[C@@H]1C[C@@H]2CN(CC(F)(F)F)C[C@@H]2C1] | Method C: MS-ESI: 238 $[M + H]^+$ |

Scheme 31: Synthesis of intermediate 65 ((1-(4-(trifluoromethyl)phenyl)cyclopropyl)methanol)

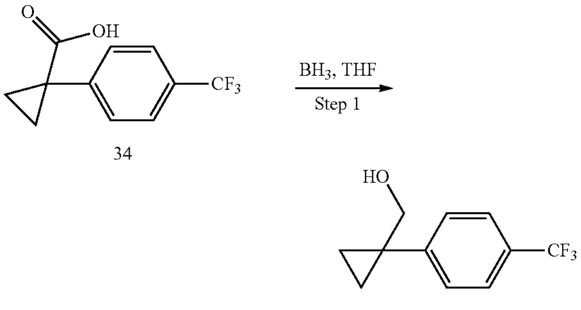

34

Intermediate 65

1-[4-(Trifluoromethyl)phenyl]cyclopropane-1-carboxylic acid (200.0 mg, 0.8 mmol, 1.0 equiv.) was dissolved in THE (5 mL) and cooled to 0° C., then $BH_3$-THF (1M, 4.3 mL, 4.3 mmol, 5.0 equiv.) was added dropwise, maintaining the solution at 0° C. The reaction mixture was stirred for 1 hour at ambient temperature then concentrated under vacuum. The residue was diluted with of water, extracted with ethyl acetate, washed with brine, dried over anhydrous $Na_2SO_4$ and concentrated under vacuum to give [1-[4-(trifluoromethyl)phenyl]cyclopropyl]methanol (150.0 mg) as a yellow oil. LCMS Method A: $[M+H]^+=217$.

Scheme 32: Synthesis of intermediate 66 (1-(4-(trifluoromethyl)phenyl)propan-2-ol)

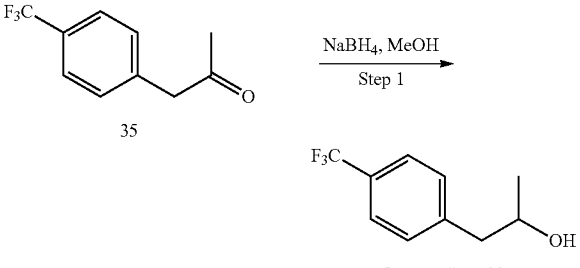

35

Intermediate 66

1-[4-(Trifluoromethyl)phenyl]propan-2-one (1.0 g, 4.9 mmol, 1.0 equiv.) was dissolved in MeOH (30 mL), then $NaBH_4$ (0.2 g, 5.8 mmol, 1.2 equiv.) was added. The reaction mixture was stirred for 2 hours at ambient temperature, then quenched by the addition of water. The resulting solution was extracted with ethyl acetate, washed with brine, dried over anhydrous $Na_2SO_4$ and concentrated under vacuum to give 1-[4-(trifluoromethyl)phenyl]propan-2-ol (0.9 g) as a light yellow oil.

Scheme 33: Synthesis of intermediate 67 (2-(1-(2,2,2-trifluoroethyl)piperidin-3-yl)ethan-1-ol)

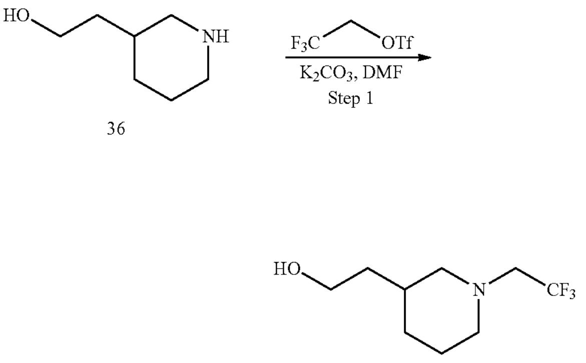

36

Intermediate 67

2-(Piperidin-3-yl)ethanol hydrochloride (2.0 g, 12.1 mmol, 1.0 equiv.) was dissolved in DMF (30 mL), then 2,2,2-trifluoroethyl trifluoromethanesulfonate (5.6 g, 24.2 mmol, 2.0 equiv.) and $K_2CO_3$ (3.3 g, 24.2 mmol, 2.0 equiv.) were added. The reaction mixture was heated to 80° C. for 2 hours, then cooled to ambient temperature and quenched by the addition of water. The resulting solution was extracted with ethyl acetate, washed with brine, dried over anhydrous $Na_2SO_4$ and concentrated under vacuum. The residue was purified by reverse flash chromatography with the following conditions: column, C18; mobile phase, MeOH in water, 10% to 50% gradient in 10 min; detector, UV 254 nm. This gave 2-[1-(2,2,2-trifluoroethyl)piperidin-3-yl]ethanol (1.4 g) as a yellow oil. LCMS Method A: $[M+H]^+=212$.

Scheme 34: Synthesis of intermediate 68 (4,4-difluoro-1-(2-hydroxyethyl)cyclohexan-1-ol)

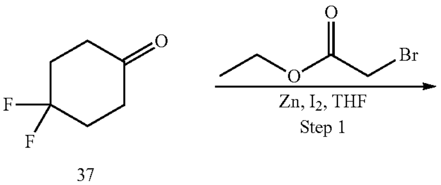

37

-continued

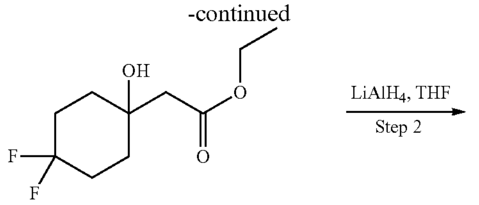

38

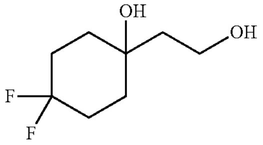

Intermediate 68

Step 1: Ethyl 2-(4,4-difluoro-1-hydroxycyclohexyl)acetate

Zinc powder (2.4 g, 37.3 mmol, 5.0 equiv.) was suspended in THE (25 mL) and cooled to 0° C., then $I_2$ (1.9 g, 7.5 mmol, 1.0 equiv.) was added. After 10 min at 0° C., 4,4-difluorocyclohexan-1-one (1.0 g, 7.5 mmol, 1.0 equiv.) and ethyl 2-bromoacetate (1.5 g, 8.9 mmol, 1.2 equiv.) were added dropwise, maintaining the reaction mixture at 0° C. The reaction mixture was heated to 65° C. for 2 hours, then cooled to ambient temperature and quenched by the addition of saturated aqueous $NaHCO_3$. The mixture was extracted with ethyl acetate, washed with brine, dried over anhydrous $Na_2SO_4$ and concentrated under vacuum. The residue was purified by flash column chromatography on silica gel, eluting with ethyl acetate/petroleum ether (1:1) to give ethyl 2-(4,4-difluoro-1-hydroxycyclohexyl)acetate (380.0 mg) as a colorless oil. LCMS Method A: $[M+H]^+$=223.

Step 2: 4,4-difluoro-1-(2-hydroxyethyl)cyclohexan-1-ol

Ethyl 2-(4,4-difluoro-1-hydroxycyclohexyl)acetate (380.0 mg, 1.7 mmol, 1.0 equiv.) was dissolved in THE (10 mL) and cooled to 0° C., then $LiAlH_4$ (97.4 mg, 2.6 mmol, 1.5 equiv.) was added. The reaction mixture was stirred for 2 hours at ambient temperature, then quenched by the addition of solid $Na_2SO_4$-$10{\cdot}H_2O$. The solids were filtered out and the filtrate was concentrated under vacuum. The residue was purified by flash column chromatography on silica gel, eluting with dichloromethane/methanol (10:1) to give 4,4-difluoro-1-(2-hydroxyethyl)cyclohexan-1-ol (120.0 mg) as colorless oil. LCMS Method A: $[M+H]^+$=181.

Scheme 35: Synthesis of intermediate 69 (2-(3-phenylbicyclo[1.1.1]pentan-1-yl)ethan-1-ol)

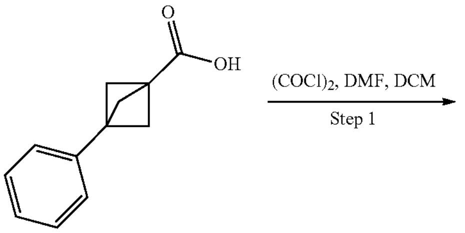

39

-continued

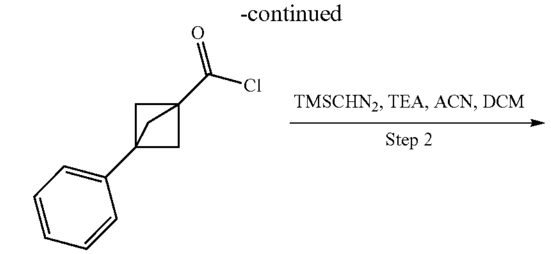

40

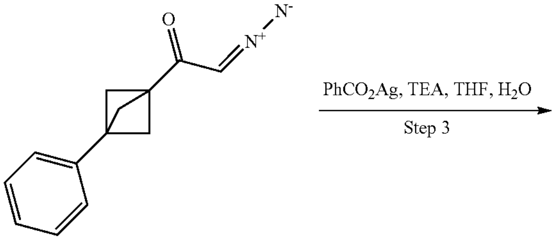

41

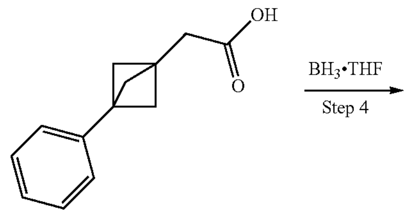

42

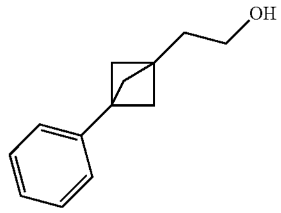

Intermediate 69

Step 1: 3-phenylbicyclo[1.1.1]pentane-1-carbonyl chloride

3-Phenylbicyclo[1.1.1]pentane-1-carboxylic acid (500.0 mg, 2.7 mmol, 1.0 equiv.) was dissolved in DCM (20 mL) and cooled to 0° C., then $(COCl)_2$ (0.35 mL, 4.0 mmol, 1.5 equiv.) was added dropwise, maintaining the solution at 0° C. This was followed by the addition of DMF (0.03 mL, 0.3 mmol, 0.1 equiv.). The reaction mixture was stirred for 2.5 hours at ambient temperature, then concentrated under vacuum to give 3-phenylbicyclo[1.1.1]pentane-1-carbonyl chloride (620 mg) as a yellow solid.

Step 2: 2-diazo-1-{3-phenylbicyclo[1.1.1]pentan-1-yl}ethanone

3-Phenylbicyclo[1.1.1]pentane-1-carbonyl chloride (600.0 mg, 2.9 mmol, 1.0 equiv.) was dissolved in DCM (10 mL) and ACN (10 mL) and cooled to 0° C. Then TEA (1.2 mL, 8.7 mmol, 3.0 equiv.) and $TMSCHN_2$ (1.3 mg, 11.6 mmol, 4.0 equiv.) were added. The reaction mixture was stirred for 4 hours at ambient temperature and then quenched by the addition of saturated aqueous citric acid. The resulting solution was extracted with ethyl acetate, washed with brine, dried over anhydrous $Na_2SO_4$ and concentrated under vacuum to give 2-diazo-1-{3-phenylbicyclo[1.1.1]pentan-1-yl}ethanone (610.0 mg) as a pale yellow solid.

Step 3: {3-phenylbicyclo[1.1.1]pentan-1-yl}acetic acid

2-Diazo-1-{3-phenylbicyclo[1.1.1]pentan-1-yl}ethanone (600.0 mg, 2.8 mmol, 1.0 equiv.) was dissolved in THF (15 mL) and $H_2O$ (5 mL), then TEA (1.6 mL, 11.3 mmol, 4.0 equiv.) and $PhCO_2Ag$ (129.5 mg, 0.6 mmol, 0.2 equiv.) were added. The reaction mixture was heated to 70° C. for 2 hours. The solid was removed by filtration and the filtrate was concentrated under vacuum. The residue was purified by reverse flash chromatography with the following conditions: column, C18 silica gel; mobile phase, ACN in water, 10% to 100% gradient in 20 min; detector, UV 254 nm. This gave {3-phenylbicyclo[1.1.1]pentan-1-yl}acetic acid (330.0 mg) as a yellow solid. LCMS Method B: $[M-H]^-=201$.

Step 4: 2-{3-phenylbicyclo[1.1.1]pentan-1-yl}ethanol

{3-Phenylbicyclo[1.1.1]pentan-1-yl}acetic acid (300.0 mg, 1.5 mmol, 1.0 equiv.) was dissolved in THE (10 mL) and cooled to 0° C., then $BH_3$·THF (1M, 1.5 mL, 1.5 mmol, 3.0 equiv.) was added dropwise. The reaction mixture was stirred for 2 hours at ambient temperature, then concentrated under vacuum. The residue was diluted with of water, extracted with ethyl acetate and concentrated under vacuum. The residue was purified by reverse flash chromatography with the following conditions: column, C18 silica gel; mobile phase, ACN in water, 10% to 100% gradient in 20 min; detector, UV 254 nm. This gave 2-{3-phenylbicyclo[1.1.1]pentan-1-yl}ethanol (130.0 mg) as a pale yellow solid. LCMS Method A: $[M+H]^+=189$.

Scheme 36: Synthesis of intermediate 70 (2-(1-(5-(trifluoromethyl)pyridin-2-yl)piperidin-4-yl)ethan-1-ol)

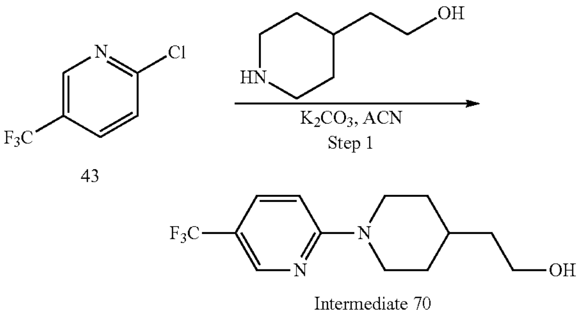

43

Intermediate 70

2-Chloro-5-(trifluoromethyl)pyridine (1.0 g, 5.5 mmol, 1.0 equiv.) was dissolved in ACN (10 mL), then 2-(piperidin-4-yl)ethan-1-ol (850 mg, 6.6 mmol, 1.2 equiv.) and $K_2CO_3$ (1.5 g, 11.0 mmol, 2.0 equiv.) were added. The reaction mixture was heated to 70° C. for 2 hours, then cooled to ambient temperature and quenched by the addition of water. Then resulting solution was extracted with ethyl acetate, washed with brine, dried over anhydrous sodium sulfate and concentrated under vacuum. The residue was purified by flash column chromatography on silica gel, eluting with dichloromethane/MeOH (10:1) to give 2-(1-(5-(trifluoromethyl)pyridin-2-yl)piperidin-4-yl)ethan-1-ol (980 mg) as a white solid. LCMS Method A: $[M+H]^+=275$.

Scheme 37: Synthesis of intermediate 71 (2-(6-(4,4-difluoropiperidin-1-yl)-5-fluoropyridin-3-yl)ethan-1-ol)

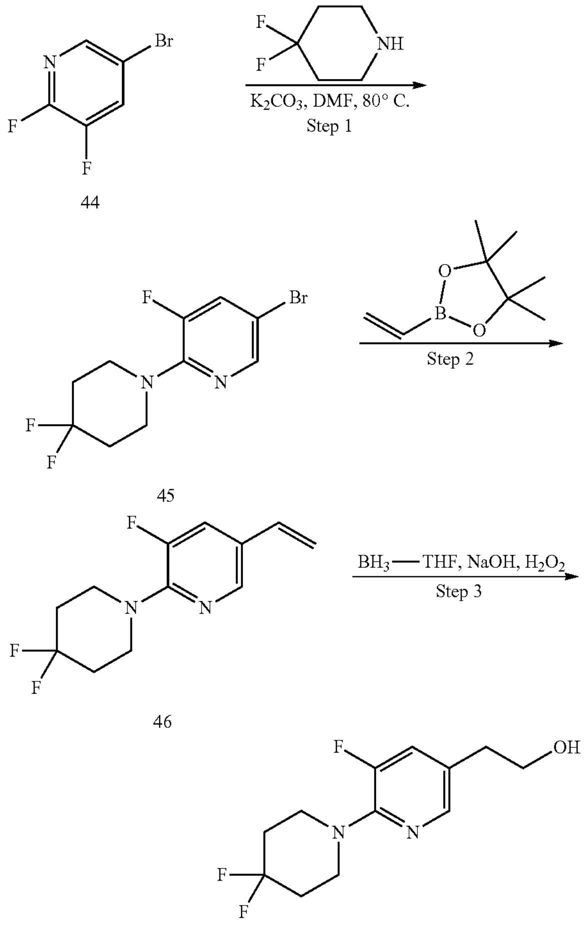

44

45

46

Intermediate 71

Step 1: 5-bromo-2-(4,4-difluoropiperidin-1-yl)-3-fluoropyridine

5-Bromo-2,3-difluoropyridine (4.0 g, 20.6 mmol, 1.0 equiv.) and 4,4-difluoropiperidine (2.7 g, 22.7 mmol, 1.1 equiv.) were dissolved in DMF (20 mL), then $K_2CO_3$ (5.7 g, 41.2 mmol, 2.0 equiv.) was added. The reaction mixture was heated to 80° C. for 2 hours, then cooled to ambient temperature and quenched by the addition of water. The resulting solution was extracted with ethyl acetate, washed with brine, dried over anhydrous sodium sulfate and concentrated under vacuum. The residue was purified by flash column chromatography on silica gel, eluting with ethyl acetate/petroleum ether (1:9) to give 5-bromo-2-(4,4-difluoropiperidin-1-yl)-3-fluoropyridine (4.5 g) as a yellow solid. LCMS Method A: $[M+H]^+=295$.

Step 2: 2-(4,4-difluoropiperidin-1-yl)-3-fluoro-5-vinylpyridine

5-Bromo-2-(4,4-difluoropiperidin-1-yl)-3-fluoropyridine (3.0 g, 10.2 mmol, 1.0 equiv.) and 2-ethenyl-4,4,5,5-tetramethyl-1,3,2-dioxaborolane (1.9 g, 12.2 mmol, 1.2 equiv.) were dissolved in 1,4-dioxane (30 mL), then Pd(dppf)$Cl_2$·$CH_2Cl_2$ (0.4 g, 0.5 mmol, 0.05 equiv.) and $Cs_2CO_3$ (6.6 g, 20.3 mmol, 2.0 equiv.) were added under an atmosphere of nitrogen. The reaction mixture was heated to 80° C. for 4 hours, then cooled to ambient temperature and quenched by the addition of water. The resulting solution was extracted with ethyl acetate, washed with brine, dried over anhydrous sodium sulfate and concentrated under vacuum. The residue was purified by flash column chromatography on silica gel, eluting with ethyl acetate/petroleum ether (1:7) to give 2-(4,4-difluoropiperidin-1-yl)-3-fluoro-5-vinylpyridine (1.1 g) as a yellow oil. LCMS Method A: $[M+H]^+=243$.

Step 3: 2-(6-(4,4-difluoropiperidin-1-yl)-5-fluoropyridin-3-yl)ethan-1-ol 2-(4,4-Difluoropiperidin-1-yl)-3-fluoro-5-vinylpyridine (1.0 g, 4.1 mmol, 1.0 equiv.) was dissolved in THE and cooled to 0° C., then $BH_3$-THF (1M, 16.5 mL, 16.5 mmol, 4.0 equiv.) was added dropwise, maintaining the solution at 0° C. The reaction mixture was stirred for 1 hour at ambient temperature. Then a solution of aqueous NaOH (1 M, 2.9 mL, 2.9 mmol, 0.7 equiv.) was added and the reaction mixture was cooled to 0° C. This was followed by the dropwise addition of $H_2O_2$ (30% wt./wt. in water, 4.8 mL, 7.2 mmol, 1.8 equiv.), maintaining the reaction mixture at 0° C. The reaction mixture was stirred for additional 1 hour at ambient temperature, then quenched by the addition of saturated aqueous $NH_4Cl$. The resulting solution was extracted with ethyl acetate, washed with brine, dried over anhydrous $Na_2SO_4$ and concentrated under vacuum. The residue was purified by flash column chromatography on silica gel, eluting with dichloromethane/MeOH (10:1) to give 2-(6-(4,4-difluoropiperidin-1-yl)-5-fluoropyridin-3-yl)ethan-1-ol (880.0 mg) as a white solid. LCMS Method A: $[M+H]^+=261$.

The intermediates in the following table were prepared using the same method described for Intermediate 71.

-continued

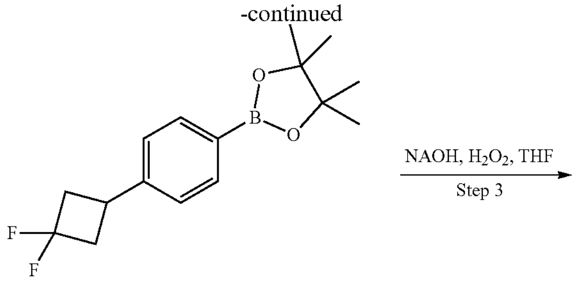

49

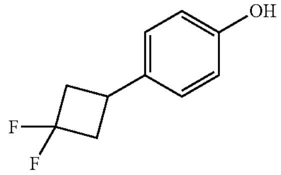

Intermediate 73

Step 1: 1-bromo-4-(3,3-difluorocyclobutyl)benzene 3-(4-Bromophenyl)cyclobutan-1-one (1.0 g, 4.4 mmol, 1.0 equiv.) was dissolved in DCM (20 mL) and cooled to 0° C., then DAST (2.2 g, 13.3 mmol, 3.0 equiv.) was added dropwise, maintaining the solution at 0° C. The reaction mixture was stirred for 4 hours at 40° C., then cooled to 0° C. and quenched by the addition of water. The resulting solution was extracted with ethyl acetate, washed with brine, dried over anhydrous $Na_2SO_4$ and concentrated under vacuum. The residue was purified by flash column chromatography on silica gel, eluting with ethyl acetate/petroleum ether (1:5) to give 1-bromo-4-(3,3-difluorocyclobutyl)benzene (870.0 mg) as a colorless oil. $^1H$ NMR (400 MHz, DMSO-$d_6$) δ 7.53 (d, J=8.4 Hz, 2H), 7.29 (d, J=8.2 Hz, 2H), 3.47-3.35 (m, 1H), 3.08-2.90 (m, 2H), 2.74-2.57 (m, 2H).

| Intermediate | Starting material | Structure | LCMS data |
|---|---|---|---|
| Intermediate 72 | 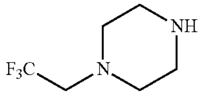 | 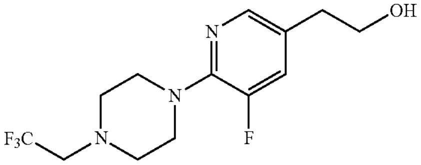 [SMILES: OCCc1cnc(N2CCN(CC(F)(F)F)CC2)c(F)c1] | Method A: MS-ESI: 308 $[M + H]^+$ |

Scheme 38: Synthesis of intermediate 73 (4-(3,3-difluorocyclobutyl)phenol)

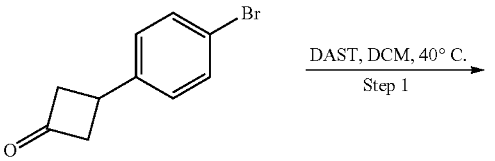

47

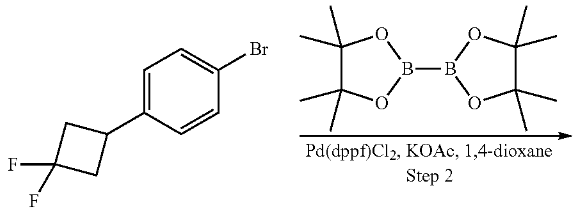

48

Step 2: 2-(4-(3,3-difluorocyclobutyl)phenyl)-4,4,5,5-tetramethyl-1,3,2-dioxaborolane 1-Bromo-4-(3,3-difluorocyclobutyl)benzene (800.0 mg, 3.2 mmol, 1.0 equiv.) was dissolved in 1,4-dioxane (150 mL), then 4,4,4',4',5,5,5',5'-octamethyl-2,2'-bi(1,3,2-dioxaborolane) (1.2 g, 4.9 mmol, 1.5 equiv.), Pd(dppf)$Cl_2$ (236.9 mg, 0.3 mmol, 0.1 equiv.) and KOAc (635.5 mg, 6.5 mmol, 2.0 equiv.) were added under an atmosphere of nitrogen. The reaction mixture was heated to 90° C. for 4 hours, then cooled to ambient temperature and concentrated under vacuum. The residue was purified by flash column chromatography on silica gel, eluting with ethyl acetate/petroleum ether (1:5) to give 2-(4-(3,3-difluorocyclobutyl)phenyl)-4,4,5,5-tetramethyl-1,3,2-dioxaborolane (805.0 mg) as a colorless oil. LCMS Method A: $[M+H]^+=295$.

Step 3: 4-(3,3-difluorocyclobutyl)phenol 2-(4-(3,3-Difluorocyclobutyl)phenyl)-4,4,5,5-tetramethyl-1,3,2-dioxaborolane (800.0 mg, 2.7 mmol, 1.0 equiv.) was dissolved in THE (20 mL) and cooled to 0° C., then aqueous NaOH (2% wt./wt., 10 mL, 5.0 mmol, 2.0 equiv.) and $H_2O_2$ (30% wt./wt., 1.0 mL, 8.8 mmol, 3.0 equiv.) were added dropwise. The reaction mixture was stirred for additional 2 hours at ambient temperature, then quenched by the addition of saturated $NH_4C_1$ aqueous. The mixture was extracted with ethyl acetate and concentrated under vacuum. The residue was purified by flash column chromatography on silica gel, eluting with ethyl acetate/petroleum ether (1:5) to give 4-(3,3-difluorocyclobutyl)phenol (320.0 mg) as a colorless oil. LCMS Method B: $[M-H]^+=183$.

Scheme 39: Synthesis of intermediate 74 (4-(tetrahydro-2H-pyran-4-yl)phenol)

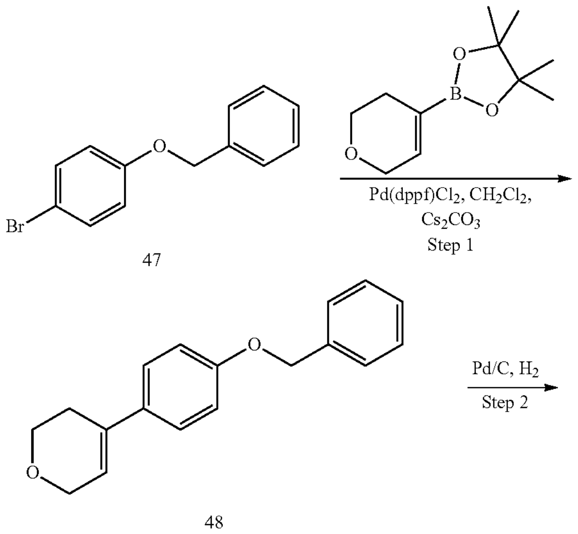

-continued

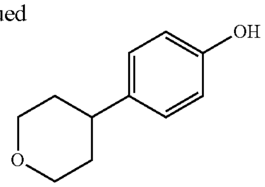

Intermediate 74

Step 1: 4-[4-(benzyloxy)phenyl]-3,6-dihydro-2H-pyran 1-(Benzyloxy)-4-bromobenzene (1.0 g, 3.8 mmol, 1.0 equiv) was dissolved in 1,4-dioxane (10 mL), then 2-(3,6-dihydro-2H-pyran-4-yl)-4,4,5,5-tetramethyl-1,3,2-dioxaborolane (1.2 g, 5.7 mmol, 1.5 equiv.), $Cs_2CO_3$ (2.5 g, 7.6 mmol, 2.0 equiv.) and $Pd(dppf)Cl_2CH_2Cl_2$ (309.0 mg, 0.4 mmol, 0.1 equiv.) were added under an atmosphere of nitrogen. The reaction mixture was heated to 90° C. for 6 hours, then cooled to ambient temperature and concentrated under vacuum. The residue was purified by flash column chromatography on silica gel, eluting with ethyl acetate/petroleum ether (1:8) to give 4-[4-(benzyloxy)phenyl]-3,6-dihydro-2H-pyran (712.0 mg) as a yellow solid. LCMS Method A: $[M+H]^+=267$.

Step 2: 4-(oxan-4-yl)phenol

4-[4-(Benzyloxy)phenyl]-3,6-dihydro-2H-pyran (500.0 mg, 1.9 mmol, 1.0 equiv.) was dissolved in EtOH (10 mL), then Pd/C (10% wt., 50.0 mg) was added under an atmosphere of nitrogen. The mixture was sparged with nitrogen, placed under an atmosphere of hydrogen gas (balloon), then stirred for 5 hours at ambient temperature. The solids were removed by filtration and the filtrate was concentrated under vacuum. The residue was purified by flash column chromatography on silica gel, eluting with ethyl acetate/petroleum ether (1:5) to give 4-(oxan-4-yl)phenol (150.0 mg) as a pale yellow solid. LCMS Method B: $[M-H]^-=177$.

The intermediates in the following table were prepared using the same method described for Intermediate 74.

| Intermediate | Starting material | Structure | LCMS data |
|---|---|---|---|
| Intermediate 75 | 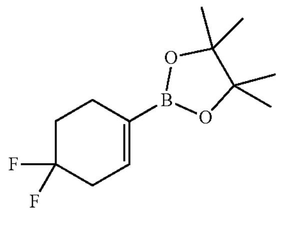 | 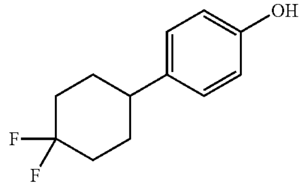 [SMILES: Oc1ccc(C2CCC(F)(F)CC2)cc1] | Method C: MS-ESI: 213 $[M + H]^+$ |
| Intermediate 76 | 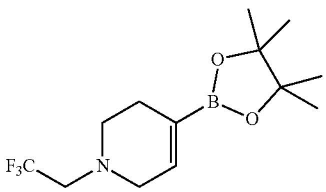 | 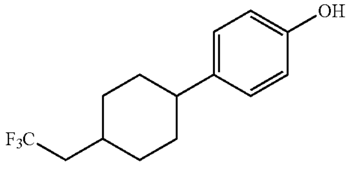 [SMILES: Oc1ccc(C2CCC(CC(F)(F)F)CC2)cc1] | Method C: MS-ESI: 260 $[M + H]^+$ |

Scheme 40: Synthesis of intermediate 77 (2-(4-methyl-1-(2,2,2-trifluoroethyl)piperidin-4-yl)phenol)

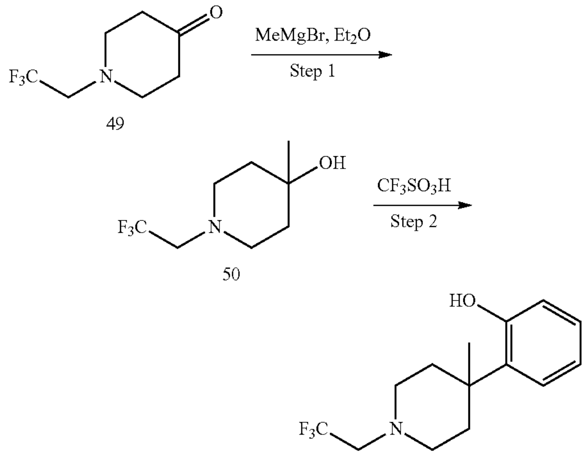

49

50

Intermediate 77

Step 1: 4-methyl-1-(2,2,2-trifluoroethyl)piperidin-4-ol 1-(2,2,2-Trifluoroethyl)piperidin-4-one (1.0 g, 5.5 mmol, 1.0 equiv.) was dissolved in $Et_2O$ (40 mL) and cooled to −55° C., then MeMgBr (1M in THF, 11.0 mL, 11.0 mmol, 2.0 equiv.) was added dropwise, maintaining the solution at −5° C. The reaction mixture was stirred for 4 hours at ambient temperature, then quenched by the addition of saturated aqueous $NH_4Cl$ at 0° C. The resulting solution was extracted with ethyl acetate, washed with brine, dried over anhydrous $Na_2SO_4$ and concentrated under vacuum to give 4-methyl-1-(2,2,2-trifluoroethyl)piperidin-4-ol (1.0 g) as a pale yellow oil. LCMS Method A: $[M+H]^+$=198.

Step 2: 2-[4-methyl-1-(2,2,2-trifluoroethyl)piperidin-4-yl]phenol

4-Methyl-1-(2,2,2-trifluoroethyl)piperidin-4-ol (600.0 mg, 3.0 mmol, 1.0 equiv.) was dissolved in $CF_3SO_3H$ (5 mL), then phenol (859.0 mg, 9.1 mmol, 3.0 equiv.) was added. The reaction mixture was stirred overnight at ambient temperature and then quenched by the addition of ice-water. The resulting solution was extracted with ethyl acetate, washed with brine, dried over anhydrous $Na_2SO_4$ and concentrated under vacuum. The residue was purified by reverse flash chromatography with the following conditions: column, silica gel; mobile phase, ACN in water, 10% to 100% gradient in 15 min; Detector, UV 254 nm. This gave 2-[4-methyl-1-(2,2,2-trifluoroethyl)piperidin-4-yl]phenol (170.0 mg) as a pale yellow oil. LCMS Method A: $[M+H]^+$=274.

Scheme 41: Synthesis of intermediate 78 (4-(4-methyl-1-(2,2,2-trifluoroethyl)piperidin-4-yl)phenol)

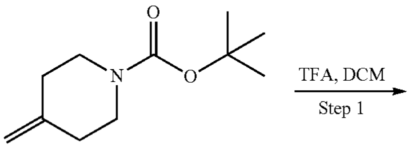

51

-continued

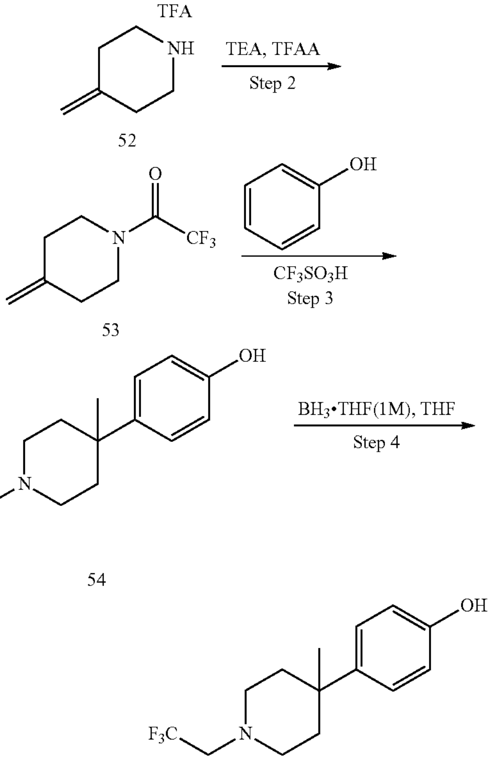

52

53

54

Intermediate 78

Step 1: 4-methylidenepiperidine TFA salt tert-Butyl 4-methylidenepiperidine-1-carboxylate (2.0 g, 10.1 mmol, 1.0 equiv.) was dissolved in DCM (40 mL), then TFA (3.1 mL, 40.6 mmol, 4.0 equiv.) was added. The reaction mixture was stirred for 1 hour at ambient temperature, then concentrated under vacuum to give 4-methylidenepiperidine TFA as a yellow solid, which was used in the next step directly without further purification. LCMS Method A: $[M+H]^+$=98.

Step 2: 2,2,2-trifluoro-1-(4-methylenepiperidin-1-yl)ethan-1-one

4-Methylidenepiperidine (1.0 g, 10.3 mmol, 1.0 equiv.) and TEA (2.9 mL, 20.6 mmol, 2.0 equiv.) were dissolved in ACN (10 mL), then TFAA (2.9 mL, 20.6 mmol, 2.0 equiv.) was added dropwise. The reaction mixture was heated to 80° C. for 2 hours, then cooled to ambient temperature and quenched by the addition of water. The resulting solution was extracted with ethyl acetate, washed with brine, dried over anhydrous $Na_2SO_4$ and concentrated under vacuum to give 2,2,2-trifluoro-1-(4-methylidenepiperidin-1-yl)ethanone (710.0 mg) as a colorless oil. LCMS Method A: $[M+H]^+$=194.

Step 3: 2,2,2-trifluoro-1-[4-(4-hydroxyphenyl)-4-methylpiperidin-1-yl]ethanone 2,2,2-Trifluoro-1-(4-methylidenepiperidin-1-yl)ethanone (700.0 mg, 3.6 mmol, 1.0 equiv.) was dissolved in $CF_3SO_3H$ (10 mL), then phenol (1.0 g, 10.9 mmol, 3.0 equiv.) was added. The reaction mixture was stirred overnight at ambient temperature, then quenched by the addition of ice-water. The resulting solution was adjusted to pH 6 with aqueous NaOH (20% wt./wt), extracted with ethyl acetate, washed with brine, dried over anhydrous $Na_2SO_4$ and concentrated under vacuum. The residue was purified by reverse flash chromatography with the following conditions: column, silica gel; mobile phase, MeCN in water, 5% to 100% gradient in 25 min; detector, UV 254 nm. This gave 2,2,2-trifluoro-1-[4-(4-hydroxyphenyl)-4-methylpiperidin-1-yl]ethanone (180.0 mg) as a yellow oil. LCMS Method B: $[M-H]^-=286$.

Step 4: 4-[4-methyl-1-(2,2,2-trifluoroethyl)piperidin-4-yl]phenol 2,2,2-Trifluoro-1-[4-(4-hydroxyphenyl)-4-methylpiperidin-1-yl]ethanone (180.0 mg, 0.6 mmol, 1.0 equiv.) was dissolved in THE (15 mL) and cooled to 0° C., then $BH_3 \cdot THF$ (1M, 2.5 mL, 2.5 mmol, 4.0 equiv.) was added dropwise. The reaction mixture was heated to 70° C. for 1 hour, then cooled to 0° C. and quenched by the addition of MeOH. The resulting solution was concentrated under vacuum and the residue was purified by flash column chromatography on silica gel, eluting with ethyl acetate/petroleum ether (1:8) to give 4-[4-methyl-1-(2,2,2-trifluoroethyl)piperidin-4-yl]phenol (150.0 mg) as a light yellow oil. LCMS Method B: $[M-H]^-=272$.

Scheme 42: Synthesis of intermediate 79 (2-(4-(trifluoromethyl)-1H-pyrazol-1-yl)ethan-1-ol)

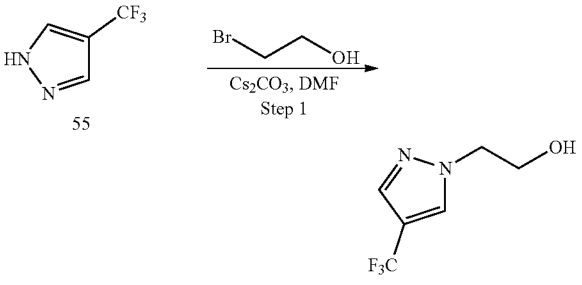

55

Intermediate 79

4-(Trifluoromethyl)-1H-pyrazole (500.0 mg, 3.7 mmol, 1.0 equiv.) and 2-bromoethanol (918.3 mg, 7.3 mmol, 2.0 equiv.) were dissolved in DMF (5 mL), then $Cs_2CO_3$ (2.4 g, 7.3 mmol, 2.0 equiv.) was added. The reaction mixture was stirred for 2 hours at ambient temperature, then concentrated under vacuum. The residue was purified by reverse flash chromatography with the following conditions: column, C18 silica gel; mobile phase, ACN in Water (10 mM $NH_4HCO_3$), 10% ACN to 50% gradient in 10 min; detector, UV 254 nm. This gave 2-[4-(trifluoromethyl)pyrazol-1-yl]ethanol (310.0 mg) as a pale yellow oil. LCMS Method A: $[M+H]^+=181$.

Scheme 43: Synthesis of intermediate 80 (2-(3-trifluoromethyl)-1H-pyrazol-1-yl)ethan-1-ol)

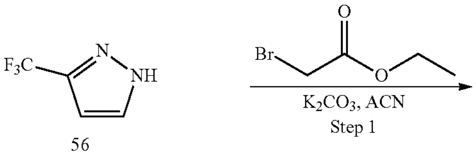

56

-continued

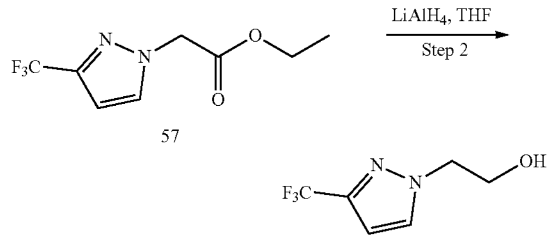

57

Intermediate 80

Step 1: ethyl 2-[3-(trifluoromethyl)pyrazol-1-yl]acetate 3-(Trifluoromethyl)-1H-pyrazole (2.0 g, 14.7 mmol, 1.0 equiv.) was dissolved in ACN (20 mL), then $K_2CO_3$ (4.1 g, 29.4 mmol, 2.0 equiv.) and ethyl bromoacetate (2.5 g, 14.7 mmol, 1.0 equiv.) were added. The reaction mixture was heated to 60° C. for 6 hours, then cooled to ambient temperature and quenched by the addition of water. The resulting solution was extracted with ethyl acetate, washed with brine, dried over anhydrous $Na_2SO_4$ and concentrated under vacuum. The residue was purified by flash column chromatography on silica gel, eluting with ethyl acetate/petroleum ether (1:5) to give ethyl 2-[3-(trifluoromethyl)pyrazol-1-yl]acetate (1.8 g) as a yellow solid. LCMS Method A: $[M+H]^+=223$.

Step 2: 2-[3-(trifluoromethyl)pyrazol-1-yl]ethanol

Ethyl 2-[3-(trifluoromethyl)pyrazol-1-yl]acetate (800.0 mg, 3.6 mmol, 1.0 equiv.) was dissolved in THE (10 mL) and cooled to 0° C., then $LiAlH_4$ (164.0 mg, 4.3 mmol, 1.2 equiv.) was added. The reaction mixture was stirred for 2 hours at 0° C. and then quenched by the addition of saturated aqueous sodium hyposulfite. The solid was removed by filtration, and the filtrate was concentrated under vacuum to give 2-[3-(trifluoromethyl)pyrazol-1-yl]ethanol (560.0 mg) as a yellow oil, which was used in the next step directly without further purification. LCMS Method A: $[M+H]^+=181$.

Scheme 44: Synthesis of intermediate 81 (tert-butyl 3-acetamido-5-(2-aminoethyl)-1H-indole-1-carboxylate)

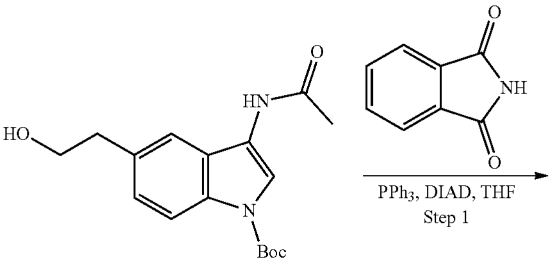

Intermediate 11

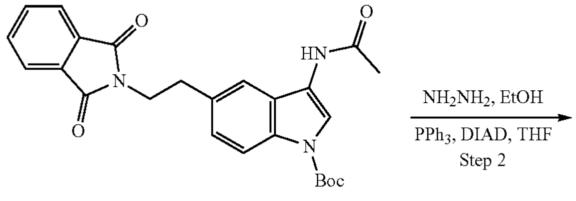

58

-continued

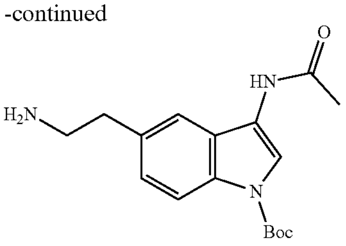

Intermediate 81

Step 1: tert-butyl 5-(hydroxymethyl)-3-(2-(methylamino)-2-oxoacetamido)-1H-indole-1-carboxylate tert-Butyl 3-acetamido-5-(2-hydroxyethyl)indole-1-carboxylate (300.0 mg, 0.9 mmol, 1.0 equiv.) was dissolved in THE (3 mL), then phthalimide (277.3 mg, 1.9 mmol, 2.0 equiv.) and $PPh_3$ (494.3 mg, 1.9 mmol, 2.0 equiv.) were added. The reaction mixture was cooled to 0° C., then DIAD (381.1 mg, 1.9 mmol, 2.0 equiv.) was added dropwise, maintaining the solution at 0° C. The reaction mixture was stirred for 6 hours at ambient temperature, then quenched by the addition of water. The resulting solution was extracted with ethyl acetate, washed with brine, dried over anhydrous $Na_2SO_4$ and concentrated under vacuum. The residue was purified by flash column chromatography on silica gel, eluting with ethyl acetate/petroleum ether (1:1) to give tert-butyl 5-[2-(1,3-dioxoisoindol-2-yl)ethyl]-3-acetamidoindole-1-carboxylate (340.0 mg) as a brown solid. LCMS Method A: $[M+H]^+$=448.

Step 2: tert-butyl 5-(2-aminoethyl)-3-acetamidoindole-1-carboxylate tert-Butyl 5-[2-(1,3-dioxoisoindol-2-yl)ethyl]-3-acetamidoindole-1-carboxylate (310.0 mg, 0.7 mmol, 1.0 equiv.) was dissolved in EtOH (3.5 mL), then hydrazine (44.4 mg, 1.4 mmol, 2.0 equiv.) was added. The reaction mixture was stirred for 5 hours at ambient temperature, then quenched by the addition of water. The resulting solution was extracted with ethyl acetate, washed with brine, dried over anhydrous $Na_2SO_4$ and concentrated under vacuum to give crude tert-butyl 5-(2-aminoethyl)-3-acetamidoindole-1-carboxylate (280.0 mg) as brown solid. LCMS Method A: $[M+H]^+$=318. The intermediate in the following table were prepared using the same method described for Intermediate 81.

| Intermediate | Starting material | Structure | LCMS data |
|---|---|---|---|
| Intermediate 82 | 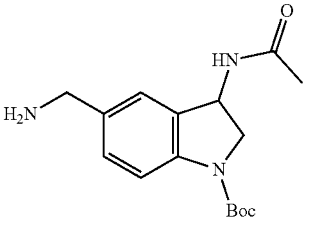 Intermediate 13 | 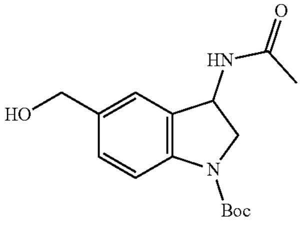 | Method A: MS-ESI: 304 $[M + H]^+$ |

Scheme 45: Synthesis of intermediate 83 (tributyl({[4-trifluoromethyl) pheny] methoxy} methyl)stannane)

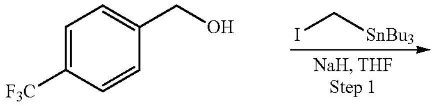

59

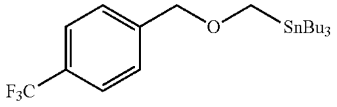

Intermediate 83

[4-(Trifluoromethyl)phenyl]methanol (5.0 g, 28.4 mmol, 1.0 equiv.) was dissolved in THE (50 mL) and cooled to 0° C., then NaH (60% wt., 1.4 g, 34.1 mmol, 1.2 equiv.) was added. After 30 min at 0° C., tributyl(iodomethyl)stannane (13.4 g, 31.2 mmol, 1.1 equiv.) was added. The reaction mixture was stirred for an additional 4 hours at ambient temperature, then cooled to 0° C. and quenched by the addition of MeOH. The resulting solution was concentrated under vacuum. The residue was purified by flash column chromatography on silica gel, eluting with dichloromethane/petroleum ether (5:1) to give tributyl({[4-(trifluoromethyl) phenyl]methoxy}methyl)stannane (9.5 g) as a colorless oil. LCMS Method A: $[M+H]^+$=481.

Scheme 46: Synthesis of intermediate 85 (5-(trans-3-(4-(trifluoromethyl)phenyl)cyclobutoxy)-1H-indol-3-amine TFA salt)

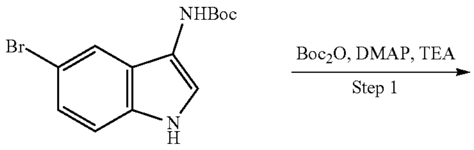

3

-continued

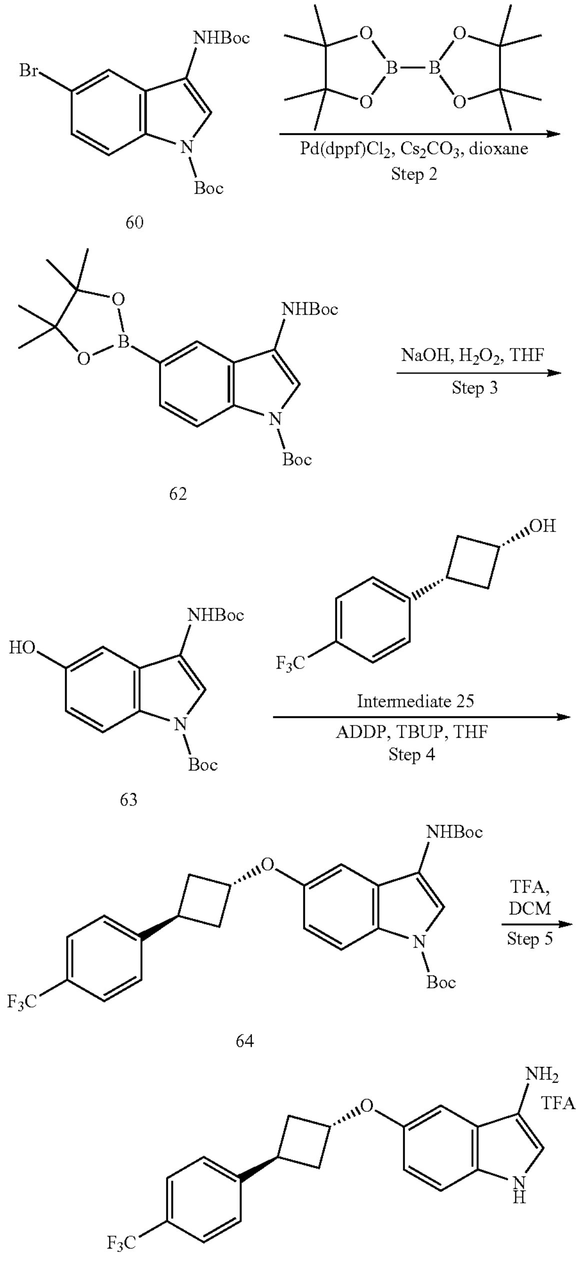

60

62

63

64

Intermediate 85

Step 1: tert-butyl 5-bromo-3-((tert-butoxycarbonyl) amino)-1H-indole-1-carboxylate tert-Butyl (5-bromo-1H-indol-3-yl)carbamate (5.0 g, 16.1 mmol, 1.0 equiv.) was dissolved in THE (80.0 mL), then $(Boc)_2O$ (4.2 g, 19.3 mmol, 1.2 equiv.), DMAP (0.2 g, 1.6 mmol, 0.1 equiv.) and TEA (4.6 mL, 32.1 mmol, 2.0 equiv.) were added. The reaction mixture was stirred for 4 hours at ambient temperature, then concentrated under vacuum. The residue was purified by flash column chromatography on silica gel, eluting with ethyl acetate/petroleum ether (1:5) to give tert-butyl 5-bromo-3-((tert-butoxycarbonyl)amino)-1H-indole-1-carboxylate (6.5 g) as a white solid.

Step 2: tert-butyl 3-((tert-butoxycarbonyl)amino)-5-(4,4,5,5-tetramethyl-1,3,2-dioxaborolan-2-yl)-1H-indole-1-carboxylate tert-Butyl 5-bromo-3-((tert-butoxycarbonyl)amino)-1H-indole-1-carboxylate (6.0 g, 14.6 mmol, 1.0 equiv.) was dissolved in 1,4-dioxane (100.0 mL), then 4,4,4',4',5,5,5',5'-octamethyl-2,2'-bi(1,3,2-dioxaborolane) (5.6 g, 21.9 mmol, 1.5 equiv.), $Pd(dppf)Cl_2$ (1.1 g, 1.5 mmol, 0.1 equiv.) and $Cs_2CO_3$ (9.5 g, 29.2 mmol, 2.0 equiv.) were added under an atmosphere of nitrogen. The reaction mixture was stirred overnight at 90° C. under nitrogen, then cooled to ambient temperature and concentrated under vacuum. The residue was purified by flash column chromatography on silica gel, eluting with ethyl acetate/petroleum ether (1:4) to give tert-butyl 3-((tert-butoxycarbonyl)amino)-5-(4,4,5,5-tetramethyl-1,3,2-dioxaborolan-2-yl)-1H-indole-1-carboxylate (6.0 g) as a white solid.

Step 3: tert-butyl 3-((tert-butoxycarbonyl)amino)-5-hydroxy-1H-indole-1-carboxylate tert-Butyl 3-((tert-butoxycarbonyl)amino)-5-(4,4,5,5-tetramethyl-1,3,2-dioxaborolan-2-yl)-1H-indole-1-carboxylate (6.0 g, 13.1 mmol, 1.0 equiv.) was dissolved in THE (80.0 mL) and cooled to 0° C. Then NaOH (1.6 g, 39.3 mmol, 3.0 equiv.) was added at 0° C., followed by the dropwise addition of $H_2O_2$ (30% w.t/wt/, 3.0 g, 26.2 mmol, 2.0 equiv), maintaining the reaction mixture at 0° C. The reaction mixture was stirred for 2 hours at ambient temperature, then quenched by the addition of brine. The resulting resolution was extracted with ethyl acetate, washed with brine, dried over anhydrous $Na_2SO_4$ and concentrated under vacuum. The residue was purified by flash column chromatography on silica gel, eluting with ethyl acetate/petroleum ether (1:1) to give tert-butyl 3-((tert-butoxycarbonyl) amino)-5-hydroxy-1H-indole-1-carboxylate (2.2 g) as a grey solid.

Step 4: tert-butyl 3-((tert-butoxycarbonyl)amino)-5-(trans-3-(4-(trifluoromethyl)phenyl)cyclobutoxy)-1H-indole-1-carboxylate tert-Butyl 3-((tert-butoxycarbonyl)amino)-5-hydroxy-1H-indole-1-carboxylate (1.0 g, 2.9 mmol, 1.0 equiv.) and cis-3-(4-(trifluoromethyl)phenyl)cyclobutan-1-ol (1.2 g, 5.7 mmol, 2.0 equiv.) were dissolved in THE (20.0 mL) and cooled to 0° C., then TBUP (1.7 g, 8.6 mmol, 3.0 equiv.) was added at 0° C. under an atmosphere of nitrogen. This was followed by the dropwise addition of ADDP (2.2 g, 8.6 mmol, 3.0 equiv.), maintaining the solution at 0° C. The reaction mixture was heated to 50° C. for 2 hours, then cooled to ambient temperature and concentrated under vacuum. The residue was purified by reverse flash chromatography with the following conditions: column, C18 silica gel; mobile phase A: 0.05% $NH_4HCO_3$ in water; mobile phase B: Acetonitrile, 45% phase B to 70% gradient in 20 min; detector, UV 254 nm. This gave tert-butyl 3-((tert-butoxycarbonyl)amino)-5-(trans-3-(4-(trifluoromethyl)phenyl)cyclobutoxy)-1H-indole-1-carboxylate (1.2 g) as an off-white solid.

Step 5: 5-(trans-3-(4-(trifluoromethyl)phenyl)cyclobutoxy)-1H-indol-3-amine TFA salt tert-Butyl 3-((tert-butoxycarbonyl)amino)-5-(trans-3-(4-(trifluoromethyl)phenyl)cyclobutoxy)-1H-indole-1-carboxylate (190.0 mg, 0.3 mmol, 1.0 equiv.) was dissolved in DCM (2.0 mL), then TFA (2.0 mL) was added. The resulting mixture was stirred for 1 hour at ambient temperature and then concentrated under vacuum to give 5-(trans-3-(4-(trifluoromethyl)phenyl)cyclobutoxy)-1H-indol-3-amine TFA salt (120.0 mg) as a white solid. LCMS Method A: $[M+H]^+$= 347.

The intermediates in the following table were prepared using the same method described for Intermediate 85.

| Intermediate | Starting material | Structure | LCMS data |
|---|---|---|---|
| Intermediate 86 | 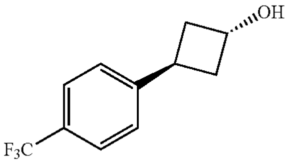 Intermediate 26 | 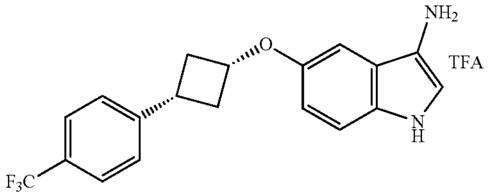 [SMILES: Nc1c[nH]c2ccc(O[C@H]3C[C@@H](c4ccc(C(F)(F)F)cc4)C3)cc12] | Method A: MS-ESI: 347 $[M + H]^+$ |
| Intermediate 87 | 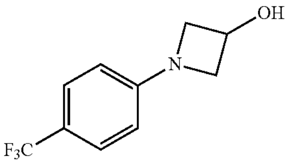 Intermediate 60 | 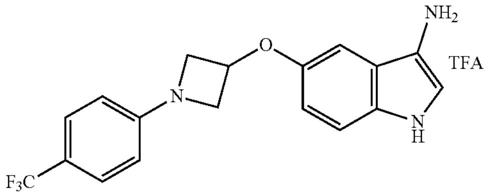 | Method A: MS-ESI: 348 $[M + H]^+$ |
| Intermediate 88 | 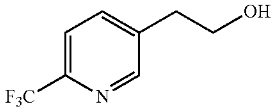 Intermediate 61 | 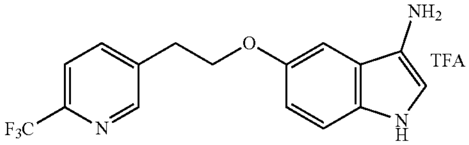 [SMILES: Nc1c[nH]c2ccc(OCCc3ccc(C(F)(F)F)nc3)cc12] | Method C: MS-ESI: 322 $[M + H]^+$ |
| Intermediate 89 | 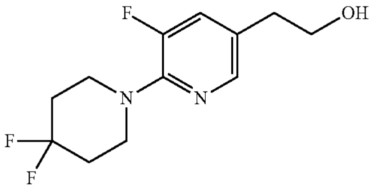 Intermediate 71 | 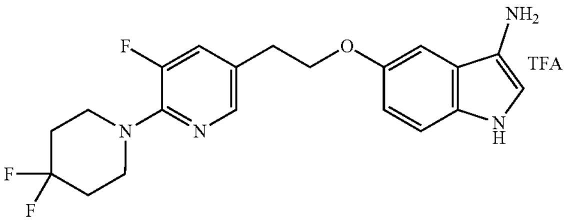 [SMILES: Nc1c[nH]c2ccc(OCCc3cnc(N4CCC(F)(F)CC4)c(F)c3)cc12] | Method C: MS-ESI: 391 $[M + H]^+$ |
| Intermediate 90 | 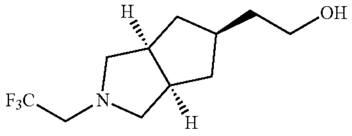 Intermediate 64 | 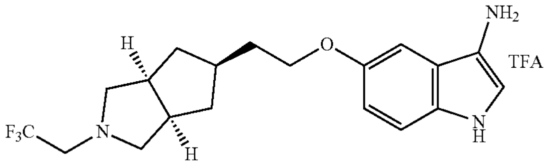 [SMILES: Nc1c[nH]c2ccc(OCC[C@@H]3C[C@@H]4CN(CC(F)(F)F)C[C@@H]4C3)cc12] | Method C: MS-ESI: 368 $[M + H]^+$ |
| Intermediate 91 | 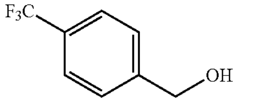 | 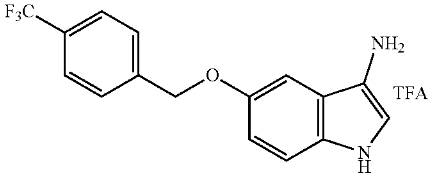 [SMILES: Nc1c[nH]c2ccc(OCc3ccc(C(F)(F)F)cc3)cc12] | Method C: MS-ESI: 307 $[M + H]^+$ |

Scheme 47: Synthesis of intermdiate 92 (5-(2-(4-(trifluoromethyl)phenoxy)ethyl)-1H-indol-3-amine TFA salt)

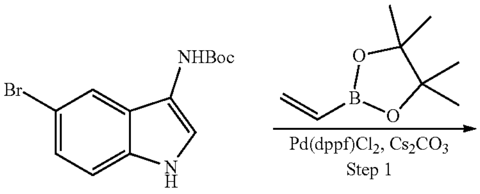

1

-continued

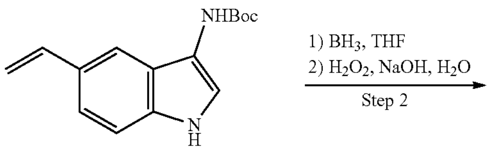

65

-continued

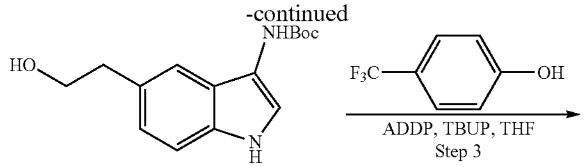

66

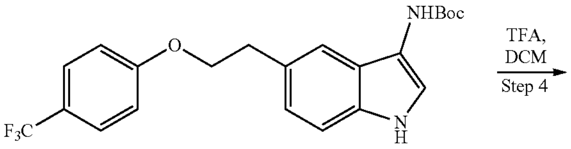

67

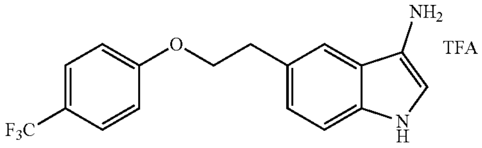

Intermediate 92

Step 1-2: tert-butyl(5-(2-hydroxyethyl)-1H-indol-3-yl)carbamate

The title compound was prepared using the same methods described for Intermediate 48 (Step 1 to 2). LCMS Method A: $[M+H]^+$=277.

Step 3: tert-butyl N-(5-[2-[4-(trifluoromethyl)phenoxy]ethyl]-1H-indol-3-yl)carbamate tert-Butyl N-[5-(2-hydroxyethyl)-1H-indol-3-yl]carbamate (338.0 mg, 1.2 mmol, 1.0 equiv.) and 4-(trifluoromethyl) phenol (198.2 mg, 1.2 mmol, 1.0 equiv.) were dissolved in THE (10 mL), then ADDP (612.4 mg, 2.4 mmol, 2.0 equiv.) and TBUP (494.9 mg, 2.4 mmol, 2.0 equiv.) were added. The reaction mixture was heated to 70° C. for 5 hours, then cooled to ambient temperature and quenched by the addition of water. The resulting solution was extracted with ethyl acetate, washed with brine, dried over anhydrous sodium sulfate and concentrated under vacuum. The residue was purified by flash column chromatography on silica gel, eluting with ethyl acetate/petroleum ether (1:1) to give tert-butyl N-(5-[2-[4-(trifluoromethyl)phenoxy]ethyl]-1H-indol-3-yl)carbamate (260.0 mg) as a brown solid. LCMS Method A: $[M+H]^+$=421.

Step 4: 5-(2-(4-(trifluoromethyl)phenoxy)ethyl)-1H-indol-3-amine TFA salt tert-Butyl N-(5-{2-[4-(trifluoromethyl)phenoxy]ethyl}-1H-indol-3-yl)carbamate (260.0 mg, 0.6 mmol, 1.0 equiv.) was dissolved in DCM (2 mL) and TFA (2 mL). The reaction mixture was stirred for 30 min at ambient temperature then concentrated under vacuum to give 5-(2-(4-(trifluoromethyl) phenoxy)ethyl)-1H-indol-3-amine TFA salt (350.0 mg) as a yellow solid. LCMS Method A: $[M+H]^+$=321.

The intermediates in the following table were prepared using the same method described for Intermediate 92.

| Intermediate | Starting material A | Starting material B | Structure | LCMS data |
|---|---|---|---|---|
| Intermediate 93 | 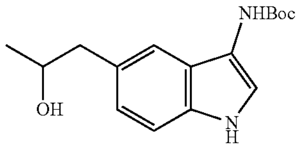 Intermediate 59 | 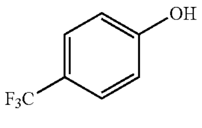 | 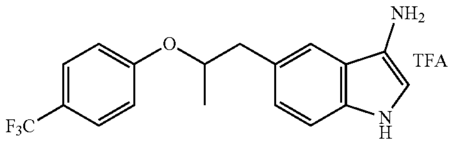 [SMILES: CC(Cc1ccc2[nH]cc(N)c2c1)Oc1ccc(C(F)(F)F)cc1] | Method A: MS-ESI: 335 $[M + H]^+$ |
| Intermediate 94 | 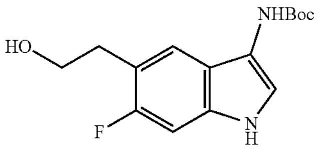 Intermediate 52 | 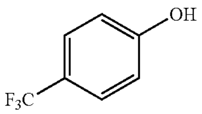 | 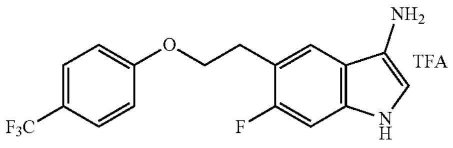 [SMILES: Nc1c[nH]c2cc(F)c(CCOc3ccc(C(F)(F)F)cc3)cc12] | Method C: MS-ESI: 339 $[M + H]^+$ |
| Intermediate 95 | 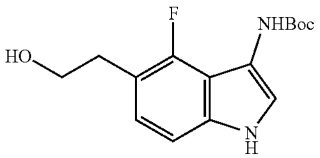 Intermediate 53 | 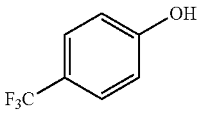 | 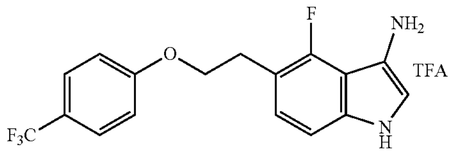 [SMILES: Nc1c[nH]c2ccc(CCOc3ccc(C(F)(F)F)cc3)c(F)c12] | Method C: MS-ESI: 339 $[M + H]^+$ |

Scheme 48: Synthesis of intermediate 96 (7-methyl-5-(4-trifluoromethyl)phenethoxy)-1H-pyrrolo[3,2-b]pyridin-3-amine TFA salt)

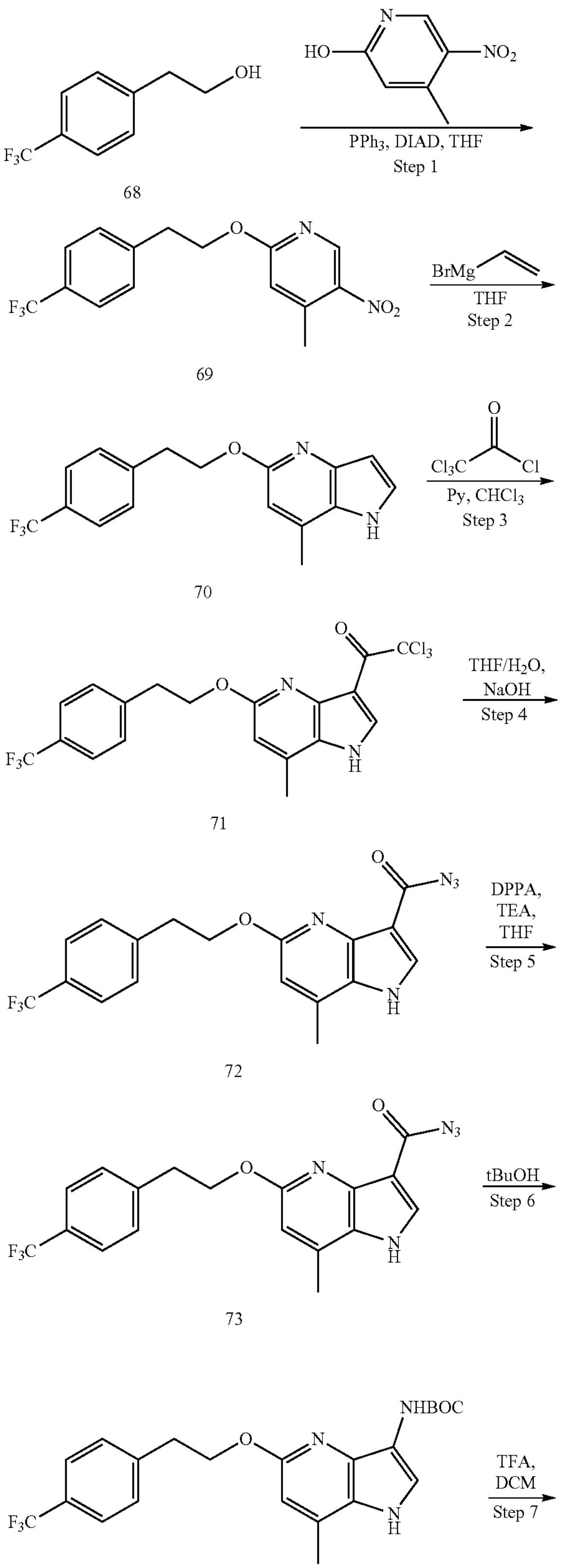

68
69
70
71
72
73
74

-continued

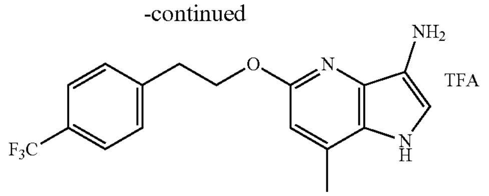

Intermediate 96

Step 1: 4-methyl-5-nitro-2-{2-[4-(trifluoromethyl)phenyl]ethoxy}pyridine

2-[4-(Trifluoromethyl)phenyl]ethanol (5.0 g, 26.3 mmol, 1.0 equiv.) was dissolved in THF (30 mL) and cooled to 0° C., then 4-methyl-5-nitropyridin-2-ol (4.1 g, 26.3 mmol, 1.0 equiv.) and DIAD (10.6 g, 52.6 mmol, 2.0 equiv.) were added. The reaction mixture was stirred for 6 hours at ambient temperature under an atmosphere of nitrogen, then concentrated under vacuum. The residue was purified by flash column chromatography on silica gel, eluting with ethyl acetate/petroleum ether (1:5) to give 4-methyl-5-nitro-2-{2-[4-(trifluoromethyl)phenyl]ethoxy}pyridine (6.2 g) as a pale yellow solid. LCMS Method A: $[M+H]^+=327$.

Step 2: 7-methyl-5-{2-[4-(trifluoromethyl)phenyl]ethoxy}-1H-pyrrolo[3,2-b]pyridine 4-Methyl-5-nitro-2-{2-[4-(trifluoromethyl)phenyl]ethoxy}pyridine (1.0 g, 3.15 mmol, 1.0 equiv.) was dissolved in THE (20 mL) and cooled to −60° C., then bromo(ethenyl)magnesium (1M in THF, 70.0 mL, 70.0 mmol, 22 equiv.) was added dropwise, maintaining the solution at −60° C. under an atmosphere of nitrogen. The reaction mixture was stirred for 8 hours at ambient temperature and then quenched by the addition of saturated aqueous $NH_4Cl$. The resulting solution was extracted with ethyl acetate, washed with brine, dried over anhydrous $Na_2SO_4$ and concentrated under vacuum. The residue was purified by flash column chromatography on silica gel, eluting with ethyl acetate/petroleum ether (1:2) to give 7-methyl-5-{2-[4-(trifluoromethyl)phenyl]ethoxy}-1H-pyrrolo[3,2-b]pyridine (380.0 mg) as a yellow solid. LCMS Method A: $[M+H]^+=321$.

Step 3: 2,2,2-trichloro-1-(7-methyl-5-{2-[4-(trifluoromethyl)phenyl]ethoxy}-1H-pyrrolo[3,2-b]pyridin-3-yl)ethanone 7-Methyl-5-{2-[4-(trifluoromethyl)phenyl]ethoxy}-1H-pyrrolo[3,2-b]pyridine (500.0 mg, 1.6 mmol, 1 equiv.) and Pyridine (246.9 mg, 3.1 mmol, 2.0 equiv.) were dissolved in $CHCl_3$ (20 mL), then trichloroacetyl chloride (851.4 mg, 4.7 mmol, 3.0 equiv.) was added dropwise. The reaction mixture was heated to 65° C. for 2 days, then concentrated vacuum. The residue was purified by reverse flash chromatography with the following conditions: column, C18 silica gel; mobile phase, ACN in water, 5% to 100% gradient in 10 min; detector, UV 254 nm. This gave 2,2,2-trichloro-1-(7-methyl-5-{2-[4-(trifluoromethyl)phenyl]ethoxy}-1H-pyrrolo[3,2-b]pyridin-3-yl)ethanone (130.0 mg) as a yellow solid. LCMS Method A: $[M+H]^+=465$.

Step 4: 7-methyl-5-{2-[4-(trifluoromethyl)phenyl]ethoxy}-1H-pyrrolo[3,2-b]pyridine-3-carboxylic acid 2,2,2-Trichloro-1-(7-methyl-5-{2-[4-(trifluoromethyl)phenyl]ethoxy}-1H-pyrrolo[3,2-b]pyridin-3-yl)ethanone (220.0 mg, 0.5 mmol, 1.0 equiv.) was dissolved in THE (15 mL) and water (3 mL), then NaOH (37.8 mg, 0.9 mmol, 2.0 equiv.) was added. The reaction mixture was heated to 65° C. for 1 hour, then cooled to ambient temperature and concentrated under vacuum. The residue was diluted with water and then adjusted to pH 5 with aqueous HCl (4M). The resulting solution was extracted with ethyl acetate, washed with brine, dried over anhydrous $Na_2SO_4$ and concentrated under vacuum to give 7-methyl-5-{2-[4-(trifluoromethyl) phenyl]ethoxy}-1H-pyrrolo[3,2-b]pyridine-3-carboxylic acid (150.0 mg) as a yellow solid. LCMS Method B: $[M-H]^+$=363.

Step 5: 7-methyl-5-{2-[4-(trifluoromethyl)phenyl] ethoxy}-1H-pyrrolo[3,2-b]pyridine-3-carbonyl azide 7-Methyl-5-{2-[4-(trifluoromethyl)phenyl]ethoxy}-1H-pyrrolo[3,2-b]pyridine-3-carboxylic acid (150.0 mg, 0.4 mmol, 1.0 equiv.) was dissolved in THE (15 mL), then TEA (0.1 mL, 0.8 mmol, 2.0 equiv.) and DPPA (226.6 mg, 0.8 mmol, 2.0 equiv.) were added. The reaction mixture was stirred for 6 hours at ambient temperature, then quenched by the addition of water. The resulting solution was extracted with ethyl acetate, washed with brine, dried over anhydrous $Na_2SO_4$ and concentrated under vacuum to give 7-methyl-5-{2-[4-(trifluoromethyl)phenyl]ethoxy}-1H-pyrrolo[3,2-b] pyridine-3-carbonyl azide (150.0 mg) as a yellow solid. LCMS Method A: $[M+H]^+$=390.

Step 6: tert-butyl N-(7-methyl-5-{2-[4-(trifluoromethyl)phenyl]ethoxy}-1H-pyrrolo[3,2-b]pyridin-3-yl) carbamate 7-Methyl-5-{2-[4-(trifluoromethyl)phenyl]ethoxy}-1H-pyrrolo[3,2-b]pyridine-3-carbonyl azide (150.0 mg, 0.4 mmol, 1.0 equiv.) was dissolved in toluene (3 mL), then t-BuOH (142.8 mg, 1.9 mmol, 5 equiv.) was added. The reaction mixture was heated to 100° C. overnight, then cooled to ambient temperature and concentrated under vacuum. The residue was purified by reverse flash chromatography with the following conditions: column, C18 silica gel; mobile phase, ACN in water, 5% to 100% gradient in 10 min; detector, UV 254 nm. This gave tert-butyl N-(7-methyl-5-{2-[4-(trifluoromethyl)phenyl]ethoxy}-1H-pyrrolo[3,2-b]pyridin-3-yl)carbamate (50.0 mg) as a yellow solid. LCMS Method A: $[M+H]^+$=436.

Step 7: 7-methyl-5-{2-[4-(trifluoromethyl)phenyl] ethoxy}-1H-pyrrolo[3,2-b]pyridin-3-amine TFA salt tert-Butyl N-(7-methyl-5-{2-[4-(trifluoromethyl)phenyl] ethoxy}-1H-pyrrolo[3,2-b]pyridin-3-yl) carbamate (50.0 mg, 0.1 mmol, 1.0 equiv.) was dissolved in DCM (2 mL) and TFA (0.5 mL). The reaction mixture was stirred for 50 min at ambient temperature and then concentrated under vacuum to give crude 7-methyl-5-{2-[4-(trifluoromethyl)phenyl] ethoxy}-1H-pyrrolo[3,2-b]pyridin-3-amine TFA salt (35.0 mg) as a light yellow solid. LCMS Method A: $[M+H]^+$=336.

The intermediates in the following table were prepared using the same method described for Intermediate 96.

| Intermediate | Structure | LCMS data |
|---|---|---|
| Intermediate 97 | 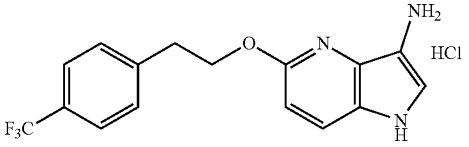 [SMILES: Nc1c[nH]c2ccc(OCCc3ccc(C(F)(F)F)cc3)nc12 ; Cl] | Method A: MS-ESI: 322 $[M+H]^+$ |

Scheme 49: Synthesis of intermediate 98 (5-(3-(4-(trifluoromethyl)-1H-pyrazol-1-yl)propyl)-1H-indol-3-amine TFA salt)

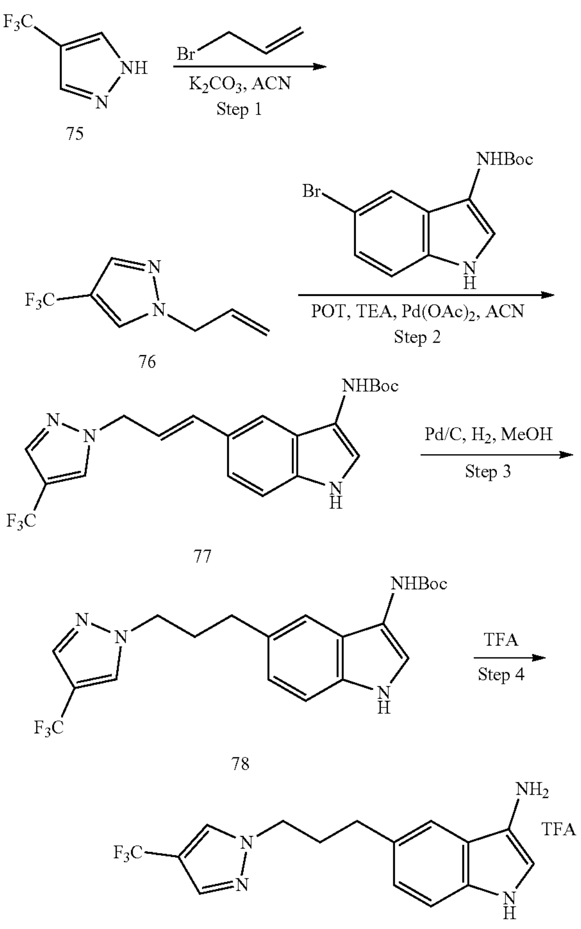

Intermediate 98

Step 1: 1-(prop-2-en-1-yl)-4-(trifluoromethyl)pyrazole 4-(Trifluoromethyl)-1H-pyrazole (500.0 mg, 3.6 mmol, 1.0 equiv.) and $K_2CO_3$ (1.0 g, 7.3 mmol, 2.0 equiv.) was dissolved in ACN (10 mL), then allyl bromide (666.7 mg, 5.5 mmol, 1.5 equiv.) was added. The reaction mixture was heated to 100° C. for 2 hours and then cooled to ambient temperature. After removing the solid by filtration, the filtrate was used in the next step directly without further manipulation. LCMS Method A: $[M+H]^+=165$.

Step 2: tert-butyl N-{5-[(1E)-3-[4-(trifluoromethyl)pyrazol-1-yl]prop-1-en-1-yl]-1H-indol-3-yl}carbamate To the above solution of 1-(prop-2-en-1-yl)-4-(trifluoromethyl)pyrazole in ACN (10 mL), tert-butyl N-(5-bromo-1H-indol-3-yl)carbamate (1.3 g, 4.2 mmol, 1.5 equiv.), TEA (0.8 mL, 5.6 mmol, 2.0 equiv.), POT (172.8 mg, 0.5 mmol, 0.2 equiv.) and $Pd(OAc)_2$ (127.4 mg, 0.5 mmol, 0.2 equiv.) were added under an atmosphere of nitrogen. The reaction mixture was heated to 100° C. for 5 hours, then cooled to ambient temperature and quenched by the addition of water. The resulting solution was extracted with ethyl acetate, washed with brine, dried over anhydrous $Na_2SO_4$ and concentrated under vacuum. The residue was purified by flash column chromatography on silica gel, eluting with ethyl acetate/petroleum ether (1:1) to give tert-butyl N-{5-[(1E)-3-[4-(trifluoromethyl)pyrazol-1-yl]prop-1-en-1-yl]-1H-indol-3-yl}carbamate (370.0 mg) as a brown oil. LCMS Method A: $[M+H]^+=407$.

Step 3: tert-butyl N-(5-{3-[4-(trifluoromethyl)pyrazol-1-yl]propyl}-1H-indol-3-yl)carbamate tert-Butyl N-{5-[(1E)-3-[4-(trifluoromethyl)pyrazol-1-yl]prop-1-en-1-yl]-1H-indol-3-yl}carbamate (300 mg, 0.7 mmol, 1.0 equiv.) was dissolved in MeOH (10 mL), placed under an atmosphere of nitrogen, then Pd/C (10% wt., 60.0 mg) was added. The mixture was sparged with nitrogen, placed under an atmosphere of hydrogen gas (balloon), then stirred for 2 hours at ambient temperature. The solids were removed by filtration and the filtrate was concentrated under vacuum to give tert-butyl N-(5-{3-[4-(trifluoromethyl)pyrazol-1-yl]propyl}-1H-indol-3-yl)carbamate (250.0 mg) as a yellow solid. LCMS Method A: $[M+H]^+=409$.

Step 4: 5-{3-[4-(trifluoromethyl)pyrazol-1-yl]propyl}-1H-indol-3-amine TFA salt tert-Butyl N-(5-{3-[4-(trifluoromethyl)pyrazol-1-yl]propyl}-1H-indol-3-yl)carbamate (210.0 mg, 0.5 mmol, 1 equiv.) was dissolved in DCM (15 mL) and TFA (5 mL). The reaction mixture was stirred for 1 hour at ambient temperature and then concentrated under vacuum. This gave 5-{3-[4-(trifluoromethyl)pyrazol-1-yl]propyl}-1H-indol-3-amine TFA salt (150.0 mg) as a brown solid. LCMS Method A: $[M+H]^+=309$.

Scheme 50: Synthesis of intermediate 100 (1-(2,2,2-trifluoroethyl)-4-(vinyloxy)piperidine)

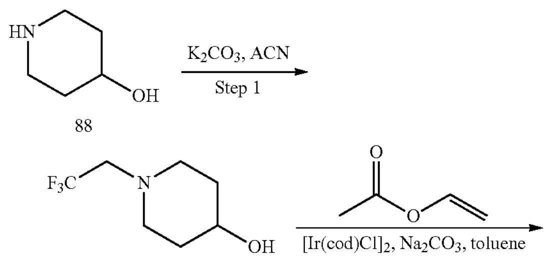

88

89

-continued

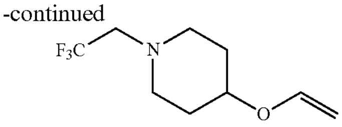

Intermediate 100

Step 1: 1-(2,2,2-trifluoroethyl)piperidin-4-ol

Piperidin-4-ol (1.0 g, 9.9 mmol, 1.0 equiv.) was dissolved in ACN (6 mL), then $K_2CO_3$ (2.7 g, 19.8 mmol, 2.0 equiv.) and 2,2,2-trifluoroethyl trifluoromethanesulfonate (2.8 g, 11.9 mmol, 1.2 equiv.) were added. The reaction mixture was heated to 70° C. for 4 hours, then cooled to ambient temperature and quenched by the addition of water. The resulting solution was extracted with ethyl acetate, washed with brine, dried over anhydrous $Na_2SO_4$ and concentrated under vacuum to give 1-(2,2,2-trifluoroethyl)piperidin-4-ol (1.5 g) as a colorless oil. LCMS Method A: $[M+H]^+=184$.

Step 2: 4-(ethenyloxy)-1-(2,2,2-trifluoroethyl)piperidine 1-(2,2,2-Trifluoroethyl)piperidin-4-ol (1.0 g, 5. mmol, 1.0 equiv.) was dissolved in toluene (5 mL), then vinyl acetate (0.9 g, 10.9 mmol, 2.0 equiv.), $Na_2CO_3$ (1.2 g, 10.9 mmol, 2.0 equiv.) and $[Ir(cod)Cl]_2$ (0.4 g, 0.5 mmol, 0.1 equiv.) were added under an atmosphere of nitrogen. The reaction mixture was heated to 100° C. overnight, then cooled to ambient temperature and concentrated under vacuum. The residue was purified by flash column chromatography on silica gel, eluting with ethyl acetate/petroleum ether (1:6) to give 4-(ethenyloxy)-1-(2,2,2-trifluoroethyl)piperidine (500.0 mg) as a pale yellow oil. LCMS Method A: $[M+H]^+=210$.

Scheme 51: Synthesis of intermediate 101 (4-(2-methylbut-3-en-2-yl)-1-(2,2,2-trifluoroethyl)piperidine)

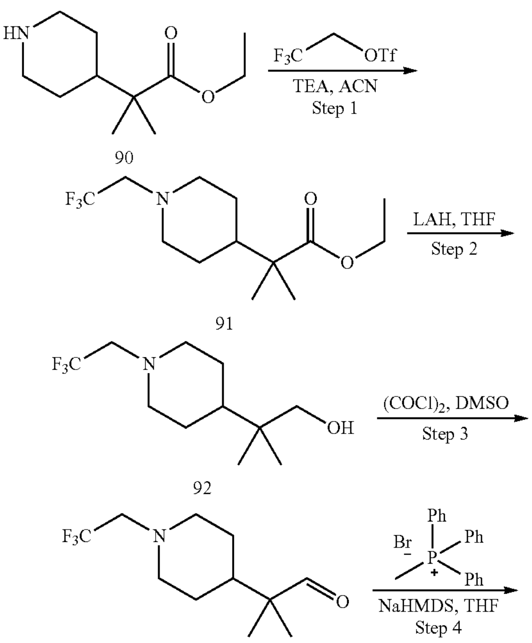

90

91

92

93

-continued

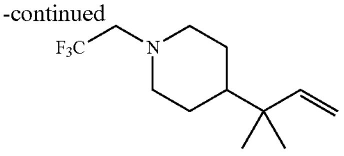

Intermediate 101

Step 1: ethyl 2-methyl-2-[1-(2,2,2-trifluoroethyl) piperidin-4-yl]propanoate Ethyl 2-methyl-2-(piperidin-4-yl)propanoate (2.0 g, 10.0 mmol, 1.0 equiv.) was dissolved in ACN (30 mL), then TEA (2.8 mL, 20.1 mmol, 2.0 equiv.) and 2,2,2-trifluoroethyl trifluoromethanesulfonate (2.8 g, 12.0 mmol, 1.2 equiv.) were added. The reaction mixture was heated to 80° C. for 4 hours, then cooled to ambient temperature and quenched by the addition of water. The resulting solution was extracted with ethyl acetate, washed with brine, dried over anhydrous $Na_2SO_4$ and concentrated under vacuum to give ethyl 2-methyl-2-[1-(2,2,2-trifluoroethyl)piperidin-4-yl] propanoate (2.3 g) as a colorless oil. LCMS Method A: $[M+H]^+$=282.

Step 2: 2-methyl-2-[1-(2,2,2-trifluoroethyl)piperidin-4-yl]propan-1-ol

Ethyl 2-methyl-2-[1-(2,2,2-trifluoroethyl)piperidin-4-yl] propanoate (2.3 g, 8.2 mmol, 1.0 equiv.) was dissolved in THE (30 mL) and cooled to 0° C., then $LiAlH_4$ (0.9 g, 24.5 mmol, 3.0 equiv.) was added, maintaining the solution at 0° C. The reaction mixture was stirred for 6 hours at ambient temperature and then quenched by the addition of MeOH. The resulting mixture was concentrated under vacuum and the residue was purified by flash column chromatography on silica gel, eluting with ethyl acetate/petroleum ether (1:4) to give 2-methyl-2-[1-(2,2,2-trifluoroethyl)piperidin-4-yl]propan-1-ol (1.1 g) as a yellow oil. LCMS Method A: $[M+H]^+$=240.

Step 3: 2-methyl-2-[1-(2,2,2-trifluoroethyl)piperidin-4-yl]propanal

Oxalyl chloride (1.0 mL, 11.5 mmol, 2.5 equiv.) was dissolved in DCM (30 mL) and cooled to −70° C., then DMSO (1.6 mL, 23.0 mmol, 5.0 equiv.) was added dropwise, maintaining the solution at −70° C. After 30 min at −70° C., a solution of 2-methyl-2-[1-(2,2,2-trifluoroethyl) piperidin-4-yl]propan-1-ol (1.1 g, 4.6 mmol, 1.0 equiv.) in DCM (10 mL) was added dropwise. The reaction mixture was stirred for an additional 4 hours at −70° C. This was followed by the addition of TEA (6.4 mL, 46.0 mmol, 10.0 equiv.). The reaction mixture was allowed to warm to ambient temperature and stir for 1 hour, then concentrated under vacuum. The residue was diluted with water, extracted with ethyl acetate, washed with brine, dried over anhydrous $Na_2SO_4$ and concentrated under vacuum.

The residue was purified by flash column chromatography on silica gel, eluting with ethyl acetate/petroleum ether (1:5) to give 2-methyl-2-[1-(2,2,2-trifluoroethyl)piperidin-4-yl] propanal (510.0 mg) as a pale yellow oil. LCMS Method A: $[M+H]^+$=238.

Step 4: 4-(2-methylbut-3-en-2-yl)-1-(2,2,2-trifluoroethyl)piperidine

Methyltriphenylphosphanium bromide (2.3 g, 6.4 mmol, 3.0 equiv.) was dissolved in THF (25 mL), then NaHMDS (1.2 g, 6.4 mmol, 3.0 equiv.) was added. After 30 min, 2-methyl-2-[1-(2,2,2-trifluoroethyl)piperidin-4-yl]propanal (510.0 mg, 2.1 mmol, 1.0 equiv.) was added. The reaction mixture was stirred for 4 hours at ambient temperature, then concentrated under vacuum. The residue was purified by flash column chromatography on silica gel, eluting with ethyl acetate/petroleum ether (1:5) to give 4-(2-methylbut-3-en-2-yl)-1-(2,2,2-trifluoroethyl)piperidine (310.0 mg) as a colorless oil. LCMS Method A: $[M+H]^+$=236.

Scheme 52: Synthesis of intermediate 102 (1-(3,3,3-trifluoropropyl)azetidine-3-carboxylic acid)

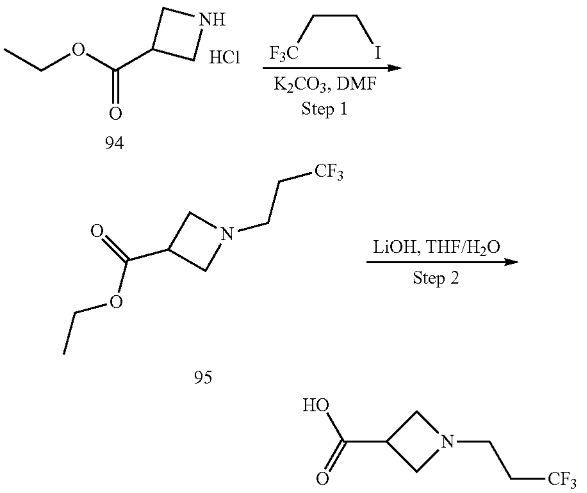

94

95

Intermediate 102

Step 1: ethyl 1-(3,3,3-trifluoropropyl)azetidine-3-carboxylate

Ethyl azetidine-3-carboxylate hydrochloride (2.6 g, 15.5 mmol, 1.0 equiv.) and 1,1,1-trifluoro-3-iodopropane (2.9 g, 13.3 mmol, 0.9 equiv.) were dissolved in ACN (10 mL), then $K_2CO_3$ (5.0 g, 36.4 mmol, 2.3 equiv.) was added. The reaction mixture was heated to 80° C. for 4 hours, then cooled to ambient temperature and quenched by the addition of water. The resulting solution was extracted with ethyl acetate, washed with brine, dried over anhydrous $Na_2SO_4$ and concentrated under vacuum to give ethyl 1-(3,3,3-trifluoropropyl)azetidine-3-carboxylate (1.8 g) as a yellow oil. LCMS Method A: [M+H]+=226.

Step 2: 1-(3,3,3-trifluoropropyl)azetidine-3-carboxylic acid

Ethyl 1-(3,3,3-trifluoropropyl)azetidine-3-carboxylate (1.0 g, 4.4 mmol, 1.0 equiv.) was dissolved in THF/$H_2O$ (10/1 mL), LiOH (0.3 g, 13.4 mmol, 3.0 equiv.) was added. The reaction mixture was stirred for 6 hours at ambient temperature and concentrated under vacuum. The residue was diluted with water, then adjusted to pH 4 with aqueous HCl (6M). The resulting solution was extracted with DCM and concentrated under vacuum to give crude 1-(3,3,3-trifluoropropyl)azetidine-3-carboxylic acid (1.2 g) as a yellow oil. LCMS Method A: $[M-H]^-$=196.

Scheme 53: Synthesis of intermediate 103 (tert-butyl 3-(cyclopropane carboxamido)-5-hydroxy-1H-indole-1-carboxylate)

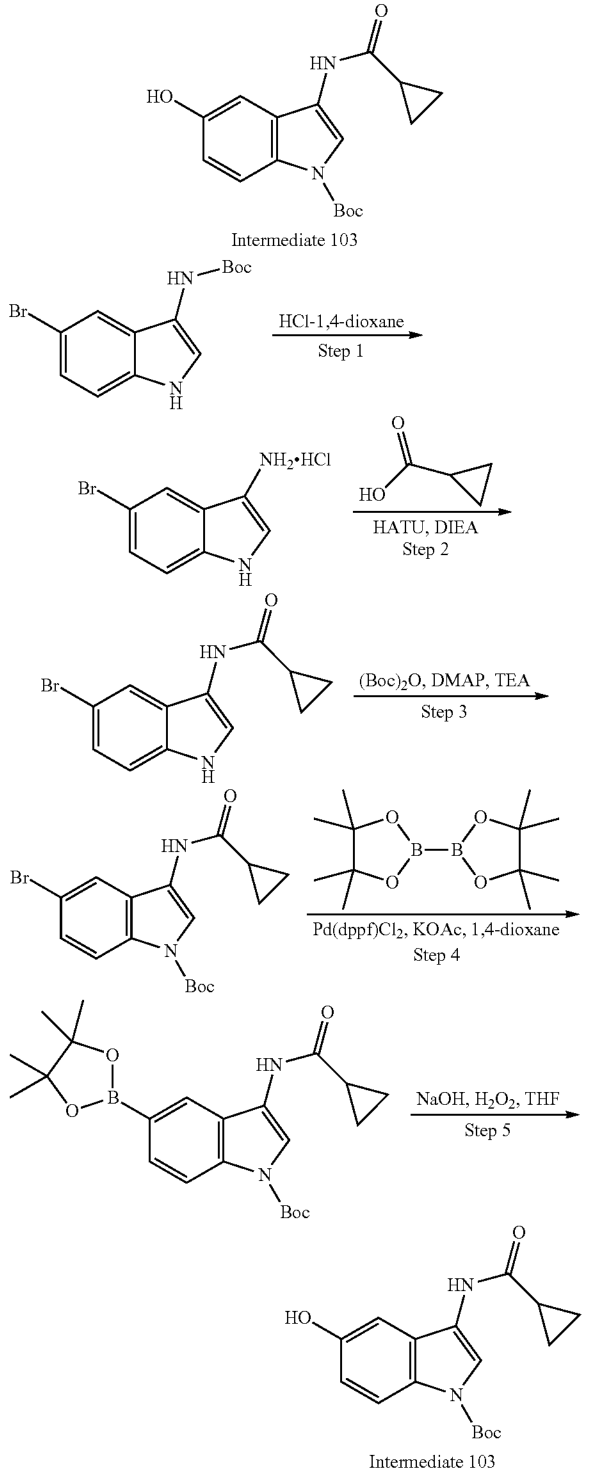

Step 1: 5-bromo-1H-indol-3-amine hydrochloride tert-Butyl (5-bromo-1H-indol-3-yl)carbamate (20.0 g, 64.2 mmol, 1.0 equiv.) was dissolved in HCl/1,4-dioxane (4 M, 150 mL). The reaction mixture was stirred for 2 hours at rt and then concentrated under vacuum to give 5-bromo-1H-indol-3-amine hydrochloride (18.7 g) as a brown solid. LCMS Method A: $[M+H]^+$=211.2.

Step 2: N-(5-bromo-1H-indol-3-yl)cyclopropanecarboxamide

Cyclopropanecarboxylic acid (172.0 mg, 2.0 mmol, 1.0 equiv.) was dissolved in DCM (20 mL), then DIEA (1.0 mL, 6.0 mmol, 3.0 equiv.), HATU (1.1 g, 3.0 mmol, 1.5 equiv.) and 5-bromo-1H-indol-3-amine hydrogen chloride (500.0 mg, 2.0 mmol, 1.0 equiv.) were added. The reaction mixture was stirred for 2 hours at rt and then quenched by the addition of water. The resulting solution was extracted with EtOAc, washed with brine, dried over anhyd. $Na_2SO_4$ and concentrated under vacuum. The residue was purified by flash column chromatography on silica gel, eluting with EtOAc/petroleum ether (1:1) to give N-(5-bromo-1H-indol-3-yl)cyclopropanecarboxamide (510.0 mg) as a white solid. LCMS Method A: $[M+H]^+$=279.2.

Step 3: tert-butyl 5-bromo-3-(cyclopropanecarboxamido)-1H-indole-1-carboxylate

N-(5-bromo-1H-indol-3-yl)cyclopropanecarboxamide (200.0 mg, 0.7 mmol, 1.0 equiv.) and $(Boc)_2O$ (156.3 mg, 0.7 mmol, 1.0 equiv.) were dissolved in THF (10 mL), then DMAP (8.7 mg, 0.07 mmol, 0.1 equiv.) and TEA (0.2 mL, 1.4 mmol, 2.0 equiv.) were added. The reaction mixture was stirred overnight at rt and then concentrated under vacuum. The residue was purified by reverse flash chromatography with the following conditions: column, C18 silica gel; mobile phase, ACN in Water (10 mmol/L $NH_4HCO_3$), 30% to 90% gradient in 30 min; detector, UV 254 nm. This resulted in tert-butyl 5-bromo-3-(cyclopropanecarboxamido)-1H-indole-1-carboxylate (106.0 mg) as a brown yellow oil. LCMS Method A: [M+H]+=379.2.

Step 4: tert-butyl 3-(cyclopropanecarboxamido)-5-(4,4,5,5-tetramethyl-1,3,2-dioxaborolan-2-yl)-1H-indole-1-carboxylate tert-Butyl 5-bromo-3-cyclopropaneamidoindole-1-carboxylate (200.0 mg, 0.5 mmol, 1.0 equiv.) and bis(pinacolato)diboron (200.9 mg, 0.8 mmol, 1.5 equiv.) were dissolved in 1,4-dioxane (10 mL), then $Pd(dppf)Cl_2$ (38.6 mg, 0.05 mmol, 0.1 equiv.) and KOAc (103.5 mg, 1.05 mmol, 2.0 equiv.) were added under an atmosphere of nitrogen. The reaction mixture was stirred overnight at 90° C., then cooled to rt and concentrated under vacuum. The residue was purified by flash column chromatography on silica gel, eluting with EtOAc/petroleum ether (1:7) to give tert-butyl 3-(cyclopropanecarboxamido)-5-(4,4,5,5-tetramethyl-1,3,2-dioxaborolan-2-yl)-1H-indole-1-carboxylate (186.0 mg) as a brown solid. LCMS Method A: $[M+H]^+$=427.2.

Step 5: tert-butyl 3-(cyclopropanecarboxamido)-5-hydroxy-1H-indole-1-carboxylate tert-Butyl 3-(cyclopropanecarboxamido)-5-(4,4,5,5-tetramethyl-1,3,2-dioxaborolan-2-yl)-1H-indole-1-carboxylate (500.0 mg, 1.2 mmol, 1.0 equiv.) was dissolved in THF (15 mL) and cooled to 0° C., then a solution of NaOH in water (30% wt./wt., 4.0 mL, 3.5 mmol, 2.0 equiv.) was added. This was followed by the addition of $H_2O_2$ (30% wt./wt. in water, 0.3 mL, 2.4 mmol, 2.0 equiv.) dropwise at 0° C. The reaction mixture was stirred overnight at rt and then concentrated under vacuum. The residue was diluted with water, extracted with EtOAc, washed with brine and concentrated under vacuum. The residue was purified by flash column chromatography on silica gel, eluting with dichloromethane/methanol (20:1) to give tert-butyl 3-(cyclopropanecarboxamido)-5-hydroxy-1H-indole-1-carboxylate (161.0 mg) as a yellow solid. LCMS Method A: $[M+H]^+$= 317.2.

The Intermediates in the Following Table were Prepared Using the Same Method Described for Intermediates 103.

| Intermediate | Starting material | Structure | LCMS data |
|---|---|---|---|
| Intermediate 104 | 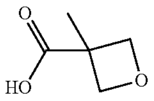 | 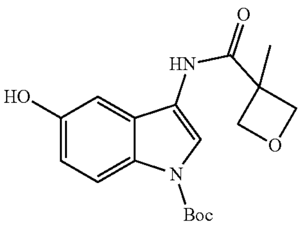 | Method A: MS-ESI: 292.0 $[M + H]^+$ |

Scheme 54: Synthesis of intermediate 105 (5-(trans-3-(6-(trifluoromethyl)pyridin-3-yl)cyclobutoxy)-1H-indol-3-amine TFA salt)

Intermediate 105

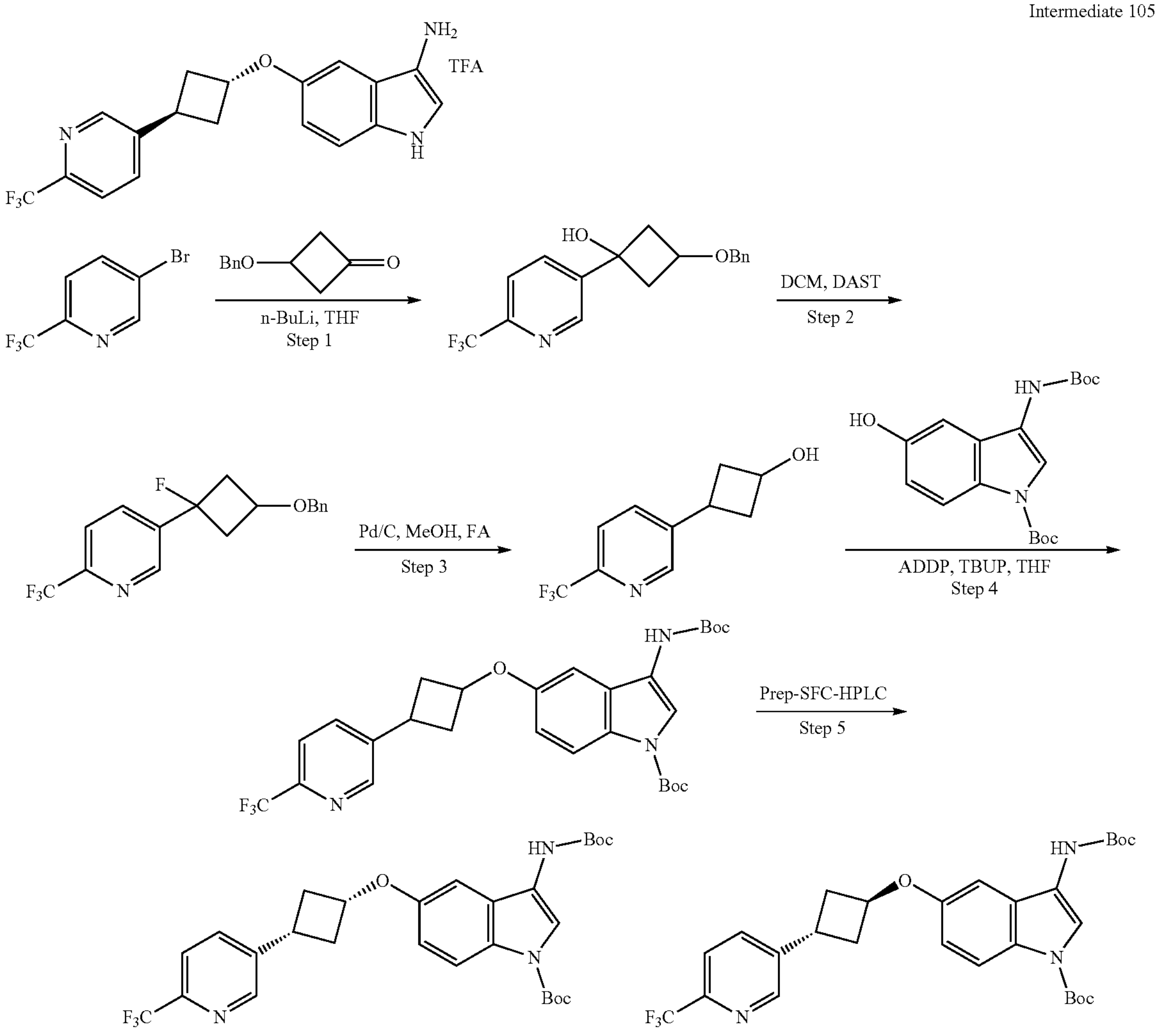

-continued

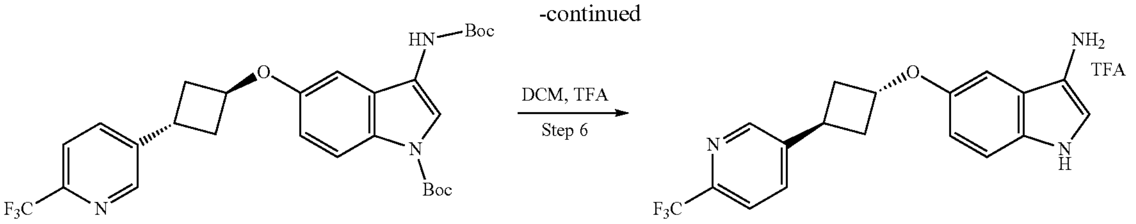

Intermediate 105

Step 1: 3-(benzyloxy)-1-(6-(trifluoromethyl)pyridin-3-yl)cyclobutan-1-ol

5-Bromo-2-(trifluoromethyl)pyridine (4.0 g, 17.6 mmol, 1.0 equiv.) was dissolved in THF (40 mL) and cooled to −70° C., then n-BuLi (2.5M in hexane, 8.5 mL, 21.3 mmol, 1.2 equiv.) added dropwise, maintaining the solution at −70° C. under an atmosphere of nitrogen. After stirred for 30 min at −70° C., 3-(benzyloxy)cyclobutan-1-one (3.7 g, 21.2 mmol, 1.2 equiv.) was added dropwise. The reaction mixture was stirred for additional 2 hours at rt and then quenched by the addition of saturated aqueous $NH_4Cl$. The resulting solution was extracted with EtOAc, washed with brine, dried over anhyd. $Na_2SO_4$ and concentrated under vacuum. The residue was purified by reverse flash column with the following conditions: column, C18 silica gel; mobile phase, MeCN in Water (0.5% $NH_4HCO_3$), 10% to 100% gradient in 25 min; detector, UV 254 nm. This resulted in 3-(benzyloxy)-1-(6-(trifluoromethyl)pyridin-3-yl)cyclobutan-1-ol (2.7 g) as a pale yellow solid. LCMS Method A: $[M+H]^+$ =324.2.

Step 2: 5-(3-(benzyloxy)-1-fluorocyclobutyl)-2-(trifluoromethyl)pyridine 3-(Benzyloxy)-1-(6-(trifluoromethyl)pyridin-3-yl)cyclobutan-1-ol (2.7 g, 8.3 mmol, 1.0 equiv.) was dissolved in DCM (10 mL) and cooled to −70° C., then DAST (2.6 g, 16.6 mmol, 2.0 equiv.) was added dropwise, maintaining the solution at −70° C. under an atmosphere of nitrogen. The reaction mixture was stirred for 2 hours at rt and then quenched by the addition of water. The resulting solution was extracted with EtOAc, washed with brine, dried over anhyd. $Na_2SO_4$ and concentrated under vacuum. The residue was purified by reverse flash column with the following conditions: column, C18 silica gel; mobile phase, MeCN in Water (0.1% $NH_4HCO_3$), 10% to 100% gradient in 30 min; detector, UV 254 nm. This resulted in 5-(3-(benzyloxy)-1-fluorocyclobutyl)-2-(trifluoromethyl)pyridine (2.5 g) as a pale yellow solid. LCMS Method A: $[M+H]^+$=326.0

Step 3: 3-(6-(trifluoromethyl)pyridin-3-yl)cyclobutan-1-ol

5-[3-(Benzyloxy)-1-fluorocyclobutyl]-2-(trifluoromethyl)pyridine (2.0 g, 6.1 mmol, 1.0 equiv.) was dissolved in MeOH (40 ml), then HCOOH (282.9 mg, 6.1 mmol, 1.0 equiv.) was added. This was followed by the addition of Pd/C (10% wt., 130.8 mg) under an atmosphere of nitrogen. The mixture was sparged with nitrogen, placed under an atmosphere of hydrogen gas (balloon), then stirred for 4 hours at 40° C. The solids were removed by filtration and the filter cake was washed with MeOH. The combined filtrate was concentrated under vacuum. The residue was purified by reverse flash column with the following conditions: column, C18 silica gel; mobile phase, MeCN in Water (0.1% $NH_4HCO_3$), 10% to 100% gradient in 30 min; detector, UV 254 nm. This resulted in 3-(6-(trifluoromethyl)pyridin-3-yl)cyclobutan-1-ol (1.0 g) as a pale yellow oil. LCMS Method A: $[M+H]^+$=261.0.

Step 4: tert-butyl 3-((tert-butoxycarbonyl)amino)-5-(trans-3-(6-(trifluoromethyl)pyridin-3-yl)cyclobutoxy)-1H-indole-1-carboxylate and tert-butyl 3-((tert-butoxycarbonyl)amino)-5-(cis-3-(6-(trifluoromethyl)pyridin-3-yl)cyclobutoxy)-1H-indole-1-carboxylate 3-[6-(Trifluoromethyl)pyridin-3-yl]cyclobutan-1-ol (1.0 g, 4.6 mmol, 1.0 equiv.) was dissolved in THE (13 mL), then tert-butyl 3-[(tert-butoxycarbonyl)amino]-5-hydroxyindole-1-carboxylate (1.6 g, 4.6 mmol, 1.0 equiv.), TBUP (1.8 g, 9.2 mmol, 2.0 equiv.) and ADDP (2.3 g, 9.2 mmol, 2.0 equiv.) were added under an atmosphere of nitrogen. The reaction mixture was stirred for 5 hours at 70° C., then cooled to rt and quenched by the addition of water. The resulting solution was extracted with EtOAc, washed with brine, dried over anhyd. $Na_2SO_4$ and concentrated under vacuum. The residue was purified by reverse flash chromatography with the following conditions: column, C18 silica gel; mobile phase, MeCN in Water (0.1% $NH_4HCO_3$), 10% to 100% gradient in 25 min; detector, UV 254 nm. This resulted in tert-butyl 3-((tert-butoxycarbonyl)amino)-5-(3-(6-(trifluoromethyl)pyridin-3-yl)cyclobutoxy)-1H-indole-1-carboxylate (1.0 g) as a pale yellow solid. The mixture was separated by Chiral-HPLC with the following conditions: Column: JW-CHIRAL-Amylose-SA, 20*250 mm, 5 um; Mobile Phase A: IPA-HPLC, Mobile Phase B: Hex (0.5% 2M $NH_3$-MeOH)-HPLC; Flow rate: 20 mL/min; Gradient: 90% B to 90% B in 14 min; Wave Length: 220/254 nm; RT1: 8.2 min; RT2: 10.22 min. This resulted in tert-butyl 3-((tert-butoxycarbonyl)amino)-5-(cis-3-(6-(trifluoromethyl)pyridin-3-yl)cyclobutoxy)-1H-indole-1-carboxylate (710.0 mg) as a pale yellow solid. LCMS Method B: $[M-H]^-$=548. And tert-butyl 3-((tert-butoxycarbonyl)amino)-5-(trans-3-(6-(trifluoromethyl)pyridin-3-yl)cyclobutoxy)-1H-indole-1-carboxylate (170.0 mg) as a pale yellow solid. LCMS Method B: $[M-H]^-$=548.1.

Step 5: 5-(trans-3-(6-(trifluoromethyl)pyridin-3-yl)cyclobutoxy)-1H-indol-3-amine TFA salt tert-Butyl 3-[(tert-butoxycarbonyl)amino]-5-[trans-3-[6-(trifluoromethyl)pyridin-3-yl]cyclobutoxy]indole-1-carboxylate (160.0 mg, 0.2 mmol, 1.0 equiv.) was dissolved in DCM (2 mL), then TFA (2 mL) was added. The reaction mixture was stirred for 1 hours at rt and then concentrated under vacuum to give crude 5-(trans-3-(6-(trifluoromethyl)

pyridin-3-yl)cyclobutoxy)-1H-indol-3-amine TFA salt (103.0 mg) as a red solid. LCMS Method B: $[M+H]^+$=348.2.

Scheme 55: Synthesis of intermediate 106 (5-(cis-3-(6-trifluoromethyl)pyridin-3-yl)cyclobutoxy)-1H-indol-3-amine TFA salt

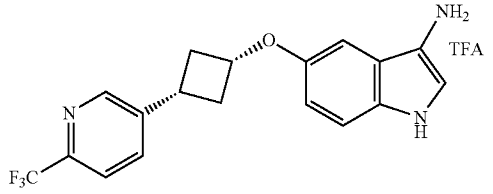

Intermediate 106

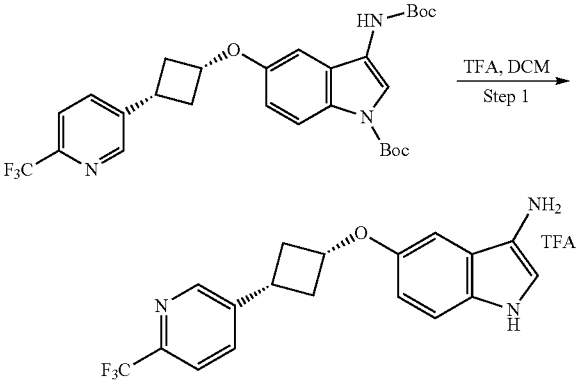

Intermediate 106 tert-Butyl 3-[(tert-butoxycarbonyl)amino]-5-[cis-3-[6-(trifluoromethyl)pyridin-3-yl]cyclobutoxy]indole-1-carboxylate (500.0 mg, 0.9 mmol, 1.0 equiv.) was dissolved in DCM (3 mL), then TFA (3 mL) was added. The reaction mixture was stirred for 1 hour at rt and then concentrated under vacuum to give crude 5-(trans-3-(6-(trifluoromethyl) pyridin-3-yl)cyclobutoxy)-1H-indol-3-amine TFA (400.0 mg) as a brown solid. LCMS Method B: $[M+H]^+$= 348.2

Scheme 56: Synthesis of intermediate 107 (5-(3-(5-trifluoromethyl)pyridin-2-yl)propyl)-1H-indol-3-amine TFA salt)

Intermediate 107

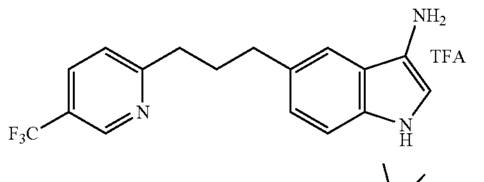

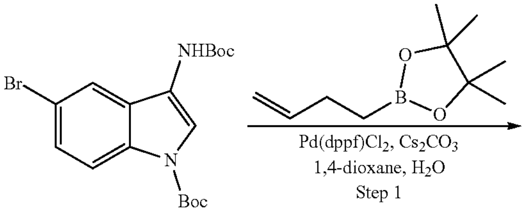

-continued

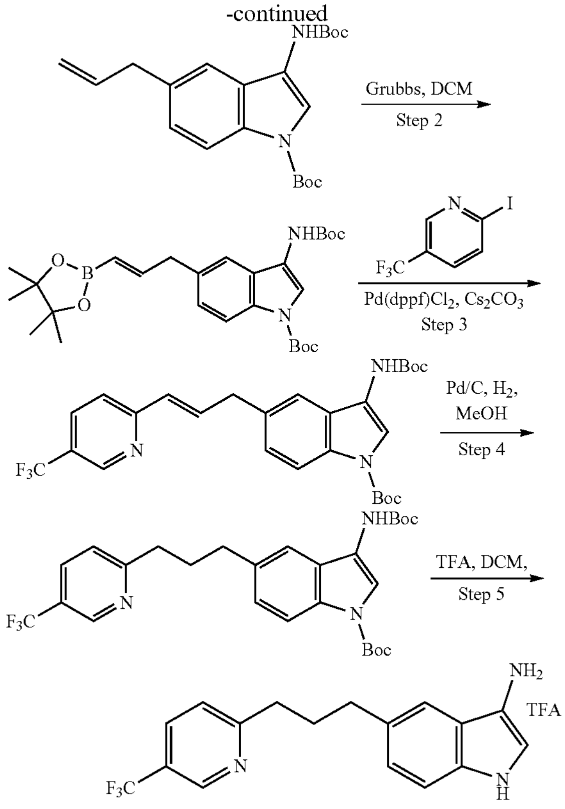

Intermediate 107

Step 1: tert-butyl 5-allyl-3-((tert-butoxycarbonyl) amino)-1H-indole-1-carboxylate tert-Butyl 5-bromo-3-((tert-butoxycarbonyl) amino)-1H-indole-1-carboxylate (4.0 g, 9.7 mmol, 1.0 equiv.), 2-(but-3-en-1-yl)-4,4,5,5-tetramethyl-1,3,2-dioxaborolane (3.3 g, 19.5 mmol, 2.0 equiv.) were dissolved in 1,4-dioxane (120 mL) and $H_2O$ (12 mL), then $Cs_2CO_3$ (6.3 g, 19.5 mmol, 2.0 equiv.) and $Pd(dppf)Cl_2$ (0.7 g, 1.0 mmol, 0.1 equiv.) were added under an atmosphere of nitrogen. The reaction mixture was stirred for 4 hours at 90° C., then cooled to rt and concentrated under vacuum. The residue was diluted with water, extracted with EtOAc, washed with brine, dried over anhyd. $Na_2SO_4$ and concentrated under vacuum. The residue was purified by flash column chromatography on silica gel, eluting with petroleum ether/EtOAc (5:1) to give tert-butyl 5-allyl-3-((tert-butoxycarbonyl) amino)-1H-indole-1-carboxylate (3.3 g) as a white solid. LCMS Method A: $[M+H]^+$= 373.2.

Step 2: tert-butyl (E)-3-((tert-butoxycarbonyl) amino)-5-(3-(4,4,5,5-tetramethyl-1,3,2-dioxaborolan-2-yl) allyl)-1H-indole-1-carboxylate tert-Butyl 5-allyl-3-((tert-butoxycarbonyl) amino)-1H-indole-1-carboxylate (1.8 g, 4.8 mmol, 1.0 equiv.) and 4,4,5,5-tetramethyl-2-vinyl-1,3,2-dioxaborolane (2.2 g, 14.5 mmol, 3.0 equiv.) were dissolved in DCM (10 mL), then Grubbs 2nd (410.2 mg, 0.5 mmol, 0.1 equiv.) was added under an atmosphere of nitrogen. The reaction mixture was stirred for 3 days at 50° C., then cooled to rt and quenched by the addition of water. The resulting solution was extracted with EtOAc, washed with brine, dried over anhyd.

$Na_2SO_4$ and concentrated under vacuum. The residue was purified by flash column chromatography on silica gel, eluting with petroleum ether/EtOAc (1:1) to give tert-butyl (E)-3-((tert-butoxycarbonyl) amino)-5-(3-(4,4,5,5-tetramethyl-1,3,2-dioxaborolan-2-yl) allyl)-1H-indole-1-carboxylate (900 mg) as a yellow solid. LCMS Method A: $[M+H]^+$=499.2.

Step 3: tert-butyl (E)-3-((tert-butoxycarbonyl) amino)-5-(3-(5-(trifluoromethyl) pyridin-2-yl) allyl)-1H-indole-1-carboxylate tert-Butyl (E)-3-((tert-butoxycarbonyl) amino)-5-(3-(4,4,5,5-tetramethyl-1,3,2-dioxaborolan-2-yl) allyl)-1H-indole-1-carboxylate (900.0 mg, 1.8 mmol, 1.0 equiv.) and 2-iodo-5-(trifluoromethyl) pyridine (985.8 mg, 3.6 mmol, 2.0 equiv.) were dissolved in 1,4-dioxane (10 mL) and $H_2O$ (1 mL), then $Pd(dppf)Cl_2$ (264.2 mg, 0.4 mmol, 0.2 equiv.) and $Cs_2CO_3$ (1.8 g, 5.4 mmol, 3.0 equiv.) were added under an atmosphere of nitrogen. The reaction mixture was stirred overnight at 90° C., then cooled to rt and concentrated under vacuum. The residue was purified by flash column chromatography on silica gel, eluting with petroleum ether/EtOAc (3:1) to give tert-butyl (E)-3-((tert-butoxycarbonyl) amino)-5-(3-(5-(trifluoromethyl) pyridin-2-yl) allyl)-1H-indole-1-carboxylate (450.0 mg) as a pale yellow solid. LCMS Method A: $[M+H]^+$=518.2.

Step 4: tert-butyl 3-((tert-butoxycarbonyl) amino)-5-(3-(5-(trifluoromethyl) pyridin-2-yl) propyl)-1H-indole-1-carboxylate tert-Butyl (E)-3-((tert-butoxycarbonyl) amino)-5-(3-(5-(trifluoromethyl) pyridin-2-yl) allyl)-1H-indole-1-carboxylate (100.0 mg, 0.2 mmol, 1.0 equiv.) was dissolved in MeOH (10 mL), then Pd/C (10% wt, 10 mg) was added under an atmosphere of nitrogen.

The mixture was sparged with nitrogen, placed under an atmosphere of hydrogen gas (balloon), then stirred for 2 hours at rt. The solids were removed by filtration and the filtrate was concentrated under vacuum to give tert-butyl 3-((tert-butoxycarbonyl) amino)-5-(3-(5-(trifluoromethyl) pyridin-2-yl) propyl)-1H-indole-1-carboxylate (60.0 mg) as a white solid. LCMS Method A: $[M+H]^+$=520.2.

Step 5: 5-(3-(5-(trifluoromethyl) pyridin-2-yl) propyl)-1H-indol-3-amine TFA salt tert-Butyl 3-((tert-butoxycarbonyl) amino)-5-(3-(5-(trifluoromethyl) pyridin-2-yl) propyl)-1H-indole-1-carboxylate (60.0 mg, 0.1 mmol, 1.0 equiv.) was dissolved in DCM (2 mL), then TFA (0.4 mL) was added. The reaction mixture was stirred for 1 hour at rt and concentrated under vacuum to give crude 5-(3-(5-(trifluoromethyl) pyridin-2-yl) propyl)-1H-indol-3-amine TFA salt (65.0 mg) as a yellow oil, that was used in the next step directly without further purification. LCMS Method B: $[M+H]^+$=320.2.

Scheme 57: Synthesis of intermediate 108 (tert-butyl 3-(2-(2-bromoethoxy)propan-2-yl)pyrrolidine-1-carboxylate)

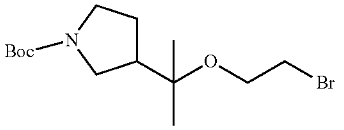

Intermediate 108

-continued

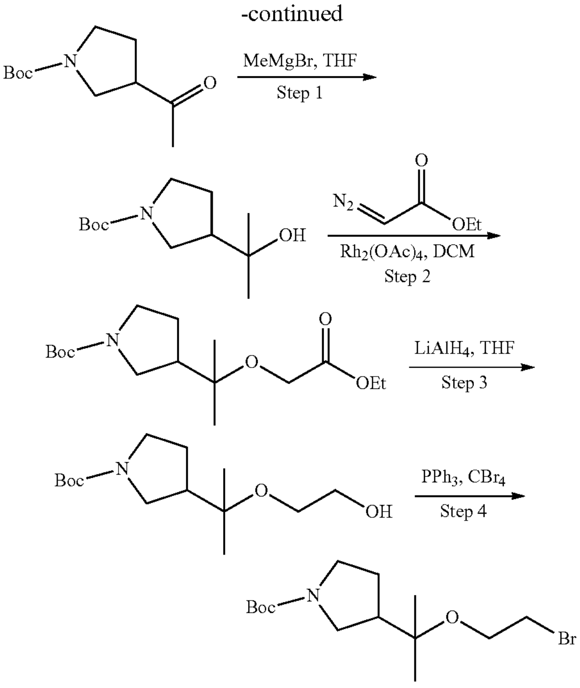

Intermediate 108

Step 1: tert-butyl 3-acetylpyrrolidine-1-carboxylate tert-Butyl 3-acetylpyrrolidine-1-carboxylate (2.0 g, 9.4 mmol, 1.0 equiv.) was dissolved in THE (20 mL) and cooled to −10° C., then MeMgBr (3M in THF, 6.3 mL, 18.9 mmol, 2.0 equiv.) was added dropwise, maintaining the solution at −10° C. under an atmosphere of nitrogen. The reaction mixture was stirred for 2 hours at 0° C., then quenched by the addition of ice-water. The resulting solution was extracted with EtOAc, washed with brine, dried over anhyd. $Na_2SO_4$ and concentrated under vacuum. The residue was purified by flash column chromatography on silica gel, eluting with dichloromethane/petroleum ether (5:1) to give tert-butyl 3-(2-hydroxypropan-2-yl) pyrrolidine-1-carboxylate (1.5 g) as a yellow oil. LCMS Method C: $[M+H]^+$=230.1.

Step 2: tert-butyl 3-(2-hydroxypropan-2-yl) pyrrolidine-1-carboxylate tert-Butyl 3-(2-hydroxypropan-2-yl) pyrrolidine-1-carboxylate (1.3 g, 5.7 mmol, 1.0 equiv.) was dissolved in DCM (15 mL) and cooled to 0° C., then ethyl diazoacetate (1.3 g, 11.3 mmol, 2.0 equiv.) and $R^h2(OAc)_4$ (0.3 g, 0.6 mmol, 0.1 equiv.) were added, maintaining the solution at 0° C. under an atmosphere of nitrogen. The reaction mixture was stirred overnight at 0° C. and then quenched by the addition of ice-water. The resulting solution was extracted with EtOAc, washed with brine, dried over anhyd. $Na_2SO_4$ and concentrated under vacuum. The residue was purified by flash column chromatography on silica gel, eluting with petroleum ether/EtOAc (5:1) to give tert-butyl 3-[2-(2-ethoxy-2-oxoethoxy) propan-2-yl] pyrrolidine-1-carboxylate (1.3 g) as a yellow oil. LCMS Method A: $[M+H]^+$=316.2

Step 3: tert-butyl 3-(2-(2-ethoxy-2-oxoethoxy) propan-2-yl) pyrrolidine-1-carboxylate tert-Butyl 3-[2-(2-ethoxy-2-oxoethoxy) propan-2-yl] pyrrolidine-1-carboxylate (1.0 g, 3.2 mmol, 1.0 equiv.) was dissolved in THE (10 mL) and cooled to 0° C., then $LiAlH_4$ (0.2 g, 4.8 mmol, 1.5 equiv.) was added in portions. The reaction mixture was stirred for 2 hours at rt and then quenched by the addition of ice-water at 0° C. The resulting solution was extracted with EtOAc, washed with brine, dried over anhyd. $Na_2SO_4$ and concentrated under vacuum to give tert-butyl 3-[2-(2-hydroxyethoxy) propan-2-yl] pyrrolidine-1-carboxylate (0.7 g) as a yellow oil. LCMS Method A: $[M+H]^+$=274.2.

Step 4: tert-butyl 3-(2-(2-hydroxyethoxy) propan-2-yl) pyrrolidine-1-carboxylate tert-Butyl 3-[2-(2-hydroxyethoxy) propan-2-yl] pyrrolidine-1-carboxylate (1.2 g, 4.4 mmol, 1.0 equiv.) was dissolved in THE (20 mL) and cooled to 0° C., then $PPh_3$ (1.7 g, 6.6 mmol, 1.5 equiv.) and $CBr_4$ (2.2 g, 6.6 mmol, 1.5 equiv.) were added under an atmosphere of nitrogen. The reaction mixture was stirred for 2 hours at 0° C. and then quenched by the addition of water. The resulting solution was extracted with EtOAc, washed with brine, dried over anhyd. $Na_2SO_4$ and concentrated under vacuum. reduced pressure. The residue was purified by flash column chromatography on silica gel, eluting with petroleum ether/EtOAc (10:1) to give tert-butyl 3-[2-(2-bromoethoxy) propan-2-yl] pyrrolidine-1-carboxylate (0.8 g) as a yellow oil. LCMS Method C: $[M+H]^+$=336.2.

Scheme 58: Synthesis of intermediate 109 (tert-butyl (3aR, 5r, 6aS)-5-vinylhexahydrocyclopenta[c]pyrrole-2(1H)-carboxylate)

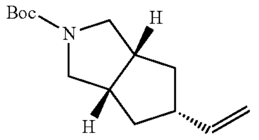

Intermediate 109

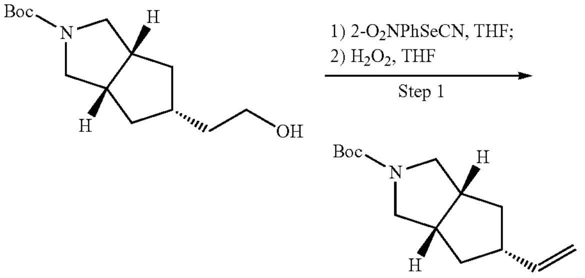

Intermediate 109 tert-Butyl (3aR,5r,6aS)-5-(2-hydroxyethyl)hexahydrocyclopenta[c]pyrrole-2(1H)-carboxylate (2.0 g, 7.8 mmol, 1.0 equiv.) and 1-nitro-2-selenocyanatobenzene (2.3 g, 10.2 mmol, 1.3 equiv.) were dissolved in THF (40 mL) and cooled to 0° C., then TBUP (2.1 g, 10.2 mmol, 1.3 equiv.) was added under an atmosphere of nitrogen. The reaction mixture was stirred for 16 hours at rt and then concentrated under vacuum. The residue was purified by flash column chromatography on silica gel, eluting with petroleum ether/EtOAc (2:1) to give intermediate product as a brown oil. Then the intermediate product was dissolved in THF (30 mL), $H_2O_2$ (30% wt., 6 mL) was added dropwise at 0° C. The resulting mixture was stirred for 2 hours at rt and then quenched by the addition of water. The resulting solution was extracted with EtOAc, washed with brine, dried over anhyd. $Na_2SO_4$ and concentrated under vacuum. The residue was purified by flash column chromatography on silica gel, eluting with petroleum ether/EtOAc (20:1) to give tert-butyl (3aR,5r,6aS)-5-vinylhexahydrocyclopenta[c]pyrrole-2(1H)-carboxylate (430.0 mg) as a yellow oil. LCMS Method A: $[M+H]^+$=238.0.

Scheme 59: Synthesis of intermediate 110 (4-(2-hydroxyethyl)-1-(trifluoromethyl)cyclohexan-1-ol)

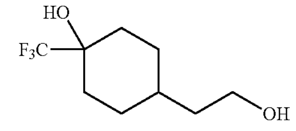

Intermediate 110

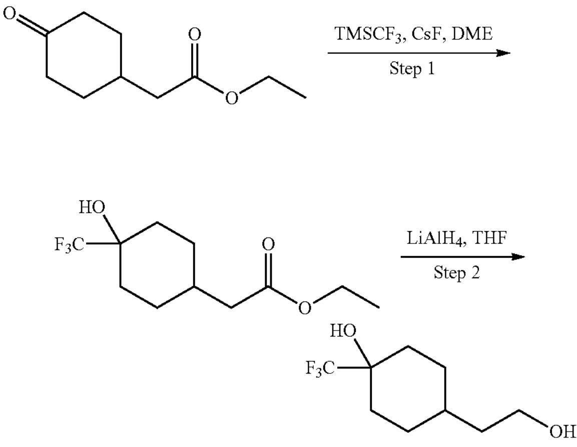

Intermediate 110

Step 1: ethyl 2-[4-hydroxy-4-(trifluoromethyl)cyclohexyl]acetate

Ethyl 2-(4-oxocyclohexyl)acetate (500.0 mg, 2.7 mmol, 1.0 equiv.) was dissolved in DME (5.0 mL), then CsF (825.0 mg, 5.4 mmol, 2.0 equiv.) and trifluoromethyltrimethylsilane (772.0 mg, 5.4 mmol, 2.0 equiv.) were added. The reaction mixture was stirred for 5 hours at rt and then concentrated under vacuum. The residue was purified by flash column chromatography on silica gel, eluting with petroleum ether/EtOAc (5:1) to give ethyl 2-[4-hydroxy-4-(trifluoromethyl)cyclohexyl]acetate (200.0 mg) as a colorless oil. LCMS Method A: $[M+H]^+$=255.1.

Step 2: 4-(2-hydroxyethyl)-1-(trifluoromethyl)cyclohexan-1-ol

Ethyl 2-[4-hydroxy-4-(trifluoromethyl)cyclohexyl]acetate (200 mg, 0.787 mmol, 1 equiv) was dissolved in THE (4 mL) and cooled to 0° C., then $LiAlH_4$ (60.0 mg, 1.6 mmol, 2.0 equiv.) was added. The reaction mixture was stirred for 5 hours at 0° C. and then quenched by the addition of ice-water. The resulting solution was extracted with EtOAc, washed with brine, dried over anhyd. $Na_2SO_4$ and concentrated under vacuum to give 4-(2-hydroxyethyl)-1-(trifluoromethyl)cyclohexan-1-ol (170.0 mg) as a colorless oil. LCMS Method A: $[M+H]^+$=213.2.

Scheme 60: Synthesis of intermediate 111 (1-(4-(trifluoromethyl)phenyl)pyrrolidin-3-ol)

Intermediate 111

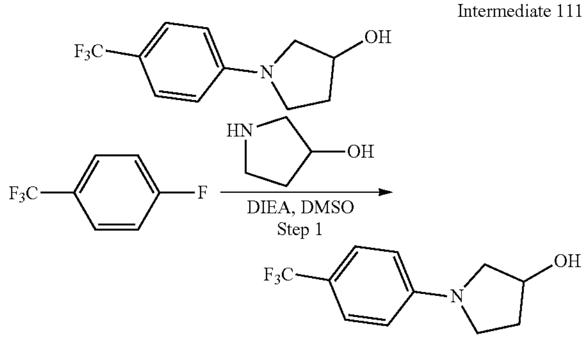

Intermediate 111

1-Fluoro-4-(trifluoromethyl)benzene (4.0 g, 24.3 mmol, 1.0 equiv.) was dissolved in DMSO (120 mL), then DIEA (8.0 mL, 48.7 mmol, 2.0 equiv.) and pyrrolidin-3-ol (2.1 g, 24.3 mmol, 1.0 equiv.) were added. The reaction mixture was stirred for 16 hours at 100° C., then cooled to rt and quenched by the addition of water. The resulting solution was extracted with EtOAc, washed with brine, dried over anhyd. $Na_2SO_4$ and concentrated under vacuum. The residue was purified by flash column chromatography on silica gel, eluting with petroleum ether/EtOAc (5:1) to give 1-[4-(trifluoromethyl)phenyl]pyrrolidin-3-ol (1.4 g) as a yellow solid. LCMS Method B: $[M+H]^+$=232.2.

Scheme 61: Synthesis of intermediate 112 (((1R, 3s, 5S)-8-(2,2,2-trifluoroethyl)-8-azabicyclo[3.2.1]octan-3-yl)methanol)

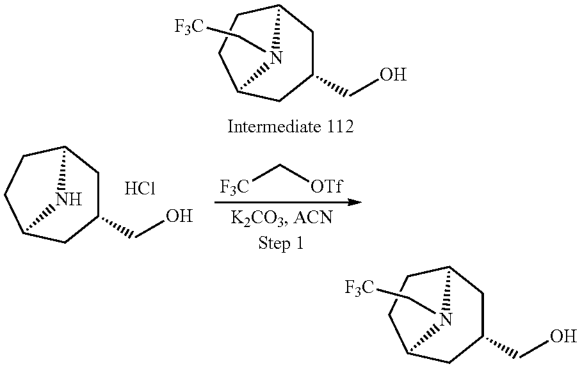

Intermediate 112

Intermediate 112

((1R,3s,5S)-8-azabicyclo[3.2.1]octan-3-yl)methanol hydrochloride (500.0 mg, 2.8 mmol, 1.0 equiv.) was dissolved in ACN (10 mL), then $K_2CO_3$ (1.2 g, 8.4 mmol, 3.0 equiv.) and 2,2,2-trifluoroethyl trifluoromethanesulfonate (720.0 mg, 3.1 mmol, 1.1 equiv.) were added. The reaction mixture was stirred for 2 hours at 80° C., then cooled to rt and quenched by the addition of water. The resulting solution was extracted with EtOAc, washed with brine, dried over anhyd. $Na_2SO_4$ and concentrated under vacuum. The residue was purified by flash column chromatography on silica gel, eluting with dichloromethane/methanol (99:1) to give [(1R,3R,5S)-8-(2,2,2-trifluoroethyl)-8-azabicyclo[3.2.1]octan-3-yl]methanol (530.0 mg) as a yellow oil. LCMS Method B: $[M-H]^-$=222.1.

Scheme 62: Synthesis of intermediate 113 (2-(4-methyl-2-trifluoromethyl)thiazol-5-yl)ethan-1-ol)

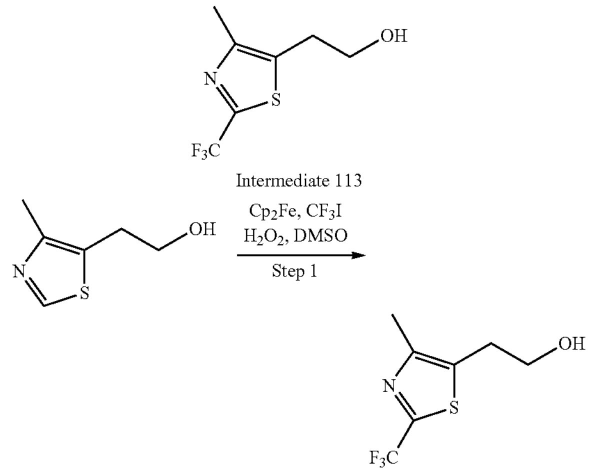

Intermediate 113

Intermediate 113

2-(4-Methylthiazol-5-yl) ethan-1-ol (3.0 g, 21.0 mmol, 1.0 equiv.) and ferrocene (2.2 g, 10.5 mmol, 0.5 equiv.) were dissolved in DMSO (10 mL), then $CF_3I$ (12.3 g, 62.9 mmol, 3.0 equiv.) was added dropwise. This was followed by the addition of $H_2O_2$ (30%, 162.6 mL, 209.5 mmol, 10.0 equiv.) dropwise at 0° C. The reaction mixture was stirred for 2 hours at rt and then quenched by the addition of aqueous $Na_2CO_3$. The resulting solution was diluted with water, extracted with EtOAc, washed with brine, dried over anhyd. $Na_2SO_4$ and concentrated under vacuum. The residue was purified by flash column chromatography on silica gel, eluting with petroleum ether/EtOAc (1:1) to give 2-(4-methyl-2-(trifluoromethyl) thiazol-5-yl) ethan-1-ol (1.7 g) as a brown oil. LCMS Method A: $[M+H]^+$=212.2.

Scheme 63: Synthesis of intermediate 114 (tert-butyl 7-(2-hydroxyethyl)-5-azaspiro[2.4]heptane-5-carboxylae)

Intermediate 114

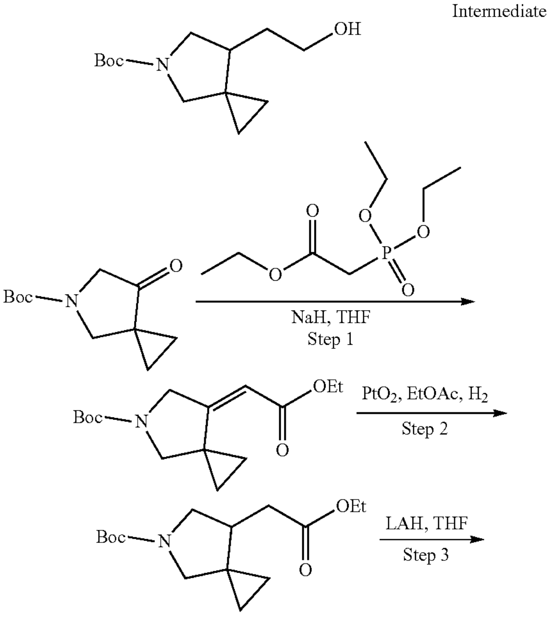

-continued

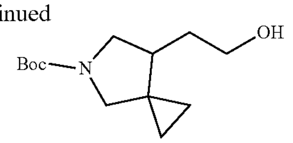

Intermediate 114

Step 1: tert-butyl (E)-7-(2-ethoxy-2-oxoethylidene)-5-azaspiro[2.4]heptane-5-carboxylate Ethyl 2-(diethoxyphosphoryl)acetate (1.6 g, 7.1 mmol, 1.5 equiv.) was dissolved in THF (15 mL) and cooled to 0° C., then NaH (60%, 284.0 mg, 7.1 mmol, 1.5 equiv.) was added. The reaction mixture was stirred for 30 min at rt, then tert-butyl 7-oxo-5-azaspiro[2.4]heptane-5-carboxylate (1.0 g, 4.7 mmol, 1.0 equiv.) was added dropwise. The resulting mixture was stirred overnight at rt and quenched by the addition of ice-water. The resulting solution was extracted with EtOAc, washed with brine, dried over anhyd. $Na_2SO_4$ and concentrated under vacuum. The residue was purified by flash column chromatography on silica gel, eluting with petroleum ether/EtOAc (1:1) to give tert-butyl (E)-7-(2-ethoxy-2-oxoethylidene)-5-azaspiro[2.4]heptane-5-carboxylate (750.0 mg) as a pale white solid. LCMS Method A: $[M+H]^+$=282.2.

Step 2: tert-butyl 7-(2-ethoxy-2-oxoethyl)-5-azaspiro[2.4]heptane-5-carboxylate tert-Butyl (E)-7-(2-ethoxy-2-oxoethylidene)-5-azaspiro[2.4]heptane-5-carboxylate (400.0 mg, 1.4 mmol, 1.0 equiv.) was dissolved in EtOAc (5.0 mL), then $PtO_2$ (40.0 mg, 0.2 mmol, 0.1 equiv.) was added. The mixture was sparged with nitrogen, placed under an atmosphere of hydrogen gas (balloon), then stirred for 2 hours at rt. The solids were removed by filtration and the filtrate was concentrated under vacuum to give tert-butyl 7-(2-ethoxy-2-oxoethyl)-5-azaspiro[2.4]heptane-5-carboxylate (380.0 mg) as an off-white solid. LCMS Method A: $[M+H]^+$=284.2.

Step 3: tert-butyl 7-(2-hydroxyethyl)-5-azaspiro[2.4]heptane-5-carboxylate tert-Butyl 7-(2-ethoxy-2-oxoethyl)-5-azaspiro[2.4]heptane-5-carboxylate (380.0 mg, 1.3 mmol, 1.0 equiv.) was dissolved in THE (8.0 mL) and cooled to 0° C., then LAH (101.8 mg, 2.7 mmol, 2.0 equiv.) was added. The reaction mixture was stirred for 2 hours at rt and then quenched by the addition of $Na_2SO_4$-$10H_2O$. The resulting mixture was filtered, the filter cake was washed with EtOAc and the combined filtrate was concentrated under vacuum. The residue was purified by flash column chromatography on silica gel, eluting with petroleum ether/EtOAc (1:1) to give tert-butyl 7-(2-hydroxyethyl)-5-azaspiro[2.4]heptane-5-carboxylate (250.0 mg) as a colorless oil. LCMS Method A: $[M+H]^+$=242.2.

The Intermediates in the Following Table were Prepared Using the Same Method Described for Intermediates 114.

| Intermediate | Starting material | Structure | LCMS data |
|---|---|---|---|
| Intermediate 115 | 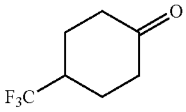 [SMILES: O=C1CCC(C(F)(F)F)CC1] | 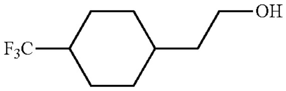 | Method A: MS-ESI: 197.2 $[M + H]^+$ |

Scheme 64: Synthesis of intermediate 116 (2-(3-(trifluoromethyl)bicyclo[1.1.1]pentan-1-yl)ethan-1-ol)

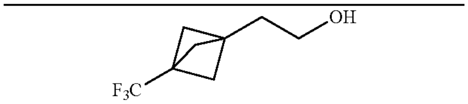

Intermediate 116

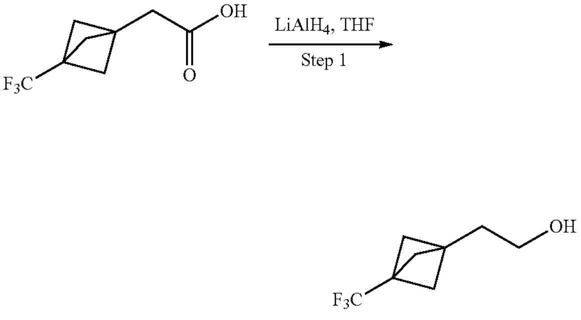

Intermediate 116

2-(3-(Trifluoromethyl)bicyclo[1.1.1]pentan-1-yl)acetic acid (250.0 mg, 1.3 mmol, 1.0 equiv.) was dissolved in THE (8 mL) and cooled to 0° C., then $LiAlH_4$ (97.7 mg, 2.6 mmol, 2.0 equiv.) was added. The resulting mixture was stirred for 2 hours at 0° C. and then quenched by the addition of $Na_2SO_4$-$10H_2O$. The resulting mixture was filtered and the filter cake was washed with EtOAc. The combined filtrate was concentrated under vacuum. The residue was purified by flash column chromatography on silica gel, eluting with petroleum ether/EtOAc (1:1) to give 2-(3-(trifluoromethyl)bicyclo[1.1.1]pentan-1-yl)ethan-1-ol (90.0 mg) as a colorless oil. LCMS Method A: $[M+H]^+$=181.2.

The Intermediates in the Following Table were Prepared Using the Same Method Described for Intermediates 116.

| Intermediate | Starting material | Structure | LCMS data |
| --- | --- | --- | --- |
| Intermediate 117 | 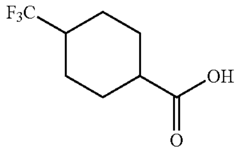 [SMILES: O=C(O)C1CCC(C(F)(F)F)CC1] | 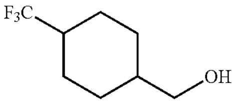 [SMILES: OCC1CCC(C(F)(F)F)CC1] | Method C: MS-ESI: 183.2 $[M + H]^+$ |

Scheme 65: Synthesis of intermediate 118 (5-(trifluoromethyl)-2,3-dihydro-1H-inden-2-ol)

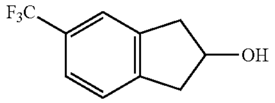

Intermediate 118

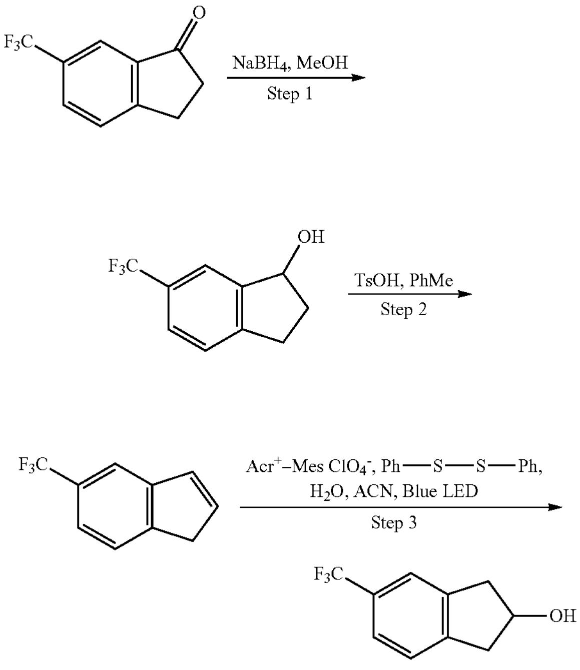

Intermediate 118

Step 1: 6-(trifluoromethyl)-2,3-dihydro-1H-inden-1-ol 6-(Trifluoromethyl)-2,3-dihydroinden-1-one (5.0 g, 24.9 mmol, 1.0 equiv.) was dissolved in MeOH (20 mL) and cooled to 0° C., then $NaBH_4$ (1.9 g, 49.9 mmol, 2.0 equiv.) was added in portions. The reaction mixture was stirred for 16 hours at rt and then quenched by the addition of eater. The resulting solution was extracted with EtOAc, washed with brine, dried over anhyd. $Na_2SO_4$ and concentrated under vacuum to give 6-(trifluoromethyl)-2,3-dihydro-1H-inden-1-ol (5.0 g) as a pale yellow oil. LCMS Method B: $[M-H]^-$=201.1.

Step 2: 5-(trifluoromethyl)-1H-indene 6-(Trifluoromethyl)-2,3-dihydro-1H-inden-1-ol (1.0 g, 4.9 mmol, 1.0 equiv.) was dissolved in toluene (5 mL), then TsOH (425.8 mg, 2.5 mmol, 0.5 equiv.) was added. The reaction mixture was stirred overnight at 110° C., then cooled to rt and concentrated under vacuum. The residue was diluted with water and the resulting solution was extracted with EtOAc, washed with brine, dried over anhyd. $Na_2SO_4$ and concentrated under vacuum. The residue was purified by flash column chromatography on silica gel, eluting with petroleum ether (100%) to give 5-(trifluoromethyl)-1H-indene (505.0 mg) as an off-white oil.

Step 3: 5-(trifluoromethyl)-2,3-dihydro-1H-inden-2-ol 5-(Trifluoromethyl)-1H-indene (500.0 mg, 2.7 mmol, 1.0 equiv.) and (phenyldisulfanyl)benzene (118.6 mg, 0.5 mmol, 0.2 equiv.) were dissolved in ACN (10 mL) and water (1 mL), then 9-Mesityl-10-methylacridinium Perchlorate (33.5 mg, 0.08 mmol, 0.03 equiv.) was added. The reaction mixture was stirred for 16 hours at 3 W blue LEDs at rt, then quenched by the addition of water. The resulting solution was extracted with EtOAc, washed with brine, dried over anhyd. $Na_2SO_4$ and concentrated under vacuum. The residue was purified by reverse flash chromatography with the following conditions: column, C18 silica gel; mobile phase, MeCN in Water (10 mmol/L $NH_4HCO_3$), 10% to 50% gradient in 10 min; detector, UV 254 nm. This gave 5-(trifluoromethyl)-2,3-dihydro-1H-inden-2-ol (300.0 mg) as an off-white solid. LCMS Method A: $[M+H]^+$=203.2 1H NMR (400 MHz, DMSO-$d_6$) δ 7.56 (s, 1H), 7.48 (dd, J=8.0, 2.0 Hz, 1H), 7.43 (d, J=8.0 Hz, 1H), 4.94 (d, J=3.6 Hz, 1H), 4.57-4.52 (m, 1H), 3.13 (dd, J=16.4, 5.6 Hz, 2H), 2.85-2.79 (m, 2H).

The Intermediates in Following Table were Prepared Using the Same Method Described for Intermediates 118.

| Intermediate | Starting material | Structure | LCMS data |
| --- | --- | --- | --- |
| Intermediate 119 | 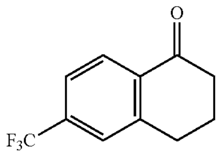 [SMILES: O=C1CCCc2cc(C(F)(F)F)ccc21] | 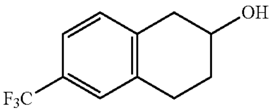 | Method A: MS-ESI: 217.2 $[M + H]^+$ |

Scheme 66: Synthesis of intermediate 120 (2-methyl-3-(4-(trifluoromethyl)phenyl)cyclobutan-1-ol)

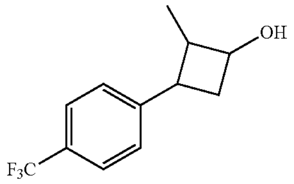

Intermediate 120

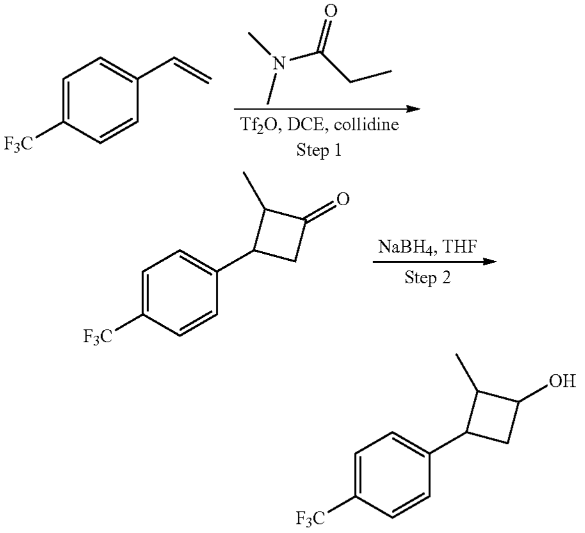

Intermediate 120

Step 1: 2-methyl-3-(4-(trifluoromethyl)phenyl)cyclobutan-1-one 1-(Trifluoromethyl)-4-vinylbenzene (5.0 g, 29.0 mmol, 1.0 equiv.) was dissolved in DCE (100 mL) and cooled to 0° C., then $Tf_2O$ (11.5 g, 40.7 mmol, 1.4 equiv.) was added dropwise, maintaining the solution at 0° C. After stirred for 30 min at 0° C., N,N-dimethylpropionamide (3.5 g, 34.8 mmol, 1.2 equiv.) and 2,4,6-trimethylpyridine (4.9 g, 40.6 mmol, 1.4 equiv.) was added. The reaction mixture was stirred for additional 2 hours at 80° C., then cooled to rt and quenched by the addition of water. The resulting solution was extracted with dichloromethane, washed with brine, dried over anhyd. $Na_2SO_4$ and concentrated under vacuum. The residue was purified by flash column chromatography on silica gel, eluting with petroleum ether/EtOAc (20:1) to give 2-methyl-3-(4-(trifluoromethyl)phenyl)cyclobutan-1-one (3.0 g) as a yellow oil. $^1H$ NMR (400 MHz, DMSO-$d_6$) δ 7.72 (d, J=8.0 Hz, 2H), 7.65 (d, J=8.0 Hz, 2H), 3.52-3.42 (m, 1H), 3.42-3.34 (m, 1H), 3.33-3.24 (m, 2H), 1.18 (d, J=7.2 Hz, 3H).

Step 2: 2-methyl-3-(4-(trifluoromethyl)phenyl)cyclobutan-1-ol

2-Methyl-3-(4-(trifluoromethyl)phenyl)cyclobutan-1-one (3.2 g, 13.8 mmol, 1.0 equiv.) was dissolved in THF (30 mL) and cooled to 0° C., then $NaBH_4$ (522.1 mg, 13.8 mmol, 1.0 equiv.) was added. The reaction mixture was stirred for 2 hours at 0° C., then quenched by the addition of water. The resulting solution was extracted with EtOAc, washed with brine, dried over anhyd. $Na_2SO_4$ and concentrated under vacuum. The residue was purified by flash column chromatography on silica gel, eluting with petroleum ether/EtOAc (5:1) to give 2-methyl-3-(4-(trifluoromethyl)phenyl)cyclobutan-1-ol (2.6 g) as a yellow oil. $^1H$ NMR (400 MHz, DMSO-$d_6$) δ 7.65 (d, J=8.0 Hz, 2H), 7.46-7.43 (m, 2H), 5.13 (d, J=7.6 Hz, 1H), 3.58-3.56 (m, 1H), 2.57-2.51 (m, 1H), 2.09-2.00 (m, 1H), 1.82-1.73 (m, 1H), 1.10 (d, J=6.4 Hz, 3H).

Scheme 67: Synthesis of intermediate 121 ((7-(trifluoromethyl)-1,2,3,4-tetrahydronaphthalen-2-yl)methanol)

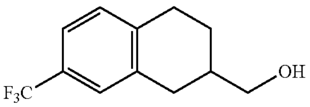

Intermediate 121

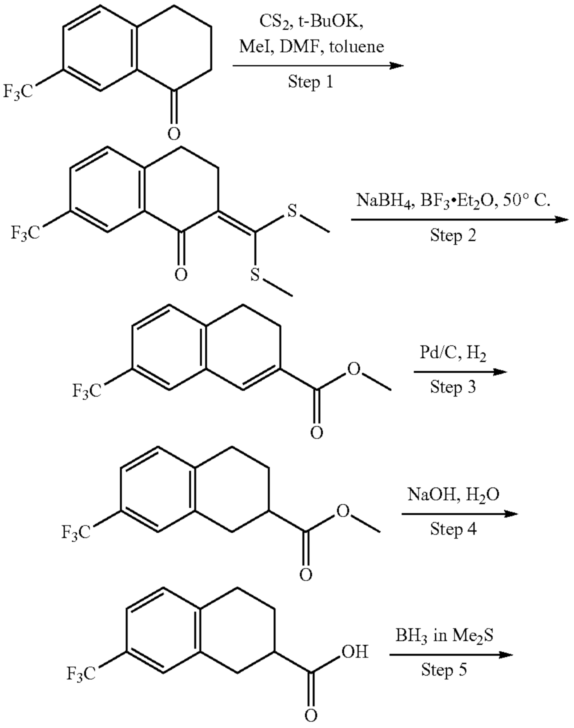

-continued

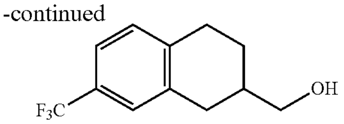

Intermediate 121

Step 1: 2-(bis(methylthio)methylene)-7-(trifluoromethyl)-3,4-dihydronaphthalen-1(2H)-one 7-(Trifluoromethyl)-3,4-dihydro-2H-naphthalen-1-one (2.0 g, 9.3 mmol, 1.0 equiv.) and t-BuOK (2.1 g, 18.7 mmol, 2.0 equiv.) were dissolved in DMF (15 mL) and toluene (15 mL), then $CS_2$ (1.4 g, 18.7 mmol, 2.0 equiv.) was added dropwise under an atmosphere of nitrogen. The reaction mixture was stirred for 4 hours at rt, then MeI (2.7 g, 18.7 mmol, 2.0 equiv.) was added dropwise. The resulting mixture was stirred overnight at rt and then quenched by the addition of water. The resulting solution was extracted with EtOAc, washed with brine, dried over anhyd. $Na_2SO_4$ and concentrated under vacuum. The residue was purified by flash column chromatography on silica gel, eluting with petroleum ether/EtOAc (8:1) to give 2-[bis(methylsulfanyl)methylidene]-7-(trifluoromethyl)-3,4-dihydronaphthalen-1-one (1.5 g) as a yellow solid. LCMS Method A: $[M+H]^+$=319.1.

Step 2: methyl 7-(trifluoromethyl)-3,4-dihydronaphthalene-2-carboxylate

2-[bis(methylsulfanyl)methylidene]-7-(trifluoromethyl)-3,4-dihydronaphthalen-1-one (1.5 g, 4.7 mmol, 1.0 equiv.) was dissolved in MeOH (15 mL) and cooled to 0° C., the $NaBH_4$ (267.0 mg, 7.1 mmol, 1.5 equiv.) was added. The reaction mixture was stirred for 30 min at rt, then $BF_3·Et_2O$ (1.2 g, 85.1 mmol, 18.0 equiv.) was added dropwise. The reaction mixture was stirred overnight at 50° C., then cooled to rt and quenched by the addition of water. The resulting solution was extracted with EtOAc, washed with brine, dried over anhyd. $Na_2SO_4$ and concentrated under vacuum. The residue was purified by flash column chromatography on silica gel, eluting with petroleum ether/EtOAc (5:1) to give 2-[bis(methylsulfanyl)methylidene]-7-(trifluoromethyl)-3,4-dihydronaphthalen-1-one (810 mg) as a yellow solid. LCMS Method A: $[M+H]^+$=257.1.

Step 3: methyl 7-(trifluoromethyl)-1,2,3,4-tetrahydronaphthalene-2-carboxylate

Methyl 7-(trifluoromethyl)-3,4-dihydronaphthalene-2-carboxylate (800.0 mg, 3.1 mmol, 1.0 equiv.) was dissolved in MeOH (10 mL), then Pd/C (166.1 mg, 1.6 mmol, 0.5 equiv.) was added under an atmosphere of nitrogen. The mixture was sparged with nitrogen, placed under an atmosphere of hydrogen gas (balloon), then stirred for 5 hours at rt. The solids were removed by filtration and the filtrate was concentrated under vacuum to give methyl 7-(trifluoromethyl)-1,2,3,4-tetrahydronaphthalene-2-carboxylate (705 mg) as a yellow oil. LCMS Method A: $[M+H]^+$=259.2.

Step 4: 7-(trifluoromethyl)-1,2,3,4-tetrahydronaphthalene-2-carboxylic acid

Methyl 7-(trifluoromethyl)-1,2,3,4-tetrahydronaphthalene-2-carboxylate (700.0 mg, 2.7 mmol, 1.0 equiv.) was dissolved in MeOH (10 mL) and $H_2O$ (5 mL), then NaOH (542.1 mg, 13.6 mmol, 5.0 equiv.) was added. The reaction mixture was stirred overnight at rt and concentrated under vacuum. The residue was diluted with water, adjusted to pH 5 with aqueous HCl. The precipitated solids were collected by filtration, washed with water and dried to give 7-(trifluoromethyl)-1,2,3,4-tetrahydronaphthalene-2-carboxylic acid (350.0 mg) as an off-white solid. LCMS Method B: $[M-H]^-$=243.1.

Step 5: (7-(trifluoromethyl)-1,2,3,4-tetrahydronaphthalen-2-yl)methanol 7-(Trifluoromethyl)-1,2,3,4-tetrahydronaphthalene-2-carboxylic acid (350.0 mg, 1.4 mmol, 1.0 equiv.) was dissolved in THE (5 mL) and cooled to 0° C., then $BH_3$-$Me_2S$ (181.1 mg, 7.2 mmol, 5.0 equiv.) was added. The reaction mixture was stirred for 4 hours at rt and then quenched by the addition of water. The resulting solution was extracted with EtOAc, washed with brine, dried over anhyd. $Na_2SO_4$ and concentrated under vacuum. The residue was purified by flash column chromatography on silica gel, eluting with petroleum ether/EtOAc (5:1) to give (7-(trifluoromethyl)-1,2,3,4-tetrahydronaphthalen-2-yl)methanol (300.0 mg) as a yellow solid. $^1$HNMR (400 MHz, DMSO-$d_6$) δ 7.40 (d, J=9.2 Hz, 2H), 7.28 (d, J=7.6 Hz, 1H), 4.62 (s, 1H), 3.38 (d, J=6.4 Hz, 2H), 2.93-2.82 (m, 2H), 2.76-2.69 (m, 1H), 2.48-2.45 (m, 1H), 1.99-1.89 (m, 1H), 1.82-1.72 (m, 1H), 1.35-1.22 (m, 1H).

Scheme 68: Synthesis of intermediate 122 (cis-3-(2-methyl-4-(trifluoromethyl)phenyl)cyclobutan-1-ol)

Intermediate 122

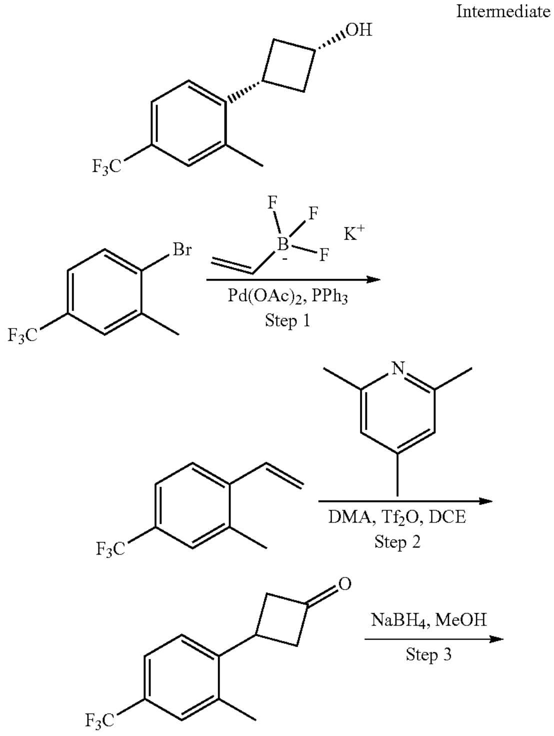

-continued

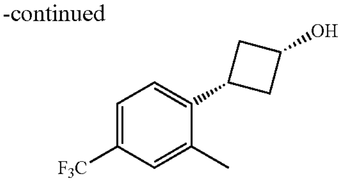

Intermediate 122

Step 1: 2-methyl-4-(trifluoromethyl)-1-vinylbenzene

1-Bromo-2-methyl-4-(trifluoromethyl)benzene (5.0 g, 20.9 mmol, 1.0 equiv.) and potassium 1-(trifluoro-lambda4-boranyl)eth-1-enide (4.2 g, 31.6 mmol, 1.5 equiv) were dissolved in THE (40 mL) and $H_2O$ (4 mL), then $Cs_2CO_3$ (13.6 g, 41.8 mmol, 2.0 equiv.), $PPh_3$ (1.1 g, 4.2 mmol, 0.2 N/equiv.) and $Pd(OAc)_2$ (0.5 g, 2.1 mmol, 0.1 equiv.) were added under an atmosphere of nitrogen. The reaction mixture was stirred for 4 hours at 70° C., then cooled to rt and quenched by the addition of water. The resulting solution was extracted with EtOAc, washed with brine, dried over anhyd. sodium sulfate and concentrated under vacuum. The residue was purified by flash column chromatography on silica gel, eluting with petroleum ether/EtOAc (99:1) to give 2-methyl-4-(trifluoromethyl)-1-vinylbenzene (2.2 g) as a yellow oil. 1H NMR (400 MHz, DMSO-$d_6$) δ 7.72 (d, J=8.0 Hz, 1H), 7.62-7.51 (m, 2H), 7.03-6.98 (m, 1H), 5.86 (dd, J=17.2 Hz, 2.1 Hz, 1H), 5.50-5.44 (m, 1H), 2.39 (s, 3H).

Step 2: 3-(2-methyl-4-(trifluoromethyl)phenyl)cyclobutan-1-one

DMA (1.1 g, 12.9 mmol, 2.4 equiv.) was dissolved in DCE (10 mL) and cooled to 0° C., then a solution of $Tf_2O$ (6.1 g, 21.5 mmol, 4.0 equiv.) in DCE (1 mL) was added dropwise under an atmosphere of nitrogen. The reaction mixture was stirred for 30 min at 0° C., then a mixture of 2,4,6-collidine (2.6 g, 21.5 mmol, 4.0 equiv.) and 2-methyl-4-(trifluoromethyl)-1-vinylbenzene (1.0 g, 5.4 mmol, 1.0 equiv.) was added dropwise, maintaining the solution at 0° C. The resulting mixture was stirred for 16 hours at 80° C., then cooled to rt and quenched by the addition of water. The resulting solution was extracted with dichloromethane, washed with brine, dried over anhyd. sodium sulfate and concentrated under vacuum. The residue was purified by flash column chromatography on silica gel, eluting with petroleum ether/EtOAc (20:1) to give 3-(2-methyl-4-(trifluoromethyl)phenyl)cyclobutan-1-one (380 mg) as a yellow oil. 1H NMR (400 MHz, DMSO-$d_6$) δ 7.62-7.60 (m, 1H), 7.56-7.53 (m, 2H), 3.88-3.79 (m, 1H), 3.50-3.41 (m, 2H), 3.30-3.24 (m, 2H), 2.37 (s, 3H).

Step 3: cis-3-(2-methyl-4-(trifluoromethyl)phenyl)cyclobutan-1-ol 3-(2-Methyl-4-(trifluoromethyl)phenyl)cyclobutan-1-one (380.0 mg, 1.7 mmol, 1.0 equiv.) was dissolved in MeOH (5 mL) and cooled to 0° C., then $NaBH_4$ (127.0 mg, 3.3 mmol, 2.0 equiv.) was added in portions. The reaction mixture was stirred for 1 hour at 0° C. and then quenched by the addition of water. The resulting solution was extracted with EtOAc, washed with brine, dried over anhyd. sodium sulfate and concentrated under vacuum to give cis-3-(2-methyl-4-(trifluoromethyl)phenyl)cyclobutan-1-ol (300.0 mg) as a yellow solid. $^1$HNMR (400 MHz, DMSO-$d_6$) δ 7.60-7.46 (m, 2H), 7.42-7.40 (m, 1H), 5.13 (d, J=7.2 Hz, 1H), 4.12-4.06 (m, 1H), 3.05-2.98 (m, 1H), 2.68-2.62 (m, 2H), 2.28 (s, 3H), 1.89-1.81 (m, 2H).

Scheme 69: Synthesis of intermediate 123 ((2-(2,2,2-trifluoroethyl)-2,4,5,6-tetrahydrocyclopenta[c]pyrazol-5-yl)methnaol) and intermediate 124 ((1-(2,2,2-trifluoroethyl)-1,4,5,6-tetrahydrocyclopenta[c]pyrazol-5-yl)methanol)

Intermediate 123

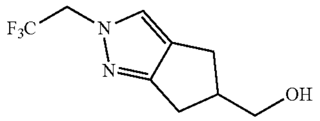

Intermediate 124

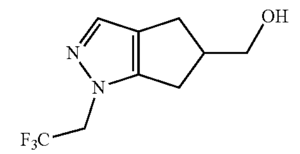

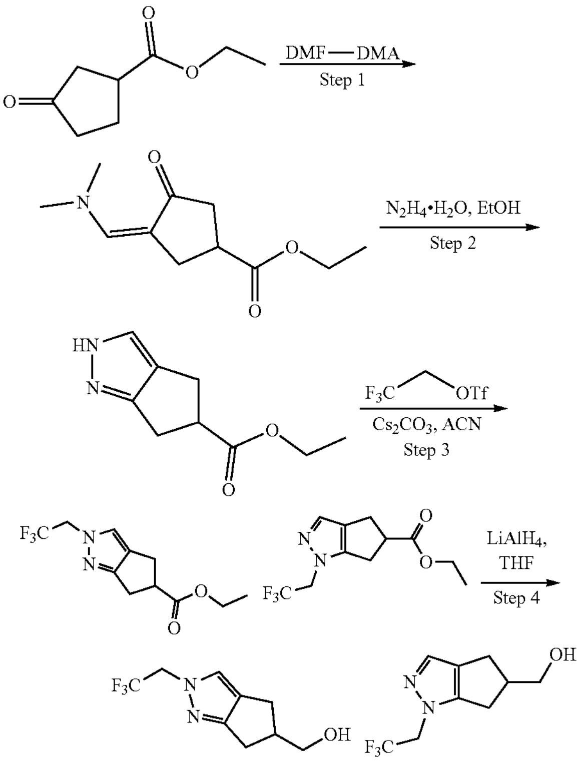

Intermediate 123 Intermediate 124

Step 1: ethyl (3Z)-3-[(dimethylamino)methylidene]-4-oxocyclopentane-1-carboxylate Ethyl 3-oxocyclopentane-1-carboxylate (4.0 g, 25.6 mmol, 1.0 equiv.) was dissolved in DMF-DMA (40.0 mL). The reaction mixture was stirred for 4 hours at 100° C., then cooled to rt and quenched by the addition of water. The resulting solution was extracted with EtOAc, washed with brine, dried over anhyd. $Na_2SO_4$ and concentrated under vacuum to give ethyl (3Z)-3-[(dimethylamino)methylidene]-4-oxocyclopentane-1-carboxylate (2.0 g) as a yellow oil. LCMS Method A: $[M+H]^+$=212.2.

Step 2: ethyl 2H,4H,5H,6H-cyclopenta[c]pyrazole-5-carboxylate

Ethyl (3Z)-3-[(dimethylamino)methylidene]-4-oxocyclopentane-1-carboxylate (2.0 g, 9.5 mmol, 1.0 equiv.) was dissolved in EtOH (20 mL), hydrazine (910.0 mg, 28.4 mmol, 3.0 equiv.) was added. The reaction mixture was stirred for 5 hours at rt and then quenched by the addition of $FeCl_3$ (900 mg). The resulting solution was filtered and the filter cake was washed with -ethanol. The combined filtrate was concentrated under vacuum. The residue was purified by Prep Chiral-HPLC with the following conditions: Column: CHIRALPAK IG, 5*15 cm, 10 m; Mobile Phase A: $CO_2$, Mobile Phase B: EtOH:DCM=1:1; Flow rate: 200 mL/min; Gradient: isocratic 30% B; Column Temperature (° C.): 35; Back Pressure(bar): 100; Wave Length: 220 nm; RT1 (min): 3.88. This resulted in ethyl 2H,4H,5H,6H-cyclopenta[c]pyrazole-5-carboxylate (920.0 mg) as an off-white solid. LCMS Method A: $[M+H]^+$=181.2.

Step 3: mixture of ethyl 2-(2,2,2-trifluoroethyl)-4H,5H,6H-cyclopenta[c]pyrazole-5-carboxylate and ethyl 1-(2,2,2-trifluoroethyl)-4H,5H,6H-cyclopenta[c]pyrazole-5-carboxylate Ethyl 2H,4H,5H,6H-cyclopenta[c]pyrazole-5-carboxylate (900.0 mg, 5.0 mmol, 1.0 equiv.) was dissolved in ACN (10 mL), $Cs_2CO_3$ (3.3 g, 10.0 mmol, 2.0 equiv.) and 2,2,2-trifluoroethyl trifluoromethanesulfonate (1.7 g, 7.5 mmol, 1.5 equiv.) were added. The reaction mixture was stirred for 16 hours at 65° C., then cooled to rt and quenched by the addition of water. The resulting solution was extracted with EtOAc, washed with brine, dried over anhyd. $Na_2SO_4$ and concentrated under vacuum to give a mixture of ethyl 2-(2,2,2-trifluoroethyl)-4H,5H,6H-cyclopenta[c]pyrazole-5-carboxylate and ethyl 1-(2,2,2-trifluoroethyl)-4H,5H,6H-cyclopenta[c]pyrazole-5-carboxylate (585.0 mg) as an off-white solid. LCMS Method A: $[M+H]^+$=263.2.

Step 4: mixture of [2-(2,2,2-trifluoroethyl)-4H,5H,6H-cyclopenta[c]pyrazol-5-yl]methanol and [1-(2,2,2-trifluoroethyl)-4H,5H,6H-cyclopenta[c]pyrazol-5-yl]methanol The mixture of ethyl 2-(2,2,2-trifluoroethyl)-4H,5H,6H-cyclopenta[c]pyrazole-5-carboxylate and ethyl 1-(2,2,2-trifluoroethyl)-4H,5H,6H-cyclopenta[c]pyrazole-5-carboxylate (200.0 mg, 0.8 mmol, 1.0 equiv.) was dissolved in THF (8 mL) and cooled to 0° C., $LiAlH_4$ (44 mg, 1.2 mmol, 1.5 equiv.) was added. The reaction mixture was stirred for 5 hours at rt and then quenched by the addition of ice-water at 0° C. The resulting solution was extracted with EtOAc, washed with brine, dried over anhyd. $Na_2SO_4$ and concentrated under vacuum. The residue was purified by silica gel column chromatography, eluting with petroleum ether/EtOAc (5:1) to give a mixture of [2-(2,2,2-trifluoroethyl)-4H,5H,6H-cyclopenta[c]pyrazol-5-yl]methanol and [1-(2,2,2-trifluoroethyl)-4H,5H,6H-cyclopenta[c]pyrazol-5-yl]methanol (81.0 mg) as an off-white solid. LCMS Method A: $[M+H]^+$=221.2.

Scheme 70: Synthesis of intermediate 125 ((2-(2,2,2-trifluoroethyl)-2-azabicyclo[2.1.1]hexan-1-yl)methanol)

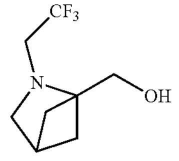

Intermediate 125

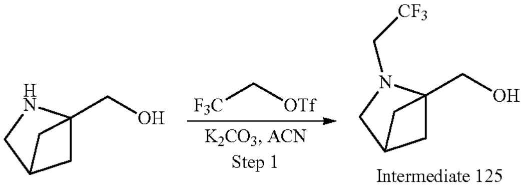

Intermediate 125

(2-Azabicyclo[2.1.1]hexan-1-yl)methanol (300.0 mg, 2.7 mmol, 1.0 equiv.) and 2,2,2-trifluoroethyl trifluoromethanesulfonate (923.0 mg, 4.0 mmol, 1.5 equiv.) were dissolved in ACN (10.0 mL), $K_2CO_3$ (732.8 mg, 5.3 mmol, 2.0 equiv.) was added at rt. The reaction mixture was stirred for 2 h at 50° C., then cooled to rt and quenched by the addition of water. The resulting solution was extracted with EtOAc, washed with brine, dried over anhyd. $Na_2SO_4$ and concentrated under vacuum. The residue was purified by flash column chromatography on silica gel, eluting with petroleum ether/EtOAc (3:1) to give (2-(2,2,2-trifluoroethyl)-2-azabicyclo[2.1.1]hexan-1-yl)methanol (400.0 mg) as a white solid. LCMS Method A: $[M+H]^+$=196.2.

Scheme 71: Synthesis of intermediate 126 (tributyl((cis-3-(4-(trifluoromethyl)phenyl)cyclobutoxy)methyl)stannane)

Intermediate 126

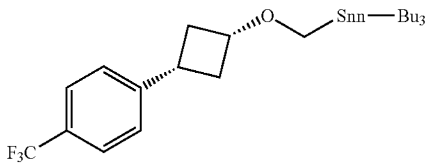

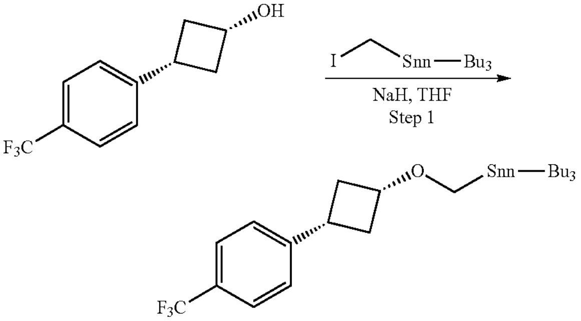

Intermediate 126 cis-3-[4-(Trifluoromethyl)phenyl]cyclobutan-1-ol (1.0 g, 4.0 mmol, 1.0 equiv.) was dissolved in THF (10 mL) and cooled to 0° C., then NaH (60% wt., 221.0 mg, 5.5 mmol, 1.4 equiv.) was added. After stirred for 15 min at 0° C., tributyl(iodomethyl)stannane (1.8 g, 4.2 mmol, 0.9 equiv.) was added. The reaction mixture was stirred for 2 hours at rt and then quenched by the addition of water. The resulting solution was extracted with dichloromethane, washed with brine and concentrated under vacuum. The residue was purified by flash column chromatography on silica gel, eluting with petroleum ether/EtOAc (99:1) to give tributyl ({[cis-3-[4-(trifluoromethyl)phenyl]cyclobutoxy]methyl}) stannane (630.0 mg) as a yellow oil.

The Intermediates in the Following Table were Prepared Using the Same Method Described for Intermediates 126.

| Intermediate | Starting material | Structure | LCMS data |
|---|---|---|---|
| Intermediate 127 | 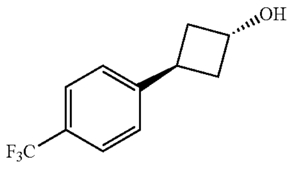 [SMILES: O[C@H]1C[C@H](c2ccc(C(F)(F)F)cc2)C1] | 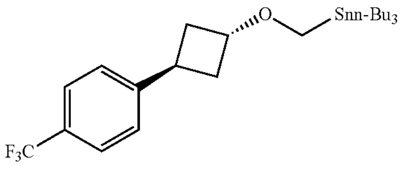 | N/A |
| Intermediate 128 | 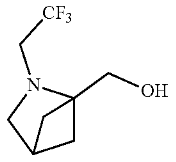 Intermediate 125 | 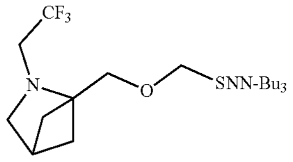 | N/A |

Scheme 72: Synthesis of intermediate 129 (3-methoxy-1-methylcyclobutane-1-carboxylic acid)

Intermediate 129

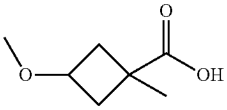

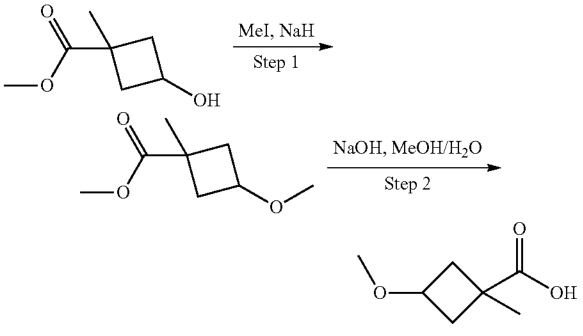

Intermediate 129

Step 1: methyl 3-methoxy-1-methylcyclobutane-1-carboxylate

Methyl 3-hydroxy-1-methylcyclobutane-1-carboxylate (1.5 g, 10.4 mmol, 1.0 equiv.) was dissolved in THE (30 mL) and cooled to 0° C., then NaH (60% wt, 624.2 mg, 15.6 mmol, 1.5 equiv.) was added under an atmosphere of nitrogen. After 5 min at 0° C., MeI (3.7 g, 26.0 mmol, 2.5 equiv.) was added. The reaction mixture was stirred for additional 1 hour at 0° C. and then quenched by the addition of ice-water. The resulting solution was extracted with EtOAc, washed with brine, dried over anhyd. $Na_2SO_4$ and concentrated under vacuum. The residue was purified by flash column chromatography on silica gel, eluting with petroleum ether/EtOAc (10:1) to give methyl 3-methoxy-1-methylcyclobutane-1-carboxylate (1.3 g) as a yellow oil.

Step 2: 3-methoxy-1-methylcyclobutane-1-carboxylic acid

Methyl 3-methoxy-1-methylcyclobutane-1-carboxylate (1.3 g, 8.5 mmol, 1.0 equiv.) was dissolved in MeOH (10 mL), then aqueous NaOH (5 mL, 2 M, 10 mmol, 1.2 equiv.) was added. The reaction mixture was stirred for 1 hour at rt and concentrated under vacuum. The residue was diluted with water, adjusted to pH 3 with aqueous HCl (4M). The resulting solution was extracted with EtOAc, washed with brine, dried over anhyd. $Na_2SO_4$ and concentrated under vacuum to afford 3-methoxy-1-methylcyclobutane-1-carboxylic acid (960 mg) as a colorless oil. LCMS Method B: $[M-H]^-=143.0$.

Scheme 73: Synthesis of intermediate 130 (2-methyloxetane-3-carboxylic acid)

Intermediate 130

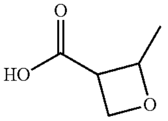

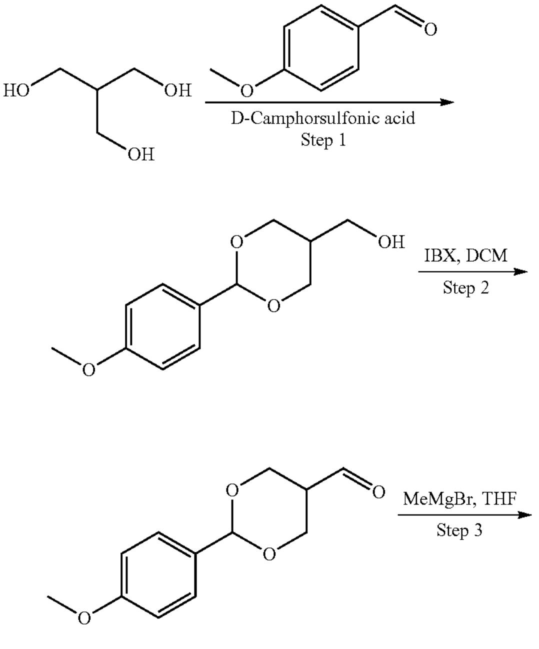

-continued

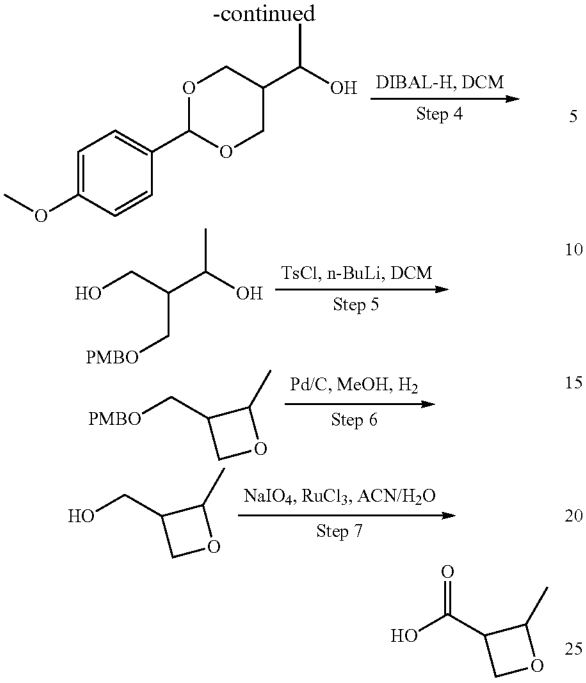

Intermediate 130

Step 1: (2-(4-methoxyphenyl)-1,3-dioxan-5-yl)methanol 2-(Hydroxymethyl)propane-1,3-diol (8.0 g, 75.4 mmol, 1.0 equiv.) and 4-methoxybenzaldehyde (12.3 g, 90.5 mmol, 1.2 equiv.) were dissolved in DCM (100 mL), then [(1S, 4R)-7,7-dimethyl-2-oxobicyclo[2.2.1]heptan-1-yl]methanesulfonic acid (3.5 g, 15.1 mmol, 0.2 equiv.) was added in portions. The reaction mixture was stirred for 2 days at 40° C., then cooled to 0° C. and quenched by the addition of TEA (5.2 mL, 37.7 mmol, 0.5 equiv.). The solution was concentrated under vacuum and the residue was purified by flash column chromatography on silica gel, eluting with petroleum ether/EtOAc (1:1) to give (2-(4-methoxyphenyl)-1,3-dioxan-5-yl)methanol (6.0 g) as a white solid. LCMS Method A: $[M+H]^+$=225.1.

Step 2: 2-(4-methoxyphenyl)-1,3-dioxane-5-carbaldehyde (2-(4-Methoxyphenyl)-1,3-dioxan-5-yl)methanol (6.0 g, 26.8 mmol, 1.0 equiv.) was dissolved in DCM (60 mL), then IBX (15.0 g, 53.5 mmol, 2.0 equiv.) was added. The reaction mixture was stirred for overnight at 40° C., then cooled to rt and remove the solid by filtration. The filter cake was washed with DCM and the combined filtrate was concentrated under vacuum to give crude 2-(4-methoxyphenyl)-1,3-dioxane-5-carbaldehyde (6.5 g) as a colorless oil. LCMS Method A: $[M+H]^+$=223.1.

Step 3: 1-(2-(4-methoxyphenyl)-1,3-dioxan-5-yl)ethan-1-ol 2-(4-Methoxyphenyl)-1,3-dioxane-5-carbaldehyde (6.5 g, 29.2 mmol, 1.0 equiv.) was dissolved in THE (80 mL) and cooled to 0° C., then MgMgBr (1M in THF, 58.5 mL, 58.5 mmol, 2.0 equiv.) was added dropwise under an atmosphere of nitrogen. The reaction mixture was stirred for 4 hours at 0° C. and then quenched by the addition of saturated aqueous $NH_4Cl$ (aq.). The resulting solution was extracted with EtOAc, washed with brine, dried over anhyd. $Na_2SO_4$ and concentrated under vacuum. The residue was purified by flash column chromatography on silica gel, eluting with petroleum ether/EtOAc (1:1) to give 1-(2-(4-methoxyphenyl)-1,3-dioxan-5-yl)ethan-1-ol (3.2 g) as a white solid. LCMS Method A: $[M+H]^+$=239.2. $^1$HNMR (400 MHz, DMSO-$d_6$) δ 7.32-7.31 (m, 2H), 6.94-6.86 (m, 2H), 5.45 (d, J=1.2 Hz, 1H), 4.66 (dd, J=5.6, 1.6 Hz, 1H), 4.35-4.33 (m, 1H), 4.10-4.00 (m, 2H), 3.95-3.88 (m, 1H), 3.68-3.65 (m, 1H), 3.41 (p, J=6.2 Hz, 1H), 1.26-1.15 (m, 3H).

Step 4: 2-(((4-methoxybenzyl)oxy)methyl)butane-1,3-diol 1-(2-(4-Methoxyphenyl)-1,3-dioxan-5-yl)ethan-1-ol (3.2 g, 13.4 mmol, 1.0 equiv.) was dissolved in DCM (50 mL) and cooled to 0° C., then DIBAL-H (1M, 26.9 mL, 26.9 mmol, 2.0 equiv.) was added dropwise, maintaining the solution at 0° C. The reaction mixture was stirred overnight at 0° C. and then quenched by the addition of $Na_2SO_4$-$10H_2O$. The resulting mixture was filtered and the filter cake was washed with DCM. The combined filtrate was concentrated under vacuum and the residue was purified by flash column chromatography on silica gel, eluting with petroleum ether/EtOAc (1:1) to give 2-(((4-methoxybenzyl)oxy)methyl)butane-1,3-diol (2.5 g) as a white solid. LCMS Method A: $[M+H]^+$=241.2. $^1$H NMR (400 MHz, DMSO-$d_6$) δ 7.23 (d, J=8.4 Hz, 2H), 6.94-6.87 (m, 2H), 4.43-4.27 (m, 3H), 4.01-3.99 (m, 1H), 3.74 (s, 3H), 3.56-3.47 (m, 1H), 3.46-3.35 (m, 4H), 1.68-1.66 (m, 1H), 1.10-1.08 (m, 3H).

Step 5: 3-(((4-methoxybenzyl)oxy)methyl)-2-methyloxetane 2-(((4-Methoxybenzyl)oxy)methyl)butane-1,3-diol (2.5 g, 10.4 mmol, 1.0 equiv.) was dissolved in DCM (25 mL) and cooled to 0° C., then n-BuLi (2.5 M in hexane, 4.2 mL, 10.4 mmol, 1.0 equiv.) was added dropwise, maintaining the solution at 0° C. under an atmosphere of nitrogen. The reaction mixture was stirred for 30 min at 0° C., then a solution of TsCl (2.0 g, 10.4 mmol, 1.0 equiv.) in DCM (10 mL) was added dropwise at 0° C. The resulting mixture was stirred for additional 2 hours at 0° C., then an addition batch of n-BuLi (2.5 M in hexane, 4.2 mL, 10.4 mmol, 1.0 equiv.) dropwise. The resulting mixture was stirred overnight at 40° C., then cooled to rt and quenched by the addition of saturated aqueous $NH_4C_1$ at 0° C. The resulting solution was extracted with EtOAc, washed with brine, dried over anhyd. $Na_2SO_4$ and concentrated under vacuum. The residue was purified by flash column chromatography on silica gel, eluting with petroleum ether/EtOAc (1:1) to give 3-(((4-methoxybenzyl)oxy)methyl)-2-methyloxetane (1.0 g) as an off-white solid. LCMS Method A: $[M+H]^+$=223.1.

Step 6: (2-methyloxetan-3-yl)methanol 3-(((4-Methoxybenzyl)oxy)methyl)-2-methyloxetane (1.0 g, 4.5 mmol, 1.0 equiv.) was dissolved in MeOH (15 mL), then Pd/C (100.0 mg, 10% wt) was added under an atmosphere of nitrogen. The mixture was sparged with nitrogen, placed under an atmosphere of hydrogen gas (balloon), then stirred overnight at rt. The solids were removed by filtration and the filtrate was concentrated under vacuum. The residue was purified by flash column chromatography on silica gel, eluting with petroleum ether/EtOAc (1:1) to give to (2-methyloxetan-3-yl)methanol (300.0 mg) as a colorless oil. LCMS Method A: $[M+H]^+$=103.0. $^1$HNMR (400 MHz, DMSO-$d_6$) δ 4.23 (t, J=5.6 Hz, 1H), 4.01-3.99 (m, 1H), 3.53-3.51 (m, 1H), 3.45-3.42 (m, 3H), 1.53-1.49 (m, 1H), 1.10 (d, J=6.4 Hz, 3H).

Step 7: 2-methyloxetane-3-carboxylic acid (2-Methyloxetan-3-yl)methanol (300.0 mg, 2.9 mmol, 1.0 equiv.) was dissolved in ACN (5 mL) and $H_2O$ (1 mL), then $NaIO_4$ (1.3 g, 5.9 mmol, 2.0 equiv.) and RuCl3·$H_2O$ (66.2 mg, 0.3 mmol, 0.1 equiv.) were added in portions. The reaction mixture was stirred overnight at rt and then quenched by the addition of water. The resulting solution was adjusted to pH 4 with conc. HCl, extracted with EtOAc, washed with brine, dried over anhyd. $Na_2SO_4$ and concentrated under vacuum to give 2-methyloxetane-3-carboxylic acid (280.0 mg) as a brown oil. LCMS Method A: $[M+H]^+$=117.2.

Scheme 74: Synthesis of intermediate 131 (1-(2-methoxyethyl)-3-methylazetidine-3-carboxylic acid)

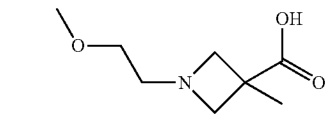

Intermediate 131

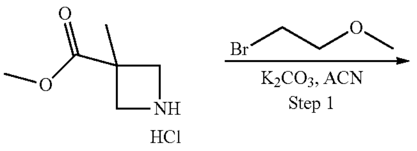

-continued

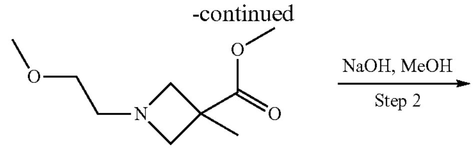

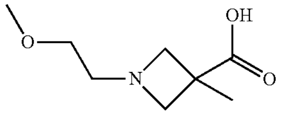

Intermediate 131

Step 1: methyl 1-(2-methoxyethyl)-3-methylazetidine-3-carboxylate

2-Bromoethyl methyl ether (0.9 g, 6.6 mmol, 1.1 equiv.) and methyl 3-methylazetidine-3-carboxylate hydrochloride (1.0 g, 6.0 mmol, 1.0 equiv.) were dissolved in ACN (10 mL), then $K_2CO_3$ (1.7 g, 12.1 mmol, 2.0 equiv.) was added. The reaction mixture was stirred for 2 hours at 80° C., then cooled to rt and quenched by the addition of water. The resulting solution was extracted with EtOAc, washed with brine, dried over anhyd. sodium sulfate and concentrated under vacuum to give methyl 1-(2-methoxyethyl)-3-methylazetidine-3-carboxylate (680 mg) as a yellow oil. LCMS Method A: $[M+H]^+$=188.1.

Step 2: 1-(2-methoxyethyl)-3-methylazetidine-3-carboxylic acid

Methyl 1-(2-methoxyethyl)-3-methylazetidine-3-carboxylate (680.0 mg, 3.6 mmol, 1.0 equiv.) was dissolved in MeOH (3 mL), then aqueous NaOH (3 mL, 2M, 6.0 mmol, 2.0 equiv.) was added dropwise. The reaction mixture was stirred for 2 hours at 80° C., then cooled to rt and concentrated under vacuum. The residue was diluted with water, adjusted to pH 2 with aqueous HCl (1M). The resulting solution was extracted with dichloromethane and concentrated under vacuum to give crude 1-(2-methoxyethyl)-3-methylazetidine-3-carboxylic acid (640 mg) as a yellow syrup. LCMS Method A: $[M+H]^+$=174.2.

The Intermediates in the Following Table were Prepared Using the Same Method Described for Intermediates 131.

| Intermediate | Starting material | Structure | LCMS data |
|---|---|---|---|
| Intermediate 132 | 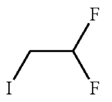 | 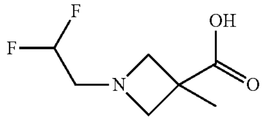 | Method C: MS-ESI: 180.2 $[M + H]^+$ |

Scheme 75: Synthesis of intermediate 133 (trans-3-acetamido-1-methylcyclobutane-1-carboxylic acid)

Intermediate 133

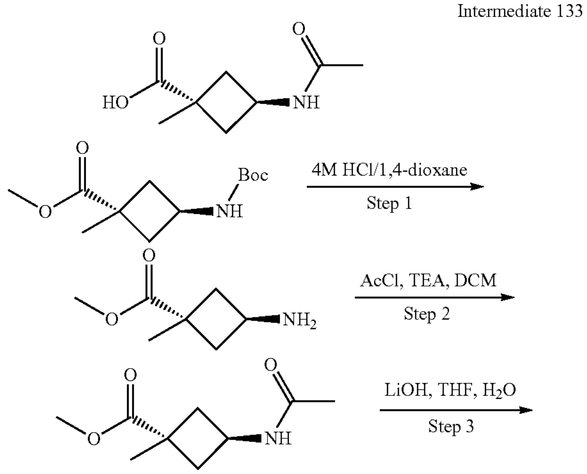

methylcyclobutane-1-carboxylate (425.0 mg) as a yellow oil. LCMS Method A: $[M+H]^+$=186.1.

Step 3: trans-3-acetamido-1-methylcyclobutane-1-carboxylic acid

Methyl trans-3-acetamido-1-methylcyclobutane-1-carboxylate (425.0 mg, 2.3 mmol, 1.0 equiv.) was dissolved in THF (10 mL) and $H_2O$ (2 mL), then LiOH (109.9 mg, 4.6 mmol, 2.0 equiv.) was added. The reaction mixture was stirred for 4 hours at rt and concentrated under vacuum. The residue was diluted with water, adjusted to pH 3 with aqueous HCl (1 M). The resulting solution was extracted with EtOAc, washed with brine, dried over anhyd. $Na_2SO_4$ and concentrated under vacuum to afford trans-3-acetamido-1-methylcyclobutane-1-carboxylic acid (630 mg) as a colorless oil. LCMS Method A: $[M+H]^+$=172.0.

The Intermediates in the Following Table were Prepared Using the Same Method Described for Intermediates 133.

| Intermediate | Starting material | Structure | LCMS data |
|---|---|---|---|
| Intermediate 134 | 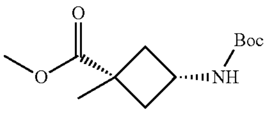 | 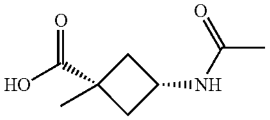 | Method A: MS-ESI: 172.0 $[M + H]^+$ |

-continued

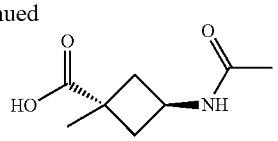

Intermediate 133

Step 1: methyl trans-3-amino-1-methylcyclobutane-1-carboxylate HCi salt

Methyl trans-3-((tert-butoxycarbonyl)amino)-1-methylcyclobutane-1-carboxylate (500.0 mg, 2.1 mmol, 1.0 equiv.) was dissolved in HCl/1,4-dioxane (5 mL). The reaction mixture was stirred for 1 hour at rt and concentrated under vacuum to give crude methyl trans-3-amino-1-methylcyclobutane-1-carboxylate (500 mg) as a white solid. LCMS Method A: $[M+H]^+$=144.1.

Step 2: methyl trans-3-acetamido-1-methylcyclobutane-1-carboxylate

Methyl trans-3-amino-1-methylcyclobutane-1-carboxylate (500.0 mg, 3.5 mmol, 1.0 equiv.) and TEA (2.4 mL, 17.5 mmol, 5.0 equiv.) were dissolved in DCM (10 mL) and cooled to 0° C., then acetyl chloride (274.1 mg, 3.5 mmol, 1.0 equiv.) was added. The reaction mixture was stirred for 2 hour at rt and then quenched by the addition of water. The resulting solution was extracted with dichloromethane, washed with brine, dried over anhyd. $Na_2SO_4$ and concentrated under vacuum to give methyl trans-3-acetamido-1-

Example 1: N-(5-(((4-(trifluoromethyl)benzyl)oxy)methyl)-1H-indol-3-yl)acetamide (Compound 111)

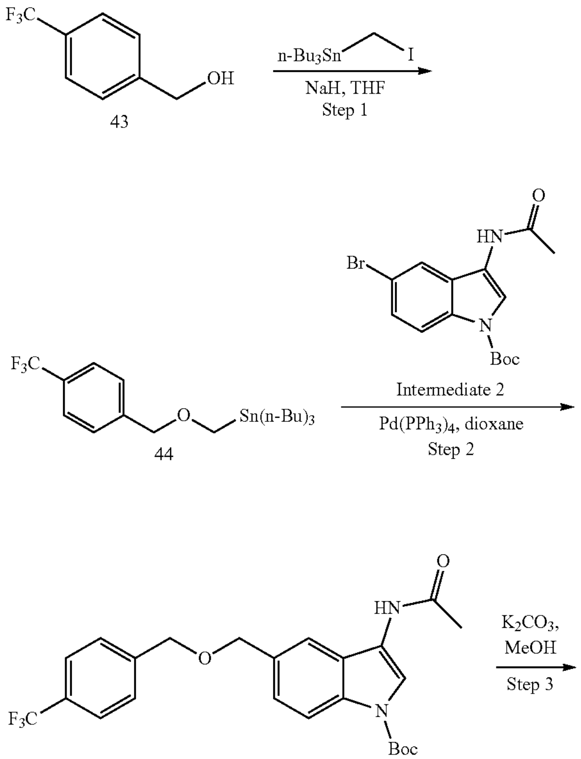

43

44

45

-continued

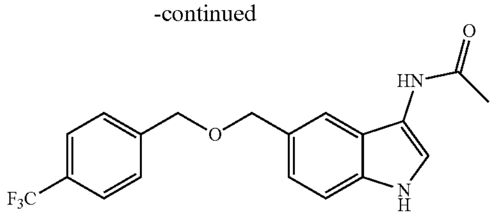

Compound 111

Step 1: tributyl([[4-(trifluoromethyl)phenyl]methoxy]methyl)stannane

[4-(trifluoromethyl)phenyl]methanol (3.0 g, 17.0 mmol, 1.0 equiv.) was dissolved in THF (100 mL) and cooled to 0° C., then NaH (60% wt., 0.8 g, 15.3 mmol, 1.2 equiv.) was added. After 1 hour at 0° C., a solution of tributyl(iodomethyl)stannane (6.6 g, 15.3 mmol, 0.9 equiv.) in THE (3 mL) was added dropwise, maintaining the solution at 0° C. The reaction mixture was stirred for an additional 72 hours at ambient temperature, then quenched by the addition of water. The resulting solution was extracted with petroleum ether and concentrated under vacuum. The residue was purified by flash column chromatography on silica gel, eluting with dichloromethane/petroleum ether (1:5) to give tributyl([[4-(trifluoromethyl)phenyl]methoxy]methyl)stannane (4.5 g) as a pale yellow oil.

Step 2: tert-butyl 3-acetamido-5-([[4-(trifluoromethyl)phenyl]methoxy]methyl)indole-1-carboxylate tert-Butyl 5-bromo-3-acetamidoindole-1-carboxylate (200.0 mg, 0.6 mmol, 1.0 equiv.) was dissolved in 1,4-dioxane (5 mL), then $Pd(PPh_3)_4$ (65.4 mg, 0.1 mmol, 0.1 equiv.) and tributyl([[4-(trifluoromethyl)phenyl]methoxy]methyl)stannane (407.0 mg, 0.8 mmol, 1.5 equiv.) were added under an atmosphere of nitrogen. The reaction mixture was heated to 100° C. for 14 hours, then cooled to ambient temperature and quenched by the addition of water. The resulting solution was extracted with ethyl acetate and concentrated under vacuum. The residue was purified by flash column chromatography on silica gel, eluting with ethyl acetate/petroleum ether (1:1) to give tert-butyl 3-acetamido-5-([[4-(trifluoromethyl)phenyl]methoxy]methyl)indole-1-carboxylate (100.5 mg) as a yellow semi-solid. LCMS Method A: $[M+H]^+$=463.

Step 3: N-[5-([[4-(trifluoromethyl)phenyl]methoxy]methyl)-1H-indol-3-yl]acetamide tert-Butyl 3-acetamido-5-([[4-(trifluoromethyl)phenyl]methoxy]methyl)indole-1-carboxylate (90.0 mg, 0.2 mmol, 1.0 equiv.) was dissolved in MeOH (5 mL), then $K_2CO_3$ (80.7 mg, 0.6 mmol, 3.0 equiv.) was added. The reaction mixture was heated to 65° C. for 2 hours, then cooled to ambient temperature and quenched by the addition of water. The resulting solution was extracted with ethyl acetate and concentrated under vacuum. The residue was purified by Prep-HPLC with the following conditions: Column: XBridge Prep OBD C18 Column, 30*150 mm, 5 m; Mobile Phase A: Water (10 mM $NH_4HCO_3$+0.1% $NH_4OH$), Mobile Phase B: ACN; Flow rate: 60 mL/min; Gradient: 35% B to 60% B in 8 min; Wave Length: 220 nm; RT1: 7.53 min. This resulted in N-[5-([[4-(trifluoromethyl)phenyl]methoxy]methyl)-1H-indol-3-yl]acetamide (35.1 mg) as a pale yellow solid. LCMS Method D: $[M+H]^+$=363. $^1$H NMR (400 MHz, DMSO-$d_6$): δ 10.78 (s, 1H), 9.84 (s, 1H), 7.80 (s, 1H), 7.74-7.70 (m, 3H), 7.60-7.58 (m, 2H), 7.33-7.31 (m, 1H), 7.13-7.10 (m, 1H), 4.63 (s, 4H), 2.09 (s, 3H).

The analogs prepared in the following table were prepared using the same method described for Example 1.

| Example # | Compound No. | Starting materials Used | Structure | LCMS data |
|---|---|---|---|---|
| 2 | 109 | (4-(trifluoromethyl) phenyl)methanol/ Intermediate 6 | 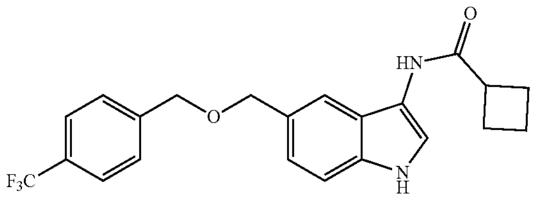 [SMILES: O=C(Nc1c[nH]c2ccc(COCc3ccc(C(F)(F)F)cc3)cc12)C1CCC1] | Method D: MS-ESI: 401 $[M - H]^-$. |
| 3 | 106 | (3-(trifluoromethyl) phenyl)methanol/ Intermediate 2 | 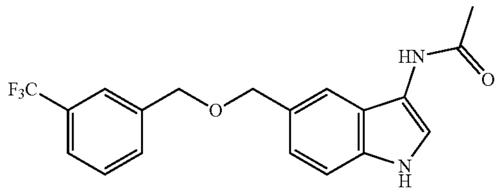 [SMILES: CC(=O)Nc1c[nH]c2ccc(COCc3cccc(C(F)(F)F)c3)cc12] | Method F: MS-ESI: 361 $[M - H]^-$. |
| 4 | 101 | (3,4-dichlorophenyl) methanol/ Intermediate 2 | 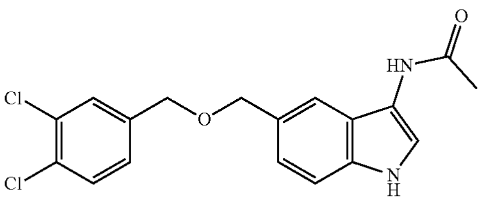 | Method F: MS-ESI: 370 $[M + H]^+$. |

Example 5: N-(5-((4-(trifluoromethyl)benzyl)oxy)-1H-indol-3-yl)propionamide (Compound 138)

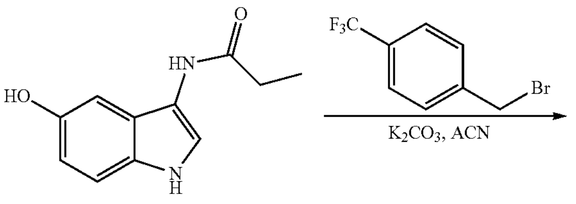

Intermediate 8

-continued

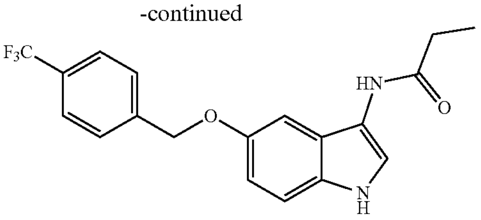

Compound 138

N-(5-hydroxy-1H-indol-3-yl)propenamide (160.0 mg, 0.8 mmol, 1.0 equiv.) and 1-(bromomethyl)-4-(trifluoromethyl) benzene (280.9 mg, 1.2 mmol, 1.5 equiv.) were dissolved in ACN (10 mL), then $K_2CO_3$ (216.6 mg, 1.6 mmol, 2.0 equiv.) was added. The reaction mixture was heated to 75° C. overnight, then cooled to ambient temperature and quenched by the addition of water. The resulting solution was extracted with ethyl acetate, washed with brine, dried over anhydrous $Na_2SO_4$ and concentrated under vacuum. The residue was purified by Prep-HPLC with the following conditions: Column: XBridge Prep OBD C18 Column, 30*150 mm, 5 m; Mobile Phase A: Water (10 mM $NH_4HCO_{3+0.1}$% $NH_4OH$), Mobile Phase B: ACN; Flow rate: 60 mL/min; Gradient: 35% B to 65% B in 7 min; Wave Length: 220 nm; RT1: 6.68 min. This resulted in N-(5-[[4-(trifluoromethyl)phenyl]methoxy]-1H-indol-3-yl)propenamide (29.2 mg) as a white solid. LCMS Method D: $[M+H]^+$= 363. $^1H$ NMR (400 MHz, DMSO-$d_6$): δ 10.62 (s, 1H), 9.66 (s, 1H), 7.79-7.77 (m, 2H), 7.73-7.68 (m, 3H), 7.45 (d, J=2.4 Hz, 1H), 7.24 (d, J=8.8 Hz, 1H), 6.86-6.83 (m, 1H), 5.21 (s, 2H), 2.41-2.33 (m, 2H), 1.12 (t, J=7.6 Hz, 3H).

The analogs prepared in the following table were prepared using the same method described for Example 5.

| Example # | Compound No. | Starting materials Used | Structure | LCMS data |
|---|---|---|---|---|
| 6 | 113 | Intermediate 27/ Intermediate 7 | 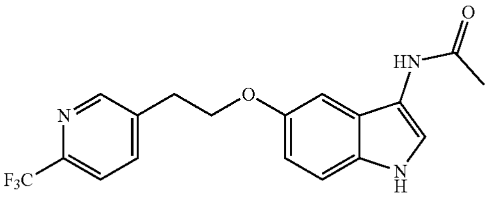 [SMILES: CC(=O)Nc1c[nH]c2ccc(OCCc3ccc(C(F)(F)F)nc3)cc12] | Method D: MS-ESI: 364 $[M + H]^+$. |
| 7 | 112 | Intermediate 28/ Intermediate 7 | 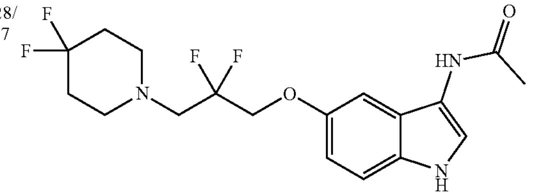 | Method F: MS-ESI: 388 $[M + H]^+$. |

Example 8: N-(5-(2-(6-(trifluoromethyl)pyridin-3-yl)ethoxy)-1H-indol-3-yl)cyclobutanecarboxamide (Compound 142)

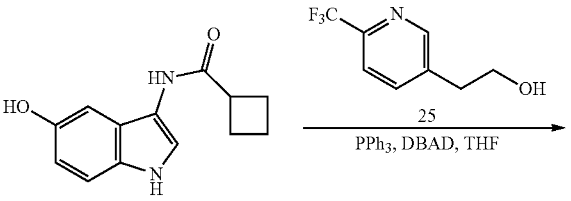

Intermediate 9

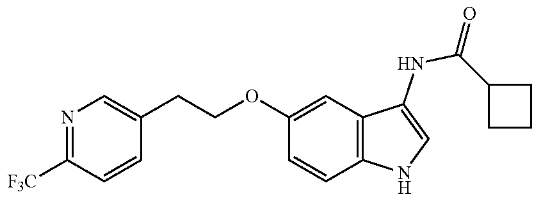

Compound 142

N-(5-Hydroxy-1H-indol-3-yl)cyclobutanecarboxamide (150.0 mg, 0.7 mmol, 1.0 equiv.) and 2-[6-(trifluoromethyl) pyridin-3-yl]ethanol (249.0 mg, 1.3 mmol, 2.0 equiv.) were dissolved in THE (10 mL), then $PPh_3$ (341.7 mg, 1.3 mmol, 2.0 equiv.) was added. This was followed by the addition of DBAD (300.0 mg, 1.3 mmol, 2.0 equiv.). The reaction mixture was stirred overnight at ambient temperature and then quenched by the addition of water. The resulting solution was extracted with ethyl acetate, washed with brine, dried over anhydrous $Na_2SO_4$ and concentrated under vacuum. The residue was purified by flash column chromatography on silica gel, eluting with ethyl acetate/petroleum ether (1:1) to give material, that was further purified by Flash-Prep-HPLC with the following conditions: Column: XBridge Prep OBD C18 Column, 30×150 mm 5 μm; Mobile Phase A: Water (10 mM $NH_4HCO_3$), Mobile Phase B: ACN; Flow rate: 60 mL/min; Gradient: 43 B to 55 B in 8 min; 254/220 nm; RT1: 6.62 min. This resulted in N-(5-[2-[6-(trifluoromethyl)pyridin-3-yl]ethoxy]-1H-indol-3-yl)cyclobutanecarboxamide (22.3 mg) as a white solid. LCMS Method D: $[M+H]^+$=404. $^1H$ NMR (400 MHz, DMSO-$d_6$): δ 10.58 (s, 1H), 9.50 (s, 1H), 8.78 (s, 1H), 8.10-8.08 (m, 1H), 7.88 (d, J=8.0 Hz, 1H), 7.71 (d, J=2.4 Hz, 1H), 7.31 (d, J=2.4 Hz, 1H), 7.20 (d, J=8.8 Hz, 1H), 6.73-6.71 (m, 1H), 4.23 (t, J=6.4 Hz, 2H), 3.33-3.30 (m, 1H), 3.22 (t, J=6.4 Hz, 2H), 2.27-2.22 (m, 2H), 2.13-2.08 (m, 2H), 1.96-1.94 (m, 1H), 1.84-1.80 (m, 1H).

The analogs prepared in the following table were prepared using the same method described for Example 8.

| Example # | Compound No. | Starting materials Used | Structure | Condition | LCMS data |
|---|---|---|---|---|---|
| 9 | 140 | tert-butyl 4-(2-hydroxy-ethyl) piperidine-1-carboxylate/ Intermediate 9 | 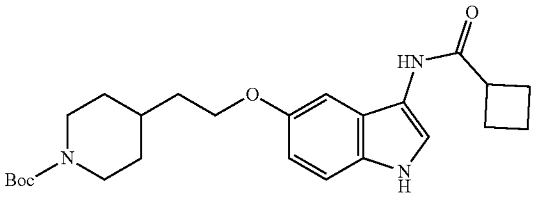 [SMILES: CC(C)(C)OC(=O)N1CCC(CCOc2ccc3[nH]cc(NC(=O)C4CCC4)c3c2)CC1] | $PPh_3$, DIAD, THF | Method D: MS-ESI: 440 $[M-H]^-$. |
| 10 | 146 | 2-(4-(trifluoro-methyl) phenyl) ethan-1-ol/ Intermediate 8 | 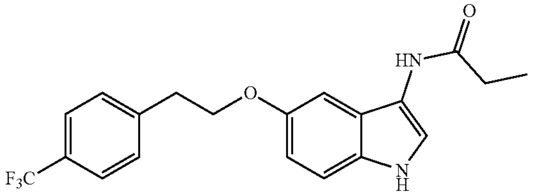 [SMILES: CCC(=O)Nc1c[nH]c2ccc(OCCc3ccc(C(F)(F)F)cc3)cc12] | $PPh_3$, DEAD, DCM | Method D: MS-ESI: 377 $[M+H]^+$. |
| 11 | 129 | Intermediate 20/ Intermediate 9 | 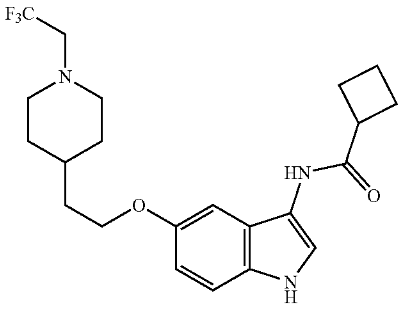 [SMILES: O=C(Nc1c[nH]c2ccc(OCCC3CCN(CC(F)(F)F)CC3)cc12)C1CCC1] | $P(n\text{-}Bu)_3$, ADDP, DCM | Method E: MS-ESI: 424 $[M+H]^+$. |
| 12 | 120 | Intermediate 22/ Intermediate 7 | 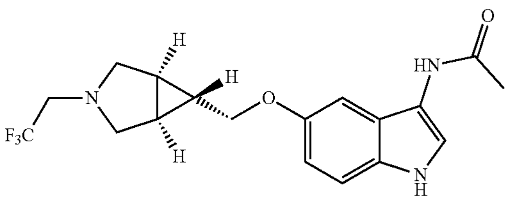 | $PPh_3$, DIAD, THF | Method F: MS-ESI: 368 $[M+H]^+$. |
| 13 | 119 | Intermediate 21/ Intermediate 7 | 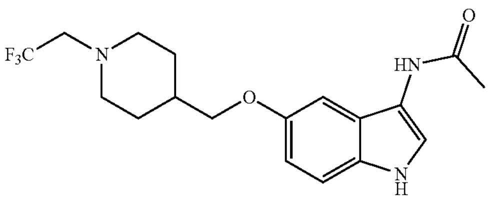 [SMILES: CC(=O)Nc1c[nH]c2ccc(OCC3CCN(CC(F)(F)F)CC3)cc12] | $PPh_3$, DIAD, THF | Method F: MS-ESI: 370 $[M+H]^+$. |

-continued

| Example # | Compound No. | Starting materials Used | Structure | Condition | LCMS data |
|---|---|---|---|---|---|
| 14 | 110 | Intermediate 24/ Intermediate 7 | 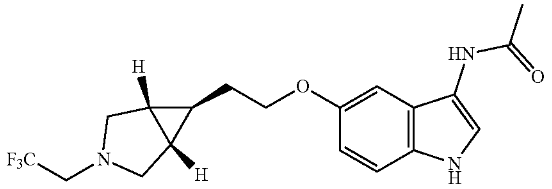 [SMILES: CC(=O)Nc1c[nH]c2ccc(OCC[C@@H]3[C@H]4CN(CC(F)(F)F)C[C@@H]34)cc12] | $P(n-Bu)_3$, ADDP, THF | Method E: MS-ESI: 382 $[M + H]^+$. |
| 15 | 105 | Intermediate 18/ Intermediate 7 | 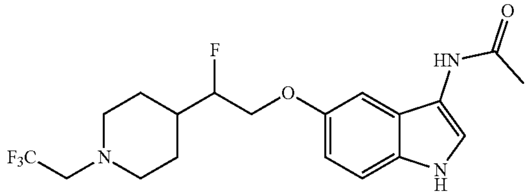 [SMILES: CC(=O)Nc1c[nH]c2ccc(OCC(F)C3CCN(CC(F)(F)F)CC3)cc12] | $P(n-Bu)_3$, ADDP, DCM | Method E: MS-ESI: 402 $[M + H]^+$. |
| 16 | 104 | Intermediate 19/ Intermediate 7 | 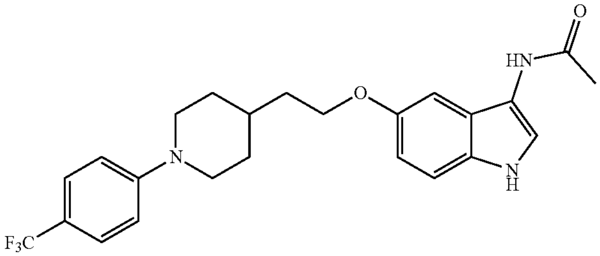 [SMILES: CC(=O)Nc1c[nH]c2ccc(OCCC3CCN(c4ccc(C(F)(F)F)cc4)CC3)cc12] | $P(n-Bu)_3$, ADDP, DCM | Method D: MS-ESI: 446 $[M + H]^+$. |
| 17 | 145 | 4-(trifluoro-methyl) phenol/ Intermediate 12 | 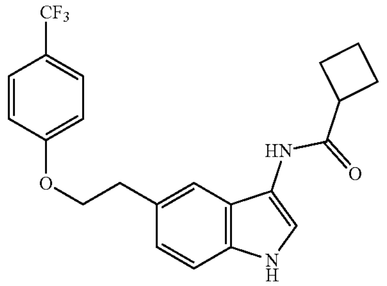 [SMILES: O=C(Nc1c[nH]c2ccc(CCOc3ccc(C(F)(F)F)cc3)cc12)C1CCC1] | $PPh_3$, DIAD, THF | Method E: MS-ESI: 403 $[M + H]^+$. |

Example 18: N-(5-(2-(4-(trifluoromethyl)phenoxy) ethyl)-1H-indol-3-yl)acetamide (Compound 127)

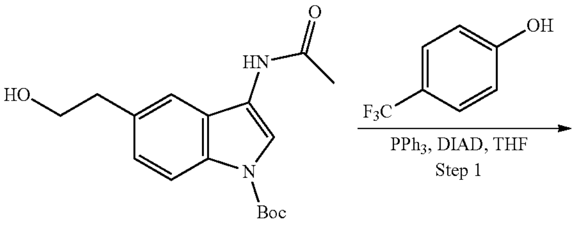

Intermediate 11

-continued

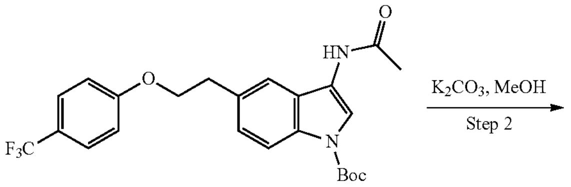

46

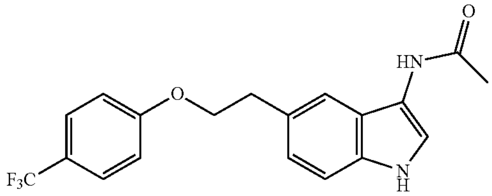

Compound 127

Step 1: tert-butyl 3-acetamido-5-[2-[4-(trifluoromethyl)phenoxy]ethyl]indole-1-carboxylate (compound 46)

tert-Butyl 3-acetamido-5-(2-hydroxyethyl)indole-1-carboxylate (300.0 mg, 0.9 mmol, 1.0 equiv.) was dissolved in THE (20 mL) and cooled to 0° C., then 4-(trifluoromethyl) phenol (229.1 mg, 1.4 mmol, 1.5 equiv.) and $PPh_3$ (494.3 mg, 1.9 mmol, 2.0 equiv.) were added. This was followed by the dropwise addition of DIAD (0.2 mL, 1.3 mmol, 2.0 equiv.). The reaction mixture was stirred for an additional 2 hours at ambient temperature and then concentrated under vacuum. The residue was purified by flash column chromatography on silica gel, eluting with ethyl acetate/petroleum ether (1:5) to give tert-butyl 3-acetamido-5-[2-[4-(trifluoromethyl)phenoxy]ethyl]indole-1-carboxylate (280.0 mg) as a pale yellow solid. LCMS Method A: $[M+H]^+=463$ Step 2: N-(5-[2-[4-(trifluoromethyl)phenoxy]ethyl]-1H-indol-3-yl)acetamide tert-Butyl 3-acetamido-5-[2-[4-(trifluoromethyl)phenoxy]ethyl]indole-1-carboxylate (100.0 mg, 0.2 mmol, 1.0 equiv.) was dissolved in MeOH (5 mL), then $K_2CO_3$ (64.8 mg, 0.5 mmol, 2.0 equiv.) was added. The reaction mixture was heated to 65° C. for 2 hours, then cooled to ambient temperature and concentrated under vacuum. The residue was purified by Prep-HPLC with the following conditions: Column: XBridge Prep OBD C18 Column, 30*150 mm 5 µm; Mobile Phase A: Water (10 mM $NH_4HCO_3$), Mobile Phase B: ACN; Flow rate: 60 mL/min; Gradient: 35% B to 65% B in 8 min, 220 nm; RT1: 7.53 min. This resulted in N-(5-[2-[4-(trifluoromethyl)phenoxy]ethyl]-1H-indol-3-yl) acetamide (36.8 mg) as a white solid. LCMS Method D: $[M+H]^+=363$. $^1H$ NMR (400 MHz, DMSO-$d_6$): δ 10.67 (s, 1H), 9.75 (s, 1H), 7.69-7.63 (m, 4H), 7.27 (d, J=8.4 Hz, 1H), 7.14 (d, J=8.8 Hz, 2H), 7.10-7.07 (m, 1H), 4.30 (t, J=7.2 Hz, 2H), 3.13 (t, J=7.2 Hz, 2H), 2.09 (s, 3H).

The analogs prepared in the following table were prepared using the same method described for Example 18.

| Example # | Compound No. | Starting materials Used | Structure | Condition | LCMS data |
|---|---|---|---|---|---|
| 19 | 103 | Intermediate 25/ Intermediate 10 | 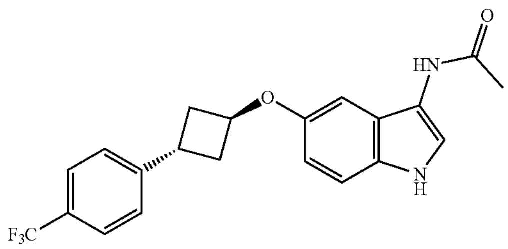 [SMILES: CC(=O)Nc1c[nH]c2ccc(O[C@H]3C[C@H](c4ccc(C(F)(F)F)cc4)C3)cc12] | P(n-Bu)$_3$, ADDP, THF | Method F: MS-ESI: 389 $[M + H]^+$. |
| 20 | 102 | Intermediate 26/ Intermediate 10 | 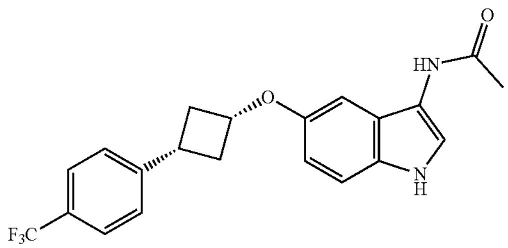 [SMILES: CC(=O)Nc1c[nH]c2ccc(O[C@H]3C[C@@H](c4ccc(C(F)(F)F)cc4)C3)cc12] | P(n-Bu)$_3$, ADDP, THF | Method F: MS-ESI: 389 $[M + H]^+$. |
| 21 | 130 | 4-(trifluoromethyl) phenol/ Intermediate 14 | 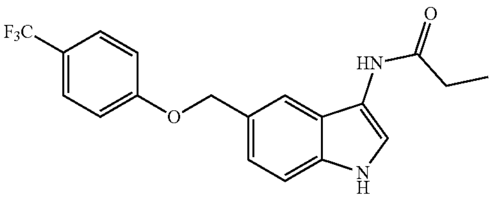 [SMILES: CCC(=O)Nc1c[nH]c2ccc(COc3ccc(C(F)(F)F)cc3)cc12] | $PPh_3$, DEAD, THF | Method D: MS-ESI: 361 $[M - H]^-$. |
| 22 | 115 | 4-(trifluoromethyl) phenol/ Intermediate 13 | 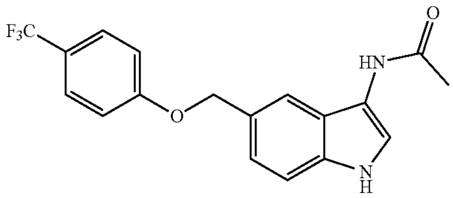 [SMILES: CC(=O)Nc1c[nH]c2ccc(COc3ccc(C(F)(F)F)cc3)cc12] | P(n-Bu)$_3$, ADDP, THF | Method F: MS-ESI: 347 $[M - H]^-$. |

-continued

| Example # | Compound No. | Starting materials Used | Structure | Condition | LCMS data |
|---|---|---|---|---|---|
| 23 | 108 | Intermediate 23/ Intermediate 10 | 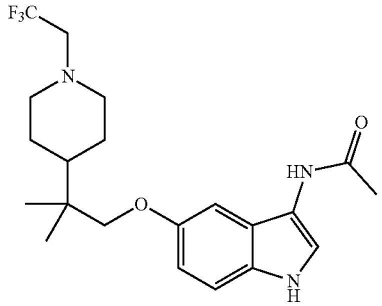 [SMILES: CC(=O)Nc1c[nH]c2ccc(OCC(C)(C)C3CCN(CC(F)(F)F)CC3)cc12] | 2-(tributyl-phosphoranyl-idene)acetonitrile | Method F: MS-ESI: 412 [M + H]$^+$. |

Example 19: N-(5-(trans-3-(4-(trifluoromethyl)phenyl)cyclobutoxy)-1H-indol-3-yl)acetamide (Compound 103)

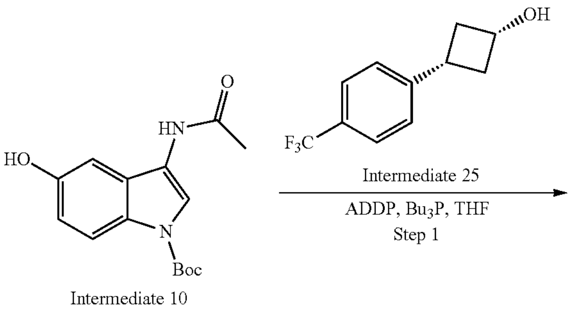

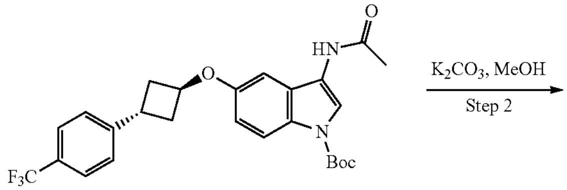

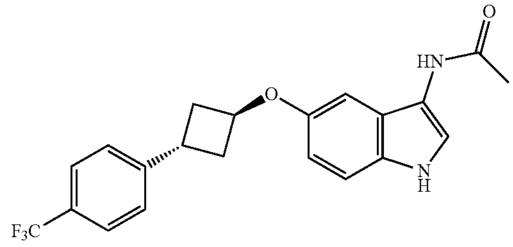

Compound 103

Step 1: tert-butyl 3-acetamido-5-(trans-3-(4-(trifluoromethyl)phenyl)cyclobutoxy)-1H-indole-1-carboxylate Cis-3-(4-(Trifluoromethyl)phenyl)cyclobutan-1-ol (2.5 g, 11.5 mmol, 1.0 equiv.) was dissolved in THE (40.0 mL) and cooled to 0° C., then tert-butyl 3-acetamido-5-hydroxy-1H-indole-1-carboxylate (4.0 g, 13.8 mmol, 1.2 equiv.) and n-$Bu_3P$ (3.5 g, 17.3 mmol, 1.5 equiv.) were added. This was followed by the addition of ADDP (5.7 g, 23.1 mmol, 2.0 equiv.) dropwise at 0° C. under a nitrogen atmosphere. The reaction mixture was heated to 70° C. for 3 hours, then cooled to ambient temperature and quenched by the addition of brine. The resulting solution was extracted with ethyl acetate, dried over anhydrous sodium sulfate and concentrated under vacuum. The residue was purified by flash column chromatography on silica gel, eluting with DCM/MeOH (10:1) to give tert-butyl 3-acetamido-5-(trans-3-(4-(trifluoromethyl)phenyl)cyclobutoxy)-1H-indole-1-carboxylate (1.5 g) as a white solid. $[M+H]^+$=489.

Step 2: N-(5-(trans-3-(4-(trifluoromethyl)phenyl)cyclobutoxy)-1H-indol-3-yl)acetamide tert-Butyl 3-acetamido-5-(trans-3-(4-(trifluoromethyl)phenyl)cyclobutoxy)-1H-indole-1-carboxylate (1.5 g, 3.0 mmol, 1.0 equiv.) was dissolved in MeOH (15 mL), then $K_2CO_3$ (848.7 mg, 6.1 mmol, 2.0 equiv.) was added. The resulting mixture was stirred for 1 hour at 70° C., then cooled to ambient temperature and quenched by the addition of water. The resulting solution was extracted with ethyl acetate, dried over anhydrous sodium sulfate and concentrated under vacuum. The residue was further purified by Prep-HPLC with the following conditions: Column: XBridge Prep OBD C18 Column, 30*150 mm, 5 μm; Mobile Phase A: water (10 mmol/L $NH_4HCO_3$), Mobile Phase B: ACN; Flow rate: 60 mL/min; Gradient: 40% B to 70% B in 7 min, 70% B; Wave Length: 220 nm; RT1 (min): 7.53. This resulted in N-(5-(trans-3-(4-(trifluoromethyl)phenyl)cyclobutoxy)-1H-indol-3-yl)acetamide (435.0 mg) as a white solid. $[M+H]^+$=389. 1H NMR (400 MHz, DMSO-$d_6$) δ 10.58 (s, 1H), 9.68 (s, 1H), 7.73-7.59 (m, 5H), 7.24-7.22 (m, 1H), 7.15 (d, J=2.0 Hz, 1H), 6.75-6.72 (m, 1H), 4.95-4.89 (m, 1H), 3.84-3.77 (m, 1H), 2.72-2.60 (m, 4H), 2.08 (s, 3H).

Examples 24/25: (E)-N-(5-(4-(trifluoromethyl)styryl)-1H-indol-3-yl)cyclobutanecarboxamide (Compound 144) and N-(5-(4-(trifluoromethyl)phenethyl)-1H-indol-3-yl)cyclobutanecarboxamide (Compound 141)

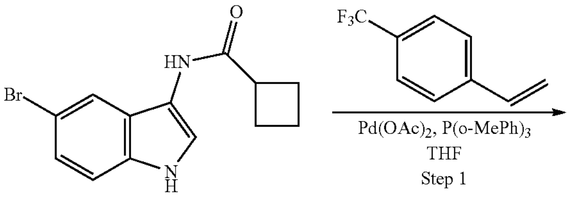

Intermediate 5

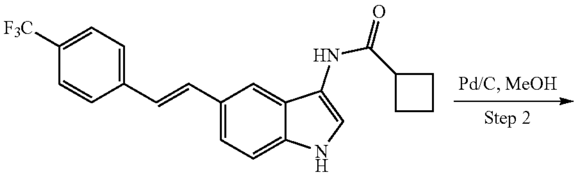

Compound 144

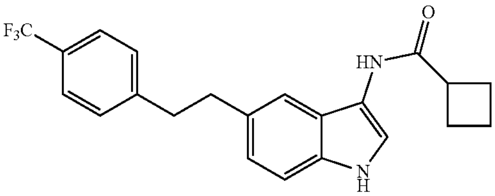

Compound 141

Step 1: (E)-N-(5-(4-(trifluoromethyl)styryl)-1H-indol-3-yl)cyclobutanecarboxamide N-(5-bromo-1H-indol-3-yl)cyclobutanecarboxamide (1.0 g, 3.4 mmol, 1.0 equiv.) was dissolved in TEA (10 mL), then 1-(trifluoromethyl)-4-vinylbenzene (704.7 mg, 4.1 mmol, 1.2 equiv.), $Pd(OAc)_2$ (76.6 mg, 0.3 mmol, 0.1 equiv.) and tri(o-tolyl)phosphine (207.6 mg, 0.7 mmol, 0.2 equiv.) were added under an atmosphere of nitrogen. The reaction mixture was heated to 100° C. for 16 hours, then cooled to ambient temperature and quenched by the addition of water. The resulting solution was extracted with ethyl acetate, washed with brine, dried over $Na_2SO_4$ and concentrated under vacuum. The residue was purified by flash column chromatography on silica gel, eluting with ethyl acetate/petroleum ether (1:2) to give material that was further purified by Flash-Prep-HPLC with the following conditions: Column: XBridge Shield RP18 OBD Column, 30*150 mm, 5 m; Flow rate: 60 mL/min; Gradient: 55% B to 70% B in 7 min; Wave Length: 254 nm; RT1: 6.97 min. This resulted in (E)-N-(5-(4-(trifluoromethyl)styryl)-1H-indol-3-yl)cyclobutanecarboxamide (33.3 mg) as a white solid. LCMS Method D: $[M+H]^+$=385. $^1$H NMR (400 MHz, DMSO-$d_6$) δ 10.91 (s, 1H), 9.71 (s, 1H), 8.03 (s, 1H), 7.82-7.80 (m, 2H), 7.74-7.72 (m, 3H), 7.53-7.42 (m, 2H), 7.35 (d, 1H), 7.20 (d, 1H), 3.38-3.34 (m, 1H), 2.30-2.23 (m, 2H), 2.18-2.10 (m, 2H), 2.04-1.96 (m, 1H), 1.88-1.81 (m, 1H).

Step 2: N-(5-(4-(trifluoromethyl)phenethyl)-1H-indol-3-yl)cyclobutanecarboxamide (E)-N-(5-(4-(trifluoromethyl)styryl)-1H-indol-3-yl)cyclobutanecarboxamide (200.0 mg, 0.5 mmol, 1.0 equiv.) was dissolved in MeOH (10 mL), then Pd/C (10% wt, 1.0 g) was added under an atmosphere of nitrogen. The mixture was sparged with nitrogen, placed under an atmosphere of hydrogen gas (balloon), then stirred for 10 hours at ambient temperature. The solids were removed by filtration and the filtrate was concentrated under vacuum. The residue was purified by flash column chromatography on silica gel, eluting with ethyl acetate/petroleum ether (1:3) to give material that was further purified by Prep-HPLC with the following conditions: Column: XBridge Prep OBD C18 Column, 30*150 mm, 5 m; Mobile Phase A: Water (10 mM $NH_4HCO_3$+0.1% $NH_4OH$), Mobile Phase B: ACN; Flow rate: 60 mL/min; Gradient: 45% B to 75% B in 7 min; Wave Length: 220 nm; RT1r: 6.5 min. This resulted in N-(5-(4-(trifluoromethyl)phenethyl)-1H-indol-3-yl)cyclobutanecarboxamide (40.2 mg) as a white solid. LCMS Method D: $[M-H]^-$=385. $^1$H NMR (400 MHz, DMSO-$d_6$) δ 10.64 (s, 1H), 9.56 (s, 1H), 7.69 (s, 1H), 7.64-7.62 (m, 3H), 7.47 (d, J=8.0 Hz, 2H), 7.23 (d, J=8.4 Hz, 1H), 7.00-6.97 (m, 1H), 3.38-3.33 (m, 1H), 3.05-2.95 (m, 4H), 2.28-2.23 (m, 2H), 2.14-2.10 (m, 1H), 2.04-1.95 (m, 1H), 1.84-1.81 (m, 1H).

The analogs prepared in following table were prepared using the same method described for Example 25.

| Example # | Compound No. | Starting materials Used | Structure | LCMS data |
|---|---|---|---|---|
| 26 | 137 | Intermediate 35/ Intermediate 5 | 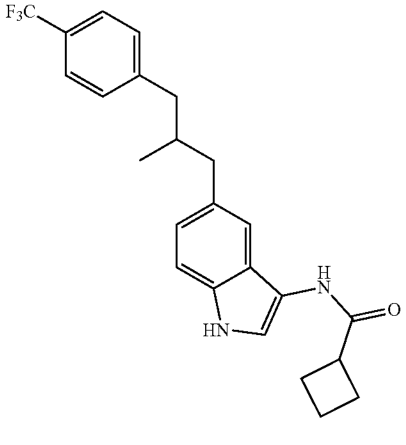 [SMILES: CC(Cc1ccc(C(F)(F)F)cc1)Cc1ccc2[nH]cc(NC(=O)C3CCC3)c2c1] | Method E: MS-ESI: 415 $[M + H]^+$. |

-continued

| Example # | Compound No. | Starting materials Used | Structure | LCMS data |
|---|---|---|---|---|
| 27 | 133 | Intermediate 36/ Intermediate 5 | 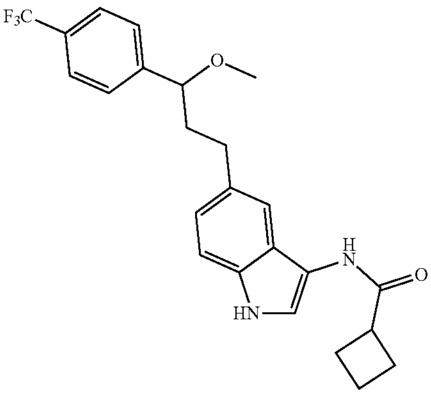 [SMILES: COC(CCc1ccc2[nH]cc(NC(=O)C3CCC3)c2c1)c1ccc(C(F)(F)F)cc1] | Method D: MS-ESI: 431 [M + H]+. |

Example 28: N-(5-(2-(1-(2,2,2-trifluoroethyl)piperidin-4-yl)ethyl)-1H-indol-3-yl)acetamide (Compound 114)

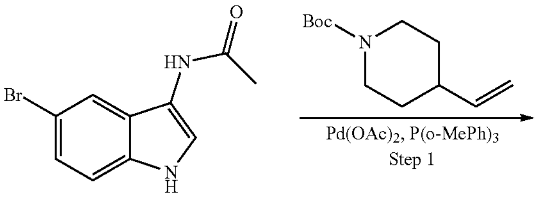

Intermediate 1

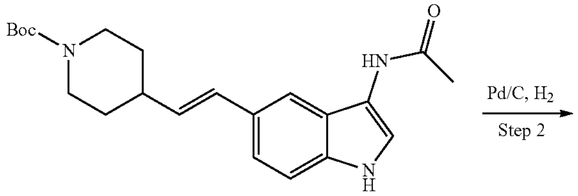

47

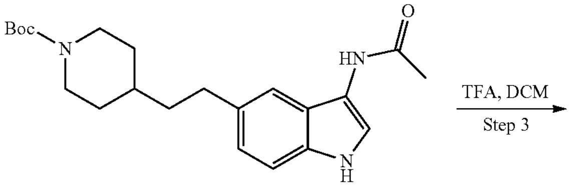

48

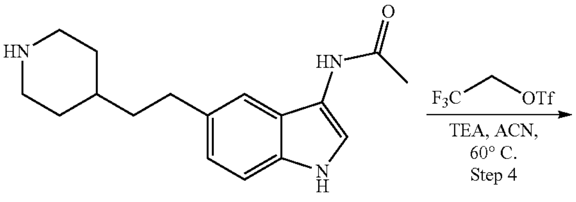

49

-continued

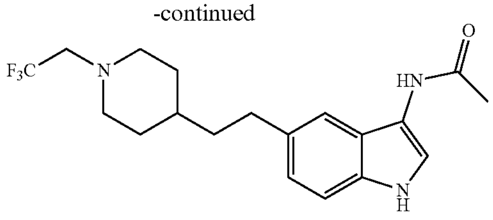

Compound 114

Step 1: tert-butyl 4-[(E)-2-(3-acetamido-1H-indol-5-yl)ethenyl]piperidine-1-carboxylate N-(5-bromo-1H-indol-3-yl)acetamide (2.0 g, 7.9 mmol, 1.0 equiv.) was dissolved in ACN (100 mL), then tert-butyl 4-ethenylpiperidine-1-carboxylate (2.5 g, 11.8 mmol, 1.5 equiv.), tri(o-tolyl)phosphine (962.0 mg, 3.2 mmol, 0.4 equiv.), $Pd(AcO)_2$ (177.4 mg, 0.8 mmol, 0.1 equiv.) and TEA (3.9 mL, 28.3 mmol, 3.6 equiv.) were added under an atmosphere of nitrogen. The reaction mixture was heated to 100° C. for 10 hours, then cooled to ambient temperature and concentrated under vacuum. The residue was purified by flash column chromatography on silica gel, eluting with ethyl acetate/petroleum ether (1:1) to give tert-butyl 4-[(E)-2-(3-acetamido-1H-indol-5-yl)ethenyl]piperidine-1-carboxylate (2.2 g) as a green solid. LCMS Method A: $[M+H]^+$= 384.

Step 2: tert-butyl 4-[2-(3-acetamido-1H-indol-5-yl)ethyl]piperidine-1-carboxylate tert-Butyl 4-[(E)-2-(3-acetamido-1H-indol-5-yl)ethenyl]piperidine-1-carboxylate (1.3 g, 3.5 mmol, 1.0 equiv.) was dissolved in MeOH (40 mL), then Pd/C (10% wt., 270.0 mg) was added. The mixture was sparged with nitrogen, placed under an atmosphere of hydrogen gas (balloon), then stirred overnight at ambient temperature. The solids were removed by filtration and the filtrate was concentrated under vacuum. The residue was purified by flash column chromatography on silica gel, eluting with ethyl acetate/petroleum ether (1:1) to give tert-butyl 4-[2-(3-acetamido-1H-indol-5-yl)ethyl]piperidine-1-carboxylate (1.0 g) as a dark blue solid. LCMS Method A: $[M+H]^+$=386.

Step 3: N-[5-[2-(piperidin-4-yl)ethyl]-1H-indol-3-yl]acetamide tert-Butyl 4-[2-(3-acetamido-1H-indol-5-yl)ethyl]piperidine-1-carboxylate (377.0 mg, 1.0 mmol, 1.0 equiv.) was dissolved in DCM (30 mL) and TFA (10 mL). The reaction mixture was stirred overnight at ambient temperature and then concentrated under vacuum to afford N-[5-[2-(piperidin-4-yl)ethyl]-1H-indol-3-yl]acetamide (744.4 mg) as a brown oil, which was used in the next step directly without further purification. LCMS Method B: $[M+H]^+$=286.

Step 4: N-(5-[2-[1-(2,2,2-trifluoroethyl)piperidin-4-yl]ethyl]-1H-indol-3-yl)acetamide N-[5-[2-(piperidin-4-yl)ethyl]-1H-indol-3-yl]acetamide (744.0 mg, 2.6 mmol, 1.0 equiv.) was dissolved in ACN (100 mL), then 2,2,2-trifluoroethyl trifluoromethanesulfonate (726.1 mg, 3.1 mmol, 1.2 equiv.) and TEA (1.5 mL, 10.5 mmol, 4.0 equiv.) were added. The resulting mixture was heated to 60° C. overnight, then cooled to ambient temperature and concentrated under vacuum. The residue was purified by Prep-HPLC with the following condition: Kinetex EVO C18 Column, 30*150, 5 um; Mobile Phase A: Water (10 mM $NH_4HCO_3$+0.1% $NH_4OH$), Mobile Phase B: ACN; Flow rate: 60 mL/min; Gradient: 50% B to 70% B in 10 min; Wave Length: 220 nm. This resulted in N-(5-[2-[1-(2,2,2-trifluoroethyl)piperidin-4-yl]ethyl]-1H-indol-3-yl)acetamide (16.4 mg) as an off-white solid. LCMS Method E: $[M+H]^+$=368. $^1H$ NMR (400 MHz, DMSO-$d_6$): δ 10.58 (s, 1H), 9.72 (s, 1H), 7.65-7.63 (m, 1H), 7.56-7.54 (m, 1H), 7.21 (d, J=8.4 Hz, 1H), 6.94-6.92 (m, 1H), 3.15-3.07 (m, 2H), 2.91-2.88 (m, 2H), 2.68-2.64 (m, 2H), 2.30-2.24 (m, 2H), 2.08 (s, 3H), 1.71-1.68 (m, 2H), 1.58-1.53 (m, 2H), 1.26-1.21 (m, 3H).

Example 29: N-(5-(4-(trifluoromethyl)phenethoxy)-1H-indol-3-yl)acetamide (Compound 136)

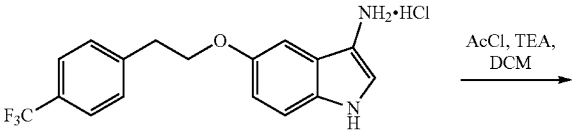

Intermediate 33

-continued

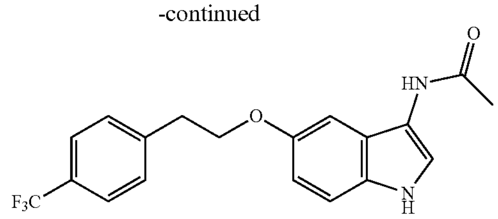

Compound 136

5-[2-[4-(trifluoromethyl)phenyl]ethoxy]-1H-indol-3-amine (350.0 mg, 1.1 mmol, 1.0 equiv.) and TEA (0.5 mL, 3.3 mmol, 3.0 equiv.) were dissolved in DCM (5 mL) and cooled to 0° C., then acetyl chloride (0.1 mL, 1.3 mmol, 1.2 equiv.) was added, maintaining the solution at 0° C. The reaction mixture was stirred for 30 min at ambient temperature, then quenched by the addition of water. The resulting solution was extracted with ethyl acetate and concentrated under vacuum. The residue was purified by flash column chromatography on silica gel, eluting with dichloromethane/methanol (10:1) to give material that was further purified by Prep-HPLC with the following conditions: Column: XBridge Prep OBD C18 Column, 30*150 mm, 5 μm; Mobile Phase A: Water (10 mM $NH_4HCO_3$), Mobile Phase B: ACN; Flow rate: 60 mL/min; Gradient: 42 B to 56 B in 8 min; 254/220 nm; RT1: 7.35 min. This resulted in N-(5-[2-[4-(trifluoromethyl)phenyl]ethoxy]-1H-indol-3-yl)acetamide (148.3 mg) as a white solid. LCMS Method F: $[M+H]^+$=363. $^1H$ NMR (400 MHz, DMSO-$d_6$): δ 10.57 (s, 1H), 9.68 (s, 1H), 7.71-7.65 (m, 2H), 7.60 (d, J=8.0 Hz, 1H), 7.55-7.52 (m, 2H), 7.32 (s, 1H), 7.22-7.19 (m, 1H), 6.73-6.70 (m, 1H), 4.20 (t, J=6.8 Hz, 2H), 3.18 (t, J=6.8 Hz, 2H), 2.07 (s, 3H).

The analogs prepared in the following table were prepared using the same method described for Example 29.

| Example # | Compound No. | Starting materials Used | Structure | LCMS data |
|---|---|---|---|---|
| 30 | 123 | 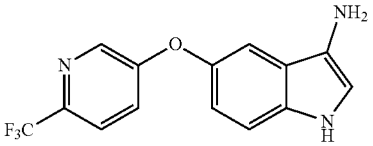 Intermediate 30 | 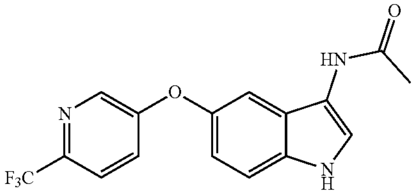 [SMILES: CC(=O)Nc1c[nH]c2ccc(Oc3ccc(C(F)(F)F)nc3)cc12] | Method E: MS-ESI: 336 $[M + H]^+$. |

-continued

| Example # | Compound No. | Starting materials Used | Structure | LCMS data |
|---|---|---|---|---|
| 31 | 116 | 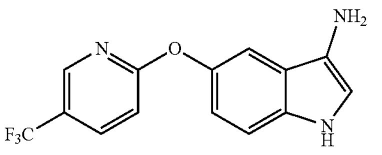 Intermediate 31 | 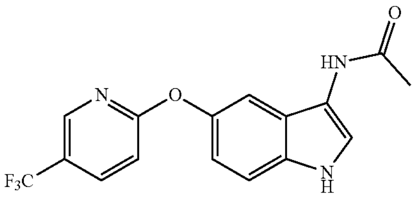 [SMILES: CC(=O)Nc1c[nH]c2ccc(Oc3ccc(C(F)(F)F)cn3)cc12] | Method D: MS-ESI: 336 [M + H]$^+$. |
| 32 | 122 | 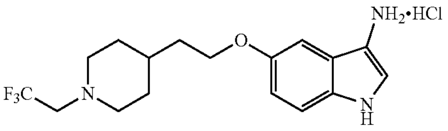 Intermediate 32 | 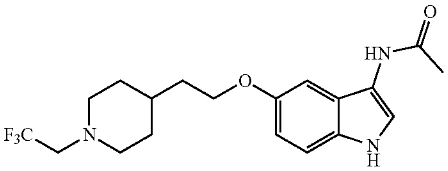 [SMILES: CC(=O)Nc1c[nH]c2ccc(OCCC3CCN(CC(F)(F)F)CC3)cc12] | Method E: MS-ESI: 384 [M + H]$^+$. |
| 33 | 124 | 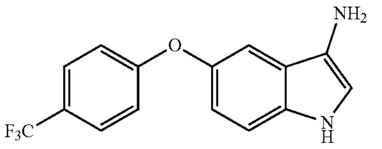 Intermediate 29 | 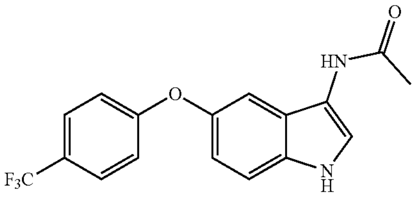 [SMILES: CC(=O)Nc1c[nH]c2ccc(Oc3ccc(C(F)(F)F)cc3)cc12] | Method F: MS-ESI: 335 [M + H]$^+$. |

Example 34: 2-methoxy-N-(5-(2-(1-(2,2,2-trifluoroethyl)piperidin-4-yl)ethoxy)-1H-indol-3-yl)acetamide (Compound 117)

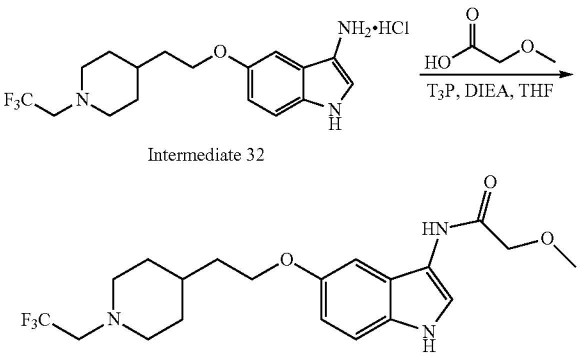

Intermediate 32

Compound 117

5-[2-[1-(2,2,2-Trifluoroethyl)piperidin-4-yl]ethoxy]-1H-indol-3-amine (200.0 mg, 0.6 mmol, 1.0 equiv.) was dissolved in THF (20 mL), then TEA (0.2 mL, 1.2 mmol, 2.0 equiv.), methoxyacetic acid (105.6 mg, 1.2 mmol, 2.0 equiv.) and $T_3P$ (wt. 50% in ethyl acetate, 0.8 mL, 1.2 mmol, 2.0 equiv.) were added. The reaction mixture was stirred for 4 hours at ambient temperature, then concentrated under vacuum. The residue was purified by reverse flash chromatography with the following conditions: column, C18 silica gel; mobile phase, ACN in water, 5% to 100% gradient in 30 min; detector, UV 254 nm. This resulted in 2-methoxy-N-(5-[2-[1-(2,2,2-trifluoroethyl)piperidin-4-yl]ethoxy]-1H-indol-3-yl)acetamide (88.5 mg) as a light yellow solid. LCMS Method D: $[M+H]^+$=414. $^1H$ NMR (400 MHz, DMSO-$d_6$): δ 10.67 (s, 1H), 9.60 (s, 1H), 7.65 (d, J=6.4 Hz, 1H), 7.27 (d, J=2.0 Hz, 1H), 7.23-7.21 (m, 1H), 6.75-6.72 (m, 1H), 4.07 (s, 2H), 4.00 (t, J=6.8 Hz, 2H), 3.37 (s, 3H), 3.17-3.09 (m, 2H), 2.93-2.90 (m, 2H), 2.34-2.28 (m, 2H), 1.71-1.68 (m, 4H), 1.53-1.47 (m, 1H), 1.30-1.27 (m, 2H).

The analogs prepared in the following table were prepared using the same method described for Example 34.

| Example # | Compound No. | Starting material A | Starting material B | Structure | LCMS data |
|---|---|---|---|---|---|
| 35 | 121 | 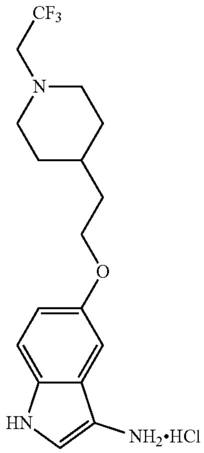 Intermediate 32 | 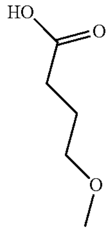 | 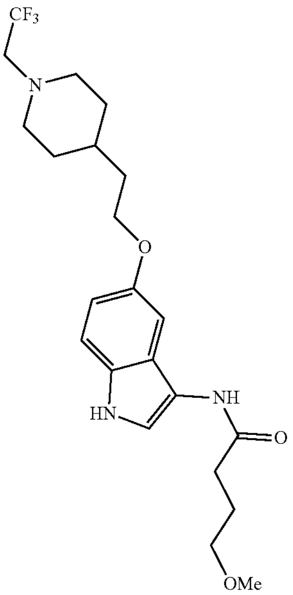 [SMILES: COCCCC(=O)Nc1c[nH]c2ccc(OCCC3CCN(CC(F)(F)F)CC3)cc12] | Method E: MS-ESI: 442 [M + H]+. |
| 36 | 118 | 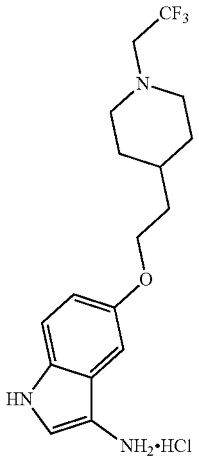 Intermediate 32 | 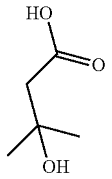 | 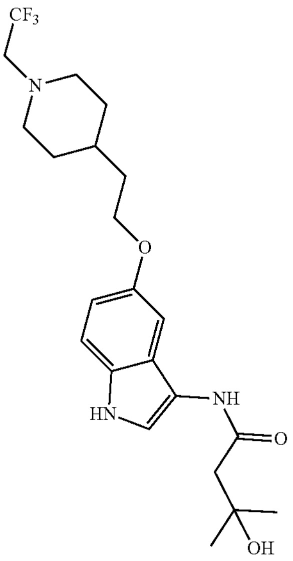 [SMILES: CC(C)(O)CC(=O)Nc1c[nH]c2ccc(OCCC3CCN(CC(F)(F)F)CC3)cc12] | Method E: MS-ESI: 442 [M + H]+. |

-continued

| Example # | Compound No. | Starting material A | Starting material B | Structure | LCMS data |
|---|---|---|---|---|---|
| 37 | 107 | 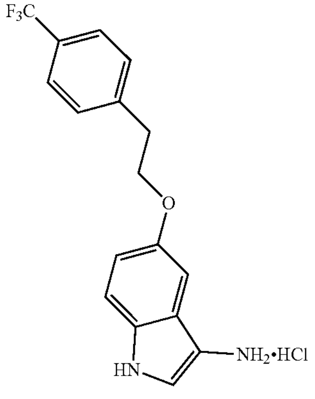 Intermediate 33 | 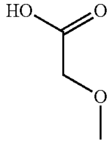 | 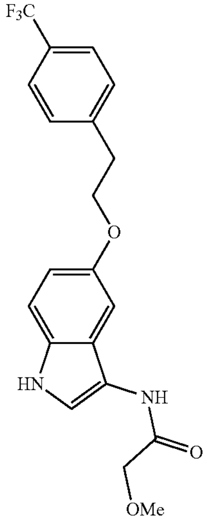 [SMILES: COCC(=O)Nc1c[nH]c2ccc(OCCc3ccc(C(F)(F)F)cc3)cc12] | Method F: MS-ESI: 393 $[M + H]^+$. |

Example 38: N-(5-(2-((6-(trifluoromethyl)pyridin-3-yl)amino)ethyl)-1H-indol-3-yl)acetamide (Compound 126)

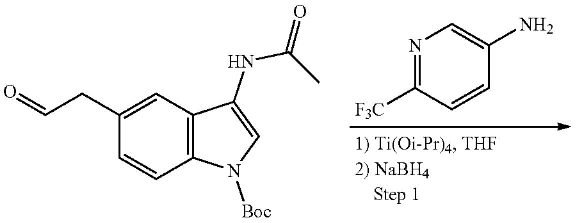

Intermediate 15

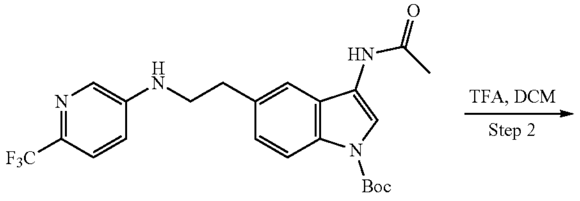

50

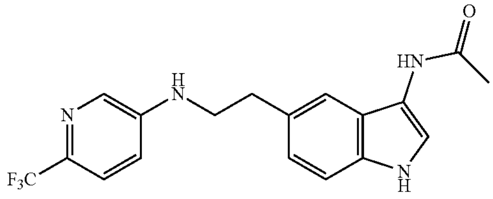

Compound 126

Step 1: tert-butyl 3-acetamido-5-(2-[[6-(trifluoromethyl)pyridin-3-yl]amino]ethyl)indole-1-carboxylate tert-Butyl 3-acetamido-5-(2-oxoethyl)indole-1-carboxylate (300.0 mg, 0.9 mmol, 1.0 equiv.) was dissolved in THE (20 mL), then 6-(trifluoromethyl)pyridin-3-amine (230.6 mg, 1.4 mmol, 1.5 equiv.) and $Ti(Oi\text{-}Pr)_4$ (539.0 mg, 1.9 mmol, 2.0 equiv.) were added. The reaction mixture was stirred for 2 hours at 70° C., then cooled to ambient temperature. This was followed by the addition of $NaBH_4$ (71.8 mg, 1.9 mmol, 2.0 equiv.). The resulting mixture was stirred for an additional 1 hour at ambient temperature, then quenched by the addition of MeOH and concentrated under vacuum. The residue was purified by flash column chromatography on silica gel, eluting with ethyl acetate/petroleum ether (1:2) to give tert-butyl 3-acetamido-5-(2-[[6-(trifluoromethyl)pyridin-3-yl]amino]ethyl)indole-1-carboxylate (200.0 mg) as a light yellow solid. LCMS Method B: $[M+H]^+$=463.

Step 2: N-[5-(2-[[6-(trifluoromethyl)pyridin-3-yl]amino]ethyl)-1H-indol-3-yl]acetamide tert-Butyl 3-acetamido-5-(2-[[6-(trifluoromethyl)pyridin-3-yl]amino]ethyl)indole-1-carboxylate (100.0 mg, 0.2 mmol, 1.0 equiv.) was dissolved in DCM (10 mL) and TFA (1 mL). The reaction mixture was stirred for 1 hour at ambient temperature, then concentrated under vacuum. The residue was purified by Prep-HPLC with the following conditions: Column: XBridge Prep OBD C18 Column, 30*150 mm, 5 μm; Mobile Phase A: Water (10 mM $NH_4HCO_3$), Mobile Phase B: ACN; Flow rate: 60 mL/min; Gradient: 25 B to 55 B in 8 min; 220 nm; RT1: 7.23 min. This resulted in N-[5-(2-[[6-(trifluoromethyl)pyridin-3-yl]amino]ethyl)-1H-indol-3-yl]acetamide (21.2 mg) as a light yellow solid. LCMS Method D: $[M+H]^+$=363. $^1H$ NMR (400 MHz, DMSO-$d_6$): δ 10.66 (s, 1H), 9.75 (s, 1H), 8.09 (d, J=2.8 Hz, 1H), 7.66-7.65 (m, 2H), 7.54 (d, J=8.4 Hz, 1H), 7.27 (d, J=8.4 Hz, 1H), 7.06-7.03 (m, 2H), 6.77 (t, J=5.6 Hz, 1H), 3.41-3.36 (m, 2H), 2.92 (t, J=7.2 Hz, 2H), 2.08 (s, 3H).

The analogs prepared in the following table were prepared using the same method described for Example 38.

| Example # | Compound No. | Intermediate | Structure | LCMS data |
|---|---|---|---|---|
| 39 | 125 | 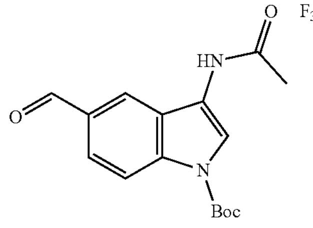 Intermediate 17 | 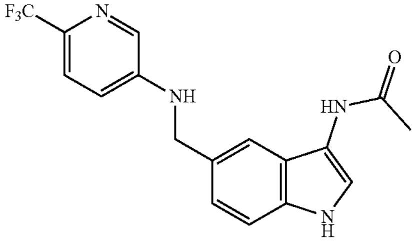 [SMILES: CC(=O)Nc1c[nH]c2ccc(CNc3ccc(C(F)(F)F)nc3)cc12] | Method D: MS-ESI: 349 $[M + H]^+$. |
| 40 | 134 | 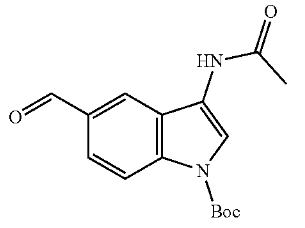 Intermediate 16 | 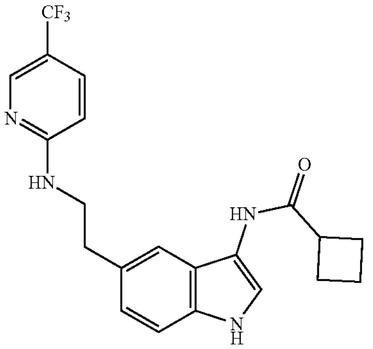 [SMILES: O=C(Nc1c[nH]c2ccc(CCNc3ccc(C(F)(F)F)cn3)cc12)C1CCC1] | Method E: MS-ESI: 403 $[M + H]^+$. |

Example 41/42: (E)-N-(5-(3-(4-(trifluoromethyl)phenyl)prop-1-en-1-yl)-1H-indol-3-yl)cyclobutanecarboxamide (Compound 135) and N-(5-(3-(4-(trifluoromethyl)phenyl)propyl)-1H-indol-3-yl)cyclobutanecarboxamide (Compound 139)

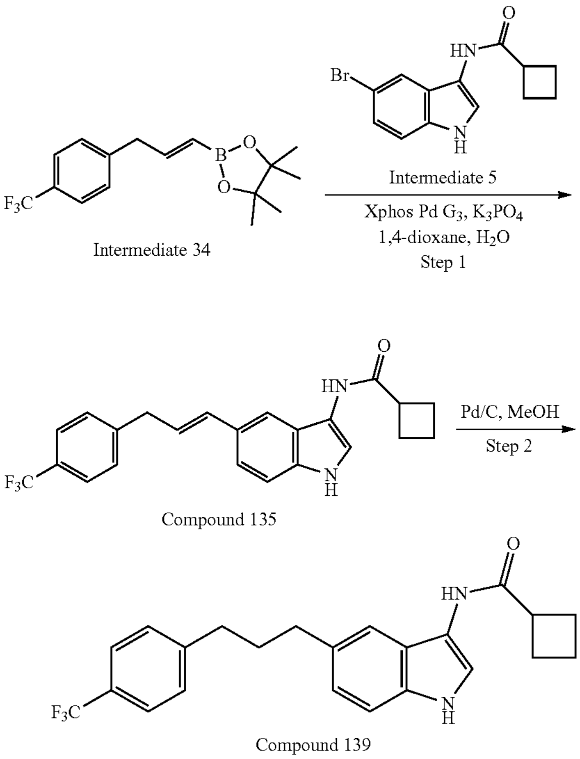

Intermediate 34

Compound 135

Compound 139

Step 1: (E)-N-(5-(3-(4-(trifluoromethyl)phenyl)prop-1-en-1-yl)-1H-indol-3-yl)cyclobutanecarboxamide (E)-4,4,5,5-tetramethyl-2-(3-(4-(trifluoromethyl)phenyl)prop-1-en-1-yl)-1,3,2-dioxaborolane (150.0 mg, 0.5 mmol, 1.0 equiv.) was dissolved in 1,4-dioxane (3 mL) and water (0.3 mL), then N-(5-bromo-1H-indol-3-yl)cyclobutane carboxamide (169.1 mg, 0.6 mmol, 1.2 equiv.), $K_3PO_4$ (306.0 mg, 1.4 mmol, 3.0 equiv.) and Xphos Pd $G_3$ (81.4 mg, 0.1 mmol, 0.2 equiv.) were added under an atmosphere of nitrogen. The reaction mixture was heated to 100° C. for 4 hours, then cooled to ambient temperature and quenched by the addition of water. The resulting solution was extracted with ethyl acetate, washed with brine, dried over anhydrous $Na_2SO_4$ and concentrated under vacuum. The residue was purified by flash column chromatography on silica gel, eluting with ethyl acetate/petroleum ether (1:1) to give material that was further purified by Prep-HPLC with the following conditions: Column: XBridge Prep OBD C18 Column, 30*150 mm, 5 m; Mobile Phase A: Water (10 mM $NH_4HCO_{3+0.1}$% $NH_4OH$), Mobile Phase B: ACN; Flow rate: 60 mL/min; Gradient: 50% B to 80% B in 7 min; Wave Length: 220 nm; RT1: 6.02 min. This resulted in (E)-N-(5-(3-(4-(trifluoromethyl)phenyl)prop-1-en-1-yl)-1H-indol-3-yl)cyclobutanecarboxamide (19.0 mg) as a white solid. LCMS Method D: $[M+H]^+$=399. $^1H$ NMR (400 MHz, DMSO-$d_6$) δ 10.75 (s, 1H), 9.62 (d, J=8.0 Hz, 1H), 7.79 (s, 1H), 7.72-7.67 (m, 3H), 7.53-7.49 (m, 2H), 7.26-7.20 (m, 2H), 6.56-6.52 (m, 1H), 6.33-6.27 (m, 1H), 3.65 (d, J=7.2 Hz, 2H), 2.34-2.33 (m, 1H), 2.27-2.22 (m, 2H), 2.14-2.09 (m, 2H), 1.96-1.92 (m, 1H), 1.84-1.81 (m, 1H).

Step 2: N-(5-(3-(4-(trifluoromethyl)phenyl)propyl)-1H-indol-3-yl)isobutyramide (E)-N-(5-(3-(4-(trifluoromethyl)phenyl)prop-1-en-1-yl)-1H-indol-3-yl)cyclobutanecarboxamide (150.0 mg, 0.4 mmol, 1.0 equiv.) was dissolved in MeOH (5 mL), then Pd/C (10% wt., 50.0 mg) was added under an atmosphere of nitrogen. The mixture was sparged with nitrogen, placed under an atmosphere of hydrogen gas (balloon), then stirred for 10 hours at ambient temperature. The solids were removed by filtration and the filtrate was concentrated under vacuum. The residue was purified by Flash-Prep-HPLC with the following conditions: Column: XBridge Prep C18 OBD Column, 30*50 mm, 5 m; Mobile Phase A: Water (10 mM $NH_4HCO_3$), Mobile Phase B: ACN; Flow rate: 60 mL/min; Gradient: 55% B to 70% B in 8 min; Wave Length: 254/220 nm; RT1: 7.73 min. This resulted in N-(5-(3-(4-(trifluoromethyl)phenyl)propyl)-1H-indol-3-yl)isobutyramide (30.0 mg) as a white solid. LCMS Method D: $[M+H]^+$=401. $^1$H NMR (400 MHz, DMSO-$d_6$) δ 10.63 (s, 1H), 9.55 (s, 1H), 7.70-7.64 (m, 3H), 7.57 (s, 1H), 7.46 (d, J=8.0 Hz, 2H), 7.23 (d, J=8.4 Hz, 1H), 6.96-6.94 (m, 1H), 3.37-3.34 (m, 1H), 2.75-2.66 (m, 4H), 2.27-2.22 (m, 2H), 2.12-2.09 (m, 2H), 2.03-1.95 (m, 3H), 1.88-1.83 (m, 1H).

The analogs prepared in the following table were prepared using the same method described for Examples 41/42.

1-(bromomethyl)-4-(trifluoromethyl)benzene (118.0 mg, 0.5 mmol, 1.0 equiv.) were dissolved in 1,4-dioxane (10 mL) and water (0.5 mL), then $Cs_2CO_3$ (402.1 mg, 1.2 mmol, 2.5 equiv.) and Pd(dppf)$Cl_2$ $CH_2Cl_2$ (80.4 mg, 0.1 mmol, 0.2 equiv.) were added under an atmosphere of nitrogen. The reaction mixture was heated to 85° C. for 16 hours, then cooled to ambient temperature and quenched by the addition of water. The resulting solution was extracted with ethyl acetate, washed with brine, dried over anhydrous $Na_2SO_4$ and concentrated under vacuum. The residue was purified by flash column chromatography on silica gel, eluting with ethyl acetate/petroleum ether (1:1) to give material that was further purified by Prep-HPLC with the following conditions: Column: YMC-Actus Triart C18 ExRS, 30 mm*150 mm, 5 μm; Mobile Phase A: Water (10 mM $NH_4HCO_3$), Mobile Phase B: ACN; Flow rate: 60 mL/min; Gradient: 40% B to 70% B in 7 min; 254/220 nm; RT1: 6.78 min. This resulted in N-(5-[[4-(trifluoromethyl)phenyl]methyl]-1H-indol-3-yl)acetamide (46.3 mg) as a white solid. LCMS Method E: $[M+H]^+$=333. $^1$H NMR (400 MHz, DMSO-$d_6$) δ 10.69 (s, 1H), 9.76 (s, 1H), 7.66-7.63 (m, 4H), 7.44 (d, 2H), 7.26 (d, J=8.0 Hz, 1H), 6.99-6.96 (m, 1H), 4.10 (s, 2H), 2.07 (s, 3H).

| Example # | Compound No. | Intermediates Used | Structure | LCMS data |
|---|---|---|---|---|
| 43 | 132 | Intermediate 34<br>Intermediate 1 | 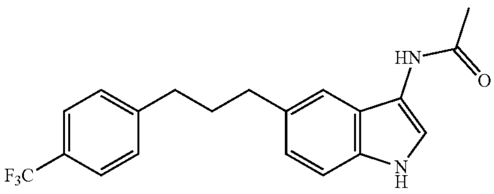 [SMILES: CC(=O)Nc1c[nH]c2ccc(CCCc3ccc(C(F)(F)F)cc3)cc12] | Method D:<br>MS-ESI:<br>359 $[M - H]^-$. |
| 44 | 143 | (E)-2-(2-ethoxyvinyl)-4,4,5,5-tetramethyl-1,3,2-dioxaborolane/<br>Intermediate 5 | 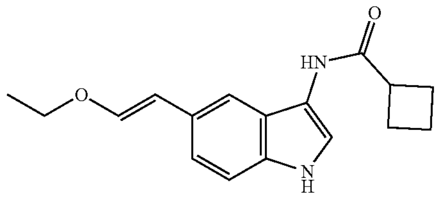 [SMILES: CCO/C=C/c1ccc2[nH]cc(NC(=O)C3CCC3)c2c1] | Method F:<br>MS-ESI:<br>285 $[M + H]^+$. |

Example 45: N-(5-(4-(trifluoromethyl)benzyl)-1H-indol-3-yl)acetamide (Compound 128)

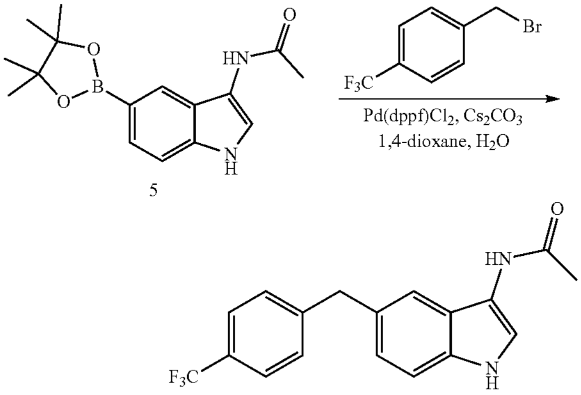

5

Compound 128

N-[5-(4,4,5,5-tetramethyl-1,3,2-dioxaborolan-2-yl)-1H-indol-3-yl] acetamide (296.4 mg, 1.0 mmol, 2 equiv.) and Example 46: N-(5-(4-(4-(trifluoromethyl)phenyl)butan-2-yl)-1H-indol-3-yl)cyclobutanecarboxamide (Compound 131)

Compound 131

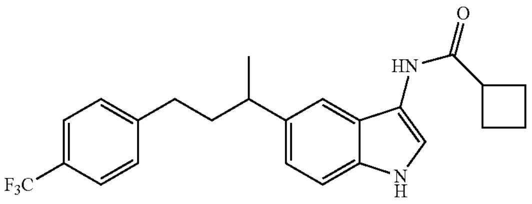

-continued

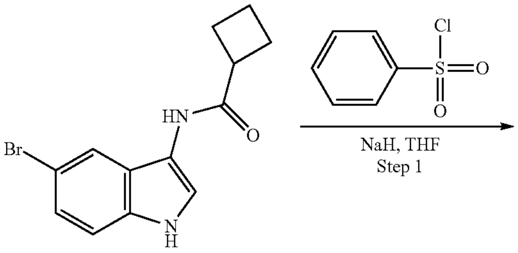

Intermediate 5

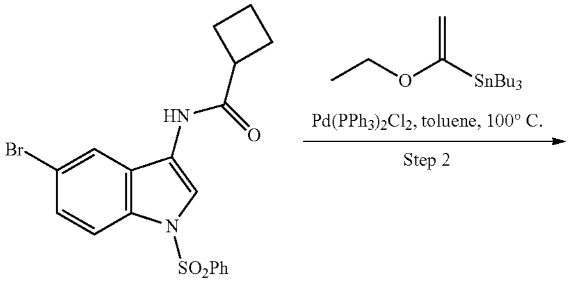

52

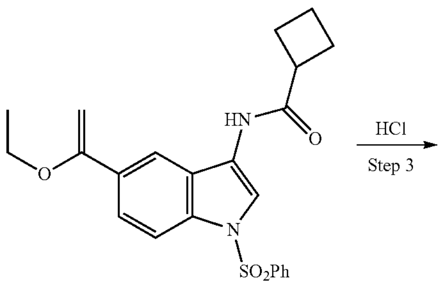

53

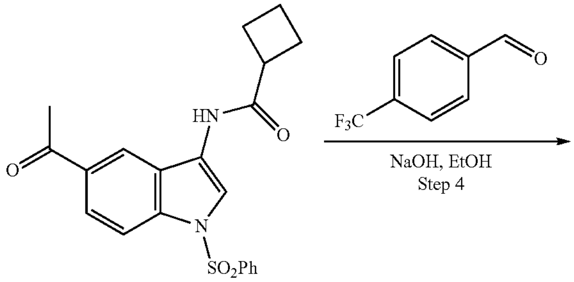

54

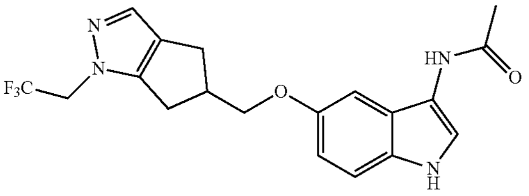

Compound 444

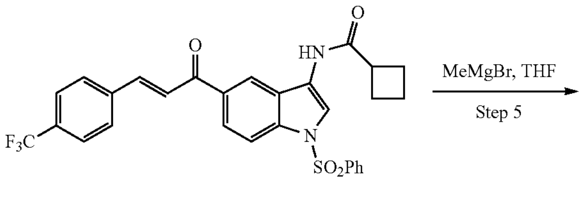

55

-continued

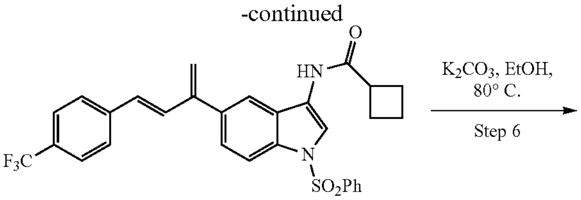

56

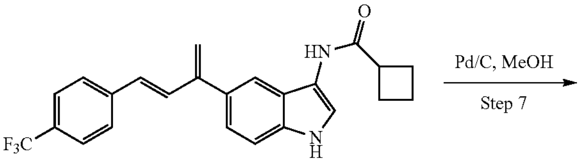

57

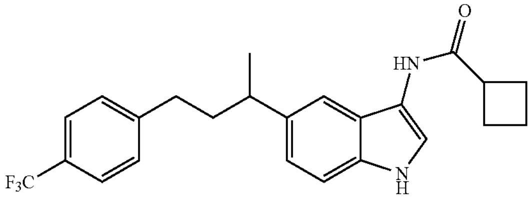

Compound 131

Step 1: N-(5-bromo-1-(phenylsulfonyl)-1H-indol-3-yl)cyclobutanecarboxamide

N-(5-bromo-1H-indol-3-yl)cyclobutanecarboxamide (3.0 g, 10.2 mmol, 1.0 equiv.) was dissolved in THF (30 mL) and cooled to 0° C., then NaH (60% wt., 0.6 g, 15.9 mmol, 1.5 equiv.) was added, maintaining the solution at 0° C. This was followed by the dropwise addition of benzenesulfonyl chloride (1.5 mL, 12.3 mmol, 1.2 equiv.), maintaining the reaction mixture at 0° C. The reaction mixture was stirred for 2 hours at ambient temperature and then quenched by the addition of water. The resulting solution was extracted with ethyl acetate, washed with brine, dried over $Na_2SO_4$ and concentrated under vacuum. The residue was purified by flash column chromatography on silica gel, eluting with ethyl acetate/petroleum ether (1:4) to give N-(5-bromo-1-(phenylsulfonyl)-1H-indol-3-yl)cyclobutanecarboxamide (1.2 g) as a yellow solid. LCMS Method A: $[M+H]^+$=433.

Step 2: N-(5-(1-ethoxyvinyl)-1-(phenylsulfonyl)-1H-indol-3-yl)cyclobutanecarboxamide N-(5-bromo-1-(phenylsulfonyl)-1H-indol-3-yl)cyclobutanecarboxamide (1.2 g, 2.8 mmol, 1.0 equiv.) was dissolved in toluene (20 mL), then tributyl(1-ethoxyethenyl)stannane (3.0 g, 8.4 mmol, 3.0 equiv.) and $Pd(PPh_3)_2Cl_2$ (380.1 mg, 0.4 mmol, 0.2 equiv.) were added under an atmosphere of nitrogen. The reaction mixture was heated to 100° C. for 14 hours, then cooled to ambient temperature and quenched by the addition of water. The resulting solution was extracted with ethyl acetate, washed with brine, dried over anhydrous $Na_2SO_4$ and concentrated under vacuum to give crude N-(5-(1-ethoxyvinyl)-1-(phenylsulfonyl)-1H-indol-3-yl)cyclobutanecarboxamide (920.0 mg) as a yellow solid. LCMS Method A: $[M+H]^+$=425.

Step 3: N-(5-acetyl-1-(phenylsulfonyl)-1H-indol-3-yl)cyclobutanecarboxamide

N-[1-(benzenesulfonyl)-5-(1-ethoxyethenyl)indol-3-yl]cyclobutanecarboxamide (1.5 g, 3.5 mmol, 1.0 equiv.) was dissolved in aqueous HCl (2 N, 20 mL). The reaction mixture was stirred for 3 hours at ambient temperature and concentrated under vacuum. The residue was purified by flash column chromatography on silica gel, eluting with ethyl acetate/petroleum ether (1:1) to give N-(5-acetyl-1-(phenylsulfonyl)-1H-indol-3-yl)cyclobutanecarboxamide (1.0 g) as a yellow solid. LCMS Method A: $[M+H]^+=397$.

Step 4: (Z)—N-(1-(phenylsulfonyl)-5-(3-(4-(trifluoromethyl)phenyl)acryloyl)-1H-indol-3-yl)cyclobutanecarboxamide N-[5-acetyl-1-(benzenesulfonyl)indol-3-yl]cyclobutanecarboxamide (1.0 g, 2.5 mmol, 1.0 equiv.) and 4-(trifluoromethyl)benzaldehyde (527.0 mg, 3.0 mmol, 1.2 equiv.) were dissolved in EtOH (20 mL) and cooled to 0° C., then NaOH aqueous (2 M, 12 mL, 24.0 mmol, 10.0 equiv.) was added dropwise, maintaining the solution at 0° C. The reaction mixture was stirred for 5 hours at ambient temperature and then quenched by the addition of water. The resulting solution was extracted with ethyl acetate, washed with brine, dried over anhydrous $Na_2SO_4$ and concentrated under vacuum to give (Z)—N-(1-(phenylsulfonyl)-5-(3-(4-(trifluoromethyl)phenyl)acryloyl)-1H-indol-3-yl)cyclobutanecarboxamide (1.2 g) as a yellow solid. LCMS Method B: $[M-H]^-=551$. $^1H$ NMR (400 MHz, DMSO-$d_6$) δ 10.25 (s, 1H), 9.93 (s, 1H), 8.78 (s, 1H), 8.13-8.09 (m, 3H), 7.98-7.96 (m, 1H), 7.91 (d, J=2.4 Hz, 1H), 7.87-7.83 (m, 3H), 7.46 (d, J=8.8 Hz, 1H), 3.46-3.42 (m, 1H), 2.30-2.26 (m, 2H), 2.16-2.14 (m, 2H), 2.02-1.98 (m, 1H), 1.88-1.85 (m, 1H).

Step 5: (Z)—N-(1-(phenylsulfonyl)-5-(4-(4-(trifluoromethyl)phenyl)buta-1,3-dien-2-yl)-1H-indol-3-yl)cyclobutanecarboxamide (E)-N-(1-(phenylsulfonyl)-5-(3-(4-(trifluoromethyl)phenyl)acryloyl)-1H-indol-3-yl)cyclobutanecarboxamide (1.2 g, 2.2 mmol, 1.0 equiv.) was dissolved in THE (50 mL) and cooled to 0° C., then MeMgBr (3 M in THF, 2.2 mL, 6.6 mmol, 3.0 equiv.) was added dropwise, maintaining the solution at 0° C. The reaction mixture was stirred for 18 hours at ambient temperature and then quenched by the addition of ice water. The resulting solution was extracted with ethyl acetate, washed with brine, dried over anhydrous $Na_2SO_4$ and concentrated under vacuum. The residue was purified by flash column chromatography on silica gel, eluting with ethyl acetate/petroleum ether (3:2) to give (Z)—N-(1-(phenylsulfonyl)-5-(4-(4-(trifluoromethyl)phenyl)buta-1,3-dien-2-yl)-1H-indol-3-yl)cyclobutanecarboxamide (1.2 g) as a yellow solid. LCMS Method A: $[M+H]^+=551$.

Step 6: (E)-N-(5-(4-(4-(trifluoromethyl)phenyl)buta-1,3-dien-2-yl)-1H-indol-3-yl)cyclobutanecarboxamide (Z)—N-(1-(phenylsulfonyl)-5-(4-(4-(trifluoromethyl)phenyl)buta-1,3-dien-2-yl)-1H-indol-3-yl)cyclobutanecarboxamide (1.2 g, 2.2 mmol, 1.0 equiv.) was dissolved in MeOH (10 mL), then $K_2CO_3$ (0.9 g, 6.3 mmol, 2.9 equiv.) was added. The reaction mixture was heated to 80° C. for 4 hours, then cooled to ambient temperature and quenched by the addition of ice-water. The resulting solution was extracted with ethyl acetate, washed with brine, dried over anhydrous $Na_2SO_4$ and concentrated under vacuum. The residue was purified by flash column chromatography on silica gel, eluting with ethyl acetate/petroleum ether (1:1) to give (E)-N-(5-(4-(4-(trifluoromethyl)phenyl)buta-1,3-dien-2-yl)-1H-indol-3-yl)cyclobutanecarboxamide (290.0 mg) as a yellow solid. LCMS Method A: $[M+H]^+=411$.

Step 7: N-(5-(4-(4-(trifluoromethyl)phenyl)butan-2-yl)-1H-indol-3-yl)cyclobutanecarboxamide (E)-N-(5-(4-(4-(trifluoromethyl)phenyl)buta-1,3-dien-2-yl)-1H-indol-3-yl)cyclobutanecarboxamide (230.0 mg, 0.6 mmol, 1.0 equiv.) was dissolved in MeOH (10 mL), then Pd/C (10% wt., 100.0 mg) was added. The mixture was sparged with nitrogen, placed under an atmosphere of hydrogen gas (balloon), then stirred for 48 hours at ambient temperature. The solids were removed by filtration and the filtrate was concentrated under vacuum. The residue was purified by flash column chromatography on silica gel, eluting with ethyl acetate/petroleum ether (1:1) to give material that was further purified by Prep-HPLC with the following conditions Column: XBridge Prep OBD C18 Column, 30*150 mm, 5 μm; Mobile Phase A: Water (10 mM $NH_4HCO_3$), Mobile Phase B: ACN; Flow rate: 60 mL/min; Gradient: 50% to 85% in 8 min; 220 nm; RT1: 7.33 min. This resulted in N-(5-(4-(4-(trifluoromethyl)phenyl)butan-2-yl)-1H-indol-3-yl)cyclobutanecarboxamide (32.1 mg) as a white solid. LCMS Method D: $[M+H]^+=415$. $^1H$ NMR (400 MHz, DMSO-$d_6$) δ 10.63 (s, 1H), 9.58 (s, 1H), 7.71 (d, J=6.4 Hz, 1H), 7.63-7.61 (m, 3H), 7.39-7.37 (m, 2H), 7.26 (d, J=8.4 Hz, 1H), 7.00-6.97 (m, 1H), 3.39-3.33 (m, 2H), 2.76-2.74 (m, 1H), 2.60-2.54 (m, 1H), 2.28-2.23 (m, 2H), 2.13-2.10 (m, 2H), 1.97-1.90 (m, 3H), 1.88-1.83 (m, 1H), 1.29 (d, J=7.2 Hz, 3H).

Example 47: N-(5-(trans-3-(4-(trifluoromethyl)phenyl)cyclobutoxy)-1H-indol-3-yl)cyclopropanecarboxamide (Compound 147)

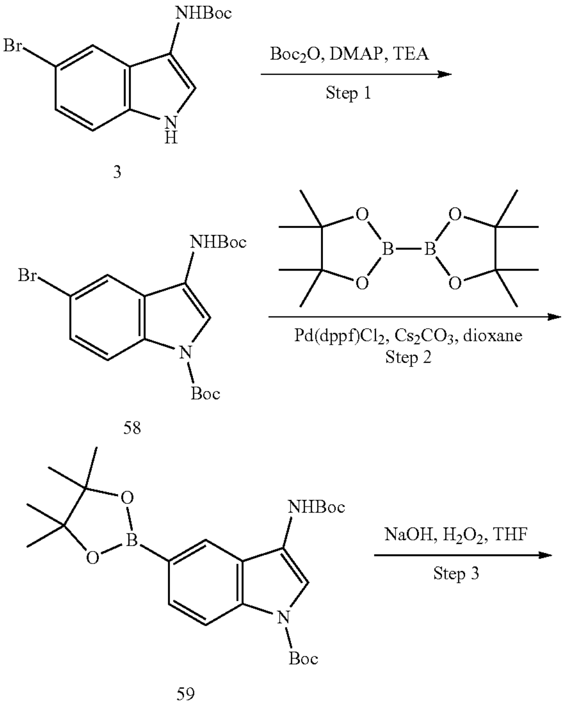

3

58

59

-continued

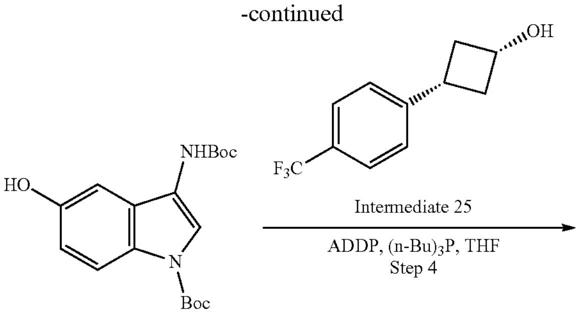

60

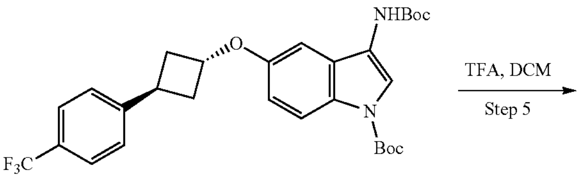

61

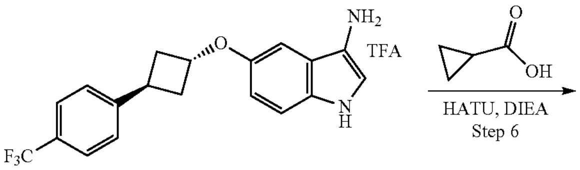

62

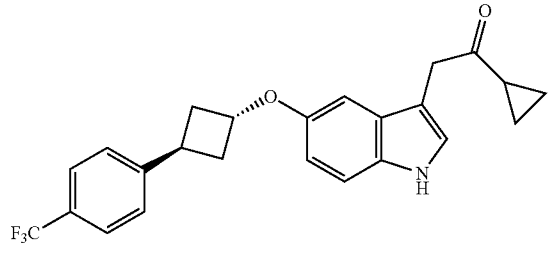

Compound 147

Step 1: tert-butyl 5-bromo-3-((tert-butoxycarbonyl)amino)-1H-indole-1-carboxylate tert-Butyl (5-bromo-1H-indol-3-yl)carbamate (5.0 g, 16.1 mmol, 1.0 equiv.) was dissolved in THE (80.0 mL), then $(BOc)_2O$ (4.2 g, 19.3 mmol, 1.2 equiv.), DMAP (0.2 g, 1.6 mmol, 0.1 equiv.) and TEA (4.6 mL, 32.1 mmol, 2.0 equiv.) were added. The reaction mixture was stirred for 4 hours at ambient temperature and then concentrated under vacuum. The residue was purified by flash column chromatography on silica gel, eluting with ethyl acetate/petroleum ether (1:5) to give tert-butyl 5-bromo-3-((tert-butoxycarbonyl)amino)-1H-indole-1-carboxylate (6.5 g) as a white solid.

Step 2: tert-butyl 3-((tert-butoxycarbonyl)amino)-5-(4,4,5,5-tetramethyl-1,3,2-dioxaborolan-2-yl)-1H-indole-1-carboxylate tert-Butyl 5-bromo-3-((tert-butoxycarbonyl)amino)-1H-indole-1-carboxylate (6.0 g, 14.6 mmol, 1.0 equiv.) was dissolved in 1,4-dioxane (100.0 mL), then 4,4,4',4',5,5,5',5'-octamethyl-2,2'-bi(1,3,2-dioxaborolane) (5.6 g, 21.9 mmol, 1.5 equiv.), $Pd(dppf)Cl_2$ (1.1 g, 1.5 mmol, 0.1 equiv.) and $Cs_2CO_3$ (9.5 g, 29.2 mmol, 2.0 equiv.) were added under an atmosphere of nitrogen. The reaction mixture was stirred overnight at 90° C. under nitrogen, then cooled to ambient temperature and concentrated under vacuum. The residue was purified by flash column chromatography on silica gel, eluting with ethyl acetate/petroleum ether (1:4) to give tert-butyl 3-((tert-butoxycarbonyl)amino)-5-(4,4,5,5-tetramethyl-1,3,2-dioxaborolan-2-yl)-1H-indole-1-carboxylate (6.0 g) as a white solid.

Step 3: tert-butyl 3-((tert-butoxycarbonyl)amino)-5-hydroxy-1H-indole-1-carboxylate tert-Butyl 3-((tert-butoxycarbonyl)amino)-5-(4,4,5,5-tetramethyl-1,3,2-dioxaborolan-2-yl)-1H-indole-1-carboxylate (6.0 g, 13.1 mmol, 1.0 equiv.) was dissolved in THE (80.0 mL) and cooled to 0° C. Then NaOH (1.6 g, 39.3 mmol, 3.0 equiv.) was added at 0° C., followed by the addition of $H_2O_2$ (3.0 g, 26.2 mmol, 2.0 equiv., 30%) dropwise, maintaining the reaction mixture at 0° C. The reaction mixture was stirred for 2 hours at ambient temperature, then quenched by the addition of brine. The resulting resolution was extracted with ethyl acetate, washed with brine, dried over anhydrous $Na_2SO_4$ and concentrated under vacuum. The residue was purified by flash column chromatography on silica gel, eluting with ethyl acetate/petroleum ether (1:1) to give tert-butyl 3-((tert-butoxycarbonyl)amino)-5-hydroxy-1H-indole-1-carboxylate (2.2 g) as a grey solid.

Step 4: tert-butyl 3-((tert-butoxycarbonyl)amino)-5-(trans-3-(4-(trifluoromethyl)phenyl)cyclobutoxy)-1H-indole-1-carboxylate tert-Butyl 3-((tert-butoxycarbonyl)amino)-5-hydroxy-1H-indole-1-carboxylate (1.0 g, 2.9 mmol, 1.0 equiv.) and cis-3-(4-(trifluoromethyl)phenyl)cyclobutan-1-ol (1.2 g, 5.7 mmol, 2.0 equiv.) were dissolved in THE (20.0 mL) and cooled to 0° C., then $n\text{-}Bu_3P$ (1.7 g, 8.6 mmol, 3.0 equiv.) was added at 0° C. under an atmosphere of nitrogen. This was followed by the addition of ADDP (2.2 g, 8.6 mmol, 3.0 equiv.) dropwise, maintaining the solution at 0° C. The reaction mixture was heated to 50° C. for 2 hours, then cooled to ambient temperature and concentrated under vacuum. The residue was purified by reverse flash chromatography with the following conditions: column, C18 silica gel; mobile phase A: 0.05% $NH_4HCO_3$ in water; mobile phase B: Acetonitrile, 45% phase B to 70% gradient in 20 min; detector, UV 254 nm. This resulted in tert-butyl 3-((tert-butoxycarbonyl)amino)-5-(trans-3-(4-(trifluoromethyl)phenyl)cyclobutoxy)-1H-indole-1-carboxylate (1.2 g) as an off-white solid.

Step 5: 5-(trans-3-(4-(trifluoromethyl)phenyl)cyclobutoxy)-1H-indol-3-amine TFA salt tert-Butyl 3-((tert-butoxycarbonyl)amino)-5-(trans-3-(4-(trifluoromethyl)phenyl) cyclobutoxy)-1H-indole-1-carboxylate (190.0 mg, 0.3 mmol, 1.0 equiv.) was dissolved in DCM (2.0 mL), then TFA (2.0 mL) was added. The resulting mixture was stirred for 1 hour at ambient temperature and then concentrated under vacuum to give 5-(trans-3-(4-(trifluoromethyl)phenyl)cyclobutoxy)-1H-indol-3-amine TFA salt (120.0 mg) as a white solid.

Step 6: N-(5-(trans-3-(4-(trifluoromethyl)phenyl)cyclobutoxy)-1H-indol-3-yl)cyclopropanecarboxamide 5-(trans-3-(4-(trifluoromethyl)phenyl)cyclobutoxy)-1H-indol-3-amine TFA salt (100.0 mg, 0.3 mmol, 1.0 equiv.)

was dissolved in THE (5.0 mL), then cyclopropanecarboxylic acid (29.8 mg, 0.3 mmol, 1.2 equiv.), HATU (131.7 mg, 0.3 mmol, 1.2 equiv.) and DIEA (0.1 mL, 0.6 mmol, 2.0 equiv.) were added. The reaction mixture was stirred for 1 hour at ambient temperature, then concentrated under vacuum. The residue was purified by reverse flash chromatography with the following conditions: column, C18 silica gel; mobile phase A: 0.05% $NH_4HCO_3$ in water; mobile phase B: Acetonitrile, 30% to 60% gradient in 30 min; detector, UV 254 nm. The resulting material was further purified by Prep-HPLC with the following conditions: Column, XBridge Prep OBD C18 Column, 30*150 mm, 5 μm; mobile phase, Aqueous (10 mmol/L $NH_4HCO_3$) and ACN (43% ACN up to 73% in 7 min). This resulted in N-(5-(trans-3-(4-(trifluoromethyl)phenyl)cyclobutoxy)-1H-indol-3-yl)cyclopropanecarboxamide (12.1 mg) as a white solid. $[M+H]^+$=415. $^1H$ NMR (400 MHz, DMSO-$d_6$) δ 10.57 (d, J=1.6 Hz, 1H), 9.91 (s, 1H), 7.72 (d, J=8.4 Hz, 2H), 7.65 (d, J=2.4 Hz, 1H), 7.61 (d, J=8.0 Hz, 2H), 7.26-7.16 (m, 2H), 6.75-6.72 (m, 1H), 4.98-4.88 (m, 1H), 3.83-3.77 (m, 1H), 2.75-2.59 (m, 4H), 1.94-1.89 (m, 1H), 0.82-0.76 (m, 4H).

Example 48: N-(5-(((4-(trifluoromethyl)benzyl)oxy)methyl)-1H-pyrrolo[2,3-b]pyridin-3-yl)acetamide (Compound 271)

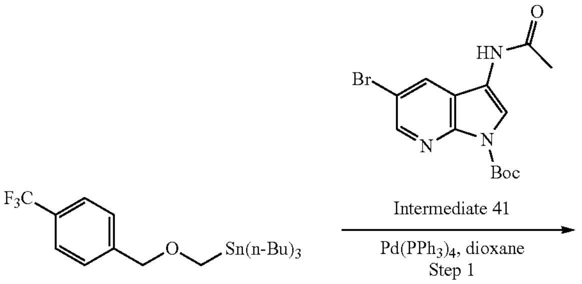

Intermediate 83

-continued

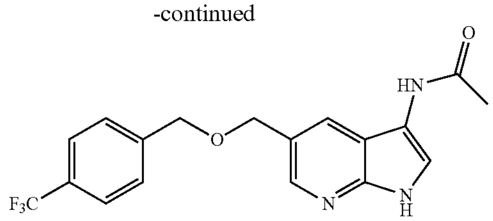

Compound 271 tert-Butyl 3-acetamido-5-bromo-1H-pyrrolo[2,3-b]pyridine-1-carboxylate (200.0 mg, 0.6 mmol, 1.0 equiv.) was dissolved in dioxane (5 mL), then tributyl(((4-(trifluoromethyl)benzyl)oxy)methyl)stannane (324.7 mg, 0.7 mmol, 1.2 equiv.), cataCXium A-Pd-G2 (37.8 mg, 0.1 mmol, 0.1 equiv.) and cataCXium A (40.5 mg, 0. mmol, 0.2 equiv.) were added under an atmosphere of nitrogen. The reaction mixture was heated to 110° C. for 6 hours, then cooled to ambient temperature and concentrated under vacuum. The residue was purified by flash column chromatography on silica gel, eluting with dichloromethane/methanol (10:1) to give material which was further purified by Prep-HPLC with the following conditions: Column: YMC-Actus Triart C18 ExRS, 30*150 mm, Sum; Mobile Phase A: Water (10 mM $NH_4HCO_3$), Mobile Phase B: ACN; Flow rate: 60 mL/min; Gradient: 33% B to 52% B in 8 min; Wave Length: 254/220 nm. This gave N-(5-(((4-(trifluoromethyl)benzyl)oxy)methyl)-1H-pyrrolo[2,3-b]pyridin-3-yl)acetamide (24.0 mg) as a white solid. LCMS Method E: $[M+H]^+$=364. $^1H$ NMR (400 MHz, DMSO-$d_6$): δ 11.33 (s, 1H), 9.99 (s, 1H), 8.23-8.21 (m, 2H), 7.76 (s, 1H), 7.74 (d, J=8.4 Hz, 2H), 7.60 (d, J=8.0 Hz, 2H), 4.68-4.66 (m, 4H), 2.08 (s, 3H).

The analogs prepared in the following table were prepared using the same method described for Example 48.

| Example # | Compound No. | Starting materials Used | Structure | LCMS data |
|---|---|---|---|---|
| 49 | 276 | 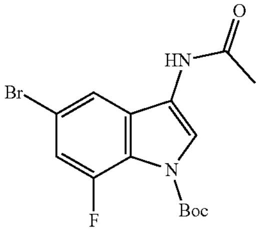 Intermediate 41 | 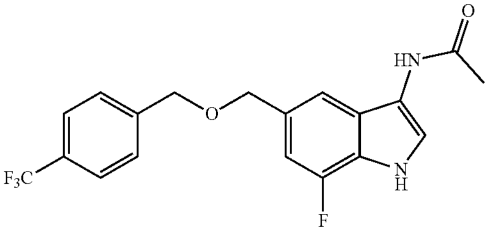 [SMILES: CC(=O)Nc1c[nH]c2c(F)cc(COCc3ccc(C(F)(F)F)cc3)cc12] | Method D: MS-ESI: 379 $[M-H]^-$. |
| 50 | 272 | 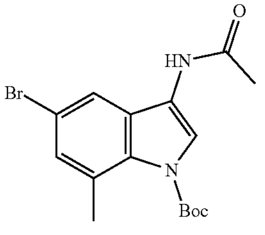 Intermediate 42 | 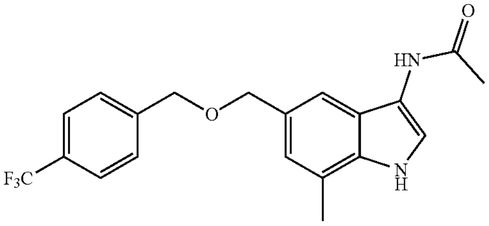 [SMILES: CC(=O)Nc1c[nH]c2c(C)cc(COCc3ccc(C(F)(F)F)cc3)cc12] | Method F: MS-ESI: 375 $[M-H]^-$. |

Example 51: N-(5-(2-((3aR,5r,6aS)-2-(2,2,2-trifluoroethyl)octahydrocyclopenta[c]pyrrol-5-yl)ethoxy)-1H-indol-3-yl)acetamide (Compound 283)

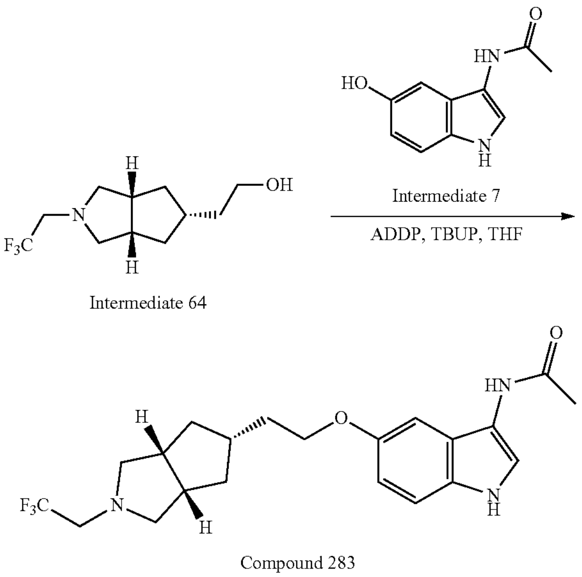

2-((3aR,5r,6aS)-2-(2,2,2-trifluoroethyl)octahydrocyclopenta[c]pyrrol-5-yl)ethan-1-ol (200.0 mg, 0.8 mmol, 1.0 equiv.) was dissolved in THE (8 mL), then N-(5-hydroxy-1H-indol-3-yl)acetamide (160.3 mg, 0.8 mmol, 1.0 equiv.), ADDP (422.0 mg, 1.7 mmol, 2.0 equiv.) and TBUP (340.5 mg, 1.7 mmol, 2.0 equiv.) were added under an atmosphere of nitrogen. The reaction mixture was stirred overnight at ambient temperature then quenched by the addition of water. The resulting solution was extracted with ethyl acetate, washed with brine, dried over anhydrous $Na_2SO_4$ and concentrated under vacuum. The residue was purified by reverse flash chromatography with the following conditions: column, C18; mobile phase, MeOH in water, 1000 to 500% gradient in 10 min; detector, UV 254 nm. The resulting material was further purified by Prep-HPLC with the following conditions: Column: Xselect CSH C18 OBD Column 30*150 mm 5 am, n; Mobile Phase A: Water (0.1% FA), Mobile Phase B: ACN; Flow rate: 60 mL/min; Gradient: 21B to 35% B in 7 min; Wave Length: 254, 220 nm, RT1: 6.23 min. This gave N-(5-(2-((3aR,5r,6aS)-2-(2,2,2-trifluoroethyl)octahydrocyclopenta[c]pyrrol-5-yl)ethoxy)-1H-indol-3-yl)acetamide (25.8 mg) as a white solid. LCMS Method D: $[M+H]^+$=410. $^1$H NMR (400 MHz, DMSO-$d_6$): δ 7.58 (s, 1H), 7.22-7.19 (m, 2H), 6.81-6.78 (m, 1H), 4.04 (t, J=6.4 Hz, 2H), 3.14-3.06 (m, 2H), 2.73-2.71 (m, 2H), 2.59-2.54 (m, 2H), 2.52-2.48 (m, 2H), 2.21 (s, 3H), 2.19-2.14 (m, 2H), 2.04-1.98 (m, 1H), 1.92-1.84 (m, 2H), 1.14-1.06 (in, 2H).

The analogs prepared in the following table were prepared using the same method described for Example 51.

| Example # | Compound No. | Starting materials Used | Structure | Condition | LCMS data |
| --- | --- | --- | --- | --- | --- |
| 52 | 255 | 4-(trifluoromethyl) phenol/ Intermediate 51 | 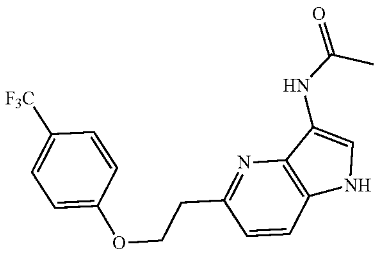 [SMILES: CC(=O)Nc1c[nH]c2ccc(CCOc3ccc(C(F)(F)F)cc3)nc12] | $PPh_3$, DIAD, THF | Method G MS-ESI: 364 $[M + H]^+$. |
| 53 | 259 | 4-(trifluoromethyl) phenol/ Intermediate 58 | 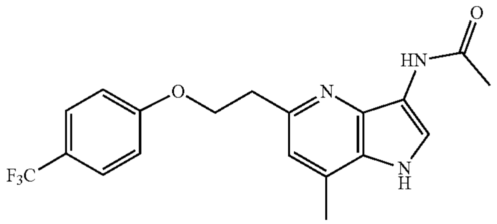 [SMILES: CC(=O)Nc1c[nH]c2c(C)cc(CCOc3ccc(C(F)(F)F)cc3)nc12] | TBUP, ADDP, THF | Method F: MS-ESI: 378 $[M + H]^+$. |
| 54 | 264 | 4-(trifluoromethyl) phenol/ Intermediate 50 | 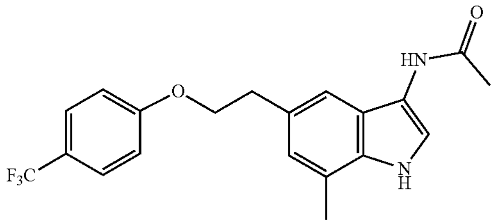 [SMILES: CC(=O)Nc1c[nH]c2c(C)cc(CCOc3ccc(C(F)(F)F)cc3)cc12] | TBUP, ADDP, THF | Method F: MS-ESI: 377 $[M + H]^+$. |

-continued

| Example # | Compound No. | Starting materials Used | Structure | Condition | LCMS data |
|---|---|---|---|---|---|
| 55 | 270 | 4-(trifluoro-methyl) phenol/ Intermediate 49 | 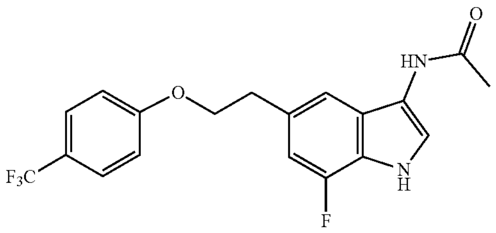 [SMILES: CC(=O)Nc1c[nH]c2c(F)cc(CCOc3ccc(C(F)(F)F)cc3)cc12] | TBUP, ADDP, THF | Method D: MS-ESI: 379 [M − H]$^-$. |
| 56 | 277 | Intermediate 45/ Intermediate 20 | 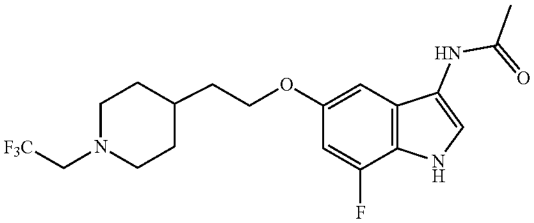 [SMILES: CC(=O)Nc1c[nH]c2c(F)cc(OCCC3CCN(CC(F)(F)F)CC3)cc12] | TBUP, ADDP, THF | Method F: MS-ESI: 402 [M + H]$^+$. |
| 57 | 278 | Intermediate 7/ Intermediate 68 | 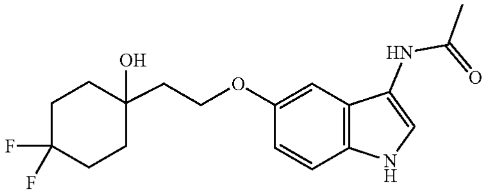 [SMILES: CC(=O)Nc1c[nH]c2ccc(OCCC3(O)CCC(F)(F)CC3)cc12] | TBUP, ADDP, THF | Method E: MS-ESI: 353 [M + H]$^+$. |
| 58 | 289 | Intermediate 7/ Intermediate 65 | 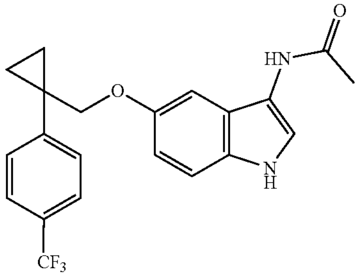 [SMILES: CC(=O)Nc1c[nH]c2ccc(OCC3(c4ccc(C(F)(F)F)cc4)CC3)cc12] | TBUP, ADDP, THF | Method G: MS-ESI: 389 [M + H]$^+$. |
| 59 | 167 | Intermediate 54/6-(trifluoro-methyl) pyridin-3-ol | 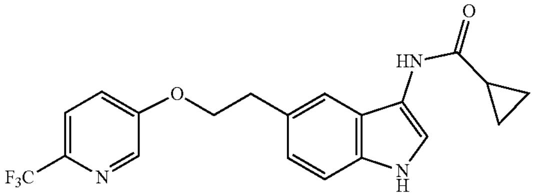 [SMILES: O=C(Nc1c[nH]c2ccc(CCOc3ccc(C(F)(F)F)nc3)cc12)C1CC1] | TBUP, ADDP, THF | Method F: MS-ESI: 390 [M + H]$^+$. |

Example 60/61: N-(5-((1-(4-(trifluoromethyl)phenyl)propan-2-yl)oxy)-1H-indol-3-yl)acetamide (Compound 286) (Front Peak, Absolute Stereochemistry Unconfirmed) and (Compound 285) (Second Peak, Absolute Stereochemistry Unconfirmed)]

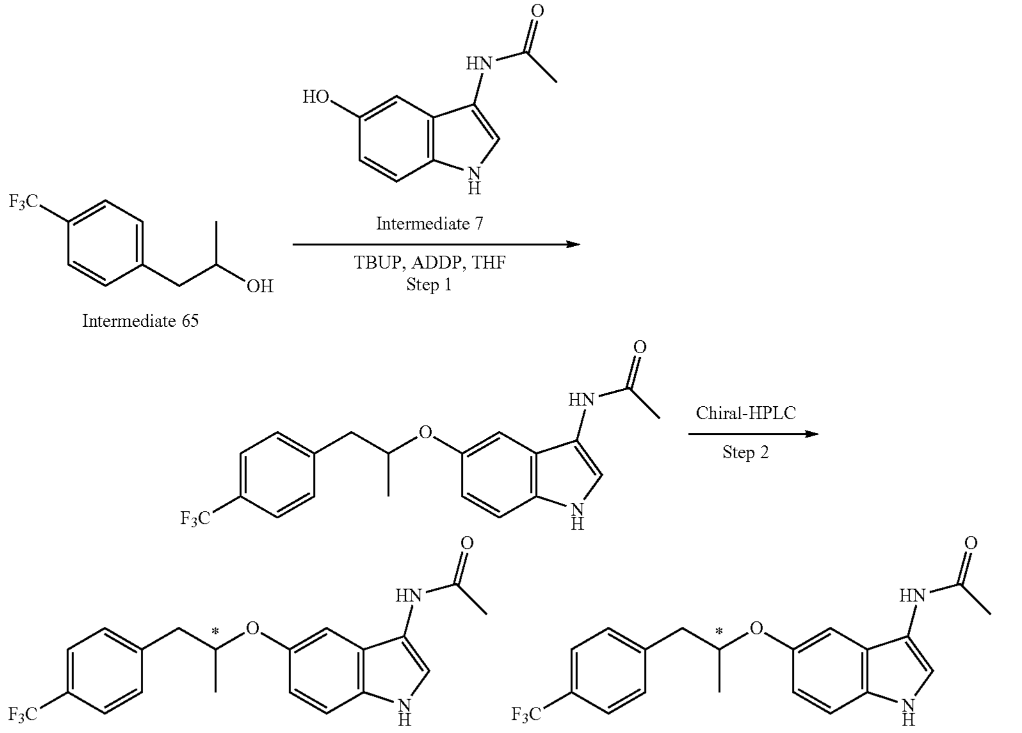

Compound 286
front peak, absolute stereochemistry unconfirmed
Example 60

Compound 285
second peak, absolute stereochemistry unconfirmed
Example 61

Step 1: N-[5-([1-[4-(trifluoromethyl)phenyl]propan-2-yl]oxy)-1H-indol-3-yl]acetamide N-(5-hydroxy-1H-indol-3-yl)acetamide (500.0 mg, 2.6 mmol, 1.0 equiv.) was dissolved in THE (20 mL), then 1-[4-(trifluoromethyl)phenyl]propan-2-ol (536.8 mg, 2.6 mmol, 1.0 equiv.), TBUP (1.1 g, 5.2 mmol, 2.0 equiv.) and ADDP (1.3 g, 5.3 mmol, 2.0 equiv.) were added under an atmosphere of nitrogen. The reaction mixture was stirred for 16 hours at ambient temperature under nitrogen, then quenched by the addition of water. The resulting solution was extracted with ethyl acetate, washed with brine, dried over anhydrous $Na_2SO_4$ and concentrated under vacuum. The residue was purified by flash column chromatography on silica gel, eluting with ethyl acetate/petroleum ether (1:1) to give N-[5-([1-[4-(trifluoromethyl)phenyl]propan-2-yl]oxy)-1H-indol-3-yl]acetamide (33 mg) as a light yellow oil. LCMS Method A: $[M+H]^+$=377.

Step 2: Example 60 (Compound 286) (Front Peak, Absolute Stereochemistry Unconfirmed) and Example 61 (Compound 285) (Second Peak, Absolute Stereochemistry Unconfirmed)

The racemic N-[5-([1-[4-(trifluoromethyl)phenyl]propan-2-yl]oxy)-1H-indol-3-yl]acetamide (20.0 mg) was separated by Prep-Chiral-HPLC with the following conditions: Column: CHIRALPAK AD-H, 2*25 cm, 5 m; Mobile Phase A: Hex (0.5% 2M $NH_3$-MeOH)-HPLC, Mobile Phase B: IPA-HPLC; Flow rate: 20 mL/min; Gradient: 20% B to 20% B in 13 min; Wave Length: 220/254 nm; RT1 (min): 9.03; RT2(min): 11.75. This gave Compound 286 (front peak, 1.3 mg) as a white solid and Compound 285 (second peak, 3.1 mg) as a white solid.

Example 60 (Compound 286): LCMS Method G: $[M+H]^+$= 377. $^1$H NMR (400 MHz, DMSO-$d_6$): δ 10.56 (s, 1H), 9.66 (s, 1H), 7.68-7.64 (m, 3H), 7.54 (d, J=8.0 Hz, 2H), 7.33 (d, J=2.4 Hz, 1H), 7.19 (d, J=8.4 Hz, 1H), 6.70-6.67 (m, 1H), 4.64-4.60 (m, 1H), 3.09-3.00 (m, 2H), 2.08 (s, 3H), 1.26 (d, J=6.0 Hz, 3H).

Example 61 (Compound 285): LCMS Method G: $[M+H]^+$= 377. $^1$H NMR (400 MHz, DMSO-$d_6$): δ 10.56 (s, 1H), 9.66 (s, 1H), 7.68-7.64 (m, 3H), 7.54 (d, J=8.0 Hz, 2H), 7.33 (d, J=2.4 Hz, 1H), 7.19 (d, J=8.4 Hz, 1H), 6.70-6.67 (m, 1H), 4.64-4.60 (m, 1H), 3.09-3.00 (m, 2H), 2.08 (s, 3H), 1.26 (d, J=6.0 Hz, 3H).

The analogs prepared in the following table were prepared using the same method described for Example 60/61.

| Example # | Compound No. | Starting materials Used | Structure | LCMS data |
|---|---|---|---|---|
| 62 | 280 | Intermediate 7/ Intermediate 67 | 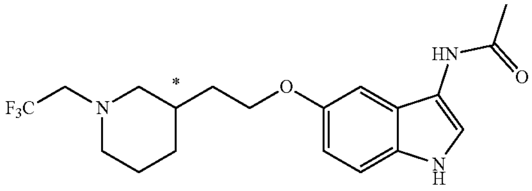 [SMILES: CC(=O)Nc1c[nH]c2ccc(OCCC3CCCN(CC(F)(F)F)C3)cc12] front peak, absolute stereochemistry unconfirmed | Method G: MS-ESI: 384 $[M + H]^+$. |
| 63 | 279 | Intermediate 7/ Intermediate 67 | 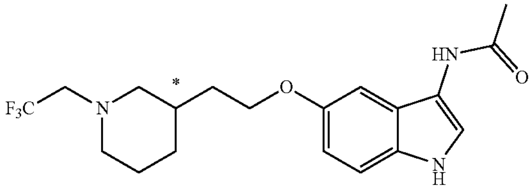 [SMILES: CC(=O)Nc1c[nH]c2ccc(OCCC3CCCN(CC(F)(F)F)C3)cc12] second peak, absolute stereochemistry unconfirmed | Method G: MS-ESI: 384 $[M + H]^+$. |

Example 64: N-(5-(2-(2-(2,2,2-trifluoroethyl)-2-azaspiro[3.3]heptan-6-yl)ethoxy)-1H-indol-3-yl) acetamide (Compound 171)

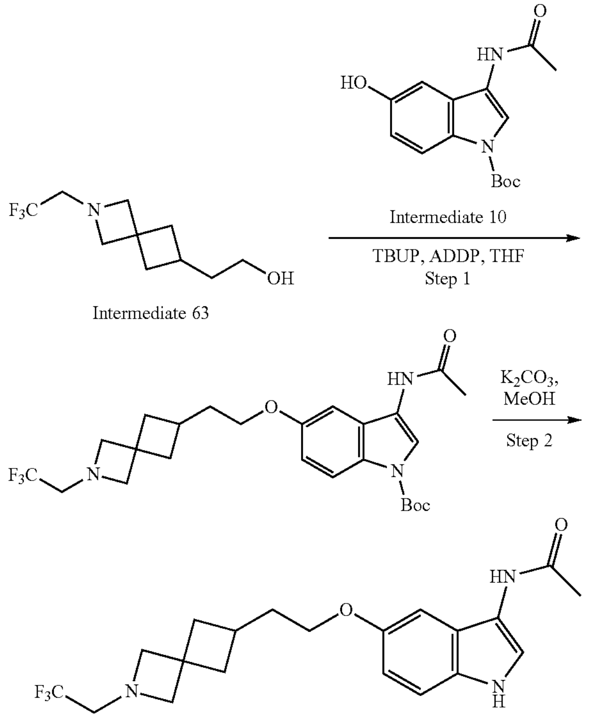

Compound 171

Step 1: tert-butyl 3-acetamido-5-{2-[2-(2,2,2-trifluoroethyl)-2-azaspiro[3.3]heptan-6-yl]ethoxy}indole-1-carboxylate 2-[2-(2,2,2-trifluoroethyl)-2-azaspiro[3.3]heptan-6-yl] ethanol (180.0 mg, 0.8 mmol, 1.0 equiv.) and tert-butyl 3-acetamido-5-hydroxyindole-1-carboxylate (234.1 mg, 0.8 mmol, 1.0 equiv.) were dissolved in THE (4 mL), then TBUP (326.3 mg, 1.6 mmol, 2.0 equiv.) and ADDP (403.7 mg, 1.6 mmol, 2.0 equiv.) were added. The reaction mixture was heated to 70° C. for 2 hours, then cooled to ambient temperature and concentrated under vacuum. The residue was purified by reverse flash chromatography with the following conditions: column, silica gel; mobile phase, ACN in water, 10% to 100% gradient in 15 min; detector, UV 254 nm. This gave tert-butyl 3-acetamido-5-{2-[2-(2,2,2-trifluoroethyl)-2-azaspiro[3.3]heptan-6-yl]ethoxy}indole-1-carboxylate (220.0 mg) as a light yellow solid. LCMS Method A: $[M+H]^+$=496.

Step 2: N-(5-(2-(2-(2,2,2-trifluoroethyl)-2-azaspiro[3.3]heptan-6-yl)ethoxy)-1H-indol-3-yl)acetamide tert-Butyl 3-acetamido-5-{2-[2-(2,2,2-trifluoroethyl)-2-azaspiro[3.3]heptan-6-yl]ethoxy}indole-1-carboxylate (200.0 mg, 0.4 mmol, 1.0 equiv.) was dissolved in MeOH (3 mL), then $K_2CO_3$ (167.3 mg, 1.2 mmol, 3.0 equiv.) was added. The reaction mixture was heated to 70° C. for 2 hours, then cooled to ambient temperature and quenched by the addition of water. The resulting solution was extracted with ethyl acetate, washed with brine, dried over anhydrous $Na_2SO_4$ and concentrated under vacuum. The residue was purified by Prep-HPLC with the following conditions: Column: XBridge Shield RP18 OBD Column, 30*150 mm, 5 m; Mobile Phase A: Water (10 mM $NH_4HCO_3$+0.1% $NH_3.H_2O$), Mobile Phase B: ACN; Flow rate: 60 mL/min; Gradient: 32% B to 53% B in 8 min; Wave Length: 220 nm; RT1: 7.58 min. This gave N-(5-(2-(2-(2,2,2-trifluoroethyl)-2-azaspiro[3.3]heptan-6-yl)ethoxy)-1H-indol-3-yl)acetamide (110.0 mg) as a pale white solid. LCMS Method E: $[M+H]^+$=396. $^1H$ NMR (400 MHz, DMSO-$d_6$): δ 10.54 (s, 1H), 9.68 (s, 1H), 7.64 (d, J=2.8 Hz, 1H), 7.27 (d, J=2.8 Hz, 1H), 7.19 (d, J=8.8 Hz, 1H), 6.71-6.89 (m, 1H), 3.87 (t, J=6.4 Hz, 2H), 3.35-3.33 (m, 2H), 3.24 (s, 2H), 3.14-3.06 (m, 2H), 2.33-2.24 (m, 3H), 2.08 (s, 3H), 1.81-1.79 (m, 4H).

The analogs prepared in following table were prepared using the same method described for Example 64.

| Example # | Compound No. | Starting materials Used | Structure | Condition | LCMS data |
|---|---|---|---|---|---|
| 65 | 281 | Intermediate 20/ Intermediate 46 | 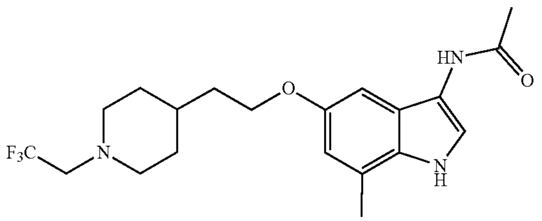 [SMILES: CC(=O)Nc1c[nH]c2c(C)cc(OCCC3CCN(CC(F)(F)F)CC3)cc12] | TBUP, ADDP, THF | Method F: MS-ESI: 398 [M + H]$^+$. |
| 66 | 267 | 2-(4-(trifluoromethyl) phenyl) ethan-1-ol/ Intermediate 47 | 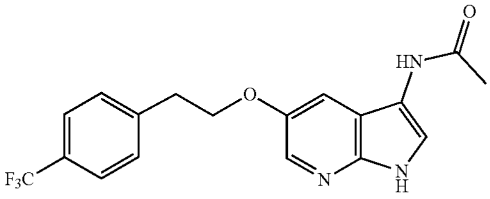 [SMILES: CC(=O)Nc1c[nH]c2ncc(OCCc3ccc(C(F)(F)F)cc3)cc12] | TBUP, ADDP, THF | Method E: MS-ESI: 364 [M + H]$^+$. |
| 67 | 262 | Intermediate 69/ Intermediate 10 | 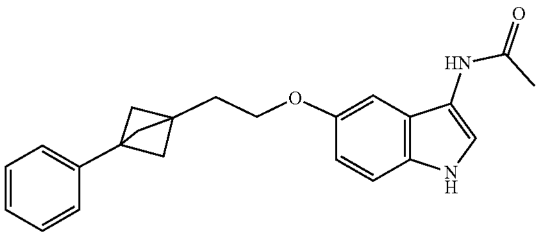 [SMILES: CC(=O)Nc1c[nH]c2ccc(OCCC34CC(c5ccccc5)(C3)C4)cc12] | TBUP, ADDP, THF | Method F: MS-ESI: 361 [M + H]$^+$. |
| 68 | 257 | Intermediate 70/ Intermediate 10 | 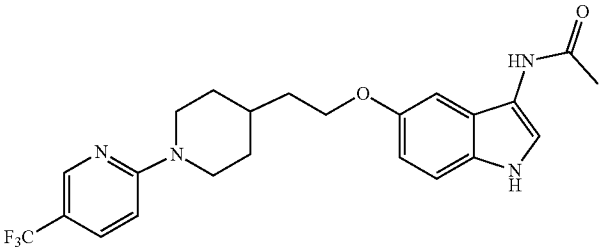 [SMILES: CC(=O)Nc1c[nH]c2ccc(OCCC3CCN(c4ccc(C(F)(F)F)cn4)CC3)cc12] | $PPh_3$, DIAD, THF | Method F: MS-ESI: 447 [M + H]$^+$. |
| 69 | 254 | Intermediate 71/ Intermediate 10 | 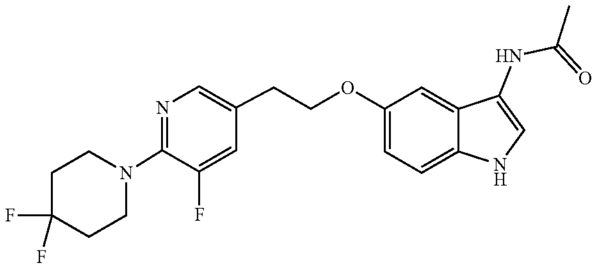 [SMILES: CC(=O)Nc1c[nH]c2ccc(OCCc3cnc(N4CCC(F)(F)CC4)c(F)c3)cc12] | TBUP, ADDP, THF | Method G: MS-ESI: 433 [M + H]$^+$. |
| 70 | 247 | (4-(trifluoromethyl) phenyl) methanol/ Intermediate 10 | 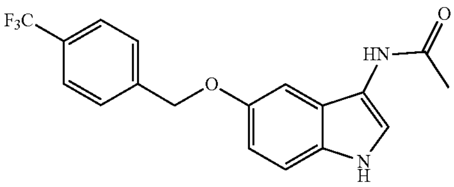 [SMILES: CC(=O)Nc1c[nH]c2ccc(OCc3ccc(C(F)(F)F)cc3)cc12] | TBUP, ADDP, THF | Method F: MS-ESI: 349 [M + H]$^+$. |

-continued

| Example # | Compound No. | Starting materials Used | Structure | Condition | LCMS data |
|---|---|---|---|---|---|
| 71 | 232 | Intermediate 11/6-(trifluoro-methyl)pyridin-3-ol | 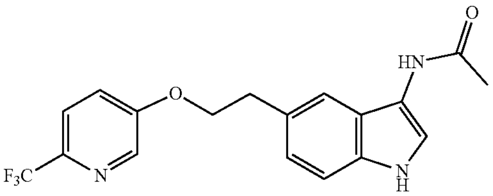 [SMILES: CC(=O)Nc1c[nH]c2ccc(CCOc3ccc(C(F)(F)F)nc3)cc12] | TBUP, ADDP, THF | Method F: MS-ESI: 364 [M + H]+. |
| 72 | 230 | Intermediate 11/4-cyclobutyl-phenol | 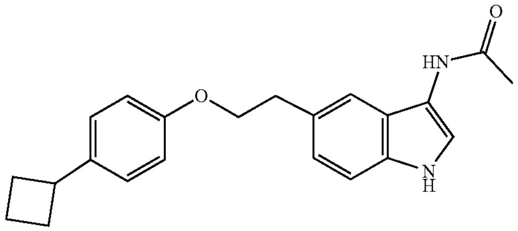 [SMILES: CC(=O)Nc1c[nH]c2ccc(CCOc3ccc(C4CCC4)cc3)cc12] | TBUP, ADDP, THF | Method F: MS-ESI: 349 [M + H]+. |
| 73 | 231 | Intermediate 11/3-(trifluoro-methyl)phenol | 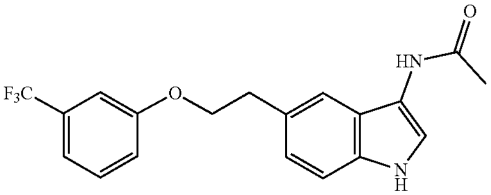 [SMILES: CC(=O)Nc1c[nH]c2ccc(CCOc3cccc(C(F)(F)F)c3)cc12] | TBUP, ADDP, THF | Method F: MS-ESI: 363 [M + H]+. |
| 74 | 214 | Intermediate 11/3,4-dichloro-phenol | 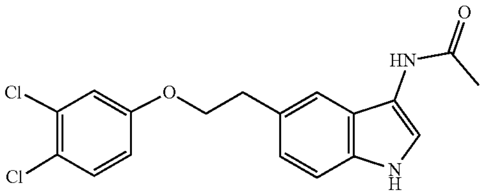 [SMILES: CC(=O)Nc1c[nH]c2ccc(CCOc3ccc(Cl)c(Cl)c3)cc12] | $PPh_3$, DIAD, THF | Method F: MS-ESI: 363 [M + H]+. |
| 75 | 228 | Intermediate 11/4-methylphenol | 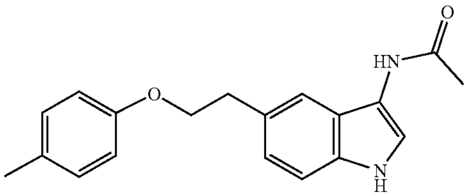 [SMILES: CC(=O)Nc1c[nH]c2ccc(CCOc3ccc(C)cc3)cc12] | TBUP, ADDP, THF | Method F: MS-ESI: 309 [M + H]+. |
| 76 | 229 | Intermediate 11/4-chlorophenol | 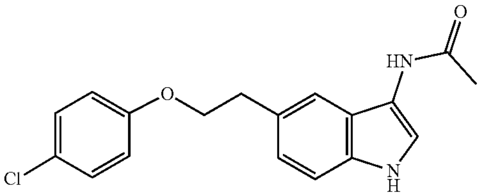 [SMILES: CC(=O)Nc1c[nH]c2ccc(CCOc3ccc(Cl)cc3)cc12] | TBUP, ADDP, THF | Method F: MS-ESI: 329 [M + H]+. |
| 77 | 225 | Intermediate 11/ Intermediate 73 | 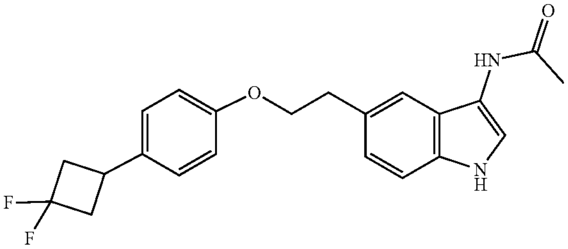 [SMILES: CC(=O)Nc1c[nH]c2ccc(CCOc3ccc(C4CC(F)(F)C4)cc3)cc12] | TBUP, ADDP, THF | Method E: MS-ESI: 385 [M + H]+. |

-continued

| Example # | Compound No. | Starting materials Used | Structure | Condition | LCMS data |
|---|---|---|---|---|---|
| 78 | 226 | Intermediate 11/ Intermediate 74 | 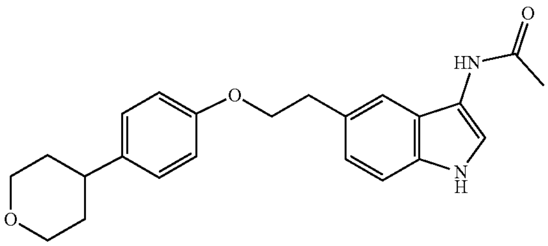 [SMILES: CC(=O)Nc1c[nH]c2ccc(CCOc3ccc(C4CCOCC4)cc3)cc12] | CMPB, toluene | Method F: MS-ESI: 379 $[M + H]^+$. |
| 79 | 224 | Intermediate 11/ Intermediate 75 | 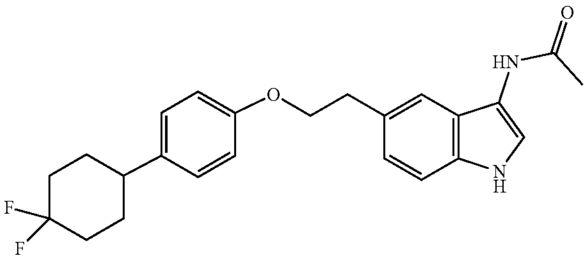 [SMILES: CC(=O)Nc1c[nH]c2ccc(CCOc3ccc(C4CCC(F)(F)CC4)cc3)cc12] | TBUP, ADDP, THF | Method F: MS-ESI: 413 $[M + H]^+$. |
| 80 | 208 | Intermediate 11/ Intermediate 77 | 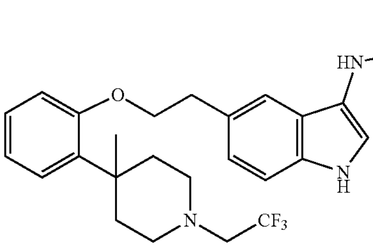 | TBUP, ADDP, THF | Method F: MS-ESI: 474 $[M + H]^+$. |
| 81 | 198 | Intermediate 11/ Intermediate 78 | 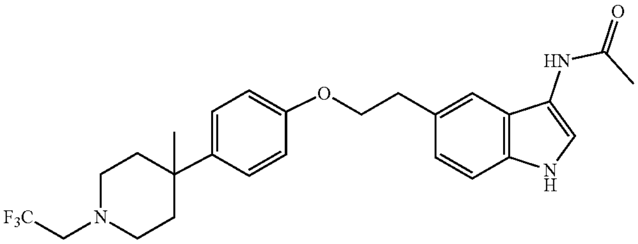 [SMILES: CC(=O)Nc1c[nH]c2ccc(CCOc3ccc(C4(C)CCN(CC(F)(F)F)CC4)cc3)cc12] | TBUP, ADDP, THF | Method F: MS-ESI: 474 [M + H]+. |
| 82 | 197 | Intermediate 79/ Intermediate 10 | 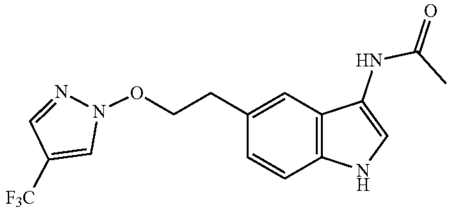 [SMILES: CC(=O)Nc1c[nH]c2ccc(CCOn3cc(C(F)(F)F)cn3)cc12] | TBUP, ADDP, THF | Method F: MS-ESI: 353 $[M + H]^+$. |
| 83 | 196 | Intermediate 80/ Intermediate A10 | 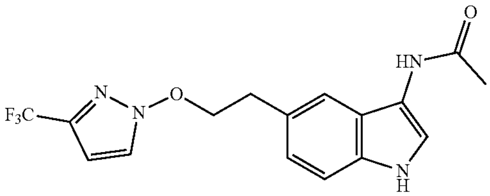 | $PPh_3$, DIAD, THF | Method D: MS-ESI: 453 $[M + H]^+$. |

-continued

| Example # | Compound No. | Starting materials Used | Structure | Condition | LCMS data |
|---|---|---|---|---|---|
| 84 | 184 | Intermediate 11/2-(trifluoromethyl) pyrimidin-5-ol | 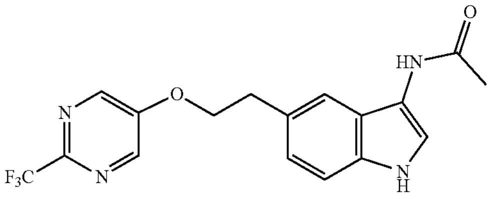 [SMILES: CC(=O)Nc1c[nH]c2ccc(CCOc3cnc(C(F)(F)F)nc3)cc12] | TBUP, ADDP, THF | Method E: MS-ESI: 365 $[M + H]^+$. |
| 85 | 273 | Intermediate 57/4-(trifluoro-methyl)phenol | 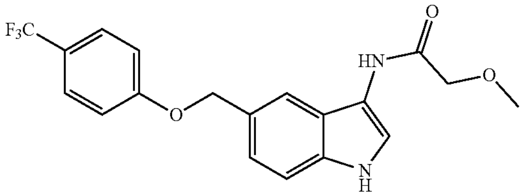 [SMILES: COCC(=O)Nc1c[nH]c2ccc(COc3ccc(C(F)(F)F)cc3)cc12] | TBUP, ADDP, THF | Method F: MS-ESI: 379 $[M + H]^+$. |
| 86 | 253 | Intermediate 72/ Intermediate 10 | 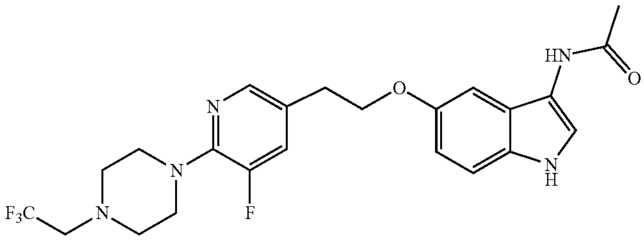 [SMILES: CC(=O)Nc1c[nH]c2ccc(OCCc3cnc(N4CCN(CC(F)(F)F)CC4)c(F)c3)cc12] | TBUP, ADDP, THF | Method G: MS-ESI: 480 $[M + H]^+$. |
| 87 | 168 | Intermediate 55/p-methylphenol | 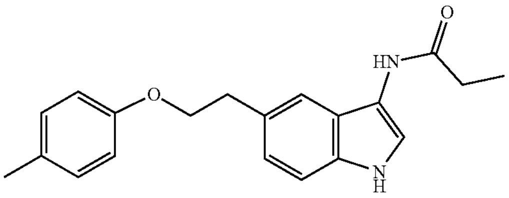 [SMILES: CCC(=O)Nc1c[nH]c2ccc(CCOc3ccc(C)cc3)cc12] | TBUP, ADDP, THF | Method E: MS-ESI: 323 $[M + H]^+$. |
| 88 | 169 | Intermediate 62/ Intermediate 10 | 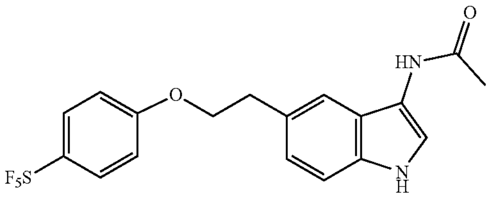 | TBUP, ADDP, THF | Method F: MS-ESI: 419 $[M - H]^-$. |
| 89 | 170 | Intermediate 11/ Intermediate 76 | 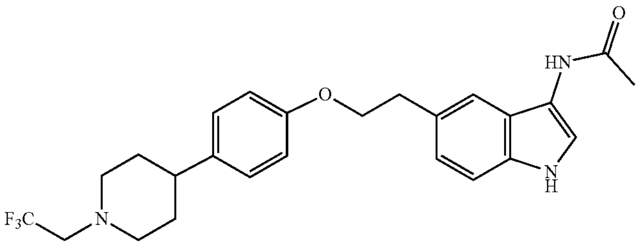 [SMILES: CC(=O)Nc1c[nH]c2ccc(CCOc3ccc(C4CCN(CC(F)(F)F)CC4)cc3)cc12] | TBUP, ADDP, THF | Method E: MS-ESI: 460 $[M + H]^+$. |

Examples 90: N-(5-(trans-3-(4-(trifluoromethyl)phenyl)cyclobutoxy)-1H-indol-3-yl)cyclopropanecarboxamide (Compound 147)

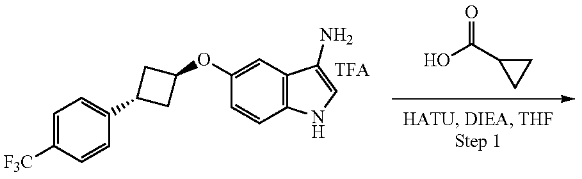

Intermediate 85

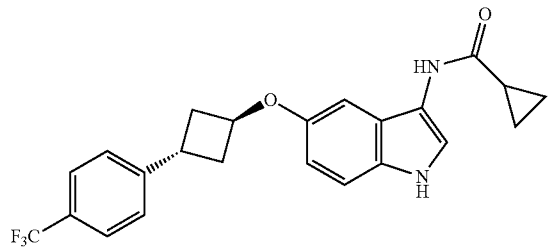

Compound 147

5-(trans-3-(4-(Trifluoromethyl)phenyl)cyclobutoxy)-1H-indol-3-amine TFA salt (100.0 mg, 0.3 mmol, 1.0 equiv.) was dissolved in THE (5 mL), then cyclopropanecarboxylic acid (29.8 mg, 0.3 mmol, 1.2 equiv.), HATU (131.7 mg, 0.3 mmol, 1.2 equiv.) and DIEA (74.6 mg, 0.6 mmol, 2.0 equiv.) were added. The reaction mixture was stirred for 1 hour at ambient temperature and then concentrated under vacuum. The residue was purified by reverse flash chromatography with the following conditions: column, C18 silica gel; mobile phase A: 0.05% $NH_4HCO_3$ in water; mobile phase B: Acetonitrile, 30% B to 60% B gradient in 30 min; detector, UV 254 nm. The resulting crude product was further purified by Prep-HPLC with the following conditions: Column, XBridgePrep OBD C18 Column, 30*150 mm, 5 m; mobile phase, Water (10 mM $NH_4HC_3$) and ACN (430 ACN up to 73% in 7 min). This gave N-(5-(trans-3-(4-(trifluoromethyl)phenyl)cyclobutoxy)-1H-indol-3-yl)cyclopropanecarboxamide (29.8 mg) as a white solid. LCMS Method 68: $[M+H]^+$=415. $^1H$ NMR (400 MHz, DMSO-$d_6$) δ 10.57 (d, J=2.0 Hz, 1H), 9.91 (s, 1H), 7.72 (d, J=8.0 Hz, 2H), 7.65 (d, J=2.4 Hz, 1H), 7.61 (d, J=8.0 Hz, 2H), 7.24-7.18 (m, 2H), 6.75-6.72 (m, 1H), 4.95-4.91 (m, 1H), 3.81-3.78 (m, 1H), 2.71-2.63 (m, 4H), 1.93-1.89 (m, 1H), 0.81-0.78 (in, 4H).

The analogs prepared in the following table were prepared using the same method described for Example 90.

| Example # | Compound No. | Starting materials Used | Structure | LCMS data |
|---|---|---|---|---|
| 91 | 258 | Intermediate 85/ 2-methoxyacetic acid | 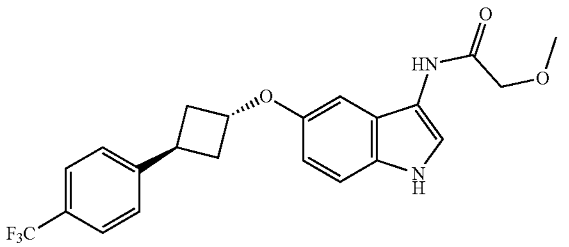 [SMILES: COCC(=O)Nc1c[nH]c2ccc(O[C@H]3C[C@H](c4ccc(C(F)(F)F)cc4)C3)cc12] | Method E: MS-ESI: 419 $[M + H]^+$. |
| 92 | 260 | Intermediate 86/ methoxyacetic acid | 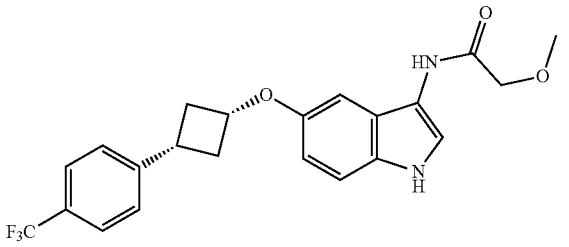 [SMILES: COCC(=O)Nc1c[nH]c2ccc(O[C@H]3C[C@@H](c4ccc(C(F)(F)F)cc4)C3)cc12] | Method E: MS-ESI: 419 $[M + H]^+$. |
| 93 | 252 | Intermediate 33/ cyclopropane-carboxylic acid | 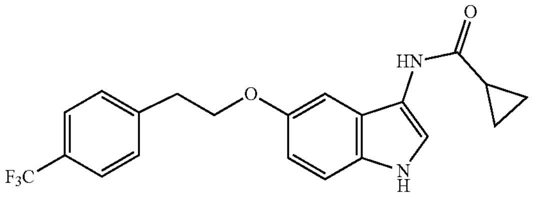 [SMILES: O=C(Nc1c[nH]c2ccc(OCCc3ccc(C(F)(F)F)cc3)cc12)C1CC1] | Method F: MS-ESI: 387 $[M + H]^+$. |
| 94 | 251 | Intermediate 33/ 1-methylcyclo-propane-1-carboxylic acid | 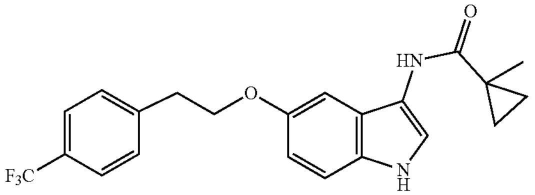 [SMILES: CC1(C(=O)Nc2c[nH]c3ccc(OCCc4ccc(C(F)(F)F)cc4)cc23)CC1] | Method F: MS-ESI: 403 $[M + H]^+$. |

-continued

| Example # | Compound No. | Starting materials Used | Structure | LCMS data |
|---|---|---|---|---|
| 95 | 249 | Intermediate 33/ 3,3-difluorocyclobutane-1-carboxylic acid | 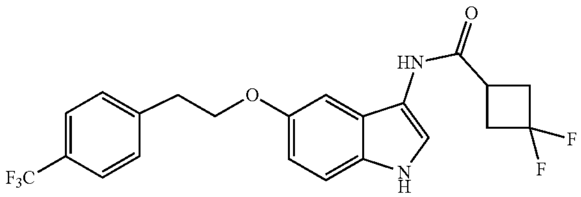 [SMILES: O=C(Nc1c[nH]c2ccc(OCCc3ccc(C(F)(F)F)cc3)cc12)C1CC(F)(F)C1] | Method F: MS-ESI: 437 [M − H]⁻. |
| 96 | 241 | Intermediate 85/ 3-methoxy-propanoic acid | 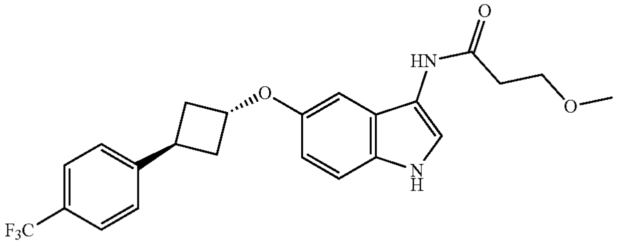 [SMILES: COCCC(=O)Nc1c[nH]c2ccc(O[C@H]3C[C@H](c4ccc(C(F)(F)F)cc4)C3)cc12] | Method E: MS-ESI: 433 [M + H]⁺. |
| 97 | 244 | Intermediate 85/ 1-(2,2,2-trifluoroethyl) azetidine-3-carboxylic acid | 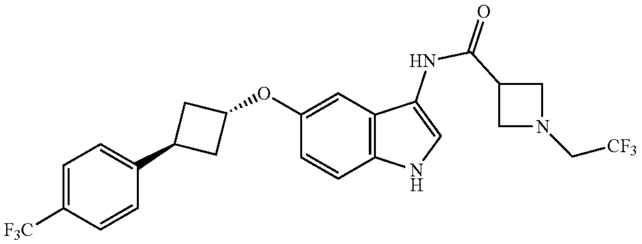 [SMILES: O=C(Nc1c[nH]c2ccc(O[C@H]3C[C@H](c4ccc(C(F)(F)F)cc4)C3)cc12)C1CN(CC(F)(F)F)C1] | Method D: MS-ESI: 512 [M + H]⁺. |
| 98 | 243 | Intermediate 86/ 1-(2,2,2-trifluoroethyl) azetidine-3-carboxylic acid | 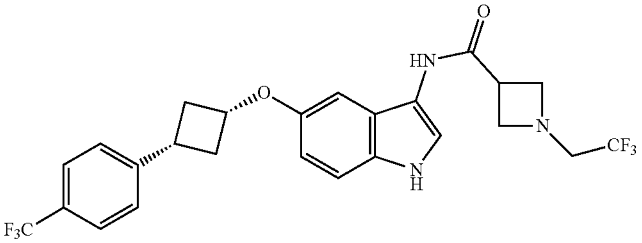 [SMILES: O=C(Nc1c[nH]c2ccc(O[C@H]3C[C@@H](c4ccc(C(F)(F)F)cc4)C3)cc12)C1CN(CC(F)(F)F)C1] | Method D: MS-ESI: 512 [M + H]⁺. |
| 99 | 227 | Intermediate 85/ Intermediate 102 | 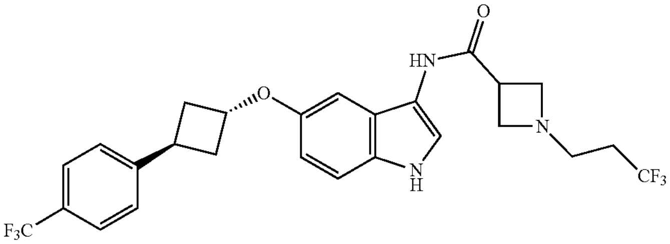 [SMILES: O=C(Nc1c[nH]c2ccc(O[C@H]3C[C@H](c4ccc(C(F)(F)F)cc4)C3)cc12)C1CN(CCC(F)(F)F)C1] | Method D: MS-ESI: 524 [M − H]⁻. |
| 100 | 221 | Intermediate 92/ cis-3-methoxycyclobutane-1-carboxylic acid | 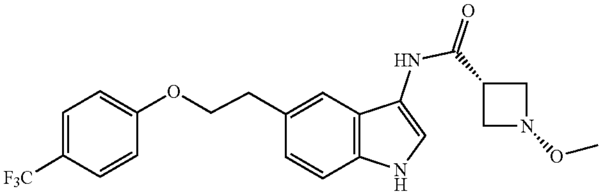 | Method F: MS-ESI: 433 [M + H]⁺. |

-continued

| Example # | Compound No. | Starting materials Used | Structure | LCMS data |
|---|---|---|---|---|
| 101 | 220 | Intermediate 92/ trans-3-methoxycyclo-butane-1-carboxylic acid | 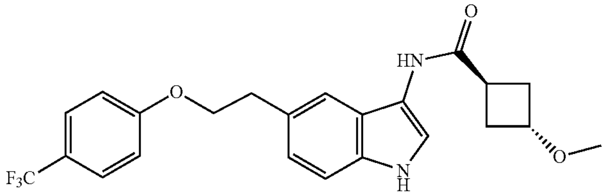 [SMILES: CO[C@H]1C[C@H](C(=O)Nc2c[nH]c3ccc(CCOc4ccc(C(F)(F)F)cc4)cc23)C1] | Method D: MS-ESI: 431 [M − H]⁻. |
| 102 | 222 | Intermediate 33/ cis-3-methoxycyclo-butane-1-carboxylic acid | 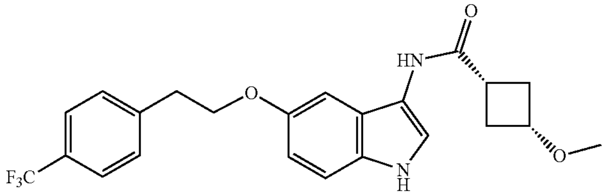 [SMILES: CO[C@H]1C[C@@H](C(=O)Nc2c[nH]c3ccc(OCCc4ccc(C(F)(F)F)cc4)cc23)C1] | Method F: MS-ESI: 433 [M + H]⁺. |
| 103 | 219 | Intermediate 92/ 1-(2,2,2-trifluoroethyl) azetidine-3-carboxylic acid | 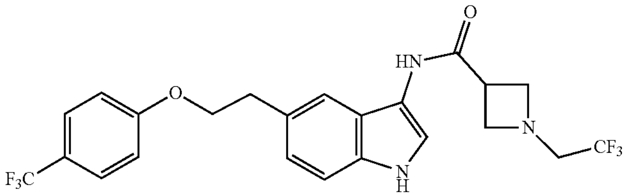 [SMILES: O=C(Nc1c[nH]c2ccc(CCOc3ccc(C(F)(F)F)cc3)cc12)C1CN(CC(F)(F)F)C1] | Method F: MS-ESI: 486 [M + H]⁺. |
| 104 | 211 | Intermediate 33/ trans-3-methoxycyclo-butane-1-carboxylic acid | 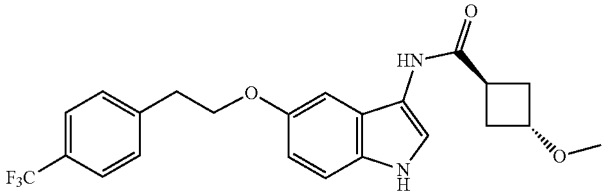 [SMILES: CO[C@H]1C[C@H](C(=O)Nc2c[nH]c3ccc(OCCc4ccc(C(F)(F)F)cc4)cc23)C1] | Method D: MS-ESI: 431 [M − H]⁻. |
| 105 | 210 | Intermediate 33/ 1-(2,2,2-trifluoroethyl) azetidine-3-carboxylic acid | 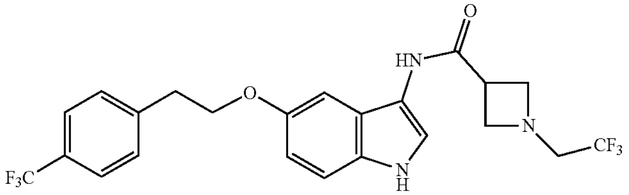 [SMILES: O=C(Nc1c[nH]c2ccc(OCCc3ccc(C(F)(F)F)cc3)cc12)C1CN(CC(F)(F)F)C1] | Method F: MS-ESI: 486 [M + H]⁺. |
| 106 | 195 | Intermediate 88/ 1-(2,2,2-trifluoroethyl) azetidine-3-carboxylic acid | 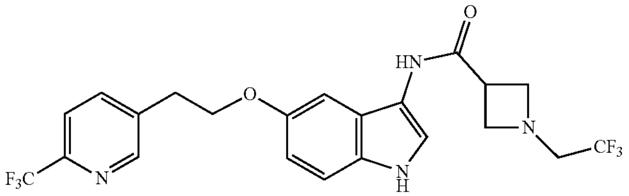 [SMILES: O=C(Nc1c[nH]c2ccc(OCCc3ccc(C(F)(F)F)nc3)cc12)C1CN(CC(F)(F)F)C1] | Method E: MS-ESI: 487 [M + H]⁺. |
| 107 | 194 | Intermediate 88/ trans-3-methoxycyclo-butane-1-carboxylic acid | 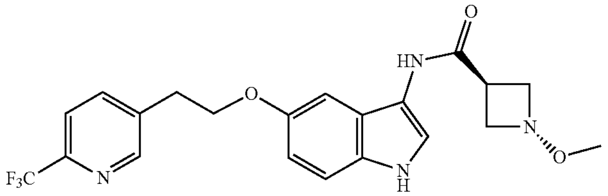 | Method D: MS-ESI: 434 [M + H]⁺. |

-continued

| Ex-ample # | Compound No. | Starting materials Used | Structure | LCMS data |
|---|---|---|---|---|
| 108 | 183 | Intermediate 89/ cyclopropane-carboxylic acid | 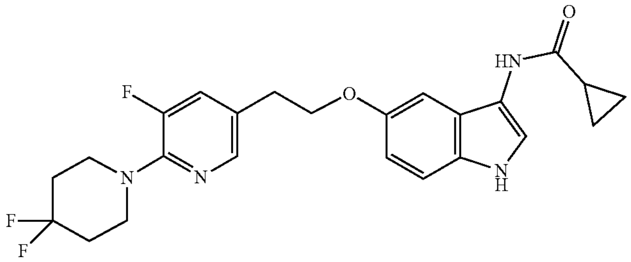 [SMILES: O=C(Nc1c[nH]c2ccc(OCCc3cnc(N4CCC(F)(F)CC4)c(F)c3)cc12)C1CC1] | Method F: MS-ESI: 459 [M + H]$^+$. |
| 109 | 182 | Intermediate 90/ cyclopropane-carboxylic acid | 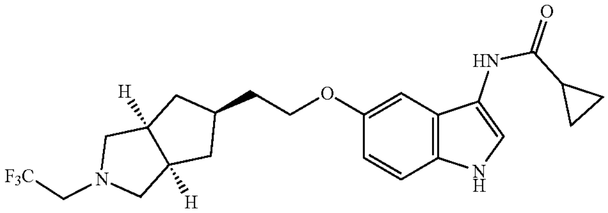 [SMILES: O=C(Nc1c[nH]c2ccc(OCC[C@@H]3C[C@@H]4CN(CC(F)(F)F)C[C@@H]4C3)cc12)C1CC1] | Method D: MS-ESI: 436 [M + H]$^+$. |
| 110 | 148 | Intermediate 85/ 3-methyloxetane-3-carboxylic acid | 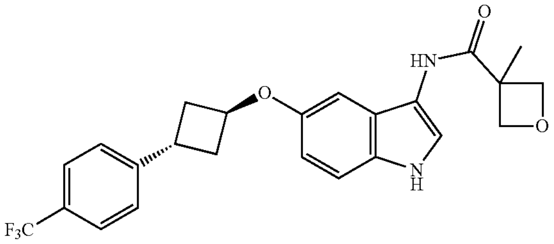 [SMILES: CC1(C(=O)Nc2c[nH]c3ccc(O[C@H]4C[C@H](c5ccc(C(F)(F)F)cc5)C4)cc23)COC1] | Method E: MS-ESI: 445 [M + H]$^+$. |
| 111 | 163 | Intermediate 33/ oxetane-3-carboxylic acid | 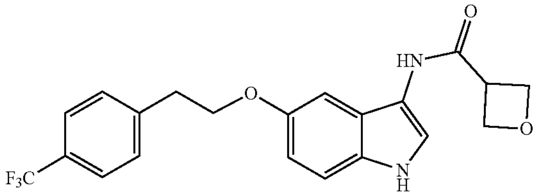 [SMILES: O=C(Nc1c[nH]c2ccc(OCCc3ccc(C(F)(F)F)cc3)cc12)C1COC1] | Method F: MS-ESI: 405 [M + H]$^+$. |
| 112 | 165 | Intermediate 92/ 3-methyloxetane-3-carboxylic acid | 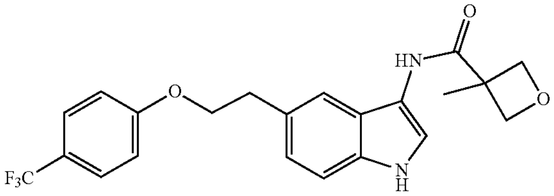 [SMILES: CC1(C(=O)Nc2c[nH]c3ccc(CCOc4ccc(C(F)(F)F)cc4)cc23)COC1] | Method F: MS-ESI: 417 [M − H]$^-$. |
| 113 | 164 | Intermediate 92/ oxetane-3-carboxylic acid | 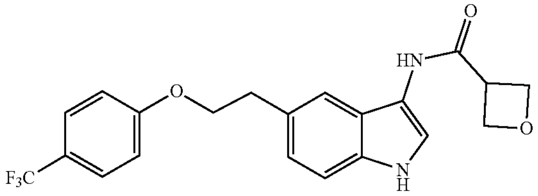 [SMILES: O=C(Nc1c[nH]c2ccc(CCOc3ccc(C(F)(F)F)cc3)cc12)C1COC1] | Method F: MS-ESI: 403 [M − H]$^-$. |

3Examples 114: N-(5-(cis-3-(4-(trifluoromethyl)phenyl)cyclobutoxy)-1H-indol-3-yl)cyclopropanecarboxamide (Compound 266)

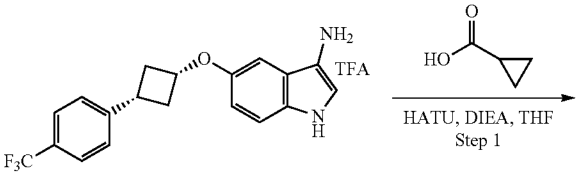

Intermediate 86

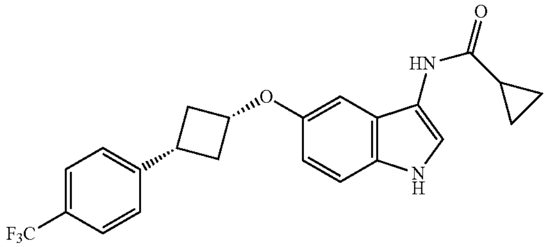

Compound 266

5-(cis-3-(4-(Trifluoromethyl)phenyl)cyclobutoxy)-1H-indol-3-amine TFA salt (100.0 mg, 0.3 mmol, 1.0 equiv.) was dissolved in THF (5 mL), then cyclopropanecarboxylic acid (29.8 mg, 0.3 mmol, 1.2 equiv.), HATU (131.7 mg, 0.3 mmol, 1.2 equiv.) and DIEA (74.6 mg, 0.6 mmol, 2.0 equiv.) were added. The reaction mixture was stirred for 1 hour at ambient temperature and then concentrated under vacuum. The residue was purified by reverse flash chromatography with the following conditions: column, C18 silica gel; mobile phase A: 0.05% $NH_4HCO_3$ in water; mobile phase B: Acetonitrile, 30% B to 60% B gradient in 30 min; detector, UV 254 nm. The resulting material was further purified by Prep-HPLC with the following conditions: Column, XBridge Prep OBD C18 Column, 30*150 mm, 5 µm; mobile phase, Water (10 mM $NH_4HCO_3$) and ACN (43% ACN up to 73% in 7 min). This gave N-(5-(trans-3-(4-(trifluoromethyl)phenyl)cyclobutoxy)-1H-indol-3-yl)cyclopropanecarboxamide (30.1 mg) as a white solid. LCMS Method E: $[M+H]^+$=415. $^1$H NMR (400 MHz, DMSO-$d_6$) δ 10.57 (d, J=2.0 Hz, 1H), 9.95 (s, 1H), 7.70-7.66 (m, 3H), 7.54 (d, J=8.0 Hz, 2H), 7.30 (d, J=2.4 Hz, 1H), 7.23 (d, J=8.8 Hz, 1H), 6.75-6.72 (m, 1H), 4.73-4.69 (m, 1H), 3.32-3.30 (m, 1H), 3.06-2.99 (m, 2H), 2.22-2.14 (m, 2H), 1.96-1.91 (m, 1H), 0.84-0.76 (m, 4H).

Example 115: 1-methyl-N-(5-(trans-3-(4-(trifluoromethyl)phenyl)cyclobutoxy)-1H-indol-3-yl)cyclopropane-1-carboxamide (Compound 261)

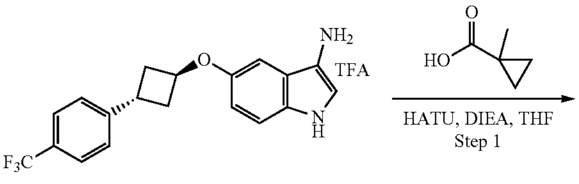

Intermediate 85

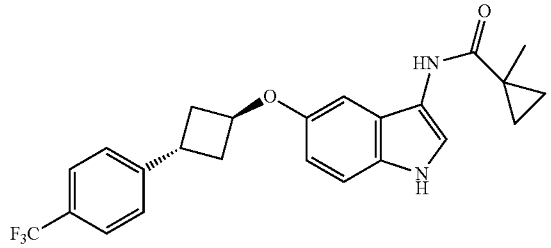

Compound 261

5-(trans-3-(4-(Trifluoromethyl)phenyl)cyclobutoxy)-1H-indol-3-amine TFA salt (100.0 mg, 0.3 mmol, 1.0 equiv.) was dissolved in THF (5 mL), then 1-methylcyclopropane-1-carboxylic acid (34.5 mg, 0.3 mmol, 1.2 equiv.), HATU (131.7 mg, 0.3 mmol, 1.2 equiv.) and DIEA (74.6 mg, 0.6 mmol, 2.0 equiv.) were added. The reaction mixture was stirred for 1 hour at ambient temperature and then concentrated under vacuum. The residue was purified by reverse flash chromatography with the following conditions: column, C18 silica gel; mobile phase A: 0.05% $NH_4HCO_3$ in water; mobile phase B: Acetonitrile, 30% B to 60% B gradient in 30 min; detector, UV 254 nm. The resulting crude product was further purified by Prep-HPLC with the following conditions: Column: XBridge Prep OBD C18 Column, 30*150 mm, 5 M m; Mobile Phase A: Water (10 mmol/L $NH_4HCO_3$), Mobile Phase B: ACN; Flow rate: 60 mL/min; Gradient: 45% B to 75% B in 7 min; Wave Length: 220 nm. This gave 1-methyl-N-(5-(trans-3-(4-(trifluoromethyl)phenyl)cyclobutoxy)-1H-indol-3-yl)cyclopropane-1-carboxamide (19.9 mg) as a white solid. LCMS Method E: $[M+H]^+$=429. $^1$H NMR (400 MHz, DMSO-$d_6$): δ 10.66 (s, 1H), 8.96 (s, 1H), 7.71 (d, J=8.4 Hz, 2H), 7.59 (d, J=8.0 Hz, 2H), 7.49 (d, J=2.0 Hz, 1H), 7.24 (d, J=8.8 Hz, 1H), 7.05 (d, J=2.0 Hz, 1H), 6.75-6.73 (m, 1H), 4.95-4.91 (m, 1H), 3.85-3.79 (m, 1H), 2.64-2.61 (m, 4H), 1.45 (s, 3H), 1.09-1.07 (m, 2H), 0.62-0.60 (m, 2H).

The analogs prepared in in the following table were prepared using the same method described for Example 115.

| Example # | Compound No. | Starting materials Used | Structure | LCMS data |
|---|---|---|---|---|
| 116 | 263 | 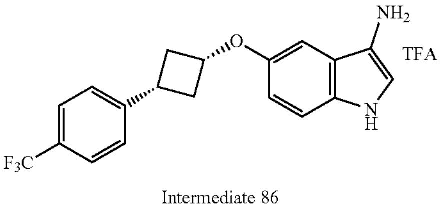 [SMILES: Nc1c[nH]c2ccc(O[C@H]3C[C@@H](c4ccc(C(F)(F)F)cc4)C3)cc12] Intermediate 86 | 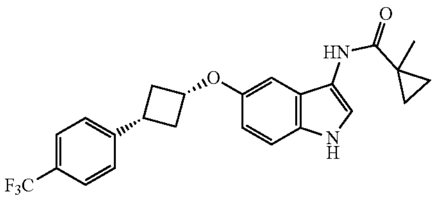 | Method E: MS-ESI: 336 $[M + H]^+$. |

Example 117: cis-3-methoxy-N-(5-(trans-3-(4-(trifluoromethyl)phenyl)cyclobutoxy)-1H-indol-3-yl)cyclobutane-1-carboxamide (Compound 246)

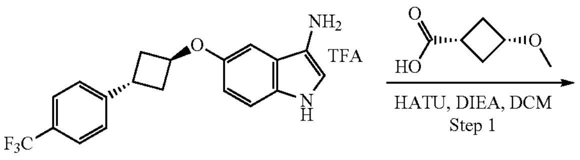

Intermediate 85

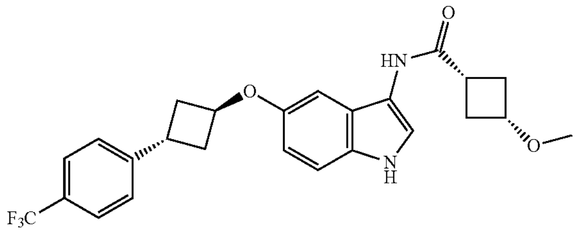

Compound 246

5-(trans-3-(4-(Trifluoromethyl)phenyl)cyclobutoxy)-1H-indol-3-amine TFA salt (250 mg, 0.7 mmol, 1.5 equiv.) was dissolved in DCM (5 mL), then cis-3-methoxycyclobutane-1-carboxylic acid (62.6 mg, 0.4 mmol, 1.0 equiv.), HATU (274.4 mg, 0.7 mmol, 1.5 equiv.) and DIEA (310.9 mg, 2.4 mmol, 5.0 equiv.) were added. The reaction mixture was stirred for 0.5 hour at ambient temperature and then quenched by the addition of water. The resulting solution was extracted with ethyl acetate, dried over anhydrous sodium sulfate and concentrated under vacuum. The residue was purified by Prep-HPLC with the following conditions: Column: XBridge Shield RP18 OBD Column, 30*150 mm, 5 μm; Mobile Phase A: Water (10 mM $NH_4HCO_3$), Mobile Phase B: ACN; Flow rate: 60 mL/min; Gradient: 46% B to 69% B in 8 min; Wave Length: 220 nm. This gave cis-3-methoxy-N-(5-(trans-3-(4-(trifluoromethyl)phenyl)cyclobutoxy)-1H-indol-3-yl)cyclobutane-1-carboxamide (53.9 mg) as a white solid. LCMS Method F: $[M+H]^+$=459. $^1H$ NMR (400 MHz, DMSO-$d_6$): δ 10.60 (s, 1H), 9.64 (s, 1H), 7.76-7.71 (m, 3H), 7.60 (d, J=8.4 Hz, 2H), 7.22 (d, J=8.8 Hz, 1H), 7.13 (d, J=2.4 Hz, 1H), 6.75-6.72 (m, 1H), 4.93-4.89 (m, 1H), 3.82-3.78 (m, 2H), 3.15 (s, 3H), 2.84-2.81 (m, 1H), 2.68-2.63 (m, 4H), 2.42-2.37 (m, 2H), 2.07-2.02 (m, 2H).

The analogs prepared in the following table were prepared using the same method described for Example 117.

| Example # | Compound No. | Starting materials Used | Structure | LCMS data |
|---|---|---|---|---|
| 118 | 242 | Intermediate 85/ trans-3-methoxy-cyclobutane-1-carboxylic acid | 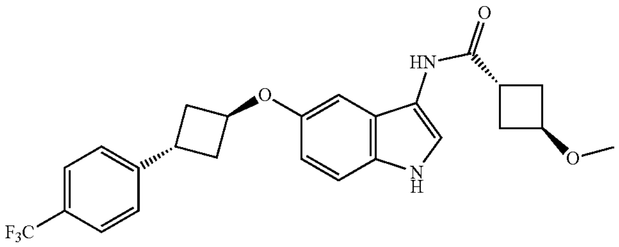 [SMILES: CO[C@H]1C[C@H](C(=O)Nc2c[nH]c3ccc(O[C@H]4C[C@H](c5ccc(C(F)(F)F)cc5)C4)cc23)C1] | Method E: MS-ESI: 459 $[M + H]^+$. |
| 119 | 245 | Intermediate 86/ cis-3-methoxycyclo-butane-1-carboxylic acid | 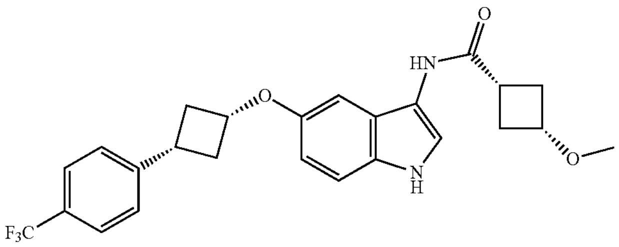 [SMILES: CO[C@H]1C[C@@H](C(=O)Nc2c[nH]c3ccc(O[C@H]4C[C@@H](c5ccc(C(F)(F)F)cc5)C4)cc23)C1] | Method E: MS-ESI: 459 $[M + H]^+$. |

Example 120: N-(5-(2-(4-(trifluoromethyl)phenoxy)propyl)-1H-indol-3-yl)acetamide (Compound 287)

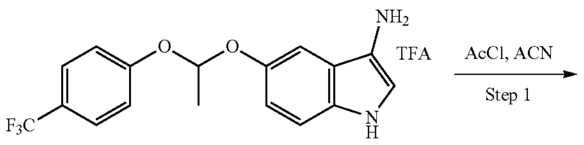

Intermediate 93

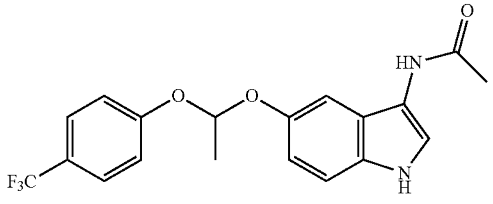

Compound 287

5-[2-[4-(Trifluoromethyl)phenoxy]propyl]-1H-indol-3-amine (100.0 mg, 0.2 mmol, 1.0 equiv.) and TEA (90.8 mg, 0.8 mmol, 3.0 equiv.) were dissolved in ACN (10 mL) and cooled to 0° C., then and AcCl (70.4 mg, 0.8 mmol, 3.0 equiv.) was added, maintaining the solution at 0° C. The reaction mixture was stirred for 4 hours at ambient temperature, then quenched by the addition of water. The resulting solution was extracted with ethyl acetate, washed with brine, dried over anhydrous sodium sulfate and concentrated under vacuum. The residue was purified by Prep-HPLC with the following conditions: Column: YMC-Actus Triart C18 ExRS, 30*150 mm, 5 m; Mobile Phase A: Water (10 mM $NH_4HCO_3$), Mobile Phase B: ACN; Flow rate: 60 mL/min; Gradient: 45% B to 67% B in 8 min; Wave Length: 220 nm; RT1: 7.7 min. This gave N-(5-[2-[4-(trifluoromethyl)phenoxy]propyl]-1H-indol-3-yl)acetamide (10.5 mg) as a white solid. LCMS Method E: $[M-H]^-$=375. $^1$H NMR (400 MHz, DMSO-$d_6$): δ 10.67 (d, J=1.2 Hz, 1H), 9.78 (s, 1H), 7.66-7.62 (m, 4H), 7.25 (d, J=8.4 Hz, 1H), 7.14 (d, J=8.4 Hz, 2H), 7.06-7.04 (m, 1H), 4.82-4.76 (m, 1H), 3.14-3.09 (m, 1H), 2.92-2.87 (m, 1H), 2.09 (s, 3H), 1.27 (d, J=6.0 Hz, 3H).

The analogs prepared in the following table were prepared using the same method described for Example 120.

| Example # | Compound No. | Starting materials Used | Structure | LCMS data |
|---|---|---|---|---|
| 121 | 250 | 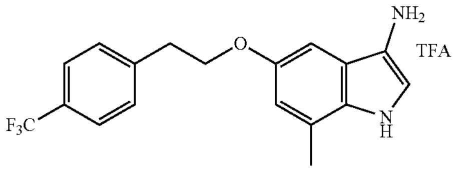 Intermediate 96 | 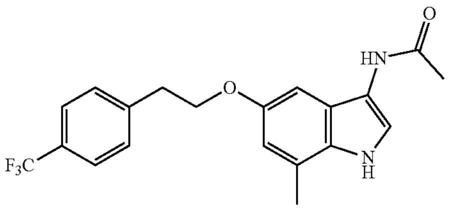 [SMILES: CC(=O)Nc1c[nH]c2c(C)cc(OCCc3ccc(C(F)(F)F)cc3)cc12] | Method F: MS-ESI: 378 $[M + H]^+$. |
| 122 | 248 | 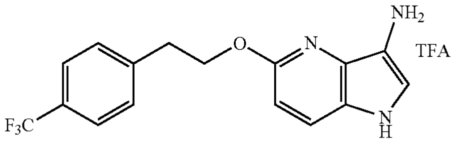 Intermediate 97 | 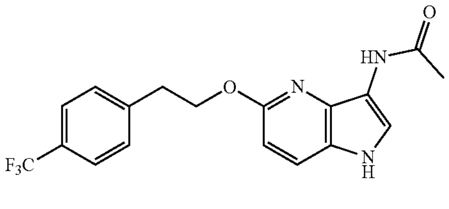 [SMILES: CC(=O)Nc1c[nH]c2ccc(OCCc3ccc(C(F)(F)F)cc3)nc12] | Method D: MS-ESI: 364 $[M + H]^+$. |
| 123 | 233 | 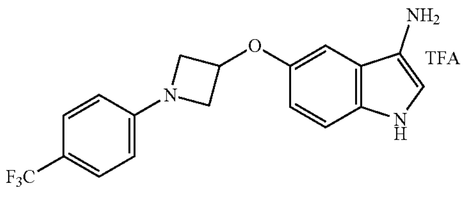 Intermediate 87 | 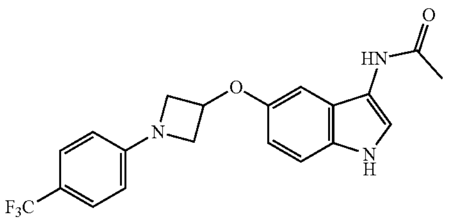 [SMILES: CC(=O)Nc1c[nH]c2ccc(OC3CN(c4ccc(C(F)(F)F)cc4)C3)cc12] | Method F: MS-ESI: 390 $[M + H]^+$. |
| 124 | 223 | 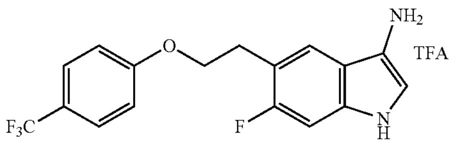 Intermediate 94 | 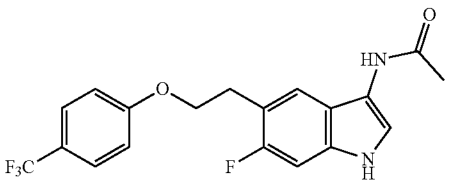 [SMILES: CC(=O)Nc1c[nH]c2cc(F)c(CCOc3ccc(C(F)(F)F)cc3)cc12] | Method F: MS-ESI: 381 $[M + H]^+$. |

-continued

| Example # | Compound No. | Starting materials Used | Structure | LCMS data |
|---|---|---|---|---|
| 125 | 213 | 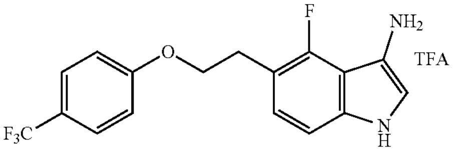 Intermediate 95 | 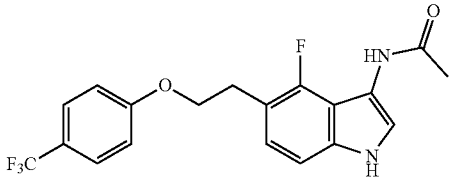 [SMILES: CC(=O)Nc1c[nH]c2ccc(CCOc3ccc(C(F)(F)F)cc3)c(F)c12] | Method E: MS-ESI: 379 [M − H]⁻. |
| 126 | 212 | 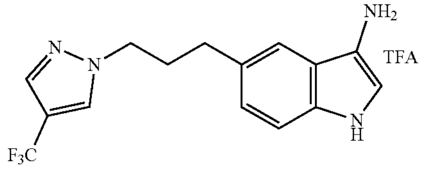 Intermediate 98 | 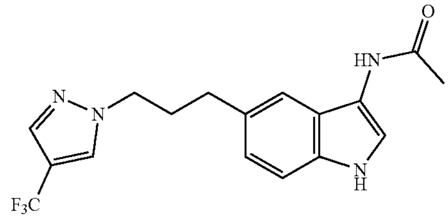 [SMILES: CC(=O)Nc1c[nH]c2ccc(CCCn3cc(C(F)(F)F)cn3)cc12] | Method E: MS-ESI: 351 [M + H]⁺. |

Example 127/128: N-(5-(2-hydroxy-3-(4-(trifluoromethyl)phenyl)propyl)-1H-indol-3-yl)cyclopropanecarboxamide (Compound 240) and N-(5-(1-hydroxy-3-(4-(trifluoromethyl)phenyl)propyl)-1H-indol-3-yl)cyclopropanecarboxamide (Compound 209)

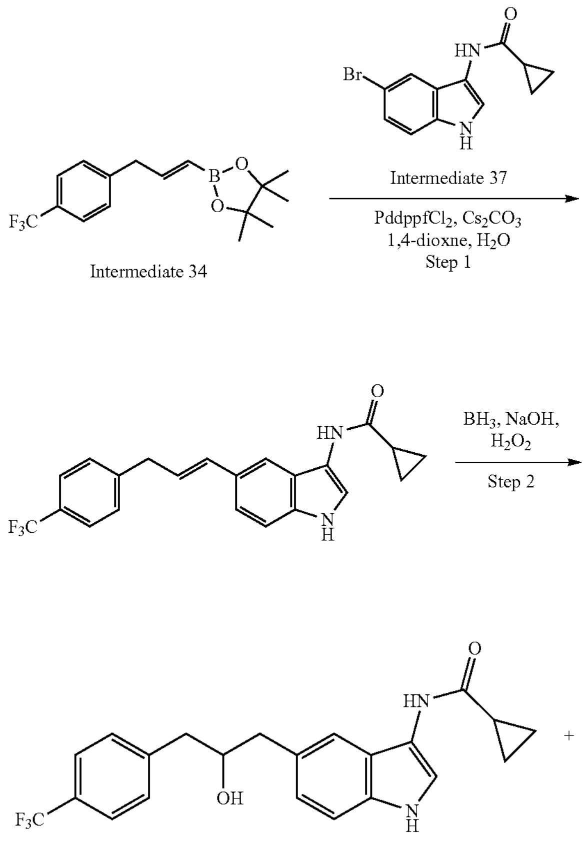

Compound 240

-continued

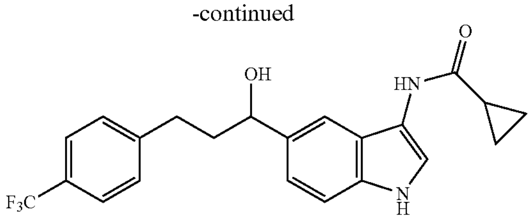

Compound 209

Step 1: (E)-N-(5-(3-(4-(trifluoromethyl)phenyl)prop-1-en-1-yl)-1H-indol-3-yl)cyclopropanecarboxamide N-(5-Bromo-1H-indol-3-yl)cyclopropanecarboxamide (500.0 mg, 1.7 mmol, 1.0 equiv.) was dissolved in 1,4-dioxane (15 mL) and water (1.5 mL), then 4,4,5,5-tetramethyl-2-[(1E)-3-[4-(trifluoromethyl)phenyl]prop-1-en-1-yl]-1,3,2-dioxaborolane (559.1 mg, 1.7 mmol, 1.0 equiv.), $Cs_2CO_3$ (1167.2 mg, 3.5 mmol, 2.0 equiv.) and Pd(dppf)$Cl_2$·$CH_2Cl_2$ (145.9 mg, 0.1 mmol, 0.1 equiv.) were added under an atmosphere of nitrogen. The reaction mixture was heated to 100° C. for 12 hours under nitrogen, then cooled to ambient temperature and concentrated under vacuum. The residue was diluted with water, extracted with ethyl acetate, washed with water, dried over anhydrous $Na_2SO_4$ and concentrated under vacuum. The residue was purified by flash column chromatography on silica gel, eluting with ethyl acetate/petroleum ether (1:5) to give (E)-N-(5-(3-(4-(trifluoromethyl)phenyl)prop-1-en-1-yl)-1H-indol-3-yl)cyclopropanecarboxamide (400.0 mg) as a white solid. LCMS Method A: $[M+H]^+$=385.

Step 2: N-(5-(2-hydroxy-3-(4-(trifluoromethyl)phenyl)propyl)-1H-indol-3-yl)cyclopropanecarboxamide and N-(5-(1-hydroxy-3-(4-(trifluoromethyl)phenyl)propyl)-1H-indol-3-yl)cyclopropanecarboxamide (E)-N-(5-(3-(4-(trifluoromethyl)phenyl)prop-1-en-1-yl)-1H-indol-3-yl)cyclopropanecarboxamide (150.0 mg, 0.4 mmol, 1.0 equiv.) was dissolved in THE (10 mL) and cooled to 0° C., then $BH_3$-THF (1M, 1.6 mL, 1.6 mmol, 4.0 equiv.) was added dropwise. After 1 hour at ambient temperature, NaOH (31.2 mg, 0.8 mmol, 2.0 equiv.) in water (0.5 mL) and $H_2O_2$ (26.6 mg, 0.8 mmol, 2.0 equiv.) were added. The reaction mixture was stirred for an additional 2 hours at ambient temperature, then quenched by the addition of saturated aqueous $NH_4Cl$. The resulting solution was extracted with ethyl acetate, washed with brine, dried over anhydrous $Na_2SO_4$ and concentrated under vacuum. The residue was purified by reverse flash chromatography with the following conditions: column, silica gel; mobile phase, ACN in water (0.5% $NH_4HCO_3$), 0% ACN to 100% gradient in 15 min; detector, UV 254 nm. The resulting material was further purified by Prep-HPLC with the following conditions: Column: Kinetex EVO prep C18, 30*150, 5 μm; Mobile Phase A: Water (10 mM $NH_4HCO_3$), Mobile Phase B: MeOH-HPLC; Flow rate: 60 mL/min; Gradient: 50% B to 70% B in 7 min; Wave Length: 220 nm. This gave N-(5-(2-hydroxy-3-(4-(trifluoromethyl)phenyl)propyl)-1H-indol-3-yl)cyclopropanecarboxamide (38.1 mg, Peak 1, RT=7.65 min) as a white solid and N-(5-(1-hydroxy-3-(4-(trifluoromethyl)phenyl)propyl)-1H-indol-3-yl)cyclopropanecarboxamide (3.8 mg, Peak 2, RT=8.00 min) as a white solid.

Peak 1: Compound 240: LCMS Method F: $[M-H]^-$=401. $^1H$ NMR (400 MHz, DMSO-$d_6$): δ 10.62 (s, 1H), 10.01 (s, 1H), 7.63-7.61 (m, 4H), 7.42 (d, J=8.0 Hz, 2H), 7.24 (d, J=8.0 Hz, 1H), 7.00-6.98 (m, 1H), 4.74 (d, J=6.4 Hz, 1H), 3.98-3.95 (m, 1H), 2.86-2.66 (m, 4H), 1.99-1.93 (m, 1H), 0.80-0.76 (m, 4H).

Peak 2: Compound 209: LCMS Method F: $[M-H]^-$=401. $^1H$ NMR (400 MHz, DMSO-$d_6$): δ 10.64 (d, J=2.0 Hz, 1H), 10.06 (s, 1H), 7.79 (s, 1H), 7.67-7.63 (m, 3H), 7.44 (d, J=8.0 Hz, 2H), 7.27 (d, J=8.4 Hz, 1H), 7.11-7.09 (m, 1H), 5.23 (d, J=4.0 Hz, 1H), 4.62-4.58 (m, 1H), 2.73-2.68 (m, 2H), 2.03-1.94 (m, 3H), 0.80-0.75 (m, 4H).

The analogs prepared in the following table were prepared using the same method described for Example 127/128.

| Example # | Compound No. | Starting materials Used | Structure | LCMS data |
|---|---|---|---|---|
| 129 | 284 | Intermediate 34/ Intermediate 1 | 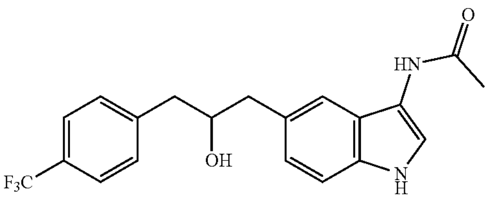 [SMILES: CC(=O)Nc1c[nH]c2ccc(CC(O)Cc3ccc(C(F)(F)F)cc3)cc12] | Method F: MS-ESI: 377 $[M + H]^+$. |
| 130 | 282 | Intermediate 34/ Intermediate 1 | 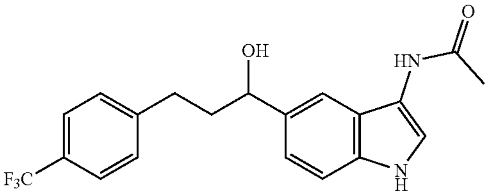 [SMILES: CC(=O)Nc1c[nH]c2ccc(C(O)CCc3ccc(C(F)(F)F)cc3)cc12] | Method F: MS-ESI: 377 $[M + H]^+$. |
| 131 | 174 | Intermediate 34/ Intermediate 38 | 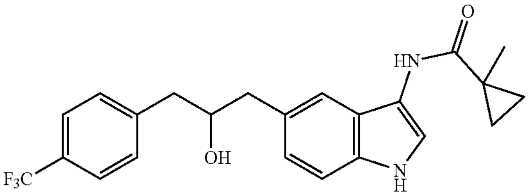 [SMILES: CC1(C(=O)Nc2c[nH]c3ccc(CC(O)Cc4ccc(C(F)(F)F)cc4)cc23)CC1] | Method F: MS-ESI: 417 $[M + H]^+$. |
| 132 | 172 | Intermediate 34/ Intermediate 38 | 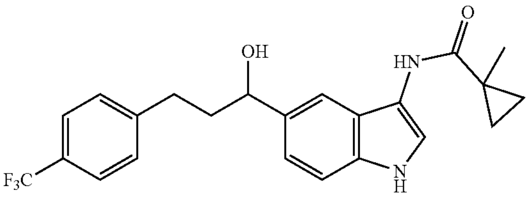 [SMILES: CC1(C(=O)Nc2c[nH]c3ccc(C(O)CCc4ccc(C(F)(F)F)cc4)cc23)CC1] | Method F: MS-ESI: 417 $[M + H]^+$. |

Example 133/134: N-(5-(2-hydroxy-3-(4-(trifluoromethyl)phenyl)propyl)-1H-indol-3-yl)cyclopropanecarboxamide [(Compound 201) (Front Peak, Absolute Stereochemistry Unconfirmed) and (Compound 200) (Second Peak, Absolute Stereochemistry Unconfirmed)]

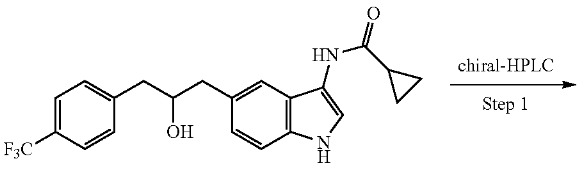

Compound 240

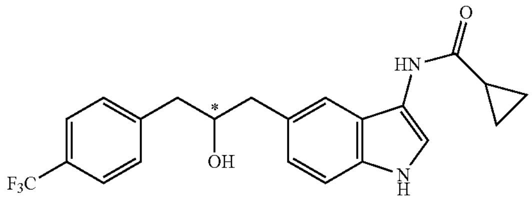

Compound 201
front peak, absolute stereochemistry unconfirmed
Example 133

+

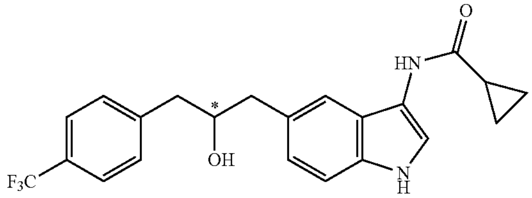

second peak, absolute stereochemistry unconfirmed
Example 134

The racemic N-(5-(2-hydroxy-3-(4-(trifluoromethyl)phenyl)propyl)-1H-indol-3-yl)cyclopropanecarboxamide (28.0 mg) was separated by Prep-Chiral-HPLC with the following conditions: Column: CHIRALPAK IC, 2*25 cm, 5 m; Mobile Phase A: Hex (0.5% 2M $NH_3$-MeOH)-HPLC, Mobile Phase B: EtOH:DCM=1:1-HPLC; Flow rate: 20 mL/min; Gradient: 15% B to 15% B in 17 min; Wave Length: 220/254 nm; RT1(min): 11.732; RT2(min): 14.323. This gave (Compound 201) (front peak, 4.9 mg) as a white solid and (Compound 200) (second peak, 5.8 mg) as a white solid.

Example 133 (Compound 201) (Peak 1): LCMS Method D: $[M-H]^-$=401. $^1$H NMR (400 MHz, DMSO-$d_6$): δ 10.61 (s, 1H), 10.00 (s, 1H), 7.63-7.61 (m, 4H), 7.42 (d, J=8.0 Hz, 2H), 7.24 (d, J=8.0 Hz, 1H), 7.00-6.98 (m, 1H), 4.74 (d, J=6.4 Hz, 1H), 3.98-3.95 (m, 1H), 2.86-2.66 (m, 4H), 1.99-1.93 (m, 1H), 0.80-0.74 (m, 4H).

Example 134 (Compound 200) (Peak 2): LCMS Method D: $[M-H]^-$=401. $^1$H NMR (400 MHz, DMSO-$d_6$): δ 10.61 (s, 1H), 10.00 (s, 1H), 7.63-7.61 (m, 4H), 7.42 (d, J=8.0 Hz, 2H), 7.24 (d, J=8.0 Hz, 1H), 7.00-6.98 (m, 1H), 4.74 (d, J=6.4 Hz, 1H), 3.98-3.95 (m, 1H), 2.86-2.66 (m, 4H), 1.99-1.93 (m, 1H), 0.80-0.74 (m, 4H).

Example 135: N-(5-(3-methyl-3-(1-(2,2,2-trifluoroethyl)piperidin-4-yl)butyl)-1H-indol-3-yl)acetamide (Compound 275)

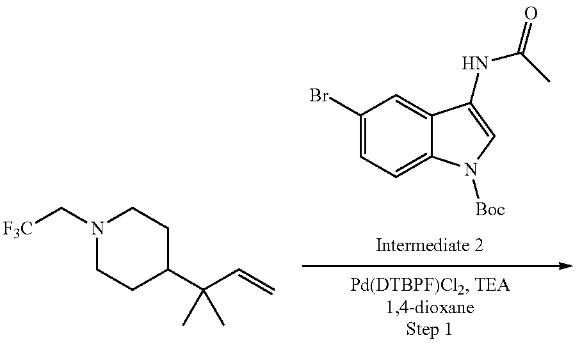

Intermediate 101

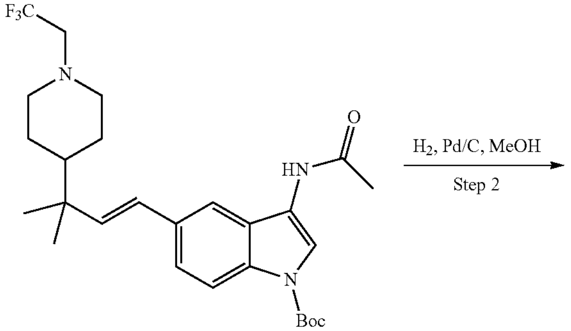

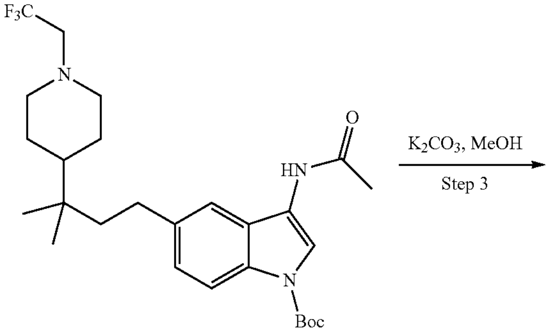

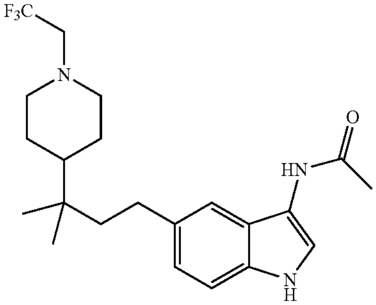

Compound 275

Step 1: tert-butyl (E)-3-acetamido-5-(3-methyl-3-(1-(2,2,2-trifluoroethyl)piperidin-4-yl)but-1-en-1-yl)-1H-indole-1-carboxylate 4-(2-Methylbut-3-en-2-yl)-1-(2,2,2-trifluoroethyl)piperidine (150.0 mg, 0.6 mmol, 1.0 equiv.) was dissolved in 1,4-dioxane (3 mL), then TEA (0.2 mL, 1.3 mmol, 2.0 equiv.), tert-butyl 5-bromo-3-acetamidoindole-1-carboxylate (225.2 mg, 0.6 mmol, 1.0 equiv.) and Pd(DtBPF)$Cl_2$ (41.6 mg, 0.1 mmol, 0.1 equiv.) were added under an atmosphere of nitrogen. The reaction mixture was heated to 120° C. overnight, then cooled to ambient temperature and concentrated under vacuum. The residue was purified by flash column chromatography on silica gel, eluting with ethyl acetate/petroleum ether (1:3) to give tert-butyl (E)-3-acetamido-5-(3-methyl-3-(1-(2,2,2-trifluoroethyl)piperidin-4-yl)but-1-en-1-yl)-1H-indole-1-carboxylate (110.0 mg) as a pale yellow solid. LCMS Method A: [M+H]+=508.

Step 2: tert-butyl 3-acetamido-5-(3-methyl-3-(1-(2,2,2-trifluoroethyl)piperidin-4-yl)butyl)-1H-indole-1-carboxylate tert-Butyl (E)-3-acetamido-5-(3-methyl-3-(1-(2,2,2-trifluoroethyl)piperidin-4-yl)but-1-en-1-yl)-1H-indole-1-carboxylate (110.0 mg, 0.2 mmol, 1.0 equiv.) was dissolved in MeOH (10 mL), then Pd/C (9.2 mg, 0.1 mmol, 0.4 equiv.) was added. The mixture was sparged with nitrogen, placed under an atmosphere of hydrogen gas (balloon), then stirred for 3 hours at ambient temperature. The solids were removed by filtration and the filtrate was concentrated under vacuum to give tert-butyl 3-acetamido-5-(3-methyl-3-(1-(2,2,2-trifluoroethyl)piperidin-4-yl)butyl)-1H-indole-1-carboxylate (105.0 mg) as a pale yellow solid. LCMS Method A: $[M+H]^+$=510.

Step 3: N-(5-(3-methyl-3-(1-(2,2,2-trifluoroethyl)piperidin-4-yl)butyl)-1H-indol-3-yl)acetamide tert-Butyl 3-acetamido-5-(3-methyl-3-(1-(2,2,2-trifluoroethyl)piperidin-4-yl)butyl)-1H-indole-1-carboxylate (80.0 mg, 0.2 mmol, 1.0 equiv.) was dissolved in MeOH (2 mL), then $K_2CO_3$ (43.4 mg, 0.3 mmol, 2.0 equiv.) was added. The reaction mixture was heated to 70° C. for 50 min, then cooled to ambient temperature and quenched by the addition of water. The resulting solution was extracted with ethyl acetate, washed with brine, dried over anhydrous $Na_2SO_4$ and concentrated under vacuum. The residue was purified by Prep-HPLC with the following conditions: Column: XBridge Prep OBD C18 Column, 30*150 mm, 5 μm; Mobile Phase A: Water (10 mM $NH_4HCO_3$), Mobile Phase B: ACN; Flow rate: 60 mL/min; Gradient: 50% B to 65% B in 8 min; Wave Length: 220 nm; RT1: 7.67 min. This gave N-(5-[3-methyl-3-[1-(2,2,2-trifluoroethyl)piperidin-4-yl]butyl]-1H-indol-3-yl)acetamide (15.9 mg) as an off-white solid. LCMS Method F: $[M+H]^+$=410. $^1$H NMR (400 MHz, DMSO-$d_6$): δ 10.57 (s, 1H), 9.71 (s, 1H), 7.64 (s, 1H), 7.59-7.55 (m, 1H), 7.24-7.19 (m, 1H), 6.91 (d, J=8.4 Hz, 1H), 3.15-3.05 (m, 2H), 3.00-2.96 (m, 2H), 2.59-2.56 (m, 2H), 2.31-2.23 (m, 2H), 2.08 (s, 3H), 1.63-1.59 (m, 2H), 1.53-1.47 (m, 2H), 1.34-1.11 (m, 3H), 0.90 (s, 6H).

The analogs prepared in the following table were prepared using the same method described for Example 135.

| Example # | Compound No. | Starting materials Used | Structure | LCMS data |
|---|---|---|---|---|
| 136 | 288 | Intermediate 100/ Intermediate 2 | 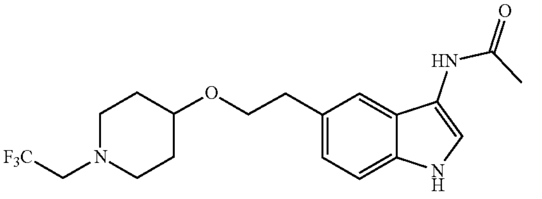 [SMILES: CC(=O)Nc1c[nH]c2ccc(CCOC3CCN(CC(F)(F)F)CC3)cc12] | Method F: MS-ESI: 384 $[M+H]^+$. |

Example 137: N-(5-((((1R,5S,6r)-3-(2,2,2-trifluoroethyl)-3-azabicyclo[3.1.0]hexan-6-yl)methoxy)methyl)-1H-indol-3-yl)acetamide (Compound 274)

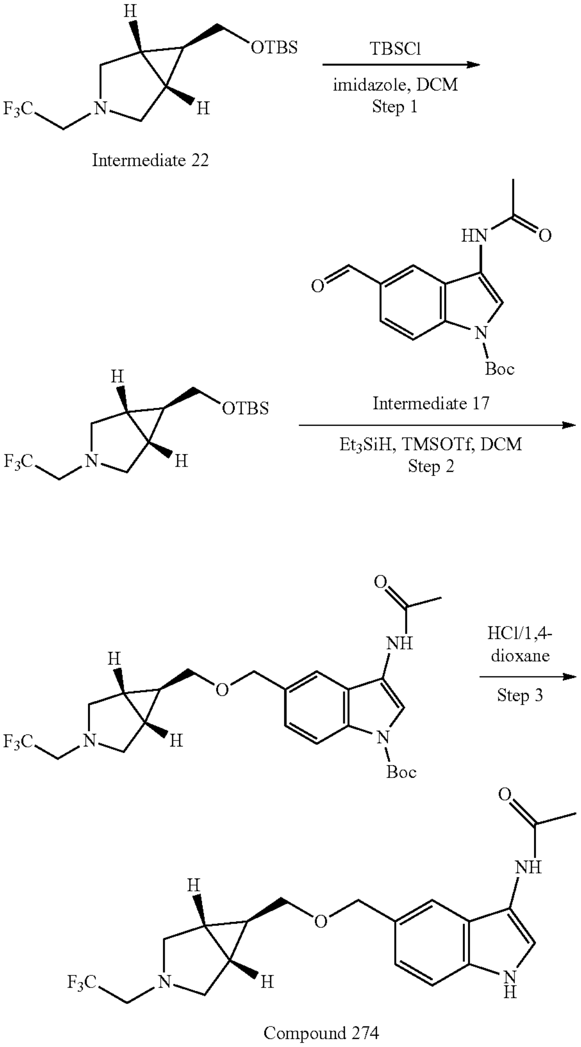

Intermediate 22
Compound 274

Step 1: (1R,5S,6S)-6-{[(tert-butyldimethylsilyl)oxy] methyl}-3-(2,2,2-trifluoroethyl)-3-azabicyclo[3.1.0] hexane

[(1R,5S,6S)-3-(2,2,2-trifluoroethyl)-3-azabicyclo[3.1.0] hexan-6-yl]methanol (2.2 g, 11.2 mmol, 1.0 equiv.) was dissolved in DCM (100 mL), then imidazole (1.5 g, 22.5 mmol, 2.0 equiv.) and TBSCl (3.4 g, 22.5 mmol, 2.0 equiv.) were added. The reaction mixture was stirred for 2 hours at ambient temperature, then quenched by the addition of water. The resulting solution was extracted with DCM, dried over anhydrous $Na_2SO_4$ and concentrated under vacuum. The residue was purified by flash column chromatography on silica gel, eluting with ethyl acetate/petroleum ether (1:1) to give (1R,5S,6S)-6-{[(tert-butyldimethylsilyl)oxy] methyl}-3-(2,2,2-trifluoroethyl)-3-azabicyclo[3.1.0]hexane (2.4 g) as an off-white oil. LCMS Method A: $[M+H]^+$=310.

Step 2: tert-butyl 3-acetamido-5-([[(1R,5S,6S)-3-(2,2,2-trifluoroethyl)-3-azabicyclo[3.1.0]hexan-6-yl] methoxy]methyl)indole-1-carboxylate (1R,5S,6S)-6-[[(tert-butyldimethylsilyl)oxy]methyl]-3-(2,2,2-trifluoroethyl)-3-azabicyclo[3.1.0]hexane (200.0 mg, 0.6 mmol, 1.0 equiv.) and tert-butyl 5-formylindole-1-carboxylate (237.8 mg, 0.9 mmol, 1.5 equiv.) were dissolved in DCM (10 mL) and cooled to 0° C., then $Et_3SiH$ (165.0 mg, 1.4 mmol, 2.2 equiv.) and TMSOTf (215.0 mg, 0.9 mmol, 1.5 equiv.) were added. The reaction mixture was stirred overnight at 0° C. and then quenched by the addition of water. The resulting solution was extracted with DCM, washed with brine, dried over anhydrous $Na_2SO_4$ and concentrated under vacuum. The residue was purified by flash column chromatography on silica gel, eluting with ethyl acetate/petroleum ether (1:1) to give tert-butyl 3-acetamido-5-([[(1R,5S,6S)-3-(2,2,2-trifluoroethyl)-3-azabicyclo[3.1.0] hexan-6-yl]methoxy]methyl)indole-1-carboxylate (100.0 mg) as a grey solid. LCMS Method A: $[M+H]^+$=482.

Step 3: N-[5-([[(1R,5S,6S)-3-(2,2,2-trifluoroethyl)-3-azabicyclo[3.1.0]hexan-6-yl]methoxy]methyl)-1H-indol-3-yl]acetamide tert-Butyl 3-acetamido-5-([[(1R,5S,6S)-3-(2,2,2-trifluoroethyl)-3-azabicyclo [3.1.0]hexan-6-yl]methoxy]methyl) indole-1-carboxylate (100.0 mg, 0.2 mmol, 1.0 equiv.) was dissolved in ethyl acetate (2 mL), then HCl/1,4-dioxane (4 M, 1 mL) was added. The reaction mixture was stirred for 2 hours at ambient temperature and then concentrated under vacuum. The residue was purified by Prep-HPLC with the following conditions: Column: Xselect CSH C18 OBD Column 30*150 mm, 5 m; Mobile Phase A: Water (0.1% FA), Mobile Phase B: ACN; Flow rate: 60 mL/min; Gradient: 15% B to 35% B in 7 min; Wave Length: 254; 220 nm; RT1: 6.47 min. This gave N-[5-([[(1R,5S,6S)-3-(2,2,2-trifluoroethyl)-3-azabicyclo[3.1.0]hexan-6-yl]methoxy] methyl)-1H-indol-3-yl]acetamide (1.4 mg) as a grey solid. LCMS Method E: $[M+H]^+$=382. LCMS Method F: $[M+H]^+$= 410. $^1H$ NMR (400 MHz, DMSO-$d_6$): δ 10.73 (s, 1H), 9.83 (s, 1H), 7.73 (s, 1H), 7.68 (s, 1H), 7.27 (d, J=8.0 Hz, 1H), 7.04 (d, J=8.0 Hz, 1H), 4.69-4.65 (m, 2H), 3.46-3.27 (m, 2H), 3.07-3.02 (m, 2H), 2.68-2.61 (m, 4H), 2.08 (s, 3H), 1.51-1.23 (m, 3H).

The analogs prepared in the following table were prepared using the same method described for Example 137.

| Example # | Compound No. | Starting materials Used | Structure | LCMS data |
|---|---|---|---|---|
| 138 | 268 | Intermediate 21/ Intermediate 17 | 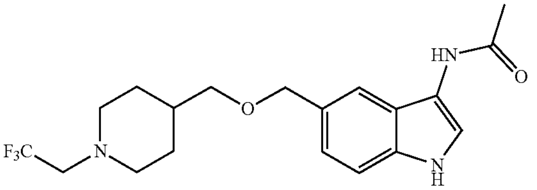 [SMILES: CC(=O)Nc1c[nH]c2ccc(COCC3CCN(CC(F)(F)F)CC3)cc12] | Method D: MS-ESI: 382 $[M-H]^+$. |

Example 139: N-(5-(2-((5-(trifluoromethyl)pyridin-2-yl)amino)ethyl)-1H-indol-3-yl)acetamide (Compound 199)

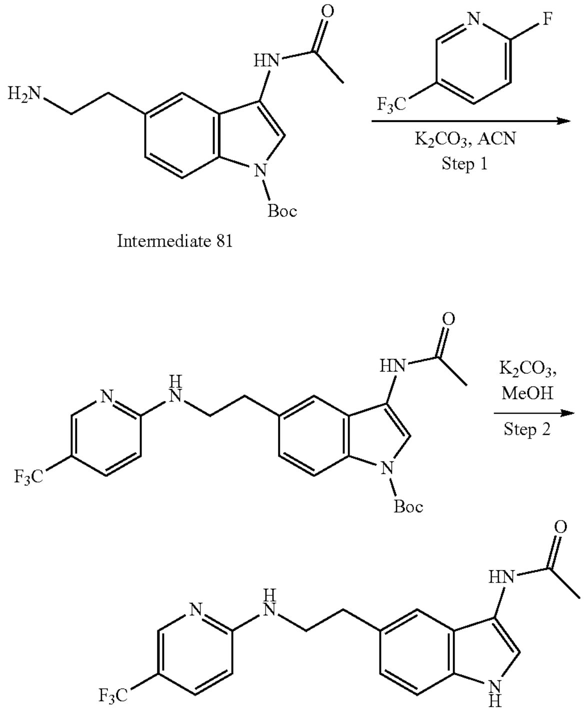

Intermediate 81

Compound 199

Step 1: tert-butyl 3-acetamido-5-(2-{[5-(trifluoromethyl) pyridin-2-yl]amino}ethyl)indole-1-carboxylate tert-Butyl 5-(2-aminoethyl)-3-acetamidoindole-1-carboxylate (270.0 mg, 0.9 mmol, 1.0 equiv.) was dissolved in ACN (3 mL), then 2-fluoro-5-(trifluoromethyl)pyridine (168.5 mg, 1.0 mmol, 1.2 equiv.) and $K_2CO_3$ (235.1 mg, 1.7 mmol, 2.0 equiv.) were added. The reaction mixture was heated to 80° C. for 6 hours, then cooled to ambient temperature and quenched by the addition of water. The resulting solution was extracted with ethyl acetate, washed with brine, dried over anhydrous $Na_2SO_4$ and concentrated under vacuum. The residue was purified by flash column chromatography on silica gel, eluting with ethyl acetate/petroleum ether (1:2) to give tert-butyl 3-acetamido-5-(2-{[5-(trifluoromethyl)pyridin-2-yl]amino}ethyl)indole-1-carboxylate (126.0 mg) as a yellow solid. LCMS Method A: $[M+H]^+$=463.

Step 2: N-[5-(2-{[5-(trifluoromethyl) pyridin-2-yl] amino}ethyl)-1H-indol-3-yl]acetamide tert-Butyl 3-acetamido-5-(2-{[5-(trifluoromethyl) pyridin-2-yl]amino}ethyl)indole-1-carboxylate (120.0 mg, 0.3 mmol, 1.0 equiv.) was dissolved in methanol (2 mL), then $K_2CO_3$ (143.5 mg, 1.0 mmol, 4.0 equiv.) was added. The reaction mixture was heated to 70° C. for 3 hours, then cooled to ambient temperature and quenched by the addition of water. The resulting solution was extracted with ethyl acetate, washed with brine, dried over anhydrous $Na_2SO_4$ and concentrated under vacuum. The residue was purified by Prep-HPLC with the following conditions: Column: X Bridge Prep OBD C18 Column, 30*150 mm, 5 μm; Mobile Phase A: Water (10 mM $NH_4HCO_3$), Mobile Phase B: ACN; Flow rate: 60 mL/min; Gradient: 33% B to 47% B in 8 min; Wave Length: 254/220 nm; RT1: 7.63 min. This gave N-[5-(2-{[5-(trifluoromethyl)pyridin-2-yl]amino}ethyl)-1H-indol-3-yl]acetamide (25.5 mg) as a white solid. LCMS Method D: $[M+H]^+$=363. $^1H$ NMR (400 MHz, DMSO-$d_6$): δ 10.65 (s, 1H), 9.79 (s, 1H), 8.33 (s, 1H), 7.66-7.64 (m, 3H), 7.44 (t, J=5.6 Hz, 1H), 7.26 (d, J=8.0 Hz, 1H), 7.01-6.99 (m, 1H), 6.60 (d, J=8.8 Hz, 1H), 3.59-3.55 (m, 2H), 2.92-2.89 (m, 2H), 2.08 (s, 3H).

The analogs prepared in the following table were prepared using the same method described for Example 139.

Example 141: N-(5-(((4-(trifluoromethyl)phenyl) sulfonamido)methyl)-1H-indol-3-yl)acetamide (Compound 265)

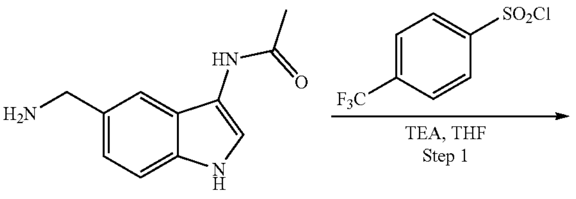

Intermediate 82

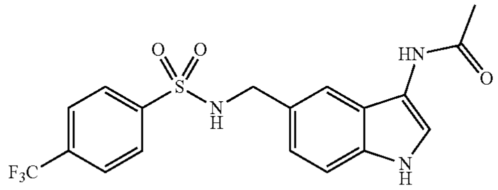

Compound 265

N-[5-(aminomethyl)-1H-indol-3-yl]acetamide (50.0 mg, 0.2 mmol, 1.0 equiv.) and TEA (0.1 mL, mg, 0.5 mmol, 2.0 equiv.) were dissolved in THE (5 mL), then 4-(trifluoromethyl)benzenesulfonyl chloride (60.1 mg, 0.2 mmol, 1.0 equiv.) was added. The reaction mixture was stirred for 2 hours at ambient temperature, then concentrated under vacuum. The residue was purified by Prep-HPLC with the following conditions: Column: XBridge Prep OBD C18 Column, 30*150 mm, 5 m; Mobile Phase A: Water (10 mM $NH_4HCO_3$), Mobile Phase B: ACN; Flow rate: 60 mL/min; Gradient: 27% B to 53% B in 7 min; Wave Length: 220 nm. This gave N-(5-[[4-(trifluoromethyl)benzenesulfonamido]methyl]-1H-indol-3-yl)acetamide (24.5 mg) as an off-white solid. LCMS Method G: $[M+H]^+$=412. $^1H$ NMR (400 MHz, DMSO-$d_6$): δ 10.72 (s, 1H), 9.82 (s, 1H), 8.32 (t, J=6.0 Hz, 1H), 8.00 (d, J=8.4 Hz, 2H), 7.92 (d, J=8.4 Hz, 2H), 7.67-7.65 (m, 2H), 7.19 (d, J=8.4 Hz, 1H), 6.92 (d, J=8.4 Hz, 1H), 4.06 (d, J=6.0 Hz, 2H), 2.08 (s, 3H).

| Example # | Compound No. | Starting materials Used | Structure | LCMS data |
|---|---|---|---|---|
| 140 | 215 | Intermediate 11 | 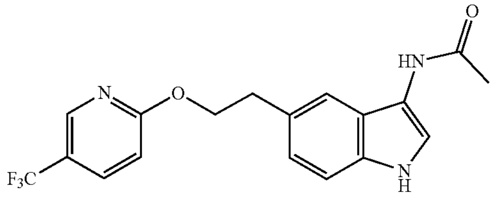 [SMILES: CC(=O)Nc1c[nH]c2ccc(CCOc3ccc(C(F)(F)F)cn3)cc12] | Method E: MS-ESI: 364 $[M+H]^+$. |

Example 142: N-(5-(2-((4-(trifluoromethyl)phenyl)thio)ethyl)-1H-indol-3-yl)acetamide (Compound 256)

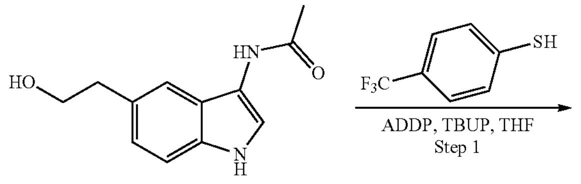

Intermediate 48

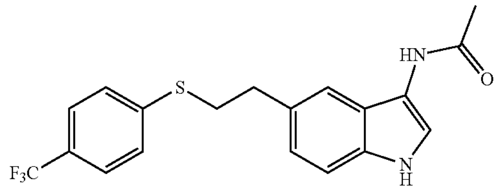

Compound 256

N-(5-(2-hydroxyethyl)-1H-indol-3-yl)acetamide (254.0 mg, 1.1 mmol, 1.0 equiv.) was dissolved in THE (5 ml), then 4-(trifluoromethyl)benzenethiol (663.5 mg, 3.7 mmol, 3.2 equiv.) and TBUP (941.8 mg, 4.7 mmol, 4.0 equiv.) were added. This was followed by the addition of ADDP (582.7 mg, 2.3 mmol, 2.0 equiv.) at 0° C. under an atmosphere of nitrogen. The reaction mixture was heated to 70° C. for 2 hours, then cooled to ambient temperature and quenched by the addition of water. The resulting solution was extracted with ethyl acetate, washed with brine, dried over anhydrous sodium sulfate and concentrated under vacuum. The residue was purified by Prep-HPLC with the following conditions: Column: XBridge Prep OBD C18 Column, 30*150 mm, 5 μm; Mobile Phase A: Water (10 mM $NH_4HCO_3$), Mobile Phase B: ACN; Flow rate: 60 mL/min; Gradient: 40% B to 65% B in 8 min; Wave Length: 220 nm; RT1: 7.68 min. LCMS Method F: $[M+H]^+$=379. $^1$H NMR (400 MHz, DMSO-$d_6$): δ 10.69 (s, 1H), 9.76 (s, 1H), 7.67-7.64 (m, 4H), 7.53 (d, J=8.4 Hz, 2H), 7.26 (d, J=8.4 Hz, 1H), 7.05-7.03 (m, 1H), 3.38-3.34 (m, 2H), 3.00 (t, J=7.6 Hz, 2H), 2.08 (s, 3H).

Example 143: N-(6-bromo-5-(4-(trifluoromethyl)phenethoxy)-1H-indol-3-yl)acetamide (Compound 173)

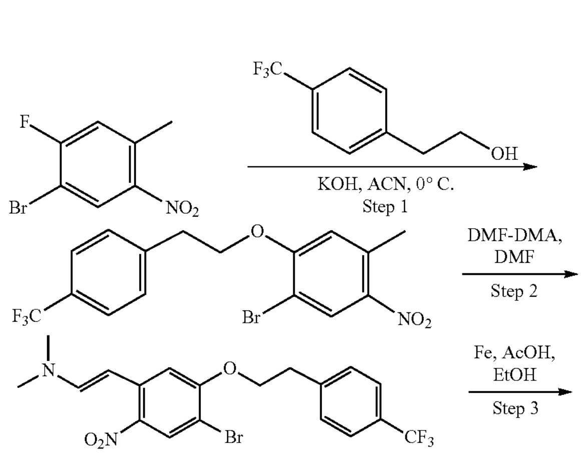

-continued

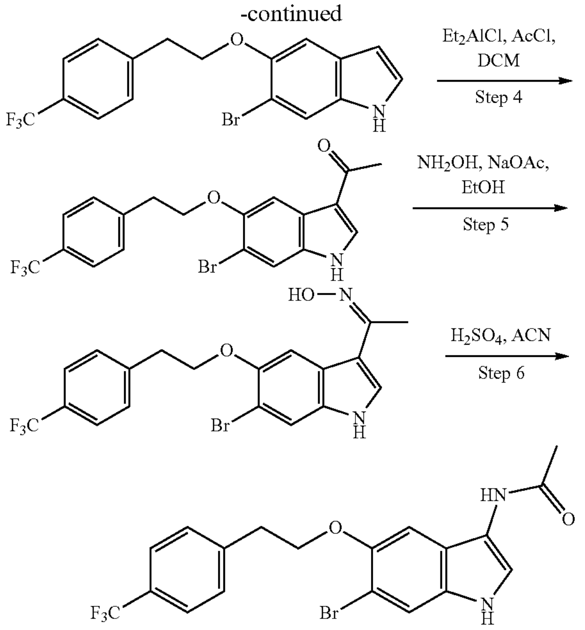

Compound 173

Step 1: 1-bromo-4-methyl-5-nitro-2-(4-(trifluoromethyl)phenethoxy)benzene

1-Bromo-2-fluoro-4-methyl-5-nitrobenzene (3.0 g, 12.8 mmol, 1.0 equiv.) and 2-(4-(trifluoromethyl)phenyl)ethan-1-ol (2.93 g, 15.4 mmol, 1.2 equiv.) were dissolved in ACN (30 mL) and cooled to 0° C., then KOH (1.1 g, 19.2 mmol, 1.5 equiv.) was added. The reaction mixture was stirred for 2 hours at 0° C. then quenched by the addition of water.

The resulting solution was extracted with ethyl acetate, washed with brine, dried over anhydrous sodium sulfate and concentrated under vacuum. The residue was purified by flash column chromatography on silica gel, eluting with ethyl acetate/petroleum ether (1:6) to give 1-bromo-4-methyl-5-nitro-2-{2-[4-(trifluoromethyl)phenyl]ethoxy}benzene (4.7 g) as a yellow solid. LCMS Method A: $[M+H]^+$=404.

Step 2: (E)-2-(4-bromo-2-nitro-5-(4-(trifluoromethyl)phenethoxy) phenyl)-N,N-dimethylethen-1-amine 1-Bromo-4-methyl-5-nitro-2-(4-(trifluoromethyl)phenethoxy)benzene (2.7 g, 6.6 mmol, 1.0 equiv.) was dissolved in DMF (20 mL), then DMF-DMA (10.0 mL, 75.4 mmol, 11.4 equiv.) was added. The reaction mixture was heated to 140° C. for 4 hours, then cooled to ambient temperature and concentrated under vacuum to give (E)-2-(4-bromo-2-nitro-5-(4-(trifluoromethyl)phenethoxy) phenyl)-N,N-dimethylethen-1-amine (2.5 g), which was used in the next step directly without further purification. LCMS Method A: $[M+H]^+$=459.

Step 3: 6-bromo-5-(4-(trifluoromethyl)phenethoxy)-1H-indole (E)-2-(4-bromo-2-nitro-5-(4-(trifluoromethyl)phenethoxy)phenyl)-N,N-dimethylethen-1-amine (2.5 g, 5.4 mmol, 1.0 equiv.) was dissolved in EtOH (30 mL) and AcOH (30 mL), then Fe (5.5 g, 98.0 mmol, 18.0 equiv.) was added. The reaction mixture was heated to 90° C. for 4 hours, then cooled to ambient temperature and quenched by the addition of water. The resulting mixture was adjusted to pH 7 with aqueous NaOH (5% wt./wt.), extracted with ethyl acetate, washed with brine, dried over anhydrous sodium sulfate and concentrated under vacuum. The residue was purified by flash column chromatography on silica gel, eluting with ethyl acetate/petroleum ether (1:2) to give 6-bromo-5-(4-(trifluoromethyl)phenethoxy)-1H-indole (850.0 mg) as a yellow solid. LCMS Method A: $[M+H]^+$=384.

Step 4: 1-(6-bromo-5-(4-(trifluoromethyl)phenethoxy)-1H-indol-3-yl)ethan-1-one

6-Bromo-5-(4-(trifluoromethyl)phenethoxy)-1H-indole (850.0 mg, 2.2 mmol, 1.0 equiv.) was dissolved in DCM (10 mL) and cooled to 0° C., then diethylaluminum chloride in hexane (1M, 3.3 mL, 3.3 mmol, 1.5 equiv.) was added dropwise. After 30 min at 0° C., AcCl (0.2 mL, 3.2 mmol, 1.0 equiv.) was added, maintaining the solution at 0° C. The reaction mixture was stirred for additional 2 hours at ambient temperature and then quenched by the addition of water. The resulting solution was extracted with ethyl acetate, washed with brine, dried over anhydrous sodium sulfate and concentrated under vacuum. The residue was purified by flash column chromatography on silica gel, eluting with ethyl acetate/petroleum ether (1:3) to give 1-(6-bromo-5-(4-(trifluoromethyl)phenethoxy)-1H-indol-3-yl)ethan-1-one (740.0 mg) as a red solid. LCMS Method B: $[M-H]^+$=424.

Step 5: (Z)-1-(6-bromo-5-(4-(trifluoromethyl)phenethoxy)-1H-indol-3-yl)ethan-1-one oxime 1-(6-Bromo-5-(4-(trifluoromethyl)phenethoxy)-1H-indol-3-yl)ethan-1-one (740.0 mg, 1.7 mmol, 1.0 equiv.) was dissolved in EtOH (10 mL), then NaOAc (284.8 mg, 3.5 mmol, 2.0 equiv.) and hydroxylamine hydrochloride (180.9 mg, 2.6 mmol, 1.5 equiv.) were added. The reaction mixture was heated to 60° C. for 5 hours, then cooled to ambient temperature and quenched by the addition of water. The resulting solution was extracted with ethyl acetate, washed with brine, dried over anhydrous sodium sulfate and concentrated under vacuum. The residue was purified by flash column chromatography on silica gel, eluting with ethyl acetate/petroleum ether (1:2) to give (Z)-1-(6-bromo-5-(4-(trifluoromethyl)phenethoxy)-1H-indol-3-yl)ethan-1-one oxime (620.0 mg) as a white solid. LCMS Method A: $[M+H]^+$=441.

Step 6: N-(6-bromo-5-(4-(trifluoromethyl)phenethoxy)-1H-indol-3-yl)acetamide (Z)-1-(6-Bromo-5-(4-(trifluoromethyl)phenethoxy)-1H-indol-3-yl)ethan-1-one oxime (300.0 mg, 0.7 mmol, 1.0 equiv.) was dissolved in ACN (5 mL) and cooled to 0° C., then concentrated $H_2SO_4$ (1 mL) was added dropwise. After 2 hours at ambient temperature, the reaction was quenched by the addition of water and adjusted to pH 7 with saturated aqueous $NaHCO_3$. The resulting solution was extracted with ethyl acetate, washed with brine, dried over anhydrous sodium sulfate and concentrated under vacuum. The residue was purified by Prep-HPLC with the following conditions: Column: XBridge Prep OBD C18 Column, 30*150 mm, 5 m; Mobile Phase A: Water (10 mM $NH_4HCO_3$), Mobile Phase B: ACN; Flow rate: 60 mL/min; Gradient: 48% B to 63% B in 8 min; Wave Length: 220 nm; RT1: 7.03 min. This gave N-(6-bromo-5-(4-(trifluoromethyl)phenethoxy)-1H-indol-3-yl)acetamide (10.7 mg) as an orange solid. LCMS Method F: $[M-H]^-$=439. $^1$H NMR (400 MHz, DMSO-$d_6$): δ 10.67 (d, J=1.6 Hz, 1H), 9.75 (s, 1H), 7.71-7.69 (m, 3H), 7.65 (d, J=8.0 Hz, 2H), 7.52 (s, 1H), 7.48 (s, 1H), 4.23 (t, J=6.8 Hz, 2H), 3.24 (t, J=6.8 Hz, 2H), 2.07 (s, 3H).

Example 144: 1-(2,2-difluoroethyl)-N-(5-(4-(trifluoromethyl)phenethoxy)-1H-indol-3-yl)azetidine-3-carboxamide (Compound 149)

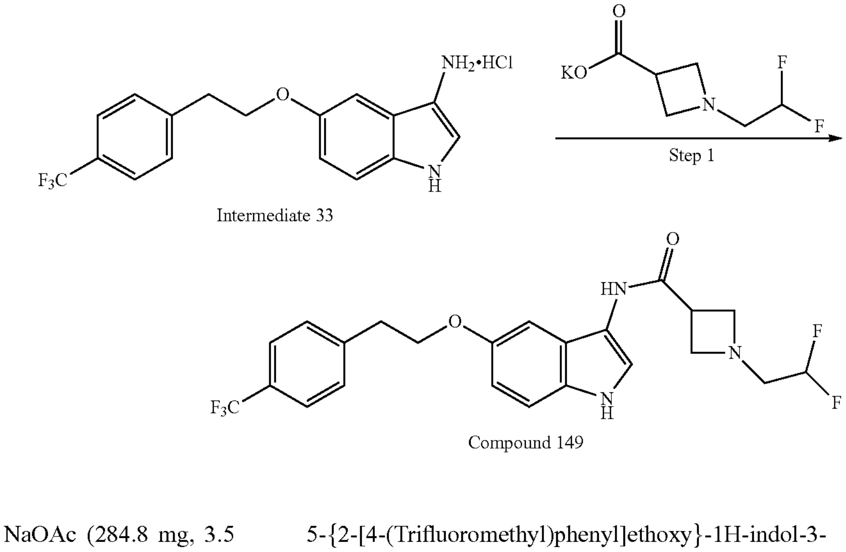

Intermediate 33

Compound 149

5-{2-[4-(Trifluoromethyl)phenyl]ethoxy}-1H-indol-3-amine hydrochloride (178.4 mg, 0.5 mmol, 1.0 equiv.) was dissolved in ACN (5 mL), then potassium 1-(2,2-difluoroethyl)azetidine-3-carboxylate (101.5 mg, 0.5 mmol, 1.0 equiv.), TCFH (210.2 mg, 0.8 mmol, 1.5 equiv.) and NMI (123.0 mg, 1.5 mmol, 3.0 equiv.) were added. The reaction mixture was stirred for 8 hours at ambient temperature and then quenched by the addition of water. The resulting solution was extracted with ethyl acetate, washed with brine, dried over anhydrous $Na_2SO_4$ and concentrated under vacuum. The residue was purified by reverse flash chromatography with the following conditions: column, silica gel; mobile phase, ACN in water (0.5% $NH_4HCO_3$), 10% ACN to 50% gradient in 15 min; detector, UV 254 nm. The resulting material was further purified by Prep-HPLC with the following conditions: Column: XBridge Shield RP18 OBD Column, 30*150 mm, 5 M m; Mobile Phase A: Water (10 mM $NH_4HCO_3$), Mobile Phase B: ACN; Flow rate: 60 mL/min; Gradient: 42% B to 62% B in 8 min; Wave Length: 220 nm; RT1: 7.15 min. This gave 1-(2,2-difluoroethyl)-N-(5-(4-(trifluoromethyl)phenethoxy)-1H-indol-3-yl)azetidine-3-carboxamide (93.5 mg) as a white solid. LCMS Method F: $[M-H]^-=466$. $^1H$ NMR (400 MHz, DMSO-$d_6$): δ 10.62 (s, 1H), 9.69 (s, 1H), 7.72-7.69 (m, 3H), 7.60 (d, J=8.0 Hz, 2H), 7.30 (d, J=2.0 Hz, 1H), 7.21 (d, J=8.8 Hz, 1H), 6.74-6.72 (m, 1H), 6.11-5.81 (t, $J_1$=56.0 Hz, $J_2$=4.4 Hz, 1H), 4.20 (t, J=6.8 Hz, 2H), 3.57-3.50 (m, 3H), 3.38-3.34 (m, 2H), 3.20-3.16 (m, 2H), 2.86-2.81 (m, 2H).

Example 145: 3-methyl-N-(5-((4-(trifluoromethyl)benzyl)oxy)-1H-indol-3-yl)oxetane-3-carboxamide (Compound 166)

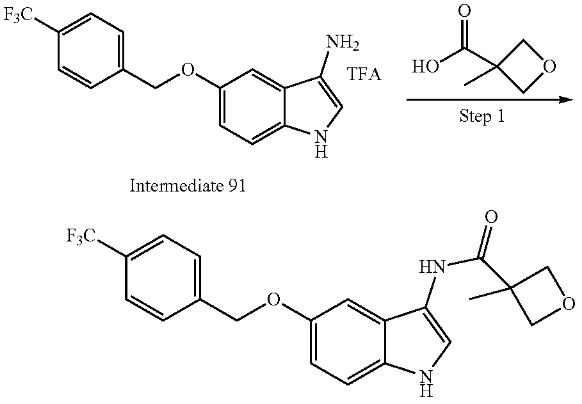

Intermediate 91

(Compound 166)

3-Methyloxetane-3-carboxylic acid (139.0 mg, 1.2 mmol, 1.0 equiv.) and HATU (682.7 mg, 1.8 mmol, 1.5 equiv.) were dissolved in DCM (5 mL), then DIEA (1.1 mL, 6.0 mmol, 5 equiv.) was added. After 2 min, 5-((4-(trifluoromethyl)benzyl)oxy)-1H-indol-3-amine TFA salt (754.9 mg, 1.8 mmol, 1.5 equiv.) was added. The reaction mixture was stirred for an additional 2 hours at ambient temperature, then quenched by the addition of water. The resulting solution was extracted with ethyl acetate, washed with brine, dried over anhydrous $Na_2SO_4$ and concentrated under vacuum. The residue was purified by flash column chromatography on silica gel, eluting with dichloromethane/methanol (10:1) to give 3-methyl-N-(5-((4-(trifluoromethyl)benzyl)oxy)-1H-indol-3-yl)oxetane-3-carboxamide (91.0 mg) as a white solid. LCMS Method F: $[M-H]^-=403$. $^1H$ NMR (400 MHz, DMSO-$d_6$): δ 10.73 (s, 1H), 9.49 (s, 1H), 7.77 (d, J=8.4 Hz, 2H), 7.72 (d, J=8.4 Hz, 2H), 7.65 (d, J=2.4 Hz, 1H), 7.36 (d, J=2.4 Hz, 1H), 7.27 (d, J=8.8 Hz, 1H), 6.88-6.86 (m, 1H), 5.21 (s, 2H), 4.88 (d, J=6.0 Hz, 2H), 4.40 (d, J=6.0 Hz, 2H), 1.65 (s, 3H).

Example 146: 3-methyl-N-(5-(4-(trifluoromethyl)phenethoxy)-1H-indol-3-yl)oxetane-3-carboxamide (Compound 238)

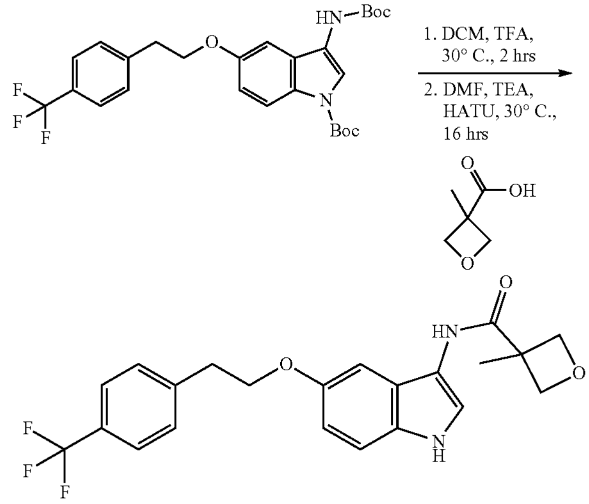

Compound 238 tert-butyl 3-{[(tert-butoxy)carbonyl]amino}-5-{2-[4-(trifluoromethyl)phenyl]ethoxy}-1H-indole-1-carboxylate (83.2 mg, 0.16 mmol, 1.0 equiv.) was dissolved in DCM (2 mL), and TFA (500 µl) was added in the mixture. The mixture was heated at 30° C. for 2 hours. The reaction mixture was concentrated by Speedvac to give a residue. The residue and 3-methyloxetane-3-carboxylic acid (37.1 mg, 0.32 mmol, 2.0 equiv.) were dissolved in DMF (2 mL), then TEA (116 µl, 0.8 mmol, 5.0 equiv.) and HATU (63.8 mg, 0.168 mmol, 1.05 equiv.) were added. The mixture was heated at 30° C. for 16 hours. The reaction mixture was concentrated by Speedvac to give a residue that was purified by prep HPLC to give 3-methyl-N-(5-(4-(trifluoromethyl)phenethoxy)-1H-indol-3-yl)oxetane-3-carboxamide (14.5 mg, 0.035 mmol) as a powder. MS-ESI, 419.2 $[M+H^+]$. $^1H$ NMR (400 MHz, DMSO-$d_6$) δ ppm 10.67 (br s, 1H), 9.46 (s, 1H), 7.71-7.64 (m, 3H), 7.63-7.56 (m, 2H), 7.27-7.24 (m, 1H), 7.22 (d, J=8.7 Hz, 1H), 6.74 (dd, J=8.8 Hz, 1H), 4.85 (d, J=6.0 Hz, 2H), 4.38 (d, J=6.0 Hz, 2H), 4.21 (t, J=6.7 Hz, 2H), 3.23-3.10 (m, 2H), 1.63 (s, 3H).

Example 147: 1-(methoxymethyl)-N-(5-{2-[4-(trifluoromethyl)phenoxy]ethyl}-1H-indol-3-yl)cyclopropane-1-carboxamide (Compound 176)

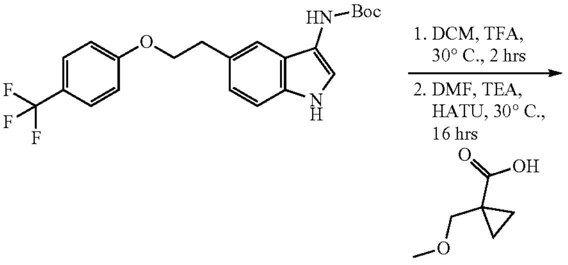

-continued

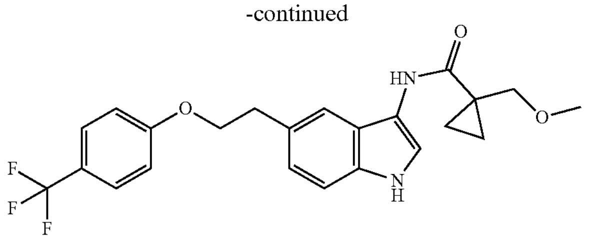

Compound 176 tert-butyl (5-(2-(4-(trifluoromethyl)phenoxy)ethyl)-1H-indol-3-yl)carbamate (83.2 mg, 0.16 mmol, 1.0 equiv.) was dissolved in DCM (2 mL), then TFA (500 µl) was added to the mixture. The reaction mixture was heated at 30° C. for 2 hours. The reaction mixture was concentrated by Speedvac to give a residue. The residue and 1-(methoxymethyl)cyclopropane-1-carboxylic acid (41.6 mg, 0.32 mmol, 2.0 equiv.) were dissolved in DMF (2 mL), then TEA (116 µl, 0.8 mmol, 5.0 equiv.) and HATU (63.8 mg, 0.168 mmol, 1.05 equiv.) were added. The mixture was heated at 30° C. for 16 hours. The reaction mixture was concentrated by Speedvac to give a residue that was purified by prep HPLC to give 1-(methoxymethyl)-N-(5-(2-(4-(trifluoromethyl)phenoxy)ethyl)-1H-indol-3-yl)cyclopropanecarboxamide (14.5 mg, 0.035 mmol) as a powder. MS-ESI, 433.2 [M+H$^+$]. $^1$H NMR (400 MHz, DMSO-$d_6$) δ ppm 10.76 (br s, 1H), 9.20 (s, 1H), 7.68-7.55 (m, 3H), 7.40 (s, 1H), 7.29 (d, J=8.2 Hz, 1H), 7.17-7.07 (m, 3H), 4.30 (t, J=6.9 Hz, 2H), 3.64 (s, 2H), 3.40 (s, 3H), 3.14 (br t, J=6.9 Hz, 2H), 1.15-1.06 (m, 2H), 0.86-0.71 (m, 2H).

Example 148: N-(5-{2-[(3aR,5S,6aS)-2-(2,2,2-trifluoroethyl)-octahydrocyclopenta[c]pyrrol-5-yl]ethoxy}-1H-indol-3-yl)oxane-4-carboxamide (Compound 152)

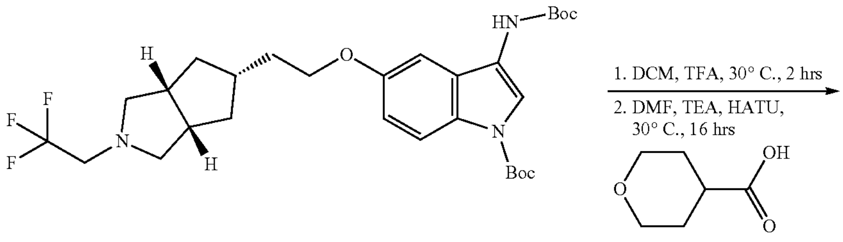

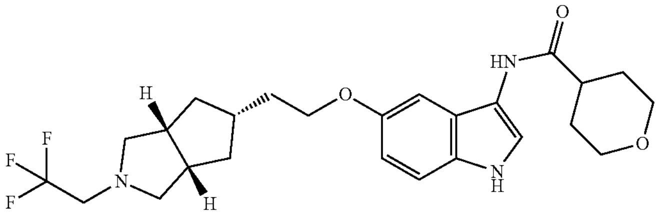

Compound 152

- tert-butyl 5-{2-[(3aR,5R,6aS)-2-(2,2,2-trifluoroethyl)-octahydrocyclopenta[c]pyrrol-5-yl]ethoxy}-3-{[(tert-butoxy)carbonyl]amino}-1H-indole-1-carboxylate (85.1 mg, 0.15 mmol, 1.0 equiv.) was dissolved in DCM (2 mL), then TFA (500 µl) was added to the mixture. The reaction mixture was heated at 30° C. for 2 hours. The reaction mixture was concentrated by Speedvac to give a residue. Then the residue and tetrahydro-2H-pyran-4-carboxylic acid (39.0 mg, 0.30 mmol, 2.0 equiv.) were dissolved in DMF (2 mL), then TEA (109 µl, 0.75 mmol, 5.0 equiv.) and HATU (59.9 mg, 0.158 mmol, 1.05 equiv.) were added. The mixture was heated at 30° C. for 16 hours. The reaction mixture was concentrated by Speedvac to give a residue that was purified by prep HPLC to give N-(5-{2-[(3aR,5S,6aS)-2-(2,2,2-trifluoroethyl)-octahydrocyclopenta[c]pyrrol-5-yl]ethoxy}-1H-indol-3-yl)oxane-4-carboxamide (14.0 mg, 0.029 mmol) as a powder. MS-ESI, 480.1 [M+H$^+$]. $^1$H NMR (400 MHz, DMSO-$d_6$) δ ppm 10.55 (d, J=2.0 Hz, 1H), 9.64 (s, 1H), 7.68 (d, J=2.5 Hz, 1H), 7.31 (d, J=2.3 Hz, 1H), 7.19 (d, J=8.8 Hz, 1H), 6.71 (dd, J=8.8, 2.4 Hz, 1H), 4.01-3.86 (m, 4H), 3.42-3.35 (m, 2H), 3.18 (q, J=10.3 Hz, 2H), 2.76-2.68 (m, 1H), 2.64 (d, J=8.4 Hz, 2H), 2.52 (d, J=1.9 Hz, 2H), 2.44-2.39 (m, 2H), 2.11-2.03 (m, 2H), 1.94-1.84 (m, 1H), 1.78 (q, J=6.5 Hz, 2H), 1.74-1.66 (m, 4H), 1.02-0.91 (m, 2H).

Example 149: 3-methoxy-N-{5-[(1S,3S)-3-[4-(trifluoromethyl)phenyl]cyclobutoxy]-1H-indol-3-yl}cyclobutane-1-carboxamide (Compound 159)

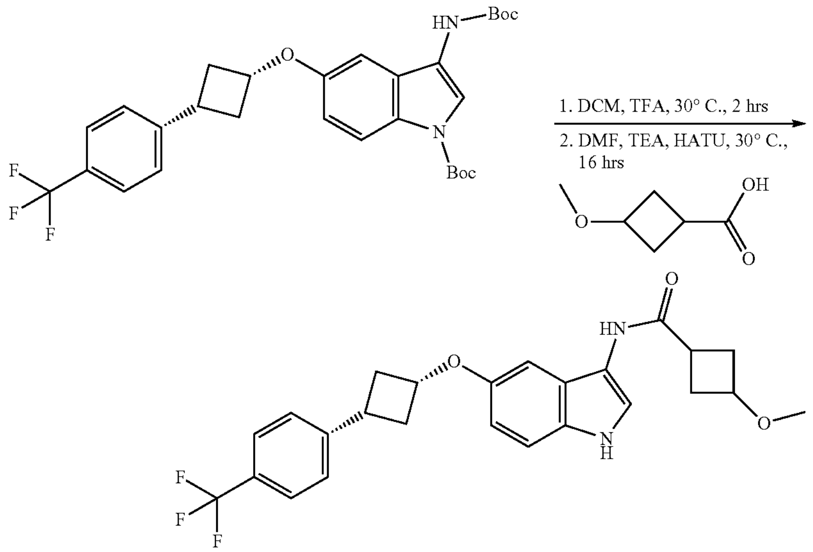

Compound 159 tert-butyl 3-{[(tert-butoxy)carbonyl]amino}-5-[(1S,3S)-3-[4-(trifluoromethyl)phenyl]cyclobutoxy]-1H-indole-1-carboxylate (81.9 mg, 0.15 mmol, 1.0 equiv.) was dissolved in DCM (2 mL), then TFA (500 μl) was added to the mixture. The reaction mixture was heated at 30° C. for 2 hours. The reaction mixture was concentrated by Speedvac to give a residue. The residue and 3-methoxycyclobutane-1-carboxylic acid (39.0 mg, 0.30 mmol, 2.0 equiv.) were dissolved in DMF (2 mL), then TEA (109 μl, 0.75 mmol, 5.0 equiv.) and HATU (59.9 mg, 0.158 mmol, 1.05 equiv.) were added. The mixture was heated at 30° C. for 16 hours. The reaction mixture was concentrated by Speedvac to give a residue that was purified by prep HPLC to give 3-methoxy-N-{5-[(1S,3S)-3-[4-(trifluoromethyl)phenyl]cyclobutoxy]-1H-indol-3-yl}cyclobutane-1-carboxamide (32.8 mg, 0.071 mmol) as a powder. MS-ESI, 459.3 [M+H+]0.1H NMR (400 MHz, DMSO-d6) δ ppm 10.60 (br s, 1H), 9.68 (s, 1H), 7.74-7.65 (m, 3H), 7.53 (d, J=8.1 Hz, 2H), 7.28-7.18 (m, 2H), 6.71 (dd, J=8.7, 2.2 Hz, 1H), 4.68 (q, J=7.2 Hz, 1H), 3.93-3.68 (m, 1H), 3.31-3.26 (m, 1H), 3.18-3.12 (m, 3H), 3.05-2.96 (m, 2H), 2.92-2.76 (m, 1H), 2.43-2.37 (m, 2H), 2.20-2.03 (m, 4H).

Example 150: 3-methoxy-N-{5-[(1S,3S)-3-[4-(trifluoromethyl)phenyl]cyclobutoxy]-1H-indol-3-yl}cyclobutane-1-carboxamide (Compound 156)

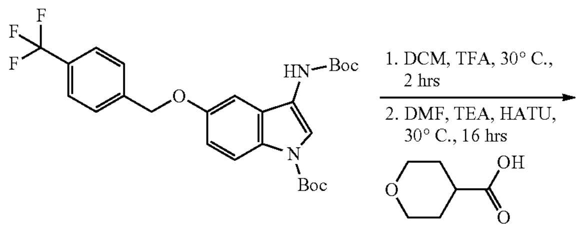

-continued

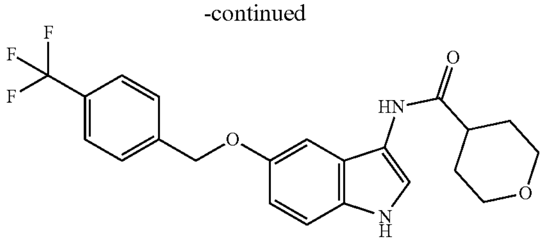

Compound 156 tert-butyl 3-{[(tert-butoxy)carbonyl]amino}-5-{[4-(trifluoromethyl)phenyl]methoxy}-1H-indole-1-carboxylate (86.0 mg, 0.17 mmol, 1.0 equiv.) was dissolved in DCM (2 mL), then TFA (500 μl) was added to the mixture. The reaction mixture was heated at 30° C. for 2 hours. The reaction mixture was concentrated by Speedvac to give the residue. Then the residue and tetrahydro-2H-pyran-4-carboxylic acid (44.2 mg, 0.34 mmol, 2.0 equiv.) were dissolved in DMF (2 mL), then TEA (123 μl, 0.85 mmol, 5.0 equiv.) and HATU (68.0 mg, 0.179 mmol, 1.05 equiv.) were added. The mixture was heated at 30° C. for 16 hours. The reaction mixture was concentrated by Speedvac to give a residue that was purified by prep HPLC to give N-(5-{[4-(trifluoromethyl)phenyl]methoxy}-1H-indol-3-yl)oxane-4-carboxamide (33.16 mg, 0.079 mmol) as a powder. MS-ESI, 419.3 $[M+H^+]$. $^1H$ NMR (400 MHz, DMSO-$d_6$) δ ppm 10.67-10.60 (m, 1H), 9.68 (s, 1H), 7.80-7.75 (m, 2H), 7.73-7.68 (m, 3H), 7.45 (d, J=2.3 Hz, 1H), 7.24 (d, J=8.8 Hz, 1H), 6.84 (dd, J=8.8, 2.3 Hz, 1H), 5.21 (s, 2H), 3.97-3.89 (m, 2H) 3.42-3.35 (m, 2H), 2.78-2.68 (m, 1H), 1.77-1.63 (in, 4H).

The analogs prepared in the following table were prepared using the above procedures with the appropriate starting material.

| Example # | Compound No. | Structure | LC-MS, MS-ESI, - - [M + H+]. |
|---|---|---|---|
| 151 | 239 | 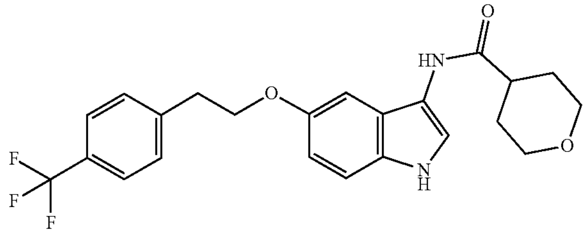 [SMILES: O=C(Nc1c[nH]c2ccc(OCCc3ccc(C(F)(F)F)cc3)cc12)C1CCOCC1] | 433.2 |
| 152 | 218 | 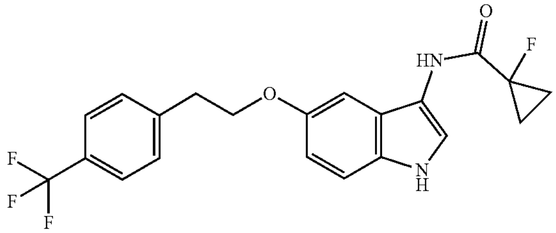 [SMILES: O=C(Nc1c[nH]c2ccc(OCCc3ccc(C(F)(F)F)cc3)cc12)C1(F)CC1] | 407.2 |
| 153 | 181 | 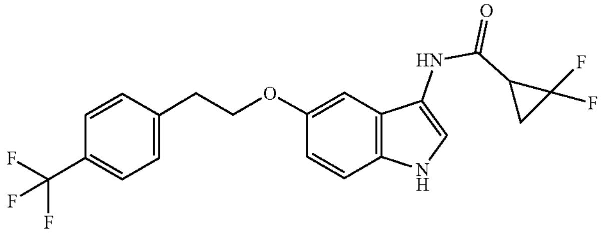 [SMILES: O=C(Nc1c[nH]c2ccc(OCCc3ccc(C(F)(F)F)cc3)cc12)C1CC1(F)F] | 425.2 |
| 154 | 180 | 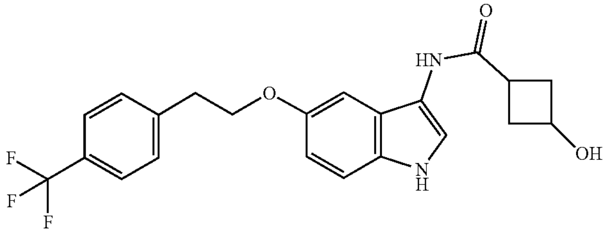 [SMILES: O=C(Nc1c[nH]c2ccc(OCCc3ccc(C(F)(F)F)cc3)cc12)C1CC(O)C1] | 419.2 |
| 155 | 238 | 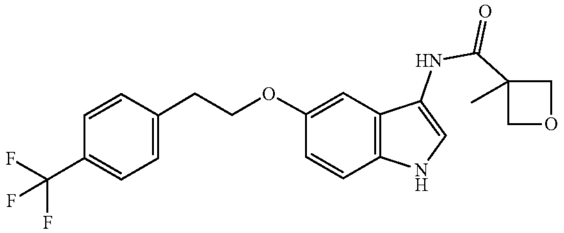 [SMILES: CC1(C(=O)Nc2c[nH]c3ccc(OCCc4ccc(C(F)(F)F)cc4)cc23)COC1] | 419.2 |
| 156 | 237 | 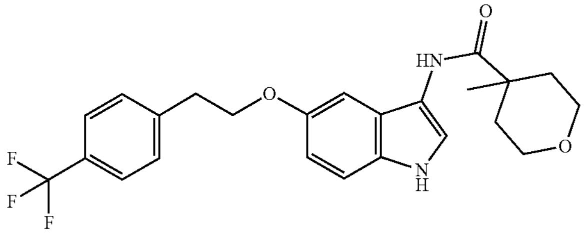 [SMILES: CC1(C(=O)Nc2c[nH]c3ccc(OCCc4ccc(C(F)(F)F)cc4)cc23)CCOCC1] | 447.2 |

-continued
| Example # | Compound No. | Structure | LC-MS, MS-ESI, - - [M + H$^+$]. |
| --- | --- | --- | --- |
| 157 | 251 | 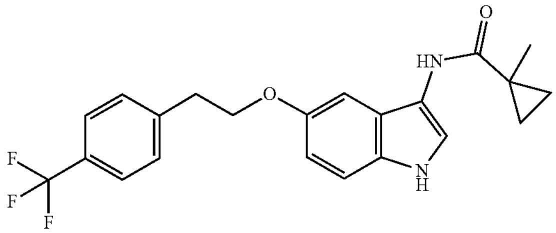 [SMILES: CC1(C(=O)Nc2c[nH]c3ccc(OCCc4ccc(C(F)(F)F)cc4)cc23)CC1] | 403.2 |
| 158 | 193 | 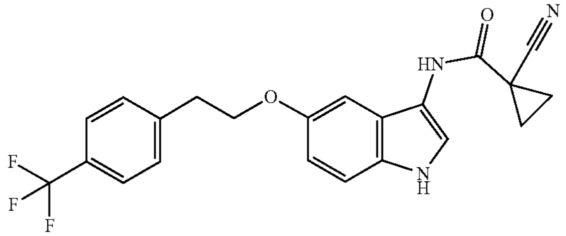 [SMILES: N#CC1(C(=O)Nc2c[nH]c3ccc(OCCc4ccc(C(F)(F)F)cc4)cc23)CC1] | 414.2 |
| 159 | 236 | 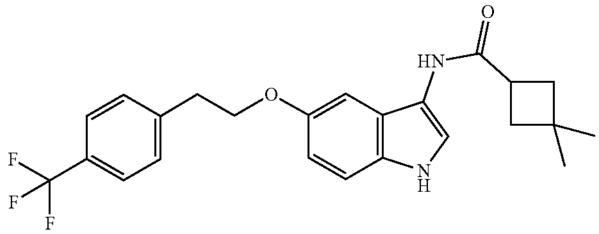 [SMILES: CC1(C)CC(C(=O)Nc2c[nH]c3ccc(OCCc4ccc(C(F)(F)F)cc4)cc23)C1] | 431.2 |
| 160 | 235 | 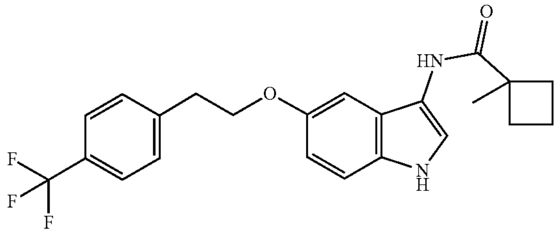 [SMILES: CC1(C(=O)Nc2c[nH]c3ccc(OCCc4ccc(C(F)(F)F)cc4)cc23)CCC1] | 417.2 |
| 161 | 234 | 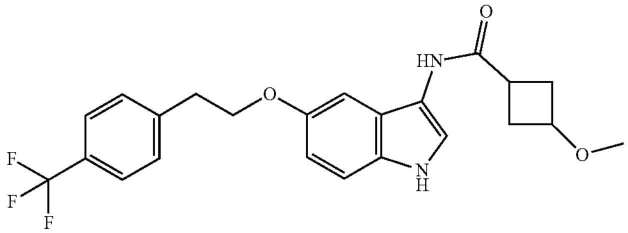 [SMILES: COC1CC(C(=O)Nc2c[nH]c3ccc(OCCc4ccc(C(F)(F)F)cc4)cc23)C1] | 433.2 |
| 162 | 192 | 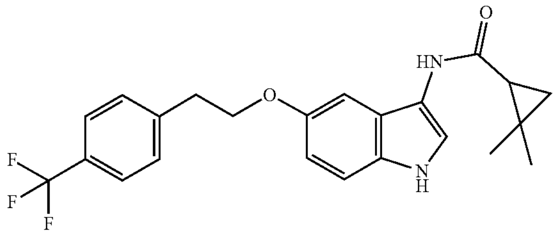 [SMILES: CC1(C)CC1C(=O)Nc1c[nH]c2ccc(OCCc3ccc(C(F)(F)F)cc3)cc12] | 417.1 |

-continued
| Example # | Compound No. | Structure | LC-MS, MS-ESI, -- [M + H+]. |
|---|---|---|---|
| 163 | 207 | 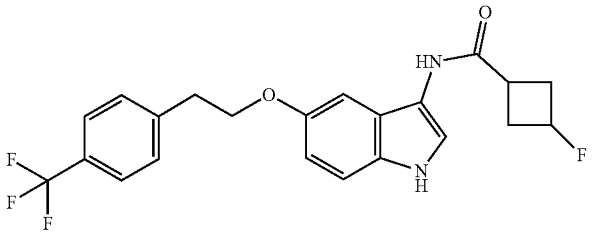 [SMILES: O=C(Nc1c[nH]c2ccc(OCCc3ccc(C(F)(F)F)cc3)cc12)C1CC(F)C1] | 421.2 |
| 164 | 191 | 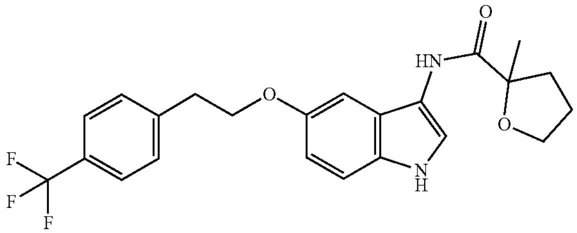 [SMILES: CC1(C(=O)Nc2c[nH]c3ccc(OCCc4ccc(C(F)(F)F)cc4)cc23)CCCO1] | 433.2 |
| 165 | 189 | 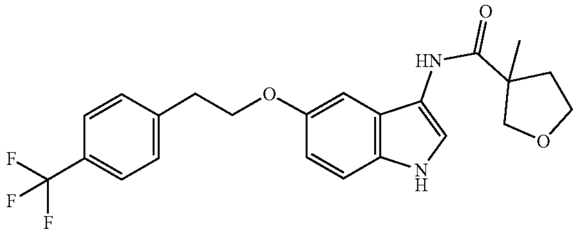 [SMILES: CC1(C(=O)Nc2c[nH]c3ccc(OCCc4ccc(C(F)(F)F)cc4)cc23)CCOC1] | 433.2 |
| 166 | 217 | 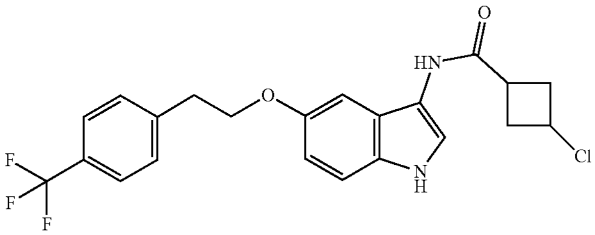 [SMILES: O=C(Nc1c[nH]c2ccc(OCCc3ccc(C(F)(F)F)cc3)cc12)C1CC(Cl)C1] | 437.1 |
| 167 | 204 | 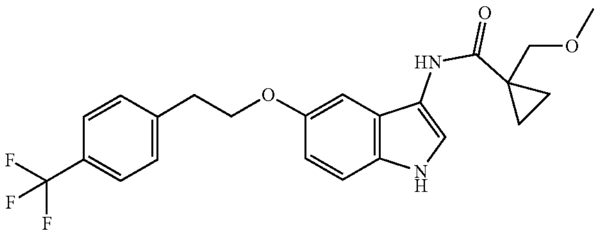 [SMILES: COCC1(C(=O)Nc2c[nH]c3ccc(OCCc4ccc(C(F)(F)F)cc4)cc23)CC1] | 433.2 |
| 168 | 187 | 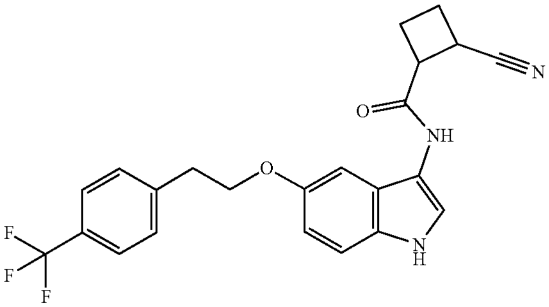 [SMILES: N#CC1CCC1C(=O)Nc1c[nH]c2ccc(OCCc3ccc(C(F)(F)F)cc3)cc12] | 428.1 |

-continued
| Example # | Compound No. | Structure | LC-MS, MS-ESI, - - [M + H⁺]. |
|---|---|---|---|
| 169 | 252 | 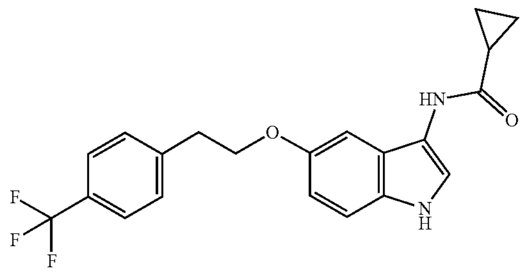 [SMILES: O=C(Nc1c[nH]c2ccc(OCCc3ccc(C(F)(F)F)cc3)cc12)C1CC1] | 389.3 |
| 170 | 186 | 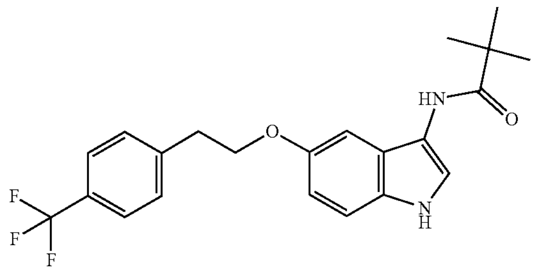 [SMILES: CC(C)(C)C(=O)Nc1c[nH]c2ccc(OCCc3ccc(C(F)(F)F)cc3)cc12] | 405.1 |
| 171 | 249 | 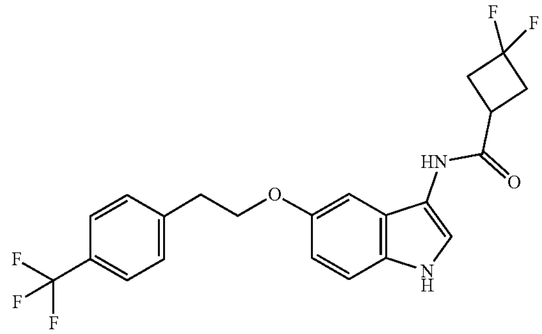 [SMILES: O=C(Nc1c[nH]c2ccc(OCCc3ccc(C(F)(F)F)cc3)cc12)C1CC(F)(F)C1] | 439.2 |
| 172 | 185 | 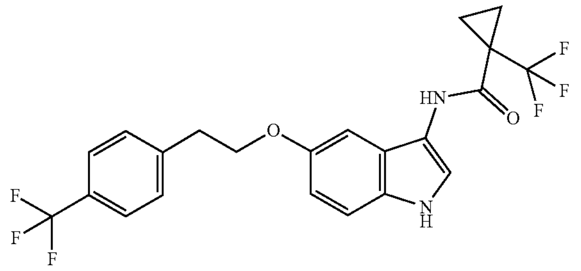 [SMILES: O=C(Nc1c[nH]c2ccc(OCCc3ccc(C(F)(F)F)cc3)cc12)C1(C(F)(F)F)CC1] | 457.1 |
| 173 | 202 | 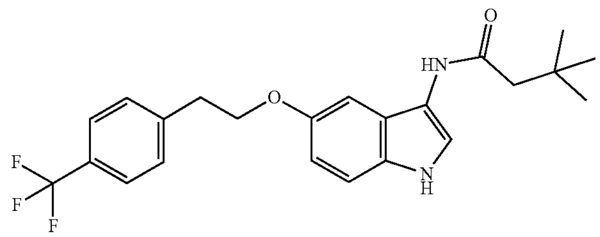 [SMILES: CC(C)(C)CC(=O)Nc1c[nH]c2ccc(OCCc3ccc(C(F)(F)F)cc3)cc12] | 419.2 |

-continued
| Example # | Compound No. | Structure | LC-MS, MS-ESI, - - [M + H+]. |
|---|---|---|---|
| 174 | 178 | 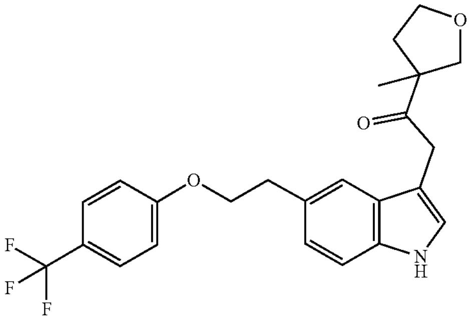 [SMILES: CC1(C(=O)Cc2c[nH]c3ccc(CCOc4ccc(C(F)(F)F)cc4)cc23)CCOC1] | 433.3 |
| 175 | 177 | 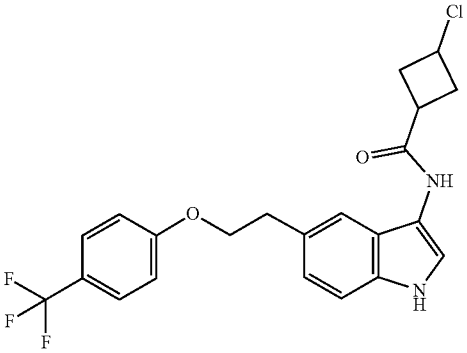 [SMILES: O=C(Nc1c[nH]c2ccc(CCOc3ccc(C(F)(F)F)cc3)cc12)C1CC(Cl)C1] | 437.2 |
| 176 | 176 | 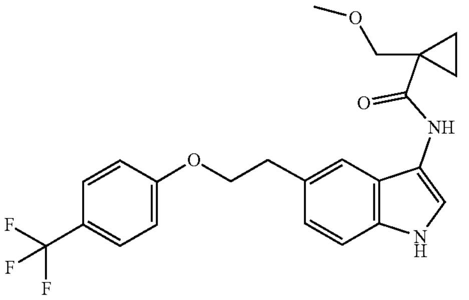 [SMILES: COCC1(C(=O)Nc2c[nH]c3ccc(CCOc4ccc(C(F)(F)F)cc4)cc23)CC1] | 433.2 |
| 177 | 175 | 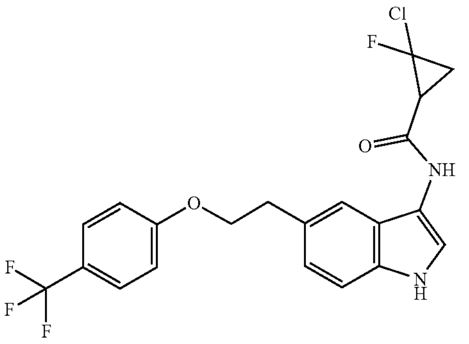 [SMILES: O=C(Nc1c[nH]c2ccc(CCOc3ccc(C(F)(F)F)cc3)cc12)C1CC1(F)Cl] | 441.1 |

-continued
| Example # | Compound No. | Structure | LC-MS, MS-ESI, -- [M + H+]. |
|---|---|---|---|
| 178 | 161 | 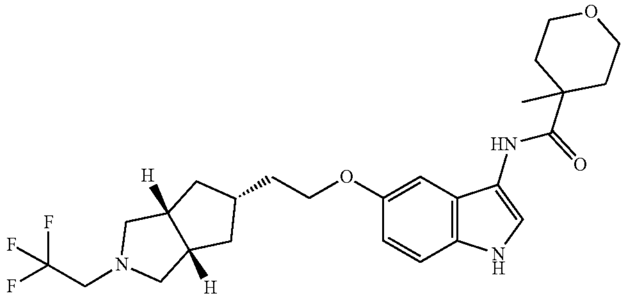 [SMILES: CC1(C(=O)Nc2c[nH]c3ccc(OCC[C@@H]4C[C@@H]5CN(CC(F)(F)F)C[C@@H]5C4)cc23)CCOCC1] | 494.4 |
| 179 | 160 | 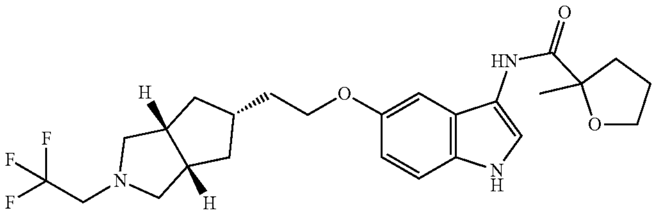 [SMILES: CC1(C(=O)Nc2c[nH]c3ccc(OCC[C@@H]4C[C@@H]5CN(CC(F)(F)F)C[C@@H]5C4)cc23)CCCO1] | 480.3 |
| 180 | 151 | 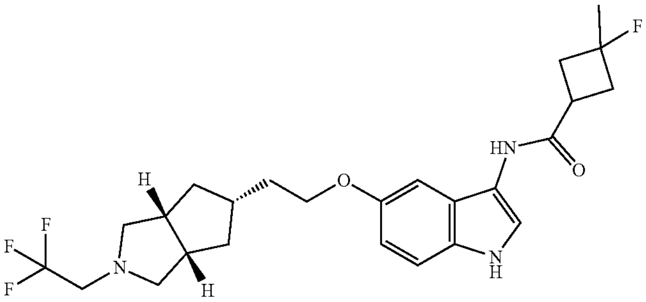 [SMILES: CC1(F)CC(C(=O)Nc2c[nH]c3ccc(OCC[C@@H]4C[C@@H]5CN(CC(F)(F)F)C[C@@H]5C4)cc23)C1] | 482.1 |
| 181 | 158 | 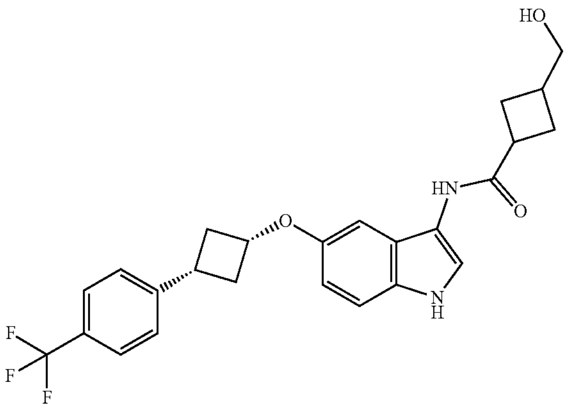 [SMILES: O=C(Nc1c[nH]c2ccc(O[C@H]3C[C@@H](c4ccc(C(F)(F)F)cc4)C3)cc12)C1CC(CO)C1] | 459.3 |

-continued
| Example # | Compound No. | Structure | LC-MS, MS-ESI, -- [M + H⁺]. |
|---|---|---|---|
| 182 | 157 | 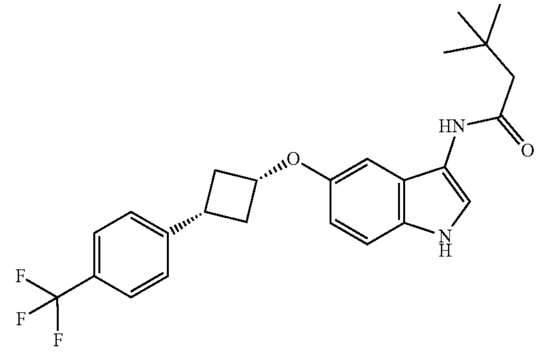 [SMILES: CC(C)(C)CC(=O)Nc1c[nH]c2ccc(O[C@H]3C[C@@H](c4ccc(C(F)(F)F)cc4)C3)cc12] | 445.4 |
| 183 | 155 | 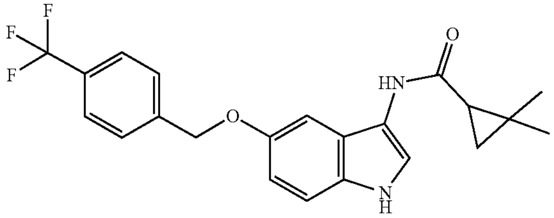 [SMILES: CC1(C)CC1C(=O)Nc1c[nH]c2ccc(OCc3ccc(C(F)(F)F)cc3)cc12] | 403.3 |
| 184 | 154 | 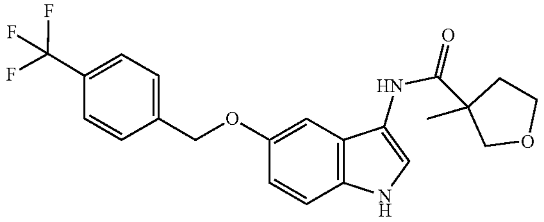 [SMILES: CC1(C(=O)Nc2c[nH]c3ccc(OCc4ccc(C(F)(F)F)cc4)cc23)CCOC1] | 419.3 |
| 185 | 153 | 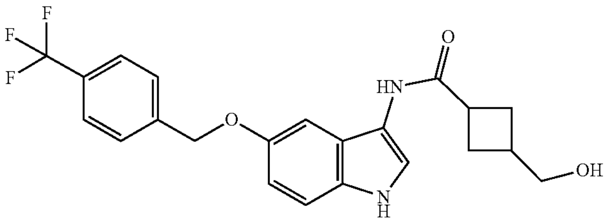 [SMILES: O=C(Nc1c[nH]c2ccc(OCc3ccc(C(F)(F)F)cc3)cc12)C1CC(CO)C1] | 419.3 |
Example 186: (1S,3S)-3-hydroxy-N-(5-(4-(trifluoromethyl)phenethoxy)-1H-indol-3-yl)cyclobutanecarboxamide (Compound 190)
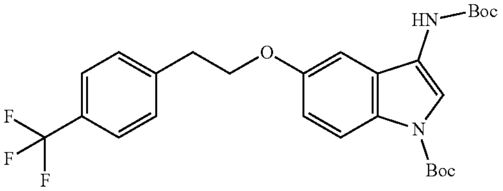
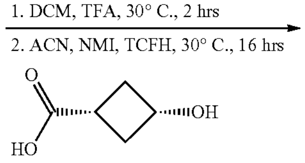

-continued

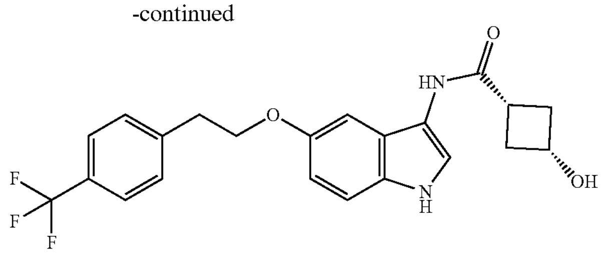

Compound 190 tert-butyl 3-{[(tert-butoxy)carbonyl] amino}1-5-{2-[4-(trifluoromethyl)phenyl]ethoxy}-1H-indole-1-carboxylate (83.2 mg, 0.16 mmol, 1.0 equiv.) was dissolved in DCM (2 mL), and TFA (500 μl) was added in the mixture. The mixture was heated at 30° C. for 2 hours. The reaction mixture was concentrated by Speedvac to give a residue. Then the residue and (1S,3S)-3-hydroxycyclobutane-1-carboxylic acid (37.1 mg, 0.32 mmol, 2.0 equiv.) were dissolved in ACN (2 mL), then NMI (0.5 mL) and TCFH (53.8 mg, 0.19 mmol, 1.2 equiv.) were added. The mixture was heated at 30° C. for 16 hours. The reaction mixture was concentrated by Speedvac to give a residue that was purified by prep HPLC to give (1S, 3S)-3-hydroxy-N-(5-{2-[4-(trifluoromethyl)phenyl]ethoxy}-1H-indol-3-yl)cyclobutane-1-carboxamide (27.0 mg, 0.064 mmol) as a powder. MS-ESI, 419.1 [M+H$^+$]. $^1$H NMR (400 MHz, DMSO-d6) δ ppm 10.61-10.52 (m, 1H), 9.57 (s, 1H), 7.69 (dd, J=5.2, 2.6 Hz, 3H), 7.59 (d, J=8.0 Hz, 2H), 7.31 (d, J=2.2 Hz, 1H), 7.19 (d, 1H), 6.71 (dd, J=8.8, 2.3 Hz, 1H), 5.14 (br d, J=6.4 Hz, 1H), 4.19 (t, J=6.7 Hz, 2H), 4.04-3.92 (m, 1H), 3.25-3.09 (m, 2H), 2.73-2.63 (m, 1H), 2.39-2.25 (m, 2H), 2.15-1.97 (m, 2H).

Example 187: (1S,3S)-3-hydroxy-N-(5-{2-[4-(trifluoromethyl)phenoxy]ethyl}-1H-indol-3-yl)cyclobutane-1-carboxamide (Compound 179)

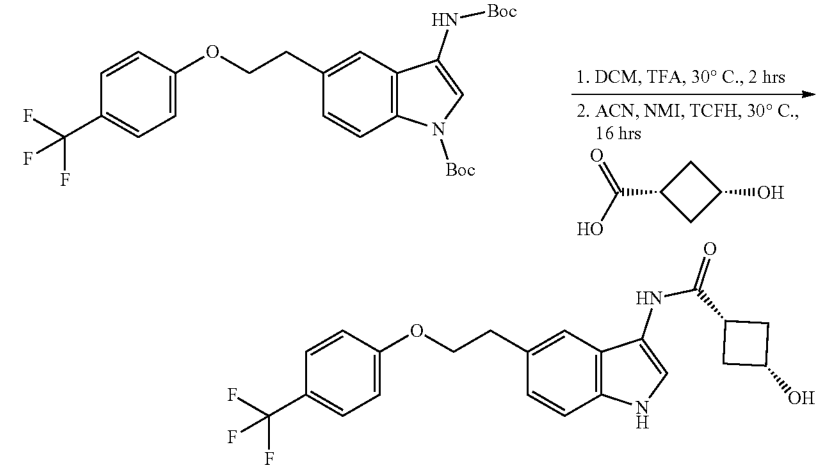

Compound 179 tert-butyl (5-(2-(4-(trifluoromethyl)phenoxy)ethyl)-1H-indol-3-yl)carbamate (83.2 mg, 0.16 mmol, 1.0 equiv.) was dissolved in DCM (2 mL), then TFA (500 μl) was added to the mixture. The reaction mixture was heated at 30° C. for 2 hours. The reaction mixture was concentrated by Speedvac to a residue. Then the residue and (1S,3S)-3-hydroxycyclobutane-1-carboxylic acid (37.1 mg, 0.32 mmol, 2.0 equiv.) were dissolved in ACN (2 mL), then NMI (0.5 mL) and TCFH (53.8 mg, 0.192 mmol, 1.2 equiv.) were added. The mixture was heated at 30° C. for 16 hours. The mixture was heated at 30° C. for 16 hours. The reaction mixture was concentrated by Speedvac to give a residue that was purified by prep HPLC to give (1S,3S)-3-hydroxy-N-(5-{2-[4-(trifluoromethyl)phenoxy]ethyl}-1H-indol-3-yl)cyclobutane-1-carboxamide (14.52 mg, 0.035 mmol) as a powder. MS-ESI, 419.2 [M+H$^+$]. $^1$H NMR (400 MHz, DMSO-$d_6$) δ ppm 10.72-10.65 (m, 1H), 9.68 (s, 1H), 7.72-7.60 (m, 4H), 7.26 (d, J=8.3 Hz, 1H), 7.16-7.05 (m, 3H), 5.14 (d, J=7.0 Hz, 1H), 4.29 (t, J=7.0 Hz, 2H), 4.04-3.92 (m, 1H), 3.16-3.07 (m, 2H), 2.78-2.68 (m, 1H), 2.39-2.27 (m, 2H), 2.15-1.95 (m, 2H).

Example 188: (1R,3S)—N-(5-{2-[(3aR,5S,6aS)-2-(2,2,2-trifluoroethyl)-octahydrocyclopenta[c]pyrrol-5-yl]ethoxy}-1H-indol-3-yl)-3-methylcyclobutane-1-carboxamide (Compound 150)

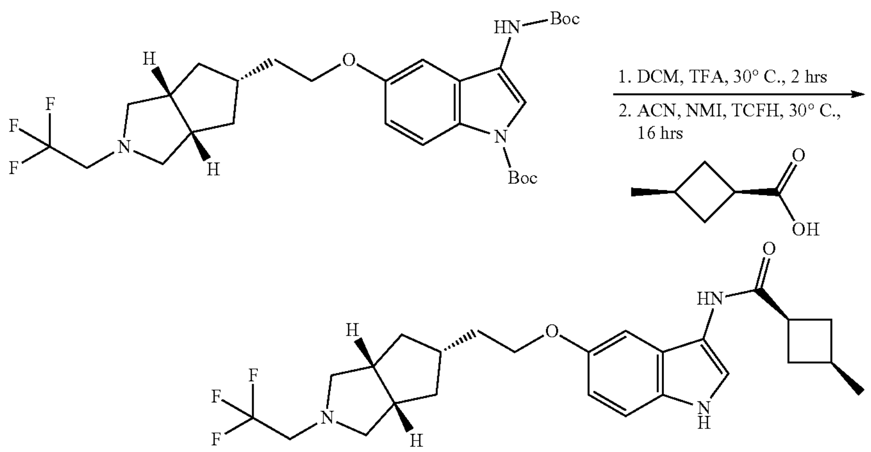

Compound 150 tert-butyl 3-{[(tert-butoxy)carbonyl]amino}-5-[(1S,3S)-3-[4-(trifluoromethyl)phenyl]cyclobutoxy]-1H-indole-1-carboxylate (81.9 mg, 0.15 mmol, 1.0 equiv.) was dissolved in DCM (2 mL), then TFA (500 μl) was added to the mixture. The reaction mixture was heated at 30° C. for 2 hours. The reaction mixture was concentrated by Speedvac to give a residue. Then the residue and (1R,3S)-3-methylcyclobutane-1-carboxylic acid (34.2 mg, 0.30 mmol, 2.0 equiv.) were dissolved in ACN (2 mL), then NMI (0.5 mL) and TCFH (50.4 mg, 0.18 mmol, 1.2 equiv.) were added. The mixture was heated at 30° C. for 16 hours. The reaction mixture was concentrated by Speedvac to give a residue that was purified by prep HPLC to give (1R,3S)—N-(5-{2-[(3aR,5S,6aS)-2-(2,2,2-trifluoroethyl)-octahydrocyclopenta[c]pyrrol-5-yl]ethoxy}-1H-indol-3-yl)-3-methylcyclobutane-1-carboxamide (30.5 mg, 0.066 mmol) as a powder. MS-ESI, 464.4 [M+H$^+$]. $^1$H NMR (400 MHz, DMSO-$d_6$) δ ppm 10.57-10.51 (m, 1H), 9.51 (s, 1H), 7.68 (d, J=2.4 Hz, 1H), 7.29 (d, J=2.3 Hz, 1H), 7.18 (d, J=8.8 Hz, 1H), 6.70 (dd, J=8.8, 2.3 Hz, 1H), 3.95 (t, J=6.5 Hz, 2H), 3.22-3.09 (m, 3H), 2.68-2.61 (m, 2H), 2.46-2.39 (m, 3H), 2.39-2.16 (m, 4H), 2.11-2.02 (m, 2H), 1.94-1.74 (m, 5H), 1.04 (d, J=6.3 Hz, 3H), 0.96 (td, J=11.7, 8.4 Hz, 2H).

The analogs prepared in the following table were prepared using the above procedures with the appropriate starting material.

| Example # | Compound No. | Structure | LC-MS, MS-ESI, -- [M+H$^+$]. |
|---|---|---|---|
| 189 | 190 | 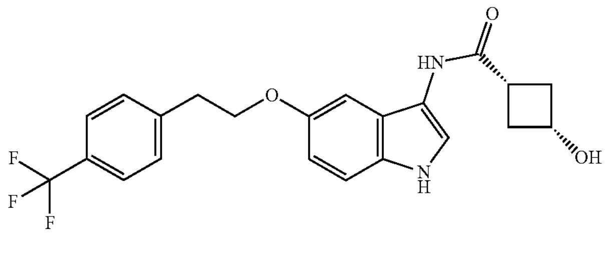 [SMILES: O=C(Nc1c[nH]c2ccc(OCCc3ccc(C(F)(F)F)cc3)cc12)[C@H]1C[C@@H](O)C1] | 419.1 |
| 190 | 206 | 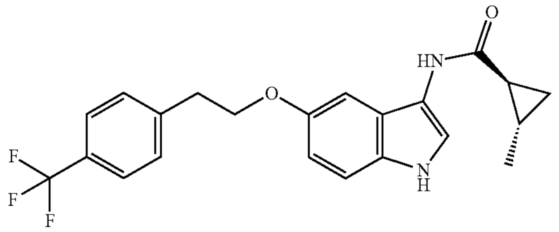 [SMILES: C[C@H]1C[C@@H]1C(=O)Nc1c[nH]c2ccc(OCCc3ccc(C(F)(F)F)cc3)cc12] | 403.2 |

-continued
| Example # | Compound No. | Structure | LC-MS, MS-ESI, -- [M+H+]. |
|---|---|---|---|
| 191 | 162 | 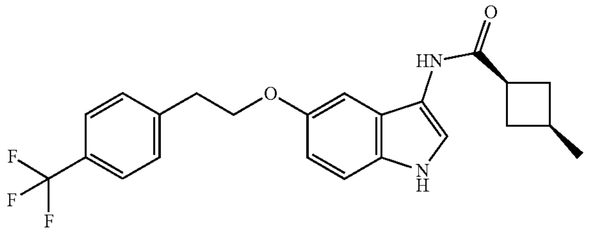 [SMILES: C[C@H]1C[C@@H](C(=O)Nc2c[nH]c3ccc(OCCc4ccc(C(F)(F)F)cc4)cc23)C1] | 417.3 |
| 192 | 205 | 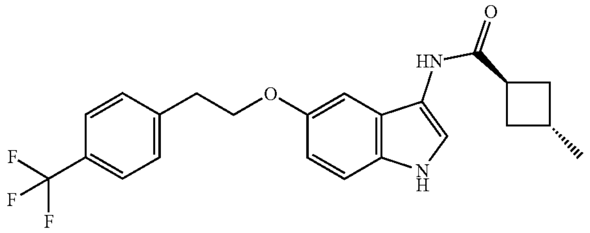 [SMILES: C[C@H]1C[C@H](C(=O)Nc2c[nH]c3ccc(OCCc4ccc(C(F)(F)F)cc4)cc23)C1] | 417.3 |
| 193 | 203 | 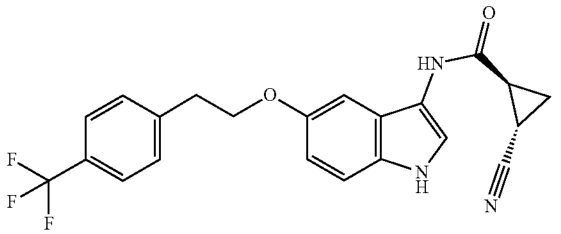 [SMILES: N#C[C@H]1C[C@@H]1C(=O)Nc1c[nH]c2ccc(OCCc3ccc(C(F)(F)F)cc3)cc12] | 414.2 |
| 194 | 188 | 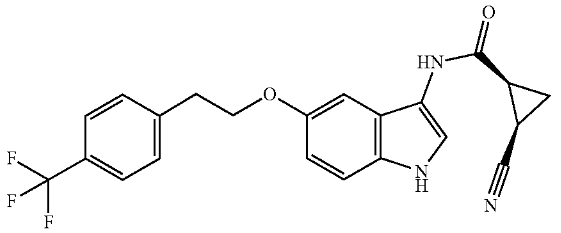 [SMILES: N#C[C@@H]1C[C@@H]1C(=O)Nc1c[nH]c2ccc(OCCc3ccc(C(F)(F)F)cc3)cc12] | 414.2 |
| 195 | 179 | 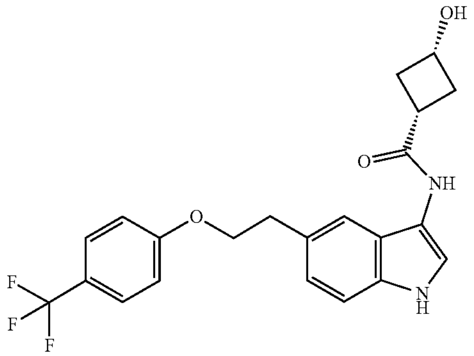 [SMILES: O=C(Nc1c[nH]c2ccc(CCOc3ccc(C(F)(F)F)cc3)cc12)[C@H]1C[C@@H](O)C1] | 419.2 |

Example 196: N-(5-(2-(cis-4-hydroxy-4-(trifluoromethyl)cyclohexyl)ethoxy)-1H-indol-3-yl)acetamide (compound 501)

Compound 501

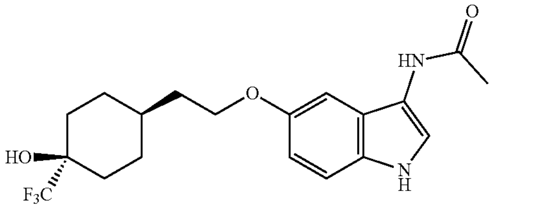

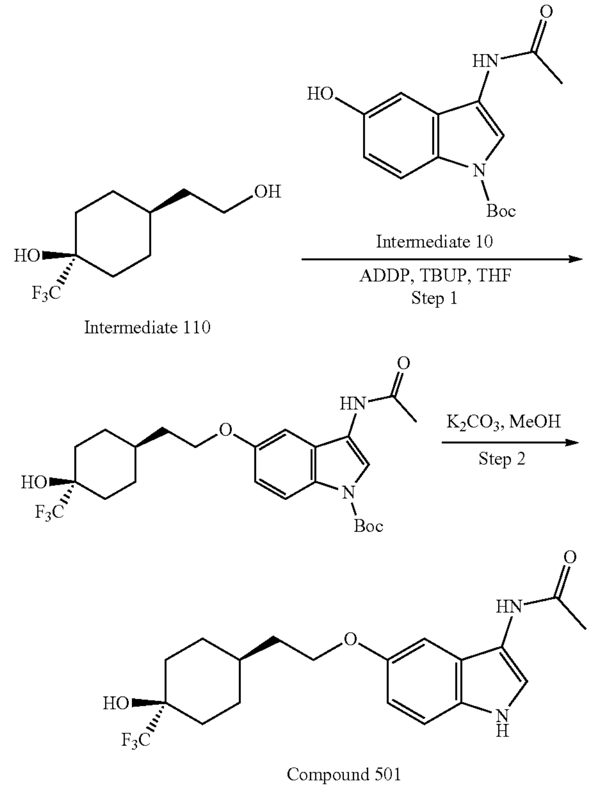

Step 1: tert-butyl 3-acetamido-5-{2-[4-hydroxy-4-(trifluoromethyl)cyclohexyl]ethoxy}indole-1-carboxylate 4-(2-hydroxyethyl)-1-(trifluoromethyl)cyclohexan-1-ol (132.0 mg, 0.6 mmol, 1.2 equiv.) and tert-butyl 3-acetamido-5-hydroxyindole-1-carboxylate (150.0 mg, 0.5 mmol, 1.0 equiv.) were dissolved in THE (10 mL), then TBUP (209.0 mg, 1.0 mmol, 2.0 equiv.) and ADDP (259.0 mg, 1.0 mmol, 2.0 equiv.) were added at 0° C. under an atmosphere of nitrogen. The reaction mixture was stirred for 16 hours at rt and concentrated under vacuum. The residue was purified by silica gel column chromatography, eluting with petroleum ether/EtOAc (5:1) to afford tert-butyl 3-acetamido-5-{2-[4-hydroxy-4-(trifluoromethyl)cyclohexyl]ethoxy}indole-1-carboxylate (200.0 mg) as a pale white solid. LCMS Method A: $[M+H]^+$=485.1.

Step 2: N-(5-(2-(cis-4-hydroxy-4-(trifluoromethyl)cyclohexyl)ethoxy)-1H-indol-3-yl)acetamide tert-Butyl 3-acetamido-5-{2-[4-hydroxy-4-(trifluoromethyl)cyclohexyl]ethoxy}indole-1-carboxylate (200.0 mg, 0.4 mmol, 1.0 equiv.) was dissolved in MeOH (5 mL), then $K_2CO_3$ (115.4 mg, 0.8 mmol, 2.0 equiv.) was added. The reaction mixture was heated to 60° C. for 16 hours, then cooled t rt and quenched by the addition of water. The resulting solution was extracted with EtOAc, washed with brine, dried over anhyd. $Na_2SO_4$ and concentrated under vacuum. The residue was purified by Prep-HPLC with the following conditions: Column: XBridge Shield RP18 OBD Column, 30*150 mm, 5 m; Mobile Phase A: Water (0.1% FA), Mobile Phase B: ACN; Flow rate: 60 mL/min; Gradient: 34% B to 46% B in 8 min; Wave Length: 254; 220 nm; RT1: 6.83 min. This gave N-(5-(2-(cis-4-hydroxy-4-(trifluoromethyl)cyclohexyl)ethoxy)-1H-indol-3-yl)acetamide (37.5 mg) as a pale white solid. LCMS Method D: $[M+H]^+$ =385.1. $^1H$ NMR (400 MHz, DMSO-$d_6$): δ 10.55 (s, 1H), 9.67 (s, 1H), 7.64 (d, J=2.4 Hz, 1H), 7.31 (d, J=2.4 Hz, 1H), 7.20 (d, J=8.8 Hz, 1H), 6.73-6.71 (m, 1H), 5.66 (s, 1H), 4.00 (t, J=6.4 Hz, 2H), 2.08 (s, 3H), 1.90-1.70 (m, 7H), 1.54-1.45 (m, 4H).

The Analogs Prepared in the Following Table were Prepared Using the Same Method Described for Example 196.

| example # | Compound # | Starting materials Used | Structure | Condition | LCMS data |
|---|---|---|---|---|---|
| 197 | 498 | Intermediate 67/ Intermediate 104 | 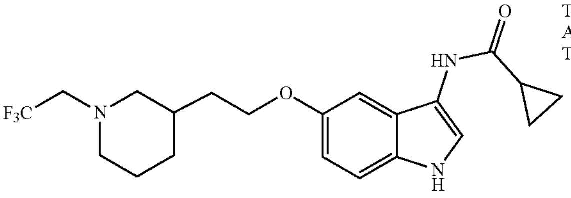 | TBUP, ADDP, THF | Method F: MS-ESI: 410.2 [M + H]$^+$. |

-continued

| example # | Compound # | Starting materials Used | Structure | Condition | LCMS data |
|---|---|---|---|---|---|
| 198 | 497 | 1-(4-(trifluoromethyl)phenyl)ethan-1-01/ Intermediate 10 | 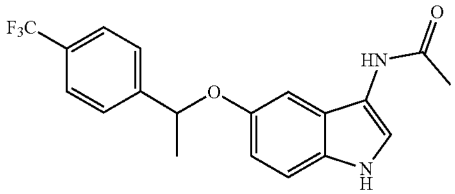 [SMILES: CC(=O)Nc1c[nH]c2ccc(OC(C)c3ccc(C(F)(F)F)cc3)cc12] | TBUP, ADDP, THF | Method E: MS-ESI: 361.1 [M − H]+. |
| 199 | 494 | Intermediate 111/ Intermediate 10 | 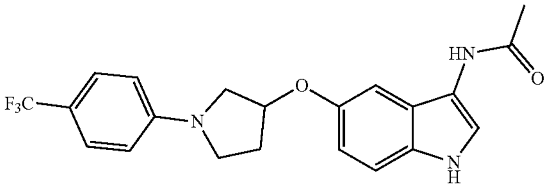 [SMILES: CC(=O)Nc1c[nH]c2ccc(OC3CCN(c4ccc(C(F)(F)F)cc4)C3)cc12] | $PPh_3$, DEAD, THF | Method F: MS-ESI: 404.0 [M + H]+. |
| 200 | 485 | Intermediate 112/ Intermediate 104 | 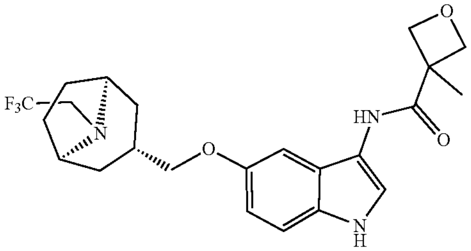 [SMILES: CC1(C(=O)Nc2c[nH]c3ccc(OC[C@@H]4C[C@H]5CC[C@@H](C4)N5CC(F)(F)F)cc23)COC1] | TBUP, ADDP, THF | Method F: MS-ESI: 452.1[M + H]+. |
| 201 | 484 | Intermediate 113/ Intermediate 10 | 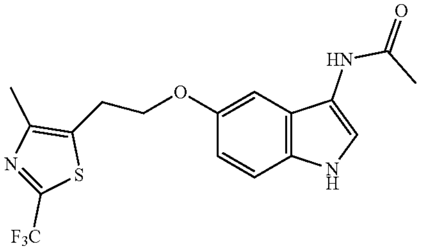 [SMILES: CC(=O)Nc1c[nH]c2ccc(OCCc3sc(C(F)(F)F)nc3C)cc12] | $PPh_3$, DIAD, Py, THF | Method D: MS-ESI: 382.1[M − H]+. |
| 202 | 479 | Intermediate 64/ Intermediate 104 | 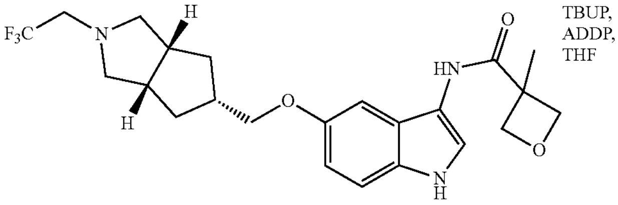 | TBUP, ADDP, THF | Method F: MS-ESI: 452.2 [M + H]+. |
| 203 | 474 | Intermediate 116/ Intermediate 10 | 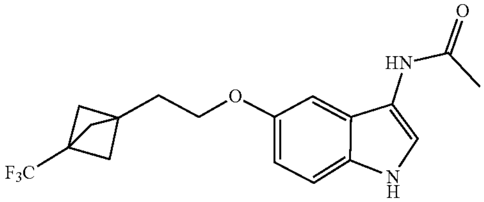 [SMILES: CC(=O)Nc1c[nH]c2ccc(OCCC34CC(C(F)(F)F)(C3)C4)cc12] | TBUP, ADDP, THF | Method F: MS-ESI: 353.2 [M + H]+. |

-continued

| example # | Compound # | Starting materials Used | Structure | Condition | LCMS data |
|---|---|---|---|---|---|
| 204 | 473 | Intermediate 118/ Intermediate 10 | 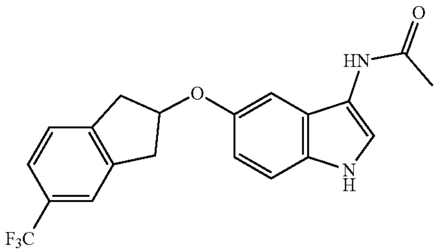 [SMILES: CC(=O)Nc1c[nH]c2ccc(OC3Cc4ccc(C(F)(F)F)cc4C3)cc12] | CMPB, toluene | Method F: MS-ESI: 375.3[M + H]+. |
| 205 | 472 | Intermediate 117/ Intermediate 10 | 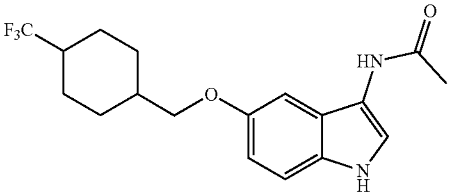 [SMILES: CC(=O)Nc1c[nH]c2ccc(OCC3CCC(C(F)(F)F)CC3)cc12] | TBUP, ADDP, THF | Method F: MS-ESI: 355.3 [M + H]+. |
| 206 | 458 | 2-(bicyclo[1.1.1] pentan-1-yl)ethan-1-ol/ Intermediate 10 | 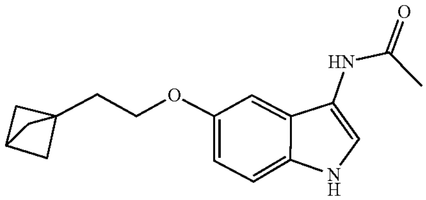 [SMILES: CC(=O)Nc1c[nH]c2ccc(OCCC34CC(C3)C4)cc12] | TBUP, ADDP, THF | Method F: MS-ESI: 285.2[M + H]+. |
| 207 | 437 | Intermediate 121/ Intermediate 10 | 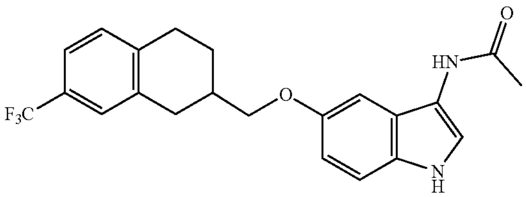 [SMILES: CC(=O)Nc1c[nH]c2ccc(OCC3CCc4ccc(C(F)(F)F)cc4C3)cc12] | TBUP, ADDP, THF | Method F: MS-ESI: 401.1[M − H]+. |
| 208 | 436 | Intermediate 119/ Intermediate 10 | 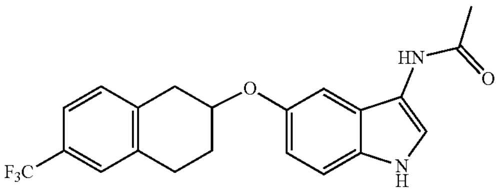 [SMILES: CC(=O)Nc1c[nH]c2ccc(OC3CCc4cc(C(F)(F)F)ccc4C3)cc12] | DBAD, $PPh_3$, THF | Method F: MS-ESI: 389.1[M + H]+. |
| 209 | 435 | Intermediate 122/ Intermediate 10 | 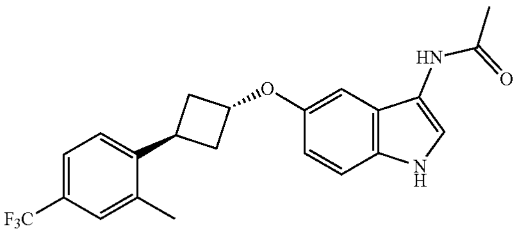 [SMILES: CC(=O)Nc1c[nH]c2ccc(O[C@H]3C[C@H](c4ccc(C(F)(F)F)cc4C)C3)cc12] | TBUP, ADDP, THF | Method E: MS-ESI: 403.2[M + H]+. |

Examples 210/211: N-(5-(2-(trans-4-(trifluoromethyl)cyclohexyl)ethoxy)-1H-indol-3-yl)acetamide [(compound 456) and N-(5-(2-(cis-4-(trifluoromethyl)cyclohexyl)ethoxy)-1H-indol-3-yl)acetamide (compound 454)

Compound 456

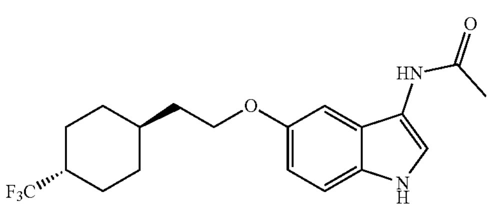

Compound 454

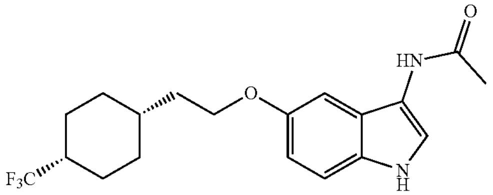

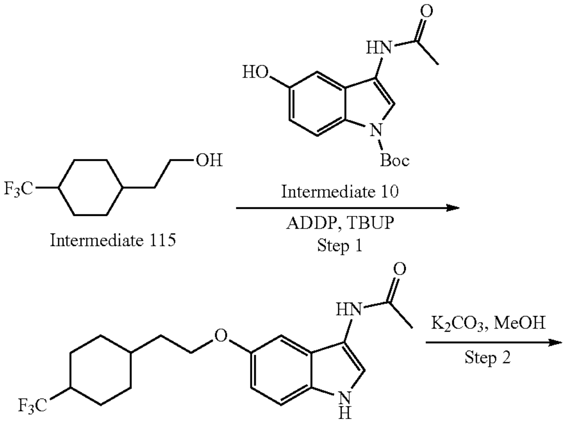

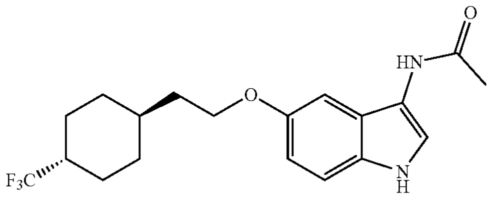

Compound 456

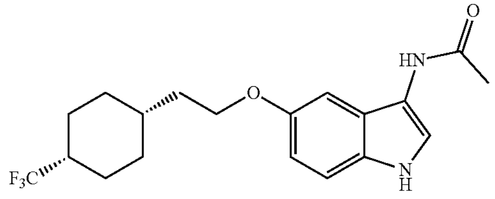

Compound 454

Step 1: tert-butyl 3-acetamido-5-(2-(4-(trifluoromethyl)cyclohexyl)ethoxy)-1H-indole-1-carboxylate tert-Butyl 3-acetamido-5-hydroxy-1H-indole-1-carboxylate (488.2 mg, 1.7 mmol, 1.0 equiv.) and 2-(4-(trifluoromethyl)cyclohexyl)ethan-1-ol (330.0 mg, 1.7 mmol, 1.0 equiv.) were dissolved in THE (5 mL) and cooled to 0° C., then TBUP (1.4 g, 6.7 mmol, 4.0 equiv.) and ADDP (842.1 mg, 3.3 mmol, 2.0 equiv.) were added under an atmosphere of nitrogen. The reaction mixture was stirred for 2 hours at 70° C., then cooled to rt and quenched by the addition of water. The resulting solution was extracted with EtOAc, washed with brine, dried over anhyd. sodium sulfate and concentrated under vacuum. The residue was purified by silica gel column chromatography, eluting with petroleum ether/EtOAc (1:1) to afford tert-butyl 3-acetamido-5-(2-(4-(trifluoromethyl)cyclohexyl)ethoxy)-1H-indole-1-carboxylate (500.0 mg) as a brown solid. LCMS Method A: $[M+H]^+$ =469.2.

Step 2: N-(5-(2-(trans-4-(trifluoromethyl)cyclohexyl)ethoxy)-1H-indol-3-yl)acetamide (Front Peak) and N-(5-(2-(cis-4-(trifluoromethyl)cyclohexyl) ethoxy)-1H-indol-3-yl)acetamide (Second Peak)

tert-Butyl 3-acetamido-5-(2-(4-(trifluoromethyl)cyclohexyl)ethoxy)-1H-indole-1-carboxylate (480 mg, 1.0 mmol, 1.0 equiv.) was dissolved in MeOH (5 mL), then $K_2CO_3$ (283.2 mg, 2.1 mmol, 2.0 equiv.) was added. The reaction mixture was stirred for 1 hour at 70° C., then cooled to rt and quenched by the addition of water. The resulting solution was extracted with EtOAc, washed with brine, dried over anhyd. sodium sulfate and concentrated under vacuum. The residue was purified by Prep-HPLC with the following conditions: Column: Xselect CSH C18 OBD Column 30*150 mm 5 m, n; Mobile Phase A: Water (0.1% FA), Mobile Phase B: ACN; Flow rate: 60 mL/min; Gradient: 47% B to 57% B in 9 min, 57% B; Wave Length: 254; 220 nm; RT1: 7.75 min, RT2: 8.15 min. This resulted in N-(5-(2-(trans-4-(trifluoromethyl)cyclohexyl)ethoxy)-1H-indol-3-yl)acetamide (front peak, absolute stereochemistry unconfirmed, assigned as Compound 456 (14.2 mg, 3.7%) as a white solid and N-(5-(2-(cis-4-(trifluoromethyl)cyclohexyl) ethoxy)-1H-indol-3-yl)acetamide (second peak, absolute stereochemistry unconfirmed, assigned as Compound 454 (16.3 mg, 4.1%) as a white solid.

Compound 456: LCMS Method E: $[M+H]^+$=369.4. $^1H$ NMR (400 MHz, DMSO-$d_6$): δ 10.57 (s, 1H), 9.70 (s, 1H), 7.65 (d, J=2.4 Hz, 1H), 7.31 (d, J=2.4 Hz, 1H), 7.20 (d, J=8.8 Hz, 1H), 6.73-6.71 (m, 1H), 3.99 (t, J=6.4 Hz, 2H), 2.31-2.29 (m, 1H), 2.08 (s, 3H), 1.92-1.90 (m, 1H), 1.81-1.76 (m, 2H), 1.67-1.60 (m, 8H).

Compound 454: LCMS Method E: $[M+H]^+$=369.4. $^1H$ NMR (400 MHz, DMSO-$d_6$): δ 10.57 (s, 1H), 9.70 (s, 1H), 7.65 (d, J=2.4 Hz, 1H), 7.31 (d, J=2.4 Hz, 1H), 7.20 (d, J=8.8 Hz, 1H), 6.73-6.71 (m, 1H), 4.00 (t, J=6.4 Hz, 2H), 2.24-2.18 (m, 1H), 2.09 (s, 3H), 1.90-1.87 (m, 4H), 1.70-1.65 (m, 2H), 1.55-1.41 (m, 2H), 1.31-1.19 (m, 2H), 1.11-1.02 (m, 2H).

The Analogs Prepared in Following Table were Prepared Using the Same Method Described for Example 210/211.

| Compound | Compound # | Starting materials Used | Structure | LCMS data |
|---|---|---|---|---|
| 212 | 448 | Intermediate 120 /Intermediate 10 | 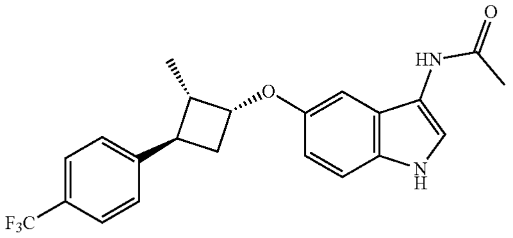 [SMILES: CC(=O)Nc1c[nH]c2ccc(O[C@@H]3C[C@@H](c4ccc(C(F)(F)F)cc4)[C@@H]3C)cc12] | Method F: MS-ESI: 401.0 [M-H]$^+$. |
| 213 | 596 | Intermediate 120 /Intermediate 10 | 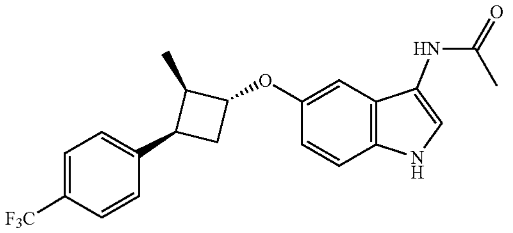 [SMILES: CC(=O)Nc1c[nH]c2ccc(O[C@@H]3C[C@@H](c4ccc(C(F)(F)F)cc4)[C@H]3C)cc12] | Method E: MS-ESI: 401.1 [M-H]$^+$. |

Examples 214/215: N-(5-((2-(2,2,2-trifluoroethyl)-2,4,5,6-tetrahydrocyclopenta[c]pyrazol-5-yl)methoxy)-1H-indol-3-yl)acetamide (compound 447) and N-(5-((1-(2,2,2-trifluoroethyl)-1,4,5,6-tetrahydrocyclopenta[c]pyrazol-5-yl)methoxy)-1H-indol-3-yl)acetamide (compound 444)

Compound 447

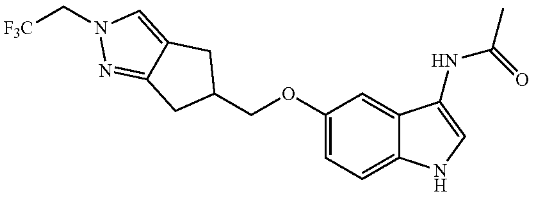

Compound 444

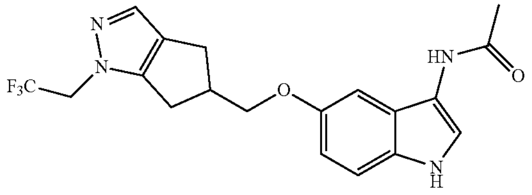

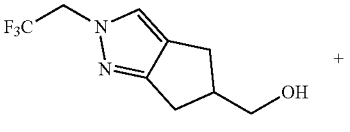

Intermediate 123

-continued

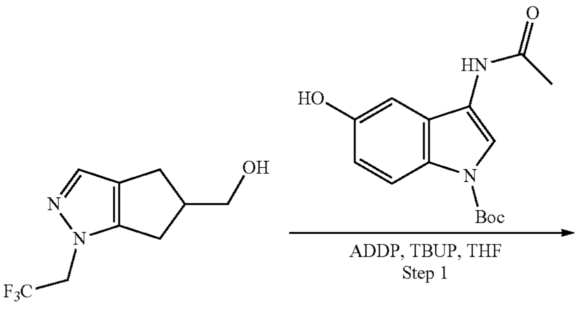

Intermediate 124

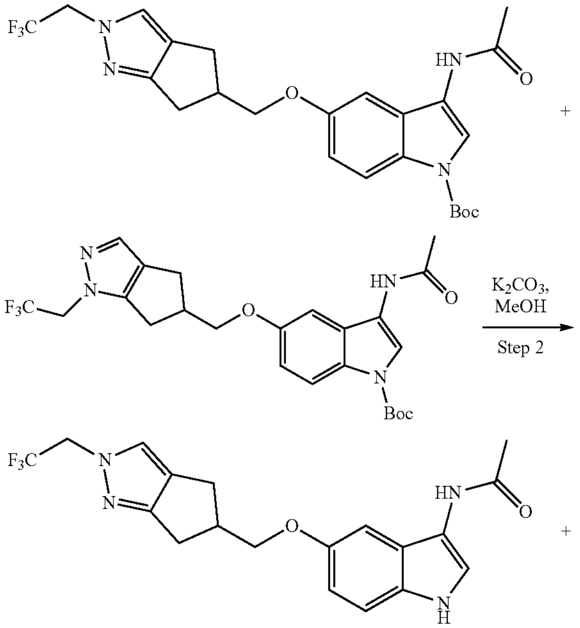

Compound 447

-continued

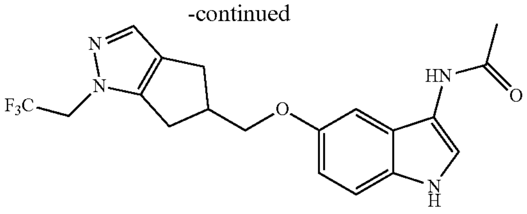

Compound 444

Step 1: mixture of tert-butyl 3-acetamido-5-{[2-(2,2,2-trifluoroethyl)-4H,5H,6H-cyclopenta[c]pyrazol-5-yl]methoxy}indole-1-carboxylate and tert-butyl 3-acetamido-5-{[1-(2,2,2-trifluoroethyl)-4H,5H,6H-cyclopenta[c]pyrazol-5-yl]methoxy}indole-1-carboxylate A mixture of [2-(2,2,2-trifluoroethyl)-4H,5H,6H-cyclopenta[c]pyrazol-5-yl]methanol and [1-(2,2,2-trifluoroethyl)-4H,5H,6H-cyclopenta[c]pyrazol-5-yl]methanol (200.0 mg, 0.9 mmol, 1.0 equiv.) and tert-butyl 3-acetamido-5-hydroxyindole-1-carboxylate (264.0 mg, 0.9 mmol, 1.0 equiv.) were dissolved in THE (8 mL) and cooled to 0° C., then TBUP (368.0 mg, 1.8 mmol, 2.0 equiv.) and ADDP (455.0 mg, 1.8 mmol, 2.0 equiv.) were added under an atmosphere of nitrogen. The reaction mixture was stirred for 16 hours at rt and then concentrated under vacuum. The residue was purified by silica gel column chromatography, eluting with petroleum ether/EtOAc (5:1) to give a mixture of tert-butyl 3-acetamido-5-{[2-(2,2,2-trifluoroethyl)-4H,5H,6H-cyclopenta[c]pyrazol-5-yl]methoxy}indole-1-carboxylate and tert-butyl 3-acetamido-5-{[1-(2,2,2-trifluoroethyl)-4H,5H,6H-cyclopenta[c]pyrazol-5-yl]methoxy}indole-1-carboxylate (150.0 mg) as an off-white solid. LCMS Method A: $[M+H]^+$=493.2.

Step 2: N-(5-((2-(2,2,2-trifluoroethyl)-2,4,5,6-tetrahydrocyclopenta[c]pyrazol-5-yl)methoxy)-1H-indol-3-yl)acetamide and N-(5-((1-(2,2,2-trifluoroethyl)-1,4,5,6-tetrahydrocyclopenta[c]pyrazol-5-yl)methoxy)-1H-indol-3-yl)acetamide tert-Butyl 3-acetamido-5-{[2-(2,2,2-trifluoroethyl)-4H,5H,6H-cyclopenta[c]pyrazol-5-yl]methoxy}indole-1-carboxylate (169.7 mg, 0.3 mmol, 1.0 equiv) was dissolved in MeOH (8 mL), $K_2CO_3$ (97 mg, 0.915 mmol, 3.0 equiv.) was added. The reaction mixture was stirred for 5 hours at 60° C., then cooled to rt and removed the solid by filtration. The filter cake was washed with MeOH, and the combined filtrate was concentrated under vacuum. The resulting mixture was separated by Prep-Chiral-HPLC with the following conditions: Column: CHIRALPAK IC, 2*25 cm, 5 μm; Mobile Phase A: Hex (0.5% 2M $NH_3$-MeOH)-HPLC, Mobile Phase B: EtOH-HPLC; Flow rate: 20 mL/min; Gradient: 20% B to 20% B in 15 min; Wave Length: 220/254 nm; RT1: 10.14 min, RT2: 14.00 min. This resulted in N-(5-((2-(2,2,2-trifluoroethyl)-2,4,5,6-tetrahydrocyclopenta[c]pyrazol-5-yl)methoxy)-1H-indol-3-yl)acetamide (34.3 mg) as an off-white solid and N-(5-((1-(2,2,2-trifluoroethyl)-1,4,5,6-tetrahydrocyclopenta[c]pyrazol-5-yl)methoxy)-1H-indol-3-yl)acetamide (11.0 mg) as an off-white solid.

Compound 447: LCMS Method E: $[M+H]^+$=393.1. $^1H$ NMR (400 MHz, DMSO-$d_6$): δ 10.57 (s, 1H), 9.70 (s, 1H), 7.66 (d, J=2.4 Hz, 1H), 7.45 (s, 1H), 7.34 (d, J=2.4 Hz, 1H), 7.21 (d, J=8.8 Hz, 1H), 6.77-6.75 (m, 1H), 5.00 (q, J=9.2 Hz, 2H), 4.00 (d, J=6.8 Hz, 2H), 3.27-3.22 (m, 1H), 2.92-2.82 (m, 2H), 2.60-2.54 (m, 2H), 2.08 (s, 3H).

Compound 444: LCMS Method E: $[M+H]^+$=393.4. $^1H$ NMR (400 MHz, DMSO-$d_6$): δ 10.58 (s, 1H), 9.69 (s, 1H), 7.65 (d, J=2.4 Hz, 1H), 7.34 (d, J=2.4 Hz, 1H), 7.26 (s, 1H), 7.21 (d, J=8.8 Hz, 1H), 6.77-6.74 (m, 1H), 5.02 (q, J=9.2 Hz, 2H), 4.99-4.00 (m, 2H), 3.46-3.43 (m, 1H), 3.02-2.96 (m, 1H), 2.86-2.80 (m, 1H), 2.72-2.67 (m, 1H), 2.52-2.50 (m, 1H), 2.08 (s, 3H).

Example 216: N-(5-(2-(5-(2,2,2-trifluoroethyl)-5-azaspiro[2.4]heptan-7-yl)ethoxy)-1H-indol-3-yl) acetamide (compound 478)

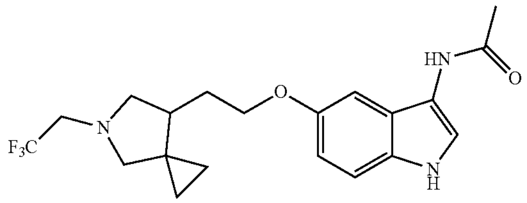

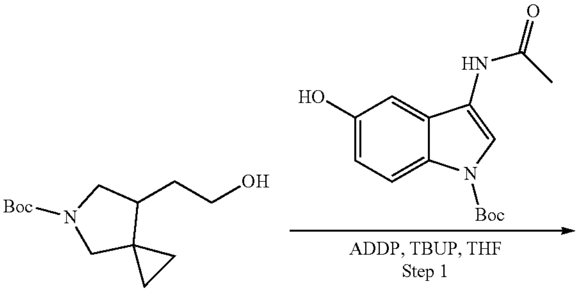

Intermediate 114

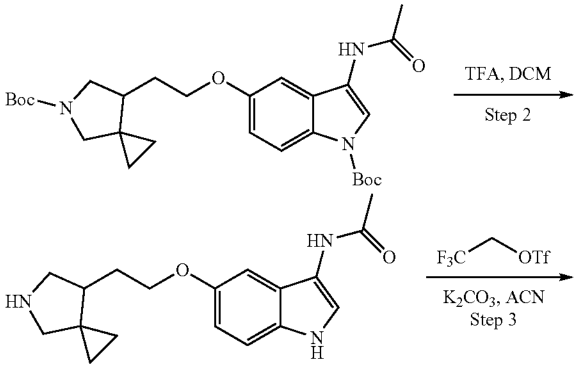

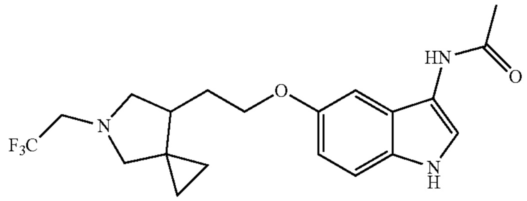

Compound 478

Step 1: tert-butyl 3-acetamido-5-(2-(5-(tert-butoxycarbonyl)-5-azaspiro[2.4]heptan-7-yl)ethoxy)-1H-indole-1-carboxylate tert-Butyl 3-acetamido-5-hydroxy-1H-indole-1-carboxylate (150.0 mg, 0.5 mmol, 1.0 equiv.) and tert-butyl 7-(2-hydroxyethyl)-5-azaspiro[2.4]heptane-5-carboxylate (249.4 mg, 1.0 mmol, 2.0 equiv.) were dissolved in THE (5 mL) and cooled to 0° C., then TBUP (209.1 mg, 1.0 mmol, 2.0 equiv.) and ADDP (258.7 mg, 1.0 mmol, 2.0 equiv.) were added, maintaining the solution at 0° C. The reaction mixture was stirred for 4 hours at rt and then concentrated under vacuum. The residue was purified by reversed-phase flash chromatography with the following conditions: column, C18 silica gel; mobile phase, MeCN in Water (10 mmol/L $NH_4HCO_3$), 30% to 70% gradient in 30 min; detector, UV 254 nm. This resulted in tert-butyl 3-acetamido-5-(2-(5-(tert-butoxycarbonyl)-5-azaspiro[2.4]heptan-7-yl)ethoxy)-1H-indole-1-carboxylate (120.0 mg) as an off-white solid. LCMS Method A: $[M+H]^+$=514.2.

Step 2: N-(5-(2-(5-azaspiro[2.4]heptan-7-yl)ethoxy)-1H-indol-3-yl)acetamide tert-Butyl 3-acetamido-5-(2-(5-(tert-butoxycarbonyl)-5-azaspiro[2.4]heptan-7-yl)ethoxy)-1H-indole-1-carboxylate (110.0 mg, 0.2 mmol, 1.0 equiv.) was dissolved in DCM (3.0 mL), then TFA (0.6 mL) was added. The reaction mixture was stirred for 2 hours at rt and then concentrated under vacuum to give N-(5-(2-(5-azaspiro[2.4]heptan-7-yl)ethoxy)-1H-indol-3-yl)acetamide (60.0 mg) as a colorless oil. LCMS Method A: $[M+H]^+$=314.2.

Step 3: N-(5-(2-(5-(2,2,2-trifluoroethyl)-5-azaspiro[2.4]heptan-7-yl)ethoxy)-1H-indol-3-yl)acetamide N-(5-(2-(5-azaspiro[2.4]heptan-7-yl)ethoxy)-1H-indol-3-yl)acetamide (60.0 mg, 0.2 mmol, 1.0 equiv.) and 2,2,2-trifluoroethyl trifluoromethanesulfonate (66.7 mg, 0.3 mmol, 1.5 equiv.) were dissolved in ACN (5.0 mL), then $K_2CO_3$ (79.4 mg, 0.6 mmol, 3.0 equiv.) was added. The reaction mixture was stirred for 2 hours at 60° C., then cooled to rt and quenched by the addition of water. The resulting solution was extracted with EtOAc, washed with brine, dried over anhyd. $Na_2SO_4$ and concentrated under vacuum. The residue was purified by Prep-HPLC with the following conditions: Column, XBridge Shield RP18 OBD Column, 30*150 mm, 5 μm; mobile phase, Water (10 mmol/L $NH_4HCO_3$+0.1% $NH_3.H_2O$) and ACN (33% ACN up to 57% in 7 min). This resulted in N-(5-(2-(5-(2,2,2-trifluoroethyl)-5-azaspiro[2.4]heptan-7-yl)ethoxy)-1H-indol-3-yl)acetamide (15.0 mg) as a white solid. LCMS Method F: $[M+H]^+$=396.1. $^1H$ NMR (400 MHz, DMSO-$d_6$) δ 10.56 (d, J=1.6 Hz, 1H), 9.68 (s, 1H), 7.64 (d, J=2.4 Hz, 1H), 7.28 (d, J=2.0 Hz, 1H), 7.20 (d, J=8.8 Hz, 1H), 6.72-6.69 (m, 1H), 3.93-3.89 (m, 2H), 3.25-3.21 (m, 3H), 2.74 (d, J=8.8 Hz, 1H), 2.69 (d, J=8.8 Hz, 1H), 2.62-2.57 (m, 1H), 2.15-2.13 (m, 1H), 2.08 (s, 3H), 1.65-1.52 (m, 2H), 0.72-0.69 (m, 1H), 0.61-0.59 (m, 1H), 0.48-0.46 (m, 1H), 0.40-0.36 (m, 1H).

Example 217/218: trans-3-hydroxy-1-methyl-N-(5-((4-(trifluoromethyl) benzyl)oxy)-1H-indol-3-yl) cyclobutane-1-carboxamide (compound 415) and cis-3-hydroxy-1-methyl-N-(5-((4-(trifluoromethyl) benzyl)oxy)-1H-indol-3-yl)cyclobutane-1-carboxamide (Compound 414)

Compound 415

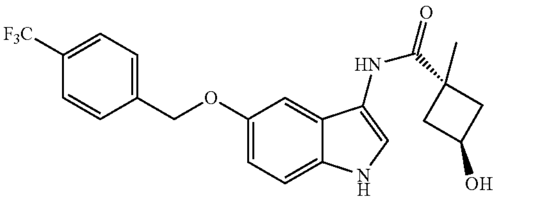

Compound 414

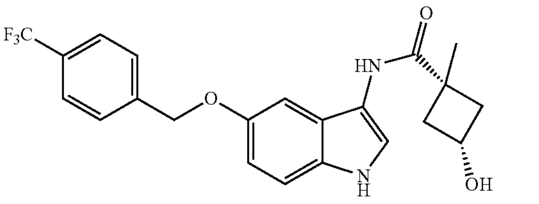

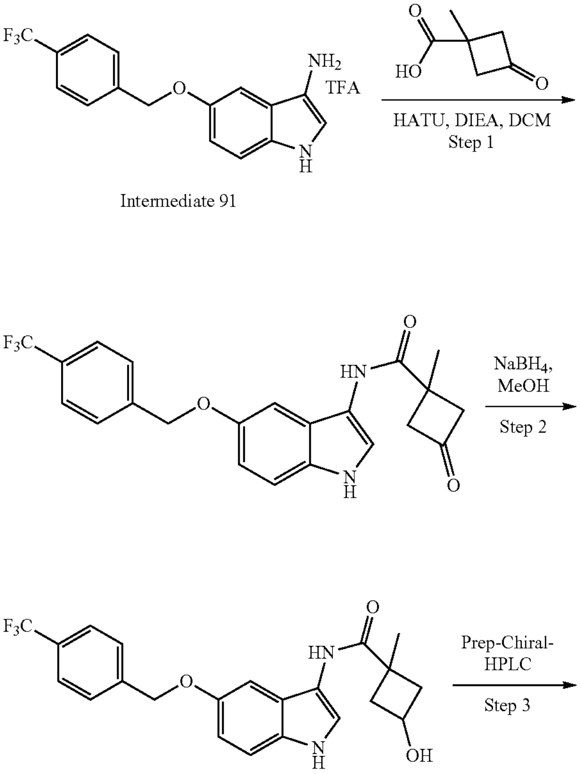

-continued

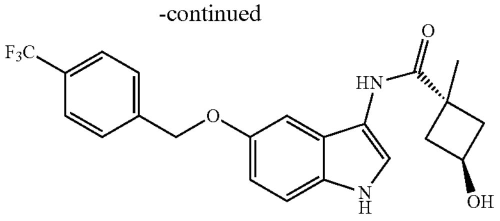

Compound 415

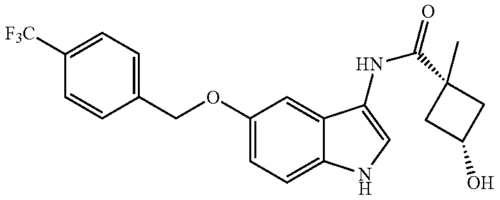

Compound 414

Step 1: 1-methyl-3-oxo-N-(5-((4-(trifluoromethyl) benzyl)oxy)-1H-indol-3-yl)cyclobutane-1-carboxamide 5-((4-(Trifluoromethyl)benzyl)oxy)-1H-indol-3-amine TFA salt (500.0 mg, 1.6 mmol, 1.0 equiv.) and 1-methyl-3-oxocyclobutane-1-carboxylic acid (209.1 mg, 1.6 mmol, 1.0 equiv.) were added in DCM (10 mL), then DIEA (0.5 mL, 3.2 mmol, 2.0 equiv.) and HATU (931.1 mg, 2.4 mmol, 1.5 equiv.) were added. The reaction mixture was stirred for 1 hour at rt and then quenched by the addition of water. The resulting solution was extracted with dichloromethane, washed with brine, dried over anhyd. $Na_2SO_4$ and concentrated under vacuum. The residue was purified by silica gel column chromatography, eluting with petroleum ether/EtOAc (3:1) to afford 1-methyl-3-oxo-N-(5-((4-(trifluoromethyl)benzyl)oxy)-1H-indol-3-yl)cyclobutane-1-carboxamide (500.0 mg) as a black solid. LCMS Method A: $[M+H]^+$ =417.2.

Step 2: 3-hydroxy-1-methyl-N-(5-((4-(trifluoromethyl)benzyl)oxy)-1H-indol-3-yl)cyclobutane-1-carboxamide 1-Methyl-3-oxo-N-(5-((4-(trifluoromethyl)benzyl)oxy)-1H-indol-3-yl)cyclobutane-1-carboxamide (500.0 mg, 1.2 mmol, 1.0 equiv.) was dissolved in MeOH (10 mL) and cooled to 0° C., then $NaBH_4$ (181.7 mg, 4.8 mmol, 4.0 equiv.) was added. The reaction mixture was stirred for 1 hour at rt and then quenched by the addition of water. The resulting solution was extracted with EtOAc, washed with brine, dried over anhyd. $Na_2SO_4$ and concentrated under vacuum. The residue was purified by reverse flash chromatography with the following conditions: column, C18 silica gel; mobile phase, MeCN in Water (10 mmol/L $NH_4HCO_3$), 10% to 50% gradient in 10 min; detector, UV 254 nm.). This resulted in 3-hydroxy-1-methyl-N-(5-((4-(trifluoromethyl) benzyl)oxy)-1H-indol-3-yl)cyclobutane-1-carboxamide (410.0 mg) as a with solid. LCMS Method A: $[M+H]^+$ =419.2.

Step 3: trans-3-hydroxy-1-methyl-N-(5-((4-(trifluoromethyl)benzyl)oxy)-1H-indol-3-yl)cyclobutane-1-carboxamide and cis-3-hydroxy-1-methyl-N-(5-((4-(trifluoromethyl)benzyl)oxy)-1H-indol-3-yl) cyclobutane-1-carboxamide The racemic 3-hydroxy-1-methyl-N-(5-((4-(trifluoromethyl)benzyl)oxy)-1H-indol-3-yl)cyclobutane-1-carboxamide (400.0 mg) was separated by Chiral-HPLC with the following conditions: Column: JW-CHIRALPAK-ID, 2*25 cm; Sum; Mobile Phase A: Hex (0.5% 2M NH3-MeOH)-HPLC, Mobile Phase B: EtOH-HPLC; Flow rate: 20 mL/min; Gradient: 20% B to 20% B in 11.5 min; Wave Length: 220/254 nm; RT1: 6.942 min, RT2: 7.015 min. This resulted in trans-3-hydroxy-1-methyl-N-(5-((4-(trifluoromethyl)benzyl)oxy)-1H-indol-3-yl)cyclobutane-1-carboxamide (125.5 mg) as an off-white solid and cis-3-hydroxy-1-methyl-N-(5-((4-(trifluoromethyl)benzyl)oxy)-1H-indol-3-yl)cyclobutane-1-carboxamide (92.4 mg) as an off-white solid.

Compound 415: LCMS Method E: $[M+H]^+$=419.2. $^1H$ NMR (400 MHz, DMSO-$d_6$): δ 10.67 (d, J=1.6 Hz, 1H), 9.20 (s, 1H), 7.78-7.70 (m, 4H), 7.60 (d, J=2.4 Hz, 1H), 7.40 (d, J=2.0 Hz, 1H), 7.24 (d, J=8.8 Hz, 1H), 6.85-6.83 (m, 1H), 5.20 (s, 2H), 5.03 (d, J=6.0 Hz, 1H), 4.03-3.89 (m, 1H), 2.84-2.79 (m, 2H), 1.82-1.77 (m, 2H), 1.49 (s, 3H).

Compound 414: LCMS Method E: $[M+H]^+$=419.2. $^1H$ NMR (400 MHz, DMSO-$d_6$): δ 10.67 (d, J=2.0 Hz, 1H), 9.03 (s, 1H), 7.80-7.70 (m, 4H), 7.58 (d, J=2.4 Hz, 1H), 7.36 (d, J=2.4 Hz, 1H), 7.25 (d, J=8.8 Hz, 1H), 6.86-6.83 (m, 1H), 5.20 (s, 2H), 4.99 (d, J=6.8 Hz, 1H), 4.18-4.13 (m, 1H), 2.27-2.19 (m, 4H), 1.41 (s, 3H).

The Analogs Prepared in the Following Table were Prepared Using the Same Method Described for Example 217/218.

| Example # | Compound # | Starting materials Used | Structure | LCMS data |
|---|---|---|---|---|
| 219 | 446 | 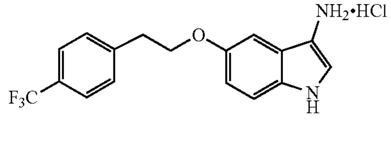 Intermediate 33 | 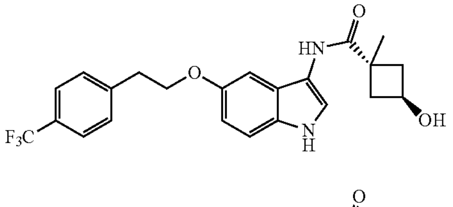 | Method F: MS-ESI: 433.1 $[M+H]^+$. |
| 220 | 445 | 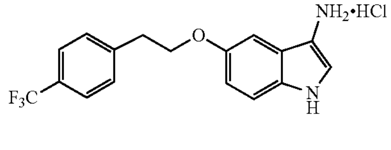 Intermediate 33 | 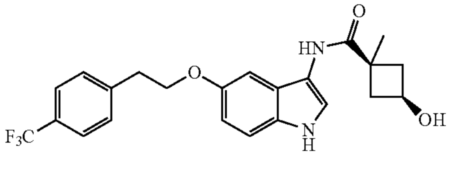 [SMILES: C[C@]1(C(=O)Nc2c[nH]c3ccc(OCCc4ccc(C(F)(F)F)cc4)cc23)C[C@@H](O)C1] | Method D: MS-ESI: 433.1 $[M+H]^+$. |

Example 221/222: cis-4-hydroxy-1-methyl-N-(5-(trans-3-(4-(trifluoromethyl)phenyl)cyclobutoxy)-1H-indol-3-yl)cyclohexane-1-carboxamide (compound 426) and trans-4-hydroxy-1-methyl-N-(5-(trans-3-(4-(trifluoromethyl)phenyl)cyclobutoxy)-1H-indol-3-yl)cyclohexane-1-carboxamide (Compound 425)
Compound 426
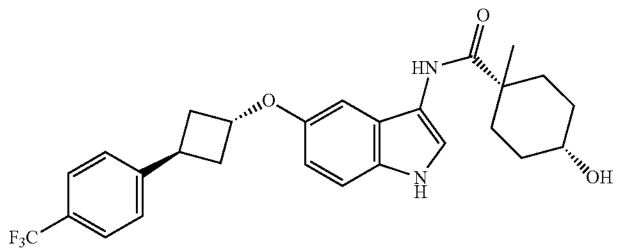
Compound 425
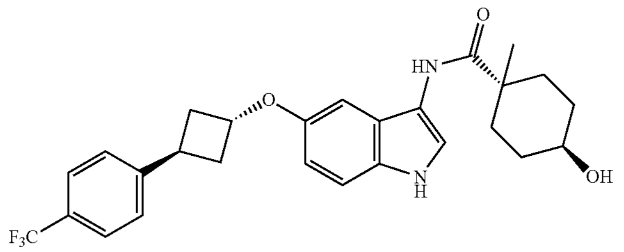
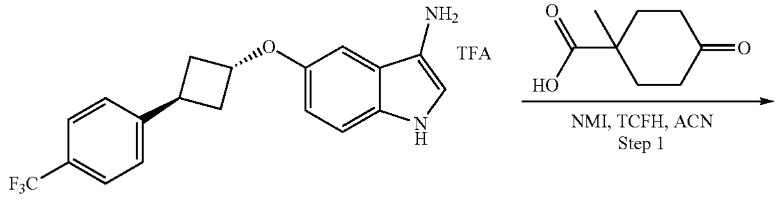
Intermediate 85
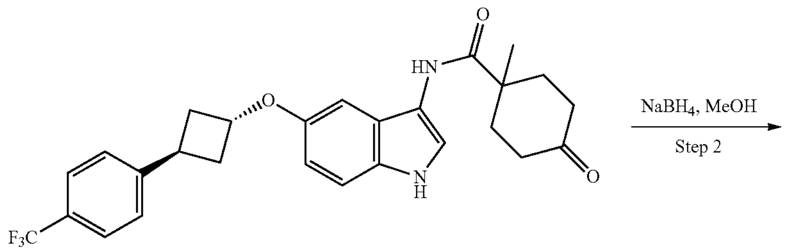
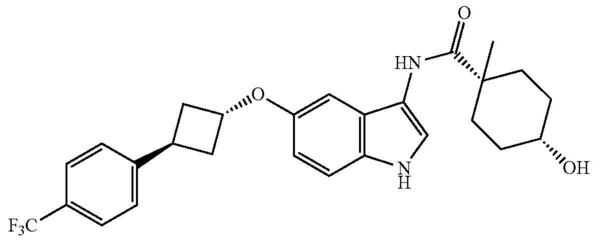
Compound 426
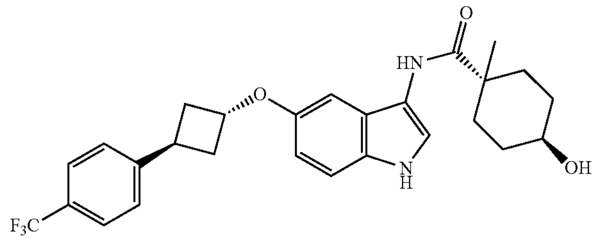
Compound 425

Step 1: 1-methyl-4-oxo-N-(5-(trans-3-(4-(trifluoromethyl)phenyl)cyclobutoxy)-1H-indol-3-yl)cyclohexane-1-carboxamide 5-[trans-3-[4-(trifluoromethyl)phenyl]cyclobutoxy]-1H-indol-3-amine TFA salt (300.0 mg, 0.9 mmol, 1.0 equiv.) and 1-methyl-4-oxocyclohexane-1-carboxylic acid (135.3 mg, 0.9 mmol, 1.0 equiv.) were dissolved in ACN (5 mL), then TCFH (1.5 g, 5.2 mmol, 6.0 equiv.) and NMI (87.6 mg, 0.9 mmol, 1.0 equiv.) were added at 0° C. The reaction mixture was stirred for 2 hours at rt and then concentrated under vacuum. The residue was purified by reverse flash chromatography with the following conditions: column, C18 silica gel; mobile phase, MeCN in Water (0.1% FA), 10% to 70% gradient in 20 min; detector, UV 254 nm. This resulted in 1-methyl-4-oxo-N-(5-(trans-3-(4-(trifluoromethyl)phenyl) cyclobutoxy)-1H-indol-3-yl)cyclohexane-1-carboxamide (140.0 mg) as a yellow green solid. LCMS Method B: $[M+H]^+$=485.2.

Step 2: cis-4-hydroxy-1-methyl-N-(5-(trans-3-(4-(trifluoromethyl)phenyl) cyclobutoxy)-1H-indol-3-yl)cyclohexane-1-carboxamide (front peak, stereochemistry unconfirmed) and trans-4-hydroxy-1-methyl-N-(5-(trans-3-(4-(trifluoromethyl)phenyl) cyclobutoxy)-1H-indol-3-yl)cyclohexane-1-carboxamide (Second Peak, Stereochemistry Unconfirmed)

1-Methyl-4-oxo-N-(5-(trans-3-(4-(trifluoromethyl)phenyl)cyclobutoxy)-1H-indol-3-yl)cyclohexane-1-carboxamide (200.0 mg, 0.4 mmol, 1.0 equiv.) was dissolved in MeOH (4 mL) and cooled to 0° C., then $NaBH_4$ (31.2 mg, 0.8 mmol, 2.0 equiv.) was added. The reaction mixture was stirred for 2 hours at rt and then quenched by the addition of ice-water. The resulting solution was extracted with EtOAc, washed with brine, dried over anhyd. $Na_2SO_4$ and concentrated under vacuum. The residue was purified by Prep-HPLC with the following conditions: Column: SunFire C18 OBD Prep Column, 19*250 mm, 5 m; Mobile Phase A: Water (0.1% FA), Mobile Phase B: ACN; Flow rate: 25 mL/min; Gradient: 45% B to 65% B in 6 min; Wave Length: 254/210 nm; RT1: 6.1 min, RT2: 6.7 min. This resulted in cis-4-hydroxy-1-methyl-N-(5-(trans-3-(4-(trifluoromethyl) phenyl) cyclobutoxy)-1H-indol-3-yl)cyclohexane-1-carboxamide (front peak, absolute stereochemistry unconfirmed, assigned as compound 426) (20.1 mg) as a white solid and trans-4-hydroxy-1-methyl-N-(5-(trans-3-(4-(trifluoromethyl)phenyl)cyclobutoxy)-1H-indol-3-yl)cyclohexane-1-carboxamide (second peak, absolute stereochemistry unconfirmed, assigned as compound 425) (48.5 mg) as a white solid.

Compound 426: LCMS Method F: $[M+H]^+$=487.3. $^1H$ NMR (400 MHz, DMSO-$d_6$): δ 10.65 (s, 1H), 8.86 (s, 1H), 7.71 (d, J=8.0 Hz, 2H), 7.58 (d, J=8.0 Hz, 2H), 7.44 (d, J=2.4 Hz, 1H), 7.23 (d, J=8.4 Hz, 1H), 6.99 (d, J=2.0 Hz, 1H), 6.74-6.72 (m, 1H), 4.92-4.87 (m, 1H), 4.41 (d, J=4.0 Hz, 1H), 3.82-3.78 (m, 1H), 3.57-3.55 (m, 1H), 2.61 (t, J=6.8 Hz, 4H), 1.88-1.81 (m, 2H), 1.70-1.65 (m, 4H), 1.49-1.42 (m, 2H), 1.24 (s, 3H).

Compound 425: LCMS Method F: $[M+H]^+$=487.3. $^1H$ NMR (400 MHz, DMSO-$d_6$): δ 10.68 (s, 1H), 8.94 (s, 1H), 7.70 (d, J=8.4 Hz, 2H), 7.58 (d, J=8.0 Hz, 2H), 7.42 (d, J=2.4 Hz, 1H), 7.24 (d, J=8.8 Hz, 1H), 6.98 (d, J=2.0 Hz, 1H), 6.74-6.72 (m, 1H), 4.92-4.86 (m, 1H), 4.46 (d, J=4.4 Hz, 1H), 3.84-3.78 (m, 1H), 3.45-3.41 (m, 1H), 2.61 (t, J=6.8 Hz, 4H), 2.32-2.29 (m, 2H), 1.72-1.68 (m, 4H), 1.36-1.30 (m, 2H), 1.27-1.16 (m, 5H).

The Analogs Prepared in the Following Table were Prepared Using the Same Method Described for Examples 221/222.

| Example # | Compound # | Starting materials Used | Structure | LCMS data |
|---|---|---|---|---|
| 223 | 419 | 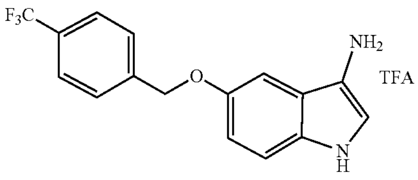 Intermediate 91 | 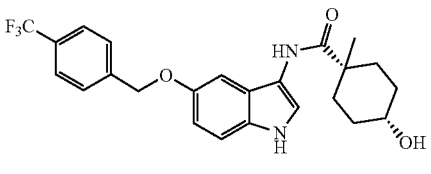 [SMILES: C[C@]1(C(=O)Nc2c[nH]c3ccc(OCc4ccc(C(F)(F)F)cc4)cc23)CC[C@@H](O)CC1] | Method F: MS-ESI: 447.3 $[M+H]^+$. |
| 224 | 418 | 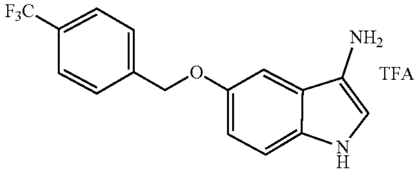 [SMILES: Nc1c[nH]c2ccc(OCc3ccc(C(F)(F)F)cc3)cc12] Intermediate 91 | 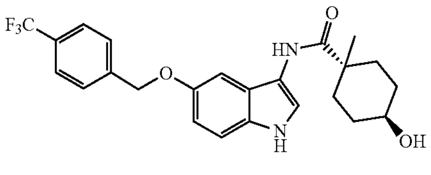 [SMILES: C[C@]1(C(=O)Nc2c[nH]c3ccc(OCc4ccc(C(F)(F)F)cc4)cc23)CC[C@H](O)CC1] | Method F: MS-ESI: 447.3 $[M+H]^+$. |

Example 225/226: trans-3-(hydroxymethyl)-1-methyl-N-(5-((4-(trifluoromethyl)benzyl)oxy)-1H-indol-3-yl)cyclobutane-1-carboxamide (Compound 417) and cis-3-(hydroxymethyl)-1-methyl-N-(5-((4-(trifluoromethyl)benzyl)oxy)-1H-indol-3-yl)cyclobutane-1-carboxamide (Compound 416)

Compound 417

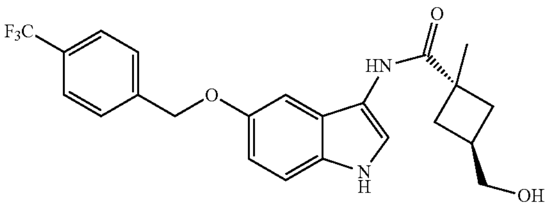

Compound 416

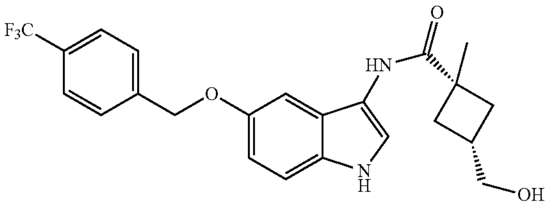

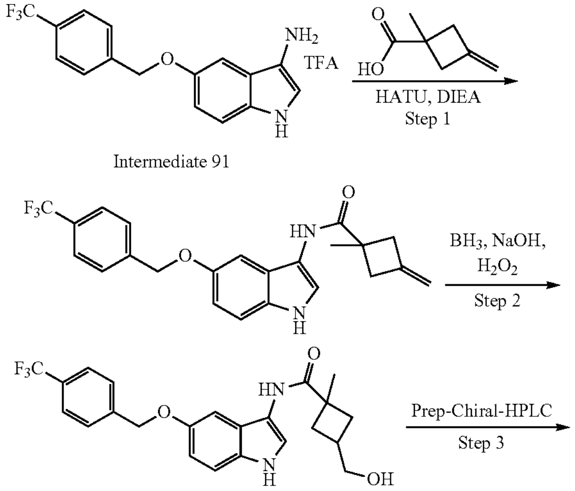

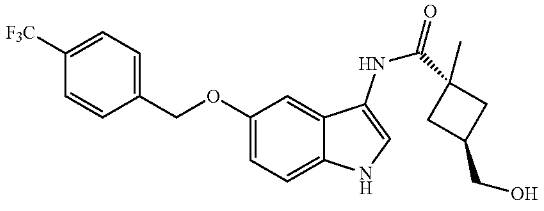

Compound 417

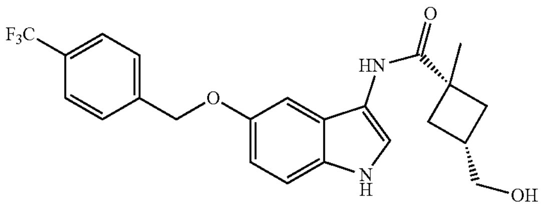

Compound 416

Step 1: 1-methyl-3-methylene-N-(5-((4-(trifluoromethyl)benzyl)oxy)-1H-indol-3-yl)cyclobutane-1-carboxamide 1-Methyl-3-methylenecyclobutane-1-carboxylic acid (350.1 mg, 2.8 mmol, 1.0 equiv.), 5-((4-(trifluoromethyl)benzyl)oxy)-1H-indol-3-amine TFA salt (850.0 mg, 2.8 mmol, 1.0 equiv.) and DIEA (2.3 mL, 13.9 mmol, 5.0 equiv.) were dissolved in DCM (10 mL), then HATU (1582.8 mg, 4.2 mmol, 1.5 equiv.) was added. The reaction mixture was stirred for 2 hours at rt and then quenched by the addition of water. The resulting solution was extracted with dichloromethane, washed with brine, dried over anhyd. $Na_2SO_4$ and concentrated under vacuum. The residue was purified by silica gel column chromatography, eluting with petroleum ether/EtOAc (1:1) to give 1-methyl-3-methylene-N-(5-((4-(trifluoromethyl)benzyl)oxy)-1H-indol-3-yl)cyclobutane-1-carboxamide (660.0 mg) as a green solid. LCMS Method A: $[M+H]^+$=415.2.

Step 2: 3-(hydroxymethyl)-1-methyl-N-(5-((4-(trifluoromethyl)benzyl)oxy)-1H-indol-3-yl)cyclobutane-1-carboxamide 1-Methyl-3-methylene-N-(5-((4-(trifluoromethyl)benzyl)oxy)-1H-indol-3-yl)cyclobutane-1-carboxamide (600.0 mg, 1.4 mmol, 1.0 equiv.) was dissolved in THE (10 mL) and cooled to 0° C., then $BH_3$-THF (5.8 mL, 1M, 5.8 mmol, 4.0 equiv.) was added dropwise, maintaining the solution at 0° C. The reaction mixture was stirred for 1 hour at 0° C., then to the above mixture were added aqueous NaOH (30% wt., 3.0 mL, 6.7 mmol, 4.6 equiv,) and $H_2O_2$ (30% wt., 1.3 mL, 3.3 mmol, 2.3 equiv,) were added dropwise at 0° C. The reaction mixture was stirred for additional 2 hours at rt and then quenched by the addition of saturated aqueous $NH_4Cl$. The resulting solution was extracted with EtOAc, washed with brine, dried over anhyd. $Na_2SO_4$ and concentrated under vacuum. The residue was purified by silica gel column chromatography, eluting with dichloromethane/methanol (10:1) to give the crude product, that was further purified by Prep-HPLC with the following conditions: Column: SunFire Prep C18 OBD Column, 19*150 mm, 5 m; Mobile Phase A: Water (0.1% FA), Mobile Phase B: ACN; Flow rate: 20 mL/min; Gradient: 60% B to 80% B in 5.5 min; Wave Length: 210/254 nm; RT1: 5.30 min. This resulted in 3-(hydroxymethyl)-1-methyl-N-(5-((4-(trifluoromethyl)benzyl)oxy)-1H-indol-3-yl) cyclobutane-1-carboxamide (150 mg). LCMS Method A: $[M+H]^+$=433.3.

Step 3: trans-3-(hydroxymethyl)-1-methyl-N-(5-((4-(trifluoromethyl)benzyl)oxy)-1H-indol-3-yl)cyclobutane-1-carboxamide (Compound 417) and cis-3-(hydroxymethyl)-1-methyl-N-(5-((4-(trifluoromethyl)benzyl)oxy)-1H-indol-3-yl)cyclobutane-1-carboxamide (Compound 416)

3-(Hydroxymethyl)-1-methyl-N-(5-((4-(trifluoromethyl)benzyl)oxy)-1H-indol-3-yl) cyclobutane-1-carboxamide (150 mg) was separated by Prep-CHIRAL-HPLC with the following conditions: Column: JW-CHIRALPAK IA-3, 4.6*50 mm, 3 m; Mobile Phase A: Hex (0.1% DEA): IPA=70: 30; Flow rate: 1 mL/min; Gradient: 0% B to 0% B. This resulted in trans-3-(hydroxymethyl)-1-methyl-N-(5-((4-(trifluoromethyl)benzyl)oxy)-1H-indol-3-yl)cyclobutane-1-carboxamide (compound 417, 98.2 mg) as a white solid and cis-3-(hydroxymethyl)-1-methyl-N-(5-((4-(trifluoromethyl)benzyl)oxy)-1H-indol-3-yl)cyclobutane-1-carboxamide (compound 416), 38.3 mg) as a white solid.

compound 417: LCMS Method D: $[M+H]^+$=433.3. $^1$H NMR (400 MHz, DMSO-$d_6$): δ 10.66 (s, 1H), 9.19 (s, 1H), 7.78-7.71 (m, 4H), 7.61 (d, J=2.4 Hz, 1H), 7.40 (d, J=2.4 Hz, 1H), 7.24 (d, J=8.8 Hz, 1H), 6.86-6.83 (m, 1H), 5.21 (s, 2H), 4.49 (t, J=5.6 Hz, 1H), 3.41-3.35 (m, 2H), 2.59-2.56 (m, 2H), 2.24-2.20 (m, 1H), 1.74-1.69 (m, 2H), 1.48 (s, 3H).

compound 416: LCMS Method D: $[M+H]^+$=433.3. $^1$H NMR (400 MHz, DMSO-$d_6$): δ 10.65 (d, J=2.0 Hz, 1H), 9.08 (s, 1H), 7.81-7.71 (m, 4H), 7.60 (d, J=2.4 Hz, 1H), 7.37 (d, J=2.4 Hz, 1H), 7.25 (d, J=8.8 Hz, 1H), 6.86-6.84 (m, 1H), 5.21 (s, 2H), 4.58 (t, J=5.2 Hz, 1H), 3.37-3.33 (m, 2H), 2.40-2.34 (m, 1H), 2.21-2.15 (m, 2H), 1.94-1.89 (m, 2H), 1.48 (s, 3H).

Example 227/228: (2R,3R)-2-methyl-N-(5-(trans-3-(4-(trifluoromethyl)phenyl)cyclobutoxy)-1H-indol-3-yl)oxetane-3-carboxamide (Compound 424) and (2S,3R)-2-methyl-N-(5-(trans-3-(4-(trifluoromethyl)phenyl)cyclobutoxy)-1H-indol-3-yl)oxetane-3-carboxamide (Compound 423)

Compound 424

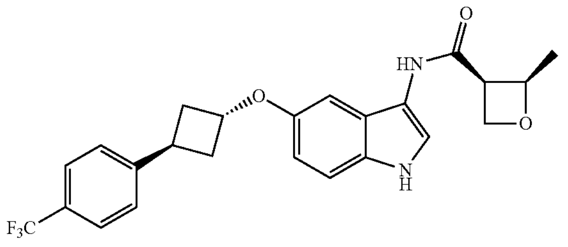

Compound 423

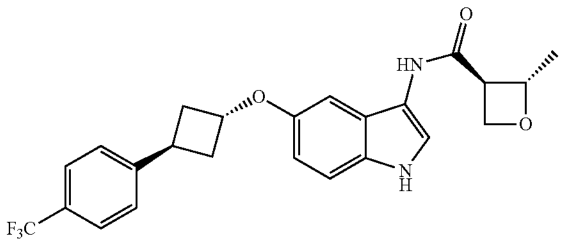

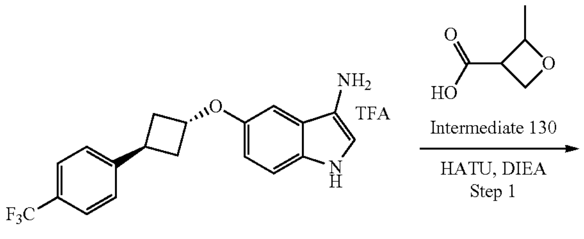

Intermediate 85

-continued

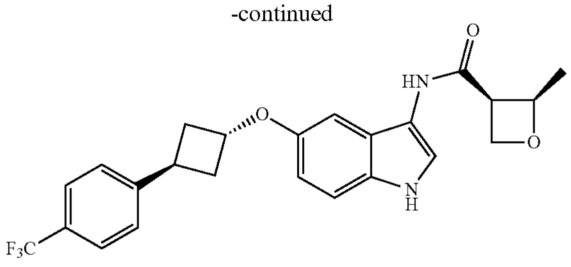

Compound 424

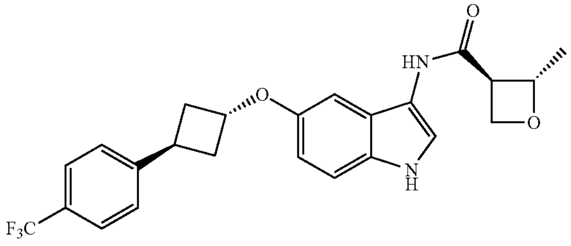

Compound 423

5-(trans-3-(4-(trifluoromethyl)phenyl)cyclobutoxy)-1H-indol-3-amine TFA salt (100.0 mg, 0.3 mmol, 1.0 equiv.) and 2-methyloxetane-3-carboxylic acid (50.3 mg, 0.4 mmol, 1.5 equiv.) were dissolved in THE (5 mL), then HATU (164.7 mg, 0.4 mmol, 1.5 equiv.) and DIEA (0.15 mL, 0.9 mmol, 3.0 equiv.) were added. The reaction mixture was stirred for 1 hour at rt and then concentrated under vacuum. The residue was purified by reverse flash chromatography with the following conditions: column, C18 silica gel; mobile phase, MeCN in Water (10 mmol/L $NH_4HCO_3$), 30% to 70% gradient in 30 min; detector, UV 254 nm. The crude product was further purified by Prep-HPLC with the following conditions: Column: SunFire Prep C18 OBD Column, 19*150 mm, 5 m; Mobile Phase A: Water (0.1% FA), Mobile Phase B: ACN; Flow rate: 20 mL/min; Gradient: 60% B to 90% B in 5.5 min; Wave Length: 210/254 nm; RT1: 5.1 min, RT2: 5.4 min. This resulted in cis-2-methyl-N-(5-(trans-3-(4-(trifluoromethyl)phenyl)cyclobutoxy)-1H-indol-3-yl)oxetane-3-carboxamide (compound 424) (6.2 mg) as an off-white solid and trans-2-methyl-N-(5-(trans-3-(4-(trifluoromethyl)phenyl)cyclobutoxy)-1H-indol-3-yl) oxetane-3-carboxamide (compound 423) (5.6 mg) as an off-white solid.

compound 424: LCMS Method F: $[M+H]^+$=445.3. $^1$H NMR (400 MHz, DMSO-$d_6$): δ 10.67 (d, J=2.4 Hz, 1H), 9.62 (s, 1H), 7.73-7.70 (m, 3H), 7.61-7.59 (m, 2H), 7.24 (d, J=8.8 Hz, 1H), 7.08 (d, J=2.0 Hz, 1H), 6.76-6.73 (m, 1H), 5.15-5.10 (m, 1H), 4.94-4.89 (m, 1H), 4.74 (t, J=6.0 Hz, 1H), 4.55-4.52 (m, 1H), 4.02-3.97 (m, 1H), 3.84-3.79 (m, 1H), 2.65-2.60 (m, 4H), 1.23 (d, J=7.2 Hz, 3H).

compound 423: LCMS Method F: $[M+H]^+$=445.1. $^1$H NMR (400 MHz, DMSO-$d_6$): δ 10.67 (d, J=1.2 Hz, 1H), 9.71 (s, 1H), 7.76-7.71 (m, 3H), 7.60 (d, J=8.4 Hz, 2H), 7.24 (d, J=8.4 Hz, 1H), 7.12 (d, J=2.0 Hz, 1H), 6.76-6.73 (m, 1H), 4.96-4.90 (m, 2H), 4.60-4.51 (m, 2H), 3.83-3.79 (m, 1H), 3.69-3.63 (m, 1H), 2.69-2.61 (m, 4H), 1.42 (d, J=6.0 Hz, 3H).

Example 229: (R)-2-hydroxy-N-(5-(trans-3-(4-(trifluoromethyl)phenyl) cyclobutoxy)-1H-indol-3-yl) butanamide (compound 429)

Compound 429

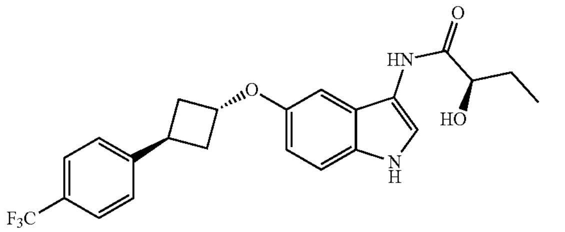

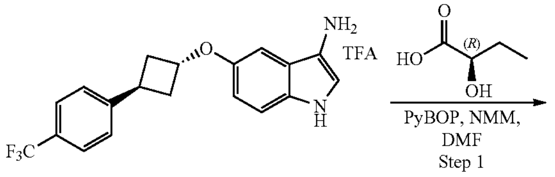

Intermediate 85

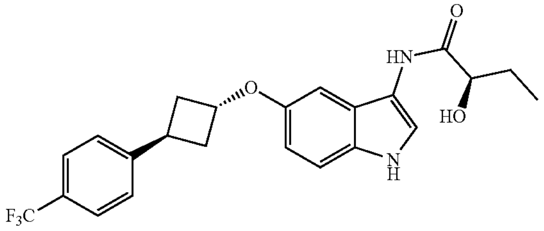

Compound 429

5-[trans-3-[4-(trifluoromethyl) phenyl] cyclobutoxy]-1H-indol-3-amine TFA salt (120.0 mg, 0.3 mmol, 1.0 equiv.) was dissolved in DMF (5 mL), (R)-2-hydroxybutyric acid (72.1 mg, 0.7 mmol, 2.0 equiv.), NMM (210.3 mg, 2.1 mmol, 6.0 equiv.) and PyBOP (180.3 mg, 0.3 mmol, 1.0 equiv.) were added. The reaction mixture was stirred for 5 hours at rt and then concentrated under vacuum. The residue was purified by reverse flash chromatography with the following conditions: column, C18 silica gel; mobile phase, MeCN in Water (0.1% FA), 5% to 70% gradient in 25 min; detector, UV 254 nm. The resulting crude product was further purified by Prep-HPLC with the following conditions: Column: SunFire Prep C18 OBD Column, 19*150 mm, 5 m; Mobile Phase A: Water (0.1% FA), Mobile Phase B: ACN; Flow rate: 20 mL/min; Gradient: 55% B to 80% B in 5.3 min; Wave Length: 210/254 nm; RT1: 5.3 min. This resulted in (2R)-2-hydroxy-N-{5-[trans-3-[4-(trifluoromethyl) phenyl] cyclobutoxy]-1H-indol-3-yl} butanamide (28.0 mg) as a white solid. LCMS Method E: $[M+H]^+$ =433.3. $^1H$ NMR (400 MHz, DMSO-$d_6$) δ 10.68 (d, J=2.6 Hz, 1H), 9.38 (s, 1H), 7.71 (d, J=8.0 Hz, 2H), 7.64-7.58 (m, 1H), 7.25 (d, J=8.8 Hz, 1H), 7.06 (d, J=2.0 Hz, 1H), 6.76-6.73 (m, 1H), 5.46 (d, J=5.6 Hz, 1H), 4.94-4.91 (m, 1H), 4.06-4.02 (m, 1H), 3.83-3.79 (m, 1H), 2.67-2.62 (m, 4H), 1.77-1.72 (m, 1H), 1.66-1.59 (m, 1H), 0.92 (t, J=7.6 Hz, 3H).

The Analogs Prepared in the Following Table were Prepared Using the Same Method Described for Example 229.

| Example # | Compound # | Starting materials Used | Structure | condition | LCMS data |
|---|---|---|---|---|---|
| 230 | 496 | Intermediate 91 /Tetramethyloxetane-3-carboxylic acid | 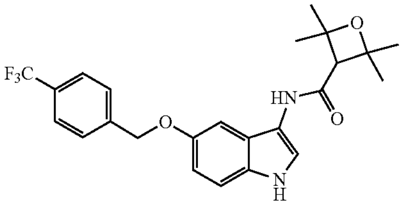 | HATU, DIEA, DCM | Method E: MS-ESI: 4475.2 $[M-H]^+$. |
| 231 | 464 | Intermediate 107 /1-methylcyclopropane-1-carboxylic acid | 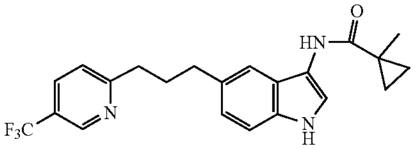 [SMILES: CC1(C(=O)Nc2c[nH]c3ccc(CCCc4ccc(C(F)(F)F)cn4)cc23)CC1] | $T_3P$, TEA, DMF | Method F: MS-ESI: 402.1$[M+H]^+$. |
| 232 | 455 | Intermediate 106 /AcCl | 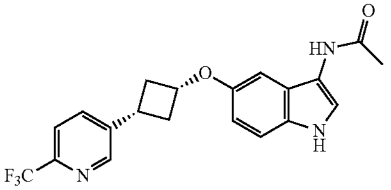 [SMILES: CC(=O)Nc1c[nH]c2ccc(O[C@H]3C[C@@H](c4ccc(C(F)(F)F)nc4)C3)cc12] | TEA, DCM | Method F: MS-ESI: 390.1$[M+H]^+$. |
| 233 | 434 | Intermediate 90 /2-(2,2,2-trifluoroethoxy)acetic acid | 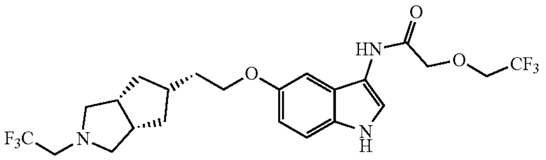 | HATU, DIEA, DCM | Method F: MS-ESI: 508.2$[M+H]^+$. |

-continued

| Example # | Compound # | Starting materials Used | Structure | condition | LCMS data |
|---|---|---|---|---|---|
| 234 | 433 | Intermediate 90 /4,4,4-trifluoro-3-hydroxybntanoic acid | 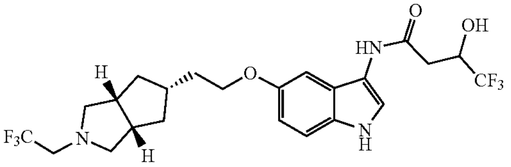 [SMILES: O=C(CC(O)C(F)(F)F)Nc1c[nH]c2ccc(OCC[C@@H]3C[C@@H]4CN(CC(F)(F)F)C[C@@H]4C3)cc12] | HATU, DIEA, DCM | Method F: MS-ESI: 508.2[M+H]$^+$. |
| 235 | 431 | Intermediate 33 /(R)-2-hydroxybutanoic acid | 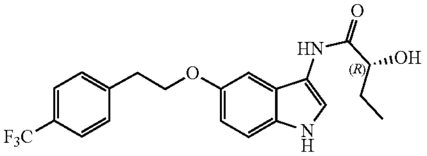 | HATU, DIEA, DCM | Method F: MS-ESI: 407.2[M+H]$^+$. |
| 236 | 430 | Intermediate 33 /(S)-2-hydroxybutanoic acid | 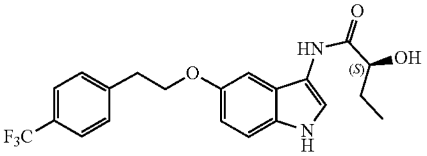 | HATU, DIEA, DCM | Method F: MS-ESI: 407.2[M+H]$^+$. |
| 237 | 428 | Intermediate 90 /2,4-dimethyloxetane-3-carboxylic acid | 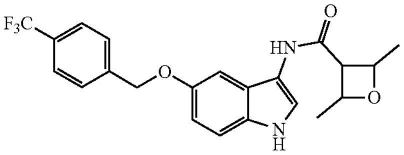 [SMILES: CC1OC(C)C1C(=O)Nc1c[nH]c2ccc(OCc3ccc(C(F)(F)F)cc3)cc12] | $T_3P$, TEA, ACN | Method E: MS-ESI: 419.2[M+H]$^+$. |
| 238 | 422 | Intermediate 86 /Intermediate 131 | 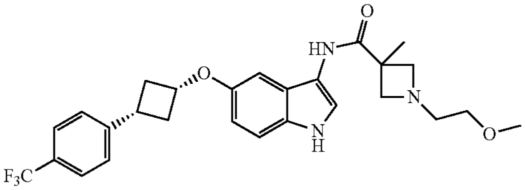 [SMILES: COCCN1CC(C)(C(=O)Nc2c[nH]c3ccc(O[C@H]4C[C@@H](c5ccc(C(F)(F)F)cc5)C4)cc23)C1] | HATU, DIEA, DCM | Method F: MS-ESI: 502.2[M+H]$^+$. |
| 239 | 421 | Intermediate 91 /Intermediate 132 | 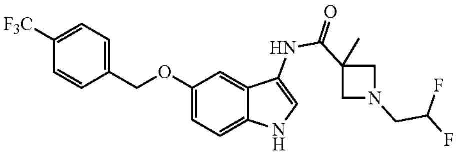 [SMILES: CC1(C(=O)Nc2c[nH]c3ccc(OCc4ccc(C(F)(F)F)cc4)cc23)CN(CC(F)F)C1] | HATU, DIEA, DCM | Method F: MS-ESI: 468.1[M+H]$^+$. |
| 240 | 420 | Intermediate 91 /l-(hydroxymethyl) cyclobutane-1-carboxylic acid | 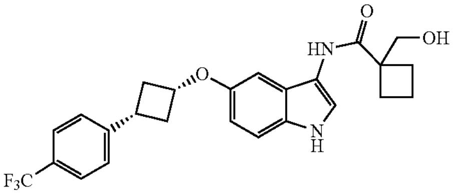 [SMILES: O=C(Nc1c[nH]c2ccc(O[C@H]3C[C@@H](c4ccc(C(F)(F)F)cc4)C3)cc12)C1(CO)CCC1] | HATU, DIEA, DCM | Method F: MS-ESI: 459.2[M+H]$^+$. |
| 241 | 413 | Intermediate 86 /Intermediate 133 | 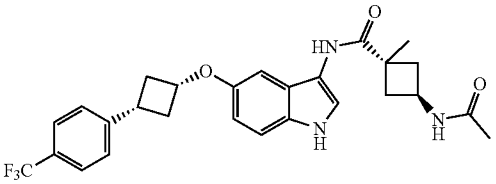 [SMILES: CC(=O)N[C@H]1C[C@](C)(C(=O)Nc2c[nH]c3ccc(O[C@H]4C[C@@H](c5ccc(C(F)(F)F)cc5)C4)cc23)C1] | $T_3P$, TEA, THF | Method F: MS-ESI: 500.2[M+H]$^+$. |
| 242 | 412 | Intermediate 86 /Intermediate 134 | 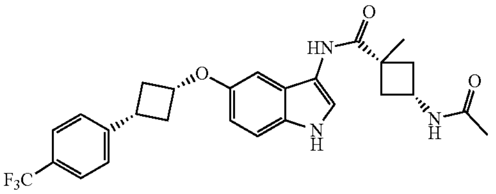 [SMILES: CC(=O)N[C@H]1C[C@@](C)(C(=O)Nc2c[nH]c3ccc(O[C@H]4C[C@@H](c5ccc(C(F)(F)F)cc5)C4)cc23)C1] | $T_3P$, TEA, THF | Method F: MS-ESI: 500.2[M+H]$^+$. |

-continued

| Example # | Compound # | Starting materials Used | Structure | condition | LCMS data |
|---|---|---|---|---|---|
| 243 | 409 | Intermediate 91 /2,2-dimethyloxetane-3-carboxylic acid | 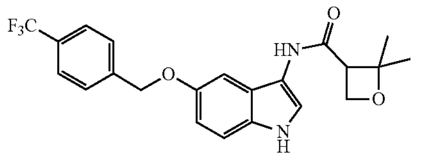 [SMILES: CC1(C)OCC1C(=O)Nc1c[nH]c2ccc(OCc3ccc(C(F)(F)F)cc3)cc12] | HATU, DIEA, DCM | Method F: MS-ESI: 419.2[M+H]+. |

Example 244: 1-(2,2-difluoroethyl)-3-methyl-N-(5-(trans-3-(4-(trifluoromethyl)phenyl)cyclobutoxy)-1H-indol-3-yl)azetidine-3-carboxamide (Compound 483)

Compound 483

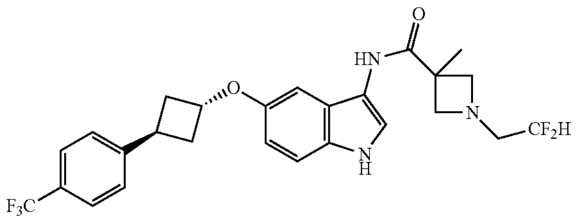

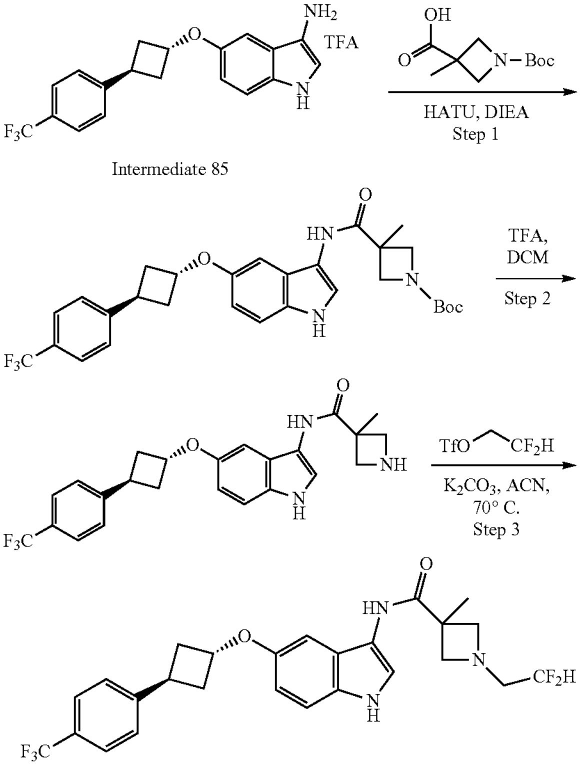

Compound 483

Step 1: tert-butyl 3-methyl-3-((5-(trans-3-(4-(trifluoromethyl)phenyl)cyclobutoxy)-1H-indol-3-yl)carbamoyl)azetidine-1-carboxylate 5-(trans-3-(4-(trifluoromethyl)phenyl)cyclobutoxy)-1H-indol-3-amine (300.0 mg, 0.9 mmol, 1.0 equiv.) and 1-(tert-butoxycarbonyl)-3-methylazetidine-3-carboxylic acid (223.7 mg, 1.0 mmol, 1.2 equiv.) were dissolved in THE (15 mL), then HATU (395.2 mg, 1.0 mmol, 1.2 equiv.) and DIEA (0.3 mL, 1.7 mmol, 2.0 equiv.) were added under an atmosphere of nitrogen. The reaction mixture was stirred overnight at rt and then concentrated under vacuum. The residue was purified by reverse flash chromatography with the following conditions: column, C18 silica gel; mobile phase, MeCN in Water (10 mmol/L $NH_4HCO_3$), 30% to 90% gradient in 20 min; detector, UV 254 nm. This resulted in tert-butyl 3-methyl-3-((5-(trans-3-(4-(trifluoromethyl)phenyl)cyclobutoxy)-1H-indol-3-yl)carbamoyl)azetidine-1-carboxylate (274.0 mg) as a brown yellow oil. LCMS Method A: $[M+H]^+$=544.2.

Step 2: 3-methyl-N-(5-(trans-3-(4-(trifluoromethyl)phenyl)cyclobutoxy)-1H-indol-3-yl)azetidine-3-carboxamide tert-Butyl 3-methyl-3-((5-(trans-3-(4-(trifluoromethyl)phenyl)cyclobutoxy)-1H-indol-3-yl)carbamoyl)azetidine-1-carboxylate (200.0 mg, 0.3 mmol, 1.0 equiv.) was dissolved in DCM (4 mL), then TFA (1 mL) was added. The reaction mixture was stirred for 4 hours at rt and concentrated under vacuum to give the crude product, which was used in the next step directly without further purification. LCMS Method A: $[M+H]^+$=444.2.

Step 3: 1-(2,2-difluoroethyl)-3-methyl-N-(5-(trans-3-(4-(trifluoromethyl)phenyl) cyclobutoxy)-1H-indol-3-yl)azetidine-3-carboxamide 3-Methyl-N-(5-(trans-3-(4-(trifluoromethyl)phenyl)cyclobutoxy)-1H-indol-3-yl)azetidine-3-carboxamide (100.0 mg, 0.2 mmol, 1.0 equiv.) and 2,2-difluoroethyl trifluoromethanesulfonate (72.4 mg, 0.3 mmol, 1.5 equiv.) were dissolved in ACN (5 mL), $K_2CO_3$ (62.3 mg, 0.5 mmol, 2.0 equiv.) was added. The reaction mixture was stirred for 4 hours at 80° C., then cooled to rt and diluted with water. The resulting solution was extracted with EtOAc, washed with brine, dried over anhyd. $Na_2SO_4$ and concentrated under vacuum. The residue was purified by Prep-HPLC with the following conditions: Column, Xselect CSH C18 OBD Column 30*150 mm Sum; mobile phase, Water (0.1% FA) and ACN (31% ACN up to 45% in 7 min). This resulted in 1-(2,2-difluoroethyl)-3-methyl-N-(5-(trans-3-(4-(trifluoromethyl)phenyl)cyclobutoxy)-1H-indol-3-yl)azetidine-3-carboxamide (33.0 mg) as a white solid. LCMS Method E: $[M+H]^+$=508.2. 1H NMR (400 MHz, DMSO-$d_6$) δ 10.67 (d, J=1.6 Hz, 1H), 9.36 (s, 1H), 8.15 (s, 1H), 7.70 (d, J=8.0 Hz, 2H), 7.68 (d, J=8.4 Hz, 3H), 7.26-7.23 (m, 1H), 7.10 (d, J=2.4 Hz, 1H), 6.76-6.74 (m, 1H), 6.10-5.82 (m, 1H), 4.94-4.91 (m, 1H), 3.83-3.79 (m, 2H), 3.64-3.60 (m, 2H), 3.22 (d, J=7.2 Hz, 2H), 2.86-2.81 (m, 2H), 2.65-2.61 (m, 4H), 1.53 (s, 3H).

Example 245: trans-3-methoxy-1-methyl-N-(5-(2-((3aR,5r,6aS)-2-(2,2,2-trifluoroethyl)octahydrocyclopenta[c]pyrrol-5-yl)ethoxy)-1H-indol-3-yl)cyclobutane-1-carboxamide (compound 427)

Compound 427

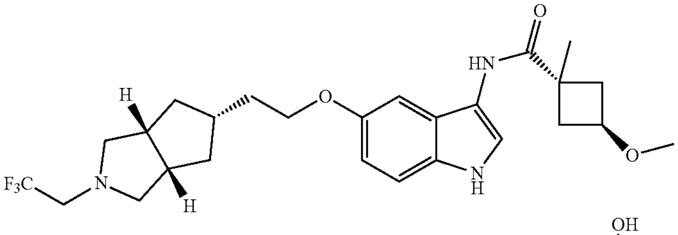

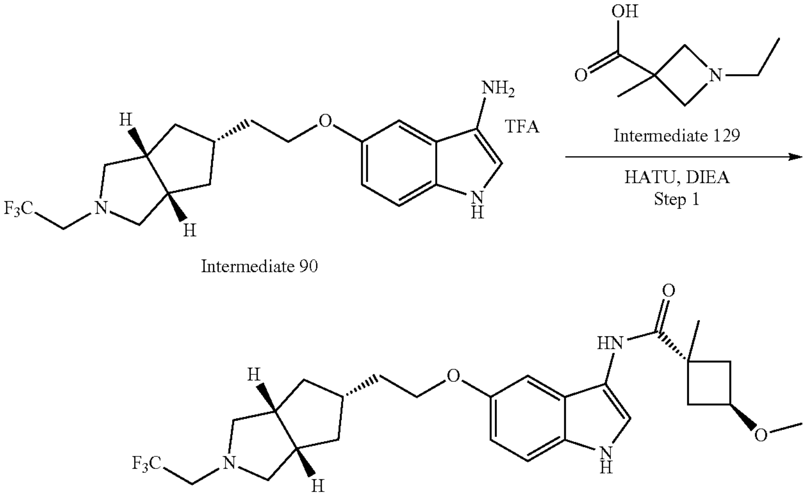

Intermediate 90

Compound 427

3-Methoxy-1-methylcyclobutane-1-carboxylic acid (627.8 mg, 4.3 mmol, 2.0 equiv.) and DIEA (1.8 mL mg, 10.9 mmol, 5.0 equiv.) were dissolved in DCM (10 mL), then HATU (1241.9 mg, 3.3 mmol, 1.5 equiv.) and 5-(2-((3aR,5r,6aS)-2-(2,2,2-trifluoroethyl)octahydrocyclopenta[c]pyrrol-5-yl)ethoxy)-1H-indol-3-amine (800.0 mg, 2.2 mmol, 1.0 equiv.) were added. The reaction mixture was stirred for 2 hours at rt and then quenched by the addition of water. The resulting solution was extracted with dichloromethane, washed with brine, dried over anhyd. $Na_2SO_4$ and concentrated under vacuum. The residue was purified by Prep-TLC (petroleum ether/EtOAc=1:1) to afford racemate, that was purified by Prep-CHIRAL-HPLC with the following conditions: Column: JW-CHIRALPAK-IF, 20*250 mm, Sum; Mobile Phase A: EtOH-HPLC, Mobile Phase B: Hex:DCM=3:1 (0.1% FA)-HPLC; Flow rate: 20 mL/min; Gradient: 80% B to 80% B in 10 min; Wave Length: 220/254 nm; RT1(min): 5.6. This resulted in trans-3-methoxy-1-methyl-N-(5-(2-((3aR,5r,6aS)-2-(2,2,2-trifluoroethyl)octahydrocyclopenta[c]pyrrol-5-yl)ethoxy)-1H-indol-3-yl)cyclobutane-1-carboxamide (87.3 mg) as a green solid. LCMS Method F: $[M+H]^+$=494.2. $^1H$ NMR (400 MHz, DMSO-$d_6$) δ 10.61 (s, 1H), 9.24 (s, 1H), 7.60 (d, J=2.0 Hz, 1H), 7.27 (d, J=2.0 Hz, 1H), 7.20 (d, J=8.4 Hz, 1H), 6.74-6.71 (m, 1H), 3.97 (t, J=6.0 Hz, 2H), 3.73-3.70 (m, 1H), 3.22-3.17 (m, 2H), 3.14 (s, 3H), 2.85-2.80 (m, 2H), 2.64 (d, J=8.4 Hz, 2H), 2.44-2.40 (m, 4H), 2.10-2.06 (m, 2H), 1.95-1.76 (m, 5H), 1.51 (s, 3H), 0.98-0.95 (m, 2H).

Example 246: N-(5-((4-(trifluoromethyl)phenyl)ethynyl)-1H-indol-3-yl)acetamide (Compound 495)

Compound 495

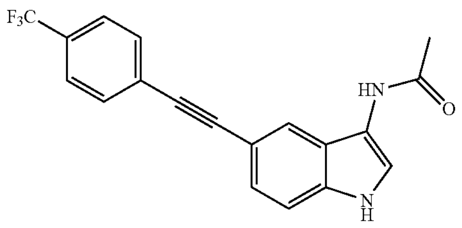

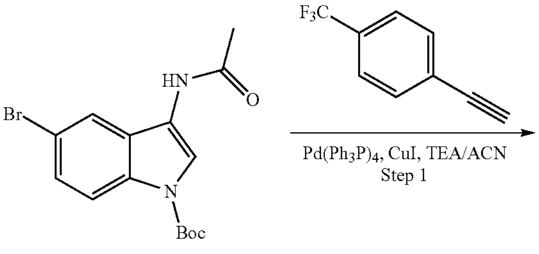

Intermediate 2

-continued

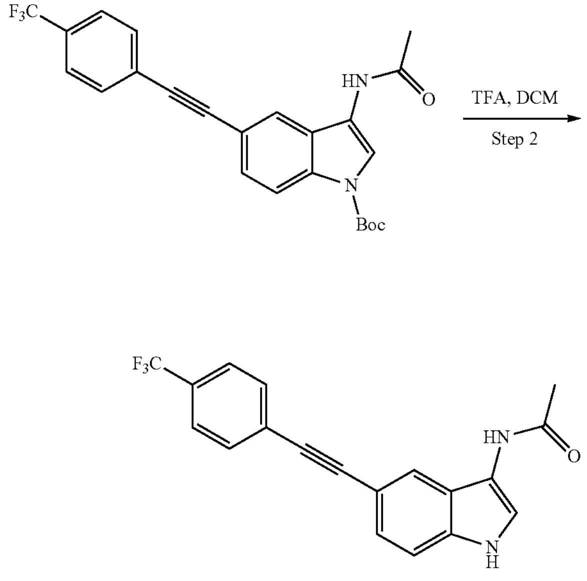

Compound 495

Step 1: tert-butyl 3-acetamido-5-((4-(trifluoromethyl)phenyl)ethynyl)-1H-indole-1-carboxylate tert-Butyl 3-acetamido-5-bromo-1H-indole-1-carboxylate (500.0 mg, 1.4 mmol, 1.0 equiv.) and 1-ethynyl-4-(trifluoromethyl)benzene (289.0 mg, 1.6 mmol, 1.2 equiv.) were dissolved in TEA (4 mL) and ACN (4 mL), then $Pd(PPh_3)_4$ (327.1 mg, 0.2 mmol, 0.2 equiv.) and CuI (26.9 mg, 0.1 mmol, 0.1 equiv.) were added under an atmosphere of nitrogen. The reaction mixture was stirred for 16 hours at 90° C., then cooled to rt and quenched by the addition of water. The resulting solution was extracted with EtOAc, washed with brine, dried over anhyd. $Na_2SO_4$ and concentrated under vacuum. The residue was purified by silica gel column chromatography, eluting with petroleum ether/EtOAc (1:1) to give tert-butyl 3-acetamido-5-((4-(trifluoromethyl)phenyl)ethynyl)-1H-indole-1-carboxylate (700.0 mg) as a brown solid. LCMS Method A: $[M+H]^+$=443.2.

Step 2: N-(5-((4-(trifluoromethyl)phenyl)ethynyl)-1H-indol-3-yl)acetamide tert-Butyl 3-acetamido-5-((4-(trifluoromethyl)phenyl)ethynyl)-1H-indole-1-carboxylate (600.0 mg, 1.3 mmol, 1.0 equiv.) was dissolved in DCM (4 mL), then TFA (2 mL) was added. The reaction mixture was stirred for 30 min at rt and concentrated under vacuum. The crude product was purified by Prep-HPLC with the following conditions: Column: XBridge Prep OBD C18 Column, 30*150 mm, 5 m; Mobile Phase A: Water (10 mmol/L $NH_4HCO_3$), Mobile Phase B: ACN; Flow rate: 60 mL/min; Gradient: 44% B to 61% B in 8 min; Wave Length: 254 nm; RT1(min): 7.55. This resulted in N-(5-((4-(trifluoromethyl)phenyl)ethynyl)-1H-indol-3-yl)acetamide (35.7 mg) as a pale brown solid. LCMS Method E: $[M-H]^-$=341.1. $^1H$ NMR (400 MHz, DMSO-$d_6$) δ 11.08 (s, 1H), 9.92 (s, 1H), 8.16 (s, 1H), 7.80-7.74 (m, 5H), 7.39 (d, J=8.4 Hz, 1H), 7.32-7.29 (m, 1H), 2.10 (s, 3H).

Example 247: N-(5-(2-((2-(1-(2,2,2-trifluoroethyl)pyrrolidin-3-yl)propan-2-yl)oxy)ethyl)-1H-indol-3-yl)acetamide (compound 499)

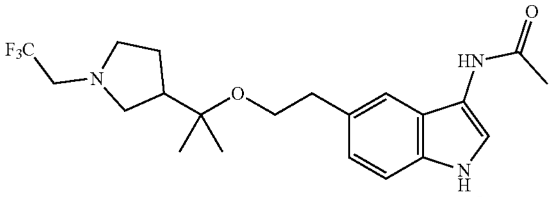

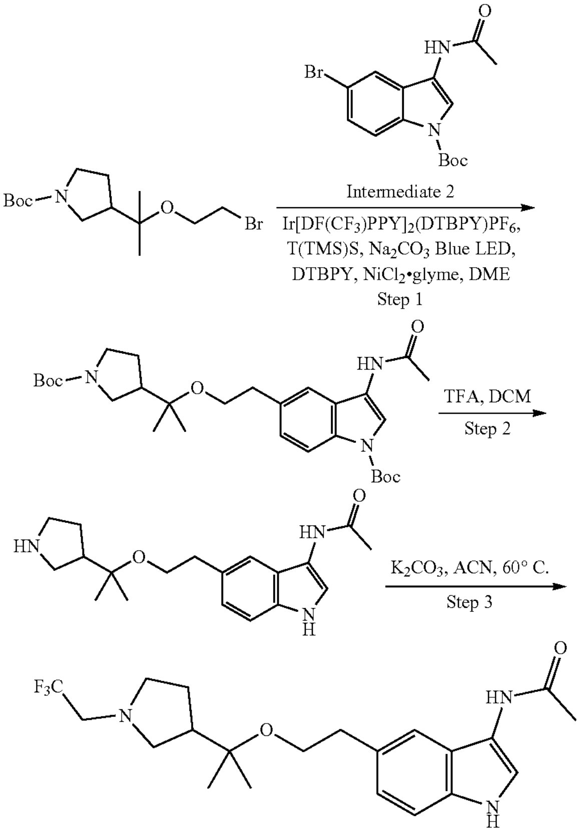

Compound 499

Step 1: tert-butyl 3-(2-(2-bromoethoxy) propan-2-yl) pyrrolidine-1-carboxylate tert-Butyl 3-(2-(2-bromoethoxy)propan-2-yl)pyrrolidine-1-carboxylate (800.0 mg, 1.7 mmol, 1.0 equiv.) and 8-(2-bromoethoxy)-1,4-dioxaspiro[4.5]decane (900.8 mg, 3.4 mmol, 2.0 equiv.) were dissolved in DME (10 mL), then tris(trimethylsilyl)silane (633.6 mg, 2.5 mmol, 1.5 equiv.), $Na_2CO_3$ (360.1 mg, 3.4 mmol, 2.0 equiv.), $Ir[DF(CF_3)PPY]_2(DTBPY)PF_6$ (190.6 mg, 0.2 mmol, 0.1 equiv.), DTBPY (45.6 mg, 0.2 mmol, 0.1 equiv.) and 1,2-dimethoxyethane dihydrochloride nickel (37.3 mg, 0.2 mmol, 0.1 equiv.) were added under an atmosphere of nitrogen. The reaction mixture was stirred overnight at rt under nitrogen atmosphere and the Blue LED light. The resulting mixture was concentrated under vacuum and the residue was purified by reverse flash chromatography with the following conditions: column, C18 silica gel; mobile phase, MeCN in Water (10 mmol/L $NH_4HCO_3$), 30% to 70% gradient in 30 min; detector, UV 254 nm. This resulted in tert-butyl 3-acetamido-5-(2-((2-(1-(tert-butoxycarbonyl)pyrrolidin-3-yl)propan-2-yl)oxy)ethyl)-1H-indole-1-carboxylate (200.0 mg) as a brown oil. LCMS Method A: $[M+H]^+$=530.2.

Step 2: N-(5-(2-((2-(pyrrolidin-3-yl)propan-2-yl)oxy)ethyl)-1H-indol-3-yl)acetamide tert-Butyl 5-[2-({2-[1-(tert-butoxycarbonyl) pyrrolidin-3-yl] propan-2-yl} oxy) ethyl]-3-acetamidoindole-1-carboxylate (200.0 mg, 0.9 mmol, 1.0 equiv.) was dissolved in DCM (5 mL), then TFA (1 mL) was added at 0° C. The reaction mixture was stirred overnight at rt and concentrated under vacuum to give crude N-(5-(2-((2-(pyrrolidin-3-yl)propan-2-yl)oxy)ethyl)-1H-indol-3-yl)acetamide, that was used in the next step directly without further purification.

Step 3: N-(5-(2-((2-(1-(2,2,2-trifluoroethyl)pyrrolidin-3-yl)propan-2-yl)oxy)ethyl)-1H-indol-3-yl)acetamide N-(5-(2-((2-(pyrrolidin-3-yl)propan-2-yl)oxy)ethyl)-1H-indol-3-yl)acetamide (60.0 mg, 0.2 mmol, 1.0 equiv.) was dissolved in ACN (2 mL), then $K_2CO_3$ (50.3 mg, 0.4 mmol, 2.0 equiv.) and 2,2,2-trifluoroethyl trifluoromethanesulfonate (42.3 mg, 0.2 mmol, 1.0 equiv.) were added. The reaction mixture was stirred for 1 hour at 60° C., then cooled to rt and concentrated under vacuum. The residue was purified by Prep-TLC (dichloromethane/MeOH=10:1) to give the crude product, that was further purified by Prep-HPLC with the following conditions: Column, Xselect CSH C18 OBD Column 30*150 mm 5 um; mobile phase, Water (0.1% FA) and ACN (15% ACN up to 30% in 7 min); Detector, UV 220/254 nm. This resulted in N-(5-(2-((2-(1-(2,2,2-trifluoroethyl)pyrrolidin-3-yl)propan-2-yl)oxy)ethyl)-1H-indol-3-yl)acetamide (12.6 mg) as a white solid. LCMS Method F: $[M+H]^+$=412.2. $^1H$ NMR (400 MHz, DMSO-$d_6$) δ 10.61 (s, 1H), 9.73 (s, 1H), 7.64 (d, J=2.0 Hz, 1H), 7.59 (s, 1H), 7.22 (d, J=8.0 Hz, 1H), 6.98 (d, J=8.4 Hz, 1H), 3.51 (t, J=7.2 Hz, 2H), 3.25-3.07 (m, 2H), 2.78 (t, J=7.2 Hz, 2H), 2.73-2.63 (m, 2H), 2.58-2.54 (m, 2H), 2.33-2.25 (m, 1H), 2.08 (s, 3H), 1.64-1.51 (m, 2H), 1.04 (s, 6H).

Example 248: N-(5-(2-((3aR,5r,6aS)-2-(2,2,2-trifluoroethyl)octahydrocyclopenta[c]pyrrol-5-yl)ethyl)-1H-indol-3-yl)acetamide (compound 457)

Compound 457

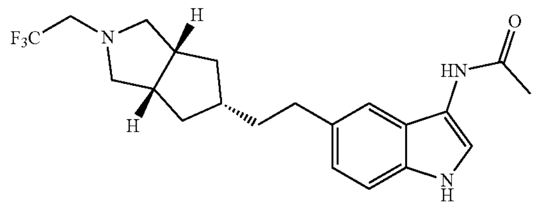

-continued

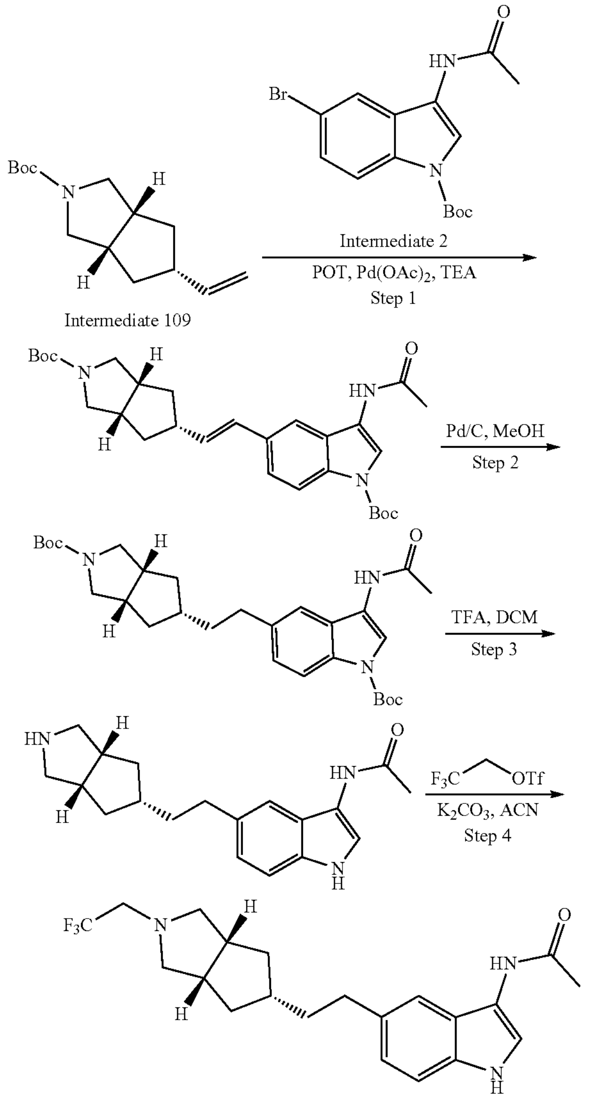

Step 1: tert-butyl 3-acetamido-5-((E)-2-((3aR,5r,6aS)-2-(tert-butoxycarbonyl)octahydrocyclopenta[c]pyrrol-5-yl)vinyl)-1H-indole-1-carboxylate tert-Butyl (3aR,5r,6aS)-5-vinylhexahydrocyclopenta[c]pyrrole-2(1H)-carboxylate (380.0 mg, 1.6 mmol, 1.0 equiv.) and tert-butyl 3-acetamido-5-bromo-1H-indole-1-carboxylate (735.2 mg, 2.1 mmol, 1.3 equiv.) were dissolved in ACN (5 mL), then $Pd(OAc)_2$ (71.9 mg, 0.3 mmol, 0.2 equiv.), $P(o\text{-}Tol)_3$ (194.9 mg, 0.6 mmol, 0.4 equiv.) and TEA (0.7 mL, 4.8 mmol, 3.0 equiv.) were added under an atmosphere of nitrogen. The reaction mixture was stirred for 16 hours at 80° C., then cooled to rt and quenched by the addition of water. The resulting solution was extracted with EtOAc, washed with brine, dried over anhyd. $Na_2SO_4$ and concentrated under vacuum. The residue was purified by flash column chromatography on silica gel, eluting with dichloromethane/methanol (15:1) to give tert-butyl 3-acetamido-5-((E)-2-((3aR,5r,6aS)-2-(tert-butoxycarbonyl)octahydrocyclopenta[c]pyrrol-5-yl)vinyl)-1H-indole-1-carboxylate (760.0 mg) as an orange solid. LCMS Method A: $[M+H]^+$ =510.2.

Step 2: tert-butyl 3-acetamido-5-(2-((3aR,5r,6aS)-2-(tert-butoxycarbonyl) octahydrocyclopenta [c]pyrrol-5-yl)ethyl)-1H-indole-1-carboxylate tert-Butyl 3-acetamido-5-((E)-2-((3aR,5r,6aS)-2-(tert-butoxycarbonyl)octahydrocyclopenta[c] pyrrol-5-yl)vinyl)-1H-indole-1-carboxylate (660.0 mg, 1.3 mmol, 1.0 equiv.) was dissolved in MeOH (10 mL), then Pd/C (137.8 mg, 10% wt.) was added under an atmosphere of nitrogen. The mixture was sparged with nitrogen, placed under an atmosphere of hydrogen gas (balloon), then stirred for 2 hours at rt. The solids were removed by filtration and the filtrate was concentrated under vacuum to give tert-butyl 3-acetamido-5-(2-((3aR,5r,6aS)-2-(tert-butoxycarbonyl)octahydrocyclopenta[c]pyrrol-5-yl)ethyl)-1H-indole-1-carboxylate (340.0 mg) as a white solid. LCMS Method A: $[M+H]^+$=512.

Step 3: N-(5-(2-((3aR,5r,6aS)-octahydrocyclopenta [c]pyrrol-5-yl)ethyl)-1H-indol-3-yl)acetamide tert-Butyl 3-acetamido-5-(2-((3aR,5r,6aS)-2-(tert-butoxycarbonyl) octahydro cyclopenta[c]pyrrol-5-yl)ethyl)-1H-indole-1-carboxylate (300.0 mg, 0.6 mmol, 1.0 equiv.) was dissolved in DCM (5 mL), then TFA (5 mL) was added. The reaction mixture was stirred for 2 hours at rt and then concentrated under vacuum to give crude N-(5-(2-((3aR,5r,6aS)-octahydrocyclopenta[c]pyrrol-5-yl)ethyl)-1H-indol-3-yl)acetamide TFA salt (320.0 mg) as a grey solid. LCMS Method A: $[M+H]^+$=512.1.

Step 4: N-(5-(2-((3aR,5r,6aS)-2-(2,2,2-trifluoroethyl)octahydrocyclopenta[c]pyrrol-5-yl)ethyl)-1H-indol-3-yl)acetamide N-(5-(2-((3aR,5r,6aS)-octahydrocyclopenta[c]pyrrol-5-yl)ethyl)-1H-indol-3-yl)acetamide (250.0 mg, 0.8 mmol, 1.0 equiv.) and $K_2CO_3$ (443.8 mg, 3.2 mmol, 4.0 equiv.) were dissolved in ACN (5 mL), then 2,2,2-trifluoroethyl trifluoromethanesulfonate (242.2 mg, 1.0 mmol, 1.3 equiv.) was added. The reaction mixture was stirred for 1 hour at 70° C., then cooled to rt and quenched by the addition of water. The resulting solution was extracted with EtOAc, washed with brine, dried over anhyd. $Na_2SO_4$ and concentrated under vacuum. The residue was purified by flash column chromatography on silica gel, eluting with petroleum ether/EtOAc (1:1) to give the crude product, that was further purified by Prep-HPLC with the following conditions: Column: YMC-Actus Triart C18 ExRS, 30*150 mm, 5 m; Mobile Phase A: Water (10 mmol/L $NH_4HCO_3$), Mobile Phase B: ACN; Flow rate: 60 mL/min; Gradient: 45% B to 75% B in 7.5 min; Wave Length: 220 nm; RT1: 7.5 min. This resulted in N-(5-(2-((3aR,5r,6aS)-2-(2,2,2-trifluoroethyl)octahydrocyclopenta[c]pyrrol-5-yl)ethyl)-1H-indol-3-yl)acetamide (20.8 mg) as a white solid. LCMS Method D: $[M+H]^+$ =394.2. $^1H$ NMR (400 MHz, DMSO-$d_6$) δ 10.60 (s, 1H), 9.74 (s, 1H), 7.63 (d, J=2.4 Hz, 1H), 7.58 (s, 1H), 7.21 (d, J=8.4 Hz, 1H), 6.93 (d, J=8.0 Hz, 1H), 3.21-3.16 (m, 2H), 2.64-2.60 (m, 4H), 2.46-2.41 (m, 4H), 2.08-2.05 (m, 5H), 2.08 (s, 5H), 1.66-1.63 (m, 3H), 0.92-0.88 (m, 2H).

Example 249: N-(5-((cis-3-(4-(trifluoromethyl)phenyl)cyclobutoxy)methyl)-1H-indol-3-yl)acetamide (Compound 500)

Compound 500

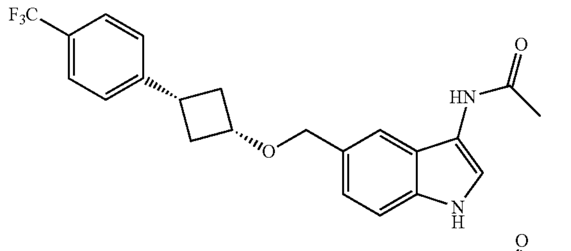

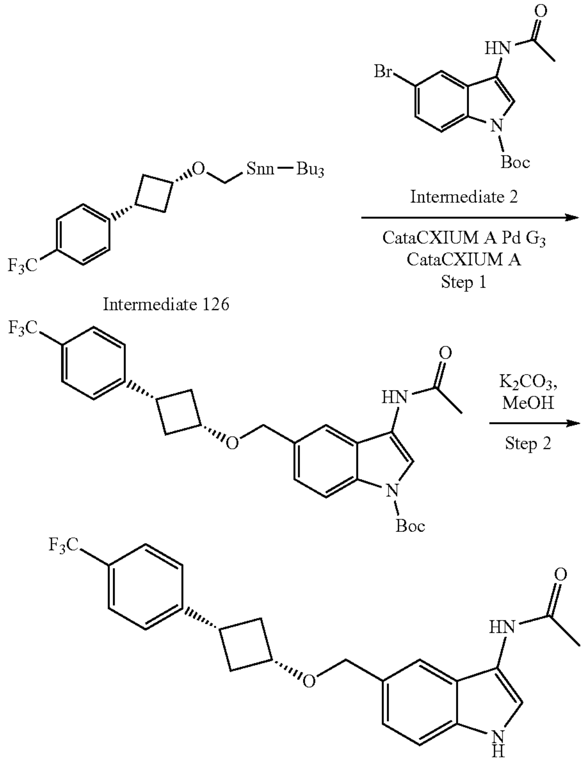

Compound 500

Step 1: tert-butyl 3-acetamido-5-((cis-3-(4-(trifluoromethyl)phenyl) cyclobutoxy)methyl)-1H-indole-1-carboxylate tert-Butyl 5-bromo-3-acetamidoindole-1-carboxylate (431.0 mg, 1.2 mmol, 1.0 equiv.) was dissolved in 1,4-dioxane (5 mL), then bis(adamantan-1-yl)(butyl)phosphane (87.5 mg, 0.2 mmol, 0.2 equiv.), Chloro[(diadamantan-1-yl)(n-butyl)phosphino][2-amino-1,1-biphenyl-2-yl]palladium (II) (81.6 mg, 0.1 mmol, 0.1 equiv.) and tributyl({[(1s,3s)-3-[4-(trifluoromethyl)phenyl]cyclobutoxy]methyl}) stannane (697.0 mg, 1.3 mmol, 1.1 equiv.) were added under an atmosphere of nitrogen. The reaction mixture was stirred for 2 hours at 100° C., then cooled to rt and quenched by the addition of water. The resulting solution was extracted with EtOAc, washed with brine, dried over anhyd. sodium sulfate and concentrated under vacuum. The residue was purified by flash column chromatography on silica gel, eluting with petroleum ether/EtOAc (1:1) to give tert-butyl 3-acetamido-5-((cis-3-(4-(trifluoromethyl)phenyl)cyclobutoxy)methyl)-1H-indole-1-carboxylate (190.0 mg) as a white solid. LCMS Method A: $[M+H]^+$=503.2.

Step 2: N-(5-((cis-3-(4-(trifluoromethyl)phenyl) cyclobutoxy)methyl)-1H-indol-3-yl)acetamide tert-Butyl 3-acetamido-5-((cis-3-(4-(trifluoromethyl)phenyl)cyclobutoxy)methyl)-1H-indole-1-carboxylate (170.0 mg, 0.3 mmol, 1.0 equiv.) was dissolved in MeOH (5 mL), then $K_2CO_3$ (93.5 mg, 0.7 mmol, 2.0 equiv.) was added. The reaction mixture was stirred for 1 hour at 70° C., then cooled to rt and quenched by the addition of water. The resulting solution was extracted with EtOAc, washed with brine, dried over anhyd. sodium sulfate and concentrated under vacuum. The crude product was purified by Prep-HPLC with the following conditions: Column: XBridge Shield RP18 OBD Column, 30*150 mm, 5 m; Mobile Phase A: Water (10 mmol/L $NH_4HCO_3$), Mobile Phase B: ACN; Flow rate: 60 mL/min; Gradient: 43% B to 61% B in 8 min; Wave Length: 220 nm; RT1(min): 7.48. This resulted in N-(5-((cis-3-(4-(trifluoromethyl)phenyl)cyclobutoxy)methyl)-1H-indol-3-yl)acetamide (61.9 mg) as a white solid. LCMS Method E: $[M-H]^-$=401.1. $^1H$ NMR (400 MHz, DMSO-$d_6$) δ 10.74 (s, 1H), 9.83 (s, 1H), 7.77 (s, 1H), 7.70-7.65 (m, 3H), 7.46 (d, J=8.0 Hz, 2H), 7.29 (d, J=8.4 Hz, 1H), 7.09-7.07 (m, 1H), 4.49 (s, 2H), 4.09-4.02 (m, 1H), 3.14-3.10 (m, 1H), 2.71-2.65 (m, 2H), 2.09 (s, 3H), 2.01-1.93 (m, 2H).

The Analogs Prepared in the Following Table were Prepared Using the Same Method Described for Examples 249.

Example 252: N-(5-(cis-2,2-dimethyl-3-(4-(trifluoromethyl) phenyl)cyclobutoxy)-1H-indol-3-yl)acetamide (Compound 432)

Compound 432

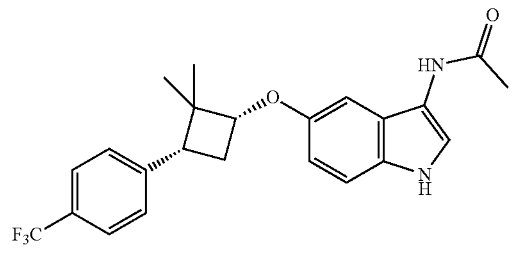

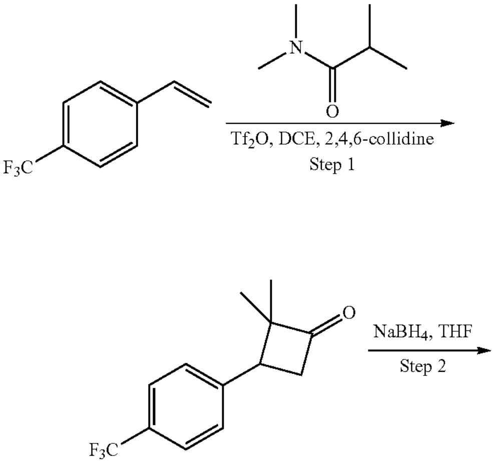

| Example # | Compound # | Starting materials Used | Structure | LCMS data |
|---|---|---|---|---|
| 250 | 492 | 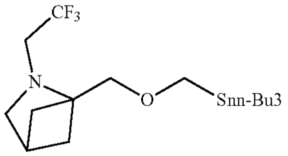 | 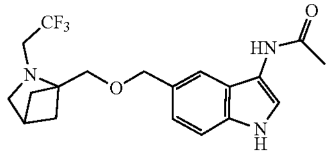 [SMILES: CC(=O)Nc1c[nH]c2ccc(COCC34CC(CN3CC(F)(F)F)C4)cc12] | Method F: MS-ESI:382.1 $[M+H]^+$. |
| 251 | 482 | Intermediate 128 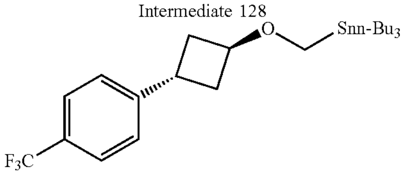 Intermediate 127 | 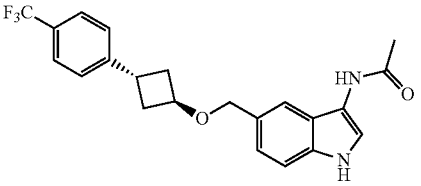 [SMILES: CC(=O)Nc1c[nH]c2ccc(CO[C@H]3C[C@H](c4ccc(C(F)(F)F)cc4)C3)cc12] | Method F: MS-ESI: 401.1 $[M-H]^+$. |

-continued

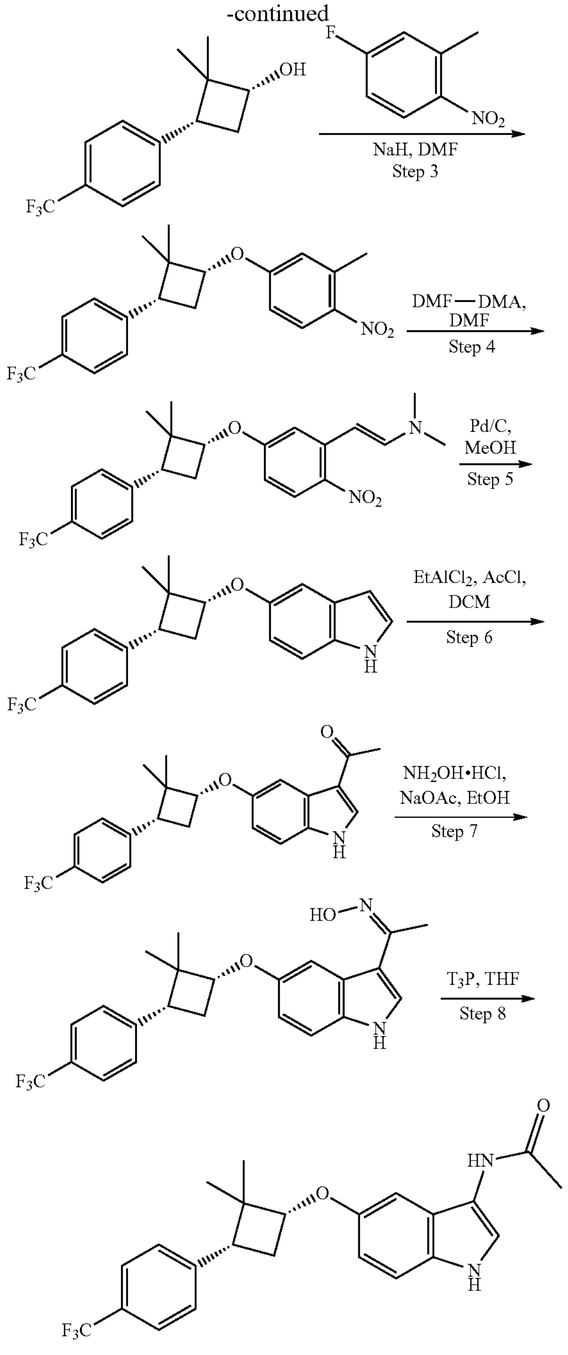

Compound 432

Step 1: 2,2-dimethyl-3-(4-(trifluoromethyl)phenyl) cyclobutan-1-one

N,N-dimethylisobutyramide (1.6 g, 13.9 mmol, 1.2 equiv.) was dissolved in DCE (20 mL) and cooled to 0° C., $Tf_2O$ (4.6 g, 16.3 mmol, 1.4 equiv.) was added under an atmosphere of nitrogen. The reaction mixture was stirred for 30 min at 0° C., then to the above mixture were added 1-(trifluoromethyl)-4-vinylbenzene (2.0 g, 11.6 mmol, 1.0 equiv.) and 2,4,6-trimethylpyridine (2.0 g, 16.3 mmol, 1.4 equiv.) dropwise, maintaining the solution at 0° C. The resulting mixture was stirred for additional 2 hours at 80° C., then cooled to rt and quenched by the addition of water. The resulting solution was extracted with dichloromethane, washed with brine, dried over anhyd. sodium sulfate and concentrated under vacuum. The residue was purified by silica gel column chromatography, eluting with petroleum ether/EtOAc (10:1) to give 2,2-dimethyl-3-(4-(trifluoromethyl)phenyl)cyclobutan-1-one (1.9 g) as a yellow oil. $^1H$ NMR (400 MHz, DMSO-$d_6$) δ 7.72 (d, J=8.0 Hz, 2H), 7.53 (d, J=8.0 Hz, 2H), 3.69 (dd, J=17.2, 8.4 Hz, 1H), 3.55 (t, J=8.8 Hz, 1H), 3.30 (dd, J=17.2, 8.4 Hz, 1H), 1.28 (s, 3H), 0.68 (s, 3H).

Step 2: cis-2,2-dimethyl-3-(4-(trifluoromethyl)phenyl)cyclobutan-1-ol 2,2-Dimethyl-3-(4-(trifluoromethyl)phenyl)cyclobutan-1-one (1.9 g, 7.9 mmol, 1.0 equiv.) was dissolved in THE (30 mL) and cooled to 0° C., then $NaBH_4$ (299.8 mg, 7.9 mmol, 1.0 equiv.) was added. The reaction mixture was stirred for 30 min at 0° C. and then quenched by the addition of water. The resulting solution was extracted with EtOAc, washed with brine, dried over anhyd. $Na_2SO_4$ and concentrated under vacuum. The residue was purified by silica gel column chromatography, eluting with petroleum ether/EtOAc (2:1) to give cis-2,2-dimethyl-3-(4-(trifluoromethyl)phenyl)cyclobutan-1-ol (1.5 g) as a yellow oil. $^1H$ NMR (400 MHz, $CDCl_3$-$d_1$) δ 7.58 (d, J=8.0 Hz, 2H), 7.24 (d, J=8.0 Hz, 2H), 4.02 (dd, J=8.4, 7.2 Hz, 1H), 2.88 (dd, J=11.2, 7.6 Hz, 1H), 2.60-2.56 (m, 1H), 2.20-2.16 (m, 1H), 1.30 (s, 3H), 0.68 (s, 3H).

Step 3: 4-(cis-2,2-dimethyl-3-(4-(trifluoromethyl) phenyl)cyclobutoxy)-2-methyl-1-nitrobenzene cis-2,2-Dimethyl-3-(4-(trifluoromethyl)phenyl)cyclobutan-1-ol (1.5 g, 6.1 mmol, 1.0 equiv.) was dissolved in DMF (20 mL) and cooled to 0° C., then NaH (60% wt., 368.4 mg, 9.2 mmol, 1.5 equiv.) was added under an atmosphere of nitrogen. After stirred for 30 min, 4-fluoro-2-methyl-1-nitrobenzene (1.4 g, 9.2 mmol, 1.5 equiv.) was added. The reaction mixture was stirred for additional 2 hours at rt and then quenched by the addition of water at 0° C. The resulting solution was extracted with EtOAc, washed with brine, dried over anhyd. $Na_2SO_4$ and concentrated under vacuum. reduced pressure. The residue was purified by silica gel column chromatography, eluting with petroleum ether/EtOAc (5:1) to give 4-(cis-2,2-dimethyl-3-(4-(trifluoromethyl)phenyl)cyclobutoxy)-2-methyl-1-nitrobenzene (1.0 g) as a yellow oil. LCMS Method A: $[M+H]^+$=380.2.

Step 4: (E)-2-(5-(cis-2,2-dimethyl-3-(4-(trifluoromethyl)phenyl)cyclobutoxy)-2-nitrophenyl)-N,N-dimethylethen-1-amine 4-(cis-2,2-dimethyl-3-(4-(trifluoromethyl)phenyl)cyclobutoxy)-2-methyl-1-nitrobenzene (1.2 g, 3.2 mmol, 1.0 equiv.) and DMF-DMA (1.9 g, 16.0 mmol, 5.0 equiv.) were dissolved in DMF (15 mL). The reaction mixture was heated to 120° C. for 16 hours, then cooled to rt and concentrated under vacuum to give (E)-2-(5-(cis-2,2-dimethyl-3-(4-(trifluoromethyl)phenyl)cyclobutoxy)-2-nitrophenyl)-N,N-dimethylethen-1-amine (1.4 g, crude) as a red oil. LCMS Method A: $[M+H]^+$=435.2.

Step 5: 5-(cis-2,2-dimethyl-3-(4-(trifluoromethyl) phenyl)cyclobutoxy)-1H-indole (E)-2-(5-(cis-2,2-dimethyl-3-(4-(trifluoromethyl)phenyl) cyclobutoxy)-2-nitrophenyl)-N,N-dimethylethen-1-amine (1.4 g, 3.2 mmol, 1.0 equiv.) was dissolved in MeOH (15 mL), then Pd/C (685.8 mg, 10% wt.) was added under an atmosphere of nitrogen. The mixture was sparged with nitrogen, placed under an atmosphere of hydrogen gas (balloon), then stirred for 16 hours at rt. The solids were removed by filtration and the filter cake was washed with MeOH. The combined filtrate was concentrated under vacuum to give 5-(cis-2,2-dimethyl-3-(4-(trifluoromethyl)phenyl)cyclobutoxy)-1H-indole (605.0 mg) as a yellow solid. LCMS Method A: $[M+H]^+$=360.1. $^1H$ NMR (400 MHz, DMSO-$d_6$) δ 10.94 (s, 1H), 7.69 (d, J=7.6 Hz, 2H), 7.43 (d, J=7.6 Hz, 2H), 7.31-7.29 (m, 2H), 7.06 (s, 1H), 6.75 (d, J=8.8 Hz, 1H), 6.34 (s, 1H), 4.52 (t, J=8.0 Hz, 1H), 3.07 (t, J=9.6 Hz, 1H), 2.70-2.63 (m, 1H), 2.45-2.37 (m, 1H), 1.38 (s, 3H), 0.68 (s, 3H).

Step 6: 1-(5-(cis-2,2-dimethyl-3-(4-(trifluoromethyl)phenyl)cyclobutoxy)-1H-indol-3-yl)ethan-1-one 5-(cis-2,2-dimethyl-3-(4-(trifluoromethyl)phenyl)cyclobutoxy)-1H-indole (450.0 mg, 1.2 mmol, 1.0 equiv.) was dissolved in DCM (10 mL) and cooled to −30° C., then $Et_2AlCl$ (1M in DCM, 1.9 mL, 1.9 mmol, 1.5 equiv.) and acetyl chloride (147.4 mg, 1.9 mmol, 1.5 equiv.) were added dropwise, maintaining the solution at −30° C. under an atmosphere of nitrogen. The reaction mixture was stirred for 2 hours at −30° C. and then quenched by the addition of ice-water. The resulting solution was extracted with dichloromethane, washed with brine, dried over anhyd. $Na_2SO_4$ and concentrated under vacuum. The residue was purified by silica gel column chromatography, eluting with petroleum ether/EtOAc (1:1) to give 1-(5-(cis-2,2-dimethyl-3-(4-(trifluoromethyl)phenyl)cyclobutoxy)-1H-indol-3-yl)ethan-1-one (428.0 mg) as a brown solid. LCMS Method A: $[M+H]^+$=402.2. $^1H$ NMR (400 MHz, DMSO-$d_6$) δ 11.82 (s, 1H), 8.25 (d, J=3.2 Hz, 1H), 7.76 (d, J=2.8 Hz, 1H), 7.68 (d, J=8.0 Hz, 2H), 7.44 (d, J=7.6 Hz, 2H), 7.36 (d, J=8.8 Hz, 1H), 6.86-6.83 (m, 1H), 4.54 (t, J=7.6 Hz, 1H), 3.14-3.10 (m, 1H), 2.68-2.58 (m, 1H), 2.45-2.41 (m, 1H), 2.43 (s, 3H), 1.43 (s, 3H), 0.66 (s, 3H).

Step 7: (Z)-1-(5-(cis-2,2-dimethyl-3-(4-(trifluoromethyl)phenyl)cyclobutoxy)-1H-indol-3-yl)ethan-1-one oxime 1-(5-(cis-2,2-dimethyl-3-(4-(trifluoromethyl)phenyl)cyclobutoxy)-1H-indol-3-yl)ethan-1-one (428.0 mg, 1.1 mmol, 1.0 equiv.) and NaOAc (174.9 mg, 2.1 mmol, 2.0 equiv.) were dissolved in EtOH (5 mL), then $NH_2OH·HCl$ (111.1 mg, 1.6 mmol, 1.5 equiv.) was added. The reaction mixture was stirred for 4 hours at 60° C., then cooled to rt and quenched by the addition of water. The resulting solution was extracted with EtOAc, washed with brine, dried over anhyd. $Na_2SO_4$ and concentrated under vacuum. The residue was purified by silica gel column chromatography, eluting with petroleum ether/EtOAc (1:1) to give (Z)-1-(5-(cis-2,2-dimethyl-3-(4-(trifluoromethyl)phenyl)cyclobutoxy)-1H-indol-3-yl)ethan-1-one oxime (340.0 mg) as a brown solid. LCMS Method A: $[M+H]^+$=417.0.

Step 8: N-(5-(cis-2,2-dimethyl-3-(4-(trifluoromethyl)phenyl)cyclobutoxy)-1H-indol-3-yl)acetamide (Z)-1-(5-(cis-2,2-dimethyl-3-(4-(trifluoromethyl)phenyl)cyclobutoxy)-1H-indol-3-yl)ethan-1-one oxime (200.0 mg, 0.5 mmol, 1.0 equiv.) was dissolved in THE (4 mL), then $T_3P$ (305.6 mg, 0.9 mmol, 2.0 equiv.) was added. The reaction mixture was stirred for 1 hour at 70° C. and then quenched by the addition of water. The resulting solution was extracted with EtOAc, washed with brine, dried over anhyd. $Na_2SO_4$ and concentrated under vacuum. The residue was purified by Prep-HPLC with the following conditions: Column: XBridge Prep OBD C18 Column, 19*250 mm, 5 m; Mobile Phase A: Water (10 mmol/L $NH_4HCO_3$), Mobile Phase B: ACN; Flow rate: 25 mL/min; Gradient: 65% B to 77% B in 6 min; Wave Length: 254 nm; RT1(min): 5.78. This resulted in N-(5-(cis-2,2-dimethyl-3-(4-(trifluoromethyl)phenyl)cyclobutoxy)-1H-indol-3-yl)acetamide (74.7 mg) as a white solid. LCMS Method F: $[M+H]^+$=417.2. $^1H$ NMR (400 MHz, DMSO-$d_6$) δ 10.60 (s, 1H), 9.71 (s, 1H), 7.69-7.65 (m, 3H), 7.43 (d, J=6.0 Hz, 2H), 7.32 (s, 1H), 7.21 (d, J=8.8 Hz, 1H), 6.75 (d, J=8.0 Hz, 1H), 4.48 (t, J=7.2 Hz, 1H), 3.12-3.08 (s, 1H), 2.74-2.67 (m, 1H), 2.42-2.37 (m, 1H), 2.09 (s, 3H), 1.36 (s, 3H), 0.72 (s, 3H).

Example 253: Synthesis of N-{5-[(1R,3R)-3-[4-(trifluoromethyl)phenyl]cyclobutoxy]-1H-indol-3-yl}oxane-4-carboxamide (Compound 493)

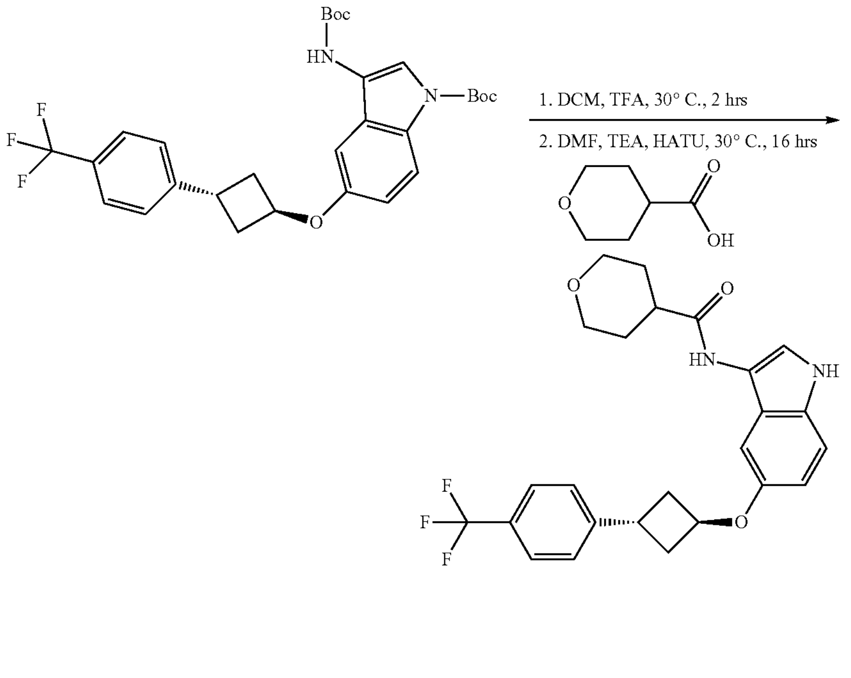

tert-butyl 3-{[(tert-butoxy)carbonyl]amino}-5-[(1R,3R)-3-[4-(trifluoromethyl)phenyl]cyclobutoxy]-1H-indole-1-carboxylate (98.3 mg, 0.18 mmol, 1.0 equiv.) was dissolved in DCM (3 mL), then TFA (1 mL) was added to the solution. The mixture was heated at 30° C. for 2 hours. The reaction mixture was concentrated by Speedvac to give a residue. Then the residue and oxane-4-carboxylic acid (46.8 mg, 0.36 mmol, 2.0 equiv.) were dissolved in DMF (2 mL), then TEA (130 μl, 0.9 mmol, 5.0 equiv.) and HATU (71.8 mg, 0.189 mmol, 1.05 equiv.) were added. The mixture was heated at 30° C. for 16 hours. The reaction mixture was concentrated by Speedvac to give a residue that was purified by prep HPLC-1-1 to give N-{5-[(1R,3R)-3-[4-(trifluoromethyl)phenyl]cyclobutoxy]-1H-indol-3-yl}oxane-4-carboxamide (24.7 mg, 0.054 mmol) as a powder. MS-ESI, 459.3 [M+H$^+$]. $^1$H NMR (400 MHz, DMSO-$d_6$), δ ppm 10.89 (br s, 1H), 9.01 (s, 1H), 7.68 (br d, J=8.1 Hz, 2H), 7.58 (br d, J=8.00 Hz, 2H), 7.28-7.12 (m, 3H), 6.73 (dd, J=8.70 Hz, 1H), 4.19 (t, J=6.60 Hz, 2H), 3.22-3.09 (m, 2H), 2.92 (q, J=7.40 Hz, 2H), 1.22 (t, J=7.30 Hz, 3H).

The compounds in the following table were prepared using the above procedures (example 253) with the appropriate starting material.

| Example # | Compound # | Structure | IUPAC Name | LC-MS, MS-ESI, -- [M+H+]. |
|---|---|---|---|---|
| 253 | 493 | 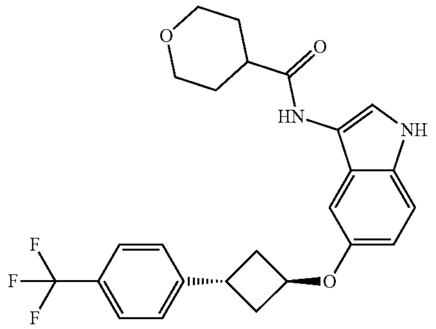 [SMILES: O=C(Nc1c[nH]c2ccc(O[C@H]3C[C@H](c4ccc(C(F)(F)F)cc4)C3)cc12)C1CCOCC1] | N-{5-[(IR,3R)-3-[4-(trifluoromethyl)phenyl]cyclobutoxy]-1H-indol-3-yl}oxane-4-carboxamide | 459.3 |
| 254 | 489 | 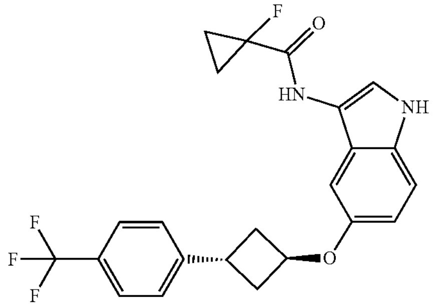 [SMILES: O=C(Nc1c[nH]c2ccc(O[C@H]3C[C@H](c4ccc(C(F)(F)F)cc4)C3)cc12)C1(F)CC1] | l-fluoro-N-{5-[(1R,3R)-3-[4-(trifluoromethyl)phenyl]cyclobutoxy]-1H-indol-3-yl}cyclopropane-1-carboxamide | 433.2 |
| 255 | 488 | 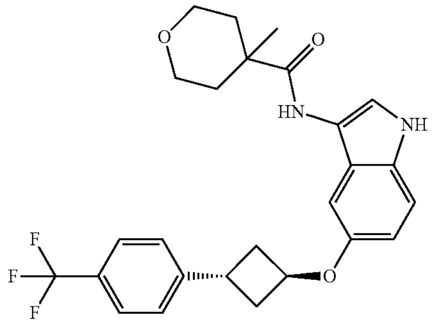 [SMILES: CC1(C(=O)Nc2c[nH]c3ccc(O[C@H]4C[C@H](c5ccc(C(F)(F)F)cc5)C4)cc23)CCOCC1] | 4-methyl-N-{5-[(1R,3R)-3-[4-(trifluoromethyl)phenyl]cyclobutoxy]-1H-indol-3-yl}oxane-4-carboxamide | 473.4 |
| 256 | 487 | 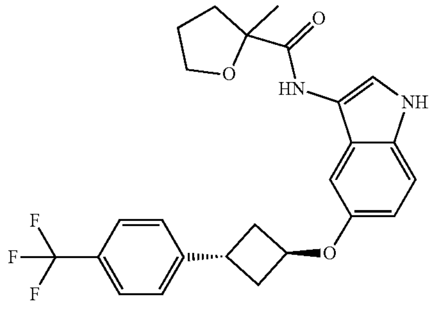 [SMILES: CC1(C(=O)Nc2c[nH]c3ccc(O[C@H]4C[C@H](c5ccc(C(F)(F)F)cc5)C4)cc23)CCCO1] | 2-methyl-N-{5-[(1R,3R)-3-[4-(trifluoromethyl)phenyl]cyclobutoxy]-1H-indol-3-yl}oxolane-2-carboxamide | 459.3 |

-continued

| Example # | Compound # | Structure | IUPAC Name | LC-MS, MS-ESI, -- [M+H+]. |
| --- | --- | --- | --- | --- |
| 257 | 469 | 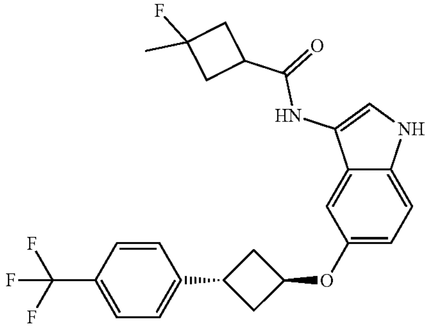 [SMILES: CC1(F)CC(C(=O)Nc2c[nH]c3ccc(O[C@H]4C[C@H](c5ccc(C(F)(F)F)cc5)C4)cc23)C1] | 3-fluoro-3-methyl-N-{5-[(1R,3R)-3-[4-(trifluoromethyl)phenyl]cyclobutoxy]-1H-indol-3-yl}cyclobutane-1-carboxamide | 461.3 |
| 258 | 468 | 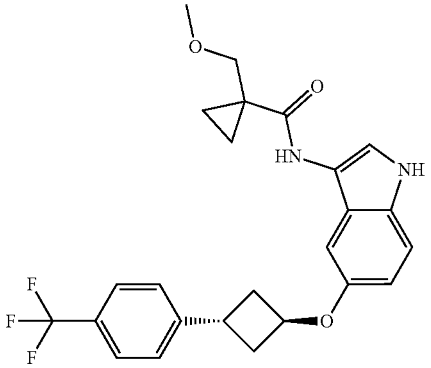 [SMILES: COCC1(C(=O)Nc2c[nH]c3ccc(O[C@H]4C[C@H](c5ccc(C(F)(F)F)cc5)C4)cc23)CC1] | l-(methoxymethyl)-N-{5-[(1R,3R)-3-[4-(trifluoromethyl)phenyl]cyclobutoxy]-1H-indol-3-yl}cyclopropane-1-carboxamide | 459.3 |
| 259 | 467 | 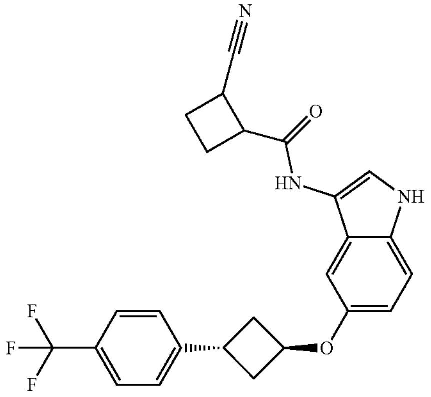 [SMILES: N#CC1CCC1C(=O)Nc1c[nH]c2ccc(O[C@H]3C[C@H](c4ccc(C(F)(F)F)cc4)C3)cc12] | 2-cyano-N-{5-[(1R,3R)-3-[4-(trifluoromethyl)phenyl]cyclobutoxy]-1H-indol-3-yl}cyclobutane-1-carboxamide | 454.3 |
| 260 | 486 | 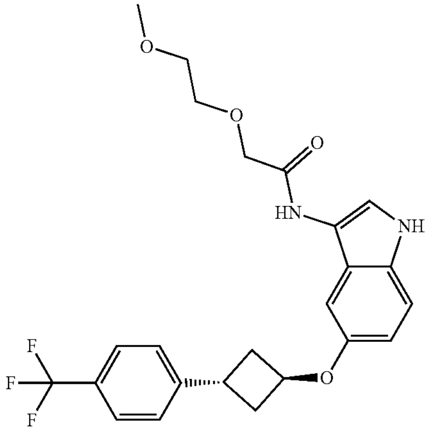 [SMILES: COCCOCC(=O)Nc1c[nH]c2ccc(O[C@H]3C[C@H](c4ccc(C(F)(F)F)cc4)C3)cc12] | 2-(2-methoxyethoxy)-N-{5-[(1R,3R)-3-[4-(trifluoromethyl)phenyl]cyclobutoxy]-1H-indol-3-yl}acetamide | 463.3 |

Example 261: Synthesis of N-{5-[(1R, 3R)-3-[4-(trifluoromethyl)phenyl]cyclobutoxy]-1H-indol-3-yl}azetidine-3-carboxamide (Compound 459)

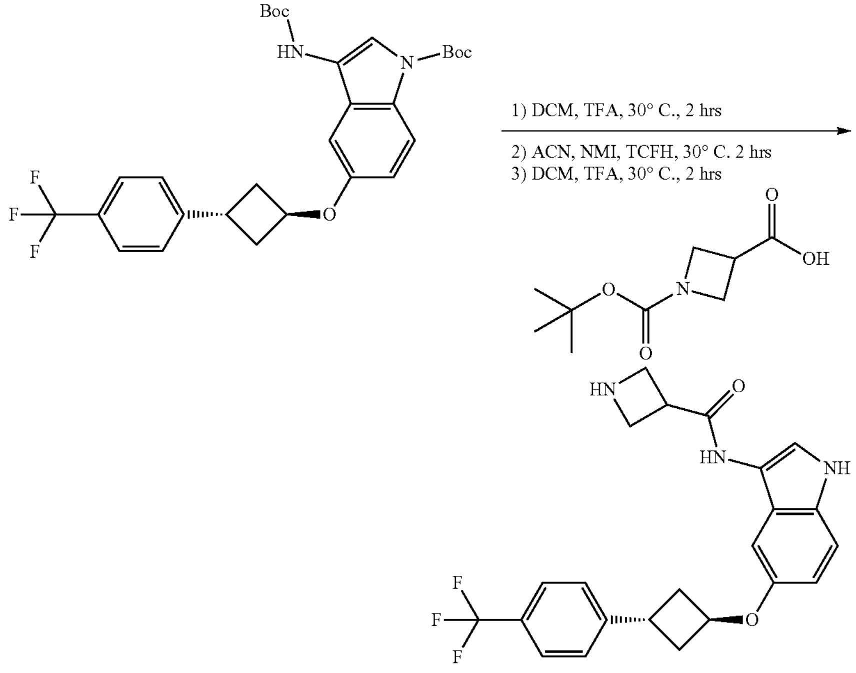

tert-butyl 3-{[(tert-butoxy)carbonyl]amino}-5-[(1R,3R)-3-[4-(trifluoromethyl)phenyl]cyclobutoxy]-1H-indole-1-carboxylate (136.5 mg, 0.25 mmol, 1.0 equiv.) was dissolved in DCM (3 mL), then TFA (1 mL) was added to the solution. The mixture was heated at 30° C. for 2 hours. The reaction mixture was concentrated by Speedvac to give a residue. Then the residue and 1-[(tert-butoxy)carbonyl] azetidine-3-carboxylic acid (100.5 mg, 0.5 mmol, 2.0 equiv.) were dissolved in ACN (1.5 mL), then NMI (500 μl) and TCFH (78.4 mg, 0.28 mmol, 1.1 equiv.) were added. The mixture was heated at 30° C. for 16 hours. The reaction mixture was concentrated by Speedvac to give a residue. The residue was diluted with $H_2O$ (1 mL) and extracted with 3*1 mL EtOAc. The combined organic layers were washed with $H_2O$ (1 mL), dried over anhydrous $Na_2SO_4$, filtered and concentrated under reduced pressure to give a residue. After that DCM (3 mL) was added dropwise and TFA (1 mL) at 30° C. for 2 hrs. The reaction mixture was concentrated by Speedvac to give a residue that was purified by prep HPLC-1 to give N-{5-[(1R, 3R)-3-[4-(trifluoromethyl) phenyl] cyclobutoxy]-1H-indol-3-yl} azetidine-3-carboxamide (4.82 mg, 0.011 mmol) as a powder. MS-ESI, 430.3 $[M+H^+]$. $^1H$ NMR (400 MHz, DMSO-$d_6$), δ ppm 11.03-10.95 (m, 1H), 9.07 (s, 1H), 7.63 (d, J=8.8 Hz, 2H), 7.55 (s, 1H), 7.29 (d, J=8.3 Hz, 1H), 7.24 (d, J=2.5 Hz, 1H), 7.14-7.06 (m, 3H), 4.27 (t, J=6.8 Hz, 2H), 3.17-3.07 (m, 2H), 2.93 (q, J=7.4 Hz, 2H), 1.23 (t, J=7.4 Hz, 3H).

The compounds in the following table were prepared using the above procedure (example 261) with the appropriate starting material.

| Example # | Compound # | Final compound | IUPAC Name | LC-MS, MS-ESI, -- [M+H+]. |
|---|---|---|---|---|
| 262 | 460 | 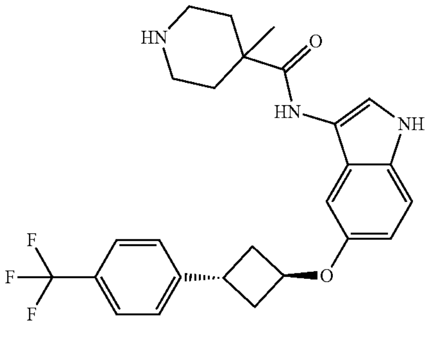 [SMILES: CC1(C(=O)Nc2c[nH]c3ccc(O[C@H]4C[C@H](c5ccc(C(F)(F)F)cc5)C4)cc23)CCNCC1] | 4-methyl-N-{5-[(1R,3R)-3-[4-(trifluoromethyl) phenyl]cyclobutoxy]-1H-indol-3-yl}piperidine-4-carboxamide | 472.3 |

-continued

| Example # | Compound # | Final compound | IUPAC Name | LC-MS, MS-ESI, -- [M+H+]. |
|---|---|---|---|---|
| 263 | 459 | 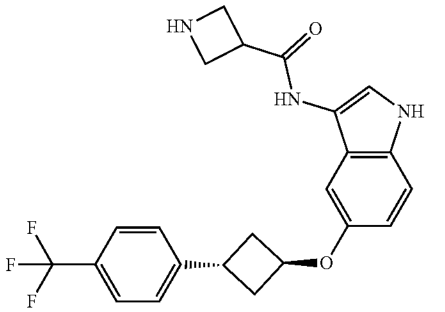 [SMILES: O=C(Nc1c[nH]c2ccc(O[C@H]3C[C@H](c4ccc(C(F)(F)F)cc4)C3)cc12)C1CNC1] | N-{5-[(1R,3R)-3-[4-(trifluoromethyl) phenyl]cyclobutoxy]-1H-indol-3-yl} azetidine-3-carboxamide | 430.3 |

The compound in the following table was prepared using steps 1) and 2) of the above procedure (example 261) with the appropriate starting material.

| Example # | Compound # | Final compound | IUPAC Name | LC-MS, MS-ESI, -- [M+H+]. |
|---|---|---|---|---|
| 264 | 466 | 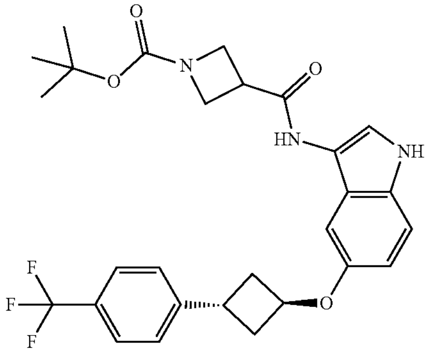 [SMILES: CC(C)(C)OC(=O)N1CC(C(=O)Nc2c[nH]c3ccc(O[C@H]4C[C@H](c5ccc(C(F)(F)F)cc5)C4)cc23)C1] | tert-butyl 3-({5-[(1R,3R)-3-[4-(trifluoromethyl) phenyl] cyclobutoxy]-1H-indol-3-yl}carbamoyl) azetidine-1-carboxylate | 529.3 |

Example 265: Synthesis of N-(5-{2-[4-(2, 2, 2-trifluoroethyl)phenoxy]ethyl}-1H-indol-3-yl)acetamide (Compound 442)

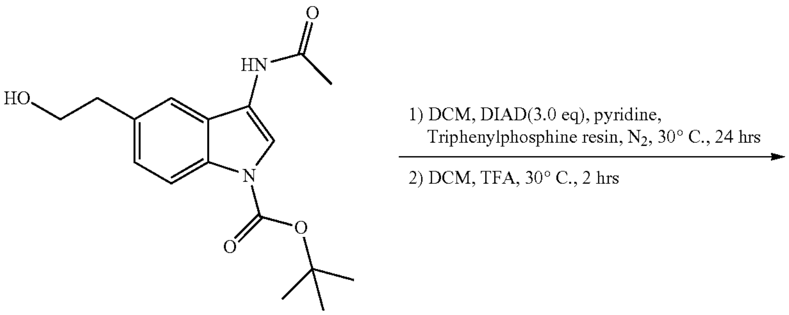

-continued

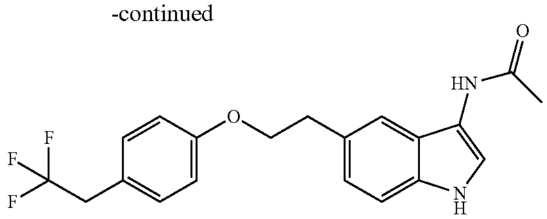

tert-butyl 3-acetamido-5-(2-hydroxyethyl)-1H-indole-1-carboxylate (66.8 mg, 0.21 mmol, 1.0 equiv.) and 4-(2,2,2-trifluoroethyl)phenol (73.9 mg, 0.42 mmol, 2.0 equiv.) were dissolved in DCM (2 mL), DIAD (127.3 mg, 0.63 mmol, 3.0 equiv.), pyridine (210 μl) and Triphenylphosphine resin (350 mg, 3.0 g/mol, 1.05 mmol, 5.0 equiv.) were added under N2 atmosphere. The mixture was heated at 30° C. for 24 hours under N2 atmosphere. The mixture was diluted with 3*1 mL DCM and extracted with $H_2O$ (1 mL). The combined organic layers were washed with $H_2O$ (1 mL), dried over anhydrous $Na_2SO_4$, filtered and concentrated under reduced pressure to give a residue. After that the residue were dissolved in DCM (2 mL), then TFA (500 μl) was added. The mixture was heated at 30° C. for 2 hours. The reaction mixture was concentrated by Speedvac to give a residue that was purified by prep HPLC-1 to give N-(5-{2-[4-(2, 2, 2-trifluoroethyl)phenoxy]ethyl}-1H-indol-3-yl) acetamide (16.24 mg, 0.041 mmol) as a powder. MS-ESI, 400.3 $[M+H^+]$. $^1H$ NMR (400 MHz, DMSO-$d_6$), δ ppm 10.67 (br s, 1H), 9.77 (s, 1H), 7.65 (d, J=9.88 Hz, 2H), 7.29-7.22 (m, 3H), 7.10-7.05 (m, 1H), 6.98-6.92 (m, 2H), 4.20 (t, J=7.03 Hz, 2H), 3.62-3.46 (m, 2H), 3.12-3.06 (m, 2H), 2.08 (s, 3H).

The compounds in the following table were prepared using the above procedure (example 265) with the appropriate starting material.

| Example # | Example # | Final compound | IUPAC Name | LC-MS, MS-ESI, -- [M+H+]. |
|---|---|---|---|---|
| 266 | 490 | 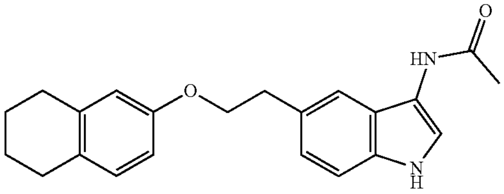 [SMILES: CC(=O)Nc1c[nH]c2ccc(CCOc3ccc4c(c3)CCCC4)cc12] | N-(5-[2-(5,6,7,8-tetrahydronaphthalen-2-yloxy)ethyl]-1H-indol-3-yl}acetamide | 349.3 |
| 267 | 462 | 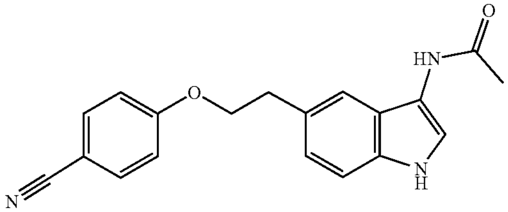 [SMILES: CC(=O)Nc1c[nH]c2ccc(CCOc3ccc(C#N)cc3)cc12] | N-{5-[2-(4-cyanophenoxy)ethyl]-1H-indol-3-yl}acetamide | 320.2 |
| 268 | 461 | 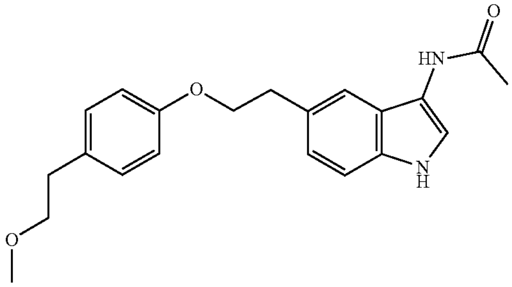 [SMILES: COCCc1ccc(OCCc2ccc3[nH]cc(NC(C)=O)c3c2)cc1] | N-(5-{2-[4-(2-methoxyethyl)phenoxy]ethyl}-1H-indol-3-yl)acetamide | 353.3 |
| 269 | 470 | 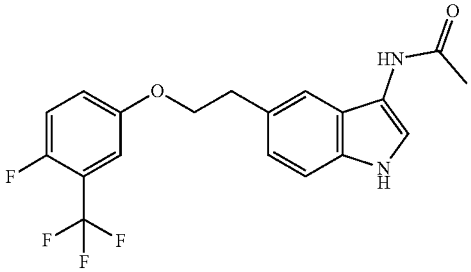 [SMILES: CC(=O)Nc1c[nH]c2ccc(CCOc3ccc(F)c(C(F)(F)F)c3)cc12] | N-(5-{2-[4-fluoro-3-(trifluoromethyl)phenoxy]ethyl}-1H-indol-3-yl)acetamide | 381.2 |

-continued

| Example # | Example # | Final compound | IUPAC Name | LC-MS, MS-ESI, -- [M+H+]. |
|---|---|---|---|---|
| 270 | 476 | 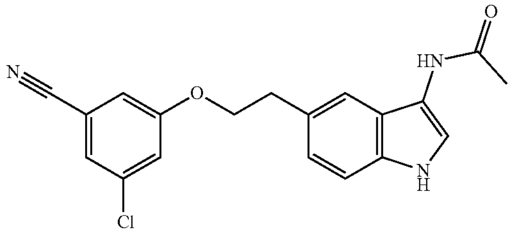 [SMILES: CC(=O)Nc1c[nH]c2ccc(CCOc3cc(Cl)cc(C#N)c3)cc12] | N-{5-[2-(3-chloro-5-cyanophenoxy)ethyl]-1H-indol-3-yl}acetamide | 354.2 |
| 271 | 453 | 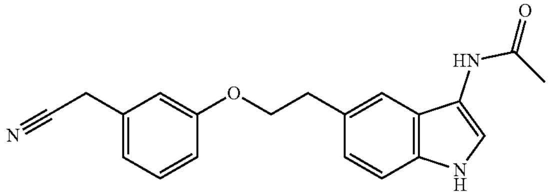 [SMILES: CC(=O)Nc1c[nH]c2ccc(CCOc3cccc(CC#N)c3)cc12] | N-(5-{2-[3-(cyanomethyl)phenoxy]ethyl}-1H-indol-3-yl)acetamide | 334.3 |
| 272 | 438 | 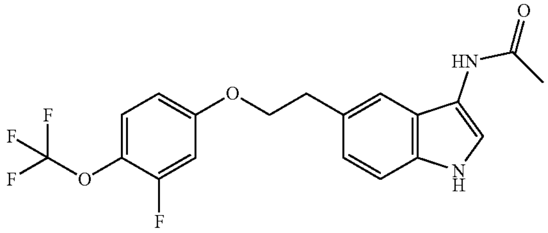 [SMILES: CC(=O)Nc1c[nH]c2ccc(CCOc3ccc(OC(F)(F)F)c(F)c3)cc12] | N-(5-{2-[3-fluoro-4-(trifluoromethoxy)phenoxy]ethyl}-1H-indol-3-yl)acetamide | 397.3 |
| 273 | 475 | 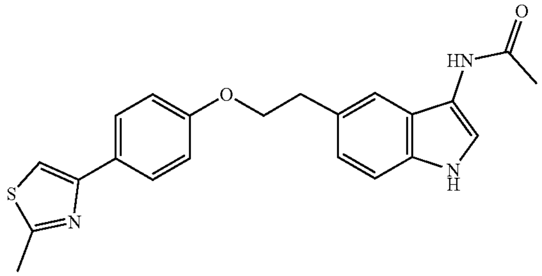 [SMILES: CC(=O)Nc1c[nH]c2ccc(CCOc3ccc(-c4csc(C)n4)cc3)cc12] | N-(5-{2-[4-(2-methyl-1,3-thiazol-4-yl)phenoxy]ethyl}-1H-indol-3-yl)acetamide | 392.2 |
| 274 | 452 | 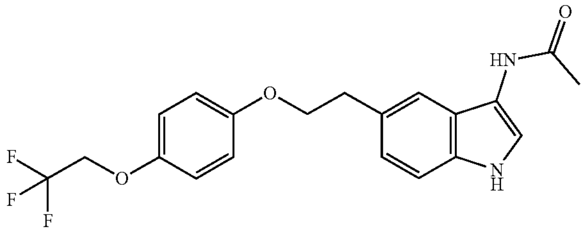 [SMILES: CC(=O)Nc1c[nH]c2ccc(CCOc3ccc(OCC(F)(F)F)cc3)cc12] | N-(5-{2-[4-(2,2,2-trifluoroethoxy)phenoxy]ethyl}-1H-indol-3-yl)acetamide | 393.2 |
| 275 | 451 | 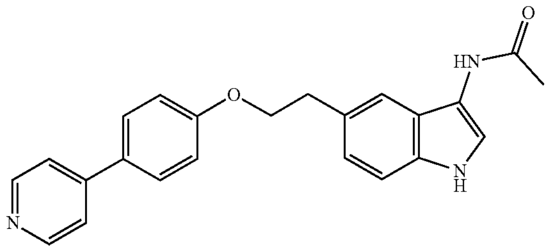 [SMILES: CC(=O)Nc1c[nH]c2ccc(CCOc3ccc(-c4ccncc4)cc3)cc12] | N-(5-{2-[4-(pyridin-4-yl)phenoxy]ethyl}-1H-indol-3-yl)acetamide | 372.2 |

-continued

| Example # | Example # | Final compound | IUPAC Name | LC-MS, MS-ESI, -- [M+H+]. |
|---|---|---|---|---|
| 276 | 442 | 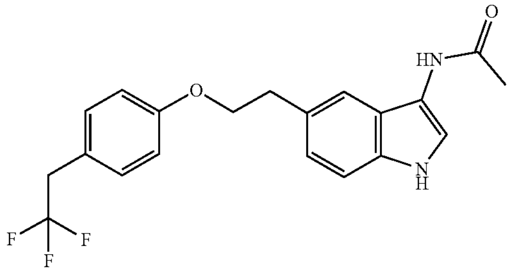 [SMILES: CC(=O)Nc1c[nH]c2ccc(CCOc3ccc(CC(F)(F)F)cc3)cc12] | N-(5-{2-[4-(2,2,2-trifluoroethyl)phenoxy]ethyl}-1H-indol-3-yl)acetamide | 400.3 |
| 277 | 441 | 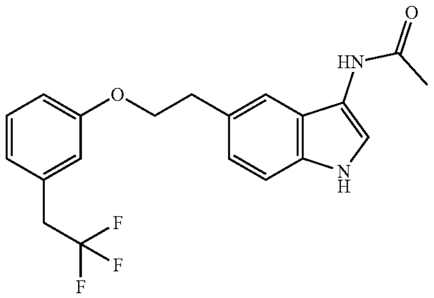 [SMILES: CC(=O)Nc1c[nH]c2ccc(CCOc3cccc(CC(F)(F)F)c3)cc12] | N-(5-{2-[3-(2,2,2-trifluoroethyl)phenoxy]ethyl}-1H-indol-3-yl)acetamide | 452.3 |
| 278 | 450 | 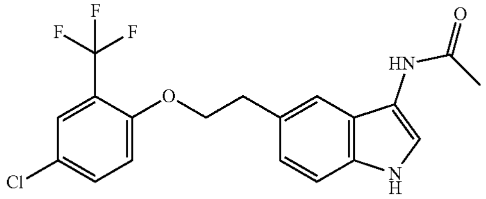 [SMILES: CC(=O)Nc1c[nH]c2ccc(CCOc3ccc(Cl)cc3C(F)(F)F)cc12] | N-(5-{2-[4-chloro-2-(trifluoromethyl)phenoxy]ethyl}-1H-indol-3-yl)acetamide | 397.2 |
| 279 | 449 | 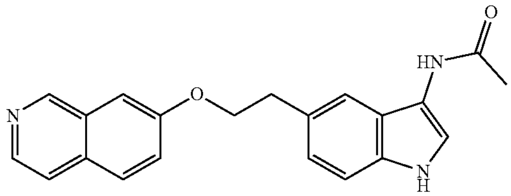 [SMILES: CC(=O)Nc1c[nH]c2ccc(CCOc3ccc4ccncc4c3)cc12] | N-{5-[2-(isoquinolin-7-yloxy)ethyl]-1H-indol-3-yl}acetamide | 346.2 |
| 280 | 411 | 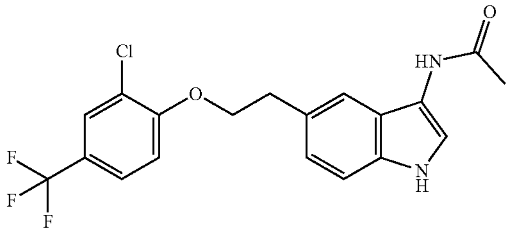 [SMILES: CC(=O)Nc1c[nH]c2ccc(CCOc3ccc(C(F)(F)F)cc3Cl)cc12] | N-(5-{2-[2-chloro-4-(trifluoromethyl)phenoxy]ethyl}-1H-indol-3-yl)acetamide | 397.1 |
| 281 | 440 | 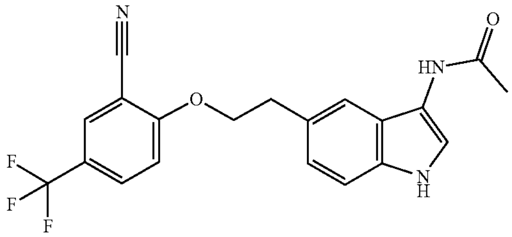 [SMILES: CC(=O)Nc1c[nH]c2ccc(CCOc3ccc(C(F)(F)F)cc3C#N)cc12] | N-(5-{2-[2-cyano-4-(trifluoromethyl)phenoxy]ethyl}-1H-indol-3-yl)acetamide | 412.3 |

-continued

| Example # | Example # | Final compound | IUPAC Name | LC-MS, MS-ESI, -- [M+H+]. |
|---|---|---|---|---|
| 282 | 410 | 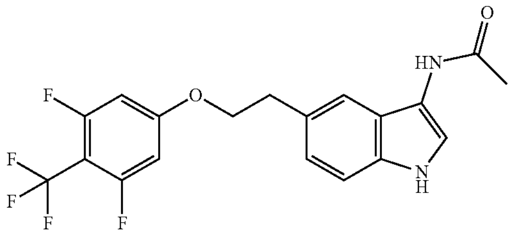 [SMILES: CC(=O)Nc1c[nH]c2ccc(CCOc3cc(F)c(C(F)(F)F)c(F)c3)cc12] | N-(5-{2-[3,5-difluoro-4-(trifluoromethyl)phenoxy]ethyl}-1H-indol-3-yl)acetamide | 399.2 |

Example 283: Synthesis of N-[5-(2-{[2-(difluoromethoxy)pyridin-4-yl]oxy}ethyl)-1H-indol-3-yl]acetamide (Compound 491)

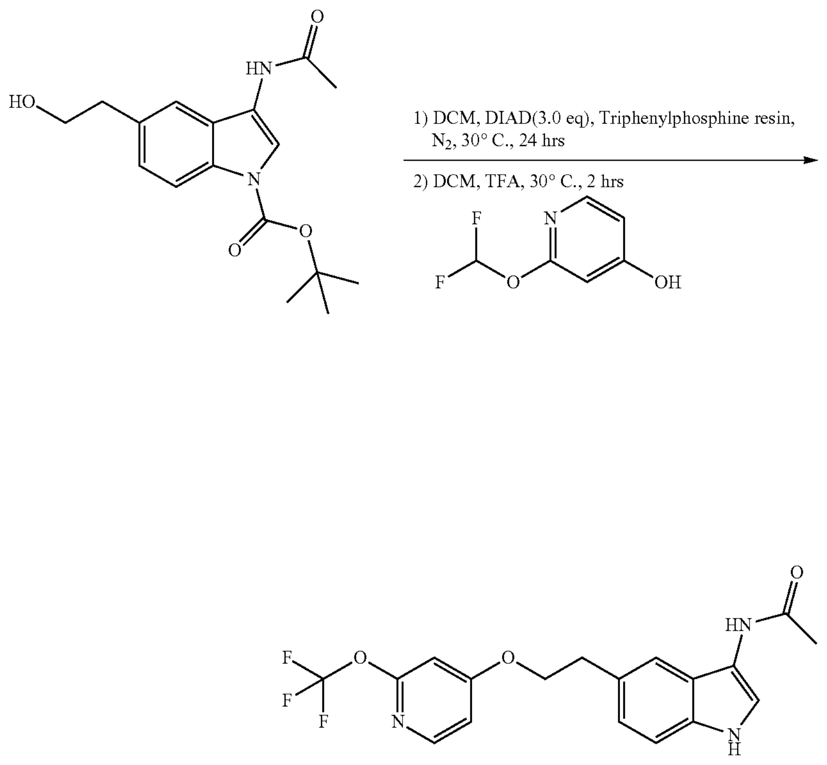

tert-butyl 3-acetamido-5-(2-hydroxyethyl)-1H-indole-1-carboxylate (66.8 mg, 0.21 mmol, 1.0 equiv.) and 2-(difluoromethoxy)pyridin-4-ol (67.6 mg, 0.42 mmol, 2.0 equiv.) were dissolved in DCM (2 mL), DIAD (127.3 mg, 0.63 mmol, 3.0 equiv.) and Triphenylphosphine resin (350 mg, 3.0 g/mol, 1.05 mmol, 5.0 equiv.) were added under $N_2$ atmosphere. The mixture was heated at 30° C. for 24 hours under N2 atmosphere. The mixture was diluted with 3*1 mL DCM and extracted with $H_2O$ (1 mL). The combined organic layers were washed with $H_2O$ (1 mL), dried over anhydrous $Na_2SO_4$, filtered and concentrated under reduced pressure to give a residue. After that the residue were dissolved in DCM (2 mL), then TFA (500 1) was added. The mixture was heated at 30° C. for 2 hours. The reaction mixture was concentrated by Speedvac to give a residue that was purified by prep HPLC-1 to give N-[5-(2-{[2-(difluoromethoxy)pyridin-4-yl]oxy}ethyl)-1H-indol-3-yl]acetamide (20.03 mg, 0.055 mmol) as a powder. MS-ESI, 362.2 [M+H$^+$]. $^1$H NMR (400 MHz, DMSO-$d_6$), δ ppm 10.69 (s, 1H), 9.78 (s, 1H), 8.04 (d, J=5.77 Hz, 1H), 7.86 (s, 1H), 7.69-7.65 (m, 1H), 7.50 (s, 1H), 7.91-7.48 (m, 1H), 7.26 (d, J=8.53 Hz, 1H), 7.06 (dd, J=8.28, 1.25 Hz, 1H), 6.85 (dd, J=5.90, 2.13 Hz, 1H), 6.66 (d, J=2.01 Hz, 1H), 4.34 (t, J=6.90 Hz, 2H), 3.11 (t, J=6.90 Hz, 2H), 2.08 (s, 3H).

The compounds in the following table were prepared using the above procedures (example 283) with the appropriate starting material.

| Example # | Compound # | Final compound | IUPAC Name | LC-MS, MS-ESI, -- [M+H+]. |
|---|---|---|---|---|
| 283 | 491 | 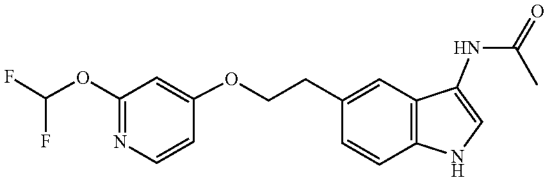 [SMILES: CC(=O)Nc1c[nH]c2ccc(CCOc3ccnc(OC(F)F)c3)cc12] | N-[5-(2-(2-(difluoromethoxy)pyridin-4-yl]oxy}ethyl)-1H-indol-3-yl]acetamide | 362.2 |
| 284 | 463 | 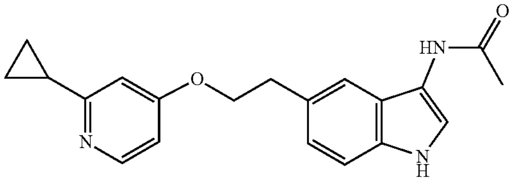 [SMILES: CC(=O)Nc1c[nH]c2ccc(CCOc3ccnc(C4CC4)c3)cc12] | N-(5-(2-(2-cyclopropylpyridin-4-yl)oxy]ethyl}-1H-indol-3-yl)acetamide | 336.3 |
| 285 | 481 | 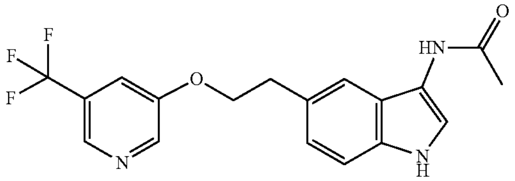 [SMILES: CC(=O)Nc1c[nH]c2ccc(CCOc3cncc(C(F)(F)F)c3)cc12] | N-[5-(2-{[5-(trifluoromethyl)pyridin-3-yl]oxy}ethyl)-1H-indol-3-yl]acetamide | 364.2 |
| 286 | 471 | 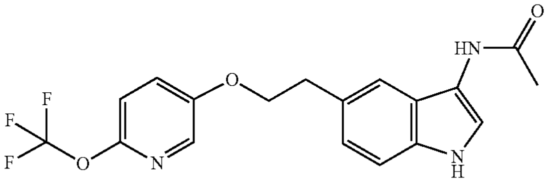 [SMILES: CC(=O)Nc1c[nH]c2ccc(CCOc3ccc(OC(F)(F)F)nc3)cc12] | N-[5-(2-{[6-(trifluoromethoxy)pyridin-3-yl]oxy}ethyl)-1H-indol-3-yl]acetamide | 380.2 |
| 287 | 477 | 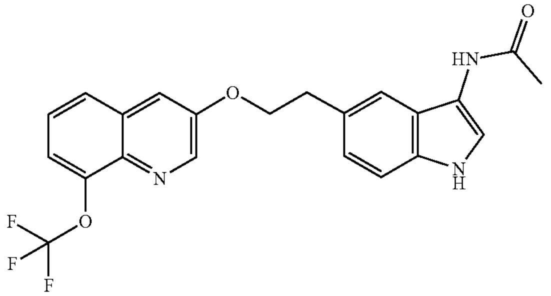 [SMILES: CC(=O)Nc1c[nH]c2ccc(CCOc3cnc4c(OC(F)(F)F)cccc4c3)cc12] | N-[5-(2-{[8-(trifluoromethoxy)quinolin-3-yl]oxy}ethyl)-1H-indol-3-yl]acetamide | 430.3 |
| 288 | 480 | 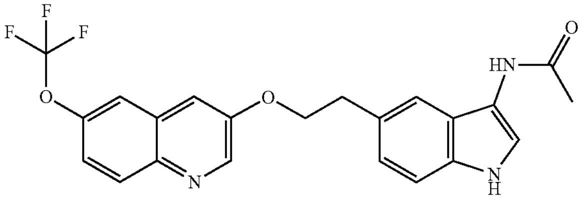 [SMILES: CC(=O)Nc1c[nH]c2ccc(CCOc3cnc4ccc(OC(F)(F)F)cc4c3)cc12] | N-[5-(2-{[6-(trifluoromethoxy)quinolin-3-yl]oxy}ethyl)-1H-indol-3-yl]acetamide | 430.3 |

Example 289: Synthesis of N-[5-(2-{[5-(difluoromethyl)pyridin-3-yl]oxy}ethyl)-1H-indol-3-yl]acetamide (compound 439)

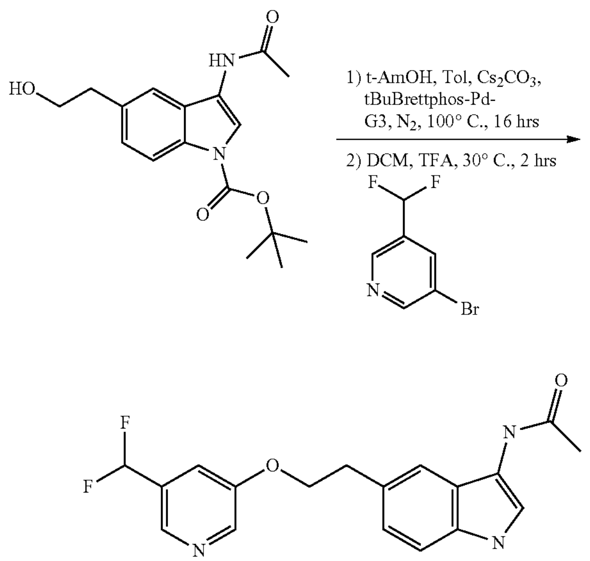

tert-butyl 3-acetamido-5-(2-hydroxyethyl)-1H-indole-1-carboxylate (66.8 mg, 0.21 mmol, 1.0 equiv.) and 3-bromo-5-(difluoromethyl)pyridine (86.5 mg, 0.42 mmol, 2.0 equiv.) were dissolved in t-AmOH (1 mL) and Tol (1 mL), $Cs_2CO_3$ (204.8 mg, 0.63 mmol, 3.0 equiv.) and tBuBrettphos-Pd-G3 (89.7 mg, 0.105 mmol, 0.5 equiv.) were added under N2 atmosphere. The mixture was heated at 100° C. for 16 hours under N2 atmosphere. The reaction mixture was concentrated by Speedvac to give a residue. The residue was diluted with $H_2O$ (1 mL) and extracted with 3*1 mL DCM. The combined organic layers were washed with $H_2O$ (1 mL), dried over anhydrous sodium sulfate anhydrous, filtered and concentrated under reduced pressure to give a residue. After that the residue were dissolved in DCM (2 mL), then TFA (500 µl) was added. The mixture was heated at 30° C. for 2 hours. The reaction mixture was concentrated by Speedvac to give a residue that was purified by prep HPLC-1 to give N-[5-(2-{[5-(difluoromethyl) pyridin-3-yl]oxy}ethyl)-1H-indol-3-yl]acetamide (13.71 mg, 0.040 mmol) as a powder. MS-ESI, 346.2 [M+H$^+$].

The compounds in the following table were prepared using the above procedures (example 289) with the appropriate starting material.

| Example # | Compound # | Final compound | IUPAC Name | LC-MS, MS-ESI, -- [M+H+]. |
|---|---|---|---|---|
| 289 | 439 | 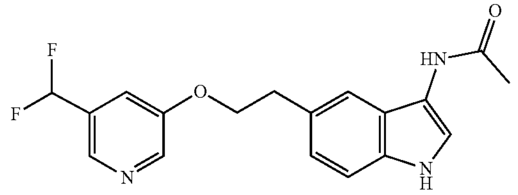 [SMILES: CC(=O)Nc1c[nH]c2ccc(CCOc3cncc(C(F)F)c3)cc12] | N-[5-(2-([5-(difluoromethyl) pyridin-3-yl] oxy}ethyl)-1H-indol-3-yl] acetamide | 346.2 |

Example 290. General Methods for the Synthesis of Compounds of Formula (I-a) and Formula (I-d)

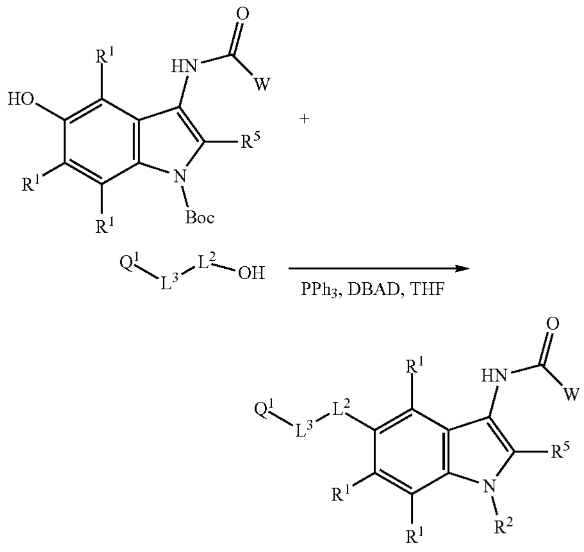

Formula (I-a)

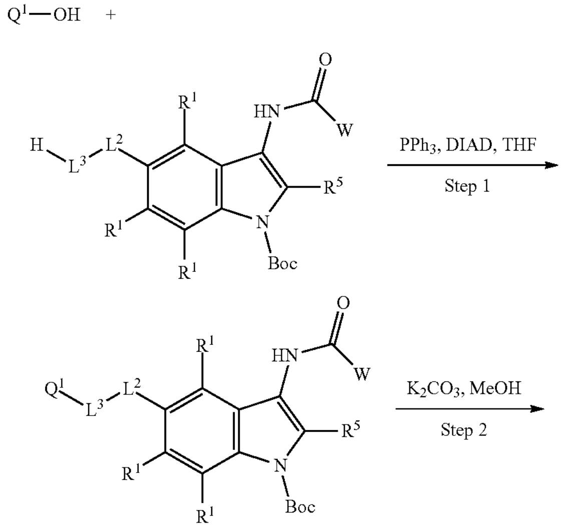

-continued

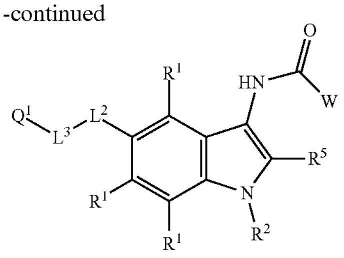

Formula (I-d)

Biological Assays

STING pathway activation by the compounds described herein was measured using THP1-Dual™ cells (KO-IFNAR2).

THP1-Dual™ KO-IFNAR2 Cells (obtained from InvivoGen) were maintained in RPMI, 10% FCS, 5 ml P/S, 2 mM L-glut, 10 mM Hepes, and 1 mM sodium pyruvate. Compounds were spotted in empty 384 well tissue culture plates (Greiner 781182) by Echo for a final concentration of 0.0017-100 μM. Cells were plated into the TC plates at 40 μL per well, 2×10E6 cells/mL. For activation with STING ligand, 2'3'cGAMP (MW 718.38, obtained from Invivogen), was prepared in Optimem media.

The following solutions were prepared for each 1×384 plate:

Solution A: 2 mL Optimem with one of the following stimuli:

60 μL of 10 mM 2'3'cGAMP→150 μM stock

Solution B: 2 mL Optimem with 60 μL Lipofectamine 2000→Incubate 5 min at RT 2 mL of solution A and 2 ml Solution B was mixed and incubated for 20 min at room temperature (RT). 20 μL of transfection solution (A+B) was added on top of the plated cells, with a final 2'3'cGAMP concentration of 15 μM. The plates were then centrifuged immediately at 340 g for 1 minute, after which they were incubated at 37° C., 5% $CO_2$, >98% humidity for 24 h. Luciferase reporter activity was then measured. $EC_{50}$ values were calculated by using standard methods known in the art.

Luciferase reporter assay: 10 μL of supernatant from the assay was transferred to white 384-plate with flat bottom and squared wells. One pouch of QUANTI-Luc™ Plus was dissolved in 25 mL of water. 100 μL of QLC Stabilizer per 25 mL of QUANTI-Luc™ Plus solution was added. 50 μL of QUANTI-Luc™ Plus/QLC solution per well was then added. Luminescence was measured on a Platereader (e.g., Spectramax I3X (Molecular Devices GF3637001)).

Luciferase reporter activity was then measured. $EC_{50}$ values were calculated by using standard methods known in the art.

Table BA shows the activity of compounds in STING reporter assay: <0.008 μM="++++++"; ≥0.008 and <0.04 μM="+++++"; ≥0.04 and <0.2 μM="++++"; ≥0.2 and <1 M="+++"; ≥1 and <5 μM="++"; ≥5 and <100 μM="+".

TABLE BA

| Compound No. | Pharmaron, THP1_IFNAR2 STING 24 h Luci Normalized: GeoMean $EC_{50}$ (μM) |
|---|---|
| 101 | +++ |
| 102 | ++++ |
| 103 | ++++ |
| 104 | +++ |
| 105 | ++ |
| 106 | +++ |
| 107 | ++++ |
| 108 | + |
| 109 | ++++ |
| 110 | +++ |
| 111 | ++++ |
| 112 | + |
| 113 | ++ |
| 114 | +++ |
| 115 | ++++ |
| 116 | + |
| 117 | +++ |
| 118 | +++ |
| 119 | + |
| 120 | + |
| 121 | +++ |
| 122 | +++ |
| 123 | + |
| 124 | ++ |
| 125 | +++ |
| 126 | ++ |
| 127 | ++++ |
| 128 | +++ |
| 129 | +++ |
| 130 | +++ |
| 131 | ++ |
| 132 | ++++ |
| 133 | +++ |
| 134 | +++ |
| 135 | +++ |
| 136 | ++++ |
| 137 | ++ |
| 138 | +++ |
| 139 | ++++ |
| 140 | +++ |
| 141 | ++ |
| 142 | +++ |
| 143 | ++ |
| 144 | + |
| 145 | +++ |
| 146 | ++++ |
| 147 | ++++ |
| 148 | +++ |
| 149 | ++++ |
| 150 | +++ |
| 151 | +++ |
| 152 | +++ |
| 153 | +++ |
| 154 | +++ |
| 155 | +++ |
| 156 | +++ |
| 157 | ++++ |
| 158 | ++++ |
| 159 | ++++ |
| 160 | +++ |
| 161 | ++++ |
| 162 | ++++ |
| 163 | ++++ |
| 164 | +++ |
| 165 | ++++ |
| 166 | ++++ |
| 167 | +++ |
| 168 | +++ |
| 169 | ++++ |
| 170 | +++ |
| 171 | ++ |
| 172 | +++ |
| 173 | + |

TABLE BA-continued

| Compound No. | Pharmaron, THP1_IFNAR2 STING 24 h Luci Normalized: GeoMean $EC_{50}$ (μM) |
|---|---|
| 174 | +++ |
| 175 | +++ |
| 176 | +++ |
| 177 | +++ |
| 178 | +++ |
| 179 | +++ |
| 180 | +++ |
| 181 | +++ |
| 182 | +++ |
| 183 | +++ |
| 184 | + |
| 185 | +++ |
| 186 | +++ |
| 187 | +++ |
| 188 | +++ |
| 189 | +++ |
| 190 | +++ |
| 191 | +++ |
| 192 | ++++ |
| 193 | +++ |
| 194 | +++ |
| 195 | +++ |
| 196 | + |
| 197 | + |
| 198 | +++ |
| 199 | ++ |
| 200 | +++ |
| 201 | +++ |
| 202 | ++++ |
| 203 | +++ |
| 204 | ++++ |
| 205 | ++++ |
| 206 | ++++ |
| 207 | ++++ |
| 208 | ++ |
| 209 | +++ |
| 210 | ++++ |
| 211 | ++++ |
| 212 | +++ |
| 213 | +++ |
| 214 | +++ |
| 215 | +++ |
| 216 | +++ |
| 217 | ++++ |
| 218 | +++ |
| 219 | ++++ |
| 220 | ++++ |
| 221 | ++++ |
| 222 | ++++ |
| 223 | ++++ |
| 224 | ++++ |
| 225 | ++++ |
| 226 | ++ |
| 227 | ++++ |
| 228 | +++ |
| 229 | +++ |
| 230 | ++++ |
| 231 | +++ |
| 232 | ++ |
| 233 | ++++ |
| 234 | ++++ |
| 235 | ++++ |
| 236 | ++++ |
| 237 | ++++ |
| 238 | ++++ |
| 239 | ++++ |
| 240 | +++ |
| 241 | ++++ |
| 242 | ++++ |
| 243 | ++++ |
| 244 | ++++ |
| 245 | ++++ |

TABLE BA-continued

| Compound No. | Pharmaron, THP1_IFNAR2 STING 24 h Luci Normalized: GeoMean $EC_{50}$ (μM) |
|---|---|
| 246 | ++++ |
| 247 | +++ |
| 248 | ++ |
| 249 | +++ |
| 250 | ++ |
| 251 | ++++ |
| 252 | ++++ |
| 253 | ++ |
| 254 | ++++ |
| 255 | ++ |
| 256 | +++ |
| 257 | +++ |
| 258 | ++++ |
| 259 | ++ |
| 260 | +++ |
| 261 | ++++ |
| 262 | ++++ |
| 263 | +++ |
| 264 | ++ |
| 265 | + |
| 266 | ++++ |
| 267 | ++ |
| 268 | ++ |
| 270 | ++ |
| 271 | ++ |
| 272 | ++ |
| 273 | ++++ |
| 274 | ++ |
| 275 | ++ |
| 276 | ++ |
| 277 | + |
| 278 | + |
| 279 | ++ |
| 280 | ++ |
| 281 | + |
| 282 | ++ |
| 283 | +++ |
| 284 | +++ |
| 285 | ++ |
| 286 | ++ |
| 287 | ++ |
| 288 | + |
| 289 | ++ |
| 290 | + |
| 291 | +++ |
| 292 | + |
| 293 | + |
| 294 | ++++ |
| 295 | ++++ |
| 296 | ++++ |
| 297 | +++ |
| 298 | +++ |
| 299 | +++ |
| 300 | ++++ |
| 301 | +++ |
| 302 | +++ |
| 303 | + |
| 304 | +++ |
| 305 | ++ |
| 306 | +++ |
| 307 | +++ |
| 308 | ++++ |
| 309 | ++++ |
| 310 | ++++ |
| 311 | ++ |
| 312 | ++++ |
| 313 | ++ |
| 314 | +++ |
| 315 | +++ |
| 316 | +++ |
| 317 | +++ |
| 318 | +++ |

TABLE BA-continued

| Compound No. | Pharmaron, THP1_IFNAR2 STING 24 h Luci Normalized: GeoMean $EC_{50}$ (μM) |
|---|---|
| 319 | +++ |
| 320 | +++ |
| 321 | +++ |
| 322 | +++ |
| 323 | +++ |
| 324 | +++ |
| 325 | +++ |
| 326 | +++ |
| 327 | +++ |
| 328 | +++ |
| 329 | +++ |
| 330 | +++ |
| 331 | ++ |
| 332 | +++ |
| 333 | ++ |
| 334 | ++++ |
| 335 | +++ |
| 336 | +++ |
| 337 | +++ |
| 338 | +++ |
| 339 | +++ |
| 340 | ++ |
| 341 | +++ |
| 342 | +++ |
| 343 | +++ |
| 344 | +++ |
| 345 | +++ |
| 346 | +++ |
| 347 | +++ |
| 348 | +++ |
| 349 | + |
| 350 | ++ |
| 351 | +++ |
| 352 | ++++ |
| 353 | +++ |
| 354 | +++ |
| 355 | +++ |
| 356 | +++ |
| 357 | +++ |
| 358 | ++ |
| 359 | ++++ |
| 360 | +++ |
| 361 | ++++ |
| 362 | +++ |
| 363 | +++ |
| 364 | ++++ |
| 365 | ++++ |
| 366 | +++ |
| 367 | +++ |
| 368 | +++ |
| 369 | +++ |
| 370 | +++ |
| 371 | +++ |
| 372 | ++ |
| 373 | ++ |
| 374 | + |
| 375 | ++ |
| 376 | +++ |
| 377 | + |
| 378 | +++ |
| 379 | +++ |
| 380 | ++++ |
| 381 | +++ |
| 382 | +++ |
| 383 | +++ |
| 384 | +++ |
| 385 | + |
| 386 | ++ |
| 387 | +++ |
| 388 | +++ |
| 389 | +++ |
| 390 | +++ |
| 391 | ++++ |
| 392 | +++ |
| 393 | +++ |
| 394 | ++++ |
| 395 | +++ |
| 396 | +++ |
| 397 | +++ |
| 398 | +++ |
| 399 | +++ |
| 400 | +++ |
| 401 | +++ |
| 402 | + |
| 404 | ++ |
| 405 | +++ |
| 406 | +++ |
| 407 | +++ |
| 408 | ++++ |
| 412 | ++ |
| 413 | ++ |
| 414 | +++ |
| 415 | ++ |
| 416 | +++ |
| 417 | +++ |
| 418 | +++ |
| 419 | +++ |
| 420 | +++ |
| 421 | +++ |
| 422 | ++ |
| 423 | +++ |
| 424 | +++ |
| 425 | +++ |
| 426 | ++++ |
| 427 | +++ |
| 428 | +++ |
| 429 | +++ |
| 430 | ++++ |
| 431 | ++++ |
| 432 | ++ |
| 433 | +++ |
| 434 | ++++ |
| 435 | ++++ |
| 436 | ++++ |
| 437 | +++ |
| 438 | ++++ |
| 439 | + |
| 440 | ++ |
| 441 | ++++ |
| 442 | ++++ |
| 443 | +++ |
| 444 | + |
| 445 | ++++ |
| 446 | ++++ |
| 447 | + |
| 448 | ++++ |
| 449 | ++ |
| 450 | +++ |
| 451 | ++ |
| 452 | ++++ |
| 453 | ++ |
| 454 | +++ |
| 455 | +++ |
| 456 | +++ |
| 457 | +++ |
| 458 | ++ |
| 459 | + |
| 460 | ++ |
| 461 | +++ |
| 462 | ++ |
| 463 | + |
| 464 | +++ |
| 465 | +++ |
| 466 | +++ |

TABLE BA-continued

| Compound No. | Pharmaron, THP1_IFNAR2 STING 24 h Luci Normalized: GeoMean $EC_{50}$ (μM) |
|---|---|
| 467 | +++ |
| 468 | +++ |
| 469 | +++ |
| 470 | +++ |
| 471 | +++ |
| 472 | +++ |
| 473 | ++ |
| 474 | +++ |
| 475 | ++ |
| 476 | ++ |
| 477 | ++ |
| 478 | ++ |
| 479 | ++++ |
| 480 | +++ |
| 481 | ++ |
| 482 | ++++ |
| 483 | ++++ |
| 484 | ++ |
| 485 | ++ |
| 486 | ++++ |
| 487 | ++++ |
| 488 | ++++ |
| 489 | +++ |
| 490 | ++++ |
| 491 | +++ |
| 492 | + |
| 493 | ++++ |
| 494 | +++ |
| 495 | ++ |
| 496 | +++ |
| 497 | ++ |
| 498 | +++ |
| 499 | + |
| 500 | ++++ |
| 501 | ++ |
| 504 | +++ |
| 505 | +++ |
| 506 | + |
| 507 | + |
| 508 | + |
| 509 | ++ |
| 510 | +++ |
| 511 | +++ |
| 512 | +++ |
| 513 | +++ |
| 514 | +++ |
| 515 | ++ |
| 516 | + |
| 517 | + |
| 518 | +++ |
| 519 | ++++ |
| 520 | ++++ |
| 521 | +++ |
| 522 | ++++ |
| 523 | +++ |
| 524 | ++++ |
| 525 | +++ |
| 526 | + |
| 527 | ++ |
| 528 | + |
| 529 | + |
| 530 | ++++ |
| 531 | ++++ |
| 532 | + |
| 533 | ++++ |
| 534 | ++++ |
| 535 | +++ |
| 536 | + |
| 537 | + |
| 538 | ++ |
| 539 | ++ |
| 540 | ++ |

TABLE BA-continued

| Compound No. | Pharmaron, THP1_IFNAR2 STING 24 h Luci Normalized: GeoMean $EC_{50}$ (μM) |
|---|---|
| 541 | + |
| 542 | +++ |
| 543 | +++ |
| 544 | +++ |
| 545 | ++++ |
| 546 | ++ |
| 547 | +++ |
| 548 | +++ |
| 549 | ++ |
| 550 | +++ |
| 551 | +++ |
| 552 | +++ |
| 553 | +++ |
| 554 | +++ |
| 555 | ++ |
| 556 | + |
| 557 | ++ |
| 558 | +++ |
| 559 | +++ |
| 560 | ++ |
| 561 | ++++ |
| 562 | +++ |
| 563 | ++++ |
| 564 | ++++ |
| 565 | +++ |
| 566 | ++++ |
| 567 | ++ |
| 568 | +++ |
| 569 | ++ |
| 570 | +++ |
| 571 | +++ |
| 572 | ++++ |
| 573 | ++++ |
| 574 | ++++ |
| 575 | +++ |
| 576 | ++++ |
| 577 | +++ |
| 578 | ++ |
| 579 | +++ |
| 580 | ++++ |
| 581 | + |
| 582 | ++++ |
| 583 | ++ |
| 584 | +++ |
| 585 | +++ |
| 586 | +++ |
| 587 | ++++ |
| 588 | ++++ |
| 589 | ++++ |
| 590 | ++ |
| 591 | +++ |
| 592 | +++ |
| 593 | ++++ |
| 594 | +++ |
| 595 | ++++ |

Numbered Clauses

The compounds, compositions, methods, and other subject matter described herein are further described in the following numbered clauses:

1. A compound of Formula (I):

Formula I

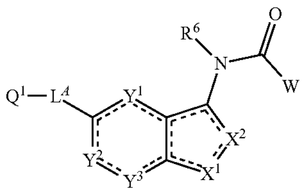

or a pharmaceutically acceptable salt thereof or a tautomer thereof, wherein:

$L^A$ is $-(L^1)_{a1}-(L^2)_{a2}-(L^3)_{a3}-(L^4)_{a4}-(L^5)_{a5}-*$, wherein * represents the point of attachment to $Q^1$;

a1, a2, a3, a4, and a5 are each independently 0 or 1, provided that a1+a2+a3+a4+a5≥1, and each of $L^1$, $L^3$, and $L^5$ is independently selected from the group consisting of: —O—, —N(H)—, —N($R^d$)—, $S(O)_{0-2}$, and —C(═O)—;

provided that when one or both of a2 and a4 is 0, then the combinations of $L^1$, $L^3$, and $L^5$ cannot form O—O, N—O, N—N, O—S, S—S, or N—$S(O)_0$ bonds, and each of $L^2$ and $L^4$ is independently selected from the group consisting of:

straight-chain $C_{1-6}$ alkylene, straight-chain $C_{2-6}$ alkenylene, or straight-chain $C_{2-6}$ alkynylene, each of which is optionally substituted with 1-6 $R^b$;

$C_{3-10}$ cycloalkylene or $C_{3-10}$ cycloalkenylene, each of which is optionally substituted with 1-3 $R^c$; and heterocyclylene or heterocycloalkenylene, each having 4-10 ring atoms wherein 1-3 ring atoms are ring heteroatoms each independently selected from the group consisting of: N, N(H), N($R^d$), O, and $S(O)_{0-2}$, wherein the heterocyclylene or heterocycloalkenylene is optionally substituted with 1-3 $R^c$;

$Q^1$ is —$R^g$;

$Y^1$, $Y^2$, and $Y^3$ are each independently selected from the group consisting of $CR^1$, C(═O), N, and $NR^2$;

$X^1$ is selected from the group consisting of O, S, N, $NR^2$, and $CR^1$;

$X^2$ is selected from the group consisting of O, S, N, $NR^4$, and $CR^5$;

each ---- is independently a single bond or a double bond, provided that the five-membered ring comprising $X^1$ and $X^2$ is heteroaryl, and that the six-membered ring comprising $Y^1$, $Y^2$, and $Y^3$ is aryl or heteroaryl;

further provided that $L^A$ cannot include a cyclic group directly attached to the 6-membered ring containing $Y^1$, $Y^2$, and $Y^3$;

each occurrence of $R^1$ and $R^5$ is independently selected from the group consisting of: H; $R^c$; $R^g$; and $-(L^g)_{bg}-R^g$;

each occurrence of $R^2$ and $R^4$ is independently selected from the group consisting of: H; $R^d$; $R^g$; and $-(L^g)_{bg}-R^g$;

$R^6$ is selected from the group consisting of: H; $R^d$; and $R^g$;

W is selected from the group consisting of:

H;

$C_{1-10}$ alkyl, $C_{2-10}$ alkenyl, or $C_{2-10}$ alkynyl, each of which is optionally substituted with 1-6 $R^{a2}$, wherein one or more of the internal optionally substituted methylene group can be replaced by one or more heteroatom selected from O or S, wherein when W is alkenyl or alkynyl, the heteroatom is not directed connected to the $sp^2$ or sp carbon;

monocyclic $C_{3-8}$ cycloalkyl or $C_{3-8}$ cycloalkenyl, each of which is optionally substituted with 1-4 substituents independently selected from the group consisting of oxo and $R^c$; and monocyclic heterocyclyl or heterocycloalkenyl of 3-8 ring atoms, wherein 1-3 ring atoms are heteroatoms, each independently selected from the group consisting of N, N(H), N($R^d$), O, and $S(O)_{0-2}$, and wherein the heterocyclyl or heterocycloalkenyl is optionally substituted with 1-4 substituents independently selected from the group consisting of oxo and $R^c$, provided that when W is heterocyclyl or heterocycloalkenyl, it is attached to the C(═O)$NR^6$ group via a ring carbon atom;

each occurrence of $R^a$ and $R^{a2}$ is independently selected from the group consisting of: —OH; -halo; —$NR^eR^f$; $C_{1-4}$ alkoxy; $C_{1-4}$ haloalkoxy; —C(═O)O($C_{1-4}$ alkyl); —C(═O)($C_{1-4}$ alkyl); —C(═O)OH; —CONR'R"; —$S(O)_{1-2}$NR'R"; —$S(O)_{1-2}$($C_{1-4}$ alkyl); and cyano;

each occurrence of $R^b$ and $R^c$ is independently selected from the group consisting of: halo; cyano; $C_{1-10}$ alkyl which is optionally substituted with 1-6 independently selected $R^a$; $C_{2-6}$ alkenyl; $C_{2-6}$ alkynyl; $C_{1-4}$ alkoxy; $C_{1-4}$ haloalkoxy; —$S(O)_{1-2}$($C_{1-4}$ alkyl); —S(O)(═NH)($C_{1-4}$ alkyl); —$NR^eR^f$; —OH; —$S(O)_{1-2}$NR'R"; —$C_{1-4}$ thioalkoxy; —$NO_2$; —C(═O)($C_{1-10}$ alkyl); —C(═O)O($C_{1-4}$ alkyl); —C(═O)OH; —C(═O)NR'R"; —NR'C(═O)($C_{1-4}$ alkyl) and —$SF_5$;

each occurrence of $R^d$ is independently selected from the group consisting of: $C_{1-6}$ alkyl optionally substituted with 1-3 independently selected $R^a$; —C(O)($C_{1-4}$ alkyl); —C(O)O($C_{1-4}$ alkyl); —CONR'R"; —$S(O)_{1-2}$NR'R"; —$S(O)_{1-2}$($C_{1-4}$ alkyl); —OH; and $C_{1-4}$ alkoxy;

each occurrence of $R^e$ and $R^f$ is independently selected from the group consisting of: H; $C_{1-6}$ alkyl optionally substituted with 1-3 substituents each independently selected from the group consisting of NR'R", —OH, halo, $C_{1-4}$ alkoxy, and $C_{1-4}$ haloalkoxy; —C(O)($C_{1-4}$ alkyl); —C(O)O($C_{1-4}$ alkyl); —CONR'R"; —$S(O)_{1-2}$NR'R"; —$S(O)_{1-2}$($C_{1-4}$ alkyl); —OH; and $C_{1-4}$ alkoxy;

each occurrence of $R^g$ is independently selected from the group consisting of:

$C_{3-12}$ cycloalkyl or $C_{3-12}$ cycloalkenyl, each of which is optionally substituted with 1-4 substituents independently selected from the group consisting of oxo, $R^c$, and $R^h$;

heterocyclyl or heterocycloalkenyl of 3-12 ring atoms, wherein 1-3 ring atoms are heteroatoms, each independently selected from the group consisting of N, N(H), N($R^d$), O, and $S(O)_{0-2}$, and wherein the heterocyclyl or heterocycloalkenyl is optionally substituted with 1-4 substituents independently selected from the group consisting of oxo, $R^c$, and $R^h$;

heteroaryl of 5-12 ring atoms, wherein 1-4 ring atoms are heteroatoms, each independently selected from the group consisting of N, N(H), N($R^d$), O, and $S(O)_{0-2}$, and wherein the heteroaryl is optionally substituted with 1-4 substituents independently selected from the group consisting of oxo, $R^c$, and $R^h$; and $C_{6-10}$ aryl optionally substituted with 1-4 substituents independently selected from the group consisting of oxo, $R^c$, and $R^h$;

each occurrence of $R^h$ is independently selected from the group consisting of:

$C_{3-12}$ cycloalkyl or $C_{3-12}$ cycloalkenyl, each of which is optionally substituted with 1-4 $R^i$;

heterocyclyl or heterocycloalkenyl of 3-12 ring atoms, wherein 1-3 ring atoms are heteroatoms, each independently selected from the group consisting of N, N(H), N($R^d$), O, and $S(O)_{0-2}$, and wherein the heterocyclyl or heterocycloalkenyl is optionally substituted with 1-4 $R^i$;

heteroaryl of 5-12 ring atoms, wherein 1-3 ring atoms are heteroatoms, each independently selected from the group consisting of N, N(H), N($R^d$), O, and $S(O)_{0-2}$, and wherein the heteroaryl is optionally substituted with 1-4 $R^i$; and $C_{6-10}$ aryl optionally substituted with 1-4 $R^i$;

each occurrence of $R^i$ is independently selected from the group consisting of: $C_{1-6}$ alkyl; $C_{1-4}$ haloalkyl; $C_{1-4}$ alkoxy; $C_{1-4}$ haloalkoxy; and halo;

each occurrence of $L^g$ is independently selected from the group consisting of: —O—, —NH—, —$NR^d$, —$S(O)_{0-2}$, C(O), and $C_{1-3}$ alkylene optionally substituted with 1-3 $R^a$; each occurrence of bg is independently 1, 2, or 3; and each occurrence of R' and R" is independently selected from the group consisting of: H; —OH; and $C_{1-4}$ alkyl.

2. The compound of clause 1, wherein a2 is 1.

3. The compound of clauses 1 or 2, wherein $L^2$ is straight-chain $C_{1-6}$ alkylene, straight-chain $C_{2-6}$ alkenylene, or straight-chain $C_{2-6}$ alkynylene, each of which is optionally substituted with 1-6 $R^b$.

4. The compound of any one of clauses 1-3, wherein $L^2$ is straight-chain $C_{1-6}$ alkylene, which is optionally substituted with 1-6 $R^b$.

5. The compound of any one of clauses 1-4, wherein $L^2$ is straight-chain $C_{1-3}$ alkylene, which is optionally substituted with 1-3 $R^b$.

6. The compound of any one of clauses 1-5, wherein $L^2$ is selected from the group consisting of —$CH_2$—, —$CHR^b$—, and —$C(R^b)_2$—.

7. The compound of any one of clauses 1-6, wherein $L^2$ is —$CH_2$—.

8. The compound of any one of clauses 1-4, wherein $L^2$ is straight-chain $C_{2-3}$ alkylene which is optionally substituted with 1-3 $R^b$.

9. The compound of any one of clauses 1-4 or 8, wherein $L^2$ is straight-chain $C_2$ alkylene which is optionally substituted with 1-3 $R^b$.

10. The compound of any one of clauses 1-4 or 8-9, wherein $L^2$ is selected from the group consisting of: —$CH_2CH_2$—, —$CH_2CH(R^b)$—*, and —$CH_2C(R^b)_2$—*, wherein the asterisk represents point of attachment to $-(L^3)_{a3}$-.

11. The compound of any one of clauses 1-4 or 8-10, wherein $L^2$ is —$CH_2CH_2$—.

12. The compound of any one of clauses 1-4 or 8, wherein $L^2$ is straight-chain $C_3$ alkylene which is optionally substituted with 1-3 $R^b$.

13. The compound of any one of clauses 1-4, 8, or 12, wherein $L^2$ is selected from the group consisting of:

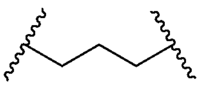,
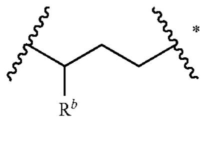,

-continued

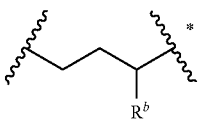, and 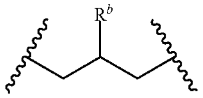, wherein the asterisk represents point of attachment to $-(L^3)_{a3}$-.

14. The compound of any one of clauses 1-3, wherein $L^2$ is straight-chain $C_{2-6}$ alkenylene, which is optionally substituted with 1-6 $R^b$.

15. The compound of any one of clauses 1-3 or 14, wherein $L^2$ is straight-chain $C_{2-4}$ alkenylene, which is optionally substituted with 1-3 $R^b$.

16. The compound of any one of clauses 1-3 or 14-15, wherein $L^2$ is selected from the group consisting of:

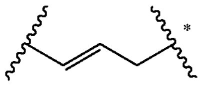 and 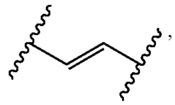, and wherein the asterisk represents the point of attachment to $-(L^3)_{a3}$-.

17. The compound of clauses 1 or 2, wherein $L^2$ is selected from the group consisting of:

$C_{3-10}$ cycloalkylene or $C_{3-10}$ cycloalkenylene, each of which is optionally substituted with 1-3 $R^c$; and heterocyclylene or heterocycloalkenylene, each having 4-10 ring atoms wherein 1-3 ring atoms are ring heteroatoms each independently selected from the group consisting of: N, N(H), N($R^d$), O, and $S(O)_{0-2}$, wherein the heterocyclylene or heterocycloalkenylene is optionally substituted with 1-3 $R^c$.

18. The compound of any one of clauses 1-2 or 17, wherein $L^2$ is selected from the group consisting of:

$C_{3-8}$ cycloalkylene, which is optionally substituted with 1-3 $R^c$; and heterocyclylene having 4-8 ring atoms wherein 1-3 ring atoms are ring heteroatoms each independently selected from the group consisting of: N, N(H), N($R^d$), O, and $S(O)_{0-2}$, wherein the heterocyclylene is optionally substituted with 1-3 $R^c$.

19. The compound of any one of clauses 1-2 or 17-18, wherein $L^2$ is:

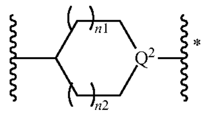

which is optionally substituted with 1-2 $R^c$, wherein n1 and n2 are independently 0, 1, or 2; $Q^2$ is CH, $CR^c$, or N; and the asterisk represents the point of attachment to $-(L^3)_{a3}$-.

20. The compound of clause 19, wherein $Q^2$ is CH.

21. The compound of clauses 19 or 20, wherein n1 and n2 are each 0.

22. The compound of any one of clauses 1-2 or 17-21, wherein $L^2$ is

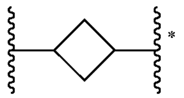
, wherein the asterisk represents the point of attachment to $-(L^3)_{a3}-$.

23. The compound of clause 1, wherein a2 is 0.

24. The compound of any one of clauses 1-23, wherein a1 is 1.

25. The compound of any one of clauses 1-24, wherein $L^1$ is selected from the group consisting of: —O—, —N(H)—, —N($R^d$)—, and —S—.

26. The compound of any one of clauses 1-25, wherein $L^1$ is —O—.

27. The compound of any one of clauses 1-23, wherein a1 is 0.

28. The compound of any one of clauses 1-27, wherein a3 is 1.

29. The compound of any one of clauses 1-28, wherein $L^3$ is selected from the group consisting of: —O—, —N(H)—, —N($R^d$)—, and —S—

30. The compound of any one of clauses 1-29, wherein $L^3$ is —O—.

31. The compound of any one of clauses 1-29, wherein $L^3$ is —N(H)— or —N($R^d$)—optionally —N(H)—.

32. The compound of any one of clauses 1-27, wherein a3 is 0.

33. The compound of any one of clauses 1-32, wherein a4 is 1.

34. The compound of any one of clauses 1-33, wherein $L^4$ is straight-chain $C_{1-3}$ alkylene, which is optionally substituted with 1-3 $R^b$.

35. The compound of any one of clauses 1-34, wherein $L^4$ is —$CH_2$—.

36. The compound of any one of clauses 1-33, wherein $L^4$ is selected from the group consisting of:

$C_{3-8}$ cycloalkylene, which is optionally substituted with 1-3 $R^c$; and heterocyclylene having 4-8 ring atoms wherein 1-3 ring atoms are ring heteroatoms each independently selected from the group consisting of: N, N(H), N($R^d$), O, and $S(O)_{0-2}$, wherein the heterocyclylene is optionally substituted with 1-3 $R^c$.

37. The compound of any one of clauses 1-33 or 36, wherein $L^4$ is:

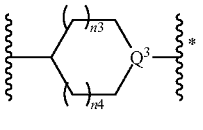

which is optionally substituted with 1-2 $R^c$, wherein n3 and n4 are independently 0, 1, or 2; $Q^3$ is CH, $CR^c$, or N; and the asterisk represents the point of attachment to $-(L^5)_{a5}-$.

38. The compound of clause 37, wherein n3 and n4 are each 1.

39. The compound of clauses 37 or 38, wherein $Q^3$ is N.

40. The compound of any one of clauses 1-33 or 36-39, wherein $L^4$ is

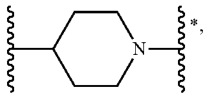

wherein the asterisk represents the point of attachment to $-(L^5)_{a5}-$.

41. The compound of any one of clauses 1-32, wherein a4 is 0.

42. The compound of any one of clauses 1-41, wherein a5 is 0.

43. The compound of clause 1, wherein one of a1, a3, and a5 is 1, and the other two are 0.

44. The compound of clauses 1 or 43, wherein one of a2 and a4 is 1, and the other is 0 or 1.

45. The compound of any one of clauses 1 or 43-44, wherein a1 and a2 are each 1.

46. The compound of any one of clauses 1 or 43-45, wherein:

a1 and a2 are each 1;

$L^1$ is —O—, —N(H)—, or —N($R^d$)—;

$L^2$ is selected from the group consisting of:

straight-chain CI-3 alkylene, which is optionally substituted with 1-3 $R^b$;

$C_{3-8}$ cycloalkylene, which is optionally substituted with 1-3 $R^c$; and heterocyclylene having 4-8 ring atoms wherein 1-3 ring atoms are ring heteroatoms each independently selected from the group consisting of: N, N(H), N($R^d$), O, and $S(O)_{0-2}$, wherein the heterocyclylene is optionally substituted with 1-3 $R^c$.

47. The compound of any one of clauses 1 or 43-46, wherein:

a1 and a2 are each 1;

$L^1$ is —O—; and $L^2$ is straight-chain CI-3 alkylene, which is optionally substituted with 1-3 $R^b$.

48. The compound of any one of clauses 1 or 43-47, wherein:

a1 and a2 are each 1;

$L^1$ is —O—; and $L^2$ is selected from the group consisting of: —$CH_2$—, —$CHR^b$—, and —$C(R^b)_2$—.

49. The compound of any one of clauses 1 or 43-47, wherein:

a1 and a2 are each 1;

$L^1$ is —O—; and $L^2$ is straight-chain $C_{2-3}$ alkylene which is optionally substituted with 1-3 $R^b$.

50. The compound of clause 49, wherein $L^2$ is straight-chain $C_2$ alkylene which is optionally substituted with 1-3 $R^b$.

51. The compound of clauses 49 or 50, wherein $L^2$ is selected from the group consisting of: —$CH_2CH_2$—, —$CH_2CH(R^b)$—*, and —$CH_2C(R^b)_2$—*, wherein the asterisk represents point of attachment to $-(L^3)_{a3}-$.

52. The compound of any one of clauses 49-51, wherein $L^2$ is —$CH_2CH_2$—.

53. The compound of any one of clauses 1 or 43-46, wherein:

a1 and a2 are each 1;

$L^1$ is —O—;

$L^2$ is selected from the group consisting of:

$C_{3-8}$ cycloalkylene, which is optionally substituted with 1-3 $R^c$; and heterocyclylene having 4-8 ring atoms wherein 1-3 ring atoms are ring heteroatoms each independently selected from the group consisting of: N, N(H), $N(R^d)$, O, and $S(O)_{0-2}$, wherein the heterocyclylene is optionally substituted with 1-3 $R^c$.

54. The compound of clause 53, wherein $L^2$ is:

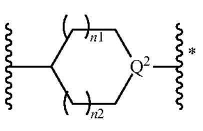

which is optionally substituted with 1-2 $R^c$, wherein n1 and n2 are independently 0, 1, or 2; $Q^2$ is CH, $CR^c$, or N; and the asterisk represents the point of attachment to $-(L^3)_{a3}-$.

55. The compound of clause 54, wherein n1 and n2 are independently 0 or 1, optionally 0; and $Q^2$ is CH; optionally wherein n1 and n2 are 0 and $Q^2$ is CH; optionally wherein $L^2$ is cyclobutane-diyl optionally substituted with 1-2 $R^c$; optionally wherein $L^2$ is cyclobutane-1,3-diyl optionally substituted with 1-2 $R^c$; optionally wherein $L^2$ is unsubstituted cyclobutane-diyl; optionally wherein $L^2$ is unsubstituted cyclobutane-1,3-diyl.

56. The compound of any one of clauses 43-55, wherein a3, a4 and a5 are each 0, optionally wherein $L^4$ is $—O—CH_2CH_2—*$, or

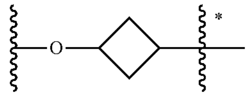 [SMILES: *OC1CC(*)C1]

(such as

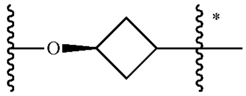 or

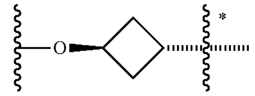), wherein * represents the point of attachment to $Q^1$.

57. The compound of any one of clauses 43-55, wherein a3 and a5 are 0; and a4 is 1.

58. The compound of clause 57, wherein $L^4$ is selected from the group consisting of:

$C_{3-8}$ cycloalkylene, which is optionally substituted with 1-3 $R^c$; and heterocyclylene having 4-8 ring atoms wherein 1-3 ring atoms are ring heteroatoms each independently selected from the group consisting of: N, N(H), $N(R^d)$, O, and $S(O)_{0-2}$, wherein the heterocyclylene is optionally substituted with 1-3 $R^c$.

59. The compound of clauses 57 or 58, wherein $L^4$ is:

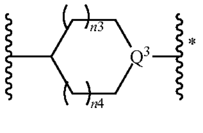

which is optionally substituted with 1-2 $R^c$, wherein n3 and n4 are independently 0, 1, or 2; $Q^3$ is CH, $CR^c$, or N; and the asterisk represents the point of attachment to $-(L^5)_{a5}-$.

60. The compound of clause 59, wherein n3 and n4 are independently 0 or 1; and $Q^3$ is N.

61. The compound of any one of clauses 1 or 43-44, wherein: a1 is 0; and a2 is 1.

62. The compound of any one of clauses 1, 43-44, or 61, wherein a1 is 0; a2 is 1; and $L^2$ is straight-chain $C_{1-6}$ alkylene, which is optionally substituted with 1-6 $R^b$.

63. The compound of clauses 61 or 62, wherein $L^2$ is straight-chain $C_{1-3}$ alkylene, which is optionally substituted with 1-3 $R^b$.

64. The compound of any one of clauses 61-63, wherein $L^2$ is selected from the group consisting of: $—CH_2—$, $—CHR^b—$, and $—C(R'')_2—$.

65. The compound of any one of clauses 61-64, wherein $L^2$ is $—CH_2—$.

66. The compound of any one of clauses 61-63, wherein $L^2$ is straight-chain $C_{2-3}$ alkylene which is optionally substituted with 1-3 $R^b$.

67. The compound of any one of clauses 61-63 or 66, wherein $L^2$ is straight-chain $C_2$ alkylene, which is optionally substituted with 1-3 $R^b$.

68. The compound of any one of clauses 61-63 or 66-67, wherein $L^2$ is selected from the group consisting of: $—CH_2CH_2—$, $—CH_2CH(R'')—*$, and $—CH_2C(R'')_2—*$, wherein the asterisk represents point of attachment to $-(L^3)_{a3}-$.

69. The compound of any one of clauses 61-63 or 66-68, wherein $L^2$ is $—CH_2CH_2—$.

70. The compound of any one of clauses 61-63 or 66, wherein $L^2$ is straight-chain $C_3$ alkylene, which is optionally substituted with 1-3 $R^b$.

71. The compound of any one of clauses 61-63, 66, or 70, wherein $L^2$ is selected from the group consisting of:

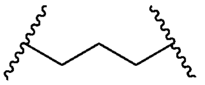, 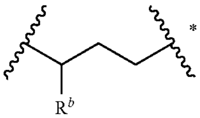, 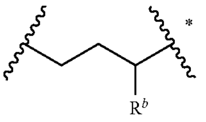, and 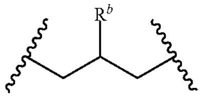, wherein the asterisk represents point of attachment to $-(L^3)_{a3}-$.

72. The compound of any one of clauses 61-71, wherein a3 is 0; a4 is 0; and a5 is 0.

73. The compound of any one of clauses 61-71, wherein a3 is 1.

74. The compound of clause 73, wherein a3 is 1; and $L^3$ is selected from the group consisting of: is —O—, —N(H)—, and $—N(R^d)—$.

75. The compound of clauses 73 or 74, wherein a3 is 1; and $L^3$ is —O—.

76. The compound of any one of clauses 61-71 or 73-74, wherein a3 is 1; and $L^3$ is —N(H)— or $—N(R^d)—$, optionally —N(H)—.

77. The compounds of any one of clauses 61-71 or 73-76, wherein a4 is 1; and $L^4$ is straight-chain $C_{1-3}$ alkylene, which is optionally substituted with 1-3 $R^b$.

78. The compound of any one of clauses 61-71 or 73-77, wherein a4 is 1; and $L^4$ is —$CH_2$—.

79. The compound of any one of clauses 61-71 or 73-77, wherein a4 is 0; and a5 is 0, optionally wherein $L^A$ is —$CH_2CH_2$—O—*, wherein * represents to point of attachment to $Q^1$.

80. The compound of clause 1, wherein a1 is 0; a2 is 1; $L^2$ is straight-chain $C_{2-4}$ alkenylene, which is optionally substituted with 1-3 $R^b$.

81. The compound of clause 80, wherein $L^2$ is selected from the group consisting of:

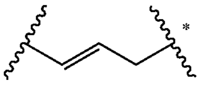 and 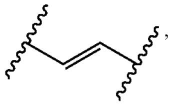

wherein the asterisk represents the point of attachment to $-(L^3)_{a3}-$.

82. The compound of clauses 80 or 81, wherein a3 is 0; a4 is 0; and a5 is 0.

83. The compound of any one of clauses 1-82, wherein $Q^1$ is selected from the group consisting of:

heteroaryl of 5-12 ring atoms, wherein 1-4 ring atoms are heteroatoms, each independently selected from the group consisting of N, N(H), N($R^d$), O, and $S(O)_{0-2}$, and wherein the heteroaryl is optionally substituted with 1-4 $R^c$; and $C_{6-10}$ aryl optionally substituted with 1-4 $R^c$.

84. The compound of any one of clauses 1-82, wherein $Q^1$ is selected from the group consisting of:

heteroaryl of 5-6 ring atoms, wherein 1-4 ring atoms are heteroatoms, each independently selected from the group consisting of N, N(H), N($R^d$), O, and $S(O)_{0-2}$, and wherein the heteroaryl is optionally substituted with 1-3 $R^c$; and phenyl optionally substituted with 1-3 $R^c$.

85. The compound of any one of clauses 1-82, wherein $Q^1$ is selected from the group consisting of:

heteroaryl of 6 ring atoms, wherein 1-2 ring atoms are ring nitrogen atoms, and wherein the heteroaryl is optionally substituted with 1-3 $R^c$; and phenyl optionally substituted with 1-3 $R^c$.

86. The compound of any one of clauses 1-85, wherein $Q^1$ is phenyl optionally substituted with 1-3 $R^c$.

87. The compound of any one of clauses 1-86, wherein $Q^1$ is selected from the group consisting of:

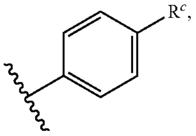 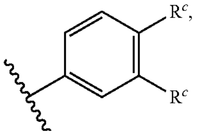 and

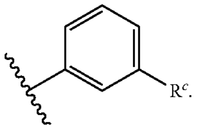

88. The compound of any one of clauses 1-85, wherein $Q^1$ is heteroaryl of 6 ring atoms, wherein 1-2 ring atoms are ring nitrogen atoms, and wherein the heteroaryl is optionally substituted with 1-3 $R^c$.

89. The compound of any one of clauses 1-85 or 88, wherein $Q^1$ is pyridyl, which is optionally substituted with 1-3 $R^c$.

90. The compound of any one of clauses 1-85 or 88-89, wherein $Q^1$ is selected from the group consisting of:

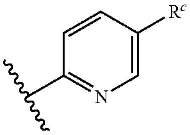 and 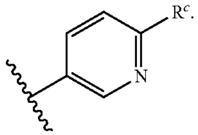

91. The compound of any one of clauses 1-82, wherein $Q^1$ is heterocyclyl or heterocycloalkenyl of 3-12 ring atoms, wherein 1-3 ring atoms are heteroatoms, each independently selected from the group consisting of N, N(H), N($R^d$), O, and $S(O)_{0-2}$, and wherein the heterocyclyl or heterocycloalkenyl is optionally substituted with 1-4 substituents independently selected from the group consisting of oxo and $R^c$.

92. The compound of any one of clauses 1-82 or 91, wherein $Q^1$ is heterocyclyl of 4-10 ring atoms, wherein 1-3 ring atoms are heteroatoms, each independently selected from the group consisting of N, N(H), N($R^d$), O, and $S(O)_{0-2}$, and wherein the heterocyclyl is optionally substituted with 1-4 substituents independently selected from the group consisting of oxo and $R^c$.

93. The compound of any one of clauses 1-82 or 91-92, wherein $Q^1$ is heterocyclyl of 4-8 ring atoms, wherein 1-2 ring atoms are heteroatoms, each independently selected from the group consisting of N, N(H), N($R^d$), O, and $S(O)_{0-2}$, provided that one ring atom is N($R^d$), and wherein the heterocyclyl is optionally substituted with 1-4 substituents independently selected from the group consisting of oxo and $R^c$.

94. The compound of any one of clauses 1-82 or 91-93, wherein $Q^1$ is

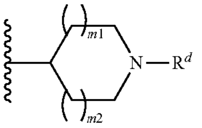 or 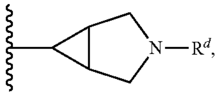

wherein m1 and m2 are each independently 0, 1, or 2; and wherein $Q^1$ is optionally substituted with 1-2 $R^c$.

95. The compound of any one of clauses 1-82 or 91-94, wherein $Q^1$ is

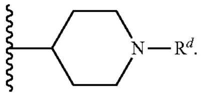

96. The compound of any one of clauses 1-82 or 91-94, wherein $Q^1$ is

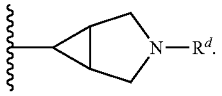

97. The compound any one of clauses 91-96, wherein each $R^d$ present in $Q^1$ is independently selected from the group consisting of: —C(O)O($C_{1-4}$ alkyl); and $C_{1-6}$ alkyl optionally substituted with 1-3 independently selected $R^a$.

98. The compound of any one of clauses 91-97, wherein each $R^d$ present in $Q^1$ is $C_{1-6}$ alkyl optionally substituted with 1-3 independently selected halo.

99. The compound of any one of clauses 91-98, wherein each $R^d$ present in $Q^1$ is:

i. $C_{1-4}$ alkyl substituted with 1-3 —F;

ii. $C_{2-3}$ alkyl substituted with 1-3 —F; or iii. —$CH_2CF_3$.

100. The compound of any one of clauses 83-99, wherein each $R^c$ present in $Q^1$ is independently selected from the group consisting of: halo; cyano; $C_{1-4}$ alkoxy; $C_{1-4}$ haloalkoxy; and $C_{1-10}$ alkyl which is optionally substituted with 1-6 independently selected $R^a$.

101. The compound of any one of clauses 83-100, wherein each $R^c$ present in $Q^1$ is independently selected from the group consisting of: halo; cyano; $C_{1-4}$ alkoxy; $C_{1-4}$ haloalkoxy; and $C_{1-6}$ alkyl which is optionally substituted with 1-6 independently selected halo.

102. The compound of any one of clauses 83-101, wherein each $R^c$ present in $Q^1$ is independently selected from the group consisting of: halo and $C_{1-3}$ alkyl which is optionally substituted with 1-6 independently selected halo.

103. The compound of any one of clauses 83-102, wherein each $R^c$ present in $Q^1$ is:

i. $C_{1-3}$ alkyl which is optionally substituted with 1-6 —F; or ii. $CF_3$.

104. The compound of any one of clauses 83-102, wherein each $R^c$ present in $Q^1$ is an independently selected halo, optionally —F or —Cl.

105. The compound of any one of clauses 1-104, wherein $Y^1$ is $CR^1$.

106. The compound of any one of clauses 1-105, wherein $Y^2$ is $CR^1$.

107. The compound of any one of clauses 1-106, wherein $Y^3$ is $CR^1$.

108. The compound of any one of clauses 1-107, wherein each occurrence of $R^1$ is independently H or $R^c$.

109. The compound of any one of clauses 1-108, wherein each occurrence of $R^1$ is H.

110. The compound of any one of clauses 1-108, wherein 1-2 occurrence of $R^1$ is $R^c$; and each remaining occurrence of $R^1$ is H.

111. The compound of any one of clauses 1-108 or 110, wherein one occurrence of $R^1$ is halo, optionally —F or —$C_1$; and each remaining occurrence of $R^1$ is H.

112. The compound of any one of clauses 1-111, wherein $Y^1$, $Y^2$, and $Y^3$ are each independently selected $CR^1$.

113. The compound of any one of clauses 1-107 or 112, wherein $Y^1$, $Y^2$, and $Y^3$ are each CH.

114. The compound of any one of clauses 1-107 or 112, wherein one of $Y^1$, $Y^2$, and $Y^3$ is $CR^e$, optionally C-halo; and each of the remaining two $Y^1$, $Y^2$, and $Y^3$ is CH.

115. The compound of any one of clauses 1-114, wherein $X^1$ is $NR^2$.

116. The compound of any one of clauses 1-115, wherein $X^1$ is NH.

117. The compound of any one of clauses 1-116, wherein $X^2$ is $CR^5$.

118. The compound of any one of clauses 1-117, wherein $X^2$ is CH.

119. The compound of any one of clauses 1-114, wherein $X^1$ is $NR^2$; and $X^2$ is $CR^5$.

120. The compound of any one of clauses 1-114 or 119, wherein $X^1$ is NH; and $X^2$ is CH.

121. The compound of any one of clauses 1-104, wherein Y, $Y^2$, and $Y^3$ are each an independently selected $CR^1$; $X^1$ is $NR^2$; and $X^2$ is $CR^5$.

122. The compound of any one of clauses 1-104 or 121, wherein $Y^1$, $Y^2$, and $Y^3$ are each CH; $X^1$ is NH; and $X^2$ is CH.

123. The compound of any one of clauses 1-122, wherein $R^6$ is H.

124. The compound of any one of clauses 1-123, wherein W is $C_{1-10}$ alkyl, $C_{2-10}$ alkenyl, or $C_{2-10}$ alkenyl, each of which is optionally substituted with 1-6 $R^{a2}$.

125. The compound of any one of clauses 1-124, wherein W is $C_{1-10}$ alkyl, which is optionally substituted with 1-6 $R^{a2}$.

126. The compound of any one of clauses 1-125, wherein W is $C_{1-6}$ alkyl, which is optionally substituted with 1-6 $R^{a2}$.

127. The compound of any one of clauses 1-126, wherein W is $C_{1-4}$ alkyl, which is optionally substituted with 1-6 $R^{a2}$.

128. The compound of any one of clauses 1-127, wherein W is unsubstituted $C_{1-4}$ alkyl.

129. The compound of any one of clauses 1-128, wherein W is selected from the group consisting of: methyl, ethyl, n-propyl, isopropyl, and isobutyl 130. The compound of any one of clauses 1-129, wherein W is methyl or ethyl.

131. The compound of any one of clauses 1-126, wherein W is $C_{1-4}$ alkyl, which is substituted with 1-6 $R^{a2}$.

132. The compound of any one of clauses 1-126 or 131, wherein each $R^{a2}$ is independently selected from the group consisting of:

i. —OH; -halo; —$NR^eR^f$; $C_{1-4}$ alkoxy; $C_{1-4}$ haloalkoxy; —C(═O)O($C_{1-4}$ alkyl); —C(═O)($C_{1-4}$ alkyl); and cyano; or ii. halo; —OH; $C_{1-4}$ alkoxy; and $C_{1-4}$ haloalkoxy.

133. The compound of any one of clauses 1-126 or 131-132, wherein W:

i. $C_{1-4}$ alkyl which is substituted with 1-3 substituents each independently selected from the group consisting of: halo; —OH; $C_{1-4}$ alkoxy; and $C_{1-4}$ haloalkoxy; or ii. selected from the group consisting of: W is

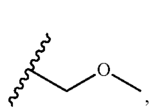
,
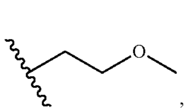
,
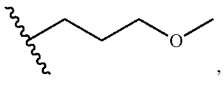
, and
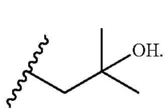

134. The compound of any one of clauses 1-123, wherein W is selected from the group consisting of:

monocyclic $C_{3-8}$ cycloalkyl or $C_{3-8}$ cycloalkenyl, each of which is optionally substituted with 1-4 substituents independently selected from the group consisting of oxo and $R^c$; and monocyclic heterocyclyl or heterocycloalkenyl of from 3-8 ring atoms, wherein 1-3 ring atoms are heteroatoms, each independently selected from the group consisting of N, N(H), N($R^d$), O, and $S(O)_{0-2}$, and wherein the heterocyclyl or heterocycloalkenyl is optionally substituted with 1-4 substituents independently selected from the group consisting of oxo and $R^c$.

135. The compound of any one of clauses 1-123 or 134, wherein W is monocyclic $C_{3-8}$ cycloalkyl or $C_{3-8}$ cycloalkenyl, each of which is optionally substituted with 1-4 substituents independently selected from the group consisting of oxo and $R^c$.

136. The compound of any one of clauses 1-123 or 134-135, wherein W is monocyclic $C_{3-8}$ cycloalkyl, which is optionally substituted with 1-4 substituents independently selected from the group consisting of oxo and $R^c$.

137. The compound of any one of clauses 1-123 or 134-136, wherein W is unsubstituted $C_{3-8}$ cycloalkyl.

138. The compound of any one of clauses 1-123 or 134-137, wherein W is cyclopropyl, cyclobutyl, cyclopentyl, or cyclohexyl.

139. The compound of any one of clauses 1-123 or 134-138, wherein W is cyclobutyl.

140. The compound of any one of clauses 1-123, wherein W is H.

141. The compound of clause 1, wherein the compound is a compound of Formula (I-a):

Formula (I-a)

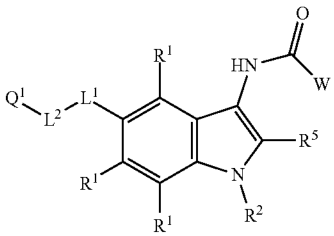

or a pharmaceutically acceptable salt thereof, wherein:

$L^1$ is selected from the group consisting of: —O—, —N(H)—, and —N($R^d$)—;

$L^2$ is selected from the group consisting of:

straight-chain $C_{1-3}$ alkylene, which is optionally substituted with 1-3 $R^b$;

$C_{3-8}$ cycloalkylene, which is optionally substituted with 1-3 $R^e$; and heterocyclylene having 4-8 ring atoms wherein 1-3 ring atoms are ring heteroatoms each independently selected from the group consisting of: N, N(H), N($R^d$), O, and $S(O)_{0-2}$, wherein the heterocyclylene is optionally substituted with 1-3 $R^c$;

$Q^1$ is —$R^g$;

each occurrence of $R^1$ and $R^5$ is independently selected from the group consisting of: H; $R^c$; $R^g$; and -$(L^g)_{bg}$-$R^g$;

each occurrence of $R^2$ is independently selected from the group consisting of: H; $R^d$; $R^g$; and -$(L^g)_{bg}$-$R^g$;

W is selected from the group consisting of:

H;

$C_{1-10}$ alkyl, $C_{2-10}$ alkenyl, or $C_{2-10}$ alkynyl, each of which is optionally substituted with 1-6 $R^{a2}$, wherein one or more of the internal optionally substituted methylene group can be replaced by one or more heteroatom selected from O or S, wherein when W is alkenyl or alkynyl, the heteroatom is not directed connected to the $sp^2$ or sp carbon;

monocyclic $C_{3-8}$ cycloalkyl or $C_{3-8}$ cycloalkenyl, each of which is optionally substituted with 1-4 substituents independently selected from the group consisting of oxo and $R^c$; and monocyclic heterocyclyl or heterocycloalkenyl of 3-8 ring atoms, wherein 1-3 ring atoms are heteroatoms, each independently selected from the group consisting of N, N(H), N($R^d$), O, and $S(O)_{0-2}$, and wherein the heterocyclyl or heterocycloalkenyl is optionally substituted with 1-4 substituents independently selected from the group consisting of oxo and $R^c$, provided that when W is heterocyclyl or heterocycloalkenyl, it is attached to the C(=O)N$R^6$ group via a ring carbon atom.

142. The compound of clause 141, wherein $L^1$ is —O—.

143. The compound of clauses 141 or 142, wherein $L^2$ is straight-chain CI-3 alkylene, which is optionally substituted with 1-3 $R^b$.

144. The compound of any one of clauses 141-143, wherein $L^2$ is selected from the group consisting of: —$CH_2$—, —CH$R^b$—, and —C$(R^b)_2$—, optionally wherein $L^2$ is —$CH_2$—.

145. The compound of any one of clauses 141-143 wherein $L^2$ is straight-chain $C_2$ alkylene which is optionally substituted with 1-3 $R^b$.

146. The compound of any one of clauses 141-143 or 145, wherein $L^2$ is selected from the group consisting of: —$CH_2CH_2$—, —$CH_2$CH(R")—*, and —$CH_2$C$(R")_2$—*, wherein the asterisk represents point of attachment to -$Q^1$.

147. The compound of clause 146, wherein $L^2$ is —$CH_2CH_2$—.

148. The compound of any one of clauses 141-143, wherein $L^2$ is straight-chain $C_3$ alkylene which is optionally substituted with 1-3 $R^b$.

149. The compound of clauses 141 or 142, wherein $L^2$ is:

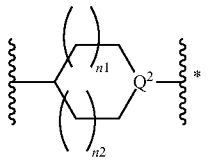

which is optionally substituted with 1-2 $R^c$, wherein n1 and n2 are independently 0, 1, or 2; $Q^2$ is CH, C$R^c$, or N; and the asterisk represents the point of attachment to $Q^1$;

150. The compound of clause 149, wherein n1 and n2 are independently 0 or 1, optionally 0; and $Q^2$ is CH; optionally wherein n1 and n2 are 0 and $Q^2$ is CH; optionally wherein $L^2$ is cyclobutane-diyl optionally substituted with 1-2 $R^c$; optionally wherein $L^2$ is cyclobutane-1,3-diyl optionally substituted with 1-2 $R^c$; optionally wherein $L^2$ is cyclobutane-diyl optionally substituted with 1-2 $R^c$; optionally wherein $L^2$ is unsubstituted cyclobutane-diyl; optionally wherein $L^2$ is unsubstituted cyclobutane-1,3-diyl.

151. The compound of clause 141, wherein $L^1$ is —O—; and $L^2$ is straight-chain $C_{2-3}$ alkylene which is optionally substituted with 1-3 $R^b$.

152. The compound of clause 151, wherein $L^2$ is:

i. straight-chain $C_2$ alkylene which is optionally substituted with 1-3 $R^b$;

ii. selected from the group consisting of: —$CH_2CH_2$—, —$CH_2$CH(R")—*, and —$CH_2$C$(R")_2$—*, wherein the asterisk represents point of attachment to -$Q^1$; or iii. —$CH_2CH_2$—.

153. The compound of clause 141, wherein $L^1$ is —O—; and $L^2$ is:

i. selected from the group consisting of: $—CH_2—$, $—CHR^b—$, and $—C(R^b)_2$; or ii. $—CH_2—$.

154. The compound of clause 1, wherein the compound is a compound of Formula (I-b):

Formula (I-b)

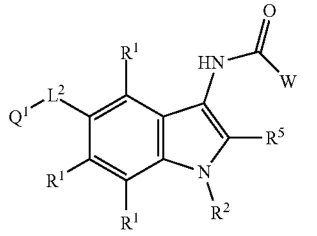

or a pharmaceutically acceptable salt thereof, wherein:

$L^2$ is straight-chain $C_{1-6}$ alkylene or straight-chain $C_{2-6}$ alkenylene, each of which is optionally substituted with 1-6 $R^b$;

$Q^1$ is $—R^g$;

each occurrence of $R^1$ and $R^5$ is independently selected from the group consisting of: H; $R^e$; $R^g$; and $-(L^g)_{bg}-R^g$;

each occurrence of $R^2$ is independently selected from the group consisting of: H; $R^d$; $R^g$; and $-(L^g)_{bg}-R^g$; and W is selected from the group consisting of:

H;

$C_{1-10}$ alkyl, $C_{2-10}$ alkenyl, or $C_{2-10}$ alkynyl, each of which is optionally substituted with 1-6 $R^{a2}$, wherein one or more of the internal optionally substituted methylene group can be replaced by one or more heteroatom selected from O or S, wherein when W is alkenyl or alkynyl, the heteroatom is not directed connected to the $sp^2$ or sp carbon;

monocyclic $C_{3-8}$ cycloalkyl or $C_{3-8}$ cycloalkenyl, each of which is optionally substituted with 1-4 substituents independently selected from the group consisting of oxo and $R^c$; and monocyclic heterocyclyl or heterocycloalkenyl of 3-8 ring atoms, wherein 1-3 ring atoms are heteroatoms, each independently selected from the group consisting of N, N(H), $N(R^d)$, O, and $S(O)_{0-2}$, and wherein the heterocyclyl or heterocycloalkenyl is optionally substituted with 1-4 substituents independently selected from the group consisting of oxo and $R^c$, provided that when W is heterocyclyl or heterocycloalkenyl, it is attached to the $C(=O)NR^6$ group via a ring carbon atom.

155. The compound of clause 154, wherein $L^2$ is straight-chain $C_{2-3}$ alkylene which is optionally substituted with 1-3 $R^b$.

156. The compound of clauses 154 or 155, wherein $L^2$ is straight-chain $C_2$ alkylene which is optionally substituted with 1-3 $R^b$.

157. The compound of any one of clauses 154-156, wherein $L^2$ is selected from the group consisting of: $—CH_2CH_2—$, $—CH_2CH(R^b)—*$, and $—CH_2C(R^b)_2—*$, wherein the asterisk represents point of attachment to $-Q^1$, optionally wherein $L^2$ is $—CH_2CH_2—$.

158. The compound of clauses 154-155, wherein $L^2$ is straight-chain $C_3$ alkylene which is optionally substituted with 1-3 $R^b$.

159. The compound of any one of clauses 154-155 or 158, wherein $L^2$ is selected from the group consisting of:

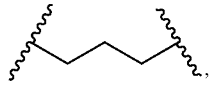,
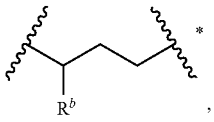,
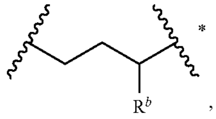, and
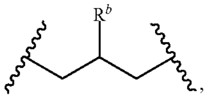, wherein the asterisk represents point of attachment to $-Q^1$, optionally wherein $L^2$ is

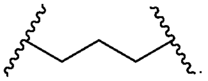 [SMILES: *CCC*].

160. The compound of clause 154, wherein $L^2$ is straight-chain $C_{2-4}$ alkenylene, which is optionally substituted with 1-3 $R^b$.

161. The compound of clauses 154 or 160, wherein $L^2$ is selected from the group consisting of:

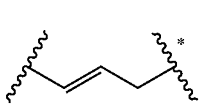 and 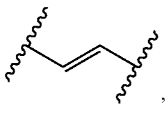, wherein the asterisk represents the point of attachment to $-Q^1$.

162. The compound of clause 1, wherein the compound is a compound of Formula (I-c):

Formula (I-c)

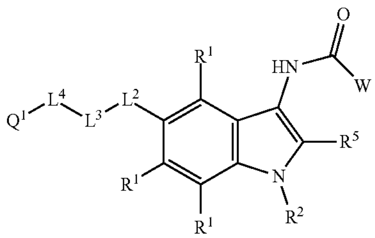

or a pharmaceutically acceptable salt thereof, wherein:

$L^2$ and $L^4$ are independently selected straight-chain $C_{1-3}$ alkylene which is optionally substituted with 1-6 $R^b$;

$L^3$ is selected from the group consisting of: $—O—$, $—N(H)—$, and $—N(R^d)—$;

$Q^1$ is $—R^g$;

each occurrence of $R^1$ and $R^5$ is independently selected from the group consisting of: H; $R^c$; $R^g$; and $-(L^g)_{bg}-R^g$;

each occurrence of $R^2$ is independently selected from the group consisting of: H; $R^d$; $R^g$; and $-(L^g)_{bg}-R^g$; and W is selected from the group consisting of:

H;

$C_{1-10}$ alkyl, $C_{2-10}$ alkenyl, or $C_{2-10}$ alkynyl, each of which is optionally substituted with 1-6 $R^{a2}$, wherein one or more of the internal optionally substituted methylene group can be replaced by one or more heteroatom selected from O or S, wherein when W is alkenyl or alkynyl, the heteroatom is not directed connected to the $sp^2$ or sp carbon;

monocyclic $C_{3-8}$ cycloalkyl or $C_{3-8}$ cycloalkenyl, each of which is optionally substituted with 1-4 substituents independently selected from the group consisting of oxo and $R^c$; and monocyclic heterocyclyl or heterocycloalkenyl of 3-8 ring atoms, wherein 1-3 ring atoms are heteroatoms, each independently selected from the group consisting of N, N(H), N($R^d$), O, and $S(O)_{0-2}$, and wherein the heterocyclyl or heterocycloalkenyl is optionally substituted with 1-4 substituents independently selected from the group consisting of oxo and $R^c$, provided that when W is heterocyclyl or heterocycloalkenyl, it is attached to the C(═O)$NR^6$ group via a ring carbon atom.

163. The compound of clause 162, wherein $L^2$ and $L^4$ are independently selected from the group consisting of: —$CH_2$—, —$CHR^b$—, and —$C(R^b)_2$.

164. The compound of clauses 162 or 163, wherein $L^2$ and $L^4$ are each —$CH_2$—.

165. The compound of any one of clauses 162-164, wherein $L^3$ is —O—.

166. The compound of any one of clauses 162-164, wherein $L^3$ is —N(H)— or —N($R^d$)—, optionally —N(H)—.

167. The compound of clause 1, wherein the compound is a compound of Formula (I-d):

Formula (I-d)

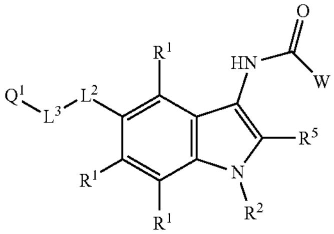

or a pharmaceutically acceptable salt thereof, wherein:

$L^2$ is straight-chain $C_{1-3}$ alkylene which is optionally substituted with 1-6 $R^b$; and $L^3$ is selected from the group consisting of: —O—, —N(H)—, and —N($R^d$)—;

$Q^1$ is —$R^g$;

each occurrence of $R^1$ and $R^5$ is independently selected from the group consisting of: H; $R^e$; $R^g$; and $-(L^g)_{bg}-R^g$;

each occurrence of $R^2$ is independently selected from the group consisting of: H; $R^d$; $R^g$; and $-(L^g)_{bg}-R^g$; and W is selected from the group consisting of:

H;

$C_{1-10}$ alkyl, $C_{2-10}$ alkenyl, or $C_{2-10}$ alkynyl, each of which is optionally substituted with 1-6 $R^{a2}$, wherein one or more of the internal optionally substituted methylene group can be replaced by one or more heteroatom selected from O or S, wherein when W is alkenyl or alkynyl, the heteroatom is not directed connected to the $sp^2$ or sp carbon;

monocyclic $C_{3-8}$ cycloalkyl or $C_{3-8}$ cycloalkenyl, each of which is optionally substituted with 1-4 substituents independently selected from the group consisting of oxo and $R^c$; and monocyclic heterocyclyl or heterocycloalkenyl of 3-8 ring atoms, wherein 1-3 ring atoms are heteroatoms, each independently selected from the group consisting of N, N(H), N($R^d$), O, and $S(O)_{0-2}$, and wherein the heterocyclyl or heterocycloalkenyl is optionally substituted with 1-4 substituents independently selected from the group consisting of oxo and $R^c$, provided that when W is heterocyclyl or heterocycloalkenyl, it is attached to the C(═O)$NR^6$ group via a ring carbon atom.

168. The compound of clause 167, wherein $L^2$ is selected from the group consisting of: —$CH_2$—, —$CHR^b$—, and —$C(R^b)_2$.

169. The compound of clause 167, wherein $L^2$ is straight-chain $C_2$ alkylene which is optionally substituted with 1-3 $R^b$.

170. The compound of clauses 167 or 169, wherein $L^2$ is selected from the group consisting of: —$CH_2CH_2$—, —$CH_2CH(R^b)$—*, and —$CH_2C(R^b)_2$—*, wherein the asterisk represents point of attachment to -$L^3$, optionally wherein $L^2$ is —$CH_2CH_2$—.

171. The compound of any one of clauses 167-170, wherein $L^3$ is —O—.

172. The compound of any one of clauses 167-170, wherein $L^3$ is —N(H)— or —N($R^d$)—, optionally —N(H)—.

173. The compound of any one of clauses 141-172, wherein $Q^1$ is selected from the group consisting of:

heteroaryl of 5-6 ring atoms, wherein 1-4 ring atoms are heteroatoms, each independently selected from the group consisting of N, N(H), N($R^d$), O, and $S(O)_{0-2}$, and wherein the heteroaryl is optionally substituted with 1-3 $R^c$; and phenyl optionally substituted with 1-3 $R^c$.

174. The compound of any one of clauses 141-173, wherein $Q^1$ is selected from the group consisting of:

heteroaryl of 6 ring atoms, wherein 1-2 ring atoms are ring nitrogen atoms, and wherein the heteroaryl is optionally substituted with 1-3 $R^c$; and phenyl optionally substituted with 1-3 $R^c$.

175. The compound of any one of clauses 141-174, wherein $Q^1$ is:

i. phenyl or pyridyl, each optionally substituted with 1-3 $R^c$;

ii.

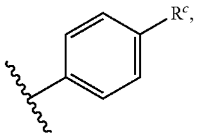

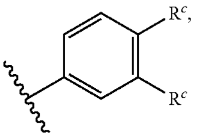

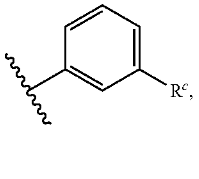

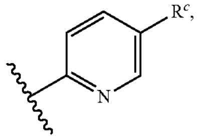

or

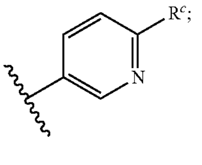

iii. any groups of i or ii, wherein each $R^c$ present in $Q^1$ is independently selected from the group consisting of:

halo and CI-3 alkyl which is optionally substituted with 1-6 independently selected halo; or iv. any groups of i or ii, wherein each $R^c$ present in $Q^1$ is independently selected from the group consisting of: —F, —Cl, and —$CF_3$.

176. The compound of any one of clauses 141-172, wherein $Q^1$ is heterocyclyl of 4-10 ring atoms, wherein 1-3 ring atoms are heteroatoms, each independently selected from the group consisting of N, N(H), N($R^d$), O, and $S(O)_{0-2}$, and wherein the heterocyclyl is optionally substituted with 1-4 substituents independently selected from the group consisting of oxo and $R^c$.

177. The compound of any one of clauses 141-172 or 176, wherein $Q^1$ is:

i.

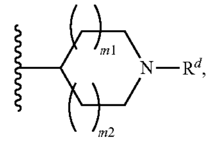

wherein m1 and m2 are each independently 0, 1, or 2;

ii.

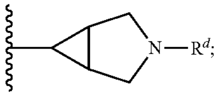

iii any groups of i or ii, wherein the $R^d$ present in $Q^1$ is selected from the group consisting of: —C(O)O($C_{1-4}$ alkyl); and $C_{1-6}$ alkyl optionally substituted with 1-3 independently selected $R^a$; or iv. any groups of i or ii, wherein the $R^d$ present in $Q^1$ is $C_{2-3}$ alkyl substituted with 1-3 —F.

178. The compound of any one of clauses 141-177, wherein each $R^1$ is H.

179. The compound of any one of clauses 141-177, wherein one occurrence of $R^1$ is $R^c$; and each remaining $R^1$ is H.

180. The compound of any one of clauses 141-179, wherein $R^2$ is H; and $R^5$ is H.

181. The compound of any one of clauses 141-180, wherein W is $C_{1-6}$ alkyl, which is optionally substituted with 1-6 $R^{a2}$.

182. The compound of any one of clauses 141-181, wherein W is unsubstituted $C_{1-4}$ alkyl.

183. The compound of any one of clauses 141-182, wherein W is methyl or ethyl.

184. The compound of any one of clauses 141-181, wherein W is $C_{1-4}$ alkyl, which is substituted with 1-6 $R^{a2}$.

185. The compound of any one of clauses 141-181 or 184, wherein W:

i. $C_{1-4}$ alkyl which is substituted with 1-3 substituents each independently selected from the group consisting of: halo; —OH; $C_{1-4}$ alkoxy; and $C_{1-4}$ haloalkoxy; or ii. selected from the group consisting of: W is

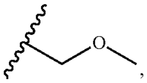

,

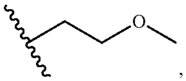

,

-continued

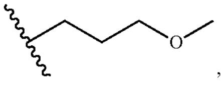

, and

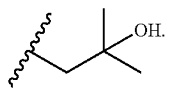

186. The compound of any one of clauses 141-181, wherein W is selected from the group consisting of:

monocyclic $C_{3-8}$ cycloalkyl or $C_{3-8}$ cycloalkenyl, each of which is optionally substituted with 1-4 substituents independently selected from the group consisting of oxo and $R^c$; and monocyclic heterocyclyl or heterocycloalkenyl of from 3-8 ring atoms, wherein 1-3 ring atoms are heteroatoms, each independently selected from the group consisting of N, N(H), N($R^d$), O, and $S(O)_{0-2}$, and wherein the heterocyclyl or heterocycloalkenyl is optionally substituted with 1-4 substituents independently selected from the group consisting of oxo and $R^c$.

187. The compound of any one of clauses 141-181 or 186, wherein W is monocyclic $C_{3-8}$ cycloalkyl, which is optionally substituted with 1-4 substituents independently selected from the group consisting of oxo and $R^c$.

188. The compound of any one of clauses 141-181 or 186-187, wherein W is:

i. unsubstituted $C_{3-8}$ cycloalkyl; or ii. cyclobutyl.

189. The compound of clause 1, wherein the compound is selected from the group consisting of compounds delineated in Table $C_1$, and a pharmaceutically acceptable salt thereof, optionally wherein the compound is compound 101-147; or 148-408; or 409-596.

190. A pharmaceutical composition comprising a compound of clauses 1-189 and one or more pharmaceutically acceptable excipients.

191. A method for inhibiting STING activity, the method comprising contacting STING with a compound or a pharmaceutically acceptable salt thereof as defined in any one of clauses 1-189; or a pharmaceutical composition as defined in clause 190.

192. The method of clause 191, wherein the inhibiting comprises antagonizing STING.

193. The method of any one of clauses 191-192, which is carried out in vitro.

194. The method of clauses 193, wherein the method comprises contacting a sample comprising one or more cells comprising STING with the compound.

195. The method of clauses 193 or 194, wherein the one or more cells are one or more cancer cells.

196. The method of clauses 194 or 195, wherein the sample further comprises one or more cancer cells, wherein the cancer is selected from the group consisting of melanoma, cervical cancer, breast cancer, ovarian cancer, prostate cancer, testicular cancer, urothelial carcinoma, bladder cancer, non-small cell lung cancer, small cell lung cancer, sarcoma, colorectal adenocarcinoma, gastrointestinal stromal tumors, gastroesophageal carcinoma, colorectal cancer, pancreatic cancer, kidney cancer, hepatocellular cancer, malignant mesothelioma, leukemia, lymphoma, myelodysplasia syndrome, multiple myeloma, transitional cell carcinoma, neuroblastoma, plasma cell neoplasms, Wilm's tumor, or hepatocellular carcinoma.

197. The method of clauses 191 or 192, which is carried out in vivo.

198. The method of clause 197, wherein the method comprises administering the compound to a subject having a disease in which increased (e.g., excessive) STING signaling contributes to the pathology and/or symptoms and/or progression of the disease.

199. The method of clause 198, wherein the subject is a human.

200. The method of clause 199, wherein the disease is cancer.

201. The method of clause 200, wherein the cancer is selected from the group consisting of melanoma, cervical cancer, breast cancer, ovarian cancer, prostate cancer, testicular cancer, urothelial carcinoma, bladder cancer, non-small cell lung cancer, small cell lung cancer, sarcoma, colorectal adenocarcinoma, gastrointestinal stromal tumors, gastroesophageal carcinoma, colorectal cancer, pancreatic cancer, kidney cancer, hepatocellular cancer, malignant mesothelioma, leukemia, lymphoma, myelodysplasia syndrome, multiple myeloma, transitional cell carcinoma, neuroblastoma, plasma cell neoplasms, Wilm's tumor, or hepatocellular carcinoma.

202. The method of clauses 200 or 201, wherein the cancer is a refractory cancer.

203. The method of clause 198, wherein the compound is administered in combination with one or more additional cancer therapies.

204. The method of clause 203, wherein the one or more additional cancer therapies comprises surgery, radiotherapy, chemotherapy, toxin therapy, immunotherapy, cryotherapy or gene therapy, or a combination thereof.

205. The method of clause 204, wherein chemotherapy comprises administering one or more additional chemotherapeutic agents.

206. The method of clause 205, wherein the one or more additional chemotherapeutic agents is selected from an alkylating agent (e.g., cisplatin, carboplatin, mechlorethamine, cyclophosphamide, chlorambucil, ifosfamide and/or oxaliplatin); an anti-metabolite (e.g., azathioprine and/or mercaptopurine); a terpenoid (e.g., a *vinca* alkaloid and/or a taxane; e.g., Vincristine, Vinblastine, Vinorelbine and/or Vindesine Taxol, Pacllitaxel and/or Docetaxel); a topoisomerase (e.g., a type I topoisomerase and/or a type 2 topoisomerase; e.g., camptothecins, such as irinotecan and/or topotecan; amsacrine, etoposide, etoposide phosphate and/or teniposide); a cytotoxic antibiotic (e.g., actinomycin, anthracyclines, doxorubicin, daunorubicin, valrubicin, idarubicin, epirubicin, bleomycin, plicamycin and/or mitomycin); a hormone (e.g., a lutenizing hormone releasing hormone agonist; e.g., leuprolidine, goserelin, triptorelin, histrelin, bicalutamide, flutamide and/or nilutamide); an antibody (e.g., Abciximab, Adalimumab, Alemtuzumab, Atlizumab, Basiliximab, Belimumab, Bevacizumab, Bretuximab vedotin, Canakinumab, Cetuximab, Ceertolizumab pegol, Daclizumab, Denosumab, Eculizumab, Efalizumab, Gemtuzumab, Golimumab, Golimumab, Ibritumomab tiuxetan, Infliximab, Ipilimumab, Muromonab-CD3, Natalizumab, Ofatumumab, Omalizumab, Palivizumab, Panitumuab, Ranibizumab, Rituximab, Tocilizumab, Tositumomab and/or Trastuzumab); an anti-angiogenic agent; a cytokine; a thrombotic agent; a growth inhibitory agent; an anti-helminthic agent; and an immune checkpoint inhibitor that targets an immune checkpoint receptor selected from the group consisting of CTLA-4, PD-1, PD-L1, PD-1-PD-L1, PD-1-PD-L2, interleukin-2 (IL-2), indoleamine 2,3-dioxygenase (IDO), IL-10, transforming growth factor-β (TGFβ), T cell immunoglobulin and mucin 3 (TIM3 or HAVCR2), Galectin 9-TIM3, Phosphatidylserine-TIM3, lymphocyte activation gene 3 protein (LAG3), MHC class II-LAG3, 4-1BB-4-1BB ligand, OX40-OX40 ligand, GITR, GITR ligand-GITR, CD27, CD70-CD27, TNFRSF25, TNFRSF25-TL1A, CD40L, CD40-CD40 ligand, HVEM-LIGHT-LTA, HVEM, HVEM-BTLA, HVEM-CD160, HVEM-LIGHT, HVEM-BTLA-CD160, CD80, CD80-PDL-1, PDL2-CD80, CD244, CD48-CD244, CD244, ICOS, ICOS—ICOS ligand, B7-H3, B7-H4, VISTA, TMIGD2, HHLA2-TMIGD2, Butyrophilins, including BTNL2, Siglec family, TIGIT and PVR family members, KIRs, ILTs and LIRs, NKG2D and NKG2A, MICA and MICB, CD244, CD28, CD86-CD28, CD86-CTLA, CD80-CD28, CD39, CD73 Adenosine-CD39-CD73, CXCR4-CXCL12, Phosphatidylserine, TIM3, Phosphatidylserine-TIM3, SIRPA-CD47, VEGF, Neuropilin, CD160, CD30, and CD155 (e.g., CTLA-4 or PD1 or PD-L1).

207. The method of any one of clauses 198-206, wherein the compound is administered intratumorally.

208. A method of treating cancer, comprising administering to a subject in need of such treatment an effective amount of a compound as defined in any one of clauses 1-189, or a pharmaceutical composition as defined in clause 190.

209. The method of clause 208, wherein the cancer is selected from the group consisting of melanoma, cervical cancer, breast cancer, ovarian cancer, prostate cancer, testicular cancer, urothelial carcinoma, bladder cancer, non-small cell lung cancer, small cell lung cancer, sarcoma, colorectal adenocarcinoma, gastrointestinal stromal tumors, gastroesophageal carcinoma, colorectal cancer, pancreatic cancer, kidney cancer, hepatocellular cancer, malignant mesothelioma, leukemia, lymphoma, myelodysplasia syndrome, multiple myeloma, transitional cell carcinoma, neuroblastoma, plasma cell neoplasms, Wilm's tumor, or hepatocellular carcinoma.

210. The method of clause 208 or 209, wherein the cancer is a refractory cancer.

211. The method of clause 208, wherein the compound is administered in combination with one or more additional cancer therapies.

212. The method of clause 211, wherein the one or more additional cancer therapies comprises surgery, radiotherapy, chemotherapy, toxin therapy, immunotherapy, cryotherapy or gene therapy, or a combination thereof.

213. The method of clause 212, wherein chemotherapy comprises administering one or more additional chemotherapeutic agents.

214. The method of clause 212, wherein the one or more additional chemotherapeutic agents is selected from an alkylating agent (e.g., cisplatin, carboplatin, mechlorethamine, cyclophosphamide, chlorambucil, ifosfamide and/or oxaliplatin); an anti-metabolite (e.g., azathioprine and/or mercaptopurine); a terpenoid (e.g., a *vinca* alkaloid and/or a taxane; e.g., Vincristine, Vinblastine, Vinorelbine and/or Vindesine Taxol, Pacllitaxel and/or Docetaxel); a topoisomerase (e.g., a type I topoisomerase and/or a type 2 topoisomerase; e.g., camptothecins, such as irinotecan and/or topotecan; amsacrine, etoposide, etoposide phosphate and/or teniposide); a cytotoxic antibiotic (e.g., actinomycin, anthracyclines, doxorubicin, daunorubicin, valrubicin, idarubicin, epirubicin, bleomycin, plicamycin and/or mitomycin); a hormone (e.g., a lutenizing hormone releasing hormone agonist; e.g., leuprolidine, goserelin, triptorelin, histrelin, bicalutamide, flutamide and/or nilutamide); an antibody (e.g., Abciximab, Adalimumab, Alemtuzumab, Atlizumab, Basiliximab, Belimumab, Bevacizumab, Bretuximab vedotin, Canakinumab, Cetuximab, Ceertolizumab pegol, Daclizumab, Denosumab, Eculizumab, Efalizumab, Gemtuzumab, Golimumab, Golimumab, Ibritumomab tiuxetan, Infliximab, Ipilimumab, Muromonab-CD3, Natalizumab, Ofatumumab, Omalizumab, Palivizumab, Panitumuab, Ranibizumab, Rituximab, Tocilizumab, Tositumomab and/or Trastuzumab); an anti-angiogenic agent; a cytokine; a thrombotic agent; a growth inhibitory agent; an anti-helminthic agent; and an immune checkpoint inhibitor that targets an immune checkpoint receptor selected from the group consisting of CTLA-4, PD-1, PD-L1, PD-1-PD-L1, PD-1-PD-L2, interleukin-2 (IL-2), indoleamine 2,3-dioxygenase (IDO), IL-10, transforming growth factor-β (TGFβ), T cell immunoglobulin and mucin 3 (TIM3 or HAVCR2), Galectin 9-TIM3, Phosphatidylserine-TIM3, lymphocyte activation gene 3 protein (LAG3), MHC class II-LAG3, 4-1BB-4-1BB ligand, OX40-OX40 ligand, GITR, GITR ligand-GITR, CD27, CD70-CD27, TNFRSF25, TNFRSF25-TL1A, CD40L, CD40-CD40 ligand, HVEM-LIGHT-LTA, HVEM, HVEM-BTLA, HVEM-CD160, HVEM-LIGHT, HVEM-BTLA-CD160, CD80, CD80-PDL-1, PDL2-CD80, CD244, CD48-CD244, CD244, ICOS, ICOS—ICOS ligand, B7-H3, B7-H4, VISTA, TMIGD2, HHLA2-TMIGD2, Butyrophilins, including BTNL2, Siglec family, TIGIT and PVR family members, KIRs, ILTs and LIRs, NKG2D and NKG2A, MICA and MICB, CD244, CD28, CD86-CD28, CD86-CTLA, CD80-CD28, CD39, CD73 Adenosine-CD39-CD73, CXCR4-CXCL12, Phosphatidylserine, TIM3, Phosphatidylserine-TIM3, SIRPA-CD47, VEGF, Neuropilin, CD160, CD30, and CD155 (e.g., CTLA-4 or PD1 or PD-L1).

215. The method of any one of clauses 208-214, wherein the compound is administered intratumorally.

216. A method of inducing an immune response in a subject in need thereof, the method comprising administering to the subject an effective amount of a compound as defined in any one of clauses 1-189, or a pharmaceutical composition as defined in clause 190.

217. The method of clause 216, wherein the subject has cancer.

218. The method of clause 217, wherein the subject has undergone and/or is undergoing and/or will undergo one or more cancer therapies.

219. The method of clause 217, wherein the cancer selected from the group consisting of melanoma, cervical cancer, breast cancer, ovarian cancer, prostate cancer, testicular cancer, urothelial carcinoma, bladder cancer, non-small cell lung cancer, small cell lung cancer, sarcoma, colorectal adenocarcinoma, gastrointestinal stromal tumors, gastroesophageal carcinoma, colorectal cancer, pancreatic cancer, kidney cancer, hepatocellular cancer, malignant mesothelioma, leukemia, lymphoma, myelodysplasia syndrome, multiple myeloma, transitional cell carcinoma, neuroblastoma, plasma cell neoplasms, Wilm's tumor, or hepatocellular carcinoma.

220. The method of clause any one of clauses 217-219, wherein the cancer is a refractory cancer.

221. The method of clause 219, wherein the immune response is an innate immune response.

222. The method of clause 221, wherein the at least one or more cancer therapies comprises surgery, radiotherapy, chemotherapy, toxin therapy, immunotherapy, cryotherapy or gene therapy, or a combination thereof.

223. The method of clause 222, wherein chemotherapy comprises administering one or more additional chemotherapeutic agents.

224. The method of clause 223, wherein the one or more additional chemotherapeutic agents is selected from alkylating agent (e.g., cisplatin, carboplatin, mechlorethamine, cyclophosphamide, chlorambucil, ifosfamide and/or oxaliplatin); an anti-metabolite (e.g., azathioprine and/or mercaptopurine); a terpenoid (e.g., a *vinca* alkaloid and/or a taxane; e.g., Vincristine, Vinblastine, Vinorelbine and/or Vindesine Taxol, Pacllitaxel and/or Docetaxel); a topoisomerase (e.g., a type I topoisomerase and/or a type 2 topoisomerase; e.g., camptothecins, such as irinotecan and/or topotecan; amsacrine, etoposide, etoposide phosphate and/or teniposide); a cytotoxic antibiotic (e.g., actinomycin, anthracyclines, doxorubicin, daunorubicin, valrubicin, idarubicin, epirubicin, bleomycin, plicamycin and/or mitomycin); a hormone (e.g., a lutenizing hormone releasing hormone agonist; e.g., leuprolidine, goserelin, triptorelin, histrelin, bicalutamide, flutamide and/or nilutamide); an antibody (e.g., Abciximab, Adalimumab, Alemtuzumab, Atlizumab, Basiliximab, Belimumab, Bevacizumab, Bretuximab vedotin, Canakinumab, Cetuximab, Ceertolizumab pegol, Daclizumab, Denosumab, Eculizumab, Efalizumab, Gemtuzumab, Golimumab, Golimumab, Ibritumomab tiuxetan, Infliximab, Ipilimumab, Muromonab-CD3, Natalizumab, Ofatumumab, Omalizumab, Palivizumab, Panitumuab, Ranibizumab, Rituximab, Tocilizumab, Tositumomab and/or Trastuzumab); an anti-angiogenic agent; a cytokine; a thrombotic agent; a growth inhibitory agent; an anti-helminthic agent; and an immune checkpoint inhibitor that targets an immune checkpoint receptor selected from the group consisting of CTLA-4, PD-1, PD-L1, PD-1-PD-L1, PD-1-PD-L2, interleukin-2 (IL-2), indoleamine 2,3-dioxygenase (IDO), IL-10, transforming growth factor-β (TGFβ), T cell immunoglobulin and mucin 3 (TIM3 or HAVCR2), Galectin 9-TIM3, Phosphatidylserine-TIM3, lymphocyte activation gene 3 protein (LAG3), MHC class II-LAG3, 4-1BB-4-1BB ligand, OX40-OX40 ligand, GITR, GITR ligand-GITR, CD27, CD70-CD27, TNFRSF25, TNFRSF25-TL1A, CD40L, CD40-CD40 ligand, HVEM-LIGHT-LTA, HVEM, HVEM-BTLA, HVEM-CD160, HVEM-LIGHT, HVEM-BTLA-CD160, CD80, CD80-PDL-1, PDL2-CD80, CD244, CD48-CD244, CD244, ICOS, ICOS—ICOS ligand, B7-H3, B7-H4, VISTA, TMIGD2, HHLA2-TMIGD2, Butyrophilins, including BTNL2, Siglec family, TIGIT and PVR family members, KIRs, ILTs and LIRs, NKG2D and NKG2A, MICA and MICB, CD244, CD28, CD86-CD28, CD86-CTLA, CD80-CD28, CD39, CD73 Adenosine-CD39-CD73, CXCR4-CXCL12, Phosphatidylserine, TIM3, Phosphatidylserine-TIM3, SIRPA-CD47, VEGF, Neuropilin, CD160, CD30, and CD155 (e.g., CTLA-4 or PD1 or PD-L1).

225. A method of treatment of a disease in which increased (e.g., excessive) STING signaling contributes to the pathology and/or symptoms and/or progression of the disease, comprising administering to a subject in need of such treatment an effective amount of a compound as defined in any one of clauses 1-189, or a pharmaceutical composition as defined in clause 190.

226. A method of treatment comprising administering to a subject having a disease in which increased (e.g., excessive) STING signaling contributes to the pathology and/or symptoms and/or progression of the disease an effective amount of a compound as defined in any one of clauses 1-189, or a pharmaceutical composition as defined in clause 190.

227. A method of treatment comprising administering to a subject a compound as defined in any one of clauses 1-189, or a pharmaceutical composition as defined in clause 190, wherein the compound or composition is administered in an amount effective to treat a disease in which increased (e.g., excessive) STING signaling contributes to the pathology and/or symptoms and/or progression of the disease, thereby treating the disease.

228. The method of any one of clauses 225-227, wherein the disease is cancer.

229. The method of clause 228, wherein the cancer is selected from the group consisting of melanoma, cervical cancer, breast cancer, ovarian cancer, prostate cancer, testicular cancer, urothelial carcinoma, bladder cancer, non-small cell lung cancer, small cell lung cancer, sarcoma, colorectal adenocarcinoma, gastrointestinal stromal tumors, gastroesophageal carcinoma, colorectal cancer, pancreatic cancer, kidney cancer, hepatocellular cancer, malignant mesothelioma, leukemia, lymphoma, myelodysplasia syndrome, multiple myeloma, transitional cell carcinoma, neuroblastoma, plasma cell neoplasms, Wilm's tumor, or hepatocellular carcinoma.

230. The method of clause 228 or 229, wherein the cancer is a refractory cancer.

231. The method of any one of clauses 228-230, wherein the compound is administered in combination with one or more additional cancer therapies.

232. The method of clause 231, wherein the one or more additional cancer therapies comprises surgery, radiotherapy, chemotherapy, toxin therapy, immunotherapy, cryotherapy or gene therapy, or a combination thereof.

233. The method of clause 232, wherein chemotherapy comprises administering one or more additional chemotherapeutic agents.

234. The method of clause 233, wherein the one or more additional chemotherapeutic agents is selected from an alkylating agent (e.g., cisplatin, carboplatin, mechlorethamine, cyclophosphamide, chlorambucil, ifosfamide and/or oxaliplatin); an anti-metabolite (e.g., azathioprine and/or mercaptopurine); a terpenoid (e.g., a *vinca* alkaloid and/or a taxane; e.g., Vincristine, Vinblastine, Vinorelbine and/or Vindesine Taxol, Pacllitaxel and/or Docetaxel); a topoisomerase (e.g., a type I topoisomerase and/or a type 2 topoisomerase; e.g., camptothecins, such as irinotecan and/or topotecan; amsacrine, etoposide, etoposide phosphate and/or teniposide); a cytotoxic antibiotic (e.g., actinomycin, anthracyclines, doxorubicin, daunorubicin, valrubicin, idarubicin, epirubicin, bleomycin, plicamycin and/or mitomycin); a hormone (e.g., a lutenizing hormone releasing hormone agonist; e.g., leuprolidine, goserelin, triptorelin, histrelin, bicalutamide, flutamide and/or nilutamide); an antibody (e.g., Abciximab, Adalimumab, Alemtuzumab, Atlizumab, Basiliximab, Belimumab, Bevacizumab, Bretuximab vedotin, Canakinumab, Cetuximab, Ceertolizumab pegol, Daclizumab, Denosumab, Eculizumab, Efalizumab, Gemtuzumab, Golimumab, Golimumab, Ibritumomab tiuxetan, Infliximab, Ipilimumab, Muromonab-CD3, Natalizumab, Ofatumumab, Omalizumab, Palivizumab, Panitumuab, Ranibizumab, Rituximab, Tocilizumab, Tositumomab and/or Trastuzumab); an anti-angiogenic agent; a cytokine; a thrombotic agent; a growth inhibitory agent; an anti-helminthic agent; and an immune checkpoint inhibitor that targets an immune checkpoint receptor selected from the group consisting of CTLA-4, PD-1, PD-L1, PD-1-PD-L1, PD-1-PD-L2, interleukin-2 (IL-2), indoleamine 2,3-dioxygenase (IDO), IL-10, transforming growth factor-β (TGFβ), T cell immunoglobulin and mucin 3 (TIM3 or HAVCR2), Galectin 9-TIM3, Phosphatidylserine-TIM3, lymphocyte activation gene 3 protein (LAG3), MHC class II-LAG3, 4-1BB-4-1BB ligand, OX40-OX40 ligand, GITR, GITR ligand-GITR, CD27, CD70-CD27, TNFRSF25, TNFRSF25-TL1A, CD40L, CD40-CD40 ligand, HVEM-LIGHT-LTA, HVEM, HVEM-BTLA, HVEM-CD160, HVEM-LIGHT, HVEM-BTLA-CD160, CD80, CD80-PDL-1, PDL2-CD80, CD244, CD48-CD244, CD244, ICOS, ICOS—ICOS ligand, B7-H3, B7-H4, VISTA, TMIGD2, HHLA2-TMIGD2, Butyrophilins, including BTNL2, Siglec family, TIGIT and PVR family members, KIRs, ILTs and LIRs, NKG2D and NKG2A, MICA and MICB, CD244, CD28, CD86-CD28, CD86-CTLA, CD80-CD28, CD39, CD73 Adenosine-CD39-CD73, CXCR4-CXCL12, Phosphatidylserine, TIM3, Phosphatidylserine-TIM3, SIRPA-CD47, VEGF, Neuropilin, CD160, CD30, and CD155 (e.g., CTLA-4 or PD1 or PD-L1).

235. The method of any one of clauses 225-234, wherein the compound is administered intratumorally.

236. A method of treatment of a disease, disorder, or condition associated with STING, comprising administering to a subject in need of such treatment an effective amount of a compound as defined in any one of clauses 1-189, or a pharmaceutical composition as defined in clause 190.

237. The method of clause 236, wherein the disease, disorder, or condition is selected from type I interferonopathies, Aicardi-Goutieres Syndrome (AGS), genetic forms of lupus, inflammation-associated disorders, and rheumatoid arthritis.

238. The method of clause 237, wherein the disease, disorder, or condition is a type I interferonopathy (e.g., STING-associated vasculopathy with onset in infancy (SAVI)).

239. The method of clause 238, wherein the type I interferonopathy is STING-associated vasculopathy with onset in infancy (SAVI)).

240. The method of clause 237, wherein the disease, disorder, or condition is Aicardi-Goutières Syndrome (AGS).

241. The method of clause 237, wherein the disease, disorder, or condition is a genetic form of lupus.

242. The method of clause 237, wherein the disease, disorder, or condition is inflammation-associated disorder.

243. The method of clause 242, wherein the inflammation-associated disorder is systemic lupus erythematosus.

244. The method of any one of clauses 191-243, wherein the method further comprises identifying the subject.

245. A combination comprising a compounds defined in any one of clauses 1 to 189 or a pharmaceutically acceptable salt or tautomer thereof, and one or more therapeutically active agents.

246. A compound defined in any one of clauses 1-189 or a pharmaceutically acceptable salt or tautomer thereof, or a pharmaceutical composition defined in clause 190, for use as a medicament.

247. A compound defined in any one of clauses 1-189 or a pharmaceutically acceptable salt or tautomer thereof, or a pharmaceutical composition defined in clause 190, for use in the treatment of a disease, condition or disorder modulated by STING inhibition.

248. A compound defined in any one of clauses 1-189 or a pharmaceutically acceptable salt or tautomer thereof, or the pharmaceutical composition defined in clause 190, for use in the treatment of a disease mentioned in any one of clauses 191-244.

249. Use of a compound defined in any one of clauses 1-189 or a pharmaceutically acceptable salt or tautomer thereof, or a pharmaceutical composition defined in clause 190, in the manufacture of a medicament for the treatment of a disease mentioned in in any one of clauses 191-244.

What is claimed is:

1. A compound of Formula (I):

Formula I

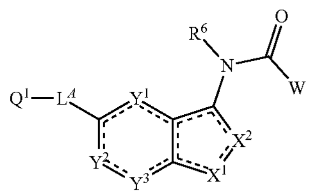

or a pharmaceutically acceptable salt thereof or a tautomer thereof, wherein:

$L^A$ is $-(L^1)_{a1}-(L^2)_{a2}(L^3)_{a3}-(L^4)_{a4}-(L^5)_{a5}-*$, wherein * represents the point of attachment to $Q^1$;

a1, a2, a3, a4, and a5 are each independently 0 or 1, provided that at +a2+a3+a4+a5≥1, and each of $L^1$, $L^3$, and $L^5$ is independently selected from the group consisting of: —O—, —N(H)—, —N($R^d$)—, $S(O)_{0-2}$, and —C(═O)—;

provided that when one or both of a2 and a4 is 0, then the combinations of $L^1$, $L^3$, and $L^5$ cannot form O—O, N—O, N—N, O—S, S—S, or N—$S(O)_0$ bonds, and each of $L^2$ and $L^4$ is independently selected from the group consisting of:

straight-chain $C_{1-6}$ alkylene, straight-chain $C_{2-6}$ alkenylene, or straight-chain $C_{2-6}$ alkynylene, each of which is optionally substituted with 1-6 $R^b$;

$C_{3-10}$ cycloalkylene or $C_{3-10}$ cycloalkenylene, each of which is optionally substituted with 1-3 $R^c$ provided the $C_{3-10}$ cycloalkylene or $C_{3-10}$ cycloalkenylene is not directly connected to the 6-membered ring containing $Y^1$, $Y^2$, and $Y^3$; and heterocyclylene or heterocycloalkenylene, each having 4-10 ring atoms wherein 1-3 ring atoms are ring heteroatoms each independently selected from the group consisting of: N, N(H), N($R^d$), O, and $S(O)_{0-2}$, wherein the heterocyclylene or heterocycloalkenylene is optionally substituted with 1-3 $R^c$, provided that the heterocyclylene or heterocycloalkenylene is not directly connected to the 6-membered ring containing $Y^1$, $Y^2$, and $Y^3$;

$Q^1$ is —$R^g$;

$Y^1$, $Y^2$, and $Y^3$ are each independently selected from the group consisting of $CR^1$, C(═O), N, and NW;

$X^1$ is NH;

$X^2$ is CH;

each ═ is independently a single bond or a double bond, provided that the five-membered ring comprising $X^1$ and $X^2$ is heteroaryl, and that the six-membered ring comprising $Y^1$, $Y^2$, and $Y^3$ is aryl or heteroaryl;

further provided that $L^A$ cannot include a cyclic group directly attached to the 6-membered ring containing $Y^1$, $Y^2$, and $Y^3$;

each occurrence of $R^1$ is independently selected from the group consisting of: H; $R^c$; $R^g$; and $-(L^g)_{bg}-R^g$;

each occurrence of $R^2$ is independently selected from the group consisting of: H; $R^d$; $R^g$; and $-(L^g)_{bg}-R^g$;

$R^6$ is selected from the group consisting of: H; $R^d$; and $R^g$;

W is selected from the group consisting of:

H;

$C_{1-10}$ alkyl, $C_{2-10}$ alkenyl, or $C_{2-10}$ alkynyl, each of which is optionally substituted with 1-6 $R^{a2}$, wherein one or more of the internal optionally substituted methylene group can be replaced by one or more heteroatom selected from O or S, wherein when W is alkenyl or alkynyl, the heteroatom is not directly connected to the $sp^2$ or sp carbon;

monocyclic $C_{3-8}$ cycloalkyl or $C_{3-8}$ cycloalkenyl, each of which is optionally substituted with 1-4 substituents independently selected from the group consisting of oxo and $R^c$; and monocyclic heterocyclyl or heterocycloalkenyl of 3-8 ring atoms, wherein 1-3 ring atoms are heteroatoms, each independently selected from the group consisting of N, N(H), N($R^d$), O, and $S(O)_{0-2}$, and wherein the heterocyclyl or heterocycloalkenyl is optionally substituted with 1-4 substituents independently selected from the group consisting of oxo and RC, provided that when W is heterocyclyl or heterocycloalkenyl, the heterocyclyl or heterocycloalkenyl is attached to the C(═O)$NR^6$ group via a ring carbon atom;

each occurrence of $R^a$ and $R^{a2}$ is independently selected from the group consisting of: —OH; —halo; —$NR^eR^f$; $C_{1-4}$ alkoxy; $C_{1-4}$ haloalkoxy; —C(═O)O($C_{1-4}$ alkyl); —C(═O)($C_{1-4}$ alkyl); —C(═O)OH; —CONR'R"; —$S(O)_{1-2}$NR'R"; —$S(O)_{1-2}$($C_{1-4}$ alkyl); and cyano;

each occurrence of $R^b$ and $R^c$ is independently selected from the group consisting of: halo; cyano; $C_{1-10}$ alkyl which is optionally substituted with 1-6 independently selected $R^a$; $C_{2-6}$ alkenyl; $C_{2-6}$ alkynyl; $C_{1-4}$ alkoxy; $C_{1-4}$ haloalkoxy; —$S(O)_{1-2}$($C_{1-4}$ alkyl); —S(O)(=NH)($C_{1-4}$ alkyl); —$NR^eR^f$; —OH; —$S(O)_{1-2}$NR'R"; —$C_{1-4}$ thioalkoxy; —$NO_2$; —C(═O)($C_{1-10}$ alkyl); —C(═O)O($C_{1-4}$ alkyl); —C(═O)OH; —C(═O)NR'R"; —NR'C(═O)($C_{1-4}$ alkyl) and —$SF_5$;

each occurrence of $R^d$ is independently selected from the group consisting of: $C_{1-6}$ alkyl optionally substituted with 1-3 independently selected $R^a$; —C(O)($C_{1-4}$ alkyl); —C(O)O($C_{1-4}$ alkyl); —CONR'R"; —$S(O)_{1-2}$NR'R"; —$S(O)_{1-2}$($C_{1-4}$ alkyl); —OH; and $C_{1-4}$ alkoxy;

each occurrence of $R^e$ and $R^f$ is independently selected from the group consisting of: H; $C_{1-6}$ alkyl optionally substituted with 1-3 substituents each independently selected from the group consisting of NR'R", —OH, halo, $C_{1-4}$ alkoxy, and $C_{1-4}$ haloalkoxy; —C(O)($C_{1-4}$ alkyl); —C(O)O($C_{1-4}$ alkyl); —CONR'R"; —$S(O)_{1-2}$NR'R"; —$S(O)_{1-2}$($C_{1-4}$ alkyl); —OH; and $C_{1-4}$ alkoxy;

each occurrence of $R^g$ is independently selected from the group consisting of:

$C_{3-12}$ cycloalkyl or $C_{3-12}$ cycloalkenyl, each of which is optionally substituted with 1-4 substituents independently selected from the group consisting of oxo, $R^c$, and $R^h$;

heterocyclyl or heterocycloalkenyl of 3-12 ring atoms, wherein 1-3 ring atoms are heteroatoms, each independently selected from the group consisting of N, N(H), N($R^d$), O, and $S(O)_{0-2}$, and wherein the heterocyclyl or heterocycloalkenyl is optionally substituted with 1-4 substituents independently selected from the group consisting of oxo, $R^c$, and $R^h$;

heteroaryl of 5-12 ring atoms, wherein 1-4 ring atoms are heteroatoms, each independently selected from the group consisting of N, N(H), N($R^d$), O, and $S(O)_{0-2}$, and wherein the heteroaryl is optionally substituted with 1-4 substituents independently selected from the group consisting of oxo, $R^c$, and $R^h$; and $C_{6-10}$ aryl optionally substituted with 1-4 substituents independently selected from the group consisting of oxo, $R^c$, and $R^h$;

each occurrence of $R^h$ is independently selected from the group consisting of:

$C_{3-12}$ cycloalkyl or $C_{3-12}$ cycloalkenyl, each of which is optionally substituted with 1-4 $R^i$;

heterocyclyl or heterocycloalkenyl of 3-12 ring atoms, wherein 1-3 ring atoms are heteroatoms, each independently selected from the group consisting of N, N(H), N($R^d$), O, and $S(O)_{0-2}$, and wherein the heterocyclyl or heterocycloalkenyl is optionally substituted with 1-4 $R^i$;

heteroaryl of 5-12 ring atoms, wherein 1-3 ring atoms are heteroatoms, each independently selected from the group consisting of N, N(H), N($R^d$), O, and $S(O)_{0-2}$, and wherein the heteroaryl is optionally substituted with 1-4 $R^i$; and $C_{6-10}$ aryl optionally substituted with 1-4 $R^i$;

each occurrence of $R^i$ is independently selected from the group consisting of: $C_{1-6}$ alkyl; $C_{1-4}$ haloalkyl; $C_{1-4}$ alkoxy; $C_{1-4}$ haloalkoxy; and halo;

each occurrence of $L^g$ is independently selected from the group consisting of: —O—, —NH—, —$NR^d$, —$S(O)_{0-2}$, C(O), and $C_{1-3}$ alkylene optionally substituted with 1-3 $R^a$;

each occurrence of bg is independently 1, 2, or 3; and each occurrence of R' and R" is independently selected from the group consisting of: H; —OH; and $C_{1-4}$ alkyl.

2. The compound of claim 1, wherein a2 is 1.

3. The compound of claim 1, wherein $L^2$ is straight-chain $C_{1-6}$ alkylene, straight-chain $C_{2-6}$ alkenylene, or straight-chain $C_{2-6}$ alkynylene, each of which is optionally substituted with 1-6 $R^b$.

4. The compound of claim 3, wherein $L^2$ is straight-chain $C_{1-6}$ alkylene, which is optionally substituted with 1-6 $R^b$.

5. The compound of claim 3, wherein $L^2$ is straight-chain $C_{1-3}$ alkylene, which is optionally substituted with 1-3 $R^b$.

6. The compound of claim 1, wherein $L^2$ is selected from the group consisting of:

$C_{3-10}$ cycloalkylene or $C_{3-10}$ cycloalkenylene, each of which is optionally substituted with 1-3 $R^c$; and heterocyclylene or heterocycloalkenylene, each having 4-10 ring atoms wherein 1-3 ring atoms are ring heteroatoms each independently selected from the group consisting of: N, N(H), N($R^d$), O, and $S(O)_{0-2}$, wherein the heterocyclylene or heterocycloalkenylene is optionally substituted with 1-3 $R^c$.

7. The compound of claim 1, wherein a1 is 1.

8. The compound of claim 1, wherein $L^1$ is selected from the group consisting of: —O—, —N(H)—, —N($R^d$)—, and —S—.

9. The compound of claim 1, wherein a1 is 0.

10. The compound of claim 1, wherein a3 is 1.

11. The compound of claim 1, wherein $L^3$ is selected from the group consisting of —O—, —N(H)—, —N($R^d$)—, and —S—.

12. The compound of claim 1, wherein a3 is 0.

13. The compound of claim 1, wherein a4 is 1.

14. The compound of claim 1, wherein:

a1 and a2 are each 1.

15. The compound of claim 14, wherein a3, a4, and a5 are each 0.

16. The compound of claim 1, wherein a1 is 0; a2 is 1.

17. The compound of claim 16, wherein a3 is 1.

18. The compound of claim 17, wherein $L^3$ is —O—.

19. The compound of claim 16, wherein a4 is 0; and a5 is 0.

20. The compound of claim 16, wherein $L^2$ is straight-chain $C_{1-6}$ alkylene, which is optionally substituted with 1-6 $R^b$.

21. The compound of claim 20, wherein $L^2$ is straight-chain $C_{1-3}$ alkylene, which is optionally substituted with 1-3 $R^b$.

22. The compound of claim 21, wherein a3 is 1, and $L^3$ is —O—.

23. The compound of claim 22, wherein a4 and a5 are each 0.

24. The compound of claim 23, wherein $L^A$ is —$CH_2CH_2$—O*.

25. The compound of claim 1, wherein $Q^1$ is selected from the group consisting of:

heteroaryl of 5-6 ring atoms, wherein 1-4 ring atoms are heteroatoms, each independently selected from the group consisting of N, N(H), N($R^d$), O, and $S(O)_{0-2}$, and wherein the heteroaryl is optionally substituted with 1-3 $R^c$; and phenyl optionally substituted with 1-3 $R^c$.

26. The compound of claim 1, wherein $Q^1$ is heterocyclyl or heterocycloalkenyl of 3-12 ring atoms, wherein 1-3 ring atoms are heteroatoms, each independently selected from the group consisting of N, N(H), N($R^d$), O, and $S(O)_{0-2}$, and wherein the heterocyclyl or heterocycloalkenyl is optionally substituted with 1-4 substituents independently selected from the group consisting of oxo and $R^c$.

27. The compound of claim 1, wherein $Y^1$ is $CR^i$; $Y^2$ is $CR^1$; and/or $Y^3$ is $CR^1$.

28. The compound of claim 1, wherein $Y^1$, $Y^2$, and $Y^3$ are each CH.

29. The compound of claim 1, wherein $R^6$ is H.

30. The compound of claim 1, wherein W is:

(i) $C_{1-10}$ alkyl, $C_{2-10}$ alkenyl, or $C_{2-10}$ alkenyl, each of which is optionally substituted with 1-6 $R^{a2}$, wherein one or more of the internal optionally substituted methylene group can be replaced by one or more heteroatom selected from O or S, wherein when W is alkenyl or alkynyl, the heteroatom is not directly connected to the $sp^2$ or sp carbon.

31. The compound of claim 1, wherein W is:

monocyclic $C_{3-8}$ cycloalkyl or $C_{3-8}$ cycloalkenyl, each of which is optionally substituted with 1-4 substituents independently selected from the group consisting of oxo and $R^c$.

32. A compound selected from the group consisting of:

101

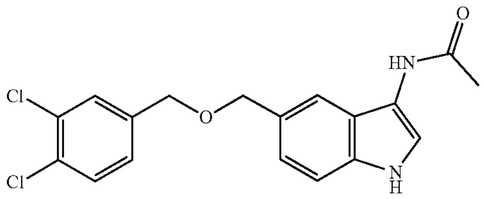 [SMILES: CC(=O)Nc1c[nH]c2ccc(COCc3ccc(Cl)c(Cl)c3)cc12]

-continued
N-(5-(((3,4-dichlorobenzyl)oxy)methyl)-1H-indol-3-yl)acetamide
102
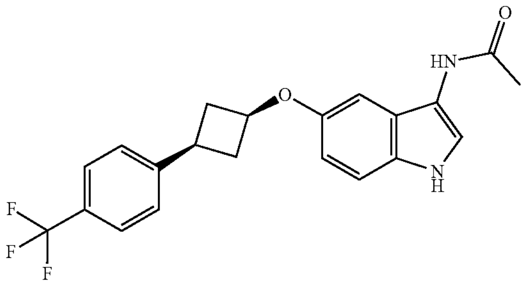 [SMILES: CC(=O)Nc1c[nH]c2ccc(O[C@H]3C[C@@H](c4ccc(C(F)(F)F)cc4)C3)cc12]
N-(5-(cis-3-(4-(trifluoromethyl)phenyl)cyclobutoxy)-1H-indol-3-yl)acetamide
103
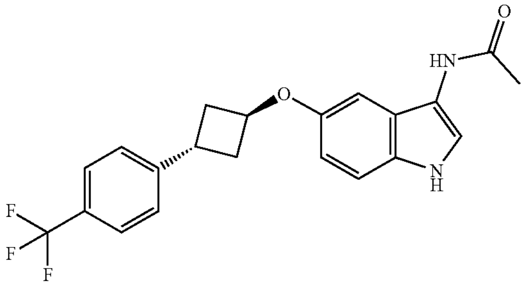 [SMILES: CC(=O)Nc1c[nH]c2ccc(O[C@H]3C[C@H](c4ccc(C(F)(F)F)cc4)C3)cc12]
N-(5-(trans-3-(4-(trifluoromethyl)phenyl)cyclobutoxy)-1H-indol-3-yl)acetamide
104
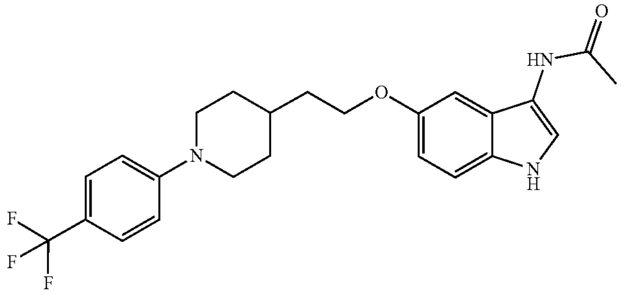 [SMILES: CC(=O)Nc1c[nH]c2ccc(OCCC3CCN(c4ccc(C(F)(F)F)cc4)CC3)cc12]
N-(5-(2-(1-(4-(trifluoromethyl)phenyl)piperidin-4-yl)ethoxy)-1H-indol-3-yl)acetamide
105
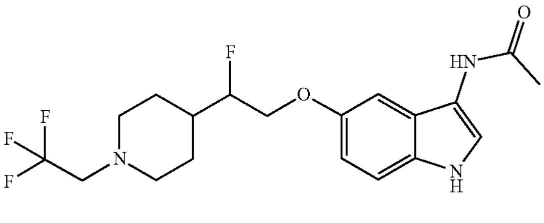 [SMILES: CC(=O)Nc1c[nH]c2ccc(OCC(F)C3CCN(CC(F)(F)F)CC3)cc12]
N-(5-(2-fluoro-2-(1-(2,2,2-trifluoroethyl)piperidin-4-yl)ethoxy)-1H-indol-3-yl)acetamide
106
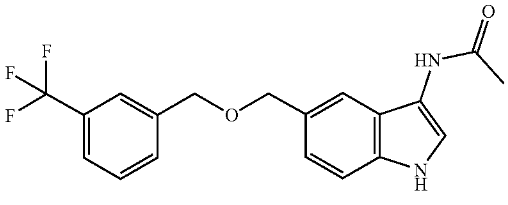 [SMILES: CC(=O)Nc1c[nH]c2ccc(COCc3cccc(C(F)(F)F)c3)cc12]

-continued

N-(5-(((3-(trifluoromethyl)benzyl)oxy)methyl)-1H-indol-3-yl)acetamide

107

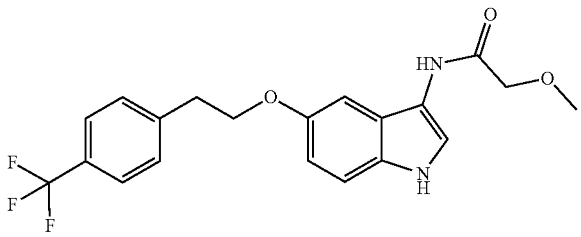 [SMILES: COCC(=O)Nc1c[nH]c2ccc(OCCc3ccc(C(F)(F)F)cc3)cc12]

2-methoxy-N-(5-(4-(trifluoromethyl)phenethoxy)-1H-indol-3-yl)acetamide

108

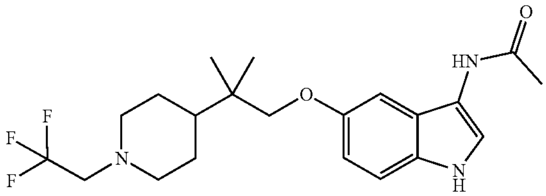 [SMILES: CC(=O)Nc1c[nH]c2ccc(OCC(C)(C)C3CCN(CC(F)(F)F)CC3)cc12]

N-(5-(2-methyl-2-(1-(2.2.2-trifluoroethyl)piperidin-4-yl)propoxy)-1H-indol-3-yl)acetamide

109

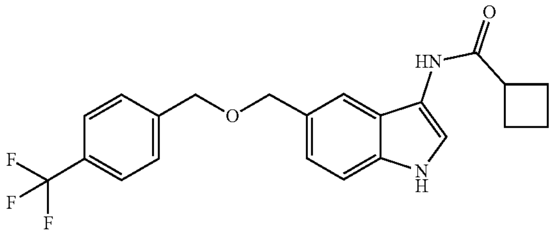 [SMILES: O=C(Nc1c[nH]c2ccc(COCc3ccc(C(F)(F)F)cc3)cc12)C1CCC1]

N-(5-(((4-(trifluoromethyl)benzyl)oxy)methyl)-1H-indol-3-yl)cyclobutanecarboxamide

110

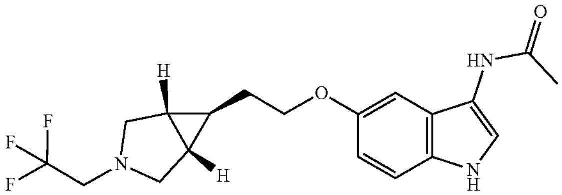 [SMILES: CC(=O)Nc1c[nH]c2ccc(OCC[C@@H]3[C@H]4CN(CC(F)(F)F)C[C@@H]34)cc12]

N-(5-(2-((1R,5S,6s)-3-(2,2,2-trifluoroethyl)-3-azabicyclo[3.1.0]hexan-6-yl)ethoxy)-1H-indol-3-yl)acetamide

111

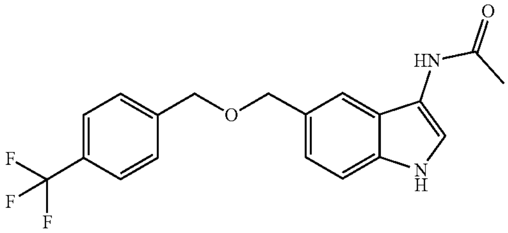 [SMILES: CC(=O)Nc1c[nH]c2ccc(COCc3ccc(C(F)(F)F)cc3)cc12]

N-(5-(((4-(trifluoromethyl)benzyl)oxy)methyl)-1H-indol-3-yl)acetamide

-continued
112
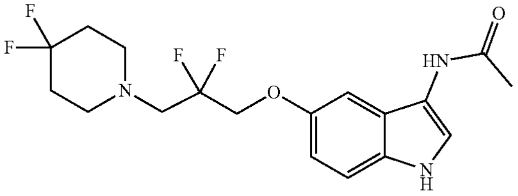 [SMILES: CC(=O)Nc1c[nH]c2ccc(OCC(F)(F)CN3CCC(F)(F)CC3)cc12]
N-(5-(3-(4,4-difluoropiperidin-1-y1)-2,2-difluoropropoxy) 1H-indol-3-y1)acetamide
113
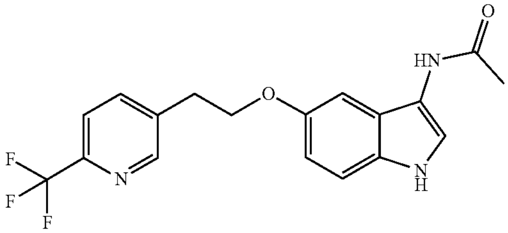 [SMILES: CC(=O)Nc1c[nH]c2ccc(OCCc3ccc(C(F)(F)F)nc3)cc12]
N-(5-(2-(6-(trifluoromethyl)pyridin-3-yl)ethoxy)-1H-indol-3-y1)acetamide
114
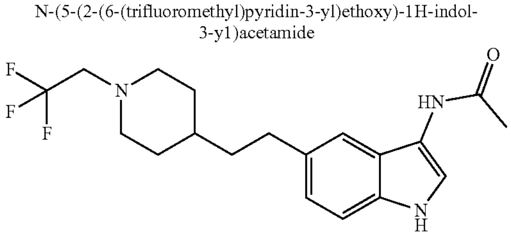
N-(5-(2-(1-(2,2.2-trifluoroethyl)piperidin-4-y1)ethyl)-1H-indol-3-yl)acetamide
115
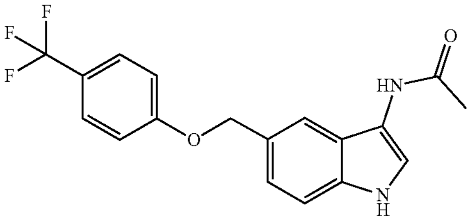 [SMILES: CC(=O)Nc1c[nH]c2ccc(COc3ccc(C(F)(F)F)cc3)cc12]
N-(5-((4-(trifluoromethyl)phenoxy)methyl)-1H-indol-3-y1)acetamide
116
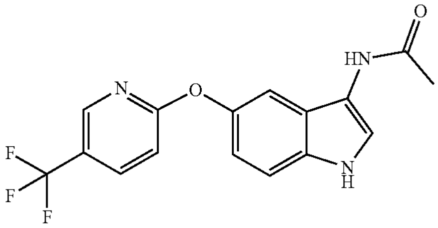 [SMILES: CC(=O)Nc1c[nH]c2ccc(Oc3ccc(C(F)(F)F)cn3)cc12]
N-(5-((5-(trifluoromethyl)pyridin-2-y1)oxy)-1H-indol-3-yl)acetamide
117
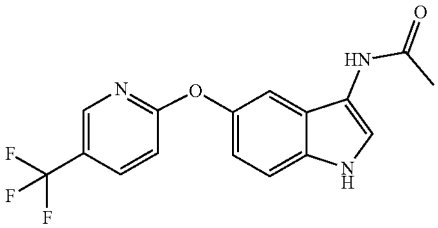 [SMILES: CC(=O)Nc1c[nH]c2ccc(Oc3ccc(C(F)(F)F)cn3)cc12]

-continued 2-methoxy-N-(5-(2-(1-(2,2,2-trifluoroethyl)piperidin-4-yl)ethoxy)-1H-indol-3-yl)acetamide

118

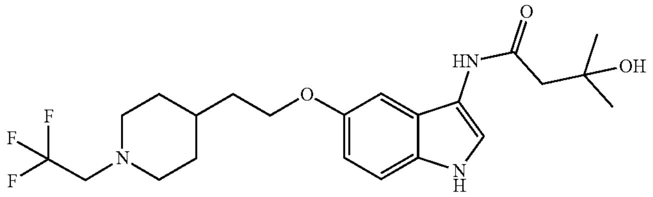 [SMILES: CC(C)(O)CC(=O)Nc1c[nH]c2ccc(OCCC3CCN(CC(F)(F)F)CC3)cc12]

3-hydroxy-3-methyl-N-(5-(2-(1-(2,2,2-trifluoroethyl)piperidin-4-y1)ethoxy)-1H-indol-3-y1)butanamide

119

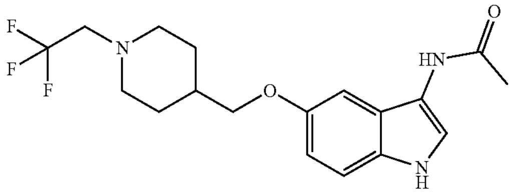 [SMILES: CC(=O)Nc1c[nH]c2ccc(OCC3CCN(CC(F)(F)F)CC3)cc12]

N-(5-((1-(2,2,2-trifluoroethyl)piperidin-4-yl)methoxy)-1H-indol-3-yl)acetamide

120

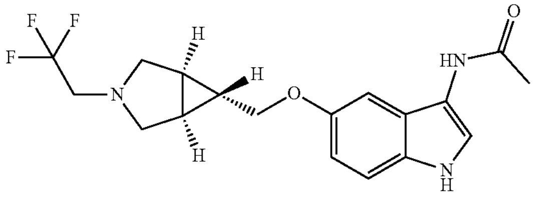 [SMILES: CC(=O)Nc1c[nH]c2ccc(OC[C@@H]3[C@H]4CN(CC(F)(F)F)C[C@@H]34)cc12]

N-(5-(((1R,5S,6r)-3-(2,2,2-trifluoroethyl)-3-azabicyclo[3.1.0]hexan-6-yl)methoxy)-1H-indol-3-yl)acetamide

121

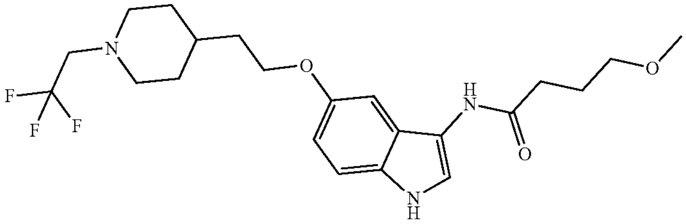 [SMILES: COCCCC(=O)Nc1c[nH]c2ccc(OCCC3CCN(CC(F)(F)F)CC3)cc12]

4-methoxy-N-(5-(2-(1-(2,2,2-trifluoroethyl)piperidin-4-yl)ethoxy)-1H-indol-3-y1)butanamide

122

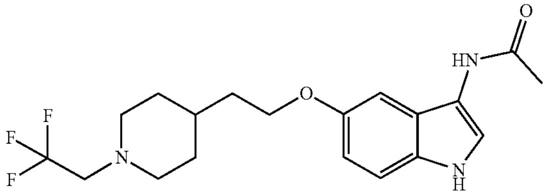 [SMILES: CC(=O)Nc1c[nH]c2ccc(OCCC3CCN(CC(F)(F)F)CC3)cc12]

N-(5-(2-(1-(2,2,2-trifluoroethyl)piperidin-4-yl)ethoxy)-1H-indol-3-yl)acetamide

-continued
123
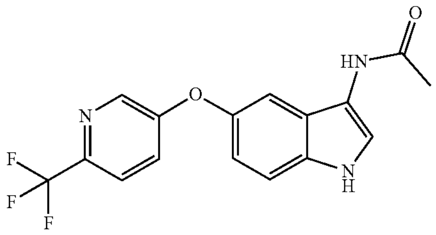 [SMILES: CC(=O)Nc1c[nH]c2ccc(Oc3ccc(C(F)(F)F)nc3)cc12]
N-(5-((6-(trifluoromethyl)pyridin-3-yl)oxy)-1H-indol-3-yl)acetamide
124
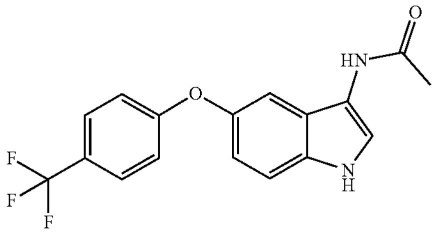 [SMILES: CC(=O)Nc1c[nH]c2ccc(Oc3ccc(C(F)(F)F)cc3)cc12]
N-(5-(4-(trifluoromethyl)phenoxy)-1H-indol-3-yl)acetamide
125
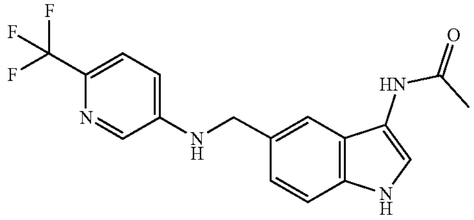 [SMILES: CC(=O)Nc1c[nH]c2ccc(CNc3ccc(C(F)(F)F)nc3)cc12]
N-(5-(((6-(trifluoromethyl)pyridin-3-yl)amino)methyl)-1H-indol-3-yl)acetamide
126
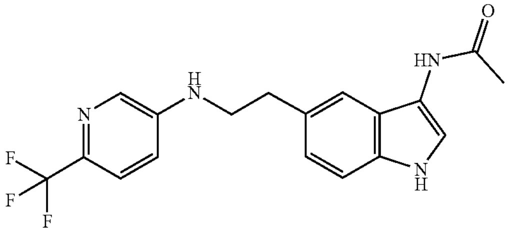 [SMILES: CC(=O)Nc1c[nH]c2ccc(CCNc3ccc(C(F)(F)F)nc3)cc12]
N-(5-(2-((6-(trifluoromethyl)pyridin-3-yl)amino)ethyl)-1H-indol-3-yl)acetamide
127
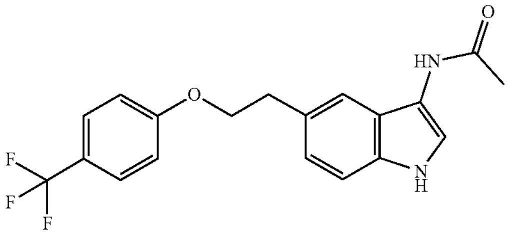 [SMILES: CC(=O)Nc1c[nH]c2ccc(CCOc3ccc(C(F)(F)F)cc3)cc12]
N-(5-(2-(4-(trifluoromethyl)phenoxy)ethyl)-1H-indol-3-yl)acetamide -continued
128
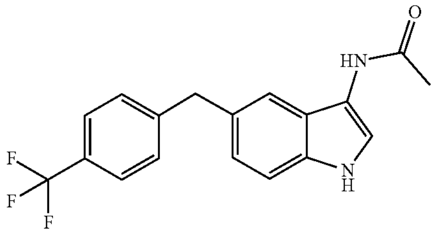 [SMILES: CC(=O)Nc1c[nH]c2ccc(Cc3ccc(C(F)(F)F)cc3)cc12]
N-(5-(4-(trifluoromethyl)benzyl)-1H-indol-3-yl)acetamide
129
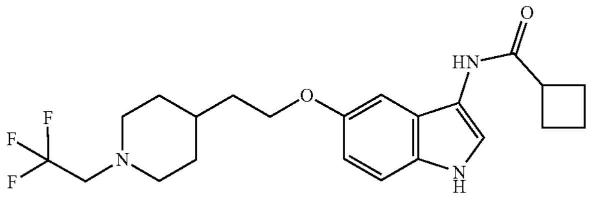 [SMILES: O=C(Nc1c[nH]c2ccc(OCCC3CCN(CC(F)(F)F)CC3)cc12)C1CCC1]
N-(5-(2-(1-(2,2,2-trifluoroethyl)piperidin-4-yl)ethoxy)-1H-indol-3-y1)cyclobutanecarboxamide
130
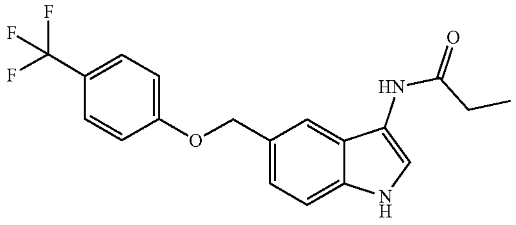 [SMILES: CCC(=O)Nc1c[nH]c2ccc(COc3ccc(C(F)(F)F)cc3)cc12]
N-(5-((4-(trifluoromethyl)phenoxy)methyl)-1H-indol-3-y1)propionamide
131
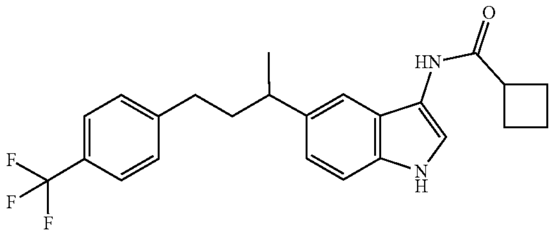 [SMILES: CC(CCc1ccc(C(F)(F)F)cc1)c1ccc2[nH]cc(NC(=O)C3CCC3)c2c1]
N-(5-(4-(4-(trifluoromethyl)phenyl)butan-2-y1)-1H-indol-3-yl)cyclobutanecarboxamide
132
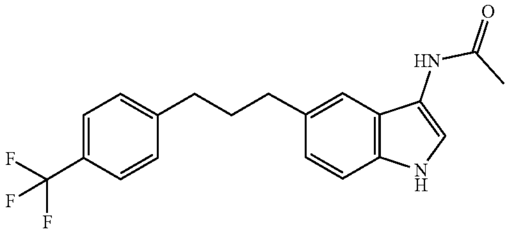 [SMILES: CC(=O)Nc1c[nH]c2ccc(CCCc3ccc(C(F)(F)F)cc3)cc12]
N-(5-(3-(4-(trifluoromethyl)phenyl)propyl)-1H-indol-3-yl)acetamide -continued

133

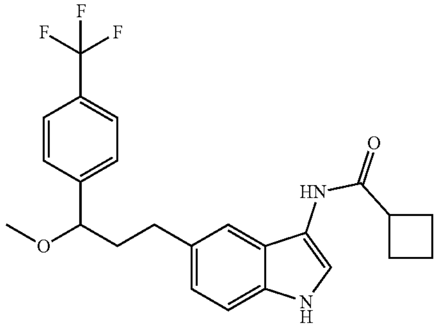 [SMILES: COC(CCc1ccc2[nH]cc(NC(=O)C3CCC3)c2c1)c1ccc(C(F)(F)F)cc1]

N-(5-(3-methoxy-3-(4-(trifluoromethyl)phenyl)propyl)-1H-indol-3-yl)cyclobutanecarboxamide

134

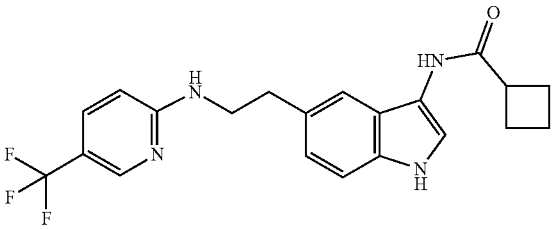 [SMILES: O=C(Nc1c[nH]c2ccc(CCNc3ccc(C(F)(F)F)cn3)cc12)C1CCC1]

N-(5-(2-((5-(trifluoromethyl)pyridin-2-yl)amino)ethyl)-1H-indol-3-yl)cyclobutanecarboxamide

135

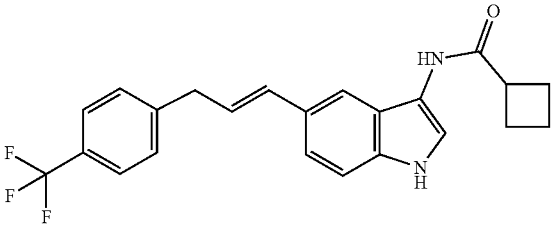 [SMILES: O=C(Nc1c[nH]c2ccc(/C=C/Cc3ccc(C(F)(F)F)cc3)cc12)C1CCC1]

(E)-N-(5-(3-(4-(trifluoromethyl)phenyl)prop-1-en-1-yl)-1H-indol-3-yl)cyclobutanecarboxamide

136

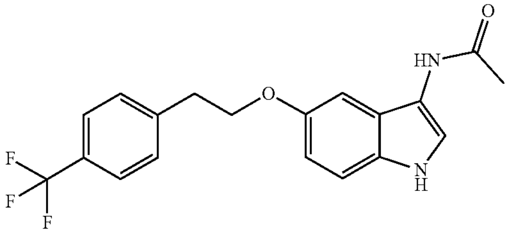 [SMILES: CC(=O)Nc1c[nH]c2ccc(OCCc3ccc(C(F)(F)F)cc3)cc12]

N-(5-(4-(trifluoromethyl)phenethoxy)-1H-indol-3-yl)acetamide

137

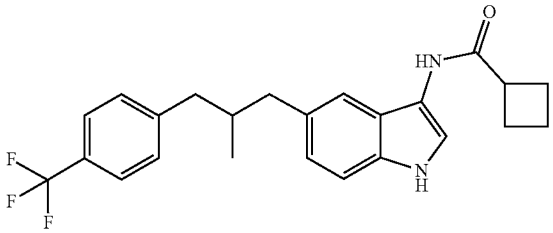 [SMILES: CC(Cc1ccc(C(F)(F)F)cc1)Cc1ccc2[nH]cc(NC(=O)C3CCC3)c2c1]

N-(5-(2-methyl-3-(4-(trifluoromethyl)phenyl)propyl)-1H-indol-3-yl)cyclobutanecarboxamide -continued
138
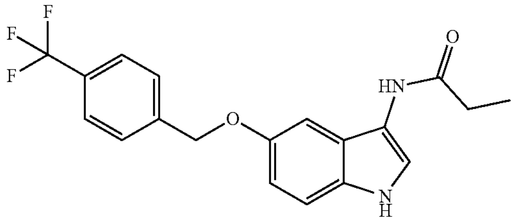 [SMILES: CCC(=O)Nc1c[nH]c2ccc(OCc3ccc(C(F)(F)F)cc3)cc12]
N-(5-((4-(trifluoromethyl)benzyl)oxy)-1H-indol-3-yl)propionamide
139
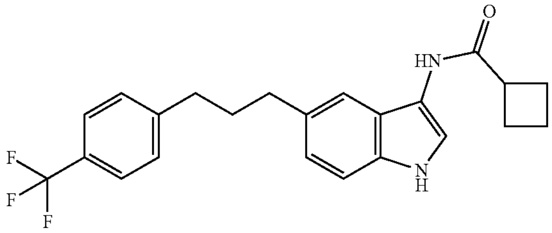 [SMILES: O=C(Nc1c[nH]c2ccc(CCCc3ccc(C(F)(F)F)cc3)cc12)C1CCC1]
N-(5-(3-(4-(trifluoromethyl)phenyl)propyl)-1H-indol-3-yl)cyclobutanecarboxamide
140
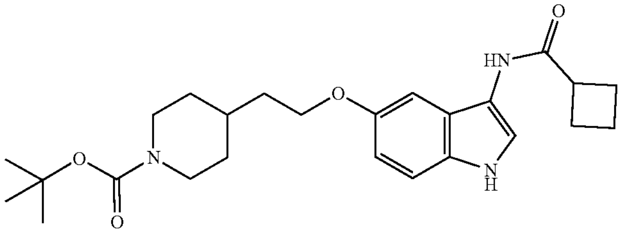 [SMILES: CC(C)(C)OC(=O)N1CCC(CCOc2ccc3[nH]cc(NC(=O)C4CCC4)c3c2)CC1]
tert-butyl 4-(2-((3-(cyclobutanecarboxamido)-1H-indol-5-yl)oxy)ethyl)piperidine-1-carboxylate
141
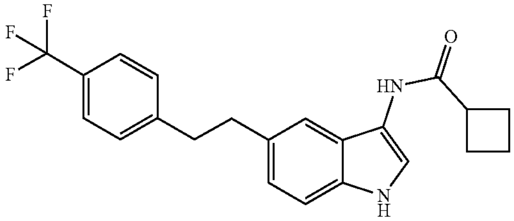 [SMILES: O=C(Nc1c[nH]c2ccc(CCc3ccc(C(F)(F)F)cc3)cc12)C1CCC1]
N-(5-(4-(trifluoromethyl)phenethyl)-1H-indol-3-yl)cyclobutanecarboxamide
142
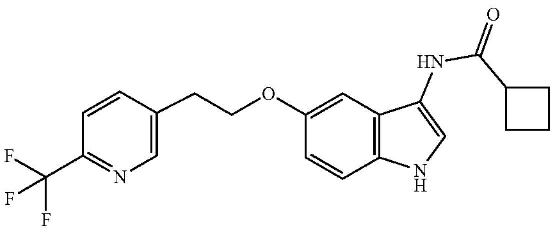 [SMILES: O=C(Nc1c[nH]c2ccc(OCCc3ccc(C(F)(F)F)nc3)cc12)C1CCC1]
N-(5-(2-(6-(trifluoromethyl)pyridin-3-yl)ethoxy)-1H-indol-3-yl)cyclobutanecarboxamide -continued
143
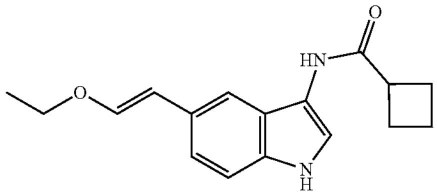 [SMILES: CCO/C=C/c1ccc2[nH]cc(NC(=O)C3CCC3)c2c1]
(E)-N-(5-(2-ethoxyvinyl)-1H-indol-3-yl)cyclobutanecarboxamide
144
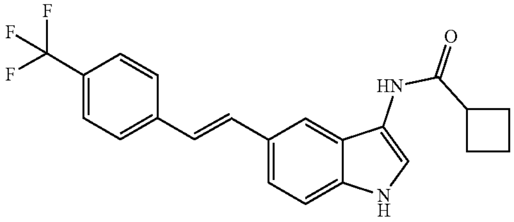 [SMILES: O=C(Nc1c[nH]c2ccc(/C=C/c3ccc(C(F)(F)F)cc3)cc12)C1CCC1]
(E)-N-(5-(4-(trifluoromethyl)styryl)-1H-indol-3-yl)cyclobutanecarboxamide
145
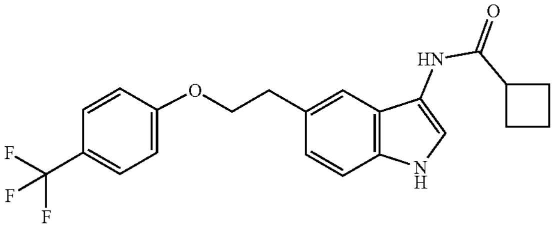 [SMILES: O=C(Nc1c[nH]c2ccc(CCOc3ccc(C(F)(F)F)cc3)cc12)C1CCC1]
N-(5-(2-(4-(trifluoromethyl)phenoxy)ethyl)-1H-indol-3-yl)cyclobutanecarboxamide
146
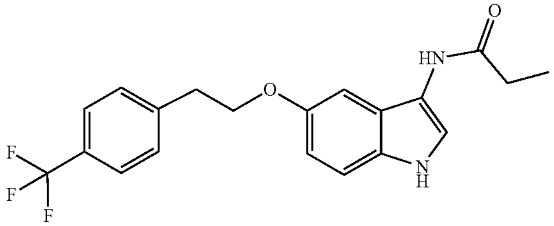 [SMILES: CCC(=O)Nc1c[nH]c2ccc(OCCc3ccc(C(F)(F)F)cc3)cc12]
N-(5-(4-(trifluoromethyl)phenethoxy)-1H-indol-3-yl)propionamide
147
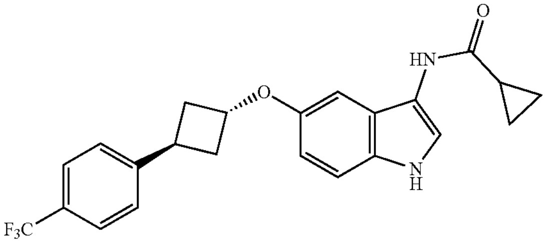 [SMILES: O=C(Nc1c[nH]c2ccc(O[C@H]3C[C@H](c4ccc(C(F)(F)F)cc4)C3)cc12)C1CC1]
trans-N-(5-(-3-(4-(trifluoromethyl)phenyl)cyclobutoxy)-1H-indol-3-yl)cyclopropanecarboxamide -continued

148

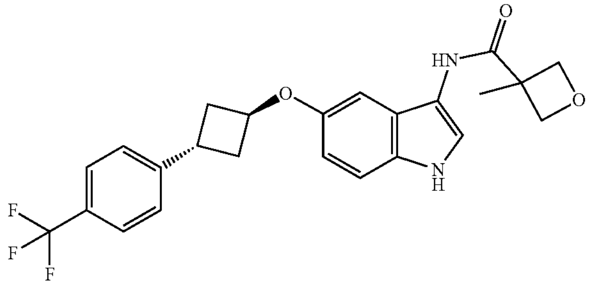 [SMILES: CC1(C(=O)Nc2c[nH]c3ccc(O[C@H]4C[C@H](c5ccc(C(F)(F)F)cc5)C4)cc23)COC1]

3-methyl-N-(5-(trans-3-(4-(trifluoromethyl)phenyl)cyclobutoxy)-1H-indol-3-yl)oxetane-3-carboxamide

149

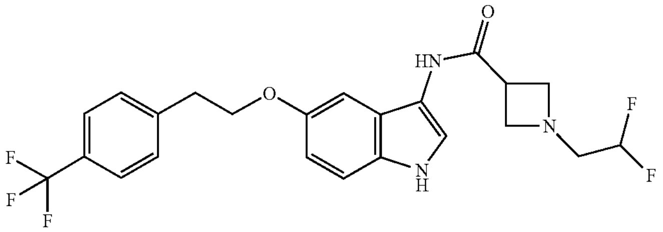 [SMILES: O=C(Nc1c[nH]c2ccc(OCCc3ccc(C(F)(F)F)cc3)cc12)C1CN(CC(F)F)C1]

1-(2,2-difluoroethyl)-N-(5-(4-(trifluoromethyl)phenethoxy)-1H-indol-3-yl)azetidine-3-carboxamide

150

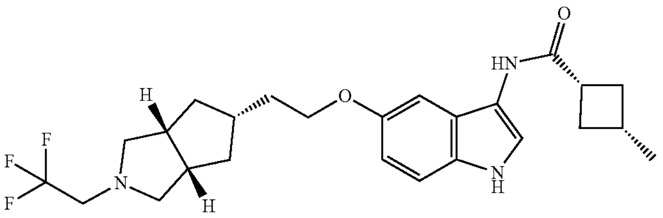 [SMILES: C[C@H]1C[C@@H](C(=O)Nc2c[nH]c3ccc(OCC[C@@H]4C[C@@H]5CN(CC(F)(F)F)C[C@@H]5C4)cc23)C1]

(1s,3S)-3-methyl-N-(5-(2-((3aR,5r,6aS)-2-(2,2,2-trifluoroethyl)octahydrocyclopenta[c]pyrrol-5-yl)ethoxy)-1H-indol-3-yl)cyclobutane-1-carboxamide

151

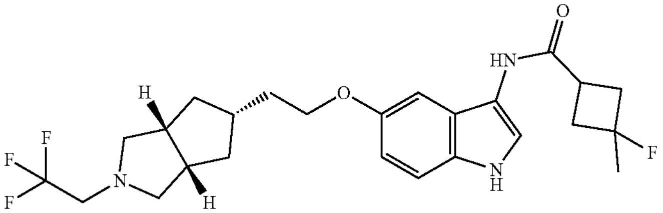 [SMILES: CC1(F)CC(C(=O)Nc2c[nH]c3ccc(OCC[C@@H]4C[C@@H]5CN(CC(F)(F)F)C[C@@H]5C4)cc23)C1]

3-fluoro-3-methyl-N-(5-(2-((3aR,5r,6aS)-2-(2,2,2-trifluoroethyl)octahydrocyclopenta[c]pyrrol-5-yl)ethoxy)-1H-indol-3-yl)cyclobutane-1-carboxamide

152

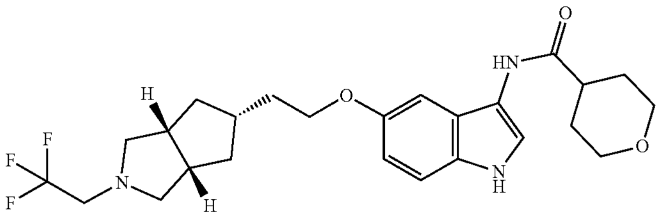 [SMILES: O=C(Nc1c[nH]c2ccc(OCC[C@@H]3C[C@@H]4CN(CC(F)(F)F)C[C@@H]4C3)cc12)C1CCOCC1]

N-(5-(2-((3aR,5r,6aS)-2-(2,2,2-trifluoroethyl)octahydrocyclopenta[c]pyrrol-5-yl)ethoxy)-1H-indol-3-yl)tetrahydro-2H-pyran-4-carboxamide -continued

153

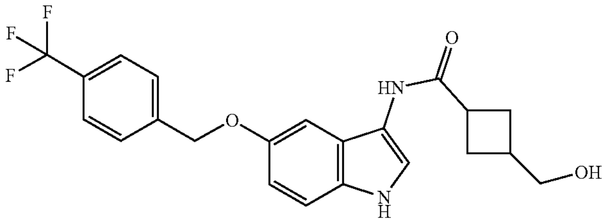 [SMILES: O=C(Nc1c[nH]c2ccc(OCc3ccc(C(F)(F)F)cc3)cc12)C1CC(CO)C1]

3-(hydroxymethyl)-N-(5-((4-(trifluoromethyl)benzyl)oxy)-1H-indol-3-yl)cyclobutane-1-carboxamide

154

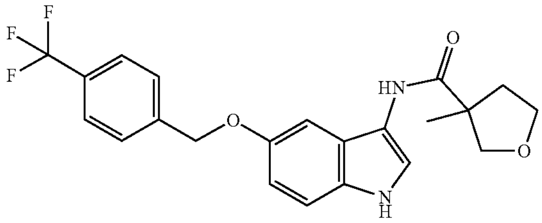 [SMILES: CC1(C(=O)Nc2c[nH]c3ccc(OCc4ccc(C(F)(F)F)cc4)cc23)CCOC1]

3-methyl-N-(5-((4-(trifluoromethyl)benzyl)oxy)-1H-indol-3-yl)tetrahydrofuran-3-carboxamide

155

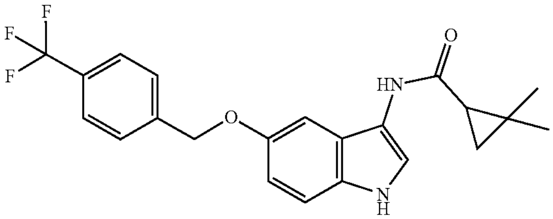 [SMILES: CC1(C)CC1C(=O)Nc1c[nH]c2ccc(OCc3ccc(C(F)(F)F)cc3)cc12]

2,2-dimethyl-N-(5-((4-(trifluoromethyl)benzyl)oxy)-1H-indol-3-yl)cyclopropane-1-carboxamide

156

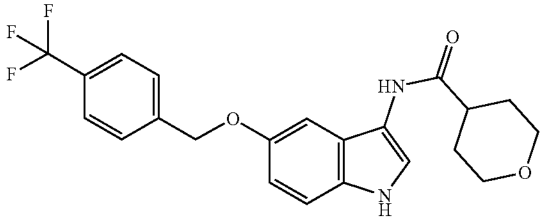 [SMILES: O=C(Nc1c[nH]c2ccc(OCc3ccc(C(F)(F)F)cc3)cc12)C1CCOCC1]

N-(5-((4-(trifluoromethyl)benzyl)oxy)-1H-indol-3-yl)tetrahydro-2H-pyran-4-carboxamide

157

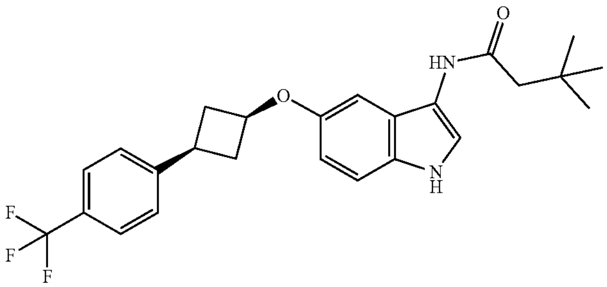 [SMILES: CC(C)(C)CC(=O)Nc1c[nH]c2ccc(O[C@H]3C[C@@H](c4ccc(C(F)(F)F)cc4)C3)cc12]

3,3-dimethyl-N-(5-(cis-3-(4-(trifluoromethyl)phenyl)cyclobutoxy)-1H-indol-3-yl)butanamide -continued

158

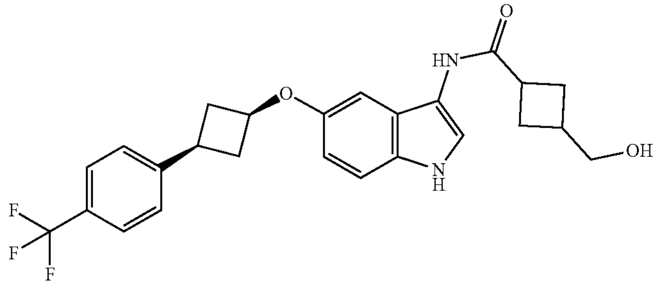

3-(hydroxymethyl)-N-(5-(cis-3-(4-(trifluoromethyl)phenyl)cyclobutoxy)-1H-indol-3-yl)cyclobutane-1-carboxamide

159

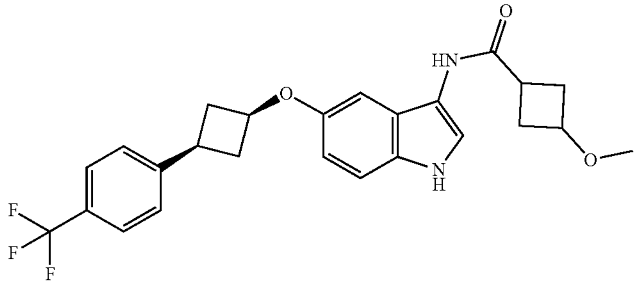 [SMILES: COC1CC(C(=O)Nc2c[nH]c3ccc(O[C@H]4C[C@@H](c5ccc(C(F)(F)F)cc5)C4)cc23)C1]

3-methoxy-N-(5-(cis-3-(4-(trifluoromethyl)phenyl)cyclobutoxy)-1H-indol-3-yl)cyclobutane-1-carboxamide

160

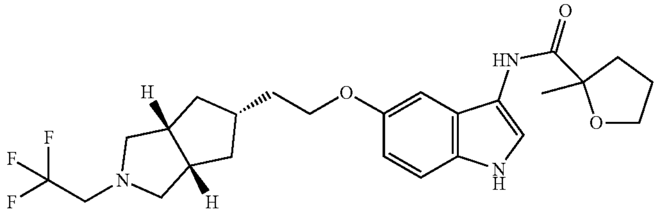 [SMILES: CC1(C(=O)Nc2c[nH]c3ccc(OCC[C@@H]4C[C@@H]5CN(CC(F)(F)F)C[C@@H]5C4)cc23)CCCO1]

2-methyl-N-(5-(2-((3aR,5r,6aS)-2-(2,2,2-trifluoroethyl)octahydrocyclopenta[c]pyrrol-5-yl)ethoxy)-1H-indol-3-yl)tetrahydrofuran-2-carboxamide

161

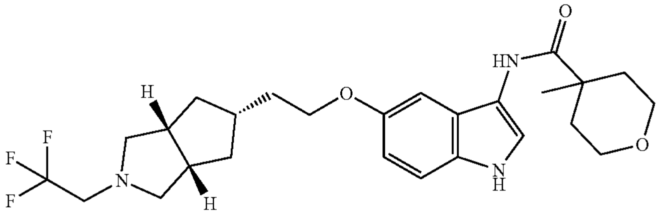 [SMILES: CC1(C(=O)Nc2c[nH]c3ccc(OCC[C@@H]4C[C@@H]5CN(CC(F)(F)F)C[C@@H]5C4)cc23)CCOCC1]

4-methyl-N-(5-(2-((3aR,5r,6aS)-2-(2,2,2-trifluoroethyl)octahydrocyclopenta[c]pyrrol-5-yl)ethoxy)-1H-indol-3-yl)tetrahydro-2H-pyran-4-carboxamide

162

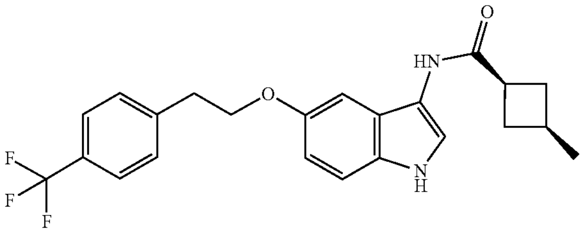 [SMILES: C[C@H]1C[C@@H](C(=O)Nc2c[nH]c3ccc(OCCc4ccc(C(F)(F)F)cc4)cc23)C1]

-continued cis-3-methyl-N-(5-(4-(trifluoromethyl)phenethoxy)-1H-indol-3-y1)cyclobutane-1-carboxamide

163

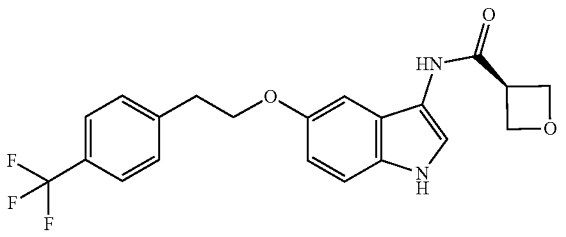

N-(5-(4-(trifluoromethyl)phenethoxy)-1H-indol-3-yl)oxetane-3-carboxamide

164

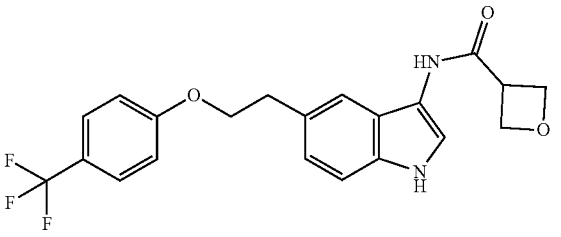 [SMILES: O=C(Nc1c[nH]c2ccc(CCOc3ccc(C(F)(F)F)cc3)cc12)C1COC1]

N-(5-(2-(4-(trifluoromethyl)phenoxy)ethyl)-1H-indol-3-yl)oxetane-3-carboxamide

165

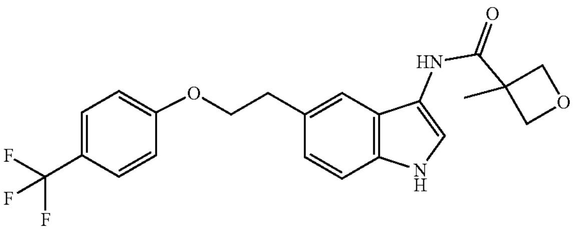 [SMILES: CC1(C(=O)Nc2c[nH]c3ccc(CCOc4ccc(C(F)(F)F)cc4)cc23)COC1]

3-methyl-N-(5-(2-(4-(trifluoromethyl)phenoxy)ethyl)-1H-indol-3-yl)oxetane-3-carboxamide

166

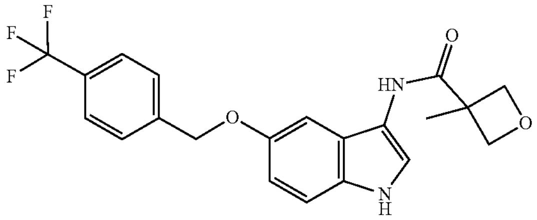 [SMILES: CC1(C(=O)Nc2c[nH]c3ccc(OCc4ccc(C(F)(F)F)cc4)cc23)COC1]

3-methyl-N-(5-((4-(trifluoromethyl)benzyl)oxy)-1H-indol-3-y1)oxetane-3-carboxamide

167

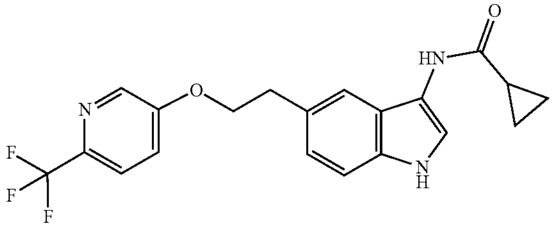 [SMILES: O=C(Nc1c[nH]c2ccc(CCOc3ccc(C(F)(F)F)nc3)cc12)C1CC1]

N-(5-(2-((6-(trifluoromethyl)pyridin-3-yl)oxy)ethyl)-1H-indol-3-y1)cyclopropanecarboxamide -continued
168
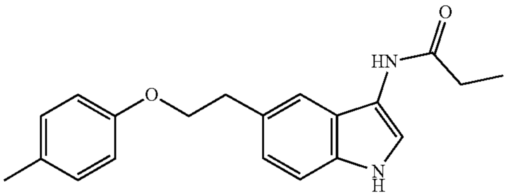 [SMILES: CCC(=O)Nc1c[nH]c2ccc(CCOc3ccc(C)cc3)cc12]
N-(5-(2-(p-tolyloxy)ethyl)-1H-indol-3-yl)propionamide
169
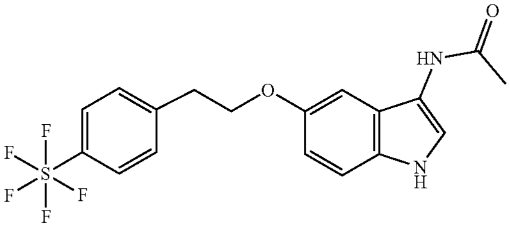 [SMILES: CC(=O)Nc1c[nH]c2ccc(OCCc3ccc(S(F)(F)(F)(F)F)cc3)cc12]
N-(5-(4-(pentafluoro-16-sulfaneyl)phenethoxy)-1H-indol-3-yl)acetamide
170
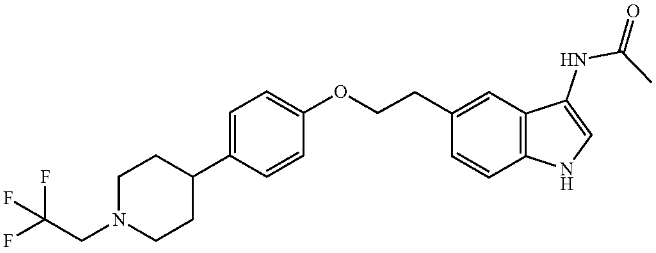 [SMILES: CC(=O)Nc1c[nH]c2ccc(CCOc3ccc(C4CCN(CC(F)(F)F)CC4)cc3)cc12]
N-(5-(2-(4-(1-(2,2.2-trifluoroethyl)piperidin-4-yl)phenoxy)ethyl)-1H-indol-3-yl)acetamide
171
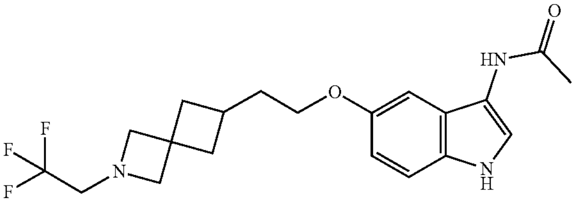 [SMILES: CC(=O)Nc1c[nH]c2ccc(OCCC3CC4(C3)CN(CC(F)(F)F)C4)cc12]
N-(5-(2-(2-(2,2,2-trifluoroethyl)-2-azaspiro[3.3 ]heptan-6-yl)ethoxy)-1H-indol-3-yl)acetamide
172
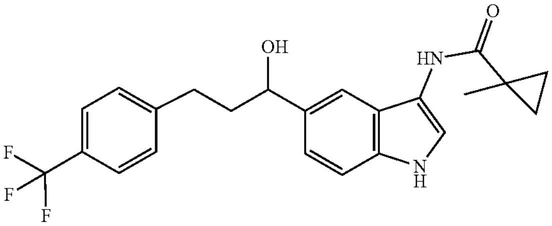 [SMILES: CC1(C(=O)Nc2c[nH]c3ccc(C(O)CCc4ccc(C(F)(F)F)cc4)cc23)CC1]
N-(5-(1-hydroxy-3-(4-(trifluoromethyl)phenyl)propyl)-1H-indol-3-yl)-1-methylcyclopropane-1-carboxamide -continued

173

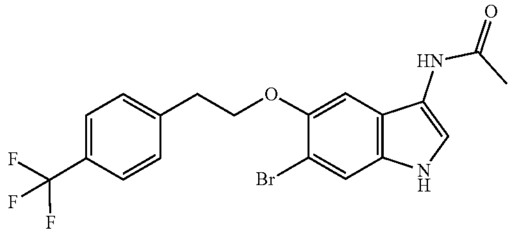 [SMILES: CC(=O)Nc1c[nH]c2cc(Br)c(OCCc3ccc(C(F)(F)F)cc3)cc12]

N-(6-bromo-5-(4-(trifluoromethyl)phenethoxy)-1H-indol-3-yl)acetamide

174

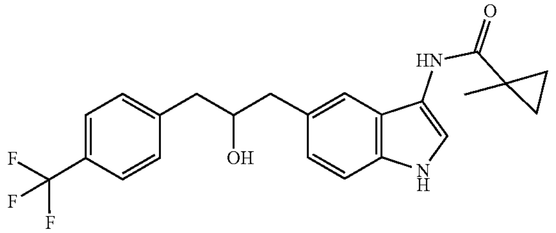

N-(5-(2-hydroxy-3-(4-(trifluoromethyl)phenyl)propyl)-1H-indol-3-y1)-1-methylcyclopropane-1-carboxamide

175

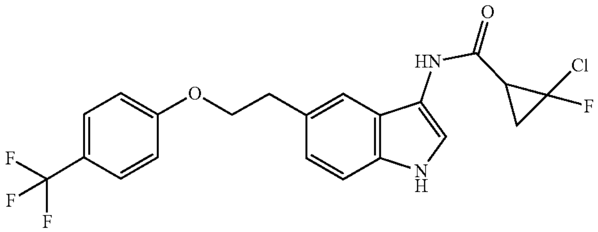 [SMILES: O=C(Nc1c[nH]c2ccc(CCOc3ccc(C(F)(F)F)cc3)cc12)C1CC1(F)Cl]

2-chloro-2-fluoro-N-(5-(2-(4-(trifluoromethyl)phenoxy)ethyl)-1H-indol-3-y1)cyclopropane-1-carboxamide

176

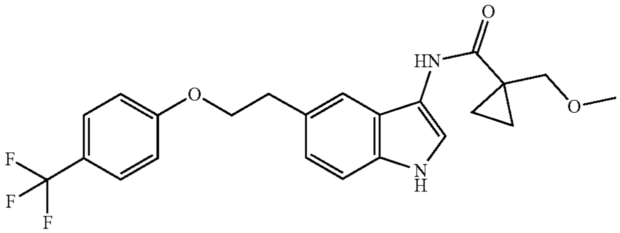 [SMILES: COCC1(C(=O)Nc2c[nH]c3ccc(CCOc4ccc(C(F)(F)F)cc4)cc23)CC1]

1-(methoxymethyl)-N-(5-(2-(4-(trifluoromethyl)phenoxy)ethyl)-1H-indol-3-yl)cyclopropane-1-carboxamide

177

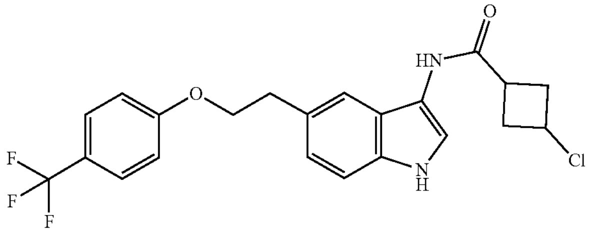 [SMILES: O=C(Nc1c[nH]c2ccc(CCOc3ccc(C(F)(F)F)cc3)cc12)C1CC(Cl)C1]

3-chloro-N-(5-(2-(4-(trifluoromethyl)phenoxy)ethyl)-1H-indol-3-y1)cyclobutane-1-carboxamide -continued

178

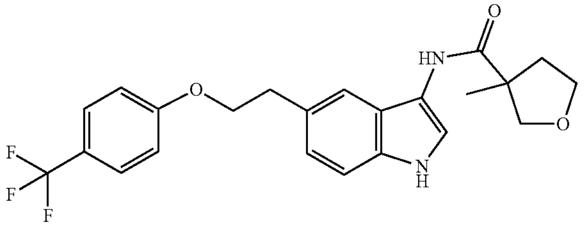 [SMILES: CC1(C(=O)Nc2c[nH]c3ccc(CCOc4ccc(C(F)(F)F)cc4)cc23)CCOC1]

3-methyl-N-(5-(2-(4-(trifluoromethyl)phenoxy)ethyl)-1H-indol-3-yl)tetrahydrofuran-3-carboxamide

179

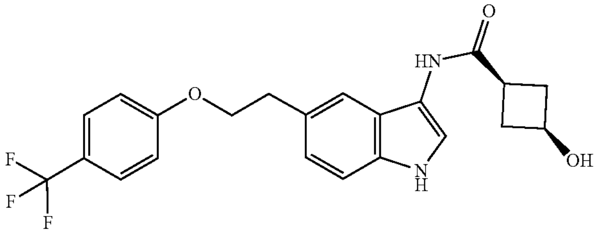 [SMILES: O=C(Nc1c[nH]c2ccc(CCOc3ccc(C(F)(F)F)cc3)cc12)[C@H]1C[C@@H](O)C1]

cis-3-hydroxy-N-(5-(2-(4-(trifluoromethyl)phenoxy)ethyl)-1H-indol-3-yl)cyclobutane-1-carboxamide

180

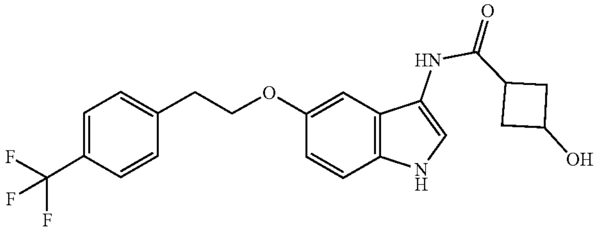 [SMILES: O=C(Nc1c[nH]c2ccc(OCCc3ccc(C(F)(F)F)cc3)cc12)C1CC(O)C1]

3-hydroxy-N-(5-(4-(trifluoromethyl)phenethoxy)-1H-indol-3-yl)cyclobutane-1-carboxamide

181

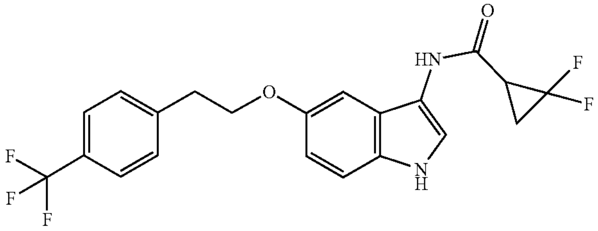 [SMILES: O=C(Nc1c[nH]c2ccc(OCCc3ccc(C(F)(F)F)cc3)cc12)C1CC1(F)F]

2,2-difluoro-N-(5-(4-(trifluoromethyl)phenethoxy)-1H-indol-3-yl)cyclopropane-1-carboxamide

182

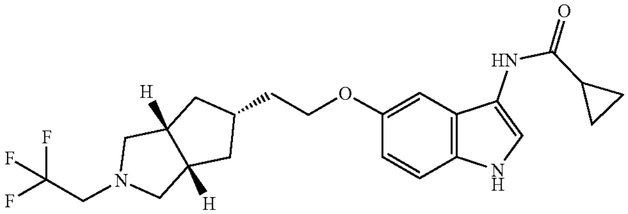 [SMILES: O=C(Nc1c[nH]c2ccc(OCC[C@@H]3C[C@@H]4CN(CC(F)(F)F)C[C@@H]4C3)cc12)C1CC1]

N-(5-(2-((3aR,5r,6aS)-2-(2,2,2-trifluoroethyl)octahydrocyclopenta[c]pyrrol-5-yl)ethoxy)1H-indol-3-yl)cyclopropanecarboxamide -continued

183

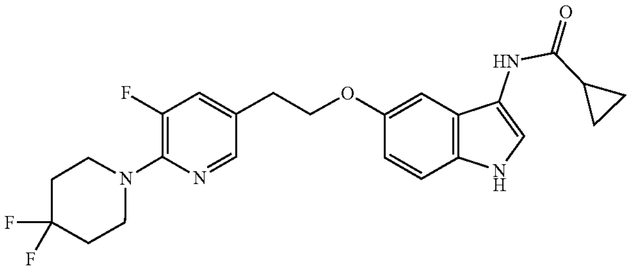 [SMILES: O=C(Nc1c[nH]c2ccc(OCCc3cnc(N4CCC(F)(F)CC4)c(F)c3)cc12)C1CC1]

N-(5-(2-(6-(4,4-difluoropiperidin-1-yl)-5-fluoropyridin-3-yl)ethoxy)-1H-indol-3-yl)cyclopropanecarboxamide

184

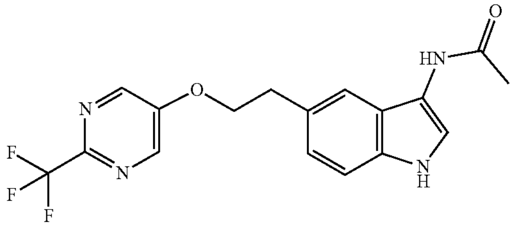 [SMILES: CC(=O)Nc1c[nH]c2ccc(CCOc3cnc(C(F)(F)F)nc3)cc12]

N-(5-(2-((2-(trifluoromethyl)pyrimidin-5-yl)oxy)ethyl)-1H-indol-3-yl)acetamide

185

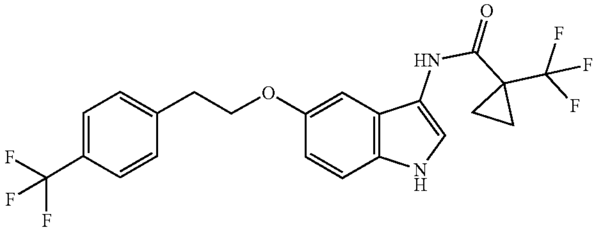 [SMILES: O=C(Nc1c[nH]c2ccc(OCCc3ccc(C(F)(F)F)cc3)cc12)C1(C(F)(F)F)CC1]

1-(trifluoromethyl)-N-(5-(4-(trifluoromethyl)phenethoxy)-1H-indol-3-yl)cyclopropane-1-carboxamide

186

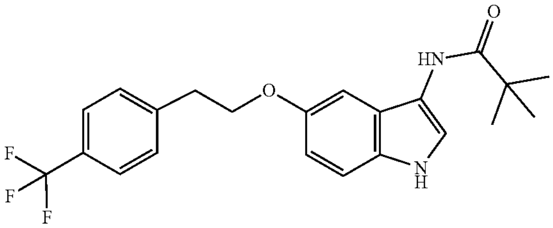 [SMILES: CC(C)(C)C(=O)Nc1c[nH]c2ccc(OCCc3ccc(C(F)(F)F)cc3)cc12]

N-(5-(4-(trifluoromethyl)phenethoxy)-1H-indol-3-yl)pivalamide

187

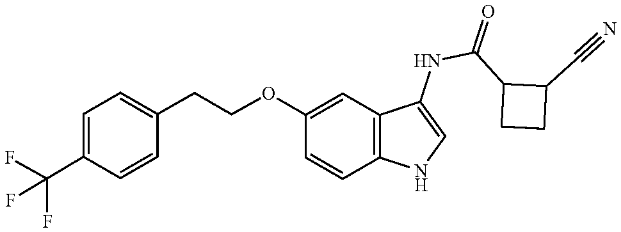 [SMILES: N#CC1CCC1C(=O)Nc1c[nH]c2ccc(OCCc3ccc(C(F)(F)F)cc3)cc12]

2-cyano-N-(5-(4-(trifluoromethyl)phenethoxy)-1H-indol-3-yl)cyclobutane-1-carboxamide -continued

188

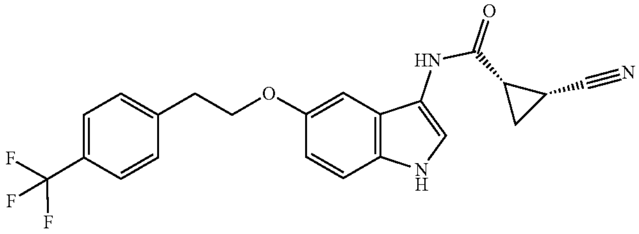 [SMILES: N#C[C@@H]1C[C@@H]1C(=O)Nc1c[nH]c2ccc(OCCc3ccc(C(F)(F)F)cc3)cc12]

(1S,2R)-2-cyano-N-(5-(4-(trifluoromethyl)phenethoxy)-1H-indol-3-yl)cyclopropane-1-carboxamide

189

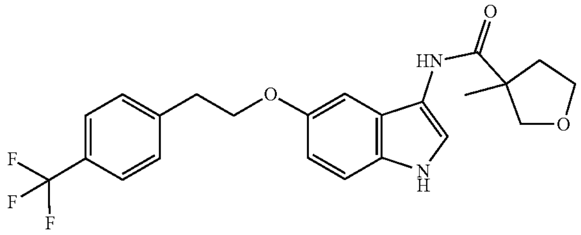 [SMILES: CC1(C(=O)Nc2c[nH]c3ccc(OCCc4ccc(C(F)(F)F)cc4)cc23)CCOC1]

3-methyl-N-(5-(4-(trifluoromethyl)phenethoxy)-1H-indol-3-yl)tetrahydrofuran-3-carboxamide

190

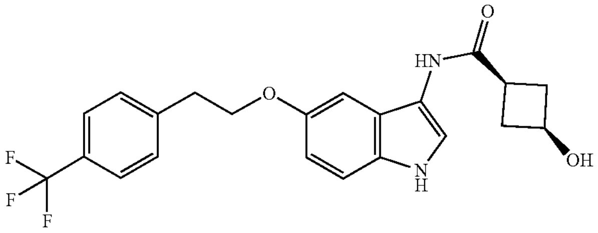 [SMILES: O=C(Nc1c[nH]c2ccc(OCCc3ccc(C(F)(F)F)cc3)cc12)[C@H]1C[C@@H](O)C1]

cis-3-hydroxy-N-(5-(4-(trifluoromethyl)phenethoxy)-1H-indol-3-yl)cyclobutane-1-carboxamide

191

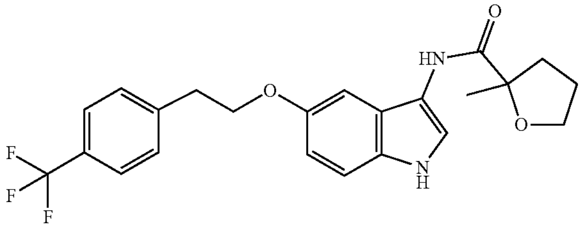 [SMILES: CC1(C(=O)Nc2c[nH]c3ccc(OCCc4ccc(C(F)(F)F)cc4)cc23)CCCO1]

2-methyl-N-(5-(4-(trifluoromethyl)phenethoxy)-1H-indol-3-yl)tetrahydrofuran-2-carboxamide

192

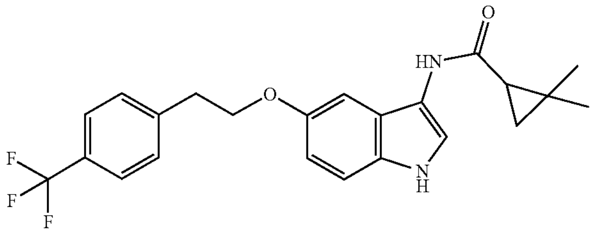 [SMILES: CC1(C)CC1C(=O)Nc1c[nH]c2ccc(OCCc3ccc(C(F)(F)F)cc3)cc12]

2,2-dimethyl-N-(5-(4-(trifluoromethyl)phenethoxy)-1H-indol-3-yl)cyclopropane-1-carboxamide -continued

193

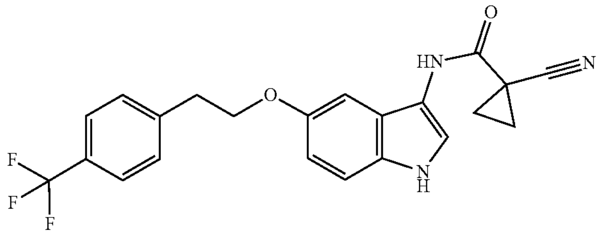 [SMILES: N#CC1(C(=O)Nc2c[nH]c3ccc(OCCc4ccc(C(F)(F)F)cc4)cc23)CC1]

1-cyano-N-(5-(4-(trifluoromethyl)phenethoxy)-1H-indol-3-y1)cyclopropane-1-carboxamide

194

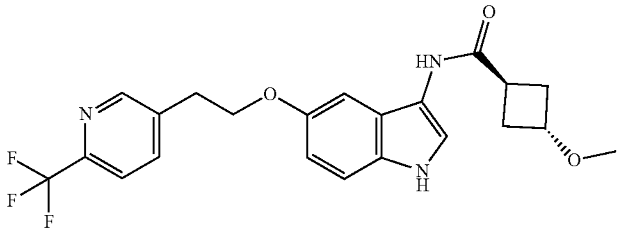 [SMILES: CO[C@H]1C[C@H](C(=O)Nc2c[nH]c3ccc(OCCc4ccc(C(F)(F)F)nc4)cc23)C1]

trans-3-methoxy-N-(5-(2-(6-(trifluoromethyl)pyridin-3-yl)ethoxy)-1H-indol-3-y1)cyclobutane-1-carboxamide

195

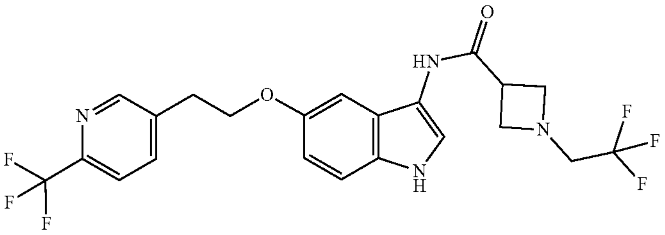 [SMILES: O=C(Nc1c[nH]c2ccc(OCCc3ccc(C(F)(F)F)nc3)cc12)C1CN(CC(F)(F)F)C1]

1-(2,2,2-trifluoroethyl)-N-(5-(2-(6-(trifluoromethyl)pyridin-3-y1)ethoxy)-1H-indol-3-y1)azetidine-3-carboxamide

196

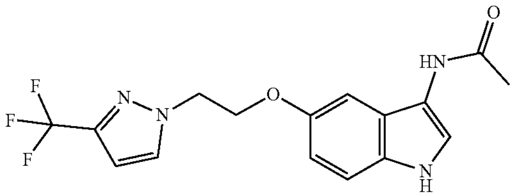 [SMILES: CC(=O)Nc1c[nH]c2ccc(OCCn3ccc(C(F)(F)F)n3)cc12]

N-(5-(2-(3-(trifluoromethyl)-1H-pyrazol-1-yl)ethoxy)-1H-indol-3-y1)acetamide

197

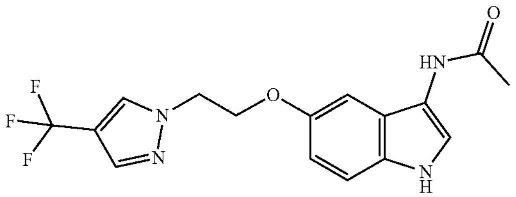 [SMILES: CC(=O)Nc1c[nH]c2ccc(OCCn3cc(C(F)(F)F)cn3)cc12]

N-(5-(2-(4-(trifluoromethyl)-1H-pyrazol-1-yl)ethoxy)-1H-indol-3-y1)acetamide

-continued

198

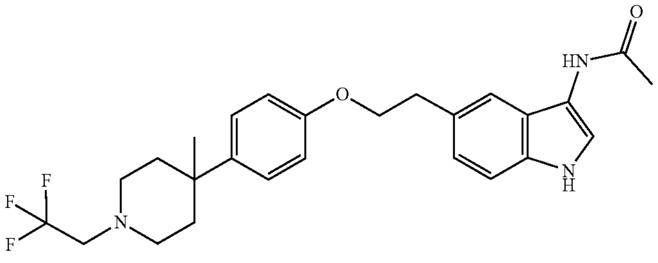 [SMILES: CC(=O)Nc1c[nH]c2ccc(CCOc3ccc(C4(C)CCN(CC(F)(F)F)CC4)cc3)cc12]

N-(5-(2-(4-(4-methyl-1-(2,2,2-trifluoroethyl)piperidin-4-y1)phenoxy)ethyl)-1H-indol-3-y1)acetamide

199

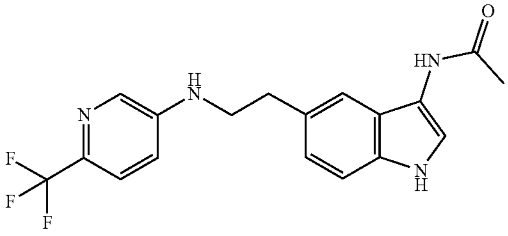 [SMILES: CC(=O)Nc1c[nH]c2ccc(CCNc3ccc(C(F)(F)F)nc3)cc12]

N-(5-(2-((5-(trifluoromethyl)pyridin-2-y1)amino)ethyl)-1H-indol-3-y1)acetamide

200

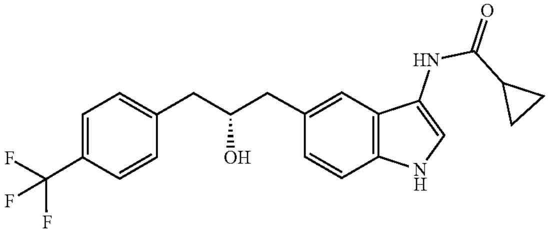 [SMILES: O=C(Nc1c[nH]c2ccc(C[C@H](O)Cc3ccc(C(F)(F)F)cc3)cc12)C1CC1]

(R)-N-(5-(2-hydroxy-3-(4-(trifluoromethyl)phenyl)propyl)-1H-indol-3-y1)cyclopropanecarboxamide

201

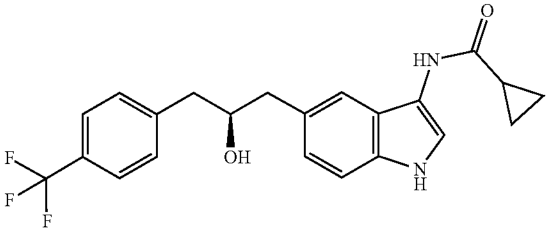

(S)-N-(5-(2-hydroxy-3-(4-(trifluoromethyl)phenyl)propyl)-1H-indol-3-y1)cyclopropanecarboxamide

202

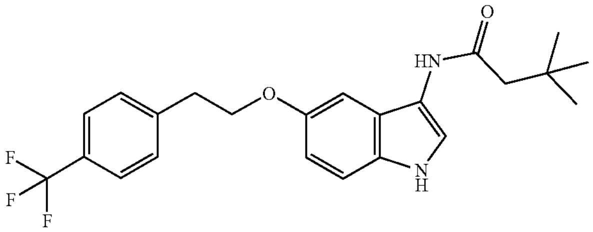 [SMILES: CC(C)(C)CC(=O)Nc1c[nH]c2ccc(OCCc3ccc(C(F)(F)F)cc3)cc12]

3,3-dimethyl-N-(5-(4-(trifluoromethyl)phenethoxy)-1H-indol-3-yl)butanamide

-continued

203

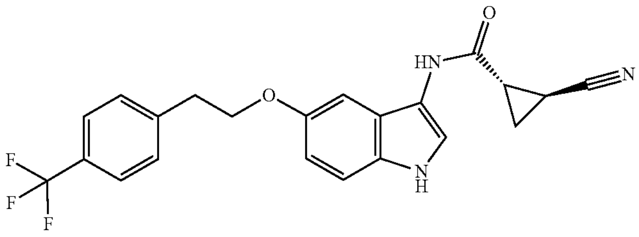

(1S,2S)-2-cyano-N-(5-(4-(trifluoromethyl)phenethoxy)-1H-indol-3-yl)cyclopropane-1-carboxamide

204

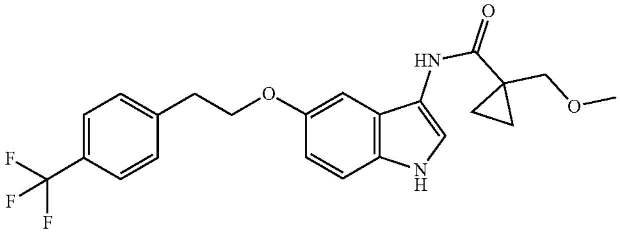 [SMILES: COCC1(C(=O)Nc2c[nH]c3ccc(OCCc4ccc(C(F)(F)F)cc4)cc23)CC1]

1-(methoxymethyl)-N-(5-(4-(trifluoromethyl)phenethoxy)-1H-indol-3-yl)cyclopropane-1-carboxamide

205

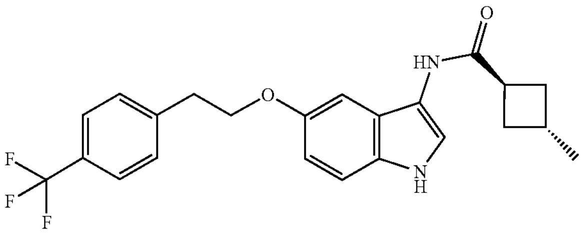

trans-3-methyl-N-(5-(4-(trifluoromethyl)phenethoxy)-1H-indol-3-yl)cyclobutane-1-carboxamide

206

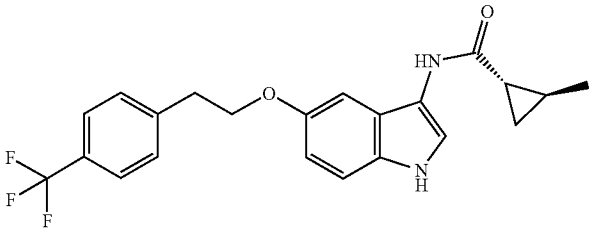 [SMILES: C[C@H]1C[C@@H]1C(=O)Nc1c[nH]c2ccc(OCCc3ccc(C(F)(F)F)cc3)cc12]

(1S,2S)-2-methyl-N-(5-(4-(trifluoromethyl)phenethoxy)-1H-indol-3-yl)cyclopropane-1-carboxamide

207

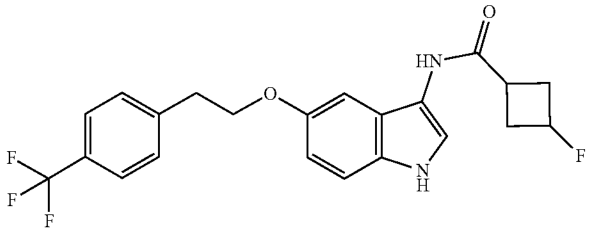

3-fluoro-N-(5-(4-(trifluoromethyl)phenethoxy)-1H-indol-3-yl)cyclobutane-1-carboxamide -continued

208

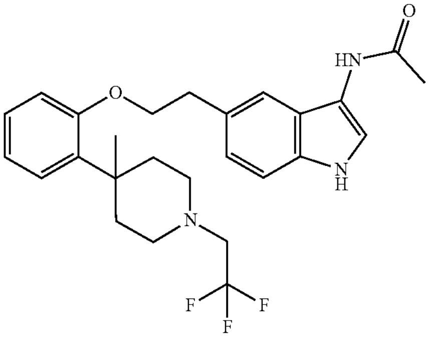 [SMILES: CC(=O)Nc1c[nH]c2ccc(CCOc3ccccc3C3(C)CCN(CC(F)(F)F)CC3)cc12]

N-(5-(2-(2-(4-methyl-1-(2,2,2-trifluoroethyl)piperidin-4-yl)phenoxy)ethyl)-1H-indol-3-yl)acetamide

209

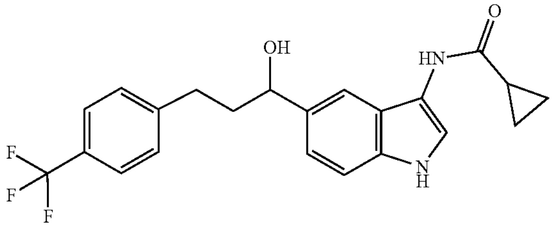 [SMILES: O=C(Nc1c[nH]c2ccc(C(O)CCc3ccc(C(F)(F)F)cc3)cc12)C1CC1]

N-(5-(1-hydroxy-3-(4-(trifluoromethyl)phenyl)propyl)-1H-indol-3-yl)cyclopropanecarboxamide

210

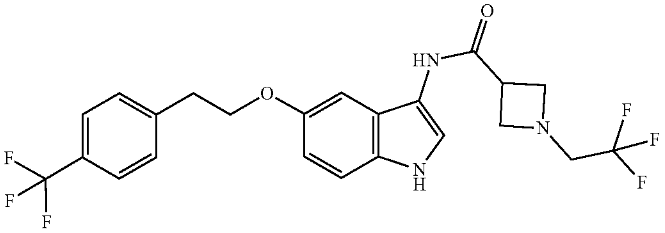 [SMILES: O=C(Nc1c[nH]c2ccc(OCCc3ccc(C(F)(F)F)cc3)cc12)C1CN(CC(F)(F)F)C1]

1-(2,2,2-trifluoroethyl)-N-(5-(4-(trifluoromethyl)phenethoxy)-1H-indol-3-yl)azetidine-3-carboxamide

211

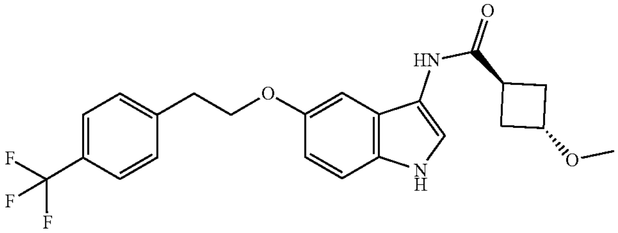 [SMILES: CO[C@H]1C[C@H](C(=O)Nc2c[nH]c3ccc(OCCc4ccc(C(F)(F)F)cc4)cc23)C1]

trans-3-methoxy-N-(5-(4-(trifluoromethyl)phenethoxy)-1H-indol-3-yl)cyclobutane-1-carboxamide

212

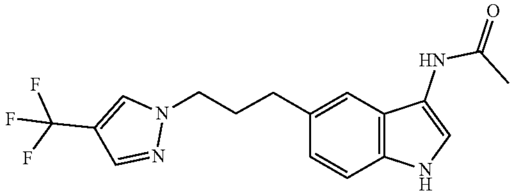

N-(5-(3-(4-(trifluoromethyl)-1H-pyrazol-1-yl)propyl)-1H-indol-3-yl)acetamide

-continued
213
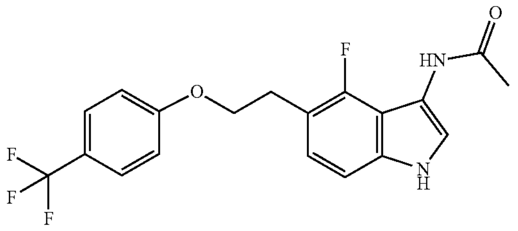
N-(4-fluoro-5-(2-(4-(trifluoromethyl)phenoxy)ethyl)-1H-indol-3-yl)acetamide
214
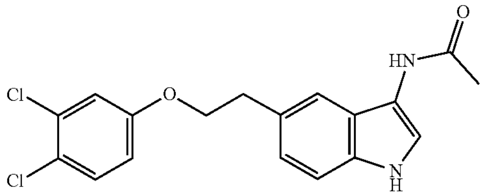 [SMILES: CC(=O)Nc1c[nH]c2ccc(CCOc3ccc(Cl)c(Cl)c3)cc12]
N-(5-(2-(3,4-dichlorophenoxy)ethyl)-1H-indol-3-yl)acetamide
215
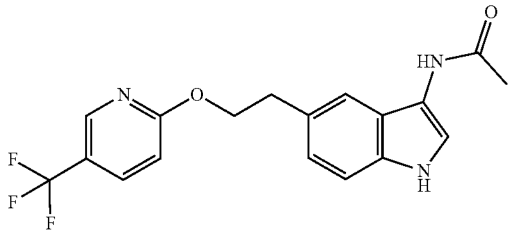 [SMILES: CC(=O)Nc1c[nH]c2ccc(CCOc3ccc(C(F)(F)F)cn3)cc12]
N-(5-(2-((5-(trifluoromethyl)pyridin-2-yl)oxy)ethyl)-1H-indol-3-yl)acetamide
216
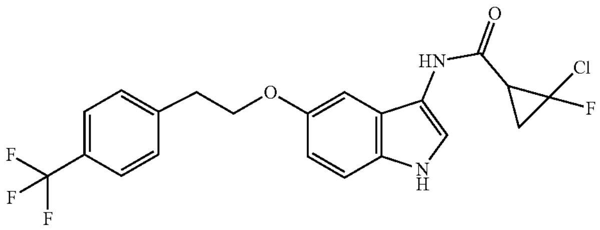 [SMILES: O=C(Nc1c[nH]c2ccc(OCCc3ccc(C(F)(F)F)cc3)cc12)C1CC1(F)Cl]
2-chloro-2-fluoro-N-(5-(4-(trifluoromethyl)phenethoxy)-1H-indol-3-yl)cyclopropane-1-carboxamide
217
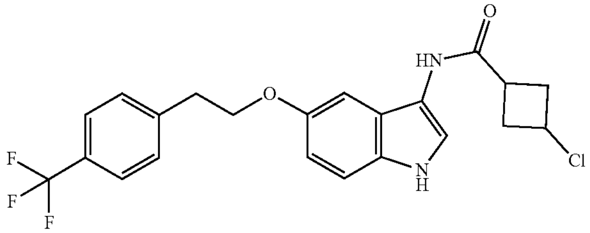 [SMILES: O=C(Nc1c[nH]c2ccc(OCCc3ccc(C(F)(F)F)cc3)cc12)C1CC(Cl)C1]
3-chloro-N-(5-(4-(trifluoromethyl)phenethoxy)-1H-indol-3-yl)cyclobutane-1-carboxamide -continued

218

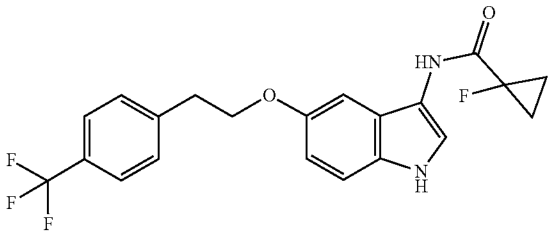 [SMILES: O=C(Nc1c[nH]c2ccc(OCCc3ccc(C(F)(F)F)cc3)cc12)C1(F)CC1]

1-fluoro-N-(5-(4-(trifluoromethyl)phenethoxy)-1H-indol-3-yl)cyclopropane-1-carboxamide

219

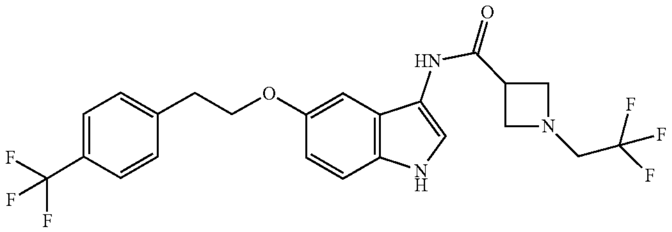 [SMILES: O=C(Nc1c[nH]c2ccc(OCCc3ccc(C(F)(F)F)cc3)cc12)C1CN(CC(F)(F)F)C1]

1-(2,2,2-trifluoroethyl)-N-(5-(2-(4-(trifluoromethyl)phenoxy)ethyl)-1H-indol-3-yl)azetidine-3-carboxamide

220

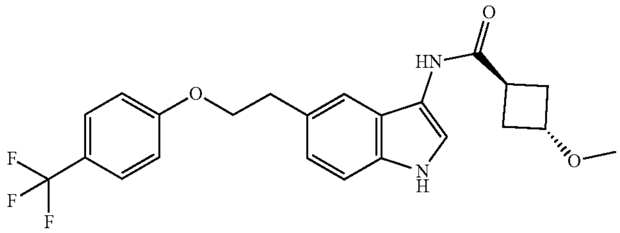 [SMILES: CO[C@H]1C[C@H](C(=O)Nc2c[nH]c3ccc(CCOc4ccc(C(F)(F)F)cc4)cc23)C1]

trans-3-methoxy-N-(5-(2-(4-(trifluoromethyl)phenoxy)ethyl)-1H-indol-3-yl)cyclobutane-1-carboxamide

221

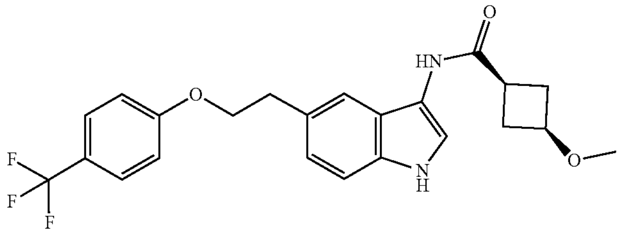 [SMILES: CO[C@H]1C[C@@H](C(=O)Nc2c[nH]c3ccc(CCOc4ccc(C(F)(F)F)cc4)cc23)C1]

cis-3-methoxy-N-(5-(2-(4-(trifluoromethyl)phenoxy)ethyl)-1H-indol-3-y1)cyclobutane-1-carboxamide

222

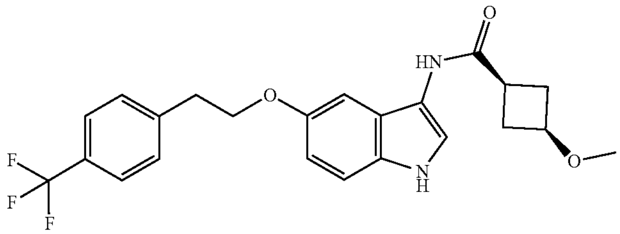 [SMILES: CO[C@H]1C[C@@H](C(=O)Nc2c[nH]c3ccc(OCCc4ccc(C(F)(F)F)cc4)cc23)C1]

cis-3-methoxy-N-(5-(4-(trifluoromethyl)phenethoxy)-1H-indol-3-y1)cyclobutane-1-carboxamide -continued
223
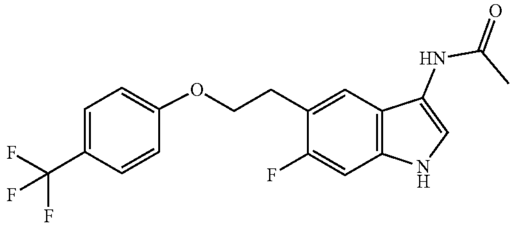 [SMILES: CC(=O)Nc1c[nH]c2cc(F)c(CCOc3ccc(C(F)(F)F)cc3)cc12]
N-(6-fluoro-5-(2-(4-(trifluoromethyl)phenoxy)ethyl)-1H-indol-3-yl)acetamide
224
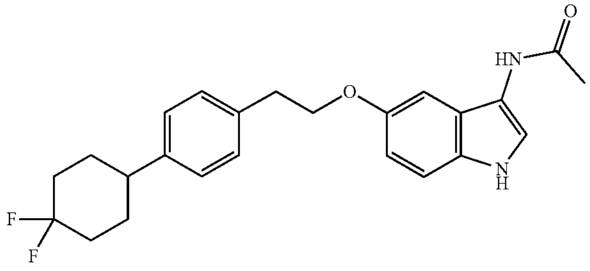 [SMILES: CC(=O)Nc1c[nH]c2ccc(OCCc3ccc(C4CCC(F)(F)CC4)cc3)cc12]
N-(5-(2-(4-(4,4-difluorocyclohexyl)phenoxy)ethyl)-1H-indol-3-yl)acetamide
225
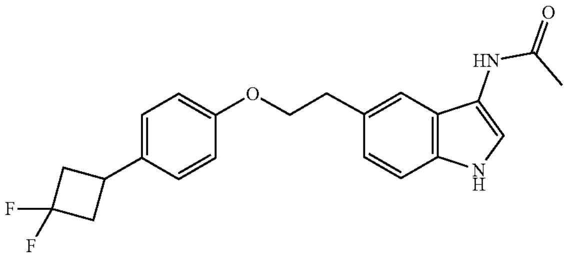 [SMILES: CC(=O)Nc1c[nH]c2ccc(CCOc3ccc(C4CC(F)(F)C4)cc3)cc12]
N-(5-(2-(4-(3,3-difluorocyclobutyl)phenoxy)ethyl)-1H-indol-3-yl)acetamide
226
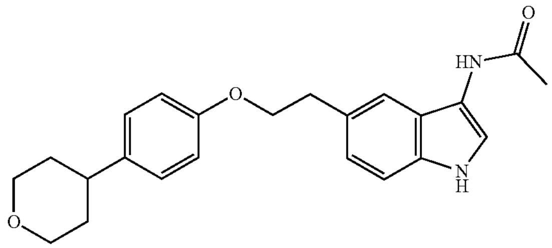 [SMILES: CC(=O)Nc1c[nH]c2ccc(CCOc3ccc(C4CCOCC4)cc3)cc12]
N-(5-(2-(4-(tetrahydro-2H-pyran-4-yl)phenoxy)ethyl)-1H-indol-3-yl)acetamide
227
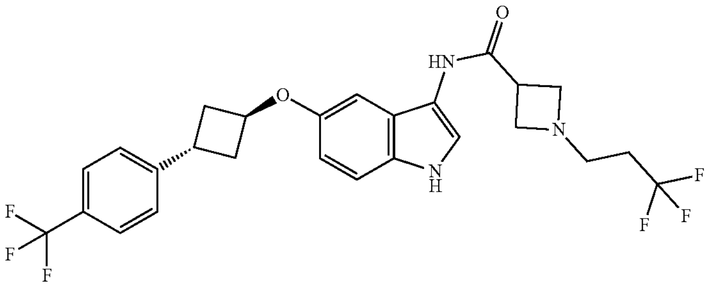 [SMILES: O=C(Nc1c[nH]c2ccc(O[C@H]3C[C@H](c4ccc(C(F)(F)F)cc4)C3)cc12)C1CN(CCC(F)(F)F)C1]
N-(5-(trans-3-(4-(trifluoromethyl)phenyl)cyclobutoxy)-1H-indol-3-yl)-1-(3,3,3-trifluoropropyl)azetidine-3-carboxamide -continued
228
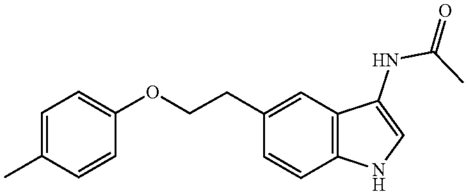 [SMILES: CC(=O)Nc1c[nH]c2ccc(CCOc3ccc(C)cc3)cc12]
N-(5-(2-(p-tolyloxy)ethyl)-1H-indol-3-yl)acetamide
229
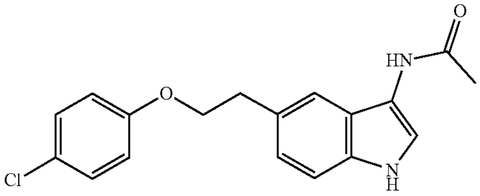 [SMILES: CC(=O)Nc1c[nH]c2ccc(CCOc3ccc(Cl)cc3)cc12]
N-(5-(2-(4-chlorophenoxy)ethyl)-1H-indol-3-yl)acetamide
230
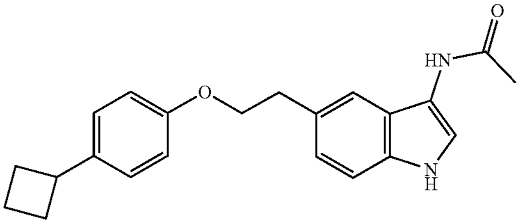 [SMILES: CC(=O)Nc1c[nH]c2ccc(CCOc3ccc(C4CCC4)cc3)cc12]
N-(5-(2-(4-cyclobutylphenoxy)ethyl)-1H-indol-3-yl)acetamide
231
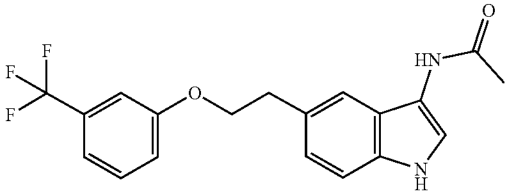 [SMILES: CC(=O)Nc1c[nH]c2ccc(CCOc3cccc(C(F)(F)F)c3)cc12]
N-(5-(2-(3-(trifluoromethyl)phenoxy)ethyl)-1H-indol-3-yl)acetamide
232
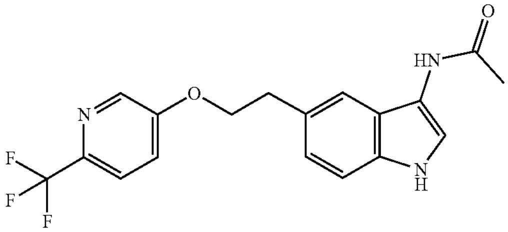
N-(5-(2-((6-(trifluoromethyl)pyridin-3-yl)oxy)ethyl)-1H-indol-3-yl)acetamide -continued

233

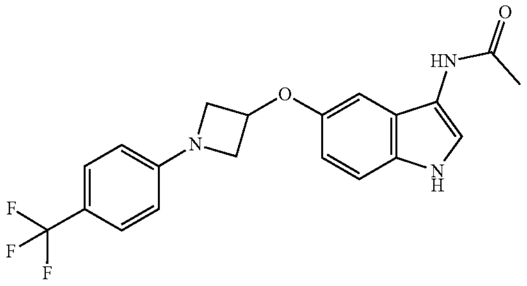 [SMILES: CC(=O)Nc1c[nH]c2ccc(OC3CN(c4ccc(C(F)(F)F)cc4)C3)cc12]

N-(5-((1-(4-(trifluoromethyl)phenyl)azetidin-3-yl)oxy)-1H-indol-3-yl)acetamide

234

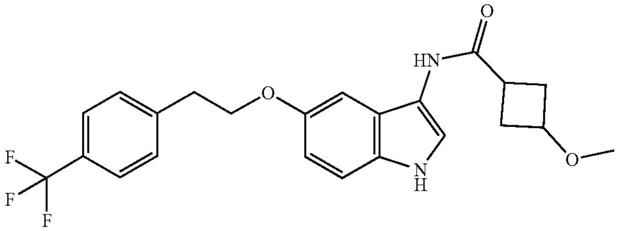 [SMILES: COC1CC(C(=O)Nc2c[nH]c3ccc(OCCc4ccc(C(F)(F)F)cc4)cc23)C1]

3-methoxy-N-(5-(4-(trifluoromethyl)phenethoxy)-1H-indol-3-yl)cyclobutane-1-carboxamide

235

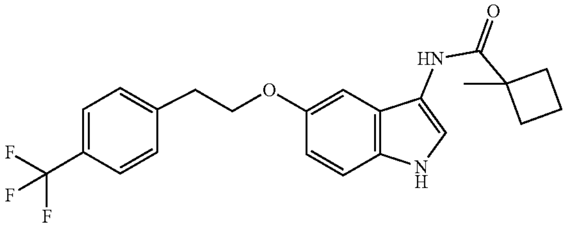 [SMILES: CC1(C(=O)Nc2c[nH]c3ccc(OCCc4ccc(C(F)(F)F)cc4)cc23)CCC1]

1-methyl-N-(5-(4-(trifluoromethyl)phenethoxy)-1H-indol-3-yl)cyclobutane-1-carboxamide

236

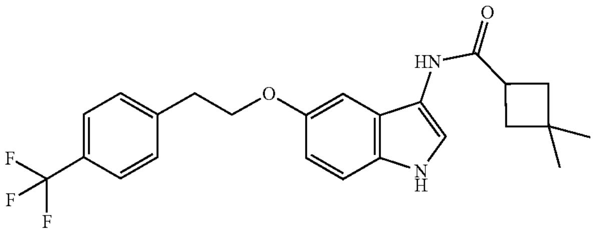 [SMILES: CC1(C)CC(C(=O)Nc2c[nH]c3ccc(OCCc4ccc(C(F)(F)F)cc4)cc23)C1]

3,3-dimethyl-N-(5-(4-(trifluoromethyl)phenethoxy)-1H-indol-3-yl)cyclobutane-1-carboxamide

237

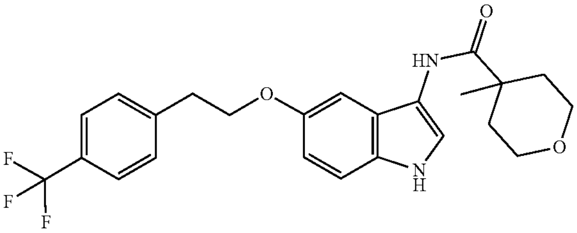 [SMILES: CC1(C(=O)Nc2c[nH]c3ccc(OCCc4ccc(C(F)(F)F)cc4)cc23)CCOCC1]

4-methyl-N-(5-(4-(trifluoromethyl)phenethoxy)-1H-indol-3-yl)tetrahydro-2H-pyran-4-carboxamide -continued

238

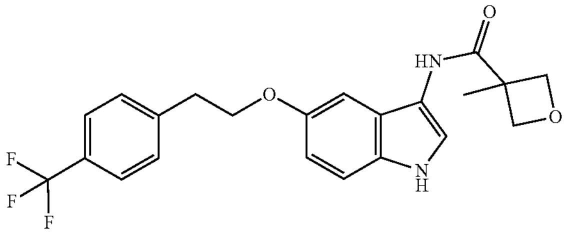 [SMILES: CC1(C(=O)Nc2c[nH]c3ccc(OCCc4ccc(C(F)(F)F)cc4)cc23)COC1]

3-methyl-N-(5-(4-(trifluoromethyl)phenethoxy)-1H-indol-3-yl)oxetane-3-carboxamide

239

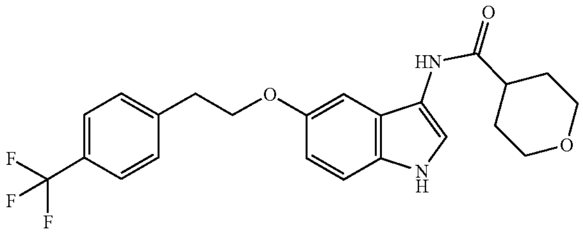 [SMILES: O=C(Nc1c[nH]c2ccc(OCCc3ccc(C(F)(F)F)cc3)cc12)C1CCOCC1]

N-(5-(4-(trifluoromethyl)phenethoxy)-1H-indol-3-yl)tetrahydro-2H-pyran-4-carboxamide

240

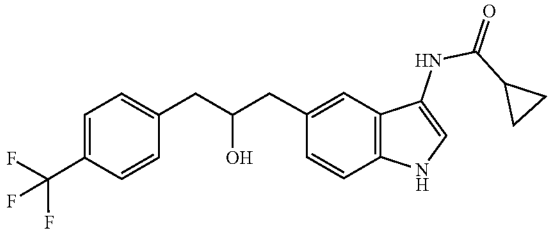

N-(5-(2-hydroxy-3-(4-(trifluoromethyl)phenyl)propyl)-1H-indol-3-yl)cyclopropanecarboxamide

241

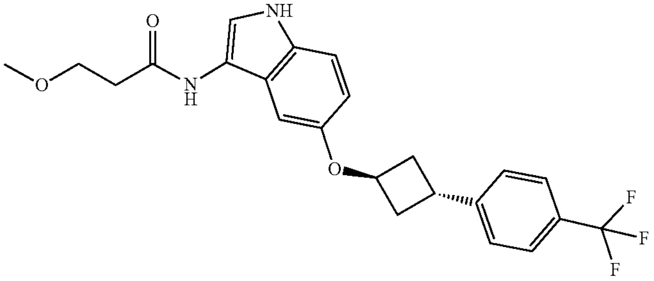 [SMILES: COCCC(=O)Nc1c[nH]c2ccc(O[C@H]3C[C@H](c4ccc(C(F)(F)F)cc4)C3)cc12]

3-methoxy-N-(5-((1r,3r)-3-(4-(trifluoromethyl)phenyl)cyclobutoxy)-1H-indol-3-yl)propanamide

242

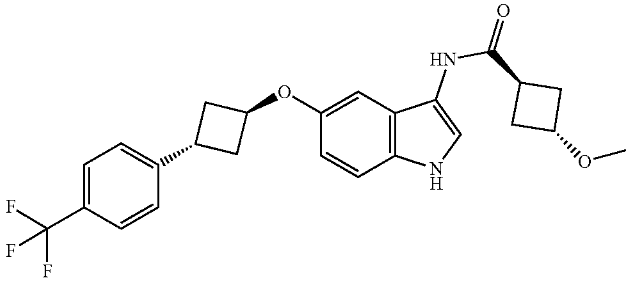 [SMILES: CO[C@H]1C[C@H](C(=O)Nc2c[nH]c3ccc(O[C@H]4C[C@H](c5ccc(C(F)(F)F)cc5)C4)cc23)C1]

trans-3-methoxy-N-(5-(trans-3-(4-(trifluoromethyl)phenyl)cyclobutoxy)-1H-indol-3-yl)cyclobutane-1-carboxamide -continued

243

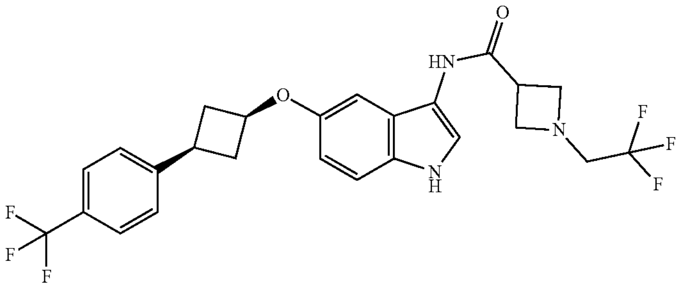 [SMILES: O=C(Nc1c[nH]c2ccc(O[C@H]3C[C@@H](c4ccc(C(F)(F)F)cc4)C3)cc12)C1CN(CC(F)(F)F)C1]

1-(2,2,2-trifluoroethyl)-N-(5-(cis-3-(4-(trifluoromethyl)phenyl)cyclobutoxy)-1H-indol-3-yl)azetidine-3-carboxamide

244

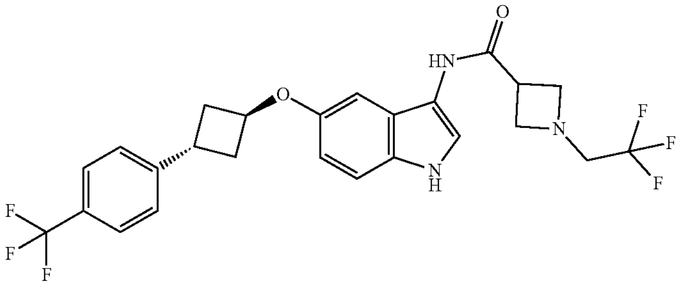 [SMILES: O=C(Nc1c[nH]c2ccc(O[C@H]3C[C@H](c4ccc(C(F)(F)F)cc4)C3)cc12)C1CN(CC(F)(F)F)C1]

1-(2,2,2-trifluoroethyl)-N-(5-(trans-3-(4-(trifluoromethyl)phenyl)cyclobutoxy)-1H-indol-3-yl)azetidine-3-carboxamide

245

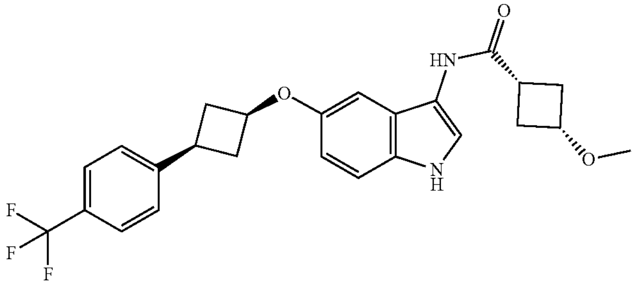 [SMILES: CO[C@H]1C[C@@H](C(=O)Nc2c[nH]c3ccc(O[C@H]4C[C@@H](c5ccc(C(F)(F)F)cc5)C4)cc23)C1]

cis-3-methoxy-N-(5-(cis-3-(4-(trifluoromethyl)phenyl)cyclobutoxy)-1H-indol-3-yl)cyclobutane-1-carboxamide

246

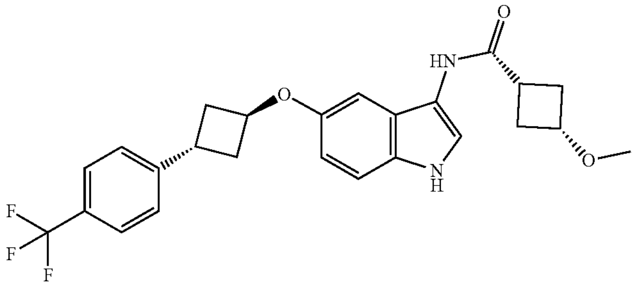

cis-3-methoxy-N-(5-(trans-3-(4-(trifluoromethyl)phenyl)cyclobutoxy)-1H-indol-3-yl)cyclobutane-1-carboxamide -continued
247
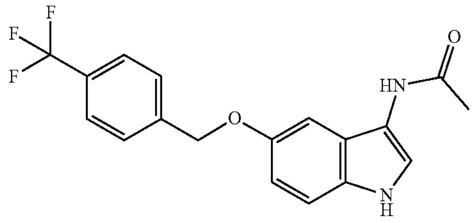 [SMILES: CC(=O)Nc1c[nH]c2ccc(OCc3ccc(C(F)(F)F)cc3)cc12]
N-(5-((4-(trifluoromethyl)benzyl)oxy)-1H-indol-3-yl)acetamide
248
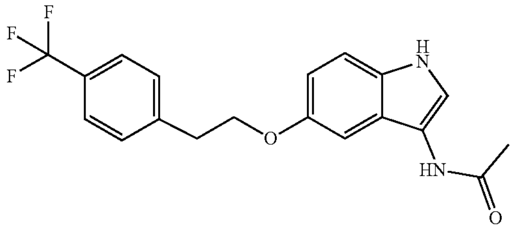 [SMILES: CC(=O)Nc1c[nH]c2ccc(OCCc3ccc(C(F)(F)F)cc3)cc12]
N-(5-(4-(trifluoromethyl)phenethoxy)-1H-pyrrolo[3,2-blpyridin-3-yl)acetamide
249
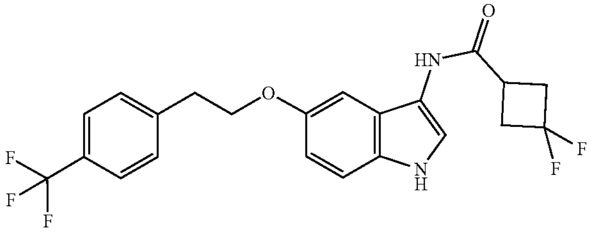 [SMILES: O=C(Nc1c[nH]c2ccc(OCCc3ccc(C(F)(F)F)cc3)cc12)C1CC(F)(F)C1]
3,3-difluoro-N-(5-(4-(trifluoromethyl)phenethoxy)-1H-indol-3-yl)cyclobutane-1-carboxamide
250
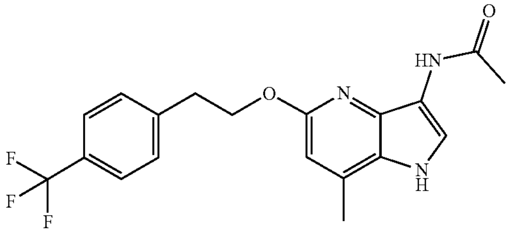 [SMILES: CC(=O)Nc1c[nH]c2c(C)cc(OCCc3ccc(C(F)(F)F)cc3)nc12]
N-(7-methyl-5-(4-(trifluoromethyl)phenethoxy)-1H-pyrrolo[3,2-b]pyridin-3-yl)acetamide
251
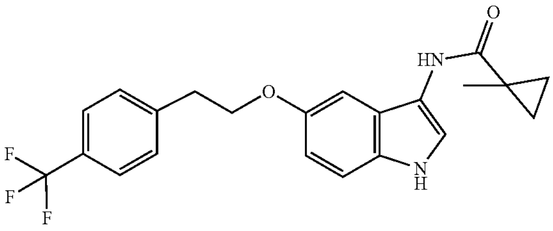
1-methyl-N-(5-(4-(trifluoromethyl)phenethoxy)-1H-indol-3-yl)cyclopropane-1-carboxamide -continued
252
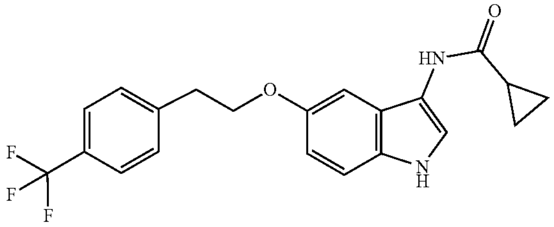 [SMILES: O=C(Nc1c[nH]c2ccc(OCCc3ccc(C(F)(F)F)cc3)cc12)C1CC1]
N-(5-(4-(trifluoromethyl)phenethoxy)-1H-indol-3-yl)cyclopropanecarboxamide
253
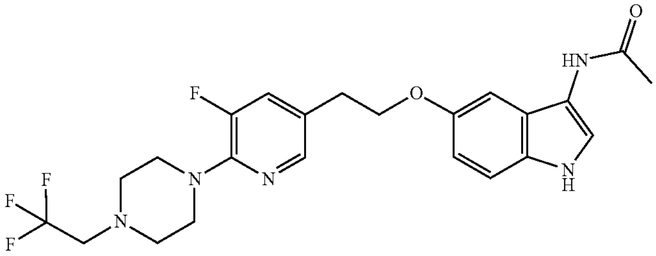 [SMILES: CC(=O)Nc1c[nH]c2ccc(OCCc3cnc(N4CCN(CC(F)(F)F)CC4)c(F)c3)cc12]
N-(5-(2-(5-fluoro-6-(4-(2,2,2-trifluoroethyl)piperazin-1-yl)pyridin-3-yl)ethoxy)-1H-indol-3-yl)acetamide
254
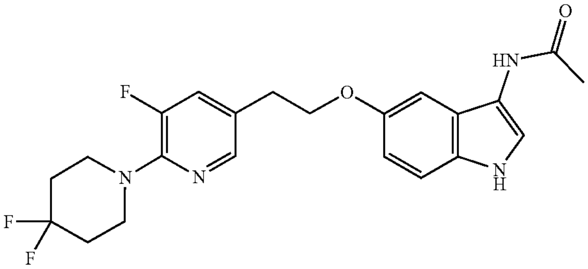 [SMILES: CC(=O)Nc1c[nH]c2ccc(OCCc3cnc(N4CCC(F)(F)CC4)c(F)c3)cc12]
N-(5-(2-(6-(4,4-difluoropiperidin-1-yl)-5-fluoropyridin-3-yl)ethoxy)-1H-indol-3-yl)acetamide
255
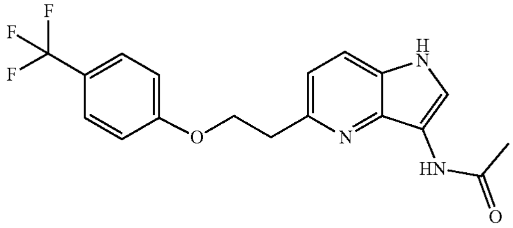 [SMILES: CC(=O)Nc1c[nH]c2ccc(CCOc3ccc(C(F)(F)F)cc3)nc12]
N-(5-(2-(4-(trifluoromethyl)phenoxy)ethyl)-1H-pyrrolo[3,2-b]pyridin-3-yl)acetamide
256
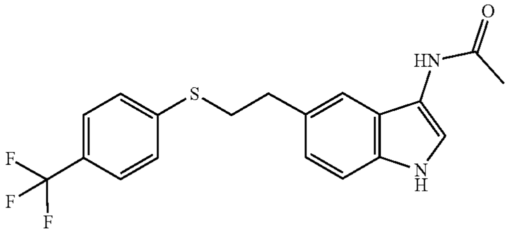
N-(5-(2-((4-(trifluoromethyl)phenyl)thio)ethyl)-1H-indol-3-yl)acetamide -continued
257
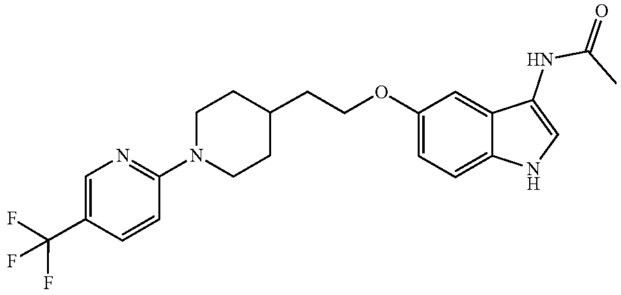 [SMILES: CC(=O)Nc1c[nH]c2ccc(OCCC3CCN(c4ccc(C(F)(F)F)cn4)CC3)cc12]
N-(5-(2-(1-(5-(trifluoromethyl)pyridin-2-yl)piperidin-4-yl)ethoxy)-1H-indol-3-y1)acetamide
258
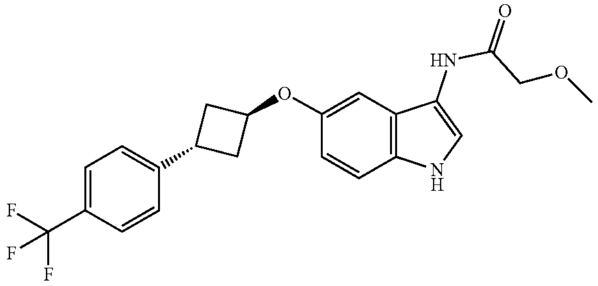 [SMILES: COCC(=O)Nc1c[nH]c2ccc(O[C@H]3C[C@H](c4ccc(C(F)(F)F)cc4)C3)cc12]
2-methoxy-N-(5-(trans-3-(4-(trifluoromethyl)phenyl)cyclobutoxy)-1H-indol-3-y1)acetamide
259
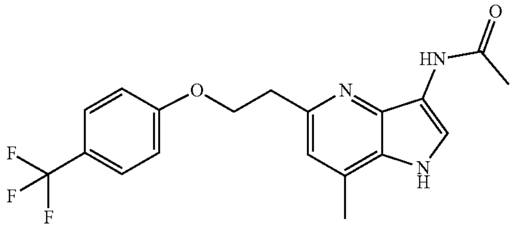 [SMILES: CC(=O)Nc1c[nH]c2c(C)cc(CCOc3ccc(C(F)(F)F)cc3)nc12]
N-(7-methyl-5-(2-(4-(trifluoromethyl)phenoxy)ethyl)-1H-pyrrolo[3,2-b]pyridin-3-yl)acetamide
260
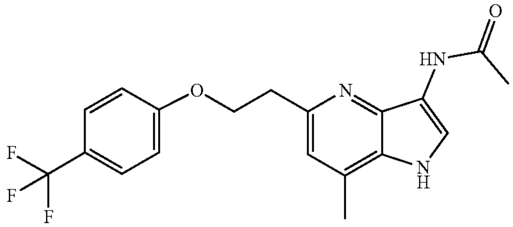 [SMILES: CC(=O)Nc1c[nH]c2c(C)cc(CCOc3ccc(C(F)(F)F)cc3)nc12]
2-methoxy-N-(5-(cis-3-(4-(trifluoromethyl)phenyl)cyclobutoxy)-1H-indol-3-yl)acetamide
261
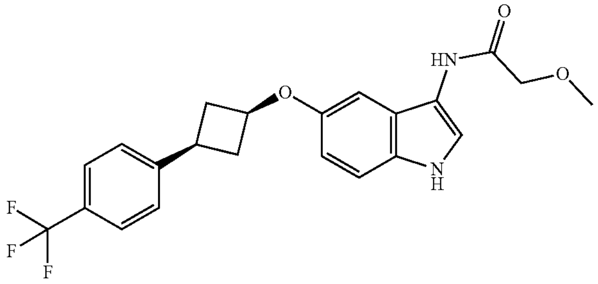 [SMILES: COCC(=O)Nc1c[nH]c2ccc(O[C@H]3C[C@@H](c4ccc(C(F)(F)F)cc4)C3)cc12]

-continued 1-methyl-N-(5-(trans-3-(4-(trifluoromethyl)phenyl)cyclobutoxy)-1H-indol-3-yl)cyclopropane-1-carboxamide

262

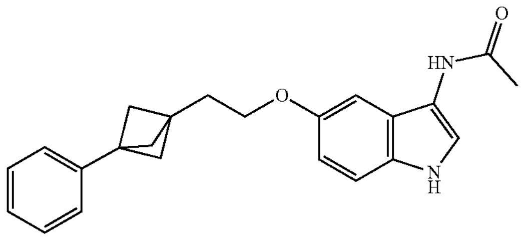 [SMILES: CC(=O)Nc1c[nH]c2ccc(OCCC34CC(c5ccccc5)(C3)C4)cc12]

N-(5-(2-(3-phenylbicyclo[1.1.1]pentan-1-yl)ethoxy)-1H-indol-3-yl)acetamide

263

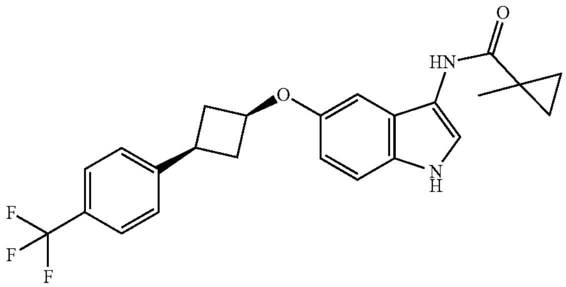 [SMILES: CC1(C(=O)Nc2c[nH]c3ccc(O[C@H]4C[C@@H](c5ccc(C(F)(F)F)cc5)C4)cc23)CC1]

1-methyl-N-(5-(cis-3-(4-(trifluoromethyl)phenyl)cyclobutoxy)-1H-indol-3-yl)cyclopropane-1-carboxamide

264

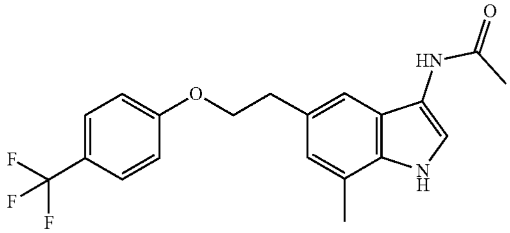 [SMILES: CC(=O)Nc1c[nH]c2c(C)cc(CCOc3ccc(C(F)(F)F)cc3)cc12]

N-(7-methyl-5-(2-(4-(trifluoromethyl)phenoxy)ethyl)-1H-indol-3-yl)acetamide

265

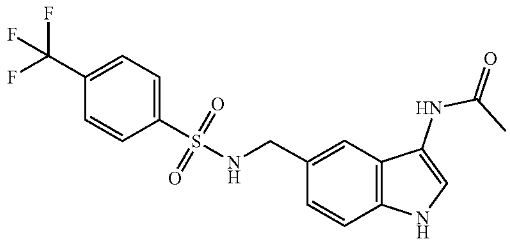 [SMILES: CC(=O)Nc1c[nH]c2ccc(CNS(=O)(=O)c3ccc(C(F)(F)F)cc3)cc12]

N-(5-(((4-(trifluoromethyl)phenyl)sulfonamido)methyl)-1H-indol-3-yl)acetamide

-continued
266
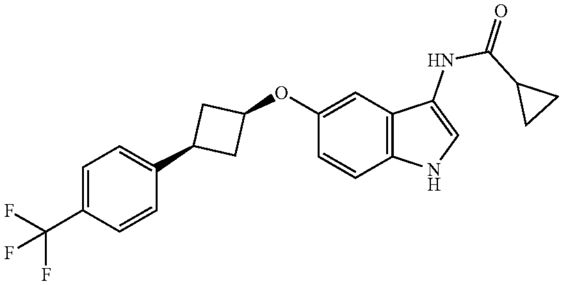 [SMILES: O=C(Nc1c[nH]c2ccc(O[C@H]3C[C@@H](c4ccc(C(F)(F)F)cc4)C3)cc12)C1CC1]
N-(5-(cis-3-(4-(trifluoromethyl)phenyl)cyclobutoxy)-1H-indol-3-y1)cyclopropanecarboxamide
267
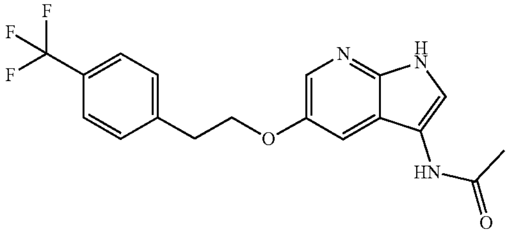 [SMILES: CC(=O)Nc1c[nH]c2ncc(OCCc3ccc(C(F)(F)F)cc3)cc12]
N-(5-(4-(trifluoromethyl)phenethoxy)-1H-pyrrolo[2,3-blpyridin-3-yl)acetamide
268
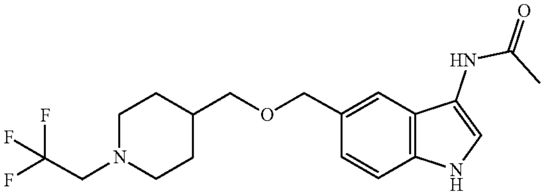 [SMILES: CC(=O)Nc1c[nH]c2ccc(COCC3CCN(CC(F)(F)F)CC3)cc12]
N-(5-(((1-(2,2,2-trifluoroethyl)piperidin-4-y1)methoxy)methyl)-1H-indol-3-yl)acetamide
270
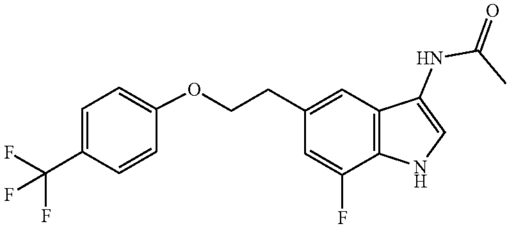 [SMILES: CC(=O)Nc1c[nH]c2c(F)cc(CCOc3ccc(C(F)(F)F)cc3)cc12]
N-(7-fluoro-5-(2-(4-(trifluoromethyl)phenoxy)ethyl)-1H-indol-3-y1)acetamide
271
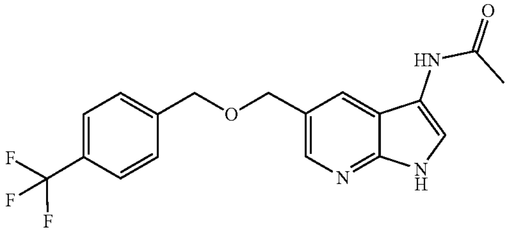 [SMILES: CC(=O)Nc1c[nH]c2ncc(COCc3ccc(C(F)(F)F)cc3)cc12]
N-(5-(((4-(trifluoromethyl)benzyl)oxy)methyl)-1H-pyrrolo[2,3-b]pyridin-3-yl)acetamide -continued
272
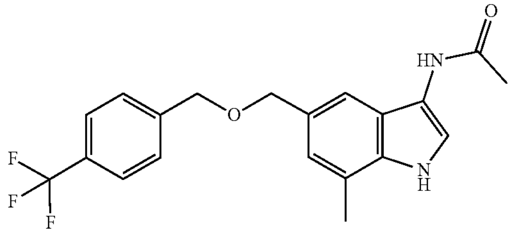 [SMILES: CC(=O)Nc1c[nH]c2c(C)cc(COCc3ccc(C(F)(F)F)cc3)cc12]
N-(7-methyl-5-(((4-(trifluoromethyl)benzyl)oxy)methyl)-1H-indol-3-yl)acetamide
273
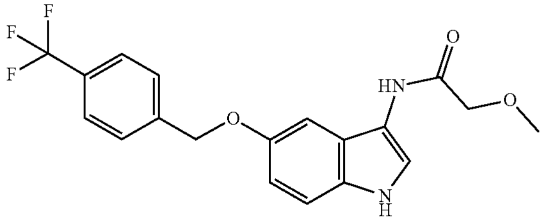 [SMILES: COCC(=O)Nc1c[nH]c2ccc(OCc3ccc(C(F)(F)F)cc3)cc12]
2-methoxy-N-(5-((4-(trifluoromethyl)phenoxy)methyl)-1H-indol-3-yl)acetamide
274
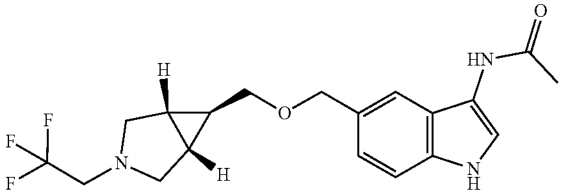 [SMILES: CC(=O)Nc1c[nH]c2ccc(COC[C@@H]3[C@H]4CN(CC(F)(F)F)C[C@@H]34)cc12]
N-(5-((((1R,5S,6r)-3-(2,2,2-trifluoroethyl)-3-azabicyclo[3.1.0]hexan-6-yl)methoxy)methyl)-1H-indol-3-yl)acetamide
275
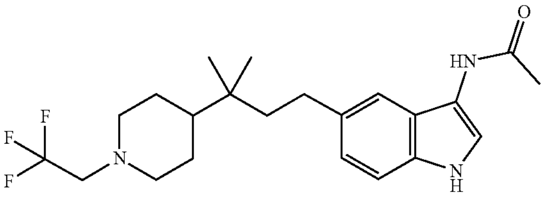 [SMILES: CC(=O)Nc1c[nH]c2ccc(CCC(C)(C)C3CCN(CC(F)(F)F)CC3)cc12]
N-(5-(3-methyl-3-(1-(2,2,2-trifluoroethyl)piperidin-4-yl)butyl)-1H-indol-3-yl)acetamide
276
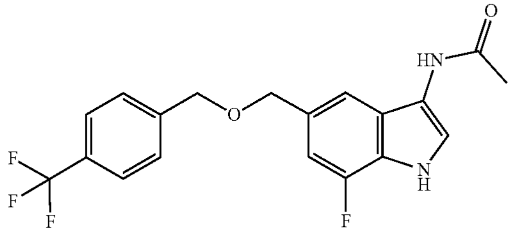
N-(7-fluoro-5-(((4-(trifluoromethyl)benzyl)oxy)methyl)-1H-indol-3-yl)acetamide -continued
277
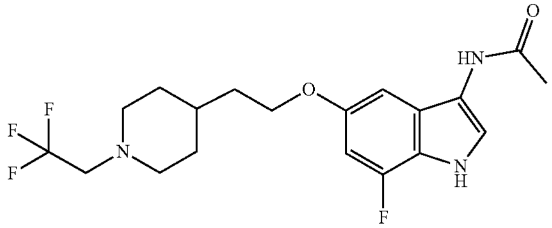 [SMILES: CC(=O)Nc1c[nH]c2c(F)cc(OCCC3CCN(CC(F)(F)F)CC3)cc12]
N-(7-fluoro-5-(2-(1-(2,2,2-trifluoroethyl)piperidin-4-y1)ethoxy)-1H-indol-3-y1)acetamide
278
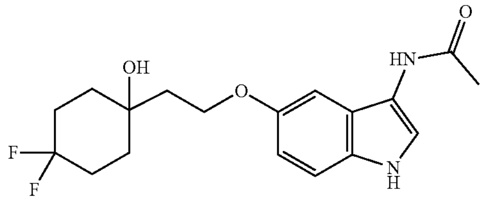 [SMILES: CC(=O)Nc1c[nH]c2ccc(OCCC3(O)CCC(F)(F)CC3)cc12]
N-(5-(2-(4,4-difluoro-1-hydroxycyclohexyl)ethoxy)-1H-indol-3-yl)acetamide
279
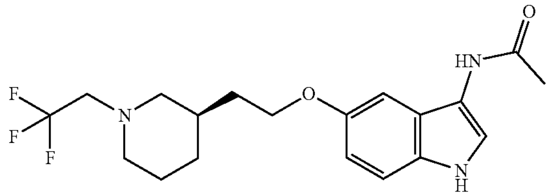 [SMILES: CC(=O)Nc1c[nH]c2ccc(OCC[C@H]3CCCN(CC(F)(F)F)C3)cc12]
(R)-N-(5-(2-(1-(2,2,2-trifluoroethyl)piperidin-3-yl)ethoxy)-1H-indol-3-y1)acetamide
280
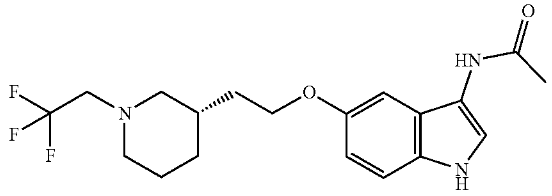 [SMILES: CC(=O)Nc1c[nH]c2ccc(OCC[C@@H]3CCCN(CC(F)(F)F)C3)cc12]
(S)-N-(5-(2-(1-(2,2.2-trifluoroethyl)piperidin-3-yl)ethoxy)-1H-indol-3-y1)acetamide
281
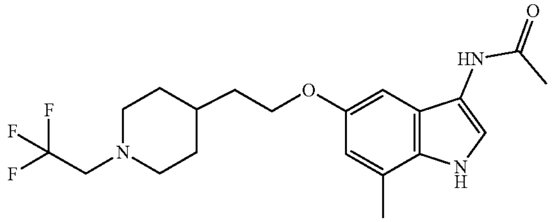 [SMILES: CC(=O)Nc1c[nH]c2c(C)cc(OCCC3CCN(CC(F)(F)F)CC3)cc12]
N-(7-methyl-5-(2-(1-(2,2,2-trifluoroethyl)piperidin-4-yl)ethoxy)-1H-indol-3-yl)acetamide
282
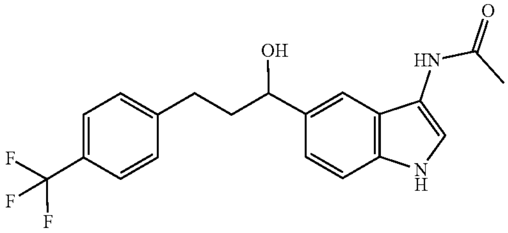 [SMILES: CC(=O)Nc1c[nH]c2ccc(C(O)CCc3ccc(C(F)(F)F)cc3)cc12]

-continued

N-(5-(1-hydroxy-3-(4-(trifluoromethyl)phenyl)propyl)-1H-indol-3-yl)acetamide

283

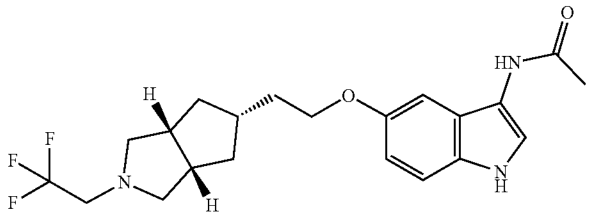 [SMILES: CC(=O)Nc1c[nH]c2ccc(OCC[C@@H]3C[C@@H]4CN(CC(F)(F)F)C[C@@H]4C3)cc12]

N-(5-(2-((3aR,5r,6aS)-2-(2,2,2-trifluoroethyl)octahydrocyclopenta[c]pyrrol-5-yl)ethoxy)-1H-indol-3-y1)acetamide

284

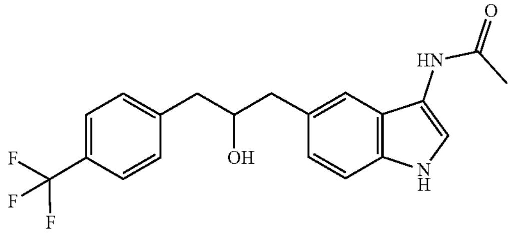 [SMILES: CC(=O)Nc1c[nH]c2ccc(CC(O)Cc3ccc(C(F)(F)F)cc3)cc12]

N-(5-(2-hydroxy-3-(4-(trifluoromethyl)phenyl)propyl)-1H-indol-3-y1)acetamide

285

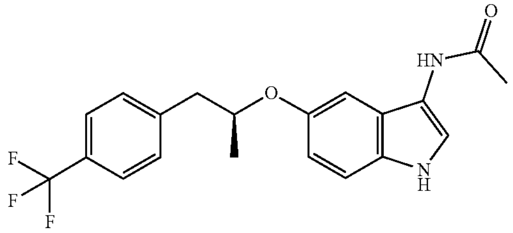 [SMILES: CC(=O)Nc1c[nH]c2ccc(O[C@@H](C)Cc3ccc(C(F)(F)F)cc3)cc12]

(S)-N-(5-((1-(4-(trifluoromethyl)phenyl)propan-2-yl)oxy)-1H-indol-3-y1)acetamide

286

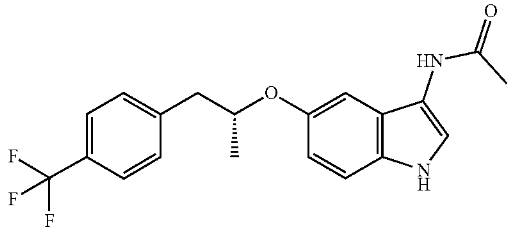 [SMILES: CC(=O)Nc1c[nH]c2ccc(O[C@H](C)Cc3ccc(C(F)(F)F)cc3)cc12]

(R)-N-(5-((1-(4-(trifluoromethyl)phenyl)propan-2-yl)oxy)-1H-indol-3-y1)acetamide

287

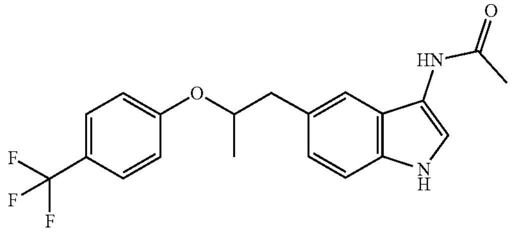 [SMILES: CC(=O)Nc1c[nH]c2ccc(CC(C)Oc3ccc(C(F)(F)F)cc3)cc12]

N-(5-(2-(4-(trifluoromethyl)phenoxy)propyl)-1H-indol-3-yl)acetamide

-continued
288
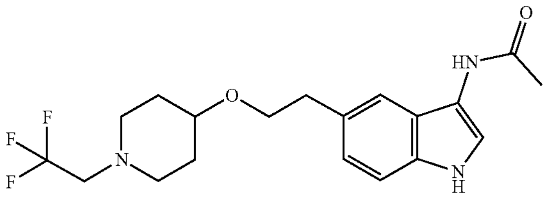 [SMILES: CC(=O)Nc1c[nH]c2ccc(CCOC3CCN(CC(F)(F)F)CC3)cc12]
N-(5-(2-((1-(2,2,2-trifluoroethyl)piperidin-4-yl)oxy)ethyl)-1H-indol-3-yl)acetamide
289
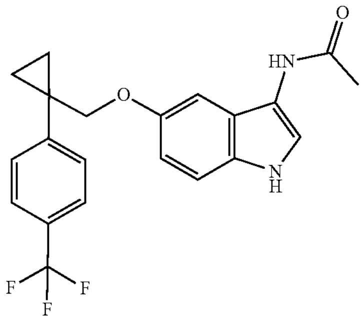 [SMILES: CC(=O)Nc1c[nH]c2ccc(OCC3(c4ccc(C(F)(F)F)cc4)CC3)cc12]
N-(5-((1-(4-(trifluoromethyl)phenyl)cyclopropyl)methoxy)-1H-indol-3-yl)acetamide
290
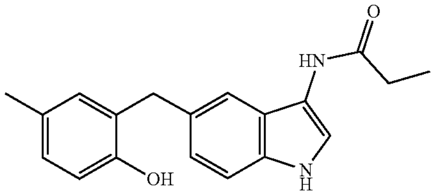 [SMILES: CCC(=O)Nc1c[nH]c2ccc(Cc3cc(C)ccc3O)cc12]
N-(5-(2-hydroxy-5-methylbenzyl)-1H-indol-3-yl)propionamide
291
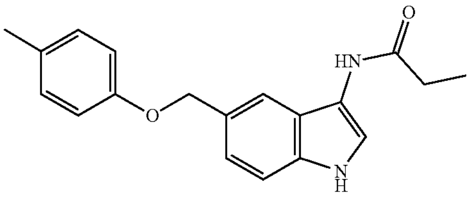 [SMILES: CCC(=O)Nc1c[nH]c2ccc(COc3ccc(C)cc3)cc12]
N-(5-((p-tolyloxy)methyl)-1H-indol-3-yl)propionamide
292
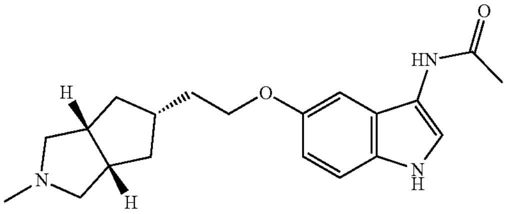 [SMILES: CC(=O)Nc1c[nH]c2ccc(OCC[C@@H]3C[C@@H]4CN(C)C[C@@H]4C3)cc12]
N-(5-(2-((3aR,5r,6aS)-2-methyloctahydrocyclopenta[c]pyrrol-5-yl)ethoxy)-1H-indol-3-yl)acetamide -continued

293

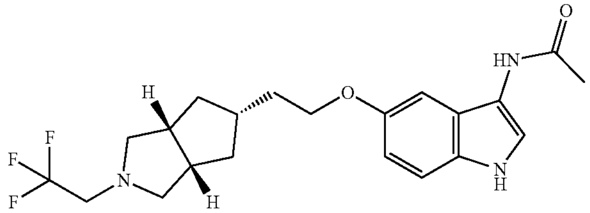 [SMILES: CC(=O)Nc1c[nH]c2ccc(OCC[C@@H]3C[C@@H]4CN(CC(F)(F)F)C[C@@H]4C3)cc12]

N-(5-(2-(((3aR,5r,6aS)-2-(2,2,2-trifluoroethyl)octahydrocyclopenta[c]pyrrol-5-yl)oxy)ethyl)-1H-indol-3-yl)acetamide

294

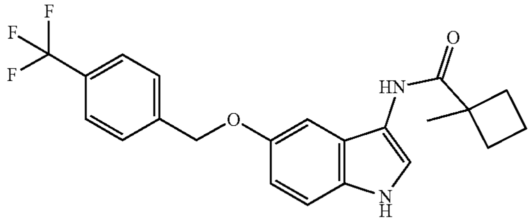 [SMILES: CC1(C(=O)Nc2c[nH]c3ccc(OCc4ccc(C(F)(F)F)cc4)cc23)CCC1]

1-methyl-N-(5-((4-(trifluoromethyl)benzyl)oxy)-1H-indol-3-yl)cyclobutane-1-carboxamide

295

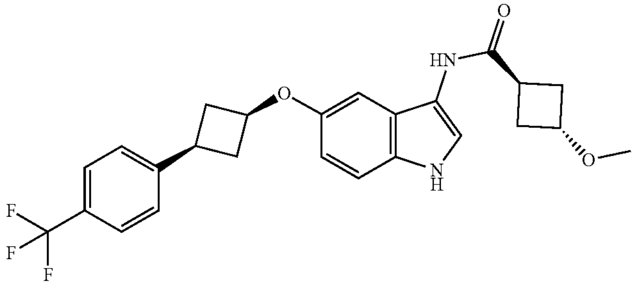 [SMILES: CO[C@H]1C[C@H](C(=O)Nc2c[nH]c3ccc(O[C@H]4C[C@@H](c5ccc(C(F)(F)F)cc5)C4)cc23)C1]

trans-3-methoxy-N-(5-(cis-3-(4-(trifluoromethyl)phenyl)cyclobutoxy)-1H-indol-3-yl)cyclobutane-1-carboxamide

296

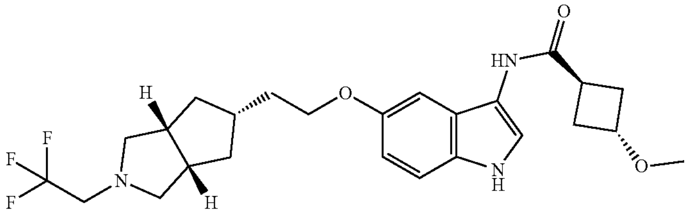 [SMILES: CO[C@H]1C[C@H](C(=O)Nc2c[nH]c3ccc(OCC[C@@H]4C[C@@H]5CN(CC(F)(F)F)C[C@@H]5C4)cc23)C1]

trans-3-methoxy-N-(5-(2-((3aR,5r,6aS)-2-(2,2,2-trifluoroethyl)octahydrocyclopenta[c]pyrrol-5-yl)ethoxy)-1H-indol-3-yl)cyclobutane-1-carboxamide

297

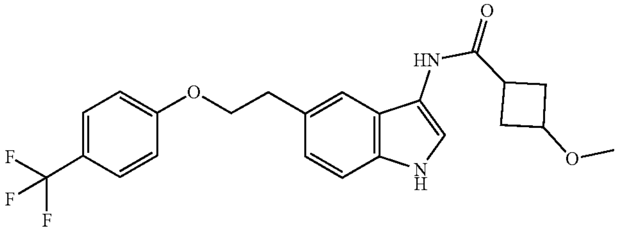 [SMILES: COC1CC(C(=O)Nc2c[nH]c3ccc(CCOc4ccc(C(F)(F)F)cc4)cc23)C1]

3-methoxy-N-(5-(2-(4-(trifluoromethyl)phenoxy)ethyl)-1H-indol-3-yl)cyclobutane-1-carboxamide -continued

298

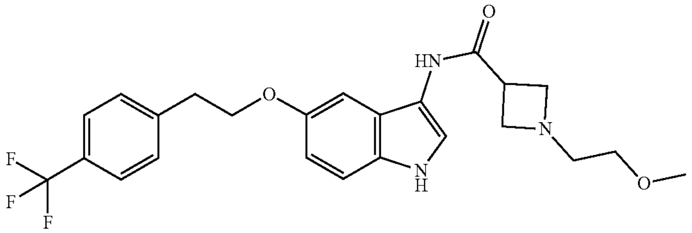 [SMILES: COCCN1CC(C(=O)Nc2c[nH]c3ccc(OCCc4ccc(C(F)(F)F)cc4)cc23)C1]

1-(2-methoxyethyl)-N-(5-(4-(trifluoromethyl)phenethoxy)-1H-indol-3-yl)azetidine-3-carboxamide

299

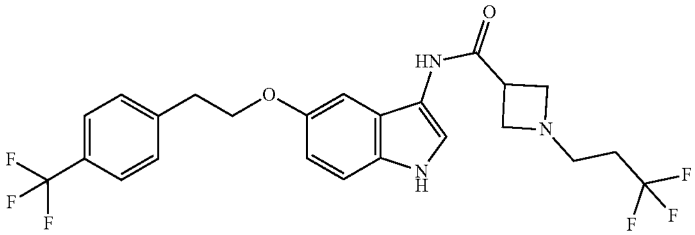 [SMILES: O=C(Nc1c[nH]c2ccc(OCCc3ccc(C(F)(F)F)cc3)cc12)C1CN(CCC(F)(F)F)C1]

N-(5-(4-(trifluoromethyl)phenethoxy)-1H-indol-3-yl)-1-(3,3,3-trifluoropropyl)azetidine-3-carboxamide

300

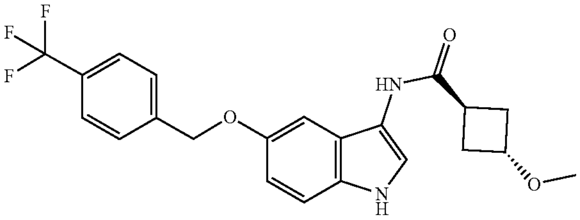 [SMILES: CO[C@H]1C[C@H](C(=O)Nc2c[nH]c3ccc(OCc4ccc(C(F)(F)F)cc4)cc23)C1]

trans-3-methoxy-N-(5-((4-(trifluoromethyl)benzyl)oxy)-1H-indol-3-yl)cyclobutane-1-carboxamide

301

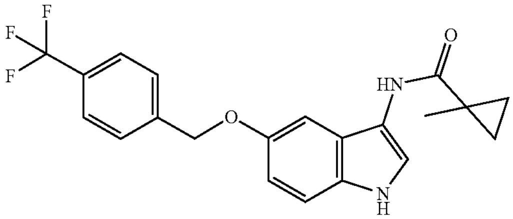 [SMILES: CC1(C(=O)Nc2c[nH]c3ccc(OCc4ccc(C(F)(F)F)cc4)cc23)CC1]

1-methyl-N-(5-((4-(trifluoromethyl)benzyl)oxy)-1H-indol-3-yl)cyclopropane-1-carboxamide

302

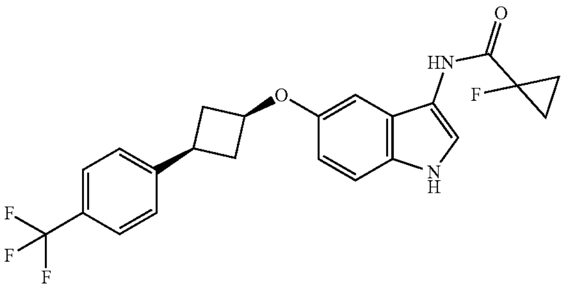 [SMILES: O=C(Nc1c[nH]c2ccc(O[C@H]3C[C@@H](c4ccc(C(F)(F)F)cc4)C3)cc12)C1(F)CC1]

1-fluoro-N-(5-(cis-3-(4-(trifluoromethyl)phenyl)cyclobutoxy)-1H-indol-3-yl)cyclopropane-1-carboxamide -continued

303

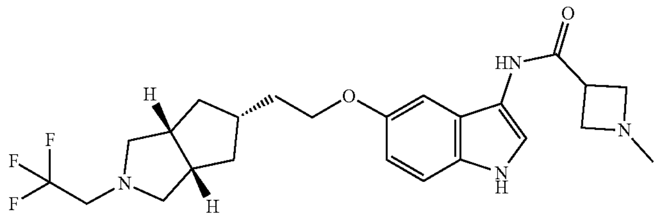 [SMILES: CN1CC(C(=O)Nc2c[nH]c3ccc(OCC[C@@H]4C[C@@H]5CN(CC(F)(F)F)C[C@@H]5C4)cc23)C1]

1-methyl-N-(5-(2-((3aR,5r,6aS)-2-(2,2,2-trifluoroethyl)octahydrocyclopenta[c]pyrrol-5-yl)ethoxy)-1H-indol-3-yl)azetidine-3-carboxamide

304

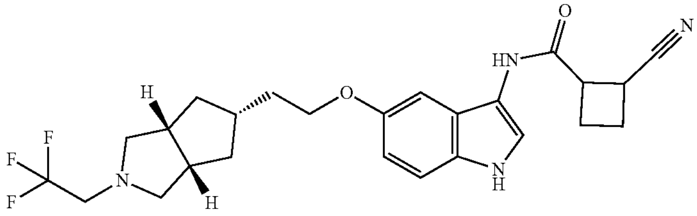 [SMILES: N#CC1CCC1C(=O)Nc1c[nH]c2ccc(OCC[C@@H]3C[C@@H]4CN(CC(F)(F)F)C[C@@H]4C3)cc12]

2-cyano-N-(5-(2-((3aR,5r,6aS)-2-(2,2,2-trifluoroethyl)octahydrocyclopenta[c]pyrrol-5-yl)ethoxy)-1H-indol-3-yl)cyclobutane-1-carboxamide

305

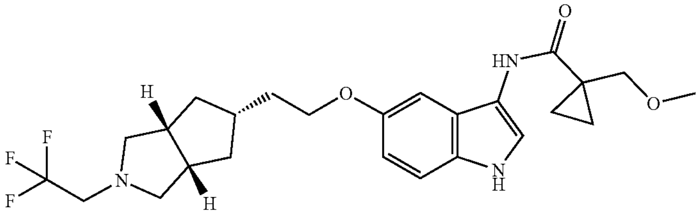 [SMILES: COCC1(C(=O)Nc2c[nH]c3ccc(OCC[C@@H]4C[C@@H]5CN(CC(F)(F)F)C[C@@H]5C4)cc23)CC1]

1-(methoxymethyl)-N-(5-(2-((3aR,5r,6aS)-2-(2,2,2-trifluoroethyl)octahydrocyclopenta[c]pyrrol-5-yl)ethoxy)-1H-indol-3-yl)cyclopropane-1-carboxamide

306

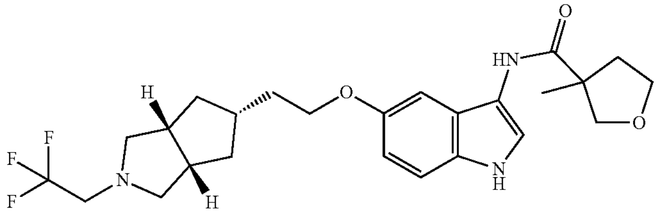 [SMILES: CC1(C(=O)Nc2c[nH]c3ccc(OCC[C@@H]4C[C@@H]5CN(CC(F)(F)F)C[C@@H]5C4)cc23)CCOC1]

3-methyl-N-(5-(2-((3aR,5r,6aS)-2-(2,2,2-trifluoroethyl)octahydrocyclopenta[c]pyrrol-5-yl)ethoxy)-1H-indol-3-yl)tetrahydrofuran-3-carboxamide

307

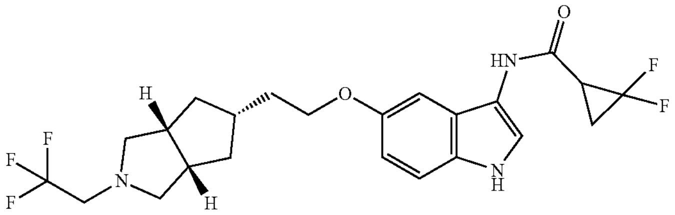 [SMILES: O=C(Nc1c[nH]c2ccc(OCC[C@@H]3C[C@@H]4CN(CC(F)(F)F)C[C@@H]4C3)cc12)C1CC1(F)F]

2,2-difluoro-N-(5-(2-((3aR,5r,6aS)-2-(2,2,2-trifluoroethyl)octahydrocyclopenta[c]pyrrol-5-yl)ethoxy)-1H-indol-3-yl)cyclopropane-1-carboxamide -continued

308

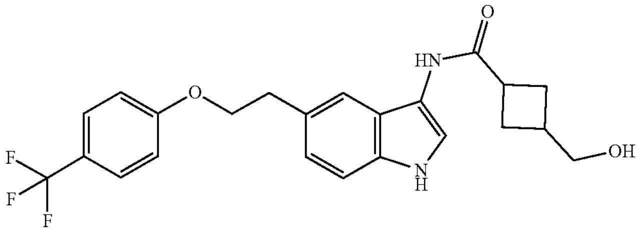 [SMILES: O=C(Nc1c[nH]c2ccc(CCOc3ccc(C(F)(F)F)cc3)cc12)C1CC(CO)C1]

3-(hydroxymethyl)-N-(5-(2-(4-(trifluoromethyl)phenoxy)ethyl)-1H-indol-3-yl)cyclobutane-1-carboxamide

309

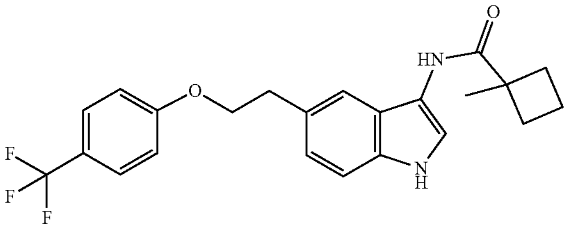 [SMILES: CC1(C(=O)Nc2c[nH]c3ccc(CCOc4ccc(C(F)(F)F)cc4)cc23)CCC1]

1-methyl-N-(5-(2-(4-(trifluoromethyl)phenoxy)ethyl)-1H-indol-3-yl)cyclobutane-1-carboxamide

310

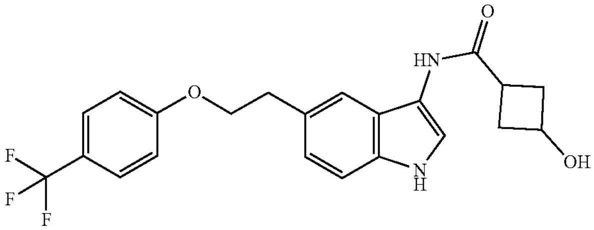 [SMILES: O=C(Nc1c[nH]c2ccc(CCOc3ccc(C(F)(F)F)cc3)cc12)C1CC(O)C1]

3-hydroxy-N-(5-(2-(4-(trifluoromethyl)phenoxy)ethyl)-1H-indol-3-yl)cyclobutane-1-carboxamide

311

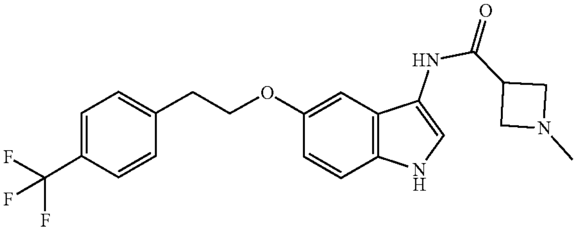 [SMILES: CN1CC(C(=O)Nc2c[nH]c3ccc(OCCc4ccc(C(F)(F)F)cc4)cc23)C1]

1-methyl-N-(5-(4-(trifluoromethyl)phenethoxy)-1H-indol-3-yl)azetidine-3-carboxamide

312

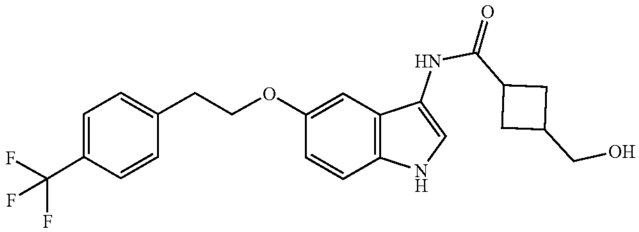 [SMILES: O=C(Nc1c[nH]c2ccc(OCCc3ccc(C(F)(F)F)cc3)cc12)C1CC(CO)C1]

3-(hydroxymethyl)-N-(5-(4-(trifluoromethyl)phenethoxy)-1H-indol-3-yl)cyclobutane-1-carboxamide -continued

313

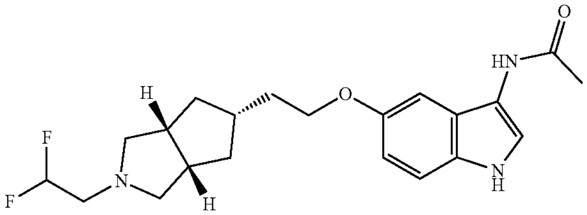 [SMILES: CC(=O)Nc1c[nH]c2ccc(OCC[C@@H]3C[C@@H]4CN(CC(F)F)C[C@@H]4C3)cc12]

N-(5-(2-((3aR,5r,6aS)-2-(2,2-difluoroethyl)octahydrocyclopenta[c]pyrrol-5-yl)ethoxy)-1H-indol-3-yl)acetamide

314

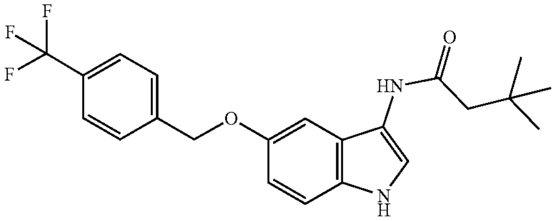 [SMILES: CC(C)(C)CC(=O)Nc1c[nH]c2ccc(OCc3ccc(C(F)(F)F)cc3)cc12]

3,3-dimethyl-N-(5-((4-(trifluoromethyl)benzyl)oxy)-1H-indol-3-yl)butanamide

315

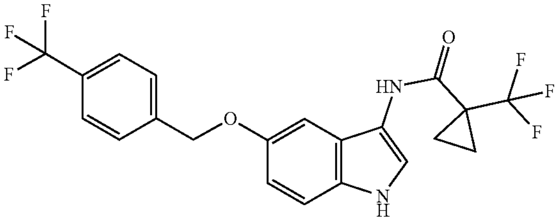 [SMILES: O=C(Nc1c[nH]c2ccc(OCc3ccc(C(F)(F)F)cc3)cc12)C1(C(F)(F)F)CC1]

1-(trifluoromethyl)-N-(5-((4-(trifluoromethyl)benzyl)oxy)-1H-indol-3-yl)cyclopropane-1-carboxamide

316

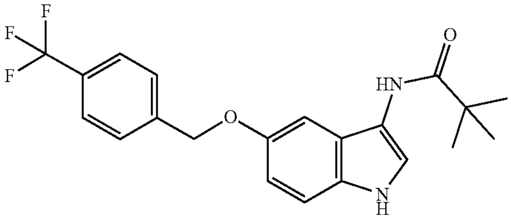 [SMILES: CC(C)(C)C(=O)Nc1c[nH]c2ccc(OCc3ccc(C(F)(F)F)cc3)cc12]

N-(5-((4-(trifluoromethyl)benzyl)oxy)-1H-indol-3-yl)pivalamide

317

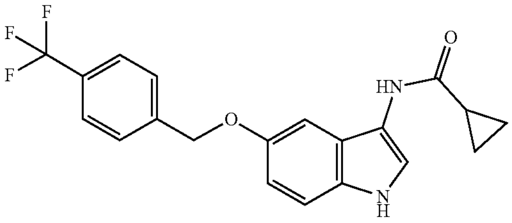 [SMILES: O=C(Nc1c[nH]c2ccc(OCc3ccc(C(F)(F)F)cc3)cc12)C1CC1]

N-(5-((4-(trifluoromethyl)benzyl)oxy)-1H-indol-3-yl)cyclopropanecarboxamide

-continued

318

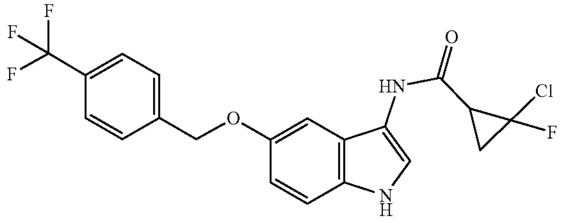

2-chloro-2-fluoro-N-(5-((4-(trifluoromethyl)benzyl)oxy)-1H-indol-3-yl)cyclopropane-1-carboxamide

319

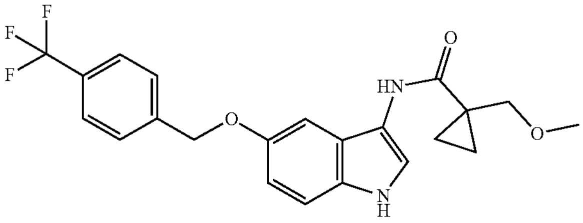 [SMILES: COCC1(C(=O)Nc2c[nH]c3ccc(OCc4ccc(C(F)(F)F)cc4)cc23)CC1]

1-(methoxymethyl)-N-(5-((4-(trifluoromethyl)benzyl)oxy)-1H-indol-3-yl)cyclopropane-1-carboxamide

320

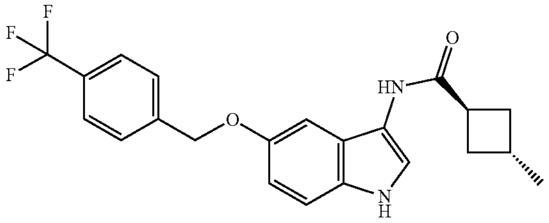 [SMILES: C[C@H]1C[C@H](C(=O)Nc2c[nH]c3ccc(OCc4ccc(C(F)(F)F)cc4)cc23)C1]

trans-3-methyl-N-(5-((4-(trifluoromethyl)benzyl)oxy)-1H-indol-3-yl)cyclobutane-1-carboxamide

321

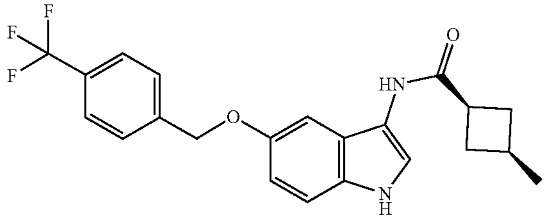 [SMILES: C[C@H]1C[C@@H](C(=O)Nc2c[nH]c3ccc(OCc4ccc(C(F)(F)F)cc4)cc23)C1]

cis-3-methyl-N-(5-((4-(trifluoromethyl)benzyl)oxy)-1H-indol-3-yl)cyclobutane-1-carboxamide

322

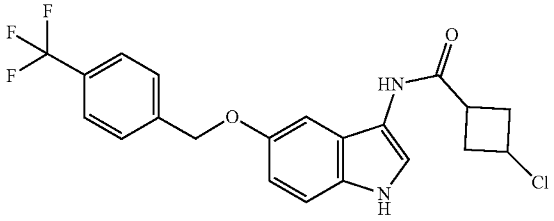 [SMILES: O=C(Nc1c[nH]c2ccc(OCc3ccc(C(F)(F)F)cc3)cc12)C1CC(Cl)C1]

3-chloro-N-(5-((4-(trifluoromethyl)benzyl)oxy)-1H-indol-3-yl)cyclobutane-1-carboxamide -continued

323

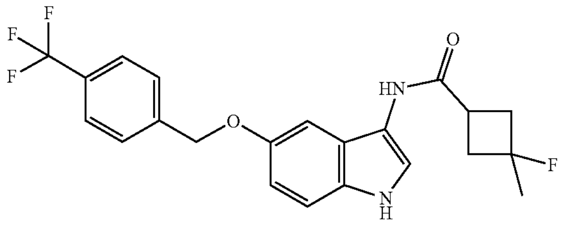 [SMILES: CC1(F)CC(C(=O)Nc2c[nH]c3ccc(OCc4ccc(C(F)(F)F)cc4)cc23)C1]

3-fluoro-3-methyl-N-(5-((4-(trifluoromethyl)benzyl)oxy)-1H-indol-3-y1)cyclobutane-1-carboxamide

324

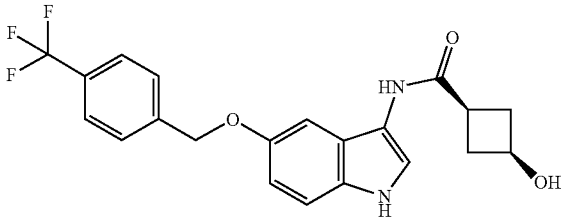 [SMILES: O=C(Nc1c[nH]c2ccc(OCc3ccc(C(F)(F)F)cc3)cc12)[C@H]1C[C@@H](O)C1]

cis-3-hydroxy-N-(5-((4-(trifluoromethyl)benzyl)oxy)-1H-indol-3-y1)cyclobutane-1-carboxamide

325

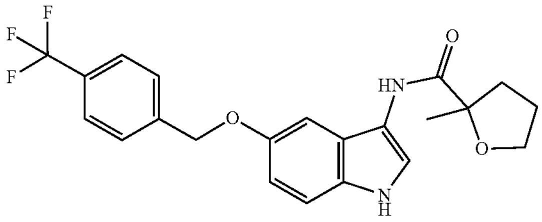 [SMILES: CC1(C(=O)Nc2c[nH]c3ccc(OCc4ccc(C(F)(F)F)cc4)cc23)CCCO1]

2-methyl-N-(5-((4-(trifluoromethyl)benzyl)oxy)-1H-indol-3-y1)tetrahydrofuran-2-carboxamide

326

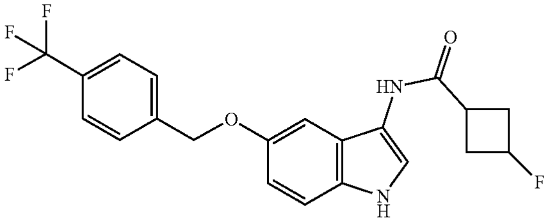 [SMILES: O=C(Nc1c[nH]c2ccc(OCc3ccc(C(F)(F)F)cc3)cc12)C1CC(F)C1]

3-fluoro-N-(5-((4-(trifluoromethyl)benzyl)oxy)-1H-indol-3-yl)cyclobutane-1-carboxamide

327

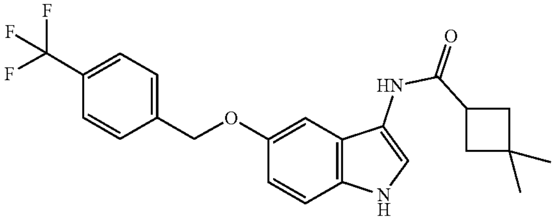 [SMILES: CC1(C)CC(C(=O)Nc2c[nH]c3ccc(OCc4ccc(C(F)(F)F)cc4)cc23)C1]

3,3-dimethyl-N-(5-((4-(trifluoromethyl)benzyl)oxy)-1H-indol-3-y1)cyclobutane-1-carboxamide -continued

328

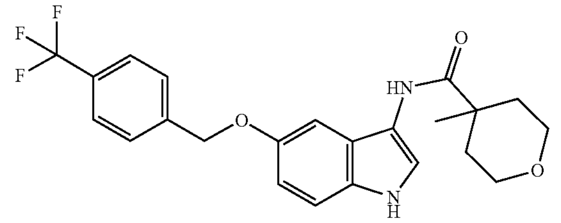 [SMILES: CC1(C(=O)Nc2c[nH]c3ccc(OCc4ccc(C(F)(F)F)cc4)cc23)CCOCC1]

4-methyl-N-(5-((4-(trifluoromethyl)benzyl)oxy)-1H-indol-3-yl)tetrahydro-2H-pyran-4-carboxamide

329

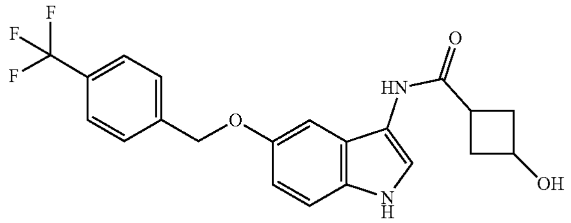 [SMILES: O=C(Nc1c[nH]c2ccc(OCc3ccc(C(F)(F)F)cc3)cc12)C1CC(O)C1]

3-hydroxy-N-(5-((4-(trifluoromethyl)benzyl)oxy)-1H-indol-3-yl)cyclobutane-1-carboxamide

330

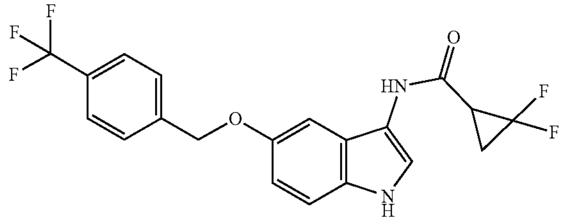 [SMILES: O=C(Nc1c[nH]c2ccc(OCc3ccc(C(F)(F)F)cc3)cc12)C1CC1(F)F]

2,2-difluoro-N-(5-((4-(trifluoromethyl)benzyl)oxy)-1H-indol-3-yl)cyclopropane-1-carboxamide

331

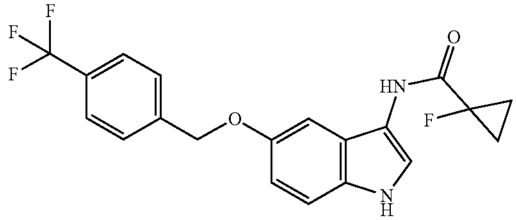 [SMILES: O=C(Nc1c[nH]c2ccc(OCc3ccc(C(F)(F)F)cc3)cc12)C1(F)CC1]

1-fluoro-N-(5-((4-(trifluoromethyl)benzyl)oxy)-1H-indol-3-yl)cyclopropane-1-carboxamide

332

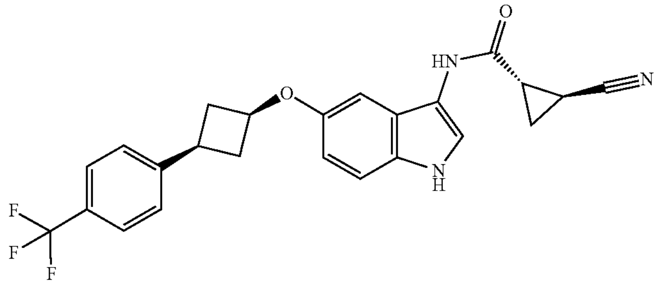 [SMILES: N#C[C@H]1C[C@@H]1C(=O)Nc1c[nH]c2ccc(O[C@H]3C[C@@H](c4ccc(C(F)(F)F)cc4)C3)cc12]

cis-2-cyano-N-(5-(cis-3-(4-(trifluoromethyl)phenyl)cyclobutoxy)-1H-indol-3-yl)cyclopropane-1-carboxamide -continued

333

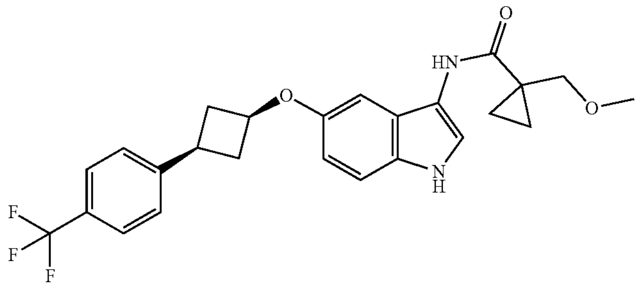 [SMILES: COCC1(C(=O)Nc2c[nH]c3ccc(O[C@H]4C[C@@H](c5ccc(C(F)(F)F)cc5)C4)cc23)CC1]

1-(methoxymethyl)-N-(5-(cis-3-(4-(trifluoromethyl)phenyl)cyclobutoxy)-1H-indol-3-yl)cyclopropane-1-carboxamide

334

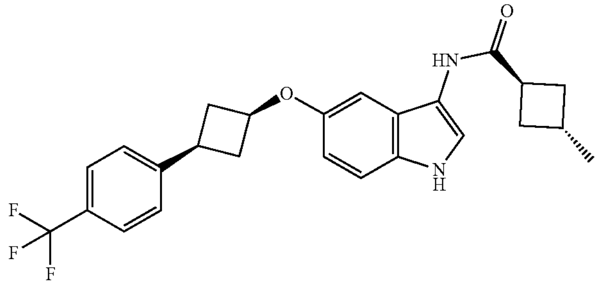 [SMILES: C[C@H]1C[C@H](C(=O)Nc2c[nH]c3ccc(O[C@H]4C[C@@H](c5ccc(C(F)(F)F)cc5)C4)cc23)C1]

trans-3-methyl-N-(5-(cis-3-(4-(trifluoromethyl)phenyl)cyclobutoxy)-1H-indol-3-yl)cyclobutane-1-carboxamide

335

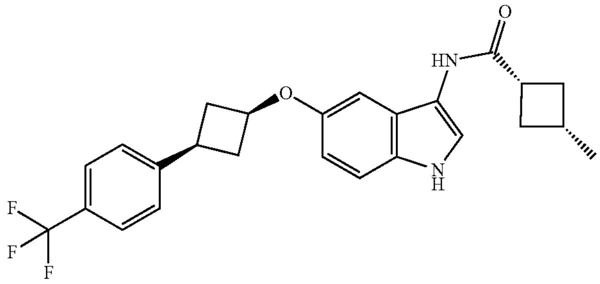 [SMILES: C[C@H]1C[C@@H](C(=O)Nc2c[nH]c3ccc(O[C@H]4C[C@@H](c5ccc(C(F)(F)F)cc5)C4)cc23)C1]

cis-3-methyl-N-(5-(cis-3-(4-(trifluoromethyl)phenyl)cyclobutoxy)-1H-indol-3-yl)cyclobutane-1-carboxamide

336

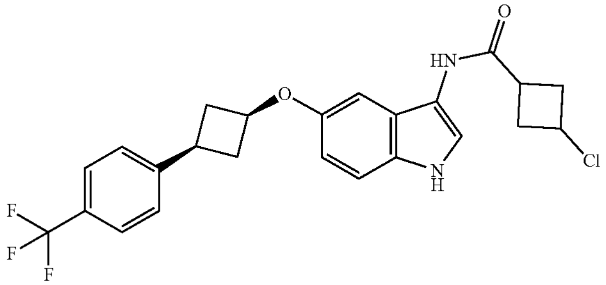 [SMILES: O=C(Nc1c[nH]c2ccc(O[C@H]3C[C@@H](c4ccc(C(F)(F)F)cc4)C3)cc12)C1CC(Cl)C1]

3-chloro-N-(5-(cis-3-(4-(trifluoromethyl)phenyl)cyclobutoxy)-1H-indol-3-yl)cyclobutane-1-carboxamide -continued

337

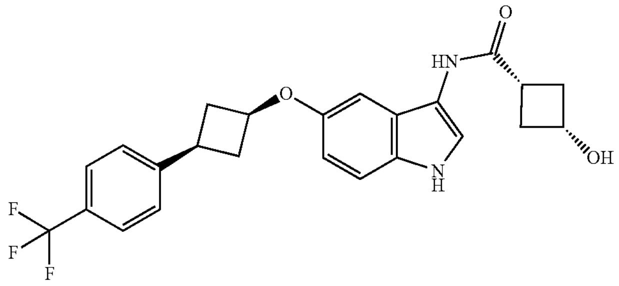 [SMILES: O=C(Nc1c[nH]c2ccc(O[C@H]3C[C@@H](c4ccc(C(F)(F)F)cc4)C3)cc12)[C@H]1C[C@@H](O)C1]

cis-3-hydroxy-N-(5-(cis-3-(4-(trifluoromethyl)phenyl)cyclobutoxy)-1H-indol-3-yl)cyclobutane-1-carboxamide

338

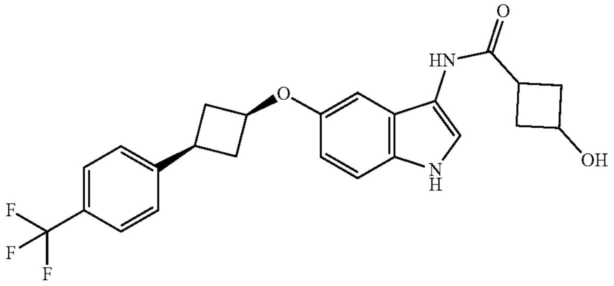 [SMILES: O=C(Nc1c[nH]c2ccc(O[C@H]3C[C@@H](c4ccc(C(F)(F)F)cc4)C3)cc12)C1CC(O)C1]

3-hydroxy-N-(5-(cis-3-(4-(trifluoromethyl)phenyl)cyclobutoxy)-1H-indol-3-yl)cyclobutane-1-carboxamide

339

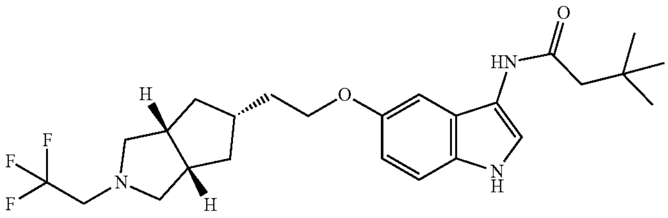 [SMILES: CC(C)(C)CC(=O)Nc1c[nH]c2ccc(OCC[C@@H]3C[C@@H]4CN(CC(F)(F)F)C[C@@H]4C3)cc12]

3,3-dimethyl-N-(5-(2-((3aR,5r,6aS)-2-(2,2,2-trifluoroethyl)octahydrocyclopenta[c]pyrrol-5-yl)ethoxy)-1H-indol-3-yl)butanamide

340

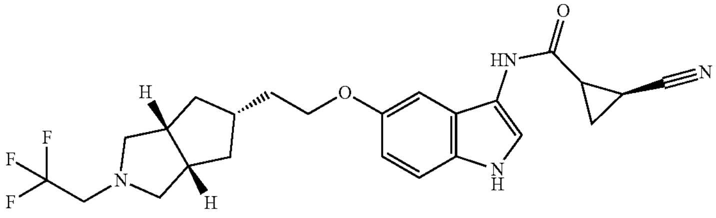 [SMILES: N#C[C@H]1CC1C(=O)Nc1c[nH]c2ccc(OCC[C@@H]3C[C@@H]4CN(CC(F)(F)F)C[C@@H]4C3)cc12]

(1S,2S)-2-cyano-N-(5-(2-((3aR,5r,6aS)-2-(2,2,2-trifluoroethyl)octahydrocyclopenta[c]pyrrol-5-yl)ethoxy).1H-indol-3-yl)cyclopropane-1-carboxamide

341

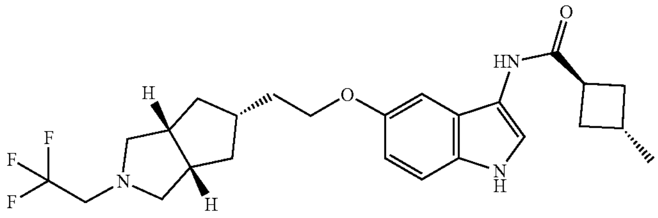 [SMILES: C[C@H]1C[C@H](C(=O)Nc2c[nH]c3ccc(OCC[C@@H]4C[C@@H]5CN(CC(F)(F)F)C[C@@H]5C4)cc23)C1]

-continued (1r,3R)-3-methyl-N-(5-(2-((3aR,5r,6aS)-2-(2,2,2-trifluoroethyl)octahydrocyclopenta[c]pyrrol-5-yl)ethoxy)-1H-indol-3-yl)cyclobutane-1-carboxamide

342

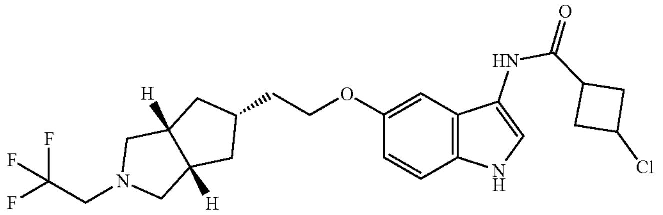 [SMILES: O=C(Nc1c[nH]c2ccc(OCC[C@@H]3C[C@@H]4CN(CC(F)(F)F)C[C@@H]4C3)cc12)C1CC(Cl)C1]

3-chloro-N-(5-(2-((3aR,5r,6aS)-2-(2,2,2-trifluoroethyl)octahydrocyclopenta[c]pyrrol-5-yl)ethoxy)-1H-indol-3-yl)cyclobutane-1-carboxamide

343

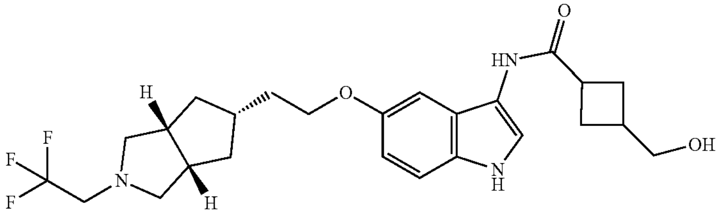 [SMILES: O=C(Nc1c[nH]c2ccc(OCC[C@@H]3C[C@@H]4CN(CC(F)(F)F)C[C@@H]4C3)cc12)C1CC(CO)C1]

3-(hydroxymethyl)-N-(5-(2-((3aR,5r,6aS)-2-(2,2,2-trifluoroethyl)octahydrocyclopenta[c]pyrrol-5-yl)ethoxy)-1H-indol-3-yl)cyclobutane-1-carboxamide

344

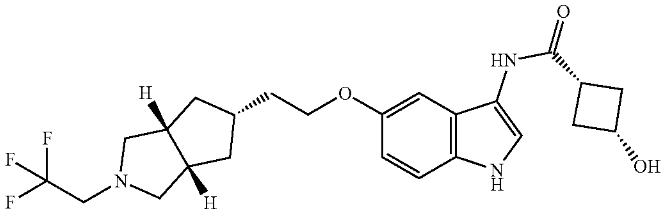 [SMILES: O=C(Nc1c[nH]c2ccc(OCC[C@@H]3C[C@@H]4CN(CC(F)(F)F)C[C@@H]4C3)cc12)[C@H]1C[C@@H](O)C1]

cis-3-hydroxy-N-(5-(2-((3aR,5r,6aS)-2-(2,2,2-trifluoroethyl)octahydrocyclopenta[c]pyrrol-5-yl)ethoxy)-1H-indol-3-yl)cyclobutane-1-carboxamide

345

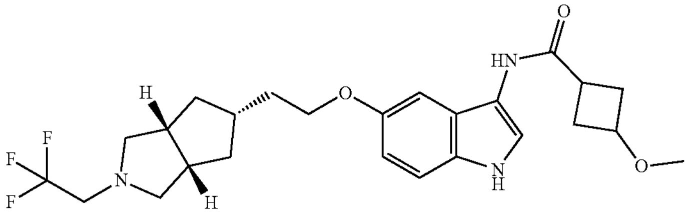 [SMILES: COC1CC(C(=O)Nc2c[nH]c3ccc(OCC[C@@H]4C[C@@H]5CN(CC(F)(F)F)C[C@@H]5C4)cc23)C1]

3-methoxy-N-(5-(2-((3aR,5r,6aS)-2-(2,2,2-trifluoroethyl)octahydrocyclopenta[c]pyrrol-5-yl)ethoxy)-1H-indol-3-yl)cyclobutane-1-carboxamide

346

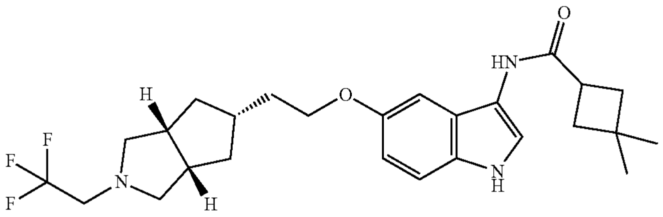 [SMILES: CC1(C)CC(C(=O)Nc2c[nH]c3ccc(OCC[C@@H]4C[C@@H]5CN(CC(F)(F)F)C[C@@H]5C4)cc23)C1]

3,3-dimethyl-N-(5-(2-((3aR,5r,6aS)-2-(2,2,2-trifluoroethyl)octahydrocyclopenta[c]pyrrol-5-yl)ethoxy)-1H-indol-3-yl)cyclobutane-1-carboxamide -continued

347

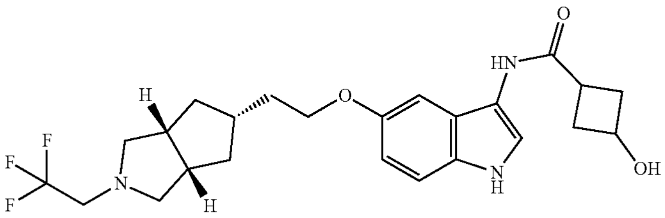 [SMILES: O=C(Nc1c[nH]c2ccc(OCC[C@@H]3C[C@@H]4CN(CC(F)(F)F)C[C@@H]4C3)cc12)C1CC(O)C1]

3-hydroxy-N-(5-(2-((3aR,5r,6aS)-2-(2,2,2-trifluoroethyl)octahydrocyclopenta[c]pyrrol-5-yl)ethoxy)-1H-indol-3-yl)cyclobutane-1-carboxamide

348

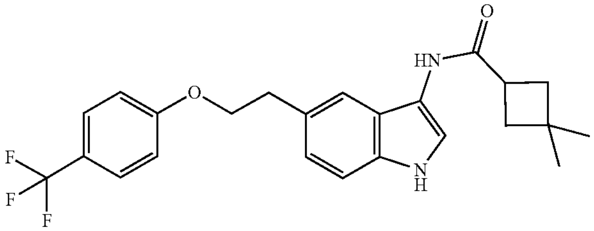 [SMILES: CC1(C)CC(C(=O)Nc2c[nH]c3ccc(CCOc4ccc(C(F)(F)F)cc4)cc23)C1]

3,3-dimethyl-N-(5-(2-(4-(trifluoromethyl)phenoxy)ethyl)-1H-indol-3-yl)cyclobutane-1-carboxamide

349

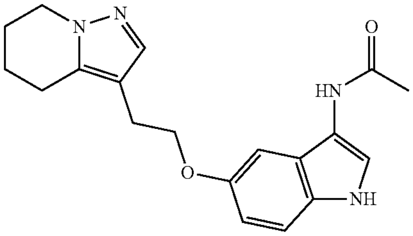 [SMILES: CC(=O)Nc1c[nH]c2ccc(OCCc3cnn4c3CCCC4)cc12]

N-(5-(2-(4,5,6,7-tetrahydropyrazolo[1,5-a]pyridin-3-yl)ethoxy)-1H-indol-3-yl)acetamide

350

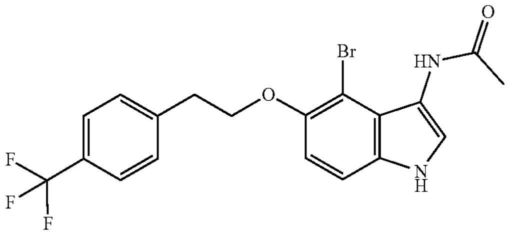 [SMILES: CC(=O)Nc1c[nH]c2ccc(OCCc3ccc(C(F)(F)F)cc3)c(Br)c12]

N-(4-bromo-5-(4-(trifluoromethyl)phenethoxy)-1H-indol-3-yl)acetamide

351

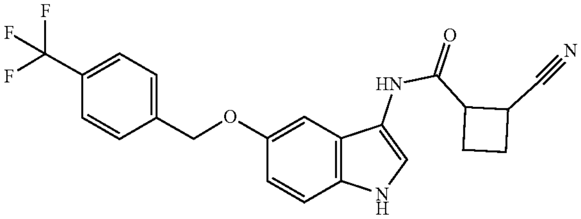 [SMILES: N#CC1CCC1C(=O)Nc1c[nH]c2ccc(OCc3ccc(C(F)(F)F)cc3)cc12]

2-cyano-N-(5-((4-(trifluoromethyl)benzyl)oxy)-1H-indol-3-yl)cyclobutane-1-carboxamide -continued
352
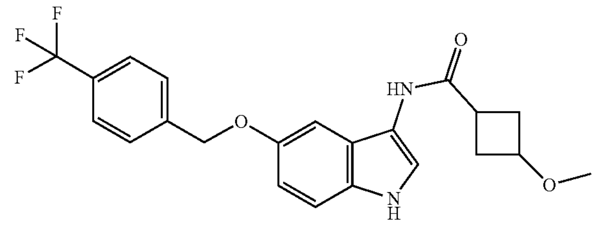 [SMILES: COC1CC(C(=O)Nc2c[nH]c3ccc(OCc4ccc(C(F)(F)F)cc4)cc23)C1]
3-methoxy-N-(5-((4-(trifluoromethyl)benzyl)oxy)-1H-indol-3-yl)cyclobutane-1-carboxamide
353
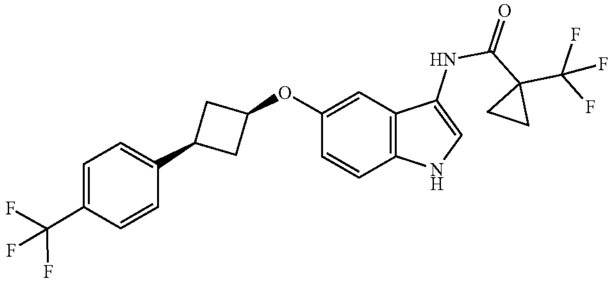 [SMILES: O=C(Nc1c[nH]c2ccc(O[C@H]3C[C@@H](c4ccc(C(F)(F)F)cc4)C3)cc12)C1(C(F)(F)F)CC1]
1-(trifluoromethyl)-N-(5-(cis-3-(4-(trifluoromethyl)phenyl)cyclobutoxy)-1H-indol-3-yl)cyclopropane-1-carboxamide
354
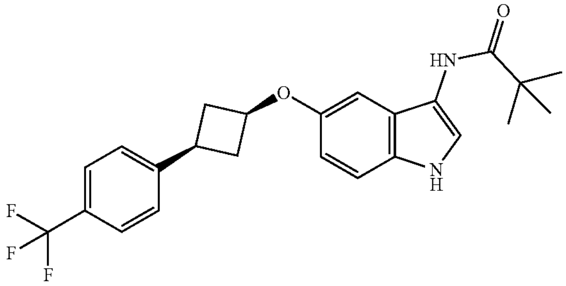 [SMILES: CC(C)(C)C(=O)Nc1c[nH]c2ccc(O[C@H]3C[C@@H](c4ccc(C(F)(F)F)cc4)C3)cc12]
N-(5-(cis-3-(4-(trifluoromethyl)phenyl)cyclobutoxy)-1H-indol-3-yl)pivalamide
355
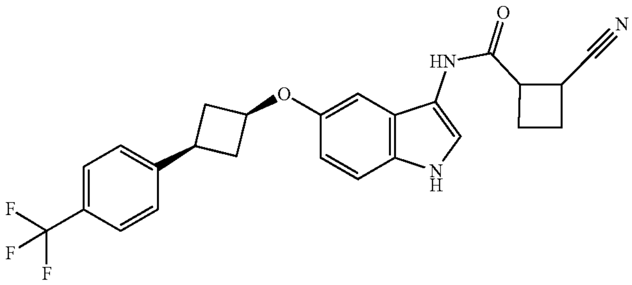 [SMILES: N#CC1CCC1C(=O)Nc1c[nH]c2ccc(O[C@H]3C[C@@H](c4ccc(C(F)(F)F)cc4)C3)cc12]
2-cyano-N-(5-(cis-3-(4-(trifluoromethyl)phenyl)cyclobutoxy)-1H-indol-3-yl)cyclobutane-1-carboxamide -continued

356

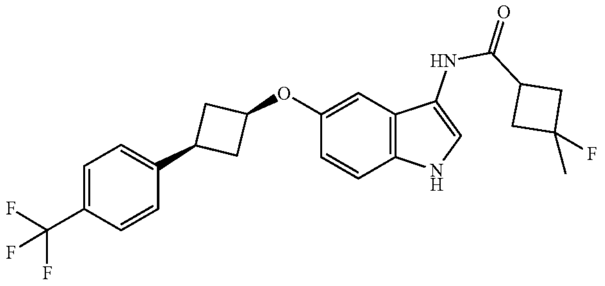 [SMILES: CC1(F)CC(C(=O)Nc2c[nH]c3ccc(O[C@H]4C[C@@H](c5ccc(C(F)(F)F)cc5)C4)cc23)C1]

3-fluoro-3-methyl-N-(5-(cis-3-(4-(trifluoromethyl)phenyl)cyclobutoxy)-1H-indol-3-yl)cyclobutane-1-carboxamide

357

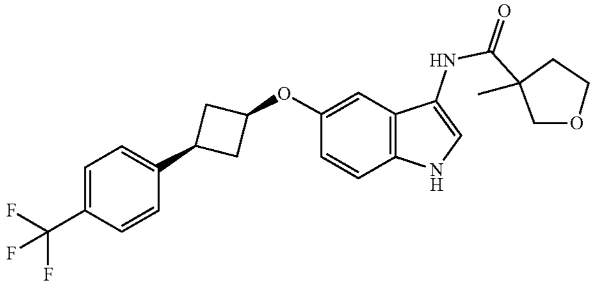 [SMILES: CC1(C(=O)Nc2c[nH]c3ccc(O[C@H]4C[C@@H](c5ccc(C(F)(F)F)cc5)C4)cc23)CCOC1]

3-methyl-N-(5-(cis-3-(4-(trifluoromethyl)phenyl)cyclobutoxy)-1H-indol-3-yl)tetrahydrofuran-3-carboxamide

358

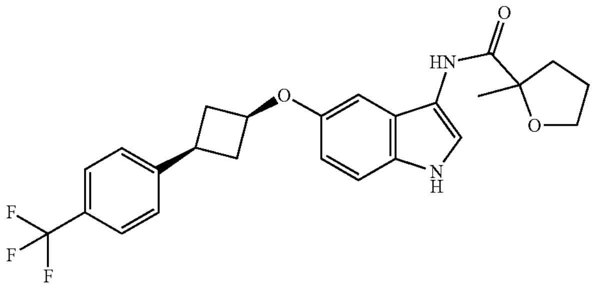 [SMILES: CC1(C(=O)Nc2c[nH]c3ccc(O[C@H]4C[C@@H](c5ccc(C(F)(F)F)cc5)C4)cc23)CCCO1]

2-methyl-N-(5-(cis-3-(4-(trifluoromethyl)phenyl)cyclobutoxy)-1H-indol-3-yl)tetrahydrofuran-2-carboxamide

359

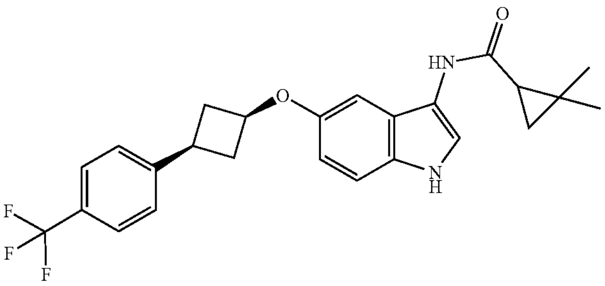 [SMILES: CC1(C)CC1C(=O)Nc1c[nH]c2ccc(O[C@H]3C[C@@H](c4ccc(C(F)(F)F)cc4)C3)cc12]

2.2-dimethyl-N-(5-(cis-3-(4-(trifluoromethyl)phenyl)cyclobutoxy)-1H-indol-3-yl)cyclopropane-1-carboxamide -continued

360

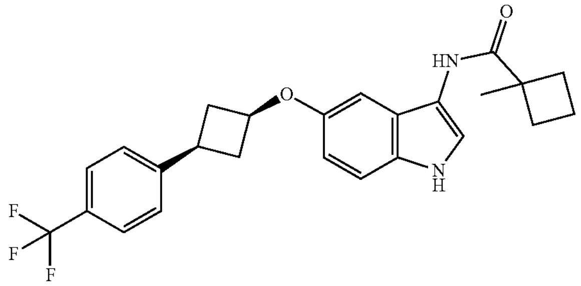 [SMILES: CC1(C(=O)Nc2c[nH]c3ccc(O[C@H]4C[C@@H](c5ccc(C(F)(F)F)cc5)C4)cc23)CCC1]

1-methyl-N-(5-(cis-3-(4-(trifluoromethyl)phenyl)cyclobutoxy)-1H-indol-3-yl)cyclobutane-1-carboxamide

361

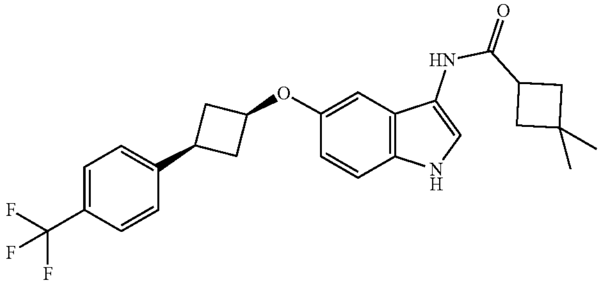 [SMILES: CC1(C)CC(C(=O)Nc2c[nH]c3ccc(O[C@H]4C[C@@H](c5ccc(C(F)(F)F)cc5)C4)cc23)C1]

3,3-dimethyl-N-(5-(cis-3-(4-(trifluoromethyl)phenyl)cyclobutoxy)-1H-indol-3-yl)cyclobutane-1-carboxamide

362

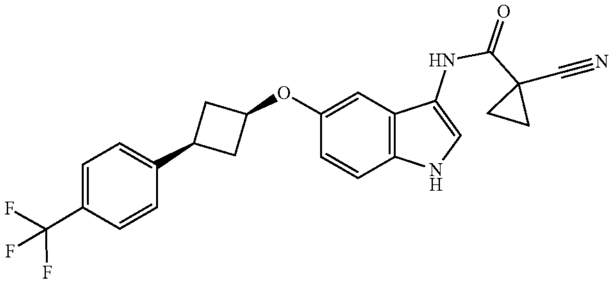 [SMILES: N#CC1(C(=O)Nc2c[nH]c3ccc(O[C@H]4C[C@@H](c5ccc(C(F)(F)F)cc5)C4)cc23)CC1]

1-cyano-N-(5-(cis-3-(4-(trifluoromethyl)phenyl)cyclobutoxy)-1H-indol-3-yl)cyclopropane-1-carboxamide

363

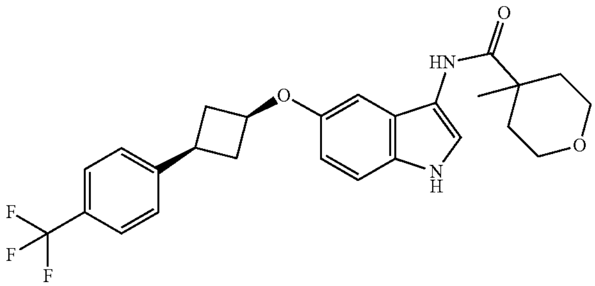 [SMILES: CC1(C(=O)Nc2c[nH]c3ccc(O[C@H]4C[C@@H](c5ccc(C(F)(F)F)cc5)C4)cc23)CCOCC1]

4-methyl-N-(5-(cis-3-(4-(trifluoromethyl)phenyl)cyclobutoxy)-1H-indol-3-yl)tetrahydro-2H-pyran-4-carboxamide -continued

364

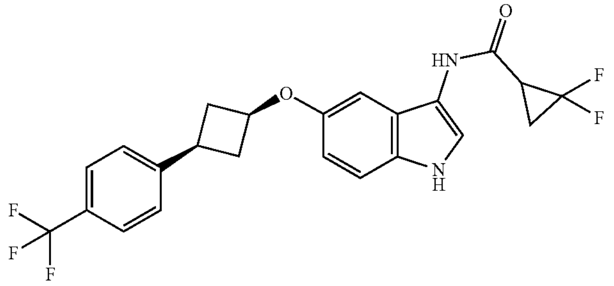 [SMILES: O=C(Nc1c[nH]c2ccc(O[C@H]3C[C@@H](c4ccc(C(F)(F)F)cc4)C3)cc12)C1CC1(F)F]

2,2-difluoro-N-(5-(cis-3-(4-(trifluoromethyl)phenyl)cyclobutoxy)-1H-indol-3-yl)cyclopropane-1-carboxamide

365

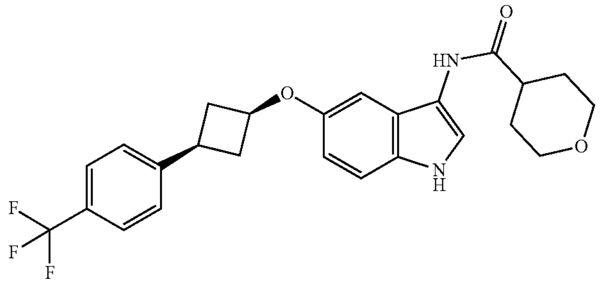 [SMILES: O=C(Nc1c[nH]c2ccc(O[C@H]3C[C@@H](c4ccc(C(F)(F)F)cc4)C3)cc12)C1CCOCC1]

N-(5-(cis-3-(4-(trifluoromethyl)phenyl)cyclobutoxy)-1H-indol-3-yl)tetrahydro-2H-pyran-4-carboxamide

366

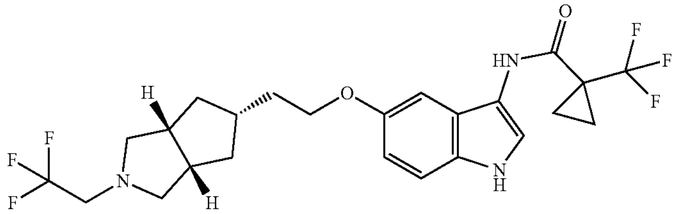 [SMILES: O=C(Nc1c[nH]c2ccc(OCC[C@@H]3C[C@@H]4CN(CC(F)(F)F)C[C@@H]4C3)cc12)C1(C(F)(F)F)CC1]

N-(5-(2-((3aR,5r,6aS)-2-(2,2,2-trifluoroethyl)octahydrocyclopenta[c]pyrrol-5-yl)ethoxy)-1H-indol-3-yl)-1-(trifluoromethyl)cyclopropane-1-carboxamide

367

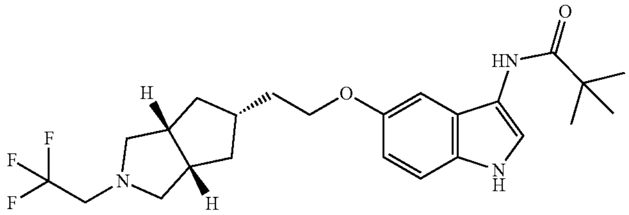 [SMILES: CC(C)(C)C(=O)Nc1c[nH]c2ccc(OCC[C@@H]3C[C@@H]4CN(CC(F)(F)F)C[C@@H]4C3)cc12]

N-(5-(2-((3aR,5r,6aS)-2-(2,2,2-trifluoroethyl)octahydrocyclopenta[c]pyrrol-5-yl)ethoxy)-1H-indol-3-yl)pivalamide

368

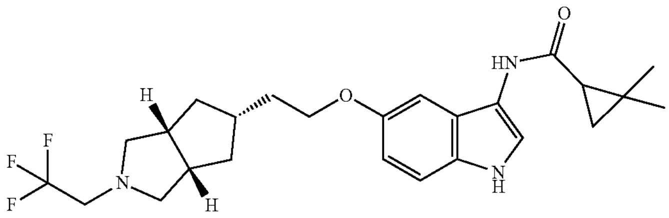 [SMILES: CC1(C)CC1C(=O)Nc1c[nH]c2ccc(OCC[C@@H]3C[C@@H]4CN(CC(F)(F)F)C[C@@H]4C3)cc12]

-continued 2,2-dimethyl-N-(5-(2-((3aR,5r,6aS)-2-(2,2,2-trifluoroethyl)octahydrocyclopenta[c]pyrrol-5-yl)ethoxy) 1H-indol-3-yl)cyclopropane-1-carboxamide

369

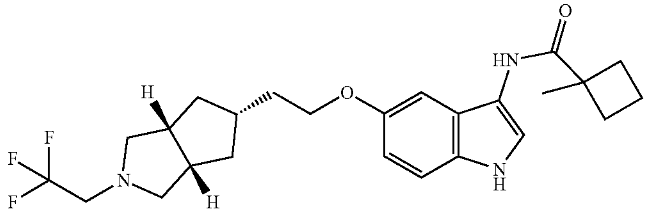 [SMILES: CC1(C(=O)Nc2c[nH]c3ccc(OCC[C@@H]4C[C@@H]5CN(CC(F)(F)F)C[C@@H]5C4)cc23)CCC1]

1-methyl-N-(5-(2-((3aR,5r,6aS)-2-(2,2,2-trifluoroethyl)octahydrocyclopenta[c]pyrrol-5-yl)ethoxy)-1H-indol-3-yl)cyclobutane-1-carboxamide

370

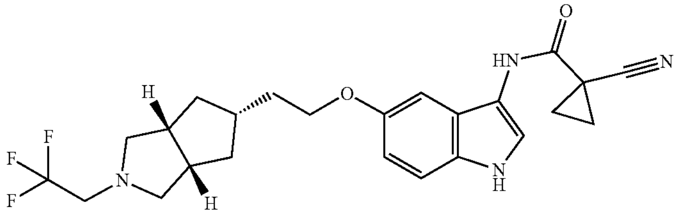 [SMILES: N#CC1(C(=O)Nc2c[nH]c3ccc(OCC[C@@H]4C[C@@H]5CN(CC(F)(F)F)C[C@@H]5C4)cc23)CC1]

1-cyano-N-(5-(2-((3aR,5r,6aS)-2-(2,2,2-trifluoroethyl)octahydrocyclopenta[c]pyrrol-5-yl)ethoxy)-1H-indol-3-yl)cyclopropane-1-carboxamide

371

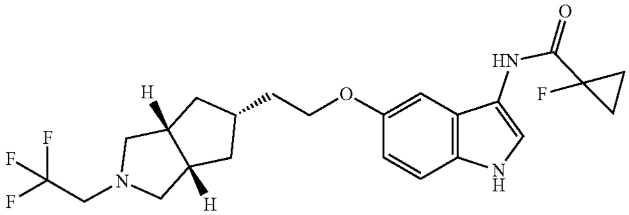 [SMILES: O=C(Nc1c[nH]c2ccc(OCC[C@@H]3C[C@@H]4CN(CC(F)(F)F)C[C@@H]4C3)cc12)C1(F)CC1]

1-fluoro-N-(5-(2-((3aR,5r,6aS)-2-(2,2,2-trifluoroethyl)octahydrocyclopenta[c]pyrrol-5-yl)ethoxy)-1H-indol-3-yl)cyclopropane-1-carboxamide

372

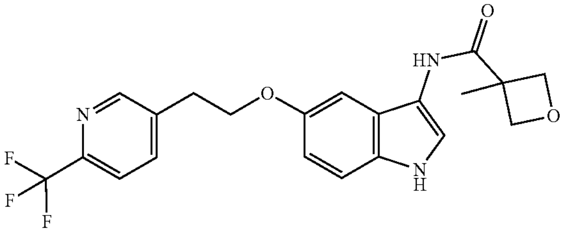 [SMILES: CC1(C(=O)Nc2c[nH]c3ccc(OCCc4ccc(C(F)(F)F)nc4)cc23)COC1]

3-methyl-N-(5-(2-(6-(trifluoromethyl)pyridin-3-yl)ethoxy)-1H-indol-3-yl)oxetane-3-carboxamide

373

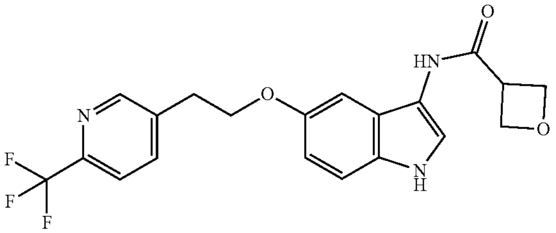 [SMILES: O=C(Nc1c[nH]c2ccc(OCCc3ccc(C(F)(F)F)nc3)cc12)C1COC1]

N-(5-(2-(6-(trifluoromethyl)pyridin-3-yl)ethoxy)-1H-indol-3-yl)oxetane-3-carboxamide -continued

374

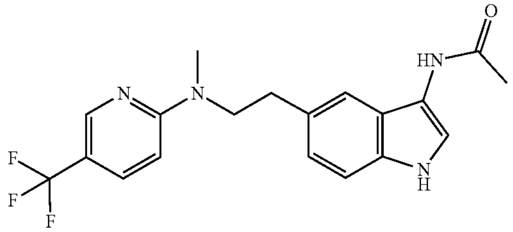 [SMILES: CC(=O)Nc1c[nH]c2ccc(CCN(C)c3ccc(C(F)(F)F)cn3)cc12]

N-(5-(2-(methyl(5-(trifluoromethyl)pyridin-2-yl)amino)ethyl)-1H-indol-3-yl)acetamide

375

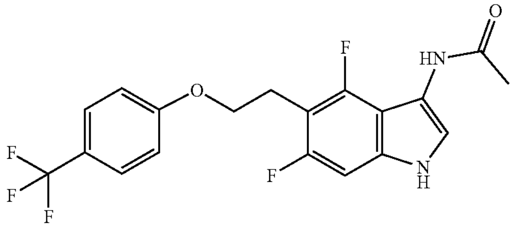 [SMILES: CC(=O)Nc1c[nH]c2cc(F)c(CCOc3ccc(C(F)(F)F)cc3)c(F)c12]

N-(4,6-difluoro-5-(2-(4-(trifluoromethyl)phenoxy)ethyl)-1H-indol-3-yl)acetamide

376

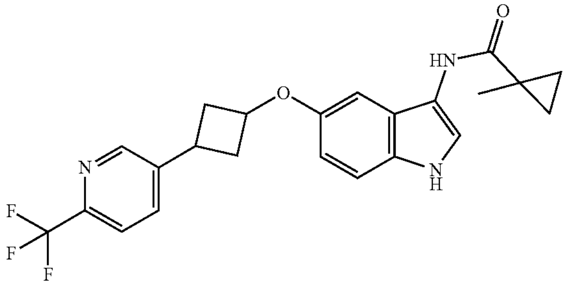 [SMILES: CC1(C(=O)Nc2c[nH]c3ccc(OC4CC(c5ccc(C(F)(F)F)nc5)C4)cc23)CC1]

1-methyl-N-(5-(3-(6-(trifluoromethyl)pyridin-3-yl)cyclobutoxy)-1H-indol-3-yl)cyclopropane-1-carboxamide

377

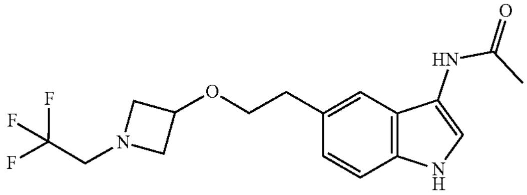 [SMILES: CC(=O)Nc1c[nH]c2ccc(CCOC3CN(CC(F)(F)F)C3)cc12]

N-(5-(2-((1-(2,2,2-trifluoroethyl)azetidin-3-yl)oxy)ethyl)-1H-indol-3-yl)acetamide

378

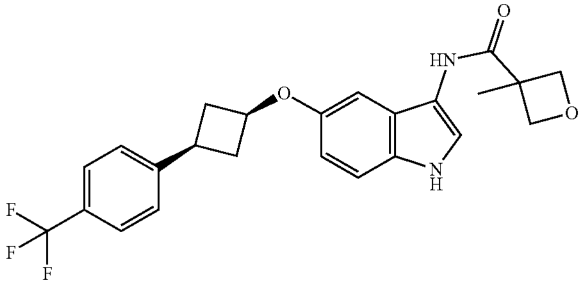 [SMILES: CC1(C(=O)Nc2c[nH]c3ccc(O[C@H]4C[C@@H](c5ccc(C(F)(F)F)cc5)C4)cc23)COC1]

3-methyl-N-(5-(cis-3-(4-(trifluoromethyl)phenyl)cyclobutoxy)-1H-indol-3-yl)oxetane-3-carboxamide -continued

379

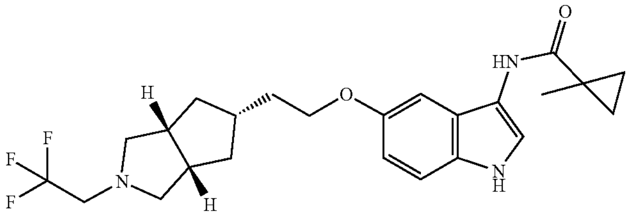 [SMILES: CC1(C(=O)Nc2c[nH]c3ccc(OCC[C@@H]4C[C@@H]5CN(CC(F)(F)F)C[C@@H]5C4)cc23)CC1]

1-methyl-N-(5-(2-((3aR,5r,6aS)-2-(2,2,2-trifluoroethyl)octahydrocyclopenta[c]pyrrol-5-yl)ethoxy)-1H-indol-3-yl)cyclopropane-1-carboxamide

380

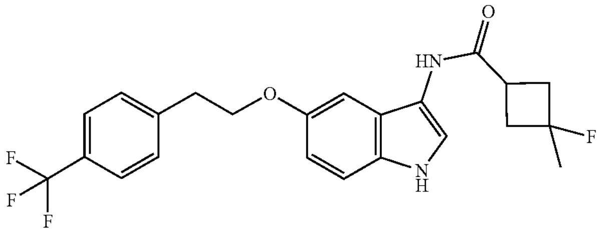 [SMILES: CC1(F)CC(C(=O)Nc2c[nH]c3ccc(OCCc4ccc(C(F)(F)F)cc4)cc23)C1]

3-fluoro-3-methyl-N-(5-(4-(trifluoromethyl)phenethoxy)-1H-indol-3-yl)cyclobutane-1-carboxamide

381

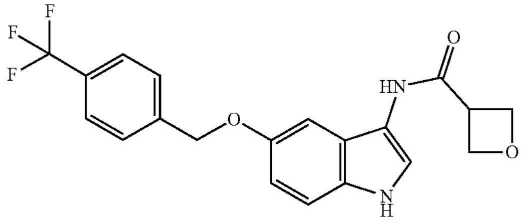 [SMILES: O=C(Nc1c[nH]c2ccc(OCc3ccc(C(F)(F)F)cc3)cc12)C1COC1]

N-(5-((4-(trifluoromethyl)benzyl)oxy)-1H-indol-3-yl)oxetane-3-carboxamide

382

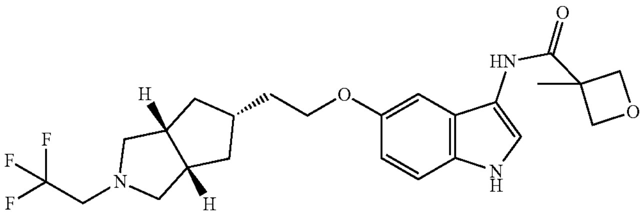 [SMILES: CC1(C(=O)Nc2c[nH]c3ccc(OCC[C@@H]4C[C@@H]5CN(CC(F)(F)F)C[C@@H]5C4)cc23)COC1]

3-methyl-N-(5-(2-((3aR,5r,6aS)-2-(2,2,2-trifluoroethyl)octahydrocyclopenta[c]pyrrol-5-yl)ethoxy)-1H-indol-3-yl)oxetane-3-carboxamide

383

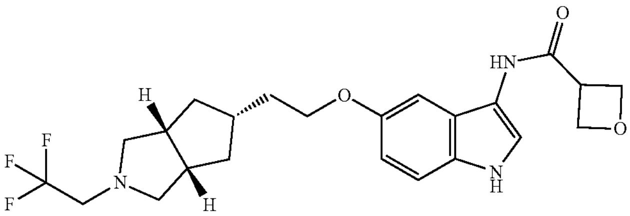 [SMILES: O=C(Nc1c[nH]c2ccc(OCC[C@@H]3C[C@@H]4CN(CC(F)(F)F)C[C@@H]4C3)cc12)C1COC1]

N-(5-(2-((3aR,5r,6aS)-2-(2,2,2-trifluoroethyl)octahydrocyclopenta[c]pyrrol-5-yl)ethoxy)-1H-indol-3-yl)oxetane-3-carboxamide -continued

384

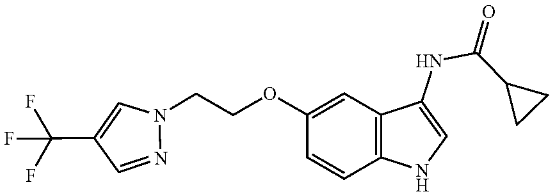 [SMILES: O=C(Nc1c[nH]c2ccc(OCCn3cc(C(F)(F)F)cn3)cc12)C1CC1]

N-(5-(3-(4-(trifluoromethyl)-1H-pyrazol-1-yl)propyl)-1H-indol-3-yl)cyclopropanecarboxamide

385

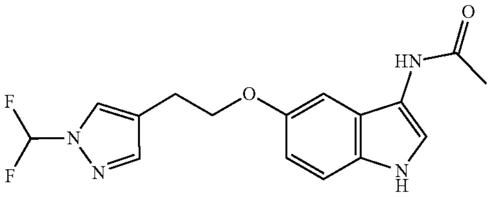 [SMILES: CC(=O)Nc1c[nH]c2ccc(OCCc3cnn(C(F)F)c3)cc12]

N-(5-(2-(1-(difluoromethyl)-1H-pyrazol-4-yl)ethoxy)-1H-indol-3-yl)acetamide

386

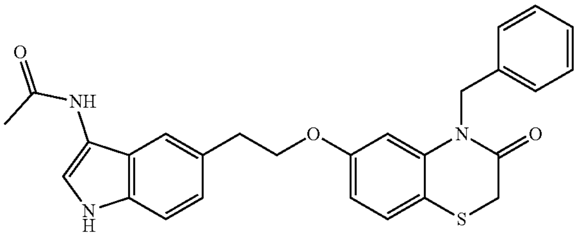 [SMILES: CC(=O)Nc1c[nH]c2ccc(CCOc3ccc4c(c3)N(Cc3ccccc3)C(=O)CS4)cc12]

N-(5-(2-((4-benzyl-3-oxo-3,4-dihydro-2H-benzo[b][1,4]thiazin-6-yl)oxy)ethyl)-1H-indol-3-yl)acetamide

387

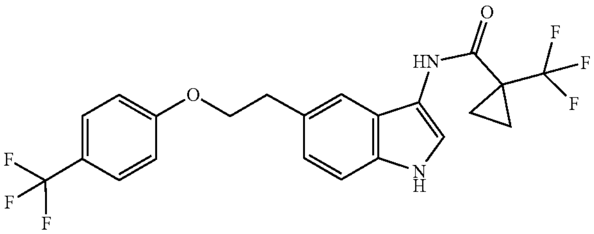 [SMILES: O=C(Nc1c[nH]c2ccc(CCOc3ccc(C(F)(F)F)cc3)cc12)C1(C(F)(F)F)CC1]

1-(trifluoromethyl)-N-(5-(2-(4-(trifluoromethyl)phenoxy)ethyl)-1H-indol-3-yl)cyclopropane-1-carboxamide

388

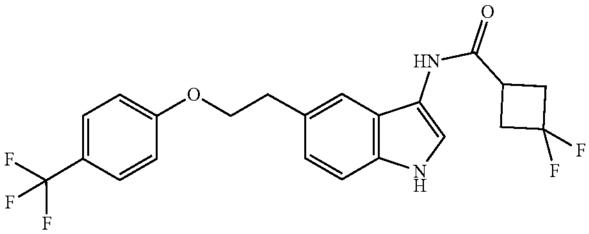 [SMILES: O=C(Nc1c[nH]c2ccc(CCOc3ccc(C(F)(F)F)cc3)cc12)C1CC(F)(F)C1]

3,3-difluoro-N-(5-(2-(4-(trifluoromethyl)phenoxy)ethyl)-1H-indol-3-yl)cyclobutane-1-carboxamide -continued

389

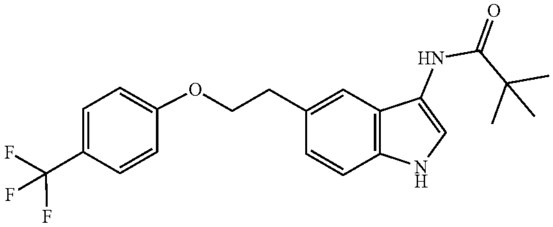 [SMILES: CC(C)(C)C(=O)Nc1c[nH]c2ccc(CCOc3ccc(C(F)(F)F)cc3)cc12]

N-(5-(2-(4-(trifluoromethyl)phenoxy)ethyl)-1H-indol-3-y1)pivalamide

390

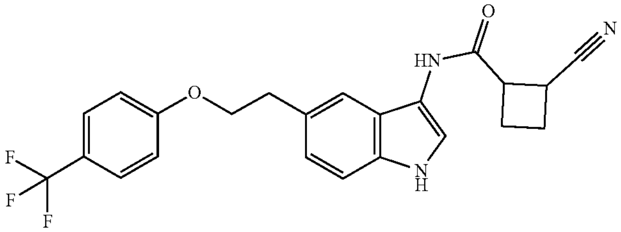 [SMILES: N#CC1CCC1C(=O)Nc1c[nH]c2ccc(CCOc3ccc(C(F)(F)F)cc3)cc12]

2-cyano-N-(5-(2-(4-(trifluoromethyl)phenoxy)ethyl)-1H-indol-3-y1)cyclobutane-1-carboxamide

391

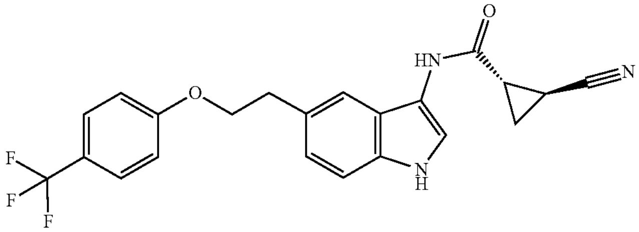 [SMILES: N#C[C@H]1C[C@@H]1C(=O)Nc1c[nH]c2ccc(CCOc3ccc(C(F)(F)F)cc3)cc12]

(1S,2S)-2-cyano-N-(5-(2-(4-(trifluoromethyl)phenoxy)ethyl)-1H-indol-3-yl)cyclopropane-1-carboxamide

392

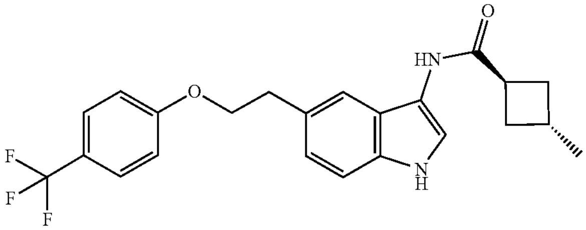 [SMILES: C[C@H]1C[C@H](C(=O)Nc2c[nH]c3ccc(CCOc4ccc(C(F)(F)F)cc4)cc23)C1]

trans-3-methyl-N-(5-(2-(4-(trifluoromethyl)phenoxy)ethyl)-1H-indol-3-y1)cyclobutane-1-carboxamide

393

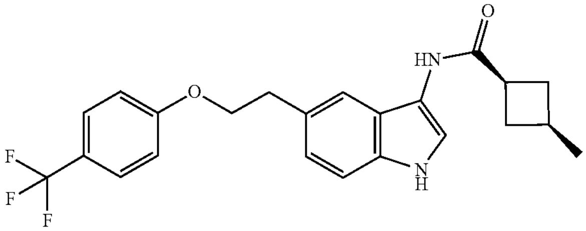 [SMILES: C[C@H]1C[C@@H](C(=O)Nc2c[nH]c3ccc(CCOc4ccc(C(F)(F)F)cc4)cc23)C1]

cis-3-methyl-N-(5-(2-(4-(trifluoromethyl)phenoxy)ethyl)-1H-indol-3-y1)cyclobutane-1-carboxamide -continued

394

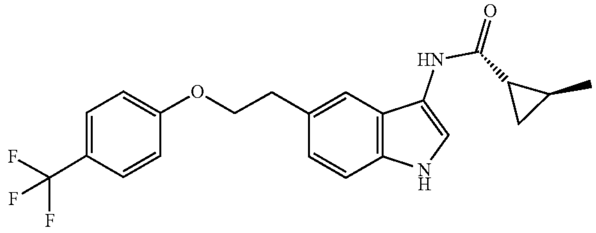

(1S,2S)-2-methyl-N-(5-(2-(4-(trifluoromethyl)phenoxy)ethyl)-1H-indol-3-yl)cyclopropane-1-carboxamide

395

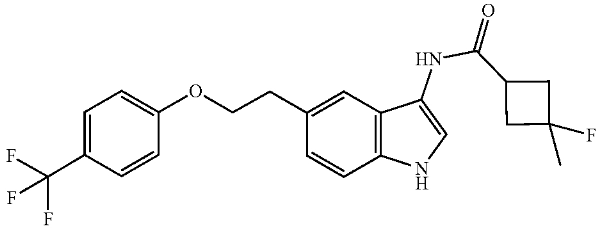 [SMILES: CC1(F)CC(C(=O)Nc2c[nH]c3ccc(CCOc4ccc(C(F)(F)F)cc4)cc23)C1]

3-fluoro-3-methyl-N-(5-(2-(4-(trifluoromethyl)phenoxy)ethyl)-1H-indol-3-yl)cyclobutane-1-carboxamide

396

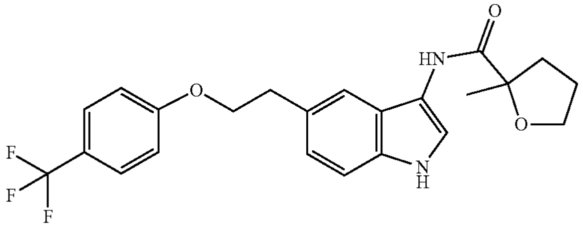 [SMILES: CC1(C(=O)Nc2c[nH]c3ccc(CCOc4ccc(C(F)(F)F)cc4)cc23)CCCO1]

2-methyl-N-(5-(2-(4-(trifluoromethyl)phenoxy)ethyl)-1H-indol-3-yl)tetrahydrofuran-2-carboxamide

397

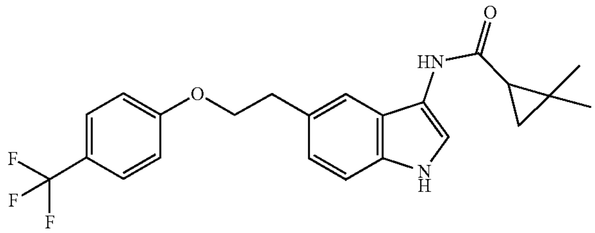 [SMILES: CC1(C)CC1C(=O)Nc1c[nH]c2ccc(CCOc3ccc(C(F)(F)F)cc3)cc12]

2,2-dimethyl-N-(5-(2-(4-(trifluoromethyl)phenoxy)ethyl)-1H-indol-3-yl)cyclopropane-1-carboxamide

398

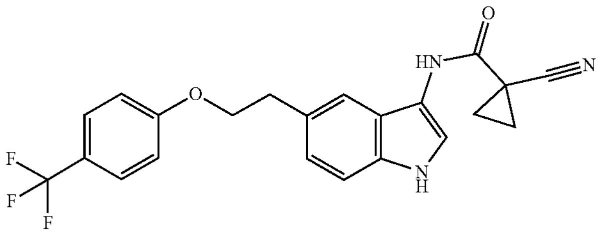 [SMILES: N#CC1(C(=O)Nc2c[nH]c3ccc(CCOc4ccc(C(F)(F)F)cc4)cc23)CC1]

1-cyano-N-(5-(2-(4-(trifluoromethyl)phenoxy)ethyl)-1H-indol-3-yl)cyclopropane-1-carboxamide -continued

399

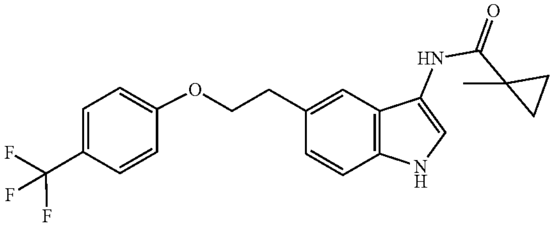

1-methyl-N-(5-(2-(4-(trifluoromethyl)phenoxy)ethyl)-1H-indol-3-yl)cyclopropane-1-carboxamide

400

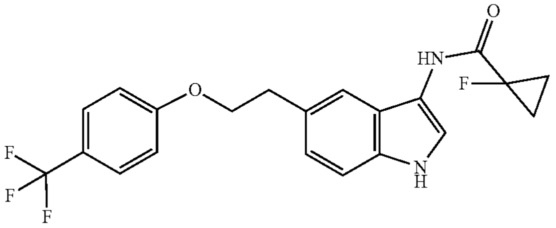 [SMILES: O=C(Nc1c[nH]c2ccc(CCOc3ccc(C(F)(F)F)cc3)cc12)C1(F)CC1]

1-fluoro-N-(5-(2-(4-(trifluoromethyl)phenoxy)ethyl)-1H-indol-3-yl)cyclopropane-1-carboxamide

401

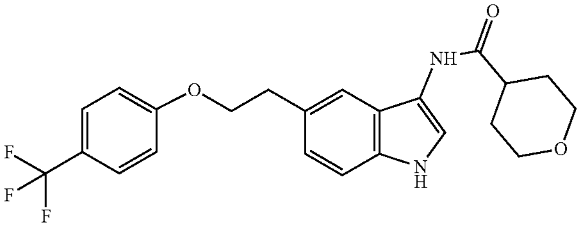 [SMILES: O=C(Nc1c[nH]c2ccc(CCOc3ccc(C(F)(F)F)cc3)cc12)C1CCOCC1]

N-(5-(2-(4-(trifluoromethyl)phenoxy)ethyl)-1H-indol-3-yl)tetrahydro-2H-pyran-4-carboxamide

402

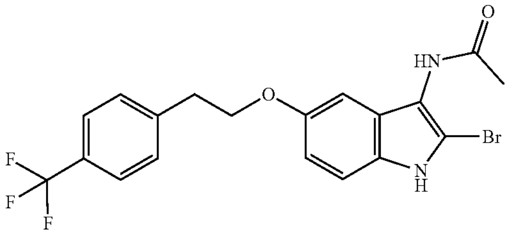 [SMILES: CC(=O)Nc1c(Br)[nH]c2ccc(OCCc3ccc(C(F)(F)F)cc3)cc12]

N-(2-bromo-5-(4-(trifluoromethyl)phenethoxy)-1H-indol-3-yl)acetamide

404

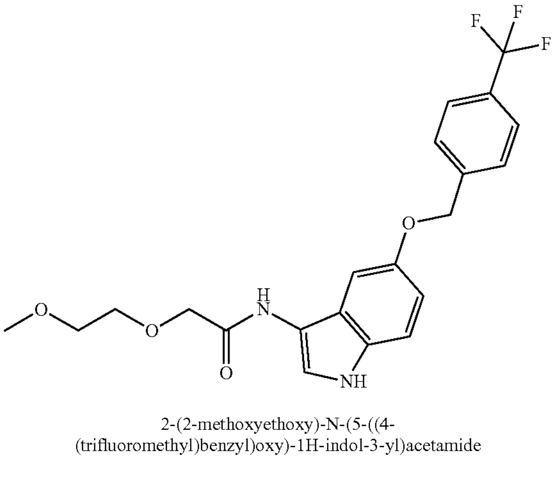

2-(2-methoxyethoxy)-N-(5-((4-(trifluoromethyl)benzyl)oxy)-1H-indol-3-yl)acetamide -continued
405
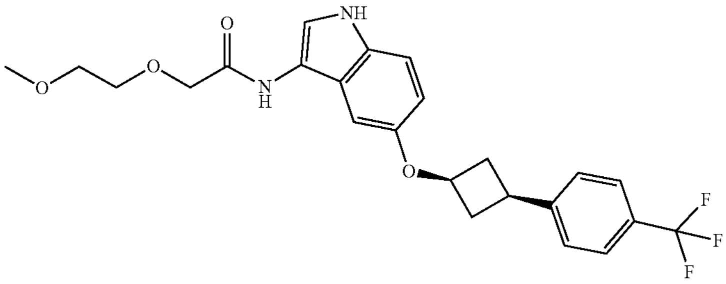 [SMILES: COCCOCC(=O)Nc1c[nH]c2ccc(O[C@H]3C[C@@H](c4ccc(C(F)(F)F)cc4)C3)cc12]
2-(2-methoxyethoxy)-N-(5-(cis-3-(4-(trifluoromethyl)phenyl)cyclobutoxy)-1H-indol-3-yl)acetamide
406
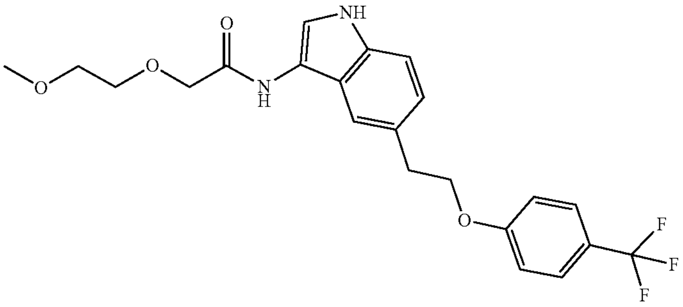 [SMILES: COCCOCC(=O)Nc1c[nH]c2ccc(CCOc3ccc(C(F)(F)F)cc3)cc12]
2-(2-methoxyethoxy)-N-(5-(2-(4-(trifluoromethyl)phenoxy)ethyl)-1H-indol-3-yl)acetamide
407
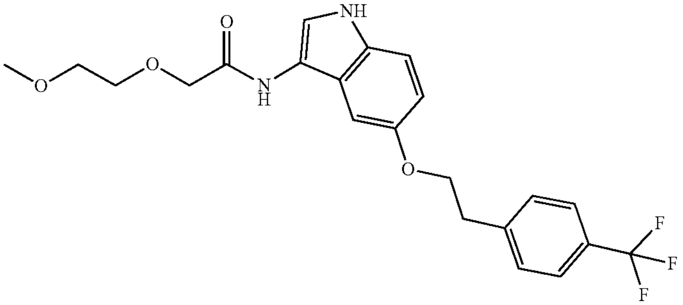
2-(2-methoxyethoxy)-N-(5-(4-(trifluoromethyl)phenethoxy)-1H-indol-3-yl)acetamide
408
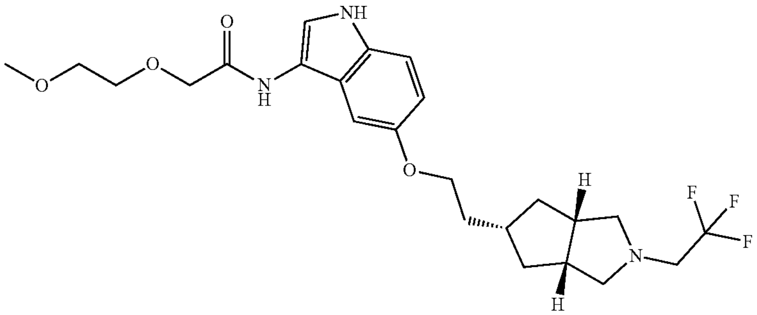 [SMILES: COCCOCC(=O)Nc1c[nH]c2ccc(OCC[C@@H]3C[C@@H]4CN(CC(F)(F)F)C[C@@H]4C3)cc12]
2-(2-methoxyethoxy)-N-(5-(2-((3aR,5r,6aS)-2-(2,2,2-trifluoroethyl)octahydrocyclopenta[c]pyrrol-5-yl)ethoxy)-1H-indol-3-yl)acetamide -continued

409

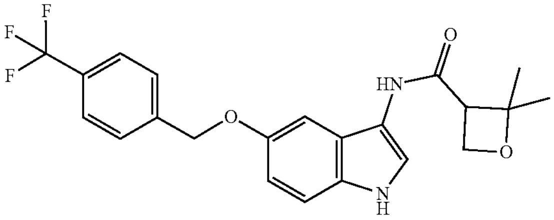 [SMILES: CC1(C)OCC1C(=O)Nc1c[nH]c2ccc(OCc3ccc(C(F)(F)F)cc3)cc12]

2,2-dimethyl-N-(5-((4-(trifluoromethyl)benzyl)oxy)-1H-indol-3-yl)oxetane-3-carboxamide

410

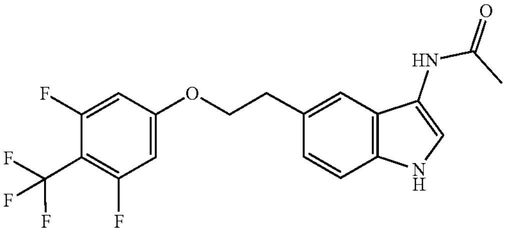 [SMILES: CC(=O)Nc1c[nH]c2ccc(CCOc3cc(F)c(C(F)(F)F)c(F)c3)cc12]

N-(5-(2-(3,5-difluoro-4-(trifluoromethyl)phenoxy)ethyl)-1H-indol-3-y1)acetamide

411

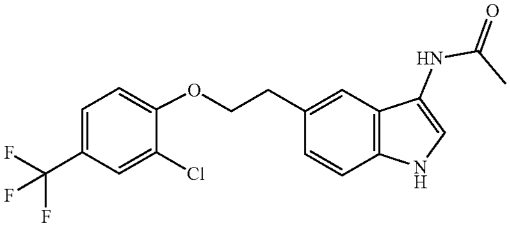 [SMILES: CC(=O)Nc1c[nH]c2ccc(CCOc3ccc(C(F)(F)F)cc3Cl)cc12]

N-(5-(2-(2-chloro-4-(trifluoromethyl)phenoxy)ethyl)-1H-indol-3-yl)acetamide

412

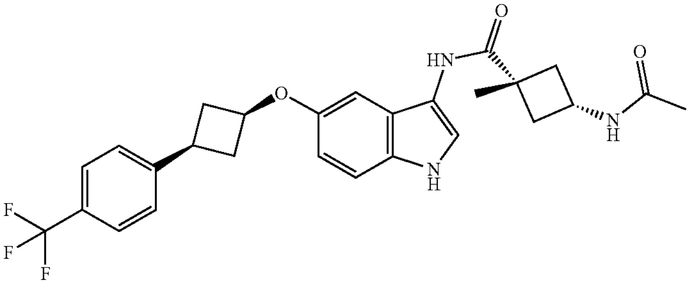 [SMILES: CC(=O)N[C@H]1C[C@@](C)(C(=O)Nc2c[nH]c3ccc(O[C@H]4C[C@@H](c5ccc(C(F)(F)F)cc5)C4)cc23)C1]

cis-3-acetamido-1-methyl-N-(5-(cis-3-(4-(trifluoromethyl)phenyl)cyclobutoxy)-1H-indol-3-y1)cyclobutane-1-carboxamide

413

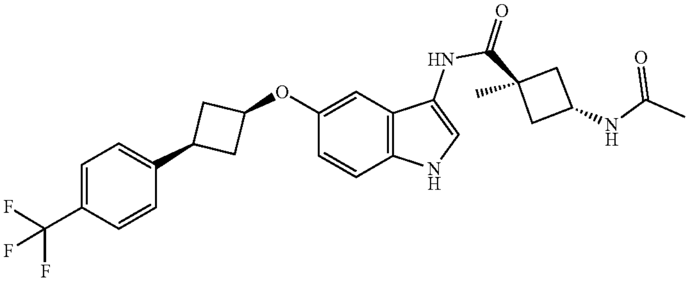 [SMILES: CC(=O)N[C@H]1C[C@](C)(C(=O)Nc2c[nH]c3ccc(O[C@H]4C[C@@H](c5ccc(C(F)(F)F)cc5)C4)cc23)C1]

trans-3-acetamido-1-methyl-N-(5-(cis-3-(4-(trifluoromethyl)phenyl)cyclobutoxy)-1H-indol-3-y1)cyclobutane-1-carboxamide -continued

414

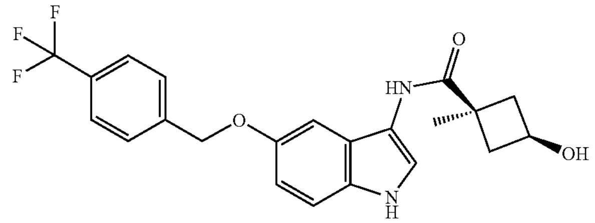 [SMILES: C[C@]1(C(=O)Nc2c[nH]c3ccc(OCc4ccc(C(F)(F)F)cc4)cc23)C[C@@H](O)C1]

cis-3-hydroxy-1-methyl-N-(5-((4-(trifluoromethyl)benzyl)oxy)-1H-indol-3-yl)cyclobutane-1-carboxamide

415

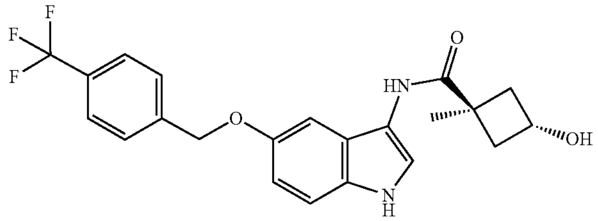 [SMILES: C[C@]1(C(=O)Nc2c[nH]c3ccc(OCc4ccc(C(F)(F)F)cc4)cc23)C[C@H](O)C1]

trans-3-hydroxy-1-methyl-N-(5-((4-(trifluoromethyl)benzyl)oxy)-1H-indol-3-yl)cyclobutane-1-carboxamide

416

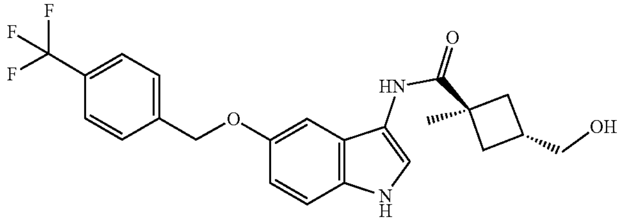 [SMILES: C[C@]1(C(=O)Nc2c[nH]c3ccc(OCc4ccc(C(F)(F)F)cc4)cc23)C[C@H](CO)C1]

trans-3-(hydroxymethyl)-1-methyl-N-(5-((4-(trifluoromethyl)benzyl)oxy)-1H-indol-3-yl)cyclobutane-1-carboxamide

417

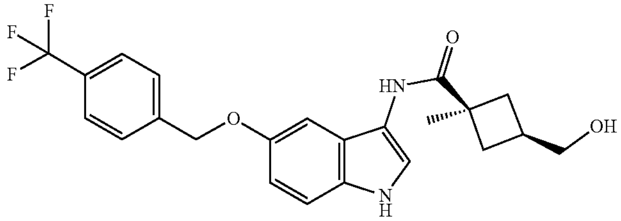 [SMILES: C[C@]1(C(=O)Nc2c[nH]c3ccc(OCc4ccc(C(F)(F)F)cc4)cc23)C[C@@H](CO)C1]

cis-3-(hydroxymethyl)-1-methyl-N-(5-((4-(trifluoromethyl)benzyl)oxy)-1H-indol-3-yl)cyclobutane-1-carboxamide

418

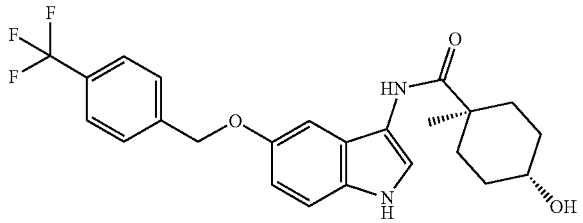 [SMILES: C[C@]1(C(=O)Nc2c[nH]c3ccc(OCc4ccc(C(F)(F)F)cc4)cc23)CC[C@H](O)CC1]

trans-4-hydroxy-1-methyl-N-(5-((4-(trifluoromethyl)benzyl)oxy)-1H-indol-3-yl)cyclohexane-1-carboxamide -continued

419

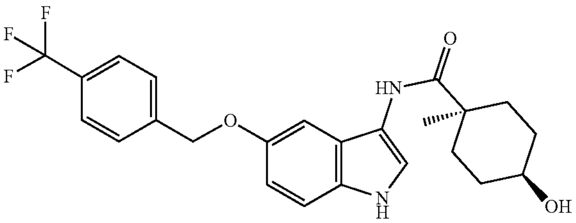 [SMILES: C[C@]1(C(=O)Nc2c[nH]c3ccc(OCc4ccc(C(F)(F)F)cc4)cc23)CC[C@@H](O)CC1]

trans-4-hydroxy-1-methyl-N-(5-((4-(trifluoromethyl)benzyl)oxy)-1H-indol-3-yl)cyclohexane-1-carboxamide

420

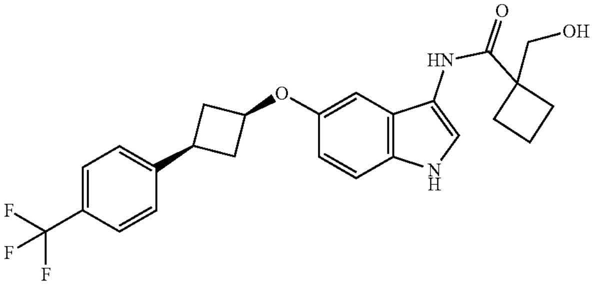 [SMILES: O=C(Nc1c[nH]c2ccc(O[C@H]3C[C@@H](c4ccc(C(F)(F)F)cc4)C3)cc12)C1(CO)CCC1]

1-(hydroxymethyl)-N-(5-(cis-3-(4-(trifluoromethyl)phenyl)cyclobutoxy)-1H-indol-3-yl)cyclobutane-1-carboxamide

421

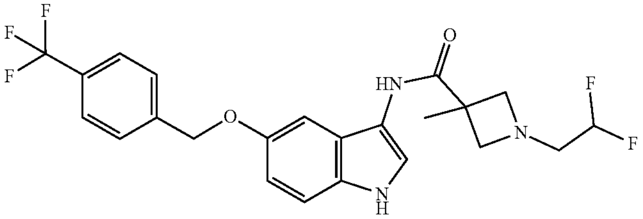 [SMILES: CC1(C(=O)Nc2c[nH]c3ccc(OCc4ccc(C(F)(F)F)cc4)cc23)CN(CC(F)F)C1]

1-(2,2-difluoroethyl)-3-methyl-N-(5-((4-(trifluoromethyl)benzyl)oxy)-1H-indol-3-yl)azetidine-3-carboxamide

422

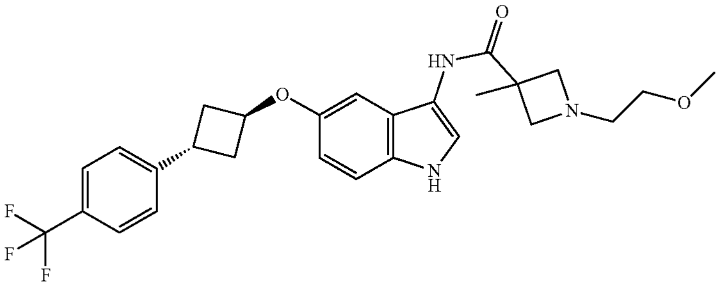 [SMILES: COCCN1CC(C)(C(=O)Nc2c[nH]c3ccc(O[C@H]4C[C@H](c5ccc(C(F)(F)F)cc5)C4)cc23)C1]

1-(2-methoxyethyl)-3-methyl-N-(5-(cis-3-(4-(trifluoromethyl)phenyl)cyclobutoxy)-1H-indol-3-yl)azetidine-3-carboxamide -continued

423

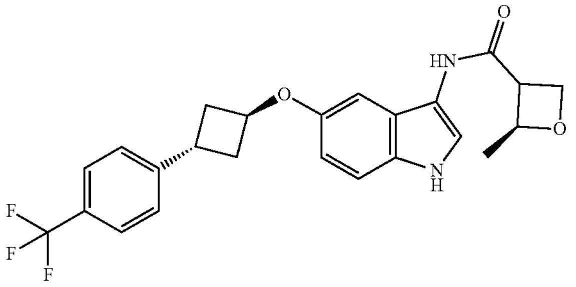 [SMILES: C[C@@H]1OCC1C(=O)Nc1c[nH]c2ccc(O[C@H]3C[C@H](c4ccc(C(F)(F)F)cc4)C3)cc12]

(2S,3R)-2-methyl-N-(5-(trans-3-(4-(trifluoromethyl)phenyl)cyclobutoxy)-1H-indol-3-yl)oxetane-3-carboxamide

424

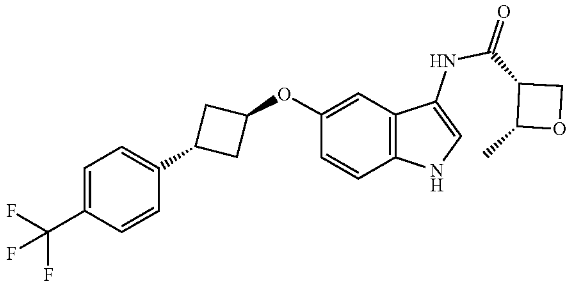 [SMILES: C[C@H]1OC[C@H]1C(=O)Nc1c[nH]c2ccc(O[C@H]3C[C@H](c4ccc(C(F)(F)F)cc4)C3)cc12]

(2R,3R)-2-methyl-N-(5-(trans-3-(4-(trifluoromethyl)phenyl)cyclobutoxy)-1H-indol-3-yl)oxetane-3-carboxamide

425

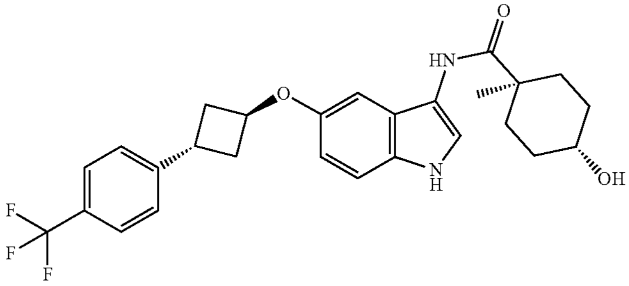 [SMILES: C[C@]1(C(=O)Nc2c[nH]c3ccc(O[C@H]4C[C@H](c5ccc(C(F)(F)F)cc5)C4)cc23)CC[C@H](O)CC1]

trans-4-hydroxy-1-methyl-N-(5-(trans-3-(4-(trifluoromethyl)phenyl)cyclobutoxy)-1H-indol-3-yl)cyclohexane-1-carboxamide

426

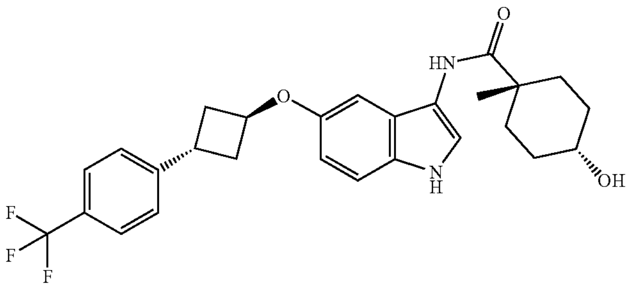 [SMILES: C[C@]1(C(=O)Nc2c[nH]c3ccc(O[C@H]4C[C@H](c5ccc(C(F)(F)F)cc5)C4)cc23)CC[C@@H](O)CC1]

cis-4-hydroxy-1-methyl-N-(5-(trans-3-(4-(trifluoromethyl)phenyl)cyclobutoxy)-1H-indol-3-yl)cyclohexane-1-carboxamide -continued

427

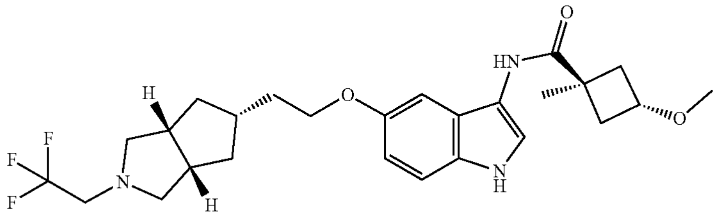 [SMILES: CO[C@H]1C[C@](C)(C(=O)Nc2c[nH]c3ccc(OCC[C@@H]4C[C@@H]5CN(CC(F)(F)F)C[C@@H]5C4)cc23)C1]

(1r,3R)-3-methoxy-1-methyl-N-(5-(2-((3aR,5r,6aS)-2-(2,2,2-trifluoroethyl)octahydrocyclopenta[c]pyrrol-5-yl)ethoxy)-1H-indol-3-yl)cyclobutane-1-carboxamide

428

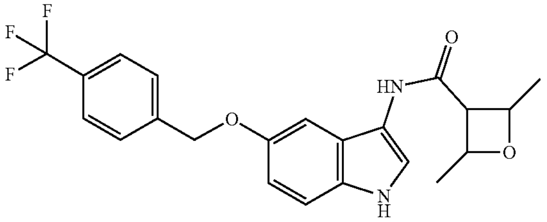 [SMILES: CC1OC(C)C1C(=O)Nc1c[nH]c2ccc(OCc3ccc(C(F)(F)F)cc3)cc12]

2.4-dimethyl-N-(5-((4-(trifluoromethyl)benzyl)oxy)-1H-indol-3-yl)oxetane-3-carboxamide

429

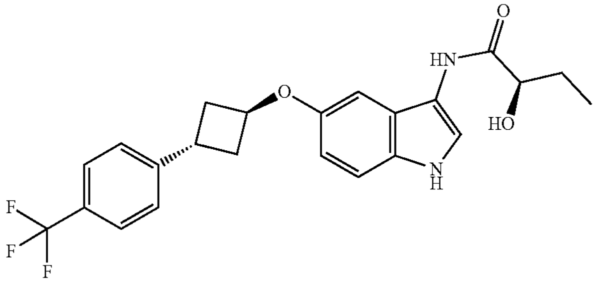 [SMILES: CC[C@@H](O)C(=O)Nc1c[nH]c2ccc(O[C@H]3C[C@H](c4ccc(C(F)(F)F)cc4)C3)cc12]

(R)-2-hydroxy-N-(5-(trans-3-(4-(trifluoromethyl)phenyl)cyclobutoxy)-1H-indol-3-yl)butanamide

430

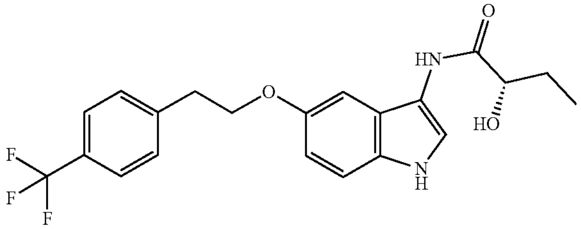 [SMILES: CC[C@H](O)C(=O)Nc1c[nH]c2ccc(OCCc3ccc(C(F)(F)F)cc3)cc12]

(S)-2-hydroxy-N-(5-(4-(trifluoromethyl)phenethoxy)-1H-indol-3-yl)butanamide

431

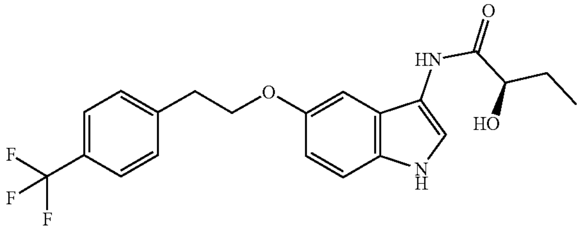 [SMILES: CC[C@@H](O)C(=O)Nc1c[nH]c2ccc(OCCc3ccc(C(F)(F)F)cc3)cc12]

(R)-2-hydroxy-N-(5-(4-(trifluoromethyl)phenethoxy)-1H-indol-3-yl)butanamide

-continued

432

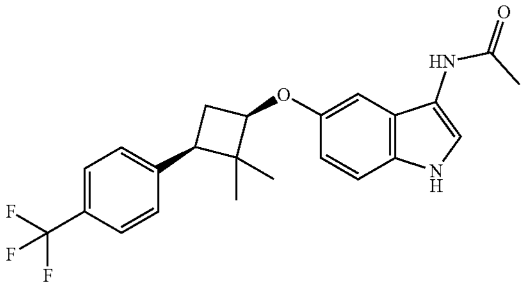 [SMILES: CC(=O)Nc1c[nH]c2ccc(O[C@@H]3C[C@H](c4ccc(C(F)(F)F)cc4)C3(C)C)cc12]

N-(5-((1R,3R)-2,2-dimethyl-3-(4-(trifluoromethyl)phenyl)cyclobutoxy)-1H-indol-3-yl)acetamide

433

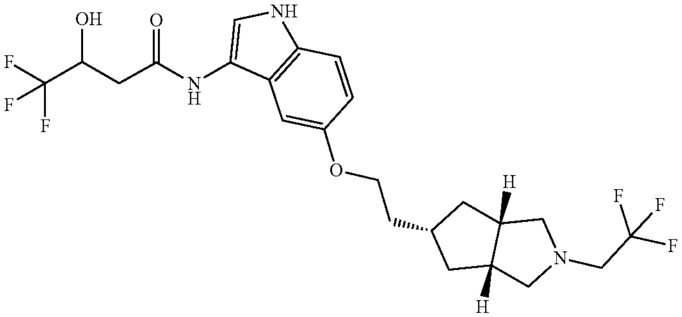 [SMILES: O=C(CC(O)C(F)(F)F)Nc1c[nH]c2ccc(OCC[C@@H]3C[C@@H]4CN(CC(F)(F)F)C[C@@H]4C3)cc12]

4,4,4-trifluoro-3-hydroxy-N-(5-(2-((3aR,5r,6aS)-2-(2,2,2-trifluoroethyl)octahydrocyclopenta[c]pyrrol-5-yl)ethoxy)-1H-indol-3-yl)butanamide

434

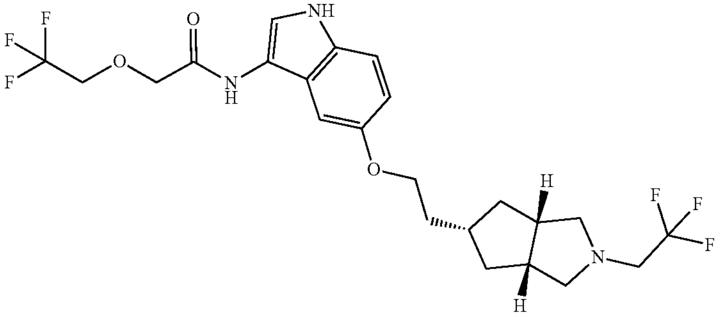 [SMILES: O=C(COCC(F)(F)F)Nc1c[nH]c2ccc(OCC[C@@H]3C[C@@H]4CN(CC(F)(F)F)C[C@@H]4C3)cc12]

2-(2,2,2-trifluoroethoxy)-N-(5-(2-((3aR,5r,6aS)-2-(2,2,2-trifluoroethyl)octahydrocyclopenta[c]pyrrol-5-yl)ethoxy)-1H-indol-3-yl)acetamide

435

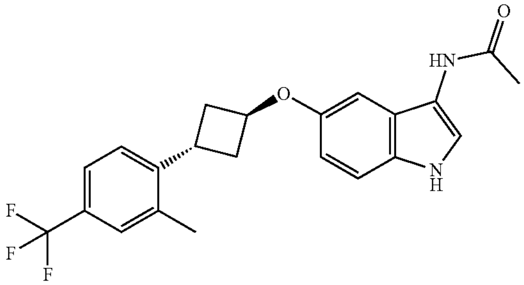 [SMILES: CC(=O)Nc1c[nH]c2ccc(O[C@H]3C[C@H](c4ccc(C(F)(F)F)cc4C)C3)cc12]

N-(5-(trans-3-(2-methyl-4-(trifluoromethyl)phenyl)cyclobutoxy)-1H-indol-3-yl)acetamide -continued
436
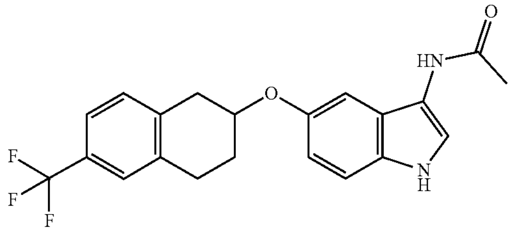 [SMILES: CC(=O)Nc1c[nH]c2ccc(OC3CCc4cc(C(F)(F)F)ccc4C3)cc12]
N-(5-((6-(trifluoromethyl)-1,2,3,4-tetrahydronaphthalen-2-yl)oxy)-1H-indol-3-yl)acetamide
437
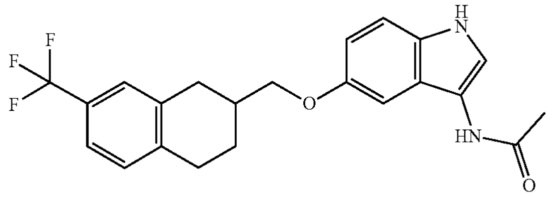 [SMILES: CC(=O)Nc1c[nH]c2ccc(OCC3CCc4ccc(C(F)(F)F)cc4C3)cc12]
N-(5-((7-(trifluoromethyl)-1,2,3,4-tetrahydronaphthalen-2-yl)methoxy)-1H-indol-3-yl)acetamide
438
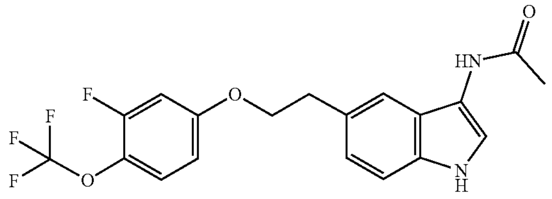 [SMILES: CC(=O)Nc1c[nH]c2ccc(CCOc3ccc(OC(F)(F)F)c(F)c3)cc12]
N-(5-(2-(3-fluoro-4-(trifluoromethoxy)phenoxy)ethyl)-1H-indol-3-yl)acetamide
439
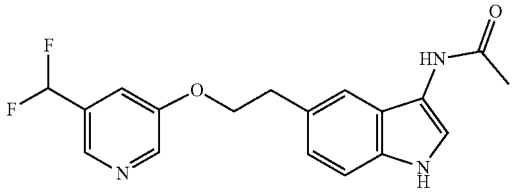 [SMILES: CC(=O)Nc1c[nH]c2ccc(CCOc3cncc(C(F)F)c3)cc12]
N-(5-(2-((5-(difluoromethyl)pyridin-3-yl)oxy)ethyl)-1H-indol-3-yl)acetamide
440
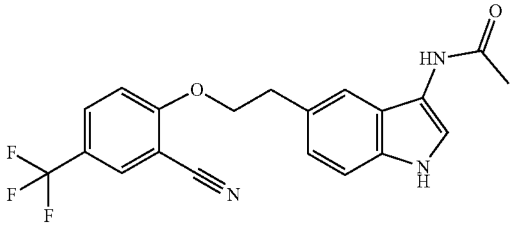 [SMILES: CC(=O)Nc1c[nH]c2ccc(CCOc3ccc(C(F)(F)F)cc3C#N)cc12]
N-(5-(2-(2-cyano-4-(trifluoromethyl)phenoxy)ethyl)-1H-indol-3-yl)acetamide
441
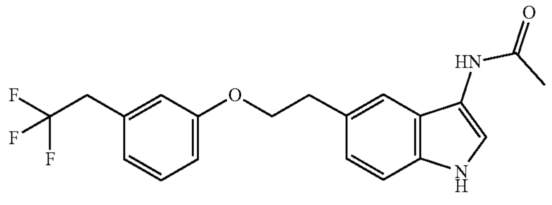 [SMILES: CC(=O)Nc1c[nH]c2ccc(CCOc3cccc(CC(F)(F)F)c3)cc12]

-continued

N-(5-(2-(3-(2,2,2-trifluoroethyl)phenoxy)ethyl)-1H-indol-3-yl)acetamide

442

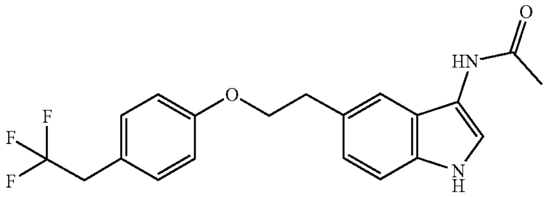 [SMILES: CC(=O)Nc1c[nH]c2ccc(CCOc3ccc(CC(F)(F)F)cc3)cc12]

N-(5-(2-(4-(2,2,2-trifluoroethyl)phenoxy)ethyl)-1H-indol-3-yl)acetamide

443

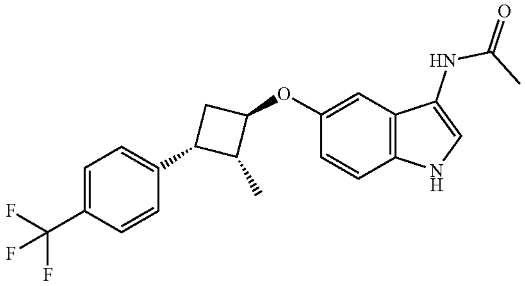 [SMILES: CC(=O)Nc1c[nH]c2ccc(O[C@@H]3C[C@@H](c4ccc(C(F)(F)F)cc4)[C@H]3C)cc12]

N-(5-((1R,2R,3R)-2-methyl-3-(4-(trifluoromethyl)phenyl)cyclobutoxy)-1H-indol-3-yl)acetamide

444

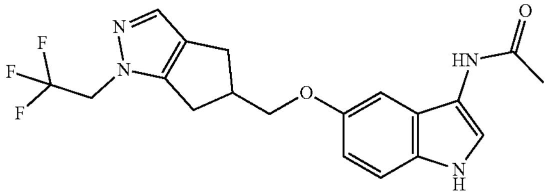 [SMILES: CC(=O)Nc1c[nH]c2ccc(OCC3Cc4cnn(CC(F)(F)F)c4C3)cc12]

N-(5-((1-(2,2,2-trifluoroethyl)-1,4,5,6-tetrahydrocyclopenta[c]pyrazol-5-yl)methoxy)-1H-indol-3-yl)acetamide

445

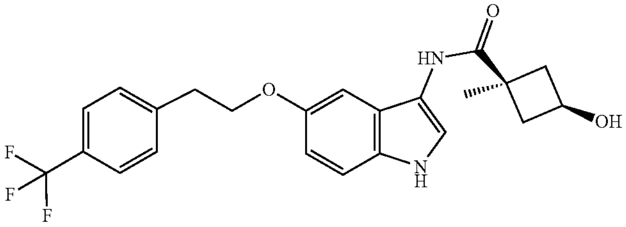 [SMILES: C[C@]1(C(=O)Nc2c[nH]c3ccc(OCCc4ccc(C(F)(F)F)cc4)cc23)C[C@@H](O)C1]

(cis)-3-hydroxy-1-methyl-N-(5-(4-(trifluoromethyl)phenethoxy)-1H-indol-3-yl)cyclobutane-1-carboxamide

446

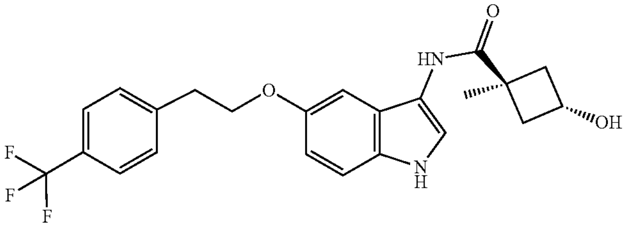 [SMILES: C[C@]1(C(=O)Nc2c[nH]c3ccc(OCCc4ccc(C(F)(F)F)cc4)cc23)C[C@H](O)C1]

trans-3-hydroxy-1-methyl-N-(5-(4-(trifluoromethyl)phenethoxy)-1H-indol-3-yl)cyclobutane-1-carboxamide -continued
447
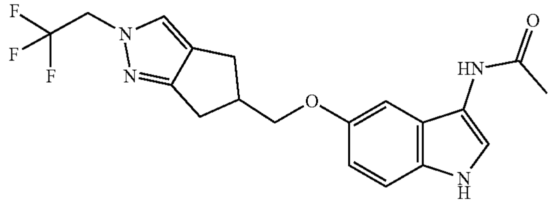 [SMILES: CC(=O)Nc1c[nH]c2ccc(OCC3Cc4cn(CC(F)(F)F)nc4C3)cc12]
N-(5-((2-(2,2,2-trifluoroethyl)-2,4,5,6-tetrahydrocyclopenta[c]pyrazol-5-yl)methoxy)-1H-indol-3-yl)acetamide
448
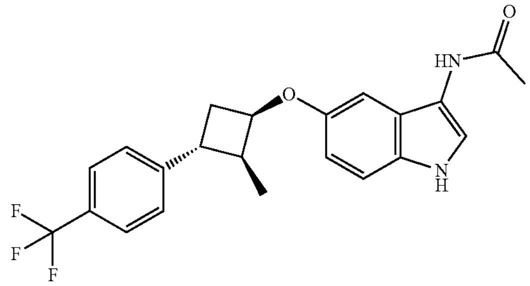 [SMILES: CC(=O)Nc1c[nH]c2ccc(O[C@@H]3C[C@@H](c4ccc(C(F)(F)F)cc4)[C@@H]3C)cc12]
N-(5-((1R,2S,3R)-2-methyl-3-(4-(trifluoromethyl)phenyl)cyclobutoxy)-1H-indol-3-yl)acetamide
449
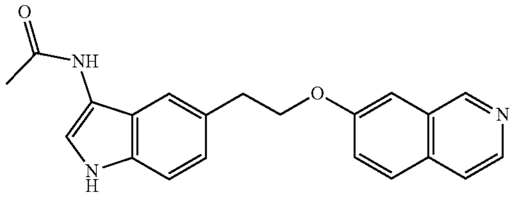 [SMILES: CC(=O)Nc1c[nH]c2ccc(CCOc3ccc4ccncc4c3)cc12]
N-(5-(2-(isoquinolin-7-yloxy)ethyl)-1H-indol-3-yl)acetamide
450
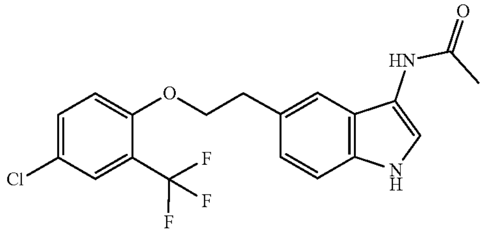 [SMILES: CC(=O)Nc1c[nH]c2ccc(CCOc3ccc(Cl)cc3C(F)(F)F)cc12]
N-(5-(2-(4-chloro-2-(trifluoromethyl)phenoxy)ethyl)-1H-indol-3-yl)acetamide
451
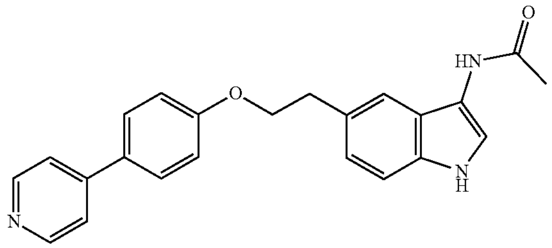 [SMILES: CC(=O)Nc1c[nH]c2ccc(CCOc3ccc(-c4ccncc4)cc3)cc12]
N-(5-(2-(4-(pyridin-4-yl)phenoxy)ethyl)-1H-indol-3-yl)acetamide -continued
452
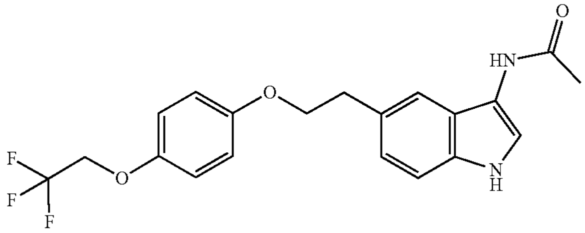 [SMILES: CC(=O)Nc1c[nH]c2ccc(CCOc3ccc(OCC(F)(F)F)cc3)cc12]
N-(5-(2-(4-(2.2,2-trifluoroethoxy)phenoxy)ethyl)-1H-indol-3-y1)acetamide
453
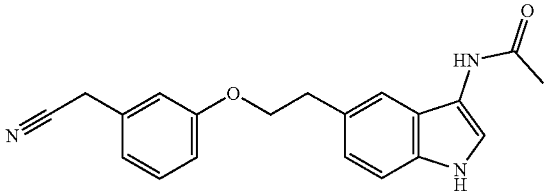 [SMILES: CC(=O)Nc1c[nH]c2ccc(CCOc3cccc(CC#N)c3)cc12]
N-(5-(2-(3-(cyanomethyl)phenoxy)ethyl)-1H-indol-3-y1)acetamide
454
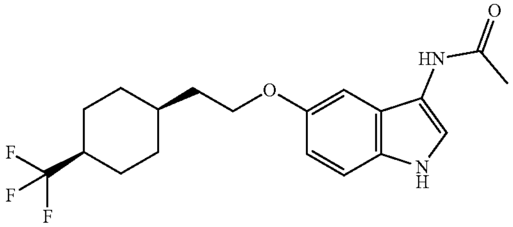 [SMILES: CC(=O)Nc1c[nH]c2ccc(OCC[C@H]3CC[C@@H](C(F)(F)F)CC3)cc12]
N-(5-(2-(cis-4-(trifluoromethyl)cyclohexyl)ethoxy)-1H-indol-3-y1)acetamide
455
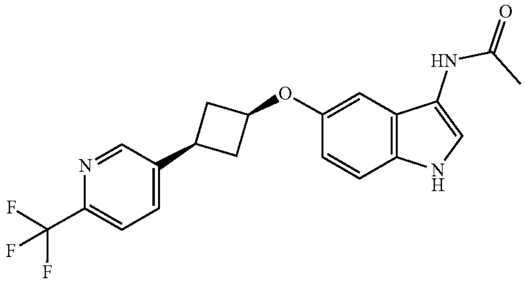 [SMILES: CC(=O)Nc1c[nH]c2ccc(O[C@H]3C[C@@H](c4ccc(C(F)(F)F)nc4)C3)cc12]
N-(5-(cis-3-(6-(trifluoromethyl)pyridin-3-yl)cyclobutoxy)-1H-indol-3-yl)acetamide
456
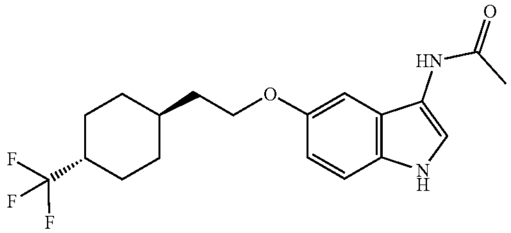 [SMILES: CC(=O)Nc1c[nH]c2ccc(OCC[C@H]3CC[C@H](C(F)(F)F)CC3)cc12]
N-(5-(2-(trans-4-(trifluoromethyl)cyclohexyl)ethoxy)-1H-indol-3-y1)acetamide -continued
457
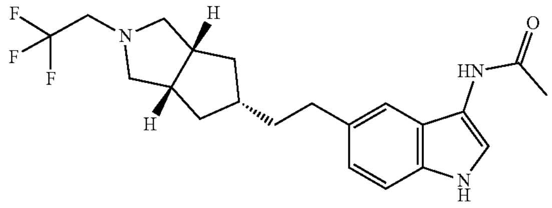 [SMILES: CC(=O)Nc1c[nH]c2ccc(CC[C@@H]3C[C@@H]4CN(CC(F)(F)F)C[C@@H]4C3)cc12]
N-(5-(2-((3aR,5r,6aS)-2-(2,2,2-trifluoroethyl)octahydrocyclopenta[c]pyrrol-5-yl)ethyl)-1H-indol-3-y1)acetamide
458
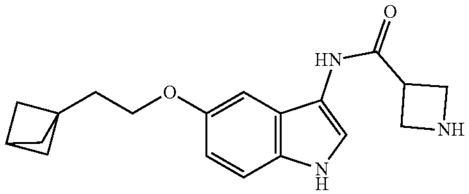 [SMILES: O=C(Nc1c[nH]c2ccc(OCCC34CC(C3)C4)cc12)C1CNC1]
N-(5-(2-(bicyclo[1.1.1]pentan-1-yl)ethoxy)-1H-indol-3-y1)acetamide
459
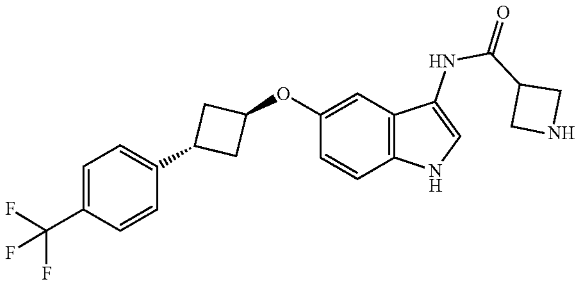 [SMILES: O=C(Nc1c[nH]c2ccc(O[C@H]3C[C@H](c4ccc(C(F)(F)F)cc4)C3)cc12)C1CNC1]
N-(5-(trans-3-(4-(trifluoromethyl)phenyl)cyclobutoxy)-1H-indol-3-y1)azetidine-3-carboxamide
460
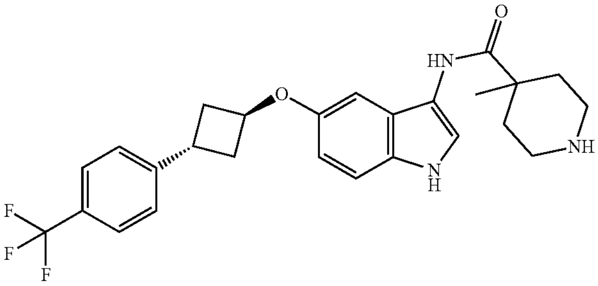 [SMILES: CC1(C(=O)Nc2c[nH]c3ccc(O[C@H]4C[C@H](c5ccc(C(F)(F)F)cc5)C4)cc23)CCNCC1]
4-methyl-N-(5-(trans-3-(4-(trifluoromethyl)phenyl)cyclobutoxy)-1H-indol-3-y1)piperidine-4-carboxamide
461
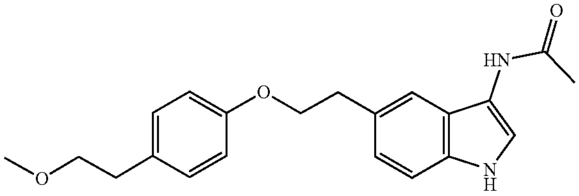 [SMILES: COCCc1ccc(OCCc2ccc3[nH]cc(NC(C)=O)c3c2)cc1]
N-(5-(2-(4-(2-methoxyethyl)phenoxy)ethyl)-1H-indol-3-yl)acetamide -continued

462

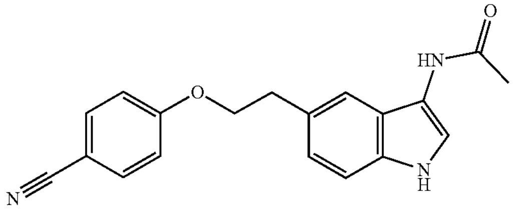 [SMILES: CC(=O)Nc1c[nH]c2ccc(CCOc3ccc(C#N)cc3)cc12]

N-(5-(2-(4-cyanophenoxy)ethyl)-1H-indol-3-yl)acetamide

463

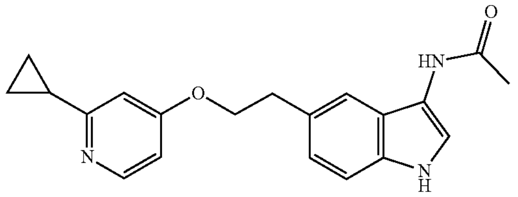 [SMILES: CC(=O)Nc1c[nH]c2ccc(CCOc3ccnc(C4CC4)c3)cc12]

N-(5-(2-((2-cyclopropylpyridin-4-yl)oxy)ethyl)-1H-indol-3-yl)acetamide

464

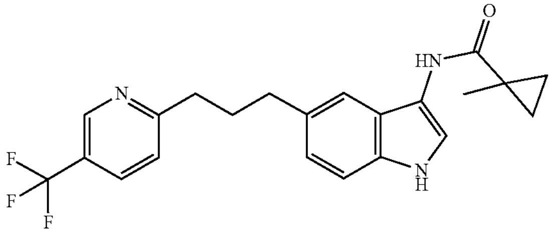 [SMILES: CC1(C(=O)Nc2c[nH]c3ccc(CCCc4ccc(C(F)(F)F)cn4)cc23)CC1]

1-methyl-N-(5-(3-(5-(trifluoromethyl)pyridin-2-yl)propyl)-1H-indol-3-yl)cyclopropane-1-carboxamide

465

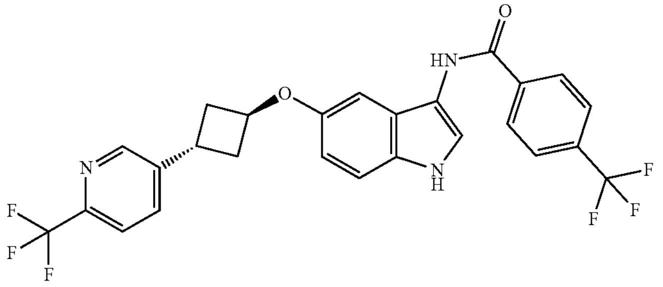 [SMILES: O=C(Nc1c[nH]c2ccc(O[C@H]3C[C@H](c4ccc(C(F)(F)F)nc4)C3)cc12)c1ccc(C(F)(F)F)cc1]

4-(trifluoromethyl)-N-(5-(trans-3-(6-(trifluoromethyl)pyridin-3-yl)cyclobutoxy)-1H-indol-3-yl)benzamide

466

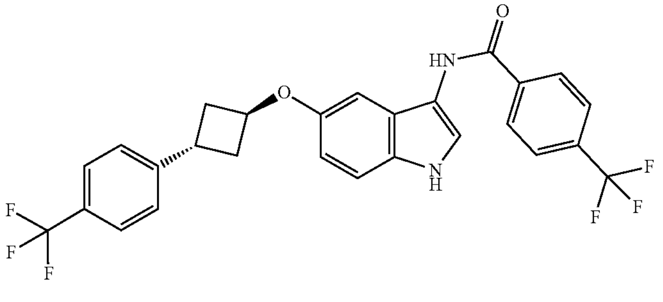 [SMILES: O=C(Nc1c[nH]c2ccc(O[C@H]3C[C@H](c4ccc(C(F)(F)F)cc4)C3)cc12)c1ccc(C(F)(F)F)cc1]

tert-butyl 3-((5-(trans-3-(4-(trifluoromethyl)phenyl)cyclobutoxy)-1H-indol-3-yl)carbamoyl)azetidine-1-carboxylate -continued

467

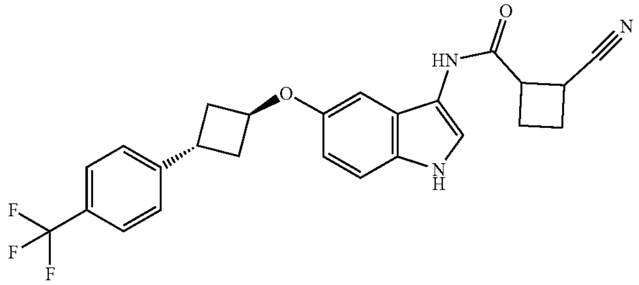 [SMILES: N#CC1CCC1C(=O)Nc1c[nH]c2ccc(O[C@H]3C[C@H](c4ccc(C(F)(F)F)cc4)C3)cc12]

2-cyano-N-(5-(trans-3-(4-(trifluoromethyl)phenyl)cyclobutoxy)-1H-indol-3-yl)cyclobutane-1-carboxamide

468

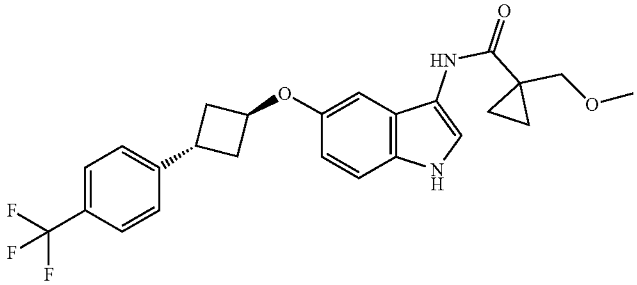 [SMILES: COCC1(C(=O)Nc2c[nH]c3ccc(O[C@H]4C[C@H](c5ccc(C(F)(F)F)cc5)C4)cc23)CC1]

1-(methoxymethyl)-N-(5-(trans-3-(4-(trifluoromethyl)phenyl)cyclobutoxy)-1H-indol-3-yl)cyclopropane-1-carboxamide

469

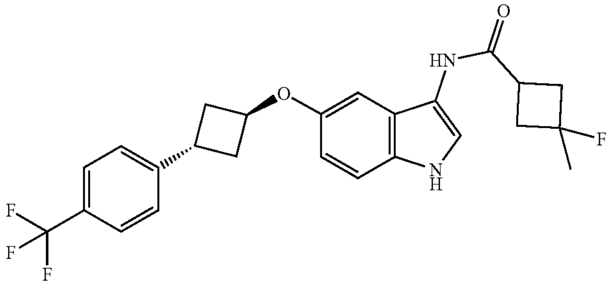 [SMILES: CC1(F)CC(C(=O)Nc2c[nH]c3ccc(O[C@H]4C[C@H](c5ccc(C(F)(F)F)cc5)C4)cc23)C1]

3-fluoro-3-methyl-N-(5-(trans-3-(4-(trifluoromethyl)phenyl)cyclobutoxy)-1H-indol-3-yl)cyclobutane-1-carboxamide

470

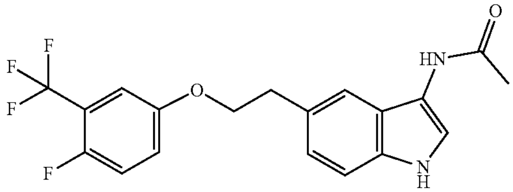 [SMILES: CC(=O)Nc1c[nH]c2ccc(CCOc3ccc(F)c(C(F)(F)F)c3)cc12]

N-(5-(2-(4-fluoro-3-(trifluoromethyl)phenoxy)ethyl)-1H-indol-3-yl)acetamide

471

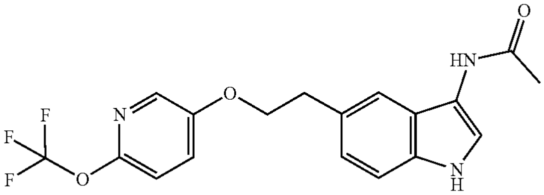 [SMILES: CC(=O)Nc1c[nH]c2ccc(CCOc3ccc(OC(F)(F)F)nc3)cc12]

N-(5-(2-((6-(trifluoromethoxy)pyridin-3-yl)oxy)ethyl)-1H-indol-3-yl)acetamide

-continued
472
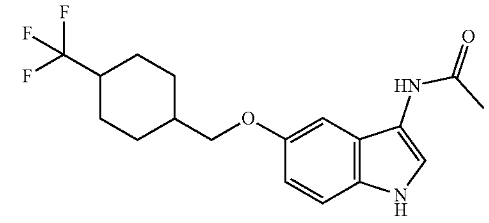 [SMILES: CC(=O)Nc1c[nH]c2ccc(OCC3CCC(C(F)(F)F)CC3)cc12]
N-(5-((4-(trifluoromethyl)cyclohexyl)methoxy)-1H-indol-3-yl)acetamide
473
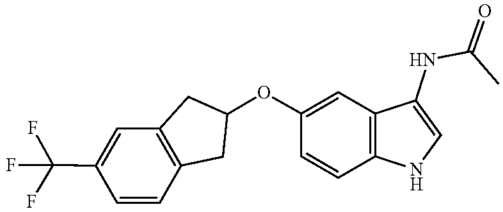 [SMILES: CC(=O)Nc1c[nH]c2ccc(OC3Cc4ccc(C(F)(F)F)cc4C3)cc12]
N-(5-((5-(trifluoromethyl)-2,3-dihydro-1H-inden-2-yl)oxy)-1H-indol-3-yl)acetamide
474
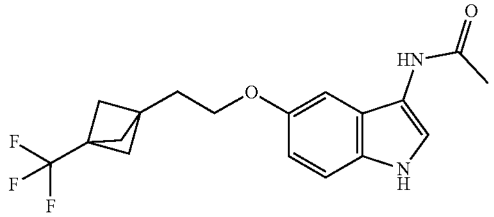 [SMILES: CC(=O)Nc1c[nH]c2ccc(OCCC34CC(C(F)(F)F)(C3)C4)cc12]
N-(5-(2-(3-(trifluoromethyl)bicyclo[ 1.1. 1]pentan-1-yl)ethoxy)-1H-indol-3-yl)acetamide
475
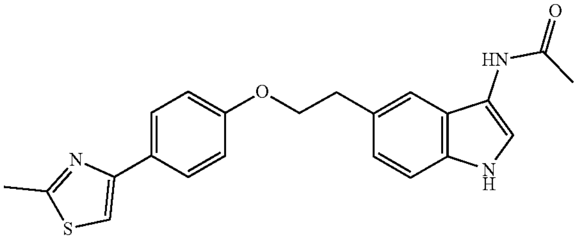 [SMILES: CC(=O)Nc1c[nH]c2ccc(CCOc3ccc(-c4csc(C)n4)cc3)cc12]
N-(5-(2-(4-(2-methylthiazol-4-yl)phenoxy)ethyl)-1H-indol-3-yl)acetamide
476
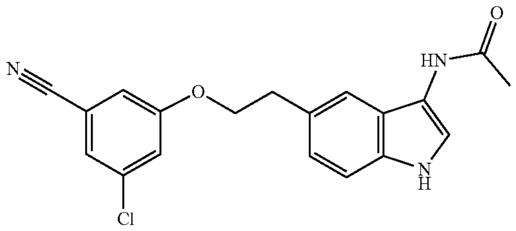 [SMILES: CC(=O)Nc1c[nH]c2ccc(CCOc3cc(Cl)cc(C#N)c3)cc12]
N-(5-(2-(3-chloro-5-cyanophenoxy)ethyl)-1H-indol-3-yl)acetamide -continued

477

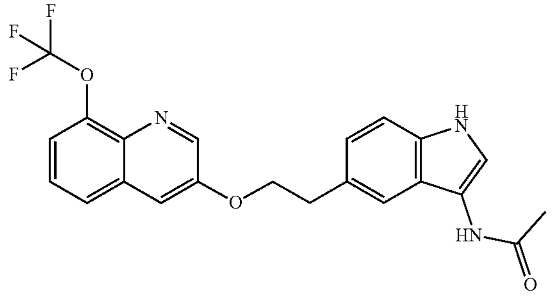 [SMILES: CC(=O)Nc1c[nH]c2ccc(CCOc3cnc4c(OC(F)(F)F)cccc4c3)cc12]

N-(5-(2-((8-(trifluoromethoxy)quinolin-3-yl)oxy)ethyl)-1H-indol-3-yl)acetamide

478

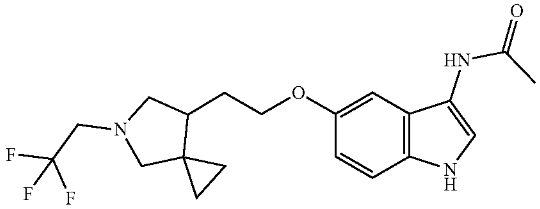 [SMILES: CC(=O)Nc1c[nH]c2ccc(OCCC3CN(CC(F)(F)F)CC34CC4)cc12]

N-(5-(2-(5-(2,2,2-trifluoroethyl)-5-azaspiro[2.4]heptan-7-yl)ethoxy)-1H-indol-3-yl)acetamide

479

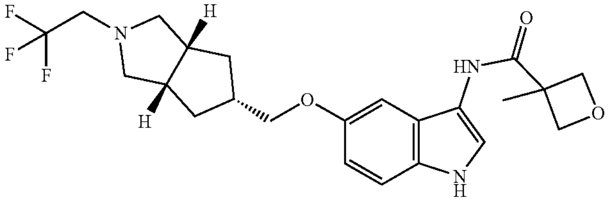 [SMILES: CC1(C(=O)Nc2c[nH]c3ccc(OC[C@@H]4C[C@@H]5CN(CC(F)(F)F)C[C@@H]5C4)cc23)COC1]

3-methyl-N-(5-(((3aR,5r,6aS)-2-(2,2,2-trifluoroethyl)octahydrocyclopenta[c]pyrrol-5-yl)methoxy)-1H-indol-3-yl)oxetane-3-carboxamide

480

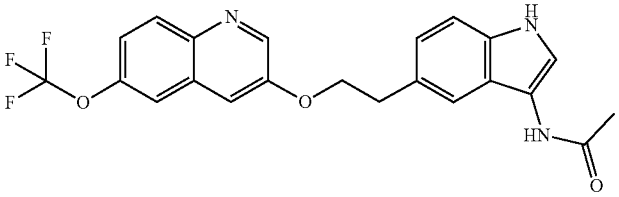 [SMILES: CC(=O)Nc1c[nH]c2ccc(CCOc3cnc4ccc(OC(F)(F)F)cc4c3)cc12]

N-(5-(2-((6-(trifluoromethoxy)quinolin-3-yl)oxy)ethyl)-1H-indol-3-yl)acetamide

481

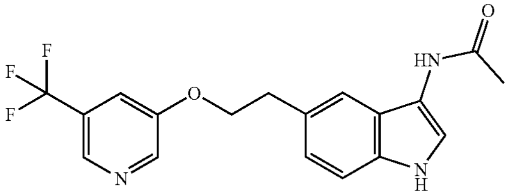 [SMILES: CC(=O)Nc1c[nH]c2ccc(CCOc3cncc(C(F)(F)F)c3)cc12]

N-(5-(2-((5-(trifluoromethyl)pyridin-3-yl)oxy)ethyl)-1H-indol-3-yl)acetamide

-continued
482
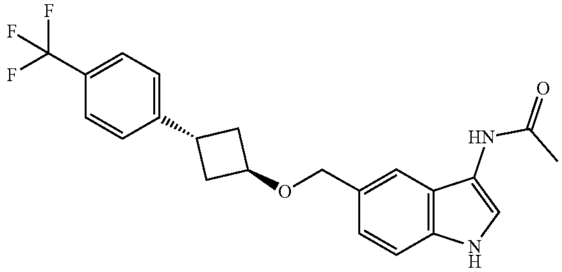 [SMILES: CC(=O)Nc1c[nH]c2ccc(CO[C@H]3C[C@H](c4ccc(C(F)(F)F)cc4)C3)cc12]
N-(5-((trans-3-(4-(trifluoromethyl)phenyl)cyclobutoxy)methyl)-1H-indol-3-yl)acetamide
483
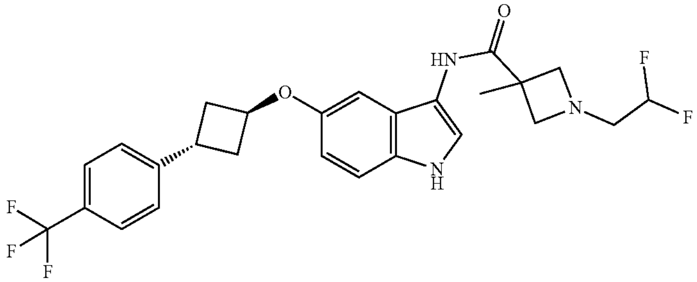 [SMILES: CC1(C(=O)Nc2c[nH]c3ccc(O[C@H]4C[C@H](c5ccc(C(F)(F)F)cc5)C4)cc23)CN(CC(F)F)C1]
1-(2,2-difluoroethyl)-3-methyl-N-(5-(trans-3-(4-(trifluoromethyl)phenyl)cyclobutoxy)-1H-indol-3-yl)azetidine-3-carboxamide
484
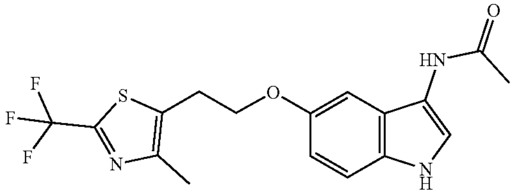 [SMILES: CC(=O)Nc1c[nH]c2ccc(OCCc3sc(C(F)(F)F)nc3C)cc12]
N-(5-(2-(4-methyl-2-(trifluoromethyl)thiazol-5-yl)ethoxy)-1H-indol-3-yl)acetamide
485
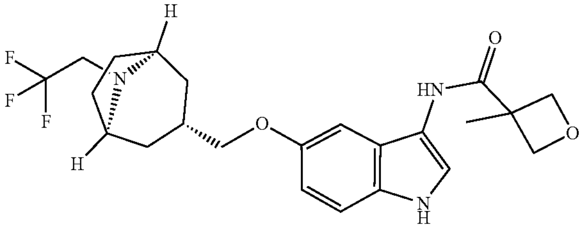 [SMILES: CC1(C(=O)Nc2c[nH]c3ccc(OC[C@@H]4C[C@H]5CC[C@@H](C4)N5CC(F)(F)F)cc23)COC1]
3-methyl-N-(5-(((1R,3s,5S)-8-(2,2,2-trifluoroethyl)-8-azabicyclo[3.2.1 ]octan-3-yl)methoxy)-1H-indol-3-yl)oxetane-3-carboxamide
486
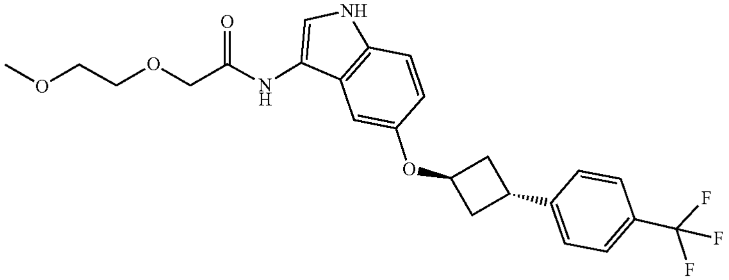 [SMILES: COCCOCC(=O)Nc1c[nH]c2ccc(O[C@H]3C[C@H](c4ccc(C(F)(F)F)cc4)C3)cc12]

-continued 2-(2-methoxyethoxy)-N-(5-((trans)-3-(4-(trifluoromethyl)phenyl)cyclobutoxy)-1H-indol-3-yl)acetamide

487

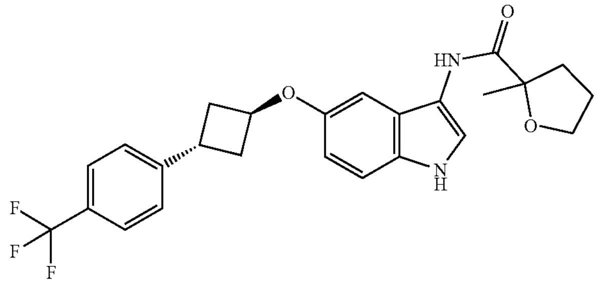 [SMILES: CC1(C(=O)Nc2c[nH]c3ccc(O[C@H]4C[C@H](c5ccc(C(F)(F)F)cc5)C4)cc23)CCCO1]

2-methyl-N-(5-(trans-3-(4-(trifluoromethyl)phenyl)cyclobutoxy)-1H-indol-3-yl)tetrahydrofuran-2-carboxamide

488

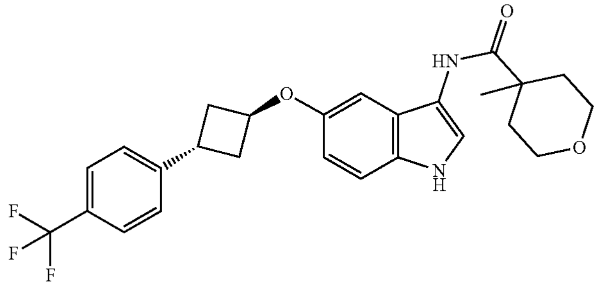 [SMILES: CC1(C(=O)Nc2c[nH]c3ccc(O[C@H]4C[C@H](c5ccc(C(F)(F)F)cc5)C4)cc23)CCOCC1]

4-methyl-N-(5-(trans-3-(4-(trifluoromethyl)phenyl)cyclobutoxy)-1H-indol-3-yl)tetrahydro-2H-pyran-4-carboxamide

489

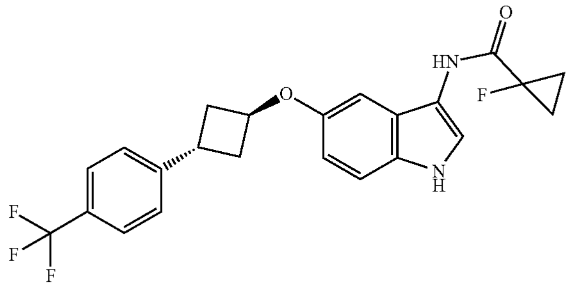 [SMILES: O=C(Nc1c[nH]c2ccc(O[C@H]3C[C@H](c4ccc(C(F)(F)F)cc4)C3)cc12)C1(F)CC1]

1-fluoro-N-(5-(trans-3-(4-(trifluoromethyl)phenyl)cyclobutoxy)-1H-indol-3-yl)cyclopropane-1-carboxamide

490

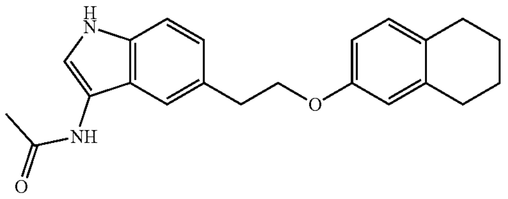 [SMILES: CC(=O)Nc1c[nH]c2ccc(CCOc3ccc4c(c3)CCCC4)cc12]

N-(5-(2-((5,6,7,8-tetrahydronaphthalen-2-yl)oxy)ethyl)-1H-indol-3-yl)acetamide

-continued
491
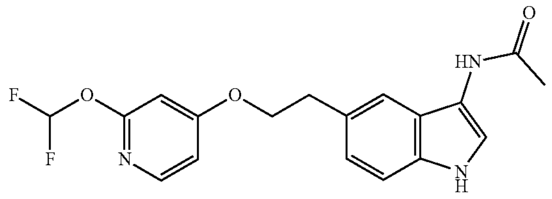 [SMILES: CC(=O)Nc1c[nH]c2ccc(CCOc3ccnc(OC(F)F)c3)cc12]
N-(5-(2-((2-(difluoromethoxy)pyridin-4-yl)oxy)ethyl)-1H-indol-3-yl)acetamide
492
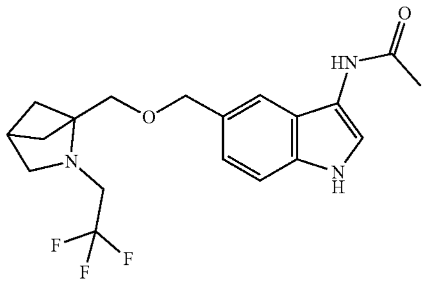 [SMILES: CC(=O)Nc1c[nH]c2ccc(COCC34CC(CN3CC(F)(F)F)C4)cc12]
N-(5-(((2-(2,2,2-trifluoroethyl)-2-azabicyclo[2.1.1 ]hexan-1-yl)methoxy)methyl)-1H-indol-3-yl)acetamide
493
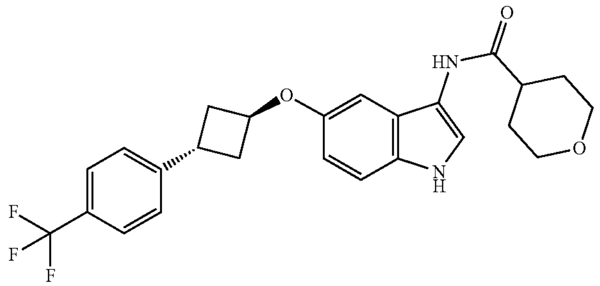 [SMILES: O=C(Nc1c[nH]c2ccc(O[C@H]3C[C@H](c4ccc(C(F)(F)F)cc4)C3)cc12)C1CCOCC1]
N-(5-(trans-3-(4-(trifluoromethyl)phenyl)cyclobutoxy)-1H-indol-3-yl)tetrahydro-2H-pyran-4-carboxamide
494
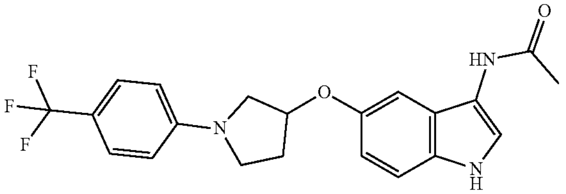 [SMILES: CC(=O)Nc1c[nH]c2ccc(OC3CCN(c4ccc(C(F)(F)F)cc4)C3)cc12]
N-(5-((1-(4-(trifluoromethyl)phenyl)pyrrolidin-3-yl)oxy)-1H-indol-3-yl)acetamide
495
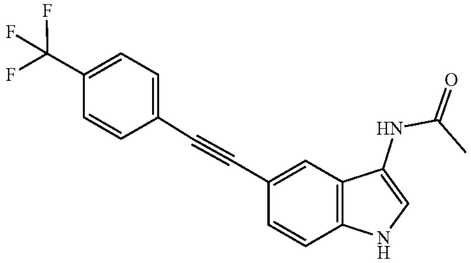 [SMILES: CC(=O)Nc1c[nH]c2ccc(C#Cc3ccc(C(F)(F)F)cc3)cc12]
N-(5-((4-(trifluoromethyl)phenyl)ethynyl)-1H-indol-3-yl)acetamide -continued
496
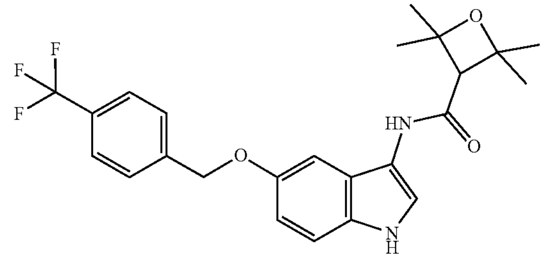 [SMILES: CC1(C)OC(C)(C)C1C(=O)Nc1c[nH]c2ccc(OCc3ccc(C(F)(F)F)cc3)cc12]
2,2,4,4-tetramethyl-N-(5-((4-(trifluoromethyl)benzyl)oxy)-1H-indol-3-yl)oxetane-3-carboxamide
497
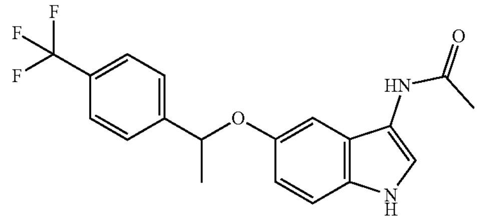 [SMILES: CC(=O)Nc1c[nH]c2ccc(OC(C)c3ccc(C(F)(F)F)cc3)cc12]
N-(5-(1-(4-(trifluoromethyl)phenyl)ethoxy)-1H-indol-3-yl)acetamide
498
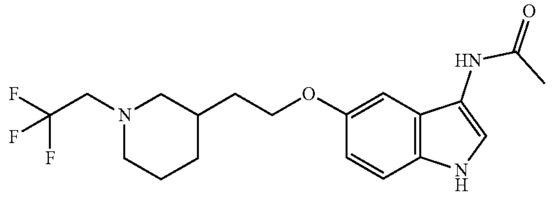 [SMILES: CC(=O)Nc1c[nH]c2ccc(OCCC3CCCN(CC(F)(F)F)C3)cc12]
N-(5-(2-(1-(2,2,2-trifluoroethyl)piperidin-3-yl)ethoxy)-1H-indol-3-yl)cyclopropanecarboxamide
499
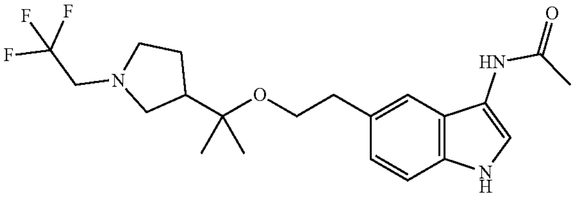 [SMILES: CC(=O)Nc1c[nH]c2ccc(CCOC(C)(C)C3CCN(CC(F)(F)F)C3)cc12]
N-(5-(2-((2-(1-(2,2,2-trifluoroethyl)pyrrolidin-3-yl)propan-2-yl)oxy)ethyl)-1H-indol-3-yl)acetamide
500
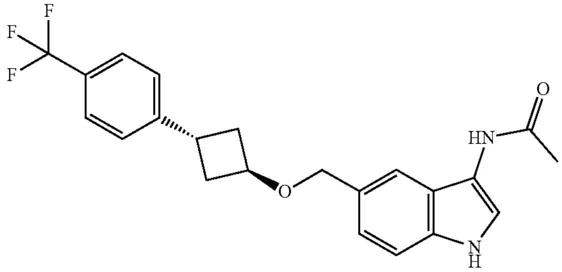 [SMILES: CC(=O)Nc1c[nH]c2ccc(CO[C@H]3C[C@H](c4ccc(C(F)(F)F)cc4)C3)cc12]
N-(5-((cis-3-(4-(trifluoromethyl)phenyl)cyclobutoxy)methyl)-1H-indol-3-yl)acetamide -continued

501

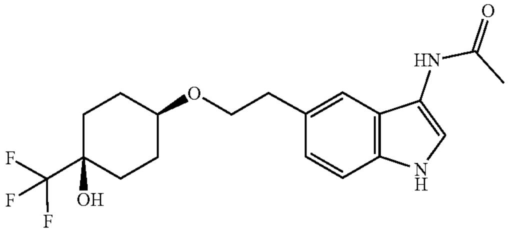 [SMILES: CC(=O)Nc1c[nH]c2ccc(CCO[C@H]3CC[C@](O)(C(F)(F)F)CC3)cc12]

N-(5-(2-(trans-4-hydroxy-4-(trifluoromethyl)cyclohexyl)ethoxy)-1H-indol-3-yl)acetamide

504

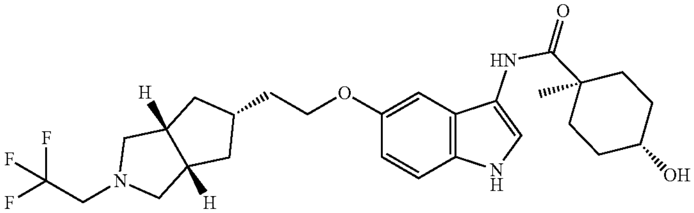 [SMILES: C[C@]1(C(=O)Nc2c[nH]c3ccc(OCC[C@@H]4C[C@@H]5CN(CC(F)(F)F)C[C@@H]5C4)cc23)CC[C@H](O)CC1]

(1r,4R)-4-hydroxy-1-methyl-N-(5-(2-((3aR,5r,6aS)-2-(2,2,2-trifluoroethyl)octahydrocyclopenta[c]pyrrol-5-yl)ethoxy)-1H-indol-3-yl)cyclohexane-1-carboxamide

505

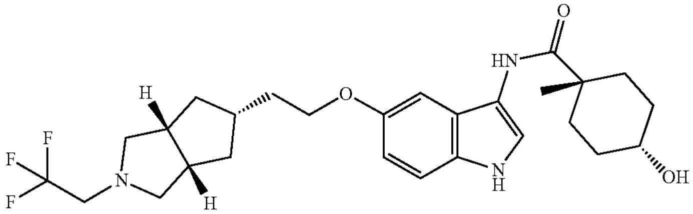 [SMILES: C[C@]1(C(=O)Nc2c[nH]c3ccc(OCC[C@@H]4C[C@@H]5CN(CC(F)(F)F)C[C@@H]5C4)cc23)CC[C@@H](O)CC1]

(1s,4S)-4-hydroxy-1-methyl-N-(5-(2-((3aR,5r,6aS)-2-(2,2,2-trifluoroethyl)octahydrocyclopenta[c]pyrrol-5-yl)ethoxy)-1H-indol-3-yl)cyclohexane-1-carboxamide

506

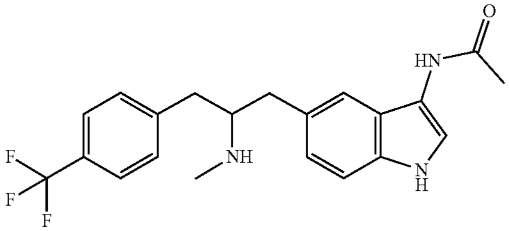 [SMILES: CNC(Cc1ccc(C(F)(F)F)cc1)Cc1ccc2[nH]cc(NC(C)=O)c2c1]

N-(5-(2-(methylamino)-3-(4-(trifluoromethyl)phenyl)propyl)-1H-indol-3-yl)acetamide

507

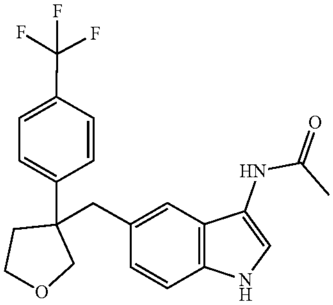 [SMILES: CC(=O)Nc1c[nH]c2ccc(CC3(c4ccc(C(F)(F)F)cc4)CCOC3)cc12]

N-(5-((3-(4-(trifluoromethyl)phenyl)tetrahydrofuran-3-yl)methyl)-1H-indol-3-yl)acetamide -continued

508

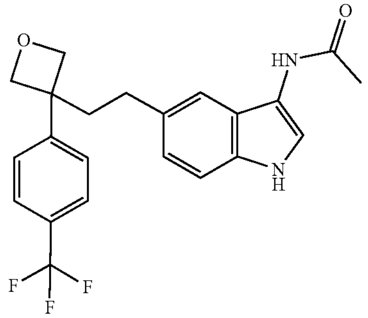 [SMILES: CC(=O)Nc1c[nH]c2ccc(CCC3(c4ccc(C(F)(F)F)cc4)COC3)cc12]

N-(5-(2-(3-(4-(trifluoromethyl)phenyl)oxetan-3-yl)ethyl)-1H-indol-3-yl)acetamide

509

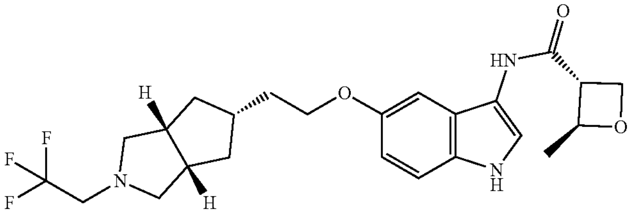 [SMILES: C[C@@H]1OC[C@H]1C(=O)Nc1c[nH]c2ccc(OCC[C@@H]3C[C@@H]4CN(CC(F)(F)F)C[C@@H]4C3)cc12]

(2S,3R)-2-methyl-N-(5-(2-((3aR,5r,6aS)-2-(2,2,2-trifluoroethyl)octahydrocyclopenta[c]pyrrol-5-yl)ethoxy)-1H-indol-3-yl)oxetane-3-carboxamide

510

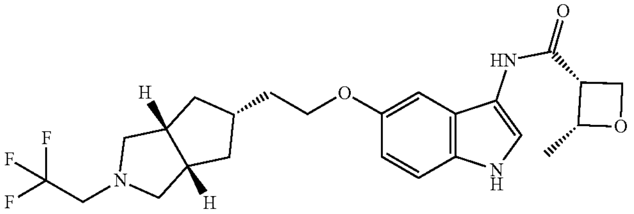 [SMILES: C[C@H]1OC[C@H]1C(=O)Nc1c[nH]c2ccc(OCC[C@@H]3C[C@@H]4CN(CC(F)(F)F)C[C@@H]4C3)cc12]

(2R,3R)-2-methyl-N-(5-(2-((3aR,5r,6aS)-2-(2,2,2-trifluoroethyl)octahydrocyclopenta[c]pyrrol-5-yl)ethoxy)-1H-indol-3-yl)oxetane-3-carboxamide

511

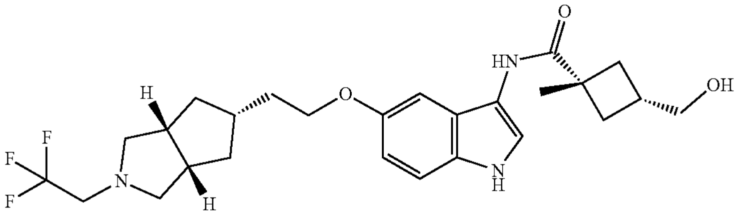 [SMILES: C[C@]1(C(=O)Nc2c[nH]c3ccc(OCC[C@@H]4C[C@@H]5CN(CC(F)(F)F)C[C@@H]5C4)cc23)C[C@@H](CO)C1]

(1s,3S)-3-(hydroxymethyl)-1-methyl-N-(5-(2-((3aR,5r,6aS)-2-(2,2,2-trifluoroethyl)octahydrocyclopenta[c]pyrrol-5-yl)ethoxy)-1H-indol-3-yl)cyclobutane-1-carboxamide

512

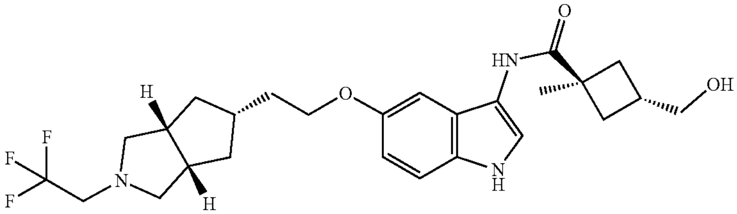 [SMILES: C[C@]1(C(=O)Nc2c[nH]c3ccc(OCC[C@@H]4C[C@@H]5CN(CC(F)(F)F)C[C@@H]5C4)cc23)C[C@H](CO)C1]

(1r,3R)-3-(hydroxymethyl)-1-methyl-N-(5-(2-((3aR,5r,6aS)-2-(2,2,2-trifluoroethyl)octahydrocyclopenta[c]pyrrol-5-yl)ethoxy)-1H-indol-3-yl)cyclobutane-1-carboxamide -continued

513

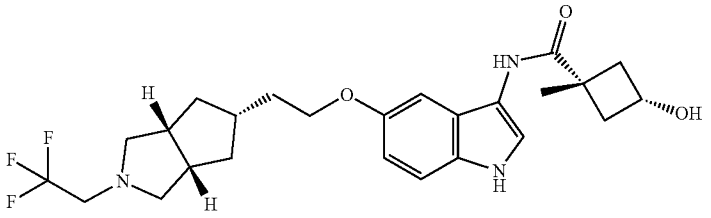 [SMILES: C[C@]1(C(=O)Nc2c[nH]c3ccc(OCC[C@@H]4C[C@@H]5CN(CC(F)(F)F)C[C@@H]5C4)cc23)C[C@@H](O)C1]

(1s,3S)-3-hydroxy-1-methyl-N-(5-(2-((3aR,5r,6aS)-2-(2,2,2-trifluoroethyl)octahydrocyclopenta[c]pyrrol-5-yl)ethoxy)-1H-indol-3-yl)cyclobutane-1-carboxamide

514

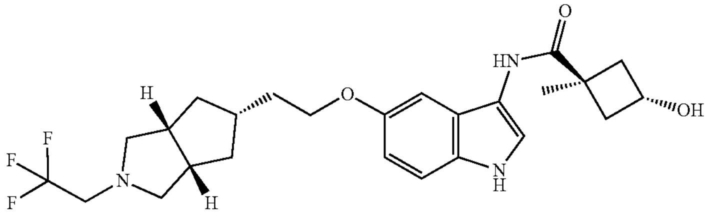 [SMILES: C[C@]1(C(=O)Nc2c[nH]c3ccc(OCC[C@@H]4C[C@@H]5CN(CC(F)(F)F)C[C@@H]5C4)cc23)C[C@H](O)C1]

(1r,3R)-3-hydroxy-1-methyl-N-(5-(2-((3aR,5r,6aS)-2-(2,2,2-trifluoroethyl)octahydrocyclopenta[c]pyrrol-5-yl)ethoxy)-1H-indol-3-y1)cyclobutane-1-carboxamide

515

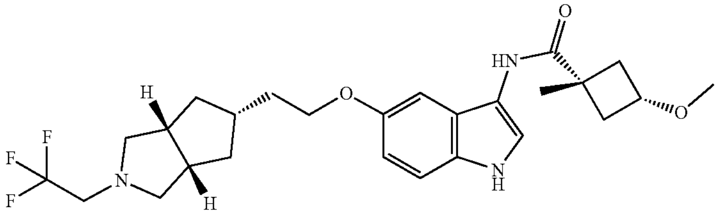 [SMILES: CO[C@H]1C[C@@](C)(C(=O)Nc2c[nH]c3ccc(OCC[C@@H]4C[C@@H]5CN(CC(F)(F)F)C[C@@H]5C4)cc23)C1]

(1s,3S)-3-methoxy-1-methyl-N-(5-(2-((3aR,5r,6aS)-2-(2,2,2-trifluoroethyl)octahydrocyclopenta[c]pyrrol-5-yl)ethoxy)-1H-indol-3-yl)cyclobutane-1-carboxamide

516

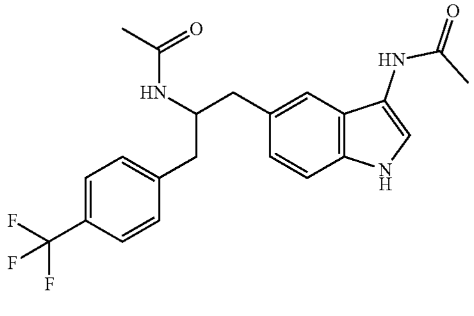 [SMILES: CC(=O)Nc1c[nH]c2ccc(CC(Cc3ccc(C(F)(F)F)cc3)NC(C)=O)cc12]

N-(1-(3-acetamido-1H-indol-5-y1)-3-(4-(trifluoromethyl)phenyl)propan-2-yl)acetamide

517

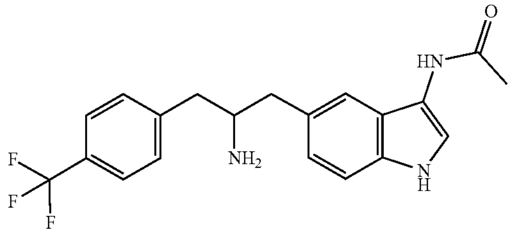 [SMILES: CC(=O)Nc1c[nH]c2ccc(CC(N)Cc3ccc(C(F)(F)F)cc3)cc12]

N-(5-(2-amino-3-(4-(trifluoromethyl)phenyl)propyl)-1H-indol-3-y1)acetamide

-continued
518
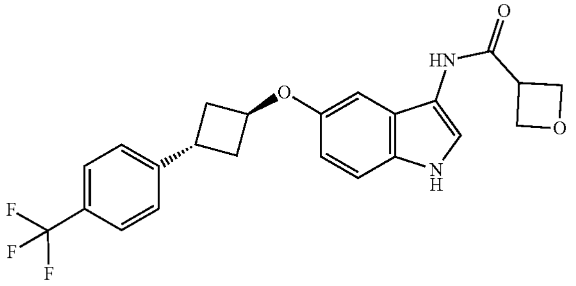 [SMILES: O=C(Nc1c[nH]c2ccc(O[C@H]3C[C@H](c4ccc(C(F)(F)F)cc4)C3)cc12)C1COC1]
N-(5-(trans-3-(4-(trifluoromethyl)phenyl)cyclobutoxy)-1H-indol-3-yl)oxetane-3-carboxamide
519
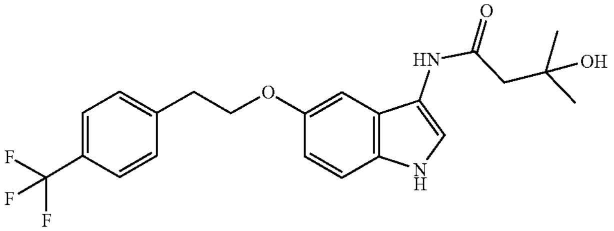 [SMILES: CC(C)(O)CC(=O)Nc1c[nH]c2ccc(OCCc3ccc(C(F)(F)F)cc3)cc12]
3-hydroxy-3-methyl-N-(5-(4-(trifluoromethyl)phenethoxy)-1H-indol-3-yl)butanamide
520
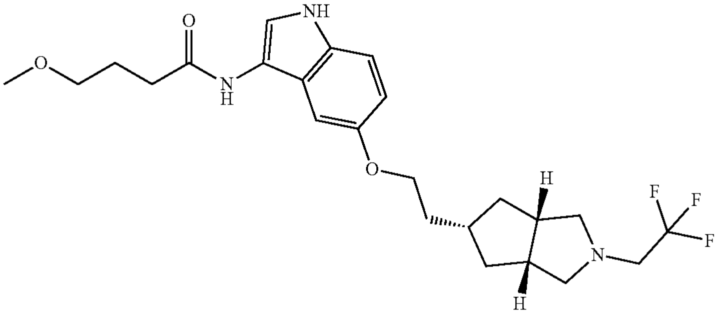 [SMILES: COCCCC(=O)Nc1c[nH]c2ccc(OCC[C@@H]3C[C@@H]4CN(CC(F)(F)F)C[C@@H]4C3)cc12]
4-methoxy-N-(5-(2-((3aR,5r,6aS)-2-(2,2,2-trifluoroethyl)octahydrocyclopenta[c]pyrrol-5-yl)ethoxy)-1H-indol-3-yl)butanamide
521
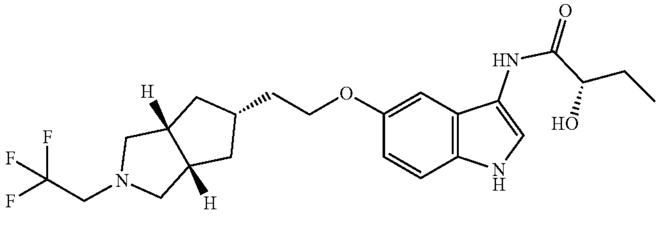 [SMILES: CC[C@H](O)C(=O)Nc1c[nH]c2ccc(OCC[C@@H]3C[C@@H]4CN(CC(F)(F)F)C[C@@H]4C3)cc12]
(S)-2-hydroxy-N-(5-(2-((3aR,5r,6aS)-2-(2,2,2-trifluoroethyl)octahydrocyclopenta[c]pyrrol-5-yl)ethoxy)-1H-indol-3-yl)butanamide
522
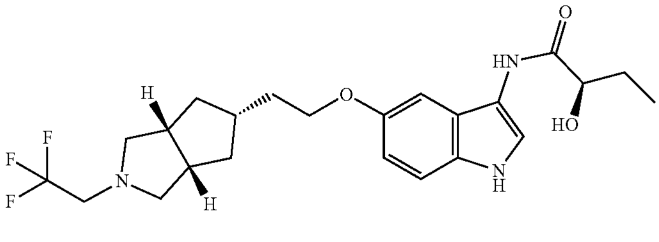 [SMILES: CC[C@@H](O)C(=O)Nc1c[nH]c2ccc(OCC[C@@H]3C[C@@H]4CN(CC(F)(F)F)C[C@@H]4C3)cc12]

-continued (R)-2-hydroxy-N-(5-(2-((3aR,5r,6aS)-2-(2,2,2-trifluoroethyl)octahydrocyclopenta[c]pyrrol-5-yl)ethoxy)-1H-indol-3-yl)butanamide

523 -

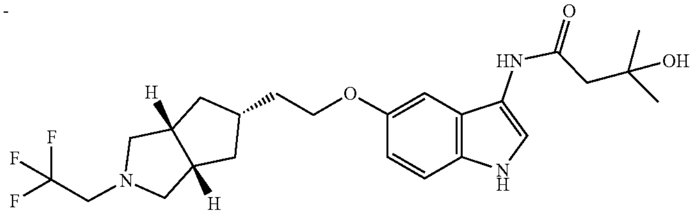

3-hydroxy-3-methyl-N-(5-(2-((3aR,5r,6aS)-2-(2,2,2-trifluoroethyl)octahydrocyclopenta[c]pyrrol-5-yl)ethoxy)-1H-indol-3-yl)butanamide

525

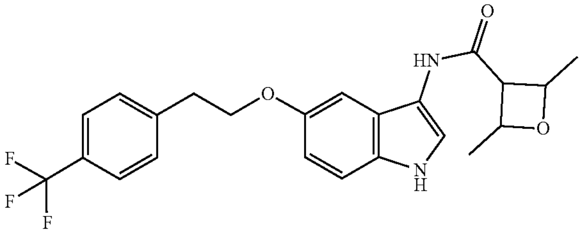 [SMILES: CC1OC(C)C1C(=O)Nc1c[nH]c2ccc(OCCc3ccc(C(F)(F)F)cc3)cc12]

2,4-dimethyl-N-(5-(4-(trifluoromethyl)phenethoxy)-1H-indol-3-yl)oxetane-3-carboxamide

526

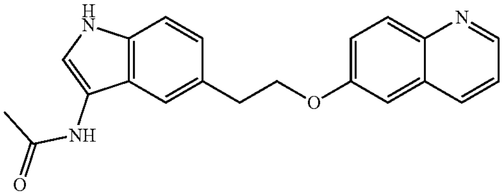 [SMILES: CC(=O)Nc1c[nH]c2ccc(CCOc3ccc4ncccc4c3)cc12]

N-(5-(2-(quinolin-6-yloxy)ethyl)-1H-indol-3-yl)acetamide

527

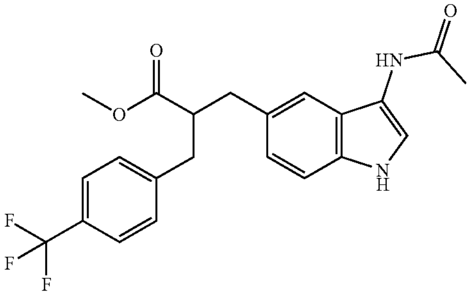 [SMILES: COC(=O)C(Cc1ccc(C(F)(F)F)cc1)Cc1ccc2[nH]cc(NC(C)=O)c2c1]

methyl 3-(3-acetamido-1H-indol-5-yl)-2-(4-(trifluoromethyl)benzyl)propanoate

528

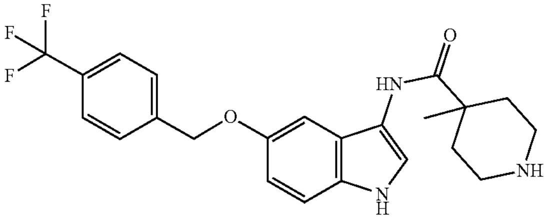 [SMILES: CC1(C(=O)Nc2c[nH]c3ccc(OCc4ccc(C(F)(F)F)cc4)cc23)CCNCC1]

4-methyl-N-(5-((4-(trifluoromethyl)benzyl)oxy)-1H-indol-3-yl)piperidine-4-carboxamide -continued
529
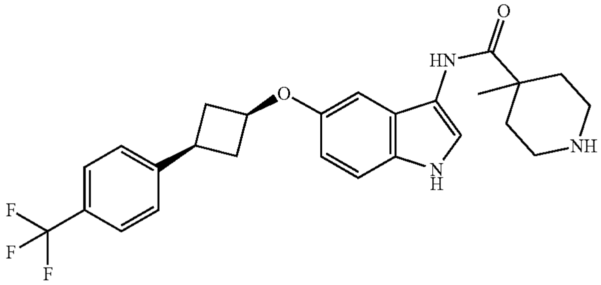 [SMILES: CC1(C(=O)Nc2c[nH]c3ccc(O[C@H]4C[C@@H](c5ccc(C(F)(F)F)cc5)C4)cc23)CCNCC1]
4-methyl-N-(5-(cis-3-(4-(trifluoromethyl)phenyl)cyclobutoxy)-1H-indol-3-yl)piperidine-4-carboxamide
530
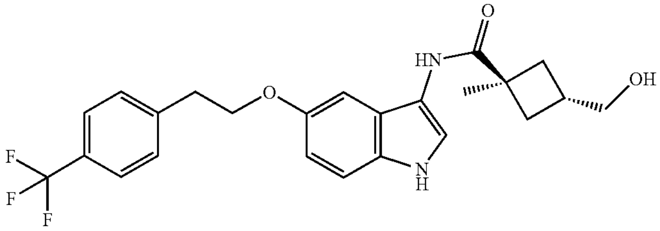 [SMILES: C[C@]1(C(=O)Nc2c[nH]c3ccc(OCCc4ccc(C(F)(F)F)cc4)cc23)C[C@H](CO)C1]
trans-3-(hydroxymethyl)-1-methyl-N-(5-(4-(trifluoromethyl)phenethoxy)-1H-indol-3-yl)cyclobutane-1-carboxamide
531
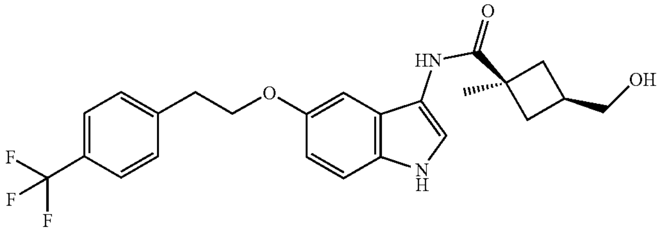 [SMILES: C[C@]1(C(=O)Nc2c[nH]c3ccc(OCCc4ccc(C(F)(F)F)cc4)cc23)C[C@@H](CO)C1]
cis-3-(hydroxymethyl)-1-methyl-N-(5-(4-(trifluoromethyl)phenethoxy)-1H-indol-3-y1)cyclobutane-1-carboxamide
532
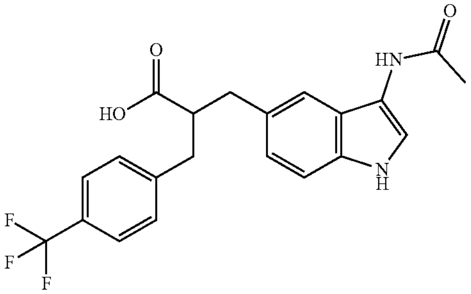 [SMILES: CC(=O)Nc1c[nH]c2ccc(CC(Cc3ccc(C(F)(F)F)cc3)C(=O)O)cc12]
3-(3-acetamido-1H-indol-5-y1)-2-(4-(trifluoromethyl)benzyl)propanoic acid
533
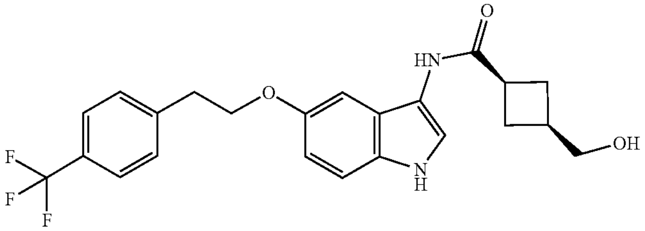 [SMILES: O=C(Nc1c[nH]c2ccc(OCCc3ccc(C(F)(F)F)cc3)cc12)[C@H]1C[C@@H](CO)C1]

-continued cis-3-(hydroxymethyl)-N-(5-(4-(trifluoromethyl)phenethoxy)-1H-indol-3-yl)cyclobutane-1-carboxamide 534 0

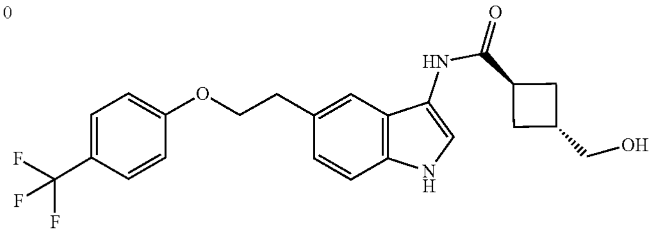

trans-3-(hydroxymethyl)-N-(5-(4-(trifluoromethyl)phenethoxy)-1H-indol-3-yl)cyclobutane-1-carboxamide

536

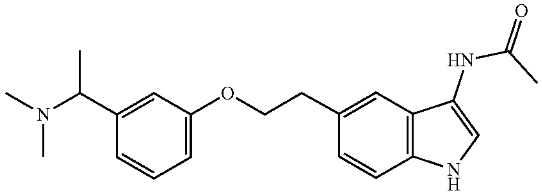 [SMILES: CC(=O)Nc1c[nH]c2ccc(CCOc3cccc(C(C)N(C)C)c3)cc12]

N-(5-(2-(3-(1-(dimethylamino)ethyl)phenoxy)ethyl)-1H-indol-3-yl)acetamide

537

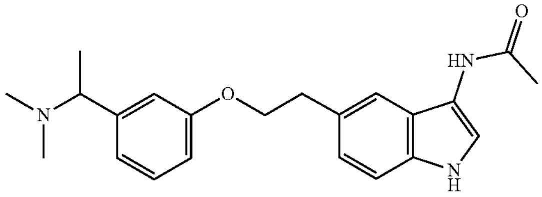 [SMILES: CC(=O)Nc1c[nH]c2ccc(CCOc3cccc(C(C)N(C)C)c3)cc12]

N-(5-(cis-3-(4-(trifluoromethyl)phenyl)cyclobutoxy)-1H-indol-3-yl)azetidine-3-carboxamide

538

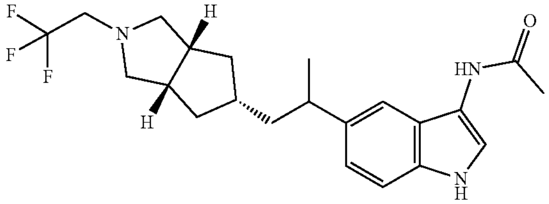 [SMILES: CC(=O)Nc1c[nH]c2ccc(C(C)C[C@@H]3C[C@@H]4CN(CC(F)(F)F)C[C@@H]4C3)cc12]

N-(5-(1-((3aR,5r,6aS)-2-(2,2,2-trifluoroethyl)octahydrocyclopenta[c]pyrrol-5-yl)propan-2-yl)-1H-indol-3-yl)acetamide

539

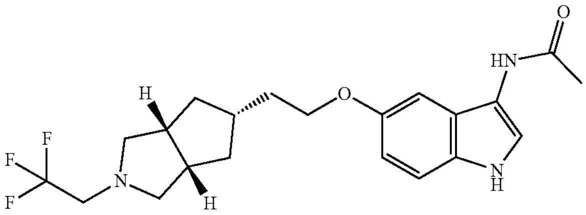 [SMILES: CC(=O)Nc1c[nH]c2ccc(OCC[C@@H]3C[C@@H]4CN(CC(F)(F)F)C[C@@H]4C3)cc12]

N-(5-(3-((3aR,5r,6aS)-2-(2,2,2-trifluoroethyl)octahydrocyclopenta[c]pyrrol-5-yl)propyl)-1H-indol-3-yl)acetamide -continued

540

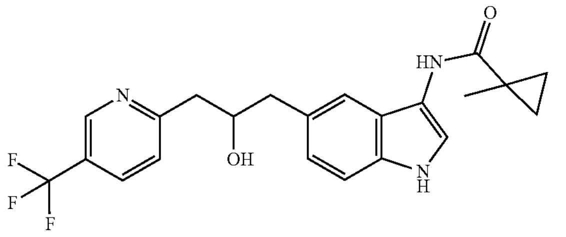 [SMILES: CC1(C(=O)Nc2c[nH]c3ccc(CC(O)Cc4ccc(C(F)(F)F)cn4)cc23)CC1]

N-(5-(2-hydroxy-3-(5-(trifluoromethyl)pyridin-2-yl)propyl)-1H-indol-3-yl)-1-methylcyclopropane-1-carboxamide

541

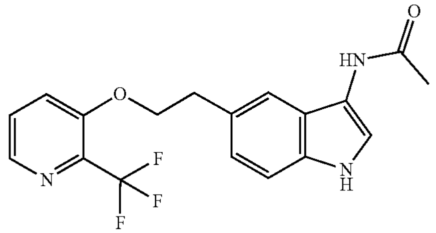 [SMILES: CC(=O)Nc1c[nH]c2ccc(CCOc3cccnc3C(F)(F)F)cc12]

N-(5-(2-((2-(trifluoromethyl)pyridin-3-yl)oxy)ethyl)-1H-indol-3-yl)acetamide

542

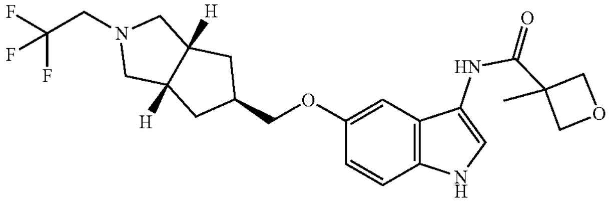 [SMILES: CC1(C(=O)Nc2c[nH]c3ccc(OC[C@H]4C[C@@H]5CN(CC(F)(F)F)C[C@@H]5C4)cc23)COC1]

3-methyl-N-(5-(((3aR,5s,6aS)-2-(2,2,2-trifluoroethyl)octahydrocyclopenta[c]pyrrol-5-yl)methoxy)-1H-indol-3-yl)oxetane-3-carboxamide

543

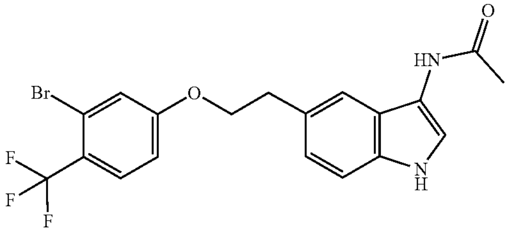 [SMILES: CC(=O)Nc1c[nH]c2ccc(CCOc3ccc(C(F)(F)F)c(Br)c3)cc12]

N-(5-(2-(3-bromo-4-(trifluoromethyl)phenoxy)ethyl)-1H-indol-3-yl)acetamide

544

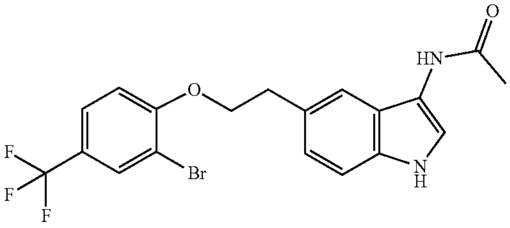 [SMILES: CC(=O)Nc1c[nH]c2ccc(CCOc3ccc(C(F)(F)F)cc3Br)cc12]

N-(5-(2-(2-bromo-4-(trifluoromethyl)phenoxy)ethyl)-1H-indol-3-yl)acetamide

-continued
545
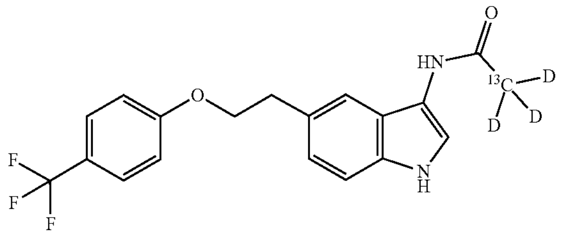 [SMILES: [2H][13C]([2H])([2H])C(=O)Nc1c[nH]c2ccc(CCOc3ccc(C(F)(F)F)cc3)cc12]
N-(5-(2-(4-(trifluoromethyl)phenoxy)ethyl)-1H-indol-3-yl)acetamide-2-13C-2,2,2-d3
546
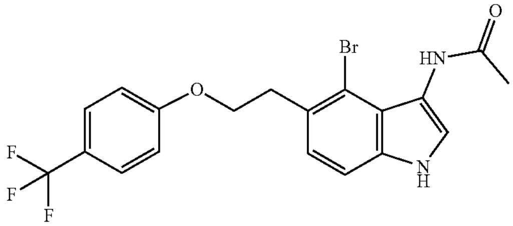 [SMILES: CC(=O)Nc1c[nH]c2ccc(CCOc3ccc(C(F)(F)F)cc3)c(Br)c12]
N-(4-bromo-5-(2-(4-(trifluoromethyl)phenoxy)ethyl)-1H-indol-3-y1)acetamide
547
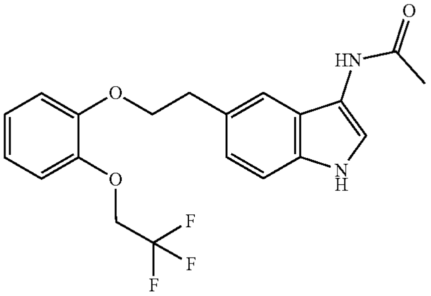 [SMILES: CC(=O)Nc1c[nH]c2ccc(CCOc3ccccc3OCC(F)(F)F)cc12]
N-(5-(2-(2-(2,2,2-trifluoroethoxy)phenoxy)ethyl)-1H-indol-3-yl)acetamide
548
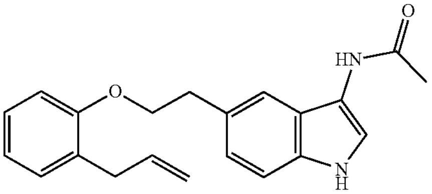 [SMILES: C=CCc1ccccc1OCCc1ccc2[nH]cc(NC(C)=O)c2c1]
N-(5-(2-(2-allylphenoxy)ethyl)-1H-indol-3-y1)acetamide
549
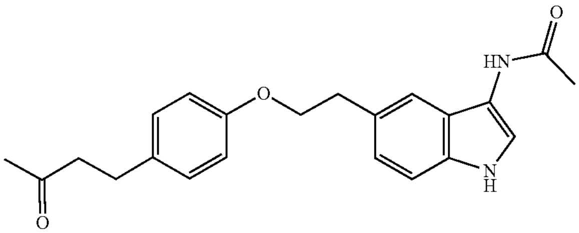 [SMILES: CC(=O)CCc1ccc(OCCc2ccc3[nH]cc(NC(C)=O)c3c2)cc1]
N-(5-(2-(4-(3-oxobutyl)phenoxy)ethyl)-1H-indol-3-y1)acetamide -continued

550

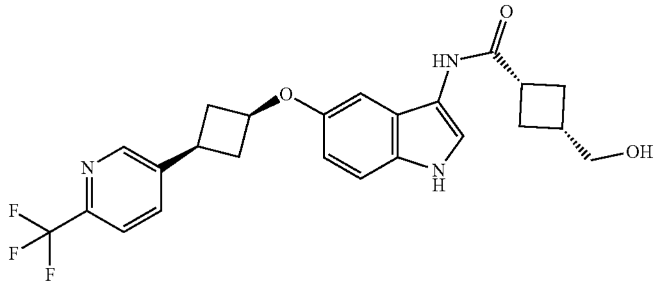 [SMILES: O=C(Nc1c[nH]c2ccc(O[C@H]3C[C@@H](c4ccc(C(F)(F)F)nc4)C3)cc12)[C@H]1C[C@@H](CO)C1]

cis-3-(hydroxymethyl)-N-(5-(cis-3-(6-(trifluoromethyl)pyridin-3-yl)cyclobutoxy)-1H-indol-3-yl)cyclobutane-1-carboxamide

551

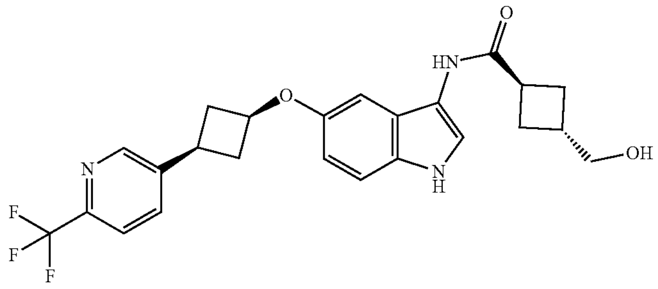 [SMILES: O=C(Nc1c[nH]c2ccc(O[C@H]3C[C@@H](c4ccc(C(F)(F)F)nc4)C3)cc12)[C@H]1C[C@H](CO)C1]

trans-3-(hydroxymethyl)-N-(5-(cis-3-(6-(trifluoromethyl)pyridin-3-yl)cyclobutoxy)-1H-indol-3-yl)cyclobutane-1-carboxamide

552

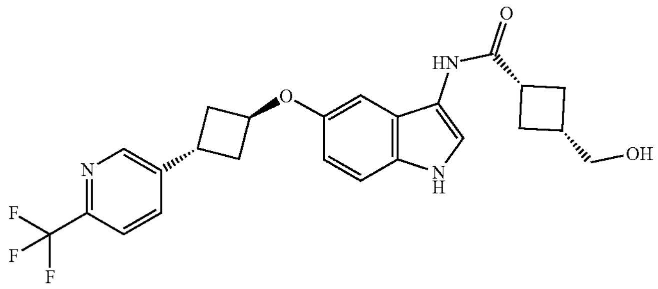 [SMILES: O=C(Nc1c[nH]c2ccc(O[C@H]3C[C@H](c4ccc(C(F)(F)F)nc4)C3)cc12)[C@H]1C[C@@H](CO)C1]

cis-3-(hydroxymethyl)-N-(5-(trans-3-(6-(trifluoromethyl)pyridin-3-yl)cyclobutoxy)-1H-indol-3-yl)cyclobutane-1-carboxamide

553

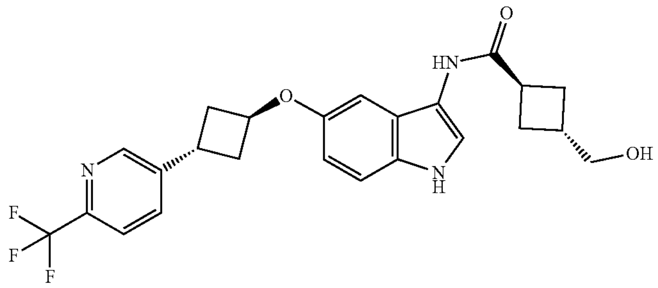 [SMILES: O=C(Nc1c[nH]c2ccc(O[C@H]3C[C@H](c4ccc(C(F)(F)F)nc4)C3)cc12)[C@H]1C[C@H](CO)C1]

trans-3-(hydroxymethyl)-N-(5-(trans-3-(6-(trifluoromethyl)pyridin-3-yl)cyclobutoxy)-1H-indol-3-yl)cyclobutane-1-carboxamide -continued
554
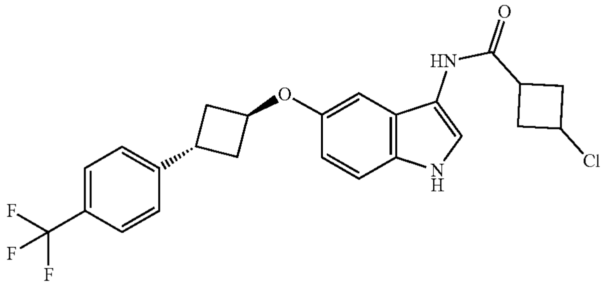 [SMILES: O=C(Nc1c[nH]c2ccc(O[C@H]3C[C@H](c4ccc(C(F)(F)F)cc4)C3)cc12)C1CC(Cl)C1]
3-chloro-N-(5-(trans-3-(4-(trifluoromethyl)phenyl)cyclobutoxy)-1H-indol-3-yl)cyclobutane-1-carboxamide
555
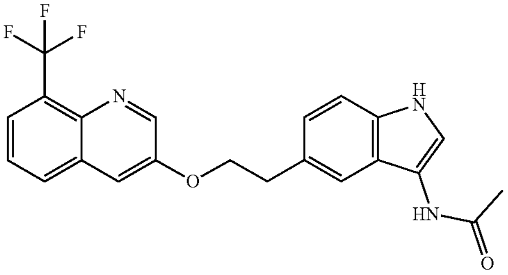 [SMILES: CC(=O)Nc1c[nH]c2ccc(CCOc3cnc4c(C(F)(F)F)cccc4c3)cc12]
N-(5-(2-((8-(trifluoromethyl)quinolin-3-yl)oxy)ethyl)-1H-indol-3-yl)acetamide
556
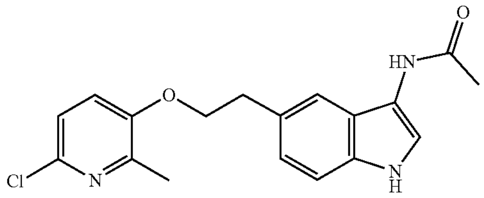 [SMILES: CC(=O)Nc1c[nH]c2ccc(CCOc3ccc(Cl)nc3C)cc12]
N-(5-(2-((6-chloro-2-methylpyridin-3-yl)oxy)ethyl)-1H-indol-3-yl)acetamide
557
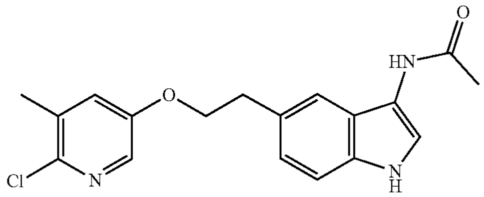 [SMILES: CC(=O)Nc1c[nH]c2ccc(CCOc3cnc(Cl)c(C)c3)cc12]
N-(5-(2-((6-chloro-5-methylpyridin-3-yl)oxy)ethyl)-1H-indol-3-yl)acetamide
558
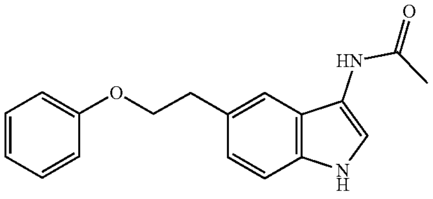 [SMILES: CC(=O)Nc1c[nH]c2ccc(CCOc3ccccc3)cc12]
N-(5-(2-phenoxyethyl)-1H-indol-3-yl)acetamide -continued

559

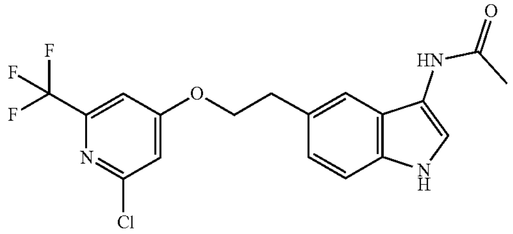 [SMILES: CC(=O)Nc1c[nH]c2ccc(CCOc3cc(Cl)nc(C(F)(F)F)c3)cc12]

N-(5-(2-((2-chloro-6-(trifluoromethyl)pyridin-4-yl)oxy)ethyl)-1H-indol-3-yl)acetamide

560

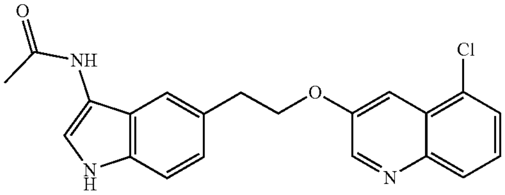 [SMILES: CC(=O)Nc1c[nH]c2ccc(CCOc3cnc4cccc(Cl)c4c3)cc12]

N-(5-(2-((5-chloroquinolin-3-yl)oxy)ethyl)-1H-indol-3-yl)acetamide

561

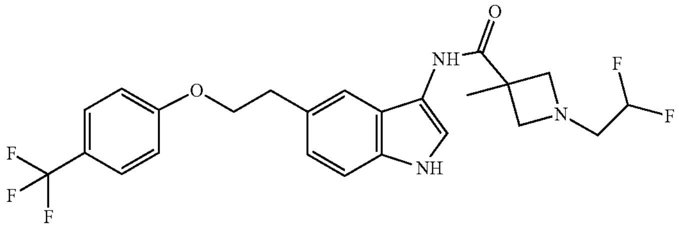 [SMILES: CC1(C(=O)Nc2c[nH]c3ccc(CCOc4ccc(C(F)(F)F)cc4)cc23)CN(CC(F)F)C1]

1-(2,2-difluoroethyl)-3-methyl-N-(5-(4-(trifluoromethyl)phenethoxy)-1H-indol-3-yl)azetidine-3-carboxamide

562

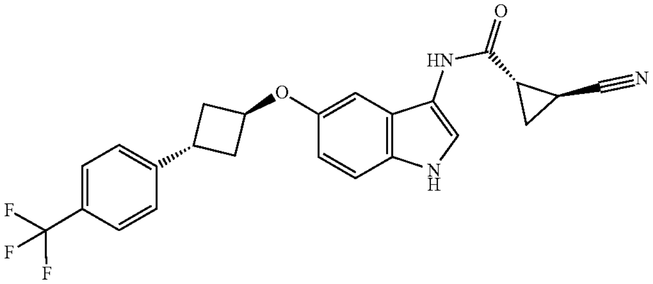 [SMILES: N#C[C@H]1C[C@@H]1C(=O)Nc1c[nH]c2ccc(O[C@H]3C[C@H](c4ccc(C(F)(F)F)cc4)C3)cc12]

(1s,2s)-2-cyano-N-(5-((trans)-3-(4-(trifluoromethyl)phenyl)cyclobutoxy)-1H-indol-3-yl)cyclopropane-1-carboxamide

563

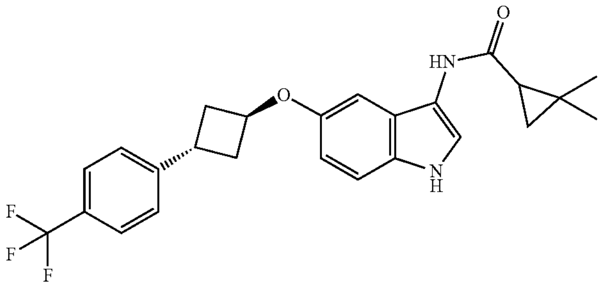 [SMILES: CC1(C)CC1C(=O)Nc1c[nH]c2ccc(O[C@H]3C[C@H](c4ccc(C(F)(F)F)cc4)C3)cc12]

2,2-dimethyl-N-(5-(trans-3-(4-(trifluoromethyl)phenyl)cyclobutoxy)-1H-indol-3-yl)cyclopropane-1-carboxamide -continued

564

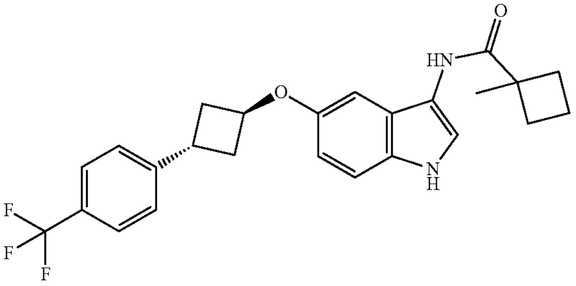 [SMILES: CC1(C(=O)Nc2c[nH]c3ccc(O[C@H]4C[C@H](c5ccc(C(F)(F)F)cc5)C4)cc23)CCC1]

1-methyl-N-(5-(trans-3-(4-(trifluoromethyl)phenyl)cyclobutoxy)-1H-indol-3-yl)cyclobutane-1-carboxamide

565

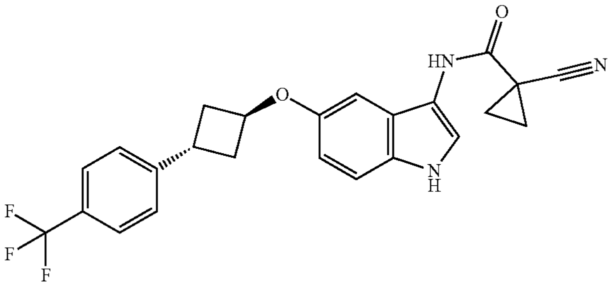 [SMILES: N#CC1(C(=O)Nc2c[nH]c3ccc(O[C@H]4C[C@H](c5ccc(C(F)(F)F)cc5)C4)cc23)CC1]

1-cyano-N-(5-(trans-3-(4-(trifluoromethyl)phenyl)cyclobutoxy)-1H-indol-3-yl)cyclopropane-1-carboxamide

567

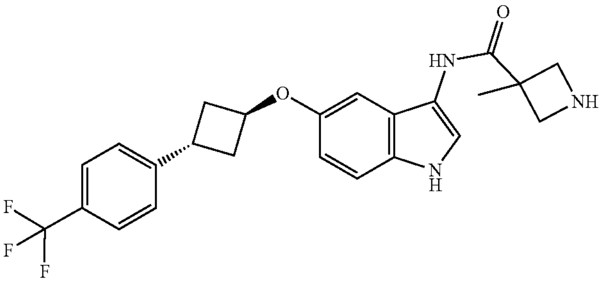 [SMILES: CC1(C(=O)Nc2c[nH]c3ccc(O[C@H]4C[C@H](c5ccc(C(F)(F)F)cc5)C4)cc23)CNC1]

3-methyl-N-(5-(trans-3-(4-(trifluoromethyl)phenyl)cyclobutoxy)-1H-indol-3-yl)azetidine-3-carboxamide

568

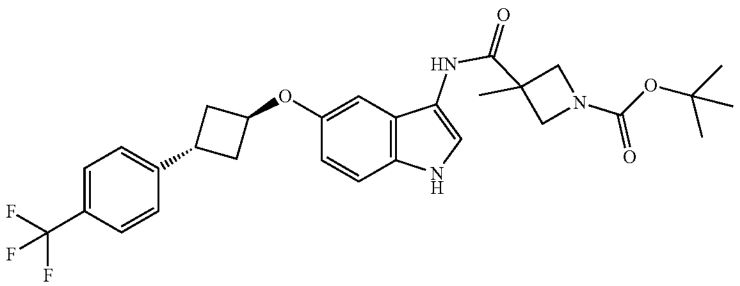 [SMILES: CC(C)(C)OC(=O)N1CC(C)(C(=O)Nc2c[nH]c3ccc(O[C@H]4C[C@H](c5ccc(C(F)(F)F)cc5)C4)cc23)C1]

tert-butyl 3-methyl-3-((5-(trans-3-(4-(trifluoromethyl)phenyl)cyclobutoxy)-1H-indol-3-yl)carbamoyl)azetidine-1-carboxylate -continued

569

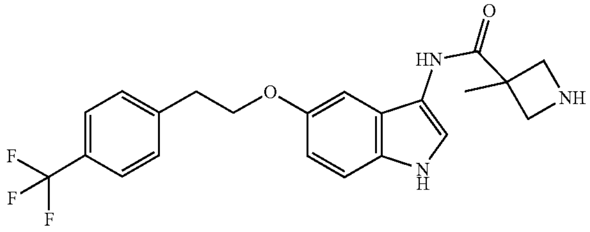 [SMILES: CC1(C(=O)Nc2c[nH]c3ccc(OCCc4ccc(C(F)(F)F)cc4)cc23)CNC1]

3-methyl-N-(5-(4-(trifluoromethyl)phenethoxy)-1H-indol-3-yl)azetidine-3-carboxamide

570

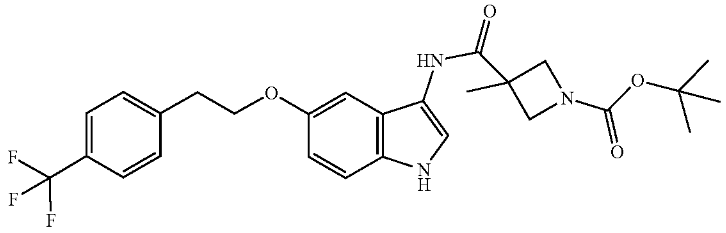 [SMILES: CC(C)(C)OC(=O)N1CC(C)(C(=O)Nc2c[nH]c3ccc(OCCc4ccc(C(F)(F)F)cc4)cc23)C1]

tert-butyl 3-methyl-3-((5-(4-(trifluoromethyl)phenethoxy 1H-indol-3-y1)carbamoyl)azetidine-1-carboxylate

571

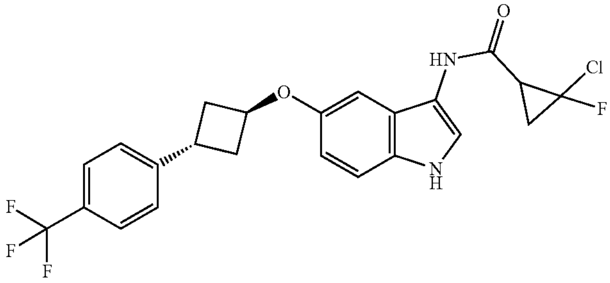 [SMILES: O=C(Nc1c[nH]c2ccc(O[C@H]3C[C@H](c4ccc(C(F)(F)F)cc4)C3)cc12)C1CC1(F)Cl]

2-chloro-2-fluoro-N-(5-(trans-3-(4-(trifluoromethyl)phenyl)cyclobutoxy)-1H-indol-3-yl)cyclopropane-1-carboxamide

572

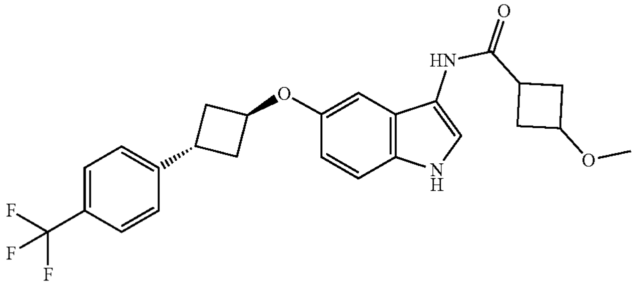

3-methoxy-N-(5-(trans-3-(4-(trifluoromethyl)phenyl)cyclobutoxy)-1H-indol-3-yl)cyclobutane-1-carboxamide

573

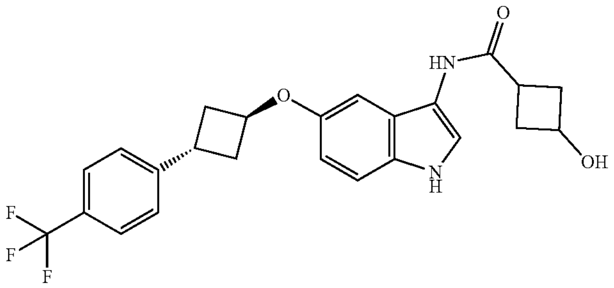 [SMILES: O=C(Nc1c[nH]c2ccc(O[C@H]3C[C@H](c4ccc(C(F)(F)F)cc4)C3)cc12)C1CC(O)C1]

-continued 3-hydroxy-N-(5-(trans-3-(4-(trifluoromethyl)phenyl)cyclobutoxy)-1H-indol-3-yl)cyclobutane-1-carboxamide

574

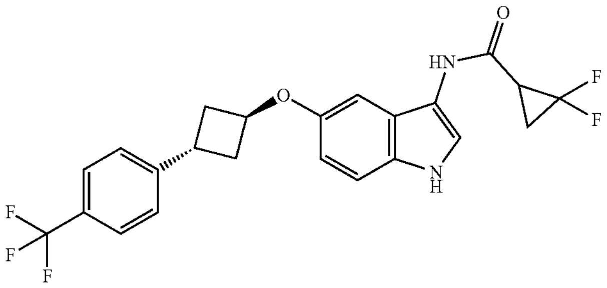 [SMILES: O=C(Nc1c[nH]c2ccc(O[C@H]3C[C@H](c4ccc(C(F)(F)F)cc4)C3)cc12)C1CC1(F)F]

2,2-difluoro-N-(5-(trans-3-(4-(trifluoromethyl)phenyl)cyclobutoxy)-1H-indol-3-yl)cyclopropane-1-carboxamide

575

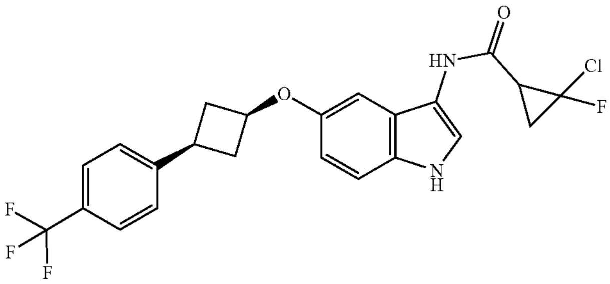

2-chloro-2-fluoro-N-(5-(cis-3-(4-(trifluoromethyl)phenyl)cyclobutoxy)-1H-indol-3-yl)cyclopropane-1-carboxamide

576

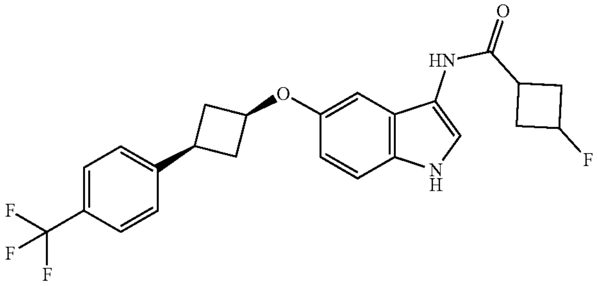 [SMILES: O=C(Nc1c[nH]c2ccc(O[C@H]3C[C@@H](c4ccc(C(F)(F)F)cc4)C3)cc12)C1CC(F)C1]

3-fluoro-N-(5-(cis-3-(4-(trifluoromethyl)phenyl)cyclobutoxy)-1H-indol-3-yl)cyclobutane-1-carboxamide

577

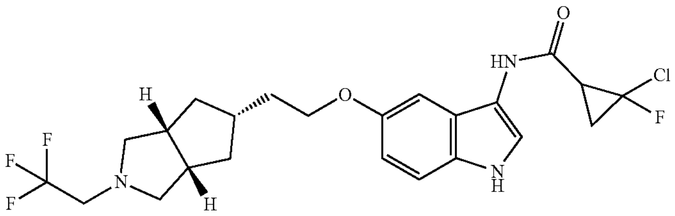 [SMILES: O=C(Nc1c[nH]c2ccc(OCC[C@@H]3C[C@@H]4CN(CC(F)(F)F)C[C@@H]4C3)cc12)C1CC1(F)Cl]

2-chloro-2-fluoro-N-(5-(2-((3aR,5r,6aS)-2-(2,2,2-trifluoroethyl)octahydrocyclopenta[c]pyrrol-5-yl)ethoxy)-1H-indol-3-yl)cyclopropane-1-carboxamide -continued

578

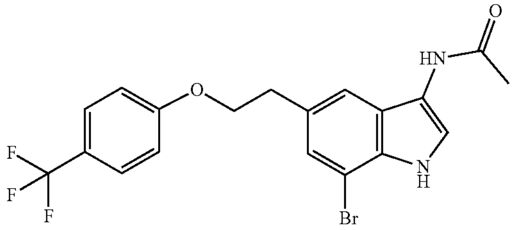

N-(7-bromo-5-(2-(4-(trifluoromethyl)phenoxy)ethyl)-1H-indol-3-y1)acetamide

579

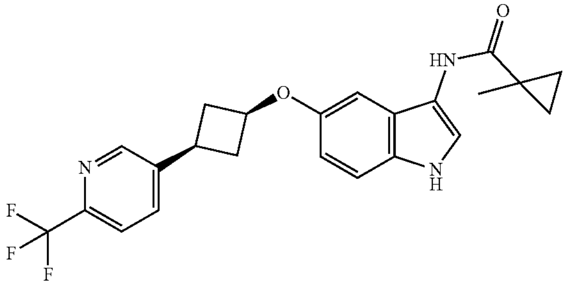 [SMILES: CC1(C(=O)Nc2c[nH]c3ccc(O[C@H]4C[C@@H](c5ccc(C(F)(F)F)nc5)C4)cc23)CC1]

1-methyl-N-(5-(cis-3-(6-(trifluoromethyl)pyridin-3-yl)cyclobutoxy)-1H-indol-3-yl)cyclopropane-1-carboxamide

580

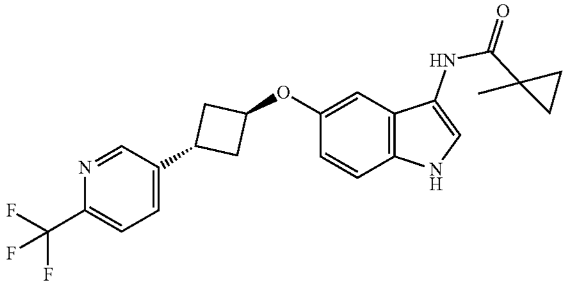 [SMILES: CC1(C(=O)Nc2c[nH]c3ccc(O[C@H]4C[C@H](c5ccc(C(F)(F)F)nc5)C4)cc23)CC1]

1-methyl-N-(5-(cis-3-(6-(trifluoromethyl)pyridin-3-yl)cyclobutoxy)-1H-indol-3-y1)cyclopropane-1-carboxamide

581

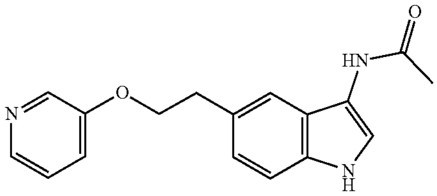 [SMILES: CC(=O)Nc1c[nH]c2ccc(CCOc3cccnc3)cc12]

N-(5-(2-(pyridin-3-yloxy)ethyl)-1H-indol-3-yl)acetamide

582

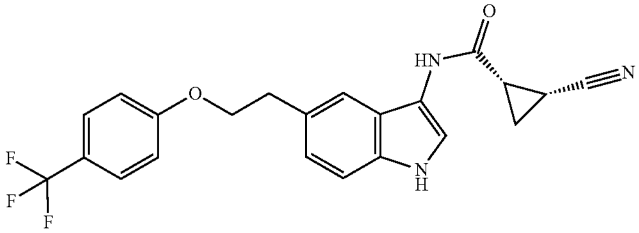 [SMILES: N#C[C@@H]1C[C@@H]1C(=O)Nc1c[nH]c2ccc(CCOc3ccc(C(F)(F)F)cc3)cc12]

(1S,2R)-2-cyano-N-(5-(2-(4-(trifluoromethyl)phenoxy)ethyl)-1H-indol-3-yl)cyclopropane-1-carboxamide -continued

584

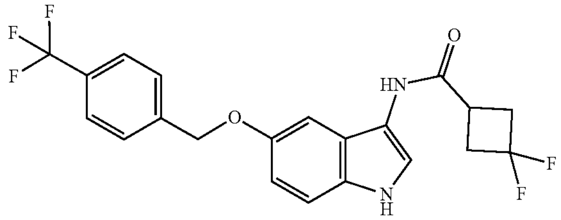 [SMILES: O=C(Nc1c[nH]c2ccc(OCc3ccc(C(F)(F)F)cc3)cc12)C1CC(F)(F)C1]

3,3-difluoro-N-(5-((4-(trifluoromethyl)benzyl)oxy)-1H-indol-3-yl)cyclobutane-1-carboxamide

585

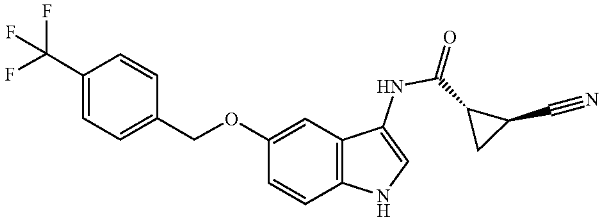 [SMILES: N#C[C@H]1C[C@@H]1C(=O)Nc1c[nH]c2ccc(OCc3ccc(C(F)(F)F)cc3)cc12]

(1S,2S)-2-cyano-N-(5-((4-(trifluoromethyl)benzyl)oxy)-1H-indol-3-yl)cyclopropane-1-carboxamide

586

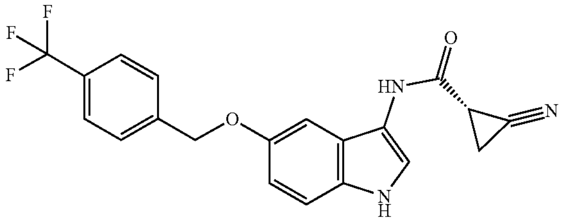

1-cyano-N-(5-((4-(trifluoromethyl)benzyl)oxy)-1H-indol-3-yl)cyclopropane-1-carboxamide

587

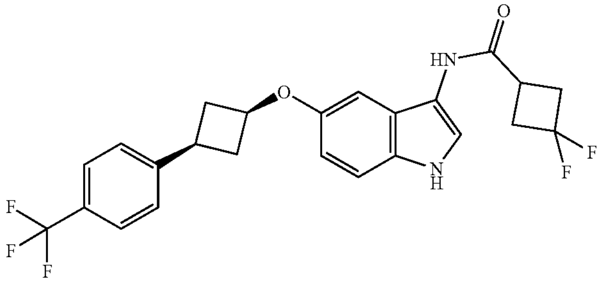

3,3-difluoro-N-(5-(cis-3-(4-(trifluoromethyl)phenyl)cyclobutoxy)-1H-indol-3-yl)cyclobutane-1-carboxamide

588

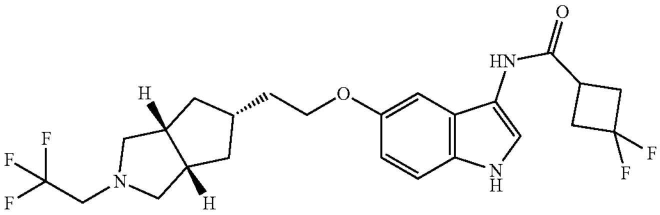 [SMILES: O=C(Nc1c[nH]c2ccc(OCC[C@@H]3C[C@@H]4CN(CC(F)(F)F)C[C@@H]4C3)cc12)C1CC(F)(F)C1]

3,3-difluoro-N-(5-(2-((3aR,5r,6aS)-2-(2,2,2-trifluoroethyl)octahydrocyclopenta[c]pyrrol-5-yl)ethoxy)-1H-indol-3-yl)cyclobutane-1-carboxamide -continued

589

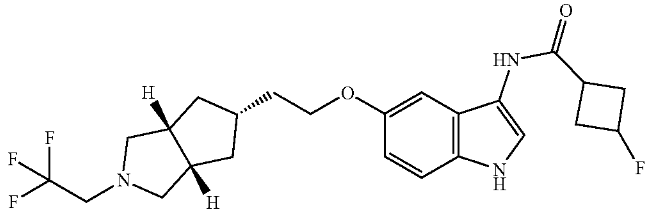 [SMILES: O=C(Nc1c[nH]c2ccc(OCC[C@@H]3C[C@@H]4CN(CC(F)(F)F)C[C@@H]4C3)cc12)C1CC(F)C1]

3-fluoro-N-(5-(2-((3aR,5r,6aS)-2-(2,2,2-trifluoroethyl)octahydrocyclopenta[c]pyrrol-5-yl)ethoxy)-1H-indol-3-yl)cyclobutane-1-carboxamide

590

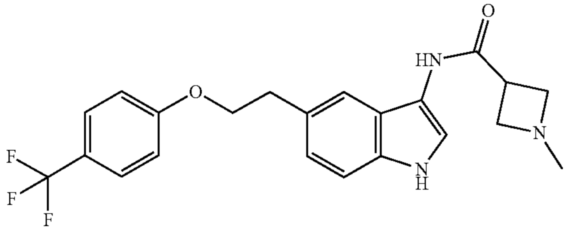 [SMILES: CN1CC(C(=O)Nc2c[nH]c3ccc(CCOc4ccc(C(F)(F)F)cc4)cc23)C1]

1-methyl-N-(5-(2-(4-(trifluoromethyl)phenoxy)ethyl)-1H-indol-3-yl)azetidine-3-carboxamide

591

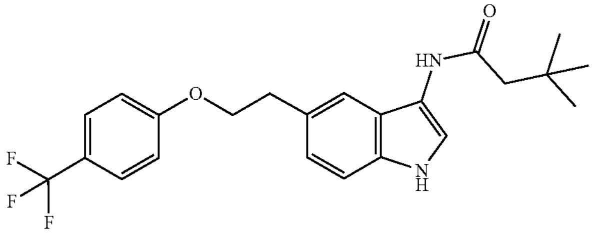 [SMILES: CC(C)(C)CC(=O)Nc1c[nH]c2ccc(CCOc3ccc(C(F)(F)F)cc3)cc12]

3,3-dimethyl-N-(5-(2-(4-(trifluoromethyl)phenoxy)ethyl)-1H-indol-3-yl)butanamide

592

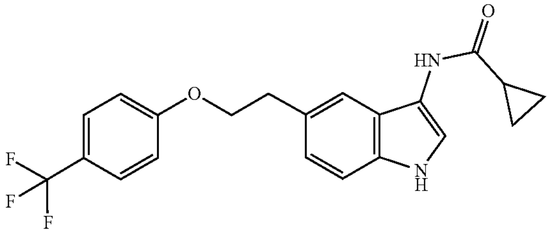 [SMILES: O=C(Nc1c[nH]c2ccc(CCOc3ccc(C(F)(F)F)cc3)cc12)C1CC1]

N-(5-(2-(4-(trifluoromethyl)phenoxy)ethyl)-1H-indol-3-yl)cyclopropanecarboxamide

593

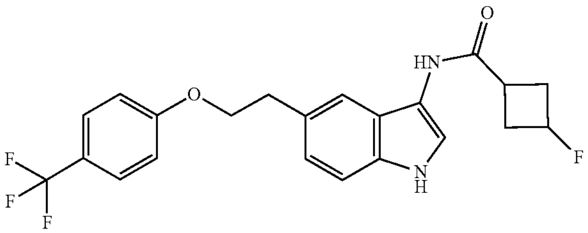 [SMILES: O=C(Nc1c[nH]c2ccc(CCOc3ccc(C(F)(F)F)cc3)cc12)C1CC(F)C1]

3-fluoro-N-(5-(2-(4-(trifluoromethyl)phenoxy)ethyl)-1H-indol-3-yl)cyclobutane-1-carboxamide -continued

594

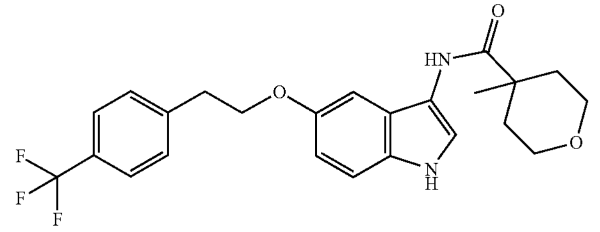 [SMILES: CC1(C(=O)Nc2c[nH]c3ccc(OCCc4ccc(C(F)(F)F)cc4)cc23)CCOCC1]

4-methyl-N-(5-(2-(4-(trifluoromethyl)phenoxy)ethyl)-1H-indol-3-yl)tetrahydro-2H-pyran-4-carboxamide

595

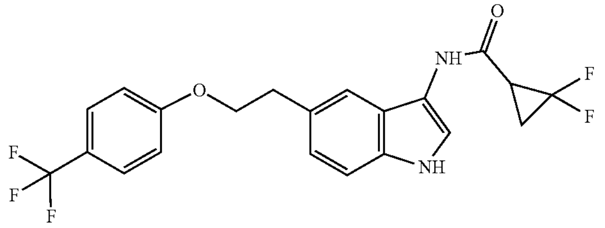 [SMILES: O=C(Nc1c[nH]c2ccc(CCOc3ccc(C(F)(F)F)cc3)cc12)C1CC1(F)F]

2,2-difluoro-N-(5-(2-(4-(trifluoromethyl)phenoxy)ethyl)-1H-indol-3-yl)cyclopropane-1-carboxamide

596

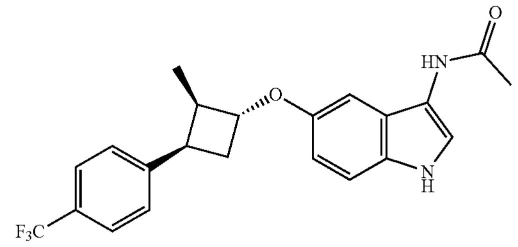 [SMILES: CC(=O)Nc1c[nH]c2ccc(O[C@@H]3C[C@@H](c4ccc(C(F)(F)F)cc4)[C@H]3C)cc12]

or a pharmaceutically acceptable salt thereof.

33. The compound of claim 1, wherein $L^1$ is —O—.

34. The compound of claim 1, wherein $L^3$ is —O—.

35. The compound of claim 1, wherein:

a1 and a2 are each 1;

$L^1$ is —O—, —N(H)—, or —N($R^d$)—; and $L^2$ is selected from the group consisting of:

straight-chain CI-3 alkylene, which is optionally substituted with 1-3 $R^b$;

$C_{3-8}$ cycloalkylene, which is optionally substituted with 1-3 $R^c$; and heterocyclylene having 4-8 ring atoms wherein 1-3 ring atoms are ring heteroatoms each independently selected from the group consisting of: N, N(H), N($R^d$), O, and $S(O)_{0-2}$, wherein the heterocyclylene is optionally substituted with 1-3 $R^C$.

36. The compound of claim 35, wherein a3, a4, and a5 are each 0.

37. The compound of claim 36, wherein $L^A$ is

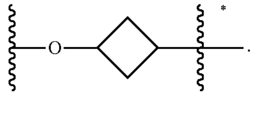

38. The compound of claim 1, wherein:

a1 and a2 are each 1;

$L^1$ is —O—; and $L^2$ is straight-chain $C_{1-3}$ alkylene, which is optionally substituted with 1-3 $R^b$.

39. The compound of claim 38, wherein a3, a4, and a5 are each 0.

40. The compound of claim 39, wherein $L^A$ is —O—$CH_2CH_2$—*.

41. The compound of claim 1, wherein W is $C_{1-10}$ alkyl, which is optionally substituted with 1-6 $R^{a2}$.

42. The compound of claim 1, wherein W is monocyclic $C_{3-8}$ cycloalkyl, which is optionally substituted with 1-4 substituents independently selected from the group consisting of oxo and $R^c$, optionally $C_{1-10}$ alkyl, which is optionally substituted with 1-6 $R^{a2}$; optionally $C_{1-4}$ alkyl, which is optionally substituted with 1-6 $R^{a2}$.

43. A compound of the following structure:

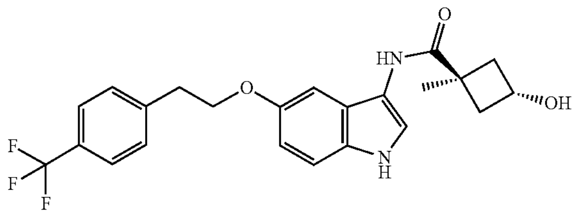 [SMILES: C[C@]1(C(=O)Nc2c[nH]c3ccc(OCCc4ccc(C(F)(F)F)cc4)cc23)C[C@H](O)C1]

trans-3-hydroxy-1-methyl-N-(5-(4-(trifluoromethyl)phenethoxy)-1H-indol-3-yl) cyclobutane-1-carboxamide.

44. A compound of the following structure:

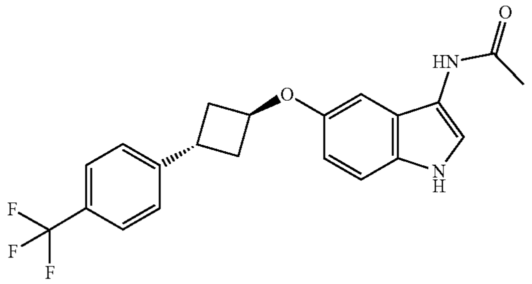 [SMILES: CC(=O)Nc1c[nH]c2ccc(O[C@H]3C[C@H](c4ccc(C(F)(F)F)cc4)C3)cc12]

N-(5-(trans-3-(4-(trifluoromethyl)phenyl)cyclobutoxy)-1H-indol-3-yl)acetamide.

45. A compound of the following structure:

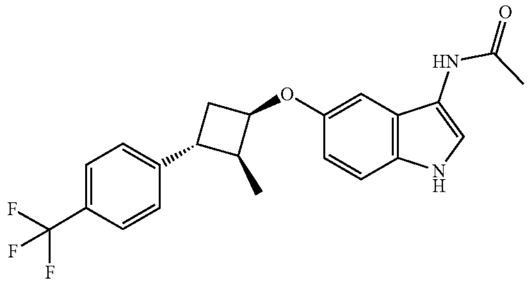 [SMILES: CC(=O)Nc1c[nH]c2ccc(O[C@@H]3C[C@@H](c4ccc(C(F)(F)F)cc4)[C@@H]3C)cc12]

N-(5-((1R,2S,3R)-2-methyl-3-(4-(trifluoromethyl)phenyl)cyclobutoxy)-1H-indol-3-yl)acetamide.

46. A compound of the following structure:

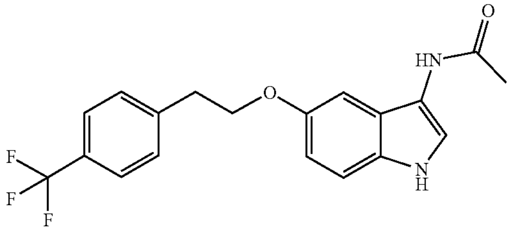 [SMILES: CC(=O)Nc1c[nH]c2ccc(OCCc3ccc(C(F)(F)F)cc3)cc12]

N-(5-(4-(trifluoromethyl)phenethoxy)-1H-indol-3-yl)acetamide.

47. A compound of the following structure:

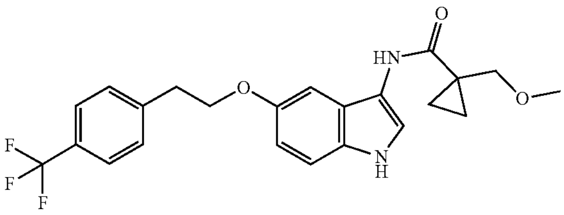 [SMILES: COCC1(C(=O)Nc2c[nH]c3ccc(OCCc4ccc(C(F)(F)F)cc4)cc23)CC1]

1-(methoxymethyl)-N-(5-(4-(trifluoromethyl) phenethoxy)-1H-indol-3-yl) cyclopropane-1-carboxamide.

48. A pharmaceutical composition comprising a compound of claim 1, or a pharmaceutically acceptable salt thereof, and one or more pharmaceutically acceptable excipients.

49. A method for inhibiting STING activity, the method comprising contacting STING with the compound of claim 1 or a pharmaceutically acceptable salt thereof.

50. A method of inducing an immune response in a subject in need thereof, the method comprising administering to the subject an effective amount of the compound of claim 1 or a pharmaceutically acceptable salt thereof.

51. A method of treatment of a disease, disorder, or condition associated with STING in a subject in need thereof, the method comprising administering to the subject an effective amount of a compound as claimed in claim 1 or a pharmaceutically acceptable salt thereof.

52. A combination comprising a compounds defined in claim 1 or a pharmaceutically acceptable salt or tautomer thereof, and one or more therapeutically active agents.

53. A method for inhibiting STING activity, the method comprising contacting STING with the compound of claim 43.

54. A method of treatment of a disease, disorder, or condition associated with STING in need thereof, the method comprising administering to the subject an effective amount of the compound of claim 51.

55. The method of claim 54, wherein the disease, disorder, or condition associated with STING is selected from the group consisting of type I interferonopathies, Aicardi-Goutières Syndrome (AGS), systemic lupus erythematosus, and rheumatoid arthritis.

56. The method of claim 54, wherein the disease, disorder, or condition associated with STING is systemic lupus erythematosus.

57. The method of claim 54, wherein the disease, disorder, or condition associated with STING is amyotrophic lateral sclerosis.

58. The method of claim 54, wherein the disease, disorder, or condition associated with STING is Parkinson's disease.

59. A method for inhibiting STING activity, the method comprising contacting STING with the compound of claim 44.

60. A method of treatment of a disease, disorder, or condition associated with STING in need thereof, the method comprising administering to the subject an effective amount of the compound of claim 44.

61. The method of claim 60, wherein the disease, disorder, or condition associated with STING is selected from the group consisting of type I interferonopathies, Aicardi-Goutières Syndrome (AGS), systemic lupus erythematosus, and rheumatoid arthritis.

62. The method of claim 60, wherein the disease, disorder, or condition associated with STING is systemic lupus erythematosus.

63. The method of claim 60, wherein the disease, disorder, or condition associated with STING is amyotrophic lateral sclerosis.

64. The method of claim 60, wherein the disease, disorder, or condition associated with STING is Parkinson's disease.

65. A method for inhibiting STING activity, the method comprising contacting STING with the compound of claim 45.

66. A method of treatment of a disease, disorder, or condition associated with STING in need thereof, the method comprising administering to the subject an effective amount of the compound of claim 45.

67. The method of claim 66, wherein the disease, disorder, or condition associated with STING is selected from the group consisting of type I interferonopathies, Aicardi-Goutières Syndrome (AGS), systemic lupus erythematosus, and rheumatoid arthritis.

68. The method of claim 66, wherein the disease, disorder, or condition associated with STING is systemic lupus erythematosus.

69. The method of claim 66, wherein the disease, disorder, or condition associated with STING is amyotrophic lateral sclerosis.

70. The method of claim 66, wherein the disease, disorder, or condition associated with STING is Parkinson's disease.

71. A method for inhibiting STING activity, the method comprising contacting STING with the compound of claim 46.

72. A method of treatment of a disease, disorder, or condition associated with STING in need thereof, the method comprising administering to the subject an effective amount of the compound of claim 46.

73. The method of claim 72, wherein the disease, disorder, or condition associated with STING is selected from the group consisting of type I interferonopathies, Aicardi-Goutières Syndrome (AGS), systemic lupus erythematosus, and rheumatoid arthritis.

74. The method of claim 72, wherein the disease, disorder, or condition associated with STING is systemic lupus erythematosus.

75. The method of claim 72, wherein the disease, disorder, or condition associated with STING is amyotrophic lateral sclerosis.

76. The method of claim 72, wherein the disease, disorder, or condition associated with STING is Parkinson's disease.

77. A method for inhibiting STING activity, the method comprising contacting STING with the compound of claim 32 or a pharmaceutically acceptable salt thereof.

78. A method of treatment of a disease, disorder, or condition associated with STING in need thereof, the method comprising administering to the subject an effective amount of the compound of claim 32 or a pharmaceutically acceptable salt thereof.

79. The method of claim 78, wherein the disease, disorder, or condition associated with STING is selected from the group consisting of type I interferonopathies, Aicardi-Goutières Syndrome (AGS), systemic lupus erythematosus, and rheumatoid arthritis.

80. The method of claim 78, wherein the disease, disorder, or condition associated with STING is systemic lupus erythematosus.

81. The method of claim 78, wherein the disease, disorder, or condition associated with STING is amyotrophic lateral sclerosis.

82. The method of claim 78, wherein the disease, disorder, or condition associated with STING is Parkinson's disease.

83. The method of claim 51, wherein the disease, disorder, or condition associated with STING is selected from the group consisting of type I interferonopathies, Aicardi-Goutières Syndrome (AGS), systemic lupus erythematosus, and rheumatoid arthritis.

84. The method of claim 51, wherein the disease, disorder, or condition associated with STING is systemic lupus erythematosus.

85. The method of claim 51, wherein the disease, disorder, or condition associated with STING is amyotrophic lateral sclerosis.

86. The method of claim 51, wherein the disease, disorder, or condition associated with STING is Parkinson's disease.

* * * * *